(12) United States Patent
Sugimoto et al.

(10) Patent No.: US 8,097,708 B2
(45) Date of Patent: Jan. 17, 2012

(54) 10A-AZALIDE COMPOUND

(75) Inventors: Tomohiro Sugimoto, Saitama (JP); Kanako Yamamoto, Saitama (JP); Akira Manaka, Saitama (JP); Haruhisa Ogita, Saitama (JP); Jun Kurosaka, Saitama (JP); Madoka Kawamura, Saitama (JP); Masato Kashimura, Saitama (JP); Naoki Sasamoto, Saitama (JP); Tomoaki Miura, Kanagawa (JP); Kenichi Kanemoto, Kanagawa (JP); Tomohiro Ozawa, Saitama (JP); Ken Chikauchi, Chiba (JP); Eiki Shitara, Kanagawa (JP); Dai Kubota, Saitama (JP)

(73) Assignees: Taisho Pharmaceutical Co., Ltd., Tokyo (JP); Meiji Seika Kaisha, Ltd., Tokyo (JP)

( * ) Notice: Subject to any disclaimer, the term of this patent is extended or adjusted under 35 U.S.C. 154(b) by 611 days.

(21) Appl. No.: 12/223,675

(22) PCT Filed: Feb. 7, 2007

(86) PCT No.: PCT/JP2007/000068
§ 371 (c)(1),
(2), (4) Date: Dec. 15, 2008

(87) PCT Pub. No.: WO2007/091393
PCT Pub. Date: Aug. 16, 2007

(65) Prior Publication Data
US 2009/0281292 A1   Nov. 12, 2009

(30) Foreign Application Priority Data

Feb. 7, 2006 (JP) ................. 2006-030207
Jan. 30, 2007 (JP) ................. 2007-020213

(51) Int. Cl.
*C07H 17/08* (2006.01)

(52) U.S. Cl. ...................................... 536/7.4

(58) Field of Classification Search ............ 536/7.4
See application file for complete search history.

(56) References Cited

U.S. PATENT DOCUMENTS

| 4,474,768 A | 10/1984 | Bright |
| 4,517,359 A | 5/1985 | Kobrehel et al. |
| 5,635,485 A | 6/1997 | Agouridas et al. |
| 5,866,549 A | 2/1999 | Or et al. |
| 6,100,404 A | 8/2000 | Agouridas et al. |
| 2007/0042974 A1 | 2/2007 | Miura et al. |

FOREIGN PATENT DOCUMENTS

| EP | 0 508 726 | 10/1992 |
| EP | 0 680 967 | 11/1995 |
| WO | 98/09978 | 3/1998 |
| WO | 02/32919 | 4/2002 |
| WO | 03/014136 | 2/2003 |
| WO | 2005/019238 | 3/2005 |

OTHER PUBLICATIONS

Lu, W. et al., *Chemoenzymatic synthesis of macrocyclic polyamines*, Tetrahedron Letters, vol. 40, pp. 4965-4968 (1999).
English language Abstract of WO 2005/019238, 2005.
English language Abstract of EP 0 680 967, 1995.
English language Abstract of WO 03/014136, 2003.

*Primary Examiner* — Elli Peselev
(74) *Attorney, Agent, or Firm* — Greenblum & Bernstein, PLC

(57) ABSTRACT

[Object]: To provide a compound having a novel structure effective against *Hemophilus influenzae* and erythromycin resistant bacteria (for example, resistant pneumococci and streptococci) as well as against conventional erythromycin sensitive bacteria.

[Solution]: A novel 10a-azalide compound represented by the formula (I), a pharmaceutically acceptable salt thereof or a solvate thereof, or an intermediate for the preparation of the same. The compound of the present invention has superior antibacterial activity against *Hemophilus influenzae*, erythromycin resistant pneumococci and the like, and therefore, the compound can be used as a therapeutic agent of infectious diseases.

17 Claims, No Drawings

10A-AZALIDE COMPOUND

TECHNICAL FIELD

The present invention relates to a novel antibiotic having an erythromycin-like structure.

BACKGROUND ART

Erythromycin A is an antibiotic which has been widely used as a therapeutic agent for infectious diseases caused by gram positive bacteria, mycoplasmas, and the like. However, due to decomposition by gastric acid, erythromycin has a drawback of inconstant pharmacokinetics. Therefore, derivatives of erythromycin having increased stability to acids were researched. As a result, macrolides having stable pharmacokinetics such as clarithromycin, azithromycin (Patent documents 1 and 2 mentioned below) and roxithromycin have been developed. These macrolide agents have been applied in a therapeutic field of respiratory infectious diseases of ambulatory patients, and therefore, they are required to have a potent antibacterial activity especially against pneumococci, streptococci, and *Hemophilus influenzae* which are frequently isolated clinically. Furthermore, since macrolide-resistant pneumococci have been highly frequently isolated from community acquired pneumonia patients, it has been considered important that they are effective against the resistant pneumococci.

As a result of various researches in recent years, Agouridas et al. found HMR3647 (telithromycin, Patent document 3 mentioned below) in 1995, and successively Or et al. found ABT-773 (cethromycin, Patent document 4 mentioned below) in 1998 as macrolides that are effective both against erythromycin resistant pneumococci and erythromycin resistant streptococci. Then, 2-fluoroketolide (Patent document 5 mentioned below) of which efficacy was further enhanced was reported.

From a structural viewpoint, marketed macrolides are mainly classified into 14-membered or 15-membered ring type macrolides which are erythromycin derivatives, and 16-membered ring type macrolides which are leucomycin derivatives. Among the erythromycin derivatives, the 15-membered ring macrolides include azithromycin mentioned above. Azithromycin, unlike the other 14-membered ring macrolides, possesses a structural feature of having a nitrogen atom in the lactone ring, and therefore the macrolide is called azalide. Nomenclature of azalides is based on the position number of a carbon atom substituted with a nitrogen atom when the carbonyl group of the lactone is assumed to be in the 1-position. In the case of azithromycin mentioned above, since the nitrogen atom is introduced in the position of the ninth carbon atom from the carbonyl group, the compound is called 9a-azalide.

In addition to the 9a-azalides, 8a-azalides (Patent document 6 mentioned below) and 11a-azalides (Patent document 7 mentioned below) are known as examples of reported azalides obtainable by chemical conversion of 14-membered ring macrolides.

As for 10a-azalides, those derived from 16-membered ring macrolides as leucomycin derivatives have recently been reported (Patent document 8 mentioned below). However, no 10a-azalides derived from 14-membered ring macrolides have been reported.

Patent document 1: U.S. Pat. No. 4,474,768
Patent document 2: U.S. Pat. No. 4,517,359
Patent document 3: EP680967
Patent document 4: WO98/09978
Patent document 5: WO02/32919
Patent document 6: EP508726
Patent document 7: WO2003/014136
Patent document 8: WO2005/019238

DISCLOSURE OF THE INVENTION

Object to be Achieved by the Invention

An object of the present invention is to provide a compound having a novel structure which is effective against *Hemophilus influenzae* and erythromycin resistant bacteria (for example, resistant pneumococci and streptococci) as well as against conventional erythromycin sensitive bacteria.

Means for Achieving the Object

The inventors of the present invention conducted various researches on azalide compounds, and as a result, succeeded in synthesis of novel azalides derived from 14-membered ring macrolides.

More specifically, the inventors of the present invention used 14-membered ring macrolides as starting materials, and oxidized 10-oxo compounds, which were obtained by oxidative cleavage of the diol moieties in the 11- and 12-positions, to derive into carboxyl compounds. Then, they performed rearrangement reactions by using the carboxyl compounds as starting materials to synthesize compounds having 10-amino group which were not reported so far. Further, by performing partial structural conversion and then intramolecular cyclization of those compounds, they succeeded in providing 10a-azalide compounds having a novel skeleton.

Further, as a result of evaluation of antibacterial activity thereof compounds, the inventors found that the 10a-azalide compounds had activities superior to those of the erythromycin derivatives as the starting materials, and accomplished the present invention.

The present invention thus relates to a 10a-azalide compound represented by the formula (I):

[Formula 1]

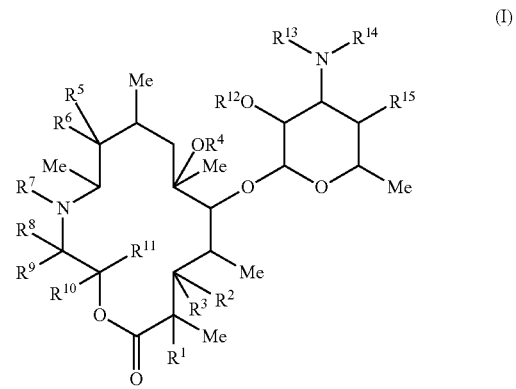

{wherein, in the formula (I), $R^1$ is:
hydrogen atom,
a halogen atom, or
a $C_{1-10}$ alkyl group which may be substituted,
$R^2$ and $R^3$ combine together to represent oxo group, or one of them is hydrogen atom, and the other is:
hydrogen atom,
hydroxyl group, a protected hydroxyl group,
a group represented by the formula —$X^{031}$—$R^{031}$,
a group represented by the formula —$X^{031}$-$A^{031}$-$X^{032}$—$R^{031}$,
a group represented by the formula —$X^{031}$-$A^{031}$-$X^{032}$-$A^{032}$-$X^{033}$—$R^{031}$,
a group represented by the formula —$X^{031}$-$A^{031}$-$X^{032}$-$A^{032}$-$X^{033}$-$A^{033}$-$X^{034}$—$R^{031}$,
or a group represented by the formula:

[Formula 2]

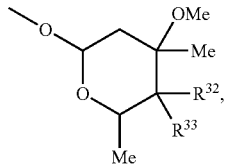

wherein $X^{031}$ is:
a group represented by the formula —O—,
a group represented by the formula —OCO—,
a group represented by the formula —$OCO_2$—, or
a group represented by the formula —OCON($R^{20}$)—,
one of $R^{32}$ and $R^{33}$ is hydrogen atom, and the other is:
hydrogen atom,
amino group,
hydroxyl group,
a protected hydroxyl group,
a group represented by the formula —OCON($R^{24}$)$R^{25}$ (in the formula, $R^{24}$ and $R^{25}$ both represent hydrogen atom, or represent groups which combine to form a cyclic amino group together with the adjacent nitrogen atom),
a group represented by the formula —$X^{331}$—$R^{331}$,
a group represented by the formula —$X^{331}$-$A^{331}$-$X^{332}$—$R^{331}$,
a group represented by the formula —$X^{331}$-$A^{331}$-$X^{332}$-$A^{332}$-$X^{333}$—$R^{331}$, or
a group represented by the formula —$X^{331}$-$A^{331}$-$X^{332}$-$A^{332}$-$X^{333}$-$A^{333}$-$X^{334}$—$R^{331}$,
wherein $X^{331}$ is:
a single bond,
a group represented by the formula —O—,
a group represented by the formula —OCO—,
a group represented by the formula —$OCO_2$—,
a group represented by the formula —OCON($R^{20}$)—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—, or
a group represented by the formula —N($R^{20}$)$SO_2$—,
or one of $R^{32}$ and $R^{33}$ is hydroxyl group, and the other is:
a group represented by the formula —$CH_2NH_2$,
a group represented by the formula —$X^{335}$—$R^{332}$,
a group represented by the formula —$X^{335}$-$A^{334}$-$X^{336}$—$R^{332}$,
a group represented by the formula —$X^{335}$-$A^{334}$-$X^{336}$-$A^{335}$-$X^{337}$—$R^{332}$, or
a group represented by the formula —$X^{335}$-$A^{334}$-$X^{336}$-$A^{335}$-$X^{337}$-$A^{336}$-$X^{338}$—$R^{332}$,
wherein $X^{335}$ is:
a single bond,
a group represented by the formula —$(CH_2)_n$—N($R^{20}$)—,
a group represented by the formula —$(CH_2)_n$—N($R^{20}$)CO—,
a group represented by the formula —$(CH_2)_n$—N($R^{20}$)$CO_2$—,
a group represented by the formula —$(CH_2)_n$—N($R^{20}$)CON($R^{21}$)—,
a group represented by the formula —$(CH_2)_n$—N($R^{20}$)O—,
a group represented by the formula —$(CH_2)_n$—OCON($R^{20}$)—,
a group represented by the formula —$(CH_2)_n$—ON($R^{20}$)CO—,
a group represented by the formula —$(CH_2)_n$—O—,
a group represented by the formula —$(CH_2)_n$—OCO—,
a group represented by the formula —$(CH_2)_n$—$OCO_2$—,
a group represented by the formula —$(CH_2)_n$—OC(N$R^{20}$)—, or
a group represented by the formula —$(CH_2)_n$—$S(O)_p$—,
or $R^{32}$ and $R^{33}$ combine together to represent:
oxo group,
oxime group,
a group represented by the formula =N—$X^{339}$—$R^{333}$,
a group represented by the formula =N—$X^{339}$-$A^{337}$-$X^{340}$—$R^{333}$,
a group represented by the formula =N—$X^{339}$-$A^{337}$-$X^{340}$-$A^{338}$-$X^{341}$—$R^{333}$,
a group represented by the formula =N—$X^{339}$-$A^{337}$-$X^{340}$-$A^{338}$-$X^{341}$-$A^{339}$-$X^{342}$—$R^{333}$, or a group represented by the formula:

[Formula 3]

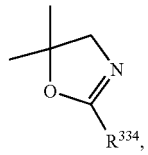

wherein $X^{339}$ is:
a single bond,
a group represented by the formula —O—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—, or
a group represented by the formula —N($R^{20}$)$SO_2$—, and
$R^{334}$ is:
a group represented by the formula —SH,
a group represented by the formula —OH,
a group represented by the formula —$X^{343}$—$R^{335}$,
a group represented by the formula —$X^{343}$-$A^{340}$-$X^{344}$—$R^{335}$,
a group represented by the formula —$X^{343}$-$A^{340}$-$X^{344}$-$A^{341}$-$X^{345}$—$R^{335}$, or
a group represented by the formula —$X^{343}$-$A^{340}$-$X^{344}$-$A^{341}$-$X^{345}$-$A^{342}$-$X^{346}$—$R^{335}$,
wherein $X^{343}$ is:
a single bond,
a group represented by the formula —S—, or
a group represented by the formula —$(CH_2)_n$ CO—,
$R^4$ is:
hydrogen atom,
a group represented by the formula —$CONHCO_2Me$,
a group represented by the formula —$X^{041}$—$R^{041}$,
a group represented by the formula —$X^{041}$-$A^{041}$-$X^{042}$—$R^{041}$, a group represented by the formula —$X^{041}$-$A^{041}$-$X^{042}$-$A^{042}$-$X^{043}$—$R^{041}$, or a group represented by the formula —$X^{041}$-$A^{041}$-$X^{042}$-$A^{042}$-$X^{043}$-$A^{043}$-$X^{044}$—$R^{041}$, wherein $X^{041}$ is:
a single bond,
a group represented by the formula —CO—,
a group represented by the formula —CON($R^{20}$)—, or
a group represented by the formula —$CO_2$—, or $R^4$ may combine with $R^6$ to form cyclic carbonate [—$CO_2$—], one of $R^5$ and $R^6$ is hydrogen atom, and the other is:
hydrogen atom,
hydroxyl group,
a protected hydroxyl group,
amino group,
a protected amino group,
a halogen atom,
a group represented by the formula —$OCONH_2$,
a group represented by the formula —$X^{061}$—$R^{061}$,
a group represented by the formula —$X^{061}$-$A^{061}$-$X^{062}$—$R^{061}$,
a group represented by the formula —$X^{061}$-$A^{061}$-$X^{062}$-$A^{062}$-$X^{063}$—$R^{061}$, or
a group represented by the formula —$X^{061}$-$A^{061}$-$X^{062}$-$A^{062}$-$X^{063}$-$A^{063}$-$X^{064}$—$R^{061}$, or may combine with $R^7$ to form cyclic carbamate [—OCO—],
wherein $X^{061}$ is:
a single bond,
a group represented by the formula —O—,
a group represented by the formula —OCO—,
a group represented by the formula —$OCO_2$—,
a group represented by the formula —OCON($R^{20}$)—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—,
a group represented by the formula —N($R^{20}$)$SO_2$—, or
a group represented by the formula —$CH_2$N($R^{20}$)—, or $R^5$ and $R^6$ combine together to represent
oxo group,
oxime group,
a group represented by the formula =N—$NH_2$,
a protected oxime group,
a group represented by the formula =N—$X^{065}$—$R^{062}$,
a group represented by the formula =N—$X^{065}$-$A^{064}$-$X^{066}$—$R^{062}$,
a group represented by the formula =N—$X^{065}$-$A^{064}$-$X^{066}$-$A^{065}$-$X^{067}$—$R^{062}$, or
a group represented by the formula =N—$X^{065}$-$A^{064}$-$X^{066}$-$A^{065}$-$X^{067}$-$A^{066}$-$X^{068}$—$R^{062}$
wherein $X^{065}$ is:
a single bond,
a group represented by the formula —O—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—, or
a group represented by the formula —N($R^{20}$)$SO_2$—, $R^7$ is:
hydrogen atom,
hydroxyl group,
a protective group of amino group,
a group represented by the formula —$X^{071}$—$R^{071}$, a group represented by the formula —$X^{071}$-$A^{071}$-$X^{072}$—$R^{071}$, or a group represented by the formula —$X^{071}$-$A^{071}$-$X^{072}$-$A^{072}$-$X^{073}$—$R^{071}$, or may combine with $R^{10}$ to form cyclic carbamate [—$CO_2CH_2$—],
wherein $X^{071}$ is:
a single bond,
a group represented by the formula —O—,
a group represented by the formula —CO—,
a group represented by the formula —$CO_2$—, or
a group represented by the formula —$SO_2$—, $R^8$ and $R^9$, which are the same or different, represent:
hydrogen atom,
a group represented by the formula —$X^{081}$—$R^{081}$,
a group represented by the formula —$X^{081}$-$A^{081}$-$X^{082}$—$R^{081}$, or
a group represented by the formula —$X^{081}$-$A^{081}$-$X^{082}$-$A^{082}$-$X^{083}$—$R^{081}$,
wherein $X^{081}$ is:
a single bond,
a group represented by the formula —CO—,
a group represented by the formula —$CO_2$—, or
a group represented by the formula —CON($R^{20}$)—, $R^{10}$ and $R^{11}$, which are the same or different, represent hydrogen atom,
a group represented by the formula —$X^{101}$—$R^{101}$,
a group represented by the formula —$X^{101}$-$A^{101}$-$X^{102}$—$R^{101}$,
a group represented by the formula —$X^{101}$-$A^{101}$-$X^{102}$-$A^{102}$-$X^{103}$—$R^{101}$, or
a group represented by the formula —$X^{101}$-$A^{101}$-$X^{102}$-$A^{102}$-$X^{103}$-$A^{103}$-$X^{104}$—$R^{101}$,
wherein $X^{101}$ is:
a single bond,
a group represented by the formula —CO—,
a group represented by the formula —$CO_2$—, or
a group represented by the formula —CON($R^{20}$)—, $R^{12}$ is:
hydrogen atom,
a protective group of hydroxyl group,
a group represented by the formula —$X^{121}$—$R^{121}$,
a group represented by the formula —$X^{121}$-$A^{121}$-$X^{122}$—$R^{121}$, or
a group represented by the formula —$X^{121}$-$A^{121}$-$X^{122}$-$A^{122}$-$X^{123}$—$R^{121}$,
wherein $X^{121}$ is:
a single bond,
a group represented by the formula —CO—,
a group represented by the formula —$CO_2$—, or
a group represented by the formula —CON($R^{20}$)—, $R^{13}$ and $R^{14}$, which are the same or different, represent
hydrogen atom,
a protective group of amino group,
a group represented by the formula —$X^{131}$—$R^{131}$,
a group represented by the formula —$X^{131}$-$A^{131}$-$X^{1132}$—$R^{131}$, or
a group represented by the formula —$X^{131}$-$A^{131}$-$X^{132}$-$A^{132}$-$X^{133}$—$R^{131}$,
wherein $X^{131}$ is:
a single bond,
a group represented by the formula —CO—,
a group represented by the formula —$CO_2$—, or
a group represented by the formula —CON($R^{20}$)—, $R^{15}$ is:
hydrogen atom,
hydroxyl group, a protected hydroxyl group,
a group represented by the formula —$X^{151}$—$R^{151}$,
a group represented by the formula —$X^{151}$-$A^{151}$-$X^{152}$—$R^{151}$, or
a group represented by the formula —$X^{151}$-$A^{151}$-$X^{152}$-$A^{152}$-$X^{153}$—$R^{151}$,
wherein $X^{151}$ is:
a single bond,
a group represented by the formula —OCO—,
a group represented by the formula —$OCO_2$—, or
a group represented by the formula —$OCON(R^{20})$—,
$X^{032}$, $X^{033}$, $X^{034}$, $X^{332}$, $X^{333}$, $X^{334}$, $X^{336}$, $X^{337}$, $X^{338}$, $X^{340}$, $X^{341}$, $X^{342}$, $X^{344}$, $X^{345}$, $X^{346}$, $X^{042}$, $X^{043}$, $X^{044}$, $X^{062}$, $X^{063}$, $X^{064}$, $X^{066}$, $X^{067}$, $X^{068}$, $X^{072}$, $X^{073}$, $X^{082}$, $X^{083}$, $X^{102}$, $X^{103}$, $X^{104}$, $X^{122}$, $X^{123}$, $X^{132}$, $X^{133}$, $X^{152}$ and $X^{153}$ mentioned above, which are the same or different, represent
a single bond
a group represented by the formula —O—,
a group represented by the formula —OCO—,
a group represented by the formula —$OCO_2$—,
a group represented by the formula —$OCON(R^{20})$—,
a group represented by the formula —$S(O)_p$—,
a group represented by the formula —$SO_2N(R^{20})$—,
a group represented by the formula —OCS—,
a group represented by the formula —CO—,
a group represented by the formula $CO_2$—,
a group represented by the formula —$CON(R^{20})$—,
a group represented by the formula —CH=N—,
a group represented by the formula —CH=N—O—,
a group represented by the formula —CH=$N(R^{20})$—,
a group represented by the formula —CH=$N(R^{20})$O—,
a group represented by the formula —CH=$N(R^{20})N(R^{21})$—,
a group represented by the formula —CH=$N(OR^{20})$—,
a group represented by the formula —CH=N—$N(R^{20})R^{21}$—,
a group represented by the formula —CS—,
a group represented by the formula —C(S)O—,
a group represented by the formula —$CSN(R^{20})$—,
a group represented by the formula —O—N=CH—,
a group represented by the formula —N=CH—,
a group represented by the formula —$N(R^{20})$—,
a group represented by the formula —$N(R^{20})$CO—,
a group represented by the formula —$N(R^{20})$CS—,
a group represented by the formula —$N(R^{20})SO_2$—,
a group represented by the formula —$N(R^{20})CO_2$—, or
a group represented by the formula —$N(R^{20})CON(R^{21})$—,
$A^{031}$, $A^{032}$, $A^{033}$, $A^{331}$, $A^{332}$, $A^{333}$, $A^{334}$, $A^{335}$, $A^{336}$, $A^{337}$, $A^{338}$, $A^{339}$, $A^{340}$, $A^{341}$, $A^{342}$, $A^{041}$, $A^{042}$, $A^{043}$, $A^{061}$, $A^{062}$, $A^{063}$, $A^{064}$, $A^{065}$, $A^{066}$, $A^{071}$, $A^{072}$, $A^{081}$, $A^{082}$, $A^{101}$, $A^{102}$, $A^{103}$, $A^{121}$, $A^{122}$, $A^{131}$, $A^{132}$, $A^{151}$ and $A^{152}$ mentioned above, which are the same or different, represent
a divalent $C_{1-10}$ aliphatic hydrocarbon group which may be substituted with
hydroxyl group,
an arylene group, or
a divalent heterocyclic group,
$R^{031}$, $R^{331}$, $R^{332}$, $R^{333}$, $R^{335}$, $R^{041}$, $R^{061}$, $R^{062}$, $R^{071}$, $R^{081}$, $R^{101}$, $R^{121}$, $R^{131}$ and $R^{151}$ mentioned above, which are the same or different, represent
a $C_{1-10}$ alkyl group which may be substituted,
a $C_{2-10}$ alkenyl group which may be substituted,
a $C_{2-10}$ alkynyl group which may be substituted,
a $C_{3-10}$ cycloalkyl group which may be substituted,
a $C_{3-10}$ cycloalkyl group condensed with an aryl group, which may be substituted,
an aryl group which may be substituted, or
a heterocyclic group which may be substituted, substituents of the groups "which may be substituted" mentioned above each mean arbitrary 1 to 5 substituents selected from the following group of substituents, and the group of substituents consists of:
carboxyl group,
a halogen atom,
oxo group,
hydroxyl group,
cyano group,
nitro group,
oxido group,
sulfonic acid group, and
thiol group,
as well as the following group which may be substituted with groups of the group A:
a $C_{1-10}$ alkyl group,
a $C_{2-12}$ alkenyl group,
a $C_{2-12}$ alkynyl group,
a $C_{3-10}$ cycloalkyl group,
a $C_{1-10}$ alkoxy group,
a $C_{1-10}$ hydroxyalkoxy group,
a $C_{2-12}$ alkenyloxy group,
a carboxy($C_{1-6}$ alkyloxy) group,
a cyano($C_{1-6}$ alkyloxy) group,
a $C_{1-10}$ alkylthio group,
a $C_{1-6}$ alkylsulfonyl group,
an arylsulfonyl group which may be substituted with a $C_{1-6}$ alkyl group or a halogen atom,
a $C_{1-10}$ haloalkylthio group,
a $C_{2-10}$ alkenylthio group,
a ($C_{1-6}$ alkoxy)($C_{1-6}$ alkyl) group,
a ($C_{1-6}$ alkoxy)($C_{1-6}$ alkoxy) group,
a $C_{1-10}$ haloalkyl group,
a $C_{2-12}$ alkanoyl group,
a $C_{2-12}$ alkanoyloxy group,
a ($C_{2-12}$ alkanoyloxy)($C_{1-6}$ alkyl) group,
a benzoyl group which may be substituted with 1 to 3 of halogen atoms or nitro groups,
a $C_{2-6}$ alkanoylamino group,
an aminosulfonyl group which may be substituted with 1 or 2 of $C_{1-6}$ alkyl groups,
a $C_{1-6}$ alkylsulfonyl group,
a $C_{1-6}$ alkylsulfonylamino group,
a benzenesulfonylamino group which may be substituted with $C_{1-6}$ alkyl,
succinimido group,
maleimido group,
phthalimido group,
a $C_{2-10}$ alkoxycarbonyl group,
a $C_{2-10}$ alkoxycarbonylalkoxy group,
tri-($C_{1-6}$ alkyl)silyloxy group,
a group represented by the formula —$N(R^{22})R^{23}$ (in the formula, $R^{22}$ and $R^{23}$ each represent hydrogen atom, a $C_{1-6}$ alkyl group, a $C_{1-6}$ hydroxyalkyl group, a $C_{3-10}$ alkoxycarbonylalkyl group or a cyano($C_{1-6}$ alkyl) group, or represent groups which combine to form, together with the adjacent nitrogen atom, a cyclic amino group, which may be substituted with "a $C_{1-6}$ alkyl group, a cyano($C_{1-6}$ alkyl) group, a $C_{3-10}$ cycloalkyl group, a $C_{2-6}$ alkanoyl group, benzoyl group, an aryloxy($C_{2-6}$ alkanoyl) group which may be substituted with "a $C_{1-6}$ alkyl group or a $C_{1-6}$ alkoxy group", a ($C_{1-6}$ alkoxy)($C_{1-6}$ alkyl) group, a $C_{2-6}$ alkoxycarbonyl group, oxo group, or hydroxyl group"),
a group represented by the formula —$CON(R^{22})R^{23}$ (in the formula, $R^{22}$ and $R^{23}$ have the same meanings as those defined above), a group represented by the formula —OCON($R^{22}$)$R^{23}$ (in the formula, $R^{22}$ and $R^{23}$ have the same meanings as those defined above), a group represented by the formula —CH$_2$N($R^{22}$)$R^{23}$ (in the formula, $R^{22}$ and $R^{23}$ have the same meanings as those defined above), a group represented by the formula —O(CH$_2$)$_m$N($R^{22}$)$R^{23}$ (in the formula, $R^{22}$ and $R^{23}$ have the same meanings as those defined above), and "an aryl group, a heterocyclic group, an aryloxy group, an arylthio group, a heterocyclyloxy group or a heterocyclylthio group" which may be substituted with 1 to 5 of groups arbitrarily selected from the group consisting of "a $C_{1-6}$ alkyl group, a $C_{1-6}$ haloalkyl group, a halogen atom, a $C_{1-6}$ alkoxy group, an aminosulfonyl group which may be substituted with 1 or 2 of $C_{1-6}$ alkyl groups, an aminosulfonylamino group which may be substituted with 1 or 2 of $C_{1-6}$ alkyl groups, an amino ($C_{1-6}$ alkyl) group which may be substituted with 1 or 2 of $C_{1-6}$ alkyl groups, a saturated heterocyclic group, a $C_{1-6}$ alkyl group substituted with a saturated heterocyclic group, carboxyl group, a $C_{2-10}$ alkoxycarbonyl group, a $C_{1-6}$ hydroxyalkyl group, cyano group, a cyano ($C_{1-6}$ alkyl) group, an amino group which may be substituted with 1 or 2 of $C_{1-6}$ alkyl groups, hydroxyl group, a $C_{1-10}$ alkylthio group, a $C_{1-6}$ alkylsulfonyl group, a $C_{1-6}$ alkylsulfonylamino group and nitro group", wherein group A consists of "an aryl group, a heterocyclic group, a heterocyclylthio group or an aryloxy group" which may be substituted with "a halogen atom, a $C_{1-6}$ alkyl group, a hydroxy($C_{1-6}$ alkyl) group, hydroxyl group or nitro group", cyano group, cyanothio group, carboxyl group, hydroxyl group, a $C_{2-10}$ alkoxycarbonyl group, and a $C_{1-10}$ alkoxy group, $R^{20}$ and $R^{21}$ mentioned above, which are the same or different, represent a group suitably selected from hydrogen atom, and a $C_{1-10}$ alkyl group which may be substituted with the aforementioned substituents, p mentioned above is an integer of 0 to 2, n mentioned above is 1 or 2, and m mentioned above is an integer of 2 to 4}, a pharmaceutically acceptable salt thereof, or a solvate thereof.

The present invention also relates to a compound represented by the formula (II), which is an intermediate for the synthesis of a 10a-azalide compound having superior antibacterial activity:

[Formula 4]

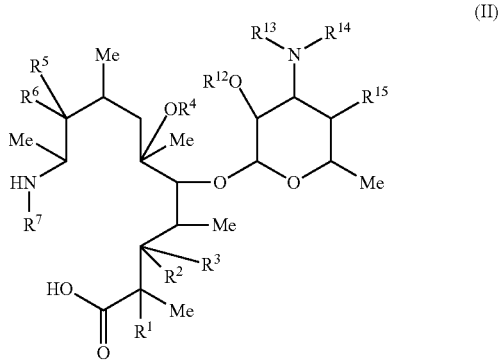

(II)

(in the formula, $R^1$, $R^2$, $R^3$, $R^4$, $R^5$, $R^6$, $R^7$, $R^{12}$, $R^{13}$, $R^{14}$ and $R^{15}$ have the same meanings as those defined above except for the case where $R^6$ and $R^7$ combine together to form cyclic carbamate [—OCO—]).

In the present invention, the symbol "$C_{x-y}$" means that the group mentioned after that has x to y of carbon atoms.

Examples of the "halogen atom" include fluorine, chlorine, bromine, and iodine.

The "$C_{1-6}$ alkyl group" is a linear or branched alkyl group having 1 to 6 carbon atoms, and examples include, for example, methyl group, ethyl group, n-propyl group, isopropyl group, n-butyl group, isobutyl group, s-butyl group, t-butyl group, n-pentyl group, isopentyl group, 1,1-dimethylpropyl group, n-hexyl group, and the like.

The "$C_{1-10}$ alkyl group" is a linear or branched alkyl group having 1 to 10 carbon atoms, and examples include, for example, the aforementioned specific examples of the "$C_{1-6}$ alkyl group", as well as, for example, 1,1,3,3-tetramethylbutyl group, n-nonanyl group, n-decanyl group, and the like.

The "$C_{2-10}$ alkenyl group" is a linear or branched alkenyl group having 2 to 10 carbon atoms corresponding to the aforementioned "alkyl group" having one or more double bonds at arbitrary positions, and examples include, for example, vinyl group, 1-propenyl group, 2-propenyl group, isopropenyl group, 2-butenyl group, 1,3-butadienyl group, 2-pentenyl group, 3-pentenyl group, 2-hexenyl group, and the like.

The "$C_{2-10}$ alkynyl group" means a linear or branched alkynyl group having 2 to 10 carbon atoms corresponding to the aforementioned "alkyl group" having one or more triple bonds at arbitrary positions, and examples include, for example, ethynyl group, 1-propynyl group, 2-propynyl group, and the like.

The "$C_{1-10}$ haloalkyl group" is an alkyl group corresponding to the aforementioned "$C_{1-10}$ alkyl group" substituted with one or two or more halogen atoms, and examples of include, for example, fluoromethyl group, difluoromethyl group, trifluoromethyl group, 2,2,2-trifluoroethyl group, 2,2,2-trichloroethyl group, pentafluoroethyl group, 3,3,3-trifluoropropyl group, perfluoropropyl group, 4-fluorobutyl group, 4-chlorobutyl group, 4-bromobutyl group, perfluorohexyl group, and the like.

The "$C_{1-6}$ alkoxy group" is a linear or branched alkoxy group having 1 to 6 carbon atoms, and examples include, for example, methoxy group, ethoxy group, 1-propoxy group, isopropoxy group, 1-butoxy group, 1-methyl-1-propoxy group, t-butoxy group, 1-pentyloxy group, and the like.

The "$C_{1-10}$ alkoxy group" is a linear or branched alkoxy group having 1 to 10 carbon atoms, and examples include, for example, besides the specific examples of the aforementioned "$C_{1-6}$ alkoxy group", for example, 1,1,3,3-tetramethylbutoxy group, n-decyloxy group, and the like.

The "$C_{2-10}$ alkoxycarbonyl group" means a group having 2 to 10 carbon atoms formed by binding the aforementioned alkoxy group and carbonyl group, and examples include, for example, methoxycarbonyl group, ethoxycarbonyl group, t-butoxycarbonyl group, and the like.

The "aryl group" is a monocyclic to tetracyclic aromatic carbon ring group having 6 to 18 carbon atoms, and examples include, for example, phenyl group, naphthyl group, anthryl group, phenanthrenyl group, tetracenyl group, pyrenyl group, and the like.

The "heterocyclic group" is a monocyclic heterocyclic group, or a condensed ring type heterocyclic group containing 1 to 5 of atoms arbitrarily selected from nitrogen atom, oxygen atom and sulfur atom as ring constituting atoms, and includes a saturated heterocyclic group, an aromatic heterocyclic group, a partially saturated monocyclic aromatic heterocyclic group and a condensed ring type heterocyclic group comprising an aromatic heterocyclic group having a single partially saturated ring. The condensed ring type heterocyclic group having a single partially saturated ring may be substituted with oxo group. When the hetero atom is sulfur atom, dioxide compounds also fall within the scope of the present invention.

As the heterocyclic group, a heterocyclic group having 2 to 10 carbon atoms in the ring system is preferred.

In this specification, a "heterocyclic group" is also referred to as "heterocyclyl group" for convenience, and these have the same meaning.

Examples of the "saturated heterocyclic group" include, for example, aziridinyl group, azetidinyl group, pyrrolidinyl group, imidazolidinyl group, pyrazolidinyl group, oxolanyl group, thiolanyl group, piperidinyl group, oxazolidinyl group, isoxazolidinyl group, piperazinyl group, oxanyl group, thianyl group, morpholinyl group, thiomorpholinyl group, and the like.

Examples of the "aromatic heterocyclic group" include, for example, pyridyl group, pyridazinyl group, pyrimidinyl group, pyrazinyl group, quinolyl group, isoquinolyl group, thienyl group (e.g., 2-thienyl group, 3-thienyl group), pyrrolyl group (e.g., 1-pyrrolyl group, 2-pyrrolyl group, 3-pyrrolyl group), thiazolyl group (e.g., 2-thiazolyl group, 4-thiazolyl group, 5-thiazolyl group), isothiazolyl group (e.g., 3-isothiazolyl group, 4-isothiazolyl group, 5-isothiazolyl group), pyrazolyl group (e.g., 1-pyrazolyl group, 3-pyrazolyl group, 4-pyrazolyl group), imidazolyl group (e.g., 1-imidazolyl group, 2-imidazolyl group, 3-imidazolyl group), furyl group (e.g., 2-furyl group, 3-furyl group), oxazolyl group (e.g., 2-oxazolyl group, 4-oxazolyl group, 5-oxazolyl group), isoxazolyl group (e.g., 3-isoxazolyl group, 4-isoxazolyl group, 5-isoxazolyl group), oxadiazolyl group (e.g., 1,2,3-oxadiazolyl group, 1,3,4-oxadiazolyl group), thiadiazolyl group (e.g., 1,2,3-thiadiazolyl group, 1,3,4-thiadiazolyl group), triazolyl group (e.g., 1,2,4-triazolyl group), benzofuranyl group (e.g., 2-benzofuranyl group, 3-benzofuranyl group, 4-benzofuranyl group, 5-benzofuranyl group), benzothienyl group (e.g., 2-benzothienyl group, 3-benzothienyl group, 4-benzothienyl group, 5-benzothienyl group), indolyl group (e.g., 2-indolyl group, 3-indolyl group, 4-indolyl group, 5-indolyl group), benzoxazolyl group (e.g., 2-benzoxazolyl group, 4-benzoxazolyl group, 5-benzoxazolyl group, 6-benzoxazolyl group), benzisoxazolyl group (e.g., 3-benzo[c]isoxazolyl group, 4-benzo[c]isoxazolyl group, 5-benzo[c]isoxazolyl group, 6-benzo[c]isoxazolyl group, 3-benzo[d]isoxazolyl group, 4-benzo[d]isoxazolyl group, 5-benzo[d]isoxazolyl group, 6-benzo[d]isoxazolyl group), indazolyl group (e.g., 3-indazolyl group, 4-indazolyl group, 5-indazolyl group, 6-indazolyl group), benzimidazolyl group (e.g., 2-benzimidazolyl group, 4-benzimidazolyl group, 5-benzimidazolyl group, 6-benzimidazolyl group), benzoxadiazolyl group (e.g., 4-benzo[1,2,5]oxadiazolyl group, 5-benzo[1,2,5]oxadiazolyl group, 4-benzo[1,2,3]oxadiazolyl group, 5-benzo[1,2,3]oxadiazolyl group), benzothiadiazolyl group (e.g., 4-benzo[1,2,5]thiadiazolyl group, 5-benzo[1,2,5]thiadiazolyl group, 4-benzo[1,2,3]thiadiazolyl group, 5-benzo[1,2,3]thiadiazolyl group), indolidinyl group (e.g., 1-indolidinyl group, 2-indolidinyl group, 3-indolidinyl group, 5-indolidinyl group), thienopyridyl group (e.g., 2-thieno[2,3-b]pyridyl group, 3-thieno[2,3-b]pyridyl group, 5-thieno[2,3-b]pyridyl group, 6-thieno[2,3-b]pyridyl group, 2-thieno[3,2-b]pyridyl group, 3-thieno[3,2-b]pyridyl group, 5-thieno[3,2-b]pyridyl group, 6-thieno[3,2-b]pyridyl group), pyrazolopyridyl group (e.g., 2-pyrazolopyridyl group, 3-pyrazolopyridyl group, 5-pyrazolopyridyl group, 6-pyrazolopyridyl group), imidazopyridyl group (e.g., 1-imidazo[1,5-a]pyridyl group, 3-imidazo[1,5-a]pyridyl group, 5-imidazo[1,5-a]pyridyl group, 7-imidazo[1,5-a]pyridyl group, 2-imidazo[1,2-a]pyridyl group, 3-imidazo[1,2-a]pyridyl group, 5-imidazo[1,2-a]pyridyl group, 7-imidazo[1,2-a]pyridyl group), imidazopyrazyl group (e.g., 1-imidazo[1,5-a]pyrazyl group, 3-imidazo[1,5-a]pyrazyl group, 5-imidazo[1,5-a]pyrazyl group, 8-imidazo[1,5-a]pyrazyl group, 2-imidazo[1,2-a]pyrazyl group, 3-imidazo[1,2-a]pyrazyl group, 5-imidazo[1,2-a]pyrazyl group, 8-imidazo[1,2-a]pyrazyl group), pyrazolopyrimidyl group (e.g., 2-pyrazolo[1,5-a]pyrimidyl group, 3-pyrazolo[1,5-a]pyrimidyl group, 5-pyrazolo[1,5-a]pyrimidyl group, 6-pyrazolo[1,5-a]pyrimidyl group, 2-pyrazolo[1,5-c]pyrimidyl group, 3-pyrazolo[1,5-c]pyrimidyl group, 4-pyrazolo[1,5-c]pyrimidyl group, 5-pyrazolo[1,5-c]pyrimidyl group), triazolopyrimidyl group (e.g., 3-[1,2,3]triazolo[1,5-a]pyrimidyl group, 5-[1,2,3]triazolo[1,5-a]pyrimidyl group, 6-[1,2,3]triazolo[1,5-a]pyrimidyl group, 3-[1,2,3]triazolo[1,5-c]pyrimidyl group, 4-[1,2,3]triazolo[1,5-c]pyrimidyl group, 5-[1,2,3]triazolo[1,5-c]pyrimidyl group, 2-[1,2,4]triazolo[1,5-a]pyrimidyl group, 5-[1,2,4]triazolo[1,5-a]pyrimidyl group, 6-[1,2,4]triazolo[1,5-a]pyrimidyl group, 7-[1,2,4]triazolo[1,5-a]pyrimidyl group, 2-[1,2,4]triazolo[1,5-c]pyrimidyl group, 5-[1,2,4]triazolo[1,5-c]pyrimidyl group, 7-[1,2,4]triazolo[1,5-c]pyrimidyl group, 8-[1,2,4]triazolo[1,5-c]pyrimidyl group), thienothienyl group (e.g., 2-thieno[2,3-b]thienyl group, 3-thieno[2,3-b]thienyl group, 2-thieno[3,2-b]thienyl group, 3-thieno[3,2-b]thienyl group), imidazothiazolyl group (e.g., 2-imidazo[2,1-b]thiazolyl group, 3-imidazo[2,1-b]thiazolyl group, 5-imidazo[2,1-b]thiazolyl group, 2-imidazo[5,1-b]thiazolyl group, 3-imidazo[5,1-b]thiazolyl group, 5-imidazo[5,1-b]thiazolyl group), and the like.

Examples of the "partially saturated monocyclic aromatic heterocyclic group and condensed ring type heterocyclic group comprising an aromatic heterocyclic group having a single partially saturated ring" include, for example, maleimido group, tetrahydrobenzofuranyl group, tetrahydrobenzothienyl group, tetrahydrobenzopyrrolyl group, 2,3-dihydro-1H-benzofuranyl group, 2,3-dihydro-1H-benzothienyl group, 2,3-dihydro-1H-indolyl group, 2,3-dihydro-1H-indazolyl group, 2,3-dihydro-1H-benzotriazolyl group, 2,3-dihydro-1H-benzoxazolyl group, 2,3-dihydro-1H-benzothiazolyl group, benzo[1,3]oxathioly group, benzo[1,3]dioxolyl group, 2H-chromenyl group, cromanyl group, indolinyl group, isoindolinyl group, and the like.

Examples of the "condensed ring type heterocyclic group having a partially saturated monocyclic ring and substituted with oxo group" include, for example, 2-oxo-1,3-dihydro-1H-indolyl ring, 3-oxo-1,2-dihydro-1H-indazolyl ring, 2-oxo-3H-benzoxazolyl ring, 2-oxo-3H-benzothiazolyl ring, 2-oxo-benzo[1,3]oxathiolyl ring, 2-oxo-benzo[1,3]dioxolyl ring, 2-oxo-chromenyl ring, and the like.

The "$C_{3-10}$ cycloalkyl group" is a cycloalkyl group having 3 to 10 carbon atoms, and examples include, for example, cyclopropyl group, cyclobutyl group, cyclopentyl group, cyclohexyl group, cycloheptyl group, adamantyl group, and the like.

The "$C_{2-12}$ alkanoyl group" is a linear or branched alkanoyl group having 2 to 12 carbon atoms, and examples include, for example, acetyl group, propionyl group, isopropionyl group, butyryl group, pivaloyl group, and the like.

The "$C_{2-12}$ alkanoyloxy group" means a group formed by binding the aforementioned $C_{2-12}$ alkanoyl group and oxy group, and examples include, for example, acetyloxy group, propionyloxy group, pivaloyloxy group, and the like.

The "($C_{2-12}$ alkanoyloxy)($C_{1-6}$ alkyl) group" means a group formed by binding the aforementioned $C_{2-12}$ alkanoyloxy group and $C_{1-6}$ alkyl group, and examples include, for example, acetyloxyethyl group, propionyloxymethyl group, pivaloyloxymethyl group, and the like.

The "$C_{2-6}$ alkanoylamino group" means a group formed by binding the aforementioned $C_{2-6}$ alkanoyl group and amino group, and examples include, for example, acetylamino group, propionylamino group, pivaloylamino group, and the like.

The "($C_{1-6}$ alkoxy)($C_{1-6}$ alkoxy) group" means a group formed by binding two of the aforementioned $C_{1-6}$ alkoxy groups, and examples include, for example, methoxymethoxy group, methoxypropoxy group, ethoxypropoxy group, heptyloxyethoxy group, and the like.

The "($C_{1-6}$ alkoxy)($C_{1-6}$ alkyl) group" means a group formed by binding the aforementioned $C_{1-6}$ alkoxy group and the aforementioned $C_{1-6}$ alkyl group, and examples include, for example, methoxymethyl group, methoxypropyl group, ethoxypropyl group, heptyloxyethyl group, and the like.

The "aryloxy group" is a group corresponding to the aforementioned "aryl group" substituting via oxygen atom, and examples include, for example, phenoxy group, naphthoxy group, and the like.

The "$C_{1-6}$ hydroxyalkyl group" means the aforementioned $C_{1-6}$ alkyl group substituted with 1 to 2 of hydroxyl groups, and examples include, for example, hydroxymethyl group, 2-hydroxyethyl group, 4-hydroxybutyl group, and the like.

The "$C_{1-10}$ alkylthio group" is a linear or branched alkylthio group having 1 to 10 carbon atoms, and examples include, for example, methylthio group, ethylthio group, n-propylthio group, isopropylthio group, n-butylthio group, 2-butylthio group, t-butylthio group, 1,1-dimethylethylthio group, n-pentylthio group, isopentylthio group, 1,1-dimethylpropylthio group, n-hexylthio group, and the like.

The "$C_{1-10}$ haloalkylthio group" is an alkylthio group consisting of the aforementioned "$C_{1-10}$ alkylthio group" substituted with one or two or more halogen atoms, and examples include, for example, fluoromethylthio group, difluoromethylthio group, trifluoromethylthio group, 2,2,2-trifluoroethylthio group, 2,2,2-trichloroethylthio group, pentafluoroethylthio group, 4-fluorobutylthio group, 4-chlorobutylthio group, 4-bromobutylthio group, perfluorohexylthio group, and the like.

The "$C_{2-10}$ alkenylthio group" is a linear or branched alkenylthio group having 2 to 10 carbon atoms, and examples include, for example, vinylthio group, allylthio group, n-propenylthio group, isopropenylthio group, n-butenylthio group, 2-butenylthio group, n-pentenylthio group, n-hexenylthio group, and the like.

The "arylthio group" is a group corresponding to the aforementioned "aryl group" substituting via sulfur atom, and examples include, for example, phenylthio group, naphthylthio group, and the like.

The "$C_{2-6}$ alkenylthio group" is a linear or branched alkenylthio group having 2 to 6 carbon atoms, and examples include, for example, vinylthio group, 1-propenylthio group, 2-propenylthio group, 2-butenylthio group, 1,3-butadienylthio group, 2-pentenylthio group, 3-pentenylthio group, 2-hexenylthio group, and the like.

The "arylsulfonyl group which may be substituted with a halogen atom" is the aforementioned sulfonyl group of which aryl group may be substituted with one or two or more halogen atoms, and examples include, for example, phenylsulfonyl group, 4-chlorophenylsulfonyl group, 4-fluorophenylsulfonyl group, 2,4-dibromophenylsulfonyl group, 2,4-difluorophenylsulfonyl group, naphthylsulfonyl group, 6-bromonaphthylsulfonyl group, and the like.

The "divalent $C_{1-10}$ aliphatic hydrocarbon group" means a $C_{1-10}$ alkylene group, a $C_{2-10}$ alkenylene group, a $C_{2-10}$ alkynylene group, a $C_{3-10}$ cycloalkylene group, or a $C_{3-10}$ cycloalkenylene group.

The "$C_{1-10}$ alkylene group" is a linear or branched alkylene group having 1 to 10 carbon atoms, and examples include, for example, —$CH_2$—, —$(CH_2)_2$—, —$(CH_2)_3$—, —$CH(CH_3)$—, —$(CH_2)_3$—, —$(CH(CH_3))_2$—, —$(CH_2)_2$—$CH(CH_3)$—, —$(CH_2)_3$—$CH(CH_3)$—, —$(CH_2)_2$—$CH(C_2H_5)$—, —$(CH_2)_6$—, —$(CH_2)_2$—$C(C_2H_5)_2$—, —$(CH_2)_3C(CH_3)_2CH_2$—, —$(CH_2)_8$—, —$(CH_2)_3C(CH_3)_2(CH_2)_3$—, —$(CH_2)_{10}$—, and the like.

The "$C_{2-10}$ alkenylene group" is a linear or branched alkenylene group of 2 to 10 carbon atoms having one or two or more double bonds in the chain, and examples include, for example, a divalent group having a double bond formed by eliminating 2 to 6 hydrogen atoms on adjacent carbon atoms of the aforementioned alkylene group.

The "$C_{2-10}$ alkynylene group" is a linear or branched alkynylene group of 2 to 10 carbon atoms having one or two or more triple bonds in the chain, and examples include, for example, a divalent group having a triple bond formed by further eliminating hydrogen atoms from carbon atoms at the double bond moiety of the aforementioned alkenylene group.

Further, the "divalent $C_{1-10}$ aliphatic hydrocarbon group" may contain a double bond and triple bond.

The "$C_{3-10}$ cycloalkylene group" is a divalent group formed by eliminating arbitrary 2 of hydrogen atoms from a cycloalkane having 3 to 10 carbon, and examples include, for example, 1,2-cyclopentylene group, 1,2-cyclohexylene group, 1,3-cyclohexylene group, 1,4-cyclohexylene group, 1,3-cycloheptylene group, and the like.

The "$C_{3-10}$ cycloalkenylene group" is a divalent group formed by eliminating arbitrary 2 of hydrogen atoms from a cycloalkene having 3 to 10 carbon atoms, and examples include, for example, 3-cyclohexen-1,2-ylene group, 2,5-cyclohexadien-1,4-ylene group, and the like.

The "arylene group" is a divalent group formed by eliminating arbitrary 2 of hydrogen atoms from a mono- to tetracyclic aromatic hydrocarbon having 6 to 18 carbon atoms, and examples include, for example, divalent groups formed by eliminating arbitrary 2 of hydrogen atoms from benzene, naphthalene, azulene, fluorene, phenanthrene, anthracene, pyrene, and the like.

The "divalent heterocyclic group" is a divalent group formed by further eliminating arbitrary 1 of hydrogen atom from the aforementioned "heterocyclic group", and examples include, for example, divalent groups formed by eliminating arbitrary 1 of hydrogen atom from pyrazolidinyl group, oxolanyl group, thiolanyl group, piperidinyl group, piperazinyl group, morpholinyl group, pyridyl group, pyridazinyl group, pyrimidinyl group, pyrazinyl group, quinolyl group, isoquinolyl group, thienyl group, pyrrolyl group, thiazolyl group, isothiazolyl group, pyrazolyl group, imidazolyl group, furyl group, oxazolyl group, isoxazolyl group, oxadiazolyl group, thiadiazolyl group, triazolyl group, benzofuranyl group, benzothienyl group, indolyl group, benzoxazolyl group, benzisoxazolyl group, indazolyl group, benzimidazolyl group, benzoxadiazolyl group, benzothiadiazolyl group, indolidinyl group, and thienopyridyl group.

The "protected hydroxyl group" means hydroxyl group protected with "a protective group of hydroxyl group".

The "protected amino group" means amino group protected with "a protective group of amino group".

The "protected oxime group" means oxime group protected with "a protective group of oxime group".

Examples of the "protective group of hydroxyl group", "protective group of amino group" and "protective group of oxime group" include a silyl type protective group such as trimethylsilyl group, triethylsilyl group and tert-butyldimethylsilyl group, an acyl type protective group such as acetyl group and benzoyl group, an ether type protective group such as benzyl group, p-methoxybenzyl group and 2-chlorobenzyl group, a carbonate type protective group such as benzyloxycarbonyl group and tert-butyloxycarbonyl group, and the like.

The "cyclic amino group formed together with the adjacent nitrogen atom" in the definitions of $R^{22}$ and $R^{23}$, or $R^{24}$ and $R^{25}$ is a 3 to 8-membered saturated cyclic amino group, one of which methylene group in the ring may be replaced with oxygen atom, or NH group, and examples include, for example, piperidinyl group, piperazinyl group, morpholino group, and the like.

The "$C_{3-10}$ cycloalkyl group condensed with an aryl group" is a group corresponding to the aforementioned $C_{3-10}$ cycloalkyl group condensed with the aforementioned aryl group, and examples include, for example, indanyl group, and the like.

In the present invention, a pharmaceutically acceptable salt means a salt used in chemotherapeutic and prophylactic treatment of bacterial infectious diseases. Examples include, for example, salts with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, paratoluenesulfonic acid, laurylsulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer, and carboxyvinyl polymer, salts with an inorganic base such as sodium salts, potassium salts and calcium salts, salts with an organic amine such as morpholine and piperidine, and salts with an amino acid.

The compounds of the present invention and pharmacologically acceptable salts thereof may exist in the form of an adduct with water or various kinds of solvents, and such an adduct or solvate also falls within the scope of the salt of the present invention. More specifically, a compound which is a solvate and is also a salt falls within the scope of the salt referred to in the present invention. Examples of the solvate include, for example, hydrate, and the like. Further, isomers of the compounds (1) may exist, and all possible isomers and mixtures thereof including the aforementioned isomers fall within the scope of the present invention. These isomers can be separated and purified according to known methods.

EFFECT OF THE PRESENT INVENTION

The compounds of the present invention have broad antibacterial activities and are effective especially against *Hemophilus influenzae*, erythromycin resistant pneumococci, and the like.

BEST MODE FOR CARRYING OUT THE INVENTION

The compounds of the present invention can be synthesized by, for example, the following methods. However, it should be understood that the preparation methods of the compounds of the present invention are not limited to these methods.

Although all of the compounds of the present invention are novel compounds not having been described in literatures, they can be prepared by known methods described in literatures, or similar methods. Examples of such literatures include S. R. Sandler et al., Organic Functional Group Preparations, Academic Press Inc., New York and London, 1968; S. R. Wagner et al., Synthetic Organic Chemistry, John Wiley, 1961; R. C. Larock, Comprehensive Organic Transformations, 1989; L. A. Paquette et al., Encyclopedia of Reagents for Organic Synthesis, 1995; Compendium of Organic Synthetic Methods, and the like.

Examples of the preparation methods are shown below. In the text of the specification, the term base means, unless specifically indicated, an organic base (e.g., an amine such as triethylamine, diisopropylethylamine, pyridine and 4-dimethylaminopyridine, a metal alkoxide such as sodium methoxide, and the like), or an inorganic base (e.g., an alkali metal carbonate such as sodium carbonate and potassium carbonate, an alkaline earth metal carbonate such as calcium carbonate, a metal hydroxide such as sodium hydroxide and potassium hydroxide, and the like).

The term solvent means, unless specifically indicated, a polar solvent (e.g., water, an alcohol type solvent such as methanol, and the like), an inert solvent (e.g., a halogenated hydrocarbon type solvent such as chloroform and methylene chloride, an ether type solvent such as diethyl ether, tetrahydrofuran and 1,4-dioxane, an aprotic solvent such as dimethylformamide, dimethyl sulfoxide and acetonitrile, an aromatic hydrocarbon type solvent such as toluene, a hydrocarbon such as cyclohexane, and the like), or a mixed solvent thereof.

The condensing agent means, unless specifically indicated, for example, a chloroformic acid ester (e.g., isobutyl chloroformate, ethyl chloroformate, methyl chloroformate and the like), an acid chloride (e.g., pivaloyl chloride, oxalyl chloride, 2,4,6-trichlorobenzoyl chloride and the like), a dehydration condensing agent (e.g., a carbodiimide reagent such as 1-ethyl-3-[3-(dimethylamino)propyl]carbodiimide hydrochloride and dicyclohexylcarbodiimide), carbonyldiimidazole, 2-chloro-1-methylpyridinium iodide salt, and the like), and the like.

<Scheme 1>

[Formula 5]

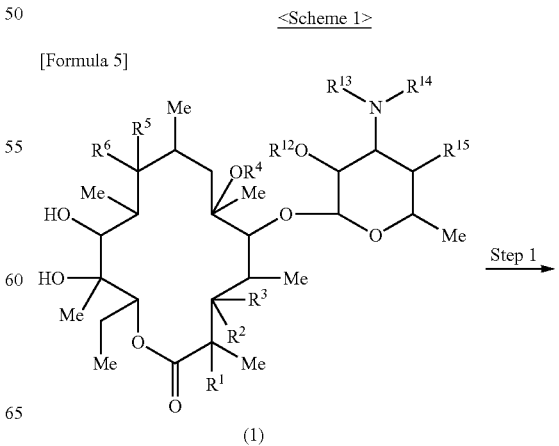

(1)

Step 1

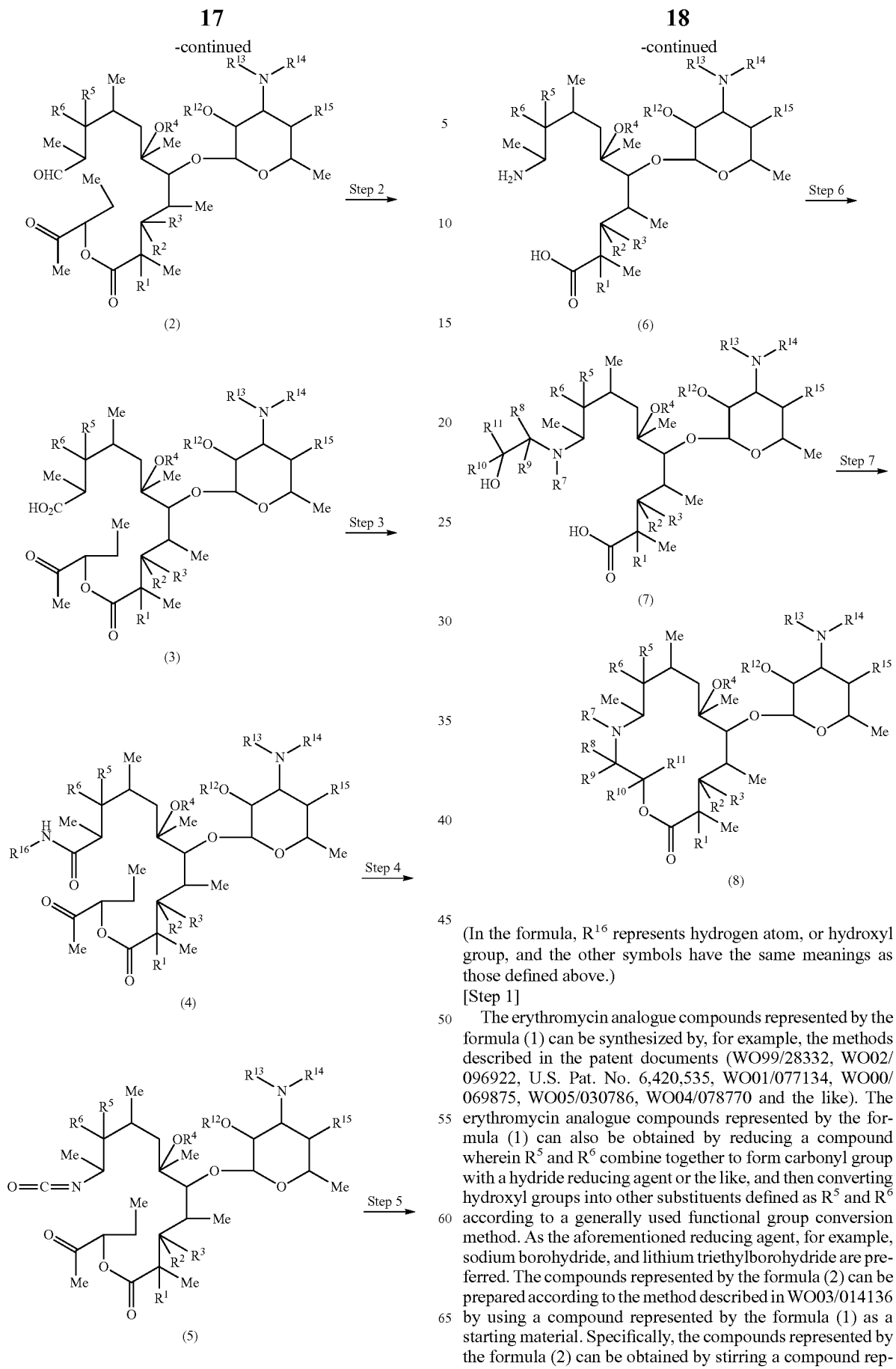

(In the formula, $R^{16}$ represents hydrogen atom, or hydroxyl group, and the other symbols have the same meanings as those defined above.)

[Step 1]

The erythromycin analogue compounds represented by the formula (1) can be synthesized by, for example, the methods described in the patent documents (WO99/28332, WO02/096922, U.S. Pat. No. 6,420,535, WO01/077134, WO00/069875, WO05/030786, WO04/078770 and the like). The erythromycin analogue compounds represented by the formula (1) can also be obtained by reducing a compound wherein $R^5$ and $R^6$ combine together to form carbonyl group with a hydride reducing agent or the like, and then converting hydroxyl groups into other substituents defined as $R^5$ and $R^6$ according to a generally used functional group conversion method. As the aforementioned reducing agent, for example, sodium borohydride, and lithium triethylborohydride are preferred. The compounds represented by the formula (2) can be prepared according to the method described in WO03/014136 by using a compound represented by the formula (1) as a starting material. Specifically, the compounds represented by the formula (2) can be obtained by stirring a compound represented by the formula (1) at room temperature with an oxidizing agent (examples include, for example, lead tetraacetate, periodic acid salts and the like, and among them, lead tetraacetate is preferred) in a solvent (chloroform is especially preferred). As the compound represented by formula (1), a compound wherein $R^5$ is a protected hydroxyl group, and $R^6$ is hydrogen atom is preferred. The compounds represented by the formula (2) can be used in the following step 2 without isolation from the reaction system.

[Step 2]

The compounds represented by the formula (3) can be obtained by stirring a compound represented by the formula (2) in a solvent in the presence of an oxidizing agent. Examples of the oxidizing agent for this reaction include, for example, sodium chlorite, sodium perchlorate, potassium permanganate, and the like, and among them, sodium chlorite is preferred. As the solvent, a mixed solvent of chloroform, tetrahydrofuran, tert-butyl alcohol and water are preferred. The reaction temperature is selected from the range of, for example, −20° C. to the boiling temperature of the solvent, and a temperature of from 0° C. to room temperature is especially preferred.

[Step 3]

The compounds represented by the formula (4) can be obtained by stirring a compound represented by the formula (3) in a condensing agent (a chloroformic acid ester is preferred) and a solvent (chloroform is preferred) in the presence or absence of an organic base (an amine such as triethylamine is preferred), then adding, for example, ammonia when $R^{16}$ is hydrogen atom, or adding, for example, hydroxylamine when $R^{16}$ is hydroxyl group, and stirring the mixture. Although ammonia is preferably added as ammonia gas, it may also be added as a solution in a solvent (for example, water, alcohol, dioxane and the like). Hydroxylamine can be used in a state of a solution in a solvent (examples of the solvent include, for example, water, alcohol, dioxane and the like, and water is especially preferred). The reaction temperature is selected from a range of, for example, −20° C. to room temperature, and a temperature of from −5° C. to 5° C. is especially preferred.

[Step 4]

The compounds represented by the formula (5) can be obtained by stirring a compound represented by the formula (4) wherein $R^{16}$ is hydrogen atom in a solvent (e.g., ethyl acetate and the like) in the presence of iodobenzene diacetate, iodobenzene bistrifluoroacetate or the like. Further, the compounds represented by the formula (5) can also be obtained by stirring a compound represented by the formula (4) wherein $R^{16}$ is hydroxyl group in a solvent (tetrahydrofuran is especially preferred) in the presence of a sulfonyl chloride (examples include, for example, p-toluenesulfonyl chloride, methanesulfonyl chloride and the like, and among them, p-toluenesulfonyl chloride is especially preferred). The compounds of the formula (5) can be used for the following step 5 without isolation from the reaction system.

[Step 5]

The compounds represented by the formula (6) can be obtained by stirring a compound represented by the formula (5) in an aqueous solution of a metal hydroxide (examples include, for example, lithium hydroxide, sodium hydroxide and the like, and among them, lithium hydroxide is preferred), or in a mixed solvent of such an aqueous solution and an alcohol solvent such as methanol and ethanol, tetrahydrofuran, or the like. The reaction temperature is selected from a range of, for example, from 0° C. to the boiling temperature of the solvent, and a temperature of from 0° C. to room temperature is especially preferred.

[Step 6]

In Step 6, it is preferable to use compounds represented by the formulas (9) to (11) for the reaction.

[Formula 6]

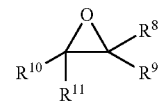

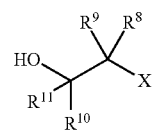

(In the formulas, X represents a leaving group (e.g., chloro group, bromo group, iodo group, methanesulfonyloxy group and the like), $R^{7'}$ represents a group defined for $R^7$ other than hydrogen atom, and the other symbols have the same meanings as those defined above.)

The compounds represented by the formula (7) wherein $R^7$ is hydrogen atom can be obtained by reacting a compound represented by the formula (6) with an epoxide represented by the formula (9) in a solvent (tetrahydrofuran is especially preferred) in the presence or absence of a Lewis acid (for example, ytterbium triflate) with heating, or by reacting a compound represented by the formula (6) with a compound represented by the formula (10) in an inert solvent in the presence of a base with heating.

The compounds represented by the formula (7) wherein $R^7$ is other than hydrogen atom can be obtained by a method of stirring a compound represented by the formula (7) wherein $R^7$ is hydrogen atom obtained by the aforementioned method, a corresponding aldehyde and a hydride reducing agent (for example, sodium triacetoxyborohydride, sodium cyanoborohydride and the like) in a solvent, or a method of reacting the compound with a compound represented by the formula (11) in an inert solvent in the presence of a base. The reaction temperature of the aforementioned reaction is selected from the range of, for example, 0° C. to the boiling temperature of the solvent.

[Step 7]

By using a compound represented by the formula (7) wherein $R^7$ is hydrogen atom as a starting material, and reacting it with a Mitsunobu reagent (for example, diethyl azodicarboxylate, diisopropyl azodicarboxylate and the like) in an inert solvent (tetrahydrofuran is especially preferred) in the presence of a phosphine reagent (for example, triphenylphosphine and the like), the compounds represented by the formula (8) wherein $R^7$ is hydrogen atom can be obtained. In this case, the reaction temperature is selected from the range of, for example, 0° C. to room temperature, and room temperature is preferred.

By a method of reacting a compound represented by the formula (8) wherein $R^7$ is hydrogen atom with a corresponding aldehyde and a hydride reducing agent (for example, sodium triacetoxyborohydride, sodium cyanoborohydride and the like) in a solvent, or a method of reacting the compound with a compound represented by the formula (11) in an inert solvent in the presence of a base, the compounds of the formula (8) wherein $R^7$ is other than hydrogen atom can be obtained.

By reacting a reaction solution obtained by reacting a compound represented by the formula (7) wherein $R^7$ is other than hydrogen atom in a condensing agent (2,4,6-trichlorobenzoyl chloride is preferred) and a solvent (tetrahydrofuran is preferred) in the presence of an organic base (an amine such as triethylamine is preferred) with a solution of a base (4-dimethylaminopyridine is preferred) in a solvent (acetonitrile is especially preferred), the compounds represented by the formula (8) wherein $R^7$ is other than hydrogen atom can be obtained. The reaction temperature is selected from the range of, for example, 0° C. to the boiling temperature of the solvent.

by the formula (12) by a method of stirring the compound represented by the formula (6) with a corresponding aldehyde and a hydride reducing agent (for example, sodium triacetoxyborohydride, sodium cyanoborohydride and the like) in a solvent, or a method of reacting it with a compound represented by the formula (11) in an inert solvent in the presence of a base, as shown in Scheme 2, and then reacting the converted compound with an epoxide represented by the formula (9) in a solvent (tetrahydrofuran is especially preferred) in the presence of a Lewis acid (for example, ytterbium triflate) with heating, or by reacting it with a compound represented by the formula (10) in an inert solvent in the presence of a base with heating.

<Scheme 2>

[Formula 7]

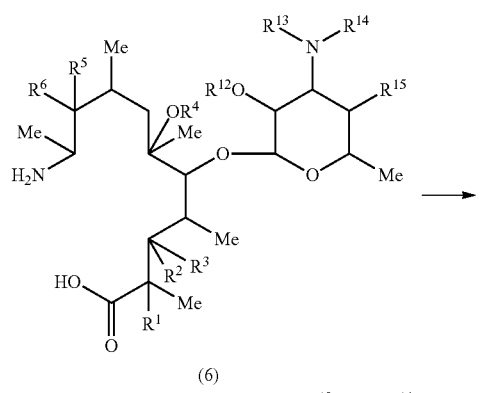

(6)

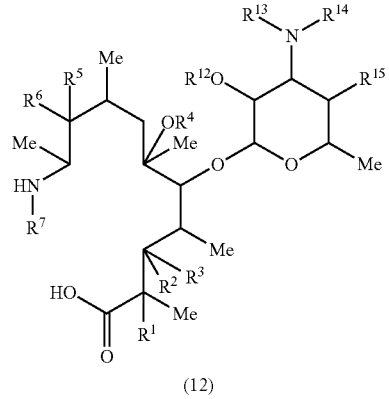

(12)

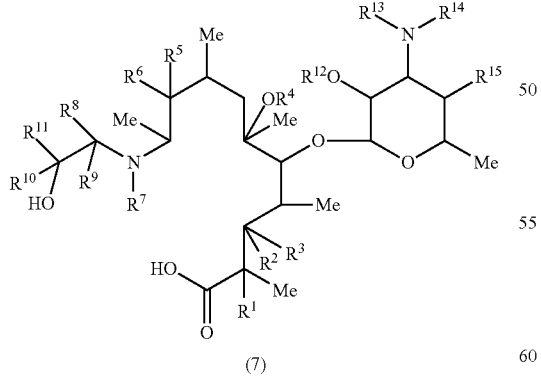

(7)

(In the formulas, the symbols have the same meanings as those defined above.)

The compounds represented by the formula (7) mentioned in Scheme 1 can also be obtained by converting a compound represented by the formula (6) into a compound represented <Scheme 3>

[Formula 8]

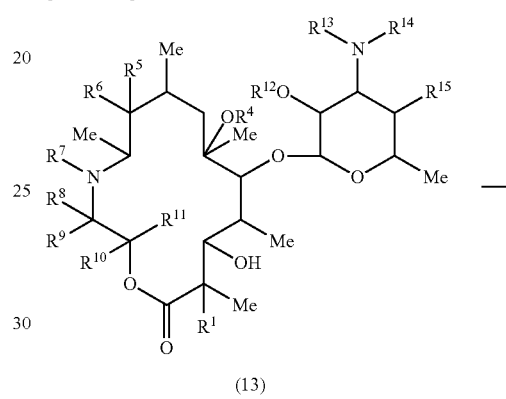

(13)

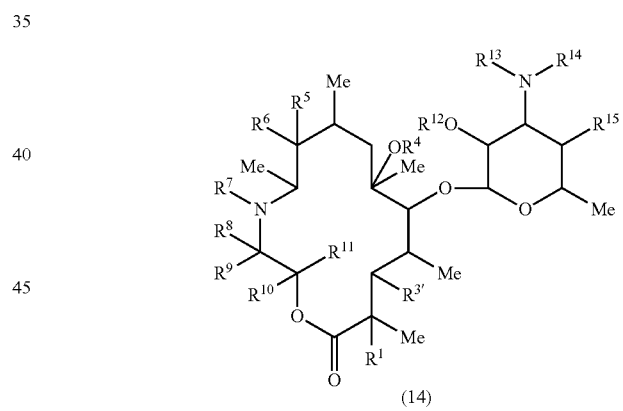

(14)

(In the formula, $R^{3'}$ is:

a group represented by the formula $—X^{031'}—R^{031}$, a group represented by the formula $—X^{031'}-A^{031}-X^{032}—R^{031}$, a group represented by the formula $—X^{031'}-A^{031}-X^{032}-A^{032}-X^{033}—R^{031}$, or a group represented by the formula $—X^{031'}-A^{031}-X^{032}-A^{032}-X^{033}-A^{033}-X^{034}—R^{031}$, wherein $X^{031'}$ is:

a group represented by the formula $—OCO—$, a group represented by the formula $—OCO_2—$, or a group represented by the formula $—OCON(R^{20})—$, $A^{031}$, $X^{032}$, $A^{032}$, $X^{033}$, $A^{033}$, $X^{034}$ and $R^{031}$ have the same meanings as those defined above, and
the other symbols in the formulas have the same meanings as those defined above.)

The compounds represented by the formula (14) wherein $X^{031'}$ is a group of the formula —OCO— can be obtained by a method similar to the methods described in the patent documents (U.S. Pat. No. 6,191,118, WO04/101584, WO05/030786 and the like). Specifically, the compounds represented by the formula (14) wherein $X^{031'}$ is a group of the formula —OCO— can be obtained by a method of reacting a compound represented by the formula (13) in an inert solvent in the presence of a corresponding carboxylic acid and a condensing agent, or with a corresponding acid anhydride or a corresponding acid chloride in an inert solvent in the presence or absence of a base. The reaction temperature is selected from the range of, for example, 0° C. to the boiling temperature of the solvent. Further, the compounds represented by the formula (14) wherein $X^{031'}$ is a group of the formula —OCON($R^{20}$)— can be obtained by a method similar to the method described in U.S. Pat. No. 5,523,399. Specifically, by a method of reacting a compound represented by the formula (13) and carbonyldiimidazole in an inert solvent at a temperature of 0° C. to the boiling temperature of the solvent, and then adding a corresponding amine, or a method of reacting the same with triphosgene in an inert solvent in the presence of a base, and then adding a corresponding amine, or a method of reacting a compound represented by the formula (13) and a corresponding isocyanate in an inert solvent, a compound represented by the formula (14) wherein $X^{031'}$ is a group of the formula —OCON($R^{20}$)— can be obtained. Further, the compounds represented by the formula (14) wherein $X^{031'}$ is a group of the formula —OCO$_2$— can be obtained by a method similar to the methods described in the patent documents WO93/013116, WO93/021200, WO93/021199 and the like. Specifically, by a method of reacting a compound represented by the formula (13) and triphosgene in an inert solvent in the presence of a base, and then reacting the resultant with a corresponding alcohol, a compound represented by the formula (14) wherein $X^{031'}$ is a group of the formula —OCO$_2$— can be obtained. The reaction temperature is selected from the range of, for example, 0° C. to the boiling temperature of the solvent.

Further, among the compounds represented by the formula (8) shown in Scheme 1, those compounds shown in Scheme 4 can also be obtained by the steps shown in Scheme 4, not only the steps shown in Scheme 1.

<Scheme 4>

[Formula 9]

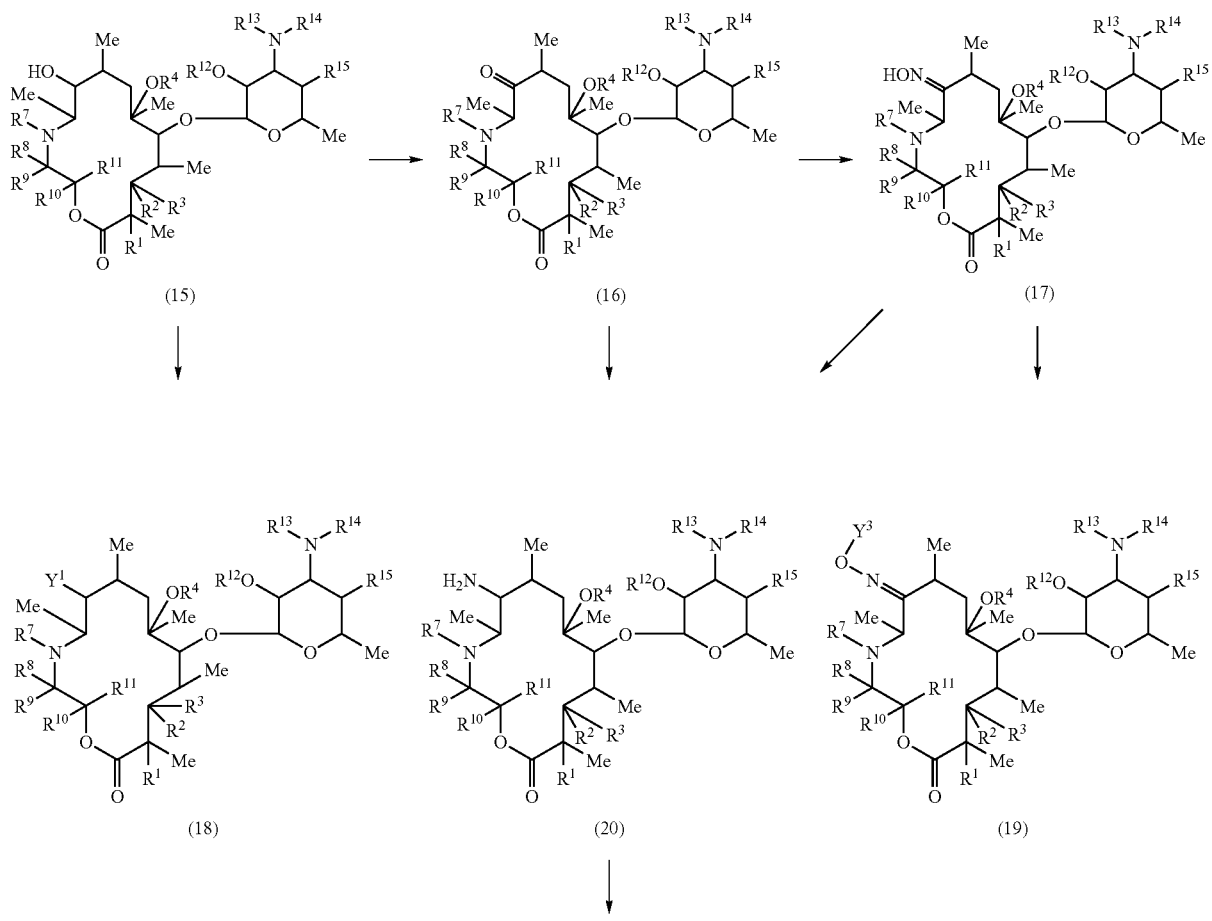

-continued

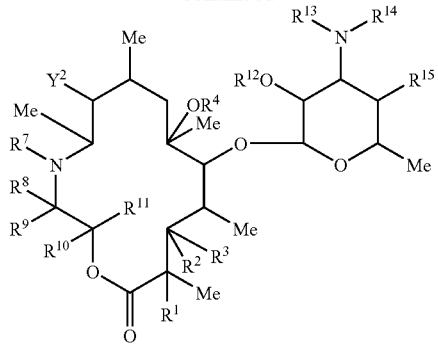

(21)

(In the formulas, $Y^1$ is:

a group represented by the formula $—X^{061'}—R^{061}$, a group represented by the formula $—X^{061'}-A^{061}-X^{062}—R^{061}$, a group represented by the formula $—X^{061'}-A^{061}-X^{062}-A^{062}-X^{063}—R^{061}$, or a group represented by the formula $—X^{061'}-A^{061}-X^{062}-A^{062}-X^{063}-A^{063}-X^{064}—R^{061}$, wherein $X^{061'}$ is:

a group represented by the formula —O—, a group represented by the formula —OCO—, a group represented by the formula $—OCO_2—$, or a group represented by the formula $—OCON(R^{20})—$, and $A^{061}, X^{062}, A^{062}, X^{063}, A^{063}, X^{064}, R^{061}$ and $R^{20}$ have the same meanings as those defined above, $Y^2$ is:

a group represented by the formula $—X^{061''}—R^{061}$, a group represented by the formula $—X^{061''}-A^{061}-X^{062}—R^{061}$, a group represented by the formula $—X^{061''}-A^{061}-X^{062}-A^{062}-X^{063}—R^{061}$, or a group represented by the formula $—X^{061''}-A^{061}-X^{062}-A^{062}-X^{063}-A^{063}-X^{064}—R^{061}$, wherein $X^{061''}$ is:

a group represented by the formula $—N(R^{20})—$, a group represented by the formula $—N(R^{20})CO—$, a group represented by the formula $—N(R^{20})CO_2—$, a group represented by the formula $—N(R^{20})CON(R^{21})—$, or a group represented by the formula $—N(R^{20})SO_2—$, and $A^{061}, X^{062}, A^{062}, X^{063}, A^{063}, X^{064}, R^{061}, R^{20}$ and $R^{21}$ have the same meanings as those defined above, $Y^3$ is:

a group represented by $R^{062}$, a group represented by the formula $-A^{064}-X^{066}—R^{062}$, a group represented by the formula $-A^{064}-X^{066}-A^{065}-X^{067}—R^{062}$, or a group represented by the formula $-A^{064}-X^{066}-A^{065}-X^{067}-A^{066}-X^{068}—R^{062}$, $A^{064}, X^{066}, A^{065}, X^{067}, A^{066}, X^{068}$ and $R^{062}$ have the same meanings as those defined above, and the other symbols have the same meanings as those defined above.)

The compounds represented by the formula (16) can be obtained by oxidizing a compound represented by the formula (15) by, for example, Swern oxidation, Corey-Kim Oxidation, or the like.

The compounds represented by the formula (17) can be obtained by reacting a compound represented by the formula (16) and a hydroxylamine salt such as hydroxylamine hydrochloride or hydroxylamine in a solvent (methanol is preferred) in the presence or absence of a base (imidazole is especially preferred).

The compounds represented by the formula (20) can be obtained by using a compound represented by the formula (16) as a starting material according to a method similar to the methods described in the literatures (Tetrahedron Letters, 1971, vol. 2, p. 195; Tetrahedron Letters, 1972, vol. 1, p. 29), specifically, by reacting the carbonyl group with hydrazine in a polar solvent to convert it into hydrazono group, and then reacting the resultant with sodium nitrite or the like, or by reacting it with hydroxylamine in a solvent to convert it into oxime group, then reacting the resultant with titanium chloride or the like to obtain an imino compound, and reducing the imino compound with a hydride reducing agent or the like.

The compounds represented by the formula (19) can be obtained by using a compound represented by the formula (17) as a starting material, and reacting it by a method similar to the method described in European Patent No. 284203 or WO93/13116 in the presence or absence of a crown ether (for example, 18-crown-6-ether and the like), specifically, reacting it with a corresponding alkyl halide or the like in an inert solvent in the presence or absence of a base.

The compounds represented by the formula (21) can be obtained by reacting a compound represented by the formula (20) and a corresponding acid chloride, a corresponding acid anhydride, a corresponding sulfonyl chloride, a corresponding isocyanate, a corresponding chloroformate or the like in an inert solvent in the presence or absence of a base.

The compounds represented by the formula (18) can be obtained by reacting a compound represented by the formula (15) and a corresponding alkyl halide, a corresponding acid chloride, a corresponding acid anhydride, a corresponding isocyanate, a corresponding chloroformate or the like in an inert solvent in the presence or absence of a base.

<Scheme 5>

[Formula 10]

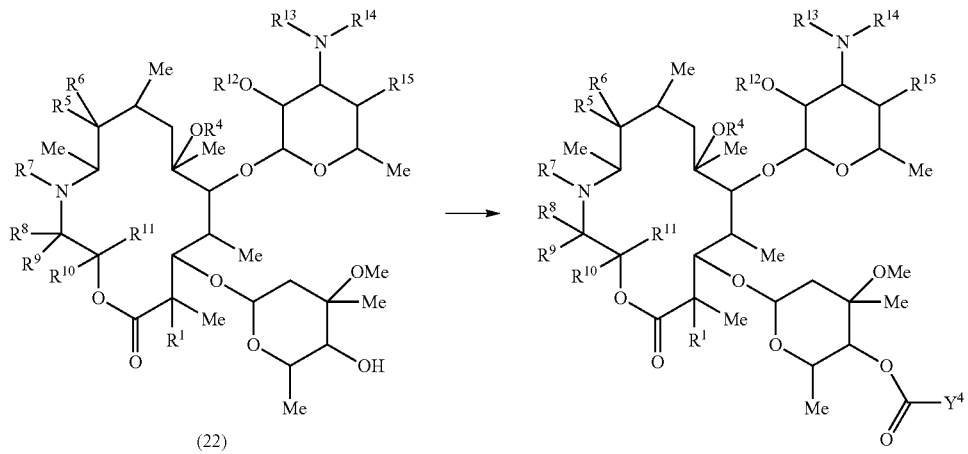

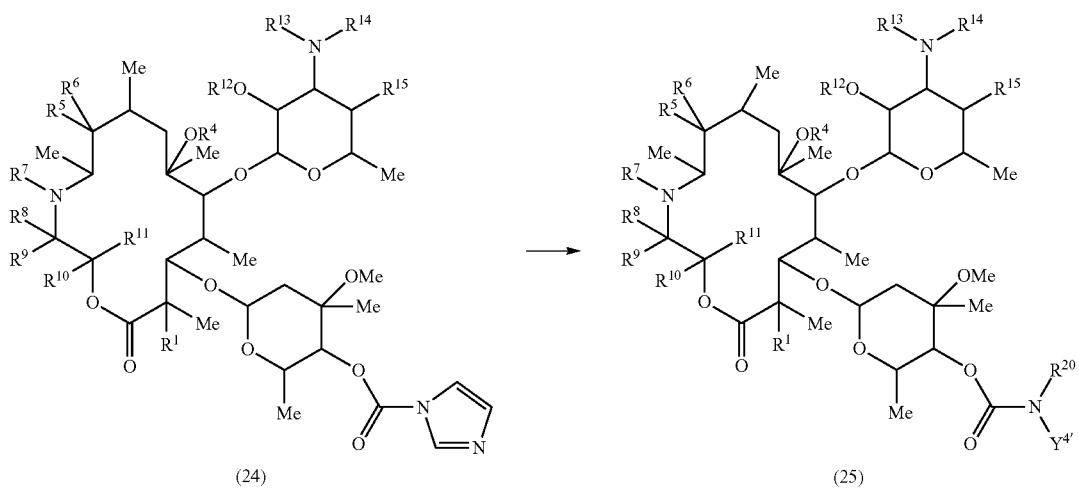

(In the formulas, $Y^4$ and $Y^{4'}$ represent:
a group represented by $R^{331}$,
a group represented by the formula $-A^{331}-X^{332}-R^{331}$,
a group represented by the formula $-A^{331}-X^{332}-A^{332}-X^{333}-R^{331}$, or
a group represented by the formula $-A^{031}-X^{332}-A^{332}-X^{333}-A^{333}-X^{334}-R^{331}$,
$A^{331}$, $X^{332}$, $A^{332}$, $X^{333}$, $A^{333}$, $X^{334}$ and $R^{331}$ have the same meanings as those defined above, and
the other symbols have the same meanings as those defined above.)

The compounds represented by the formula (23) can be obtained by using a compound represented by the formula (22) as a starting material, according to a method similar to the method described in European Patent No. 895999, specifically, by condensing it with a corresponding carboxylic acid by a generally used method.

Further, the compounds represented by the formula (25) can be obtained by using a compound represented by the formula (22) as a starting material according to a method similar to the method described in European Patent No. 895999, specifically, by reacting it with a corresponding amine, via an imidazocarbonyl compound represented by the formula (24).

<Scheme 6>
[Formula 11]
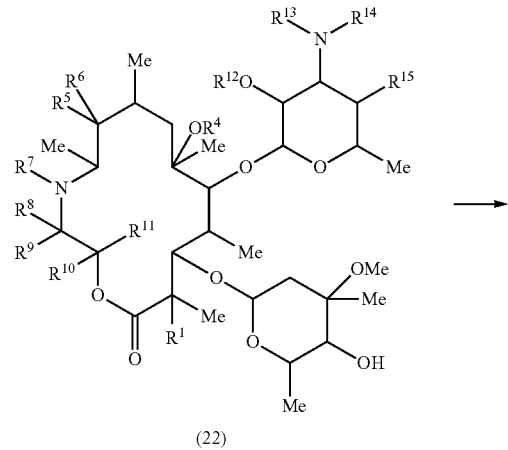
(22)
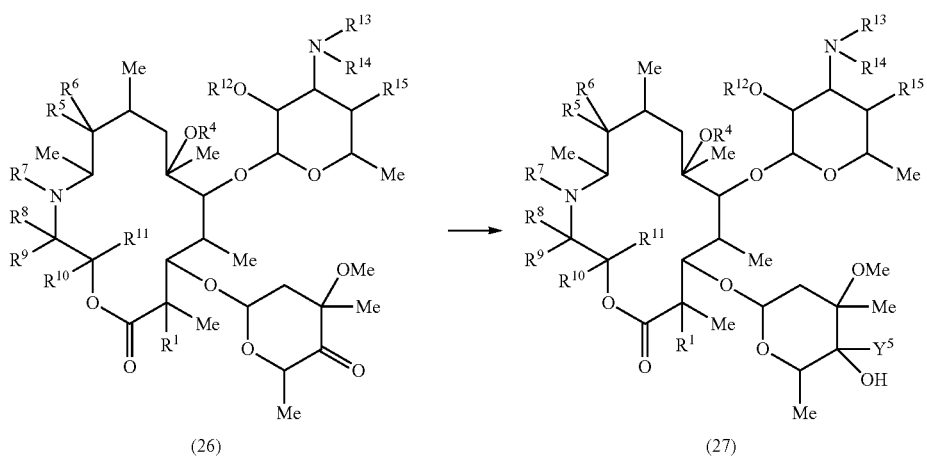
(26) (27)
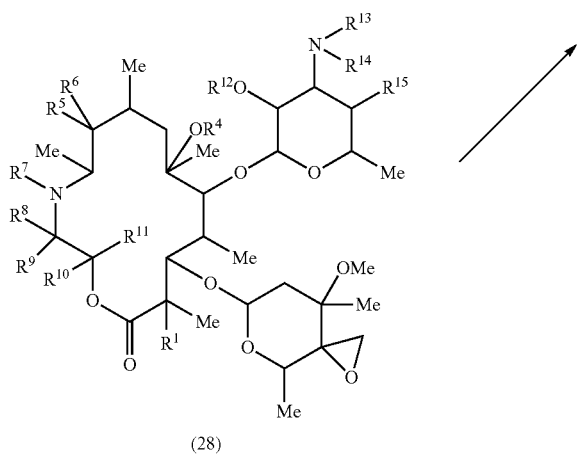
(28)

(In the formulas, $Y^5$ is:
a group represented by the formula $-X^{335}-R^{332}$,
a group represented by the formula $-X^{335}-A^{334}-X^{336}-R^{332}$,
a group represented by the formula $-X^{335}-A^{334}-X^{336}-A^{335}-X^{337}-R^{332}$, or
a group represented by the formula $-X^{335}-A^{334}-X^{336}-A^{335}-X^{337}-A^{336}-X^{338}-R^{332}$,
$X^{335}$, $A^{334}$, $X^{336}$, $A^{335}$, $X^{337}$, $A^{336}$, $X^{338}$ and $R^{332}$ have the same meanings as those defined above, and
the other symbols have the same meanings as those defined above.)

The compounds represented by the formula (27) can be obtained via a compound represented by the formula (26) obtainable by oxidizing a compound represented by the formula (22) by, for example, Swern oxidation, Corey-Kim Oxidation or the like according to a method similar to the method described in Japanese Patent Unexamined Publication (KOHYO) No. 2000-514097, specifically, by reacting it with a corresponding Grignard reagent or the like by a method well known to those skilled in the art, or by reacting a corresponding amine or the like, via an epoxy compound represented by the formula (28).

(29) according to a method similar to the method described in Japanese Patent Unexamined Publication (KOHYO) No. 2000-514097, specifically, by reacting it with a reagent of the formula $R^{334}-CN$, $R^{334}-CO_2H$, $R^{334}-C=NH(OCH_3)$ or the like in a solvent in the presence of a base, acid or a Lewis acid at a temperature of from room temperature to the boiling temperature of the solvent.

<Scheme 8>

[Formula 13]

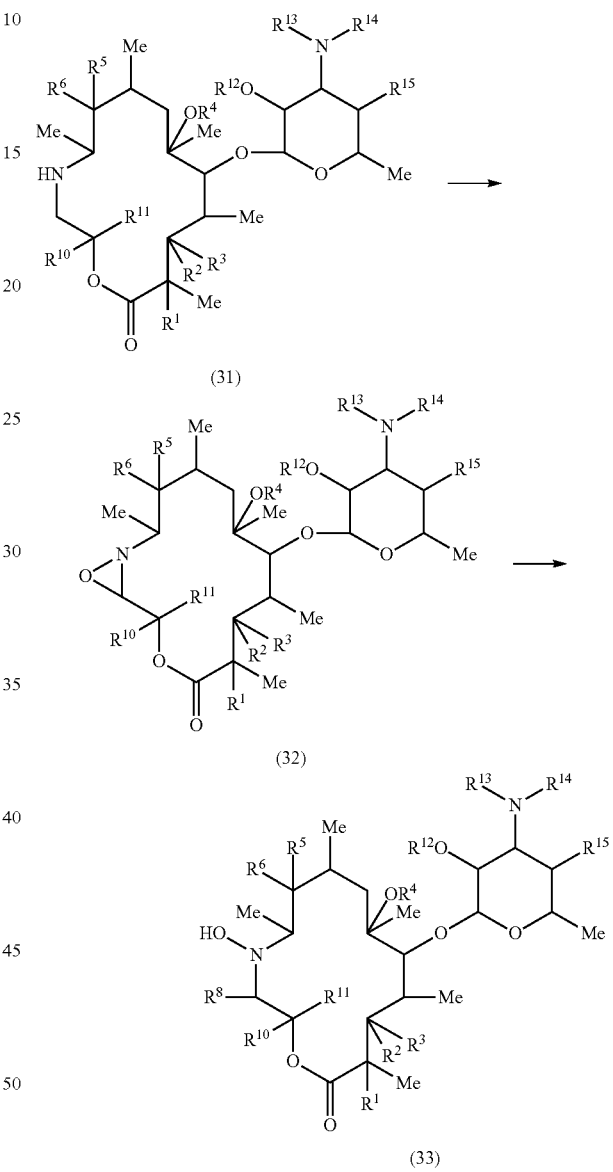

(In the formulas, the symbols have the same meanings as those defined above.)

The compounds represented by the formula (33) can be obtained by reacting a compound represented by the formula (31) according to a method similar to the method described in the literature (The Journal of Antibiotics, 1998, vol. 8, p. 1029), specifically, by oxidizing the compound, then treating the resultant with triphenylphosphine to convert into a compound represented by the formula (32), and then reacting the resultant according to a method similar to the method described in WO01/074792, specifically, reacting it with a corresponding Grignard reagent or the like.

<Scheme 7>

[Formula 12]

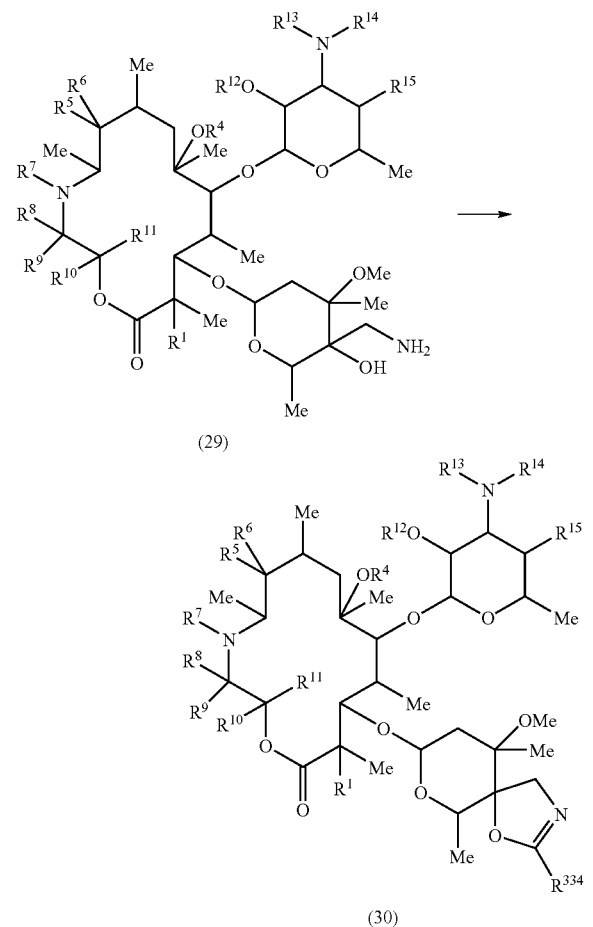

(In the formulas, the symbols have the same meanings as those defined above.)

The compounds represented by the formula (30) can be obtained by reacting a compound represented by the formula <Scheme 9>

[Formula 14]

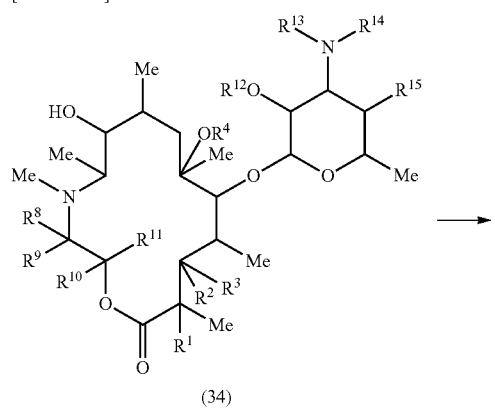

(34)

→

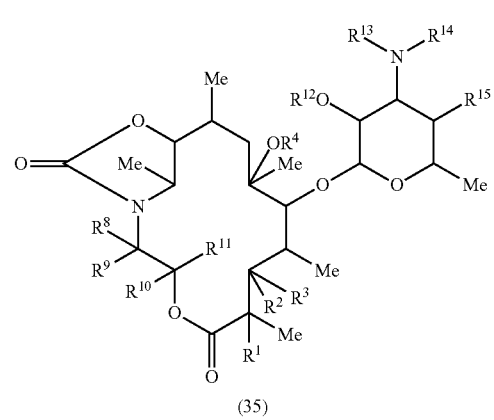

(35)

(In the formulas, the symbols have the same meanings as those defined above.)

The compounds represented by the formula (35) can be obtained by reacting a compound represented by the formula (34) with a chloroformic acid ester, triphosgene or the like in a solvent (chloroform is especially preferred) in the presence of a base (pyridine is preferred).

<Scheme 10>

[Formula 15]

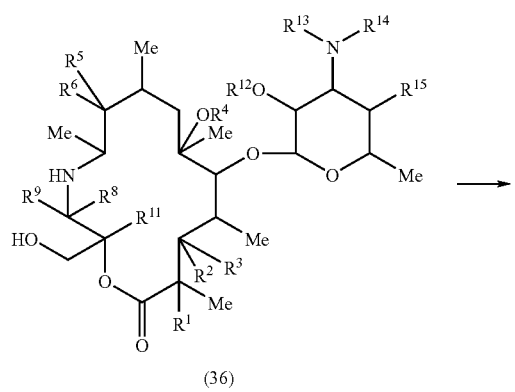

(36)

→

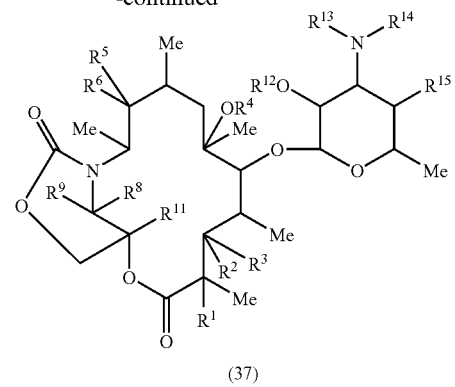

(37)

(In the formula, the symbols have the same meanings as those defined above.)

The compounds represented by the formula (37) can be obtained by reacting a compound represented by the formula (36) with triphosgene or the like in an inert solvent (chloroform or dichloromethane is desirable) in the presence of a base (pyridine is desirable).

<Scheme 11>

[Formula 16]

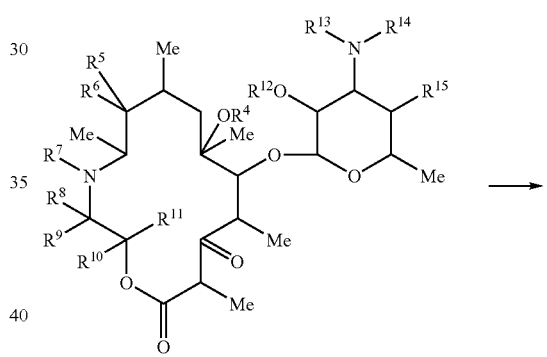

(38)

→

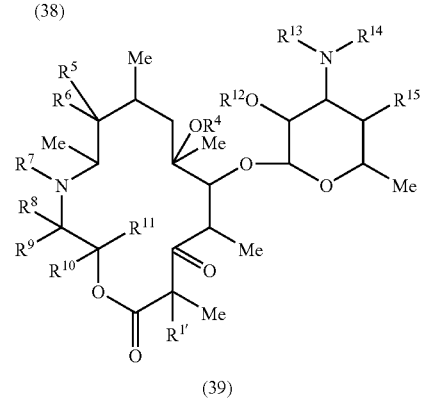

(39)

(In the formulas, $R^{1'}$ represents a halogen atom, and the other symbols have the same meanings as those defined above.)

The compounds represented by the formula (39) can be obtained by reacting a compound represented by the formula (38) according to a method similar to the method described in WO00/069875, specifically, by reaction with a corresponding halogenating reagent or the like (for example, N-fluorobenzenesulfonimide and the like) in an inert solvent in the presence or absence of a base.

<Scheme 12>

[Formula 17]

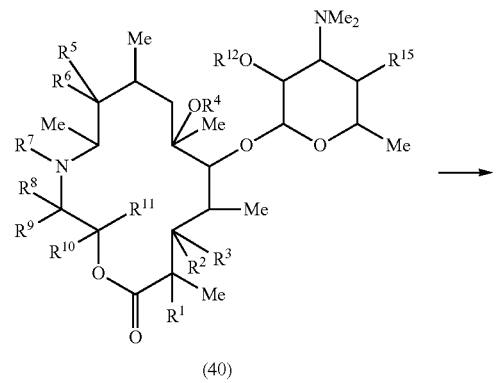

(40)

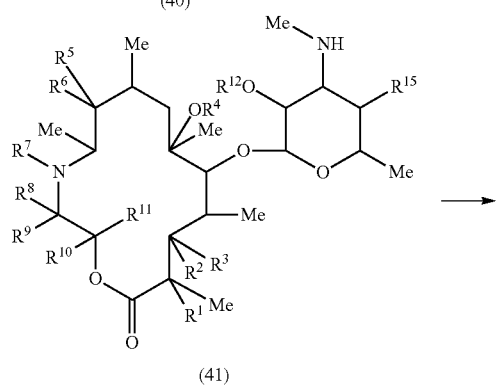

(41)

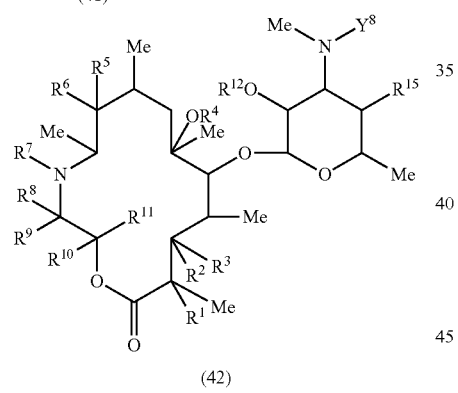

(42)

(In the formulas, $Y^8$ is:
a group represented by the formula $—X^{131}—R^{131}$,
a group represented by the formula $—X^{131}-A^{131}-X^{132}—R^{131}$,
a group represented by the formula $—X^{131}-A^{131}-X^{132}-A^{132}-X^{133}—R^{131}$, or
a protective group of amino group,
$X^{131}, A^{131}, X^{132}, A^{132}, X^{133}$ and $R^{131}$ have the same meanings as those defined above, and
the other symbols have the same meanings as those defined above.)

The compounds represented by the formula (42) can be obtained by reacting a compound represented by the formula (40) according to a method similar to the method described in WO04/013153, specifically, by converting it into a demethylated compound represented by the formula (41), and then reacting the resultant with a corresponding reagent in an inert solvent in the presence or absence of a base.

<Scheme 13>

[Formula 18]

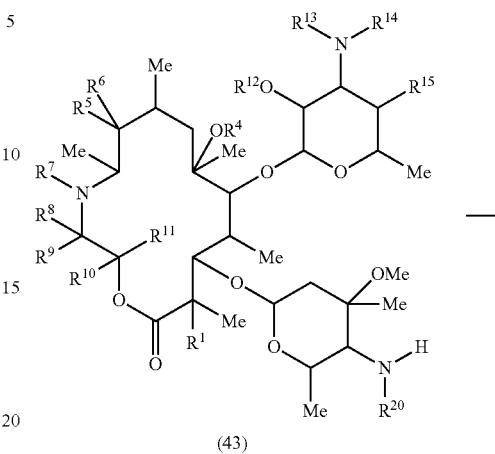

(43)

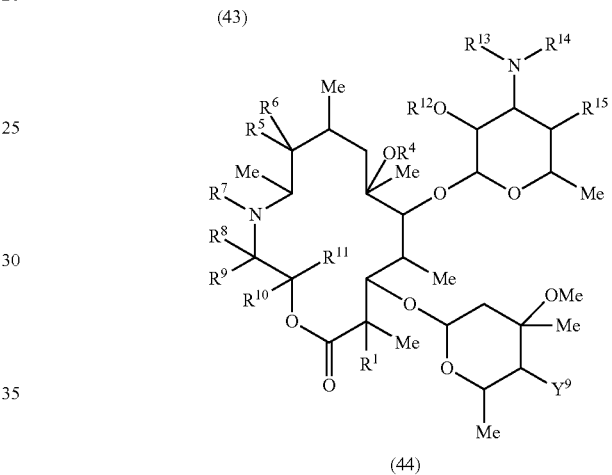

(44)

(In the formula, $Y^9$ is:
a group represented by the formula $—X^{331'}—R^{331}$,
a group represented by the formula $—X^{331'}-A^{331}-X^{332}—R^{331}$
a group represented by the formula $—X^{331'}-A^{331}-X^{332}-A^{332}-X^{333}—R^{331}$
a group represented by the formula $—X^{331'}-A^{331}-X^{332}-A^{332}-X^{333}-A^{333}-X^{334}—R^{331}$,
wherein $X^{331'}$ is:
a group represented by the formula $—N(R^{20})—$,
a group represented by the formula $—N(R^{20})CO—$,
a group represented by the formula $—N(R^{20})CO_2—$,
a group represented by the formula $—N(R^{20})CON(R^{21})—$, or
a group represented by the formula $—N(R^{20})SO_2—$, and
$A^{331}, X^{332}, A^{332}, X^{333}, A^{333}, X^{334}$ and $R^{331}$ have the same meanings as those defined above, and the other symbols have the same meanings as those defined above)

The compounds represented by the formula (43) can be obtained according to a method similar to the method described in European Patent No. 549040, specifically, by using a compound represented by the formula (26) as a starting material, and reducing imino group, that is produced in a solvent and in the presence of a corresponding ammonium salt in the presence or absence of an acid (for example, acetic acid and the like), with a hydride reducing agent (for example, sodium triacetoxyborohydride, sodium cyanoborohydride and the like).

The compounds wherein $R^{20}$ is hydrogen atom can also be obtained by reacting a compound represented by the formula (26) with hydroxylamine in a solvent to convert into an oxime compound, and then hydrogenating the resultant with a reducing agent such as platinum oxide or Raney nickel, or by reaction with titanium chloride or the like and reducing the resulting imino compound with a hydride reducing agent (for example, sodium triacetoxyborohydride, sodium cyanoborohydride and the like).

The compounds represented by the formula (44) wherein $X^{331'}$ is a group of the formula —NH— can be obtained by a method of using a compound represented by the formula (43) as a starting material, and stirring with a corresponding aldehyde and a hydride reducing agent (for example, sodium triacetoxyborohydride, sodium cyanoborohydride and the like) in a solvent, or by reaction with a corresponding halide, sulfonyloxy compound or the like in an inert solvent (N,N'-dimethylformamide is preferred) in the presence of a base. The compounds represented by the formula (44) wherein $X^{331'}$ is a group of the formula —N($R^{20}$)— can also be obtained by a method of using a compound wherein $X^{331'}$ mentioned above is a group of the formula —NH— as a starting material, and stirring with a corresponding aldehyde and a hydride reducing agent (e.g., sodium triacetoxyborohydride, sodium cyanoborohydride and the like) in a solvent. The compounds represented by the formula (44) wherein $X^{331'}$ is a group of the formula —N($R^{20}$)CO— can be obtained by a method of reacting a compound represented by the formula (44) in the presence of a corresponding carboxylic acid and a condensing agent, or with a corresponding acid anhydride or a corresponding an acid chloride in the presence or absence of a base, in an inert solvent. The compounds represented by the formula (44) wherein $X^{331'}$ is a group of the formula —N($R^{20}$)$CO_2$— can be obtained by using a compound represented by the formula (43) as a starting material, and reaction with a corresponding chloroformate reagent in an inert solvent. The compounds represented by the formula (44) wherein $X^{031'}$ is a group of the formula —N($R^{20}$)CON($R^{21}$)— can also be obtained by a method of using a compound represented by the formula (43) as a starting material, and reaction with N,N'-carbonyldiimidazole or triphosgene in an inert solvent (N,N'-dimethylformamide, tetrahydrofuran, chloroform or dichloromethane is preferred), and then reacting the resultant with a corresponding amine reagent in an inert solvent, or a method of reacting a compound represented by the formula (29) with a corresponding isocyanate reagent in an inert solvent. The compounds represented by the formula (44) wherein $X^{331'}$ is a group of the formula —N($R^{20}$)$SO_2$— can be obtained by using a compound represented by the formula (43) as a starting material, and reaction with a corresponding chlorosulfonyl reagent in an inert solvent (chloroform or dichloromethane is preferred) in the presence or absence of a base (triethylamine or pyridine is preferred).

Hydroxyl group, amino group, carboxyl group and oxime group contained in the compounds represented by the formulas (1) to (44) mentioned in these synthesis methods may be protected with selectively removable protective groups known in this field, and by removing them at a desired stage, the 10a-azalide compounds represented by the formula (I) and intermediates represented by the formula (II) for the synthesis of 10a-azalides can be provided. Examples of the known protective group include a silyl type protective group such as trimethylsilyl group, triethylsilyl group and tert-butyldimethylsilyl group, an acyl type protective group such as acetyl group and benzoyl group, an ether type protective group such as benzyl group, p-methoxybenzyl group and 2-chlorobenzyl group, a carbonate type protective group such as benzyloxycarbonyl group and tert-butyloxycarbonyl group, and the like. However, besides those mentioned above, protective groups described in Protective Groups in Organic Syntheses (Third Edition, 1999, Ed. by P. G. M. Wuts, T. Green), and the like can also be used. Further, the substituents of the compounds represented by the formulas (1) to (44) mentioned in these synthesis methods can be interchangeably converted by known methods.

The preparation methods of the compounds of the present invention are not limited by the aforementioned methods or the methods specifically described in the examples, and the substituents of the compounds of the present invention can be interchangeably converted by known methods using the compounds of the present invention as intermediates.

The intermediates and the objective compounds mentioned in the aforementioned preparation methods can be isolated and purified by purification methods commonly used in organic synthetic chemistry, for example, neutralization, filtration, extraction, washing, drying, concentration, recrystallization using a solvent such as ethyl acetate, ethyl acetate-hexane, isopropyl alcohol, ethanol, hydrated ethanol, acetone and hydrated acetone, various chromatography techniques, and the like. The intermediates can also be used in subsequent reactions without particular purification.

The compounds (I) and the compounds (II) include those of which isomers can exist, and all possible isomers including the above compounds and mixtures thereof fall within the scope of the present invention.

The compounds of the present invention and pharmaceutically acceptable salts thereof may exist in the forms of adducts with water or various kinds of solvents, and these adducts also fall within the scope of the salts of the present invention.

EXAMPLES

The present invention will be further explained in detail with reference to reference examples, examples and test example.

Reference Example 1

Synthesis of benzyl(oxiran-2-ylmethyl)carbamic acid

N-Benzyloxycarbonyl-3-amino-1,2-propanediol (5 g) obtained by the method described in the patent document (WO02/072068) was dissolved in pyridine (20 ml), and the solution was added with p-toluenesulfonyl chloride (4.66 g). The mixture was stirred at room temperature for 3 hours, and then further added with p-toluenesulfonyl chloride (2.3 g), and the mixture was stirred at room temperature for 2.5 days. The reaction mixture was added with 2 N hydrochloric acid and ethyl acetate, the layers were separated, and the organic layer was washed successively with saturated aqueous sodium hydrogencarbonate and saturated brine, then dried over anhydrous magnesium sulfate and filtered. The filtrate was concentrated under reduced pressure, and the resulting residue was dissolved in methanol (100 ml). The solution was added with potassium carbonate (8.32 g), and the mixture was stirred at room temperature for 2.5 hours. The reaction mixture was added with distilled water and ethyl acetate, the layers were separated, and the organic layer was washed with saturated brine, then dried over anhydrous magnesium sulfate and filtered. The filtrate was concentrated under reduced pressure, and the resulting residue was purified by silica gel column chromatography (hexane:ethyl acetate=2:1) to obtain the title compound (4.35 g).

MS (ESI) m/z=230.0 [M+Na]$^+$ $^1$H-NMR (300 MHz, CDCl$_3$) δ (ppm): 2.60 (dd, J=4.66, 2.64 Hz, 1H), 2.79 (t, J=4.35 Hz, 1H), 3.07-3.16 (m, 1H), 3.22-3.34 (m, 1H), 3.57-3.69 (m, 1H), 4.93 (s, 1H), 5.12 (s, 2H), 7.27-7.46 (m, 5H)

Reference Example 2

Synthesis of 2-(3-bromophenyl)-N-{2-[(2R)-oxiran-2-yl]ethyl}acetamide (1) 4-Bromo-1-butene (25 g) was dissolved in dimethyl sulfoxide (160 ml), the solution was added with sodium azide (18.1 g), and the mixture was stirred at room temperature for 18 hours. The reaction mixture was added with distilled water and diethyl ether, the layers were separated, and the organic layer was washed successively with distilled water and saturated brine, then dried over anhydrous magnesium sulfate and filtered. The filtrate was concentrated under ordinary pressure to obtain 4-azido-1-butene (8.43 g).

(2) The compound obtained in (1) mentioned above (1.00 g) was dissolved in tetrahydrofuran (20 ml), the solution was added with triphenylphosphine (2.94 g), and the mixture was stirred at room temperature for 45 minutes. The mixture was added with distilled water (0.93 ml), and the mixture was stirred for 18 hours. Then, the mixture was added with 3-bromophenylacetic acid (2.77 g), 1-hydroxybenzotriazole (1.98 g), and 1-ethyl-3-(3-dimethylaminopropyl)carbodiimide hydrochloride (3.55 g) under ice cooling, and the mixture was stirred at room temperature for 18 hours. The reaction mixture was added with saturated aqueous sodium hydrogencarbonate, and the mixture was extracted with ethyl acetate. The organic layer was washed with saturated brine, then dried over anhydrous magnesium sulfate and filtered. The filtrate was concentrated under reduced pressure, and the resulting residue was purified by silica gel column chromatography (hexane:ethyl acetate=2:1 to 1:1) to obtain an amide compound (1.90 g).

(3) Potassium hexacyanoferrate(III) (57.1 g), potassium carbonate (24.0 g), hydroquinidine 1,4-phthalazinediyl diether (450 mg), and potassium osmate(VI) dihydrate (42.6 mg) were dissolved in a mixed solvent of t-butyl alcohol (270 ml) and distilled water (300 ml), and the solution was added with a solution of the compound obtained in (2) mentioned above (15.5 g) in t-butyl alcohol (30 ml) under ice cooling. The mixture was stirred for 4 hours under ice cooling, and then added with sodium hydrogensulfite until foaming ceased. The mixture was added with chloroform, the layers were separated, and the organic layer was washed with saturated brine, then dried over anhydrous magnesium sulfate and filtered. The filtrate was concentrated under reduced pressure, and the resulting residue was purified by silica gel column chromatography (chloroform to chloroform:methanol:28% aqueous ammonia=10:1:0.1) to obtain a diol compound (17.6 g).

(4) By using the compound obtained in (3) mentioned above (17.5 g) as a starting material, the title compound (8.43 g) was obtained in the same manner as that of Reference Example 1.

MS (ESI) m/z=306.1 [M+Na]$^+$ $^1$H-NMR (600 MHz, CDCl$_3$) δ (ppm): 1.42-1.58 (m, 1H), 1.86-1.97 (m, 1H), 2.36-2.49 (m, 1H), 2.67-2.76 (m, 1H), 2.86-2.95 (m, 1H), 3.39 (q, J=6.11 Hz, 2H), 3.49 (s, 2H), 5.80-5.95 (m, 1H), 7.07-7.44 (m, 4H)

Reference Example 3

Synthesis of 2-(3-bromophenyl)-N-[2-(2-oxiran-2-yl)ethyl]acetamide (1) 4-Azidobutane-1,2-diol (2.0 g) obtained by the method described in the literature (Heterocycles, 2003, vol. 61, p. 481) was dissolved in methanol (10 ml), and the solution was added with 5% palladium-carbon (0.4 g) and 2 N hydrochloric acid (2 ml), and the mixture was stirred under hydrogen atmosphere of 1 atm, and at room temperature for 4 hours. The reaction mixture was filtered, and then the filtrate was concentrated under reduced pressure to obtain 4-aminobutane-1,2-diol hydrochloride (1.8 g).

(2) 3-Bromophenylacetic acid (3.05 g) was dissolved in chloroform (30 ml), the solution was added with 1-ethyl-3-(3-dimethylaminopropyl)carbodiimide hydrochloride (2.72 g) under ice cooling, and the mixture was stirred at same temperature for 30 minutes. The reaction mixture was added dropwise with a solution of the compound obtained in (1) mentioned above (1.67 g) in methanol (10 ml), and the mixture was stirred at room temperature for 5 hours. The reaction mixture was concentrated under reduced pressure, and then the resulting residue was purified by silica gel column chromatography (chloroform:methanol:28% aqueous ammonia=20:1:0.1) to obtain an amide compound (2.58 g).

(3) By using the compound obtained in (2) mentioned above (2.48 g) as a starting material, the title compound (0.97 g) was obtained in the same manner as that of Reference Example 1.

$^1$H-NMR (300 MHz, CDCl$_3$) δ (ppm): 1.45-1.58 (m, 1H), 1.90-2.02 (m, 1H), 2.46 (dd, J=4.74, 2.56 Hz, 1H), 2.71-2.76 (m, 1H), 2.89-2.97 (m, 1H), 3.41 (q, J=6.22 Hz, 2H), 3.52 (s, 2H), 5.79 (s, 1H), 7.19-7.25 (m, 2H), 7.38-7.49 (m, 2H)

Reference Example 4

Synthesis of (2R)-4-aminobutane-1,2-diol (2R)-4-Azidobutane-1,2-diol (12 g) obtained by the method described in the literature (Heterocycles, 2003, vol. 61, p. 481) was dissolved in methanol (60 ml), the solution was added with 5% palladium-carbon (2.4 g), and the mixture was stirred at room temperature for 7 hours under a hydrogen atmosphere of 1 atm. The reaction mixture was filtered, and the filtrate was concentrated under reduced pressure. The resulting residue was dissolved in methanol (60 ml), the solution was added with 5% palladium-carbon (2.4 g), and the mixture was stirred at room temperature for 1.5 days under a hydrogen atmosphere of 1 atm. The reaction mixture was filtered, and the filtrate was concentrated under reduced pressure to obtain the title compound (9.56 g).

MS (ESI) m/z=105.9 [M+H]$^+$ $^1$H-NMR (300 MHz, CD$_3$OD) δ (ppm): 1.52-1.68 (m, 1H), 1.67-1.83 (m, 1H), 2.79-3.00 (m, 2H), 3.27-3.34 (m, 1H), 3.42-3.53 (m, 1H), 3.63-3.75 (m, 1H)

Reference Example 5

Synthesis of 2-(2-bromophenyl)-N-{2-[(2R)-oxiran-2-yl]ethyl}acetamide

By using the compound obtained in Reference Example 4 (3.45 g) and 2-bromophenylacetic acid (8.46 g) as starting materials, the title compound (2.20 g) was obtained in the same manners as those of Reference Example 3, (2) and Reference Example 1.

MS (ESI) m/z=306.0 [M+Na]$^+$ $^1$H-NMR (300 MHz, CDCl$_3$) δ (ppm): 1.47-1.62 (m, 1H), 1.86-1.99 (m, 1H), 2.44 (dd, J=4.82, 2.64 Hz, 1H), 2.71 (dd, J=4.66, 4.20 Hz, 1H), 2.88-2.97 (m, 1H), 3.34-3.48 (m, 2H), 3.71 (s, 2H), 5.75 (s, 1H), 7.13-7.22 (m, 1H), 7.28-7.39 (m, 2H), 7.57-7.63 (m, 1H)

Reference Example 6

Synthesis of 2-(4-bromophenyl)-N-{2-[(2R)-oxiran-2-yl]ethyl}acetamide

By using the compound obtained in Reference Example 4 (3.25 g) and 4-bromophenylacetic acid (7.31 g) as starting materials, the title compound (2.24 g) was obtained in the same manners as those of Reference Example 3, (2) and Reference Example 1.

MS (ESI) m/z=306.0 [M+Na]$^+$ $^1$H-NMR (300 MHz, CDCl$_3$) δ (ppm): 1.42-1.56 (m, 1H), 1.89-2.03 (m, 1H), 2.45 (dd, J=4.82, 2.64 Hz, 1H), 2.70-2.76 (m, 1H), 2.88-2.97 (m, 1H), 3.40 (q, J=6.22 Hz, 2H), 3.50 (s, 2H), 5.66-5.86 (m, 1H), 7.12-7.19 (m, 2H), 7.44-7.51 (m, 2H)

Reference Example 7

Synthesis of 2-(3-bromophenyl)-N-methyl-N-{2-[(2R)-oxiran-2-yl]ethyl}acetamide (1) 4-Bromo-1-butene (6.65 g) was dissolved in dimethylformamide (50 ml), the solution was added with N-methylbenzylamine (5.97 g), and the mixture was stirred at 60° C. for 2 hours. The reaction mixture was added with ethyl acetate and distilled water, the layers were separated, and the organic layer was washed successively with distilled water and brine, then dried over anhydrous magnesium sulfate and filtered. The filtrate was concentrated under reduced pressure, and the resulting residue was purified by silica gel column chromatography (hexane:ethyl acetate=2:1) to obtain a coupling compound (2.54 g).

(2) AD-mix-β (19.97 g) was dissolved in a mixed solvent of t-butyl alcohol (70 ml) and distilled water (70 ml), and the solution was added with the compound obtained in (1) mentioned above (2.50 g) under ice cooling. The mixture was stirred for 6 hours under ice cooling, and then added with sodium hydrogensulfite until foaming ceased. The mixture was added with chloroform, the layers were separated, and the organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain a diol compound (2.45 g).

(3) The compound obtained in (2) mentioned above (2.40 g) was dissolved in methanol, the solution was added with 20% palladium hydroxide-carbon (1 g), and the mixture was stirred at room temperature for 6 hours under a hydrogen atmosphere of 1 atm. The reaction mixture was filtered, and then the filtrate was concentrated under reduced pressure to obtain an amine compound (1.49 g).

(4) 3-Bromophenylacetic acid (3.23 g) was dissolved in chloroform (30 ml), the solution was added with 1-ethyl-3-(3-dimethylaminopropyl)carbodiimide hydrochloride (2.88 g) under ice cooling, and the mixture was stirred at room temperature for 1 hour. The reaction mixture was added with a solution of the compound obtained in (3) mentioned above (1.49 g) in methanol (10 ml), and the mixture was stirred at room temperature for 72 hours. The reaction mixture was concentrated under reduced pressure, and the resulting residue was purified by silica gel column chromatography (chloroform:methanol:28% aqueous ammonia=20:1:0.1 to 10:1:0.1) to obtain an amide compound (843 mg).

(5) By using the compound obtained in (4) mentioned above (843 mg) as a starting material, the title compound (393 mg) was obtained in the same manner as that of Reference Example 1.

MS (ESI) m/z=298.0 [M+H]$^+$

Reference Example 8

Synthesis of 2-(3-bromophenyl)-N-[(2R)-oxiran-2-ylmethyl]acetamide (1) By using 3-bromophenylacetic acid (10 g) and allylamine (4.18 ml) as starting materials, an amide compound (10.58 g) was obtained in the same manner as that of Reference Example 3, (2).

(2) By using the compound obtained in (1) mentioned above (5 g) as a starting material, a diol compound (6.48 g) was obtained in the same manner as that of Reference Example 7, (2).

(3) By using the compound obtained in (2) mentioned above (6.3 g) as a starting material, the title compound (1.73 g) was obtained in the same manner as that of Reference Example 1.

MS (ESI) m/z=292.0 [M+Na]$^+$ $^1$H-NMR (300 MHz, CDCl$_3$) δ (ppm): 2.51 (dd, J=4.59, 2.56 Hz, 1H), 2.74-2.79 (m, 1H), 3.05-3.12 (m, 1H), 3.21-3.33 (m, 1H), 3.54 (s, 2H), 3.68-3.78 (m, 1H), 5.53-5.68 (m, 1H), 7.18-7.25 (m, 2H), 7.40-7.47 (m, 2H)

Reference Example 9

Synthesis of 2-(3-bromophenyl)-N-{3-[(2R)-oxiran-2-yl]propyl}acetamide (1) 5-Bromo-1-pentene (6.65 g) was dissolved in dimethylformamide (50 ml), the solution was added with potassium phthalimide (13.7 g) under ice cooling, and the mixture was stirred at 60° C. for 2 hours. The deposited solid was separated by filtration, and the filtrate was added with diethyl ether. Then, the mixture was washed successively with distilled water and saturated brine, and then the organic layer was dried over anhydrous magnesium sulfate and filtered. The filtrate was concentrated under reduced pressure to obtain a phthalimide compound (15.7 g).

(2) The compound obtained in (1) mentioned above (15.7 g) was dissolved in ethanol (100 ml), the solution was added with hydrazine monohydrate (7.7 ml) under ice cooling, and the mixture was stirred at 60° C. for 20 minutes. The reaction mixture was added with diluted hydrochloric acid under ice cooling to make the mixture acidic, and the deposited solid was separated by filtration. The filtrate was concentrated under reduced pressure, and the resulting residue was added with potassium hydroxide under ice cooling to make the residue basic, and the mixture was extracted with diethyl ether. The organic layer was washed with saturated brine, then dried over anhydrous magne-

Reference Example 10

Synthesis of N-(3-bromobenzyl)-3-[(2R)-oxiran-2-yl]propanamide (1) 4-Pentenoic acid (2.96 g) was added with thionyl chloride (1.96 ml), and the mixture was stirred at 70° C. for 2 hours. The reaction mixture was added with a solution of 3-bromobenzylamine (5.0 g) and triethylamine (11.2 ml) in chloroform (50 ml) under ice cooling, and the mixture was stirred at room temperature for 1 hour. The reaction mixture was added with saturated brine, the layers were separated, and the organic layer was dried over anhydrous magnesium sulfate and filtered. The filtrate was concentrated under reduced pressure, and the resulting residue was purified by silica gel column chromatography (hexane:ethyl acetate=5:1) to obtain an amide compound (2.01 g).

(2) By using the compound obtained in (1) mentioned above (2.01 g) as a starting material, the title compound (1.36 g) was obtained in the same manners as those of Reference Example 7, (2) and Reference Example 1.

MS (ESI) m/z=284.0 [M+H]$^+$

Reference Example 11

Synthesis of 3-(3-bromophenyl)-N-[(2R)-oxiran-2-ylmethyl]propanamide

By using 3-(3-bromophenyl)propionic acid (2.5 g) and allylamine 0.80 ml) as starting materials, the title compound (1.01 g) was obtained in the same manners as those of Reference Example 3, (2) Reference Example 7, (2) and Reference Example 1.

MS (ESI) m/z=306.0 [M+Na]$^+$ $^1$H-NMR (300 MHz, CDCl$_3$) δ (ppm): 2.41-2.52 (m, 3H), 2.75 (t, J=4.27 Hz, 1H), 2.95 (t, J=7.54 Hz, 2H), 3.02-3.10 (m, 1H), 3.24-3.37 (m, 1H), 3.63-3.75 (m, 1H), 5.54 (s, 1H), 7.09-7.20 (m, 2H), 7.30-7.40 (m, 2H)

Reference Example 12

Synthesis of N-(3-bromophenyl)-4-[(2R)-oxiran-2-yl]butanamide

By using 5-hexenoic acid (3.65 g) and 3-bromoaniline (5.0 g) as starting materials, the title compound (690 mg) was obtained in the same manners as those of Reference Example 10, (1), Reference Example 7, (2) and Reference Example 1.

MS (ESI) m/z=284.0 [M+H]$^+$ $^1$H-NMR (300 MHz, CDCl$_3$) δ (ppm): 1.26-1.39 (m, 1H), 1.55-1.77 (m, 3H), 2.44 (dd, J=4.90, 2.72 Hz, 1H), 2.75 (dd, J=4.82, 4.04 Hz, 1H), 2.83-2.91 (m, 1H), 3.29 (q, J=6.63 Hz, 2H), 3.51 (s, 2H), 5.71 (br.s., 1H), 7.18-7.24 (m, 2H), 7.39-7.46 (m, 2H)

(3) By using the compound obtained in (2) mentioned above (2.5 g) as a starting material, the title compound (1.39 g) was obtained in the same manners as those of Reference Example 3, (2), Reference Example 7, (2) and Reference Example 1.

MS (ESI) m/z=298.0 [M+H]$^+$

Reference Example 13

Synthesis of 2-(1-naphthyl)-N-{2-[(2R)-oxiran-2-yl]ethyl}acetamide

By using the compound obtained in Reference Example 4 (1.24 g) and 1-naphthylacetic acid (2.64 g) as starting materials, the title compound (0.51 g) was obtained in the same manners as those of Reference Example 3, (2) and Reference Example 1.

MS (ESI) m/z=256.1 [M+H]$^+$ $^1$H-NMR (300 MHz, CDCl$_3$) δ (ppm): 1.35-1.50 (m, 1H), 1.65-1.80 (m, 1H), 2.18 (dd, J=4.82, 2.64 Hz, 1H), 2.42-2.47 (m, 1H), 2.49-2.55 (m, 1H), 2.66-2.76 (m, 1H), 3.20-3.40 (m, 1H), 4.03 (s, 2H), 5.57 (s, 1H), 7.27-7.61 (m, 4H), 7.79-8.00 (m, 3H)

Reference Example 14

Synthesis of 2-(5-bromopyridin-3-yl)-N-{2-[(2R)-oxiran-2-yl]ethyl}acetamide

By using the compound obtained in Reference Example 4 (1.29 g) and 5-bromo-3-pyridylacetic acid (2.21 g) as starting materials, the title compound (0.45 g) was obtained in the same manners as those of Reference Example 3, (2) and Reference Example 1.

MS (ESI) m/z=307.0 [M+Na]$^+$ $^1$H-NMR (300 MHz, CDCl$_3$) δ (ppm): 1.43-1.57 (m, 1H), 2.01-2.13 (m, 1H), 2.51 (dd, J=4.66, 2.80 Hz, 1H), 2.75-2.79 (m, 1H), 2.95-3.02 (m, 1H), 3.41-3.49 (m, 2H), 3.50 (s, 2H), 5.94 (s, 1H), 7.85 (t, J=2.10 Hz, 1H), 8.44 (d, J=1.87 Hz, 1H), 8.60 (d, J=2.18 Hz, 1H)

Reference Example 15

Synthesis of 3-bromo-N-{3-[(2R)-oxiran-2-yl]propyl}benzamide (1) The compound obtained in Reference Example 9, (2) (5.08 g) was dissolved in chloroform (50 ml), the solution was added with 3-bromobenzoic acid (7 g) and 1-ethyl-3-(3-dimethylaminopropyl)carbodiimide hydrochloride (8.01 g), and the mixture was stirred at room temperature for 18 hours. The reaction mixture was concentrated under reduced pressure, and the resulting residue was added with saturated aqueous ammonium chloride and chloroform, and the layers were separated. The organic layer was washed with saturated brine, then dried over anhydrous magnesium sulfate and filtered. The filtrate was concentrated under reduced pressure, and the resulting residue was purified by silica gel column chromatography (chloroform:methanol=30:1) to obtain an amide compound (6.95 g).

(2) By using the compound obtained in (1) mentioned above (3 g) as a starting material, the title compound (2.54 g) was obtained in the same manners as those of Reference Example 7, (2) and Reference Example 1.

MS (ESI) m/z=306.0 [M+Na]$^+$ $^1$H-NMR (300 MHz, CDCl$_3$) δ (ppm): 1.38-1.53 (m, 1H), 1.69-1.97 (m, 3H), 2.56 (dd, J=4.82, 2.80 Hz, 1H), 2.80-2.86 (m, 1H), 2.94-3.03 (m, 1H), 3.41-3.65 (m, 2H), 6.50 (s, 1H), 7.31 (t, J=7.93 Hz, 1H), 7.60-7.65 (m, 1H), 7.68-7.73 (m, 1H), 7.94 (t, J=1.87 Hz, 1H)

Reference Example 16

Synthesis of 2-(3-bromophenyl)furan 1,3-Dibromobenzene (1.0 g) was dissolved in toluene (20 ml), the solution was added with tri-n-butyl-(2-furyl)tin 1.59 g) and tetrakistriphenylphosphine palladium (0.25 g), and the mixture was stirred for 30 minutes under reflux by heating. The reaction mixture was concentrated under reduced pressure, and then the residue was dissolved in hexane. The solution was filtered through silica gel, and the filtrate was concentrated under reduced pressure. The resulting residue was dissolved in diethyl ether, the solution was added with cesium fluoride (1.01 g), and the mixture was stirred at room temperature for 30 minutes. The reaction mixture was added with a mixed solvent of hexane:ethyl acetate=10:1, and the mixture was filtered. The filtrate was concentrated under reduced pressure, and the resulting residue was purified by silica gel column chromatography (hexane alone) to obtain the title compound (0.59 g).

MS (TOF) m/z=222.0[M]$^+$
$^1$H-NMR (300 MHz, CDCl$_3$) δ (ppm): 6.48 (dd, J=3.42, 1.71 Hz, 1H), 6.67 (dd, J=3.42, 0.62 Hz, 1H), 7.24 (t, J=7.85 Hz, 1H), 7.35-7.41 (m, 1H), 7.48 (dd, J=1.79, 0.70 Hz, 1H), 7.55-7.62 (m, 1H), 7.82 (t, J=1.79 Hz, 1H)

Reference Example 17

Synthesis of 3-bromo-N-{5-[(2R)-oxiran-2-yl]pentyl}benzamide (1) By using 7-bromo-1-heptene (5 g) as a starting material, an amine compound (2.87 g) was obtained in the same manners as those of Reference Example 9, (1) and (2).

(2) By using the compound obtained in (1) mentioned above (1.50 g) and 3-bromobenzoic acid (4.01 g) as starting materials, the title compound (1.55 g) was obtained in the same manners as those of Reference Example 3, (2), Reference Example 7, (2) and Reference Example 1.

MS (ESI) m/z=312.2 [M+H]$^+$
$^1$H-NMR (200 MHz, CDCl$_3$) δ (ppm): 1.32-1.74 (m, 8H), 2.47 (dd, J=5.05, 2.86 Hz, 1H), 2.71-2.80 (m, 1H), 2.84-2.98 (m, 1H), 3.37-3.51 (m, 2H), 6.24-6.43 (m, 1H), 7.24-7.37 (m, 1H), 7.55-7.76 (m, 2H), 7.86-7.96 (m, 1H)

Reference Example 18

Synthesis of 3-bromo-N-[(2R)-oxiran-2-ylmethyl]benzamide

By using 3-bromobenzoic acid (5 g) and allylamine (1.86 ml) as starting materials, the title compound (0.75 g) was obtained in the same manners as those of Reference Example 3, (2), Reference Example 7, (2) and Reference Example 1.

MS (ESI) m/z=277.9 [M+Na]$^+$
$^1$H-NMR (300 MHz, CDCl$_3$) δ (ppm): 2.66 (dd, J=4.43, 2.88 Hz, 1H), 2.83-2.88 (m, 1H), 3.19-3.27 (m, 1H), 3.45-3.59 (m, 1H), 3.90-4.00 (m, 1H), 6.23-6.36 (m, 1H), 7.31-7.38 (m, 1H), 7.58-7.71 (m, 2H), 7.91-7.97 (m, 1H)

Reference Example 19

Synthesis of 3-bromo-N-{2-[(2R)-oxiran-2-yl]ethyl}benzamide

By using the compound obtained in Reference Example 4 (1.40 g) and 3-bromobenzoic acid (2.94 g) as starting materials, the title compound (0.61 g) was obtained in the same manners as those of Reference Example 3, (2) and Reference Example 1.

MS (ESI) m/z=291.9 [M+Na]$^+$
$^1$H-NMR (300 MHz, CDCl$_3$) δ (ppm): 1.56-1.71 (m, 1H), 2.14-2.27 (m, 1H), 2.61 (dd, J=4.74, 2.72 Hz, 1H), 2.81-2.87 (m, 1H), 3.06-3.14 (m, 1H), 3.60-3.69 (m, 2H), 6.61 (s, 1H), 7.31 (t, J=7.93 Hz, 1H), 7.60-7.65 (m, 1H), 7.67-7.72 (m, 1H), 7.94 (t, J=1.79 Hz, 1H)

Reference Example 20

Synthesis of N-(3-bromophenyl)-N'-{3-[(2R)-oxiran-2-yl]propyl}urea (1) The compound obtained in Reference Example 9, (2) (0.37 g) was dissolved in tetrahydrofuran (3 ml), the solution was added with triethylamine (0.42 ml) and 3-bromophenyl isocyanate (0.315 ml), and the mixture was stirred at room temperature for 1 hour. The reaction mixture was concentrated under reduced pressure, the resulting residue was added with distilled water and chloroform, and the layers were separated. The organic layer was washed with saturated brine, then dried over anhydrous magnesium sulfate and filtered. The filtrate was concentrated under reduced pressure, and the resulting residue was purified by silica gel column chromatography (chloroform: methanol=30:1) to obtain an urea compound (0.95 g).

(2) By using the compound obtained in (1) mentioned above (0.9 g) as a starting material, the title compound (0.33 g) was obtained in the same manners as those of Reference Example 7, (2) and Reference Example 1.

MS (ESI) m/z=321.1 [M+Na]$^+$
$^1$H-NMR (200 MHz, CDCl$_3$) δ (ppm): 1.33-1.52 (m, 1H), 1.60-1.92 (m, 3H), 2.52 (dd, J=4.83, 2.64 Hz, 1H), 2.80 (t, J=4.40 Hz, 1H), 2.87-3.03 (m, 1H), 3.25-3.40 (m, 2H), 4.96 (s, 1H), 6.48 (s, 1H), 7.06-7.30 (m, 3H), 7.53-7.60 (m, 1H)

Reference Example 21

Synthesis of 2-(3-azidopropyl)oxirane (1) 4-Penten-1-ol (20.0 g) was dissolved in pyridine, the solution was added with p-toluenesulfonyl chloride (48.7 g) under ice cooling, and the mixture was stirred for 2 hours. The reaction mixture was added with hexane and distilled water, the layers were separated, and the organic layer was washed 4 times with 1 N hydrochloric acid, then dried over anhydrous magnesium sulfate and filtered. The filtrate was concentrated under reduced pressure to obtain a tosyl compound (54.1 g).

(2) The compound obtained in (1) mentioned above (54.0 g) was dissolved in dimethyl sulfoxide (500 ml), the solution was added with sodium azide (14.6 g), and the mixture was stirred at room temperature for 18 hours. The reaction mixture was added with pentane, the layers were separated, and then the organic layer was concentrated under ordinary pressure to obtain an azide compound (11.8 g).

(3) The compound obtained in (2) mentioned above (20.7 g) was dissolved in dichloromethane (250 ml), and the solution was added portionwise with m-chloroperbenzoic acid (28.2 g) under ice cooling. The mixture was stirred at room temperature for 18 hours, and then filtered, the filtrate was successively washed with 10% aqueous sodium hydroxide and saturated aqueous sodium thiosulfate, then dried over anhydrous magnesium sulfate and filtered. The filtrate was concentrated under ordinary pressure to obtain the title compound (23.7 g).
MS (ESI) m/z=150.9 [M+Na]+
$^1$H-NMR (200 MHz, CDCl$_3$) δ (ppm): 1.66 (m, 4H), 2.50 (dd, J=4.83, 2.64 Hz, 1H), 2.73-2.81 (m, 1H), 2.89-2.97 (m, 1H), 3.36 (t, J=6.15 Hz, 2H)

Reference Example 22

Synthesis of 2-(5-bromopentyl)oxirane

7-Bromo-1-heptene (5.10 g) was dissolved in chloroform (29 ml), the solution was added with m-chloroperbenzoic acid (6.21 g) under ice cooling, and the mixture was stirred at room temperature for 3 hours. The reaction mixture was added with diethyl ether and saturated aqueous sodium thiosulfate, the layers were separated, and the organic layer was washed with saturated aqueous sodium hydrogencarbonate, then dried over anhydrous magnesium sulfate and filtered. The filtrate was concentrated under ordinary pressure to obtain the title compound (5.27 g).
MS (TOF)=193.0 [M+H]+
$^1$H-NMR (600 MHz, CDCl$_3$) δ (ppm): 1.36-1.63 (m, 6H), 1.82-1.91 (m, 2H), 2.46 (dd, J=5.04, 2.75 Hz, 1H), 2.74 (dd, J=5.04, 3.67 Hz, 1H), 2.87-2.93 (m, 1H), 3.40 (t, J=6.88 Hz, 2H)

Reference Example 23

Synthesis of 3-bromo-N-{4-[(2R)-oxiran-2-yl]butyl}benzamide (1) By using 6-bromo-1-hexene (5 g) as a starting material, an amine compound (3.16 g) was obtained in the same manners as those of Reference Example 9, (1) and (2).
(2) By using the compound obtained in (1) mentioned above (3.16 g) and 3-bromobenzoic acid (5.5 g) as starting materials, the title compound (2.58 g) was obtained in the same manners as those of Reference Example 3, (2), Reference Example 7, (2) and Reference Example 1.
MS (ESI) m/z=298.1 [M+H]+
$^1$H-NMR (200 MHz, CDCl$_3$) δ (ppm): 1.48-1.80 (m, 6H), 2.48 (dd, J=5.05, 2.86 Hz, 1H), 2.76 (dd, J=5.05, 4.18 Hz, 1H), 2.85-2.99 (m, 1H), 3.30-3.55 (m, 2H), 6.32-6.55 (m, 1H), 7.22-7.38 (m, 1H), 7.56-7.76 (m, 2H), 7.86-7.99 (m, 1H)

Reference Example 24

Synthesis of N-{3-[(2R)-oxiran-2-yl]propyl}-1-naphthamide (1) The compound obtained in Reference Example 9, (2) (1.0 g) was dissolved in chloroform (10 ml), the solution was added with triethylamine (4.9 ml) and 1-naphthyl chloride (1.8 ml) under ice cooling, and the mixture was stirred at room temperature for 40 minutes. The reaction mixture was added with saturated aqueous sodium hydrogencarbonate, and the mixture was extracted with chloroform. The organic layer was washed with 0.5 N hydrochloric acid, then dried over anhydrous magnesium sulfate and filtered. The filtrate was concentrated under reduced pressure, and the resulting residue was purified by silica gel column chromatography (hexane:ethyl acetate=2:1) to obtain an amide compound (2.27 g).
(2) By using the compound obtained in (1) mentioned above (2.04 g) as a starting material, the title compound (1.06 g) was obtained in the same manners as those of Reference Example 7, (2) and Reference Example 1.
MS (ESI) m/z=256.2 [M+H]+
$^1$H-NMR (200 MHz, CDCl$_3$) δ (ppm): 1.45-1.94 (m, 4H), 2.50 (dd, J=5.05, 2.86 Hz, 1H), 2.74-2.81 (m, 1H), 2.89-3.03 (m, 1H), 3.58 (q, J=6.59 Hz, 2H), 6.15-6.36 (m, 1H), 7.35-7.61 (m, 4H), 7.79-7.97 (m, 2H), 8.19-8.36 (m, 1H)

Reference Example 25

Synthesis of methyl 4-[(2R)-oxiran-2-yl]butanoate (1) 5-Hexenoic acid (6.5 g) was dissolved in toluene (65 ml), the solution was added with p-toluenesulfonic acid monohydrate (490 mg) and benzyl alcohol (30 ml) under ice cooling, and the mixture was stirred for 3.5 hours under reflux by heating. The reaction mixture was left to cool, and then concentrated under reduced pressure, and the resulting residue was purified by silica gel column chromatography (hexane:ethyl acetate=30:1 to 20:1) to obtain an ester compound (13.7 g).
(2) By using the compound obtained in (1) mentioned above (11.2 g) as a starting material, the title compound (7.04 g) was obtained in the same manners as those of Reference Example 2, (3) and Reference Example 1.
MS (ESI) m/z=167.0 [M+Na]+
$^1$H-NMR (200 MHz, CDCl$_3$) δ (ppm): 1.40-1.90 (m, 4H), 2.25-2.96 (m, 5H), 3.66 (s, 3H)

Reference Example 26

Synthesis of benzyl oxiran-2-ylacetate (1) By using vinylacetic acid (15 g) as a starting material, an ester compound (42.4 g) was obtained in the same manner as that of Reference Example 25, (1).
(2) The compound obtained in (1) mentioned above (22.1 g) was dissolved in chloroform (90 ml), the solution was added with m-chloroperbenzoic acid (19.6 g) under ice cooling, and the mixture was stirred at room temperature for 48 hours. The reaction mixture was added with saturated aqueous sodium hydrogencarbonate, the layers were separated, and the organic layer was washed successively with saturated aqueous sodium hydrogencarbonate, and saturated aqueous sodium thiosulfate, then dried over anhydrous magnesium sulfate and filtered. The filtrate was concentrated under reduced pressure, and the resulting residue was purified by silica gel column chromatography (hexane:ethyl acetate=10:1 to 5:1) to obtain the title compound (10.7 g).
MS (ESI) m/z=215.0 [M+Na]+
$^1$H-NMR (600 MHz, CDCl$_3$) δ (ppm): 2.56 (dd, J=4.81, 2.52 Hz, 1H), 2.61 (t, J=5.50 Hz, 2H), 2.80-2.86 (m, 1H), 3.26-3.36 (m, 1H), 5.16 (s, 2H), 7.29-7.46 (m, 5H)

Reference Example 27

Synthesis of benzyl 5-oxiran-2-ylpentanoate (1) By using 6-heptenoic acid (5.18 g) as a starting material, an ester compound (9.67 g) was obtained in the same manner as that of Reference Example 25, (1).
(2) By using the compound obtained in (1) mentioned above (4.72 g) as a starting material, the title compound (4.56 g) was obtained in the same manner as that of Reference Example 26, (2).
MS (ESI) m/z=257.1 [M+Na]+

$^1$H-NMR (600 MHz, CDCl$_3$) δ (ppm): 1.39-1.60 (m, 4H), 1.66-1.75 (m, 2H), 2.37 (t, J=7.57 Hz, 2H), 2.44 (dd, J=5.04, 2.75 Hz, 1H), 2.72-2.74 (m, 1H), 2.85-2.91 (m, 1H), 5.11 (s, 2H), 7.28-7.41 (m, 5H)

Reference Example 28

Synthesis of oxiran-2-ylmethyl (3-bromobenzyl)carbamate (1) 3-Bromobenzylamine (1 g) was dissolved in chloroform (30 ml), the solution was added with allyl chloroformate (0.57 ml) and triethylamine (3.75 ml), and the mixture was stirred at room temperature for 1 hour. The reaction mixture was added with distilled water and chloroform, the layers were separated, and the organic layer was dried over anhydrous magnesium sulfate and filtered. The filtrate was concentrated under reduced pressure, and the resulting residue was purified by silica gel column chromatography (chloroform:methanol=20:1) to obtain a carbamate compound (0.65 g).

(2) By using the compound obtained in (1) mentioned above (0.64 g) as a starting material, the title compound (0.43 g) was obtained in the same manner as that of Reference Example 26, (2).
MS (ESI) m/z=308.1 [M+Na]$^+$
$^1$H-NMR (200 MHz, CDCl$_3$) δ (ppm): 2.60-2.71 (m, 1H), 2.85 (t, J=4.61 Hz, 1H), 3.17-3.29 (m, 1H), 3.93 (dd, J=12.31, 6.59 Hz, 1H), 4.36 (d, J=6.15 Hz, 2H), 4.48 (dd, J=12.09, 2.86 Hz, 1H), 5.12 (s, 1H), 7.17-7.25 (m, 2H), 7.32-7.49 (m, 2H)

Reference Example 29

Synthesis of 3-bromobenzyl(oxiran-2-ylmethyl)carbamate (1) Allyl isocyanate (0.78 ml) was dissolved in toluene (10 ml), the solution was added with 3-bromobenzyl alcohol (1.5 g), and the mixture was stirred for 9 hours under reflux by heating. The reaction mixture was concentrated under reduced pressure, and the resulting residue was purified by silica gel column chromatography (chloroform:methanol=50:1) to obtain a carbamate compound (1.66 g).

(2) By using the compound obtained in (1) mentioned above (0.65 g) as a starting material, the title compound (0.55 g) was obtained in the same manner as that of Reference Example 26, (2).
MS (ESI) m/z=308.1 [M+Na]$^+$
$^1$H-NMR (200 MHz, CDCl$_3$) δ (ppm): 2.60 (dd, J=4.40, 2.64 Hz, 1H), 2.74-2.85 (m, 1H), 3.05-3.17 (m, 1H), 3.18-3.39 (m, 1H), 3.55-3.73 (m, 1H), 4.96 (s, 1H), 5.08 (s, 2H), 7.15-7.35 (m, 2H), 7.39-7.55 (m, 2H)

Reference Example 30

Synthesis of allyl(oxiran-2-ylmethyl)carbamate (1) 3-Amino-1,2-propanediol (5 g) was dissolved in distilled water (280 ml), and the solution was added dropwise with allyl chloroformate (6.4 ml) under ice cooling. The mixture was further added dropwise with 0.4 N aqueous sodium hydroxide (140 ml). After the addition, the reaction mixture was stirred at room temperature for 36 hours. The reaction mixture was concentrated under reduced pressure, the resulting residue was added with 3 N hydrochloric acid to make the residue acidic, the mixture was extracted successively with chloroform and ethyl acetate, and then the organic layers were dried over anhydrous magnesium sulfate and filtered. The filtrate was concentrated under reduced pressure to obtain a carbamate compound (3.40 g).

(2) By using the compound obtained in (1) mentioned above (3.0 g) as a starting material, the title compound (1.72 g) was obtained in the same manner as that of Reference Example 1.
MS (ESI) m/z=180.0 [M+Na]$^+$
$^1$H-NMR (600 MHz, CDCl$_3$) δ (ppm): 2.56-2.65 (m, 1H), 2.75-2.82 (m, 1H), 3.06-3.13 (m, 1H), 3.40-3.51 (m, 1H), 3.56-3.66 (m, 1H), 4.06-4.10 (m, 2H), 5.18-5.24 (m, 2H), 5.85-5.97 (m, 1H)

Reference Example 31

Synthesis of (2R)-2-[4-(benzyloxy)butyl]oxirane (1) 5-Hexen-1-ol (25.08 g) was dissolved in dimethylformamide (250 ml), and the solution was slowly added with sodium hydride (7.22 g) on an ice bath, and after foaming ceased, the mixture was added dropwise with a solution of benzyl alcohol (38.04 g) in dimethylformamide (30 ml). After the addition, the reaction mixture was warmed to room temperature, and stirred for 3 hours. The reaction mixture was added with saturated aqueous ammonium chloride, and the mixture was extracted with diethyl ether. The organic layer was washed with saturated brine, then dried over anhydrous magnesium sulfate and filtered. The filtrate was concentrated under reduced pressure, and the resulting residue was purified by silica gel column chromatography (hexane:ethyl acetate=20:1) to obtain a benzyl ether compound (48.33 g).

(2) By using the compound obtained in (1) mentioned above as a starting material, the title compound (8.00 g) was obtained in the same manners as those of Reference Example 7, (2) and Reference Example 1.
MS (ESI) m/z=229.1 [M+Na]$^+$
$^1$H-NMR (200 MHz, CDCl$_3$) δ (ppm): 1.43-1.81 (m, 6H), 2.46 (dd, J=4.83, 2.64 Hz, 1H), 2.75 (dd, J=4.83, 3.96 Hz, 1H), 2.83-2.96 (m, 1H), 3.49 (t, J=6.15 Hz, 2H), 4.51 (s, 2H), 7.19-7.44 (m, 5H)

Reference Example 32

Synthesis of (2R)-2-[2-(benzyloxy)ethyl]oxirane (1) (S)-Aspartic acid (25.04 g) and potassium bromide (102.98 g) were dissolved in 2.5 M sulfuric acid, and the solution was added dropwise with an aqueous solution (45 ml) of sodium nitrite (23.23 g) over 1 hour with maintaining the internal temperature to be in the range of −5 to 0° C. on a sodium chloride-ice bath. After the addition, the reaction mixture was stirred for 2.5 hours with maintaining the internal temperature to be −5° C. The reaction mixture was extracted with ethyl acetate, and the organic layer was dried over anhydrous sodium sulfate and filtered. The filtrate was concentrated under reduced pressure to obtain a bromo compound (33.18 g).

(2) The compound obtained in (1) mentioned above (12.92 g) was dissolved in tetrahydrofuran (100 ml), the solution was added with a solution of a borane-tetrahydrofuran complex (1.01 M) in tetrahydrofuran (200 ml) on an ice bath, and the mixture was stirred at the same temperature for 3 hours. Then, the mixture was added with a mixed solvent of distilled water-tetrahydrofuran (1:1, 25 ml) on an ice bath. After the foaming ceased, the mixture was added with potassium carbonate (45.1 g), and the mixture was warmed to room temperature, and stirred for 1 hour. The reaction mixture was filtered, then the filtration residue was washed with diethyl ether, and the wash and the filtrate were combined and concentrated under reduced pressure. The resulting residue was purified by silica gel column chromatography (hexane:ethyl acetate=4:1 to 1:1) to obtain a diol compound (9.16 g).

(3) Sodium hydride (3.90 g) was added to tetrahydrofuran (108 ml), and then the mixture was slowly added dropwise with a solution of the compound obtained in (2) mentioned above (9.16 g) in tetrahydrofuran (20 ml) at an internal temperature in the range of −10 to −5° C. on an ice-ethanol bath. The mixture was stirred for 30 minutes at the same temperature, and then added with benzyl bromide (7.1 ml) and tetra-n-butylammonium iodide (2.00 g), and the mixture was further stirred for 30 minutes at an internal temperature of −10° C. Then, the mixture was stirred at room temperature for 2 hours, and then added to saturated aqueous ammonium chloride, and the mixture was extracted with chloroform. The organic layer was washed successively with distilled water and saturated brine, then dried over anhydrous magnesium sulfate and filtered. The filtrate was concentrated under reduced pressure, and the resulting residue was purified by silica gel column chromatography (hexane:ethyl acetate=10:1 to 4:1) to obtain the title compound (5.22 g).

MS (ESI) m/z=201.1 [M+Na]$^+$ $^1$H-NMR (200 MHz, CDCl$_3$) δ (ppm): 1.70-2.00 (m, 2H), 2.53 (dd, J=4.83, 2.64 Hz, 1H), 2.79 (dd, J=5.05, 3.74 Hz, 1H), 2.96-3.17 (m, 1H), 3.63 (t, J=6.59 Hz, 2H), 4.54 (s, 2H), 7.29-7.39 (m, 5H)

Reference Example 33

Synthesis of 1-(oxiran-2-ylmethyl)piperidine

Piperidine (3 ml) was dissolved in t-butyl alcohol (1.2 ml), and the solution was added dropwise with (±)-epichlorohydrin (2.45 ml) on an ice bath. The mixture was slowly warmed to room temperature as it was, and stirred for 18 hours. Then, the mixture was added dropwise with a solution of potassium t-butoxide (3.39 g) in tetrahydrofuran (18 ml) under ice cooling so that the internal temperature should not exceed 15° C. After the addition, the reaction mixture was stirred at room temperature for 2 hours. The reaction mixture was concentrated under reduced pressure, the resulting residue was added to distilled water, and the mixture was extracted with chloroform. The organic layer was washed with saturated brine, then dried over anhydrous magnesium sulfate and filtered. The filtrate was concentrated under reduced pressure, and the resulting residue was purified by silica gel column chromatography (chloroform:methanol=50:1) to obtain the title compound (1.55 g).

MS (ESI) m/z=142.0 [M+H]$^+$ $^1$H-NMR (200 MHz, CDCl$_3$) δ (ppm): 1.36-1.52 (m, 2H), 1.53-1.70 (m, 4H), 2.29 (dd, J=13.19, 6.59 Hz, 1H), 2.36-2.61 (m, 5H), 2.67 (m, 1H), 2.78 (dd, J=5.05, 4.18 Hz, 1H), 3.05-3.16 (m, 1H)

Reference Example 34

Synthesis of benzyl 4-(oxiran-2-ylmethyl)piperazine-1-carboxylate

By using 1-benzyloxycarbonylpiperazine (6 ml) and (±)-epichlorohydrin (2.4 ml) as starting materials, the title compound (7.80 g) was obtained in the same manner as that of Reference Example 33.

MS (ESI) m/z=299.2 [M+Na]$^+$ $^1$H-NMR (200 MHz, CDCl$_3$) δ (ppm): 2.27 (dd, J=13.40, 6.81 Hz, 1H), 2.40-2.67 (m, 4H), 2.49 (dd, J=5.27, 2.64 Hz, 1H), 2.72-2.86 (m, 2H), 3.04-3.17 (m, 1H), 3.56 (t, J=5.05 Hz, 4H), 5.13 (s, 2H), 7.30-7.42 (m, 5H)

Reference Example 35

Synthesis of 1-(oxiran-2-ylmethyl)pyrrolidine

By using pyrrolidine (3 ml) and (±)-epichlorohydrin (2.9 ml) as starting materials, the title compound (2.10 g) was obtained in the same manner as that of Reference Example 33.

MS (ESI) m/z=127.9 [M+H]$^+$ $^1$H-NMR (200 MHz, CDCl$_3$) δ (ppm): 1.76-1.87 (m, 4H), 2.43 (dd, J=12.75, 6.59 Hz, 1H), 2.49-2.56 (m, 1H), 2.55-2.69 (m, 4H), 2.73-2.86 (m, 2H), 3.06-3.19 (m, 1H)

Reference Example 36

Synthesis of (2R)-(4-azidobutyl)oxirane (1) 6-Bromo-1-hexene (5.06 g) was dissolved in dimethyl sulfoxide (120 ml), the solution was added with sodium azide (2.42 g), and the mixture was stirred at room temperature for 16 hours. The reaction mixture was added to distilled water, the mixture was extracted with diethyl ether, and the organic layer was washed with saturated brine, then dried over anhydrous magnesium sulfate and filtered. The filtrate was concentrated under ordinary pressure to obtain an azido compound (14.01 g).

(2) By using the compound obtained in (1) mentioned above (14.01 g) as a starting material, the title compound (6.26 g) was obtained in the same manners as those of Reference Example 7, (2) and Reference Example 1.

MS (TOF)=142.1 [M+H]$^+$ $^1$H-NMR (200 MHz, CDCl$_3$) δ (ppm): 1.43-1.79 (m, 6H), 2.48 (dd, J=4.83, 2.64 Hz, 1H), 2.76 (dd, J=4.83, 3.96 Hz, 1H), 2.85-2.99 (m, 1H), 3.30 (t, J=6.59 Hz, 2H)

Reference Example 37

Synthesis of 3-nitrobenzyl[(2R)-oxiran-2-ylmethyl]carbamate

By using allyl isocyanate (0.7 g) and 3-nitrobenzyl alcohol (1.17 g) as starting materials, the title compound (1.7 g) was obtained in the same manners as those of Reference Example 29, (1) and Reference Example 26, (2).

MS (ESI) m/z=275.1 [M+Na]$^+$ $^1$H-NMR (200 MHz, CDCl$_3$) δ (ppm): 2.62 (dd, J=4.61, 2.42 Hz, 1H), 2.73-2.90 (m, 1H), 3.05-3.20 (m, 1H), 3.18-3.41 (m, 1H), 3.53-3.77 (m, 1H), 5.04 (s, 1H), 5.21 (s, 2H), 7.54 (t, J=7.69 Hz, 1H), 7.63-7.74 (m, 1H), 8.12-8.28 (m, 2H)

Reference Example 38

3-cyanobenzyl[(2R)-oxiran-2-ylmethyl]carbamate

By using allyl isocyanate (0.7 g) and 3-cyanobenzyl alcohol (1.02 g) as starting materials, the title compound (1.34 g) was obtained in the same manners as those of Reference Example 29, (1) and Reference Example 26, (2).

MS (ESI) m/z=255.1 [M+Na]$^+$ $^1$H-NMR (200 MHz, CDCl$_3$) δ (ppm): 2.61 (dd, J=4.40, 2.64 Hz, 1H), 2.76-2.85 (m, 1H), 3.06-3.18 (m, 1H), 3.19-3.35 (m, 1H), 3.55-3.76 (m, 1H), 4.91-5.08 (m, 1H), 5.14 (s, 2H), 7.39-7.71 (m, 4H)

Reference Example 39

Synthesis of oxiran-2-ylmethyl benzylcarbamate (1) Benzylamine (5.0 g) was dissolved in chloroform (80 ml), the solution was added with saturated aqueous sodium hydrogencarbonate (80 ml) at room temperature, and then added with allyl chloroformate (6.75 g) under ice cooling, and the mixture was stirred at room temperature for 30 minutes. The reaction mixture was added with chloroform, the layers were separated, and the organic layer was dried over anhydrous magnesium sulfate and filtered. The filtrate was concentrated under reduced pressure, and the resulting residue was purified by silica gel column chromatography (hexane:ethyl acetate:triethylamine=10:10:0.2) to obtain a carbamate compound (8.86 g).
(2) By using the compound obtained in (1) mentioned above (8.86 g) as a starting material, the title compound (7.64 g) was obtained in the same manner as that of Reference Example 26, (2).
MS (ESI) m/z=230.1 [M+Na]$^+$
$^1$H-NMR (600 MHz, CDCl$_3$) δ (ppm): 2.56-2.68 (m, 1H), 2.76-2.91 (m, 1H), 3.10-3.29 (m, 1H), 3.90 (dd, J=12.15, 6.19 Hz, 1H), 4.36 (d, J=5.96 Hz, 2H), 4.45 (dd, J=12.15, 2.98 Hz, 1H), 5.08-5.22 (m, 1H), 7.15-7.42 (m, 5H)

Reference Example 40

Synthesis of pyridin-3-ylmethyl[(2R)-oxiran-2-ylmethyl]carbamate (1) By using allyl isocyanate (1.0 g) and 3-pyridinemethanol (1.19 g) as starting materials, a carbamate compound (2.13 g) was obtained in the same manner as that of Reference Example 29, (1).
(2) By using the compound obtained in (1) mentioned above (1.0 g) as a starting material, the title compound (0.40 g) was obtained in the same manners as those of Reference Example 7, (2) and Reference Example 1.
MS (ESI) m/z=209.1 [M+H]$^+$
$^1$H-NMR (600 MHz, CDCl$_3$) δ (ppm): 2.56-2.60 (m, 1H), 2.78 (t, J=4.36 Hz, 1H), 3.10 (s, 1H), 3.22-3.29 (m, 1H), 3.59-3.66 (m, 1H), 5.00 (s, 1H), 5.12 (s, 2H), 7.29 (dd, J=7.79, 5.04 Hz, 1H), 7.68 (d, J=7.79 Hz, 1H), 8.55-8.58 (m, 1H), 8.61 (s, 1H)

Reference Example 41

Synthesis of 4-({3-[(2R)-oxiran-2-yl]propoxy}methyl)quinoline (1) The compound obtained in Reference Example 21, (1) (1.5 g) was dissolved in tetrahydrofuran (50 ml), the solution was added with 4-(hydroxymethyl)quinoline (0.99 g) obtained by the method described in the literature (Synthesis, 1994, p. 1278), potassium hydroxide (0.385 g) and 18-crown-6-ether (1.81 g), and the mixture was stirred at room temperature for 6 hours. The reaction mixture was added with distilled water and ethyl acetate, the layers were separated, and the organic layer was washed with saturated brine, then dried over anhydrous magnesium sulfate and filtered. The filtrate was concentrated under reduced pressure, and the resulting residue was purified by silica gel column chromatography (chloroform:methanol 30:1) to obtain an ether compound (1.08 g).
(2) By using the compound obtained in (1) mentioned above (1.05 g) as a starting material, the title compound (0.46 g) was obtained in the same manners as those of Reference Example 7, (2) and Reference Example 1.
MS (ESI) m/z=244.1 [M+H]$^+$
$^1$H-NMR (200 MHz, CDCl$_3$) δ (ppm): 1.51-1.96 (m, 4H), 2.48 (dd, J=5.05, 2.86 Hz, 1H), 2.72-2.80 (m, 1H), 2.90-3.02 (m, 1H), 3.63-3.73 (m, 2H), 4.98-5.01 (m, 2H), 7.49 (d, J=4.40 Hz, 1H), 7.52-7.64 (m, 1H), 7.67-7.79 (m, 1H), 7.94-8.03 (m, 1H), 8.10-8.20 (m, 1H), 8.90 (d, J=4.40 Hz, 1H)

Reference Example 42

Synthesis of 4-oxiran-2-ylbutanenitrile

By using 5-hexenenitrile (3.0 g) as a starting material, the title compound (5.03 g) was obtained in the same manner as that of Reference Example 26, (2).
MS (ESI) m/z=134.0 [M+Na]$^+$
$^1$H-NMR (200 MHz, CDCl$_3$) δ (ppm): 1.45-1.69 (m, 1H), 1.74-1.97 (m, 3H), 2.33-2.56 (m, 3H), 2.74-2.82 (m, 1H), 2.87-3.02 (m, 1H)

Reference Example 43

Synthesis of methyl(oxiran-2-ylmethyl)carbamate (1) Allylamine (4.5 ml) was dissolved in chloroform (50 ml), the solution was added dropwise with methyl chloroformate (2.32 ml) under ice cooling, and the mixture was stirred at room temperature for 2 hours. The reaction mixture was washed successively with 2 N hydrochloric acid and saturated aqueous sodium hydrogencarbonate, then dried over anhydrous magnesium sulfate and filtered. The filtrate was concentrated under reduced pressure to obtain a carbamate compound (3.93 g).
(2) By using the compound obtained in (1) mentioned above (3.90 g) as a starting material, the title compound (3.32 g) was obtained in the same manner as that of Reference Example 26, (2).
MS (ESI) m/z=154.0 [M+Na]$^+$
$^1$H-NMR (200 MHz, CDCl$_3$) δ (ppm): 2.61 (dd, J=4.83, 2.64 Hz, 1H), 2.75-2.83 (m, 1H), 3.07-3.15 (m, 1H), 3.18-3.34 (m, 1H), 3.54-3.69 (m, 1H), 3.69 (s, 3H), 4.90 (br.s., 1H)

Reference Example 44

Synthesis of ethyl(oxiran-2-ylmethyl)carbamate (1) By using allylamine (4.5 ml) and ethyl chloroformate (2.87 ml) as starting materials, a carbamate compound (5.84 g) was obtained in the same manner as that of Reference Example 43, (1).
(2) By using the compound obtained in (1) mentioned above (3.84 g) as a starting material, the title compound (2.43 g) was obtained in the same manner as that of Reference Example 26, (2).
MS (ESI) m/z=168.0 [M+Na]$^+$
$^1$H-NMR (200 MHz, CDCl$_3$) δ (ppm): 1.25 (t, J=7.03 Hz, 3H), 2.61 (dd, J=4.40, 2.64 Hz, 1H), 2.73-2.86 (m, 1H), 3.06-3.15 (m, 1H), 3.18-3.34 (m, 1H), 3.52-3.68 (m, 1H), 4.13 (q, J=7.33 Hz, 2H), 4.85 (br.s., 1H)

Reference Example 45

Synthesis of oxiran-2-ylmethyl methylcarbamate

By using 40% aqueous methylamine (7.3 ml) and allyl chloroformate (3 ml) as starting materials, the title compound (989 mg) was obtained in the same manners as those of Reference Example 43, (1) and Reference Example 26, (2).

MS (ESI) m/z=154.0 [M+Na]$^+$
$^1$H-NMR (200 MHz, CDCl$_3$) δ (ppm): 2.61-2.67 (m, 1H), 2.78-2.87 (m, 1H), 2.81 (d, J=4.83 Hz, 3H), 3.16-3.27 (m, 1H), 3.89 (dd, J=12.31, 6.59 Hz, 1H), 4.44 (dd, J=12.31, 2.64 Hz, 1H), 4.78 (br.s., 1H)

Reference Example 46

Synthesis of oxiran-2-ylmethyl dimethylcarbamate

By using 50% aqueous dimethylamine (9.03 ml) and allyl chloroformate (3 ml) as starting materials, the title compound (1.10 g) was obtained in the same manners as those of Reference Example 43, (1) and Reference Example 26, (2).

MS (ESI) m/z=168.0 [M+Na]$^+$
$^1$H-NMR (200 MHz, CDCl$_3$) δ (ppm): 2.65 (dd, J=4.83, 2.64 Hz, 1H), 2.84 (dd, J=4.83, 3.96 Hz, 1H), 2.94 (s, 6H), 3.19-3.28 (m, 1H), 3.91 (dd, J=12.31, 6.15 Hz, 1H), 4.44 (dd, J=12.31, 3.08 Hz, 1H)

Reference Example 47

[3-(1,1-Dimethyl-3,5-dioxane-4-yl)phenyl]acetic acid (1) (1,1-Dimethyl-3,5-dioxacyclohexan-4-yl)-3-bromomethylbenzene (0.90 g) obtained by the method described in the literature (Tetrahedron, 1997, vol. 53, p. 6755) was dissolved in dimethyl sulfoxide (3 ml), the solution was added with sodium cyanide (0.17 g), and the mixture was stirred at 30° C. for 2 hours. The mixture was further added with sodium cyanide (0.34 g), and the mixture was stirred at 30° C. for 1 hour. The reaction mixture was added with 1 N aqueous sodium hydroxide and ethyl acetate, the layers were separated, and the organic layer was washed with saturated brine, then dried over anhydrous magnesium sulfate and filtered. The filtrate was concentrated under reduced pressure to obtain a cyano compound (0.78 g).

(2) The compound obtained in (1) mentioned above (0.78 g) was dissolved in ethanol (10 ml), the solution was added with 5 N aqueous sodium hydroxide, and the mixture was stirred for 3 hours under reflux by heating. The reaction mixture was added with 3 N hydrochloric acid, thereby made acidic, and concentrated under reduced pressure, and the resulting residue was added with distilled water and ethyl acetate, the layers were separated, and the organic layer was dried over anhydrous magnesium sulfate and filtered. The filtrate was concentrated under reduced pressure to obtain the title compound (0.71 g).

MS (ESI) m/z=273.0 [M+Na]$^+$
$^1$H-NMR (300 MHz, CDCl$_3$) δ (ppm): 0.80 (s, 3H), 1.29 (s, 3H), 3.60-3.69 (m, 4H), 3.73-3.81 (m, 2H), 5.39 (s, 1H), 7.29 (t, J=1.63 Hz, 1H), 7.34 (t, J=7.77 Hz, 1H), 7.39-7.46 (m, 2H)

Reference Example 48

Synthesis of 8-(2-aminoethoxy)-1-ethylquinolin-4(1H)-one hydrochloride (1) 8-Benzyloxy-1-ethyl-4-oxo-1,4-dihydroquinoline-3-carboxylic acid ethyl ester (0.6 g) obtained by the method described in the patent document (WO04/101584) was dissolved in tetrahydrofuran (5 ml), the solution was added with 2 N aqueous sodium hydroxide (5 ml), and the mixture was stirred at 85° C. for 2.5 hours. The reaction mixture was further added with ethanol (6 ml) and 2 N aqueous sodium hydroxide (6 ml), and the mixture was stirred at 85° C. for 0.5 hour. The reaction mixture was concentrated under reduced pressure, and the concentrate was added with concentrated hydrochloric acid (2.5 ml). The deposited solid was separated by filtration, the resulting solid was washed with distilled water, and then dissolved in toluene, and the solution was filtered. The filtrate was concentrated under reduced pressure to obtain a carboxylic acid (0.5 g).

(2) The compound obtained in (1) mentioned above (0.5 g) was dissolved in dimethylformamide (10 ml), the solution was added with sodium cyanide (0.76 g), and the mixture was stirred at 120° C. for 1 hour. The mixture was added with dimethyl sulfoxide (10 ml), the reaction mixture was stirred at 120° C. for 8 hours, and then added with saturated aqueous ammonium chloride and diethyl ether, and the layers were separated. The organic layer was washed successively with 2 N aqueous sodium hydroxide and saturated brine, then dried over anhydrous magnesium sulfate and filtered. The filtrate was concentrated under reduced pressure to obtain 8-benzyloxy-1-ethyl-4-oxo-1,4-dihydroquinoline (20 mg). The aqueous layer was added with concentrated hydrochloric acid and thereby made acidic, and the deposited solid was separated by filtration. The resulting solid was dissolved in dimethyl sulfoxide (10 ml), the solution was added with sodium cyanide (0.5 g), and the mixture was stirred at 150° C. for 12 hours and at 140° C. for 11 hours. The reaction mixture was left to cool, and then added with saturated aqueous sodium hydrogencarbonate, and the mixture was extracted with diethyl ether. The organic layer was washed with saturated brine, then dried over anhydrous magnesium sulfate and filtered. The filtrate was concentrated under reduced pressure to further obtain 8-benzyloxy-1-ethyl-4-oxo-1,4-dihydroquinoline (0.17 g).

(3) By using the compound obtained in (2) mentioned above (0.19 g) as a starting material, the title compound (0.1 g) was obtained according to the method described in the patent document (WO04/101584).

MS (ESI) m/z=233.0 [M+H]$^+$
$^1$H-NMR (200 MHz, DMSO-d6) δ (ppm): 1.21-1.40 (m, 3H), 3.19-3.43 (m, 2H), 4.39 (t, J=5.27 Hz, 2H), 4.52 (q, J=7.03 Hz, 2H), 6.06 (d, J=7.47 Hz, 1H), 7.22-7.45 (m, 2H), 7.77-8.01 (m, 2H)

Reference Example 49

Synthesis of 2-(1,2,3,4-tetrahydroquinolin-8-yloxy)ethanamine hydrochloride (1) 8-Hydroxyquinoline (2 g) was dissolved in acetonitrile (50 ml), the solution was added with potassium carbonate (5.7 g) and N-(2-chloroethyl)dibenzylamine hydrochloride (4.1 g), and the mixture was stirred for 6 hours under reflux by heating. The reaction mixture was filtered, and then the filtrate was concentrated under reduced pressure. The resulting residue was diluted with chloroform, washed successively with 2 N aqueous sodium hydroxide and saturated brine, then dried over anhydrous magnesium sulfate and filtered. The filtrate was concentrated under reduced pressure, and the resulting residue was purified by silica gel column chromatography (hexane:ethyl acetate=3:1 to 0:1) to obtain a dibenzylamine compound (2.1 g).

(2) The compound obtained in (1) mentioned above (1 g) was dissolved in methanol (20 ml), the solution was added with 10% palladium-carbon (0.5 g) and concentrated hydrochloric acid (0.23 ml), and the mixture was stirred at room temperature for 12 hours under a hydrogen atmosphere of 1 atm. The reaction mixture was filtered through Celite, and then the filtrate was concentrated under reduced pressure. The resulting residue was dissolved in methanol (20 ml), the solution was added with 10% palladium-carbon (0.5 g) and concentrated hydrochloric acid (0.23 ml), and the mixture was stirred at room temperature for 60 hours under a hydrogen atmosphere of 1 atm. The reaction mixture was filtered through Celite, and then the filtrate was concentrated under reduced pressure to obtain the title compound (0.52 g).
MS (ESI) m/z=193.0 [M+H]$^+$
$^1$H-NMR (200 MHz, CD$_3$OD) δ (ppm): 1.94-2.16 (m, 2H), 2.86 (t, J=6.37 Hz, 2H), 3.24-3.38 (m, 2H), 3.38-3.50 (m, 2H), 4.20-4.38 (m, 2H), 6.58-7.22 (m, 3H)

Reference Example 50

Synthesis of 2-phenoxyethylamine hydrochloride

By using phenol as a starting material, the title compound was obtained in the same manner as that of Reference Example 49.
MS (ESI) m/z=137.9 [M+H]$^+$
$^1$H-NMR (200 MHz, DMSO-d6) δ (ppm): 3.19 (t, J=5.27 Hz, 2H), 4.05-4.25 (m, 2H), 6.88-7.11 (m, 3H), 7.18-7.44 (m, 2H)

Reference Example 51

Synthesis of 8-(4-aminobutoxy)-1-ethyl-4-oxo-1,4-dihydroquinoline-3-carboxylic acid hydrochloride (1) 8-Hydroxy-1-ethyl-4-oxo-1,4-dihydroquinoline-3-carboxylic acid ethyl ester (300 mg) obtained by the method described in the patent document (WO04/101584) was dissolved in dimethylformamide (2 ml), the solution was added with 1,4-dibromobutane (737 mg) and potassium carbonate (159 mg), and the mixture was stirred at 100° C. for 3 hours. The reaction mixture was added with ethyl acetate and distilled water, the layers were separated, and the organic layer was washed with distilled water, then dried over anhydrous magnesium sulfate and filtered. The filtrate was concentrated under reduced pressure, and the resulting residue was dissolved in dimethylformamide (2 ml). The solution was added with dibenzylamine (343 mg) and potassium carbonate (238 mg), and the mixture was stirred at 100° C. for 3 hours. The reaction mixture was added with ethyl acetate and distilled water, the layers were separated, and the organic layer was washed with distilled water, then dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain a dibenzyl compound (343 mg).
(2) The compound obtained in (1) mentioned above (400 mg) was dissolved in tetrahydrofuran (4 ml), the solution was added with 2 N aqueous sodium hydroxide (2 ml), and the mixture was stirred at room temperature for 18 hours, and further stirred at 50° C. for 2 hours. The reaction mixture was added with dry ice, and added with ethyl acetate. The layers were separated, and the organic layer was dried over anhydrous magnesium sulfate and filtered. The filtrate was concentrated under reduced pressure, and the resulting residue was dissolved in 4 N hydrochloric acid in dioxane (5 ml) and methanol (5 ml). The solution was added with 5% palladium-carbon (400 mg), and the mixture was stirred at room temperature for 18 hours under a hydrogen atmosphere of 1 atm. The reaction mixture was filtered, and then the filtrate was concentrated under reduced pressure. The resulting residue was dissolved in methanol, the solution was added with a mixed solvent of hexane:ethyl acetate=1:1 to deposit solid, and the solid was separated by filtration to obtain the title compound (71 mg).
$^1$H-NMR (300 MHz, DMSO-d6) δ (ppm): 1.43 (t, J=6.92 Hz, 3H), 1.70-2.01 (m, 2H), 3.27-3.52 (m, 2H), 4.24 (t, J=6.06 Hz, 2H), 4.77-4.89 (m, 2H), 7.57-7.63 (m, 2H), 7.98-8.04 (m, 1H), 8.93 (s, 1H)

Reference Example 52

2-(Quinolin-8-yloxy)ethanamine (1) By using 8-quinolinol (1.0 g) and N-(2-bromoethyl)phthalimide (1.75 g) as starting materials, a phthalimide compound (230 mg) was obtained in the same manner as that of Reference Example 49 (1).
(2) The compound obtained in (1) mentioned above (220 mg) was dissolved in ethanol (3 ml), the solution was added with hydrazine monohydrate (50.4 µl), and the mixture was stirred for 4 hours under reflux by heating, and further stirred at room temperature for 18 hours. The reaction mixture was concentrated under reduced pressure, and the resulting residue was added with 1 N hydrochloric acid. The mixture was filtered, and then the filtrate was added with 5 N aqueous sodium hydroxide, and thereby made alkaline. The filtrate was added with chloroform, the layers were separated, and the organic layer was washed with saturated brine, then dried over anhydrous magnesium sulfate and filtered. The filtrate was concentrated under reduced pressure to obtain the title compound (83 mg).
MS (ESI) m/z=188.9 [M+H]$^+$
$^1$H-NMR (200 MHz, CDCl$_3$) δ (ppm): 3.24-3.42 (m, 2H), 4.23-4.38 (m, 2H), 7.09 (dd, J=6.81, 1.98 Hz, 1H), 7.33-7.54 (m, 3H), 8.05-8.24 (m, 1H), 8.96 (dd, J=4.18, 1.54 Hz, 1H)

Reference Example 53

Synthesis of ethyl 1-ethyl-4-oxo-8-(3-oxopropoxy)-1,4-dihydroquinoline-3-carboxylate (1) By using 8-hydroxy-1-ethyl-4-oxo-1,4-dihydroquinoline-3-carboxylic acid ethyl ester (0.2 g) obtained by the method described in the patent document (WO04/101584) and 3-bromo-1-propanol (0.13 g) as starting materials, an alcohol compound (223 mg) was obtained in the same manner as that of Reference Example 49, (1).
(2) The compound obtained in (1) mentioned above (46 mg) was dissolved in chloroform (3 ml), the solution was added with the Dess-Martin reagent (90 mg), and the mixture was stirred at room temperature for 30 minutes. The reaction mixture was added with saturated aqueous sodium hydrogencarbonate and chloroform, the layers were separated, and the organic layer was dried over anhydrous magnesium sulfate and filtered. The filtrate was concentrated under reduced pressure to obtain the title compound (140 mg) in an unpurified state.

Reference Example 54

Synthesis of N-ethyl-N-[(1S)-1-(2-methoxyphenyl)ethyl]ethane-1,2-diamine (1) (1S)-1-(2-Methoxyphenyl)ethanamine (8.86 g) obtained by the method described in the patent document (Japanese Patent Unexamined Publication No. 54-154724) was dissolved in chloroform (100 ml), the solution was added with acetic anhydride (12.0 g) and 4-dimethylaminopyridine (14.3 g), and the mixture was stirred at 70° C. for 30 minutes. The reaction mixture was left to cool, then successively washed with 1 N hydrochloric acid and 10% aqueous sodium hydroxide, then dried over anhydrous magnesium sulfate and filtered. The filtrate was concentrated under reduced pressure to obtain an acetyl compound (11.23 g).

(2) Lithium aluminum hydride (3.3 g) was added to tetrahydrofuran (200 ml). The mixture was added with the compound obtained in (1) mentioned above (11.2 g) over 15 minutes under reflux by heating. The mixture was stirred for 3 hours under reflux by heating, then left to cool, and successively added with distilled water (3.3 ml), 15% aqueous sodium hydroxide (3.3 ml) and distilled water (3.3 ml), and the mixture was stirred for 2 hours. The reaction mixture was filtered, and the resulting filtrate was further washed with tetrahydrofuran. The filtrate and wash were concentrated under reduced pressure to obtain an N-ethyl compound (10.86 g).

(3) Phthalimide acetaldehyde (633 mg) obtained by the method described in the literature (Tetrahedron Letters, 2001, vol. 42, p. 315) was dissolved in chloroform (20 ml), the solution was added with the compound obtained in (2) mentioned above (0.6 g) and sodium triacetoxyborohydride (1.06 g), and the mixture was stirred at room temperature for 2 hours. The reaction mixture was added with saturated aqueous sodium hydrogencarbonate and chloroform, the layers were separated, and then the organic layer was dried over anhydrous magnesium sulfate and filtered. The filtrate was concentrated under reduced pressure, and the resulting residue was purified by silica gel column chromatography (hexane:ethyl acetate=2:1) to obtain a phthalimide compound (0.93 g).

(4) The compound obtained in (3) mentioned above (0.93 g) was dissolved in ethanol (20 ml), the solution was added with hydrazine monohydrate (0.38 ml), and the mixture was stirred for 3 hours under reflux by heating, and further stirred at room temperature for 18 hours. The reaction mixture was concentrated under reduced pressure, the resulting residue was added with 1 N hydrochloric acid, and thereby made acidic, and the deposited solid was separated by filtration. The filtrate was neutralized with potassium carbonate, and then added with chloroform, the layers were separated, and the organic layer was dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain the title compound (484 mg).

MS (ESI) m/z=223.2 [M+H]$^+$ $^1$H-NMR (200 MHz, CDCl$_3$) δ (ppm): 0.98 (t, J=7.03 Hz, 3H), 1.29 (d, J=7.03 Hz, 3H), 2.38-2.72 (m, 6H), 3.82 (s, 3H), 4.37 (q, J=7.03 Hz, 1H), 6.83-6.97 (m, 2H), 7.15-7.25 (m, 1H), 7.36 (dd, J=7.47, 1.76 Hz, 1H)

Reference Example 55

Synthesis of 5-{ethyl[(1S)-1-(2-methoxyphenyl)ethyl]amino}pentanoic acid (1) The compound obtained in Reference Example 54, (2) (1.0 g) was dissolved in dimethylformamide (5 ml), the solution was added with ethyl 5-bromopentanoate (1.21 g), and the mixture was stirred at 100° C. for 2 hours. The reaction mixture was added with ethyl acetate and distilled water, the layers were separated, and the organic layer was dried over anhydrous magnesium sulfate and filtered. The filtrate was concentrated under reduced pressure to obtain an ethyl ester (1.07 g).

(2) The compound obtained in (1) mentioned above (1.07 g) was dissolved in 3 N hydrochloric acid (15 ml), and the solution was stirred at 80° C. for 5 hours. The reaction mixture was added with ethyl acetate, the layers were separated, and the organic layer was concentrated under reduced pressure. The resulting the residue was added with 10% aqueous sodium hydroxide, and the aqueous layer was extracted with ethyl acetate. The aqueous layer was neutralized with dry ice, the mixture was added with chloroform, and the layers were separated. The organic layer was concentrated under reduced pressure to obtain the title compound (201 mg).

MS (ESI) m/z=280.1 [M+Na]$^+$ $^1$H-NMR (300 MHz, CDCl$_3$) δ (ppm): 1.15 (t, J=7.15 Hz, 3H), 1.55 (d, J=6.68 Hz, 3H), 1.53-1.80 (m, 4H), 2.08-2.31 (m, 2H), 2.68-2.86 (m, 3H), 2.91-3.04 (m, 1H), 3.83 (s, 3H), 4.65-4.79 (m, 1H), 6.88 (d, J=8.08 Hz, 1H), 6.99 (t, J=7.54 Hz, 1H), 7.28 (t, J=7.77 Hz, 1H), 7.59 (d, J=7.31 Hz, 1H)

Reference Example 56

Synthesis of 6-{ethyl[(1S)-1-(2-methoxyphenyl)ethyl]amino}hexanoic acid

By using the compound obtained in Reference Example 54, (2) (1.0 g) and ethyl 6-bromohexanoate (1.31 g) as starting materials, the title compound (400 mg) was obtained in the same manner as that of Reference Example 55.

MS (ESI) m/z=294.1 [M+Na]$^+$ $^1$H-NMR (300 MHz, CDCl$_3$) δ (ppm): 1.11 (t, J=7.15 Hz, 3H), 1.21-1.35 (m, 2H), 1.49-1.68 (m, 4H), 1.52 (d, J=6.84 Hz, 3H), 2.17-2.31 (m, 2H), 2.66-2.97 (m, 4H), 3.82 (s, 3H), 4.60 (q, J=6.42 Hz, 1H), 6.87 (d, J=7.46 Hz, 1H), 6.98 (t, J=7.31 Hz, 1H), 7.22-7.29 (m, 1H), 7.61 (dd, J=7.69, 1.48 Hz, 1H)

Reference Example 57

Synthesis of N-ethyl-N-[(1S)-1-(2-methoxyphenyl)ethyl]propane-1,3-diamine (1) The compound obtained in Reference Example 54, (2) (1.0 g) was dissolved in dimethylformamide (10 ml), the solution was added with N-(3-bromopropyl)phthalimide (1.65 g) and potassium carbonate (0.85 g), and the mixture was stirred at 100° C. for 2.5 hours. The reaction mixture was added with distilled water and ethyl acetate, the layers were separated, and the organic layer was washed with saturated brine, then dried over anhydrous magnesium sulfate and filtered. The filtrate was concentrated under reduced pressure, and the resulting residue was purified by silica gel column chromatography (chloroform alone to chloroform:methanol=100:1 to 20:1) to obtain a phthalimide compound (1.58 g).

(2) By using the compound obtained in (1) mentioned above (1.73 g) as a starting material, the title compound (0.99 g) was obtained in the same manner as that of Reference Example 54, (4).

$^1$H-NMR (300 MHz, CDCl$_3$) δ (ppm): 1.01 (t, J=7.07 Hz, 3H), 1.28 (d, J=6.68 Hz, 3H), 1.49-1.61 (m, 2H), 2.42-2.74 (m, 6H), 3.81 (s, 3H), 4.32 (q, J=6.84 Hz, 1H), 6.86 (dd, J=8.24, 1.09 Hz, 1H), 6.89-6.98 (m, 1H), 7.16-7.23 (m, 1H), 7.40 (dd, J=7.62, 1.71 Hz, 1H)

Reference Example 58

Synthesis of N-ethyl-N-[(1S)-1-(2-methoxyphenyl)ethyl]butane-1,4-diamine

By using the compound obtained in Reference Example 54, (2) (1.0 g) and N-(4-bromobutyl)phthalimide (1.73 g) as starting materials, the title compound (0.98 g) was obtained in the same manners as those of Reference Example 57, (1) and Reference Example 54, (4).

$^1$H-NMR (300 MHz, CDCl$_3$) δ (ppm): 0.99 (t, J=7.07 Hz, 3H), 1.28 (d, J=6.68 Hz, 3H), 1.30-1.58 (m, 4H), 2.35-2.72 (m, 6H), 3.81 (s, 3H), 4.30 (q, J=6.74 Hz, 1H), 6.85 (dd, J=8.24, 1.09 Hz, 1H), 6.90-6.97 (m, 1H), 7.15-7.22 (m, 1H), 7.42 (dd, J=7.69, 1.79 Hz, 1H)

Reference Example 59

Synthesis of 4-{ethyl[(1S)-1-(2-methoxyphenyl)ethyl]amino}butanoic acid (1) Ethyl 4-bromobutanoate (5.0 g) was dissolved in toluene (100 ml), the solution was added with benzyl alcohol (51.3 ml) and concentrated hydrochloric acid (1 ml), and the mixture was heated with evaporating toluene. The reaction mixture was left to cool, and then concentrated under reduced pressure, and the resulting residue was purified by silica gel column chromatography (hexane:acetone=10:1). The resulting compound was added with benzyl alcohol (250 ml) and p-toluenesulfonic acid monohydrate (100 mg), and the mixture was stirred at 100° C. The reaction mixture was concentrated, and the resulting residue was purified by silica gel column chromatography (hexane:acetone=10:1) to obtain benzyl 4-bromobutanoate (3.9 g).

(2) By using the compound obtained in (1) mentioned above (1.72 g) and the compound obtained in Reference Example 54, (2) (1.0 g) as starting materials, a benzyl ester compound (91 mg) was obtained in the same manner as that of Reference Example 55, (1).

(3) The compound obtained in (2) mentioned above (550 mg) was dissolved in tetrahydrofuran (10 ml), the solution was added with 5% palladium-carbon (200 mg), and the mixture was stirred at room temperature for 18 hours under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=10:1:0.1) to obtain the title compound (560 mg).

MS (ESI) m/z=266.1 [M+Na]$^+$ $^1$H-NMR (300 MHz, DMSO-d6) δ (ppm): 0.93 (t, J=6.99 Hz, 3H), 1.22 (d, J=6.99 Hz, 3H), 1.59 (t, 2H), 2.11 (t, J=7.23 Hz, 2H), 2.31-2.64 (m, 4H), 3.76 (s, 3H), 4.28 (q, J=6.74 Hz, 1H), 6.88-6.98 (m, 2H), 7.16-7.25 (m, 1H), 7.35 (dd, J=7.54, 1.63 Hz, 1H)

Reference Example 60

Synthesis of N-(2-methoxyphenyl)propane-1,3-diamine

By using 3-bromopropylphthalimide (25.0 g) and o-anisidine (10 g) as starting materials, the title compound (4.9 g) was obtained in the same manners as those of Reference Example 57, (1) and Reference Example 54, (4).

MS (ESI) m/z=180.9 [M+H]$^+$ $^1$H-NMR (200 MHz, CDCl$_3$) δ (ppm): 1.74-1.95 (m, 2H), 2.87 (t, J=6.81 Hz, 2H), 3.21 (t, J=6.81 Hz, 2H), 3.84 (s, 3H), 6.56-6.92 (m, 4H)

Reference Example 61

Synthesis of N-benzyl-N-ethylethane-1,2-diamine

By using 2-bromoethylphthalimide and ethylbenzylamine as starting materials, the title compound (5.1 g) was obtained in the same manners as those of Reference Example 57, (1) and Reference Example 54, (4).

MS (ESI) m/z=179.0 [M+H]$^+$ $^1$H-NMR (300 MHz, CDCl$_3$) δ (ppm): 1.05 (t, J=7.15 Hz, 3H), 2.46-2.59 (m, 4H), 2.73 (t, J=5.98 Hz, 2H), 3.57 (s, 2H), 7.18-7.37 (m, 5H)

Reference Example 62

Synthesis of N-[(1S)-1-(2-methoxyphenyl)ethyl]-N-methylethane-1,2-diamine (1) (1S)-1-(2-Methoxyphenyl)ethanamine (100 mg) was dissolved in chloroform (10 ml), the solution was added with phthalimide acetaldehyde (125 mg) and sodium triacetoxyborohydride (210 mg), and the mixture was stirred at room temperature for 1 hour. The mixture was further added with 37% aqueous formaldehyde (340 ml) and sodium triacetoxyborohydride (210 mg), and the mixture was stirred at room temperature for 1 hour. The reaction mixture was added with saturated aqueous sodium hydrogencarbonate, the layers were separated, and the organic layer was dried over anhydrous magnesium sulfate and filtered. The filtrate was concentrated under reduced pressure to obtain a phthalimide compound (244 mg).

(2) By using the compound obtained in (1) mentioned above as a starting material, the title compound (114 mg) was obtained in the same manner as that of Reference Example 54, (4).

$^1$H-NMR (600 MHz, CDCl$_3$) δ (ppm): 1.29 (d, J=6.88 Hz, 3H), 2.17 (s, 3H), 2.34-2.40 (m, 1H), 2.44-2.51 (m, 1H), 2.70-2.79 (m, 2H), 3.81 (s, 3H), 4.15 (q, J=6.88 Hz, 1H), 6.86 (d, J=7.79 Hz, 1H), 6.94 (m, 1H), 7.20 (m, 1H), 7.35 (dd, J=7.57, 1.60 Hz, 1H)

Reference Example 63

Synthesis of N-ethyl-N-(1-pyrazin-2-ylethyl)ethane-1,2-diamine (1) 1-(Pyrazin-2-yl)ethylamine (0.45 g) obtained by the method described in the patent document (WO0/100213) was dissolved in chloroform (20 ml), the solution was added with phthalimide acetaldehyde (0.76 g) and sodium triacetoxyborohydride (1.16 g), and the mixture was stirred at room temperature for 2 hours. The mixture was further added with acetaldehyde (0.342 ml) and sodium triacetoxyborohydride (1.16 g), and the mixture was stirred at room temperature for 3.5 hours. The reaction mixture was added with saturated aqueous sodium hydrogencarbonate and chloroform, the layers were separated, and the organic layer was washed with saturated brine, then dried over anhydrous magnesium sulfate and filtered. The filtrate was concentrated under reduced pressure to obtain an N-ethyl compound.

(2) By using the compound obtained in (1) mentioned above as a starting material, the title compound (0.66 g) was obtained in the same manner as that of Reference Example 54, (4).

MS (ESI) m/z=195.1 [M+H]$^+$
$^1$H-NMR (600 MHz, CDCl$_3$) δ (ppm): 1.04 (t, J=7.11 Hz, 3H), 1.41 (d, J=6.88 Hz, 3H), 2.45-2.52 (m, 2H), 2.55-2.64 (m, 2H), 2.65-2.74 (m, 2H), 4.09 (q, J=6.88 Hz, 1H), 8.40 (d, J=2.29 Hz, 1H), 8.47-8.50 (m, 1H), 8.72 (d, J=1.38 Hz, 1H)

Reference Example 64

Synthesis of N-ethyl-N-[1-(2-methoxypyrazin-3-yl)ethyl]ethane-1,2-diamine (1) 1-(2-Methoxy-3-pyrazinyl)-1-ethanone (0.5 g) obtained by the method described in the literature (Journal of Organic Chemistry, 1989, vol. 54, p. 640) was dissolved in methanol, the solution was added with ammonium acetate (2.53 g) and sodium cyanoborohydride (0.145 g), and the mixture was stirred at room temperature for 3 days. The reaction mixture was added with 2 N hydrochloric acid, and the mixture was concentrated under reduced pressure, and then added with 5 N aqueous sodium hydroxide and thereby made alkaline. The mixture was added with chloroform, the layers were separated, and the organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain an amine compound (245 mg).

(2) By using the compound obtained in (1) mentioned above (245 mg) as a starting material, the title compound (53 mg) was obtained in the same manners as those of Reference Example 63, (1) and Reference Example 54, (4).

MS (ESI) m/z=225.1 [M+H]$^+$
$^1$H-NMR (200 MHz, CDCl$_3$) δ (ppm): 0.97 (t, J=7.25 Hz, 3H), 1.35 (d, J=7.03 Hz, 3H), 2.40-2.92 (m, 6H), 3.98 (s, 3H), 4.34-4.47 (m, 1H), 7.98 (d, J=2.64 Hz, 1H), 8.07 (d, J=3.08 Hz, 1H)

Reference Example 65

Synthesis of N-ethyl-N-(1-pyridin-3-ylethyl)ethane-1,2-diamine

By using 3-acetylpyridine (1.0 g) as a starting material, the title compound (146 mg) was obtained in the same manners as those of Reference Example 64, (1), Reference Example 63, (1) and Reference Example 54, (4).

MS (ESI) m/z=194.1 [M+H]$^+$
$^1$H-NMR (200 MHz, CDCl$_3$) δ (ppm): 1.03 (t, J=7.03 Hz, 3H), 1.33-1.42 (m, 3H), 2.35-2.60 (m, 4H), 2.63-2.73 (m, 2H), 3.93 (q, J=6.59 Hz, 1H), 7.21-7.28 (m, 1H), 7.63-7.73 (m, 1H), 8.48 (dd, J=4.83, 1.76 Hz, 1H), 8.60 (d, J=2.20 Hz, 1H)

Reference Example 66

Synthesis of N-ethyl-N-[1-(4-methoxypyridin-3-yl)ethyl]ethane-1,2-diamine

By using 3-acetyl-4-methoxypyridine (500 mg) obtained by the method described in the patent document (Japanese Patent Unexamined Publication No. 10-287678) as a starting material, the title compound (97 mg) was obtained in the same manners as those of Reference Example 64, (1), Reference Example 63, (1) and Reference Example 54, (4).

MS (ESI) m/z=224.2 [M+H]$^+$
$^1$H-NMR (200 MHz, CDCl$_3$) δ (ppm): 0.98 (t, J=7.03 Hz, 3H), 1.34 (d, J=7.03 Hz, 3H), 2.39-2.74 (m, 6H), 3.87 (s, 3H), 4.32 (q, J=7.03 Hz, 1H), 6.77 (d, J=5.71 Hz, 1H), 8.39 (d, J=5.71 Hz, 1H), 8.46 (s, 1H)

Reference Example 67

Synthesis of N,N-dimethyl-1,4-butanediamine (1) N-Benzyloxycarbonyl-1,4-butanediamine (1.0 g) was dissolved in methanol (15 ml), and the solution was added with 37% aqueous formaldehyde (3.1 ml) and sodium triacetoxyborohydride (1.23 g). The mixture was stirred at room temperature for 2 hours, and then further added with sodium triacetoxyborohydride (820 mg), and the mixture was stirred at room temperature for 1 hour. The reaction mixture was added with saturated aqueous sodium hydrogencarbonate and ethyl acetate, the layers were separated, and the organic layer was washed successively with distilled water and saturated brine, then dried over anhydrous magnesium sulfate and filtered. The resulting filtrate was concentrated under reduced pressure to obtain a dimethylamino compound (950 mg).

(2) By using the compound obtained in (1) mentioned above (280 mg) as a starting material, the title compound (80 mg) was obtained in the same manner as that of Reference Example 4.

MS (GC) m/z=293 [M−15]$^+$
$^1$H-NMR (400 MHz, CDCl$_3$) δ (ppm): 1.65 (quint, J=7.20 Hz, 2H), 1.75 (quint, J=7.20 Hz, 2H), 2.29 (s, 6H), 2.38 (t, J=7.20 Hz, 2H), 2.87 (t, J=7.20 Hz, 2H)

Reference Example 68

Synthesis of N-(2-aminomethyl)methanesulfonamide (1) N-Benzyloxycarbonyl-1,2-diaminoethane hydrochloride (1.0 g) was suspended in dichloromethane (15 ml), the suspension was added with triethylamine (1.45 ml) and methanesulfonyl chloride (0.4 ml) under ice cooling, and the mixture was stirred for 20 minutes under ice cooling. The reaction mixture was added with distilled water, the layers were separated, and the organic layer was washed successively with saturated aqueous sodium hydrogencarbonate and saturated brine. The organic layer was dried over anhydrous magnesium sulfate and filtered, and then the filtrate was concentrated under reduced pressure to obtain a methanesulfonyl compound (1.0 g).

(2) By using the compound obtained in (1) mentioned above (1.0 g) as a starting material, the title compound (530 mg) was obtained in the same manner as that of Reference Example 4.

MS (GC) m/z=139 [M+H]$^+$
$^1$H-NMR (400 MHz, CDCl$_3$) δ (ppm): 2.91 (t, J=5.60 Hz, 2H), 2.99 (s, 3H), 3.16 (t, J=5.60 Hz, 2H)

Reference Example 69

Synthesis of N-(2-aminomethyl)acetamide

By using N-benzyloxycarbonyl-1,2-diaminoethane hydrochloride (1.0 g) and acetyl chloride (370 μl) as starting materials, the title compound (440 mg) was obtained in the same manners as those of Reference Example 68, (1) and Reference Example 4.

MS (GC) m/z=103 [M+H]$^+$
$^1$H-NMR (400 MHz, CDCl$_3$) δ (ppm): 2.01 (s, 3H), 2.84 (t, J=6.00 Hz, 2H), 3.16 (q, J=5.6 Hz, 2H), 6.01 (brs, 1H)

Reference Example 70

Synthesis of 1-[1-(2-methoxyphenyl)ethyl]pyrrolidin-3-amine 3-t-Butoxycarbonylaminopyrrolidine (560 mg) was dissolved in methanol (5 ml), the solution was added with acetic acid (170 μl), 2-methoxyacetophenone (140 μl) and sodium cyanoborohydride (45 mg), and the mixture was stirred at 50° C. for 20 hours. The reaction mixture was added with 5 N hydrochloric acid (10 ml), the mixture was stirred at room temperature for 2 hours, and then made basic with potassium carbonate, and methanol was evaporated under reduced pressure. The reaction mixture was added with chloroform, the layers were separated, the organic layer was dried over anhydrous magnesium sulfate and filtered, and then the filtrate was concentrated under reduced pressure to obtain the title compound (83 mg).

MS (ESI) m/z=221 [M+H]$^+$
$^1$H-NMR (400 MHz, CDCl$_3$) δ (ppm): 1.30-1.33 (m, 3H), 1.38-1.52 (m, 1H), 2.12-2.21 (m, 1H), 2.26-2.35 (m, 1H), 2.37-2.56 (m, 1H), 2.60-2.81 (m, 2H), 3.44-3.50 (m, 1H), 3.78-3.84 (m, 4H), 6.86 (d, J=8.28 Hz, 1H), 6.94-6.99 (m, 1H), 7.17-7.21 (m, 1H), 7.49-7.52 (m, 1H)

Reference Example 71

Synthesis of 1-[1-(2-methoxyphenyl)ethyl]piperazine

By using N-t-butoxycarbonylpiperazine (560 mg) as a starting material, the title compound (149 mg) was obtained in the same manner as that of Reference Example 70.

MS (ESI) m/z=221 [M+H]$^+$
$^1$H-NMR (400 MHz, CDCl$_3$) δ (ppm): 1.30 (d, J=6.80 Hz, 3H), 2.32-2.56 (m, 4H), 2.86 (t, J=4.80 Hz, 4H), 3.81 (s, 3H), 3.93 (q, J=6.80 Hz, 1H), 6.84-6.89 (m, 1H), 6.92-6.98 (m, 1H), 7.17-7.22 (m, 1H), 7.40-7.45 (m, 1H)

Reference Example 72

Synthesis of N-ethyl-N-[(1S)-1-(3-methoxyphenyl)ethyl]ethane-1,2-diamine

By using (S)-1-(3-methoxyphenyl)ethylamine (200 mg) as a starting material, the title compound (135 mg) was obtained in the same manners as those of Reference Example 63, (1) and Reference Example 54, (4).

MS (ESI) m/z=223.2 [M+H]$^+$
$^1$H-NMR (200 MHz, CDCl$_3$) δ (ppm): 1.02 (t, J=7.25 Hz, 3H), 1.33 (d, J=6.59 Hz, 3H), 2.35-2.76 (m, 6H), 3.77-3.92 (m, 1H), 3.81 (s, 3H), 6.72-6.82 (m, 1H), 6.89-7.01 (m, 2H), 7.16-7.28 (m, 1H)

Reference Example 73

Synthesis of N-ethyl-N-[(1S)-1-(4-methoxyphenyl)ethyl]ethane-1,2-diamine

By using (S)-1-(4-methoxyphenyl)ethylamine (200 mg) as a starting material, the title compound (167 mg) was obtained in the same manners as those of Reference Example 63, (1) and Reference Example 54, (4).

MS (ESI) m/z=223.2 [M+H]$^+$
$^1$H-NMR (200 MHz, CDCl$_3$) δ (ppm): 1.02 (t, J=7.25 Hz, 3H), 1.32 (d, J=6.59 Hz, 3H), 2.31-2.77 (m, 6H), 3.75-3.94 (m, 1H), 3.80 (s, 3H), 6.85 (d, J=8.79 Hz, 2H), 7.27 (d, J=8.79 Hz, 2H)

Reference Example 74

Synthesis of N-ethyl-N-[(1S)-1-(4-fluorophenyl)ethyl]ethane-1,2-diamine

By using (S)-1-(4-fluorophenyl)ethylamine (200 mg) as a starting material, the title compound (186 mg) was obtained in the same manners as those of Reference Example 63, (1) and Reference Example 54, (4).

MS (ESI) m/z=211.1 [M+H]$^+$
$^1$H-NMR (200 MHz, CDCl$_3$) δ (ppm): 1.02 (t, J=7.03 Hz, 3H), 1.32 (d, J=6.59 Hz, 3H), 2.33-2.73 (m, 6H), 3.80-3.93 (m, 1H), 6.99 (t, J=8.79 Hz, 2H), 7.27-7.36 (m, 2H)

Reference Example 75

Synthesis of N-[(1S)-1-(4-chlorophenyl)ethyl]-N-ethylethane-1,2-diamine

By using (S)-4-chloro-α-methylbenzylamine (200 mg) as a starting material, the title compound (179 mg) was obtained in the same manners as those of Reference Example 63, (1) and Reference Example 54, (4).

MS (ESI) m/z=227.1 [M+H]$^+$
$^1$H-NMR (200 MHz, CDCl$_3$) δ (ppm): 1.01 (t, J=7.25 Hz, 3H), 1.32 (d, J=7.03 Hz, 3H), 2.33-2.74 (m, 6H), 3.85 (q, J=6.59 Hz, 1H), 7.24-7.34 (m, 4H)

Reference Example 76

Synthesis of N-ethyl-N-[(1S)-1-(4-methylphenyl)ethyl]ethane-1,2-diamine

By using (S)-1-(p-tolyl)-ethylamine (200 mg) as a starting material, the title compound (219 mg) was obtained in the same manners as those of Reference Example 63, (1) and Reference Example 54, (4).

MS (ESI) m/z=207.2 [M+H]$^+$
$^1$H-NMR (200 MHz, CDCl$_3$) δ (ppm): 1.02 (t, J=7.03 Hz, 3H), 1.33 (d, J=7.03 Hz, 3H), 2.33 (s, 3H), 2.34-2.72 (m, 6H), 3.77-3.93 (m, 1H), 7.06-7.26 (m, 4H)

Reference Example 77

Synthesis of N-ethyl-N-[(1S)-1-(2-fluorophenyl)ethyl]ethane-1,2-diamine

By using (S)-1-(2-fluorophenyl)ethylamine (200 mg) as a starting material, the title compound (236 mg) was obtained in the same manners as those of Reference Example 63, (1) and Reference Example 54, (4).

MS (ESI) m/z=211.1 [M+H]$^+$ $^1$H-NMR (600 MHz, CDCl$_3$) δ (ppm): 0.99 (t, J=7.11 Hz, 3H), 1.34 (d, J=6.88 Hz, 3H), 2.38-2.69 (m, 6H), 4.26 (q, J=6.88 Hz, 1H), 6.96-7.02 (m, 1H), 7.05-7.12 (m, 1H), 7.15-7.21 (m, 1H), 7.32-7.39 (m, 1H)

Reference Example 78

Synthesis of N-[1-[4-(benzyloxy)phenyl]ethyl]-N-ethylethane-1,2-diamine (1) 4'-hydroxyacetophenone (3.0 g) was dissolved in acetone (50 ml), the solution was added with benzyl bromide (2.88 ml) and potassium carbonate (4.57 g), and the mixture was stirred for 4 hours under reflux by heating. The reaction mixture was added with distilled water and ethyl acetate, the layers were separated, and the organic layer was dried over anhydrous magnesium sulfate and filtered. The filtrate was concentrated under reduced pressure to obtain a benzyl ether compound (5.0 g).

(2) By using the compound obtained in (1) mentioned above (1.0 g) as a starting material, the title compound (161 mg) was obtained in the same manners as those of Reference Example 64, (1), Reference Example 63, (1) and Reference Example 54, (4).

MS (ESI) m/z=298.9 [M+H]$^+$ $^1$H-NMR (200 MHz, CDCl$_3$) δ (ppm): 1.02 (t, J=7.25 Hz, 3H), 1.33 (d, J=7.03 Hz, 3H), 2.31-2.73 (m, 6H), 3.85 (q, J=6.74 Hz, 1H), 5.05 (s, 2H), 6.93 (d, J=8.79 Hz, 2H), 7.19-7.50 (m, 7H)

Reference Example 79

Synthesis of N-ethyl-N-[1-(3-fluorophenyl)ethyl]ethane-1,2-diamine (1) By using 3'-fluoroacetophenone (5.0 g) as a starting material, an amine compound (2.77 g) was obtained in the same manner as that of Reference Example 64, (1).

(2) By using the compound obtained in (1) mentioned above (1.0 g) as a starting material, the title compound (525 mg) was obtained in the same manners as those of Reference Example 63, (1) and Reference Example 54, (4).

MS (ESI) m/z=211.1 [M+H]$^+$ $^1$H-NMR (200 MHz, CDCl$_3$) δ (ppm): 1.02 (t, J=7.03 Hz, 3H), 1.33 (d, J=7.03 Hz, 3H), 2.32-2.78 (m, 6H), 3.87 (q, J=6.89 Hz, 1H), 6.82-7.00 (m, 1H), 7.02-7.17 (m, 2H), 7.19-7.33 (m, 1H)

Reference Example 80

Synthesis of N-[1-(3-chlorophenyl)ethyl]-N-ethyl-ethane-1,2-diamine (1) By using 3'-chloroacetophenone (5.0 g) as a starting material, an amine compound (2.62 g) was obtained in the same manner as that of Reference Example 64, (1).

(2) By using the compound obtained in (1) mentioned above (1.0 g) as a starting material, the title compound (474 mg) was obtained in the same manners as those of Reference Example 63, (1) and Reference Example 54, (4).

MS (ESI) m/z=227.1 [M+H]$^+$ $^1$H-NMR (200 MHz, CDCl$_3$) δ (ppm): 1.02 (t, J=7.03 Hz, 3H), 1.33 (d, J=7.03 Hz, 3H), 2.36-2.73 (m, 6H), 3.85 (q, J=6.74 Hz, 1H), 7.14-7.40 (m, 4H)

Reference Example 81

Synthesis of N-[1-(4-ethoxyphenyl)ethyl]-N-ethyl-ethane-1,2-diamine (1) By using 4'-ethoxyacetophenone (5.0 g) as a starting material, an amine compound (3.58 g) was obtained in the same manner as that of Reference Example 64, (1).

(2) By using the compound obtained in (1) mentioned above (1.0 g) as a starting material, the title compound (532 mg) was obtained in the same manners as those of Reference Example 63, (1) and Reference Example 54, (4).

MS (ESI) m/z=237.2 [M+H]$^+$ $^1$H-NMR (200 MHz, CDCl$_3$) δ (ppm): 1.02 (t, J=7.03 Hz, 3H), 1.32 (d, J=7.03 Hz, 3H), 1.41 (t, J=7.03 Hz, 3H), 2.32-2.71 (m, 6H), 3.84 (q, J=6.59 Hz, 1H), 4.02 (q, J=7.03 Hz, 2H), 6.84 (d, J=8.79 Hz, 2H), 7.25 (d, J=8.35 Hz, 2H)

Reference Example 82

Synthesis of N-[1-(1-methyl-1H-pyrrol-3-yl)ethyl]ethane-1,2-diamine

3-Acetyl-1-methylpyrrole (1.0 g) and ethylenediamine (1.46 g) were dissolved in toluene (10 ml), the solution was added with p-toluenesulfonic acid monohydrate (154 mg), and the mixture was refluxed for 2 hours by heating. The reaction mixture was added to a suspension of sodium borohydride (307 mg) in tetrahydrofuran, then the mixture was added with methanol, and the mixture was stirred at room temperature for 16 hours. The reaction mixture was made acidic with 1 N hydrochloric acid, and then the solvent was evaporated under reduced pressure. The mixture was added with distilled water and potassium carbonate, and thereby neutralized, and then the mixture was extracted with chloroform, and the organic layer was dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain the title compound (1.14 g).

$^1$H-NMR (200 MHz, CDCl$_3$) δ (ppm): 1.37 (d, J=6.59 Hz, 3H), 2.35-2.67 (m, 2H), 2.72-2.83 (m, 2H), 3.06 (s, 3H), 3.87 (q, J=6.59 Hz, 1H), 7.55 (d, J=8.35 Hz, 2H), 7.89 (d, J=8.79 Hz, 2H)

Reference Example 83

Synthesis of N-ethyl-N-[1-(2-methylphenyl)ethyl]ethane-1,2-diamine (1) By using 2'-methylacetophenone (5.0 g) as a starting material, an amine compound (2.05 g) was obtained in the same manner as that of Reference Example 64, (1).

(2) By using the compound obtained in (1) mentioned above (1.0 g) as a starting material, the title compound (514 mg) was obtained in the same manners as those of Reference Example 63, (1) and Reference Example 54, (4).

MS (ESI) m/z=207.1 [M+H]$^+$ $^1$H-NMR (200 MHz, CDCl$_3$) δ (ppm): 1.02 (t, J=7.25 Hz, 3H), 1.30 (d, J=7.03 Hz, 3H), 2.27-2.74 (m, 6H), 2.41 (s, 3H), 4.08 (q, J=6.59 Hz, 1H), 7.07-7.23 (m, 3H), 7.32-7.43 (m, 1H)

Reference Example 84

Synthesis of N-ethyl-N-[1-(3-methylphenyl)ethyl]ethane-1,2-diamine (1) By using 3'-methylacetophenone (5.0 g) as a starting material, an amine compound (3.06 g) was obtained in the same manner as that of Reference Example 64, (1).
(2) By using the compound obtained in (1) mentioned above (1.0 g) as a starting material, the title compound (550 mg) was obtained in the same manners as those of Reference Example 63, (1) and Reference Example 54, (4).
MS (ESI) m/z=207.1 [M+H]$^+$
$^1$H-NMR (200 MHz, CDCl$_3$) δ (ppm): 1.03 (t, J=7.03 Hz, 3H), 1.34 (d, J=7.03 Hz, 3H), 2.35 (s, 3H), 2.37-2.73 (m, 6H), 3.84 (q, J=6.74 Hz, 1H), 6.99-7.25 (m, 4H)

Reference Example 85

Synthesis of N-ethyl-N-[1-(4-ethylphenyl)ethyl]ethane-1,2-diamine (1) By using 4'-ethylacetophenone (5.0 g) as a starting material, an amine compound (3.10 g) was obtained in the same manner as that of Reference Example 64, (1).
(2) By using the compound obtained in (1) mentioned above (1.0 g) as a starting material, the title compound (675 mg) was obtained in the same manners as those of Reference Example 63, (1) and Reference Example 54, (4).
MS (ESI) m/z=221.1 [M+H]$^+$
$^1$H-NMR (200 MHz, CDCl$_3$) δ (ppm): 1.03 (t, J=7.03 Hz, 3H), 1.24 (t, J=7.69 Hz, 3H), 1.34 (d, J=6.59 Hz, 3H), 2.33-2.71 (m, 8H), 3.80-3.92 (m, 1H), 7.10-7.18 (m, 2H), 7.21-7.30 (m, 2H)

Reference Example 86

Synthesis of N-[1-[3-(dimethylamino)phenyl]ethyl]-N-ethylethane-1,2-diamine (1) By using 3'-dimethylaminoacetophenone (5.0 g) as a starting material, an amine compound (2.46 g) was obtained in the same manner as that of Reference Example 64, (1).
(2) By using the compound obtained in (1) mentioned above (1.0 g) as a starting material, the title compound (396 mg) was obtained in the same manners as those of Reference Example 63, (1) and Reference Example 54, (4).
MS (ESI) m/z=236.1 [M+H]$^+$
$^1$H-NMR (200 MHz, CDCl$_3$) δ (ppm): 1.03 (t, J=7.03 Hz, 3H), 1.35 (d, J=6.59 Hz, 3H), 2.37-2.74 (m, 6H), 2.94 (s, 6H), 3.81 (q, J=6.89 Hz, 1H), 6.56-6.81 (m, 3H), 7.18 (t, J=7.91 Hz, 1H)

Reference Example 87

Synthesis of N-ethyl-N-[1-(3-nitrophenyl)ethyl]ethane-1,2-diamine

By using 3'-nitroacetophenone (500 mg) as a starting material, the title compound (71 mg) was obtained in the same manners as those of Reference Example 64, (1), Reference Example 63, (1) and Reference Example 54, (4).
MS (ESI) m/z=238.1 [M+H]$^+$
$^1$H-NMR (600 MHz, CDCl$_3$) δ (ppm): 1.03 (t, J=7.11 Hz, 3H), 1.38 (d, J=6.42 Hz, 3H), 2.42-2.62 (m, 4H), 2.66-2.75 (m, 2H), 3.97 (q, J=6.57 Hz, 1H), 7.47 (t, J=8.02 Hz, 1H), 7.72 (d, J=7.34 Hz, 1H), 8.06-8.11 (m, 1H), 8.21-8.25 (m, 1H)

Reference Example 88

Synthesis of N-ethyl-N-[(1S)-1-[2-(trifluoromethyl)phenyl]ethyl]ethane-1,2-diamine By using (S)-1-[2-(trifluoromethyl)phenyl]ethylamine (200 mg) as a starting material, the title compound (115 mg) was obtained in the same manners as those of Reference Example 63, (1) and Reference Example 54, (4).
MS (ESI) m/z=261.1 [M+H]$^+$
$^1$H-NMR (200 MHz, CDCl$_3$) δ (ppm): 0.97 (t, J=7.03 Hz, 3H), 1.31 (d, J=6.59 Hz, 3H), 2.28-2.51 (m, 1H), 2.52-2.86 (m, 5H), 4.01-4.23 (m, 1H), 7.23-7.36 (m, 1H), 7.44-7.65 (m, 2H), 7.85 (d, J=7.91 Hz, 1H)

Reference Example 89

Synthesis of N-ethyl-N-[(1S)-1-[3-(trifluoromethyl)phenyl]ethyl]ethane-1,2-diamine By using (S)-1-[3-(trifluoromethyl)phenyl]ethylamine (200 mg) as a starting material, the title compound (98 mg) was obtained in the same manners as those of Reference Example 63, (1) and Reference Example 54, (4).
MS (ESI) m/z=261.1 [M+H]$^+$
$^1$H-NMR (200 MHz, CDCl$_3$) δ (ppm): 1.03 (t, J=7.03 Hz, 3H), 1.36 (d, J=6.59 Hz, 3H), 2.32-2.78 (m, 6H), 3.86-3.99 (m, 1H), 7.33-7.67 (m, 4H)

Reference Example 90

Synthesis of N-ethyl-N-[(1S)-1-[4-(trifluoromethyl)phenyl]ethyl]ethane-1,2-diamine By using (S)-1-[4-(trifluoromethyl)phenyl]ethylamine (200 mg) as a starting material, the title compound (108 mg) was obtained in the same manners as those of Reference Example 63, (1) and Reference Example 54, (4).
MS (ESI) m/z=261.1 [M+H]$^+$
$^1$H-NMR (200 MHz, CDCl$_3$) δ (ppm): 1.03 (t, J=7.03 Hz, 3H), 1.36 (d, J=7.03 Hz, 3H), 2.32-2.77 (m, 6H), 3.92 (q, J=6.74 Hz, 1H), 7.42-7.61 (m, 4H)

Reference Example 91

Synthesis of N-[(1S)-1-(4-bromophenyl)ethyl]-N-ethylethane-1,2-diamine

By using (S)-1-(4-bromophenyl)ethylamine (200 mg) as a starting material, the title compound (61 mg) was obtained in the same manners as those of Reference Example 63, (1) and Reference Example 54, (4).
MS (ESI) m/z=271.0 [M+H]$^+$
$^1$H-NMR (200 MHz, CDCl$_3$) δ (ppm): 1.01 (t, J=7.25 Hz, 3H), 1.31 (d, J=7.03 Hz, 3H), 2.32-2.76 (m, 6H), 3.83 (q, J=6.74 Hz, 1H), 7.18-7.29 (m, 2H), 7.37-7.48 (m, 2H)

Reference Example 92

Synthesis of N-ethyl-N-[(1S)-1-phenylethyl]ethane-1,2-diamine (1) By using (S)-(−)-1-phenylethylamine (210 mg) as a starting material, the title compound (230 mg) was obtained in the same manners as those of Reference Example 63, (1) and Reference Example 54, (4).

MS (ESI) m/z=193.1 [M+H]$^+$ $^1$H-NMR (600 MHz, CDCl$_3$) δ (ppm): 0.96 (t, J=7.11 Hz, 3H), 1.28 (d, J=6.88 Hz, 3H), 1.50 (brs, 2H), 2.33-2.63 (m, 6H), 3.81 (q, J=6.72 Hz, 1H), 7.13-7.18 (m, 1H), 7.22-7.26 (m, 2H), 7.27-7.30 (m, 2H)

Reference Example 93

Synthesis of N-ethyl-N-[(1S)-1-(1-naphthyl)ethyl] ethane-1,2-diamine (1) By using (S)-(−)-1-(1-naphthyl)ethylamine (240 mg) as a starting material, the title compound (220 mg) was obtained in the same manners as those of Reference Example 63, (1) and Reference Example 54, (4).

MS (ESI) m/z=243.1 [M+H]$^+$ $^1$H-NMR (600 MHz, CDCl$_3$) δ (ppm): 1.06 (t, J=7.11 Hz, 3H), 1.25 (brs, 2H), 1.44 (d, J=6.42 Hz, 3H), 2.36-2.56 (m, 4H), 2.69 (q, J=7.18 Hz, 2H), 4.65 (q, J=6.57 Hz, 1H), 7.33-7.55 (m, 4H), 7.71 (d, J=8.25 Hz, 1H), 7.80 (d, J=7.79 Hz, 1H), 8.42 (d, J=8.25 Hz, 1H)

Reference Example 94

Synthesis of N-ethyl-N-[(1S)-1-(2-naphthyl)ethyl] ethane-1,2-diamine (1) By using (S)-(−)-1-(2-naphthyl)ethylamine (240 mg) as a starting material, the title compound (160 mg) was obtained in the same manners as those of Reference Example 63, (1) and Reference Example 54, (4).

MS (ESI) m/z=243.1 [M+H]$^+$ $^1$H-NMR (600 MHz, CDCl$_3$) δ (ppm): 1.04 (t, J=7.11 Hz, 3H), 1.43 (brs, 2H), 1.39-1.46 (d, J=6.88 Hz, 3H), 2.43-2.72 (m, 6H), 4.02 (q, J=6.72 Hz, 1H), 7.41-7.49 (m, 2H), 7.54-7.60 (m, 2H), 7.70 (s, 1H), 7.75-7.83 (m, 2H)

Reference Example 95

Synthesis of N-[1-(1-methyl-1H-pyrrol-2-yl)ethyl] ethane-1,2-diamine

By using 2-acetyl-1-methylpyrrole (1.0 g) as a starting material, the title compound (424 mg) was obtained in the same manner as that of Reference Example 82.

$^1$H-NMR (200 MHz, CDCl$_3$) δ (ppm): 1.43 (d, J=6.59 Hz, 3H), 2.51-2.80 (m, 4H), 3.66 (s, 3H), 3.87 (q, J=6.59 Hz, 1H), 5.99-6.08 (m, 2H), 6.52-6.56 (m, 1H)

Reference Example 96

Synthesis of N-[1-[4-(methylsulfonyl)phenyl]ethyl] ethane-1,2-diamine

4′-(Methylsulfonyl)acetophenone (1.0 g) and ethylenediamine (908 mg) were dissolved in methanol (10 ml), and the solution was heated at 50° C. for 3 hours. The reaction mixture was added with a suspension of sodium borohydride (286 mg) in tetrahydrofuran (50 ml), and then added with methanol (6 ml), and the mixture was stirred at room temperature for 16 hours. The reaction mixture was made acidic with 1 N hydrochloric acid, and the solvent was evaporated under reduced pressure. The mixture was added with distilled water and potassium carbonate and thereby neutralized, then the mixture was extracted with chloroform, and the organic layer was dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain the title compound (553 mg).

MS (ESI) m/z=243.1 [M+H]$^+$ $^1$H-NMR (200 MHz, CDCl$_3$) δ (ppm): 1.37 (d, J=6.59 Hz, 3H), 2.35-2.67 (m, 2H), 2.72-2.83 (m, 2H), 3.06 (s, 3H), 3.87 (q, J=6.59 Hz, 1H), 7.55 (d, J=8.35 Hz, 2H), 7.89 (d, J=8.79 Hz, 2H)

Reference Example 97

Synthesis of N-[1-(1-ethyl-1H-pyrazol-5-yl)ethyl] ethane-1,2-diamine

By using 1-(2-ethyl-2H-pyrazol-3-yl)-ethanone (250 mg) as a starting material, the title compound (72 mg) was obtained in the same manner as that of Reference Example 82.

MS (ESI) m/z=183.1 [M+H]$^+$ $^1$H-NMR (200 MHz, CDCl$_3$) δ (ppm): 1.40-1.49 (m, 6H), 2.47-2.82 (m, 4H), 3.95 (q, J=6.59 Hz, 1H), 4.21 (q, J=7.03 Hz, 2H), 6.12 (d, J=1.76 Hz, 1H), 7.43 (d, J=1.76 Hz, 1H)

Reference Example 98

Synthesis of 3-[1-[(2-aminoethyl)amino]ethyl]-N-methylthiophene-2-sulfonamide

By using 3-acetyl-2-(methylaminosulfonyl)thiophene (1.0 g) as a starting material, the title compound (762 mg) was obtained in the same manner as that of Reference Example 82.

MS (ESI) m/z=264.1 [M+H]$^+$

Reference Example 99

Synthesis of N-[1-(1-methyl-1H-pyrazol-5-yl)ethyl] ethane-1,2-diamine

By using 1-(2-methyl-2H-pyrazol-3-yl)-ethanone (250 mg) as a starting material, the title compound (34 mg) was obtained in the same manner as that of Reference Example 82.

$^1$H-NMR (200 MHz, CDCl$_3$) δ (ppm): 1.42 (d, J=6.59 Hz, 3H), 2.50-2.88 (m, 4H), 3.90-4.02 (m, 1H), 4.14 (s, 3H), 6.45-6.52 (m, 1H), 7.37-7.45 (m, 1H)

Reference Example 100

Synthesis of N-[1-(1,3-dimethyl-1H-pyrazol-5-yl) ethyl]ethane-1,2-diamine

By using 1-(2,5-dimethyl-2H-pyrazol-3-yl)-ethanone (250 mg) as a starting material, the title compound (57 mg) was obtained in the same manner as that of Reference Example 82.

MS (ESI) m/z=183.1 [M+H]$^+$ $^1$H-NMR (200 MHz, CDCl$_3$) δ (ppm): 1.39 (d, J=6.59 Hz, 3H), 2.23 (s, 3H), 2.49-2.68 (m, 2H), 2.73-2.83 (m, 2H), 3.81 (s, 3H), 3.88 (q, J=6.59 Hz, 1H), 5.91 (s, 1H)

Reference Example 101

Synthesis of N-(1-[3-[(diethylamino)methyl]-4-methoxyphenyl]ethyl)ethane-1,2-diamine By using 1-(3-[(diethylamino)methyl]-4-methoxyphenyl)ethanone (250 mg) as a starting material, the title compound (130 mg) was obtained in the same manner as that of Reference Example 82.
$^1$H-NMR (200 MHz, CDCl$_3$) δ (ppm): 0.97-1.15 (m, 6H), 1.31-1.38 (m, 3H), 2.43-2.80 (m, 8H), 3.53-3.62 (m, 2H), 3.64-3.78 (m, 1H), 3.78-3.84 (m, 3H), 6.75-6.86 (m, 1H), 7.09-7.19 (m, 1H), 7.27-7.37 (m, 1H)

Reference Example 102

Synthesis of N-[1-[4-methoxy-3-(pyrrolidin-1-ylmethyl)phenyl]ethyl]ethane-1,2-diamine By using 1-[4-methoxy-3-(pyrrolidin-1-ylmethyl)phenyl]ethanone (250 mg) as a starting material, the title compound (70 mg) was obtained in the same manner as that of Reference Example 82.
$^1$H-NMR (200 MHz, CDCl$_3$) δ (ppm): 1.34 (d, J=6.59 Hz, 3H), 1.73-1.86 (m, 4H), 2.40-2.79 (m, 8H), 3.63-3.78 (m, 3H), 3.81 (s, 3H), 6.77-6.87 (m, 1H), 7.11-7.30 (m, 2H)

Reference Example 103

Synthesis of 2-[1-[(2-aminoethyl)amino]ethyl]phenol

By using 2'-hydroxyacetophenone (1.0 g) as a starting material, the title compound (303 mg) was obtained in the same manner as that of Reference Example 82.
MS (ESI) m/z=181.0 [M+H]$^+$
$^1$H-NMR (200 MHz, CDCl$_3$) δ (ppm): 1.47 (d, J=6.59 Hz, 3H), 2.61-2.71 (m, 2H), 2.74-3.03 (m, 2H), 3.92 (q, J=6.74 Hz, 1H), 6.71-6.84 (m, 2H), 6.91-7.00 (m, 1H), 7.08-7.19 (m, 1H)

Reference Example 104

Synthesis of N-[1-(2-nitrophenyl)ethyl]ethane-1,2-diamine

By using 2'-nitroacetophenone (1.0 g) as a starting material, the title compound (110 mg) was obtained in the same manner as that of Reference Example 82.
MS (ESI) m/z=210.1 [M+H]$^+$
$^1$H-NMR (200 MHz, CDCl$_3$) δ (ppm): 1.44 (d, J=6.59 Hz, 3H), 2.30-2.47 (m, 1H), 2.50-2.65 (m, 1H), 2.69-2.81 (m, 2H), 4.28 (q, J=6.59 Hz, 1H), 7.29-7.42 (m, 1H), 7.52-7.65 (m, 1H), 7.70-7.84 (m, 2H)

Reference Example 105

Synthesis of N-[1-(2-chlorophenyl)ethyl]ethane-1,2-diamine

By using 2'-chloroacetophenone (1.0 g) as a starting material, the title compound (529 mg) was obtained in the same manner as that of Reference Example 82.
MS (ESI) m/z=199.0 [M+H]$^+$
$^1$H-NMR (200 MHz, CDCl$_3$) δ (ppm): 1.35 (d, J=6.59 Hz, 3H), 2.41-2.66 (m, 2H), 2.73-2.83 (m, 2H), 4.29 (q, J=6.59 Hz, 1H), 7.09-7.37 (m, 3H), 7.47-7.54 (m, 1H)

Reference Example 106

Synthesis of 3-[1-[(2-aminoethyl)amino]ethyl]phenol

3'-Hydroxyacetophenone (1.0 g) and ethylenediamine (1.47 ml) were dissolved in methanol (10 ml), and the solution was stirred at room temperature for 16 hours. The mixture was added with sodium borohydride (277.9 mg), and the mixture was stirred at room temperature for 5 hours. The reaction mixture was added with 1 N hydrochloric acid, and then the solvent was evaporated. The residue was added with potassium carbonate and distilled water, thereby made alkaline, and then extracted with a mixed solvent of chloroform-ethanol (10:1), and the organic layer was dried over anhydrous sodium sulfate and filtered. The filtrate was concentrated under reduced pressure, and the resulting residue was purified by silica gel column chromatography (chloroform:methanol:28% aqueous ammonia=10:1:0.1 to 5:1:0.1) to obtain the title compound (59.1 mg).
MS (ESI) m/z=181.0 [M+H]$^+$
$^1$H-NMR (200 MHz, CDCl$_3$) δ (ppm): 1.36 (d, J=6.59 Hz, 3H), 2.44-2.85 (m, 4H), 3.72 (q, J=6.45 Hz, 1H), 6.63-6.91 (m, 3H), 7.09-7.21 (m, 1H)

Reference Example 107

Synthesis of N-[1-(2-ethoxyphenyl)ethyl]ethane-1,2-diamine

By using 2'-ethoxyacetophenone (1.0 g) as a starting material, the title compound (882 mg) was obtained in the same manner as that of Reference Example 106.
MS (ESI) m/z=209.1 [M+H]$^+$
$^1$H-NMR (200 MHz, CDCl$_3$) δ (ppm): 1.33-1.48 (m, 6H), 2.46-2.59 (m, 2H), 2.70-2.84 (m, 2H), 3.97-4.20 (m, 3H), 6.80-6.98 (m, 2H), 7.11-7.34 (m, 2H)

Reference Example 108

Synthesis of N-[1-(4-nitrophenyl)ethyl]ethane-1,2-diamine

By using 4'-nitroacetophenone (1.0 g) as a starting material, the title compound (639 mg) was obtained in the same manner as that of Reference Example 82.
MS (ESI) m/z=210.1 [M+H]$^+$
$^1$H-NMR (200 MHz, CDCl$_3$) δ (ppm): 1.37 (d, J=6.59 Hz, 3H), 2.35-2.49 (m, 1H), 2.52-2.67 (m, 1H), 2.73-2.82 (m, 2H), 3.89 (q, J=6.59 Hz, 1H), 7.51 (d, J=8.79 Hz, 2H), 8.19 (d, J=8.79 Hz, 2H)

Reference Example 109

Synthesis of N-[1-(3-methoxyphenyl)ethyl]ethane-1,2-diamine

By using 3'-methoxyacetophenone (1.0 g) as a starting material, the title compound (1.16 g) was obtained in the same manner as that of Reference Example 106.
MS (ESI) m/z=195.1 [M+H]$^+$
$^1$H-NMR (200 MHz, CDCl$_3$) δ (ppm): 1.36 (d, J=6.59 Hz, 3H), 2.41-2.65 (m, 2H), 2.72-2.81 (m, 2H), 3.74 (q, J=6.30 Hz, 1H), 3.81 (s, 3H), 6.73-6.82 (m, 1H), 6.86-6.95 (m, 2H), 7.17-7.31 (m, 1H)

Reference Example 110

Synthesis of 4-[1-[(2-aminoethyl)amino]ethyl]phenol

By using 4'-hydroxyacetophenone (1.0 g) as a starting material, the title compound (59.1 mg) was obtained in the same manner as that of Reference Example 106.
MS (ESI) m/z=181.0 [M+H]+
$^1$H-NMR (200 MHz, CDCl$_3$) δ (ppm): 1.35 (d, J=6.59 Hz, 3H), 2.42-2.86 (m, 4H), 3.62-3.79 (m, 1H), 6.65 (d, J=8.79 Hz, 2H), 7.11 (d, J=8.35 Hz, 2H)

Reference Example 111

Synthesis of N-[1-[4-(dimethylamino)phenyl]ethyl]ethane-1,2-diamine

By using 4'-dimethylaminoacetophenone (1.0 g) as a starting material, the title compound (370 mg) was obtained in the same manner as that of Reference Example 82.
MS (ESI) m/z=208.1 [M+H]+
$^1$H-NMR (200 MHz, CDCl$_3$) δ (ppm): 1.35 (d, J=6.59 Hz, 3H), 2.41-2.65 (m, 2H), 2.70-2.81 (m, 2H), 2.93 (s, 6H), 3.62-3.76 (m, 1H), 6.72 (d, J=8.79 Hz, 2H), 7.18 (d, J=8.79 Hz, 2H)

Reference Example 112

Synthesis of N-[(1S)-1-[3,5-bis(trifluoromethyl)phenyl]ethyl]-N-ethylethane-1,2-diamine By using (S)-1-[3,5-bis(trifluoromethyl)phenyl]ethylamine (210 mg) as a starting material, the title compound (210 mg) was obtained in the same manners as those of Reference Example 63, (1) and Reference Example 54, (4).
MS (ESI) m/z=329.2 [M+H]+
$^1$H-NMR (200 MHz, CDCl$_3$) δ (ppm): 1.04 (t, J=7.03 Hz, 3H), 1.39 (d, J=6.59 Hz, 3H), 1.51 (br.s., 2H), 2.38-2.78 (m, 6H), 3.98 (q, 1H), 7.75 (s, 1H), 7.85 (s, 2H)

Reference Example 113

Synthesis of N-ethyl-N-[(1R)-1-(3-methoxyphenyl)ethyl]ethane-1,2-diamine

By using (R)-1-(3-methoxyphenyl)ethylamine (500 mg) as a starting material, the title compound (390 mg) was obtained in the same manners as those of Reference Example 63, (1) and Reference Example 54, (4).
MS (ESI) m/z=223.1 [M+H]+
$^1$H-NMR (200 MHz, CDCl$_3$) δ (ppm): 1.03 (t, J=7.03 Hz, 3H), 1.34 (d, J=7.03 Hz, 3H), 2.36-2.75 (m, 6H), 3.78-3.91 (m, 1H), 3.81 (s, 3H), 6.72-6.82 (m, 1H), 6.84-6.99 (m, 2H), 7.16-7.28 (m, 1H)

Reference Example 114

Synthesis of 4-[1-[(2-aminoethyl)amino]ethyl]-2-[(diethylamino)methyl]phenol

By using 1-(3-[(diethylamino)methyl]-4-hydroxyphenyl)ethanone (250 mg) as a starting material, the title compound (89 mg) was obtained in the same manner as that of Reference Example 82.
MS (ESI) m/z=266.1 [M+H]+
$^1$H-NMR (200 MHz, CDCl$_3$) δ (ppm): 1.10 (t, J=7.03 Hz, 6H), 1.33 (d, J=6.59 Hz, 3H), 2.41-2.79 (m, 8H), 3.66 (q, J=6.59 Hz, 1H), 3.75 (s, 2H), 6.74 (d, J=7.91 Hz, 1H), 6.89-6.94 (m, 1H), 7.03-7.11 (m, 1H)

Reference Example 115

Synthesis of 4-[1-[(2-aminoethyl)amino]ethyl]-2-(piperidin-1-ylmethyl)phenol

By using 1-(4-hydroxy-3-piperidin-1-ylmethyl-phenyl)-ethanone (250 mg) as a starting material, the title compound (137 mg) was obtained in the same manner as that of Reference Example 82.
MS (ESI) m/z=300.2 [M+Na]+
$^1$H-NMR (200 MHz, CDCl$_3$) δ (ppm): 1.42-1.70 (m, 6H), 2.37-2.82 (m, 8H), 3.59-3.73 (m, 3H), 6.75 (d, J=8.35 Hz, 1H), 6.87-6.95 (m, 3H), 7.03-7.11 (m, 3H)

Reference Example 116

Synthesis of N-[1-[4-methoxy-3-(piperidin-1-ylmethyl)phenyl]ethyl]ethane-1,2-diamine By using 1-[4-methoxy-3-(piperidin-1-ylmethyl)phenyl]ethanone (250 mg) as a starting material, the title compound (69 mg) was obtained in the same manner as that of Reference Example 96.
$^1$H-NMR (200 MHz, CDCl$_3$) δ (ppm): 1.35 (d, J=6.59 Hz, 3H), 1.39-1.67 (m, 6H), 2.39-2.79 (m, 8H), 3.54 (s, 2H), 3.72 (q, J=6.59 Hz, 1H), 3.80 (s, 3H), 6.82 (d, J=8.35 Hz, 1H), 7.12-7.20 (m, 1H), 7.24-7.32 (m, 1H)

Reference Example 117

Synthesis of N-[1-[4-methoxy-3-(morpholin-4-ylmethyl)phenyl]ethyl]ethane-1,2-diamine By using 1-[4-methoxy-3-(morpholin-4-ylmethyl)phenyl]ethanone (250 mg) as a starting material, the title compound (181 mg) was obtained in the same manner as that of Reference Example 96.
$^1$H-NMR (200 MHz, CDCl$_3$) δ (ppm): 1.35 (d, J=6.59 Hz, 3H), 2.41-2.80 (m, 8H), 3.56 (s, 2H), 3.66-3.76 (m, 5H), 3.81 (s, 3H), 6.83 (d, J=8.35 Hz, 1H), 7.13-7.30 (m, 2H)

Reference Example 118

Synthesis of 2-(4-[1-[(2-aminoethyl)amino]ethyl]phenoxy)-N,N-dimethylacetamide

By using 2-(4-acetylphenoxy)-N,N-dimethylacetamide (250 mg) as a starting material, the title compound (162 mg) was obtained in the same manner as that of Reference Example 96.
MS (ESI) m/z=266.2 [M+H]+
$^1$H-NMR (200 MHz, CDCl$_3$) δ (ppm): 1.33 (d, J=6.59 Hz, 3H), 2.36-2.65 (m, 2H), 2.69-2.82 (m, 2H), 2.99 (s, 3H), 3.10 (s, 3H), 3.72 (q, J=6.59 Hz, 1H), 4.67 (s, 2H), 6.86-6.94 (m, 2H), 7.18-7.29 (m, 2H)

Reference Example 119

Synthesis of N-[1-[4-(2-morpholin-4-yl-2-oxoethoxy)phenyl]ethyl]ethane-1,2-diamine By using 1-[4-(2-morpholin-4-yl-2-oxoethoxy)phenyl]ethanone (250 mg) as a starting material, the title compound (168 mg) was obtained in the same manner as that of Reference Example 96.

MS (ESI) m/z=308.2 [M+H]⁺

¹H-NMR (200 MHz, CDCl₃) δ (ppm): 1.34 (d, J=6.59 Hz, 3H), 2.39-2.82 (m, 4H), 3.56-3.78 (m, 9H), 4.68 (s, 2H), 6.90 (d, J=8.79 Hz, 2H), 7.17-7.30 (m, 2H)

Reference Example 120

Synthesis of N-[1-[4-(4-methylpiperazin-1-yl)phenyl]ethyl]ethane-1,2-diamine

By using 1-[4-(4-methylpiperazino)phenyl]-1-ethanone (250 mg) as a starting material, the title compound (62 mg) was obtained in the same manner as that of Reference Example 96.

MS (ESI) m/z=263.2 [M+H]⁺

¹H-NMR (200 MHz, CDCl₃) δ (ppm): 1.34 (d, J=6.59 Hz, 3H), 2.35 (s, 3H), 2.41-2.80 (m, 8H), 3.15-3.24 (m, 4H), 3.70 (q, J=6.59 Hz, 1H), 6.89 (d, J=8.79 Hz, 2H), 7.20 (d, J=8.35 Hz, 2H)

Reference Example 121

Synthesis of N-(3-[1-[(2-aminoethyl)amino]ethyl]phenyl)methanesulfonamide

By using N-(3-acetylphenyl)methanesulfonamide (250 mg) as a starting material, the title compound (189 mg) was obtained in the same manner as that of Reference Example 96.

MS (ESI) m/z=258.1 [M+H]⁺

¹H-NMR (200 MHz, CDCl₃) δ (ppm): 1.35 (d, J=6.59 Hz, 3H), 2.37-2.87 (m, 4H), 3.02 (s, 3H), 3.70-3.85 (m, 1H), 7.05-7.39 (m, 4H)

Reference Example 122

Synthesis of 1-(4-[1-[(2-aminoethyl)amino]ethyl]phenyl)pyridin-4(1H)-one

By using 1-(4-acetylphenyl)pyridin-4(1H)-one (250 mg) as a starting material, the title compound (287 mg) was obtained in the same manner as that of Reference Example 96.

MS (ESI) m/z=258.2 [M+H]⁺

¹H-NMR (200 MHz, CDCl₃) δ (ppm): 1.38 (d, J=6.59 Hz, 3H), 2.36-2.71 (m, 2H), 2.72-2.87 (m, 2H), 3.85 (q, J=6.74 Hz, 1H), 6.50 (d, J=7.47 Hz, 2H), 7.21-7.35 (m, 2H), 7.40-7.65 (m, 4H)

Reference Example 123

Synthesis of 1-[4-[1-[(2-aminoethyl)amino]ethyl]phenyl]piperidin-4-ol

By using 1-[4-(4-hydroxypiperidin-1-yl)phenyl]ethanone (250 mg) as a starting material, the title compound (146 mg) was obtained in the same manner as that of Reference Example 96.

MS (ESI) m/z=264.2 [M+H]⁺

¹H-NMR (200 MHz, CDCl₃) δ (ppm): 1.36 (d, J=6.59 Hz, 3H), 1.57-1.82 (m, 2H), 1.92-2.11 (m, 2H), 2.39-2.66 (m, 2H), 2.69-3.03 (m, 4H), 3.42-3.95 (m, 4H), 6.90 (d, J=8.35 Hz, 2H), 7.19 (d, J=8.35 Hz, 2H)

Reference Example 124

Synthesis of N'-[3-[1-[(2-aminoethyl)amino]ethyl]phenyl]-N,N-dimethylsulfamide

By using N'-(3-acetylphenyl)-N,N-dimethylsulfamide (250 mg) as a starting material, the title compound (299 mg) was obtained in the same manner as that of Reference Example 96.

MS (ESI) m/z=287.1 [M+H]⁺

¹H-NMR (200 MHz, CDCl₃) δ (ppm): 1.35 (d, J=6.59 Hz, 3H), 2.33-2.82 (m, 4H), 2.85 (s, 6H), 3.69-3.83 (m, 1H), 7.00-7.33 (m, 4H)

Reference Example 125

Synthesis of N-[1-[4-(2-pyridin-4-ylaziridin-1-yl)phenyl]ethyl]ethane-1,2-diamine By using 1-[4-(2-pyridin-4-ylaziridin-1-yl)phenyl]ethanone (250 mg) as a starting material, the title compound (272 mg) was obtained in the same manner as that of Reference Example 96.

MS (ESI) m/z=283.2 [M+H]⁺

¹H-NMR (200 MHz, CDCl₃) δ (ppm): 1.35 (d, J=6.59 Hz, 3H), 2.32-2.66 (m, 4H), 2.69-2.83 (m, 2H), 3.05 (dd, J=6.37, 3.30 Hz, 1H), 3.73 (q, J=6.30 Hz, 1H), 6.98 (d, J=8.35 Hz, 2H), 7.22 (d, J=8.35 Hz, 2H), 7.30 (d, J=6.15 Hz, 2H), 8.57 (d, J=6.15 Hz, 2H)

Reference Example 126

Synthesis of N-[1-(1-methyl-1H-pyrazol-4-yl)ethyl]ethane-1,2-diamine 1-(1-Methyl-1H-pyrazol-4-yl)-ethanone (250 mg) and ethylenediamine (362 mg) were dissolved in methanol (10 ml), the solution was added with acetic acid (1.21 g) and sodium cyanoborohydride (189 mg), and the mixture was stirred at room temperature for 48 hours. The reaction mixture was added with saturated aqueous sodium hydrogencarbonate and tetrahydrofuran, the layers were separated, and then the organic layer was dried over anhydrous magnesium sulfate and filtered. The filtrate was concentrated under reduced pressure, and the resulting residue was purified by silica gel column chromatography (chloroform:methanol: 28% aqueous ammonia=10:1:0.1) to obtain the title compound (163 mg).

MS (ESI) m/z=169.1 [M+H]⁺

¹H-NMR (200 MHz, CDCl₃) δ (ppm): 1.26 (d, J=6.59 Hz, 3H), 2.53-2.80 (m, 4H), 3.69 (q, J=6.59 Hz, 1H), 3.77 (s, 3H), 7.34 (s, 1H), 7.53 (s, 1H)

Reference Example 127

Synthesis of 4-[1-[(2-aminoethyl)amino]ethyl]benzenesulfonamide

By using 4-acetyl-benzenesulfonamide (250 mg) as a starting material, the title compound (49 mg) was obtained in the same manner as that of Reference Example 96.

MS (ESI) m/z=244.1 [M+H]⁺

¹H-NMR (200 MHz, CDCl₃) δ (ppm): 1.22 (d, J=6.15 Hz, 3H), 2.36-2.68 (m, 4H), 3.64-3.83 (m, 1H), 7.45-7.56 (m, 2H), 7.70-7.82 (m, 2H)

Reference Example 128

Synthesis of N-[(1S)-1-(2-methoxyphenyl)ethyl]ethane-1,2-diamine

By using (1S)-1-(2-methoxyphenyl)ethylamine (70 mg) as a starting material, the title compound (71 mg) was obtained in the same manners as those of Reference Example 54, (3) and (4).
MS (ESI) m/z=195.1 [M+H]⁺
¹H-NMR (200 MHz, CDCl₃) δ (ppm): 1.36 (d, J=6.59 Hz, 3H), 2.47-2.58 (m, 2H), 2.71-2.82 (m, 2H), 3.83 (s, 3H), 4.12 (q, J=6.59 Hz, 1H), 6.82-7.01 (m, 2H), 7.13-7.36 (m, 2H)

Reference Example 129

Synthesis of N-[1-(3-ethylphenyl)ethyl]ethane-1,2-diamine

By using 3'-ethylacetophenone (500 mg) as a starting material, the title compound (571 mg) was obtained in the same manner as that of Reference Example 96.
MS (ESI) m/z=193.1 [M+H]⁺
¹H-NMR (200 MHz, CDCl₃) δ (ppm): 1.24 (t, J=7.47 Hz, 3H), 1.37 (d, J=6.59 Hz, 3H), 2.38-2.85 (m, 6H), 3.74 (q, J=6.89 Hz, 1H), 7.02-7.31 (m, 4H)

Reference Example 130

Synthesis of N-[1-[4-(4,5-bis[[(triethylsilyl)oxy]methyl]-1H-1,2,3-triazol-1-yl)phenyl]ethyl]ethane-1,2-diamine (1) 1-[4-(4,5-Bis[[(triethylsilyl)oxy]methyl]-1H-1,2,3-triazol-1-yl)phenyl]ethanone (100 mg) was dissolved in dimethylformamide (2 ml), the solution was added with t-butyldimethylchlorosilane (134.1 mg) and imidazole (165.2 mg), and the mixture was stirred at room temperature for 16 hours and at 50° C. for 6 hours. The mixture was further added with t-butyldimethylchlorosilane (134.1 mg) and imidazole (165.2 mg), and the mixture was stirred at room temperature for 16 hours. The mixture was added with distilled water and ethyl acetate, the layers were separated, and the organic layer was concentrated under reduced pressure. The resulting residue was purified by silica gel column chromatography (chloroform) to obtain a protected compound (199 mg).
(2) By using the compound obtained in (1) mentioned above (195 mg) as a starting material, the title compound (138 mg) was obtained in the same manner as that of Reference Example 96.
MS (ESI) m/z=520.4 [M+H]⁺
¹H-NMR (200 MHz, CDCl₃) δ (ppm): 0.00 (s, 6H), 0.13 (s, 6H), 0.82 (s, 9H), 0.92 (s, 9H), 1.39 (d, J=6.59 Hz, 3H), 2.42-2.69 (m, 2H), 2.73-2.85 (m, 2H), 3.78-3.95 (m, 1H), 4.77 (s, 2H), 4.92 (s, 2H), 7.41-7.66 (m, 4H)

Reference Example 131

Synthesis of 3-[(1S)-1-[(2-aminoethyl)amino]ethyl]phenol

By using (S)-1-(3-hydroxyphenyl)ethylamine (400 mg) obtained by the method described in the literature (Journal Medicinal Chemistry, 2004, vol. 47, p. 2887) as a starting material, the title compound (71 mg) was obtained in the same manners as those of Reference Example 54, (3) and (4).
¹H-NMR (600 MHz, CDCl₃) δ (ppm): 1.34 (d, J=6.42 Hz, 3H), 2.49-2.55 (m, 1H), 2.59-2.64 (m, 1H), 2.72-2.80 (m, 2H), 3.70 (q, J=6.57 Hz, 1H), 6.68 (dd, J=8.02, 2.52 Hz, 1H), 6.80 (d, J=7.34 Hz, 1H), 6.82-6.85 (m, 1H), 7.15 (t, J=7.79 Hz, 1H)

Reference Example 132

Synthesis of N-[1-[4-[[t-butyl(dimethyl)silyl]oxy]-3,5-dimethoxyphenyl]ethyl]ethane-1,2-diamine 3',5'-Dimethoxy-4'-hydroxyacetophenone (1.00 g) was dissolved in dimethylformamide (4 ml), the solution was added with imidazole (1.04 g) and t-butyldimethylchlorosilane (769 mg), and the mixture was stirred at room temperature for 10 hours. The reaction mixture was added with ethyl acetate and saturated aqueous ammonium chloride, the layers were separated, and the organic layer was successively washed 3 times with distilled water, dried over anhydrous magnesium sulfate and filtered. The filtrate was concentrated under reduced pressure to obtain a crude product. This product was dissolved in methanol (20 ml), the solution was added with ethylenediamine (289 mg), and the mixture was stirred at room temperature for 15 hours. The reaction mixture was added with a suspension of sodium borohydride (289 mg) in tetrahydrofuran (30 ml), and then added with methanol (6 ml), and the mixture was stirred at room temperature for 1.5 hours. The reaction mixture was concentrated under reduced pressure, and then added with chloroform and saturated aqueous ammonium chloride, the layers were separated, and then the organic layer was dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain the title compound (417 mg).
MS (ESI) m/z=355.3 [M+H]⁺
¹H-NMR (200 MHz, CDCl₃) δ (ppm): 0.12 (s, 6H), 1.01 (s, 9H), 1.34 (d, J=6.59 Hz, 3H), 2.40-2.66 (m, 2H), 2.71-2.81 (m, 2H), 3.60-3.73 (m, 1H), 3.79 (s, 6H), 6.50 (s, 2H)

Reference Example 133

Synthesis of 2-amino-3-(dimethylamino)propan-1-ol

Lithium aluminum hydride (555 mg) was suspended in tetrahydrofuran (30 ml), the suspension was added with 4-aza-DL-leucine dihydrochloride (2.0 g) under reflux by heating, and the mixture was stirred for 3 hours. The reaction mixture was added successively with distilled water, 15% aqueous sodium hydroxide and distilled water, and the mixture was stirred for 12 hours. The reaction mixture was filtered, and the resulting filtrate was concentrated under reduced pressure to obtain the title compound (140 mg).
MS (ESI) m/z=119.0 [M+H]⁺
¹H-NMR (600 MHz, DMSO-d6) δ (ppm): 2.08-2.16 (m, 1H), 2.11 (s, 6H), 3.20-3.39 (m, 4H)

Reference Example 134

Synthesis of 1-methylpyrrolidin-3-amine

By using 3-amino-1-N-t-butoxycarbonyl-pyrrolidine (2.0 g) as a starting material, the title compound (240 mg) was obtained in the same manner as that of Reference Example 133.
MS (ESI) m/z=101.0 [M+H]⁺

Reference Example 135

Synthesis of 2-(4-methylpiperazin-1-yl)ethanamine (1) 1-Methylpiperazine (873 µl) was dissolved in dimethylformamide (20 ml), the solution was added with N-(2-bromoethyl)phthalimide (1.0 g), and the mixture was stirred at room temperature for 52 hours. The reaction mixture was added with ethyl acetate and distilled water, the layers were separated, and the organic layer was successively washed twice with distilled water, then dried over anhydrous magnesium sulfate and filtered. The filtrate was concentrated under reduced pressure, and the resulting residue was purified by silica gel column chromatography (hexane:acetone:triethylamine=100:10:0.2) to obtain a phthalimide compound (580 mg).

(2) The compound obtained in (1) mentioned above (580 mg) was dissolved in ethanol (20 ml), the solution was added with hydrazine monohydrate (515 µl), and the mixture was stirred at room temperature for 24 hours. The reaction mixture was filtered, then the filtrate was concentrated under reduced pressure, and the resulting residue was purified by silica gel column chromatography (chloroform:methanol:28% aqueous ammonia=10:1:0.1) to obtain the title compound (90 mg).

MS (ESI) m/z=144.0 [M+H]$^+$ $^1$H-NMR (600 MHz, CDCl$_3$) δ (ppm): 2.27 (s, 3H), 2.36-2.61 (m, 10H), 2.78 (t, J=6.19 Hz, 2H)

Reference Example 136

Synthesis of benzyl 4-(2-aminoethyl)piperazine-1-carboxylate

N-(2-Aminoethyl)piperazine (4.93 g) was dissolved in tetrahydrofuran (40 ml), and the solution was added with triethylamine (10.6 ml). The mixture was added with a solution of benzyl chloroformate (4.9 ml) in tetrahydrofuran (40 ml) under ice cooling, and the mixture was stirred at room temperature for 1 hour. The reaction mixture was added with ethyl acetate and saturated aqueous sodium hydrogencarbonate, the layers were separated, and then the organic layer was dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain the title compound (400 mg).

MS (ESI) m/z=264.0 [M+H]$^+$ $^1$H-NMR (600 MHz, CDCl$_3$) δ (ppm): 2.37-2.45 (m, 6H), 2.79 (t, J=6.19 Hz, 2H), 3.49-3.53 (m, 4H), 5.12 (s, 2H), 7.28-7.37 (m, 5H)

Reference Example 137

Synthesis of (1R,2R)-2-[(5-aminopentyl)amino]-1-(4-nitrophenyl)propane-1,3-diol (1) (1S,2S)-(+)-2-Amino-1-(4-nitrophenyl)-1,3-propanediol (5.0 g) was dissolved in dimethylformamide (50 ml), the solution was added with N-(5-bromopentyl)phthalimide (7.8 g), and the mixture was stirred at 70° C. for 6 hours. The reaction mixture was added with ethyl acetate and distilled water, the layers were separated, and then the organic layer was washed twice with distilled water, then dried over anhydrous magnesium sulfate and filtered. The filtrate was concentrated under reduced pressure, and the resulting residue was purified by silica gel column chromatography (chloroform:methanol:28% aqueous ammonia=40:1:0.1) to obtain a phthalimide compound (3.0 g).

(2) The compound obtained in (1) mentioned above (1.0 g) was dissolved in ethanol (10 ml), the solution was added with hydrazine monohydrate (340 µl), and the mixture was heated for 4 hours with stirring. The reaction mixture was concentrated under reduced pressure, and then added with 1 N hydrochloric acid, and the mixture was stirred and then filtered. The filtrate was concentrated under reduced pressure, and the resulting residue was purified by silica gel column chromatography (NH-form, chloroform:methanol=9:1) to obtain the title compound (130 mg).

MS (ESI) m/z=298.2 [M+H]$^+$ $^1$H-NMR (200 MHz, CDCl$_3$) δ (ppm): 1.20-1.56 (m, 4H), 2.32-2.77 (m, 7H), 3.35 (dd, J=11.21, 3.74 Hz, 1H), 3.60-3.75 (m, 1H), 4.69 (d, J=7.03 Hz, 1H), 7.59 (d, J=8.79 Hz, 2H), 8.19 (d, J=8.79 Hz, 2H)

Reference Example 138

Synthesis of (1R,2R)-2-[(6-aminohexyl)amino]-1-(4-nitrophenyl)propane-1,3-diol (1) By using (1S,2S)-(+)-2-amino-1-(4-nitrophenyl)-1,3-propanediol (5.0 g) and N-(6-bromohexyl)phthalimide (8.16 g) as starting materials, a phthalimide compound (6.1 g) was obtained in the same manner as that of Reference Example 137, (1).

(2) By using the compound obtained in (1) mentioned above (3.0 g) as a starting material, the title compound (1.05 g) was obtained in the same manner as that of Reference Example 137, (2).

MS (ESI) m/z=312.2 [M+H]$^+$ $^1$H-NMR (200 MHz, CDCl$_3$) δ (ppm): 1.19-1.55 (m, 6H), 2.25-2.73 (m, 7H), 3.37 (dd, J=11.21, 3.74 Hz, 1H), 3.70 (dd, J=11.21, 3.74 Hz, 1H), 4.69 (d, J=6.59 Hz, 1H), 7.59 (d, J=8.35 Hz, 2H), 8.20 (d, J=8.79 Hz, 2H)

Reference Example 139

Synthesis of (1R,2R)-2-[(2-aminoethyl)amino]-1-(4-nitrophenyl)propane-1,3-diol (1)(1S,2S)-(+)-2-Amino-1-(4-nitrophenyl)-1,3-propanediol (3.0 g) was dissolved in dimethylformamide (30 ml), the solution was added with N-(2-bromoethyl)phthalimide (4.30 g) and triethylamine (2.85 g), and the mixture was stirred at 70° C. for 10 hours. The reaction mixture was added with ethyl acetate and distilled water, and the layers were separated, and then the organic layer was washed twice with distilled water, dried over anhydrous magnesium sulfate and filtered. The filtrate was concentrated under reduced pressure, and the resulting residue was purified by silica gel column chromatography (chloroform:methanol:28% aqueous ammonia=40:1:0.1) to obtain a phthalimide compound (1.94 g).

(2) The compound obtained in (1) mentioned above (1.94 g) was dissolved in ethanol (100 ml), the solution was added with hydrazine monohydrate (755 mg), and the mixture was refluxed by heating for 10 hours. The reaction mixture was concentrated under reduced pressure, and then added with 1 N hydrochloric acid, and the mixture was stirred, and then filtered. The filtrate was made basic with 10% aqueous sodium hydroxide, and extracted with chloroform, and the organic layer was dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain the title compound (1.35 g).

MS (ESI) m/z=256.2 [M+H]$^+$ $^1$H-NMR (200 MHz, CDCl$_3$) δ (ppm): 2.64-2.92 (m, 5H), 3.33-3.47 (m, 1H), 3.67 (dd, J=11.65, 3.74 Hz, 1H), 4.63 (d, J=7.03 Hz, 1H), 7.58 (d, J=8.35 Hz, 2H), 8.21 (d, J=9.23 Hz, 2H)

Reference Example 140

Synthesis of (1R,2R)-2-[(3-aminopropyl)amino]-1-(4-nitrophenyl)propane-1,3-diol

By using (1S,2S)-(+)-2-amino-1-(4-nitrophenyl)-1,3-propanediol (3.0 g) and N-(3-bromopropyl)phthalimide (4.53 g) as starting materials, the title compound (2.54 g) was obtained in the same manner as that of Reference Example 139.

MS (ESI) m/z=270.2 [M+H]$^+$ $^1$H-NMR (200 MHz, CDCl$_3$) δ (ppm): 1.55-1.74 (m, 2H), 2.48-2.90 (m, 5H), 3.39 (dd, J=11.43, 3.96 Hz, 1H), 3.61-3.83 (m, 1H), 4.69 (d, J=7.03 Hz, 1H), 7.59 (d, J=8.35 Hz, 2H), 8.20 (d, J=8.79 Hz, 2H)

Reference Example 141

Synthesis of (1R,2R)-2-[(4-aminobutyl)amino]-1-(4-nitrophenyl)propane-1,3-diol

By using (1S,2S)-(+)-2-amino-1-(4-nitrophenyl)-1,3-propanediol (3.0 g) and N-(4-bromobutyl)phthalimide (4.77 g) as starting materials, the title compound (2.76 g) was obtained in the same manner as that of Reference Example 139.

MS (ESI) m/z=284.2 [M+H]$^+$ $^1$H-NMR (200 MHz, CDCl$_3$) δ (ppm): 1.41-1.56 (m, 4H), 2.33-2.76 (m, 5H), 3.37 (dd, J=11.43, 3.96 Hz, 1H), 3.63-3.76 (m, 1H), 4.69 (d, J=7.03 Hz, 1H), 7.59 (d, J=8.35 Hz, 2H), 8.20 (d, J=8.79 Hz, 2H)

Reference Example 142

Synthesis of N-(2-[[t-butyl(dimethyl)silyl]oxy]ethyl)-N-ethylethane-1,2-diamine (1) 2-Ethylaminoethanol (5.0 g) was dissolved in dimethylformamide (100 ml), the solution was added with imidazole (22.9 g) and t-butyldimethylchlorosilane (16.9 g), and the mixture was stirred at room temperature for 16 hours. The reaction mixture was added with ethyl acetate and saturated aqueous ammonium chloride, the layers were separated, and then the organic layer was washed 3 times with distilled water, dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain a protected compound (786 mg).

(2) The compound obtained in (1) mentioned above (410 mg) and phthalimide acetaldehyde (419 mg) were dissolved in chloroform (5 ml), the solution was added with sodium triacetoxyborohydride (642 mg), and the mixture was stirred at room temperature for 1 hour. The reaction mixture was added with saturated aqueous sodium hydrogencarbonate and chloroform, the layers were separated, and then the organic layer was dried over anhydrous magnesium sulfate and filtered. The filtrate was concentrated under reduced pressure, and the resulting residue was purified by silica gel column chromatography (hexane:ethyl acetate=5:1) to obtain a phthalimide compound. This phthalimide compound was dissolved in ethanol, the solution was added with hydrazine monohydrate (0.29 ml), and the mixture was stirred at room temperature for 18 hours. The reaction mixture was concentrated under reduced pressure, and the deposited solid was separated by filtration and washed with ethanol. The filtrate was concentrated under reduced pressure, and the resulting residue was purified by silica gel column chromatography (chloroform:methanol:28% aqueous ammonia=10:1:0.1) to obtain the title compound (294 mg).

MS (ESI) m/z=247.2 [M+H]$^+$ $^1$H-NMR (200 MHz, CDCl$_3$) δ (ppm): 0.06 (s, 6H), 0.90 (s, 9H), 0.94-1.10 (m, 3H), 2.47-2.77 (m, 8H), 3.66 (t, J=6.59 Hz, 2H)

Reference Example 143

Synthesis of 2-amino-1-(4-nitrophenyl)ethanol (1) 4-Nitrostyrene (2.0 g) was dissolved in a mixed solvent of acetonitrile-distilled water (3:2, 50 ml), the solution was added with N-bromosuccinimide (2.63 g), and the mixture was stirred at room temperature for 3 hours. The reaction mixture was concentrated under reduced pressure, and then extracted with diethyl ether, and the organic layer was dried over anhydrous sodium sulfate and filtered. The filtrate was concentrated under reduced pressure, and the resulting residue was dissolved in methanol (130 ml). The solution was added with potassium carbonate (1.5 g), and the mixture was stirred at room temperature for 4 hours. The mixture was added with distilled water, the mixture was concentrated under reduced pressure, and extracted with ethyl acetate, and the organic layer was dried over anhydrous magnesium sulfate and filtered. The filtrate was concentrated under reduced pressure to obtain an epoxy compound (2.67 g).

(2) The compound obtained in (1) mentioned above (500 mg) was added with a 8 N solution of ammonia in methanol (5 ml), and the mixture was stirred at room temperature for 1 day. The reaction mixture was evaporated under reduced pressure, and the resulting residue was purified by silica gel column chromatography (chloroform:methanol:28% aqueous ammonia=20:1:0.1 to 10:1:0.1) to obtain the title compound (221 mg).

MS (ESI) m/z=183.0 [M+H]$^+$ $^1$H-NMR (200 MHz, DMSO-d6) δ (ppm): 2.52-2.80 (m, 2H), 4.51-4.68 (m, 1H), 5.46-5.68 (m, 1H), 7.60 (d, J=8.35 Hz, 2H), 8.19 (d, J=8.79 Hz, 2H)

Reference Example 144

Synthesis of 2-amino-3-(4-nitrophenyl)propan-1-ol

Lithium aluminum hydride (271 mg) was suspended in tetrahydrofuran, the suspension was added with 4-nitro-DL-phenylalanine (1.0 g) under ice cooling, and the mixture was stirred for 1 hour. The reaction mixture was added successively with distilled water, 15% aqueous sodium hydroxide and distilled water, and the mixture was stirred for 12 hours. The reaction mixture was filtered, and the resulting filtrate was concentrated under reduced pressure to obtain the title compound (516 mg).

MS (ESI) m/z=197.0 [M+H]$^+$ $^1$H-NMR (600 MHz, DMSO-d6) δ (ppm): 2.50-2.54 (m, 1H), 2.79-2.89 (m, 2H), 3.16-3.27 (m, 2H), 4.64-4.69 (m, 1H), 7.47 (d, J=8.71 Hz, 2H), 8.12 (d, J=8.71 Hz, 2H)

Reference Example 145

Synthesis of N-(2-[[t-butyl(dimethyl)silyl]oxy] ethyl)-N-[(1S)-1-(2-methoxyphenyl)ethyl]ethane-1, 2-diamine (1) (R)-1-(2-Methoxyphenyl)ethylamine (250 mg) and (2-bromoethoxy)-t-butyldimethylsilane (396 mg) were dissolved in dimethylformamide (5 ml), and the solution was stirred at 100° C. for 4 hours. The reaction mixture was added with saturated aqueous sodium hydrogencarbonate and ethyl acetate, the layers were separated, and the organic layer was dried over anhydrous sodium sulfate and filtered. The filtrate was concentrated under reduced pressure, and the resulting residue was purified by silica gel column chromatography (chloroform:methanol:28% aqueous ammonia=60:1:0.1) to obtain an adduct compound (407 mg).
(2) By using the compound obtained in (1) mentioned above (400 mg) as a starting material, the title compound (268 mg) was obtained in the same manners as those of Reference Example 54, (3) and (4).
$^1$H-NMR (200 MHz, CDCl$_3$) δ (ppm): 0.00 (s, 6H), 0.86 (s, 9H), 1.31 (d, J=7.03 Hz, 3H), 2.38-2.86 (m, 6H), 3.40-3.69 (m, 2H), 3.81 (s, 3H), 4.38 (q, J=6.89 Hz, 1H), 6.80-6.99 (m, 2H), 7.11-7.39 (m, 2H)

Reference Example 146

Synthesis of 4-[[2-[[t-butyl(dimethyl)silyl]oxy]ethyl] (ethyl)amino]butan-1-ol

The compound obtained in Reference Example 142, (1) (1.0 g) was dissolved in dimethylformamide (50 ml), the solution was added with potassium carbonate (3.3 g) and 4-bromo-1-butanol (1.13 g), and the mixture was stirred at 100° C. for 2 hours. The reaction mixture was added with ethyl acetate and distilled water, the layers were separated, and then the organic layer was washed twice with distilled water, dried over anhydrous magnesium sulfate and filtered. The filtrate was concentrated under reduced pressure, and the resulting residue was purified by silica gel column chromatography (chloroform:methanol:28% aqueous ammonia=30:1:0.1) to obtain the title compound (77 mg).
MS (ESI) m/z=276.3 [M+H]$^+$
$^1$H-NMR (200 MHz, CDCl$_3$) δ (ppm): 0.06 (s, 6H), 0.89 (s, 9H), 1.01 (t, J=7.03 Hz, 3H), 1.44-1.72 (m, 4H), 2.41-2.64 (m, 6H), 3.40-3.49 (m, 2H), 3.59-3.72 (m, 2H)

Reference Example 147

Synthesis of 1-amino-3-[(2-methoxyphenyl)amino]propan-2-ol (1) N-(2,3-Epoxypropyl)phthalimide (800 mg) and o-anisidine (485 mg) were dissolved in ethanol (10 ml), and the solution was stirred for 6 hours under reflux by heating. The reaction mixture was concentrated under reduced pressure, and the resulting residue was purified by silica gel column chromatography (hexane:ethyl acetate=1:1 to 1:3) to obtain an adduct compound (831 mg).
(2) By using the compound obtained in (1) mentioned above (816 mg) as a starting material, the title compound (170 mg) was obtained in the same manner as that of Reference Example 54, (4).
MS (ESI) m/z=197.1 [M+H]$^+$
$^1$H-NMR (200 MHz, CDCl$_3$) δ (ppm): 2.96-3.44 (m, 4H), 3.84 (s, 3H), 4.11-4.30 (m, 1H), 4.36-4.56 (m, 1H), 6.56-6.95 (m, 4H)

Reference Example 148

Synthesis of 1-amino-3-[ethyl[(1S)-1-(2-methoxyphenyl)ethyl]amino]propan-2-ol (1) By using N-(2,3-epoxypropyl)phthalimide (470 mg) and (1S)-1-(2-methoxyphenyl)ethanamine (350 mg) obtained by the method described in the patent document (Japanese Patent Unexamined Publication No. 54-154724) as starting materials, an adduct compound (495 mg) was obtained in the same manner as that of Reference Example 147, (1).
(2) By using the compound obtained in (1) mentioned above (485 mg) and acetaldehyde (334 mg) as starting materials, an N-ethyl compound (452 mg) was obtained in the same manner as that of Reference Example 54, (3).
(3) By using the compound obtained in (2) mentioned above (441 mg) as a starting material, the title compound (296 mg) was obtained in the same manner as that of Reference Example 54, (4).
MS (ESI) m/z=253.2 [M+H]$^+$
$^1$H-NMR (200 MHz, CDCl$_3$) δ (ppm): 0.86-1.07 (m, 3H), 1.23-1.38 (m, 3H), 2.33-2.80 (m, 6H), 3.45-3.72 (m, 1H), 3.79-3.90 (m, 3H), 4.33-4.50 (m, 1H), 6.82-7.39 (m, 4H)

Reference Example 149

Synthesis of N-(5-aminopentyl)-2,2-dichloroacetamide (1) 5-Amino-1-pentanol (1.0 g) was dissolved in tetrahydrofuran (10 ml), the solution was added with a solution of dichloroacetyl chloride (1.0 ml) in tetrahydrofuran (10 ml) under ice cooling, and the mixture was stirred at room temperature for 1 hour. The reaction mixture was filtered, the filtrate was concentrated under reduced pressure, and the resulting residue was purified by silica gel column chromatography (chloroform:methanol:28% aqueous ammonia=40:1:0.1) to obtain a dichloroacetyl compound (446 mg).
(2) The compound obtained in (1) mentioned above (445 mg) was dissolved in chloroform (10 ml), the solution was added with pyridine (10 ml) and a solution of p-toluenesulfonyl chloride (5.94 g) in chloroform (20 ml) under ice cooling, and the mixture was stirred at room temperature for 12 hours. The mixture was added with saturated brine and chloroform, the layers were separated, and then the organic layer was dried over anhydrous magnesium sulfate and filtered. The filtrate was concentrated under reduced pressure, and the resulting residue was purified by silica gel column chromatography (hexane:ethyl acetate=6:1) to obtain a p-toluenesulfonyl compound (204 mg).
(3) The compound obtained in (2) mentioned above (204 mg) was dissolved in dimethylformamide (2 ml), the solution was added with potassium phthalimide (154 mg), and the mixture was stirred at 70° C. for 2 hours and at 100° C. for 2 hours. The reaction mixture was added with ethyl acetate and saturated aqueous sodium hydrogencarbonate, the layers were separated, and then dried over anhydrous magnesium sulfate and filtered. The filtrate was concentrated under reduced pressure, and the resulting residue was purified by silica gel column chromatography (hexane:ethyl acetate=10:1) to obtain a phthalimide compound (160 mg).

(4) The compound obtained in (3) mentioned above (160 mg) was dissolved in ethanol (3 ml), the solution was added with hydrazine monohydrate (67.8 μl), and the mixture was stirred at 80° C. for 4 hours. The reaction mixture was filtered, then the filtrate was concentrated under reduced pressure, and the resulting residue was purified by silica gel column chromatography (chloroform:methanol:28% aqueous ammonia=10:1:0.1) to obtain the title compound (47 mg).
MS (ESI) m/z=213.0 [M+H]$^+$
$^1$H-NMR (200 MHz, CDCl$_3$) δ (ppm): 1.29-1.87 (m, 6H), 2.71 (t, J=6.59 Hz, 2H), 3.25-3.42 (m, 2H), 5.95 (s, 1H), 6.85-7.10 (m, 1H)

Reference Example 150

Synthesis of N-(3-[[t-butyl(dimethyl)silyl]oxy]propyl)-N-ethylethane-1,2-diamine (1) N-(2-Bromoethyl)phthalimide (9 g) was dissolved in dimethylformamide (25 ml), the solution was added with ethylbenzylamine (5.27 g) and potassium carbonate (5.39 g), and the mixture was stirred at 100° C. for 6 hours. The reaction mixture was added with 2 N hydrochloric acid and chloroform, the layers were separated, and the organic layer was dried over anhydrous magnesium sulfate and filtered. The filtrate was added with a mixed solvent of ethyl acetate-hexane (1:1), and the deposited crystals were dried under reduced pressure to obtain a phthalimide compound (8.43 g).

(2) By using the compound obtained in (1) mentioned above (485 mg) as a starting material, a debenzylated compound (1.50 g) was obtained in the same manner as that of Reference Example 7, (3).

(3) The compound obtained in (2) mentioned above (500 mg) was dissolved in dimethylformamide (10 ml), the solution was added with (3-bromopropoxy)-t-butyldimethylsilane (796 μl) and potassium carbonate (475 mg), and the mixture was stirred at 100° C. for 2 hours. The reaction mixture was added with saturated aqueous ammonium chloride and ethyl acetate, the layers were separated, and the organic layer was washed successively with saturated aqueous ammonium chloride and saturated brine, then dried over anhydrous magnesium sulfate and filtered. The filtrate was concentrated under reduced pressure, and the resulting residue was purified by silica gel column chromatography (hexane:acetone=10:1) to obtain an adduct compound (387 mg).

(4) By using the compound obtained in (3) mentioned above (387 mg) as a starting material, the title compound (191 mg) was obtained in the same manner as that of Reference Example 54, (4).
MS (ESI) m/z=261.3 [M+H]$^+$
$^1$H-NMR (200 MHz, CDCl$_3$) δ (ppm): 0.01-0.10 (m, 6H), 0.89 (s, 9H), 0.95-1.11 (m, 3H), 1.52-1.75 (m, 3H), 2.40-2.65 (m, 5H), 2.66-2.77 (m, 2H), 3.54-3.73 (m, 2H)

Reference Example 151

Synthesis of 6-(dimethylamino)hexanal

By using 6-dimethylamino-1-hexanol (100 mg) as a starting material, the title compound (37.8 mg) was obtained in the same manner as that of Reference Example 53, (2).
$^1$H-NMR (200 MHz, CDCl$_3$) δ (ppm): 1.28-1.79 (m, 6H), 2.25-2.61 (m, 4H), 2.36 (s, 6H), 9.72-9.80 (m, 1H)

Reference Example 152

Synthesis of t-butyl(dimethyl)[[(1R)-1-methyl-3-oxiran-2-ylpropyl]oxy]silane (1)(R)-(−)-5-Hexen-2-ol (1 g) was dissolved in dimethylformamide (10 ml), the solution was added with imidazole (2.04 g) and t-butyldimethylchlorosilane (2.26 g) under ice cooling, and the mixture was stirred at room temperature for 18 hours. The reaction mixture was added with ethyl acetate and saturated aqueous ammonium chloride, the layers were separated, and the organic layer was dried over anhydrous magnesium sulfate and filtered. The filtrate was concentrated under reduced pressure, and the resulting residue was purified by silica gel column chromatography (hexane:ethyl acetate=40:1) to obtain a protected compound (1.7 g).

(2) By using the compound obtained in (1) mentioned above (1.7 g) as a starting material, the title compound (1.58 g) was obtained in the same manner as that of Reference Example 26, (2).
MS (ESI) m/z=253.1 [M+Na]$^+$
$^1$H-NMR (600 MHz, CDCl$_3$) δ (ppm): 0.02-0.05 (m, 6H), 0.85-0.88 (m, 9H), 1.10-1.15 (m, 3H), 1.44-1.68 (m, 4H), 2.44-2.47 (m, 1H), 2.72-2.75 (m, 1H), 2.88-2.93 (m, 1H), 3.75-3.87 (m, 1H)

Reference Example 153

Synthesis of t-butyl(dimethyl)[[(1S)-1-methyl-3-oxiran-2-ylpropyl]oxy]silane

By using (S)-(+)-5-hexen-2-ol (1 g) as a starting material, the title compound (1.48 g) was obtained in the same manners as those of Reference Example 152, (1) and Reference Example 26, (2).
MS (ESI) m/z=253.1 [M+Na]$^+$
$^1$H-NMR (600 MHz, CDCl$_3$) δ (ppm): 0.01-0.05 (m, 6H), 0.85-0.89 (m, 9H), 1.10-1.14 (m, 3H), 1.44-1.68 (m, 4H), 2.43-2.47 (m, 1H), 2.72-2.75 (m, 1H), 2.88-2.93 (m, 1H), 3.77-3.87 (m, 1H)

Reference Example 154

Synthesis of 3-(oxiran-2-ylmethyl)-1,3-oxazolidin-2-one (1) 2-Oxazolidinone (3 g) was dissolved in acetone (130 ml), the solution was added with allyl bromide (5.8 ml) and cesium carbonate (33.7 g), and the mixture was stirred at 60° C. for 24 hours. The reaction mixture was filtered, the filtrate was concentrated under reduced pressure, and the resulting residue was purified by silica gel column chromatography (hexane:ethyl acetate=1:1) to obtain an adduct compound (4.18 g).

(2) By using the compound obtained in (1) mentioned above (4.10 g) as a starting material, the title compound (511 mg) was obtained in the same manner as that of Reference Example 26, (2).
MS (ESI) m/z=143.8 [M+H]$^+$
$^1$H-NMR (200 MHz, CDCl$_3$) δ (ppm): 2.54-2.65 (m, 1H), 2.79-2.86 (m, 1H), 2.97-3.19 (m, 2H), 3.55-3.93 (m, 3H), 4.29-4.44 (m, 2H)

Reference Example 155

Synthesis of
3-(2-oxiran-2-ylethyl)-1,3-oxazolidin-2-one

By using 2-oxazolidinone (2.20 g) and 4-bromo-1-butene (4.42 g) as starting materials, the title compound (389 mg) was obtained in the same manners as those of Reference Example 154, (1) and Reference Example 26, (2).

MS (ESI) m/z=157.9 [M+H]$^+$
$^1$H-NMR (200 MHz, CDCl$_3$) δ (ppm): 1.56-1.82 (m, 1H), 1.85-2.09 (m, 1H), 2.47-2.61 (m, 1H), 2.73-2.86 (m, 1H), 2.91-3.06 (m, 1H), 3.38-3.54 (m, 2H), 3.55-3.74 (m, 2H), 4.25-4.47 (m, 2H)

Reference Example 156

Synthesis of
3-(3-oxiran-2-ylpropyl)-1,3-oxazolidin-2-one

By using 2-oxazolidinone (3 g) and 5-bromo-1-pentene (5.3 ml) as starting materials, the title compound (1.22 g) was obtained in the same manners as those of Reference Example 154, (1) and Reference Example 26, (2).

MS (ESI) m/z=171.8 [M+H]$^+$
$^1$H-NMR (200 MHz, CDCl$_3$) δ (ppm): 1.37-1.59 (m, 1H), 1.60-1.84 (m, 3H), 2.50 (dd, J=4.83, 2.64 Hz, 1H), 2.78 (d, J=4.83 Hz, 1H), 2.89-3.02 (m, 1H), 3.27-3.38 (m, 2H), 3.51-3.64 (m, 2H), 4.24-4.41 (m, 2H)

Reference Example 157

Synthesis of benzyl 3-oxiran-2-ylpropionate (1) 4-Pentenoic acid (15 g) was dissolved in toluene (100 ml), the solution was added with p-toluenesulfonic acid monohydrate (1.29 g) and benzyl alcohol (78 ml) under ice cooling, and the mixture was stirred under reflux by heating for 3.5 hours. The reaction mixture was left to cool, and then concentrated under reduced pressure, and the resulting residue was purified by silica gel column chromatography (hexane:ethyl acetate=30:1 to 20:1) to obtain an ester compound (37.5 g).

(2) By using the compound obtained in (1) mentioned above (6.0 g) as a starting material, the title compound (6.3 g) was obtained in the same manner as that of Reference Example 26, (2).

MS (ESI) m/z=229.0 [M+Na]$^+$
$^1$H-NMR (200 MHz, CDCl$_3$) δ (ppm): 1.67-2.11 (m, 2H), 2.41-2.61 (m, 3H), 2.68-2.79 (m, 1H), 2.89-3.06 (m, 1H), 5.13 (s, 2H), 7.28-7.43 (m, 5H)

Reference Example 158

Synthesis of 5-oxiran-2-ylpentanenitrile

By using 6-heptenenitrile (2.5 g) as a starting material, the title compound (2.91 g) was obtained in the same manner as that of Reference Example 26, (2).

MS (ESI) m/z=148.0 [M+Na]$^+$
$^1$H-NMR (200 MHz, CDCl$_3$) δ (ppm): 1.42-1.86 (m, 6H), 2.32-2.44 (m, 2H), 2.48 (dd, J=5.05, 2.86 Hz, 1H), 2.77 (dd, J=5.27, 3.96 Hz, 1H), 2.85-3.01 (m, 1H)

Reference Example 159

Synthesis of 2-[3-(benzyloxy)butyl]oxirane (1) 5-Hexen-2-ol (2.9 g) was dissolved in dimethylformamide (55 ml), the solution was added portionwise with sodium hydride (1.06 g) under ice cooling, and the mixture was stirred at room temperature for 1 hour. The reaction mixture was added with benzyl chloride (4.0 m), and the mixture was stirred at room temperature for 5 hours. The reaction mixture was added with saturated aqueous ammonium chloride, and the mixture was extracted with diethyl ether. The organic layer was washed with saturated brine, then dried over anhydrous magnesium sulfate and filtered. The filtrate was concentrated under reduced pressure, and the resulting residue was purified by silica gel column chromatography (hexane:ethyl acetate=20:1 to 10:1) to obtain a benzyl ether compound (5.16 g).

(2) By using the compound obtained in (1) mentioned above (5.09 g) as a starting material, the title compound (3.21 g) was obtained in the same manner as that of Reference Example 26, (2).

MS (ESI) m/z=229.1 [M+Na]$^+$
$^1$H-NMR (200 MHz, CDCl$_3$) δ (ppm): 1.17-1.25 (m, 3H), 1.46-1.82 (m, 4H), 2.37-2.51 (m, 1H), 2.68-2.78 (m, 1H), 2.84-2.97 (m, 1H), 3.47-3.65 (m, 1H), 4.37-4.65 (m, 2H), 7.16-7.47 (m, 5H)

Reference Example 160

Synthesis of
benzyl[3-[(2R)-oxiran-2-yl]propyl]carbamate (1) 5-Bromo-1-pentene (25 g) was dissolved in dimethylformamide (120 ml), the solution was added with potassium phthalimide (34.2 g) under ice cooling, and the mixture was stirred at 60° C. for 2 hours. The deposited solid was separated by filtration, and the filtrate was added with diethyl ether. Then, the mixture was washed successively with distilled water and saturated brine, and then the organic layer was dried over anhydrous magnesium sulfate and filtered. The filtrate was concentrated under reduced pressure, the resulting residue was dissolved in ethanol (200 ml), the solution was added with hydrazine monohydrate (24.4 ml) under ice cooling, and the mixture was stirred at 60° C. for 20 minutes. The reaction mixture was added with diluted hydrochloric acid under ice cooling and thereby made acidic, and the deposited solid was separated by filtration. The filtrate was concentrated under reduced pressure, the resulting residue was added with potassium hydroxide under ice cooling, thereby made basic, and extracted with chloroform, and the organic layer was filtered. The filtrate was added with saturated aqueous sodium hydrogencarbonate (200 ml), the mixture was added with benzyl chloroformate (31.5 g) on an ice bath, and the mixture was stirred at room temperature for 1 hour. The reaction mixture was extracted with chloroform, and the organic layer was dried over anhydrous magnesium sulfate and filtered. The filtrate was concentrated under reduced pressure, and the resulting residue was purified by silica gel column chromatography (hexane:ethyl acetate=1:1) to obtain a carbamate compound (9.13 g).

(2) By using the compound obtained in (1) mentioned above (9.10 g) as a starting material, a diol compound (9.39 g) was obtained in the same manner as that of Reference Example 2, (3).

(3) By using the compound obtained in (2) mentioned above (9.39 g) as a starting material, the title compound (9.38 g) was obtained in the same manner as that of Reference Example 1.

MS (ESI) m/z=258.1 [M+Na]$^+$

¹H-NMR (200 MHz, CDCl₃) δ (ppm): 1.39-1.82 (m, 3H), 2.35-2.56 (m, 2H), 2.65-2.80 (m, 1H), 2.84-2.98 (m, 1H), 3.14-3.34 (m, 2H), 5.01-5.17 (m, 2H), 7.14-7.47 (m, 5H)

Reference Example 161

Synthesis of 1-(2-oxiran-2-ylethyl)pyridin-2(1H)-one (1) 2-Hydroxypyridine (5 g) was dissolved in 1,4-dioxane (70 ml), the solution was added with 4-bromo-1-butene (5.87 ml) and cesium carbonate (17.1 g), and the mixture was stirred at room temperature for 48 hours. The reaction mixture was filtered, the filtrate was concentrated under reduced pressure, and the resulting residue was purified by silica gel column chromatography (hexane:ethyl acetate=1:1) to obtain an adduct compound (5.18 g).
(2) By using the compound obtained in (1) mentioned above (3.0 g) as a starting material, the title compound (479 mg) was obtained in the same manner as that of Reference Example 26, (2).
MS (ESI) m/z=188.0 [M+Na]⁺
¹H-NMR (200 MHz, CDCl₃) δ (ppm): 1.66-1.85 (m, 1H), 2.15-2.36 (m, 1H), 2.49 (dd, J=4.83, 2.64 Hz, 1H), 2.79 (dd, J=4.83, 3.96 Hz, 1H), 2.89-3.04 (m, 1H), 4.05-4.16 (m, 2H), 6.11-6.22 (m, 1H), 6.51-6.62 (m, 1H), 7.25-7.40 (m, 2H)

Reference Example 162

Synthesis of 1-(3-oxiran-2-ylpropyl)pyridin-2(1H)-one (1) By using 5-bromo-1-pentene (5.07 ml) as a starting material, an adduct compound (3.79 g) was obtained in the same manner as that of Reference Example 161, (1).
(2) By using the compound obtained in (1) mentioned above (3.79 g) as a starting material, the title compound (4.06 g) was obtained in the same manner as that of Reference Example 26, (2).
MS (ESI) m/z=202.0 [M+Na]⁺
¹H-NMR (200 MHz, CDCl₃) δ (ppm): 1.37-1.58 (m, 1H), 1.64-2.04 (m, 3H), 2.50 (dd, J=5.27, 2.64 Hz, 1H), 2.76 (dd, J=4.83, 3.96 Hz, 1H), 2.91-3.02 (m, 1H), 3.86-4.13 (m, 2H), 6.10-6.20 (m, 1H), 6.52-6.61 (m, 1H), 7.29-7.37 (m, 2H)

Reference Example 163

Synthesis of N-[1-(4-benzyloxy-3-methoxyphenyl)-ethyl]-N-ethylethane-1,2-diamine (1) 1-(4-Hydroxy-3-methoxyphenyl)ethanone (1.66 g) was dissolved in acetone (100 ml), the solution was successively added with potassium carbonate (1.66 g) and benzyl bromide (1.4 ml), and the mixture was stirred at room temperature for 21 hours. The reaction mixture was concentrated under reduced pressure, the resulting the residue was added with ethyl acetate and distilled water, the layers were separated, and the organic layer was dried over anhydrous magnesium sulfate, and then filtered. The filtrate was concentrated under reduced pressure, and the resulting residue was purified by silica gel column chromatography (hexane:ethyl acetate=2:1) to obtain a benzyl ether compound (1.74 g).
(2) By using the compound obtained in (1) mentioned above (1.74 g) as a starting material, the title compound (320 mg) was obtained in the same manners as those of Reference Example 64, (1), Reference Example 63, (1) and Reference Example 54, (4).
MS (ESI) m/z=329 [M+H]⁺

Reference Example 164

Synthesis of N-[1-(2,6-bisbenzyloxyphenyl)-ethyl]-N-ethylethane-1,2-diamine

By using 1-(2,6-dihydroxyphenyl)ethanone (1.53 g) as a starting material, the title compound (325 mg) was obtained in the same manners as those of Reference Example 163, (1), Reference Example 64, (1), Reference Example 63, (1) and Reference Example 54, (4).
MS (ESI) m/z=405 [M+H]⁺
¹H-NMR (400 MHz, CDCl₃) δ (ppm): 0.89 (t, J=7.30 Hz, 3H), 1.46 (d, J=7.07 Hz, 3H), 2.45-2.60 (m, 4H), 2.63-2.73 (m, 2H), 4.67 (q, J=7.06 Hz, 1H), 5.07 (s, 4H), 6.62 (d, J=8.28 Hz, 2H), 7.13 (t, J=8.28 Hz, 1H), 7.31-7.47 (m, 10H)

Reference Example 165

Synthesis of N-[1-(4-ethoxy-3-piperidin-1-ylmethylphenyl)-ethyl]-N-ethylethane-1,2-diamine By using 1-[4-ethoxy-3-(piperidin-1-ylmethyl)phenyl]ethanone (520 mg) as a starting material, the title compound (44.3 mg) was obtained in the same manners as those of Reference Example 64, (1), Reference Example 63, (1) and Reference Example 54, (4).
MS (FAB) m/z=334 [M+H]⁺
¹H-NMR (400 MHz, CDCl₃) δ (ppm): 1.02 (t, J=7.06 Hz, 3H), 1.32 (d, J=6.58 Hz, 3H), 1.40 (t, J=7.06 Hz, 3H), 1.54-1.65 (m, 6H), 2.35-2.67 (m, 10H), 3.65 (s, 2H), 3.84 (q, J=6.82 Hz, 1H), 4.01 (q, J=6.82 Hz, 2H), 6.78 (d, J=8.28 Hz, 1H), 7.15 (dd, J=2.19, 8.52 Hz, 1H), 7.34 (d, J=1.95 Hz, 1H)

Reference Example 166

Synthesis of 2-[5-[1-[(2-aminoethyl)ethylamino]ethyl]-2-methoxyphenyl]acetonitrile By using 2-(5-acetyl-2-methoxyphenyl)acetonitrile (420 mg) as a starting material, the title compound (137 mg) was obtained in the same manners as those of Reference Example 64, (1), Reference Example 63, (1) and Reference Example 54, (4).
MS (ESI) m/z=262 [M+H]⁺
¹H-NMR (400 MHz, CDCl₃) δ (ppm): 1.02 (t, J=7.07 Hz, 3H), 1.32 (d, J=6.82 Hz, 3H), 2.37-2.69 (m, 6H), 3.68 (s, 2H), 3.83 (q, J=6.82 Hz, 1H), 3.85 (s, 3H), 6.83 (d, J=5.12 Hz, 1H), 7.28 (dd, J=2.19, 8.52 Hz, 1H), 7.34 (d, J=1.95 Hz, 1H)

Reference Example 167

Synthesis of N-ethyl-N-[1-(5-methylisoxazol-4-yl)ethyl]ethane-1,2-diamine

By using 1-(5-methylisoxazol-4-yl)ethanone (1.0 g) as a starting material, the title compound (412 mg) was obtained in the same manners as those of Reference Example 64, (1), Reference Example 63, (1) and Reference Example 54, (4).
MS (ESI) m/z=198 [M+H]⁺
¹H-NMR (300 MHz, CDCl₃) δ (ppm): 1.03 (t, J=7.14 Hz, 3H), 1.31 (d, J=6.87 Hz, 3H), 2.28-2.60 (m, 4H), 2.42 (s, 3H), 2.62-2.75 (m, 2H), 2.85 (q, J=6.86 Hz, 1H), 8.12 (s, 1H)

Reference Example 168

Synthesis of N-[1-(4-ethoxy-3-morpholin-4-ylmethylphenyl)ethyl]-N-ethylethane-1,2-diamine By using 1-[4-ethoxy-3-(morpholinomethyl)phenyl]ethanone (527 mg) as a starting material, the title compound (177 mg) was obtained in the same manners as those of Reference Example 64, (1), Reference Example 63, (1) and Reference Example 54, (4).

MS (FAB) m/z=336 [M+H]$^+$
$^1$H-NMR (300 MHz, CDCl$_3$) δ (ppm): 1.01 (t, J=7.14 Hz, 3H), 1.32 (d, J=6.59 Hz, 3H), 1.41 (t, J=7.14 Hz, 3H), 2.32-2.68 (m, 10H), 3.57 (s, 2H), 3.72 (t, J=4.67 Hz, 4H), 3.83 (q, J=6.86 Hz, 1H), 4.02 (q, J=6.86 Hz, 2H), 6.79 (d, J=8.24 Hz, 1H), 7.16 (dd, J=2.20, 8.24 Hz, 1H), 7.32 (d, J=1.92 Hz, 1H)

Reference Example 169

Synthesis of [5-[[1-[(2-aminoethyl)ethylamino]ethyl]thiophen-2-yl]acetonitrile

By using 2-(5-acetylthiophen-2-yl)acetonitrile (826 mg) as a starting material, the title compound (291 mg) was obtained in the same manners as those of Reference Example 64, (1), Reference Example 63, (1) and Reference Example 54, (4).

MS (FAB) m/z=238 [M+H]$^+$
$^1$H-NMR (300 MHz, CDCl$_3$) δ (ppm): 1.06 (t, J=7.42 Hz, 3H), 1.36 (d, J=6.87 Hz, 3H), 2.37-2.60 (m, 4H), 2.64-2.82 (m, 2H), 3.85 (s, 2H), 4.08 (q, J=6.32 Hz, 1H), 6.70 (dd, J=1.37, 3.57 Hz, 1H), 6.86-6.89 (m, 1H)

Reference Example 170

Synthesis of N-ethyl-N-[1-(3-methylpyrazin-2-yl)ethyl]ethane-1,2-diamine

By using 1-(3-methylpyrazin-2-yl)ethanone (0.5 g) as a starting material, the title compound (245 mg) was obtained in the same manners as those of Reference Example 64, (1), Reference Example 63, (1) and Reference Example 54, (4).

MS (ESI) m/z=209 [M+H]$^+$
$^1$H-NMR (300 MHz, CDCl$_3$) δ (ppm): 1.04 (t, J=7.14 Hz, 3H), 1.38 (d, J=6.59 Hz, 3H), 2.39-2.71 (m, 6H), 2.71 (s, 3H), 4.28 (q, J=6.59 Hz, 1H), 8.34 (dd, J=2.20, 4.89 Hz, 2H)

Reference Example 171

Synthesis of N-ethyl-N-(1-pyridin-4-ylethyl)ethane-1,2-diamine

By using 1-(pyridin-4-yl)ethanone (2.0 g) as a starting material, the title compound (439 mg) was obtained in the same manners as those of Reference Example 64, (1), Reference Example 63, (1) and Reference Example 54, (4).

MS (FAB) m/z=194 [M+H]$^+$
$^1$H-NMR (300 MHz, CDCl$_3$) δ (ppm): 1.03 (t, J=7.14 Hz, 3H), 1.34 (d, J=6.87 Hz, 3H), 2.37-2.61 (m, 4H), 2.65-2.74 (m, 2H), 3.86 (q, J=6.87 Hz, 1H), 7.30 (d, J=5.77 Hz, 2H), 8.53 (dd, J=3.02, 4.67 Hz, 2H)

Reference Example 172

Synthesis of N-ethyl-N-[1-(1-ethyl-3-methyl-1H-pyrazol-4-yl)ethyl]ethane-1,2-diamine By using 1-(1-ethyl-3-methyl-1H-pyrazol-4-yl)ethanone (0.5 g) as a starting material, the title compound (205 mg) was obtained in the same manners as those of Reference Example 64, (1), Reference Example 63, (1) and Reference Example 54, (4).

MS (FAB) m/z=225 [M+H]$^+$
$^1$H-NMR (300 MHz, CDCl$_3$) δ (ppm): 1.03 (t, J=7.15 Hz, 3H), 1.25 (d, J=6.86 Hz, 3H), 1.45 (t, J=7.14 Hz, 3H), 2.27 (s, 3H), 2.35-2.51 (m, 4H), 2.59-2.72 (m, 2H), 3.89 (q, J=6.87 Hz, 1H), 4.07 (q, J=7.14 Hz, 2H), 7.17 (s, 1H)

Reference Example 173

Synthesis of N-[1-(2,4-dimethyloxazol-5-yl)ethyl]-N-ethylethane-1,2-diamine

By using 1-(2,4-dimethyloxazol-5-yl)ethanone (500 mg) as a starting material, the title compound (260 mg) was obtained in the same manners as those of Reference Example 64, (1), Reference Example 63, (1) and Reference Example 54, (4).

MS (ESI) m/z=212 [M+H]$^+$
$^1$H-NMR (300 MHz, CDCl$_3$) δ (ppm): 1.04 (t, J=7.1 Hz, 3H), 1.37 (d, J=6.9 Hz, 3H), 2.11 (s, 3H), 2.27-2.41 (m, 5H), 2.59-2.74 (m, 4H), 3.93 (q, J=6.9 Hz, 1H)

Reference Example 174

Synthesis of N-[1-[3-(1H-tetrazol-1-yl)phenyl]ethyl]-N-ethylethane-1,2-diamine

By using 1-[3-(1H-tetrazol-1-yl)phenyl]ethanone (565 mg) as a starting material, the title compound (190 mg) was obtained in the same manners as those of Reference Example 64, (1), Reference Example 63, (1) and Reference Example 54, (4).

MS (FAB) m/z=261 [M+H]$^+$
$^1$H-NMR (300 MHz, CDCl$_3$) δ (ppm): 1.05 (t, J=7.0 Hz, 3H), 1.38 (d, J=6.6 Hz, 3H), 2.46-2.75 (m, 6H), 3.97 (q, J=6.6 Hz, 1H), 7.49-7.58 (m, 3H), 7.79 (s, 1H), 9.05 (s, 1H)

Reference Example 175

Synthesis of N-ethyl-N-[1-(1,3,5-trimethyl-1H-pyrazol-4-yl)ethyl]ethane-1,2-diamine By using 1-(1,3,5-trimethyl-1H-pyrazol-4-yl)ethanone (500 mg) as a starting material, the title compound (228 mg) was obtained in the same manners as those of Reference Example 64, (1), Reference Example 63, (1) and Reference Example 54, (4).

MS (ESI) m/z=225 [M+H]$^+$
$^1$H-NMR (300 MHz, CDCl$_3$) δ (ppm): 0.95 (t, J=7.0 Hz, 3H), 1.30 (d, J=6.9 Hz, 3H), 2.23 (m, 6H), 2.46-2.71 (m, 6H), 3.66-3.71 (m, 4H)

Reference Example 176

Synthesis of N-ethyl-N-[1-(4-morpholinophenyl)ethyl]ethane-1,2-diamine

By using 1-(4-morpholinophenyl)ethanone (1.0 g) as a starting material, the title compound (178 mg) was obtained in the same manners as those of Reference Example 64, (1), Reference Example 63, (1) and Reference Example 54, (4).

MS (FAB) m/z=278 [M+H]$^+$ $^1$H-NMR (300 MHz, CDCl$_3$) δ (ppm): 1.01 (t, J=7.1 Hz, 3H), 1.30-1.38 (m, 3H), 2.34-2.67 (m, 6H), 3.13-3.17 (m, 4H), 3.79-3.88 (m, 5H), 6.86 (d, J=8.6 Hz, 2H), 7.25 (d, J=8.6 Hz, 2H)

Reference Example 177

Synthesis of N-ethyl-N-[1-[4-(morpholinosulfonyl) phenyl]ethyl]ethane-1,2-diamine By using 1-[4-(morpholinosulfonyl)phenyl]ethanone (539 mg) as a starting material, the title compound (187 mg) was obtained in the same manners as those of Reference Example 64, (1), Reference Example 63, (1) and Reference Example 54, (4).
MS (ESI) m/z=342 [M+H]$^+$
$^1$H-NMR (300 MHz, CDCl$_3$) δ (ppm): 1.03 (t, J=7.1 Hz, 3H), 1.36 (d, J=6.6 Hz, 3H), 2.41-2.62 (m, 4H), 2.68 (t, J=6.0 Hz, 2H), 2.99-3.02 (m, 4H), 3.74-3.77 (m, 4H), 3.93 (q, J=6.6 Hz, 1H), 7.55 (d, J=8.2 Hz, 2H), 7.69 (d, J=8.2 Hz, 2H)

Reference Example 178

Synthesis of N-ethyl-N-[1-(1-ethyl-5-methyl-1H-pyrazol-4-yl)ethyl]ethane-1,2-diamine By using 1-(1-ethyl-5-methyl-1H-pyrazol-4-yl)ethanone (500 mg) as a starting material, the title compound (73 mg) was obtained in the same manners as those of Reference Example 64, (1), Reference Example 63, (1) and Reference Example 54, (4).
MS (FAB) m/z=225 [M+H]$^+$
$^1$H-NMR (300 MHz, CDCl$_3$) δ (ppm): 1.03 (t, J=7.1 Hz, 3H), 1.28 (d, J=6.9 Hz, 3H), 1.39 (t, J=7.2 Hz, 3H), 2.26 (s, 3H), 2.36-2.52 (m, 4H), 2.63 (t, J=6.3 Hz, 2H), 3.87 (q, J=6.9 Hz, 1H), 4.09 (q, J=7.2 Hz, 2H), 7.27 (s, 1H)

Reference Example 179

Synthesis of N-ethyl-N-[1-[4-methoxy-3-[(1-methyl-1H-tetrazol-5-ylthio)methyl]phenyl]ethyl]ethane-1,2-diamine By using 1-[4-methoxy-3-[(1-methyl-1H-tetrazol-5-ylthio)methyl]phenyl]ethanone (500 mg) as a starting material, the title compound (267 mg) was obtained in the same manners as those of Reference Example 64, (1), Reference Example 63, (1) and Reference Example 54, (4).
MS (ESI) m/z=351 [M+H]$^+$
$^1$H-NMR (300 MHz, CDCl$_3$) δ (ppm): 1.00 (t, J=7.1 Hz, 3H), 1.26 (d, J=6.6 Hz, 3H), 2.33-2.65 (m, 6H), 3.77-3.82 (m, 4H), 3.85 (s, 3H), 4.53 (s, 2H), 6.82 (d, J=8.5 Hz, 1H), 7.26-7.27 (m, 1H), 7.31 (d, J=1.9 Hz, 1H)

Reference Example 180

Synthesis of 2-[4-[1-(2-aminoethylamino)ethyl]phenoxy]-N,N-diethylacetamide

By using 2-(4-acetylphenoxy)-N,N-diethylacetamide (250 mg), ethylenediamine (400 μl) and acetic acid (700 μl) as starting materials, the title compound (52.9 mg) was obtained in the same manner as that of Reference Example 64, (1).
MS (FAB) m/z=294 [M+H]$^+$
$^1$H-NMR (400 MHz, CD$_3$OD) δ (ppm): 1.14 (t, J=7.1 Hz, 3H), 1.24 (t, J=7.1 Hz, 3H), 1.34 (d, J=6.6 Hz, 3H), 2.42-2.56 (m, 2H), 2.71 (t, J=6.1 Hz, 2H), 3.38-3.46 (m, 4H), 3.70 (q, J=6.6 Hz, 1H), 4.88 (s, 2H), 6.92 (d, J=8.7 Hz, 2H), 7.26 (d, J=8.7 Hz, 2H)

Reference Example 181

Synthesis of 2-[4-[1-(2-aminoethylamino)ethyl]phenoxy]-1-(pyrrolidin-1-yl)ethanone By using 2-(4-acetylphenoxy)-1-(pyrrolidin-1-yl)ethanone (250 mg), ethylenediamine (400 μl) and acetic acid (700 μl) as starting materials, the title compound (163.8 mg) was obtained in the same manner as that of Reference Example 64, (1).
MS (FAB) m/z=292 [M+H]$^+$
$^1$H-NMR (400 MHz, CD$_3$OD) δ (ppm): 1.34 (d, J=6.6 Hz, 3H), 1.86-2.04 (m, 4H), 2.42-2.55 (m, 2H), 2.70 (t, J=6.3 Hz, 2H), 3.45-3.73 (m, 5H), 4.70 (s, 2H), 6.92 (d, J=8.7 Hz, 2H), 7.25 (d, J=8.7 Hz, 2H)

Reference Example 182

Synthesis of N-[1-[4-(1H-tetrazol-1-yl)phenyl]ethyl]ethane-1,2-diamine

By using 1-[4-(1H-tetrazol-1-yl)phenyl]ethanone (250 mg), ethylenediamine (400 μl) and acetic acid (700 μl) as starting materials, the title compound (60.5 mg) was obtained in the same manner as that of Reference Example 64, (1).
MS (FAB) m/z=233 [M+H]$^+$
$^1$H-NMR (400 MHz, CD$_3$OD) δ (ppm): 1.42 (d, J=6.5 Hz, 3H), 2.55-2.72 (m, 2H), 2.83-2.92 (m, 2H), 3.90 (q, J=6.5 Hz, 1H), 7.64 (d, J=8.5 Hz, 2H), 7.84 (d, J=8.5 Hz, 2H), 9.76 (s, 1H)

Reference Example 183

Synthesis of 4-[1-(2-aminoethylamino)ethyl]-2-methoxyphenol (1) 1-(4-Hydroxy-3-methoxyphenyl)ethanone (1 g) was dissolved in dimethylformamide (5 ml), the solution was added with imidazole (1.3 g) and t-butyldimethylchlorosilane (1 g), and the mixture was stirred at room temperature for 4.5 hours. The reaction mixture was added with saturated aqueous ammonium chloride and ethyl acetate, the layers were separated, and the organic layer was washed successively with distilled water and saturated brine, then dried over anhydrous magnesium sulfate and filtered. The filtrate was concentrated under reduced pressure, and the resulting residue was purified by silica gel column chromatography (hexane:ethyl acetate=10:1) to obtain 1-(4-t-butyldimethylsilyloxy-3-methoxyphenyl)ethanone (1.6 g).
(2) By using the compound obtained in (1) mentioned above (560 mg) as a starting material, the title compound (90.3 mg) was obtained in the same manner as that of Reference Example 96.
MS (ESI) m/z=211 [M+H]$^+$
$^1$H-NMR (400 MHz, CD$_3$OD) δ (ppm): 1.35 (d, J=6.82 Hz, 3H), 2.42-2.57 (m, 2H), 2.70 J=6.57 Hz, 2H), 3.66 (q, J=6.82 Hz, 1H), 3.85 (s, 3H), 6.73 (d, J=0.93 Hz, 2H), 6.93 (s, 1H)

Reference Example 184

Synthesis of 6-[1-(2-aminoethylamino)ethyl]-3-(t-butyldimethylsilyloxy)-2-methylphenol By using 1-(2,4-dihydroxy-3-methylphenyl)ethanone (1.0 g) as a starting material, the title compound (103 mg) was obtained in the same manners as those of Reference Example 183, (1) and Reference Example 96.

MS (ESI) m/z=325 [M+H]$^+$ $^1$H-NMR (400 MHz, CD$_3$OD) δ (ppm): 0.08 (s, 6H), 1.02 (s, 9H), 1.38 (d, J=6.58 Hz, 3H), 2.01 (s, 3H), 2.53-2.82 (m, 4H), 3.85 (q, J=6.82 Hz, 1H), 6.25 (d, J=8.03 Hz, 1H), 6.66 (d, J=8.04 Hz, 1H)

Reference Example 185

Synthesis of 6-[1-(2-aminoethylamino)ethyl]-2,3-dimethoxyphenol

By using 1-(2-hydroxy-3,4-dimethoxyphenyl)ethanone (200 mg) as a starting material, the title compound (23.5 mg) was obtained in the same manners as those of Reference Example 183, (1) and Reference Example 96.

MS (ESI) m/z=241 [M+H]$^+$ $^1$H-NMR (400 MHz, CD$_3$OD) δ (ppm): 1.40 (d, J=6.82 Hz, 3H), 2.54-2.82 (m, 4H), 3.77 (s, 3H), 3.79 (s, 3H), 3.94 (q, J=6.82 Hz, 1H), 6.44 (d, J=8.52 Hz, 1H), 6.75 (d, J=8.76 Hz, 1H)

Reference Example 186

Synthesis of 4-[1-(2-aminoethylamino)ethyl]-2-methoxymethylphenol

By using 1-[4-hydroxy-3-(methoxymethyl)phenyl]ethanone (250 mg) as a starting material, the title compound (72.9 mg) was obtained in the same manners as those of Reference Example 183, (1) and Reference Example 96.

MS (ESI) m/z=225 [M+H]$^+$ $^1$H-NMR (400 MHz, CD$_3$OD) δ (ppm): 1.34 (d, J=6.57 Hz, 3H), 2.40-2.54 (m, 2H), 2.68 (t, J=6.58 Hz, 2H), 3.39 (s, 3H), 3.66 (q, J=6.58 Hz, 1H), 4.48 (s, 2H), 6.75 (d, J=8.28 Hz, 1H), 7.08 (dd, J=2.19, 8.28 Hz, 1H), 7.19 (d, J=2.20 Hz, 1H)

Reference Example 187

Synthesis of 2-[1-(2-aminoethylamino)ethyl]-4-methoxyphenol

By using 1-(2-hydroxy-5-methoxyphenyl)ethanone (363 mg) as a starting material, the title compound (224 mg) was obtained in the same manners as those of Reference Example 183, (1) and Reference Example 96.

MS (ESI) m/z=325 [M+H]$^+$ $^1$H-NMR (400 MHz, CD$_3$OD) δ (ppm): 1.39 (d, J=6.82 Hz, 3H), 2.51-2.58 (m, 2H), 2.62-2.79 (m, 2H), 3.70 (s, 3H), 3.89 (q, J=6.82 Hz, 1H), 6.61-6.68 (m, 3H)

Reference Example 188

Synthesis of 2-[1-(2-aminoethylamino)ethyl]benzene-1,3-diol

By using 1-(2,6-dihydroxyphenyl)ethanone (329 mg) as a starting material, the title compound (93.6 mg) was obtained in the same manners as those of Reference Example 183, (1) and Reference Example 96.

MS (ESI) m/z=197 [M+H]$^+$ $^1$H-NMR (400 MHz, CD$_3$OD) δ (ppm): 1.37 (d, J=6.57 Hz, 3H), 2.56-2.82 (m, 4H), 4.41 (q, J=6.82 Hz, 1H), 6.20 (d, J=8.04 Hz, 2H), 6.84 (t, J=8.04 Hz, 1H)

Reference Example 189

Synthesis of 2-(3,4-dihydro-1H-isoquinolin-2-yl)ethylamine

By using 1,2,3,4-tetrahydroisoquinoline (335 mg) as a starting material, the title compound (458 mg) was obtained in the same manners as those of Reference Example 54, (3) and (4).

MS (FAB) m/z=177 [M+H]$^+$ $^1$H-NMR (400 MHz, CDCl$_3$) δ (ppm): 2.60 (t, J=5.86 Hz, 2H), 2.75 (t, J=5.86 Hz, 2H), 2.96 (q, J=6.35 Hz, 4H), 3.64 (s, 2H), 6.99-7.04 (m, 1H), 7.07-7.15 (m, 3H)

Reference Example 190

Synthesis of (S)-N-[1-(2-methoxyphenyl)ethyl]-2-nitro-N-(4-oxobutyl)benzenesulfonamide (1) (1S)-1-(2-Methoxyphenyl)ethanamine (2.45 g) obtained by the method described in the patent document (Japanese Patent Unexamined Publication No. 54-154724) was dissolved in dichloromethane (20 ml), the solution was added with ortho-nitrobenzenesulfonyl chloride (3.52 g) and triethylamine (2.64 ml) under ice cooling, and the mixture was stirred for 1 hour under ice cooling. The reaction mixture was added with 1 N hydrochloric acid and chloroform, the layers were separated, and then the organic layer was washed with saturated brine. The organic layer was dried over anhydrous sodium sulfate and filtered. The filtrate was concentrated under reduced pressure to obtain a protected compound (4.91 g) as a crude product.

(2) The compound obtained in (1) mentioned above (3.00 g) was dissolved in dimethylformamide (45 ml), the solution was added with 5-bromo-1-pentene (1.58 ml), sodium iodide (0.266 g) and potassium carbonate (2.46 g), and the mixture was stirred at 80° C. for 4 hours and further stirred at 100° C. for 3 hours. The reaction mixture was left to cool, and then added with distilled water, chloroform and saturated brine, the layers were separated, and then the organic layer was dried over anhydrous sodium sulfate and filtered. The filtrate was concentrated under reduced pressure, and the resulting residue was purified by silica gel column chromatography (hexane:ethyl acetate) to obtain N-pentenyl compound (2.32 g).

(3) The compound obtained in (2) mentioned above (567 mg) was dissolved in acetone/distilled water=3/1 (11 ml), the solution was added with 4 wt % aqueous osmium tetraoxide (445 μl) and sodium periodate (1.05 g), and the mixture was stirred at room temperature for 30 minutes. The reaction mixture was added with saturated brine and chloroform, the layers were separated, and then the organic layer was dried over anhydrous sodium sulfate and filtered. The filtrate was concentrated under reduced pressure, and the resulting residue was purified by silica gel column chromatography (hexane:ethyl acetate) to obtain the title compound (293 mg).

MS (ESI) m/z=407 [M+H]$^+$ $^1$H-NMR (300 MHz, CDCl$_3$) δ (ppm): 1.67-1.92 (m, 5H), 2.34-2.51 (m, 2H), 3.19-3.41 (m, 2H), 3.45 (s, 3H), 5.30 (q, J=7.2 Hz, 1H), 6.67 (d, J=8.1 Hz, 1H), 6.92 (t, J=7.5 Hz, 1H), 7.19-7.25 (m, 1H), 7.37 (d, J=7.5 Hz, 1H), 7.43-7.60 (m, 3H), 7.66 (d, J=8.1 Hz, 1H), 9.64 (s, 1H)

Reference Example 191

Synthesis of (S)-4-[ethyl[1-(2-methoxyphenyl)ethyl]amino]butanoic acid

The compound obtained in Reference Example 190 (100 mg) was dissolved in t-butanol-distilled water-tetrahydrofuran (2.4:0.6:0.4, 3.4 ml), the solution was successively added with 2-methyl-2-butene (115 µl), sodium dihydrogenphosphate (38.4 mg) and 80% sodium chlorite (94.5 mg), and the mixture was stirred at room temperature for 1.5 hours. The reaction mixture was added with 1 N hydrochloric acid, thereby adjusted to pH 2, and extracted with ethyl acetate. The organic layer was washed with aqueous sodium thiosulfate, and the organic layer was dried over anhydrous magnesium sulfate, and then filtered. The filtrate was concentrated under reduced pressure, and the resulting residue was purified by preparative thin layer chromatography (chloroform:methanol=10:1) to obtain the title compound (93.9 mg).

MS (ESI) m/z=423 [M+H]$^+$ $^1$H-NMR (300 MHz, CDCl$_3$) δ (ppm): 1.71 (d, J=7.14 Hz, 3H), 1.73-1.96 (m, 2H), 2.21-2.48 (m, 2H), 3.20-3.49 (m, 2H), 3.45 (s, 3H), 5.32 (q, J=7.14 Hz, 1H), 6.67 (d, J=8.25 Hz, 1H), 6.87-6.94 (m, 1H), 7.18-7.26 (m, 1H), 7.34-7.40 (m, 1H), 7.41-7.62 (m, 3H), 7.67 (dd, J=1.38, 7.97 Hz, 1H)

Reference Example 192

Synthesis of 2-[ethyl(4-hydroxybutyl)amino]-N,N-dimethylpropanamide (1) 4-(t-Butyldimethylsilyloxy)-1-butanol (12.5 g) was dissolved in dichloromethane (250 ml), the solution was added with molecular sieves 4A (79 g) and pyridinium chlorochromate (15.8 g), and the mixture was stirred at room temperature for 2 hours. The reaction mixture was added with diethyl ether (250 ml), and added with Florisil (79 g), and then the reaction mixture was filtered through Celite. The filtrate was concentrated under reduced pressure, and the resulting residue was purified by silica gel column chromatography (hexane:ethyl acetate=50:1) to obtain an aldehyde compound (2.98 g).

(2) Alanine methyl ester hydrochloride (350 mg) was added to chloroform, and the mixture was successively added with triethylamine (350 µl), the compound obtained in (1) mentioned above (1.01 g), and sodium triacetoxyborohydride (0.5 g). The mixture was stirred at room temperature for 19 hours, and then added with acetaldehyde (710 µl) and sodium triacetoxyborohydride (638 mg), and the mixture was stirred at room temperature for 2.5 hours. The reaction mixture was added with saturated aqueous sodium hydrogencarbonate, the layers were separated, and the organic layer was dried over anhydrous magnesium sulfate and filtered. The filtrate was concentrated under reduced pressure, and the resulting residue was purified by silica gel column chromatography (hexane:ethyl acetate=50:1 to 15:1) to obtain an amine compound (233 mg).

(3) The compound obtained in (2) mentioned above (233 mg) was dissolved in methanol (4.7 ml), the solution was added with 1 N aqueous potassium hydroxide (1.47 ml), and the mixture was stirred at room temperature for 13 hours, and then further stirred at 40° C. for 3.5 hours. The reaction mixture was left to cool to room temperature, added with 1 N hydrochloric acid, thereby adjusted to pH 7, and then concentrated under reduced pressure. The resulting residue was dissolved in tetrahydrofuran-distilled water (1:1, 4.48 ml), the solution was added with triethylamine (206 µl) and isobutyl chloroformate (107 µl) under ice cooling, and the mixture was stirred for 20 minutes. The reaction mixture was added with 50% aqueous dimethylamine (773 µl), and the mixture was warmed to room temperature and stirred for 1 hour. The reaction mixture was added with saturated aqueous sodium hydrogencarbonate and chloroform, the layers were separated, the organic layer was concentrated under reduced pressure, and the resulting residue was purified by silica gel column chromatography (chloroform:methanol=100:1 to 20:1) to obtain a dimethylamide compound (50.4 mg).

(4) The compound obtained in (3) mentioned above (50.4 mg) was dissolved in tetrahydrofuran (1.0 ml), the solution was added with a hydrogen fluoride/pyridine complex (11.9 µl), and the mixture was stirred at room temperature for 8.5 hours. The reaction mixture was added with saturated aqueous sodium hydrogencarbonate and chloroform, and the layers were separated. The organic layer was concentrated under reduced pressure, and the resulting residue was purified by silica gel column chromatography (chloroform:methanol=100:1 to 5:1) to obtain the title compound (31.1 mg).

MS (CI) m/z=217 [M+H]$^+$ $^1$H-NMR (300 MHz, CDCl$_3$) δ (ppm): 1.07 (t, J=7.14 Hz, 3H), 1.18 (d, J=6.87 Hz, 3H), 1.48-1.64 (m, 4H), 2.42-2.70 (m, 4H), 2.95 (s, 3H), 3.13 (s, 3H), 3.56-3.62 (m, 2H), 3.85 (q, J=6.60 Hz, 1H)

Reference Example 193

Synthesis of (S)-2-[ethyl[1-(2-methoxyphenyl)ethyl]amino]ethanol (1) (1S)-1-(2-Methoxyphenyl)ethanamine (0.25 g) obtained by the method described in the patent document (Japanese Patent Unexamined Publication No. 54-154724) was dissolved in chloroform, the solution was added with 2-(t-butyldimethylsilyloxy)-acetaldehyde (0.35 ml) and sodium triacetoxyborohydride (0.42 g) under ice cooling, and the mixture was stirred for 1 hour under ice cooling and then stirred at room temperature for 2 hours. The reaction mixture was added with acetaldehyde (0.173 ml) and sodium triacetoxyborohydride (0.79 g), and the mixture was stirred overnight at room temperature. The reaction mixture was added with saturated aqueous sodium hydrogencarbonate and chloroform, the layers were separated, and then the organic layer was washed with saturated brine. The organic layer was dried over sodium sulfate and filtered, then the filtrate was concentrated under reduced pressure, and the resulting residue was purified by preparative thin layer chromatography (chloroform:methanol=8:1) to obtain a tertiary amine compound (73.5 mg).

(2) The compound obtained in (1) mentioned above (73.5 mg) was dissolved in tetrahydrofuran (1.5 ml), the solution was added with a hydrogen fluoride-pyridine complex (55 µl), and the mixture was stirred at room temperature for 1.5 hours. The reaction mixture was added with saturated aqueous sodium hydrogencarbonate and chloroform, the layers were separated, and then the organic layer was dried over sodium sulfate and filtered. The filtrate was concentrated under reduced pressure, and the resulting residue was purified by preparative thin layer chromatography (chloroform:methanol=5:1) to obtain the title compound (44.2 mg).

MS (ESI) m/z=224 [M+H]$^+$ $^1$H-NMR (300 MHz, CDCl$_3$) δ (ppm): 0.95 (t, J=7.2 Hz, 3H), 1.32 (d, J=6.9 Hz, 3H), 2.53 (q, J=7.2 Hz, 2H), 2.58-2.73

(m, 2H), 2.94 (br, 1H), 3.43-3.60 (m, 2H), 3.84 (s, 3H), 4.42 (q, J=6.9 Hz, 1H), 6.87-6.96 (m, 2H), 7.21-7.30 (m, 2H)

Reference Example 194

Synthesis of (S)-N-(1-(2-methoxyphenyl)ethyl)-1H-imidazole-1-carboxamide (S)-1-(2-Methoxyphenyl)ethanamine (100 mg) obtained by the method described in the patent document (Japanese Patent Unexamined Publication No. 54-154724) was dissolved in dimethylformamide (0.65 ml), the solution was added with N,N'-carbonyldiimidazole (321 mg), and the mixture was stirred at room temperature for 1 hour. The reaction mixture was added with distilled water and ethyl acetate, the layers were separated, and the organic layer was washed successively with distilled water and saturated brine. The organic layer was dried over anhydrous sodium sulfate and filtered, and then the filtrate was concentrated under reduced pressure to obtain the title compound (147 mg).
MS (ESI) m/z=246 [M+H]$^+$

Reference Example 195

Synthesis of (S)-2-[ethyl[1-(2-methoxyphenyl)ethyl]amino]acetic acid 2,2,2-trifluoroacetic acid salt (1) The compound obtained in Reference Example 190, (1) (101 mg) was dissolved in dimethylformamide (2 ml), the solution was added with t-butyl bromoacetate (70.2 mg), potassium iodide (59.8 mg) and potassium carbonate (62.2 mg), and under an argon atmosphere, the mixture was stirred at 80° C. for 20 hours, and then further stirred at 100° C. for 2 days. The reaction mixture was added with distilled water and ethyl acetate, the layers were separated, and then the organic layer was washed with saturated brine. The organic layer was dried over anhydrous magnesium sulfate and filtered, then the filtrate was concentrated under reduced pressure, and the resulting residue was purified by silica gel column chromatography (hexane:ethyl acetate=4:1) to obtain an ester compound (65.1 mg).
(2) The compound obtained in (1) mentioned above (152 mg) was dissolved in dimethylformamide (2 ml), the solution was added with thiophenol (172 μl) and potassium carbonate (233 mg), and the mixture was stirred at room temperature for 22 hours under an argon atmosphere. The reaction mixture was added with distilled water and ethyl acetate, the layers were separated, and then the organic layer was dried over anhydrous magnesium sulfate and filtered. The filtrate was concentrated under reduced pressure, and the resulting residue was purified by silica gel column chromatography (hexane:ethyl acetate=4:1) to obtain a deprotected compound (86 mg).
(3) By using the compound obtained in (2) mentioned above (26.5 mg) as a starting material, a tertiary amine compound was obtained as a crude product in the same manner as that of Reference Example 193, (1). The resulting compound was dissolved in dichloromethane (1 ml), the solution was added with trifluoroacetic acid (0.5 ml), and then the reaction mixture was stirred at room temperature for 20 hours, and concentrated under reduced pressure to obtain the title compound (24.9 mg).
$^1$H-NMR (400 MHz, CDCl$_3$) δ (ppm): 1.48 (t, J=7.3 Hz, 3H), 1.71 (d, J=7.1 Hz, 3H), 3.31 (q, J=7.3 Hz, 2H), 3.79 (d, J=16.8 Hz, 1H), 3.91 (d, J=16.8 Hz, 1H), 4.03 (s, 3H), 4.85 (q, J=7.1 Hz, 1H), 7.03 (d, J=8.5 Hz, 1H), 7.10-7.13 (m, 1H), 7.24-7.26 (m, 1H), 7.46-7.52 (m, 1H)

Reference Example 196

Synthesis of (S)-N-[1-(2-methoxyphenyl)ethyl]-2-nitro-N-(4-oxopropyl)benzenesulfonamide By using the compound obtained in Reference Example 190, (1) (336 mg) and 4-bromo-1-butene (504 μl) as starting materials, the title compound (104 mg) was obtained in the same manners as those of Reference Example 190, (2) and (3).
MS (ESI) m/z=393 [M+H]$^+$
$^1$H-NMR (300 MHz, CDCl$_3$) δ (ppm): 1.61 (t, J=7.2 Hz, 3H), 2.36-2.47 (m, 1H), 2.68-2.79 (m, 1H), 3.52 (s, 3H), 3.61-3.67 (m, 2H), 5.41 (q, J=7.2 Hz, 1H), 6.73 (d, J=8.1 Hz, 1H), 6.91 (dt, J=7.5, 0.9 Hz, 1H), 7.22-7.33 (m, 2H), 7.48-7.61 (m, 3H), 7.70 (dd, J=7.8, 1.2 Hz, 1H), 9.57 (s, 1H)

Reference Example 197

Synthesis of (S)-2-amino-3-(4-methoxyphenyl)propan-1-ol (1) Lithium aluminum hydride (512 mg) was suspended in ice-cooled tetrahydrofuran (15 ml) under an argon atmosphere, and the suspension was added with (S)-2-t-butoxycarbonylamino-3-(4-methoxyphenyl)propanoic acid (1.0 g). The mixture was stirred for 30 minutes, then warmed to room temperature, and further stirred for 3 hours. The reaction mixture was ice-cooled again, and successively added with distilled water (512 μl), 15% aqueous sodium hydroxide (512 μl) and distilled water (1.54 ml), and the mixture was stirred for 30 minutes, and filtered through Celite. The filtrate was concentrated under reduced pressure, and the resulting residue was purified by silica gel column chromatography (hexane:ethyl acetate=4:1 to 3:2) to obtain an alcohol compound (718 mg).
(2) The compound obtained in (1) mentioned above (718 mg) was dissolved in dioxane-methanol (3.5:1, 4.5 ml), the solution was added with a 4 N hydrochloric acid solution in dioxane (3.59 ml) under ice cooling, and the mixture was stirred for 1.5 hours, then warmed to room temperature, and stirred for 2 hours. The reaction mixture was added with diethyl ether-hexane (1:1, 14 ml), and the deposited solid was taken by filtration. The resulting filtration product was suspended in chloroform-methanol (10:1, 20 ml), and filtered through NH silica gel, and then the filtrate was concentrated under reduced pressure to obtain the title compound (315 mg).
MS (CI) m/z=182 [M+H]$^+$
$^1$H-NMR (400 MHz, CDCl$_3$) δ (ppm): 2.47 (dd, J=8.49, 13.64 Hz, 1H), 2.70 (dd, J=5.36, 13.64 Hz, 1H), 3.04-3.12 (m, 1H), 3.37 (dd, J=7.31, 10.72 Hz, 1H), 3.63 (dd, J=3.90, 10.47 Hz, 1H), 3.80 (s, 3H), 6.84-6.88 (m, 2H), 7.04-7.14 (m, 2H)

Reference Example 198

Synthesis of 2-hydroxy-2-(4-methoxyphenyl)ethylamine

2-Amino-4'-methoxyacetophenone hydrochloride (500 mg) was dissolved in methanol (10 ml), the solution was added with sodium borohydride (188 mg), and the mixture was stirred at room temperature for 2 hours. The reaction mixture was added with sodium borohydride (188 mg), and further stirred for 30 minutes. The reaction mixture was added with 5 N aqueous sodium hydroxide (1 ml), the mixture was stirred for 10 minutes, and then added with chloroform, and the layers were separated. The organic layer was washed with saturated brine, dried over anhydrous magnesium sulfate and filtered, and then the filtrate was concentrated under reduced pressure to obtain the title compound (240 mg).

MS (FAB) m/z=168 [M+H]$^+$ $^1$H-NMR (400 MHz, CDCl$_3$) δ (ppm): 2.80 (dd, J=7.8, 12.7 Hz, 1H), 2.98 (dd, J=4.1, 7.8 Hz, 1H), 3.81 (s, 3H), 4.59 (dd, J=4.1, 7.8 Hz, 1H), 6.89 (m, 2H), 7.28 (m, 2H)

Reference Example 199

Synthesis of 2-(benzyloxy)ethyl oxiran-2-ylethylcarbamate (1) Allyl isocyanate (2.38 g) was dissolved in toluene (29 ml), the solution was added with benzyloxyethanol (4.1 ml) and 1,4-diazabicyclo[2.2.2]octane (963 mg), and the mixture was stirred at room temperature for 5 hours. The reaction mixture was added with distilled water and ethyl acetate, the layers were separated, and the organic layer was washed successively with distilled water and saturated brine, then dried over anhydrous sodium sulfate and filtered. The filtrate was concentrated under reduced pressure, and the resulting residue was purified by silica gel column chromatography (hexane:ethyl acetate=10:1 to 5:1) to obtain 2-(benzyloxy)ethyl allylcarbamate (5.1 g).

(2) By using the compound obtained in (1) mentioned above (5.1 g) as a starting material, the title compound (4.86 g) was obtained in the same manner as that of Reference Example 26, (2).

MS (FAB) m/z=252 [M+H]$^+$ $^1$H-NMR (300 MHz, CDCl$_3$) δ (ppm): 2.60 (dd, J=2.47, 4.67 Hz, 1H), 2.78 (t, J=4.40 Hz, 1H), 3.07-3.14 (m, 1H), 3.26 (ddd, J=5.22, 6.32, 4.8 Hz, 1H), 3.55-3.65 (m, 1H), 3.66 (t, J=4.67 Hz, 2H), 4.26 (t, J=4.67 Hz, 2H), 4.56 (s, 2H), 7.22-7.40 (m, 5H)

Reference Example 200

Synthesis of propargyl oxiran-2-ylmethylcarbamate

By using allyl isocyanate (2.40 g) and propargyl alcohol (1.7 ml) as starting materials, the title compound (3.35 g) was obtained in the same manners as those of Reference Example 199, (1) and Reference Example 26, (2).

MS (FAB) m/z=155 [M+H]$^+$ $^1$H-NMR (300 MHz, CDCl$_3$) δ (ppm): 2.49 (t, J=2.47 Hz, 1H), 2.62 (dd, J=2.75, 4.67 Hz, 1H), 2.81 (t, J=4.67 Hz, 1H), 3.09-3.17 (m, 1H), 3.23-3.35 (m, 1H), 3.58-3.70 (m, 1H), 4.69 (d, J=2.20 Hz, 2H), 5.00-5.20 (m, 1H)

Reference Example 201

Synthesis of 2-(6-t-butyldimethylsilyloxyhexyl)oxirane

By using 7-octen-1-ol (5.0 g) as a starting material, the title compound (7.9 g) was obtained in the same manners as those of Reference Example 183, (1) and Reference Example 26, (2).

MS (CI) m/z=259 [M+H]$^+$ $^1$H-NMR (400 MHz, CDCl$_3$) δ (ppm): 0.05 (s, 6H), 0.89 (s, 9H), 1.29-1.58 (m, 10H), 2.46 (dd, J=2.68, 5.12 Hz, 1H), 2.75 (dd, J=4.14, 5.11 Hz, 1H), 2.87-2.95 (m, 1H), 3.60 (t, J=6.82 Hz, 2H)

Reference Example 202

Synthesis of 2-(5-t-butyldimethylsilyloxypentyl)oxirane

By using 6-hepten-1-ol (5.0 g) as a starting material, the title compound (8.74 g) was obtained in the same manners as those of Reference Example 183, (1) and Reference Example 26, (2).

MS (CI) m/z=245 [M+H]$^+$ $^1$H-NMR (400 MHz, CDCl$_3$) δ (ppm): 0.05 (s, 6H), 0.89 (s, 9H), 1.34-1.58 (m, 8H), 2.47 (dd, J=2.68, 5.11 Hz, 1H), 2.75 (dd, J=4.14, 5.11 Hz, 1H), 2.87-2.94 (m, 1H), 3.61 (t, J=6.58 Hz, 2H)

Reference Example 203

Synthesis of 2-[(1-triethylsilyloxycyclohexyl)methyl]oxirane (1) 1-Allylcyclohexanol (5.0 g) was dissolved in dichloromethane (50 ml), the solution was added with 2,6-lutidine (4.98 ml) and triethylsilyl trifluoromethanesulfonate (8.06 ml) under ice cooling, and the mixture was stirred for 2 hours, and then at room temperature for 12 hours. The reaction mixture was added with 10% aqueous citric acid and hexane, the layers were separated, the organic layer was washed with saturated brine, dried over anhydrous magnesium sulfate and filtered, and then the filtrate was concentrated under reduced pressure to obtain a triethylsilyl compound (8.9 g).

(2) By using the compound obtained in (1) mentioned above (8.9 g) as a starting material, the title compound (8.52 g) was obtained in the same manner as that of Reference Example 26, (2).

$^1$H-NMR (400 MHz, CDCl$_3$) δ (ppm): 0.61 (q, J=7.80 Hz, 6H), 0.96 (t, J=7.04 Hz, 9H), 1.29-1.45 (m, 4H), 1.49-1.83 (m, 8H), 2.46 (dd, J=2.68, 5.11 Hz, 1H), 2.78 (t, J=4.14 Hz, 1H), 3.08-3.14 (m, 1H)

Reference Example 204

Synthesis of 2-(2-triethylsilyloxy-2-phenylpropyl)oxirane

By using 2-phenyl-4-penten-2-ol (2.5 g) as a starting material, the title compound (1.63 g) was obtained in the same manners as those of Reference Example 203, (1) and Reference Example 26, (2).

$^1$H-NMR (400 MHz, CDCl$_3$) δ (ppm): 0.54-0.66 (m, 6H), 0.90-0.98 (m, 9H), 1.70-1.76 (m, 3H), 1.81-1.91 (m, 1H), 1.94-2.10 (m, 1H), 2.13-2.41 (m, 1H), 2.53-2.65 (m, 1H), 2.71-3.07 (m, 1H), 7.20-7.49 (m, 5H)

Reference Example 205

Synthesis of 2-(2-triethylsilyloxy-2-methylbutyl)oxirane

By using 3-methyl-5-hexen-3-ol (2.5 g) as a starting material, the title compound (4.23 g) was obtained in the same manners as those of Reference Example 203, (1) and Reference Example 26, (2).

¹H-NMR (400 MHz, CDCl₃) δ (ppm): 0.05-0.63 (m, 6H), 0.85-0.99 (m, 12H), 1.23-1.31 (m, 3H), 1.51-1.72 (m, 4H), 2.43-2.47 (m, 1H), 2.75-2.80 (m, 1H), 3.03-3.12 (m, 1H)

Reference Example 206

Synthesis of 2-O-t-butyldimethylsilyl-1-(oxiran-2-yl)propan-2-ol (1) By using 4-penten-2-ol (5.0 g) as a starting material, 2-O-t-butyldimethylsilyl-4-penten-2-ol (8.4 g) was obtained in the same manner as that of Reference Example 183, (1).
(2) By using the compound obtained in (1) mentioned above (6.0 g) as a starting material, the title compound (6.13 g) was obtained in the same manner as that of Reference Example 26, (2).
MS (FAB) m/z=252 [M+H]⁺
¹H-NMR (300 MHz, CDCl₃) δ (ppm): 0.06-0.14 (m, 6H), 0.90 and 0.91 (s, 9H), 1.19 and 1.23 (d, J=6.04 Hz, 3H), 1.45-1.61 (m, 1H), 1.65-1.81 (m, 1H), 2.45-2.54 (m, 1H), 2.74-2.84 (m, 1H), 2.89-3.08 (m, 1H), 3.88-4.12 (m, 1H)

Reference Example 207

Synthesis of 1,2-di-O-t-butyldimethylsilyl-4-(oxiran-2-yl)butane-1,2-diol

By using 5-hexene-1,2-diol (5.0 g) as a starting material, the title compound (8.00 g) was obtained in the same manners as those of Reference Example 183, (1) and Reference Example 26, (2).
MS (ESI) m/z=361 [M+H]⁺
¹H-NMR (300 MHz, CDCl₃) δ (ppm): 0.07 (s, 6H), 0.08 (s, 6H), 0.89 (s, 9H), 0.91 (s, 9H), 1.45-1.85 (m, 4H), 2.45-2.51 (m, 1H), 2.76 (t, J=4.40 Hz, 1H), 2.89-2.97 (m, 1H), 3.36-3.45 (m, 1H), 3.50-3.58 (m, 1H), 3.65-3.76 (m, 1H)

Reference Example 208

Synthesis of allyl(S)-(oxiran-2-ylmethyl)carbamate (1) By using (S)-3-amino-1,2-propanediol (2.9 g) as a starting material, a carbamate compound (1.15 g) was obtained in the same manner as that of Reference Example 30, (1).
(2) The compound obtained in (1) mentioned above (1.15 g) was dissolved in chloroform, the solution was added with pyridine (1.9 ml) and p-toluenesulfonyl chloride (1.50 g), and the mixture was stirred at room temperature for 4.5 hours. The reaction mixture was added with p-toluenesulfonyl chloride (125 mg), and the mixture was further stirred at room temperature for 1.5 hours. The reaction mixture was added with 2 N hydrochloric acid, the layers were separated, and the organic layer was washed successively with saturated aqueous sodium hydrogencarbonate and saturated brine, then dried over anhydrous sodium sulfate and filtered. The filtrate was concentrated under reduced pressure, the resulting residue was dissolved in methanol (15 ml), the solution was added with a 1 N solution of sodium methoxide in methanol (15.2 ml), and the mixture was stirred for 1.5 hours under ice cooling. The reaction mixture was added with 20% aqueous ammonium chloride, and methanol was evaporated under reduced pressure. The concentrate was added with ethyl acetate, the layers were separated, and the organic layer was washed successively with saturated brine, then dried over anhydrous sodium sulfate and filtered. The filtrate was concentrated under reduced pressure, and the resulting residue was purified by silica gel column chromatography (hexane:ethyl acetate=4:1 to 3:1) to obtain the title compound (670 mg).
MS (FAB) m/z=158 [M+H]⁺
¹H-NMR (300 MHz, CDCl₃) δ (ppm): 2.62 (dd, J=2.75, 4.67 Hz, 1H), 2.80 (dd, J=3.85, 4.67 Hz, 1H), 3.05-3.20 (m, 1H), 3.20-3.35 (m, 1H), 3.50-3.70 (m, 1H), 4.58 (d, J=5.77 Hz, 2H), 4.82-5.07 (m, 1H), 5.17-5.40 (m, 2H), 5.83-6.02 (m, 1H)

Reference Example 209

Synthesis of (S)-2-allyloxirane

By using (S)-epichlorohydrin (5.0 g) as a starting material, the title compound (1.05 g) was obtained according to the method described in the literature (Journal of American Chemical Society, 2004, vol. 126, p. 2495).
MS (EI) m/z=84 [M]⁺
¹H-NMR (400 MHz, CDCl₃) δ (ppm): 2.27-2.40 (m, 2H), 2.52 (dd, J=2.68, 4.87 Hz, 1H), 2.77 (dd, J=4.14, 4.87 Hz, 1H), 2.97-3.03 (m, 1H), 5.09-5.21 (m, 2H), 5.78-5.89 (m, 1H)

Reference Example 210

Synthesis of 2-(2-t-butyldimethylsilyloxybenzyl)oxirane

By using 2-allylphenol (4.0 g) as a starting material, the title compound (6.3 g) was obtained in the same manners as those of Reference Example 183, (1) and Reference Example 26, (2).
MS (EI) m/z=265 [M+H]⁺
¹H-NMR (400 MHz, CDCl₃) δ (ppm): 0.25 (s, 3H), 0.26 (s, 3H), 1.02 (s, 9H), 2.53 (dd, J=2.68, 4.87 Hz, 1H), 2.72-2.79 (m, 2H), 2.98 (dd, J=5.36, 14.37 Hz, 1H), 3.17-3.23 (m, 1H), 6.81 (dd, J=1.22, 8.28 Hz, 1H), 6.88-6.94 (m, 1H), 7.09-7.15 (m, 1H), 7.21 (dd, J=1.71, 7.55 Hz, 1H)

Reference Example 211

Synthesis of allyl 2-[(oxiran-2-yl)ethyl]carbamate (1) Acetyl chloride (2.6 ml) was added to methanol (240 ml) under ice cooling, the mixture was stirred for 10 minutes, and then added with (S)-4-(benzyloxycarbonylamino)-2-hydroxybutanoic acid (30 g), and the mixture was gradually warmed from ice cooling temperature to room temperature, and stirred for 16.5 hours. The reaction mixture was added with saturated aqueous sodium hydrogencarbonate, and methanol was evaporated under reduced pressure. The concentrate was added with ethyl acetate, the layers were separated, and the organic layer was washed successively with saturated aqueous sodium hydrogencarbonate and saturated brine, then dried over anhydrous sodium sulfate and filtered. The filtrate was concentrated under reduced pressure, the resulting residue was added with dichloromethane to dissolve the residue, and the mixture was added with molecular sieves 4A (140 g) and pyridinium chlorochromate (30.7 g). The mixture was stirred at room temperature for 2.5 hours, and then further added with pyridinium chlorochromate (21.1 g), and the mixture was stirred at room temperature for 3.5 hours. The reaction mixture was added with diethyl ether and Florisil, and filtered through Celite under reduced pressure. The filtrate was concentrated under reduced pressure, and the resulting residue was purified by silica gel column chromatography (hexane:ethyl acetate=3:1 to 1:2) to obtain 4-(benzyloxycarbonylamino)-2-oxobutanoic acid methyl ester (17 g).

(2) A suspension of lithium borohydride (4.51 g) in diethyl ether (350 ml) was added with a solution of the compound obtained in (1) mentioned above (16.5 g) in diethyl ether (150 ml) under ice cooling, and then the mixture was stirred at room temperature for 20 hours. The reaction mixture was added with 20% aqueous ammonium chloride and concentrated hydrochloric acid (20 ml), and the mixture was stirred at room temperature for 20 minutes, and then made alkaline with sodium hydrogencarbonate. The organic layer and the aqueous layer were separated, and the aqueous layer was extracted twice with ethyl acetate. The organic layers were combined, dried over anhydrous sodium sulfate and filtered, then the filtrate was concentrated under reduced pressure, and the resulting residue was purified by silica gel column chromatography (chloroform:methanol=70:1 to 10:1) to obtain a 1,2-diol compound (11.3 g).

(3) The compound obtained in (2) mentioned above (11.6 g) was dissolved in methanol (120 m), the solution was added with 10% palladium-carbon (580 mg), and the mixture was stirred at room temperature for 16 hours under a hydrogen atmosphere of 1 atm. The reaction mixture was filtered, and the filtrate was concentrated under reduced pressure to obtain 4-amino-1,2-butanediol (6.10 g).

(4) By using the compound obtained in (3) mentioned above (3.0 g) as a starting material, a carbamate compound (3.40 g) was obtained in the same manner as that of Reference Example 30, (1).

(5) By using the compound obtained in (4) mentioned above (3.40 g) as a starting material, the title compound (1.65 g) was obtained in the same manner as that of Reference Example 208, (2).

MS (ESI) m/z=172 [M+H]$^+$ $^1$H-NMR (300 MHz, CDCl$_3$) δ (ppm): 1.54-1.68 (m, 1H), 1.88-2.04 (m, 1H), 2.53 (dd, J=2.75, 4.67 Hz, 1H), 2.79 (t, J=4.95 Hz, 1H), 2.95-3.05 (m, 1H), 3.28-3.46 (m, 2H), 4.57 (d, J=5.22 Hz, 2H), 5.04 (brs, 1H), 5.17-5.28 (m, 2H), 5.84-6.01 (m, 1H)

Reference Example 212

Synthesis of 2-methoxy-4-(oxiran-2-ylmethyl)phenyl acetate

By using 4-allyl-2-methoxyphenyl acetate (5.0 g) as a starting material, the title compound (5.2 g) was obtained in the same manner as that of Reference Example 26, (2).

MS (GC) m/z=222 [M]$^+$ $^1$H-NMR (400 MHz, CDCl$_3$) δ (ppm): 2.32 (s, 3H), 2.56 (dd, J=2.68, 4.88 Hz, 1H), 2.81-2.90 (m, 3H), 3.14-3.18 (m, 1H), 3.84 (s, 3H), 6.82-6.87 (m, 2H), 6.97 (d, J=8.08 Hz, 1H)

Reference Example 213

Synthesis of 2-(2-t-butyldimethylsilyloxy-2-phenylethyl)oxirane

By using 1-phenyl-3-buten-1-ol (2.5 g) as a starting material, the title compound (4.43 g) was obtained in the same manners as those of Reference Example 183, (1) and Reference Example 26, (2).

MS (CI) m/z=278 [M+H]$^+$ $^1$H-NMR (400 MHz, CDCl$_3$) δ (ppm): −0.15-−0.11 (m, 3H), 0.02-0.08 (m, 3H), 0.87-0.92 (m, 9H), 1.61-1.81 (m, 1H), 1.90-2.10 (m, 1H), 2.41-2.48 (m, 1H), 2.65-2.81 (m, 1H), 2.82-3.19 (m, 1H), 4.83-4.93 (m, 1H), 7.21-7.37 (m, 1H)

Reference Example 214

Synthesis of 2-(2-t-butyldimethylsilyloxyhexyl)oxirane

By using 1-octen-4-ol (10.0 g) as a starting material, the title compound (18.25 g) was obtained in the same manners as those of Reference Example 183, (1) and Reference Example 26, (2).

MS (CI) m/z=259 [M+H]$^+$ $^1$H-NMR (400 MHz, CDCl$_3$) δ (ppm): 0.04-0.10 (m, 6H), 0.86-0.94 (m, 12H), 1.22-1.38 (m, 4H), 1.45-1.76 (m, 4H), 2.44-2.52 (m, 1H), 2.74-2.82 (m, 1H), 3.00-3.08 (m, 1H), 3.82-3.92 (m, 1H)

Reference Example 215

Synthesis of 2-(2-t-butyldimethylsilyloxy-3-methylbutyl)oxirane

By using 2-methyl-5-hexen-3-ol (10.0 g) as a starting material, the title compound (18.6 g) was obtained in the same manners as those of Reference Example 183, (1) and Reference Example 26, (2).

MS (CI) m/z=244 [M]$^+$ $^1$H-NMR (400 MHz, CDCl$_3$) δ (ppm): 0.04-0.11 (m, 6H), 0.83-0.93 (m, 15H), 1.45-1.66 (m, 2H), 1.74-1.86 (m, 1H), 2.43-2.54 (m, 1H), 2.74-2.83 (m, 1H), 2.98-3.06 (m, 1H), 3.61-3.76 (m, 1H)

Reference Example 216

Synthesis of 2-(2-t-butyldimethylsilyloxypentyl)oxirane

By using 1-hepten-4-ol (10.0 g) as a starting material, the title compound (16.1 g) was obtained in the same manners as those of Reference Example 183, (1) and Reference Example 26, (2).

MS (CI) m/z=245 [M+H]$^+$ $^1$H-NMR (400 MHz, CDCl$_3$) δ (ppm): 0.04-0.09 (m, 6H), 0.86-0.94 (m, 12H), 1.25-1.76 (m, 6H), 2.43-2.52 (m, 1H), 2.74-2.83 (m, 1H), 2.99-3.08 (m, 1H), 3.81-3.92 (m, 1H)

Reference Example 217

Synthesis of 1-O-t-butyldimethylsilyl-4-methoxy-2-(oxiran-2-ylmethyl)phenol

By using 2-allyl-4-methoxyphenol (1.0 g) as a starting material, the title compound (600 mg) was obtained in the same manners as those of Reference Example 183, (1) and Reference Example 26, (2).

MS (GC) m/z=294 [M]$^+$ $^1$H-NMR (400 MHz, CDCl$_3$) δ (ppm): 2.31-2.35 (m, 1H), 2.48-2.58 (m, 2H), 2.67-2.75 (m, 1H), 2.95-3.01 (m, 1H), 3.55 (s, 3H), 6.46 (dd, J=3.43, 8.08 Hz, 1H), 6.52 (d, J=8.08 Hz, 1H), 6.58 (d, J=3.43 Hz, 1H)

Reference Example 218

Synthesis of 1-O-t-butyldimethylsilyl-1-(4-methoxyphenyl)-2-(oxiran-2-yl)ethanol By using 1-(4-methoxyphenyl)-3-buten-1-ol (4.0 g) as a starting material, the title compound (5.4 g) was obtained in the same manners as those of Reference Example 183, (1) and Reference Example 26, (2).
MS (GC) m/z=293 [M-15]$^+$
$^1$H-NMR (400 MHz, CDCl$_3$) δ (ppm): 2.31-2.35 (m, 1H), 2.48-2.58 (m, 2H), 2.67-2.75 (m, 1H), 2.95-3.01 (m, 1H), 3.55 (s, 3H), 6.46 (dd, J=3.43, 8.08 Hz, 1H), 6.52 (d, J=8.08 Hz, 1H), 6.58 (d, J=3.43 Hz, 1H)

Reference Example 219

Synthesis of benzyl 4-(oxiran-2-yl)butanate

By using 5-pentenoic acid (5.0 g) as a starting material, the title compound (10.0 g) was obtained in the same manners as those of Reference Example 25, (1) and Reference Example 26, (2).
MS (GC) m/z=220 [M]$^+$ Reference Example 220

Synthesis of 2-(2-methoxyphenyl)propan-1-amine (1) 2-(2-Methoxyphenyl)acetonitrile (2.0 g) was dissolved in anhydrous tetrahydrofuran (40 ml), and the solution was added with a 1 M solution of lithium hexamethyldisilazide in hexane (14.3 ml) at −78° C. under an argon atmosphere. The mixture was stirred at −78° C. for 1 hour, and then added with iodomethane (0.89 ml), and the mixture was stirred at −78° C. for 1.5 hours, and stirred overnight with warming to room temperature. The reaction mixture was added with 0.2 N hydrochloric acid, the mixture was extracted with ethyl acetate, and the organic layer was dried over anhydrous sodium sulfate and filtered. The filtrate was concentrated under reduced pressure, and the resulting residue was purified by silica gel column chromatography (hexane:ethyl acetate=24:1 to 3:1) to obtain a methyl compound (2.13 g).
(2) The compound obtained in (1) mentioned above (1.00 g) was dissolved in anhydrous tetrahydrofuran (30 ml), the solution was added with a 2 M solution of a borane/dimethyl sulfide complex in tetrahydrofuran (4.31 ml) under an argon atmosphere, and the mixture was stirred for 3 hours under reflux by heating. The reaction mixture was added with concentrated hydrochloric acid, and the mixture was concentrated under reduced pressure. The resulting residue was dissolved in chloroform, and the solution was dried over anhydrous sodium sulfate, and then filtered. The filtrate was concentrated under reduced pressure to obtain an amine hydrochloride (1.39 g).
(3) The compound obtained in (2) mentioned above (636 mg) was dissolved in dichloromethane (10 ml), then adsorbed to NH silica gel (Fuji Silysia), and then eluted with ethyl acetate. The elute was concentrated under reduced pressure, and the precipitates deposited during the concentration was taken by filtration to obtain the title compound (99.5 mg).
MS (EI): m/z=165 [M]$^+$ $^1$H-NMR (400 MHz, CDCl$_3$) δ (ppm): 1.40 (d, J=7.06 Hz, 3H), 3.08 (dd, J=7.79, 12.42 Hz, 1H), 3.19 (dd, J=6.82, 12.66 Hz, 1H), 3.48-3.59 (m, 1H), 3.85 (s, 3H), 6.88 (d, J=8.28 Hz, 1H), 6.89-6.94 (m, 1H), 7.17-7.26 (m, 2H)

Syntheses of Examples 1 to 6

Preparation methods of the compounds represented by the formula (A) having R and R' defined in the examples are shown below.

[Formula 19]

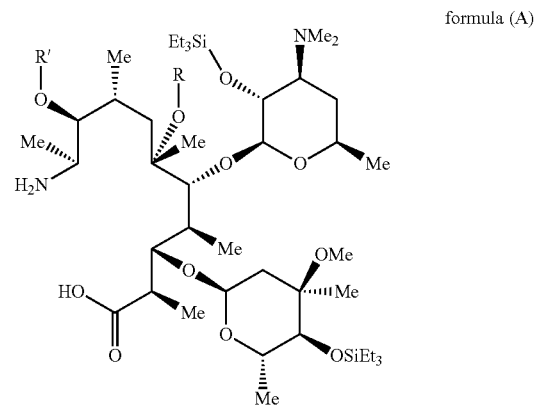

formula (A)

Example 1

Synthesis of the Compound of the Formula (A) Wherein R=Methyl and R'=Triethylsilyl (1) (9S)-9,2',4''-O-Tris(triethylsilyl)-9-dihydro-6-O-methylerythromycin A (200 g) was dissolved in chloroform (400 ml), the solution was added with 90% lead tetraacetate (90.2 g) under ice cooling, and the mixture was stirred for 10 minutes. The mixture was further added successively with a solution of 2-methyl-2-butene (51.3 g) in tetrahydrofuran (800 ml), t-butyl alcohol (400 ml) and an aqueous solution (400 ml) of sodium chlorite (33.1 g), and the mixture was stirred at room temperature for 18 hours. The reaction mixture was added with saturated aqueous sodium hydrogencarbonate (700 ml), the mixture was stirred and then added with ethyl acetate (1000 ml), and the layers were separated. The organic layer was washed successively with saturated aqueous sodium hydrogencarbonate (500 ml) and saturated brine (500 ml), then dried over anhydrous magnesium sulfate and filtered. The resulting filtrate was concentrated under reduced pressure to obtain a 10-carboxy compound (218.9 g).
(2) A solution of the compound obtained in (1) mentioned above (218.9 g) in toluene (500 ml) was concentrated under reduced pressure, the resulting residue was dissolved in chloroform (500 ml), and the solution was added with triethylamine (28.1 ml). Then, the mixture was added dropwise with isobutyl chloroformate (25.0 g) under ice cooling, and the mixture was stirred at the same temperature for 30 minutes. Then, the mixture was added with 50% aqueous hydroxylamine (12.1 g) under ice cooling, and the mixture was stirred at the same temperature for 1 hour. The reaction mixture was added with saturated aqueous ammonium chloride (500 ml), the layers were separated, and the organic layer was washed with saturated brine (500 ml), then dried over anhydrous magnesium sulfate and filtered. The filtrate was concentrated under reduced pressure to obtain a 10-hydroxamic acid compound (219.9 g).

(3) A solution of the compound obtained in (2) mentioned above (219.9 g) in toluene (500 ml) was concentrated under reduced pressure, and the resulting residue was dissolved in tetrahydrofuran (800 ml). The solution was successively added with triethylamine (77.0 ml) and p-toluenesulfonyl chloride (38.4 g), the mixture was stirred at room temperature for 40 minutes, and then further added with an aqueous solution (260 ml) of lithium hydroxide (38.4 g), and the mixture was stirred at room temperature for 1 hour. The reaction mixture was added with saturated aqueous ammonium chloride (500 ml), thereby neutralized, and then concentrated under reduced pressure, the resulting residue was added with chloroform (1000 ml), and the layers were separated. The organic layer was washed with saturated aqueous sodium hydrogencarbonate (500 ml), then dried over anhydrous magnesium sulfate and filtered. The filtrate was concentrated under reduced pressure, and the resulting residue was purified by silica gel column chromatography (chloroform:methanol:28% aqueous ammonia=40:1:0.1 to 15:1:0.1) to obtain the title compound (44.3 g).

MS (ESI) m/z=993.8 [M+H]$^+$ $^1$H-NMR (500 MHz, CDCl$_3$) δ (ppm): 0.51-0.70 (m, 18H), 0.84-1.00 (m, J=7.84, 7.84 Hz, 30H), 1.06-1.12 (m, 6H), 1.13-1.17 (m, 7H), 1.22 (d, J=6.50 Hz, 3H), 1.24 (d, J=6.88 Hz, 3H), 1.30 (s, 3H), 1.30-1.35 (m, 1H), 1.42 (dd, J=14.72, 4.78 Hz, 1H), 1.55-1.72 (m, 3H), 2.15-2.19 (m, 1H), 2.18 (s, 6H), 2.31-2.38 (m, 1H), 2.43-2.52 (m, 1H), 2.52-2.60 (m, 1H), 3.12 (dd, J=9.75, 7.07 Hz, 1H), 3.18 (d, J=9.17 Hz, 1H), 3.28 (s, 3H), 3.29 (s, 3H), 3.32-3.43 (m, 2H), 3.51-3.60 (m, 1H), 3.72 (d, J=7.65 Hz, 1H), 3.83-3.88 (m, 1H), 4.19-4.29 (m, 1H), 4.43 (d, J=7.26 Hz, 1H), 4.85 (d, J=4.59 Hz, 1H)

Example 2

Synthesis of the Compound of the Formula (A) Wherein R=Hydrogen Atom and R'=Triethylsilyl (1) By using (9S)-9,2',4"-O-tris(triethylsilyl)-9-dihydroerythromycin A (100 g) as a starting material, a 10-carboxy compound (53.4 g) was obtained in the same manner as that of Example 1, (1).

(2) The compound obtained in (1) mentioned above (53 g) was dissolved in tetrahydrofuran (700 ml), and the solution was added with triethylamine (8.0 ml). Then, the mixture was added dropwise with isobutyl chloroformate (7.0 ml) under ice cooling, and then the mixture was stirred for 30 minutes. Then, the reaction mixture was bubbled with ammonia gas for 1 hour under ice cooling. The reaction mixture was filtered, then the filtrate was concentrated under reduced pressure, and the resulting residue was purified by silica gel column chromatography (hexane:acetone:triethylamine=30:10:0.2) to obtain a 10-amide compound (36.1 g).

(3) The compound obtained in (2) mentioned above (17.3 g) was dissolved in ethyl acetate (340 ml), the solution was added with iodobenzenediacetate (10.2 g), and the mixture was stirred at room temperature for 14 hours. The reaction mixture was added with saturated aqueous sodium hydrogencarbonate, the layers were separated, and the organic layer was dried over sodium sulfate and filtered. The filtrate was concentrated under reduced pressure, and the resulting residue was dissolved in tetrahydrofuran (90 ml). The solution was added with an aqueous solution (30 ml) of lithium hydroxide (3.3 g), and the mixture was stirred at room temperature for 2.5 hours. The reaction mixture was added with saturated ammonium chloride, and the mixture was concentrated under reduced pressure. The residue was added with ethyl acetate, the layers were separated, and the organic layer was washed with saturated brine, and then dried over sodium sulfate and filtered. The filtrate was concentrated under reduced pressure, and the resulting residue was purified by silica gel column chromatography (chloroform:methanol:28% aqueous ammonia=9:1:0.1) to obtain the title compound (6.8 g).

MS (ESI) m/z=979.9 [M+H]$^+$ $^1$H-NMR (300 MHz, CDCl$_3$) δ (ppm): 0.49-0.76 (m, 18H), 0.84-1.04 (m, 30H), 1.03-1.37 (m, 23H), 1.37-1.72 (m, 3H), 1.77-1.93 (m, 1H), 2.01-2.18 (m, 1H), 2.19 (s, 6H), 2.32 (d, J=15.23 Hz, 1H), 2.38-2.56 (m, 2H), 3.13-3.29 (m, 3H), 3.30 (s, 3H), 3.37-3.54 (m, 1H), 3.56 (d, J=6.84 Hz, 1H), 3.62 (s, 1H), 3.64-3.80 (m, 1H), 4.13 (d, J=4.97 Hz, 1H), 4.17-4.30 (m, 1H), 4.60 (d, J=6.68 Hz, 1H), 4.64 (d, J=4.35 Hz, 1H)

Example 3

Synthesis of the Compound of the Formula (A) Wherein R=Hydrogen Atom and R'=Benzyl (1) (9S)-2'-O-Acetyl-9-dihydroerythromycin A (8.51 g) obtained by the method described in the literature (Journal of Organic Chemistry, 1982, vol. 47, p. 5019) was dissolved in tetrahydrofuran (85 ml), the solution was added with benzyl bromide (1.37 ml), and the mixture was stirred at room temperature for 3 minutes. Then, the mixture was added with potassium hydroxide (3.1 g), and the mixture was stirred at room temperature for 1.5 hours. The reaction mixture was added with saturated aqueous ammonium chloride, and the aqueous layer was extracted with ethyl acetate. The resulting organic layer was successively washed with saturated aqueous ammonium chloride, distilled water and saturated brine, then dried over anhydrous magnesium sulfate and filtered. The filtrate was concentrated under reduced pressure to obtain a 9-O-benzyl compound (8.6 g).

(2) The compound obtained in (1) mentioned above (8.6 g) was dissolved in methanol (500 ml), and the solution was stirred for 8 hours under reflux by heating. The reaction mixture was concentrated under reduced pressure, and the resulting residue was purified by silica gel column chromatography (chloroform:methanol:28% aqueous ammonia=40:1:0.1 to 30:1:0.1) to obtain a deacetylated compound (5.54 g).

(3) The compound obtained in (2) mentioned above (5.54 g) was dissolved in dimethylformamide (70 ml), and the solution was successively added with imidazole (3.4 g) and triethylchlorosilane (2.8 ml). The reaction mixture was stirred at room temperature for 63 hours, and then successively added with imidazole (850 mg) and triethylchlorosilane (0.7 ml), and the mixture was stirred at room temperature for 24 hours. The reaction mixture was added with saturated aqueous ammonium chloride and ethyl acetate, the layers were separated, and the aqueous layer was extracted with ethyl acetate. The organic layer was successively washed with saturated aqueous ammonium chloride, distilled water and saturated brine, then dried over anhydrous magnesium sulfate and filtered. The filtrate was concentrated under reduced pressure, and the resulting residue was purified by silica gel column chromatography (acetone:hexane=40:1 to 20:1) to obtain (9S)-9-O-benzyl-2',4"-O-bis(triethylsilyl)-9-dihydroerythromycin A (5.8 g).

(4) By using the compound obtained in (3) mentioned above (2.0 g) as a starting material, the title compound (264 mg) was obtained in the same manner as that of Example 1.
MS (ESI) m/z=955.9 [M+H]$^+$
$^1$H-NMR (300 MHz, CDCl$_3$) δ (ppm): 0.45-1.42 (m, 60H), 1.49-1.90 (m, 4H), 2.08-2.55 (m, 3H), 2.18 (s, 6H), 2.63-2.82 (m, 1H), 3.10-3.34 (m, 2H), 3.29 (s, 3H), 3.34-3.50 (m, 2H), 3.52-3.87 (m, 3H), 4.04-4.35 (m, 2H), 4.45-4.82 (m, 3H), 7.12-7.45 (m, 5H)

Example 4

Synthesis of the compound of the formula (A) wherein R=hydrogen atom and R'=2-(N-benzyloxycarbonyl)aminoethyl (1) By using (9S)-2'-O-acetyl-9-dihydroerythromycin A (10 g) and 2-bromoethylamine hydrobromide (3.95 g) as starting materials, a 9-O-(2-aminoethyl) compound (4.8 g) was obtained in the same manner as that of Example 3, (1).
(2) The compound obtained in (1) mentioned above (4.7 g) was dissolved in chloroform, the solution was successively added with an aqueous solution (25 ml) of sodium hydrogencarbonate (961 mg) and benzyl chloroformate (0.9 ml), and the mixture was stirred at room temperature for 1 hour. The layers of the reaction mixture were separated, and the aqueous layer was extracted with ethyl acetate. The organic layer was washed successively with distilled water and saturated brine, then dried over anhydrous magnesium sulfate and filtered. The filtrate was concentrated under reduced pressure to obtain an N-benzyloxycarbonyl compound (4.9 g).
(3) By using the compound obtained in (2) mentioned above (4.9 g) as a starting material, the title compound (313 mg) was obtained in the same manners as those of Example 3, (2), (3), and Example 1.
MS (ESI) m/z=1042.9 [M+H]$^+$
$^1$H-NMR (600 MHz, CDCl$_3$) δ (ppm): 0.46-0.71 (m, 18H), 0.80-1.88 (m, 46H), 2.04-2.31 (m, 2H), 2.17 (s, 6H), 2.34-2.52 (m, 2H), 2.55-2.69 (m, 1H), 2.94-3.85 (m, 10H), 3.27 (s, 3H), 4.09-4.29 (m, 2H), 4.45-4.76 (m, 2H), 5.01-5.15 (m, 2H), 7.18-7.40 (m, 5H)

Example 5

Synthesis of the compound of the formula (A) wherein R=hydrogen atom and R'=2-benzyloxyethyl By using (9S)-2'-O-acetyl-9-dihydroerythromycin A (10 g) and benzyl 2-bromoethyl ether (4.73 g) as starting materials, the title compound (321 mg) was obtained in the same manners as those of Example 3, (1), (2), (3) and Example 1.
MS (ESI) m/z=1000.0 [M+H]$^+$
$^1$H-NMR (600 MHz, CDCl$_3$) δ (ppm): 0.49-0.70 (m, 18H), 0.79-1.86 (m, 46H), 2.09-2.22 (m, 1H), 2.17 (s, 6H), 2.24-2.38 (m, 1H), 2.38-2.55 (m, 2H), 3.10-3.37 (m, 4H), 3.31 (s, 3H), 3.42-3.81 (m, 5H), 3.85-3.94 (m, 1H), 4.04-4.26 (m, 2H), 4.46-4.60 (m, 2H), 4.66-4.85 (m, 2H), 7.13-7.41 (m, 5H)

Example 6

Synthesis of the Compound of the Formula (A) Wherein R=Propargyl and R'=Triethylsilyl By using (9S)-9,2',4''-O-tris(triethylsilyl)-9-dihydro-6-O-propargylerythromycin A (48.4 g) as a starting material, the title compound (13.8 g) was obtained in the same manner as that of Example 1.
MS (ESI) m/z=1017.9 [M+H]$^+$ Syntheses of Examples 7 to 108

Preparation methods of the compounds of the formula (B) having R defined in Table 1 are shown below.

TABLE 1

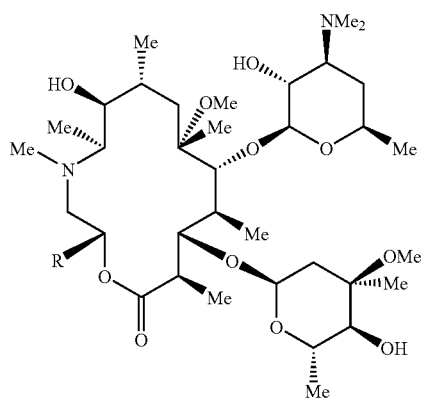

formula (B)

| Example | R | ESI MS (M + H) | $^1$H-NMR, CDCl$_3$, δ (ppm) |
|---|---|---|---|
| 7 | (branched alkyl with Me) | 719.2 | (300 MHz): 0.82 (d, J = 6.99 Hz, 6H) 0.90 (t, J = 7.38 Hz, 3H) 1.06-1.28 (m, 5H) 1.11 (d, J = 7.31 Hz, 3H) 1.17 (d, J = 7.46 Hz, 3H) 1.24 (s, 3H) 1.29 (d, J = 6.22 Hz, 3H) 1.33 (s, 3H) 1.50-1.91 (m, 5H) 2.11-2.54 (m, 7H) 2.29 (s, 6H) 2.37 (s, 3H) 2.76-2.95 (m, 2H) 3.01 (t, J = 8.63 Hz, 1H) 3.18-3.23 (m, 1H) 3.24 (s, 3H) 3.33 (s, 3H) 3.39-3.52 (m, 2H) 3.71 (d, J = 8.24 Hz, 1H) 4.02-4.10 (m, 1H) 4.17 (d, J = 4.35 Hz, 1H) 4.40 (d, J = 7.15 Hz, 1H) 4.61-4.68 (m, 1H) 4.95 (d, J = 4.51 Hz, 1H) |

TABLE 1-continued formula (B)

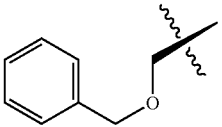

| Example | R | ESI MS (M + H) | $^1$H-NMR, CDCl$_3$, δ (ppm) |
|---|---|---|---|
| 8 | H | 691.5 | (500 MHz): 0.81-0.89 (m, 6H) 1.10 (d, J = 7.65 Hz, 3H) 1.10-1.29 (m, 5H) 1.18 (d, J = 7.65 Hz, 3H) 1.25 (s, 3H) 1.30 (d, J = 6.12 Hz, 3H) 1.34 (s, 3H) 1.53-1.58 (m, 1H) 1.64-1.73 (m, 1H) 1.85-1.94 (m, 1H) 2.17-2.60 (m, 16H) 2.76-2.83 (m, 1H) 2.84-2.92 (m, 1H) 3.02 (t, J = 9.94 Hz, 1H) 3.21-3.25 (m, 1H) 3.26 (s, 3H) 3.34 (s, 3H) 3.46-3.55 (m, 2H) 3.73 (d, J = 7.65 Hz, 1H) 3.75-3.86 (m, 1H) 4.03-4.09 (m, 1H) 4.15 (d, J = 3.82 Hz, 1H) 4.36-4.40 (m, 1H) 4.42 (d, J = 6.88 Hz, 1H) 4.88 (d, J = 4.59 Hz, 1H) |
| 9 |  | 811.5 | (300 MHz): 0.80-0.88 (m, 6H) 1.10 (d, J = 7.15 Hz, 3H) 1.10-1.22 (m, 2H) 1.16 (d, J = 7.31 Hz, 3H) 1.20-1.26 (m, 3H) 1.24 (s, 3H) 1.29 (d, J = 6.06 Hz, 3H) 1.33 (s, 3H) 1.54 (dd, J = 15.31, 4.90 Hz, 1H) 1.63-1.72 (m, 1H) 1.81-1.93 (m, 1H) 2.17-2.55 (m, 7H) 2.30 (s, 6H) 2.33 (s, 3H) 2.76-2.86 (m, 1H) 2.90 (d, J = 13.99 Hz, 1H) 3.01 (t, J = 9.71 Hz, 1H) 3.17-3.25 (m, 1H) 3.24 (s, 3H) 3.33 (s, 3H) 3.40-3.52 (m, 2H) 3.53-3.70 (m, 2H) 3.71 (d, J = 7.93 Hz, 1H) 4.06 (dd, J = 9.17, 6.37 Hz, 1H) 4.15 (d, J = 4.04 Hz, 1H) 4.40 (d, J = 6.84 Hz, 1H) 4.53 (s, 2H) 4.93 (d, J = 4.82 Hz, 1H) 4.98 (s, 1H) 7.25-7.39 (m, 5H) |
| 10 | 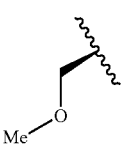 | 719.3 | |
| 11 |  | 735.3 | (500 MHz): 0.85 (d, 6H) 1.11 (d, J = 7.65 Hz, 3H) 1.12-1.35 (m, 2H) 1.18 (d, J = 7.65 Hz, 2H) 1.24 (d, J = 6.12 Hz, 3H) 1.25 (s, 3H) 1.30 (d, J = 6.12 Hz, 3H) 1.33 (s, 3H) 1.52-1.71 (m, 2H) 1.84-1.91 (m, 1H) 2.21-2.54 (m, 6H) 2.30 (s, 6H) 2.35 (s, 3H) 2.79-2.91 (m, 2H) 3.02 (t, J = 9.94 Hz, 1H) 3.20-3.24 (m, 1H) 3.25 (s, 3H) 3.34 (s, 3H) 3.36 (s, 3H) 3.43-3.52 (m, 3H) 3.57 (dd, J = 9.94, 6.12 Hz, 1H) 3.72 (d, J = 7.65 Hz, 1H) 4.03-4.10 (m, 1H) 4.12-4.16 (m, 1H) 4.41 (d, J = 7.65 Hz, 1H) 4.90-4.95 (m, 2H) |
| 12 | 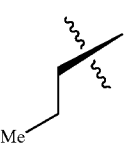 | 705.4 | (300 MHz): 0.81-0.91 (m, 6H) 1.06-1.23 (m, 2H) 1.11 (d, J = 7.31 Hz, 3H) 1.16 (d, J = 7.46 Hz, 3H) 1.19-1.27 (m, 9H) 1.29 (d, J = 6.22 Hz, 3H) 1.32 (s, 3H) 1.55 (dd, J = 15.15, 4.90 Hz, 1H) 1.60-1.70 (m, 1H) 1.90 (s, 1H) 2.08-2.21 (m, 1H) 2.21-2.42 (m, 4H) 2.29 (s, 6H) 2.37 (s, 3H) 2.45-2.54 (m, 2H) 2.70-2.81 (m, 1H) 2.89 (d, J = 14.77 Hz, 1H) 3.02 (t, J = 8.39 Hz, 1H) 3.17-3.25 (m, 1H) 3.26 (s, 3H) 3.34 (s, 3H) 3.38-3.57 (m, 2H) 3.72 (d, J = 7.77 Hz, 1H) 3.99-4.11 (m, 1H) 4.13 (s, 1H) 4.42 (d, J = 7.15 Hz, 1H) 4.86 (s, 1H) 4.90 (d, J = 4.51 Hz, 1H) |
| 13 | 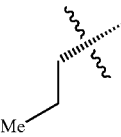 | 733.4 | (300 MHz): 0.82 (d, J = 6.99 Hz, 6H) 0.91 (t, J = 7.07 Hz, 3H) 1.10 (d, J = 7.46 Hz, 3H) 1.11-1.91 (m, 15H) 1.16 (d, J = 7.31 Hz, 3H) 1.29 (d, J = 6.22 Hz, 3H) 1.33 (s, 3H) 2.06-2.54 (m, 7H) 2.30 (s, 6H) 2.37 (s, 3H) 2.74-2.85 (m, 1H) 2.88-2.96 (m, 1H) 3.01 (t, J = 9.87 Hz, 1H) 3.18-3.25 (m, 1H) 3.23 (s, 3H) 3.33 (s, 3H) 3.37-3.53 (m, 2H) 3.71 (d, J = 8.24 Hz, 1H) 4.01-4.11 (m, 1H) 4.17 (d, J = 5.28 Hz, 1H) 4.39 (d, J = 7.15 Hz, 1H) 4.69-4.77 (m, 1H) 4.95 (d, J = 4.97 Hz, 1H) |
| 14 | 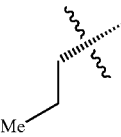 | 733.5 | (300 MHz): 0.92 (t, J = 7.23 Hz, 3H) 0.95-1.79 (m, 27H) 1.13 (d, J = 7.31 Hz, 3H) 1.29 (s, 3H) 2.06-2.39 (m, 6H) 2.24 (s, 3H) 2.31 (s, 6H) 2.45-2.85 (m, 3H) 3.01 (t, J = 9.64 Hz, 1H) 3.21-3.41 (m, 8H) 3.48-3.60 (m, 1H) 3.82 (d, J = 6.84 Hz, 1H) 3.96-4.07 (m, 1H) 4.27-4.34 (m, 1H) 4.53 (d, J = 7.62 Hz, 1H) 4.66 (d, J = 4.97 Hz, 1H) 4.86-5.00 (m, 1H) |

TABLE 1-continued formula (B)

[Structure of macrolide compound with R substituent]

| Example | R | ESI MS (M + H) | ¹H-NMR, CDCl₃, δ (ppm) |
|---|---|---|---|
| 15 | [sec-pentyl group] | 747.5 | (300 MHz): 0.82 (d, J = 6.84 Hz, 6H) 0.89 (t, J = 6.84 Hz, 3H) 1.04-1.37 (m, 6H) 1.10 (d, J = 7.46 Hz, 3H) 1.16 (d, J = 7.46 Hz, 3H) 1.21-1.25 (m, 3H) 1.24 (s, 3H) 1.29 (d, J = 6.37 Hz, 3H) 1.33 (s, 3H) 1.48-1.59 (m, 1H) 1.59-1.93 (m, 3H) 2.07-2.20 (m, 1H) 2.21-2.42 (m, 4H) 2.29 (s, 6H) 2.37 (s, 3H) 2.41-2.54 (m, 2H) 2.80 (dd, J = 7.46, 5.44 Hz, 1H) 2.91 (d, J = 16.16 Hz, 1H) 3.01 (t, J = 9.56 Hz, 1H) 3.16-3.23 (m, 1H) 3.23 (s, 3H) 3.33 (s, 3H) 3.38-3.52 (m, 2H) 3.71 (d, J = 8.08 Hz, 1H) 4.00-4.12 (m, 1H) 4.17 (d, J = 5.28 Hz, 1H) 4.39 (d, J = 7.31 Hz, 1H) 4.71 (s, 1H) 4.95 (d, J = 4.35 Hz, 1H) |
| 16 | [benzyloxymethyl group] | 811.5 | (300 MHz): 0.95 (d, J = 6.99 Hz, 3H) 1.00 (d, J = 7.31 Hz, 3H) 1.01-1.23 (m, 2H) 1.08-1.18 (m, 6H) 1.11-1.27 (m, 9H) 1.29 (s, 3H) 1.47-1.81 (m, 3H) 1.92-2.99 (m, 9H) 2.23 (s, 3H) 2.29 (s, 6H) 3.19-3.29 (m, 1H) 3.30 (s, 3H) 3.35 (s, 3H) 3.42-3.58 (m, 2H) 3.64 (t, J = 4.97 Hz, 2H) 3.80 (d, J = 6.68 Hz, 1H) 3.89-4.09 (m, 1H) 4.36 (s, 1H) 4.45-4.52 (m, 2H) 4.52 (s, 2H) 5.20 (s, 1H) 7.27-7.39 (m, 5H) |
| 17 | [Cbz-NH-ethyl group] | 854.6 | (300 MHz): 0.78-0.90 (m, 6H) 1.05-1.16 (m, 6H) 1.12-1.22 (m, 2H) 1.20-1.24 (m, 3H) 1.24 (s, 3H) 1.29 (d, J = 6.37 Hz, 3H) 1.32 (s, 3H) 1.49-1.58 (m, 1H) 1.60-1.71 (m, 1H) 1.87 (s, 1H) 2.18-2.39 (m, 5H) 2.29 (s, 6H) 2.35 (s, 3H) 2.40-2.54 (m, 2H) 2.73-2.84 (m, 1H) 2.91-3.01 (m, 1H) 3.01 (t, J = 9.87 Hz, 1H) 3.16-3.23 (m, 1H) 3.24 (s, 3H) 3.33 (s, 3H) 3.34-3.56 (m, 4H) 3.70 (d, J = 8.08 Hz, 1H) 3.98-4.14 (m, 2H) 4.40 (d, J = 7.31 Hz, 1H) 4.85 (s, 1H) 4.90 (d, J = 4.82 Hz, 1H) 5.05 (s, 1H) 5.09 (s, 2H) 7.28-7.39 (m, 5H) |
| 18 | [Cbz-NH-propyl group] | 854.5 | (300 MHz): 0.88-0.99 (m, 6H) 1.02-1.23 (m, 2H) 1.07 (d, J = 7.15 Hz, 3H) 1.13 (d, J = 7.46 Hz, 3H) 1.18-1.30 (m, 12H) 1.47-1.71 (m, 2H) 1.80-2.63 (m, 7H) 2.16 (s, 3H) 2.27 (s, 6H) 2.76 (t, J = 10.26 Hz, 1H) 2.93-3.10 (m, 2H) 3.15-3.70 (m, 5H) 3.27 (s, 3H) 3.37 (s, 3H) 3.77 (d, J = 6.37 Hz, 1H) 3.94-4.06 (m, 1H) 4.39 (d, J = 5.60 Hz, 1H) 4.50 (s, 1H) 4.56 (d, J = 7.46 Hz, 1H) 4.90-5.16 (m, 2H) 5.37-5.50 (m, 1H) 7.03 (s, 1H) 7.27-7.40 (m, 5H) |
| 19 | [pyrrol-1-yl-methyl group] | 770.6 | (300 MHz): 0.80-0.87 (m, 6H) 0.92 (d, J = 7.31 Hz, 3H) 1.08 (d, J = 7.46 Hz, 3H) 1.12-1.17 (m, 1H) 1.18-1.25 (m, 1H) 1.20-1.24 (m, 3H) 1.22 (s, 3H) 1.28 (d, J = 6.22 Hz, 3H) 1.33 (s, 3H) 1.49 (dd, J = 15.39, 4.97 Hz, 1H) 1.62-1.73 (m, 1H) 1.86 (s, 1H) 2.19-2.36 (m, 5H) 2.30 (s, 6H) 2.40 (s, 3H) 2.42-2.54 (m, 2H) 2.64-2.75 (m, 1H) 2.93-3.08 (m, 2H) 3.16-3.26 (m, 1H) 3.21 (s, 3H) 3.30 (s, 3H) 3.39-3.54 (m, 2H) 3.68 (d, J = 7.93 Hz, 1H) 3.97-4.08 (m, 3H) 4.09-4.21 (m, 1H) 4.38 (d, J = 6.99 Hz, 1H) 4.85 (d, J = 4.51 Hz, 1H) 4.99 (s, 1H) 6.10 (t, J = 2.10 Hz, 2H) 6.63 (t, J = 2.10 Hz, 2H) |
| 20 | [pyrrol-1-yl-methyl group] | 770.5 | (300 MHz): 0.79-0.88 (m, 6H) 0.92 (d, J = 5.91 Hz, 3H) 1.08 (d, J = 7.48 Hz, 3H) 1.12-1.18 (m, 1H) 1.19-1.25 (m, 1H) 1.19-1.25 (m, 6H) 1.28 (d, J = 6.06 Hz, 3H) 1.33 (s, 3H) 1.45-1.54 (m, 1H) 1.61-1.73 (m, 1H) 1.86 (s, 1H) 2.19-2.36 (m, 5H) 2.31 (s, 6H) 2.40 (s, 3H) 2.43-2.57 (m, 2H) 2.66-2.75 (m, 1H) 2.94-3.08 (m, 2H) 3.16-3.26 (m, 1H) 3.21 (s, 3H) 3.30 (s, 3H) 3.39-3.51 (m, 2H) 3.68 (d, J = 7.93 Hz, 1H) 3.97-4.19 (m, 4H) 4.38 (d, J = 6.99 Hz, 1H) 4.85 (d, J = 4.20 Hz, 1H) 5.00 (s, 1H) 6.10 (t, J = 2.41 Hz, 2H) 6.63 (t, J = 2.10 Hz, 2H) |

TABLE 1-continued formula (B)

| Example | R | ESI MS (M + H) | $^1$H-NMR, CDCl$_3$, δ (ppm) |
|---|---|---|---|
| 21 | (CH$_2$-N(Me)Me group) | 748.5 | (300 MHz): 0.80-0.90 (m, 6H) 1.12 (d, 3H) 1.11-1.24 (m, 2H) 1.17 (d, J = 7.31 Hz, 3H) 1.21-1.28 (m, 3H) 1.25 (s, 3H) 1.30 (d, J = 6.22 Hz, 3H) 1.34 (s, 3H) 1.50-1.56 (m, 1H) 1.60-1.72 (m, 1H) 1.81-1.96 (m, 1H) 2.13-2.57 (m, 9 H) 2.24 (s, 6H) 2.30 (s, 6H) 2.39 (s, 3H) 2.80 (dd, J = 6.61, 5.21 Hz, 1H) 2.89 (d, J = 15.39 Hz, 1H) 3.02 (t, J = 9.87 Hz, 1H) 3.18-3.24 (m, 1H) 3.25 (s, 3H) 3.34 (s, 3H) 3.38-3.56 (m, 2H) 3.72 (d, J = 7.62 Hz, 1H) 4.07 (dd, J = 9.71, 6.45 Hz, 1H) 4.17 (d, J = 5.60 Hz, 1H) 4.41 (d, J = 7.46 Hz, 1H) 4.86-4.92 (m, 1H) 4.94 (d, J = 4.35 Hz, 1H) |
| 22 | (morpholinomethyl) | 790.8 | (300 MHz): 0.79-0.87 (m, 6H) 1.11 (d, J = 7.15 Hz, 3H) 1.11-1.26 (m, 2H) 1.18 (d, J = 7.62 Hz, 3H) 1.21-1.25 (m, 3H) 1.24 (s, 3H) 1.29 (d, J = 6.22 Hz, 3H) 1.33 (s, 3H) 1.49-1.56 (m, 1H) 1.66 (d, J = 13.21 Hz, 1H) 1.87 (s, 1H) 2.19-2.62 (m, 13H) 2.29 (s, 6H) 2.37 (s, 3H) 2.76-2.83 (m, 1H) 2.88 (d, J = 15.39 Hz, 1H) 2.96-3.07 (m, 1H) 3.15-3.23 (m, 1H) 3.23 (s, 3H) 3.33 (s, 3H) 3.46 (t, 2H) 3.65 (t, J = 5.05 Hz, 4H) 3.71 (d, J = 8.24 Hz, 1H) 4.06 (dd, J = 9.25, 6.14 Hz, 1H) 4.12 (d, J = 4.20 Hz, 1H) 4.39 (d, J = 7.31 Hz, 1H) 4.93 (d, J = 4.51 Hz, 1H) 4.98 (s, 1H) |
| 23 | (3-(furan-2-yl)phenylacetamido-ethyl) | 918.8 | (500 MHz): 0.78-0.86 (m, 6H) 1.04-1.11 (m, 6H) 1.19-1.33 (m, 2H) 1.22 (d, J = 6.12 Hz, 3H) 1.24 (s, 3H) 1.29 (d, J = 6.12 Hz, 3H) 1.31 (s, 3H) 1.47-1.91 (m, 5H) 2.05-2.40 (m, 15H) 2.40-2.56 (m, 2H) 2.70-2.78 (m, 1H) 2.82-2.92 (m, 1H) 3.01 (t, J = 9.94 Hz, 1H) 3.18-3.25 (m, 1H) 3.22 (s, 3H) 3.31 (s, 3H) 3.33-3.52 (m, 3H) 3.58 (s, 2H) 3.69 (d, J = 8.41 Hz, 1H) 3.98-4.12 (m, 2H) 4.39 (d, J = 6.88 Hz, 1H) 4.67-4.80 (m, 1H) 4.86 (d, J = 4.59 Hz, 1H) 5.64-5.87 (m, 1H) 6.44-6.49 (m, 1H) 6.67 (d, J = 3.82 Hz, 1H) 7.16 (d, J = 7.65 Hz, 1H) 7.33-7.38 (m, 1H) 7.44-7.47 (m, 1H) 7.55-7.60 (m, 2H) |
| 24 | (3-(furan-2-yl)phenylacetamido-ethyl) | 918.7 | (500 MHz): 0.75-0.88 (m, 6H) 1.03-1.11 (m, 6H) 1.10-1.21 (m, 2H) 1.22 (d, J = 6.12 Hz, 3H) 1.24 (s, 3H) 1.29 (d, J = 6.12 Hz, 3H) 1.31 (s, 3H) 1.52 (dd, 1H) 1.58-1.91 (m, 4H) 2.07-2.15 (m, 1H) 2.18-2.37 (m, 4H) 2.26-2.34 (m, 9H) 2.38-2.54 (m, 2H) 2.67-2.80 (m, 1H) 2.82-2.92 (m, 1H) 2.96-3.05 (m, 2H) 3.22 (s, 3H) 3.18-3.21 (m, 1H) 3.26-3.42 (m, 2H) 3.31 (s, 3H) 3.42-3.52 (m, 1H) 3.57 (s, 2H) 3.69 (d, J = 8.41 Hz, 1H) 3.97-4.12 (m, 2H) 4.39 (d, J = 6.88 Hz, 1H) 4.72 (s, 1H) 4.86 (d, J = 4.59 Hz, 1H) 5.64-5.97 (m, 1H) 6.44-6.48 (m, 1H) 6.67 (d, J = 3.82 Hz, 1H) 7.16 (d, J = 7.65 Hz, 1H) 7.35 (t, J = 8.03 Hz, 1H) 7.46 (d, J = 1.53 Hz, 1H) 7.55-7.60 (m, 2H) |
| 25 | (benzo[d]isoxazol-3-yl-acetamido-ethyl) | 893.5 | (300 MHz): 0.76-0.89 (m, 6H) 1.05-1.16 (m, 6H) 1.13-1.21 (m, 2H) 1.23 (d, J = 6.06 Hz, 3H) 1.26 (s, 3H) 1.30 (d, J = 6.37 Hz, 3H) 1.32 (s, 3H) 1.46-1.97 (m, 5H) 2.06-2.35 (m, 4H) 2.29 (s, 6H) 2.32 (s, 3H) 2.38 (d, J = 15.54 Hz, 1H) 2.42-2.55 (m, 2H) 2.71-2.84 (m, 1H) 2.88 (d, J = 13.99 Hz, 1H) 2.96-3.12 (m, 2H) 3.16-3.24 (m, 1H) 3.24 (s, 3H) 3.34 (s, 3H) 3.36-3.56 (m, 3H) 3.71 (d, J = 8.08 Hz, 1H) 3.95 (s, 2H) 3.99-4.17 (m, 2H) 4.40 (d, J = 7.15 Hz, 1H) 4.75 (s, 1H) 4.89 (d, J = 4.66 Hz, 1H) 6.59 (s, 1H) 7.29-7.40 (m, 1H) 7.51-7.65 (m, 2H) 7.79 (d, J = 7.93 Hz, 1H) |

TABLE 1-continued formula (B)

| Example | R | ESI MS (M + H) | ¹H-NMR, CDCl₃, δ (ppm) |
|---|---|---|---|
| 26 | 2-(furan-2-yl)phenylacetamide | 918.6 | (300 MHz): 0.75-0.88 (m, 6H) 1.03-1.12 (m, 6H) 1.10-1.22 (m, 2H) 1.23 (d, J = 6.06 Hz, 3H) 1.25 (s, 3H) 1.30 (d, J = 6.37 Hz, 3H) 1.32 (s, 3H) 1.54 (dd, J = 15.23, 4.82 Hz, 1H) 1.66 (d, J = 11.19 Hz, 1H) 1.71-1.93 (m, 3H) 2.02-2.14 (m, 1H) 2.16-2.29 (m, 3H) 2.27-2.32 (m, 9H) 2.36 (d, J = 15.54 Hz, 1H) 2.39-2.54 (m, 2H) 2.71 (dd, J = 7.38, 5.52 Hz, 1H) 2.85 (d, J = 14.61 1H) 2.94-3.10 (m, 2H) 3.19 (d, J = 7.15 Hz, 1H) 3.23 (s, 3H) 3.25-3.52 (m, 3H) 3.32 (s, 3H) 3.69 (d, J = 8.08 Hz, 1H) 3.77 (s, 2H) 3.95-4.13 (m, 2H) 4.39 (d, J = 7.31 Hz, 1H) 4.63 (s, 1H) 4.88 (d, J = 4.51 Hz, 1H) 5.78 (s, 1H) 6.48 (dd, J = 3.42, 1.87 Hz, 1H) 6.57 (dd, J = 3.34, 0.70 Hz, 1H) 7.29-7.39 (m, 3H) 7.52-7.56 (m, 1H) 7.64-7.71 (m, 1H) |
| 27 | 4-(furan-2-yl)phenylacetamide | 918.6 | (300 MHz): 0.76-0.89 (m, 6H) 1.04-1.11 (m, J = 7.31 Hz, 6H) 1.10-1.22 (m, 2H) 1.18-1.26 (m, 6H) 1.29 (d, J = 6.22 Hz, 3H) 1.32 (s, 3H) 1.49 (dd, J = 15.31, 4.74 Hz, 1H) 1.60-1.94 (m, 4H) 2.04-2.40 (m, 5H) 2.29 (s, 6H) 2.33 (s, 3H) 2.41-2.54 (m, 2H) 2.70-2.79 (m, 1H) 2.89 (d, J = 14.46 Hz, 1H) 2.94-3.10 (m, 2H) 3.17-3.22 (m, 1H) 3.23 (s, 3H) 3.31 (s, 3H) 3.32-3.52 (m, 3H) 3.56 (s, 2H) 3.69 (d, J = 7.93 Hz, 1H) 3.97-4.13 (m, 2H) 4.39 (d, J = 7.15 Hz, 1H) 4.75 (s, 1H) 4.86 (d, J = 4.35 Hz, 1H) 5.83 (s, 1H) 6.47 (dd, J = 3.34, 1.79 Hz, 1H) 6.65 (d, J = 3.42 Hz, 1H) 7.27-7.34 (m, 2H) 7.43-7.49 (m, 1H) 7.65 (d, J = 8.24 Hz, 2H) |
| 28 | 3-(pyridin-2-yl)phenylacetamide | 929.6 | (300 MHz): 0.76-0.91 (m, 6H) 1.02-1.17 (m, 6H) 1.11-1.22 (m, 2H) 1.20-1.27 (m, 3H) 1.24 (s, 3H) 1.30 (d, J = 6.53 Hz, 3H) 1.32 (s, 3H) 1.51 (dd, J = 15.23, 4.66 Hz, 1H) 1.59-1.97 (m, 4H) 2.07-2.38 (m, 4H) 2.30 (s, 6H) 2.32 (s, 3H) 2.38-2.56 (m, 2H) 2.68-2.81 (m, 1H) 2.88 (d, J = 15.70 Hz, 1H) 2.94-3.10 (m, 2H) 3.13-3.22 (m, 1H) 3.22 (s, 3H) 3.27-3.55 (m, 3H) 3.32 (s, 3H) 3.65 (s, 2H) 3.70 (d, J = 7.93 Hz, 1H) 3.93-4.15 (m, 2H) 4.39 (d, J = 7.15 Hz, 1H) 4.75 (s, 1H) 4.87 (d, J = 4.66 Hz, 1H) 5.87 (s, 1H) 7.20-7.27 (m, 1H) 7.31-7.39 (m, 1H) 7.47 (t, J = 7.46 Hz, 1H) 7.70-7.79 (m, 2H) 7.85-7.98 (m, 2H) 8.69 (d, J = 4.66 Hz, 1H) |
| 29 | 3-(pyridin-3-yl)phenylacetamide | 929.6 | (300 MHz): 0.76-0.92 (m, 6H) 1.04-1.13 (m, 6H) 1.10-1.23 (m, 2H) 1.20-1.26 (m, 3H) 1.23-1.26 (m, 3H) 1.30 (d, J = 6.68 Hz, 3H) 1.32 (s, 3H) 1.50 (dd, J = 15.08, 4.82 Hz, 1H) 1.60-1.96 (m, 4H) 2.07-2.39 (m, 4H) 2.29 (s, 6H) 2.32 (s, 3H) 2.39-2.55 (m, 2H) 2.68-2.81 (m, 1H) 2.87 (d, J = 16.63 Hz, 1H) 2.93-3.08 (m, 2H) 3.15-3.22 (m, 1H) 3.23 (s, 3H) 3.32 (s, 3H) 3.30-3.55 (m, 3H) 3.63 (s, 2H) 3.70 (d, J = 7.93 Hz, 1H) 3.93-4.13 (m, 2H) 4.40 (d, J = 7.31 Hz, 1H) 4.78 (s, 1H) 4.86 (d, J = 4.35 Hz, 1H) 5.95 (s, 1H) 7.29-7.41 (m, 2H) 7.41-7.57 (m, 3H) 7.84-7.95 (m, 1H) 8.55-8.64 (m, 1H) 8.85 (d, J = 2.18 Hz, 1H) |

TABLE 1-continued formula (B)

[Structure of formula (B): macrolide with NMe2 sugar, OMe sugars, macrocyclic lactone with N-Me, and R group on the ring]

| Example | R | ESI MS (M + H) | ¹H-NMR, CDCl₃, δ (ppm) |
|---------|---|----------------|------------------------|
| 30 | [3-(furan-2-yl)phenyl]-CH₂-C(O)-N(Me)-CH₂-CH(~)- | 932.6 | (300 MHz): 0.78-0.85 (m, 6H) 1.06-1.12 (m, 6H) 1.11-1.35 (m, 8H) 1.17 (d, J = 7.62 Hz, 3H) 1.29 (d, J = 6.22 Hz, 3H) 1.46-2.08 (m, 5H) 2.08-2.52 (m, 7H) 2.27 (s, 3H) 2.29 (s, 6H) 2.34-2.37 (m, 3H) 2.75-2.88 (m, 1H) 2.91-3.05 (m, 2H) 3.17-3.57 (m, 5H) 3.23 (s, 3H) 3.32 (s, 3H) 3.66-3.76 (m, 3H) 4.00-4.09 (m, 1H) 4.13-4.19 (m, 1H) 4.39 (d, J = 7.46 Hz, 1H) 4.65-4.74 (m, 1H) 4.90-4.94 (m, 1H) 6.43-6.48 (m, 1H) 6.66 (dd, J = 3.34, 0.70 Hz, 1H) 7.11-7.17 (m, 1H) 7.33 (t, J = 7.85 Hz, 1H) 7.44-7.46 (m, 1H) 7.53-7.59 (m, 2H) |
| 31 | [3-(furan-2-yl)phenyl]-CH₂-C(O)-NH-CH₂-(~) | 904.5 | (300 MHz): 0.74-0.87 (m, 6H) 0.93 (d, J = 7.15 Hz, 3H) 1.04 (d, J = 8.08 Hz, 3H) 1.04-1.21 (m, 2H) 1.22 (d, J = 6.22 Hz, 3H) 1.25 (s, 3H) 1.28 (d, J = 6.37 Hz, 3H) 1.30 (s, 3H) 1.43-1.71 (m, 2H) 1.76-1.92 (m, 1H) 2.06-2.73 (m, 9H) 2.25-2.33 (m, 9H) 2.81-3.07 (m, 2H) 3.14-3.26 (m, 1H) 3.20 (s, 3H) 3.27-3.37 (m, 1H) 3.31 (s, 3H) 3.38-3.52 (m, 1H) 3.59 (s, 2H) 3.67 (d, J = 7.31 Hz, 1H) 3.95-4.13 (m, 1H) 4.38 (d, J = 7.15 Hz, 1H) 4.76 (s, 1H) 4.82 (d, J = 4.35 Hz, 1H) 5.86 (s, 1H) 6.47 (dd, J = 3.42, 1.87 Hz, 1H) 6.68 (d, J = 3.89 Hz, 1H) 7.14 (d, J = 8.08 Hz, 1H) 7.37 (t, J = 7.54 Hz, 1H) 7.43-7.48 (m, 1H) 7.51-7.64 (m, 2H) |
| 32 | [3-(furan-2-yl)phenyl]-CH₂-C(O)-NH-CH₂-CH₂-CH(~)- | 932.6 | (300 MHz): 0.78-0.85 (m, 6H) 1.06-1.34 (m, 14H) 1.29 (d, J = 6.22 Hz, 3H) 1.32 (s, 3H) 1.36-1.73 (m, 6H) 1.79-1.90 (m, 1H) 2.04-2.13 (m, 1H) 2.18-2.52 (m, 6H) 2.29 (s, 9H) 2.71-2.81 (m, 1H) 2.83-2.92 (m, 1H) 2.95-3.06 (m, 1H) 3.16-3.52 (m, 5H) 3.24 (s, 3H) 3.33 (s, 3H) 3.59 (s, 2H) 3.70 (d, J = 8.24 Hz, 1H) 4.00-4.15 (m, 2H) 4.39 (d, J = 7.15 Hz, 1H) 4.63-4.72 (m, 1H) 4.91 (d, J = 4.20 Hz, 1H) 5.46-5.54 (m, 1H) 6.48 (dd, J = 3.34, 1.79 Hz, 1H) 6.68 (d, J = 3.42 Hz, 1H) 7.15 (d, J = 7.77 Hz, 1H) 7.37 (t, J = 7.69 Hz, 1H) 7.48 (d, J = 1.09 Hz, 1H) 7.56-7.63 (m, 2H) |
| 33 | [3-(furan-2-yl)phenyl]-CH₂-NH-C(O)-CH₂-CH(~)- | 918.5 | (300 MHz): 0.83 (d, J = 6.99 Hz, 6H) 1.09 (d, J = 7.46 Hz, 3H) 1.13 (d, J = 7.46 Hz, 3H) 1.23 (d, J = 6.06 Hz, 3H) 1.22 (s, 3H) 1.29 (d, J = 8.22 Hz, 3H) 1.32 (s, 3H) 1.46-1.70 (m, 2H) 1.81-2.52 (m, 12H) 2.29 (s, 6H) 2.38 (s, 3H) 2.74-2.84 (m, 1H) 2.91-3.05 (m, 2H) 3.18-3.24 (m, 3H) 3.23 (s, 3H) 3.31 (s, 3H) 3.32-3.51 (m, 2H) 3.70 (d, J = 7.93 Hz, 1H) 3.99-4.09 (m, 1H) 4.10-4.16 (m, 1H) 4.39 (d, J = 6.99 Hz, 1H) 4.47 (d, J = 5.60 Hz, 2H) 4.74-4.82 (m, 1H) 4.89 (d, J = 4.35 Hz, 1H) 5.88-5.96 (m, 1H) 6.47 (dd, J = 3.34, 1.79 Hz, 1H) 6.67 (dd, J = 3.42, 0.78 Hz, 1H) 7.15-7.20 (m, 1H) 7.32-7.38 (m, 1H) 7.47 (dd, J = 1.67, 0.76 Hz, 1H) 7.56-7.60 (m, 2H) |

TABLE 1-continued formula (B)

| Example | R | ESI MS (M + H) | 1H-NMR, CDCl3, δ (ppm) |
|---|---|---|---|
| 34 | 3-(furan-2-yl)phenyl-CH2CH2-C(O)NH-CH2- | 918.6 | (300 MHz): 0.79-0.91 (m, 6H) 1.05-1.13 (m, 6H) 1.11-1.27 (m, 2H) 1.20-1.26 (m, 6H) 1.29 (d, J = 6.37 Hz, 3H) 1.32 (s, 3H) 1.49-1.58 (m, 1H) 1.62-1.73 (m, 1H) 1.78-1.97 (m, 1H) 2.12-2.39 (m, 4H) 2.29-2.30 (m, 6H) 2.32-2.34 (m, 3H) 2.39-2.56 (m, 4H) 2.71-2.64 (m, 1H) 2.86-3.09 (m, 4H) 3.15-3.24 (m, 1H) 3.23-3.26 (m, 3H) 3.25-3.41 (m, 3H) 3.31-3.32 (m, 3H) 3.40-3.53 (m, 1H) 3.70 (d, J = 7.77 Hz, 1H) 3.94-4.12 (m, 2H) 4.40 (d, J = 7.77 Hz, 1H) 4.70-4.94 (m, 2H) 5.93 (s, 1H) 6.47 (dd, J = 3.42, 1.71 Hz, 1H) 6.61-6.67 (m, 1H) 7.09 (d, J = 7.77 Hz, 1H) 7.26-7.34 (m, 1H) 7.43-7.47 (m, 1H) 7.48-7.54 (m, 2H) |
| 35 | 3-(furan-2-yl)phenyl-NH-C(O)-CH2CH2CH2- | 918.6 | (300 MHz): 0.86 (d, J = 6.84 Hz, 6H) 1.10 (d, J = 7.31 Hz, 3H) 1.11-1.27 (m, 2H) 1.17 (d, J = 7.31 Hz, 3H) 1.23 (d, J = 6.06 Hz, 3H) 1.23 (s, 3H) 1.30 (d, J = 6.37 Hz, 3H) 1.33 (s, 3H) 1.48-1.93 (m, 7H) 2.14-2.53 (m, 9H) 2.29 (s, 6H) 2.37 (s, 3H) 2.78-2.86 (m, 1H) 2.88-2.97 (m, 1H) 2.97-3.06 (m, 1H) 3.21 (dd, J = 10.26, 7.31 Hz, 1H) 3.27 (s, 3H) 3.32 (s, 3H) 3.36-3.53 (m, 2H) 3.72 (d, J = 7.93 Hz, 1H) 4.01-4.15 (m, 2H) 4.41 (d, J = 7.31 Hz, 1H) 4.86-4.92 (m, 1H) 4.94 (d, J = 4.51 Hz, 1H) 6.46 (dd, J = 3.34, 1.79 Hz, 1H) 6.67 (dd, J = 3.42, 0.78 Hz, 1H) 7.32 (t, J = 7.85 Hz, 1H) 7.38-7.42 (m, 1H) 7.46 (dd, J = 1.79, 0.70 Hz, 1H) 7.46-7.51 (m, 1H) 7.84 (s, 1H) |
| 36 | naphthalen-1-yl-CH2-C(O)NH-CH2- | 902.6 | (300 MHz): 0.73-0.86 (m, 6H) 1.00 (d, 3H) 1.06 (d, J = 7.15 Hz, 3H) 1.08-1.21 (m, 2H) 1.23 (d, J = 6.06 Hz, 3H) 1.26 (s, 3H) 1.28-1.35 (m, 6H) 1.46-1.73 (m, 4H) 1.75-1.91 (m, 1H) 1.93-2.08 (m, 1H) 2.10-2.54 (m, 5H) 2.23-2.26 (m, 3H) 2.27-2.30 (m, 6H) 2.60-2.70 (m, 1H) 2.78 (d, J = 15.85 Hz, 1H) 2.87-3.11 (m, 3H) 3.12-3.40 (m, 2H) 3.21-3.22 (m, 3H) 3.30-3.33 (m, 3H) 3.40-3.54 (m, 1H) 3.68 (d, J = 7.77 Hz, 1H) 3.98-4.10 (m, 2H) 4.01 (s, 2H) 4.38 (d, J = 7.46 Hz, 1H) 4.50 (s, 1H) 4.84 (d, J = 4.35 Hz, 1H) 5.67 (s, 1H) 7.36-7.58 (m, 4H) 7.77-7.90 (m, 2H) 7.92-7.99 (m, 1H) |
| 37 | 5-(furan-2-yl)pyridin-3-yl-CH2-C(O)NH-CH2- | 919.5 | (300 MHz): 0.80-0.91 (m, 6H) 1.04-1.17 (m, 6H) 1.10-1.20 (m, 2H) 1.23 (d, J = 5.91 Hz, 3H) 1.25 (s, 3H) 1.30 (d, J = 6.22 Hz, 3H) 1.32 (s, 3H) 1.45-1.97 (m, 5H) 2.02-2.56 (m, 6H) 2.28-2.30 (m, 6H) 2.32-2.35 (m, 3H) 2.61-3.09 (m, 5H) 3.15-3.23 (m, 1H) 3.24 (s, 3H) 3.33 (s, 3H) 3.35-3.53 (m, 2H) 3.56 (s, 2H) 3.71 (d, J = 8.08 Hz, 1H) 3.96-4.11 (m, 2H) 4.41 (d, J = 7.46 Hz, 1H) 4.73-4.94 (m, 2H) 6.08 (s, 1H) 6.50 (dd, J = 3.57, 2.02 Hz, 1H) 6.78 (d, J = 3.57 Hz, 1H) 7.49-7.54 (m, 1H) 7.89-7.95 (m, 1H) 8.40 (d, J = 2.18 Hz, 1H) 8.84 (d, J = 2.02 Hz, 1H) |

TABLE 1-continued

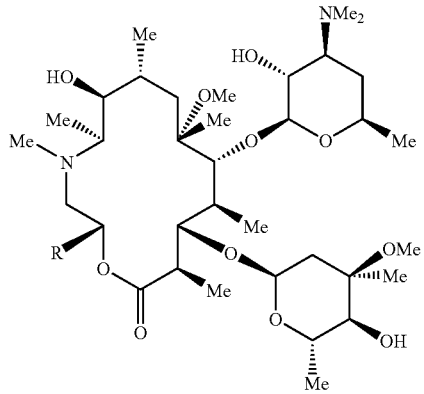

formula (B)

| Example | R | ESI MS (M + H) | $^1$H-NMR, CDCl$_3$, δ (ppm) |
|---|---|---|---|
| 38 | 3-(furan-2-yl)-N-(butyl)benzamide linker | 918.7 | (500 MHz): 0.84 (d, 6H) 1.09 (d, J = 7.40 Hz, 3H) 1.16 (d, J = 7.40 Hz, 3H) 1.15-1.76 (m, 8H) 1.21-1.23 (m, 3H) 1.23 (s, 3H) 1.28 (d, J = 6.31 Hz, 3H) 1.32 (s, 3H) 1.77-1.93 (m, 2H) 2.14-2.58 (m, 14H) 2.73-2.86 (m, 1H) 2.86-2.97 (m, 1H) 3.00 (t, J = 9.74 Hz, 1H) 3.17-3.27 (m, 1H) 3.24 (s, 3H) 3.31 (s, 3H) 3.34-3.60 (m, 4H) 3.71 (d, J = 7.68 Hz, 1H) 3.99-4.08 (m, 1H) 4.08-4.17 (m, 1H) 4.40 (d, J = 7.13 Hz, 1H) 4.77-4.88 (m, 1H) 4.91 (d, J = 4.66 Hz, 1H) 6.25-6.44 (m, 1H) 6.49 (dd, J = 3.29, 1.92 Hz, 1H) 6.71-6.77 (m, 1H) 7.44 (t, J = 7.68 Hz, 1H) 7.47-7.49 (m, 1H) 7.60-7.67 (m, 1H) 7.76-7.80 (m, 1H) 8.03-8.09 (m, 1H) |
| 39 | allyloxymethyl | 761.5 | (300 MHz): 0.78-0.89 (m, 6H) 1.10 (d, J = 7.31 Hz, 3H) 1.16 (d, J = 7.62 Hz, 3H) 1.18-1.27 (m, 2H) 1.20-1.27 (m, 3H) 1.24 (s, 3H) 1.29 (d, J = 6.22 Hz, 3H) 1.33 (s, 3H) 1.47-1.65 (m, 2H) 1.77-1.93 (m, 1H) 2.18-2.58 (m, 6H) 2.30 (s, 6H) 2.34 (s, 3H) 2.73-2.95 (m, 2H) 2.96-3.08 (m, 1H) 3.17-3.24 (m, 1H) 3.24 (s, 3H) 3.33 (s, 3H) 3.36-3.66 (m, 4H) 3.71 (d, J = 7.93 Hz, 1H) 3.95-4.01 (m, 2H) 4.01-4.10 (m, 1H) 4.10-4.18 (m, 1H) 4.40 (d, J = 7.46 Hz, 1H) 4.86-4.98 (m, 2H) 5.10-5.34 (m, 2H) 5.77-5.97 (m, 1H) |
| 40 | propargyloxymethyl | 759.5 | (300 MHz): 0.78-0.89 (m, 6H) 1.10 (d, J = 7.31 Hz, 3H) 1.17 (d, J = 7.46 Hz, 3H) 1.14-1.26 (m, J = 7.46 Hz, 2H) 1.20-1.26 (m, 6H) 1.29 (d, J = 6.22 Hz, 3H) 1.33 (s, 3H) 1.48-1.62 (m, 2H) 1.79-1.95 (m, 1H) 2.30 (s, 3H) 2.30 (s, 6H) 2.33-2.40 (m, 1H) 2.36 (s, 3H) 2.41-2.55 (m, 2H) 2.43 (t, J = 2.41 Hz, 1H) 2.76-2.85 (m, 1H) 2.90 (d, J = 14.14 Hz, 1H) 3.02 (t, J = 9.71 Hz, 1H) 3.16-3.23 (m, 1H) 3.24 (s, 3H) 3.33 (s, 3H) 3.35-3.52 (m, 2H) 3.55-3.64 (m, 1H) 3.67-3.79 (m, 2H) 4.01-4.16 (m, 2H) 4.16 (dd, J = 2.33, 1.71 Hz, 2H) 4.41 (d, J = 7.15 Hz, 1H) 4.88-5.01 (m, 2H) |
| 41 | 3-(furan-2-yl)phenyl allyl ether linker | | (300 MHz): 0.77-0.90 (m, 6H) 1.01-1.27 (m, 2H) 1.03-1.17 (m, 6H) 1.19-1.27 (m, 6H) 1.29 (d, J = 6.06 Hz, 3H) 1.33 (s, 3H) 1.44-1.75 (m, 2H) 1.78-1.93 (m, 1H) 2.15-2.58 (m, 6H) 2.30-2.32 (m, 6H) 2.35-2.37 (m, 3H) 2.71-3.10 (m, 3H) 3.16-3.34 (m, 1H) 3.23-3.25 (m, 3H) 3.30-3.32 (m, 3H) 3.36-3.58 (m, 4H) 3.71 (d, J = 8.24 Hz, 1H) 3.78-4.19 (m, 4H) 4.39 (d, J = 7.46 Hz, 1H) 4.81-5.06 (m, 3H) 6.09 (d, J = 5.28 Hz, 1H) 6.41-6.50 (m, 1H) 6.64 (d, J = 3.42 Hz, 1H) 7.04-7.15 (m, 1H) 7.17-7.34 (m, 2H) 7.40-7.55 (m, 2H) |
| 42 | 3-(furan-2-yl)phenyl propargyl ether linker | 901.6 | (300 MHz): 0.78-0.90 (m, 6H) 1.08 (d, J = 7.15 Hz, 3H) 1.09-1.22 (m, 2H) 1.17 (d, J = 7.46 Hz, 3H) 1.21-1.26 (m, 3H) 1.23 (s, 3H) 1.29 (d, J = 6.22 Hz, 3H) 1.33 (s, 3H) 1.46-1.70 (m, 2H) 1.79-1.96 (m, 1H) 2.18-2.58 (m, 6H) 2.30 (s, 6H) 2.38 (s, 3H) 2.76-3.07 (m, 3H) 3.17-3.24 (m, 1H) 3.25 (s, 3H) 3.32 (s, 3H) 3.36-3.54 (m, 2H) 3.60-3.89 (m, 3H) 4.05 (dd, J = 9.48, 6.37 Hz, 1H) 4.09-4.19 (m, 1H) 4.33-4.47 (m, 3H) 4.92 (d, J = 4.20 Hz, 1H) 4.99 (s, 1H) 6.48 (dd, J = 3.42, 1.71 Hz, 1H) 6.69 (dd, J = 3.42, 0.78 Hz, 1H) 7.30-7.35 (m, 2H) 7.45-7.49 (m, 1H) 7.59-7.66 (m, 1H) 7.73-7.77 (m, 1H) |

TABLE 1-continued

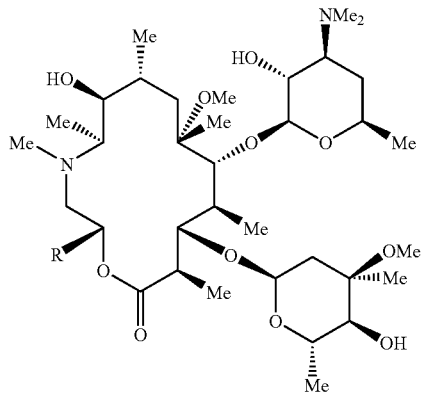

formula (B)

| Example | R | ESI MS (M + H) | $^1$H-NMR, CDCl$_3$, δ (ppm) |
|---|---|---|---|
| 43 | 3-(furan-2-yl)phenyl-(CH$_2$)$_3$-O- | 905.6 | (300 MHz): 0.79-0.90 (m, 6H) 1.02-1.37 (m, 2H) 1.06-1.13 (m, 3H) 1.16 (d, J = 7.46 Hz, 3H) 1.20-1.26 (m, 3H) 1.23-1.24 (m, 3H) 1.29 (d, J = 6.22 Hz, 3H) 1.33 (s, 3H) 1.54 (dd, J = 15.62, 5.05 Hz, 1H) 1.67 (d, J = 13.21 Hz, 1H) 1.78-1.95 (m, 3H) 2.16-2.41 (m, 5H) 2.29-2.31 (m, 6H) 2.34-2.36 (m, 3H) 2.42-2.55 (m, 2H) 2.64-2.75 (m, 2H) 2.76-2.86 (m, 1H) 2.91 (d, J = 15.39 Hz, 1H) 2.96-3.07 (m, 1H) 3.16-3.24 (m, 1H) 3.23-3.26 (m, 3H) 3.32 (s, 3H) 3.37-3.58 (m, 6H) 3.71 (d, J = 7.93 Hz, 1H) 3.99-4.21 (m, 2H) 4.40 (d, J = 7.15 Hz, 1H) 4.89-5.00 (m, 2H) 6.44-6.49 (m, 1H) 6.61-6.67 (m, 1H) 7.03-7.11 (m, 1H) 7.14-7.18 (m, 1H) 7.19-7.34 (m, 1H) 7.45-7.53 (m, 2H) |
| 44 | 3-(furan-2-yl)benzamido-(CH$_2$)$_5$- | 946.8 | (500 MHz): 0.78-0.86 (m, 6H) 1.04-1.88 (m, 16H) 1.08 (d, J = 7.13 Hz, 3H) 1.14 (d, J = 7.40 Hz, 3H) 1.23 (d, J = 9.87 Hz, 3H) 1.27 (d, J = 6.31 Hz, 3H) 1.31 (s, 3H) 2.05-2.60 (m, 15H) 2.75-2.82 (m, 1H) 2.88-3.01 (m, 2H) 3.17-3.52 (m, 5H) 3.21 (s, 3H) 3.30 (s, 3H) 3.69 (d, J = 7.68 Hz, 1H) 4.00-4.07 (m, 1H) 4.09-4.14 (m, 1H) 4.38 (d, J = 7.13 Hz, 1H) 4.76 (d, 1H) 4.89 (d, J = 4.39 Hz, 1H) 6.24-6.32 (m, 1H) 6.48 (dd, J = 3.43, 1.78 Hz, 1H) 6.73 (d, J = 3.57 Hz, 1H) 7.43 (t, J = 7.82 Hz, 1H) 7.48 (d, J = 1.10 Hz, 1H) 7.63 (d, J = 7.95 Hz, 1H) 7.77 (ddd, J = 7.95, 1.37, 1.10 Hz, 1H) 8.05 (t, J = 1.51 Hz, 1H) |
| 45 | 3-(furan-2-yl)benzamido-(CH$_2$)$_2$- | 890.7 | (600 MHz): 0.82-0.94 (m, 6H) 1.09 (d, J = 7.34 Hz, 3H) 1.12 (d, J = 7.34 Hz, 3H) 1.14-1.27 (m, 2H) 1.20-1.23 (m, 3H) 1.22-1.22 (m, 3H) 1.28 (d, J = 6.42 Hz, 3H) 1.33 (s, 3H) 1.52 (dd, J = 15.36, 4.81 Hz, 1H) 1.57-1.83 (m, J = 11.92 Hz, 3H) 1.90 (s, 1H) 2.18-2.31 (m, 3H) 2.28-2.30 (m, 6H) 2.33 (d, J = 15.13 Hz, 1H) 2.41 (s, 3H) 2.43-2.51 (m, 2H) 2.57 (s, 1H) 2.79-2.89 (m, 1H) 3.00 (s, 1H) 3.04-3.14 (m, 1H) 3.20 (dd, J = 10.32, 7.11 Hz, 1H) 3.26 (s, 3H) 3.30 (s, 3H) 3.42-3.51 (m, 1H) 3.55-3.62 (m, 1H) 3.71 (d, J = 7.79 Hz, 1H) 3.98-4.16 (m, 2H) 4.40 (d, J = 6.88 Hz, 1H) 4.88 (d, J = 4.59 Hz, 1H) 5.04 (s, 1H) 6.45-6.52 (m, 1H) 6.75 (d, J = 3.21 Hz, 1H) 7.00 (s, 1H) 7.43 (t, J = 7.79 Hz, 1H) 7.46-7.49 (m, 1H) 7.62 (d, J = 7.79 Hz, 1H) 7.78 (d, J = 9.17 Hz, 1H) 8.06 (s, 1H) |
| 46 | 3-(furan-2-yl)benzamido-(CH$_2$)$_2$- | 904.7 | (600 MHz): 0.79-0.90 (m, 6H) 1.10 (d, J = 7.79 Hz, 3H) 1.12-1.25 (m, 2H) 1.17-1.26 (m, J = 7.34 Hz, 9H) 1.29 (d, J = 6.42 Hz, 3H) 1.32 (s, 3H) 1.54 (dd, J = 15.13, 5.04 Hz, 1H) 1.57-1.78 (m, 2H) 1.81-1.96 (m, 2H) 2.14-2.42 (m, 4H) 2.28-2.32 (m, 6H) 2.37-2.38 (m, 3H) 2.43-2.57 (m, 2H) 2.79-2.89 (m, 1H) 2.89-2.96 (m, 1H) 2.97-3.04 (m, 1H) 3.07-3.30 (m, 3H) 3.24 (s, 3H) 3.32 (s, 3H) 3.42-3.52 (m, 2H) 3.72 (d, J = 7.79 Hz, 1H) 3.72-3.80 (m, 1H) 4.00-4.08 (m, 1H) 4.11 (s, 1H) 4.41 (d, J = 7.34 Hz, 1H) 4.93 (d, J = 4.59 Hz, 1H) 4.99 (s, 1H) 6.45-6.50 (m, 1H) 6.76 (d, J = 3.21 Hz, 1H) 7.44 (t, J = 7.79 Hz, 1H) 7.46-7.50 (m, 1H) 7.67 (d, J = 7.34 Hz, 1H) 7.78 (d, J = 7.79 Hz, 1H) 8.12 (s, 1H) |

TABLE 1-continued

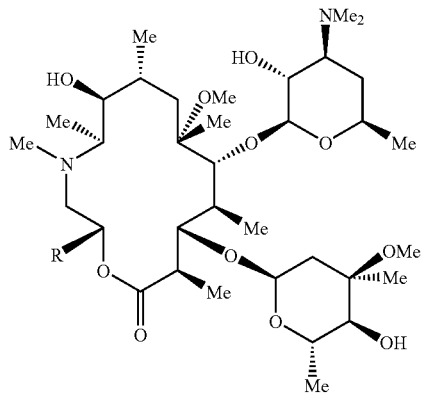

formula (B)

| Example | R | ESI MS (M + H) | $^1$H-NMR, CDCl$_3$, δ (ppm) |
|---|---|---|---|
| 47 | 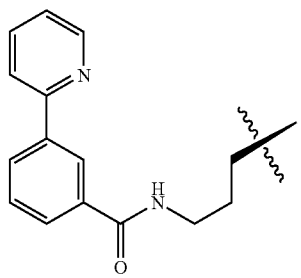 | 929.7 | (600 MHz): 0.78-0.87 (m, 6H) 1.08 (d, J = 7.34 Hz, 3H) 1.11-1.26 (m, 2H) 1.15 (d, J = 7.34 Hz, 3H) 1.20-1.24 (m, 3H) 1.22-123 (m, 3H) 1.28 (d, J = 6.42 Hz, 3H) 1.31 (s, 3H) 1.52 (dd, J = 15.13, 5.04 Hz, 1H) 1.56-1.74 (m, 3H) 1.77-1.92 (m, 3H) 2.13-2.32 (m, 3H) 2.28-2.31 (m, 6H) 2.34 (d, J = 15.13 Hz, 1H) 2.37 (s, 3H) 2.40-2.54 (m, 2H) 2.76-2.84 (m, 1H) 2.87-3.03 (m, 2H) 3.18-3.22 (m, 1H) 3.23-3.25 (m, 3H) 3.31 (s, 3H) 3.34-3.58 (m, 4H) 3.70 (d, J = 7.79 Hz, 1H) 4.00-4.08 (m, 1H) 4.12 (s, 1H) 4.39 (d, J = 6.88 Hz, 1H) 4.80 (s, 1H) 4.91 (d, J = 5.04 Hz, 1H) 6.49 (s, 1H) 7.25-7.29 (m, 1H) 7.54 (t, J = 7.79 Hz, 1H) 7.75-7.83 (m, 2H) 7.86 (d, J = 7.79 Hz, 1H) 8.11 (d, J = 7.80 Hz, 1H) 8.38 (s, 1H) 8.68-8.72 (m, 1H) |
| 48 | 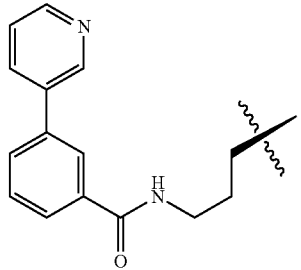 | | (600 MHz): 0.77-0.86 (m, 6H) 1.06 (d, J = 7.34 Hz, 3H) 1.13 (d, J = 7.34 Hz, 3H) 1.15-1.25 (m, 2H) 1.20 (d, J = 6.42 Hz, 3H) 1.21 (s, 3H) 1.26 (d, J = 6.42 Hz, 3H) 1.30 (s, 3H) 1.51 (dd, J = 15.36, 4.81 Hz, 1H) 1.53-1.73 (m, 3H) 1.73-1.92 (m, 3H) 2.09-2.60 (m, 6H) 2.30-2.32 (m, 6H) 2.33-2.35 (m, 3H) 2.73-2.83 (m, 1H) 2.84-3.03 (m, 2H) 3.15-3.21 (m, 1H) 3.21-3.23 (m, 3H) 3.28-3.30 (m, 3H) 3.33-3.60 (m, 4H) 3.69 (d, J = 7.79 Hz, 1H) 3.96-4.13 (m, 2H) 4.38 (d, J = 7.34 Hz, 1H) 4.68-4.91 (m, 2H) 7.34-7.40 (m, 1H) 7.52 (t, J = 7.79 Hz, 1H) 7.69 (d, J = 7.79 Hz, 1H) 7.77 (s, 1H) 7.92 (s, 1H) 8.01 (s, 1H) 8.59 (d, J = 5.04 Hz, 1H) 8.82-8.88 (m, 1H) |
| 49 | 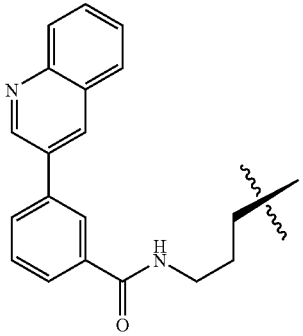 | 979.8 | (600 MHz): 0.76-0.90 (m, 6H) 1.08 (d, J = 7.34 Hz, 3H) 1.14 (d, J = 7.34 Hz, 3H) 1.15-1.25 (m, 2H) 1.21-1.23 (m, 3H) 1.22-1.22 (m, 3H) 1.27 (d, J = 6.42 Hz, 3H) 1.31 (s, 3H) 1.45-1.96 (m, 7H) 2.10-2.66 (m, 6H) 2.29-2.31 (m, 6H) 2.32-2.34 (m, 3H) 2.75-2.84 (m, 1H) 2.86-3.04 (m, 2H) 3.17-3.28 (m, 1H) 3.23-3.24 (m, 3H) 3.30 (s, 3H) 3.33-3.62 (m, 4H) 3.70 (d, J = 7.79 Hz, 1H) 3.96-4.19 (m, 2H) 4.39 (d, J = 7.79 Hz, 1H) 4.80-4.96 (m, 2H) 7.55-7.62 (m, 2H) 7.74 (t, J = 7.79 Hz, 1H) 7.77-7.89 (m, 1H) 7.84 (d, J = 8.25 Hz, 1H) 7.91 (d, J = 7.79 Hz, 1H) 8.14 (d, J = 8.71 Hz, 1H) 8.19 (s, 1H) 8.38 (s, 1H) 9.20 (s, 1H) |

TABLE 1-continued formula (B)

| Example | R | ESI MS (M + H) | $^1$H-NMR, CDCl$_3$, δ (ppm) |
|---|---|---|---|
| 50 | 3-(furan-2-yl)phenyl-NH-C(O)-NH-CH(CH3)-CH2CH2- | 933.8 | (600 MHz): 0.80-0.93 (m, 6H) 1.08 (d, J = 7.34 Hz, 3H) 1.14 (d, J = 7.34 Hz, 3H) 1.16-1.26 (m, 2H) 1.20-1.24 (m, 3H) 1.21-1.23 (m, 3H), 1.28 (d, J = 5.96 Hz, 3H) 1.33 (s, 3H) 1.46-1.60 (m, 3H) 1.64 (d, J = 12.38 Hz, 1H) 1.75 (s, 2H) 1.93 (s, 1H) 2.11-2.39 (m, 4H) 2.26-2.28 (m, 6H) 2.33-2.36 (m, 3H) 2.39-2.59 (m, 2H) 2.74-2.83 (m, 1H) 2.91 (s, 1H) 3.00 (t, J = 9.86 Hz, 1H) 3.19 (dd, J = 10.09, 7.34 Hz, 1H) 3.22-3.40 (m, 2H) 3.23-3.25 (m, 3H) 3.29-3.32 (m, 3H) 3.41-3.52 (m, 2H) 3.71 (d, J = 7.79 Hz, 1H) 3.96-4.09 (m, 2H) 4.40 (d, J = 6.88 Hz, 1H) 4.69-5.01 (m, 2H) 6.41-6.46 (m, 1H) 6.62 (d, J = 3.21 Hz, 1H) 7.23-7.29 (m, 2H) 7.29-7.34 (m, 1H) 7.42 (s, 1H) 7.68 (s, 1H) |
| 51 | H$_2$N-CH$_2$CH$_2$-CH(CH$_3$)- |  | (600 MHz): 0.81 (d, J = 6.88 Hz, 6H) 1.08 (d, J = 7.34 Hz, 3H) 1.10-1.25 (m, 2H) 1.15 (d, J = 7.34 Hz, 3H) 1.21 (d, J = 5.96 Hz, 3H) 1.22 (s, 3H) 1.27 (d, J = 6.42 Hz, 3H) 1.31 (s, 3H) 1.35-1.42 (m, 1H) 1.45-1.60 (m, 3H) 1.61-1.65 (m, 1H) 1.73-1.79 (m, 1H) 1.80-1.86 (m, 1H) 2.10-2.17 (m, 1H) 2.22-2.43 (m, 4H) 2.27 (s, 6H) 2.36 (s, 3H) 2.43-2.49 (m, 1H) 2.68 (t, J = 6.88 Hz, 2H) 2.76-2.81 (m, 1H) 2.91 (d, J = 14.21 Hz, 1H) 2.99 (d, J = 9.63 Hz, 1H) 3.19 (dd, J = 10.09, 7.34 Hz, 1H) 3.22 (s, 3H) 3.31 (s, 3H) 3.37-3.41 (m, 1H) 3.42-3.48 (m, 1H) 3.69 (d, J = 8.25 Hz, 1H) 4.02-4.07 (m, 1H) 4.12-4.16 (m, 1H) 4.38 (d, J = 7.34 Hz, 1H) 4.69-4.74 (m, 1H) 4.92 (d, J = 4.58 Hz, 1H) |
| 52 | Cl-CH$_2$-CH(CH$_3$)- | 739.6 | (600 MHz): 0.79-0.89 (m, 6H) 1.09 (d, J = 7.34 Hz, 3H) 1.12-1.27 (m, 2H) 1.18 (d, J = 7.34 Hz, 3H) 1.22 (d, J = 5.96 Hz, 3H) 1.23 (s, 3H) 1.28 (d, J = 6.42 Hz, 3H) 1.32 (s, 3H) 1.54 (dd, J = 15.13, 5.04 Hz, 1H) 1.66 (d, J = 11.00 Hz, 1H) 1.79-1.89 (m, 1H) 2.21-2.42 (m, 5H) 2.29 (s, 6H) 2.38 (s, 3H) 2.43-2.52 (m, 2H) 2.77-2.88 (m, 1H) 2.96 (d, J = 14.67 Hz, 1H) 3.00 (d, J = 7.34 Hz, 1H) 3.17-3.23 (m, 1H) 3.22 (s, 3H) 3.32 (s, 3H) 3.38-3.50 (m, 2H) 3.59-3.73 (m, 2H) 3.70 (d, J = 7.79 Hz, 1H) 4.00-4.08 (m, 1H) 4.08-4.16 (m, 1H) 4.39 (d, J = 6.88 Hz, 1H) 4.85-4.95 (m, 1H) 4.90 (d, J = 5.04 Hz, 1H) |
| 53 | 3-(thiophen-2-yl)phenyl-C(O)-NH-CH$_2$CH$_2$-CH(CH$_3$)- | 934.7 | (600 MHz): 0.78-0.88 (m, 6H) 1.08 (d, J = 7.34 Hz, 3H) 1.09-1.26 (m, 2H) 1.15 (d, J = 7.34 Hz, 3H) 1.20-1.23 (m, 3H) 1.21-1.23 (m, 3H) 1.28 (d, J = 5.96 Hz, 3H) 1.31 (s, 3H) 1.52 (dd, J = 15.36, 4.81 Hz, 1H) 1.55-1.72 (m, 3H) 1.75-1.91 (m, 3H) 2.12-2.32 (m, 4H) 2.27-2.29 (m, 6H) 2.34 (d, J = 15.59 Hz, 1H) 2.36 (s, 3H) 2.42-2.51 (m, 2H) 2.75-2.83 (m, 1H) 2.93 (d, J = 14.67 Hz, 1H) 3.00 (t, J = 8.25 Hz, 1H) 3.20 (dd, J = 10.32, 7.11 Hz, 1H) 3.24 (s, 3H) 3.31 (s, 3H) 3.34-3.41 (m, 1H) 3.41-3.50 (m, 2H) 3.50-3.60 (m, 1H) 3.70 (d, J = 7.79 Hz, 1H) 4.01-4.07 (m, 1H) 4.11 (s, 1H) 4.39 (d, J = 7.34 Hz, 1H) 4.81 (s, 1H) 4.91 (d, J = 4.58 Hz, 1H) 6.39 (s, 1H) 7.09 (dd, J = 5.04, 3.67 Hz, 1H) 7.30 (d, J = 5.04 Hz, 1H) 7.38 (d, J = 3.67 Hz, 1H) 7.42 (t, J = 7.79 Hz, 1H) 7.63 (d, J = 7.79 Hz, 1H) 7.71 (d, J = 8.71 Hz, 1H) 7.98-8.06 (m, 1H) |

TABLE 1-continued formula (B)

| Example | R | ESI MS (M + H) | ¹H-NMR, CDCl₃, δ (ppm) |
|---|---|---|---|
| 54 | 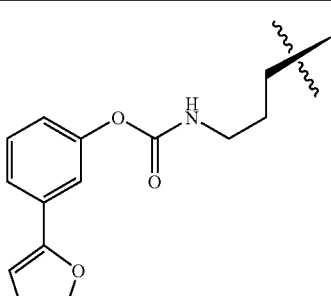 | 934.7 | (600 MHz): 0.77-0.90 (m, 6H) 1.09 (d, J = 7.34 Hz, 3H) 1.12-1.26 (m, 2H) 1.17 (d, J = 7.34 Hz, 3H) 1.20-1.24 (m, 3H) 1.22-1.23 (m, 3H) 1.28 (d, J = 6.42 Hz, 3H) 1.32 (s, 3H) 1.53 (dd, J = 15.13, 4.59 Hz, 1H) 1.55-1.74 (m, 3H) 1.76-1.91 (m, 3H) 2.08-2.58 (m, 7H) 2.29-2.32 (m, 6H) 2.37-2.40 (m, 3H) 2.76-2.86 (m, 1H) 2.88-3.05 (m, 2H) 3.17-3.34 (m, 2H) 3.22-3.25 (m, 3H) 3.31-3.32 (m, 3H) 3.34-3.52 (m, 3H) 3.70 (d, J = 8.25 Hz, 1H) 4.01-4.08 (m, 1H) 4.13 (s, 1H) 4.39 (d, J = 7.34 Hz, 1H) 4.77 (s, 1H) 4.92 (d, J = 4.58 Hz, 1H) 5.14 (s, 1H) 6.43-6.47 (m, 1H) 6.64 (d, J = 3.21 Hz, 1H) 7.01 (d, J = 8.25 Hz, 1H) 7.34 (t, J = 8.02 Hz, 1H) 7.43 (d, J = 14.67 Hz, 2H) 7.49 (d, J = 7.79 Hz, 1H) |
| 55 | 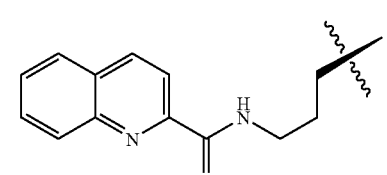 | 903.7 | (600 MHz): 0.76-0.86 (m, 6H) 1.03-1.25 (m, 2H) 1.09 (d, J = 7.34 Hz, 3H) 1.17 (d, J = 7.34 Hz, 3H) 1.20-1.23 (m, 3H) 1.21-1.22 (m, 3H) 1.28 (d, J = 6.42 Hz, 3H) 1.31 (s, 3H) 1.52 (dd, J = 15.13, 5.04 Hz, 1H) 1.59-1.96 (m, 6H) 2.10-2.32 (m, 4H) 2.26-2.29 (m, 6H) 2.35 (d, J = 15.59 Hz, 1H) 2.37 (s, 3H) 2.40-2.50 (m, 2H) 2.77-2.85 (m, 1H) 2.93 (d, J = 14.67 Hz, 1H) 3.00 (t, J = 9.40 Hz, 1H) 3.20 (dd, J = 10.32, 7.11 Hz, 1H) 3.23 (s, 3H) 3.31 (s, 3H) 3.35-3.49 (m, 2H) 3.49-3.60 (m, 2H) 3.70 (d, J = 8.25 Hz, 1H) 4.01-4.08 (m, 1H) 4.15 (s, 1H) 4.38 (d, J = 7.34 Hz, 1H) 4.79 (s, 1H) 4.93 (d, J = 4.59 Hz, 1H) 7.58-7.64 (m, 1H) 7.74-7.78 (m, 1H) 7.87 (d, J = 8.25 Hz, 1H) 8.11 (d, J = 8.71 Hz, 1H) 8.25-8.36 (m, 2H) |
| 56 | 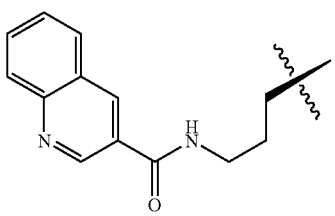 | 903.7 | (600 MHz): 0.78-0.90 (m, 6H) 1.08 (d, J = 7.34 Hz, 3H) 1.08-1.25 (m, 2H) 1.16 (d, J = 7.34 Hz, 3H) 1.19-1.23 (m, 3H) 1.21-1.23 (m, 3H) 1.28 (d, J = 6.42 Hz, 3H) 1.31 (s, 3H) 1.52 (dd, J = 15.13, 5.04 Hz, 1H) 1.61-1.66 (m, 1H) 1.66-1.94 (m, 5H) 2.15-2.31 (m, 4H) 2.26-2.28 (m, 6H) 2.34 (d, J = 15.13 Hz, 1H) 2.36 (s, 3H) 2.41-2.53 (m, 2H) 2.75-2.86 (m, 1H) 2.93 (d, J = 4.21 Hz, 1H) 3.00 (t, J = 9.40 Hz, 1H) 3.20 (dd, J = 10.32, 7.11 Hz, 1H) 3.23 (s, 3H) 3.31 (s, 3H) 3.34-3.57 (m, 3H) 3.58-3.68 (m, 1H) 3.70 (d, J = 7.79 Hz, 1H) 4.00-4.08 (m, 1H) 4.12 (s, 1H) 4.40 (d, J = 7.34 Hz, 1H) 4.84 (s, 1H) 4.91 (d, J = 4.58 Hz, 1H) 6.69 (s, 1H) 7.60 (t, J = 6.88 Hz, 1H) 7.79 (t, J = 6.88 Hz, 1H) 7.92 (d, J = 7.79 Hz, 1H) 8.14 (d, J = 8.71 Hz, 1H) 8.62 (s, 1H) 9.28 (s, 1H) |
| 57 | 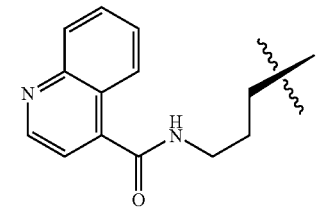 | 903.7 | (600 MHz): 0.75-0.86 (m, 6H) 1.05 (d, J = 7.34 Hz, 3H) 1.06-1.23 (m, 2H) 1.10 (d, J = 7.79 Hz, 3H) 1.19 (d, J = 5.96 Hz, 3H) 1.19 (s, 3H) 1.25 (d, J = 5.96 Hz, 3H) 1.29 (s, 3H) 1.49 (dd, J = 15.36, 4.81 Hz, 1H) 1.54-1.91 (m, 6H) 2.11-2.28 (m, 4H) 2.24-2.26 (m, 6H) 2.30 (d, J = 15.13 Hz, 1H) 2.35 (s, 3H) 2.38-2.49 (m, 2H) 2.72-2.80 (m, 1H) 2.92 (d, J = 14.21 Hz, 1H) 2.97 (t, J = 9.17 Hz, 1H) 3.17 (dd, J = 10.09, 7.34 Hz, 1H) 3.19 (s, 3H) 3.28 (s, 3H) 3.31-3.39 (m, 1H) 3.40-3.47 (m, 1H) 3.47-3.63 (m, 2H) 3.66 (d, J = 7.79 Hz, 1H) 3.97-4.04 (m, 1H) 4.08 (s, 1H) 4.36 (d, J = 7.34 Hz, 1H) 4.78 (s, 1H) 4.86 (d, J = 4.58 Hz, 1H) 6.29 (s, 1H) 7.40 (d, J = 4.58 Hz, 1H) 7.55-7.60 (m, 1H) 7.70-7.75 (m, 1H) 8.10 (d, J = 8.71 Hz, 1H) 8.18 (d, J = 7.79 Hz, 1H) 8.90 (d, J = 4.13 Hz, 1H) |

TABLE 1-continued formula (B)

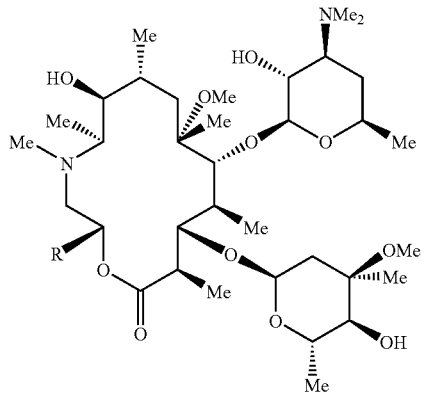

| Example | R | ESI MS (M + H) | ¹H-NMR, CDCl₃, δ (ppm) |
|---|---|---|---|
| 58 | ![Br-pentyl] | 839.5 | (600 MHz): 0.78-0.84 (m, 6H) 1.09 (d, J = 7.34 Hz, 3H) 1.15 (d, J = 7.34 Hz, 3H) 1.17-1.27 (m, 2H) 1.22 (d, J = 6.42 Hz, 3H) 1.23 (s, 3H) 1.28 (d, J = 5.96 Hz, 3H) 1.32 (s, 3H) 1.33-1.89 (m, 7H) 1.53 (dd, J = 15.13, 4.59 Hz, 1H) 1.61-1.71 (m, 1H) 1.71-1.79 (m, 1H) 1.80-1.88 (m, 1H) 2.08-2.19 (m, 1H) 2.21-2.55 (m, 5H) 2.30 (s, 6H) 2.36 (s, 3H) 2.75-2.83 (m, 1H) 2.91 (d, J = 14.67 Hz, 1H) 3.00 (t, J = 9.40 Hz, 1H) 3.18-3.24 (m, 1H) 3.22 (s, 3H) 3.32 (s, 3H) 3.36-3.43 (m, 2H) 3.43-3.49 (m, 1H) 3.51 (t, J = 6.65 Hz, 2H) 3.70 (d, J = 8.25 Hz, 1H) 4.02-4.09 (m, 1H) 4.12-4.17 (m, 1H) 4.38 (d, J = 7.34 Hz, 1H) 4.67-4.75 (m, 1H) 4.93 (d, J = 4.59 Hz, 1H) |
| 59 | ![furan-phenyl-amide] | 918.7 | (600 MHz): 0.79-0.88 (m, 6H) 1.09 (d, J = 7.34 Hz, 3H) 1.10-1.25 (m, 2H) 1.15 (d, J = 7.34 Hz, 3H) 1.20-1.23 (m, 3H) 1.21-1.23 (m, 3H) 1.28 (d, J = 6.42 Hz, 3H) 1.31 (s, 3H) 1.53 (dd, J = 15.13, 4.59 Hz, 1H) 1.55-1.74 (m, 3H) 1.75-1.95 (m, 3H) 2.13-2.39 (m, 4H) 2.27-2.29 (m, 6H) 2.35-2.36 (m, 3H) 2.41-2.52 (m, 2H) 2.76-2.83 (m, 1H) 2.92 (d, J = 14.67 Hz, 1H) 3.00 (t, J = 9.40 Hz, 1H) 3.20 (dd, J = 10.09, 6.88 Hz, 1H) 3.24 (s, 3H) 3.31 (s, 3H) 3.34-3.50 (m, 3H) 3.50-3.58 (m, 1H) 3.70 (d, J = 8.25 Hz, 1H) 4.01-4.08 (m, 1H) 4.13 (s, 1H) 4.39 (d, J = 7.34 Hz, 1H) 4.80 (s, 1H) 4.91 (d, J = 4.59 Hz, 1H) 6.36 (s, 1H) 6.49 (dd, J = 3.44, 1.60 Hz, 1H) 6.74 (d, J = 2.75 Hz, 1H) 7.50 (d, J = 1.38 Hz, 1H) 7.68-7.73 (m, 2H) 7.79 (d, J = 8.25 Hz, 2H) |
| 60 | ![furan-phenyl-amide meta] | 932.7 | (500 MHz): 0.74-0.93 (m, 6H) 1.07 (d, J = 7.40 Hz, 3H) 1.09 (d, J = 7.68 Hz, 3H) 1.25 (dd, J = 30.17, 6.03 Hz, 8H) 1.18-1.25 (m, 6H) 1.28 (d, J = 6.03 Hz, 3H) 1.30-1.32 (m, 3H) 1.75-1.90 (m, 3H) 2.09-2.40 (m, 4H) 2.32 (s, 6H) 2.37 (s, 3H) 2.40-2.58 (m, 2H) 2.71-2.82 (m, 1H) 2.87-2.96 (m, 1H) 2.96-3.03 (m, 1H) 3.18-3.27 (m, 1H) 3.22 (s, 3H) 3.29 (s, 3H) 3.33-3.54 (m, 4H) 3.69 (d, J = 7.95 Hz, 1H) 3.98-4.07 (m, 1H) 4.07-4.16 (m, 1H) 4.38 (d, J = 7.13 Hz, 1H) 4.64-4.83 (m, 1H) 4.88 (d, J = 4.39 Hz, 1H) 6.14-6.28 (m, 1H) 6.48 (dd, J = 3.43, 1.78 Hz, 1H) 6.73 (d, J = 3.02 Hz, 1H) 7.43 (t, J = 7.68 Hz, 1H) 7.48 (d, J = 1.10 Hz, 1H) 7.62 (d, J = 7.13 Hz, 1H) 7.75-7.81 (m, 1H) 8.01-8.08 (m, 1H) |
| 61 | ![naphthalene-amide] | 902.7 | (500 MHz): 0.78-0.88 (m, 6H) 1.08 (d, J = 7.40 Hz, 3H) 1.15 (d, J = 7.40 Hz, 3H) 1.17-1.35 (m, 8H) 1.28 (d, J = 6.03 Hz, 3H) 1.32 (s, 3H) 1.52 (dd, J = 15.08, 4.94 Hz, 1H) 1.56-1.77 (m, 3H) 1.78-1.97 (m, 3H) 2.12-2.36 (m, 10H) 2.38 (s, 3H) 2.41-2.54 (m, 2H) 2.73-2.85 (m, 1H) 2.88-3.05 (m, 2H) 3.15-3.27 (m, 1H) 3.23 (s, 3H) 3.29-3.33 (m, 3H) 3.34-3.50 (m, 2H) 3.50-3.65 (m, 2H) 3.70 (d, J = 7.95 Hz, 1H) 3.98-4.09 (m, 1H) 4.08-4.19 (m, 1H) 4.39 (d, J = 7.40 Hz, 1H) 4.72-4.86 (m, 1H) 4.91 (d, J = 4.39 Hz, 1H) 6.03-6.16 (m, 1H) 7.41-7.47 (m, 1H) 7.48-7.56 (m, 2H) 7.58 (dd, J = 7.13, 1.10 Hz, 1H) 7.85 (d, J = 9.05 Hz, 1H) 7.90 (d, J = 8.23 Hz, 1H) 8.28 (d, J = 8.23 Hz, 1H) |
| 62 | ![methyl ester chain] | 791.6 | (500 MHz): 0.74-0.87 (m, 6H) 1.09 (d, J = 7.13 Hz, 3H) 1.16 (d, J = 7.40 Hz, 3H) 1.18-1.91 (m, 14H) 1.28 (d, J = 6.31 Hz, 3H) 1.31 (s, 3H) 1.53 (dd, J = 15.22, 5.07 Hz, 1H) 2.05-2.39 (m, 16H) 2.38-2.54 (m, 2H) 2.74-2.84 (m, 1H) 2.88-2.96 (m, 1H) 3.00 (t, J = 9.74 Hz, 1H) 3.16-3.25 (m, 1H) 3.22 (s, 3H) 3.32 (s, 3H) 3.35-3.42 (m, 1H) 3.43-3.51 (m, 1H) 3.66 (s, 3H) 3.69 (d, J = 7.95 Hz, 1H) 4.00-4.09 (m, 1H) 4.10-4.18 (m, 1H) 4.38 (d, J = 7.13 Hz, 1H) 4.66-4.78 (m, 1H) 4.93 (d, J = 4.39 Hz, 1H) |

TABLE 1-continued formula (B)

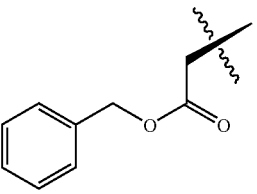

| Example | R | ESI MS (M + H) | $^1$H-NMR, CDCl$_3$, δ (ppm) |
|---|---|---|---|
| 63 | 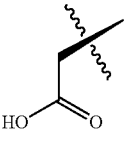 | 839.6 | (500 MHz): 0.77-0.83 (m, 6H) 1.05 (d, J = 7.40 Hz, 3H) 1.07 (d, J = 7.40 Hz, 3H) 1.17-1.26 (m, 2H) 1.22 (d, J = 6.03 Hz, 3H) 1.22 (s, 3H) 1.28 (d, J = 6.31 Hz, 3H) 1.32 (s, 3H) 1.49-1.55 (m, 1H) 1.63-1.74 (m, 1H) 1.76-1.90 (m, 1H) 2.16-2.38 (m, 13H) 2.38-2.53 (m, 2H) 2.59 (dd, J = 15.91, 4.66 Hz, 1H) 2.65-2.73 (m, 1H) 2.77-2.91 (m, 2H) 2.98-3.07 (m, 2H) 3.15-3.24 (m, 1H) 3.21-3.22 (m, 3H) 3.31 (s, 3H) 3.36-3.54 (m, 2H) 3.68 (d, J = 7.95 Hz, 1H) 3.99-4.07 (m, 1H) 4.08-4.17 (m, 1H) 4.37 (d, J = 7.13 Hz, 1H) 4.89 (d, J = 4.66 Hz, 1H) 5.07-5.15 (m, 3H) 7.27-7.40 (m, 5H) |
| 64 | 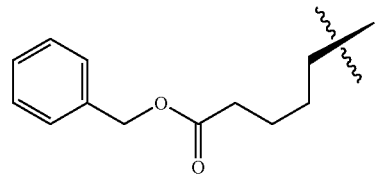 | 749.6 | (500 MHz): 0.73-0.96 (m, 6H) 1.09 (d, J = 7.65 Hz, 3H) 1.15 (d, J = 7.65 Hz, 3H) 1.18-1.47 (m, 14H) 1.50-1.77 (m, 2H) 1.89-2.91 (m, 8H) 2.35 (br. s., 6H) 2.63 (s, 3H) 3.01 (d, J = 9.17 Hz, 1H) 3.17-3.25 (m, 1H) 3.26-3.82 (m, 6H) 3.32 (s, 3H) 3.63 (s, 3H) 3.83-3.96 (m, 1H) 3.96-4.07 (m, 1H) 4.41 (d, J = 6.88 Hz, 1H) 4.85 (d, J = 4.59 Hz, 1H) 5.06-5.15 (m, 1H) |
| 65 | 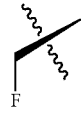 | 881.7 | (500 MHz): 0.78-0.85 (m, 6H) 1.09 (d, J = 6.88 Hz, 3H) 1.13 (d, J = 7.65 Hz, 3H) 1.19-1.91 (m, 17H) 1.28 (d, J = 6.12 Hz, 3H) 1.32 (s, 3H) 2.05-2.17 (m, 1H) 2.16-2.62 (m, 17H) 2.73-2.82 (m, 1H) 2.86-2.95 (m, 1H) 3.00 (t, J = 9.94 Hz, 1H) 3.16-3.30 (m, 1H) 3.22 (s, 3H) 3.32 (s, 3H) 3.39 (s, 1H) 3.44-3.51 (m, 1H) 3.70 (d, J = 7.65 Hz, 1H) 3.99-4.10 (m, 1H) 4.11-4.19 (m, 1H) 4.38 (d, J = 7.65 Hz, 1H) 4.63-4.75 (m, 1H) 4.93 (d, J = 4.59 Hz, 1H) 5.10 (s, 2H) 7.28-7.40 (m, 5H) |
| 66 |  | 723.6 | (600 MHz): 0.77-0.93 (m, 6H) 1.04-1.37 (m, 20H) 1.51-1.58 (m, 1H) 1.61-1.71 (m, 1H) 1.81-1.92 (m, 1H) 2.18-2.57 (m, 6H) 2.29 (s, 6H) 2.32 (s, 3H) 2.79-2.88 (m, 1H) 2.90-3.06 (m, 2H) 3.15-3.52 (m, 3H) 3.24 (s, 3H) 3.32 (s, 3H) 3.70 (d, J = 8.25 Hz, 1H) 3.99-4.15 (m, 2H) 4.35-4.63 (m, 3H) 4.86-4.94 (m, 1H) 4.94-5.04 (m, 1H) |
| 67 | 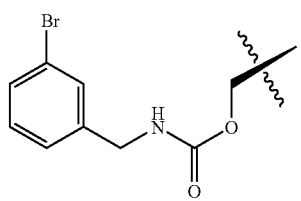 | 717.5 | (600 MHz): 0.75-0.92 (m, 6H) 1.05-1.38 (m, 20H) 1.54 (dd, J = 15.13, 5.04 Hz, 1H) 1.55-1.72 (m, 1H) 1.81-1.94 (m, 1H) 2.16-2.54 (m, J = 34.85 Hz, 6H) 2.29 (s, 6H) 2.35 (s, 3H) 2.77-3.05 (m, 3H) 3.16-3.55 (m, 3H) 3.25 (s, 3H) 3.32 (s, 3H) 3.72 (d, J = 7.79 Hz, 1H) 4.00-4.09 (m, 1H) 4.10-4.21 (m, 1H) 4.41 (d, J = 7.34 Hz, 1H) 4.87-4.93 (m, 1H) 5.09-5.31 (m, 3H) 5.81-5.96 (m, 1H) |
| 68 |  | 932.7 | (600 MHz): 0.78-0.91 (m, 6H) 1.08 (d, J = 7.34 Hz, 3H) 1.13 (d, J = 6.88 Hz, 3H) 1.17-1.26 (m, 2H) 1.22 (d, J = 6.42 Hz, 3H) 1.23 (s, 3H) 1.28 (d, J = 6.42 Hz, 3H) 1.31 (s, 3H) 1.53 (dd, J = 15.36, 4.81 Hz, 1H) 1.56-1.72 (m, 1H) 1.76-1.92 (m, 1H) 2.16-2.39 (m, 4H) 2.29-2.32 (m, 6H) 2.33-2.35 (m, 3H) 2.40-2.54 (m, 2H) 2.74-2.84 (m, 1H) 2.93 (d, J = 15.13 Hz, 1H) 3.00 (t, J = 9.40 Hz, 1H) 3.17-3.25 (m, 1H) 3.22-3.24 (m, 3H) 3.32 (s, 3H) 3.35-3.51 (m, 2H) 3.70 (d, J = 8.25 Hz, 1H) 4.01-4.07 (m, 1H) 4.07-4.13 (m, 1H) 4.18-4.37 (m, 4H) 4.39 (d, J = 7.34 Hz, 1H) 4.91 (d, J = 4.58 Hz, 1H) 4.94-5.06 (m, 2H) 7.15-7.22 (m, 2H) 7.37-7.45 (m, 2H) |

TABLE 1-continued formula (B)

| Example | R | ESI MS (M + H) | ¹H-NMR, CDCl₃, δ (ppm) |
|---------|---|----------------|------------------------|
| 69 | 3-bromobenzyl carbamate-methyl | 932.7 | (600 MHz): 0.78-0.90 (m, 6H) 1.08 (d, J = 7.34 Hz, 3H) 1.10-1.27 (m, 2H) 1.12 (d, J = 7.34 Hz, 3H) 1.22 (d, J = 5.96 Hz, 3H) 1.23 (s, 3H) 1.28 (d, J = 5.96 Hz, 3H) 1.31 (s, 3H) 1.54 (dd, J = 15.13, 5.04 Hz, 1H) 1.57-1.71 (m, 1H) 1.80-1.92 (m, 1H) 2.12-2.39 (m, 13H) 2.40-2.58 (m, 2H) 2.73-2.83 (m, 1H) 2.91-3.04 (m, 1H) 3.17-3.26 (m, 1H) 3.22-3.24 (m, 3H) 3.32 (s, 3H) 3.33-3.43 (m, 2H) 3.44-3.54 (m, 2H) 3.70 (d, J = 7.34 Hz, 1H) 4.00-4.12 (m, 2H) 4.40 (d, J = 6.88 Hz, 1H) 4.84 (s, 1H) 4.88 (d, J = 4.58 Hz, 1H) 5.04 (s, 2H) 5.07 (s, 1H) 7.17-7.29 (m, 2H) 7.42 (d, J = 7.34 Hz, 1H) 7.48 (s, 1H) |
| 70 | allyl carbamate-methyl | 804.7 | (600 MHz): 0.79-0.89 (m, 6H) 1.09 (d, J = 7.34 Hz, 3H) 1.10-1.26 (m, 2H) 1.16 (d, J = 7.79 Hz, 3H) 1.22 (d, J = 5.96 Hz, 3H) 1.23 (s, 3H) 1.28 (d, J = 6.42 Hz, 3H) 1.32 (s, 3H) 1.54 (dd, J = 15.36, 4.81 Hz, 1H) 1.63-1.74 (m, 1H) 1.80-1.93 (m, 1H) 2.17-2.40 (m, 4H) 2.28-2.32 (m, 6H) 2.34-2.36 (m, 3H) 2.41-2.55 (m, 2H) 2.75-2.85 (m, 1H) 2.93-3.05 (m, 2H) 3.15-3.29 (m, 1H) 3.22-3.24 (m, 3H) 3.31-3.55 (m, 4H) 3.31-3.33 (m, 3H) 3.70 (d, J = 7.79 Hz, 1H) 3.99-4.15 (m, 2H) 4.40 (d, J = 6.88 Hz, 1H) 4.54 (d, J = 5.50 Hz, 2H) 4.83 (s, 1H) 4.89 (d, J = 4.58 Hz, 1H) 5.04 (s, 1H) 5.19 (d, J = 11.00 Hz, 1H) 5.28 (d, J = 16.97 Hz, 1H) 5.84-5.96 (m, 1H) |
| 71 | 4-(benzyloxy)butyl | 853.8 | (600 MHz): 0.77-0.84 (m, 6H) 1.09 (d, J = 7.34 Hz, 3H) 1.13 (d, J = 7.34 Hz, 3H) 1.14-1.26 (m, 2H) 1.21 (d, J = 6.42 Hz, 3H) 1.22 (s, 3H) 1.28 (d, J = 6.42 Hz, 3H) 1.31 (s, 3H) 1.37-1.88 (m, 8H) 1.53 (dd, J = 15.13, 5.04 Hz, 1H) 2.06-2.17 (m, 1H) 2.19-2.38 (m, 4H) 2.28 (s, 6H) 2.35 (s, 3H) 2.39-2.52 (m, 2H) 2.74-2.82 (m, 1H) 2.90 (d, J = 15.59 Hz, 1H) 3.00 (t, J = 8.94 Hz, 1H) 3.17-3.24 (m, 1H) 3.22 (s, 3H) 3.31 (s, 3H) 3.36-3.50 (m, 2H) 3.44 (t, J = 6.42 Hz, 2H) 3.69 (d, J = 7.79 Hz, 1H) 4.01-4.08 (m, 1H) 4.12-4.18 (m, 1H) 4.38 (d, J = 7.34 Hz, 1H) 4.47 (s, 2H) 4.66-4.74 (m, 1H) 4.92 (d, J = 4.59 Hz, 1H) 7.25-7.27 (m, 1H) 7.29-7.36 (m, 4H) |
| 72 | 3-(benzyloxy)propyl | 839.7 | (600 MHz): 0.81 (d, J = 6.88 Hz, 6H) 1.08 (d, J = 6.88 Hz, 3H) 1.09-1.27 (m, 2H) 1.14 (d, J = 7.34 Hz, 3H) 1.21-1.23 (m, 3H) 1.23 (s, 3H) 1.28 (d, J = 6.42 Hz, 3H) 1.31 (s, 3H) 1.50-1.72 (m, 5H) 1.78-1.86 (m, 2H) 2.11-2.17 (m, 1H) 2.18-2.51 (m, 6H) 2.30 (s, 6H) 2.37 (s, 3H) 2.75-2.81 (m, 1H) 2.90-2.96 (m, 1H) 3.00 (t, J = 10.09 Hz, 1H) 3.22 (s, 3H) 3.21-3.25 (m, 1H) 3.32 (s, 3H) 3.37-3.41 (m, 3H) 3.41-3.51 (m, 3H) 3.70 (d, J = 7.79 Hz, 1H) 4.02-4.07 (m, 1H) 4.13-4.18 (m, 1H) 4.39 (d, J = 7.34 Hz, 1H) 4.48 (s, 2H) 4.69-4.75 (m, 1H) 4.92 (d, J = 4.58 Hz, 1H) 7.26-7.36 (m, 5H) |
| 73 | 4-hydroxybutyl | 749.7 | (600 MHz): 0.81 (d, J = 6.42 Hz, 6H) 1.05-1.35 (m, 2H) 1.08 (d, J = 7.34 Hz, 3H) 1.15 (d, J = 7.34 Hz, 3H) 1.21 (d, J = 5.96 Hz, 3H) 1.22 (s, 3H) 1.28 (d, J = 6.42 Hz, 3H) 1.31 (s, 3H) 1.47-1.87 (m, 7H) 2.11-2.19 (m, 1H) 2.20-2.39 (m, 4H) 2.27 (s, 6H) 2.36 (s, 3H) 2.38-2.49 (m, 2H) 2.76-2.81 (m, 1H) 2.92 (d, J = 14.67 Hz, 1H) 3.00 (t, J = 9.17 Hz, 1H) 3.18-3.21 (m, 1H) 3.21-3.24 (m, 3H) 3.31 (s, 3H) 3.36-3.49 (m, 2H) 3.62-3.67 (m, 2H) 3.69 (d, J = 8.25 Hz, 1H) 4.01-4.07 (m, 1H) 4.11-4.16 (m, 1H) 4.38 (d, J = 7.34 Hz, 1H) 4.72-4.77 (m, 1H) 4.92 (d, J = 4.58 Hz, 1H) |

TABLE 1-continued

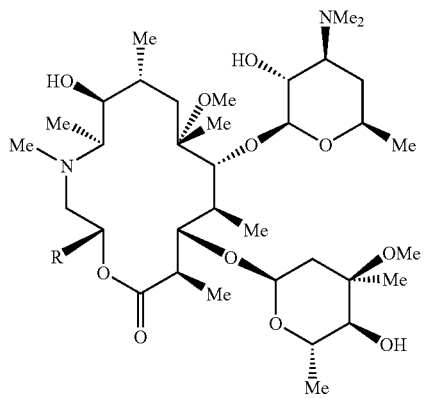

formula (B)

| Example | R | ESI MS (M + H) | $^1$H-NMR, CDCl$_3$, δ (ppm) |
|---|---|---|---|
| 74 | 3-(furan-2-yl)-phenyl-SO$_2$NH-CH$_2$CH$_2$-CH(Me)- | 954.7 | (600 MHz): 0.78-0.84 (m, 6H) 1.07 (d, J = 6.88 Hz, 3H) 1.10 (d, J = 7.34 Hz, 3H) 1.20-1.32 (m, 5H) 1.22 (d, J = 6.42 Hz, 3H) 1.28 (d, J = 6.42 Hz, 3H) 1.30 (s, 3H) 1.41-1.88 (m, 7H) 2.00-2.13 (m, 1H) 2.16-2.47 (m, 15H) 2.71-2.78 (m, 1H) 2.84-2.93 (m, 1H) 2.98-3.03 (m, 2H) 3.18-3.27 (m, 2H) 3.20 (s, 3H) 3.31 (s, 3H) 3.32-3.39 (m, 1H) 3.44-3.50 (m, 1H) 3.69 (d, J = 7.79 Hz, 1H) 4.00-4.14 (m, 2H) 4.39 (d, J = 6.88 Hz, 1H) 4.64-4.68 (m, 1H) 4.89 (d, J = 5.04 Hz, 1H) 6.50 (dd, J = 3.21, 1.83 Hz, 1H) 6.77 (d, J = 3.21 Hz, 1H) 7.50-7.51 (m, 1H) 7.51-7.54 (m, 1H) 7.72 (d, J = 8.71 Hz, 1H) 7.84 (d, J = 7.34 Hz, 1H) 8.13 (s, 1H) |
| 75 | 6-(furan-2-yl)-pyridine-2-carboxamide | 919.7 | (600 MHz): 0.74-0.84 (m, 6H) 1.05 (d, J = 7.34 Hz, 3H) 1.07-1.23 (m, 2H) 1.13 (d, J = 7.79 Hz, 3H) 1.17-1.20 (m, 3H) 1.18-1.19 (m, 3H) 1.25 (d, J = 5.96 Hz, 3H) 1.28 (s, 3H) 1.49 (dd, J = 15.13, 5.04 Hz, 1H) 1.53-1.73 (m, 3H) 1.74-1.98 (m, 3H) 2.07-2.36 (m, 6H) 2.23-2.26 (m, 3H) 2.32-2.34 (m, 3H) 2.37-2.47 (m, 2H) 2.72-2.81 (m, 1H) 2.90 (d, J = 15.13 Hz, 1H) 2.97 (t, J = 9.40 Hz, 1H) 3.17 (dd, J = 10.32 7.11 Hz, 1H) 3.19 (s, 3H) 3.28 (s, 3H) 3.31-3.52 (m, 4H) 3.66 (d, J = 7.79 Hz, 1H) 3.98-4.05 (m, 1H) 4.11 (s, 1H) 4.35 (d, J = 7.34 Hz, 1H) 4.74 (s, 1H) 4.89 (d, J = 5.04 Hz, 1H) 6.52 (dd, J = 3.21, 1.83 Hz, 1H) 7.07 (d, J = 3.21 Hz, 1H) 7.52 (d, J = 0.92 Hz, 1H) 7.75-7.78 (m, 1H) 7.82 (t, J = 7.79 Hz, 1H) 7.99-8.02 (m, 1H) 8.10 (t, J = 6.19 Hz, 1H) |
| 76 | 5-(furan-2-yl)-pyridine-3-carboxamide | 919.8 | (600 MHz): 0.79-0.90 (m, 6H) 1.08 (d, J = 7.34 Hz, 3H) 1.10-1.26 (m, 2H) 1.15 (d, J = 7.34 Hz, 3H) 1.21 (d, J = 5.96 Hz, 3H) 1.22 (s, 3H) 1.28 (d, J = 5.96 Hz, 3H) 1.31 (s, 3H) 1.52 (dd, J = 15.36, 4.81 Hz, 1H) 1.55-1.71 (m, 3H) 1.72-1.94 (m, 3H) 2.15-2.31 (m, 3H) 2.26-2.29 (m, 6H) 2.34 (d, J = 15.59 Hz, 1H) 2.36 (s, 3H) 2.39-2.51 (m, 2H) 2.75-2.84 (m, 1H) 2.93 (d, J = 12.84 Hz, 1H) 3.00 (t, J = 9.40 Hz, 1H) 3.20 (dd, J = 10.09, 7.34 Hz, 1H) 3.23 (s, 3H) 3.31 (s, 3H) 3.35-3.52 (m, 3H) 3.53-3.63 (m, 1H) 3.70 (d, J = 7.79 Hz, 1H) 4.00-4.07 (m, 1H) 4.09 (s, 1H) 4.39 (d, J = 7.34 Hz, 1H) 4.83 (s, 1H) 4.90 (d, J = 4.58 Hz, 1H) 6.50-6.53 (m, 1H) 6.83 (d, J = 3.21 Hz, 1H) 7.54 (d, J = 1.83 Hz, 1H) 8.30-8.38 (m, 1H) 8.83 (d, J = 1.83 Hz, 1H) 9.00 (d, J = 1.83 Hz, 1H) |
| 77 | 5-(furan-2-yl)-thiophene-2-carboxamide | 924.7 | (600 MHz): 0.83-0.94 (m, 6H) 1.14 (d, J = 7.34 Hz, 3H) 1.15-1.31 (m, 2H) 1.21 (d, J = 7.34 Hz, 3H) 1.26 (d, J = 5.96 Hz, 3H) 1.27 (s, 3H) 1.33 (d, J = 6.42 Hz, 3H) 1.36 (s, 3H) 1.54-1.73 (m, 4H) 1.74-2.10 (m, 3H) 2.16-2.45 (m, 4H) 2.31-2.34 (m, 6H) 2.45-2.58 (m, 2H) 2.79-2.89 (m, 1H) 2.96 (d, J = 13.30 Hz, 1H) 3.01-3.09 (m, 1H) 3.25 (dd, J = 10.09, 7.34 Hz, 1H) 3.28 (s, 3H) 3.36 (s, 3H) 3.38-3.61 (m, 4H) 3.75 (d, J = 7.79 Hz, 1H) 4.06-4.13 (m, 1H) 4.17 (s, 1H) 4.44 (d, J = 6.88 Hz, 1H) 4.84 (s, 1H) 4.96 (d, J = 4.59 Hz, 1H) 6.39 (s, 1H) 6.48-6.52 (m, 1H) 6.62-6.65 (m, 1H) 7.21 (d, J = 4.13 Hz, 1H) 7.45-7.52 (m, 2H) |

TABLE 1-continued formula (B)

| Example | R | ESI MS (M + H) | ¹H-NMR, CDCl₃, δ (ppm) |
|---|---|---|---|
| 78 | (5-(furan-2-yl)furan-2-yl)-C(=O)-NH-CH₂CH₂-CH(Me)- | 908.8 | (600 MHz): 0.77-0.88 (m, 6H) 1.08 (d, J = 7.34 Hz, 3H) 1.10-1.25 (m, 2H) 1.16 (d, J = 7.34 Hz, 3H) 1.21 (d, J = 6.42 Hz, 3H) 1.22 (s, 3H) 1.28 (d, J = 5.96 Hz, 3H) 1.31 (s, 3H) 1.52 (dd, J = 15.13, 5.04 Hz, 1H) 1.55-1.71 (m, 3H) 1.72-1.94 (m, 3H) 2.12-2.20 (m, 1H) 2.21-2.35 (m, 3H) 2.26-2.28 (m, 6H) 2.34-2.37 (m, 3H) 2.39-2.51 (m, 2H) 2.76-2.84 (m, 1H) 2.92 (d, J = 15.59 Hz, 1H) 3.00 (t, J = 9.63 Hz, 1H) 3.20 (dd, J = 10.09, 7.34 Hz, 1H) 3.23 (s, 3H) 3.31 (s, 3H) 3.34-3.53 (m, 4H) 3.69 (d, J = 8.25 Hz, 1H) 4.01-4.07 (m, 1H) 4.12 (s, 1H) 4.38 (d, J = 6.88 Hz, 1H) 4.78 (s, 1H) 4.91 (d, J = 4.58 Hz, 1H) 6.44-6.51 (m, 2H) 6.60 (d, J = 3.21 Hz, 1H) 6.70 (d, J = 3.67 Hz, 1H) 7.14 (d, J = 3.67 Hz, 1H) 7.43-7.47 (m, 1H) |
| 79 | PhCH₂-O-CH₂CH₂-CH(Me)- | 825.8 | (600 MHz): 0.73-0.80 (m, 6H) 1.03-1.06 (m, 7H) 1.19 (d, J = 6.42 Hz, 3H) 1.19-1.20 (m, 3H) 1.21-1.23 (m, 1H) 1.25 (d, J = 6.42 Hz, 3H) 1.29 (s, 3H) 1.50 (dd, J = 15.13, 5.04 Hz, 1H) 1.62 (d, J = 12.38 Hz, 1H) 1.74-1.85 (m, 2H) 1.97-2.17 (m, 2H) 2.18-2.30 (m, 3H) 2.26 (s, 6H) 2.33 (s, 3H) 2.34-2.49 (m, 3H) 2.70-2.77 (m, 1H) 2.92-3.00 (m, 2H) 3.13-3.20 (m, 1H) 3.19 (s, 3H) 3.28 (s, 3H) 3.34-3.46 (m, 3H) 3.46-3.51 (m, 1H) 3.66 (d, J = 8.25 Hz, 1H) 3.98-4.05 (m, 1H) 4.10-4.15 (m, 1H) 4.34 (d, J = 6.88 Hz, 1H) 4.42 (s, 2H) 4.85-4.93 (m, 1H) 4.90 (d, J = 4.58 Hz, 1H) 7.20-7.32 (m, 5H) |
| 80 | piperidin-1-yl-CH₂-CH(Me)- | 788.7 | (600 MHz): 0.74-0.79 (m, 6H) 1.04 (d, J = 7.34 Hz, 3H) 1.06-1.21 (m, 2H) 1.11 (d, J = 7.34 Hz, 3H) 1.16 (d, J = 6.42 Hz, 3H) 1.18 (s, 3H) 1.23 (d, J = 6.42 Hz, 3H) 1.27 (s, 3H) 1.31-1.36 (m, 2H) 1.40-1.52 (m, 5H) 1.60 (d, J = 12.38 Hz, 1H) 1.64-1.85 (m, 2H) 2.13-2.48 (m, 12H) 2.24 (s, 6H) 2.31 (s, 3H) 2.69-2.77 (m, 1H) 2.81 (d, J = 15.13 Hz, 1H) 2.95 (t, J = 9.86 Hz, 1H) 3.10-3.21 (m, 1H) 3.17 (s, 3H) 3.27 (s, 3H) 3.36-3.46 (m, 2H) 3.65 (d, J = 7.79 Hz, 1H) 3.96-4.03 (m, 1H) 4.06-4.12 (m, 1H) 4.33 (d, J = 7.34 Hz, 1H) 4.75-4.96 (m, 1H) 4.88 (d, J = 5.04 Hz, 1H) |
| 81 | HO-CH₂CH₂CH₂-CH(Me)- | 763.7 | (600 MHz): 0.77-0.85 (m, 6H) 1.09 (d, J = 7.34 Hz, 3H) 1.13-1.26 (m, 2H) 1.15 (d, J = 7.34 Hz, 2H) 1.21 (d, J = 5.96 Hz, 3H) 1.22 (s, 3H) 1.28 (d, J = 6.42 Hz, 3H) 1.31 (s, 3H) 1.36-1.91 (m, 10H) 2.09-2.20 (m, 1H) 2.20-2.32 (m, 3H) 2.29 (s, 6H) 2.33-2.52 (m, 3H) 2.36 (s, 3H) 2.76-2.83 (m, 1H) 2.92 (d, J = 17.42 Hz, 1H) 3.00 (t, J = 9.40 Hz, 1H) 3.17-3.25 (m, 1H) 3.22 (s, 3H) 3.32 (s, 3H) 3.35-3.51 (m, 2H) 3.59-3.65 (m, 2H) 3.69 (d, J = 8.25 Hz, 1H) 4.01-4.08 (m, 1H) 4.11-4.17 (m, 1H) 4.38 (d, J = 7.34 Hz, 1H) 4.68-4.78 (m, 1H) 4.93 (d, J = 4.59 Hz, 1H) |

TABLE 1-continued formula (B)

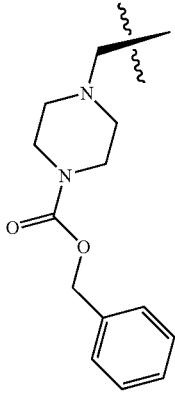

| Example | R | ESI MS (M + H) | $^1$H-NMR, CDCl$_3$, δ (ppm) |
|---|---|---|---|
| 82 | 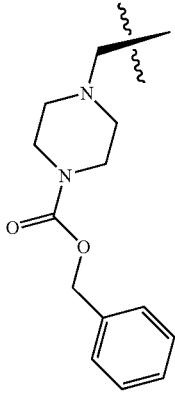 | 923.8 | (600 MHz): 0.80-0.85 (m, 6H) 1.08 (d, J = 7.34 Hz, 3H) 1.15 (d, J = 7.34 Hz, 3H) 1.17-1.26 (m, 2H) 1.22 (d, J = 6.42 Hz, 3H) 1.23 (s, 3H) 1.28 (d, J = 6.42 Hz, 3H) 1.32 (s, 3H) 1.48-1.93 (m, 3H) 2.18-2.60 (m, 13H) 2.35 (s, 6H) 2.37 (s, 3H) 2.72-2.82 (m, 1H) 2.87 (d, J = 16.51 Hz, 1H) 3.00 (t, J = 9.86 Hz, 1H) 3.16-3.25 (m, 1H) 3.22 (s, 3H) 3.32 (s, 3H) 3.39-3.52 (m, 6H) 3.70 (d, J = 7.79 Hz, 1H) 4.01-4.07 (m, 1H) 4.07-4.13 (m, 1H) 4.39 (d, J = 7.34 Hz, 1H) 4.91 (d, J = 4.59 Hz, 1H) 4.94-4.98 (m, 1H) 5.11 (s, 2H) 7.27-7.38 (m, 5H) |
| 83 | 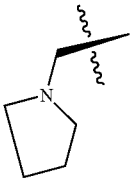 | 774.7 | (600 MHz): 0.78-0.87 (m, 6H) 1.09 (d, J = 7.34 Hz, 3H) 1.11-1.27 (m, 8H) 1.15 (d, J = 7.79 Hz, 3H) 1.28 (d, J = 6.42 Hz, 3H) 1.32 (s, 3H) 1.53 (dd, J = 15.13, 5.04 Hz, 1H) 1.60-1.80 (m, 4H) 1.65 (d, J = 12.84 Hz, 1H) 1.80-1.89 (m, 1H) 2.21-2.40 (m, 5H) 2.29 (s, 6H) 2.38 (s, 3H) 2.42-2.53 (m, 6H) 2.56 (dd, J = 12.15, 7.11 Hz, 1H) 2.66-2.75 (m, 1H) 2.75-2.83 (m, 1H) 2.88 (d, J = 14.21 Hz, 1H) 2.98-3.03 (m, 1H) 3.17-3.25 (m, 1H) 3.23 (s, 3H) 3.32 (s, 3H) 3.41-3.51 (m, 2H) 3.70 (d, J = 8.25 Hz, 1H) 4.01-4.09 (m, 1H) 4.12-4.18 (m, 1H) 4.39 (d, J = 7.34 Hz, 1H) 4.85-4.91 (m, 1H) 4.93 (d, J = 4.59 Hz, 1H) |
| 84 | 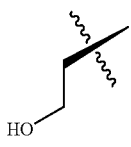 | 735.6 | (600 MHz): 0.83 (d, J = 6.88 Hz, 3H) 0.85 (d, J = 4.59 Hz, 3H) 1.08 (d, J = 7.34 Hz, 3H) 1.10-1.24 (m, 2H) 1.15 (d, J = 7.34 Hz, 3H) 1.19 (d, J = 5.96 Hz, 3H) 1.21 (s, 3H) 1.25 (d, J = 5.96 Hz, 3H) 1.29 (s, 3H) 1.52 (dd, J = 15.36, 4.81 Hz, 1H) 1.58-1.70 (m, 1H) 1.71-1.81 (m, 2H) 1.81-1.91 (m, 1H) 2.15-2.31 (m, 5H) 2.26 (s, 6H) 2.32-2.54 (m, 3H) 2.35 (s, 3H) 2.73-2.82 (m, 1H) 2.90-3.01 (m, 1H) 2.98 (t, J = 9.86 Hz, 1H) 3.16-3.21 (m, 2H) 3.22 (s, 3H) 3.30 (s, 3H) 3.41-3.50 (m, 2H) 3.60-3.67 (m, 1H) 3.70 (d, J = 7.79 Hz, 1H) 3.98-4.06 (m, 1H) 4.06-4.13 (m, 1H) 4.38 (d, J = 7.34 Hz, 1H) 4.87 (d, J = 4.58 Hz, 1H) 4.93-5.01 (m, 1H) |
| 85 | 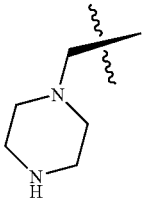 | 789.8 | (600 MHz): 0.78-0.86 (m, 6H) 1.08 (d, J = 7.34 Hz, 3H) 1.10-1.26 (m, 2H) 1.16 (d, J = 7.34 Hz, 3H) 1.21 (d, J = 5.96 Hz, 3H) 1.22 (s, 3H) 1.27 (d, J = 6.42 Hz, 3H) 1.31 (s, 3H) 1.53 (dd, J = 15.36, 4.81 Hz, 1H) 1.60-1.66 (m, 1H) 1.79-1.90 (m, 1H) 2.20-2.33 (m, 3H) 2.27 (s, 6H) 2.34-2.54 (m, 9H) 2.35 (s, 3H) 2.74-2.90 (m, 6H) 2.99 (d, J = 9.17 Hz, 1H) 3.16-3.23 (m, 1H) 3.22 (s, 3H) 3.32 (s, 3H) 3.41-3.49 (m, 2H) 3.69 (d, J = 8.25 Hz, 1H) 4.01-4.07 (m, 1H) 4.08-4.14 (m, 1H) 4.37 (d, J = 7.34 Hz, 1H) 4.92 (d, J = 4.58 Hz, 1H) 4.93-4.98 (m, 1H) |

TABLE 1-continued formula (B)

| Example | R | ESI MS (M + H) | $^1$H-NMR, CDCl$_3$, δ (ppm) |
|---|---|---|---|
| 86 | (4-aminopentyl group) | | (600 MHz): 0.78-0.85 (m, 6H) 0.91 (t, J = 7.34 Hz, 2H) 1.09 (d, J = 7.34 Hz, 3H) 1.11-1.27 (m, 2H) 1.15 (d, J = 7.34 Hz, 3H) 1.22 (d, J = 5.96 Hz, 3H) 1.22 (s, 3H) 1.28 (d, J = 6.42 Hz, 3H) 1.32 (s, 3H) 1.33-1.90 (m, 6H) 1.53 (dd, J = 15.13, 5.04 Hz, 1H) 2.10-2.53 (m, 6H) 2.29 (s, 6H) 2.36 (s, 3H) 2.68 (t, J = 7.11 Hz, 2H) 2.75-2.82 (m, 1H) 2.91 (d, J = 14.67 Hz, 1H) 3.00 (d, J = 9.63 Hz, 1H) 3.17-3.24 (m, 1H) 3.22 (s, 3H) 3.32 (s, 3H) 3.35-3.43 (m, 1H) 3.42-3.51 (m, 1H) 3.70 (d, J = 8.25 Hz, 1H) 4.00-4.08 (m, 1H) 4.10-4.17 (m, 1H) 4.38 (d, J = 7.34 Hz, 1H) 4.67-4.78 (m, 1H) 4.93 (d, J = 4.59 Hz, 1H) |
| 87 | (4-methylpiperazin-1-yl)methyl | 803.8 | (600 MHz): 0.77-0.88 (m, 6H) 1.08 (d, J = 7.34 Hz, 3H) 1.10-1.21 (m, 2H) 1.16 (d, J = 7.34 Hz, 3H) 1.22 (d, J = 6.42 Hz, 3H) 1.22-1.23 (m, 3H) 1.27 (d, J = 6.42 Hz, 3H) 1.32 (s, 3H) 1.53 (dd, J = 15.36, 4.81 Hz, 1H) 1.66-1.73 (m, 1H) 1.79-1.91 (m, 1H) 2.15-2.65 (m, 16H) 2.30 (s, 3H) 2.33 (s, 6H) 2.36 (s, 3H) 2.74-2.81 (m, 1H) 2.88 (d, J = 14.67 Hz, 1H) 3.00 (d, J = 9.63 Hz, 1H) 3.17-3.26 (m, 4H) 3.32 (s, 3H) 3.39-3.52 (m, 2H) 3.70 (d, J = 7.79 Hz, 1H) 3.99-4.07 (m, 1H) 4.08-4.14 (m, 1H) 4.38 (d, J = 7.34 Hz, 1H) 4.92 (d, J = 4.59 Hz, 1H) 4.93-4.99 (m, 1H) |
| 88 | (imidazol-1-yl)methyl | 771.7 | (600 MHz): 0.82 (d, J = 6.88 Hz, 3H) 0.85 (d, J = 6.42 Hz, 3H) 0.88-0.99 (m, 3H) 1.07 (d, J = 7.34 Hz, 3H) 1.09-1.25 (m, 8H) 1.27 (d, J = 6.42 Hz, 3H) 1.32 (s, 3H) 1.49 (dd, J = 15.36, 4.81 Hz, 1H) 1.65 (d, J = 13.76 Hz, 1H) 1.74-1.91 (m, 1H) 2.18-2.36 (m, 4H) 2.28 (s, 6H) 2.39 (s, 3H) 2.43-2.53 (m, 2H) 2.65-2.74 (m, 1H) 2.94-3.01 (m, 1H) 3.06 (d, J = 15.59 Hz, 1H) 3.15-3.21 (m, 1H) 3.20 (s, 3H) 3.29 (s, 3H) 3.35-3.49 (m, 2H) 3.66 (d, J = 7.79 Hz, 1H) 3.97-4.05 (m, 2H) 4.08 (dd, J = 14.21, 3.21 Hz, 1H) 4.19-4.29 (m, 1H) 4.37 (d, J = 6.88 Hz, 1H) 4.82 (d, J = 4.58 Hz, 1H) 4.91-5.02 (m, 1H) 6.90 (s, 1H) 7.02 (s, 1H) 7.46 (s, 1H) |
| 89 | [4-(pyridin-3-yl)imidazol-1-yl]methyl | 847.5 | (600 MHz): 0.75-0.91 (m, 9H) 1.03 (d, J = 7.34 Hz, 3H) 1.06-1.28 (m, 11H) 1.29 (s, 3H) 1.43 (dd, J = 15.13, 4.59 Hz, 1H) 1.51-1.88 (m, 2H) 2.15-2.34 (m, 11H) 2.39 (s, 3H) 2.42-2.54 (m, 2H) 2.66-2.74 (m, 1H) 2.94 (t, J = 9.40 Hz, 1H) 3.05-3.20 (m, 2H) 3.17 (s, 3H) 3.24 (s, 3H) 3.25-3.47 (m, 2H) 3.63 (d, J = 8.25 Hz, 1H) 3.92-4.03 (m, 2H) 4.11 (dd, J = 14.21, 2.75 Hz, 1H) 4.21-4.29 (m, 1H) 4.33 (d, J = 7.34 Hz, 1H) 4.77 (d, J = 4.59 Hz, 1H) 4.93-5.04 (m, 1H) 7.24 (s, 1H) 7.26 (dd, J = 8.02, 4.81 Hz, 1H) 7.51 (s, 1H) 8.03 (td, J = 7.91, 2.06, 1.95 Hz, 1H) 8.43 (dd, J = 4.81, 1.60 Hz, 1H) 8.90 (d, J = 1.83 Hz, 1H) |
| 90 | (methoxycarbonyl)methyl | 749.6 | (500 MHz): 0.85-0.96 (m, 6H) 1.11 (d, J = 7.65 Hz, 3H) 1.15-1.34 (m, 8H) 1.18 (d, J = 6.88 Hz, 3H) 1.26 (d, J = 6.12 Hz, 3H) 1.30 (s, 3H) 1.53 (dd, J = 14.91, 4.97 Hz, 1H) 1.65-1.73 (m, 1H) 1.89-2.00 (m, 1H) 2.15-2.42 (m, 13H) 2.44-2.54 (m, 1H) 2.55-2.63 (m, 1H) 2.64-2.76 (m, 1H) 2.90-2.97 (m, 1H) 2.97-3.03 (m, 1H) 3.03-3.13 (m, 1H) 3.19-3.29 (m, 1H) 3.26 (s, 3H) 3.33 (s, 3H) 3.44-3.56 (m, 2H) 3.70-3.77 (m, 1H) 3.73 (s, 3H) 3.99-4.08 (m, 1H) 4.08-4.27 (m, 1H) 4.44 (d, J = 6.88 Hz, 1H) 4.72-4.78 (m, 1H) 5.06-5.15 (m, 1H) |

TABLE 1-continued formula (B)

| Example | R | ESI MS (M + H) | $^1$H-NMR, CDCl$_3$, δ (ppm) |
|---|---|---|---|
| 91 | H$_2$N-C(=O)-(CH$_2$)$_4$- | 790.7 | (500 MHz): 0.74-0.87 (m, 6H) 1.09 (d, J = 7.13 Hz, 3H) 1.15 (d, J = 7.40 Hz, 3H) 1.18-1.91 (m, 17H) 1.28 (d, J = 6.31 Hz, 3H) 1.32 (s, 3H) 2.09-2.58 (m, 9H) 2.31 (s, 6H) 2.37 (s, 3H) 2.71-2.85 (m, 1H) 2.86-2.96 (m, 1H) 3.00 (t, J = 9.60 Hz, 1H) 3.18-3.25 (m, 4H) 3.32 (s, 3H) 3.35-3.43 (m, 1H) 3.43-3.52 (m, 1H) 3.66-3.73 (m, J = 7.95 Hz, 1H) 3.99-4.08 (m, 1H) 4.09-4.19 (m, 1H) 4.39 (d, J = 7.40 Hz, 1H) 4.65-4.80 (m, 1H) 4.92 (d, J = 4.66 Hz, 1H) 5.17-5.32 (m, 1H) 5.33-5.53 (m, 1H) |
| 92 | 3-NH$_2$-C$_6$H$_4$-CH$_2$-O-C(=O)-NH- | 869.7 | (600 MHz): 0.78-0.88 (m, 6H) 1.08 (d, J = 7.79 Hz, 3H) 1.12 (d, J = 7.34 Hz, 3H) 1.17-1.30 (m, 2H) 1.21 (d, J = 5.96 Hz, 3H) 1.23 (s, 3H) 1.28 (d, J = 6.42 Hz, 3H) 1.31 (s, 3H) 1.53 (dd, J = 15.13, 4.59 Hz, 1H) 1.61-1.70 (m, 1H) 1.79-1.92 (m, 1H) 2.18-2.37 (m, 4H) 2.27-2.30 (m, 6H) 2.34-2.35 (m, 3H) 2.42-2.52 (m, 2H) 2.73-2.83 (m, 1H) 2.93-3.04 (m, 2H) 3.16-3.41 (m, 3H) 3.22-3.24 (m, 3H) 3.30-3.32 (m, 3H) 3.42-3.58 (m, 3H) 3.64-3.77 (m, 1H) 3.69 (d, J = 8.25 Hz, 1H) 3.99-4.14 (m, 2H) 4.39 (d, J = 6.88 Hz, 1H) 4.85 (s, 1H) 4.89 (d, J = 4.59 Hz, 1H) 4.94-5.10 (m, 3H) 6.60 (d, J = 9.17 Hz, 1H) 6.63 (s, 1H) 6.69 (d, J = 7.34 Hz, 1H) 7.11 (t, J = 7.79 Hz, 1H) |
| 93 | 3-NC-C$_6$H$_4$-CH$_2$-O-C(=O)-NH- | 879.7 | (600 MHz): 0.77-0.90 (m, 6H) 1.08 (d, J = 7.34 Hz, 3H) 1.13 (d, J = 7.34 Hz, 3H) 1.16-1.30 (m, 2H) 1.22 (d, J = 5.96 Hz, 3H) 1.23-1.24 (m, 3H) 1.28 (d, J = 5.96 Hz, 3H) 1.32 (s, 3H) 1.48-1.58 (m, 2H) 1.79-1.93 (m, 1H) 2.07-2.40 (m, 14H) 2.39-2.56 (m, 2H) 2.74-2.83 (m, 1H) 2.93-3.05 (m, 2H) 3.17-3.27 (m, 1H) 3.22-3.24 (m, 3H) 3.32 (s, 3H) 3.33-3.56 (m, 4H) 3.70 (d, J = 7.79 Hz, 1H) 3.96-4.16 (m, 2H) 4.40 (d, J = 6.88 Hz, 1H) 4.79-4.91 (m, 2H) 5.10 (s, 2H) 5.16 (s, 1H) 7.45 (t, J = 7.79 Hz, 1H) 7.52-7.69 (m, 3H) |
| 94 | 3-(2-furyl)-C$_6$H$_4$-CH$_2$-O-C(=O)-NH- | 920.8 | (600 MHz): 0.77-0.91 (m, 6H) 1.02-1.37 (m, 20H) 1.47-1.56 (m, 1H) 1.61-1.72 (m, 1H) 1.80-1.93 (m, 1H) 2.17-2.54 (m, 6H) 2.30 (s, 6H) 2.35 (s, 3H) 2.72-2.82 (m, 1H) 2.93-3.05 (m, 2H) 3.15-3.56 (m, 5H) 3.23 (s, 3H) 3.31 (s, 3H) 3.69 (d, J = 7.79 Hz, 1H) 3.99-4.13 (m, 2H) 4.39 (d, J = 7.34 Hz, 1H) 4.78-4.92 (m, 2H) 5.03-5.16 (m, 3H) 6.42-6.51 (m, 1H) 6.62-6.71 (m, 1H) 7.19-7.69 (m, 5H) |
| 95 | C$_6$H$_5$-O-C(=O)-NH- | 854.7 | (600 MHz): 0.81-0.89 (m, 6H) 1.10 (d, J = 7.34 Hz, 3H) 1.15-1.26 (m, 2H) 1.19 (d, J = 7.34 Hz, 3H) 1.22 (d, J = 5.96 Hz, 3H) 1.23 (s, 3H) 1.28 (d, J = 5.96 Hz, 3H) 1.32 (s, 3H) 1.55 (dd, J = 15.13, 5.04 Hz, 1H) 1.62-1.72 (m, 1H) 1.77-1.93 (m, 3H) 2.19-2.42 (m, 7H) 2.29 (s, 6H) 2.38 (s, 3H) 2.44-2.52 (m, 2H) 2.78-2.87 (m, 1H) 2.90-3.04 (m, 2H) 3.17-3.26 (m, 4H) 3.25 (s, 3H) 3.32 (s, 3H) 3.38-3.51 (m, 3H) 3.71 (d, J = 7.79 Hz, 1H) 4.00-4.08 (m, 1H) 4.09-4.18 (m, 1H) 4.40 (d, J = 7.34 Hz, 1H) 4.86-4.98 (m, 1H) 4.93 (d, J = 4.59 Hz, 1H) 5.34-5.50 (brs, 1H) 7.11 (d, J = 7.34 Hz, 1H) 7.18 (t, J = 7.34 Hz, 1H) 7.34 (t, J = 8.02 Hz, 2H) |

TABLE 1-continued formula (B)

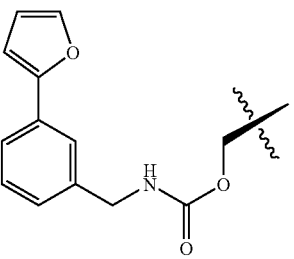

| Example | R | ESI MS (M + H) | $^1$H-NMR, CDCl$_3$, δ (ppm) |
|---|---|---|---|
| 96 |  | 920.8 | (500 MHz): 0.75-0.90 (m, 6H) 1.06 (d, J = 7.13 Hz, 3H) 1.11 (d, J = 7.40 Hz, 3H) 1.11-1.39 (m, 2H) 1.20-1.24 (m, 6H) 1.27 (d, J = 6.31 Hz, 3H) 1.31 (s, 3H) 1.41-2.06 (m, 3H) 2.15-2.55 (m, 14H) 2.55-2.69 (m, 1H) 2.72-2.84 (m, 1H) 2.88-2.97 (m, 1H) 3.00 (d, J = 6.86 Hz, 1H) 3.20-3.32 (m, 1H) 3.22 (s, 3H) 3.30 (s, 3H) 3.35-3.54 (m, 2H) 3.69 (d, J = 7.68 Hz, 1H) 3.97-4.13 (m, 2H) 4.16-4.47 (m, 5H) 4.84-4.91 (m, 1H) 4.93-5.08 (m, 2H) 6.46 (dd, J = 3.29, 1.92 Hz, 1H) 6.66 (dd, J = 3.43, 0.69 Hz, 1H) 7.14-7.19 (m, 1H) 7.34 (m, 1H) 7.44-7.48 (m, 1H) 7.53-7.61 (m, 2H) |
| 97 |  | 854.8 | (500 MHz): 0.74-0.88 (m, 6H) 1.06 (d, J = 6.88 Hz, 3H) 1.09-1.75 (m, 4H) 1.13 (d, J = 7.65 Hz, 3H) 1.21-1.25 (m, 6H) 1.28 (d, J = 6.12 Hz, 3H) 1.31 (s, 3H) 1.81-1.90 (m, 1H) 2.12-2.56 (m, 16H) 2.73-2.85 (m, 1H) 2.90-2.99 (m, 1H) 3.01 (t, J = 9.56 Hz, 1H) 3.22 (s, 3H) 3.25-3.36 (m, 1H) 3.31 (s, 3H) 3.36-3.45 (m, 1H) 3.46-3.57 (m, 1H) 3.70 (d, J = 7.65 Hz, 1H) 3.98-4.05 (m, 1H) 4.05-4.13 (m, 1H) 4.17-4.38 (m, 4H) 4.41 (d, J = 6.88 Hz, 1H) 4.89 (d, J = 4.59 Hz, 1H) 4.92-5.02 (m, 1H) 7.26-7.36 (m, 5H) |
| 98 | 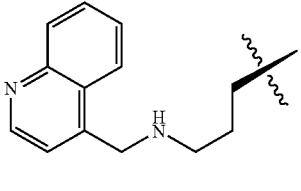 | 855.8 | (600 MHz): 0.78-0.89 (m, 6H) 1.08 (d, J = 7.79 Hz, 3H) 1.10 (d, J = 7.34 Hz, 3H) 1.15-1.28 (m, 2H) 1.21 (d, J = 5.96 Hz, 3H) 1.23 (s, 3H) 1.28 (d, J = 5.96 Hz, 3H) 1.31 (s, 3H) 1.53 (dd, J = 15.36, 4.81 Hz, 1H) 1.65 (d, J = 13.30 Hz, 1H) 1.80-1.91 (m, 1H) 2.18-2.38 (m, 4H) 2.27-2.29 (m, 6H) 2.33-2.35 (m, 3H) 2.40-2.54 (m, 2H) 2.71-2.83 (m, 1H) 2.92-3.05 (m, 2H) 3.19 (dd, J = 10.09, 7.34 Hz, 1H) 3.22 (s, 3H) 3.30-3.32 (m, 3H) 3.30-3.54 (m, 4H) 3.69 (d, J = 8.25 Hz, 1H) 3.97-4.13 (m, 2H) 4.39 (d, J = 6.88 Hz, 1H) 4.84 (s, 1H) 4.88 (d, J = 4.59 Hz, 1H) 5.09 (s, 2H) 5.15 (s, 1H) 7.26-7.30 (m, 1H) 7.67 (d, J = 7.79 Hz, 1H) 8.55 (d, J = 5.04 Hz, 1H) 8.58 (s, 1H) |
| 99 | 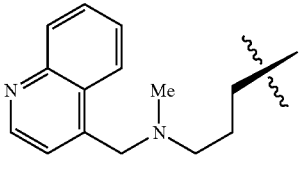 | 889.7 | (600 MHz): 0.77-0.86 (m, 6H) 1.09 (d, J = 7.34 Hz, 3H) 1.09-1.26 (m, 2H) 1.13 (d, J = 7.79 Hz, 3H) 1.21 (d, J = 5.96 Hz, 3H) 1.22 (s, 3H) 1.28 (d, J = 6.42 Hz, 3H) 1.31 (s, 3H) 1.46-1.69 (m, 6H) 1.84 (s, 1H) 2.08-2.20 (m, 1H) 2.21-2.31 (m, 2H) 2.27-2.29 (m, 6H) 2.32-2.37 (m, 1H) 2.35-2.36 (m, 3H) 2.37-2.51 (m, 2H) 2.74 (t, J = 6.65 Hz, 2H) 2.76-2.82 (m, 1H) 2.92 (d, J = 14.21 Hz, 1H) 3.00 (d, J = 8.71 Hz, 1H) 3.20 (dd, J = 10.09, 7.34 Hz, 1H) 3.22 (s, 3H) 3.31 (s, 3H) 3.33-3.50 (m, 2H) 3.69 (d, J = 8.25 Hz, 1H) 4.01-4.08 (m, 1H) 4.14 (m, 1H) 4.25 (s, 2H) 4.38 (d, J = 7.34 Hz, 1H) 4.74 (s, 1H) 4.92 (d, J = 4.58 Hz, 1H) 7.43 (d, J = 4.13 Hz, 1H) 7.53-7.59 (m, 1H) 7.67-7.73 (m, 1H) 8.07 (d, J = 8.25 Hz, 1H) 8.11 (d, J = 7.79 Hz, 1H) 8.86 (d, J = 4.13 Hz, 1H) |
| 100 |  | | (600 MHz): 0.72-0.85 (m, 6H) 1.00-1.35 (m, 2H) 1.06 (d, J = 5.04 Hz, 3H) 1.11 (d, J = 7.79 Hz, 3H) 1.18-1.25 (m, 6H) 1.27 (d, J = 6.42 Hz, 3H) 1.29-1.31 (m, 3H) 1.38-1.68 (m, 6H) 1.74-1.86 (m, 1H) 1.92-2.42 (m, 12H) 2.21-2.22 (m, 6H) 2.45 (t, J = 6.88 Hz, 2H) 2.71-2.81 (m, 1H) 2.90 (none, 1H) 2.85-2.92 (m, 1H) 2.99 (t, J = 9.63 Hz, 1H) 3.16-3.23 (m, 1H) 3.19-3.21 (m, 3H) 3.28-3.30 (m, 3H) 3.33-3.41 (m, 1H) 3.42-3.56 (m, 1H) 3.68 (d, J = 7.79 Hz, 1H) 3.82-3.92 (m, 2H) 3.95-4.07 (m, 1H) 4.07-4.18 (m, 1H) 4.38 (d, J = 7.79 Hz, 1H) 4.66 (s, 1H) 4.90 (d, J = 4.58 Hz, 1H) 7.38 (d, J = 4.13 Hz, 1H) 7.49-7.55 (m, 1H) 7.65-7.71 (m, 1H) 8.09 (d, J = 8.25 Hz, 1H) 8.21 (d, J = 8.71 Hz, 1H) 8.83 (d, J = 4.13 Hz, 1H) |

TABLE 1-continued formula (B)

| Example | R | ESI MS (M + H) | ¹H-NMR, CDCl₃, δ (ppm) |
|---|---|---|---|
| 101 | quinolin-4-ylmethoxy-propyl group | 890.6 | (600 MHz): 0.78-0.84 (m, 6H) 1.05-1.10 (m, 3H) 1.06-1.29 (m, 2H) 1.13 (d, J = 7.34 Hz, 3H) 1.21-1.25 (m, 6H) 1.28 (d, J = 5.96 Hz, 3H) 1.31 (s, 3H) 1.57-1.91 (m, 7H) 2.06-2.17 (m, 1H) 2.18-2.47 (m, 12H) 2.34-2.36 (m, 3H) 2.75-2.83 (m, 1H) 2.90-2.97 (m, 1H) 3.01 (t, J = 10.09 Hz, 1H) 3.16-3.27 (m, 1H) 3.21-3.22 (m, 3H) 3.31 (s, 3H) 3.39 (s, 1H) 3.47 (s, 1H) 3.54-3.65 (m, 2H) 3.70 (d, J = 7.79 Hz, 1H) 4.03 (s, 1H) 4.14 (s, 1H) 4.39 (s, 1H) 4.74 (s, 1H) 4.91 (s, 1H) 4.96 (s, 2H) 7.45 (d, J = 4.58 Hz, 1H) 7.53-7.59 (m, 1H) 7.69-7.74 (m, 1H) 7.98 (d, J = 8.25 Hz, 1H) 8.12 (d, J = 8.25 Hz, 1H) 8.89 (d, J = 4.13 Hz, 1H) |
| 102 | cyanomethyl-substituted group | 730.5 | (500 MHz): 0.82-0.93 (m, 6H) 1.10 (d, J = 7.64 Hz, 3H) 1.12-1.31 (m, 2H) 1.18-1.23 (m, 6H) 1.24 (s, 3H) 1.29 (d, J = 6.12 Hz, 3H) 1.33 (s, 3H) 1.51-1.71 (m, 2H) 1.83-1.93 (m, 1H) 2.18-2.41 (m, 4H) 2.30 (s, 6H) 2.37 (d, J = 15.29 Hz, 1H) 2.40 (s, 3H) 2.44-2.61 (m, 2H) 2.66-2.75 (m, 2H) 2.82-2.87 (m, 1H) 2.97-3.08 (m, 2H) 3.16-3.23 (m, 1H) 3.24 (s, 3H) 3.29-3.38 (m, 1H) 3.33 (s, 3H) 3.43-3.52 (m, 1H) 3.70 (d, J = 7.64 Hz, 1H) 3.92-4.10 (m, 2H) 4.41 (d, J = 7.26 Hz, 1H) 4.89 (d, J = 4.59 Hz, 1H) 4.94-5.03 (m, 1H) |
| 103 | cyanoethyl-substituted group | 744.5 | (500 MHz): 0.82-0.93 (m, 6H) 1.10 (d, J = 7.64 Hz, 3H) 1.12-1.31 (m, 2H) 1.18-1.23 (m, 6H) 1.24 (s, 3H) 1.29 (d, J = 6.12 Hz, 3H) 1.33 (s, 3H) 1.51-1.71 (m, 2H) 1.83-1.93 (m, 1H) 2.18-2.41 (m, 4H) 2.30 (s, 6H) 2.37 (d, J = 15.29 Hz, 1H) 2.40 (s, 3H) 2.44-2.61 (m, 2H) 2.66-2.75 (m, 2H) 2.82-2.87 (m, 1H) 2.97-3.08 (m, 2H) 3.16-3.23 (m, 1H) 3.24 (s, 3H) 3.29-3.38 (m, 1H) 3.33 (s, 3H) 3.43-3.52 (m, 1H) 3.70 (d, J = 7.64 Hz, 1H) 3.92-4.10 (m, 2H) 4.41 (d, J = 7.26 Hz, 1H) 4.89 (d, J = 4.59 Hz, 1H) 4.94-5.03 (m, 1H) |
| 104 | cyanopropyl-substituted group | 758.6 | (500 MHz): 0.75-0.88 (m, 6H) 1.09 (d, J = 7.26 Hz, 3H) 1.11-1.27 (m, 2H) 1.15 (d, J = 7.26 Hz, 3H) 1.22 (d, J = 6.12 Hz, 3H) 1.23 (s, 3H) 1.28 (d, J = 6.50 Hz, 3H) 1.32 (s, 3H) 1.54 (dd, J = 15.29, 4.97 Hz, 1H) 1.57-1.98 (m, 7H) 2.11-2.20 (m, 1H) 2.19-2.52 (m, 7H) 2.28 (s, 6H) 2.37 (s, 3H) 2.73-2.84 (m, 1H) 2.94 (d, J = 14.91 Hz, 1H) 3.00 (t, J = 9.75 Hz, 1H) 3.15-3.22 (m, 1H) 3.22 (s, 3H) 3.32 (s, 3H) 3.33-3.42 (m, 1H) 3.42-3.50 (m, 1H) 3.69 (d, J = 8.03 Hz, 1H) 4.00-4.09 (m, 1H) 4.09-4.18 (m, 1H) 4.38 (d, J = 7.26 Hz, 1H) 4.69-4.81 (m, 1H) 4.92 (d, J = 4.59 Hz, 1H) |
| 105 | methoxycarbonylamino-methyl group | 778.5 | (600 MHz): 0.81-0.86 (m, 6H) 1.09 (d, J = 7.34 Hz, 3H) 1.10-1.25 (m, 2H) 1.16 (d, J = 7.34 Hz, 3H) 1.22 (d, J = 5.96 Hz, 3H) 1.23 (s, 3H) 1.28 (d, J = 5.96 Hz, 3H) 1.32 (s, 3H) 1.54 (dd, J = 15.13, 5.04 Hz, 1H) 1.59-1.68 (m, 1H) 1.82-1.88 (m, 1H) 2.20-2.32 (m, 3H) 2.24 (d, J = 10.09 Hz, 1H) 2.29 (s, 6H) 2.35 (d, J = 14.67 Hz, 1H) 2.35 (s, 3H) 2.43-2.51 (m, 2H) 2.77-2.83 (m, 1H) 2.95-2.99 (m, 1H) 3.00 (t, J = 9.86 Hz, 1H) 3.18-3.22 (m, 1H) 3.23 (s, 3H) 3.32 (s, 3H) 3.31-3.42 (m, 2H) 3.42-3.54 (m, 2H) 3.64 (s, 3H) 3.70 (d, J = 7.79 Hz, 1H) 4.02-4.06 (m, 1H) 4.07-4.13 (m, 1H) 4.39 (d, J = 6.88 Hz, 1H) 4.80-4.84 (m, 1H) 4.90 (d, J = 4.58 Hz, 1H) 4.96-5.02 (m, 1H) |
| 106 | ethoxycarbonylamino-methyl group | 792.5 | (600 MHz): 0.80-0.87 (m, 6H) 1.09 (d, J = 7.34 Hz, 3H) 1.09-1.26 (m, 5H) 1.16 (d, J = 7.34 Hz, 3H) 1.21 (d, J = 5.96 Hz, 3H) 1.23 (s, 3H) 1.28 (d, J = 6.42 Hz, 3H) 1.32 (s, 3H) 1.54 (dd, J = 14.90, 4.81 Hz, 1H) 1.61-1.68 (m, 1H) 1.82-1.89 (m, 1H) 2.21-2.38 (m, 5H) 2.28 (s, 6H) 2.35 (s, 3H) 2.42-2.51 (m, 2H) 2.78-2.82 (m, 1H) 2.95-2.98 (m, 1H) 3.00 (t, J = 10.09 Hz, 1H) 3.18-3.22 (m, 1H) 3.23 (s, 3H) 3.32 (s, 3H) 3.32-3.42 (m, 2H) 3.42-3.51 (m, 2H) 3.69 (d, J = 7.79 Hz, 1H) 4.01-4.12 (m, 4H) 4.39 (d, J = 6.88 Hz, 1H) 4.79-4.84 (m, 1H) 4.90 (d, J = 4.58 Hz, 1H) 4.92-4.96 (m, 1H) |

TABLE 1-continued

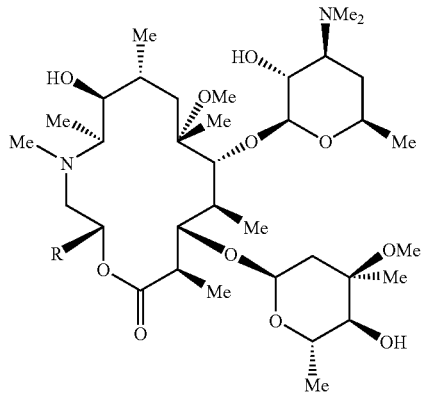

formula (B)

| Example | R | ESI MS (M + H) | $^1$H-NMR, CDCl$_3$, δ (ppm) |
|---|---|---|---|
| 107 | ![Me-NH-C(=O)-O-CH(Me)-] | 778.5 | (600 MHz): 0.80-0.86 (m, 6H) 1.09 (d, J = 7.34 Hz, 3H) 1.10-1.25 (m, 2H) 1.15 (d, J = 7.34 Hz, 3H) 1.22 (d, J = 6.42 Hz, 3H) 1.23 (s, 3H) 1.28 (d, J = 6.42 Hz, 3H) 1.32 (s, 3H) 1.52-1.56 (m, 1H) 1.61-1.68 (m, 1H) 1.83-1.87 (m, 1H) 2.21-2.38 (m, 5H) 2.29 (s, 6H) 2.34 (s, 3H) 2.43-2.50 (m, 2H) 2.78 (d, J = 4.59 Hz, 3H) 2.79-2.83 (m, 1H) 2.89-2.94 (m, 1H) 3.00 (t, J = 10.09 Hz, 1H) 3.19-3.22 (m, 1H) 3.23 (s, 3H) 3.32 (s, 3H) 3.38-3.50 (m, 2H) 3.70 (d, J = 7.79 Hz, 1H) 4.02-4.07 (m, 1H) 4.08-4.13 (m, 1H) 4.17-4.25 (m, 2H) 4.39 (d, J = 6.88 Hz, 1H) 4.55-4.60 (m, 1H) 4.91 (d, J = 4.59 Hz, 1H) 4.93-4.97 (m, 1H) |
| 108 | ![Me2N-C(=O)-O-CH(Me)-] | 792.6 | (600 MHz): 0.79-0.84 (m, 6H) 1.09 (d, J = 7.34 Hz, 3H) 1.10-1.25 (m, 2H) 1.15 (d, J = 7.34 Hz, 3H) 1.21 (d, J = 5.96 Hz, 3H) 1.22 (s, 3H) 1.28 (d, J = 6.42 Hz, 3H) 1.32 (s, 3H) 1.53 (dd, J = 15.13, 5.04 Hz, 1H) 1.63-1.69 (m, 1H) 1.80-1.87 (m, 1H) 2.25 (d, J = 10.55 Hz, 1H) 2.24-2.38 (m, 4H) 2.28 (s, 6H) 2.34 (s, 3H) 2.42-2.50 (m, 2H) 2.79-2.84 (m, 1H) 2.85 (s, 3H) 2.90 (s, 3H) 2.95 (d, J = 16.05 Hz, 1H) 3.00 (t, J = 9.86 Hz, 1H) 3.18-3.22 (m, 1H) 3.22 (s, 3H) 3.32 (s, 3H) 3.41-3.50 (m, 2H) 3.69 (d, J = 7.79 Hz, 1H) 4.02-4.07 (m, 1H) 4.11-4.13 (m, 1H) 4.15-4.19 (m, 1H) 4.27 (dd, J = 11.46, 4.13 Hz, 1H) 4.38 (d, J = 7.34 Hz, 1H) 4.92 (d, J = 4.59 Hz, 1H) 4.95-5.00 (m, 1H) |

Example 7

(1) The compound obtained in Example 1 (10.0 g) was dissolved in tetrahydrofuran (30 ml), the solution was added with (R)-1,2-epoxybutane (3.62 g) and ytterbium triflate monohydrate (624 mg), and the mixture was stirred at 90° C. for 1.25 hours in a sealed tube. The reaction mixture was concentrated under reduced pressure, and the resulting residue was purified by silica gel column chromatography (chloroform:methanol:28% aqueous ammonia=30:1:0.1) to obtain a 10a-N-(2-hydroxybutyl) compound (4.62 g).

(2) The compound obtained in (1) mentioned above (4.62 g) was dissolved in chloroform (25 ml), the solution was added with 37% aqueous formaldehyde (2.2 ml) and sodium triacetoxyborohydride (1.38 g), and the mixture was stirred at room temperature for 30 minutes. The reaction mixture was added with saturated aqueous sodium hydrogencarbonate, the layers were separated, and the organic layer was dried over anhydrous magnesium sulfate and filtered. The filtrate was concentrated under reduced pressure to obtain a 10a-N-methyl compound (4.55 g).

(3) The compound obtained in (2) mentioned above (4.55 g) was dissolved in tetrahydrofuran (20 ml), the solution was added with triethylamine (469 mg) and 2,4,6-trichlorobenzoyl chloride (1.13 g), and the mixture was stirred at room temperature for 3 hours. This solution was added dropwise to a solution of 4-dimethylaminopyridine (12.9 g) in acetonitrile (420 ml) under reflux by heating. The reaction mixture was concentrated under reduced pressure, the resulting residue was added with ethyl acetate and saturated aqueous ammonium chloride, the layers were separated, and the organic layer was washed successively with saturated aqueous ammonium chloride and saturated brine, then dried over anhydrous magnesium sulfate and filtered. The filtrate was concentrated under reduced pressure, and the resulting residue was purified by silica gel column chromatography (hexane:acetone:triethylamine=65:5:0.1) to obtain a cyclized compound (2.46 g).

(4) The compound obtained in (3) mentioned above (600 mg) was dissolved in tetrahydrofuran (10 ml), the solution was added with a hydrogen fluoride-pyridine complex (161 mg), and the mixture was stirred at room temperature for 15 hours. The reaction mixture was saturated neutralized with aqueous sodium hydrogencarbonate, and then added with 10% aqueous sodium hydroxide and ethyl acetate, the layers were separated, and the organic layer was dried over anhydrous magnesium sulfate and filtered. The filtrate was concentrated under reduced pressure, and the resulting residue was purified by silica gel column chromatography (chloroform:methanol:28% aqueous ammonia=20:1:0.1 to 10:1:0.1) to obtain the compound shown in Table 1 (311 mg).

Example 8

(1) The compound obtained in Example 1 (1.06 g) was dissolved in toluene (10 ml), the solution was added with triethylamine (866 mg) and 2-bromoethanol (666 mg), and the mixture was stirred for 2 hours under reflux by heating. The reaction mixture was concentrated under reduced pressure, and the resulting residue was purified by silica gel column chromatography (chloroform:methanol:28% aqueous ammonia=25:1:0.1) to obtain a 10a-(N-2-hydroxyethyl) compound (1.49 g).

(2) By using the compound obtained in (1) mentioned above (1.49 g) as a starting material, the compound shown in Table 1 (135 mg) was obtained in the same manners as those of Example 7, (2), (3) and (4).

Example 9

By using the compound obtained in Example 1 (1.0 g) and benzyl(S)-(+)-glycidyl ether (0.83 g) as starting materials, the compound shown in Table 1 (89 mg) was obtained in the same manner as that of Example 7.

Example 10

By using the compound obtained in Example 1 (700 mg) and (S)-1,2-epoxybutane (254 mg) as starting materials, the compound shown in Table 1 (21.6 mg) was obtained in the same manner as that of Example 7.

Example 11

By using the compound obtained in Example 1 (1.0 g) and (S)-glycidyl methyl ether (266 mg) as starting materials, the compound shown in Table 1 (80 mg) was obtained in the same manner as that of Example 7.

Example 12

By using the compound obtained in Example 1 (0.5 g) and (R)-(+)-propylene oxide (0.18 ml) as starting materials, the compound shown in Table 1 (10.9 mg) was obtained in the same manner as that of Example 7.

Example 13

By using the compound obtained in Example 1 (1.0 g) and 1,2-epoxypentane (434 mg) as starting materials, the compound shown in Table 1 (51 mg) was obtained in the same manner as that of Example 7.

Example 14

By using the compound obtained in Example 1 (1.0 g) and 1,2-epoxypentane (434 mg) as starting materials, the compound shown in Table 1 (5 mg) was obtained in the same manner as that of Example 7.

Example 15

By using the compound obtained in Example 1 (0.5 g) and (R)-(+)-1,2-epoxyhexane (0.303 ml) as starting materials, the compound shown in Table 1 (32.8 mg) was obtained in the same manner as that of Example 7.

Example 16

By using the compound obtained in Example 1 (1.0 g) and benzyl(R)-(−)-glycidyl ether (0.83 g) as starting materials, the compound shown in Table 1 (12.5 mg) was obtained in the same manner as that of Example 7.

Example 17

(1) By using the compound obtained in Example 1 (2.0 g) and the compound obtained in Reference Example 1 (2.78 g) as starting materials, a 10a-N-methyl compound (406 mg) was obtained in the same manners as those of Example 7, (1) and (2).
(2) By using the compound obtained in (1) mentioned above (200 mg) as a starting material, a cyclized compound (78 mg) was obtained in the same manner as that of Example 7, (3).
(3) By using the compound obtained in (2) mentioned above (78 mg) as a starting material, the compound shown in Table 1 (52.3 mg) was obtained in the same manner as that of Example 7, (4).

Example 18

By using the compound obtained in Example 1 (2.0 g) and the compound obtained in Reference Example 1 (2.78 g) as starting materials, the compound shown in Table 1 (31.3 mg) was obtained in the same manner as that of Example 7.

Example 19

By using the compound obtained in Example 1 (1.5 g) and N-glycidylpyrrole (0.93 g) obtained by the method described in the patent document (Japanese Patent Unexamined Publication No. 49-017899) as starting materials, the compound shown in Table 1 (102.3 mg) was obtained in the same manner as that of Example 7.

Example 20

By using the compound obtained in Example 1 (1.5 g) and N-glycidylpyrrole (0.93 g) obtained by the method described in the patent document (Japanese Patent Unexamined Publication No. 49-017899) as starting materials, the compound shown in Table 1 (2.7 mg) was obtained in the same manner as that of Example 7.

Example 21

(1) The compound obtained in Example 17, (1) (0.2 g) was dissolved in methanol (5 ml), the solution was added with 5% palladium-carbon (50 mg), and the mixture was stirred at room temperature for 1 day under a hydrogen atmosphere of 1 atm. The reaction mixture was filtered, and then the filtrate was concentrated under reduced pressure. The resulting residue was dissolved in methanol (5 ml), the solution was added with 5% palladium-carbon (50 mg), and the mixture was stirred at room temperature for 1 hour under a hydrogen atmosphere of 1 atm. The reaction mixture was filtered, and then the filtrate was concentrated under reduced pressure to obtain a debenzyloxycarbonylated compound (167 mg).
(2) The compound obtained in (1) mentioned above (161 mg) was dissolved in chloroform (5 ml), the solution was added with 37% aqueous formaldehyde (0.12 ml) and sodium triacetoxyborohydride (95 mg), and the mixture was stirred at room temperature for 1.5 hours. The mixture was further added with 37% aqueous formaldehyde (0.12 ml) and sodium triacetoxyborohydride (95 mg), and the mixture was stirred at room temperature for 30 minutes. The reaction mixture was added with saturated aqueous sodium hydrogencarbonate and chloroform, the layers were separated, and the organic layer was washed with saturated brine, then dried over anhydrous magnesium sulfate and filtered. The resulting filtrate was concentrated under reduced pressure to obtain a dimethylamino compound (201 mg).

(3) By using the compound obtained in (2) mentioned above (201 mg) as a starting material, the compound shown in Table 1 (25.3 mg) was obtained in the same manners as those of Example 7, (3) and (4).

Example 22

By using the compound obtained in Example 1 (1.0 g) and 4-(2,3-epoxypropyl)morpholine (0.43 g) as starting materials, the compound shown in Table 1 (42.0 mg) was obtained in the same manner as that of Example 7.

Example 23

(1) By using the compound obtained in Example 1 (2.33 g) and the compound obtained in Reference Example 2 (2.0 g) as starting materials, a cyclized compound (859 mg) was obtained in the same manners as those of Example 7, (1), (2) and (3).

(2) Tri-O-tolylphosphine (20.1 mg) was dissolved in toluene (4 ml), the solution was successively added with tris(dibenzylideneacetone)dipalladium(0) (30.2 mg), tri-n-butyl(2-furyl)tin (236 mg) and a solution of the compound obtained in (1) mentioned above (420 mg) in toluene (13 ml), and the mixture was stirred for 1.5 hours under reflux by heating. The reaction mixture was concentrated under reduced pressure, and the resulting residue was purified by silica gel column chromatography (chloroform:methanol:28% aqueous ammonia=10:1:0.1) to obtain an biaryl compound (403 mg).

(3) By using the compound obtained in (2) mentioned above (403 mg) as a starting material, the compound shown in Table 1 (264 mg) was obtained in the same manner as that of Example 7, (4).

Example 24

By using the compound obtained in Example 1 (553 mg) and the compound obtained in Reference Example 3 (950 mg) as starting materials, the compound shown in Table 1 (4.5 mg) was obtained in the same manners as those of Example 23 (Example 7, (1), (2) and (3), Example 23, (2) and Example 7, (4)).

Example 25

(1) By using the compound obtained in Example 1 (3.63 g) and 2-(2-azidoethyl)oxirane (4.14 g) obtained by the method described in the literature (Tetrahedron, 1987, vol. 43, p. 1799) as starting materials, a cyclized compound (468 mg) was obtained in the same manners as those of Example 7, (1), (2) and (3).

(2) The compound obtained in (1) mentioned above (0.1 g) was dissolved in chloroform (3 ml), the solution was added with a 1 M solution of trimethylphosphine in tetrahydrofuran (0.18 ml) under ice cooling, and the mixture was stirred at room temperature for 1.5 hours. A solution of 2-(1,2-benzisoxazol-3-yl)acetic acid (24.1 mg), 1-ethyl-3-(3-dimethylaminopropyl)carbodiimide hydrochloride (26.1 mg) and 1-hydroxybenzotriazole monohydrate (20.8 mg) in chloroform (3 ml) separately stirred at room temperature for 1.5 hours was added to the reaction mixture, and the mixture was stirred at room temperature for 18 hours. A solution (2 ml) of 2-(1,2-benzisoxazol-3-yl)acetic acid (24.1 mg), 1-ethyl-3-(3-dimethylaminopropyl)carbodiimide hydrochloride (26.1 mg) and 1-hydroxybenzotriazole monohydrate (20.8 mg) in chloroform separately stirred at room temperature for 1.5 hours was added to the reaction mixture, and the mixture was stirred at room temperature for 2.5 days. The reaction mixture was added with saturated aqueous sodium hydrogencarbonate and chloroform, the layers were separated, and the organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=30:1:0.1) to obtain an amide compound (20.0 mg).

(3) By using the compound obtained in (2) mentioned above (20.0 mg) as a starting material, the compound shown in Table 1 (13.1 mg) was obtained in the same manner as that of Example 7, (4).

Example 26

(1) By using the compound obtained in Example 1 (0.5 g) and the compound obtained in Reference Example 5 (0.43 g) as starting materials, a cyclized compound (231 mg) was obtained in the same manners as those of Example 7, (1), (2) and (3).

(2) By using the compound obtained in (1) mentioned above (70 mg) as a starting material, the compound shown in Table 1 (25.0 mg) was obtained in the same manners as those of Example 23, (2) and Example 7, (4).

Example 27

By using the compound obtained in Example 1 (0.5 g) and the compound obtained in Reference Example 6 (0.43 g) as starting materials, the compound shown in Table 1 (35.3 mg) was obtained in the same manner as that of Example 23 (Example 7, (1), (2), (3), Example 23, (2) and Example 7, (4)).

Example 28

By using the compound obtained in Example 23, (1) (70 mg) and tri-n-butyl-(2-pyridyl)tin (30.3 mg) as starting materials, the compound shown in Table 1 (23.2 mg) was obtained in the same manners as those of Example 23, (2) and Example 7, (4).

Example 29

By using the compound obtained in Example 23, (1) (70 mg) and tri-n-butyl-(3-pyridyl)tin (30.3 mg) as starting materials, the compound shown in Table 1 (20.5 mg) was obtained in the same manners as those of Example 23, (2) and Example 7, (4).

Example 30

By using the compound obtained in Example 1 (433 mg) and the compound obtained in Reference Example 7 (390 mg) as starting materials, the compound shown in Table 1 (44.2 mg) was obtained in the same manner as that of Example 23 (Example 7, (1), (2), (3), Example 23, (2) and Example 7, (4)).

Example 31

By using the compound obtained in Example 1 (0.5 g) and the compound obtained in Reference Example 8 (0.41 g) as starting materials, the compound shown in Table 1 (23.3 mg) was obtained in the same manner as that of Example 23 (Example 7, (1), (2), (3), Example 23, (2) and Example 7, (4)).

Example 32

By using the compound obtained in Example 1 (866 mg) and the compound obtained in Reference Example 9 (1.30 g) as starting materials, the compound shown in Table 1 (35.9 mg) was obtained in the same manner as that of Example 23 (Example 7, (1), (2), (3), Example 23, (2) and Example 7, (4)).

Example 33

By using the compound obtained in Example 1 (909 mg) and the compound obtained in Reference Example 10 (1.30 g) as starting materials, the compound shown in Table 1 (57.2 mg) was obtained in the same manner as that of Example 23 (Example 7, (1), (2), (3), Example 23, (2) and Example 7, (4)).

Example 34

By using the compound obtained in Example 1 (0.5 g) and the compound obtained in Reference Example 11 (0.43 g) as starting materials, the compound shown in Table 1 (24.0 mg) was obtained in the same manner as that of Example 23 (Example 7, (1), (2), (3), Example 23, (2) and Example 7, (4)).

Example 35

By using the compound obtained in Example 1 (793 mg) and the compound obtained in Reference Example 12 (680 mg) as starting materials, the compound shown in Table 1 (96.5 mg) was obtained in the same manner as that of Example 23 (Example 7, (1), (2), (3), Example 23, (2) and Example 7, (4)).

Example 36

By using the compound obtained in Example 1 (0.5 g) and the compound obtained in Reference Example 13 (0.39 g) as starting materials, the compound shown in Table 1 (104.6 mg) was obtained in the same manner as that of Example 7.

Example 37

By using the compound obtained in Example 1 (0.5 g) and the compound obtained in Reference Example 14 (0.43 g) as starting materials, the compound shown in Table 1 (29.8 mg) was obtained in the same manner as that of Example 23 (Example 7, (1), (2), (3), Example 23, (2) and Example 7, (4)).

Example 38

By using the compound obtained in Example 1 (0.5 g) and the compound obtained in Reference Example 15 (0.43 g) as starting materials, the compound shown in Table 1 (68.2 mg) was obtained in the same manner as that of Example 23 (Example 7, (1), (2), (3), Example 23, (2) and Example 7, (4)).

Example 39

By using the compound obtained in Example 1 (1.0 g) and allyl glycidyl ether (0.57 g) as starting materials, the compound shown in Table 1 (85.0 mg) was obtained in the same manner as that of Example 7.

Example 40

By using the compound obtained in Example 1 (1.0 g) and propargyl glycidyl ether (0.54 ml) as starting materials, the compound shown in Table 1 (95.3 mg) was obtained in the same manner as that of Example 7.

Example 41

Palladium(II) acetate (1.2 mg) was dissolved in 1,2-dimethoxyethane (2 ml), the solution was successively added with triphenylphosphine (5.5 mg) and the compound obtained in Reference Example 16 (17.6 mg) under a nitrogen atmosphere, and the mixture was stirred at room temperature for 15 minutes. The reaction mixture was successively added with the compound obtained in Example 39 (40 mg), tetrabutylammonium bromide (33.9 mg) and diisopropylethylamine (18.8 µl) under a nitrogen atmosphere, and the mixture was stirred for 5 hours under reflux by heating. The reaction mixture was concentrated under reduced pressure, and the resulting residue was purified by preparative thin layer chromatography (ethyl acetate:methanol:28% aqueous ammonia=5:1:0.1) to obtain the compound shown in Table 1 (2.3 mg).

Example 42

The compound obtained in Example 40 (85 mg) was dissolved in acetonitrile (3 ml), the solution was successively added with the compound obtained in Reference Example 16 (37.5 mg), triethylamine (1 ml), and tetrakistriphenylphosphine palladium (6.5 mg), and the mixture was stirred for 2.5 hours under reflux by heating. The reaction mixture was concentrated under reduced pressure, and the resulting residue was purified by silica gel column chromatography (chloroform:methanol:28% aqueous ammonia=20:1:0.1 to 10:1:0.1) to obtain the compound shown in Table 1 (43.2 mg).

Example 43

The compound obtained in Example 42 (30 mg) was dissolved in methanol (1.5 ml), the solution was added with 5% palladium-carbon (6 mg), and the mixture was stirred at room temperature for 18 hours under a hydrogen atmosphere of 1 atm. The reaction mixture was filtered, and then the filtrate was concentrated under reduced pressure. The resulting residue was purified by silica gel column chromatography (chloroform:methanol:28% aqueous ammonia=10:1:0.1) to obtain the compound shown in Table 1 (22.9 mg).

Example 44

By using the compound obtained in Example 1 (1.0 g) and the compound obtained in Reference Example 17 (943 mg) as starting materials, the compound shown in Table 1 (19 mg) was obtained in the same manner as that of Example 23 (Example 7, (1), (2), (3), Example 23, (2) and Example 7, (4)).

Example 45

By using the compound obtained in Example 1 (0.3 g) and the compound obtained in Reference Example 18 (0.23 g) as starting materials, the compound shown in Table 1 (14 mg) was obtained in the same manner as that of Example 23 (Example 7, (1), (2), (3), Example 23, (2) and Example 7, (4)).

Example 46

By using the compound obtained in Example 1 (0.3 g) and the compound obtained in Reference Example 19 (0.245 g) as starting materials, the compound shown in Table 1 (12 mg) was obtained in the same manner as that of Example 23 (Example 7, (1), (2), (3), Example 23, (2) and Example 7, (4)).

Example 47

(1) By using the compound obtained in Example 1 (2.33 g) and the compound obtained in Reference Example 15 (2.0 g) as starting materials, a cyclized compound (0.37 g) was obtained in the same manners as those of Example 7, (1), (2) and (3).

(2) By using the compound obtained in (1) mentioned above (30 mg) and tri-n-butyl-(2-pyridyl)tin (13.0 mg) as starting materials, the compound shown in Table 1 (6.1 mg) was obtained in the same manners as those of Example 23, (2) and Example 7, (4).

Example 48

By using the compound obtained in Example 47, (1) (30 mg) and tri-n-butyl-(3-pyridyl)tin (13.0 mg) as starting materials, the compound shown in Table 1 (1.2 mg) was obtained in the same manners as those of Example 23, (2) and Example 7, (4).

Example 49

(1) Palladium(II) acetate (0.5 mg) was dissolved in 1,2-dimethoxyethane (0.3 ml), and the solution was successively added with triphenylphosphine (3.1 mg) and quinoline-3-boronic acid (6.1 mg) under a nitrogen atmosphere. The mixture was successively added with sodium carbonate (5.0 mg), distilled water (0.5 ml), and a solution of the compound obtained in Example 47, (1) (30 mg) in 1,2-dimethoxyethane (0.2 ml), and the mixture was stirred at 80° C. for 2 hours under a nitrogen atmosphere. The reaction mixture was concentrated under reduced pressure, the resulting residue was added with distilled water and ethyl acetate, the layers were separated, and the organic layer was dried over anhydrous magnesium sulfate and filtered. The filtrate was concentrated under reduced pressure, and the resulting residue was purified by silica gel column chromatography (hexane:acetone:triethylamine=30:10:0.2) to obtain a biaryl compound (12.6 mg).

(2) By using the compound obtained in (1) mentioned above (12.6 mg) as a starting material, the compound shown in Table 1 (3.8 mg) was obtained in the same manner as that of Example 7, (4).

Example 50

By using the compound obtained in Example 1 (0.33 g) and the compound obtained in Reference Example 20 (0.30 g) as starting materials, the compound shown in Table 1 (19.2 mg) was obtained in the same manner as that of Example 23 (Example 7, (1), (2), (3), Example 23, (2) and Example 7, (4)).

Example 51

(1) By using the compound obtained in Example 1 (9.59 g) and the compound obtained in Reference Example 21 (7.36 g) as starting materials, a cyclized compound (895 mg) was obtained in the same manners as those of Example 7, (1), (2) and (3).

(2) From the compound obtained in (1) mentioned above (50 mg), an azide compound (37 mg) was obtained in the same manner as that of Example 7, (4).

(3) The compound obtained in (2) mentioned above (32 mg) was dissolved in methanol, the solution was added with 5% palladium-carbon (30 mg), and the mixture was stirred at room temperature for 3 hours under a hydrogen atmosphere of 1 atm. The reaction mixture was filtered, then the filtrate was concentrated under reduced pressure, and the resulting residue was purified by silica gel column chromatography (NH-form silica gel, chloroform:methanol=50:1) to obtain the compound shown in Table 1 (21.5 mg).

Example 52

(1) By using the compound obtained in Example 1 (1.21 g) and (R)-epichlorohydrin as starting materials, a chloromethyl compound (130 mg) was obtained in the same manners as those of Example 7, (1), (2) and (3).

(2) By using the compound obtained in (1) mentioned above (25 mg) as a starting material, the compound shown in Table 1 (15 mg) was obtained in the same manner as that of Example 7, (4).

Example 53

By using the compound obtained in Example 47, (1) (30 mg) and tri-n-butyl-(2-thienyl)tin (13.2 mg) as starting materials, the compound shown in Table 1 (11.4 mg) was obtained in the same manners as those of Example 23, (2) and Example 7, (4).

Example 54

(1) The compound obtained in Example 51, (1) (50 mg) was dissolved in methanol (5 ml), the solution was added with 5% palladium-carbon (10 mg), and the mixture was stirred at room temperature for 1 day under a hydrogen atmosphere of 1 atm. The reaction mixture was filtered, and then the filtrate was concentrated under reduced pressure to obtain an amine compound (55 mg).

(2) (Method A)

The compound obtained in (1) mentioned above (15 mg) was dissolved in tetrahydrofuran (0.5 ml), the solution was added with 4-dimethylaminopyridine (1.7 mg) and N,N'-carbonyldiimidazole (3.3 mg), and the mixture was stirred at room temperature for 30 minutes. The mixture was added with 3-bromophenol (11.9 mg), and the mixture was stirred for 5 hours under reflux by heating. The reaction mixture was concentrated under reduced pressure, the resulting residue was added with toluene (5 ml), and the mixture was stirred for 7 hours under reflux by heating. The reaction mixture was concentrated under reduced pressure, and the resulting residue was purified by preparative thin layer chromatography (hexane:acetone:triethylamine=30:10:0.2) to obtain a carbamate compound (8.0 mg).

(3) (Method B)

The compound obtained in (1) mentioned above (15 mg) was dissolved in chloroform (0.4 ml), and the solution was added with saturated aqueous sodium hydrogencarbonate (0.2 ml). Then, the mixture was added with triphosgene (4.1 mg) under ice cooling, and the mixture was stirred for 30 minutes. The layers of the reaction mixture were separated, and the organic layer was concentrated under reduced pressure. The resulting residue was dissolved in toluene (0.5 ml), the solution was added with 3-bromophenol (11.9 mg), and the mixture was stirred at 85° C. for 3 hours. The reaction mixture was concentrated under reduced pressure, and the resulting residue was purified by preparative thin layer chromatography (hexane:acetone:triethylamine=30:10:0.2) to obtain a carbamate compound (6.8 mg).

(4) By using the compound obtained in (2) or (3) mentioned above (15 mg) as a starting material, the compound shown in Table 1 (3.9 mg) was obtained in the same manners as those of Example 23, (2) and Example 7, (4).

Example 55

(1) The compound obtained in Example 54, (1) (20 mg) was dissolved in chloroform (0.5 ml), the solution was added with triethylamine (26 µl) and 2-quinolinecarbonyl chloride (17.6 mg), and the mixture was stirred at room temperature for 1 hour. The reaction mixture was added with saturated aqueous sodium hydrogencarbonate and chloroform, the layers were separated, and the organic layer was dried over anhydrous sodium sulfate and filtered. The filtrate was concentrated under reduced pressure, and the resulting residue was purified by silica gel column chromatography (hexane:acetone:triethylamine=50:10:0.2) to obtain an amide compound (19.5 mg).

(2) By using the compound obtained in (1) mentioned above (19.5 mg) as a starting material, the compound shown in Table 1 (11.9 mg) was obtained in the same manner as that of Example 7, (4).

Example 56

By using the compound obtained in Example 54, (1) (20 mg) and 3-quinolinecarbonyl chloride (17.6 mg) obtained by the method described in the literature (Bioorganic & Medicinal Chemistry, 2005, vol. 13, p. 2031) as starting materials, the compound shown in Table 1 (8.0 mg) was obtained in the same manners as those of Example 55, (1) and Example 7, (4).

Example 57

By using the compound obtained in Example 54, (1) (20 mg) and 4-quinolinecarbonyl chloride (17.6 mg) obtained by the method described in the literature (Bioorganic & Medicinal Chemistry, 2005, vol. 13, p. 2031) as starting materials, the compound shown in Table 1 (8.6 mg) was obtained in the same manners as those of Example 55, (1) and Example 7, (4).

Example 58

By using the compound obtained in Example 1 (2.82 g) and the compound obtained in Reference Example 22 as starting materials, the compound shown in Table 1 (14 mg) was obtained in the same manner as that of Example 7.

Example 59

(1) By using the compound obtained in Example 54, (1) (35 mg) and 4-bromobenzoyl chloride (21.2 mg) as starting materials, an amide compound (44.5 mg) was obtained in the same manner as that of Example 55, (1).
(2) By using the compound obtained in (1) mentioned above (27.6 mg) as a starting material, the compound shown in Table 1 (8.1 mg) was obtained in the same manners as those of Example 23, (2) and Example 7, (4).

Example 60

By using the compound obtained in Example 1 (1.6 g) and the compound obtained in Reference Example 23 (1.44 g) as starting materials, the compound shown in Table 1 (12.6 mg) was obtained in the same manner as that of Example 23 (Example 7, (1), (2), (3), Example 23, (2) and Example 7, (4)).

Example 61

By using the compound obtained in Example 1 (1.0 g) and the compound obtained in Reference Example 24 (771 mg) as starting materials, the compound shown in Table 1 (8.6 mg) was obtained in the same manner as that of Example 7.

Example 62

By using the compound obtained in Example 1 (4.89 g) and the compound obtained in Reference Example 25 (3.25 g) as starting materials, the compound shown in Table 1 (8.7 mg) was obtained in the same manner as that of Example 7.

Example 63

(1) By using the compound obtained in Example 1 (1.77 g) and the compound obtained in Reference Example 26 (2.05 g) as starting materials, a cyclized compound (205 mg) was obtained in the same manners as those of Example 7, (1), (2) and (3).
(2) By using the compound obtained in (1) mentioned above (32.1 mg) as a starting material, the compound shown in Table 1 (15.5 mg) was obtained in the same manner as that of Example 7, (4).

Example 64

The compound obtained in Example 63 (8.3 mg) was dissolved in ethyl acetate (1.5 ml), the solution was added with 5% palladium-carbon (4.2 mg), and the mixture was stirred at room temperature for 1 hour under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=10:1:0.1) to obtain the compound shown in Table 1 (8.2 mg).

Example 65

(1) By using the compound obtained in Example 1 (2.12 g) and the compound obtained in Reference Example 27 (3.00 g) as starting materials, a cyclized compound (127 mg) was obtained in the same manners as those of Example 7, (1), (2) and (3).
(2) By using the compound obtained in (1) mentioned above (39.5 mg) as a starting material, the compound shown in Table 1 (21.3 mg) was obtained in the same manner as that of Example 7, (4).

Example 66

By using the compound obtained in Example 1 (2.0 g) and epifluorohydrin (919 mg) as starting materials, the compound shown in Table 1 (51 mg) was obtained in the same manner as that of Example 7.

Example 67

By using the compound obtained in Example 1 (2.0 g) and (R)-2-vinyloxirane (460 mg) as starting materials, the compound shown in Table 1 (26 mg) was obtained in the same manner as that of Example 7.

Example 68

(1) By using the compound obtained in Example 1 (0.30 g) and the compound obtained in Reference Example 28 (0.43 g) as starting materials, a cyclized compound (95.3 mg) was obtained in the same manners as those of Example 7, (1), (2) and (3).
(2) By using the compound obtained in (1) mentioned above (10 mg) as a starting material, the compound shown in Table 1 (7.6 mg) was obtained in the same manner as that of Example 7, (4).

Example 69

(1) By using the compound obtained in Example 1 (0.38 g) and the compound obtained in Reference Example 29 (0.55 g) as starting materials, a cyclized compound (73 mg) was obtained in the same manners as those of Example 7, (1), (2) and (3).
(2) By using the compound obtained in (1) mentioned above (10 mg) as a starting material, the compound shown in Table 1 (5.3 mg) was obtained in the same manner as that of Example 7, (4).

Example 70

(1) By using the compound obtained in Example 1 (0.5 g) and the compound obtained in Reference Example 30 (0.76 g) as starting materials, a cyclized compound (45.2 mg) was obtained in the same manners as those of Example 7, (1), (2) and (3).
(2) By using the compound obtained in (1) mentioned above (10 mg) as a starting material, the compound shown in Table 1 (6.6 mg) was obtained in the same manner as that of Example 7, (4).

Example 71

(1) By using the compound obtained in Example 1 (0.98 g) and the compound obtained in Reference Example 31 as starting materials, a cyclized compound (0.32 g) was obtained in the same manners as those of Example 7, (1), (2) and (3).
(2) By using the compound obtained in (1) mentioned above (130 mg) as a starting material, the compound shown in Table 1 (69 mg) was obtained in the same manner as that of Example 7, (4).

Example 72

By using the compound obtained in Example 1 (375 mg) and 2-[3-(benzyloxy)propyl]oxirane (435 mg) obtained by the method described in the literature (European Journal of Organic Chemistry, 2000, p. 1219) as starting materials, the compound shown in Table 1 (32 mg) was obtained in the same manner as that of Example 7.

Example 73

The compound obtained in Example 72 (28 mg) was dissolved in methanol, the solution was added with 20% palladium hydroxide-carbon (30 mg), and the mixture was stirred at room temperature for 3 hours under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=10:1:0.1) to obtain the compound shown in Table 1 (26.7 mg).

Example 74

(1) The compound obtained in Example 51, (1) (20 mg) was dissolved in ethyl acetate, the solution was added with 5% palladium-carbon (20 mg), and the mixture was stirred at room temperature for 3 hours under a hydrogen atmosphere of 1 atm. The reaction mixture was filtered, and then the filtrate was concentrated under reduced pressure. The resulting residue was dissolved in chloroform (1 ml), the solution was added with triethylamine (9.1 mg) and 3-bromobenzenesulfonyl chloride (4.6 mg), and the mixture was stirred at room temperature for 2 hours. The reaction mixture was concentrated under reduced pressure, and the resulting residue was purified by silica gel column chromatography (hexane:acetone:triethylamine=30:10:0.2) to obtain a bromo compound (11.4 mg).
(2) By using the compound obtained in (1) mentioned above (11.4 mg) as a starting material, the compound shown in Table 1 (2.0 mg) was obtained in the same manners as those of Example 23, (2) and Example 7, (4).

Example 75

(1) The compound obtained in Example 54, (1) (50 mg) was dissolved in a mixed solvent of chloroform-methanol (2:1, 1.5 ml), the solution was added with 6-bromopicolinic acid (27.8 mg), 1-ethyl-3-(3-dimethylaminopropyl)carbodiimide hydrochloride (26.3 mg), and 4-dimethylaminopyridine (5.6 mg), and the mixture was stirred at room temperature for 18 hours. The reaction mixture was concentrated under reduced pressure, and the resulting residue was purified by silica gel column chromatography (hexane:acetone:triethylamine=30:10:0.2) to obtain an amide compound (65.5 mg).
(2) By using the compound obtained in (1) mentioned above (60 mg) as a starting material, the compound shown in Table 1 (38.0 mg) was obtained in the same manners as those of Example 23, (2) and Example 7, (4).

Example 76

By using the compound obtained in Example 54, (1) (50 mg) and 5-bromonicotinic acid (27.8 mg) as starting materials, the compound shown in Table 1 (16.9 mg) was obtained in the same manners as those of Example 75, (1), Example 23, (2) and Example 7, (4).

Example 77

By using the compound obtained in Example 54, (1) (50 mg) and 5-bromo-2-thiophenecarboxylic acid (28.6 mg) as starting materials, the compound shown in Table 1 (30.8 mg) was obtained in the same manners as those of Example 75, (1), Example 23, (2) and Example 7, (4).

Example 78

By using the compound obtained in Example 54, (1) (50 mg) and 5-bromo-2-furancarboxylic acid (26.1 mg) as starting materials, the compound shown in Table 1 (21.6 mg) was obtained in the same manners as those of Example 75, (1), Example 23, (2) and Example 7, (4).

Example 79

(1) By using the compound obtained in Example 1 (4.00 g) and the compound (2.16 g) obtained by the method described in the literature (Synthesis, 1992, p. 621, Reference Example 32) as starting materials, a cyclized compound (0.78 g) was obtained in the same manners as those of Example 7, (1), (2) and (3).
(2) By using the compound obtained in (1) mentioned above (130 mg) as a starting material, the compound shown in Table 1 (68 mg) was obtained in the same manner as that of Example 7, (4).

Example 80

By using the compound obtained in Example 1 (1.20 g) and the compound obtained in Reference Example 33 as starting materials, the compound shown in Table 1 (73 mg) was obtained in the same manner as that of Example 7.

Example 81

The compound obtained in Example 71 (12 mg) was dissolved in a mixed solvent of methanol-ethyl acetate (1:1, 2 ml), the solution was added with 20% palladium hydroxide-carbon (12 mg), and the mixture was stirred at room temperature for 60 hours under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=50:1:0.1 to 20:1:0.1) to obtain the compound shown in Table 1 (8 mg).

Example 82

(1) By using the compound obtained in Example 1 (4.00 g) and the compound obtained in Reference Example 34 as starting materials, a cyclized compound (0.76 g) was obtained in the same manners as those of Example 7, (1), (2) and (3).
(2) By using the compound obtained in (1) mentioned above (0.38 g) as a starting material, the compound shown in Table 1 (0.25 g) was obtained in the same manner as that of Example 7, (4).

Example 83

By using the compound obtained in Example 1 (1.00 g) and the compound obtained in Reference Example 35 as starting materials, the compound shown in Table 1 (50 mg) was obtained in the same manner as that of Example 7.

Example 84

By using the compound obtained in Example 79 (40 mg) as a starting material, the compound shown in Table 1 (34 mg) was obtained in the same manner as that of Example 81.

Example 85

The compound obtained in Example 82 (160 mg) was dissolved in methanol (20 ml), the solution was added with 5% palladium-carbon (160 mg), and the mixture was stirred at room temperature for 18 hours under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=50:1:0.1 to 10:1:0.1) to obtain the compound shown in Table 1 (75 mg).

Example 86

(1) By using the compound obtained in Example 1 (4.00 g) and the compound obtained in Reference Example 36 as starting materials, a cyclized compound (0.51 g) was obtained in the same manners as those of Example 7, (1), (2) and (3).
(2) By using the compound obtained in (1) mentioned above (96 mg) as a starting material, a deprotected compound (60 mg) was obtained in the same manner as that of Example 7, (4).
(3) By using the compound obtained in (2) mentioned above (34 mg) as a starting material, the compound shown in Table 1 (21 mg) was obtained in the same manner as that of Example 21, (1).

Example 87

By using the compound obtained in Example 85 (10 mg) as a starting material, the compound shown in Table 1 (6 mg) was obtained in the same manner as that of Example 7, (2).

Example 88

(1) The compound obtained in Example 52, (1) (68 mg) was dissolved in dimethylformamide (2 ml), the solution was added with imidazole (13 mg) and potassium carbonate (26 mg), and the mixture was stirred at 70° C. for 5 hours, and further stirred at 120° C. for 3 hours. The reaction mixture was added with distilled water and chloroform, and the layers were separated. The organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=100:1:0.1) to obtain an imidazolyl compound (18 mg).
(2) By using the compound obtained in (1) mentioned above (18 mg) as a starting material, the compound shown in Table 1 (11 mg) was obtained in the same manner as that of Example 7, (4).

Example 89

By using the compound obtained in Example 52, (1) (38 mg) and 3-(4,5-dihydroxy-1H-imidazol-4-yl)-pyridine (25 mg) obtained by the method described in the literature (Journal of Medicinal Chemistry, 2005, vol. 48, p. 224) as starting materials, the compound shown in Table 1 (6 mg) was obtained in the same manners as those of Example 88, (1) and Example 7, (4).

Example 90

(1) By using the compound obtained in Example 1 (3 g) and methyl-(S)-glycidate (925 mg) as starting materials, a cyclized compound (910 mg) was obtained in the same manners as those of Example 7, (1), (2) and (3).

(2) By using the compound obtained in (1) mentioned above (30.7 mg) as a starting material, the compound shown in Table 1 (16.2 mg) was obtained in the same manner as that of Example 7, (4).

Example 91

(1) By using the compound obtained in Example 65, (1) (36.5 mg) as a starting material, a carboxylic acid compound (31.6 mg) was obtained in the same manner as that of Example 64.
(2) The compound obtained in (1) mentioned above (10.1 mg) was dissolved in chloroform (1.0 ml), the solution was added with triethylamine (6.2 μl) and isobutyl chloroformate (5.8 μl) under ice cooling, and the mixture was stirred at the same temperature for 1 hour. The mixture was added with a 0.5 N solution of ammonia in 1,4-dioxane, and the mixture was stirred at room temperature for 1.5 hours. The reaction mixture was neutralized with saturated aqueous ammonium chloride, and then extracted with ethyl acetate, and the organic layer was dried over anhydrous magnesium sulfate and filtered. The filtrate was concentrated under reduced pressure, and the resulting residue was purified by silica gel column chromatography (hexane:acetone:triethylamine=10:10:0.2) to obtain an amide compound (10.5 mg).
(3) By using the compound obtained in (2) mentioned above (10.1 mg) as a starting material, the compound shown in Table 1 (2.8 mg) was obtained in the same manner as that of Example 7, (4).

Example 92

(1) By using the compound obtained in Example 1 (0.5 g) and the compound obtained in Reference Example 37 (0.64 g) as starting materials, a nitro compound (24.0 mg) was obtained in the same manner as that of Example 7.
(2) The compound obtained in (1) mentioned above (20 mg) was dissolved in a mixed solvent of 2-propanol-distilled water (2:1, 3 ml), the solution was added with iron (12.4 mg) and ammonium chloride (2.4 mg), and the mixture was stirred at 90° C. for 1 hour. The reaction mixture was filtered, then the filtrate was concentrated under reduced pressure, and the resulting residue was purified by silica gel column chromatography (chloroform:methanol:28% aqueous ammonia=10:1:0.1) to obtain the compound shown in Table 1 (6.5 mg).

Example 93

By using the compound obtained in Example 1 (0.5 g) and the compound obtained in Reference Example 38 (0.585 g) as starting materials, the compound shown in Table 1 (47.2 mg) was obtained in the same manner as that of Example 7.

Example 94

By using the compound obtained in Example 69, (1) (30 mg) as a starting material, the compound shown in Table 1 (11 mg) was obtained in the same manners as those of Example 23, (2) and Example 7, (4).

Example 95

(1) By using the compound obtained in Example 1 (4.00 g) and 2-(2-azidoethyl)oxirane obtained by the method described in the literature (Tetrahedron, 1987, vol. 43, p. 1799) as starting materials, a cyclized compound (0.29 g) was obtained in the same manners as those of Example 7, (1), (2) and (3).
(2) The compound obtained in (1) mentioned above (57 mg) was dissolved in methanol (5 ml), the solution was added with 5% palladium-carbon (57 mg), and the mixture was stirred at room temperature for 2 hours under a hydrogen atmosphere of 1 atm. The reaction mixture was filtered, and then the filtrate was concentrated under reduced pressure. The resulting residue was dissolved in tetrahydrofuran (1 ml), the solution was added with phenyl chloroformate (8 μl) and triethylamine (8 μl), and the mixture was stirred at room temperature for 1 hour. The reaction mixture was concentrated under reduced pressure, and the resulting residue was added with saturated aqueous sodium hydrogencarbonate and chloroform, and the layers were separated. The organic layer was dried over anhydrous magnesium sulfate and filtered. The filtrate was concentrated under reduced pressure, and the resulting residue was purified by silica gel column chromatography (hexane:acetone:triethylamine=25:5:0.1) to obtain a carbamate compound (35 mg).
(3) By using the compound obtained in (2) mentioned above (35 mg) as a starting material, the compound shown in Table 1 (13 mg) was obtained in the same manner as that of Example 7, (4).

Example 96

By using the compound obtained in Example 68, (1) (20.6 mg) as a starting material, the compound shown in Table 1 (9.1 mg) was obtained in the same manners as those of Example 23, (2) and Example 7, (4).

Example 97

(1) By using the compound obtained in Example 1 (2.41 g) and the compound obtained in Reference Example 39 (2.52 g) as starting materials, a cyclized compound (253 mg) was obtained in the same manners as those of Example 7, (1), (2) and (3).
(2) By using the compound obtained in (1) mentioned above (21.6 mg) as a starting material, the compound shown in Table 1 (5.6 mg) was obtained in the same manner as that of Example 7, (4).

Example 98

By using the compound obtained in Example 1 (0.465 g) and the compound obtained in Reference Example 40 (0.39 g) as starting materials, the compound shown in Table 1 (10.8 mg) was obtained in the same manner as that of Example 7.

Example 99

(1) The compound obtained in Example 54, (1) (45 mg) was dissolved in chloroform (4 ml), the solution was added with 4-quinolinecarboxaldehyde (6.5 mg) and sodium triacetoxyborohydride (13.1 mg), and the mixture was stirred at room temperature for 2 hours. The reaction mixture was added with saturated aqueous sodium hydrogencarbonate and chloroform, the layers were separated, and the organic layer was dried over anhydrous magnesium sulfate and filtered. The filtrate was concentrated under reduced pressure, and the resulting residue was purified by preparative thin layer chromatography (hexane:acetone:triethylamine=10:10:0.2) to obtain an N-(4-quinolylmethyl) compound (40.8 mg).

(2) By using the compound obtained in (1) mentioned above (40 mg) as a starting material, the compound shown in Table 1 (14.3 mg) was obtained in the same manner as that of Example 7, (4).

Example 100

The compound obtained in Example 99 (6.0 mg) was dissolved in chloroform (0.5 ml), the solution was added with 37% aqueous formaldehyde (2.7 µl) and sodium triacetoxyborohydride (2.15 mg), and the mixture was stirred at room temperature for 18 hours. The reaction mixture was added with saturated aqueous sodium hydrogencarbonate and chloroform, the layers were separated, and the organic layer was dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) to obtain the compound shown in Table 1 (1.1 mg).

Example 101

By using the compound obtained in Example 1 (0.37 g) and the compound obtained in Reference Example 41 (0.45 g) as starting materials, the compound shown in Table 1 (47 mg) was obtained in the same manner as that of Example 7.

Example 102

By using the compound obtained in Example 1 (693 mg) and oxiran-2-ylacetonitrile (870 mg) obtained by the method described in the literature (Journal of Organic Chemistry, 2001, vol. 66, 6, p. 2171) as starting materials, the compound shown in Table 1 (8.0 mg) was obtained in the same manner as that of Example 7.

Example 103

(1) By using the compound obtained in Example 1 (700 mg) and 3-oxiran-2-ylpropanenitrile (2.05 g) obtained by the method described in the literature (Journal of the Chemical Society, Perkin Transactions II, 1987, 9, p. 1253) as starting materials, a cyclized compound (122 mg) was obtained in the same manners as those of Example 7, (1), (2) and (3).

(2) By using the compound obtained in (1) mentioned above (83.0 mg) as a starting material, the compound shown in Table 1 (44.0 mg) was obtained in the same manner as that of Example 7, (4).

Example 104

(1) By using the compound obtained in Example 1 (700 mg) and the compound obtained in Reference Example 42 (2.35 g) as starting materials, a cyclized compound (99.7 mg) was obtained in the same manners as those of Example 7, (1), (2) and (3).

(2) By using the compound obtained in (1) mentioned above (68.1 mg) as a starting material, the compound shown in Table 1 (33.0 mg) was obtained in the same manner as that of Example 7, (4).

Example 105

By using the compound obtained in Example 1 (500 mg) and the compound obtained in Reference Example 43 (989 mg) as starting materials, the compound shown in Table 1 (6.4 mg) was obtained in the same manner as that of Example 7.

Example 106

By using the compound obtained in Example 1 (500 mg) and the compound obtained in Reference Example 44 (1.1 g) as starting materials, the compound shown in Table 1 (21.7 mg) was obtained in the same manner as that of Example 7.

Example 107

By using the compound obtained in Example 1 (500 mg) and the compound obtained in Reference Example 45 (989 mg) as starting materials, the compound shown in Table 1 (2.75 mg) was obtained in the same manner as that of Example 7.

Example 108

By using the compound obtained in Example 1 (500 mg) and the compound obtained in Reference Example 46 (1.1 g) as starting materials, the compound shown in Table 1 (28.5 mg) was obtained in the same manner as that of Example 7.

Syntheses of Examples 109 and 110

Preparation methods of the compounds represented by the formula (C) having R defined in the examples are shown below.

[Formula 20]

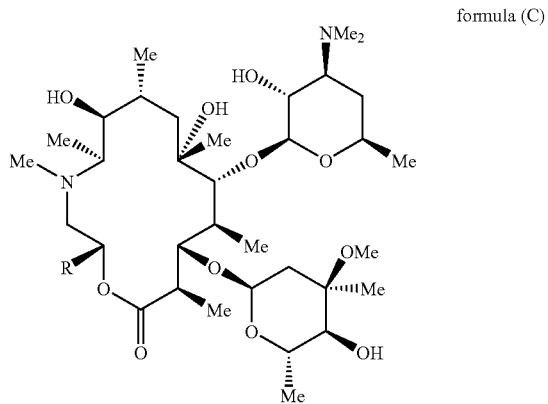

formula (C)

Example 109

Synthesis of the Compound of the Formula (C) Wherein R=Hydrogen Atom

By using the compound obtained in Example 2 (780 mg) as a starting material, the title compound (12 mg) was obtained in the same manners as those of Example 8, (1), Example 7, (2), (3) and (4).

MS (ESI) m/z=677.3 [M+H]$^+$

Example 110

Synthesis of the Compound of the Formula (C) Wherein R=Ethyl

By using the compound obtained in Example 2 (0.5 g) and (R)-1,2-epoxybutane as starting materials, the title compound (39 mg) was obtained in the same manner as that of Example 7.

MS (ESI) m/z=705.4 [M+H]+

$^1$H-NMR (300 MHz, CDCl$_3$) δ (ppm): 0.90 (t, J=7.38 Hz, 3H), 0.93-1.01 (m, 6H), 1.10 (d, J=7.31 Hz, 3H), 1.16-1.72 (m, 15H), 1.19 (d, J=7.15 Hz, 3H), 1.29 (d, J=6.22 Hz, 3H), 2.03-2.40 (m, 6H), 2.27 (s, 3H), 2.31 (s, 6H), 2.42-2.78 (m, 4H), 3.02 (t, J=8.94 Hz, 1H), 3.19-3.27 (m, 1H), 3.31 (s, 1H), 3.31 (s, 3H), 3.51-3.65 (m, 2H), 3.99-4.11 (m, 1H), 4.31-4.36 (m, 1H), 4.50 (d, J=7.31 Hz, 1H), 4.73-4.80 (m, 1H), 4.83 (d, J=4.51 Hz, 1H), 4.95 (s, 1H)

Syntheses of Examples 111 to 125

Preparation methods of the compounds represented by the formula (D) having R$^{1D}$, R$^{2D}$ and R$^{3D}$ defined in Table 2 are shown below.

TABLE 2 formula (D)

| Example | R$^{2D}$ | R$^{3D}$ | ESI MS (M + H) | $^1$H-NMR, CDCl$_3$, δ (ppm) |
|---|---|---|---|---|
| 111 | ⟨structure: -C(Me)$_2$-OH⟩ | H | 561.3 | (500 MHz): 0.90 (t, J = 7.26 Hz, 3H) 0.97 (d, J = 6.12 Hz, 3H) 1.04 (d, J = 6.88 Hz, 6H) 1.23 (d, J = 6.88 Hz, 3H) 1.22-1.75 (m, 6H) 1.26 (d, J = 6.12 Hz, 3H) 1.26-1.29 (m, 3H) 1.82-1.90 (m, 1H) 2.06-2.13 (m, 1H) 2.26 (s, 6H) 2.36 (s, 3H) 2.45-2.64 (m, 3H) 2.86-2.92 (m, 1H) 3.11 (s, 3H) 3.26 (dd, J = 9.94, 7.65 Hz, 1H) 3.49-3.58 (m, 1H) 3.84-3.94 (m, 2H) 3.97-4.01 (m, 1H) 4.36-4.42 (m, 1H) 4.50 (d, J = 7.65 Hz, 1H) 4.84-4.91 (m, 1H) |
| 112 | ⟨structure: -C(Me)$_2$-O-C(O)-CH$_2$-(2-pyridyl)⟩ | H | 680.6 | (300 MHz): 0.82-0.95 (m, 9H) 0.97-1.31 (m, 2H) 1.02 (d, J = 6.84 Hz, 3H) 1.07 (d, J = 7.31 Hz, 3H) 1.17 (d, J = 6.06 Hz, 3H) 1.26 (s, 3H) 1.45-1.99 (m, 4H) 2.09-2.28 (m, 2H) 2.30 (s, 6H) 2.38 (s, 3H) 2.43-2.64 (m, 3H) 2.77-2.88 (m, 1H) 2.97-3.07 (m, 1H) 3.14-3.51 (m, 3H) 3.21 (s, 3H) 3.87 (d, J = 4.04 Hz, 1H) 3.89-3.98 (m, 2H) 4.11 (d, J = 7.15 Hz, 1H) 4.69-4.78 (m, 1H) 5.23-5.33 (m, 1H) 7.19 (ddd, J = 7.54, 4.90, 1.09 Hz, 1H) 7.37 (dt, J = 7.81, 0.99 Hz, 1H) 7.67 (td, J = 7.69, 1.87 Hz, 1H) 8.53 (ddd, J = 4.90, 1.79, 0.93 Hz, 1H) |

TABLE 2-continued

| | | | | |
|---|---|---|---|---|
| 113 |  | 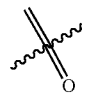 | 758.6 | (300 MHz): 0.77 (d, J = 6.53 Hz, 3H) 0.83 (d, J = 7.15 Hz, 3H) 1.15-1.22 (m, 1H) 1.22 (d, J = 6.06 Hz, 3H) 1.22-1.27 (m, 1H) 1.29 (s, 3H) 1.30-1.38 (m, 6H) 1.61-1.94 (m, 4H) 2.00 (d, J = 15.70 Hz, 1H) 2.21-2.62 (m, 3H) 2.30 (s, 6H) 2.37 (s, 3H) 2.75-2.83 (m, 1H) 2.83 (s, 3H) 2.86-3.03 (m, 1H) 3.16-3.34 (m, 2H) 3.36-3.57 (m, 3H) 3.57 (s, 2H) 3.84-4.01 (m, 2H) 4.41 (d, J = 7.31 Hz, 1H) 4.68-4.81 (m, 1H) 5.88 (t, J = 6.06 Hz, 1H) 6.47 (dd, J = 3.42, 1.87 Hz, 1H) 6.69 (dd, J = 3.42, 0.78 Hz, 1H) 7.14-7.21 (m, 1H) 7.37 (t, 1H) 7.44-7.49 (m, 1H) 7.55-7.63 (m, 2H) |
| 114 | 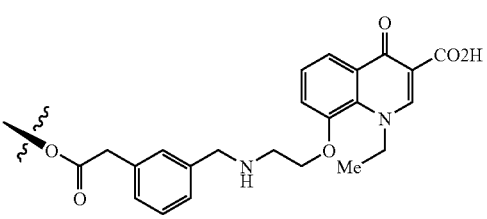 | H | | (600 MHz): 0.79-0.99 (m, 12H) 1.07-1.25 (m, 2H) 1.12 (d, J = 7.34 Hz, 3H) 1.19 (d, J = 5.96 Hz, 3H) 1.28 (s, 3H) 1.50 (t, J = 7.11 Hz, 3H) 1.52-1.77 (m, 3H) 1.85-1.99 (m, 1H) 2.08-2.28 (m, 3H) 2.30 (s, 6H) 2.39 (s, 3H) 2.44-2.62 (m, 2H) 2.77-2.89 (m, 1H) 2.99-3.10 (m, 1H) 3.14-3.31 (m, 5H) 3.22-3.24 (m, 3H) 3.64-3.75 (m, 3H) 3.87 (s, 1H) 3.91 (s, 2H) 4.02 (s, 1H) 4.21-4.35 (m, 2H) 4.60-4.83 (m, 3H) 5.31 (s, 1H) 7.26 (t, J = 7.11 Hz, 2H) 7.30-7.35 (m, 2H) 7.37 (s, 1H) 7.50 (t, J = 8.02 Hz, 1H) 8.20 (dd, J = 8.25, 1.38 Hz, 1H) 8.66 (s, 1H) |
| 115 | 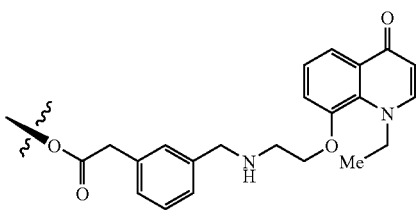 | H | 923.5 | (600 MHz): 0.79-0.96 (m, 12H) 1.04-1.30 (m, 2H) 1.09 (d, J = 7.34 Hz, 3H) 1.15 (d, J = 6.42 Hz, 3H) 1.24 (s, 3H) 1.36 (t, J = 7.11 Hz, 3H) 1.45-1.75 (m, 3H) 1.86-1.96 (m, 1H) 2.05-2.23 (m, 3H) 2.26 (s, 6H) 2.35 (s, 3H) 2.41-2.59 (m, 2H) 2.76-2.86 (m, 1H) 2.96-3.28 (m, 6H) 3.19 (s, 3H) 3.60-4.07 (m, 4H) 3.65-3.70 (m, 2H) 3.87 (s, 2H) 4.17-4.24 (m, 2H) 4.48 (q, J = 6.88 Hz, 2H) 6.26 (d, J = 7.79 Hz, 1H) 7.09-7.16 (m, 1H) 7.17-7.35 (m, 5H) 7.44 (d, J = 7.79 Hz, 1H) 8.10 (d, J = 6.42 Hz, 1H) |
| 116 | 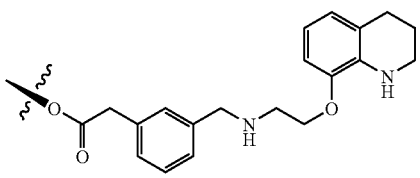 | H | 883.4 | (600 MHz): 0.76-0.96 (m, 12H) 1.03-1.28 (m, 2H) 1.06-1.11 (m, 3H) 1.15 (d, J = 6.42 Hz, 3H) 1.23-1.24 (m, 3H) 1.46-1.72 (m, 3H) 1.85-1.99 (m, 3H) 2.10-2.40 (m, 3H) 2.25-2.29 (m, 6H) 2.34-2.37 (m, 3H) 2.43-2.57 (m, 2H) 2.76 (t, J = 6.42 Hz, 2H) 2.79-2.85 (m, 1H) 2.98-3.24 (m, 4H) 2.99-3.05 (m, 2H) 3.20 (s, 3H) 3.28-3.33 (m, 2H) 3.60-4.01 (m, 4H) 3.67 (s, 2H) 3.84 (s, 2H) 4.09 (t, J = 5.27 Hz, 2H) 6.49-6.64 (m, 2H) 7.17-7.38 (m, 5H) |

TABLE 2-continued
| 117 | 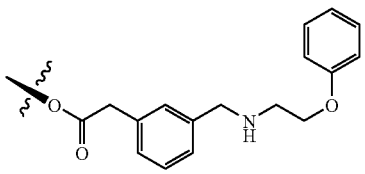 | H | 828.4 | (600 MHz): 0.75-0.91 (m, 9H) 0.92 (d, J = 6.88 Hz, 3H) 1.09 (d, J = 7.34 Hz, 3H) 1.09-1.19 (m, 2H) 1.14 (d, J = 6.42 Hz, 3H) 1.24 (s, 3H) 1.44-1.69 (m, 3H) 1.85-1.95 (m, 1H) 2.06-2.28 (m, 3H) 2.25 (s, 6H) 2.36 (s, 3H) 2.43-2.57 (m, 2H) 2.77-2.85 (m, 1H) 2.99-3.02 (m, 2H) 3.01-3.05 (m, 1H) 3.11-3.24 (m, 3H) 3.20 (s, 3H) 3.62-3.70 (m, 3H) 3.78-3.89 (m, 2H) 3.85 (s, 2H) 3.92-4.01 (m, 1H) 4.06-4.09 (m, 2H) 6.87-6.96 (m, 3H) 7.17-7.36 (m, 6H) |
| --- | --- | --- | --- | --- |
| 118 | 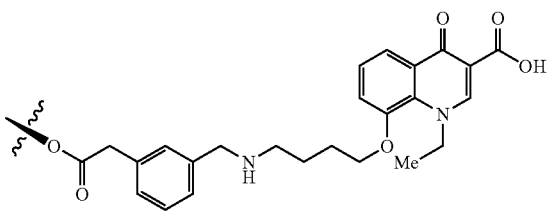 | H | 995.6 | |
| 119 | 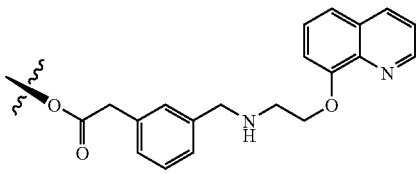 | H | 879.4 | (600 MHz): 0.78 (d, J = 7.34 Hz, 3H) 0.81-0.89 (m, 6H) 0.95 (d, J = 6.88 Hz, 3H) 1.02 (d, J = 7.34 Hz, 3H) 1.06-1.22 (m, 2H) 1.11 (d, J = 6.42 Hz, 3H) 1.19 (s, 3H) 1.44-1.53 (m, 2H) 1.54-1.66 (m, 1H) 1.79-1.90 (m, 1H) 2.01 (s, 1H) 2.12-2.46 (m, 4H) 2.26-2.29 (m, 9H) 2.73-2.83 (m, 1H) 2.95-3.06 (m, 1H) 3.13-3.23 (m, 3H) 3.19 (s, 3H) 3.23-3.33 (m, 2H) 3.59-3.72 (m, 2H) 3.73-3.85 (m, 2H) 3.87-3.97 (m, 3H) 4.28-4.41 (m, 3H) 7.07 (d, J = 7.34 Hz, 1H) 7.18 (d, J = 7.34 Hz, 1H) 7.22-7.32 (m, 2H) 7.35-7.42 (m, 2H) 7.44 (t, J = 8.02 Hz, 1H) 7.49 (s, 1H) 8.09-8.14 (m, 1H) 8.86-8.92 (m, 1H) |
| 120 | 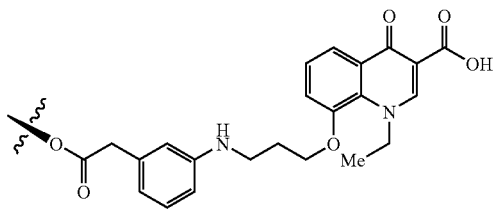 | H | | (600 MHz): 0.80-0.90 (m, 12H) 0.92 (d, J = 6.88 Hz, 3H) 1.08 (d, J = 7.34 Hz, 3H) 1.06-1.26 (m, 2H) 1.15 (d, J = 5.96 Hz, 3H) 1.24 (s, 3H) 1.49-1.69 (m, 5H) 1.86-1.94 (m, 1H) 2.07-2.42 (m, 5H) 2.28 (s, 6H) 2.36 (s, 3H) 2.43-2.56 (m, 2H) 2.77-2.83 (m, 1H) 2.99-3.08 (m, 1H) 3.17 (dd, J = 10.09, 7.34 Hz, 1H) 3.20 (s, 3H) 3.35-3.41 (m, 2H) 3.54-3.64 (m, 2H) 3.77-3.91 (m, 2H) 3.95-4.03 (m, 1H) 4.30 (t, J = 6.42 Hz, 2H) 4.66-4.70 (m, 1H) 4.72 (q, J = 6.88 Hz, 2H) 5.24 (br. s., 1H) 6.52 (d, J = 8.25 Hz, 1H) 6.64-6.68 (m, 2H) 7.11 (t, J = 7.57 Hz, 1H) 7.31 (d, J = 7.79 Hz, 1H) 7.48 (t, J = 8.02 Hz, 1H) 8.17 (d, J = 6.88 Hz, 1H) 8.63 (s, 1H) |

TABLE 2-continued
| | | | | |
|---|---|---|---|---|
| 121 | 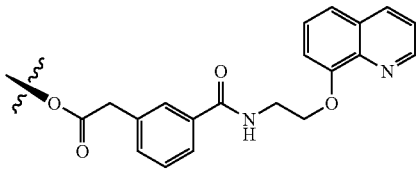 | H | 893.6 | (600 MHz): 0.68-1.01 (m, 6H) 0.75 (d, J = 7.34 Hz, 3H) 0.95 (d, J = 6.88 Hz, 3H) 1.12-1.32 (m, 8H) 1.17 (d, J = 5.96 Hz, 3H) 1.33-1.74 (m, 3H) 1.83-2.27 (m, 3H) 2.26-2.37 (m, 9H) 2.37-2.56 (m, 3H) 2.61-2.70 (m, 1H) 2.98 (d, J = 15.13 Hz, 1H) 3.16-3.28 (m, 2H) 3.21 (s, 3H) 3.43-3.51 (m, 1H) 3.67-3.93 (m, 3H) 4.15-4.30 (m, 3H) 4.34 (td, J = 9.40, 2.29 Hz, 2H) 4.58-4.74 (m, 1H) 5.08-5.28 (m, 1H) 7.06 (d, J = 7.79 Hz, 1H) 7.33-7.41 (m, 5H) 7.46 (m, 1H) 7.80 (s, 1H) 7.86 (d, J = 7.79 Hz, 1H) 8.14 (dd, J = 8.25, 1.38 Hz, 1H) 9.08 (br s, 1H) |
| 122 | 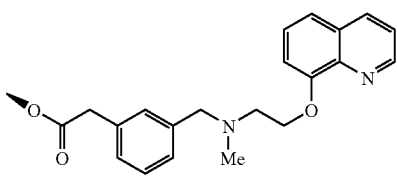 | H | 893.7 | (600 MHz): 0.79-0.86 (m, 6H) 0.86-0.90 (m, 6H) 0.87 (d, J = 6.88 Hz, 3H) 0.99-1.18 (m, 2H) 1.06 (d, J = 7.34 Hz, 3H) 1.13 (d, J = 5.96 Hz, 3H) 1.22 (s, 3H) 1.41-1.69 (m, 3H) 1.75-1.94 (m, 1H) 2.05-2.30 (m, 3H) 2.23-2.28 (m, 6H) 2.33-2.36 (m, 6H) 2.41-2.56 (m, 2H) 2.72-2.82 (m, 1H) 2.94-3.04 (m, 1H) 3.04 (t, J = 6.88 Hz, 2H) 3.10-3.23 (m, 4H) 3.17-3.19 (m, 3H) 3.59-3.69 (m, 4H) 3.81-3.86 (m, 1H) 3.98 (s, 1H) 4.27-4.38 (m, 3H) 7.00-7.05 (m, 1H) 7.16-7.28 (m, 2H) 7.31 (s, 1H) 7.34-7.44 (m, 4H) 8.08-8.12 (m, 1H) 8.89-8.92 (m, 1H) |
| 123 | 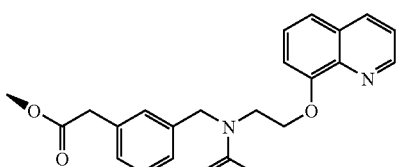 | H | 921.7 | (600 MHz): 0.79-0.93 (m, 9H) 1.04-1.11 (m, 3H) 1.09-1.31 (m, 2H) 1.12-1.20 (m, 6H) 1.22-1.27 (m, 3H) 1.43-1.63 (m, 3H) 1.86-1.94 (m, 1H) 2.14 (s, 3H) 2.20-2.41 (m, 3H) 2.21-2.31 (m, 6H) 2.33-2.36 (m, 3H) 2.42-2.59 (m, 2H) 2.73-2.83 (m, 1H) 2.95-3.06 (m, 1H) 3.07-3.34 (m, 4H) 3.19-3.20 (m, 3H) 3.58-3.71 (m, 2H) 3.80-3.92 (m, 5H) 4.01 (s, 1H) 4.42-4.50 (m, 2H) 4.61-4.75 (m, 1H) 7.09-7.15 (m, 1H) 7.18-7.32 (m, 3H) 7.35-7.48 (m, 4H) 8.09-8.16 (m, 1H) 8.89-8.96 (m, 1H) |

TABLE 2-continued

| 124 | 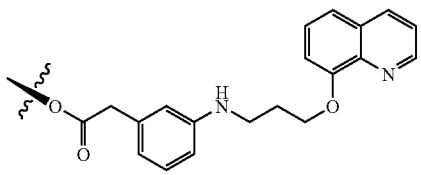 | H | 879.6 | (600 MHz): 0.81-0.91 (m, 9H) 0.93 (d, J = 6.88 Hz, 3H) 1.04-1.21 (m, 8H) 1.23 (s, 3H) 1.44-1.69 (m, 5H) 1.87-1.93 (m, 1H) 2.06-2.61 (m, 5H) 2.24 (s, 6H) 2.36 (s, 3H) 2.77-2.84 (m, 1H) 3.00-3.26 (m, 3H) 3.20 (s, 3H) 3.42 (t, J = 5.96 Hz, 2H) 3.51-3.61 (m, 3H) 3.85-4.00 (m, 2H) 4.38 (t, J = 5.96 Hz, 2H) 4.68-4.79 (m, 1H) 4.94-5.04 (m, 1H) 5.15-5.27 (m, 1H) 6.60 (t, J = 6.65 Hz, 2H) 6.71 (s, 1H) 7.07 (t, J = 7.79 Hz, 2H) 7.38-7.41 (m, 1H) 7.42-7.44 (m, 1H) 7.45 (t, J = 4.13 Hz, 1H) 8.13 (dd, J = 8.48, 1.60 Hz, 1H) 9.01 (dd, J = 4.13, 1.83 Hz, 1H) |
|---|---|---|---|---|
| 125 | 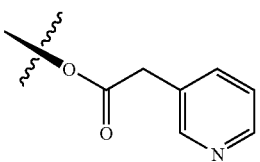 | H | 680.6 | (600 MHz): 0.78-0.92 (m, 9H) 0.95 (d, J = 6.88 Hz, 3H) 1.03-1.20 (m, 2H) 1.08 (d, J = 7.34 Hz, 3H) 1.15 (d, J = 5.96 Hz, 3H) 1.25 (s, 3H) 1.49-1.57 (m, 1H) 1.57-1.72 (m, 2H) 1.82-1.93 (m, 1H) 2.09-2.23 (m, 2H) 2.30 (s, 3H) 2.37 (s, 6H) 2.43-2.58 (m, 3H) 2.80-2.88 (m, 1H) 2.96-3.07 (m, 1H) 3.10-3.26 (m, 3H) 3.19 (s, 3H) 3.70 (d, J = 2.29 Hz, 2H) 3.77-3.86 (m, 1H) 3.94-4.09 (m, 1H) 4.62-4.77 (m, 1H) 5.18-5.46 (m, 1H) 7.27 (dd, J = 7.79, 5.04 Hz, 1H) 7.71 (d, J = 7.79 Hz, 1H) 8.52 (dd, J = 4.81, 1.60 Hz, 1H) 8.54 (d, J = 2.29 Hz, 1H) |

$R^{1D}$ in the compounds represented by the formula (D) is ethyl group except for the compound of Example 113.
$R^{1D}$ in the compound of Example 113 is a group represented by the formula:

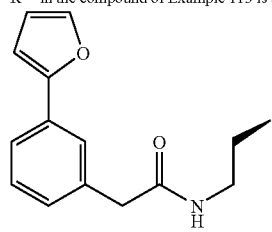

Example 111

The compound obtained in Example 7, (3) (5.35 g) was dissolved in ethanol (20 ml) and 1 N hydrochloric acid (20 ml), and the solution was stirred at room temperature for 2 days. The reaction mixture was neutralized with 10% aqueous sodium hydroxide, and then added with ethyl acetate, and the layers were separated. The organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=20:1:0.1 to 10:1:0.1) to obtain the compound shown in Table 2 (3.87 g).

Example 112

(1) The compound obtained in Example 111 (3.86 g) was dissolved in acetone (20 ml), the solution was added with acetic anhydride (617 mg), and the mixture was stirred for 18 hours. The reaction mixture was concentrated under reduced pressure, the resulting residue was added with ethyl acetate and saturated aqueous sodium hydrogencarbonate, the layers were separated, and the organic layer was dried over anhydrous magnesium sulfate and filtered. The filtrate was concentrated under reduced pressure to obtain a 2'-O-acetyl compound (1.81 g) as a crude product. The resulting crude product (1.81 g) was dissolved in dimethylformamide, the solution was added with imidazole (714 mg) and triethylchlorosilane (543 mg), and the mixture was stirred at room temperature for 15 hours. The reaction mixture was added with ethyl acetate and distilled water, the layers were separated, and the organic layer was washed successively with saturated aqueous ammonium chloride and distilled water, then dried over anhydrous magnesium sulfate and filtered. The filtrate was concentrated under reduced pressure, and the resulting residue was purified by silica gel column chromatography (hexane:acetone:triethylamine=30:10:0.2) to obtain a 2'-O-acetyl-9-O-triethylsilyl-3-hydroxy compound (1.09 g).

(2) The compound obtained in (1) mentioned above (46 mg) was dissolved in toluene (1 ml), the solution was added with 2-pyridylacetic acid hydrochloride (66 mg), 1-ethyl-3-(3-dimethylaminopropyl)carbodiimide hydrochloride (74 mg) and 4-dimethylaminopyridine (16 mg), and the mixture was stirred at room temperature for 18 hours. The reaction mixture was added with ethyl acetate and saturated aqueous ammonium chloride, the layers were separated, and the organic layer was washed with saturated brine, then dried over anhydrous magnesium sulfate and filtered. The filtrate was concentrated under reduced pressure, the resulting residue was dissolved in methanol (2 ml), and the solution was stirred at room temperature for 30 hours. The reaction mixture was concentrated under reduced pressure to obtain a condensed compound.

(3) By using the compound obtained in (2) mentioned above as a starting material, the compound shown in Table 2 (19 mg) was obtained in the same manner as that of Example 7, (4).

Example 113

(1) By using the compound obtained in Example 23, (2) (0.7 g) as a starting material, a 2'-O-acetyl-9-O-triethylsilyl-3-hydroxy compound (114 mg) was obtained in the same manners as those of Example 111 and Example 112, (1).

(2) N-Chlorosuccinimide (146 mg) was dissolved in toluene (3 ml), the solution was added with dimethyl sulfide (0.16 ml) at −20° C., and the mixture was stirred at the same temperature for 10 minutes. The filtrate was added with a solution (3 ml) of the compound obtained in (1) mentioned above (100 mg) in toluene, and the mixture was stirred at the same temperature for 10 minutes. The mixture was added with triethylamine (0.30 ml), and the mixture was stirred at the same temperature for 30 minutes. The reaction mixture was added with saturated aqueous sodium hydrogencarbonate and ethyl acetate, the layers were separated, and the organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=20:1:0.1) to obtain a 3-ketone compound (105 mg)

(3) The compound obtained in (2) mentioned above (93 mg) was dissolved in methanol (5 ml), and the solution was stirred at room temperature for 3 days. The reaction mixture was concentrated under reduced pressure, and the resulting residue was dissolved in ethanol (1 ml). The solution was added with 1 N hydrochloric acid (1 ml), and the mixture was stirred at room temperature for 18 hours. The reaction mixture was added with saturated aqueous sodium hydrogencarbonate and ethyl acetate, the layers were separated, and the organic layer was washed with saturated brine, then dried over anhydrous magnesium sulfate and filtered. The filtrate was concentrated under reduced pressure, and the resulting residue was purified by silica gel column chromatography (chloroform:methanol: 28% aqueous ammonia=30:1:0.1 to 10:1:0.1) and preparative thin layer chromatography (chloroform:methanol: 28% aqueous ammonia=10:1:0.1) to obtain the compound shown in Table 2 (34.2 mg).

Example 114

(1) The compound obtained in Example 112, (1) (250 mg) was dissolved in toluene (1 ml), the solution was added with the compound obtained in Reference Example 47 (262 mg), 1-ethyl-3-(3-dimethylaminopropyl)carbodiimide hydrochloride (201 mg) and 4-dimethylaminopyridine (43 mg), and the mixture was stirred at room temperature for 1 day. The mixture was further added with dichloromethane (5 ml), and the mixture was stirred at room temperature for 2.5 days. The reaction mixture was added with ethyl acetate and distilled water, the layers were separated, and the organic layer was washed with saturated brine, then dried over anhydrous magnesium sulfate and filtered. The filtrate was concentrated under reduced pressure, and the resulting residue was purified by silica gel column chromatography (hexane:acetone:triethylamine=50:10:0.2) to obtain a 3-O-acyl compound (123 mg).

(2) The compound obtained in (1) mentioned above (120 mg) was dissolved in ethanol (2 ml), the solution was added with 1 N hydrochloric acid (2 ml), and the mixture was stirred at room temperature for 18 hours. The reaction mixture was concentrated under reduced pressure, and the resulting residue was added with 1 N aqueous sodium hydroxide and ethyl acetate. The layers were separated, and the organic layer was washed with saturated brine, then dried over anhydrous magnesium sulfate and filtered. The filtrate was concentrated under reduced pressure, and the resulting residue was purified by silica gel column chromatography (hexane:acetone:triethylamine=30:10:0.2) to obtain an aldehyde compound (39 mg).

(3) The compound obtained in (2) mentioned above (38 mg) was dissolved in a mixed solvent of chloroform-dimethylformamide (3:2, 2.5 ml), the solution was added with a solution (0.5 ml) of 8-(2-aminoethoxy)-1-ethyl-4-oxo-1,4-dihydro-quinoline-3-carboxylic acid hydrochloride (48 mg) obtained by the method described in the patent document (WO04/101584) in dimethylformamide and sodium triacetoxyborohydride (32 mg), and the mixture was stirred at room temperature for 18 hours. The mixture was further added with a solution (0.5 ml) of 8-(2-aminoethoxy)-1-ethyl-4-oxo-1,4-dihydro-quinoline-3-carboxylic acid hydrochloride (25 mg) in dimethylformamide and sodium triacetoxyborohydride (16 mg), and the mixture was stirred for 4 hours. The reaction mixture was added with saturated aqueous sodium hydrogencarbonate and 1 N aqueous sodium hydroxide, and the mixture was extracted with ethyl acetate. The organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=20:1:0.1 to 10:1:0.1) to obtain a 2'-acetyl compound (17.3 mg).

(4) The compound obtained in (3) mentioned above (14.4 mg) was dissolved in methanol (0.8 ml), and the solution was stirred at room temperature for 3.5 days. The reaction mixture was concentrated under reduced pressure, and the resulting residue was purified by silica gel column chromatography (chloroform:methanol=10:1 to chloroform:

methanol:28% aqueous ammonia=20:1:0.1 to 10:1:0.1) to obtain the compound shown in Table 2 (6.8 mg).

Example 115

(1) The compound obtained in Example 114, (2) (0.34 g) was dissolved in methanol (50 ml), and the solution was stirred at 70° C. for 2 hours, and further stirred at room temperature for 9 hours. The reaction mixture was concentrated under reduced pressure to obtain a deprotected compound (0.31 g).
(2) The compound obtained in (1) mentioned above (50 mg) was dissolved in dimethylformamide (1.3 ml) and methanol (1.3 ml), the solution was added with the compound obtained in Reference Example 48 (16.2 mg) and acetic acid (0.15 ml), and the mixture was stirred at room temperature for 40 minutes. The mixture was added with sodium cyanoborohydride (13 mg), and the mixture was stirred at room temperature for 6 hours. The mixture was added with chloroform and saturated aqueous sodium hydrogencarbonate, the layers were separated, and the organic layer was washed with saturated brine. The organic layer was dried over anhydrous magnesium sulfate. The filtrate was concentrated under reduced pressure, and the resulting residue was purified by silica gel column chromatography (chloroform:methanol:28% aqueous ammonia=9:1:0.1) to obtain the compound shown in Table 2 (22 mg).

Example 116

By using the compound obtained in Example 115, (1) (50 mg) and the compound obtained in Reference Example 49 (19 mg) as starting materials, the compound shown in Table 2 (26 mg) was obtained in the same manner as that of Example 115, (2).

Example 117

By using the compound obtained in Example 115, (1) (50 mg) and the compound obtained in Reference Example 50 (12.3 mg) as starting materials, the compound shown in Table 2 (26 mg) was obtained in the same manner as that of Example 115, (2).

Example 118

By using the compound obtained in Example 115, (1) (20 mg) and the compound obtained in Reference Example 51 (8.6 mg) as starting materials, the compound shown in Table 2 (1.9 mg) was obtained in the same manner as that of Example 115, (2).

Example 119

By using the compound obtained in Example 115, (1) (14.9 mg) and the compound obtained in Reference Example 52 (4.0 mg) as starting materials, the compound shown in Table 2 (11.2 mg) was obtained in the same manner as that of Example 115, (2).

Example 120

(1) By using the compound obtained in Example 112, (1) (200 mg) and 3-nitrophenylacetic acid (152 mg) as starting materials, a nitrophenylacetic acid ester compound (266 mg) was obtained in the same manner as that of Example 114, (1).
(2) The compound obtained in (1) mentioned above (260 mg) was dissolved in methanol, and the solution was stirred for 3 hours under reflux by heating. The reaction mixture was left to cool, and then added with 5% palladium-carbon (100 mg), and the mixture was stirred at room temperature for 5 hours under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=20:1:0.1 to 10:1:0.1) to obtain an amine compound (180 mg).
(3) The compound obtained in (2) mentioned above (116 mg) was dissolved in methanol (4 ml), the solution was added with the compound obtained in Reference Example 53 (140 mg), sodium acetate (12 mg) and acetic acid (41 µl), and the mixture was stirred at room temperature for 15 minutes. The mixture was added with sodium cyanoborohydride (18 mg), and the mixture was stirred at room temperature for 2 hours. The reaction mixture was added with saturated aqueous sodium hydrogencarbonate and ethyl acetate, the layers were separated, and the organic layer was washed with saturated brine, then dried over anhydrous magnesium sulfate and filtered. The filtrate was concentrated under reduced pressure, and the resulting residue was purified by column chromatography (chloroform:methanol:28% aqueous ammonia=20:1:0.1 to 10:1:0.1) to obtain an adduct compound (106 mg).
(4) The compound obtained in (3) mentioned above (70 mg) was dissolved in 1 N hydrochloric acid (1 ml) and ethanol (0.1 ml), and the solution was stirred at 80° C. for 3 hours. The reaction mixture was added with saturated aqueous sodium hydrogencarbonate and chloroform, the layers were separated, and the organic layer was dried over anhydrous magnesium sulfate and filtered. The filtrate was concentrated under reduced pressure, and the resulting residue was purified by column chromatography (chloroform:methanol=10:1 to chloroform:methanol:28% aqueous ammonia=10:1:0.1) to obtain the compound shown in Table 2 (7.8 mg).

Example 121

(1) The compound obtained in Example 114, (2) (63 mg) and sulfamic acid (21 mg) were dissolved in tetrahydrofuran (2 ml), the solution was added with an aqueous solution (2 ml) of sodium chlorite (19 mg), and the mixture was stirred at room temperature for 3 hours. The reaction mixture was added with saturated aqueous sodium hydrogencarbonate and chloroform, and the layers were separated. The organic layer was dried over anhydrous magnesium sulfate and filtered. The filtrate was concentrated under reduced pressure to obtain a carboxyl compound (62 mg).
(2) The compound obtained in (1) mentioned above (62 mg) and the compound obtained in Reference Example 52 (31 mg) were dissolved in dichloromethane (5 ml), the solution was added with 1-ethyl-3-(3-dimethylaminopropyl)carbodiimide hydrochloride (31 mg), 1-hydroxybenzotriazole monohydrate (11 mg) and triethylamine (34 µl), and the mixture was stirred at room temperature for 15 hours. The reaction mixture was added with saturated aqueous sodium hydrogencarbonate and chloroform, the layers were separated, and the organic layer was dried over anhydrous magnesium sulfate and filtered. The filtrate was concentrated under reduced pressure, and the resulting residue was dissolved in methanol (50 ml), and the solution was stirred at 80° C. for 3 hours. The reaction mixture was concentrated under reduced pressure, and the resulting residue was purified by preparative thin layer chromatography (chloroform:methanol:28% aqueous ammonia=10:1:0.1) to obtain the compound shown in Table 2 (12 mg).

Example 122

By using the compound obtained in Example 119 (5.0 mg) as a starting material, the compound shown in Table 2 (6.5 mg) was obtained in the same manner as that of Example 7, (2).

Example 123

(1) By using the compound obtained in Example 114, (2) (60 mg) and the compound obtained in Reference Example 52 (15.1 mg) as starting materials, a 2'-acetyl compound (9.0 mg) was obtained in the same manner as that of Example 115, (2).
(2) The compound obtained in (1) mentioned above (6 mg) was dissolved in chloroform (0.5 ml), the solution was added with acetic anhydride (0.61 μl), and the mixture was stirred at room temperature for 2 hours. The reaction mixture was concentrated under reduced pressure, and the resulting residue was purified by preparative thin layer chromatography (chloroform:methanol:28% aqueous ammonia=10:1:0.1) to obtain an N-acyl compound (7.3 mg).
(3) The compound obtained in (2) mentioned above (7.3 mg) was dissolved in methanol (0.5 ml), and the solution was stirred at room temperature for 3 days. The reaction mixture was concentrated under reduced pressure, and the resulting residue was purified by preparative thin layer chromatography (chloroform:methanol:28% aqueous ammonia=10:1:0.1) to obtain the compound shown in Table 2 (4.5 mg).

Example 124

By using 3-(quinoline-8-yloxy)propanal (10 mg) obtained from 8-quinolinol in the same manner as that of Reference Example 53 and the compound obtained in Example 120, (2) (35 mg) as starting materials, the compound shown in Table 2 (3.6 mg) was obtained in the same manners as those of Example 120, (3) and (4).

Example 125

(1) By using the compound obtained in Example 112, (1) (97 mg) and 3-pyridylacetic acid hydrochloride as starting materials, an acyl compound (94 mg) was obtained in the same manner as that of Example 112, (2).
(2) The compound obtained in (1) mentioned above (94 mg) was dissolved in ethanol (1 ml), the solution was added with 1 N hydrochloric acid (1 ml), and the mixture was stirred at room temperature for 15 hours. The reaction mixture was added with saturated aqueous sodium hydrogencarbonate and chloroform, and the layers were separated. The organic layer was dried over anhydrous magnesium sulfate and filtered. The filtrate was concentrated under reduced pressure, and the resulting residue was purified by silica gel column chromatography (chloroform:methanol:28% aqueous ammonia=30:1:0.1 to 10:1:0.1) to obtain a 2'-O-acetyl compound (74 mg).
(3) The compound obtained in (2) mentioned above (23 mg) was dissolved in methanol (5 ml), and the solution was stirred at room temperature for 15 hours. The reaction mixture was concentrated under reduced pressure, and the resulting residue was purified by silica gel column chromatography (chloroform:methanol:28% aqueous ammonia=20:1:0.1) to obtain the compound shown in Table 2 (22 mg).

Syntheses of Examples 126 to 171

Preparation methods of the compounds of the formula (E) having $R^{1E}$, $R^{2E}$ and $R^{3E}$ defined in Table 3 are shown below.

TABLE 3 formula (E)

| Example | R$^{1E}$ | R$^{2E}$ | R$^{3E}$ | ESI MS (M + H) | $^1$H-NMR, CDCl$_3$, δ (ppm) |
|---|---|---|---|---|---|
| 126 | Et | (carbamate with 2-methoxyphenyl ethyl / N-ethyl substituent) | H | 968.0 | (600 MHz): 0.78-0.85 (m, 6H) 0.86-0.95 (m, 6H) 1.08-1.35 (m, 20H) 1.31 (s, 3H) 1.49-1.88 (m, 5H) 2.09-2.67 (m, 10H) 2.24 (s, 6H) 2.36 (s, 3H) 2.78-2.83 (m, 1H) 2.86-2.94 (m, 1H) 3.15-3.46 (m, 4H) 3.23 (s, 3H) 3.32 (s, 3H) 3.53-3.60 (m, 1H) 3.71 (d, J = 8.25 Hz, 1H) 3.84 (s, 3H) 4.18-4.25 (m, 1H) 4.32-4.46 (m, 3H) 4.54 (d, J = 9.63 Hz, 1H) 4.60-4.67 (m, 1H) 4.95-4.99 (m, 1H) 5.56 (s, 1H) 6.84-6.94 (m, 2H) 7.18-7.30 (m, 2H) |
| 127 | Et | =O | =O | 717.3 | (300 MHz): 0.84 (t, J = 7.31 Hz, 3H) 0.92 (t, J = 7.46 Hz, 3H) 1.08 (d, J = 7.31 Hz, 3H) 1.12-1.32 (m, 2H) 1.18 (d, J = 7.46 Hz, 3H) 1.22 (d, J = 6.06 Hz, 3H) 1.30 (s, 3H) 1.38 (d, J = 6.84 Hz, 3H) 1.43 (s, 3H) 1.52-1.96 (m, 5H) 2.08-2.56 (m, 5H) 2.28 (s, 6H) 2.32 (d, J = 6.99 Hz, 1H) 2.38 (s, 3H) 2.76-2.96 (m, 2H) 3.18-3.28 (m, 1H) 3.24 (s, 3H) 3.30 (s, 3H) 3.30-3.51 (m, 2H) 3.71 (d, J = 6.84 Hz, 1H) 4.25-4.32 (m, 2H) 4.49-4.60 (m, 1H) 4.62-4.75 (m, 1H) 5.26 (t, J = 7.07 Hz, 1H) |
| 128 | Et | =NOH | =NOH | 732.5 | (300 MHz): 0.80-0.95 (m, 9H) 1.06 (d, J = 7.31 Hz, 3H) 1.12-1.26 (m, 2H) 1.18 (d, J = 6.99 Hz, 3H) 1.22 (d, J = 6.06 Hz, 3H) 1.29 (s, 3H) 1.48 (d, J = 6.99 Hz, 3H) 1.52 (s, 3H) 1.53-1.73 (m, 4H) 1.85-1.97 (m, 1H) 2.09-2.37 (m, 4H) 2.29 (s, 6H) 2.38 (s, 3H) 2.43-2.57 (m, 2H) 2.81-2.89 (m, 1H) 2.91-3.00 (m, 1H) 3.16-3.29 (m, 2H) 3.22 (s, 3H) 3.31 (s, 3H) 3.43-3.59 (m, 1H) 3.83-3.96 (m, 1H) 3.97-4.05 (m, 1H) 4.43 (d, J = 7.62 Hz, 1H) 4.66-4.79 (m, 1H) 5.01-5.11 (m, 1H) 5.16-5.28 (m, 1H) |

| | | | | | |
|---|---|---|---|---|---|
| 129 | Et | ⋎NH₂ / H | H / ⋎NH₂ | 718.4 | mixture of diastereomers (300 MHz): 0.73-0.97 (m, 9H) 1.01-1.35 (m, 20H) 1.44-1.94 (m, 3H) 1.98-2.61 (m, 7H) 2.30 (s, 6H) 2.37 (s, 3H) 2.72-2.97 (m, 3H) 3.16-3.28 (m, 1H) 3.25 (s, 3H) 3.28-3.36 (m, 3H) 3.37-3.59 (m, 2H) 3.68-3.77 (m, 1H) 3.98-4.21 (m, 2H) 4.35-4.51 (m, 1H) 4.59-4.73 (m, 2H) 4.90-5.01 (m, 1H) |
| 130 | Et | [N-cyclopropyl-Cl-quinolone-CO₂H with O-CH₂CH₂-O-CH₂CH₂-C(O)O-] | H | 1096.5 | (300 MHz): 0.79-0.99 (m, 9H) 0.99-1.35 (m, 24H) 1.39-1.93 (m, 5H) 2.13-2.51 (m, J = 16.32 Hz, 5H) 2.31 (s, 6H) 2.37 (s, 3H) 2.52-2.93 (m, 5H) 3.17-3.22 (m, 1H) 3.23 (s, 3H) 3.33 (s, 3H) 3.38-3.47 (m, 1H) 3.55-3.74 (m, 3H) 3.88-3.99 (m, 4H) 4.14-4.20 (m, 1H) 4.29-4.35 (m, 2H) 4.36-4.47 (m, 1H) 4.52 (d, J = 6.06 Hz, 1H) 4.66-4.72 (m, 1H) 4.73 (d, J = 9.64 Hz, 1H) 5.00 (d, J = 5.13 Hz, 1H) 7.91 (s, 1H) 8.15 (s, 1H) 8.84 (s, 1H) |
| 131 | Et | [N-cyclopropyl-Cl-quinolone-CO₂H with NH-CH₂CH₂-O-CH₂CH₂-C(O)O-] | H | 1095.5 | (300 MHz): 0.83 (d, J = 6.84 Hz, 6H) 0.90 (t, J = 7.38 Hz, 3H) 0.94-1.92 (m, 23H) 1.11 (s, 3H) 1.29 (s, 3H) 2.12-2.93 (m, J = 15.23 Hz, 10H) 2.31 (s, 6H) 2.36 (s, 3H) 3.16-3.60 (m, 6H) 3.22 (s, 3H) 3.32 (s, 3H) 3.69 (d, J = 7.46 Hz, 1H) 3.75-3.85 (m, 4H) 4.16-4.20 (m, 1H) 4.39-4.45 (m, 1H) 4.50 (d, J = 7.15 Hz, 1H) 4.64-4.70 (m, 1H) 4.73 (d, J = 9.95 Hz, 1H) 4.97-5.06 (m, 2H) 7.54 (s, 1H) 8.05 (d, J = 8.74 (s, 1H) |
| 132 | Et | [2-methoxybenzyl-N(Et)-CH₂CH₂-NH-C(O)O-] | H | 953.7 | (600 MHz): 0.77-0.85 (m, 6H) 0.89 (t, J = 7.34 Hz, 3H) 0.99 (t, J = 7.11 Hz, 3H) 1.06-1.21 (m, 2H) 1.10-1.18 (m, 15H) 1.29-1.30 (m, 3H) 1.48-1.65 (m, 3H) 1.69-1.79 (m, 1H) 1.79-1.89 (m, 1H) 2.11-2.31 (m, 3H) 2.25-2.27 (m, 6H) 2.35 (s, 3H) 2.40 (d, J = 15.13 Hz, 1H) 2.45-2.64 (m, 4H) 2.66-2.77 (m, 2H) 2.77-2.84 (m, 1H) 2.85-2.92 (m, 1H) 3.16-3.45 (m, 4H) 3.22-3.23 (m, 3H) 3.31-3.32 (m, 3H) 3.55-3.60 (m, 1H) 3.60-3.63 (m, 1H) 3.71 (d, J = 7.79 Hz, 1H) 3.73-3.76 (m, 1H) 3.83 (s, 3H) 4.20 (s, 1H) 4.34-4.42 (m, 1H) 4.44 (d, J = 6.42 Hz, 1H) 4.54 (d, J = 10.09 Hz, 1H) 4.64 (s, 1H) 4.96 (d, J = 5.04 Hz, 1H) 5.51-5.57 (m, 1H) 6.85 (d, J = 8.25 Hz, 1H) 6.89 (t, J = 7.57 Hz, 1H) 7.18-7.29 (m, 2H) |
| 133 | Et | [(S)-1-(2-methoxyphenyl)ethyl-NH-CH₂CH₂CH₂-C(O)O-] | H | 924.5 | (300 MHz): 0.83 (d, J = 6.84 Hz, 6H) 0.90 (t, J = 7.31 Hz, 3H) 1.01-1.37 (m, 17H) 1.05 (t, J = 7.15 Hz, 3H) 1.31 (s, 3H) 1.46-1.92 (m, 5H) 2.13-2.68 (m, 8H) 2.29 (s, 6H) 2.36 (s, 3H) 2.66-2.94 (m, 4H) 3.19-3.23 (m, 3H) 3.24 (s, 3H) 3.32 (s, 3H) 3.37-3.45 (m, 1H) 3.57-3.67 (m, 1H) 3.71 (d, J = 7.31 Hz, 1H) 3.82 (s, 3H) 4.09-4.22 (m, 2H) 4.36-4.48 (m, 1H) 4.49 (d, J = 7.15 Hz, 1H) 4.63-4.73 (m, 2H) 4.99 (d, J = 4.82 Hz, 1H) 6.86 (d, J = 8.08 Hz, 1H) 6.95 (t, J = 7.46 Hz, 1H) 7.17-7.24 (m, 1H) 7.30-7.35 (m, 1H) |

TABLE 3-continued

| | | | | |
|---|---|---|---|---|
| 134 | Et | [structure] | H | 952.6 | (300 MHz): 0.83 (d, J = 6.84 Hz, 6H) 0.90 (t, J = 7.46 Hz, 3H) 0.99 (t, J = 6.84 Hz, 3H) 1.00-1.34 (m, 14H) 1.10 (s, 3H) 1.12 (d, J = 7.15 Hz, 3H) 1.30 (s, 3H) 1.46-1.91 (m, 5H) 2.13-2.68 (m, 10H) 2.29 (s, 6H) 2.36 (s, 3H) 2.72-3.02 (m, 4H) 3.20-3.23 (m, 1H) 3.24 (s, 3H) 3.32 (s, 3H) 3.37-3.44 (m, 1H) 3.59-3.74 (m, 2H) 3.80 (s, 3H) 4.13-4.19 (m, 1H) 4.28-4.45 (m, 2H) 4.50 (d, J = 7.31 Hz, 1H) 4.61-4.72 (m, 2H) 4.98 (d, J = 4.35 Hz, 1H) 6.85 (d, J = 8.08 Hz, 1H) 6.92 (t, J = 7.54 Hz, 1H) 7.15-7.23 (m, 1H) 7.37 (d, J = 7.31 Hz, 1H) |
| 135 | Et | [structure] | H | 980.7 | |
| 136 | Et | [structure] | H | 994.7 | (300 MHz): 0.83 (d, J = 7.15 Hz, 6H) 0.90 (t, J = 7.31 Hz, 3H) 0.97 (t, J = 6.99 Hz, 3H) 1.04-1.35 (m, 18H) 1.09 (s, 3H) 1.26 (d, J = 6.53 Hz, 3H) 1.31 (s, 3H) 1.35-1.93 (m, 7H) 2.12-2.67 (m, 12H) 2.30 (s, 6H) 2.36 (s, 3H) 2.77-2.94 (m, 2H) 3.18-3.23 (m, 1H) 3.24 (s, 3H) 3.33 (s, 3H) 3.36-3.45 (m, 1H) 3.58-3.67 (m, 1H) 3.70 (d, J = 7.77 Hz, 1H) 3.81 (s, 3H) 4.17 (d, J = 4.51 Hz, 1H) 4.24-4.33 (m, 1H) 4.36-4.47 (m, 1H) 4.50 (d, J = 7.15 Hz, 1H) 4.62-4.72 (m, 2H) 4.99 (d, J = 4.66 Hz, 1H) 6.85 (d, J = 8.08 Hz, 1H) 6.92 (t, J = 7.38 Hz, 1H) 7.18 (td, J = 7.69, 1.40 Hz, 1H) 7.40 (d, J = 6.68 Hz, 1H) |
| 137 | Et | [structure] | H | | (300 MHz): 0.79-0.86 (m, 6H) 0.90 (t, J = 7.31 Hz, 3H) 1.06-1.28 (m, 2H) 1.06-1.21 (m, 15H) 1.28-1.34 (m, 3H) 1.45-1.95 (m, 5H) 2.07-2.65 (m, 6H) 2.28-2.31 (m, 6H) 2.37-2.37 (m, 3H) 2.68-2.77 (m, 2H) 2.77-2.96 (m, 2H) 3.13-3.35 (m, 3H) 3.23-3.25 (m, 3H) 3.32-3.34 (m, 3H) 3.41 (d, J = 8.70 Hz, 1H) 3.51-3.63 (m, 1H) 3.71 (d, J = 7.93 Hz, 1H) 3.76 (s, 2H) 3.84 (s, 3H) 4.14-4.23 (m, 1H) 4.29-4.42 (m, 1H) 4.45 (d, J = 0.84 Hz, 1H) 4.54 (d, J = 9.79 Hz, 1H) 4.65 (s, 1H) 4.98 (d, J = 4.51 Hz, 1H) 5.39 (t, J = 5.28 Hz, 1H) 6.83-6.95 (m, 2H) 7.15-7.30 (m, 2H) |
| 138 | Et | [structure] | H | 939.6 | (300 MHz): 0.78-0.87 (m, 6H) 0.91 (t, J = 7.07 Hz, 3H) 1.05-1.28 (m, 17H) 1.31-1.33 (m, 3H) 1.46-1.95 (m, 5H) 2.11-2.48 (m, 6H) 2.17-2.22 (m, 3H) 2.27-2.29 (m, 6H) 2.37-2.38 (m, 3H) 2.56 (t, J = 5.67 Hz, 2H) 2.74-2.97 (m, 2H) 3.14-3.50 (m, 3H) 3.24 (s, 4H) 3.24 (s, 3H) 3.33 (s, 3H) 3.51-3.79 (m, 4H) 3.86 (s, 3H) 4.19-4.26 (m, 1H) 4.33-4.50 (m, 2H) 4.56 (d, J = 9.79 Hz, 1H) 4.66 (s, 1H) 4.97-5.01 (m, 1H) 5.55-5.64 (m, 1H) 6.83-6.96 (m, 1H) 7.19-7.30 (m, 2H) |

TABLE 3-continued

| | | | |
|---|---|---|---|
| 139 | Et | [structure] | H | 1045.6 | (600 MHz): 0.76-0.85 (m, 6H) 0.89 (t, J = 7.34 Hz, 3H) 1.03-1.22 (m, 2H) 1.08-1.19 (m, 15H) 1.31 (s, 3H) 1.49-1.67 (m, 3H) 1.69-1.80 (m, 1H) 1.80-1.89 (m, 1H) 2.09-2.20 (m, 1H) 2.20-2.31 (m, 2H) 2.24-2.30 (m, 6H) 2.36 (s, 3H) 2.39 (d, J = 15.13 Hz, 1H) 2.46-2.66 (m, 4H) 2.77-2.85 (m, 1H) 2.89 (d, J = 14.67 Hz, 1H) 3.16-3.42 (m, 4H) 3.21-3.24 (m, 3H) 3.31-3.33 (m, 3H) 3.56-3.68 (m, 1H) 3.64 (d, J = 8.25 Hz, 4H) 3.73 (d, J = 8.25 Hz, 1H) 3.81 (s, 6H) 4.22 (s, 1H) 4.35-4.43 (m, 1H) 4.45 (d, J = 7.34 Hz, 1H) 4.52 (d, J = 9.63 Hz, 1H) 4.64 (s, 1H) 4.96 (d, J = 4.59 Hz, 1H) 5.59 (s, 1H) 6.83 (d, J = 8.25 Hz, 2H) 6.88 (t, J = 7.57 Hz, 2H) 7.19 (t, J = 7.79 Hz, 2H) 7.33 (d, J = 6.42 Hz, 2H) |
| 140 | Et | [structure] | H | 981.7 | (600 MHz): 0.78-0.85 (m, 6H) 0.89 (t, J = 7.34 Hz, 3H) 1.01 (s, 3H) 1.05-1.33 (m, 23H) 1.46-1.94 (m, 7H) 2.10-2.19 (m, 1H) 2.20-2.69 (m, 9H) 2.25-2.29 (m, 6H) 2.35-2.37 (m, 3H) 2.76-2.84 (m, 1H) 2.89 (d, J = 15.13 Hz, 1H) 3.13-3.25 (m, 3H) 3.22-3.24 (m, 3H) 3.30 (s, 3H) 3.39 (s, 1H) 3.56 (s, 1H) 3.71 (d, J = 7.79 Hz, 1H) 3.81 (s, 3H) 4.19 (s, 1H) 4.33-4.42 (m, 2H) 4.44 (d, J = 7.34 Hz, 1H) 4.53 (d, J = 9.63 Hz, 1H) 4.63 (s, 1H) 4.96 (d, J = 4.59 Hz, 1H) 5.73 (s, 1H) 6.86 (d, J = 7.79 Hz, 1H) 6.90-6.97 (m, 1H) 7.17-7.24 (m, 1H) 7.28-7.35 (m, 1H) |
| 141 | Et | [structure] | H | 995.7 | (600 MHz): 0.76-0.84 (m, 6H) 0.89 (t, J = 7.34 Hz, 3H) 0.97 (s, 3H) 1.06-1.23 (m, 2H) 1.12 (d, J = 7.34 Hz, 3H) 1.13-1.18 (m, 15H) 1.26 (s, 2H) 1.30 (s, 3H) 1.42 (s, 2H) 1.48-1.64 (m, 3H) 1.75 (s, 1H) 1.83 (s, 1H) 2.09-2.19 (m, 1H) 2.20-2.69 (m, 9H) 2.26-2.28 (m, 6H) 2.35-2.37 (m, 3H) 2.76-2.84 (m, 1H) 2.89 (d, J = 15.13 Hz, 1H) 3.08-3.21 (m, 3H) 3.22 (s, 3H) 3.32 (s, 3H) 3.35-3.46 (m, 1H) 3.48-3.57 (m, 1H) 3.69 (d, J = 8.25 Hz, 1H) 3.80 (s, 3H) 4.18-4.31 (m, 2H) 4.32-4.44 (m, 2H) 4.53 (d, J = 9.63 Hz, 1H) 4.63 (s, 1H) 4.97 (d, J = 4.58 Hz, 1H) 5.01 (s, 1H) 6.84 (d, J = 8.25 Hz, 1H) 6.89-6.96 (m, 1H) 7.14-7.22 (m, 1H) 7.34-7.43 (m, 1H) |
| 142 | Et | [structure] | H | (600 MHz): 0.80-0.85 (m, 6H) 0.89 (t, J = 7.34 Hz, 3H) 1.02-1.35 (m, 23H) 1.30 (s, 3H) 1.49-1.89 (m, 7H) 2.14-2.64 (m, 12H) 2.28 (s, 6H) 2.35 (s, 3H) 2.78-2.84 (m, 1H) 2.85-2.91 (m, 1H) 3.18-3.23 (m, 1H) 3.23 (s, 3H) 3.31 (s, 3H) 3.38-3.44 (m, 1H) 3.59-3.65 (m, 1H) 3.69 (d, J = 7.79 Hz, 1H) 3.80 (s, 3H) 4.14-4.18 (m, 1H) 4.28-4.33 (m, 1H) 4.37-4.43 (m, 1H) 4.49 (d, J = 6.88 Hz, 1H) 4.63-4.70 (m, 2H) 4.97 (d, J = 5.04 Hz, 1H) 6.84 (d, J = 8.25 Hz, 1H) 6.89-6.94 (m, 1H) 7.16-7.21 (m, 1H) 7.34-7.38 (m, 1H) |

| | | | | |
|---|---|---|---|---|
| 143 | Et | ![structure] | 939.6 | (600 MHz): 0.78-0.83 (m, 6H) 0.88 (t, J = 7.34 Hz, 3H) 1.04-1.20 (m, 8H) 1.07 (s, 3H) 1.09 (d, J = 7.34 Hz, 3H) 1.14 (d, J = 7.34 Hz, 3H) 1.28 (s, 3H) 1.49-1.59 (m, 2H) 1.63-1.68 (m, 1H) 1.69-1.77 (m, 1H) 1.80-1.86 (m, 1H) 2.11-2.46 (m, 5H) 2.27 (s, 6H) 2.34 (s, 3H) 2.51-2.57 (m, 1H) 2.76-2.83 (m, 1H) 2.86 (d, J = 14.21 Hz, 1H) 3.17 (dd, J = 10.32, 7.11 Hz, 1H) 3.21 (s, 3H) 3.28 (s, 3H) 3.34-3.49 (m, 3H) 3.52-3.64 (m, 3H) 3.67 (d, J = 8.25 Hz, 3H) 3.95 (s, 3H) 4.13-4.17 (m, 1H) 4.31-4.37 (m, 1H) 4.42 (d, J = 7.34 Hz, 1H) 4.50 (d, J = 9.63 Hz, 1H) 4.60-4.67 (m, 1H) 4.95 (d, J = 4.59 Hz, 1H) 5.35 (t, J = 5.73 Hz, 1H) 6.95 (d, J = 7.79 Hz, 1H) 7.01-7.08 (m, 1H) 7.41-7.45 (m, 1H) 8.12 (t, J = 5.50 Hz, 1H) 8.16 (dd, J = 8.25, 1.83 Hz, 1H) |
| 144 | Et | ![structure] | 975.6 | (600 MHz): 0.77 (d, J = 6.88 Hz, 6H) 0.85 (t, J = 7.34 Hz, 3H) 1.04-1.25 (m, 8H) 1.08 (d, J = 7.34 Hz, 3H) 1.10 (s, 3H) 1.17 (d, J = 5.96 Hz, 3H) 1.27 (s, 3H) 1.47-1.52 (m, 1H) 1.55 (dd, J = 15.13, 5.04 Hz, 1H) 1.65-1.75 (m, 2H) 1.77-1.84 (m, 1H) 2.08-2.42 (m, 5H) 2.25 (s, 6H) 2.31 (s, 3H) 2.51-2.57 (m, 1H) 2.74-2.80 (m, 1H) 2.84 (d, J = 14.21 Hz, 1H) 2.91-3.00 (m, 2H) 3.15 (dd, J = 10.32, 7.11 Hz, 1H) 3.19 (s, 3H) 3.25-3.41 (m, 3H) 3.29 (s, 3H) 3.52-3.57 (m, 1H) 3.65 (d, J = 8.25 Hz, 1H) 3.93 (s, 3H) 4.13-4.17 (m, 1H) 4.33-4.37 (m, 1H) 4.40 (d, J = 6.88 Hz, 1H) 4.47 (d, J = 9.63 Hz, 1H) 4.60 (d, 1H) 4.93 (d, J = 5.04 Hz, 1H) 5.11-5.15 (m, 1H) 5.25 (t, J = 5.73 Hz, 1H) 6.99 (d, J = 8.25 Hz, 1H) 7.02 (td, J = 7.57, 0.92 Hz, 1H) 7.50 (td, J = 7.91, 1.61 Hz, 1H) 7.82 (dd, J = 7.79, 1.83 Hz, 1H) |
| 145 | Et | ![structure] | 954.6 | (600 MHz): 0.77 (d, J = 6.42 Hz, 6H) 0.84 (t, J = 7.34 Hz, 3H) 1.02-1.16 (m, 17H) 1.24 (s, 3H) 1.46-1.55 (m, 2H) 1.58-1.62 (m, 1H) 1.66-1.73 (m, 1H) 1.76-1.83 (m, 1H) 2.07-2.28 (m, 3H) 2.22 (s, 6H) 2.30 (s, 3H) 2.33 (d, J = 15.13 Hz, 1H) 2.36-2.44 (m, 1H) 2.47-2.53 (m, 1H) 2.73-2.78 (m, 1H) 2.80-2.85 (m, 1H) 3.14 (dd, J = 10.32, 7.57 Hz, 1H) 3.17 (s, 3H) 3.24 (s, 3H) 3.26-3.42 (m, 5H) 3.49-3.54 (m, 1H) 3.64 (d, J = 7.79 Hz, 1H) 3.78 (s, 3H) 4.09-4.13 (m, 1H) 4.29-4.34 (m, 1H) 4.38 (d, J = 7.34 Hz, 1H) 4.46 (d, J = 10.09 Hz, 1H) 4.57-4.62 (m, 1H) 4.91 (d, J = 5.04 Hz, 1H) 5.27 (s, 1H) 5.34 (t, J = 4.81 Hz, 1H) 6.77-6.82 (m, 1H) 6.87 (td, J = 7.57, 1.38 Hz, 1H) 6.92 (td, J = 7.79, 1.38 Hz, 1H) 7.91 (dd, J = 7.79, 1.38 Hz, 1H) |
| 146 | Et | ![structure] | 925.5 | (600 MHz): 0.76 (d, J = 6.88 Hz, 6H) 0.84 (t, J = 7.34 Hz, 3H) 1.06 (d, J = 7.34 Hz, 14H) 1.06 (d, J = 7.34 Hz, 3H) 1.25 (s, 3H) 1.45-1.64 (m, 3H) 1.65-1.73 (m, 1H) 1.75-1.83 (m, 3H) 2.07-2.12 (m, 1H) 2.18-2.43 (m, 4H) 2.23 (s, 6H) 2.31 (s, 3H) 2.47-2.53 (m, 1H) 2.74-2.78 (m, 1H) 2.84 (d, J = 15.13 Hz, 1H) 3.10-3.17 (m, 3H) 3.17 (s, 3H) 3.25-3.42 (m, 3H) 3.45-3.51 (m, 1H) 3.64 (d, J = 8.71 Hz, 1H) 4.36 (d, J = 7.34 Hz, 3H) 4.15-4.20 (m, 1H) 4.29-4.34 (m, 1H) 4.36 (d, J = 7.34 Hz, 1H) 4.50 (d, J = 9.63 Hz, 1H) 4.55-4.61 (m, 1H) 4.92 (d, J = 4.58 Hz, 1H) 6.52 (dd, J = 7.79, 1.38 Hz, 1H) 6.61 (td, J = 7.79, 1.38 Hz, 1H) 6.71 (dd, J = 7.79, 1.38 Hz, 1H) 6.80 (td, J = 7.57, 1.38 Hz, 1H) |

TABLE 3-continued

| | | | | |
|---|---|---|---|---|
| 147 | Et | [structure: benzyl-N(Et)-CH2CH2-NH-C(=O)-O-] | H | 923.6 | (300 MHz): 0.83 (d, J = 6.84 Hz, 6H) 0.91 (t, J = 7.31 Hz, 3H) 1.02 (t, J = 7.23 Hz, 3H) 1.06-1.27 (m, 17H) 1.32 (s, 3H) 1.45-1.91 (m, 5H) 2.11-2.62 (m, 10H) 2.29 (s, 6H) 2.37 (s, 3H) 2.78-2.95 (m, 2H) 3.15-3.48 (m, J = 35.28 Hz, 4H) 3.24 (s, 3H) 3.36 (s, 3H) 3.58 (d, J = 3.57 Hz, 2H) 3.59-3.67 (m, 1H) 3.73 (d, J = 8.24 Hz, 1H) 4.18-4.26 (m, 1H) 4.36-4.44 (m, 1H) 4.48 (d, J = 7.46 Hz, 1H) 4.52-4.58 (m, 1H) 4.60-4.71 (m, 1H) 4.98 (d, J = 3.26 Hz, 1H) 5.24-5.29 (m, 1H) 7.21-7.32 (m, 5H) |
| 148 | Et | [structure: 2-pyridylmethyl-N(Et)-CH2CH2-NH-C(=O)-O-] | H | | (600 MHz): 0.81 (d, J = 6.42 Hz, 6H) 0.89 (t, J = 7.34 Hz, 3H) 1.04 (t, J = 7.11 Hz, 3H) 1.01-1.22 (m, 14H) 1.12 (s, 3H) 1.30 (s, 3H) 1.49-1.64 (m, 3H) 1.69-1.78 (m, 1H) 1.80-1.89 (m, 1H) 2.10-2.46 (m, 4H) 2.24 (s, 6H) 2.35 (s, 3H) 2.40 (d, J = 15.13 Hz, 1H) 2.53-2.66 (m, 5H) 2.78-2.84 (m, 1H) 2.89 (d, J = 14.67 Hz, 1H) 3.16-3.45 (m, 4H) 3.23 (s, 3H) 3.36 (s, 3H) 3.61-3.66 (m, 1H) 3.67-3.73 (m, 2H) 3.76-3.80 (m, 1H) 4.16-4.22 (m, 1H) 4.35-4.43 (m, 1H) 4.47 (d, J = 6.88 Hz, 1H) 4.52 (d, J = 10.09 Hz, 1H) 4.61-4.67 (m, 1H) 4.96 (d, J = 4.59 Hz, 1H) 5.88 (t, J = 4.59 Hz, 1H) 7.14 (dd, J = 7.34, 5.04 Hz, 1H) 7.32 (d, J = 7.79 Hz, 1H) 7.61 (td, J = 7.57, 1.83 Hz, 1H) 8.59 (d, J = 4.58 Hz, 1H) |
| 149 | Et | [structure: 3-pyridylmethyl-N(Et)-CH2CH2-NH-C(=O)-O-] | H | 922.7 | (600 MHz): 0.81 (d, J = 6.42 Hz, 6H) 0.89 (t, J = 7.34 Hz, 3H) 1.01 (t, J = 7.11 Hz, 3H) 1.04-1.27 (m, 17H) 1.30 (s, 3H) 1.50-1.79 (m, 4H) 1.80-1.87 (m, 1H) 2.11-2.19 (m, 1H) 2.22-2.61 (m, 6H) 2.29 (s, 6H) 2.36 (s, 3H) 2.41 (d, J = 15.59 Hz, 1H) 2.58 (t, J = 5.96 Hz, 2H) 2.78-2.83 (m, 1H) 2.88 (d, J = 14.21 Hz, 1H) 3.17-3.46 (m, 4H) 3.22 (s, 3H) 3.34 (s, 3H) 3.56-3.61 (m, 2H) 3.66-3.71 (m, 1H) 3.70 (d, J = 8.25 Hz, 1H) 4.20-4.26 (m, 1H) 4.35-4.47 (m, 1H) 4.54 (d, J = 10.09 Hz, 2H) 4.59-4.67 (m, 1H) 4.97 (d, J = 4.58 Hz, 1H) 5.18-5.21 (m, 1H) 7.23 (dd, J = 7.34, 5.04 Hz, 1H) 7.62 (d, J = 7.79 Hz, 1H) 8.47-8.51 (m, 2H) |
| 150 | Et | [structure: 4-pyridylmethyl-N(Et)-CH2CH2-NH-C(=O)-O-] | H | 924.9 | (600 MHz): 0.81 (d, J = 6.42 Hz, 6H) 0.89 (t, J = 7.34 Hz, 3H) 1.01 (t, J = 7.11 Hz, 3H) 1.03-1.27 (m, 17H) 1.30 (s, 3H) 1.52-1.56 (m, 1H) 1.57-1.62 (m, 1H) 1.62-1.68 (m, 1H) 1.70-1.79 (m, 1H) 1.80-1.88 (m, 1H) 2.11-2.19 (m, 1H) 2.22-2.65 (m, 7H) 2.31 (s, 6H) 2.36 (s, 3H) 2.41 (d, J = 15.59 Hz, 1H) 2.58 (t, J = 5.96 Hz, 2H) 2.78-2.84 (m, 1H) 2.88 (d, J = 13.76 Hz, 1H) 3.19-3.44 (m, 4H) 3.22 (s, 3H) 3.34 (s, 3H) 3.54-3.61 (m, 2H) 3.70 (d, J = 7.79 Hz, 1H) 4.19-4.27 (m, 1H) 4.36-4.41 (m, 1H) 4.44 (d, J = 6.88 Hz, 1H) 4.54 (d, J = 9.63 Hz, 1H) 4.63 (d, 1H) 4.97 (d, J = 4.13 Hz, 1H) 5.22 (br. s., 1H) 7.23 (d, J = 5.50 Hz, 2H) 8.51 (d, J = 5.04 Hz, 2H) |

TABLE 3-continued

| | | | | |
|---|---|---|---|---|
| 151 | Et | ![naphthalen-2-ylmethyl carbamate structure] | H | (600 MHz): 0.79 (d, J = 6.88 Hz, 6H) 0.83-0.89 (m, 3H) 1.00 (t, J = 7.11 Hz, 3H) 1.03-1.23 (m, 17H) 1.24-1.29 (m, 3H) 1.46-1.76 (m, 4H) 1.78-1.87 (m, 1H) 2.09-2.44 (m, 5H) 2.23 (s, 6H) 2.33 (s, 3H) 2.48-2.62 (m, 5H) 2.75-2.81 (m, 1H) 2.82-2.89 (m, 1H) 3.14-3.42 (m, 3H) 3.20 (s, 3H) 3.33 (s, 3H) 3.54-3.62 (m, 1H) 3.65-3.73 (m, 2H) 3.76 (s, 2H) 4.16-4.22 (m, 1H) 4.35-4.39 (m, 1H) 4.43 (d, J = 6.88 Hz, 1H) 4.51 (d, J = 10.09 Hz, 1H) 4.61 (br s., 1H) 4.94 (d, J = 4.58 Hz, 1H) 5.26 (t, J = 4.59 Hz, 1H) 7.38-7.48 (m, 3H) 7.66 (s, 1H) 7.72-7.83 (m, 3H) |
| 152 | Et | ![naphthalen-1-ylmethyl carbamate structure] | H | (600 MHz): 0.82 (d, J = 6.42 Hz, 6H) 0.89 (t, J = 7.34 Hz, 3H) 1.07 (t, J = 7.11 Hz, 3H) 1.07-1.22 (m, 17H) 1.30 (s, 3H) 1.48-1.68 (m, 3H) 1.70-1.79 (m, 1H) 1.81-1.88 (m, 1H) 2.11-2.45 (m, 5H) 2.26 (s, 6H) 2.36 (s, 3H) 2.51-2.69 (m, 3H) 2.65 (t, J = 5.96 Hz, 2H) 2.78-2.84 (m, 1H) 2.88 (d, J = 14.67 Hz, 1H) 3.17-3.45 (m, 4H) 3.22 (s, 3H) 3.33 (s, 3H) 3.52-3.58 (m, 1H) 3.69-3.73 (m, 1H) 3.97-4.04 (m, 2H) 4.18-4.25 (m, 1H) 4.34-4.39 (m, 1H) 4.42-4.45 (m, 1H) 4.50 (d, J = 9.63 Hz, 1H) 4.61-4.66 (m, 1H) 4.96 (d, J = 4.59 Hz, 1H) 5.12-5.15 (m, 1H) 7.45-7.48 (m, 2H) 7.49-7.53 (m, 2H) 7.76 (d, J = 8.25 Hz, 1H) 7.84 (d, J = 7.79 Hz, 1H) 8.20 (d, J = 8.71 Hz, 1H) |
| 153 | Et | ![quinolin-3-ylmethyl carbamate structure] | H | 974.9 (600 MHz): 0.81 (d, J = 6.88 Hz, 6H) 0.89 (t, J = 7.34 Hz, 3H) 1.05 (t, J = 7.11 Hz, 3H) 1.17 (d, 17H) 1.30 (s, 3H) 1.50-1.78 (m, 4H) 1.81-1.87 (m, 1H) 2.12-2.20 (m, 1H) 2.20-2.46 (m, 3H) 2.27 (s, 6H) 2.36 (s, 3H) 2.40 (d, J = 15.13 Hz, 1H) 2.52-2.61 (m, 3H) 2.64 (t, J = 5.96 Hz, 2H) 2.78-2.83 (m, 1H) 2.88 (d, J = 13.76 Hz, 1H) 3.17-3.44 (m, 3H) 3.22 (s, 3H) 3.34 (s, 3H) 3.54-3.59 (m, 1H) 3.66-3.72 (m, 2H) 3.74-3.81 (m, 2H) 4.21-4.26 (m, 1H) 4.36-4.47 (m, 2H) 4.54 (d, J = 10.09 Hz, 1H) 4.61-4.67 (m, 1H) 4.97 (d, J = 4.58 Hz, 1H) 5.22 (t, J = 4.36 Hz, 1H) 7.54 (t, J = 7.57 Hz, 1H) 7.68 (t, J = 8.25 Hz, 1H) 7.80 (d, J = 7.79 Hz, 1H) 8.03 (s, 1H) 8.08 (d, J = 8.71 Hz, 1H) 8.83 (d, J = 2.29 Hz, 1H) |
| 154 | Et | ![quinolin-4-ylmethyl carbamate structure] | H | 974.9 (600 MHz): 0.81 (d, J = 6.42 Hz, 6H) 0.89 (t, J = 7.34 Hz, 3H) 1.07 (t, J = 7.11 Hz, 3H) 1.09-1.24 (m, 17H) 1.30 (s, 3H) 1.50-1.62 (m, 3H) 1.71-1.78 (m, 1H) 1.80-1.88 (m, 1H) 2.11-2.18 (m, 1H) 2.22-2.45 (m, 3H) 2.26 (s, 6H) 2.35 (s, 3H) 2.40 (d, J = 15.13 Hz, 1H) 2.52-2.58 (m, 3H) 2.58-2.64 (m, 2H) 2.68 (t, J = 5.50 Hz, 2H) 2.78-2.83 (m, 1H) 2.88 (d, J = 13.30 Hz, 1H) 3.17-3.21 (m, 1H) 3.22 (s, 3H) 3.21-3.47 (m, 3H) 3.34 (s, 3H) 3.52-3.57 (m, 1H) 3.70 (d, J = 8.25 Hz, 1H) 4.04 (s, 2H) 4.22-4.26 (m, 1H) 4.35-4.40 (m, 1H) 4.43 (d, J = 7.34 Hz, 1H) 4.52 (d, J = 10.09 Hz, 1H) 4.60-4.66 (m, 1H) 4.96 (d, J = 4.59 Hz, 1H) 5.14 (t, J = 4.81 Hz, 1H) 7.47 (d, J = 4.59 Hz, 1H) 7.56 (t, J = 7.11 Hz, 1H) 7.70 (t, J = 7.57 Hz, 1H) 8.11 (d, J = 8.25 Hz, 1H) 8.13 (d, J = 8.25 Hz, 1H) 8.84 (d, J = 4.58 Hz, 1H) |

TABLE 3-continued

| # | R | Structure | R' | NMR |
|---|---|---|---|---|
| 155 | | (thiophene-CH2-N(Et)-CH2CH2-NH-C(O)-O-) | H | (600 MHz): 0.82 (d, J = 6.42 Hz, 6H) 0.89 (t, J = 7.34 Hz, 3H) 1.04 (t, J = 7.11 Hz, 3H) 1.06-1.28 (m, 17H) 1.31 (s, 3H) 1.50-1.69 (m, 3H) 1.70-1.78 (m, 1H) 1.81-1.88 (m, 1H) 2.13-2.20 (m, 1H) 2.21-2.46 (m, 3H) 2.30 (s, 6H) 2.36 (s, 3H) 2.40 (d, J = 15.13 Hz, 1H) 2.52-2.63 (m, J = 5.96, 5.96 Hz, 3H) 2.58 (t, J = 5.96 Hz, 2H) 2.79-2.83 (m, 1H) 2.86-2.92 (m, 1H) 3.23 (s, 3H) 3.19-3.23 (m, 1H) 3.25-3.30 (m, 2H) 3.34 (s, 3H) 3.37-3.43 (m, 1H) 3.60-3.66 (m, 1H) 3.71 (d, J = 8.25 Hz, 1H) 3.77-3.84 (m, 2H) 4.17-4.21 (m, 1H) 4.36-4.42 (m, 1H) 4.46-4.49 (m, 1H) 4.54 (d, J = 10.09 Hz, 1H) 4.62-4.67 (m, 1H) 4.97 (d, J = 4.13 Hz, 1H) 5.33 (t, J = 4.36 Hz, 1H) 6.87 (d, J = 3.67 Hz, 1H) 6.93 (dd, J = 5.04, 3.21 Hz, 1H) 7.19 (d, J = 5.04 Hz, 1H) |
| 156 | | (furan-CH2-N(Et)-CH2CH2-NH-C(O)-O-) | Et | (600 MHz): 0.78-0.84 (m, 6H) 0.89 (t, J = 7.11 Hz, 3H) 0.95-1.33 (m, 17H) 1.04 (t, J = 7.11 Hz, 3H) 1.30 (s, 3H) 1.50-1.88 (m, 5H) 2.12-2.62 (m, 10H) 2.28 (s, 6H) 2.35 (s, 3H) 2.79-2.93 (m, 2H) 3.11-3.46 (m, 4H) 3.23 (s, 3H) 3.34 (s, 3H) 3.53-3.75 (m, 2H) 4.17-4.20 (m, 1H) 4.34-4.57 (m, 3H) 4.60-4.69 (m, 1H) 4.97 (d, J = 4.58 Hz, 1H) 5.40 (br. s., 1H) 6.14 (d, J = 3.21 Hz, 1H) 6.28-6.31 (m, 1H) 7.34-7.37 (m, 1H) |
| 157 | | (2-methoxyphenyl-CH(Me)-N(Et)-CH2CH2-NH-C(O)-O-) | H | (600 MHz): 0.80-0.86 (m, 6H) 0.92 (t, J = 6.88 Hz, 3H) 1.06-1.27 (m, 14H) 1.10 (d, J = 7.34 Hz, 3H) 1.29 (d, J = 6.88 Hz, 3H) 1.31 (s, 3H) 1.48-1.56 (m, 1H) 1.60 (dd, J = 15.13, 5.04 Hz, 1H) 1.82-1.93 (m, 1H) 2.19-2.44 (m, 5H) 2.24 (s, 6H) 2.32 (s, 3H) 2.46-2.65 (m, 5H) 2.75-2.82 (m, 1H) 2.82-2.90 (m, 1H) 3.15-3.28 (m, 3H) 3.24 (s, 3H) 3.31 (s, 3H) 3.44-3.52 (m, 1H) 3.56-3.67 (m, 1H) 3.72 (s, 3H) 3.81-3.89 (m, 1H) 3.84 (s, 3H) 4.17 (br. s., 1H) 4.31-4.41 (m, 3H) 4.45 (d, J = 5.96 Hz, 1H) 4.52 (d, J = 9.63 Hz, 1H) 4.89 (br. s., 1H) 5.51 (br. s., 1H) 6.86 (d, J = 8.25 Hz, 1H) 6.90 (t, J = 7.34 Hz, 1H) 7.20 (t, J = 7.79 Hz, 1H) 7.27 (d, J = 6.88 Hz, 1H) |
| 158 | | (2-methoxyphenyl-CH(Me)-N(Me)-CH2CH2-NH-C(O)-O-) | H | (600 MHz): 0.80-0.86 (m, 6H) 1.08-1.28 (m, 5H) 1.10 (d, J = 7.34 Hz, 3H) 1.15 (s, 3H) 1.17 (d, J = 6.42 Hz, 3H) 1.19 (d, J = 5.96 Hz, 3H) 1.29 (d, J = 6.42 Hz, 3H) 1.32 (s, 3H) 1.55-1.65 (m, 2H) 1.82-1.95 (m, 1H) 2.11 (s, 3H) 2.19-2.35 (m, 3H) 2.25 (s, 6H) 2.32 (s, 3H) 2.39 (d, J = 14.67 Hz, 1H) 2.42-2.61 (m, 4H) 2.76-2.82 (m, 1H) 2.82-2.92 (m, 1H) 3.16-3.31 (m, 3H) 3.25 (s, 3H) 3.32 (s, 3H) 3.42-3.55 (m, 1H) 3.59-3.66 (m, 1H) 3.72 (d, J = 7.34 Hz, 1H) 3.84 (s, 3H) 3.84-3.90 (m, 1H) 4.14-4.21 (m, 2H) 4.32-4.41 (m, 2H) 4.46 (d, 1H) 4.53 (d, J = 10.09 Hz, 1H) 4.85-4.92 (m, 1H) 5.49 (br. s., 1H) 6.87 (d, J = 7.79 Hz, 1H) 6.91 (t, J = 7.34 Hz, 1H) 7.20 (t, J = 7.11 Hz, 1H) 7.25-7.27 (m, 1H) |

| | | | |
|---|---|---|---|
| 159 | Et | [structure with OMe phenyl, Me, NMe] | (600 MHz): 0.81 (d, J = 6.88 Hz, 6H) 0.89 (t, J = 7.34 Hz, 3H) 1.08-1.25 (m, 14H) 1.12 (d, J = 7.34 Hz, 3H) 1.29 (d, J = 6.88 Hz, 3H) 1.31 (s, 3H) 1.49-1.69 (m, 3H) 1.71-1.78 (m, 1H) 1.81-1.87 (m, 1H) 2.08-2.57 (m, 6H) 2.11 (s, 3H) 2.24 (s, 6H) 2.36 (s, 3H) 2.78-2.84 (m, 1H) 2.87-2.92 (m, 1H) 3.16-3.35 (m, 4H) 3.23 (s, 3H) 3.32 (s, 3H) 3.36-3.46 (m, 2H) 3.55-3.60 (m, 1H) 3.71 (d, J = 8.25 Hz, 1H) 3.84 (s, 3H) 4.14-4.24 (m, 2H) 4.37-4.42 (m, 1H) 4.44 (d, J = 6.88 Hz, 1H) 4.54 (d, J = 9.63 Hz, 1H) 4.60-4.67 (m, 1H) 4.97 (d, J = 4.59 Hz, 1H) 5.54 (br. s., 1H) 6.87 (d, J = 8.25 Hz, 1H) 6.91 (t, J = 7.34 Hz, 1H) 7.18-7.22 (m, 1H) 7.26 (dd, J = 7.57-1.60 Hz, 1H) |
| 160 | Me | [structure with OMe phenyl, Me, NMe] | 939.9 (600 MHz): 0.79-0.88 (m, 6H) 1.09-1.13 (m, 3H) 1.13-1.20 (m, 12H) 1.20-1.33 (m, 2H) 1.20-1.26 (m, 3H) 1.26-1.32 (m, 6H) 1.56-1.63 (m, 1H) 1.64-1.80 (m, 1H) 1.81-1.93 (m, 1H) 2.05-2.31 (m, 3H) 2.24-2.26 (m, 6H) 2.36 (s, 3H) 2.40 (d, J = 15.13 Hz, 1H) 2.43-2.59 (m, 4H) 2.71-2.79 (m, 1H) 2.81-2.93 (m, 1H) 3.17-3.30 (m, 3H) 3.24-3.25 (m, 3H) 3.34-3.48 (m, 1H) 3.56-3.65 (m, 1H) 3.72 (d, J = 8.25 Hz, 1H) 3.84 (s, 3H) 4.11-4.24 (m, 2H) 4.34-4.42 (m, 1H) 4.46 (d, J = 6.42 Hz, 1H) 4.53 (d, J = 9.63 Hz, 1H) 4.84 (s, 1H) 4.91 (d, J = 4.59 Hz, 1H) 5.50 (s, 1H) 6.87 (d, J = 8.25 Hz, 1H) 6.91 (t, J = 7.34 Hz, 1H) 7.20 (t, J = 7.79 Hz, 1H) 7.24-7.28 (m, 1H) |
| 161 | Me | [structure with OMe phenyl, Me, NEt] | 953.9 (600 MHz): 0.80-0.88 (m, 6H) 0.93 (t, J = 6.88 Hz, 3H) 1.11 (d, J = 7.34 Hz, 3H) 1.13 (s, 3H) 1.15 (d, J = 7.34 Hz, 3H) 1.16-1.20 (m, 6H) 1.18-1.27 (m, 2H) 1.20-1.24 (m, 3H) 1.26-1.33 (m, 6H) 1.49-1.56 (m, 1H) 1.60 (dd, J = 15.13, 4.59 Hz, 1H) 1.87 (s, 1H) 2.09-2.18 (m, 1H) 2.19-2.31 (m, 2H) 2.24-2.26 (m, 6H) 2.36 (s, 3H) 2.40 (d, J = 15.13 Hz, 1H) 2.44-2.66 (m, 6H) 2.71-2.79 (m, 1H) 2.82-2.93 (m, 1H) 3.16-3.23 (m, 3H) 3.23-3.26 (m, 3H) 3.32 (s, 3H) 3.36-3.45 (m, 1H) 3.55-3.64 (m, 1H) 3.72 (d, J = 7.79 Hz, 1H) 3.84 (s, 3H) 4.17 (s, 1H) 4.32-4.42 (m, 2H) 4.46 (d, J = 7.34 Hz, 1H) 4.52 (d, J = 9.63 Hz, 1H) 4.85 (s, 1H) 4.91 (d, J = 4.58 Hz, 1H) 5.53 (s, 1H) 6.86 (d, J = 8.25 Hz, 1H) 6.91 (t, J = 7.11 Hz, 1H) 7.20 (t, J = 8.48 Hz, 1H) 7.28 (d, J = 6.88 Hz, 1H) |
| 162 | Et | [structure with pyrazine, Me, NEt] | 939.7 mixture of diastereomers. (600 MHz): 0.77-0.85 (m, 6H) 0.90 (t, J = 7.34 Hz, 3H) 1.01 (t, J = 7.11 Hz, 3H) 1.06-1.26 (m, 17H) 1.30 (s, 3H) 1.42 (q, J = 6.88 Hz, 3H) 1.48-1.58 (m, 2H) 1.60 (dd, J = 15.36, 4.81 Hz, 1H) 1.75 (s, 1H) 1.84 (s, 1H) 2.08-2.60 (m, 8H) 2.23-2.26 (m, 6H) 2.35-2.37 (m, 3H) 2.60-2.71 (m, 2H) 2.77-2.85 (m, 1H) 2.85-2.94 (m, 1H) 3.15-3.26 (m, 1H) 3.22-3.23 (m, 3H) 3.31-3.46 (m, 3H) 3.35 (s, 3H) 3.56-3.67 (m, 1H) 3.71 (d, J = 7.79 Hz, 1H) 4.11 (s, 1H) 4.20 (s, 1H) 4.38 (s, 1H) 4.48 (s, 1H) 4.53 (d, J = 10.09 Hz, 1H) 4.64 (s, 1H) 4.97 (d, J = 4.58 Hz, 1H) 5.55 (s, 1H) 8.42 (d, J = 2.29 Hz, 1H) 8.50-8.65 (m, 2H), and |

TABLE 3-continued

| # | | Structure | | MS | NMR |
|---|---|---|---|---|---|
| 163 | Et | (pyrazine-OMe structure with carbamate) | H | | (600 MHz): 0.77-0.85 (m, 6H) 0.90 (t, J = 7.34 Hz, 3H) 1.04 (t, J = 7.11 Hz, 3H) 1.06-1.26 (m, 17H) 1.30 (s, 3H) 1.42 (d, J = 6.88 Hz, 3H) 1.48-1.58 (m, 2H) 1.60 (dd, J = 15.36, 4.81 Hz, 1H) 1.75 (s, 1H) 1.84 (s, 1H) 2.08-2.60 (m, 8H) 2.23-2.26 (m, 6H) 2.35-2.37 (m, 3H) 2.60-2.71 (m, 2H) 2.77-2.85 (m, 3H) 2.85-2.94 (m, 1H) 3.15-3.26 (m, 1H) 3.22-3.23 (m, 3H) 3.31-3.46 (m, 3H) 3.35 (s, 3H) 3.56-3.67 (m, 1H) 3.71 (d, J = 7.79 Hz, 1H) 4.03-4.09 (m, 1H) 4.20 (s, 1H) 4.38 (s, 1H) 4.48 (s, 1H) 4.53 (d, J = 9.63 Hz, 1H) 4.64 (s, 1H) 4.97 (d, J = 4.58 Hz, 1H) 5.44 (s, 1H) 8.42 (d, J = 2.29 Hz, 1H) 8.50-8.65 (m, 2H) |
| 164 | Et | (pyrazine-OMe structure with carbamate) | H | 969.6 | (500 MHz): 0.78-0.85 (m, 6H) 0.85-0.93 (m, 6H) 1.06-1.35 (m, 2H) 1.11 (d, J = 7.40 Hz, 3H) 1.13-1.20 (m, 12H) 1.29 (s, 3H) 1.32 (d, J = 6.86 Hz, 3H) 1.48-1.65 (m, 3H) 1.73 (s, 1H) 1.84 (s, 1H) 2.09-2.46 (m, 5H) 2.22-2.23 (m, 6H) 2.35-2.36 (m, 3H) 2.47-2.70 (m, 5H) 2.76-2.84 (m, 1H) 2.88 (d, J = 13.44 Hz, 1H) 3.14-3.35 (m, 3H) 3.22-3.23 (m, 3H) 3.33 (s, 3H) 3.36-3.43 (m, 1H) 3.59-3.68 (m, 1H) 3.71 (d, J = 7.95 Hz, 1H) 4.00 (s, 3H) 4.16 (s, 1H) 4.33-4.43 (m, 2H) 4.47 (d, J = 7.13 Hz, 1H) 4.53 (d, J = 9.60 Hz, 1H) 4.64 (s, 1H) 4.96 (d, J = 4.66 Hz, 1H) 6.00 (t, J = 4.80 Hz, 1H) 7.96 (d, J = 2.47 Hz, 1H) 8.14 (d, J = 2.74 Hz, 1H) |
| 165 | Et | (pyrazine-OMe structure with carbamate) | H | 969.8 | (500 MHz): 0.76-0.84 (m, 6H) 0.85-0.93 (m, 6H) 1.05-1.20 (m, 2H) 1.10 (d, J = 7.13 Hz, 3H) 1.11-1.19 (m, 12H) 1.29 (s, 3H) 1.33 (d, J = 6.86 Hz, 3H) 1.45 (d, J = 11.52 Hz, 1H) 1.48-1.56 (m, 1H) 1.59 (dd, J = 15.08, 4.94 Hz, 1H) 1.68-1.78 (m, 1H) 1.78-1.87 (m, 1H) 2.18-2.31 (m, 3H) 2.22-2.23 (m, 6H) 2.35 (s, 3H) 2.35-2.76 (m, 7H) 2.76-2.83 (m, 1H) 2.88 (d, J = 13.99 Hz, 1H) 3.12-3.33 (m, 3H) 3.21-3.22 (m, 3H) 3.30-3.31 (m, 3H) 3.33-3.44 (m, 1H) 3.48-3.57 (m, 1H) 3.69 (d, J = 7.95 Hz, 1H) 3.99 (s, 3H) 4.18 (s, 1H) 4.31-4.40 (m, 2H) 4.42 (d, J = 7.13 Hz, 1H) 4.52 (d, J = 9.87 Hz, 1H) 4.63 (s, 1H) 4.95 (d, J = 4.94 Hz, 1H) 5.81 (t, J = 4.94 Hz, 1H) 7.96 (d, J = 2.74 Hz, 1H) 8.08 (d, J = 2.74 Hz, 1H) |
| | Et | (pyridine structure with carbamate) | H | 938.7 | mixture of diastereomers. (600 MHz): 0.81 (d, J = 6.42 Hz, 6H) 0.89 (t, J = 7.34 Hz, 3H) 1.00 (t, J = 6.19 Hz, 3H) 1.06-1.26 (m, 17H) 1.30 (s, 3H) 1.35-1.38 (m, 3H) 1.50-1.68 (m, 3H) 1.71-1.78 (m, 1H) 1.81-1.87 (m, 1H) 2.11-2.19 (m, 1H) 2.21-2.51 (m, 5H) 2.29 (s, 6H) 2.36 (s, 3H) 2.40 (d, J = 15.13 Hz, 1H) 2.52-2.65 (m, 3H) 2.78-2.84 (m, 1H) 2.88 (d, J = 12.84 Hz, 1H) 3.18-3.25 (m, 2H) 3.22 (s, 3H) 3.34 (s, 3H) 3.35-3.48 (m, 2H) 3.54-3.60 (m, 1H) 3.71 (d, J = 7.79 Hz, 1H) 3.87-3.94 (m, 1H) 4.21-4.25 (m, 1H) 4.36-4.42 (m, 1H) 4.24-4.47 (m, 1H) 4.52-4.56 (m, 1H) 4.60-4.66 (m, 1H) 4.97 (d, J = 4.13 Hz, 1H) 5.12-5.17 (m, 1H) 7.23 (dd, J = 7.57, 4.81 Hz, 1H) 7.63 (dd, J = 7.79, 1.83 Hz, 1H) 8.48 (d, J = 4.58 Hz, 1H) 8.53 (s, 1H), and |

TABLE 3-continued

| | | | | |
|---|---|---|---|---|
| 166 | Et | 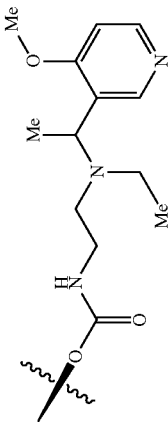 | H | 968.8 | (600 MHz): 0.81 (d, J = 6.42 Hz, 6H) 0.89 (t, J = 7.34 Hz, 3H) 0.98 (t, J = 6.19 Hz, 3H) 1.06-1.26 (m, 17H) 1.30 (s, 3H) 1.35-1.38 (m, 3H) 1.50-1.68 (m, 3H) 1.71-1.78 (m, 1H) 1.81-1.87 (m, 1H) 2.11-2.19 (m, 1H) 2.21-2.51 (m, 5H) 2.29 (s, 6H) 2.36 (s, 3H) 2.40 (d, J = 15.13 Hz, 1H) 2.52-2.65 (m, 3H) 2.78-2.84 (m, 1H) 2.88 (d, J = 12.84 Hz, 1H) 3.18-3.25 (m, 2H) 3.22 (s, 3H) 3.34 (s, 3H) 3.35-3.48 (m, 2H) 3.54-3.60 (m, 1H) 3.71 (d, J = 7.79 Hz, 1H) 3.87-3.94 (m, 1H) 4.21-4.25 (m, 1H) 4.36-4.42 (m, 1H) 4.42-4.47 (m, 1H) 4.52-4.56 (m, 1H) 4.60-4.66 (m, 1H) 4.97 (d, J = 4.13 Hz, 1H) 5.12-5.17 (m, 1H) 7.23 (dd, J = 7.57, 4.81 Hz, 1H) 7.63 (dd, J = 7.79, 1.83 Hz, 1H) 8.48 (d, J = 4.58 Hz, 1H) 8.53 (s, 1H)
mixture of diastereomers. (600 MHz): 0.81 (d, J = 6.88 Hz, 6H) 0.90 (t, J = 7.11 Hz, 3H) 0.89-0.96 (m, 3H) 1.05-1.26 (m, 17H) 1.29-1.32 (m, 3H) 1.33-1.36 (m, 3H) 1.50-1.87 (m, 5H) 2.14-2.18 (m, 1H) 2.23-2.68 (m, 9H) 2.30 (s, 6H) 2.36 (s, 3H) 2.78-2.84 (m, 1H) 2.87-2.93 (m, 1H) 3.18-3.49 (m, 4H) 3.22 (s, 3H) 3.32 (s, 3H) 3.51-3.58 (m, 1H) 3.69-3.73 (m, 1H) 3.90 (s, 3H) 4.20-4.25 (m, 1H) 4.30-4.34 (m, 1H) 4.36-4.40 (m, 1H) 4.41-4.45 (m, 1H) 4.52-4.56 (m, 1H) 4.60-4.66 (m, 1H) 4.97 (d, J = 4.58 Hz, 1H) 5.46-5.51 (m, 1H) 6.78 (d, J = 5.50 Hz, 1H) 8.38-8.41 (m, 2H), and (600 MHz): (d, J = 6.88 Hz, 6H) 0.90 (t, J = 7.11 Hz, 3H) 0.89-0.96 (m, 3H) 1.05-1.26 (m, 17H) 1.29-1.32 (m, 3H) 1.33-1.36 (m, 3H) 1.50-1.87 (m, 5H) 2.14-2.18 (m, 1H) 2.23-2.68 (m, 9H) 2.28 (s, 6H) 2.36 (s, 3H) 2.78-2.84 (m, 1H) 2.87-2.93 (m, 1H) 3.18-3.49 (m, 4H) 3.22 (s, 3H) 3.31 (s, 3H) 3.51-3.58 (m, 1H) 3.69-3.73 (m, 1H) 3.90 (s, 3H) 4.20-4.25 (m, 1H) 4.30-4.34 (m, 1H) 4.36-4.40 (m, 1H) 4.41-4.45 (m, 1H) 4.52-4.56 (m, 1H) 4.60-4.66 (m, 1H) 4.97 (d, J = 4.58 Hz, 1H) 5.46-5.51 (m, 1H) 6.78 (d, J = 5.50 Hz, 1H) 8.38-8.41 (m, 2H) |
| 167 | Et | | OH | Me | 733.6 | (600 MHz): 0.75-0.81 (m, 6H) 0.86 (t, J = 7.34 Hz, 3H) 1.03 (s, 3H) 1.07 (d, J = 7.34 Hz, 3H) 1.08-1.23 (m, 8H) 1.11 (s, 3H) 1.17 (d, J = 5.96 Hz, 3H) 1.28 (s, 3H) 1.44-1.68 (m, 3H) 1.71 (dd, J = 15.36, 5.27 Hz, 1H) 1.77-1.85 (m, 1H) 2.05 (d, J = 15.59 Hz, 1H) 2.09-2.16 (m, 1H) 2.15-2.25 (m, 2H) 2.26 (s, 6H) 2.32 (s, 3H) 2.36-2.43 (m, 1H) 2.43-2.52 (m, 1H) 2.73-2.80 (m, 1H) 2.81-2.88 (m, 1H) 3.14-3.20 (m, 1H) 3.20 (s, 3H) 3.25 (s, 3H) 3.35-3.42 (m, 1H) 3.42-3.49 (m, 1H) 3.64 (d, J = 7.79 Hz, 1H) 4.12-4.18 (m, 1H) 4.37 (d, J = 7.34 Hz, 1H) 4.47 (q, J = 6.42 Hz, 1H) 4.58-4.64 (m, 1H) 4.93 (d, J = 5.04 Hz, 1H) |

TABLE 3-continued

| | | | | |
|---|---|---|---|---|
| 168 | Et | [structure] | OH | (600 MHz): 0.78-0.83 (m, 6H) 0.87-0.94 (m, 3H) 0.96-1.34 (m, 28H) 1.36-1.70 (m, 7H) 1.80-1.91 (m, 2H) 2.02 (d, J = 15.13 Hz, 1H) 2.12-2.20 (m, 1H) 2.22-2.29 (m, 2H) 2.28 (s, 6H) 2.36 (s, 3H) 2.40-2.68 (m, 5H) 2.73-2.81 (m, 1H) 2.83-2.91 (m, 1H) 2.94-3.02 (m, 1H) 3.18-3.21 (m, 1H) 3.22 (s, 3H) 3.27 (s, 3H) 3.32-3.38 (m, 1H) 3.47-3.56 (m, 1H) 3.71 (d, J = 8.25 Hz, 1H) 3.81 (s, 3H) 4.16-4.34 (m, 2H) 4.37 (d, J = 7.34 Hz, 1H) 4.39-4.47 (m, 1H) 4.56-4.67 (m, 1H) 4.96 (d, J = 4.58 Hz, 1H) 6.86 (d, J = 8.71 Hz, 1H) 6.94 (t, J = 5.96 Hz, 1H) 7.19 (t, 1H) 7.44-7.49 (m, 1H) |
| 169 | Et | [structure] | OH | 953.7 (600 MHz): 0.79 (d, J = 6.88 Hz, 6H) 0.87 (t, 3H) 0.92 (t, J = 7.11 Hz, 3H) 0.95-0.99 (m, 3H) 1.03-1.24 (m, 14H) 1.25 (d, J = 6.88 Hz, 3H) 1.29 (s, 3H) 1.35-1.83 (m, 8H) 1.86 (dd, J = 15.13, 5.04 Hz, 1H) 2.02 (d, J = 14.67 Hz, 1H) 2.10-2.27 (m, 3H) 2.25 (s, 6H) 2.34 (s, 3H) 2.36-2.65 (m, 6H) 2.71-2.80 (m, 1H) 2.88 (d, J = 14.67 Hz, 1H) 3.13-3.20 (m, 1H) 3.21 (s, 3H) 3.25 (s, 3H) 3.33-3.48 (m, 2H) 3.69 (d, J = 8.25 Hz, 1H) 3.78 (s, 3H) 4.13-4.44 (m, 4H) 4.54-4.65 (m, 1H) 4.95 (d, J = 5.04 Hz, 1H) 6.82 (d, J = 8.25 Hz, 1H) 6.90 (t, J = 7.57 Hz, 1H) 7.17 (t, 1H) 7.29 (d, J = 7.79 Hz, 1H) |
| 170 | Et | [structure] | OH | 981.9 (600 MHz): 0.81 (d, J = 6.88 Hz, 3H) 0.84-0.93 (m, 6H) 0.97 (t, J = 6.65 Hz, 3H) 1.04-1.33 (m, 12H) 1.09 (d, J = 7.34 Hz, 3H) 1.15 (d, J = 7.34 Hz, 3H) 1.19 (d, J = 6.42 Hz, 3H) 1.24 (s, 3H) 1.31 (s, 3H) 1.34-1.83 (m, 8H) 1.86 (dd, J = 14.90, 5.27 Hz, 1H) 2.03 (d, J = 14.67 Hz, 1H) 2.10-2.21 (m, 1H) 2.23-2.29 (m, 2H) 2.27 (s, 6H) 2.36 (s, 3H) 2.38-2.56 (m, 5H) 2.59-2.67 (m, 1H) 2.73-2.81 (m, 1H) 2.89 (d, J = 11.46 Hz, 1H) 3.17-3.23 (m, 1H) 3.22 (s, 3H) 3.27 (s, 3H) 3.36-3.44 (m, 1H) 3.51-3.57 (m, 1H) 3.70 (d, J = 7.79 Hz, 1H) 3.80 (s, 3H) 4.13-4.40 (m, 2H) 4.25-4.31 (m, 1H) 4.36 (d, J = 7.34 Hz, 1H) 4.58-4.69 (m, 1H) 4.96 (d, J = 5.04 Hz, 1H) 6.84 (d, J = 7.79 Hz, 1H) 6.92 (t, J = 7.57 Hz, 1H) 7.18 (t, J = 7.11 Hz, 1H) 7.39 (d, J = 5.96 Hz, 1H) |
| 171 | Et | [structure] | OH | 995.9 FAB MASS (600 MHz): 0.77-0.90 (m, 9H) 0.93-1.36 (m, 23H) 1.31 (s, 3H) 1.36-1.88 (m, 7H) 2.05-2.17 (m, 2H) 2.25 (s, 6H) 2.23-2.54 (m, 8H) 2.37 (s, 3H) 2.58-2.66 (m, 1H) 2.69-2.75 (m, 1H) 2.79-2.91 (m, 2H) 3.13-3.21 (m, 1H) 3.20 (s, 3H) 3.30 (s, 1H) 3.30 (s, 3H) 3.37-3.45 (m, 1H) 3.55 (dd, J = 14.44, 6.19 Hz, 1H) 3.67 (d, J = 8.71 Hz, 1H) 3.76-3.82 (m, 1H) 3.80 (s, 3H) 4.29-4.37 (m, 3H) 4.55-4.65 (m, 2H) 4.98 (d, J = 4.59 Hz, 1H) 6.51 (br s, 1H) 6.84 (d, J = 8.25 Hz, 1H) 6.92 (t, J = 7.57 Hz, 1H) 7.18 (t, J = 7.34 Hz, 1H) 7.33-7.41 (m, 1H) |

Example 126

(1) The compound obtained in Example 7, (3) (5.78 g) was dissolved in ethanol (75 ml), the solution was added with ice-cooled 1 N hydrochloric acid (30 ml), and the mixture was stirred for 30 minutes. The reaction mixture was neutralized with 10% aqueous sodium hydroxide, and then added with ethyl acetate, and the layers were separated. The organic layer was washed with saturated brine, then dried over anhydrous magnesium sulfate and filtered. The filtrate was concentrated under reduced pressure, and the resulting residue was purified by silica gel column chromatography (hexane:acetone=20:1 to 10:1) to obtain a 4"-hydroxy compound (3.97 g).

(2) The compound obtained in (1) mentioned above (3.00 g) was dissolved in tetrahydrofuran (20 ml) and dimethylformamide (10 ml), the solution was added with N,N'-carbonyldiimidazole (1.54 g) and added with sodium hydride (228 mg) under ice cooling, and the mixture was stirred for 1 hour. The mixture was successively added with distilled water, ethyl acetate and saturated aqueous ammonium chloride, the layers were separated, and the organic layer was successively washed 3 times with distilled water, then dried over anhydrous magnesium sulfate and filtered. The filtrate was concentrated under reduced pressure, and the resulting residue was purified by silica gel column chromatography (hexane:acetone:triethylamine=50:10:0.2) to obtain a 4"-O-imidazolylcarbonyl compound (3.11 g).

(3) The compound obtained in (2) mentioned above (530 mg) was dissolved in tetrahydrofuran (3 ml), and the solution was added with the compound obtained in Reference Example 54 (170 mg). Then, the reaction mixture was concentrated to about 1 ml under reduced pressure. The reaction mixture was left for 2 days, and then concentrated under reduced pressure, and the resulting residue was purified by silica gel column chromatography (chloroform:methanol:28% aqueous ammonia=30:1:0.1) to obtain a carbamate compound (621 mg).

(4) By using the compound obtained in (3) mentioned above (621 mg) as a starting material, the compound shown in Table 3 (393 mg) was obtained in the same manner as that of Example 7, (4).

Example 127

By using the compound obtained in Example 126 (1) (0.28 g) as a starting material, the compound shown in Table 3 (0.18 g) was obtained in the same manners as those of Example 113, (2) and Example 7, (4).

Example 128

The compound obtained in Example 127 (0.17 g) was dissolved in methanol (5 ml), the solution was added with hydroxylamine hydrochloride (49 mg), and the mixture was stirred at room temperature for 14 hours. The reaction mixture was concentrated under reduced pressure, and the resulting residue was added with chloroform and 0.1 N aqueous sodium hydroxide. The layers were separated, and the organic layer was washed with saturated brine, then dried over anhydrous magnesium sulfate and filtered. The filtrate was concentrated under reduced pressure to obtain the compound shown in Table 3 (0.177 g).

Example 129

The compound obtained in Example 128 (0.15 g) was dissolved in ethanol (15 ml), the solution was added with Raney nickel (0.7 g), and the mixture was stirred at room temperature for 31 hours under a hydrogen atmosphere of 3.5 kgt/cm$^2$. The reaction mixture was filtered through Celite, and then the filtrate was concentrated under reduced pressure. The resulting residue was purified by silica gel column chromatography (chloroform:methanol:28% aqueous ammonia=9:1:0.1) and preparative thin layer chromatography (chloroform:methanol:28% aqueous ammonia=9:1:0.1) to obtain the compound shown in Table 3 (2 mg).

Example 130

(1) 6-[2-(2-Carboxyethoxy)ethoxy]-7-chloro-1-cyclopropyl-4-oxo-1,4-dihydroquinoline-3-carboxylic acid (84 mg) obtained by the method described in the patent document (WO04/101585) was dissolved in dichloromethane (2 ml), the solution was added with 1-ethyl-3-(3-dimethylaminopropyl)carbodiimide hydrochloride (61 mg) under ice cooling, and the mixture was stirred for 30 minutes. The mixture was further added with the compound obtained in Example 126, (1) (100 mg) and 4-dimethylaminopyridine (130 mg), and the mixture was stirred at room temperature for 18 hours. The reaction mixture was added with ethyl acetate and saturated aqueous sodium hydrogencarbonate, and the layers were separated. The organic layer was washed successively with saturated aqueous ammonium chloride and saturated brine, and then the organic layer was dried over anhydrous magnesium sulfate and filtered. The filtrate was concentrated under reduced pressure, and the resulting residue was purified by column chromatography (chloroform:methanol:28% aqueous ammonia=20:1:0.1) to obtain a coupling compound (38.9 mg).

(2) By using the compound obtained in (1) mentioned above (38.9 mg) as a starting material, the compound shown in Table 3 (7.1 mg) was obtained in the same manner as that of Example 7, (4).

Example 131

(1) 6-{[2-(2-Carboxyethoxy)ethyl]amino}-7-chloro-1-cyclopropyl-4-oxo-1,4-dihydroquinoline-3-carboxylic acid (84 mg) obtained by the method described in the patent document (WO04/101585) was dissolved in dichloromethane (1 ml), the solution was added with triethylamine (19 mg) and pivaloyl chloride (23 mg) under ice cooling, and the mixture was stirred for 30 minutes. The mixture Was further added with the compound obtained in Example 126, (1) (100 mg) and 4-dimethylaminopyridine (9.5 mg), and the mixture was stirred at room temperature for 18 hours. The reaction mixture was purified by column chromatography (chloroform:methanol:28% aqueous ammonia=20:1:0.1) to obtain a coupling compound (97 mg).

(2) By using the compound obtained in (1) mentioned above (97 mg) as a starting material, the compound shown in Table 3 (10.9 mg) was obtained in the same manner as that of Example 7, (4).

Example 132

(1) By using the compound obtained in Example 126, (2) (650 mg) and ethylenediamine (78.1 µl) as starting materials, an amine compound (420 mg) was obtained in the same manner as those of Example 126, (3) and Example 7, (4).

(2) By using the compound obtained in (1) mentioned above (100 mg) and 2-methoxybenzaldehyde (17 mg) as starting materials, an N-benzyl compound (70 mg) was obtained in the same manner as that of Example 7, (2).

(3) By using the compound obtained in (2) mentioned above (10 mg) and acetaldehyde (3.0 μl) as starting materials, the compound shown in Table 3 (5.8 mg) was obtained in the same manner as that of Example 7, (2).

Example 133

(1) The compound obtained in Example 126, (1) (100 mg) was dissolved in toluene (10 ml), the solution was added with triethylamine (200 μl) and 3-chloropropenyl chloride (50 μl), and the mixture was stirred at room temperature for 20 minutes. The reaction mixture was added with ethyl acetate and saturated aqueous sodium hydrogencarbonate, the layers were separated, and the organic layer was dried over anhydrous magnesium sulfate and filtered. The filtrate was concentrated under reduced pressure, and the resulting residue was purified by column chromatography (hexane:acetone:triethylamine=50:1:0.1) to obtain a coupling compound (125 mg). By using the resulting coupling compound (125 mg) as a starting material, a 4"-O-vinyl ester compound (78.7 mg) was obtained in the same manner as that of Example 7, (4).

(2) The compound obtained in (1) mentioned above (32 mg) was dissolved in acetonitrile (1 ml), the solution was added with (1S)-1-(2-methoxyphenyl)ethanamine (63 mg) obtained by the method described in the patent document (Japanese Patent Unexamined Publication No. 54-154724) and diisopropylethylamine (50 μl), and the mixture was stirred at 100° C. for 3 hours in a sealed tube. The reaction mixture was concentrated under reduced pressure, and the resulting residue was purified by silica gel column chromatography (chloroform:methanol:28% aqueous ammonia=20:1:0.1) to obtain the compound shown in Table 3 (37 mg).

Example 134

The compound obtained in Example 133 (37 mg) was dissolved in chloroform (5 ml), and the solution was added with acetaldehyde (11 μl) and sodium triacetoxyborohydride (13 mg), and the mixture was stirred at room temperature for 1 hour. The reaction mixture was added with chloroform and saturated aqueous sodium hydrogencarbonate, the layers were separated, and the organic layer was dried over anhydrous magnesium sulfate and filtered. The filtrate was concentrated under reduced pressure, and the resulting residue was purified by column chromatography (chloroform:methanol:28% aqueous ammonia=10:1:0.1) to obtain the compound shown in Table 3 (2.8 mg).

Example 135

The compound obtained in Example 126, (1) (50 mg) was dissolved in toluene (1 ml), the solution was added with the compound obtained in Reference Example 55 (30 mg), 1-ethyl-3-(3-dimethylaminopropyl)carbodiimide hydrochloride (30 mg) and 4-dimethylaminopyridine (65 mg), and the mixture was stirred at 80° C. for 5 hours. The reaction mixture was added with ethyl acetate and saturated aqueous ammonium chloride, the layers were separated, and the organic layer was dried over anhydrous magnesium sulfate and filtered. The filtrate was concentrated under reduced pressure, and the resulting residue was purified by column chromatography (hexane:acetone:triethylamine=50:1:0.1) to obtain a coupling compound (11.3 mg). By using the resulting coupling compound (11.3 mg) as a starting material, the compound shown in Table 3 (2.5 mg) was obtained in the same manner as that of Example 7, (4).

Example 136

By using the compound obtained in Example 126, (1) (50 mg) and the compound obtained in Reference Example 56 (31 mg) as starting materials, the compound shown in Table 3 (17.8 mg) was obtained in the same manner as that of Example 135.

Example 137

By using the compound obtained in Example 132, (1) (20 mg) and 2-methoxybenzaldehyde (3.4 mg) as starting materials, the compound shown in Table 3 (10 mg) was obtained in the same manner as that of Example 7, (2).

Example 138

By using the compound obtained in Example 132, (1) (20 mg) and 2-methoxybenzaldehyde (3.4 mg) as starting materials, and then using 37% aqueous formaldehyde (10.1 mg) as a starting material, the compound shown in Table 3 (5.3 mg) was obtained in the same manner as that of Example 7, (2).

Example 139

By using the compound obtained in Example 132, (1) (20 mg) and 2-methoxybenzaldehyde (3.4 mg) as starting materials, the compound shown in Table 3 (19.1 mg) was obtained in the same manner as that of Example 7, (2).

Example 140

By using the compound obtained in Example 126, (2) (20 mg) and the compound obtained in Reference Example 57 (9.1 mg) as starting materials, the compound shown in Table 3 (10.1 mg) was obtained in the same manners as those of Example 126, (3) and Example 7, (4).

Example 141

By using the compound obtained in Example 126, (2) (20 mg) and the compound obtained in Reference Example 58 (9.6 mg) as starting materials, the compound shown in Table 3 (13.9 mg) was obtained in the same manners as those of Example 126, (3) and Example 7, (4).

Example 142

By using the compound obtained in Example 126, (1) (100 mg) and the compound obtained in Reference Example 59 (84 mg) as starting materials, the compound shown in Table 3 (2.6 mg) was obtained in the same manner as that of Example 135.

Example 143

(1) The compound obtained in Example 126, (2) (500 mg) was dissolved in tetrahydrofuran (2 ml), the solution was added with ethylenediamine (64 μl), and the mixture was stirred at room temperature for 2 days. The reaction mixture was concentrated under reduced pressure, and the resulting residue was purified by column chromatography (hexane:acetone:triethylamine=10:1:0.1) to obtain an amine compound (350 mg).

(2) The compound obtained in (1) mentioned above (50 mg) was dissolved in chloroform (1 ml), the solution was added with triethylamine (24 mg) and 2-methoxybenzoyl chloride (12 mg), and the mixture was stirred at room temperature for 1 hour. The reaction mixture was purified by column chromatography (NH-form) to obtain a coupling compound (56.4 mg). By using the resulting coupling compound (56.4 mg) as a starting material, the compound shown in Table 3 (32.9 mg) was obtained in the same manner as that of Example 7, (4).

Example 144

By using the compound obtained in Example 143, (1) (50 mg) and 2-methoxybenzenesulfonyl chloride (15 mg) as starting materials, the compound shown in Table 3 (40.2 mg) was obtained in the same manner as that of Example 143, (2).

Example 145

By using the compound obtained in Example 143, (1) (50 mg) and 2-methoxyphenyl isocyanate (11 mg) as starting materials, the compound shown in Table 3 (36.0 mg) was obtained in the same manner as that of Example 143, (2).

Example 146

By using the compound obtained in Example 126, (2) (50 mg) and the compound obtained in Reference Example 60 (17.3 mg) as starting materials, the compound shown in Table 3 (21.1 mg) was obtained in the same manners as those of Example 126, (3) and Example 7, (4).

Example 147

By using the compound obtained in Example 126, (2) (667 mg) and the compound obtained in Reference Example 61 (173 mg) as starting materials, the compound shown in Table 3 (463 mg) was obtained in the same manners as those of Example 126, (3) and Example 7, (4).

Example 148

(1) The compound obtained in Example 147 (450 mg) was dissolved in methanol (10 ml), the solution was added with 20% palladium hydroxide-carbon (300 mg), and the mixture was stirred at room temperature for 2 days under a hydrogen atmosphere of 1 atm. The reaction mixture was filtered, and then the filtrate was concentrated under reduced pressure to obtain a debenzylated compound (429 mg).

(2) The compound obtained in (1) mentioned above (30 mg) was dissolved in chloroform, the solution was added with 2-pyridinecarboxaldehyde (19 mg) and sodium triacetoxyborohydride (30 mg), and the mixture was stirred at room temperature for 18 hours. The reaction mixture was added with chloroform and saturated aqueous sodium hydrogencarbonate, the layers were separated, and the organic layer was dried over anhydrous magnesium sulfate and filtered. The filtrate was concentrated under reduced pressure, and the resulting residue was purified by column chromatography (chloroform:methanol:28% aqueous ammonia=20:1:0.1) to obtain the compound shown in Table 3 (20.4 mg).

Example 149

By using the compound obtained in Example 148, (1) (30 mg) and 3-pyridinecarboxaldehyde as starting materials, the compound shown in Table 3 (12.9 mg) was obtained in the same manner as that of Example 148, (2).

Example 150

By using the compound obtained in Example 148, (1) (30 mg) and 4-pyridinecarboxaldehyde as starting materials, the compound shown in Table 3 (19.8 mg) was obtained in the same manner as that of Example 148, (2).

Example 151

By using the compound obtained in Example 148, (1) (30 mg) and 2-naphthaldehyde as starting materials, the compound shown in Table 3 (4.5 mg) was obtained in the same manner as that of Example 148, (2).

Example 152

By using the compound obtained in Example 148, (1) (30 mg) and 1-naphthaldehyde as starting materials, the compound shown in Table 3 (4.0 mg) was obtained in the same manner as that of Example 148, (2).

Example 153

By using the compound obtained in Example 148, (1) (30 mg) and 3-quinolinecarboxaldehyde as starting materials, the compound shown in Table 3 (10.7 mg) was obtained in the same manner as that of Example 148, (2).

Example 154

By using the compound obtained in Example 148, (1) (30 mg) and 4-quinolinecarboxaldehyde as starting materials, the compound shown in Table 3 (22.5 mg) was obtained in the same manner as that of Example 148, (2).

Example 155

By using the compound obtained in Example 148, (1) (30 mg) and 2-thiophenecarboxaldehyde as starting materials, the compound shown in Table 3 (2.8 mg) was obtained in the same manner as that of Example 148, (2).

Example 156

By using the compound obtained in Example 148, (1) (30 mg) and furfural as starting materials, the compound shown in Table 3 (10.1 mg) was obtained in the same manner as that of Example 148, (2).

Example 157

(1) By using the compound obtained in Example 8, (1) (1.39 g) as a starting material, a cyclized compound (708 mg) was obtained in the same manners as those of Example 7, (2) and (3).

(2) By using the compound obtained in (1) mentioned above (700 mg) as a starting material, 4"-O-imidazolylcarbonyl compound (329 mg) was obtained in the same manners as those of Example 126, (1) and (2).

223

(3) By using the compound obtained in (2) mentioned above (50 mg) and the compound obtained in Reference Example 54 as starting materials, the compound shown in Table 3 (21.0 mg) was obtained in the same manners as those of Example 126, (3) and Example 7, (4).

Example 158

By using the compound obtained in Example 157, (2) (50 mg) and the compound obtained in Reference Example 62 as starting materials, the compound shown in Table 3 (24.0 mg) was obtained in the same manners as those of Example 126, (3) and Example 7, (4).

Example 159

By using the compound obtained in Example 126, (2) (50 mg) and the compound obtained in Reference Example 62 (15 mg) as starting materials, the compound shown in Table 3 (39.2 mg) was obtained in the same manners as those of Example 126, (3) and Example 7, (4).

Example 160

(1) By using the compound obtained in Example 1 (1.14 g) and (R)-(+)-propylene oxide (0.2 g) as starting materials, a cyclized compound (189 mg) was obtained in the same manners as those of Example 7, (1), (2) and (3).
(2) By using the compound obtained in (1) mentioned above (60 mg) as starting materials, a 4"-O-imidazolylcarbonyl compound (40.5 mg) was obtained in the same manners as those of Example 126, (1) and (2).
(3) By using the compound obtained in (2) mentioned above (20 mg) and the compound obtained in Reference Example 62 (6.1 mg) as starting materials, the compound shown in Table 3 (11.1 mg) was obtained in the same manners as those of Example 126, (3) and Example 7, (4).

Example 161

By using the compound obtained in Example 160, (2) (20 mg) and the compound obtained in Reference Example 54 (6.5 mg) as starting materials, the compound shown in Table 3 (10.5 mg) was obtained in the same manners as those of Example 126, (3) and Example 7, (4).

Example 162

By using the compound obtained in Example 126, (2) (40 mg) and the compound obtained in Reference Example 63 (19.1 mg) as starting materials, the compound shown in Table 3 (29 mg) was obtained in the same manners as those of Example 126, (3) and Example 7, (4).

Example 163

By using the compound obtained in Example 126, (2) (90.6 mg) and the compound obtained in Reference Example 64 (50 mg) as starting materials, the compound shown in Table 3 (21 mg) was obtained in the same manners as those of Example 126, (3) and Example 7, (4).

Example 164

By using the compound obtained in Example 126, (2) (90.6 mg) and the compound obtained in Reference Example 64 (50 mg) as starting materials, the compound shown in Table 3 (35 mg) was obtained in the same manners as those of Example 126, (3) and Example 7, (4).

Example 165

By using the compound obtained in Example 126, (2) (100 mg) and the compound obtained in Reference Example 65 (37 mg) as starting materials, the compound shown in Table 3 (32.1 mg) as a mixture of diastereomers was obtained in the same manners as those of Example 126, (3) and Example 7, (4).

Example 166

By using the compound obtained in Example 126, (2) (100 mg) and the compound obtained in Reference Example 66 (43 mg) as starting materials, the compound shown in Table 3 (46.8 mg) as a mixture of diastereomers was obtained in the same manners as those of Example 126, (3) and Example 7, (4).

Example 167

(1) The compound obtained in Example 126, (1) (1.79 g) was dissolved in chloroform (purity: 99.5% or higher, 19 ml), the solution was successively added with 1-ethyl-3-(3-dimethylaminopropyl)carbodiimide hydrochloride (1.09 g), dimethyl sulfoxide (1.34 ml) and pyridinium trifluoroacetate (1.09 g), and the mixture was stirred at room temperature for 2 hours. The reaction mixture was added with saturated aqueous sodium hydrogencarbonate and chloroform, the layers were separated, and the organic layer was dried over anhydrous magnesium sulfate and filtered. The filtrate was concentrated under reduced pressure, and the resulting residue was purified by silica gel column chromatography (chloroform:methanol:28% aqueous ammonia=50:1:0.1 to 30:1:0.1) to obtain a 4"-ketone compound (1.52 g).
(2) The compound obtained in (1) mentioned above (15 mg) was dissolved in dichloromethane (3 ml), the solution was added with a 0.84 M solution of methylmagnesium iodide in ether (140 µl) on a dry ice-acetone bath, and the mixture was stirred at the same temperature for 2 hours. The mixture was further stirred at −20° C. for 20 minutes. The reaction mixture was added with saturated aqueous ammonium chloride and chloroform, and the layers were separated. The organic layer was dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) to obtain a 4"-methyl adduct compound (7 mg).
(3) By using the compound obtained in (2) mentioned above (7 mg) as a starting material, the compound shown in Table 3 (5 mg) was obtained in the same manner as that of Example 7, (4).

Example 168

(1) Trimethylsulfoxonium iodide (304 mg) was dissolved in tetrahydrofuran (16 ml), the solution was added with sodium hydride (33 mg) on an ice bath, and the mixture was stirred at the same temperature for 2 hours. Then, the mixture was added with a solution (16 ml) of the compound obtained in Example 167, (1) (0.87 g) in dimethyl sulfoxide, and the mixture was stirred at room temperature for 2 hours. The reaction mixture was added with saturated aqueous ammonium chloride, the mixture was extracted with diethyl ether, and the organic layer was washed with saturated brine, then dried over anhydrous magnesium sulfate and filtered. The filtrate was concentrated under reduced pressure, and the resulting residue was purified by silica gel column chromatography (chloroform:methanol: 28% aqueous ammonia=50:1:0.1) to obtain an epoxy compound (0.76 g).

(2) The compound obtained in (1) mentioned above (21 mg) was dissolved in ethanol (1 ml), the solution was added with the compound obtained in Reference Example 57 (52 mg) and potassium iodide (37 mg), and the mixture was stirred at 90° C. for 20 hours. The reaction mixture was concentrated under reduced pressure, and the resulting residue was added with saturated brine and chloroform, and the layers were separated. The organic layer was dried over anhydrous magnesium sulfate and filtered. The filtrate was concentrated under reduced pressure, and the resulting residue was purified by column chromatography (chloroform:methanol:28% aqueous ammonia=50:1:0.1 to 30:1:0.1) to obtain an amine compound (35 mg).

(3) By using the compound obtained in (2) mentioned above (35 mg) as a starting material, the compound shown in Table 3 (20 mg) was obtained in the same manner as that of Example 7, (4).

Example 169

(1) By using the compound obtained in Example 168, (1) (73 mg) and the compound obtained in Reference Example 54 as starting materials, an amine compound (40 mg) was obtained in the same manner as that of Example 168, (2).

(2) The compound obtained in (1) mentioned above (40 mg) and ammonium chloride (29 mg) were dissolved in a mixed solvent of methanol-distilled water (2:1, 3 ml), and the solution was stirred at 90° C. for 60 hours. The reaction mixture was added with saturated aqueous sodium hydrogencarbonate and chloroform, the layers were separated, and the organic layer was dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) to obtain the compound shown in Table 3 (10 mg).

Example 170

By using the compound obtained in Example 168, (1) (55 mg) and the compound obtained in Reference Example 58 as starting materials, the compound shown in Table 3 (24 mg) was obtained in the same manners as those of Example 168, (2) and Example 7, (4).

Example 171

(1) The compound obtained in Example 168, (1) (0.43 g) was dissolved in a mixed solvent of methanol-distilled water (2:1, 4.5 ml), the solution was added with sodium azide (0.29 g) and ammonium chloride (0.19 g), and the mixture was stirred at 90° C. for 64 hours. The reaction mixture was added with distilled water and chloroform, and the layers were separated. The organic layer was dried over anhydrous magnesium sulfate and filtered. The filtrate was concentrated under reduced pressure, and the resulting residue was purified by silica gel column chromatography (chloroform:methanol:28% aqueous ammonia=50:1:0.1 to 20:1:0.1) to obtain an azide compound (0.27 g).

(2) The compound obtained in (1) mentioned above (127 mg) was dissolved in tetrahydrofuran (5 ml), the solution was added with a 1 M solution of trimethylphosphine in tetrahydrofuran (1 ml), and the mixture was stirred at room temperature for 5 hours. Then, the mixture was added with distilled water (10 ml), and the mixture was further stirred at room temperature for 60 hours, and extracted with chloroform. The organic layer was dried over anhydrous magnesium sulfate and filtered. The filtrate was concentrated under reduced pressure, and the resulting residue was purified by column chromatography (chloroform:methanol:28% aqueous ammonia=10:1:0.1) to obtain an amine compound (83 mg).

(3) The compound obtained in (2) mentioned above (24 mg) was dissolved in toluene (5 ml), the solution was added with the compound obtained in Reference Example 59 (26 mg), 1-ethyl-3-(3-dimethylaminopropyl)carbodiimide hydrochloride (19 mg) and 1-hydroxybenzotriazole monohydrate (5 mg), and the mixture was stirred at room temperature for 16 hours. The reaction mixture was concentrated under reduced pressure, then the resulting residue was added with distilled water and chloroform, and the layers were separated. The organic layer was dried over anhydrous magnesium sulfate and filtered. The filtrate was concentrated under reduced pressure, the resulting residue was dissolved in methanol (100 ml), and the solution was stirred at room temperature for 16 hours and further stirred at 80° C. for 2 hours. The reaction mixture was concentrated under reduced pressure, and the resulting residue was purified by column chromatography (chloroform:methanol:28% aqueous ammonia=20:1:0.1 to 10:1:0.1) to obtain the compound shown in Table 3 (15 mg).

Example 172

Synthesis of the Compound Represented by the Formula (F)

[Formula 21]

formula (F)

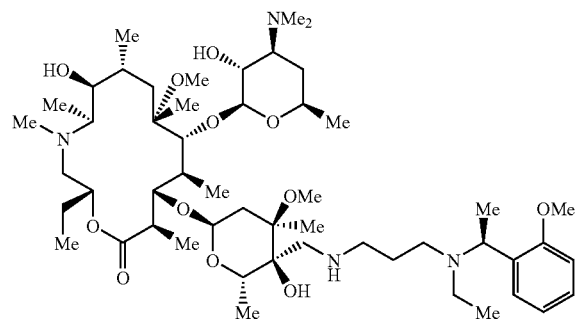

(1) Trimethylsulfonium tetrafluoroborate (73 mg) was dissolved in tetrahydrofuran (4 ml), the solution was slowly added with a 0.5 M solution of potassium bistrimethylsilylamide in toluene (0.8 ml) on a sodium chloride-ice bath under a nitrogen atmosphere, and the mixture was stirred for 2 hours at the same temperature on the ice bath. Then, the mixture was added with a solution of the compound obtained in Example 167, (1) (100 mg) in ethylene glycol dimethyl ether (1 ml) on a dry ice-acetone bath, and the mixture was stirred at the same temperature for 2 hours.

The reaction mixture was added with saturated aqueous ammonium chloride and chloroform, the layers were separated, and the organic layer was washed with saturated brine, then dried over anhydrous magnesium sulfate and filtered. The filtrate was concentrated under reduced pressure, and the resulting residue was purified by silica gel column chromatography (hexane:acetone:triethylamine=50:5:0.1) to obtain an epoxy compound (95 mg).

(2) By using the compound obtained in (1) mentioned above (40 mg) as a starting material, the title compound (9 mg) was obtained in the same manners as those of Example 168, (2) and Example 7, (4).

$^1$H-NMR (600 MHz, CDCl$_3$) δ (ppm): 0.77-0.83 (m, 6H), 0.89 (t, J=7.34 Hz, 3H), 0.98 (t, J=6.65 Hz, 3H), 1.04-1.38 (m, 11H), 1.09 (d, J=10.09 Hz, 3H), 1.15 (d, J=7.34 Hz, 3H), 1.27 (d, J=6.88 Hz, 4H), 1.32 (s, 3H), 1.40-1.66 (m, 5H), 1.68-1.88 (m, 2H), 2.01 (dd, J=15.36, 5.27 Hz, 1H), 2.11-2.32 (m, 3H), 2.19 (d, J=15.13 Hz, 1H), 2.26 (s, 6H), 2.36 (s, 3H), 2.40-2.66 (m, 5H), 2.75 (d, J=12.84 Hz, 1H), 2.81 (m, 1H), 2.91 (d, J=12.84 Hz, 1H), 3.16-3.20 (m, 1H), 3.21 (s, 3H), 3.34 (s, 3H), 3.38-3.46 (m, 1H), 3.49-3.56 (m, 1H), 3.67 (d, J=7.79 Hz, 1H), 3.77-3.86 (m, 2H), 3.80 (s, 3H), 4.26-4.33 (m, 1H), 4.39-4.49 (m, 3H), 4.60-4.67 (m, 1H), 4.85 (d, J=5.04 Hz, 1H), 6.84 (d, J=7.79 Hz, 1H), 6.92 (m, 1H), 7.17 (t, J=7.57 Hz, 1H), 7.38 (d, J=5.50 Hz, 1H)

Example 173

Synthesis of the Compound Represented by the Formula (G)

[Formula 22]

formula (G)

(1) By using the compound obtained in Example 2 (5.0 g) as a starting material, a cyclized compound (400 mg) was obtained in the same manners as those of Example 7, (1), (2) and (3).

(2) By using the compound obtained in (1) mentioned above (150 mg) as a starting material, the title compound (36.7 mg) was obtained in the same manners as those of Example 126, (1), (2), (3) and Example 7, (4).

MS (ESI) m/z=953.7 [M+H]$^+$ $^1$H-NMR (600 MHz, CDCl$_3$) δ (ppm): 0.79:1:0.1 (m, 12H), 1.16 (d, 20H), 1.28 (d, J=6.88 Hz, 3H), 1.48-1.65 (m, 6H), 2.00-2.10 (m, 1H), 2.14-2.65 (m, 9H), 2.23-2.29 (m, 9H), 2.69-2.80 (m, 1H), 3.15-3.34 (m, 4H), 3.27-3.31 (m, 3H), 3.58-3.73 (m, 2H), 3.83 (s, 3H), 3.84-3.90 (m, 1H), 4.28-4.44 (m, 3H), 4.48-4.56 (m, 2H), 4.80-4.85 (m, 1H), 5.52 (s, 1H), 6.86 (d, J=8.25 Hz, 1H), 6.91 (t, J=7.57 Hz, 1H), 7.17-7.23 (m, 1H), 7.24-7.30 (m, 1H)

Example 174

Synthesis of the Compound Represented by the Formula (H)

[Formula 23]

formula (H)

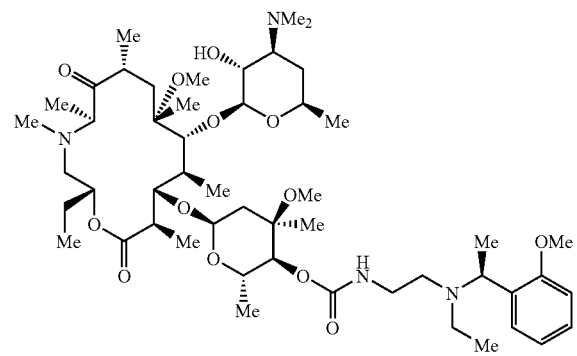

The compound obtained in Example 126 was dissolved in acetone, the solution was added with acetic anhydride (13.7 mg), and the mixture was stirred at room temperature for 48 hours. The reaction mixture was concentrated under reduced pressure, and the resulting residue was added with saturated aqueous sodium hydrogencarbonate and ethyl acetate. The layers were separated, and the organic layer was dried over anhydrous magnesium sulfate and filtered. The filtrate was concentrated under reduced pressure, and by using the resulting residue as a starting material, a compound was obtained in the same manner as that of Example 113, (2). The resulting compound was dissolved in methanol, and the solution was stirred under reflux by heating for 3 hours. The reaction mixture was concentrated under reduced pressure, and the resulting residue was purified by silica gel column chromatography (chloroform:methanol:28% aqueous ammonia=20:1:0.1) to obtain the title compound (36.4 mg).

MS (ESI) m/z=965.5 [M+H]$^+$ $^1$H-NMR (300 MHz, CDCl$_3$) δ (ppm): 0.90 (t, J=7.38 Hz, 3H), 0.93 (t, J=6.99 Hz, 3H), 1.04 (d, J=6.68 Hz, 3H), 1.07 (d, J=6.84 Hz, 3H), 1.08-1.32 (m, 22H), 1.34-1.68 (m, 5H), 2.02-2.18 (m, 2H), 2.12 (s, 3H), 2.25 (s, 6H), 2.35-2.83 (m, 9H), 3.16-3.35 (m, 4H), 3.25 (s, 3H), 3.31 (s, 3H), 3.57-3.66 (m, 2H), 3.69 (d, J=6.68 Hz, 1H), 3.85 (s, 3H), 3.94-3.99 (m, 1H), 4.33-4.42 (m, 2H), 4.46 (d, J=7.15 Hz, 1H), 4.53 (d, J=9.79 Hz, 1H), 4.93 (d, J=4.35 Hz, 1H), 4.94-5.03 (m, 1H), 5.55 (s, 1H), 6.85-6.90 (m, 1H), 6.91-6.95 (m, 1H), 7.18-7.25 (m, 1H), 7.27-7.31 (m, 1H)

Example 175

Synthesis of the Compound Represented by the Formula (I)

[Formula 24]

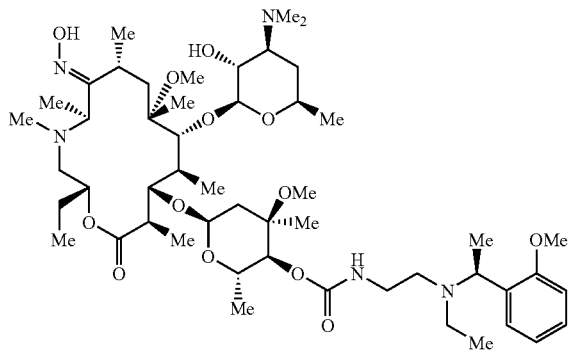

formula (I)

The compound obtained in Example 174 (28 mg) was dissolved in methanol (1 ml), the solution was added with hydroxylamine hydrochloride (10 mg) and imidazole (11.8 mg), and the mixture was stirred for 5 hours under reflux by heating. The reaction mixture was concentrated under reduced pressure, and the resulting residue was added with saturated aqueous ammonium chloride and chloroform. The layers were separated, and the organic layer was dried over anhydrous magnesium sulfate and filtered. The filtrate was concentrated under reduced pressure, and the resulting residue was purified by column chromatography (chloroform: methanol=10:1 to chloroform:methanol:28% aqueous ammonia=20:1:0.1) to obtain the title compound (24.6 mg).

MS (ESI) m/z=980.7 [M+H]$^+$ $^1$H-NMR (300 MHz, CDCl$_3$) δ (ppm): 0.85-0.96 (m, 6H), 1.02-1.29 (m, 22H), 1.26-1.33 (m, 6H), 1.46-1.77 (m, 5H), 1.91-2.09 (m, 2H), 2.07 (s, 3H), 2.23 (s, 6H), 2.33-2.75 (m, 9H), 3.19-3.35 (m, J=5.13 Hz, 3H), 3.29 (s, 3H), 3.30 (s, 3H), 3.45-3.88 (m, 4H), 3.82 (s, 3H), 3.93 (d, J=3.57 Hz, 1H), 4.29-4.42 (m, 2H), 4.52 (d, J=9.95 Hz, 1H), 4.57 (d, J=6.99 Hz, 1H), 4.83-4.88 (m, 1H), 4.90 (d, J=4.20 Hz, 1H), 5.44 (t, J=4.82 Hz, 1H), 6.86 (d, J=8.39 Hz, 1H), 6.91 (t, J=7.46 Hz, 1H), 7.18-7.31 (m, 2H)

Syntheses of Examples 176 to 205

Preparation methods of compounds represented by the formula (J) having R$^{1J}$, R$^{2J}$ and R$^{3J}$ defined in Table 4 are shown below.

TABLE 4 formula (J)

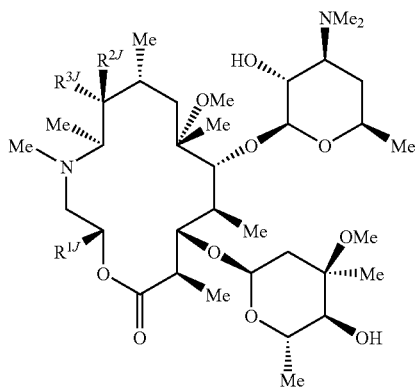

| Example | R$^{2J}$ | R$^{3J}$ | ESI MS (M + H) | $^1$H-NMR, CDCl$_3$, δ (ppm) |
|---|---|---|---|---|
| 176 |  |  | 717.4 | (300 MHz): 0.89 (t, J = 7.46 Hz, 3H) 0.99-1.40 (m, 5H) 1.04 (d, J = 6.68 Hz, 3H) 1.08 (d, J = 6.68 Hz, 3H) 1.12 (d, J = 7.46 Hz, 3H) 1.23 (d, J = 6.22 Hz, 3H) 1.25 (s, 3H) 1.29 (d, J = 6.22 Hz, 3H) 1.33 (s, 3H) 1.47-1.62 (m, 3H) 1.62-1.70 (m, 1H) 2.02-2.20 (m, 2H) 2.12 (s, 3H) 2.29 (s, 6H) 2.38 (d, J = 14.61 Hz, 1H) 2.42 ~ 2.57 (m, 2H) 2.68-2.76 (m, 2H) 2.76-2.87 (m, 1H) 3.01 (d, J = 9.33 Hz, 1H) 3.18-3.35 (m, 3H) 3.25 (s, 3H) 3.32 (s, 3H) 3.42-3.57 (m, 1H) 3.62 (q, J = 6.68 Hz, 1H) 3.68 (d, J = 7.15 Hz, 1H) 3.93 (dd, J = 8.24, 2.02 Hz, 1H) 3.98-4.10 (m, 1H) 4.40 (d, J = 7.15 Hz, 1H) 4.91 (d, J = 4.51 Hz, 1H) 4.93-5.02 (m, 1H) |

TABLE 4-continued formula (J)

| Example | R[2J] | R[3J] | ESI MS (M + H) | $^1$H-NMR, CDCl$_3$, δ (ppm) |
|---|---|---|---|---|
| 177 | (isopropenyl ester, O-C(=O)-C(=CH$_2$)-) | (isopropenyl ester, O-C(=O)-C(=CH$_2$)-) | 689.5 | (300 MHz): 1.06 (d, J = 6.68 Hz, 3H) 1.11 (d, J = 7.46 Hz, 3H) 1.14 (d, J = 6.99 Hz, 3H) 1.18 (d, J = 7.15 Hz, 3H) 1.19-1.30 (m, 1H) 1.22-1.24 (m, 3H) 1.25 (s, 3H) 1.27 (d, J = 6.22 Hz, 3H) 1.31 (s, 3H) 1.43-1.70 (m, 3H) 2.02-2.25 (m, 3H) 2.20 (s, 3H) 2.29 (s, 6H) 2.38 (d, J = 15.23 Hz, 1H) 2.42-2.51 (m, 1H) 2.64-2.88 (m, 3H) 2.97-3.12 (m, 2H) 3.22 (s, 3H) 3.24-3.30 (m, 1H) 3.32 (s, 3H) 3.44-3.56 (m, 1H) 3.69 (d, J = 6.84 Hz, 1H) 3.82 (q, J = 6.74 Hz, 1H) 3.92 (dd, J = 6.45, 2.10 Hz, 1H) 3.97-4.09 (m, 2H) 4.30-4.38 (m, 1H) 4.41 (d, J = 7.31 Hz, 1H) 4.80 (d, J = 4.66 Hz, 1H) |
| 178 | Me-C(=O)-O- (acetate) | H | 761.6 | (300 MHz): 0.84-0.91 (m, 6H) 1.02 (d, J = 6.53 Hz, 3H) 1.12 (d, J = 7.46 Hz, 3H) 1.09-1.28 (m, 7H) 1.17 (d, J = 6.99 Hz, 3H) 1.22 (d, J = 6.22 Hz, 3H) 1.29 (d, J = 6.22 Hz, 3H) 1.37-1.88 (m, 6H) 2.00-2.28 (m, 3H) 2.05 (s, 3H) 2.17 (s, 3H) 2.29 (s, 6H) 2.37-2.74 (m, 4H) 2.90-2.98 (m, 1H) 3.03 (t, J = 9.71 Hz, 1H) 3.26 (s, 3H) 3.31-3.39 (m, 1H) 3.35 (s, 3H) 3.50-3.59 (m, 1H) 3.72 (d, J = 6.99 Hz, 1H) 3.98-4.12 (m, 2H) 4.50 (d, J = 7.15 Hz, 1H) 4.73-4.79 (m, 1H) 4.84-4.95 (m, 2H) |
| 179 | H$_2$N-C(=O)-O- (carbamate) | H | 762.6 | (300 MHz): 0.88 (t, J = 7.54 Hz, 3H) 0.95 (d, J = 6.84 Hz, 3H) 1.03 (d, J = 6.68 Hz, 3H) 1.12 (d, J = 7.31 Hz, 3H) 1.10-1.28 (m, 7H) 1.17 (d, J = 6.99 Hz, 3H) 1.22 (d, J = 6.06 Hz, 3H) 1.29 (d, J = 6.22 Hz, 3H) 1.35-1.73 (m, 5H) 1.99-2.27 (m, 4H) 2.16 (s, 3H) 2.29 (s, 6H) 2.37-2.74 (m, 5H) 2.91-3.07 (m, 2H) 3.26 (s, 3H) 3.32-3.58 (m, 2H) 3.34 (s, 3H) 3.72 (d, J = 6.99 Hz, 1H) 4.06 (d, 2H) 4.49 (d, J = 7.31 Hz, 1H) 4.56 (s, 2H) 4.58-4.65 (m, 1H) 4.87 (d, J = 4.66 Hz, 1H) 4.88-4.96 (m, 1H) |
| 180 | (isopropenyl ester) | (isopropenyl ester) | 916.5 | (300 MHz): 1.02 (d, J = 6.68 Hz, 3H) 1.04-1.12 (m, 6H) 1.14 (d, J = 7.31 Hz, 3H) 1.16-1.21 (m, 1H) 1.22 (d, J = 6.06 Hz, 3H) 1.25 (s, 3H) 1.30 (d, J = 6.22 Hz, 3H) 1.33 (s, 3H) 1.35-1.42 (m, 1H) 1.47-1.73 (m, 4H) 1.97-2.13 (m, 2H) 2.06 (s, 3H) 2.20 (d, J = 10.57 Hz, 1H) 2.28 (s, 6H) 2.36 (d, J = 15.54 Hz, 1H) 2.39-2.58 (m, 2H) 2.60-2.93 (m, 3H) 3.01 (t, 1H) 3.06-3.26 (m, 2H) 3.20 (s, 3H) 3.31 (s, 3H) 3.40-3.72 (m, 4H) 3.58 (s, 2H) 3.86 (d, J = 7.31 Hz, 1H) 4.02 (dd, J = 9.25, 5.98 Hz, 1H) 4.39 (d, J = 7.15 Hz, 1H) 4.86 (d, J = 4.35 Hz, 1H) 4.90 (s, 1H) 5.93-6.04 (m, 1H) 6.47 (dd, J = 3.26, 1.87 Hz, 1H) 6.68 (d, J = 3.42 Hz, 1H) 7.15-7.22 (m, 1H) 7.35 (t, J = 7.69 Hz, 1H) 7.46 (d, J = 1.09 Hz, 1H) 7.53-7.63 (m, 2H) |
| 181 | HO-CH$_2$-C(=O)-O- (glycolate) | H | 777.7 | (600 MHz): 0.86 (t, J = 7.57 Hz, 3H) 0.90 (d, J = 6.88 Hz, 3H) 0.99 (d, J = 5.96 Hz, 3H) 1.09 (d, J = 7.79 Hz, 3H) 1.16 (d, J = 7.34 Hz, 3H) 1.17-1.30 (m, 2H) 1.21 (d, J = 6.42 Hz, 3H) 1.23-1.24 (m, 6H) 1.28 (d, J = 6.42 Hz, 3H) 1.48-1.67 (m, 4H) 1.94-2.05 (m, 2H) 2.09-2.17 (m, 4H) 2.17-2.25 (m, 1H) 2.29 (s, 6H) 2.38 (d, J = 15.13 Hz, 1H) 2.42-2.60 (m, 1H) 2.68 (s, 1H) 2.93-3.05 (m, 2H) 3.25 (s, 3H) 3.26-3.31 (m, 1H) 3.32 (s, 3H) 3.47-3.55 (m, 1H) 3.64 (d, J = 7.34 Hz, 1H) 3.95-4.05 (m, 2H) 4.09-4.17 (m, 2H) 4.48 (d, J = 6.88 Hz, 1H) 4.79-4.89 (m, 3H) |

TABLE 4-continued formula (J)

| Example | R²ᴶ | R³ᴶ | ESI MS (M + H) | ¹H-NMR, CDCl₃, δ (ppm) |
|---|---|---|---|---|
| 182 | H₂N-CH₂-C(=O)-O-⁂ | H | 776.7 | (600 MHz): 0.81-0.92 (m, 6H) 0.99 (s, 3H) 1.10 (d, J = 7.34 Hz, 3H) 1.16 (d, J = 7.34 Hz, 3H) 1.17-1.30 (m, 2H) 1.21 (d, J = 5.96 Hz, 3H) 1.22-1.25 (m, 6H) 1.27 (d, J = 6.42 Hz, 3H) 1.48-1.72 (m, 4H) 1.94-2.06 (m, 2H) 2.08-2.24 (m, 5H) 2.29 (S, 6H) 2.39 (d, J = 15.59 Hz, 1H) 2.43-2.61 (m, 2H) 2.68 (s, 1H) 2.93-2.98 (m, 1H) 2.98-3.05 (m, 1H) 3.23 (s, 3H) 3.28-3.36 (m, 1H) 3.32-3.33 (m, 3H) 3.41 (s, 2H) 3.48-3.56 (m, 1H) 3.67 (d, J = 6.88 Hz, 1H) 3.94-4.07 (m, 2H) 4.48 (d, J = 5.50 Hz, 1H) 4.81 (s, 1H) 4.83-4.91 (m, 2H) |
| 183 | Me₂N-CH₂-C(=O)-O-⁂ | H | 804.7 | (600 MHz): 0.82-0.90 (m, 6H) 0.98 (s, 3H) 1.09 (d, J = 7.34 Hz, 3H) 1.15 (d, J = 7.34 Hz, 3H) 1.17-1.27 (m, 2H) 1.21 (d, J = 5.96 Hz, 3H) 1.22-1.26 (m, 6H) 1.29 (d, J = 5.96 Hz, 3H) 1.48-1.59 (m, 3H) 1.59-1.65 (m, 1H) 1.95-2.06 (m, 2H) 2.07-2.23 (m, 5H) 2.27 (s, 6H) 2.32 (s, 6H) 2.39 (d, J = 15.13 Hz, 1H) 2.42-2.50 (m, 1H) 2.52-2.61 (m, 2H) 2.68 (s, 1H) 2.90-2.97 (m, 1H) 3.02 (t, J = 9.63 Hz, 1H) 3.14 (s, 2H) 3.24 (s, 3H) 3.28-3.38 (m, 1H) 3.32-3.33 (m, 3H) 3.52 (s, 1H) 3.68 (d, J = 7.34 Hz, 1H) 3.98 (s, 1H) 4.01-4.08 (m, 1H) 4.47 (s, 1H) 4.80 (s, 1H) 4.83-4.93 (m, 2H) |
| 184 | phthalimido-CH₂CH₂-NH-CH₂-C(=O)-O-⁂ | H | 949.9 | (600 MHz): 0.82-0.89 (m, 6H) 0.97 (s, 3H) 1.09 (d, J = 7.34 Hz, 3H) 1.16 (d, J = 7.34 Hz, 3H) 1.18-1.32 (m, 2H) 1.21 (d, J = 5.96 Hz, 3H) 1.22-1.26 (m, 3H) 1.24-1.25 (m, 3H) 1.28 (d, J = 5.96 Hz, 3H) 1.47-1.67 (m, 4H) 1.90-2.07 (m, 2H) 2.09-2.22 (m, 4H) 2.25-2.36 (m, 6H) 2.38 (d, J = 15.59 Hz, 1H) 2.40-2.64 (m, 3H) 2.65-2.74 (m, 1H) 2.91 (t, J = 6.19 Hz, 2H) 2.92-2.98 (m, 1H) 3.01 (t, J = 9.17 Hz, 1H) 3.22 (s, 3H) 3.29-3.32 (m, 1H) 3.32-3.34 (m, 3H) 3.40 (d, J = 4.13 Hz, 2H) 3.48-3.57 (m, 1H) 3.67 (d, J = 7.34 Hz, 1H) 3.79 (t, J = 6.19 Hz, 2H) 3.95-4.07 (m, 2H) 4.46 (d, J = 8.71 Hz, 1H) 4.81 (s, 1H) 4.85 (d, J = 5.04 Hz, 1H) 4.88 (s, 1H) 7.70 (dd, J = 5.50, 3.21 Hz, 2H) 7.83 (dd, J = 5.50, 3.21 Hz, 2H) |
| 185 | Cbz-NH-CH₂-C(=O)-O-⁂ | H | 910.8 | (600 MHz): 0.82-0.91 (m, 6H) 0.97 (s, 3H) 1.09 (d, J = 7.34 Hz, 3H) 1.16 (d, J = 7.34 Hz, 3H) 1.19-1.31 (m, 2H) 1.20 (d, J = 5.96 Hz, 3H) 1.23-1.27 (m, 6H) 1.29 (d, J = 6.42 Hz, 3H) 1.45-1.69 (m, 4H) 1.93-2.09 (m, 2H) 2.14-2.16 (m, 3H) 2.17-2.28 (m, 1H) 2.29-2.31 (m, 6H) 2.38 (d, J = 15.13 Hz, 1H) 2.41-2.61 (m, 3H) 2.66-2.74 (m, 1H) 2.92-3.04 (m, 2H) 3.21-3.34 (m, 1H) 3.23-3.24 (m, 3H) 3.31-3.33 (m, 3H) 3.46-3.55 (m, 1H) 3.66 (d, J = 7.34 Hz, 1H) 3.87-4.07 (m, 4H) 4.45 (d, J = 6.42 Hz, 1H) 4.81 (s, 1H) 4.84-4.91 (m, 2H) 5.11 (s, 2H) 5.27 (s, 1H) 7.27-7.38 (m, 5H) |

TABLE 4-continued formula (J)

| Example | R$^{2J}$ | R$^{3J}$ | ESI MS (M + H) | $^1$H-NMR, CDCl$_3$, δ (ppm) |
|---|---|---|---|---|
| 186 | benzyl-NH-CH$_2$-C(O)-O-~ | H | 866.8 | (600 MHz): 0.81-0.91 (m, 6H) 1.00 (s, 3H) 1.10 (d, J = 7.34 Hz, 3H) 1.15 (d, J = 7.34 Hz, 3H) 1.16-1.32 (m, 11H) 1.20 (d, J = 5.96 Hz, 3H) 1.46-1.59 (m, 3H) 1.60-1.67 (m, 1H) 1.94-2.05 (m, 2H) 2.11-2.14 (m, 3H) 2.15-2.24 (m, 1H) 2.27-2.30 (m, 6H) 2.39 (d, J = 15.13 Hz, 1H) 2.41-2.63 (m, 3H) 2.68 (s, 1H) 2.92-3.04 (m, 2H) 3.18 (s, 2H) 3.27-3.35 (m, 1H) 3.32-3.33 (m, 3H) 3.37 (s, 3H) 3.47-3.57 (m, 1H) 3.67 (d, J = 7.34 Hz, 1H) 3.79 (d, J = 1.83 Hz, 2H) 3.94-4.06 (m, 2H) 4.46 (d, J = 5.50 Hz, 1H) 4.80-4.91 (m, 3H) 7.20-7.25 (m, 1H) 7.27-7.33 (m, 4H) |
| 187 | benzyl-N(Me)-CH$_2$-C(O)-O-~ | H | 880.8 | (600 MHz): 0.80-0.90 (m, 6H) 1.00 (s, 3H) 1.09 (d, J = 7.34 Hz, 3H) 1.10-1.32 (m, 2H) 1.15 (d, J = 7.34 Hz, 3H) 1.20 (d, J = 5.96 Hz, 3H) 1.22-1.31 (m, 9H) 1.46-1.71 (m, 4H) 1.92-2.04 (m, 2H) 2.06-2.24 (m, 4H) 2.29-2.34 (m, 6H) 2.37-2.38 (m, 3H) 2.38-2.42 (m, 1H) 2.42-2.61 (m, 3H) 2.68 (s, 1H) 2.92-2.98 (m, 1H) 3.01 (t, J = 9.63 Hz, 1H) 3.16 (s, 3H) 3.23 (d, J = 4.13 Hz, 2H) 3.30-3.36 (m, 1H) 3.32-3.33 (m, 3H) 3.49-3.56 (m, 1H) 3.66 (d, J = 7.34 Hz, 1H) 3.68 (s, 2H) 3.94-4.06 (m, 2H) 4.46 (d, J = 6.42 Hz, 1H) 4.79-4.91 (m, 3H) 7.20-7.24 (m, 1H) 7.26-7.34 (m, 4H) |
| 188 | Me-CH$_2$-NH-C(O)-O-~ | H | 790.7 | (600 MHz): 0.86 (t, J = 7.57 Hz, 3H) 0.91 (d, J = 6.88 Hz, 3H) 1.01 (d, J = 6.42 Hz, 3H) 1.07-1.11 (m, 6H) 1.11-1.29 (m, 2H) 1.15 (d, J = 6.88 Hz, 3H) 1.20 (d, J = 5.96 Hz, 3H) 1.22-1.30 (m, 9H) 1.48-1.59 (m, 3H) 1.60-1.66 (m, 1H) 1.97-2.09 (m, 2H) 2.12-2.14 (m, 3H) 2.15-2.23 (m, 1H) 2.28-2.29 (m, 6H) 2.40 (d, J = 15.13 Hz, 1H) 2.45-2.58 (m, 3H) 2.64-2.71 (m, 1H) 2.92 (s, 1H) 3.01 (t, J = 8.94 Hz, 1H) 3.12-3.26 (m, 2H) 3.22-3.22 (m, 3H) 3.29-3.38 (m, 1H) 3.33-3.34 (m, 3H) 3.49-3.56 (m, 1H) 3.70 (d, J = 7.34 Hz, 1H) 3.98-4.10 (m, 2H) 4.41-4.50 (m, 2H) 4.61 (s, 1H) 4.81-4.96 (m, 2H) |
| 189 | Br-CH$_2$-CH$_2$-NH-C(O)-O-~ | H | 868.6 | (600 MHz): 0.87 (t, J = 7.57 Hz, 3H) 0.91 (d, J = 6.88 Hz, 3H) 1.03 (d, J = 6.42 Hz, 3H) 1.04-1.32 (m, J = 45.85 Hz, 2H) 1.08 (s, 3H) 1.16 (d, J = 6.88 Hz, 3H) 1.19-1.34 (m, 12H) 1.46-1.62 (m, 4H) 1.93-2.08 (m, 2H) 2.08-2.44 (m, 5H) 2.13-2.17 (m, 9H) 2.63-2.76 (m, 1H) 2.93-3.08 (m, 2H) 3.14-3.26 (m, 5H) 3.27-3.37 (m, 1H) 3.31-3.32 (m, 3H) 3.38-3.49 (m, 2H) 3.49-3.74 (m, 2H) 3.91-4.13 (m, 2H) 4.47 (d, J = 6.42 Hz, 1H) 4.85 (d, J = 4.13 Hz, 1H) 4.87-5.03 (m, 2H) |

TABLE 4-continued formula (J)

| Example | R²ᴶ | R³ᴶ | ESI MS (M + H) | ¹H-NMR, CDCl₃, δ (ppm) |
|---|---|---|---|---|
| 190 | H₂N-CH₂CH₂-NH-C(O)O-⁓ | H | 805.7 | (600 MHz): 0.86 (t, J = 7.57 Hz, 3H) 0.91 (d, J = 6.88 Hz, 3H) 1.01 (d, J = 6.42 Hz, 3H) 1.05-1.31 (m, 2H) 1.10 (d, J = 7.79 Hz, 3H) 1.15 (d, J = 7.34 Hz, 3H) 1.20 (d, J = 5.96 Hz, 3H) 1.22-1.31 (m, 9H) 1.46-1.72 (m, 4H) 1.96-2.10 (m, 2H) 2.13-2.16 (m, 3H) 2.15-2.25 (m, 1H) 2.28-2.31 (m, 6H) 2.39 (d, J = 15.13 Hz, 1H) 2.44-2.59 (m, 3H) 2.65-2.72 (m, 1H) 2.72-2.84 (m, 2H) 2.93 (s, 1H) 3.01 (d, J = 9.63 Hz, 1H) 3.12-3.28 (m, 2H) 3.22-3.23 (m, 3H) 3.28-3.40 (m, 1H) 3.32-3.34 (m, 3H) 3.48-3.57 (m, 1H) 3.69 (d, J = 6.42 Hz, 1H) 3.94-4.10 (m, 2H) 4.47 (d, J = 6.42 Hz, 1H) 4.62 (s, 1H) 4.79-5.01 (m, 3H) |
| 191 | Me₂N-CH₂CH₂-NH-C(O)O-⁓ | H | 833.8 | (600 MHz): 0.84 (t, J = 7.34 Hz, 3H) 0.90 (d, J = 6.42 Hz, 3H) 1.00 (d, J = 6.88 Hz, 3H) 1.06-1.30 (m, 2H) 1.08 (d, J = 7.34 Hz, 3H) 1.13 (d, J = 6.88 Hz, 3H) 1.18 (d, J = 5.96 Hz, 3H) 1.20-1.23 (m, 6H) 1.27 (d, J = 6.42 Hz, 3H) 1.46-1.58 (m, 3H) 1.59-1.65 (m, 1H) 1.90-2.04 (m, 2H) 2.04-2.20 (m, 12H) 2.27-2.28 (m, 6H) 2.38 (d, J = 15.59 Hz, 1H) 2.44-2.56 (m, 3H) 2.64 (s, 1H) 2.90 (s, 1H) 2.99 (s, 1H) 3.11-3.27 (m, 2H) 3.20-3.21 (m, 3H) 3.28-3.33 (m, 1H) 3.31-3.32 (m, 3H) 3.48-3.56 (m, 1H) 3.68-3.72 (m, 1H) 3.94-4.09 (m, 2H) 4.43-4.50 (m, 1H) 4.59-4.67 (m, 1H) 4.79-4.92 (m, 2H) 5.03-5.09 (m, 1H) |
| 192 | PhCH₂-O-C(O)-NH-CH₂CH₂-NH-C(O)O-⁓ | H | 939.9 | (600 MHz): 0.86 (t, J = 7.57 Hz, 3H) 0.89 (d, J = 6.42 Hz, 3H) 0.98 (d, J = 6.42 Hz, 3H) 1.06-1.33 (m, 2H) 1.10 (d, J = 7.34 Hz, 3H) 1.15 (d, J = 7.34 Hz, 3H) 1.20 (d, J = 5.96 Hz, 3H) 1.23 (s, 3H) 1.26 (s, 3H) 1.28 (d, J = 6.42 Hz, 3H) 1.46-1.69 (m, 4H) 2.01-2.10 (m, 2H) 2.14-2.23 (m, 1H) 2.15-2.16 (m, 3H) 2.29-2.31 (m, 6H) 2.38 (d, J = 15.59 Hz, 1H) 2.42-2.60 (m, 3H) 2.66-2.75 (m, 1H) 2.93 (s, 1H) 3.00 (t, J = 9.86 Hz, 1H) 3.21-3.22 (m, 3H) 3.25-3.37 (m, 5H) 3.31-3.32 (m, 3H) 3.51 (s, 1H) 3.67 (d, J = 7.34 Hz, 1H) 3.96-4.10 (m, 2H) 4.44 (d, J = 7.34 Hz, 1H) 4.59 (s, 1H) 4.85 (d, J = 4.13 Hz, 1H) 4.89-4.94 (m, 1H) 4.97 (s, 1H) 5.08 (s, 2H) 5.18 (s, 1H) 7.27-7.39 (m, 5H) |
| 193 | PhCH₂-NH-CH₂CH₂-NH-C(O)O-⁓ | H | 895.9 | (600 MHz): 0.86 (t, J = 7.34 Hz, 3H) 0.90 (d, J = 6.88 Hz, 3H) 1.00 (d, J = 6.42 Hz, 3H) 1.05-1.33 (m, 2H) 1.10 (d, J = 7.34 Hz, 3H) 1.16 (d, J = 6.88 Hz, 3H) 1.19 (d, J = 6.42 Hz, 3H) 1.22-1.32 (m, 9H) 1.46-1.74 (m, 4H) 1.96-2.11 (m, 2H) 2.12-2.24 (m, 1H) 2.14-2.17 (m, 3H) 2.28-2.31 (m, 6H) 2.39 (d, J = 15.13 Hz, 1H) 2.43-2.61 (m, 3H) 2.65-2.76 (m, 3H) 2.93 (s, 1H) 3.01 (t, J = 9.17 Hz, 1H) 3.18-3.38 (m, 3H) 3.21-3.24 (m, 3H) 3.32-3.34 (m, 3H) 3.47-3.58 (m, 1H) 3.65-3.84 (m, 3H) 3.95-4.09 (m, 2H) 4.46 (d, J = 6.88 Hz, 1H) 4.63 (s, 1H) 4.80-4.94 (m, 2H) 5.00 (s, 1H) 7.18-7.37 (m, 5H) |

TABLE 4-continued formula (J)

| Example | R2J | R3J | ESI MS (M + H) | 1H-NMR, CDCl3, δ (ppm) |
|---|---|---|---|---|
| 194 | H2N-N= | H2N-N= | 731.4 | (300 MHz): 0.88 (t, J = 7.54 Hz, 3H) 0.98 (d, J = 6.37 Hz, 3H) 1.07 (d, J = 7.46 Hz, 3H) 1.08-1.84 (m, 8H) 1.11-1.29 (m, 18H) 1.89 (s, 3H) 1.99-2.12 (m, 1H) 2.30 (s, 6H) 2.31-2.54 (m, 2H) 2.55-2.78 (m, 3H) 2.94-3.08 (m, 1H) 3.16-3.26 (m, 1H) 3.33 (s, 3H) 3.44 (s, 3H) 3.47-3.71 (m, 4H) 3.86-4.12 (m, 2H) 4.48 (d, J = 7.15 Hz, 1H) 4.82 (d, J = 4.35 Hz, 1H) 4.85-4.96 (m, 1H) 5.36-5.80 (m, 2H) |
| 195 | H2N- | H | 718.5 | (300 MHz): 0.80-1.00 (m, 9H) 1.10-1.19 (m, 6H) 1.14-1.31 (m, 2H) 1.21-1.25 (m, 3H) 1.24 (s, 3H) 1.31 (d, J = 6.37 Hz, 3H) 1.35 (s, 3H) 1.46-1.82 (m, 5H) 1.89-2.57 (m, 5H) 2.26-2.31 (m, 9H) 2.37 (d, J = 14.92 Hz, 1H) 2.65-2.86 (m, 2H) 3.02 (t, J = 9.56 Hz, 1H) 3.12-3.53 (m, 3H) 3.30-3.34 (m, 6H) 3.74 (d, J = 8.39 Hz, 1H) 3.96-4.11 (m, 2H) 4.38 (d, J = 7.31 Hz, 1H) 4.62-4.78 (m, 1H) 4.81-4.94 (m, 1H) |
| 196 | Me-SO2-HN- | H | 796.4 | (300 MHz): 0.84-0.91 (m, 3H) 0.99 (d, J = 7.46 Hz, 3H) 1.04 (d, J = 7.15 Hz, 3H) 1.10 (d, J = 7.15 Hz, 3H) 1.08-1.28 (m, 2H) 1.19 (d, J = 6.99 Hz, 3H) 1.23 (d, J = 6.22 Hz, 3H) 1.25 (s, 3H) 1.28-1.33 (m, 6H) 1.42-1.71 (m, 4H) 1.89-2.01 (m, 1H) 2.03-2.52 (m, 14H) 2.59-2.72 (m, 1H) 2.76-2.93 (m, 2H) 2.95 (s, 3H) 3.03 (t, J = 9.64 Hz, 1H) 3.14-3.32 (m, 2H) 3.32 (s, 3H) 3.34 (s, 3H) 3.43-3.57 (m, 1H) 3.76 (d, J = 8.08 Hz, 1H) 3.97-4.10 (m, 2H) 4.45 (d, J = 6.99 Hz, 1H) 4.87-4.93 (m, 1H) 5.08-5.26 (m, 1H) 6.04-6.21 (m, 1H) |
| 197 | H2N-CH2CH2-NH- | H | 761.7 | |
| 198 | H2N-CH2CH2-N(C(O)OCH2Ph)- | H | 895.7 | |

TABLE 4-continued formula (J)

| Example | R[2J] | R[3J] | ESI MS (M + H) | $^1$H-NMR, CDCl$_3$, δ (ppm) |
|---|---|---|---|---|
| 199 | Me-C(=O)-NH-⦚ | H | 759.5 | (600 MHz): 0.84 (t, J = 7.11 Hz, 3H) 0.93 (d, J = 7.34 Hz, 3H) 1.00 (d, J = 6.88 Hz, 3H) 1.12 (d, J = 3.67 Hz, 3H) 1.14-1.28 (m, 2H) 1.16 (d, J = 6.88 Hz, 3H) 1.20 (d, J = 5.96 Hz, 3H) 1.21-1.22 (m, 3H) 1.24 (s, 3H) 1.28 (d, J = 6.42 Hz, 3H) 1.40-1.48 (m, 2H) 1.54 (dd, J = 15.13, 5.04 Hz, 1H) 1.62-1.69 (m, 1H) 2.01 (s, 3H) 2.11-2.32 (m, 15H) 2.35 (d, J = 15.13 Hz, 1H) 2.44-2.54 (m, 1H) 2.58-2.67 (m, 1H) 2.76-2.88 (m, 1H) 2.99 (d, J = 9.17 Hz, 1H) 3.14-3.23 (m, 1H) 3.25 (s, 3H) 3.28 (s, 3H) 3.41-3.49 (m, 2H) 3.69 (d, J = 8.25 Hz, 1H) 3.97-4.06 (m, 1H) 4.07-4.16 (m, 1H) 4.39 (d, J = 6.88 Hz, 1H) 4.78-4.95 (m, 2H) 7.01 (br. s., 1H) |
| 200 | Ph-CH$_2$-O-CH$_2$-C(=O)-NH-⦚ | H | 866.9 | (600 MHz): 0.83 (t, J = 7.11 Hz, 3H) 0.94 (d, J = 6.42 Hz, 3H) 1.02 (d, J = 6.42 Hz, 3H) 1.12 (d, J = 7.34 Hz, 3H) 1.16 (d, J = 6.88 Hz, 3H) 1.17-1.21 (m, 1H) 1.20 (d, J = 5.96 Hz, 3H) 1.23 (s, 3H) 1.24-1.30 (m, 7H) 1.42-1.51 (m, 2H) 1.54 (dd, J = 15.36, 4.81 Hz, 1H) 1.94-2.06 (m, 1H) 2.07-2.50 (m, 16H) 2.54-2.68 (m, 1H) 2.75-2.83 (m, 1H) 2.88-2.96 (m, 1H) 2.99 (d, J = 9.17 Hz, 1H) 3.17-3.35 (m, 2H) 3.21 (s, 3H) 3.30 (s, 3H) 3.43-3.50 (m, 1H) 3.67 (d, J = 8.25 Hz, 1H) 3.94 (s, 2H) 3.96-4.18 (m, 2H) 4.40 (d, J = 7.34 Hz, 1H) 4.61 (s, 2H) 4.83-4.91 (m, 2H) 7.11 (br. s., 1H) 7.27-7.38 (m, 5H) |
| 201 | HO-CH$_2$-C(=O)-NH-⦚ | H | 766.8 | (600 MHz): 0.81-0.93 (m, 3H) 0.97 (d, J = 7.34 Hz, 3H) 1.02-1.19 (m, 7H) 1.19-1.27 (m, 4H) 1.21 (d, J = 5.96 Hz, 3H) 1.23 (s, 3H) 1.26 (s, 3H) 1.29 (d, J = 5.96 Hz, 3H) 1.41-1.50 (m, 2H) 1.55 (dd, J = 15.13, 4.59 Hz, 1H) 1.64 (d, J = 11.46 Hz, 1H) 2.08-2.40 (m, 4H) 2.26-2.28 (m, 9H) 2.37 (d, J = 15.13 Hz, 1H) 2.40-2.52 (m, 2H) 2.63-2.70 (m, 1H) 2.80-2.88 (m, 1H) 3.00 (d, J = 9.63 Hz, 1H) 3.19 (dd, J = 10.32, 7.11 Hz, 1H) 3.26 (s, 3H) 3.29 (s, 3H) 3.42-3.51 (m, 2H) 3.72 (d, J = 8.25 Hz, 1H) 3.99-4.14 (m, 4H) 4.40 (d, J = 6.88 Hz, 1H) 4.76-4.82 (m, 1H) 4.83-4.91 (m, 1H) |
| 202 | H$_2$N-CH$_2$-C(=O)-NH-⦚ | H | 774.5 | (600 MHz): 0.86 (t, J = 7.11 Hz, 3H) 0.96-1.01 (m, 6H) 1.04-1.17 (m, 7H) 1.17-1.26 (m, 4H) 1.20 (d, J = 5.96 Hz, 3H) 1.22 (s, 3H) 1.25 (s, 3H) 1.28 (d, J = 6.42 Hz, 3H) 1.42-1.52 (m, 2H) 1.54 (dd, J = 15.13, 4.59 Hz, 1H) 1.67 (d, J = 13.30 Hz, 1H) 1.79-1.93 (m, 1H) 1.93-2.25 (m, 2H) 2.14-2.16 (m, 3H) 2.28-2.34 (m, 6H) 2.37 (d, J = 15.13 Hz, 1H) 2.48-2.63 (m, 1H) 2.72-2.85 (m, 2H) 2.99 (d, J = 9.17 Hz, 1H) 3.15-3.26 (m, 1H) 3.23 (s, 3H) 3.29 (s, 3H) 3.33-3.40 (m, 2H) 3.43-3.50 (m, 1H) 3.69 (d, J = 8.71 Hz, 1H) 3.94-4.05 (m, 1H) 4.09-4.18 (m, 1H) 4.41 (d, J = 7.34 Hz, 1H) 4.77-4.92 (m, 2H) 7.53 (br. s., 1H) |
| 203 | Me$_2$N-CH$_2$-C(=O)-NH-⦚ | H | 803.7 | |

TABLE 4-continued formula (J)

| Example | $R^{2J}$ | $R^{3J}$ | ESI MS (M + H) | $^{1}$H-NMR, CDCl$_3$, δ (ppm) |
|---|---|---|---|---|
| 204 | Me-CH$_2$-NH-C(O)-NH-⁓ | H | 789.9 | (600 MHz): 0.83 (t, J = 7.34 Hz, 3H) 0.93 (d, J = 7.34 Hz, 3H) 1.00 (d, J = 6.88 Hz, 3H) 1.04-1.14 (m, 7H) 1.19 (d, J = 6.88 Hz, 3H) 1.21 (d, J = 6.42 Hz, 3H) 1.22-1.28 (m, 7H) 1.30 (d, J = 5.96 Hz, 3H) 1.36-1.47 (m, 2H) 1.56 (dd, J = 15.13, 5.04 Hz, 1H) 1.62-1.69 (m, 1H) 1.74-1.88 (m, 1H) 2.12-2.20 (m, 1H) 2.20-2.33 (m, 12H) 2.37 (d, J = 15.13 Hz, 1H) 2.41-2.49 (m, 1H) 2.58-2.66 (m, 1H) 2.80-2.91 (m, 2H) 2.98-3.04 (m, 1H) 3.13-3.33 (m, 4H) 3.26 (s, 3H) 3.30 (s, 3H) 3.41-3.49 (m, 1H) 3.69 (d, J = 8.25 Hz, 1H) 3.99-4.11 (m, 2H) 4.38 (d, J = 7.34 Hz, 1H) 4.90 (d, J = 4.13 Hz, 1H) 4.93-5.12 (m, 2H) 5.46 (br. s., 1H) |
| 205 | Me-N(Me)-C(Me)$_2$-⁓ | H | 746.8 | (600 MHz): 0.88 (t, J = 7.34 Hz, 3H) 1.04 (d, J = 6.42 Hz, 3H) 1.07-1.20 (m, 2H) 1.10 (d, J = 7.34 Hz, 3H) 1.16 (d, J = 7.34 Hz, 3H) 1.21 (d, J = 5.96 Hz, 3H) 1.22-1.25 (m, 7H) 1.27 (d, J = 6.42 Hz, 3H) 1.33 (s, 3H) 1.50-1.75 (m, J = 15.13, 5.04 Hz, 3H) 1.55 (dd, J = 15.13, 5.04 Hz, 1H) 1.93-2.10 (m, 2H) 2.15-2.41 (m, 17H) 2.38 (d, J = 15.13 Hz, 1H) 2.44-2.60 (m, 3H) 2.62-2.69 (m, 1H) 3.01 (d, J = 9.17 Hz, 1H) 3.19-3.30 (m, 1H) 3.27 (s, 3H) 3.32 (s, 3H) 3.46-3.55 (m, 1H) 3.72 (d, J = 7.34 Hz, 1H) 3.98-4.09 (m, 2H) 4.41-4.49 (m, 1H) 4.86 (d, J = 4.58 Hz, 1H) 4.95-5.04 (m, 1H) |

$R^{1J}$ in the compounds represented by the formula (J) is ethyl group except for the compounds of Examples 177 and 180. $R^{1J}$ in the compound of Example 177 is hydrogen atom, and $R^{1J}$ in the compound of Example 180 is a group represented by the formula:

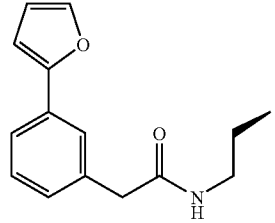

Example 176

(1) The compound obtained in Example 126, (1) (1.34 g) was dissolved in chloroform (25 ml), the solution was added with pyridine (2.28 ml) and triphosgene (1.30 g) under ice cooling, and the mixture was stirred for 30 minutes. The mixture was further added with benzyl alcohol (3.05 g), the mixture was stirred for 1 hour, and then added with distilled water, and the layers were separated. The organic layer was dried over anhydrous magnesium sulfate and filtered. The filtrate was concentrated under reduced pressure, and the resulting residue was purified by silica gel column chromatography (hexane:acetone:triethylamine=650:50:0.1) to obtain a 4″-O-benzyloxycarbonyl compound (1.59 g).

(2) By using the compound obtained in (1) mentioned above (1.59 g) as a starting material, a desilylated compound (1.08 g) was obtained in the same manner as that of Example 7, (4).

(3) The compound obtained in (2) mentioned above (1.08 g) was dissolved in acetone (10 ml), the solution was added with acetic anhydride (155 mg), and the mixture was stirred for 18 hours. The reaction mixture was concentrated under reduced pressure, and the resulting residue was added with ethyl acetate and saturated aqueous sodium hydrogencarbonate. The layers were separated, and the organic layer was dried over anhydrous magnesium sulfate and filtered. The resulting filtrate was concentrated under reduced pressure to obtain a 2′-O-acetyl compound (1.00 g).

(4) N-Chlorosuccinimide (746 mg) was suspended in toluene (30 ml), the mixture was added dropwise with dimethyl sulfide (1.35 ml) at −25° C., and the mixture was stirred at the same temperature for 15 minutes. The mixture was added dropwise with a solution of the compound obtained in (3) mentioned above (500 mg) in toluene (5 ml), and the mixture was stirred at the same temperature for 15 minutes. The mixture was further added with triethylamine (1.56 ml), the mixture was warmed to room temperature 10 minutes later, and then added with ethyl acetate and saturated aqueous sodium hydrogencarbonate, and the layers were separated. The organic layer was dried over anhydrous magnesium sulfate and filtered. The filtrate was concentrated under reduced pressure, and the resulting residue was purified by silica gel column chromatography (hexane:acetone:triethylamine=10:10:0.1) to obtain a 9-ketone compound (465 mg).

(5) The compound obtained in (4) mentioned above (460 mg) was dissolved in methanol, the solution was stirred at room temperature for 40 hours. The reaction mixture was added with 5% palladium-carbon (450 mg), and the mixture was stirred at room temperature for 1.5 hours under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=20:1:0.1 to 10:1:0.1) to obtain the compound shown in Table 4 (308 mg).

Example 177

By using the compound obtained in Example 157, (1) (240 mg) as a starting material, the compound shown in Table 4 (31.0 mg) was obtained in the same manners as those of Example 126, (1) and Example 176.

Example 178

The compound obtained in Example 176, (3) (50 mg) was dissolved in chloroform (0.5 ml) and pyridine (0.5 ml), the solution was added with acetic anhydride (29 mg) and 4-dimethylaminopyridine (14 mg), and the mixture was stirred at room temperature for 18 hours. The reaction mixture was concentrated under reduced pressure, and the resulting residue was purified by column chromatography (chloroform:methanol:28% aqueous ammonia=20:1:0.1). By using the resulting 9-O-acetyl compound (51.6 mg) as a starting material, the compound shown in Table 4 (31.8 mg) was obtained in the same manner as that of Example 176, (5).

Example 179

The compound obtained in Example 176, (3) (50 mg) was dissolved in chloroform (1 ml), the solution was added with trichloroacetyl isocyanate (8 µl), and the mixture was stirred for 10 minutes. The reaction mixture was added with methanol (6 µl) and potassium carbonate (9.3 mg), and the mixture was stirred at room temperature for 18 hours. The reaction mixture was concentrated under reduced pressure, the resulting residue was purified by column chromatography (chloroform:methanol:28% aqueous ammonia=20:1:0.1), and by using the resulting 9-O-carbamoyl compound (38.6 mg) as a starting material, the compound shown in Table 4 (14.5 mg) was obtained in the same manner as that of Example 176, (5).

Example 180

By using the compound obtained in Example 23, (2) (0.98 g) as a starting material, the compound shown in Table 4 (207 mg) was obtained in the same manner as that of Example 176.

Example 181

(1) The compound obtained in Example 176, (3) (50 mg) was dissolved in chloroform (2 ml), the solution was added with pyridine (1 ml), benzyl chloroacetate (26.4 µl) and 4-dimethylaminopyridine (13.6 mg), and the mixture was stirred at room temperature for 1 hour. The reaction mixture was added with saturated aqueous ammonium chloride and chloroform, and the layers were separated. The organic layer was washed with saturated brine, and then the organic layer was dried over anhydrous magnesium sulfate and filtered. The filtrate was concentrated under reduced pressure, and the resulting residue was purified by silica gel column chromatography (hexane:acetone:triethylamine=30:10:0.2) to obtain a 9-O-acyl compound (52.9 mg).

(2) The compound obtained in (1) mentioned above (35 mg) was dissolved in methanol (1 ml), the solution was stirred at room temperature for 18 hours, further stirred at 45° C. for 8 hours and stirred at room temperature for 18 hours. The solution was added with 5% palladium-carbon (20 mg), and the mixture was stirred at room temperature for 4 days under a hydrogen atmosphere. The reaction mixture was filtered, the filtrate was concentrated under reduced pressure, and the resulting residue was purified by silica gel column chromatography (chloroform:methanol:28% aqueous ammonia=30:1:0.1 to 10:1:0.1) to obtain the compound shown in Table 4 (13.0 mg).

Example 182

(1) The compound obtained in Example 176, (3) (250 mg) was dissolved in chloroform (2 ml), the solution was added with pyridine (5 ml), chloroacetic anhydride (478 mg) and 4-dimethylaminopyridine (160 mg), and the mixture was stirred at room temperature for 3 hours. The reaction mixture was added with saturated aqueous ammonium chloride and chloroform, the layers were separated, and the organic layer was washed with saturated brine, then dried over anhydrous magnesium sulfate and filtered. The filtrate was concentrated under reduced pressure, and the resulting residue was purified by silica gel column chromatography (chloroform alone) to chloroform:methanol:28% aqueous ammonia=20:1:0.1) to obtain a 9-O-acyl compound (217 mg).

(2) The compound obtained in (1) mentioned above (215 mg) was dissolved in dimethylformamide (5 ml), the solution was added with sodium azide (21.6 mg), and the mixture was stirred at 80° C. for 3.5 hours. The reaction mixture was added with distilled water and ethyl acetate, the layers were separated, and the organic layer was washed successively with distilled water and saturated brine, then dried over anhydrous magnesium sulfate and filtered. The filtrate was concentrated under reduced pressure, and the resulting residue was purified by silica gel column chromatography (chloroform alone to chloroform:methanol:28% aqueous ammonia=20:1:0.1) to obtain an azide compound (158 mg).

(3) The compound obtained in (2) mentioned above (155 mg) was dissolved in ethyl acetate (5 ml), the solution was added with 5% palladium-carbon (30 mg), and the mixture was stirred at room temperature for 18 hours under a hydrogen atmosphere. The reaction mixture was filtered, and the filtrate was concentrated under reduced pressure. The resulting residue was dissolved in ethyl acetate (5 ml), the solution was added with 5% palladium-carbon (100 mg), and the mixture was stirred at room temperature for 4 hours under a hydrogen atmosphere. The reaction mixture was filtered, and the filtrate was concentrated under reduced pressure to obtain an amine compound.
(4) The compound obtained in (3) mentioned above was dissolved in methanol (5 ml), and the solution was stirred at 50° C. for 3 hours and stirred at room temperature for 18 hours. The reaction mixture was concentrated under reduced pressure, and the resulting residue was purified by silica gel column chromatography (chloroform:methanol: 28% aqueous ammonia=30:1:0.1) to obtain the compound shown in Table 4 (78 mg).

Example 183

By using the compound obtained in Example 182 (20 mg) as a starting material, the compound shown in Table 4 (10.9 mg) was obtained in the same manner as that of Example 7, (2).

Example 184

The compound obtained in Example 182 (10 mg) was dissolved in chloroform (0.5 ml), the solution was added with phthalimide acetaldehyde (2.9 mg) and sodium triacetoxyborohydride (4.1 mg), and the mixture was stirred at room temperature for 1 hour. The mixture was further added with phthalimide acetaldehyde (12 mg) and sodium triacetoxyborohydride (16 mg), and the mixture was stirred at room temperature for 1 hour. The reaction mixture was added with saturated aqueous sodium hydrogencarbonate and chloroform, the layers were separated, and the organic layer was washed with saturated brine, then dried over anhydrous magnesium sulfate and filtered. The filtrate was concentrated under reduced pressure, and the resulting residue was purified by silica gel column chromatography (NH-form, chloroform alone) and preparative thin layer chromatography (chloroform:methanol:28% aqueous ammonia=10:1:0.1) to obtain the compound shown in Table 4 (2.1 mg).

Example 185

(1) The compound obtained in Example 182, (3) (10 mg) was dissolved in chloroform (0.5 ml), the solution was added with triethylamine (2 µl) and benzyloxychloroformate (2 µl), and the mixture was stirred at room temperature for 1 hour. The reaction mixture was added with distilled water and chloroform, the layers were separated, and the organic layer was dried over anhydrous magnesium sulfate and filtered. The filtrate was concentrated under reduced pressure to obtain an N-benzyloxycarbonyl compound (12.5 mg).
(2) By using the compound obtained in (1) mentioned above (12 mg) as a starting material, the compound shown in Table 4 (4.3 mg) was obtained in the same manner as that of Example 182, (4).

Example 186

By using the compound obtained in Example 182 (20 mg) and benzaldehyde (3.0 mg) as starting materials, the compound shown in Table 4 (9.3 mg) was obtained in the same manner as that of Example 7, (2).

Example 187

By using the compound obtained in Example 186 (5.8 mg) as a starting material, the compound shown in Table 4 (2.7 mg) was obtained in the same manner as that of Example 7, (2).

Example 188

(1) The compound obtained in Example 176, (3) (10 mg) was dissolved in toluene (0.1 ml), the solution was added with ethyl isocyanate (44 µl) and 4-dimethylaminopyridine (21.3 mg), and the mixture was stirred at 120° C. for 6 hours. The mixture was further added with ethyl isocyanate (88 µl), and the mixture was stirred at 120° C. for 3 hours. The reaction mixture was concentrated under reduced pressure, and the resulting residue was purified by preparative thin layer chromatography (hexane:acetone:triethylamine=10:10:0.2) to obtain a carbamate compound (10.6 mg).
(2) By using the compound obtained in (1) mentioned above (15 mg) as a starting material, the compound shown in Table 4 (3.5 mg) was obtained in the same manner as that of Example 181, (2).

Example 189

(1) The compound obtained in Example 176, (3) (100 mg) was dissolved in toluene (0.5 ml), the solution was added with 2-bromoethyl isocyanate (101 µl), and the mixture was stirred at 120° C. for 1.5 hours. The reaction mixture was concentrated under reduced pressure, and the resulting residue was purified by silica gel column chromatography (hexane:acetone=20:1 to hexane:acetone:triethylamine=10:10:0.2) to obtain a carbamate compound (100 mg).
(2) By using the compound obtained in (1) mentioned above (100 mg) as a starting material, the compound shown in Table 4 (55 mg) was obtained in the same manner as that of Example 181, (2).

Example 190

(1) The compound obtained in Example 189 (20 mg) was dissolved in dimethylformamide (0.5 ml), the solution was added with sodium azide (2.2 mg), and the mixture was stirred at 120° C. for 3 hours. The reaction mixture was added with distilled water and ethyl acetate, the layers were separated, and the organic layer was washed with saturated brine, then dried over anhydrous magnesium sulfate and filtered. The filtrate was concentrated under reduced pressure to obtain an azide compound (18 mg).
(2) The compound obtained in (1) mentioned above (18 mg) was dissolved in a mixed solvent of methanol-ethyl acetate (1:1, 0.3 ml), the solution was added with 5% palladium-carbon (9 mg), and the mixture was stirred at room temperature for 2.5 hours under hydrogen atmosphere. The reaction mixture was filtered, the filtrate was concentrated under reduced pressure, and the resulting residue was purified by silica gel column chromatography (chloroform: methanol:28% aqueous ammonia=10:1:0.1) to obtain the compound shown in Table 4 (7.9 mg).

Example 191

By using the compound obtained in Example 190 (15 mg) as a starting material, the compound shown in Table 4 (3.8 mg) was obtained in the same manner as that of Example 7, (2).

Example 192

By using the compound obtained in Example 190 (15 mg) as a starting material, the compound shown in Table 4 (1.3 mg) was obtained in the same manners as those of Example 185, (1) and Example 182, (4).

Example 193

By using the compound obtained in Example 190 (30 mg) and benzaldehyde (4.35 mg) as starting materials, the compound shown in Table 4 (4.4 mg) was obtained in the same manner as that of Example 7, (2).

Example 194

The compound obtained in Example 176 (0.22 g) was dissolved in ethanol (7 ml), the solution was added with hydrazine monohydrate (0.15 ml), and the mixture was stirred for 7 hours under reflux by heating. The reaction mixture was added with distilled water and chloroform, the layers were separated, and the organic layer was washed with saturated brine, then dried over anhydrous magnesium sulfate and filtered. The filtrate was concentrated under reduced pressure, and the resulting residue was dissolved in ethanol (7 ml), the solution was added with hydrazine monohydrate (0.15 ml), and the mixture was stirred for 7 hours under reflux by heating. The reaction mixture was added with distilled water and chloroform, and the layers were separated. The organic layer was washed with saturated brine, then dried over anhydrous magnesium sulfate and filtered. The filtrate was concentrated under reduced pressure to obtain the compound shown in Table 4 (0.19 g).

Example 195

The compound obtained in Example 194 (190 mg) was dissolved in a mixed solvent of methanol-distilled water (2:1, 4.5 ml), and the solution was added with 3 N hydrochloric acid (150 µl) on a sodium chloride-ice bath. The mixture was slowly added with an aqueous solution (0.6 ml) of sodium nitrite (90 mg). The mixture was further added with 3 N hydrochloric acid (360 µl), and the mixture was adjusted to pH 4, and stirred at the same temperature for 15 minutes. The mixture was successively added with potassium carbonate (201 mg), methanol (1 ml) and sodium borohydride (10 mg), and the mixture was further stirred at the same temperature for 30 minutes. The reaction mixture was adjusted to pH 2 with 3 N hydrochloric acid, and further stirred for 30 minutes. The reaction mixture was added with saturated aqueous sodium hydrogencarbonate and chloroform, the layers were separated, and the organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=30:1:0.1 to 10:1:0.1) to obtain the compound shown in Table 4 (110 mg).

Example 196

The compound obtained in Example 195 (25 mg) was dissolved in diethyl ether (3 ml), the solution was added with methanesulfonyl chloride (50 µl) and an aqueous solution (1 ml) of sodium hydrogencarbonate (15 mg), and the mixture was stirred at room temperature for 50 minutes. The reaction mixture was added with diethyl ether and distilled water, the layers were separated, and the organic layer was dried over anhydrous magnesium sulfate and filtered. The filtrate was concentrated under reduced pressure, and the resulting residue was purified by silica gel column chromatography (chloroform:methanol:28% aqueous ammonia=9:1:0.1) to obtain the compound shown in Table 4 (15 mg).

Example 197

(1) By using the compound obtained in Example 195 (58 mg) and phthalimide acetaldehyde as starting materials, a phthalimide compound (38 mg) was obtained in the same manner as that of Example 7, (2).

(2) The compound obtained in (1) mentioned above (38 mg) was dissolved in ethanol (1 ml), the solution was added with hydrazine monohydrate (1 µl), and the mixture was stirred at room temperature for 16 hours. The reaction mixture was added with saturated aqueous sodium hydrogencarbonate and chloroform, and the layers were separated. The organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=20:1:0.1 to 5:1:0.1) to obtain the compound shown in Table 4 (5 mg).

Example 198

(1) The compound obtained in Example 197, (1) (16 mg) was dissolved in diethyl ether (3 ml), the solution was added with an aqueous solution (1 ml) of sodium hydrogencarbonate (10 mg) and benzyl chloroformate (6 µl), and the mixture was vigorously stirred for 2 hours. The reaction mixture was added with saturated aqueous sodium hydrogencarbonate and diethyl ether, the layers were separated, and the organic layer was washed with saturated brine, then dried over anhydrous magnesium sulfate and filtered. The filtrate was concentrated under reduced pressure, the resulting residue was dissolved in methanol (10 ml), and the solution was stirred at room temperature for 14 hours. The reaction mixture was concentrated under reduced pressure, and the resulting residue was purified by silica gel column chromatography (chloroform:methanol:28% aqueous ammonia=20:1:0.1 to 10:1:0.1) to obtain a 9-N-benzyloxycarbonyl compound (10 mg).

(2) By using the compound obtained in (1) mentioned above (38 mg) as a starting material, the compound shown in Table 4 (7 mg) was obtained in the same manner as that of Example 197, (2).

Example 199

By using the compound obtained in Example 195 (20 mg) and acetyl chloride (3 µl) as starting materials, the compound shown in Table 4 (11 mg) was obtained in the same manner as that of Example 198, (1).

Example 200

By using the compound obtained in Example 195 (30 mg) and benzyl chloroacetate (13 μl) as starting materials, the compound shown in Table 4 (12 mg) was obtained in the same manner as that of Example 198, (1).

Example 201

By using the compound obtained in Example 200 (15 mg) as a starting material, the compound shown in Table 4 (10 mg) was obtained in the same manner as that of Example 81.

Example 202

(1) By using the compound obtained in Example 195 (58 mg) and chloroacetyl chloride (13 μl) as starting materials, a chloromethyl compound (38 mg) was obtained in the same manner as that of Example 198, (1).

(2) The compound obtained in (1) mentioned above (38 mg) was dissolved in dimethylformamide (1 ml), the solution was added with sodium azide (9 mg), and the mixture was stirred for 4 hours on an oil bath at 120° C. The reaction mixture was added with saturated aqueous ammonium chloride and chloroform, the layers were separated, and the organic layer was washed with saturated brine, then dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) to obtain an azide compound (21 mg).

(3) The compound obtained in (2) mentioned above (21 mg) was dissolved in a mixed solvent of methanol-ethyl acetate (1:1, 1 ml), the solution was added with 5% palladium-carbon (21 mg), and the mixture was stirred at room temperature for 5 hours under a hydrogen atmosphere of 1 atm. The reaction mixture was filtered, then the filtrate was concentrated under reduced pressure, and the resulting residue was purified by preparative thin layer chromatography (chloroform:methanol:28% aqueous ammonia=10:1:0.1) to obtain the compound shown in Table 4 (14 mg).

Example 203

By using the compound obtained in Example 202 (8 mg) as a starting material, the compound shown in Table 4 (6 mg) was obtained in the same manner as that of Example 7, (2).

Example 204

The compound obtained in Example 195 (16 mg) was dissolved in dichloromethane (1 ml), the solution was added with ethyl isocyanate (4 μl), and the mixture was stirred at room temperature for 3 hours. The reaction mixture was added with distilled water and chloroform, the layers were separated, and the organic layer was washed with saturated brine, then dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) to obtain the compound shown in Table 4 (9 mg).

Example 205

By using the compound obtained in Example 195 (10 mg) as a starting material, the compound shown in Table 4 (7 mg) was obtained in the same manner as that of Example 7, (2).

Example 206

Synthesis of the Compound Represented by the Formula (K)

[Formula 25]

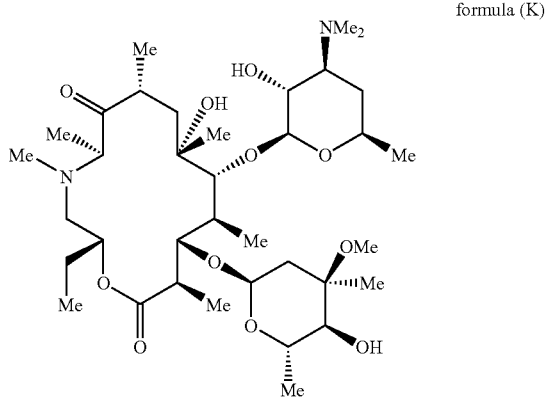

formula (K)

(1) By using the compound obtained in Example 3 as a starting material, a cyclized compound (995 mg) was obtained in the same manners as those of Example 7, (1), (2) and (3).

(2) The compound obtained in (1) mentioned above (500 mg) was dissolved in methanol (5 ml), the solution was added with 20% palladium hydroxide-carbon (100 mg), and the mixture was stirred at room temperature for 24 hours under a hydrogen atmosphere of 1 atm. The reaction mixture was filtered through Celite, then the filtrate was concentrated under reduced pressure, and the resulting residue was purified by silica gel column chromatography (chloroform:methanol:28% aqueous ammonia=100:1:0.1) to obtain a debenzylated compound (500 mg).

(3) By using the compound obtained in (2) mentioned above (400 mg) as a starting material, a 9-ketone compound (421 mg) was obtained in the same manner as that of Example 113, (2).

(4) By using the compound obtained in (3) mentioned above (10 mg) as a starting material, the title compound (5 mg) was obtained in the same manner as that of Example 7, (4).

MS (ESI) m/z=703.5 [M+H]$^+$ $^1$H-NMR (600 MHz, CDCl$_3$) δ (ppm): 0.90 (t, J=7.57 Hz, 3H), 0.93 (d, J=6.42 Hz, 3H), 1.01 (d, J=6.88 Hz, 3H), 1.07 (d, J=7.34 Hz, 3H), 1.11 (d, J=7.34 Hz, 3H), 1.21 (d, J=5.96 Hz, 3H), 1.22 (s, 3H), 1.23-1.25 (m, 1H), 1.26 (d, J=5.96 Hz, 3H), 1.30 (s, 3H), 1.52 (dd, J=15.36, 4.81 Hz, 1H), 1.55-1.88 (m, 5H), 1.95-2.05 (m, 1H), 2.15 (d, J=11.00 Hz, 1H), 2.21 (d, J=14.67 Hz, 1H), 2.29 (s, 6H), 2.37 (d, J=15.13 Hz, 1H), 2.43 (s, 3H), 2.44-2.50 (m, 1H), 2.57 (q, J=6.72 Hz, 1H), 2.66-2.77 (m, 2H), 2.98 (t, J=9.63 Hz, 1H), 3.05 (d, J=13.76 Hz, 1H), 3.18-3.25 (m, 1H), 3.34 (s, 3H), 3.41-3.51 (m, 1H), 3.62 (d, J=7.79 Hz, 1H), 3.97-4.04 (m, 2H), 4.39 (d, J=7.34 Hz, 1H), 4.61-4.65 (m, 1H), 4.80 (d, J=4.59 Hz, 1H), 6.04 (br.s., 1H)

Syntheses of Examples 207 to 213

Preparation methods of compounds represented by the formula (L) having $R^{1L}$, $R^{2L}$ and $R^{3L}$ defined in Table 5 are shown below.

TABLE 5 formula (L)

| Example | $R^{1L}$ | $R^{2L}$ | $R^{3L}$ | ESI MS (M + H) | $^1$H-NMR, CDCl$_3$, δ (ppm) |
|---------|----------|----------|----------|----------------|------------------------------|
| 207 | -O-C(=O)-CH$_2$-(3-pyridyl) | H | Et | 692.5 | (600 MHz): 0.90 (t, J = 7.34 Hz, 3H) 0.97 (d, J = 6.88 Hz, 2H) 1.05 (d, J = 6.42 Hz, 3H) 1.08 (d, J = 7.34 Hz, 3H) 1.10-1.20 (m, 2H) 1.16 (d, J = 6.42 Hz, 3H) 1.22 (d, J = 6.42 Hz, 3H) 1.28 (s, 3H) 1.39 (d, J = 15.13 Hz, 1H) 1.48-1.81 (m, 4H) 1.96-2.03 (m, 1H) 2.05-2.11 (m, 1H) 2.26 (s, 6H) 2.31-2.38 (m, 1H) 2.72-2.80 (m, 1H) 3.02 (dd, J = 15.13, 9.63 Hz, 1H) 3.11 (dd, J = 10.09, 7.34 Hz, 1H) 3.13-3.19 (m, 1H) 3.21 (s, 3H) 3.54 (dd, J = 10.09, 2.75 Hz, 1H) 3.62-3.73 (m, J = 2.75 Hz, 2H) 3.69 (d, J = 2.75 Hz, 2H) 3.79 (d, J = 4.59 Hz, 2H) 3.95 (d, J = 7.34 Hz, 1H) 4.96-5.02 (m, 1H) 5.20 (d, J = 10.55 Hz, 1H) 7.28 (dd, J = 7.79, 4.13 Hz, 1H) 7.71 (dt, J = 8.14, 1.95, 1.83 Hz, 1H) 8.53 (dd, J = 5.04, 1.38 Hz, 1H) 8.54 (d, J = 1.83 Hz, 1H) |
| 208 | -O-C(=O)-CH$_2$-(2-pyridyl) | H | Et | 692.5 | (600 MHz): 0.90 (t, J = 7.57 Hz, 3H) 1.05 (t, 9H) 1.08-1.25 (m, 2H) 1.17 (d, J = 5.96 Hz, 3H) 1.21 (d, J = 6.42 Hz, 3H) 1.29 (s, 3H) 1.41 (d, J = 14.67 Hz, 1H) 1.49-1.66 (m, 3H) 1.96-2.03 (m, 1H) 2.05-2.12 (m, 1H) 2.29 (s, 6H) 2.49-2.57 (m, 1H) 2.73-2.79 (m, 1H) 3.01 (dd, J = 15.13, 9.63 Hz, 1H) 3.15 (dd, J = 10.32, 7.11 Hz, 1H) 3.22 (s, 3H) 3.33-3.40 (m, 1H) 3.53 (dd, J = 10.32, 2.52 Hz, 1H) 3.67-3.73 (m, 2H) 3.84 (d, J = 4.58 Hz, 1H) 3.90 (d, J = 3.21 Hz, 2H) 4.11 (d, J = 7.34 Hz, 1H) 4.96-5.02 (m, 1H) 5.20 (d, J = 10.55 Hz, 1H) 7.18-7.21 (m, 1H) 7.34 (d, J = 7.79 Hz, 1H) 7.66 (dt, J = 7.57, 1.83 Hz, 1H) 8.51-8.53 (m, 1H) |
| 209 | cladinosyl | H | Et | 731.5 | (500 MHz): 0.92 (t, J = 7.62 Hz, 3H) 1.07 (d, J = 7.62 Hz, 3H) 1.07 (d, J = 6.70 Hz, 3H) 1.17 (d, J = 7.31 Hz, 3H) 1.17-1.30 (m, 2H) 1.22 (d, J = 6.10 Hz, 3H) 1.24 (s, 3H) 1.25 (d, J = 6.40 Hz, 3H) 1.29 (d, J = 6.40 Hz, 3H) 1.37 (s, 3H) 1.44-1.68 (m, 5H) 1.75-1.82 (m, 1H) 2.05-2.12 (m, 1H) 2.27 (s, 3H) 2.27 (s, 6H) 2.66-2.73 (m, 1H) 2.98-3.10 (m, 2H) 3.16 (dd, J = 10.21, 7.16 Hz, 1H) 3.22 (s, 3H) 3.31 (s, 3H) 3.42-3.48 (m, 1H) 3.58 (dd, J = 10.21, 3.50 Hz, 1H) 3.66 (d, J = 7.92 Hz, 1H) 3.74-3.79 (m, 1H) 3.89-3.92 (m, 1H) 3.95 (d, J = 8.23 Hz, 1H) 3.97-4.04 (m, 1H) 4.35 (d, J = 7.31 Hz, 1H) 4.81-4.86 (m, 1H) 4.89 (d, J = 4.57 Hz, 1H) |

TABLE 5-continued formula (L)

| Example | R1L | R2L | R3L | ESI MS (M + H) | 1H-NMR, CDCl3, δ (ppm) |
|---------|-----|-----|-----|----------------|------------------------|
| 210 | cladinosyl | H | 3-(furan-2-yl)phenyl-CH2-C(O)NH-CH2- | 930.6 | (300 MHz): 0.81-1.40 (m, 17H) 1.13 (d, J = 7.31 Hz, 3H) 1.32 (d, J = 6.22 Hz, 3H) 1.36 (s, 3H) 1.41-1.81 (m, 5H) 1.97-2.12 (m, 2H) 2.21-2.51 (m, 3H) 2.28 (s, 6H) 2.61-2.73 (m, 1H) 2.78-2.92 (m, 1H) 2.99-3.72 (m, 8H) 3.12 (s, 3H) 3.30 (s, 3H) 3.60 (s, 2H) 3.79-3.86 (m, 1H) 3.89 (d, J = 7.62 Hz, 1H) 4.00 (d, 1H) 4.34 (d, J = 6.99 Hz, 1H) 4.81 (d, J = 4.35 Hz, 1H) 4.82-4.91 (m, 1H) 6.15-6.23 (m, 1H) 6.47 (dd, J = 3.34, 1.79 Hz, 1H) 6.67 (d, J = 2.49 Hz, 1H) 7.19 (d, J = 7.46 Hz, 1H) 7.35 (t, J = 7.93 Hz, 1H) 7.46 (d, J = 1.55 Hz, 1H) 7.55-7.61 (m, 2H) |
| 211 | =O | =O | 3-(furan-2-yl)phenyl-CH2-C(O)NH-CH2- | 770.5 | (300 MHz): 1.05 (d, J = 6.84 Hz, 3H) 1.12-1.91 (m, 15H) 1.29 (s, 3H) 1.39 (d, J = 6.99 Hz, 3H) 2.02-2.16 (m, 1H) 2.27 (s, 6H) 2.40-2.52 (m, 1H) 2.69-3.08 (m, 4H) 3.14-3.23 (m, 1H) 3.46-3.68 (m, 3H) 3.59 (s, 3H) 3.65 (s, 2H) 3.72-3.81 (m, 1H) 3.97-4.06 (m, 2H) 4.32 (d, J = 7.77 Hz, 1H) 4.87-4.98 (m, 1H) 6.17-6.23 (m, 1H) 6.47 (dd, J = 3.11, 2.02 Hz, 1H) 6.68 (d, J = 2.80 Hz, 1H) 7.17-7.22 (m, 1H) 7.36 (t, J = 7.77 Hz, 1H) 7.46-7.48 (m, 1H) 7.55-7.61 (m, 2H) |
| 212 | cladinosyl | H | 3-(furan-2-yl)phenyl-C(O)NH-CH2-CH2- | 930.5 | (600 MHz): 1.03-1.07 (m, 6H) 1.14 (d, J = 7.34 Hz, 3H) 1.15-1.27 (m, 2H) 1.21 (d, J = 5.96 Hz, 3H) 1.23 (s, 3H) 1.25 (s, 3H) 1.28 (d, J = 5.96 Hz, 3H) 1.36 (s, 3H) 1.47 (d, J = 16.51 Hz, 1H) 1.51 (dd, J = 15.13, 5.04 Hz, 1H) 1.54-1.84 (m, 6H) 2.02-2.12 (m, 1H) 2.20-2.37 (m, 8H) 2.66-2.75 (m, 1H) 3.01 (t, J = 9.86 Hz, 1H) 3.08 (dd, J = 15.13, 9.63 Hz, 1H) 3.13-3.22 (m, 1H) 3.20 (s, 3H) 3.29 (s, 3H) 3.35-3.51 (m, 3H) 3.59 (dd, J = 10.09, 3.67 Hz, 1H) 3.66 (d, J = 7.79 Hz, 1H) 3.74-3.79 (m, 1H) 3.85-3.91 (m, 1H) 3.93 (d, J = 7.79 Hz, 1H) 3.95-4.03 (m, 1H) 4.35 (d, J = 6.88 Hz, 1H) 4.85 (d, J = 4.59 Hz, 1H) 4.89 (s, 1H) 6.48 (dd, J = 3.67, 1.83 Hz, 1H) 6.49-6.53 (m, 1H) 6.73-6.76 (m, 1H) 7.42 (t, J = 7.79 Hz, 1H) 7.47 (d, J = 1.83 Hz, 1H) 7.62-7.66 (m, 1H) 7.75-7.79 (m, 1H) 8.03-8.07 (m, 1H) |

TABLE 5-continued

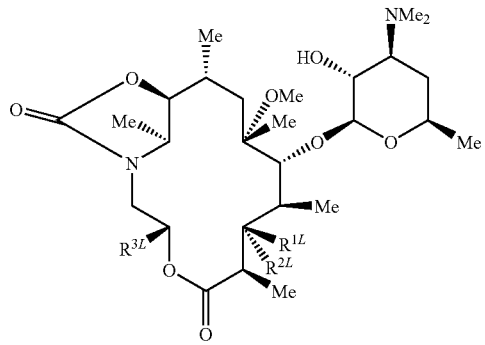

formula (L)

| Example | $R^{1L}$ | $R^{2L}$ | $R^{3L}$ | ESI MS (M + H) | $^1$H-NMR, CDCl$_3$, δ (ppm) |
|---|---|---|---|---|---|
| 213 | | | 3-(furan-2-yl)benzamide propyl | 770.5 | (600 MHz): 1.04 (d, J = 6.88 Hz, 3H) 1.20 (d, J = 5.96 Hz, 3H) 1.21-1.29 (m, 11H) 1.35 (d, J = 6.88 Hz, 3H) 1.45-1.79 (m, 6H) 2.08-2.20 (m, 1H) 2.27 (s, 6H) 2.38-2.53 (m, 1H) 2.76 (s, 3H) 2.86-2.95 (m, 1H) 3.04 (dd, J = 15.13, 10.55 Hz, 1H) 3.13-3.23 (m, 1H) 3.35-3.53 (m, 2H)3.53-3.81 (m, 4H) 4.00-4.11 (m, 2H) 4.29 (d, J = 7.34 Hz, 1H) 4.83-4.90 (m, 1H) 6.47 (dd, J = 3.67, 1.83 Hz, 1H) 6.48-6.55 (m, 1H) 6.77 (d, J = 4.13 Hz, 1H) 7.41 (t, J = 7.79 Hz, 1H) 7.45-7.49 (m, 1H) 7.61-7.65 (m, 1H) 7.74-7.78 (m, 1H) 8.04-8.07 (m, 1H) |

Example 207

(1) The compound obtained in Example 125, (2) (74 mg) and pyridine (83 μl) were dissolved in chloroform, the solution was added with triphosgene (91 mg), and the mixture was stirred at room temperature for 9 hours. The reaction mixture was added with saturated aqueous sodium hydrogencarbonate and chloroform, the layers were separated, and the organic layer was dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) to obtain a 9,10a-cyclic carbamate compound (52 mg).
(2) By using the compound obtained in (1) mentioned above (52 mg) as a starting material, the compound shown in Table 5 (40 mg) was obtained in the same manner as that of Example 125, (3).

Example 208

By using the compound obtained in Example 112 (97 mg) as a starting material, the compound shown in Table 5 (19 mg) was obtained in the same manners as those of Example 176, (3), Example 207, (1) and Example 125, (3).

Example 209

(1) By using the compound obtained in Example 176, (3) (50 mg) as a starting material, a 9,10a-cyclic carbamate compound (14.4 mg) was obtained in the same manner as that of Example 207, (1).
(2) By using the compound obtained in (1) mentioned above as a starting material, the compound shown in Table 5 (5.0 mg) was obtained in the same manner as that of Example 176, (5).

Example 210

(1) By using the compound obtained in Example 23 (32 mg) as a starting material, a 9,10a-cyclic carbamate compound (10.5 mg) was obtained in the same manners as those of Example 176, (3) and Example 207 (1).
(2) By using the compound obtained in (1) mentioned above (10.5 mg) as a starting material, the compound shown in Table 5 (4.4 mg) was obtained in the same manner as that of Example 125, (3).

Example 211

(1) The compound obtained in Example 210, (1) (32 mg) was dissolved in 1 N hydrochloric acid (1 ml) and ethanol (1 ml), and the solution was stirred at room temperature for 18 hours. The reaction mixture was neutralized with 1 N aqueous sodium hydroxide, and then extracted with chloroform, and the organic layer was dried over anhydrous magnesium sulfate and filtered. The filtrate was concentrated under reduced pressure, and the resulting residue was purified by column chromatography (chloroform:methanol:28% aqueous ammonia=20:1:0.1), and by using the resulting compound (7.5 mg) as a starting material, a 2'-O-acetyl compound (7.4 mg) was obtained in the same manner as that of Example 113, (2).
(2) By using the compound obtained in (1) mentioned above (7.4 mg) as a starting material, the compound shown in Table 5 (5.0 mg) was obtained in the same manner as that of Example 125, (3).

Example 212

(1) By using the compound obtained in Example 38 (82 mg) as a starting material, a 9,10a-cyclic carbamate compound (23.0 mg) was obtained in the same manners as those of Example 176, (3) and Example 207, (1).

(3) By using the compound obtained in (2) mentioned above (5.0 mg) as a starting material, the compound shown in Table 5 (2.8 mg) was obtained in the same manner as that of Example 125, (3).

Example 213

By using the compound obtained in Example 212, (1) (17 mg) as a starting material, the compound shown in Table 5 (2.5 mg) was obtained in the same manners as those of Example 211, (1) and Example 125, (3).

Syntheses of Examples 214 to 235

Preparation methods of compounds represented by the formula (M) having $R^{1M}$, $R^{2M}$, and $R^{3M}$ defined in Table 6 are shown below.

TABLE 6

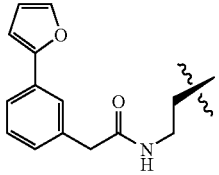

formula (M)

| Example | $R^{1M}$ | $R^{3M}$ | ESI MS (M + H) | $^1$H-NMR, CDCl$_3$, δ (ppm) |
|---|---|---|---|---|
| 214 | Et | H | 732.5 | (300 MHz): 0.89 (t, J = 7.54 Hz, 3H) 1.06 (d, J = 6.84 Hz, 3H) 1.10 (d, J = 7.46 Hz, 3H) 1.20 (t, 16H) 1.30 (s, 3H) 1.46-1.72 (m, 5H) 1.89-2.77 (m, 8H) 2.11 (s, 3H) 2.28 (s, 6H) 2.96-3.06 (m, 1H) 3.25-3.30 (m, 1H) 3.27 (s, 3H) 3.34 (s, 3H) 3.44-3.62 (m, 3H) 3.68 (d, J = 6.99 Hz, 1H) 3.92 (dd, J = 5.28, 1.55 Hz, 1H) 3.96-4.08 (m, 1H) 4.48 (d, J = 7.46 Hz, 1H) 4.80-4.92 (m, 1H) 4.89 (d, J = 4.97 Hz, 1H) |
| 215 | H | H | 704.4 | (300 MHz): 1.03-1.40 (m, 16H) 1.05 (d, J = 6.99 Hz, 3H) 1.11 (d, J = 7.77 Hz, 3H) 1.28 (s, 3H) 1.48-1.70 (m, 5H) 1.97-2.54 (m, 5H) 2.19 (s, 3H) 2.29 (s, 6H) 2.63-2.91 (m, 3H) 3.01 (t, J = 9.64 Hz, 1H) 3.23-3.37 (m, 1H) 3.25 (s, 3H) 3.34 (s, 3H) 3.47-3.59 (m, 1H) 3.63-3.74 (m, 2H) 3.94-4.06 (m, 2H) 4.20-4.31 (m, 1H) 4.50 (d, J = 7.31 Hz, 1H) 4.66 (d, J = 4.35 Hz, 1H) |
| 216 | 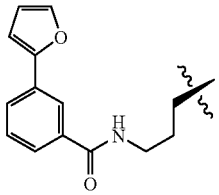 | H | 931.7 | (300 MHz): 1.00-1.17 (m, 12H) 1.23 (d, J = 6.37 Hz, 3H) 1.24-1.29 (m, 1H) 1.26 (s, 3H) 1.26-1.29 (m, 3H) 1.32 (s, 3H) 1.38-1.74 (m, 5H) 2.04-2.24 (m, 3H) 2.17 (s, 3H) 2.30 (s, 6H) 2.32-2.57 (m, 3H) 2.64-2.95 (m, 3H) 3.02 (t, J = 9.79 Hz, 1H) 3.25 (s, 3H) 3.30-3.33 (m, 1H) 3.33 (s, 3H) 3.39 (d, J = 7.15 Hz, 1H) 3.43-3.62 (m, 3H) 3.58 (s, 2H) 3.66 (d, J = 6.22 Hz, 1H) 3.80 (d, J = 7.15 Hz, 1H) 3.95-4.08 (m, 1H) 4.45 (d, J = 7.31 Hz, 1H) 4.60 (s, 1H) 4.86 (d, J = 4.66 Hz, 1H) 6.23 (s, 1H) 6.46 (dd, J = 3.42, 1.87 Hz, 1H) 6.68 (dd, J = 3.26, 0.78 Hz, 1H) 7.15-7.22 (m, 1H) 7.35 (t, J = 7.69 Hz, 1H) 7.44-7.48 (m, 1H) 7.54-7.62 (m, 2H) |
| 217 | (furan-phenyl-C(O)NH-CH(Me)-) | H | 931.4 | (600 MHz): 1.07-1.15 (m, 6H) 1.16-1.21 (m, 6H) 1.25 (d, J = 5.96 Hz, 3H) 1.26-1.32 (m, 7H) 1.35-1.36 (m, 3H) 1.46-1.88 (m, 7H) 2.01-2.06 (m, 1H) 2.15-2.35 (m, 1H) 2.26-2.30 (m, 3H) 2.31-2.32 (m, 6H) 2.36-2.52 (m, 2H) 2.68-2.82 (m, 3H) 3.04 (t, J = 9.63 Hz, 1H) 3.24-3.42 (m, 1H) 3.26-3.28 (m, 3H) 3.35-3.36 (m, 3H) 3.42-3.49 (m, 1H) 3.49-3.58 (m, 1H) 3.59-3.81 (m, 3H) 3.68 (d, J = 8.71 Hz, 1H) 3.85-3.89 (m, 1H) 4.02-4.09 (m, 1H) 4.48 (d, J = 7.34 Hz, 1H) 4.71 (s, 1H) 4.89-4.93 (m, 1H) 6.50-6.54 (m, 1H) 6.78 (d, J = 2.75 Hz, 1H) 7.13-7.18 (m, 1H) 7.39-7.43 (m, 1H) 7.44-7.53 (m, 3H) |

TABLE 6-continued formula (M)

| Example | R[1M] | R[3M] | ESI MS (M + H) | $^1$H-NMR, CDCl$_3$, δ (ppm) |
|---|---|---|---|---|
| 218 | Et | H | 693.6 | (600 MHz): 0.86 (t, J = 7.57 Hz, 3H) 0.97-1.25 (m, 8H) 0.99 (d, J = 6.88 Hz, 3H) 1.08 (d, J = 6.88 Hz, 3H) 1.15 (d, J = 6.42 Hz, 3H) 1.27 (s, 3H) 1.42-1.66 (m, 3H) 1.97-2.05 (m, 1H) 2.25 (s, 3H) 2.30 (s, 6H) 2.44-2.64 (m, 3H) 2.68-2.73 (m, 1H) 2.75-2.81 (m, 1H) 3.12 (s, 3H) 3.21 (dd, J = 10.09, 7.34 Hz, 1H) 3.24-3.28 (m, 1H) 3.33-3.39 (m, 1H) 3.40-3.47 (m, 1H) 3.72 (d, J = 4.13 Hz, 1H) 3.87-3.96 (m, 2H) 4.11 (d, J = 7.34 Hz, 1H) 4.86-4.93 (m, 1H) 5.11 (d, J = 11.00 Hz, 1H) 7.18 (dd, J = 7.79, 4.13 Hz, 1H) 7.36 (d, J = 8.25 Hz, 1H) 7.66 (td, J = 7.57, 1.83 Hz, 1H) 8.52 (d, J = 4.58 Hz, 1H) |
| 219 | allyl-O-C(O)-NH-CH(CH$_3$)- | H | 817.7 | (500 MHz): 1.04-1.09 (m, 6H) 1.11 (d, J = 6.86 Hz, 3H) 1.15 (d, J = 7.13 Hz, 3H) 1.19-1.33 (m, 7H) 1.21 (d, J = 6.31 Hz, 3H) 1.30 (s, 3H) 1.45-1.74 (m, 3H) 1.94-2.10 (m, 2H) 2.13-2.23 (m, 4H) 2.29 (s, 6H) 2.37 (d, J = 15.08 Hz, 1H) 2.42-2.52 (m, 1H) 2.57-2.67 (m, 1H) 2.68-2.75 (m, 1H) 2.78-2.85 (m, 1H) 3.00 (t, J = 9.87 Hz, 1H) 3.14-3.36 (m, 2H) 3.22 (s, 3H) 3.32 (s, 3H) 3.39-3.60 (m, 4H) 3.65 (d, J = 7.13 Hz, 1H) 3.86 (d, J = 6.03 Hz, 1H) 3.95-4.05 (m, 1H) 4.45 (d, J = 7.13 Hz, 1H) 4.50-4.62 (m, 2H) 4.73-4.86 (m, 2H) 5.12-5.23 (m, 2H) 5.29 (d, J = 16.45 Hz, 1H) 5.82-5.99 (m, 1H) |
| 220 | Bn-O-C(O)-NH-CH(CH$_3$)- | H | 867.8 | (600 MHz): 1.01-1.08 (m, 6H) 1.08-1.16 (m, 6H) 1.18-1.56 (m, 4H) 1.20-1.26 (m, 9H) 1.29 (s, 3H) 1.96-2.07 (m, 2H) 2.13-2.17 (m, 6H) 2.21-2.48 (m, 6H) 2.58-2.84 (m, 2H) 2.96-3.05 (m, 1H) 3.22 (s, 3H) 3.24-3.33 (m, 1H) 3.31-3.32 (m, 3H) 3.36-3.59 (m, 5H) 3.65 (d, J = 7.34 Hz, 1H) 3.82-3.87 (m, 1H) 3.95-4.02 (m, 1H) 4.46 (d, J = 7.34 Hz, 1H) 4.77-4.87 (m, 2H) 5.09 (d, J = 4.58 Hz, 2H) 5.16 (s, 1H) 7.29-7.38 (m, 5H) |
| 221 | Bn-O-CH$_2$CH$_2$-CH(CH$_3$)- | H | 852.7 | (600 MHz): 1.04 (d, J = 6.42 Hz, 3H) 1.08 (d, J = 7.34 Hz, 3H) 1.12 (d, J = 6.88 Hz, 3H) 1.14 (d, J = 7.34 Hz, 3H) 1.21 (d, J = 5.96 Hz, 3H) 1.22-1.28 (m, 4H) 1.23 (s, 3H) 1.29 (s, 3H) 1.51-1.69 (m, 7H) 1.90-1.96 (m, 1H) 1.99-2.05 (m, 1H) 2.10 (s, 3H) 2.15 (d, J = 10.55 Hz, 1H) 2.29 (s, 6H) 2.30-2.35 (m, 1H) 2.37 (d, J = 15.13 Hz, 1H) 2.43-2.52 (m, 1H) 2.56-2.62 (m, 1H) 2.65-2.74 (m, 2H) 3.00 (t, J = 9.86 Hz, 1H) 3.25 (s, 3H) 3.26-3.33 (m, 2H) 3.32 (s, 3H) 3.42-3.49 (m, 2H) 3.49-3.54 (m, 1H) 3.54-3.60 (m, 1H) 3.67 (d, J = 6.88 Hz, 1H) 3.88-3.91 (m, 1H) 3.99-4.02 (m, 1H) 4.47 (d, J = 7.34 Hz, 1H) 4.48 (s, 2H) 4.88 (d, J = 4.59 Hz, 1H) 4.88-4.94 (m, 1H) 7.26-7.36 (m, 5H) |

TABLE 6-continued formula (M)

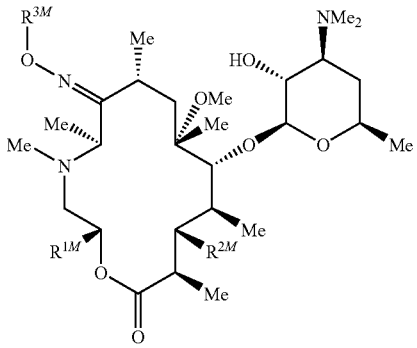

| Example | R$^{1M}$ | R$^{3M}$ | ESI MS (M + H) | $^1$H-NMR, CDCl$_3$, δ (ppm) |
|---|---|---|---|---|
| 222 | HO-CH₂CH₂-C(Me)(H)- (R configuration) | H | 762.7 | (600 MHz): 1.05-1.09 (m, 6H) 1.12 (d, J = 6.88 Hz, 3H) 1.15 (d, J = 7.34 Hz, 3H) 1.17-1.29 (m, 7H) 1.21 (d, J = 5.96 Hz, 3H) 1.30 (s, 3H) 1.50-1.74 (m, 7H) 1.99-2.10 (m, 2H) 2.16 (s, 3H) 2.21-2.25 (m, 1H) 2.30 (s, 6H) 2.37 (d, J = 15.13 Hz, 1H) 2.45-2.60 (m, 2H) 2.68-2.74 (m, 1H) 2.76-2.83 (m, 1H) 3.00 (t, J = 9.63 Hz, 1H) 3.24 (s, 3H) 3.29-3.31 (m, 1H) 3.32 (s, 3H) 3.43-3.48 (m, 1H) 3.49-3.54 (m, 1H) 3.54-3.60 (m, 1H) 3.61-3.70 (m, 3H) 3.87 (d, J = 5.50 Hz, 1H) 3.97-4.04 (m, 1H) 4.46 (d, J = 6.88 Hz, 1H) 4.80-4.85 (m, 1H) 4.87 (d, J = 4.58 Hz, 1H) |
| 223 | Et | CH₂=CH-CH₂-C(Me)(H)- | 772.8 | (500 MHz): 0.87 (t, J = 7.26 Hz, 3H) 1.04 (d, J = 6.88 Hz, 3H) 1.07 (d, J = 7.65 Hz, 3H) 1.10 (d, J = 6.88 Hz, 3H) 1.15 (d, J = 6.88 Hz, 3H) 1.24 (d, 13H) 1.58 (d, 5H) 1.90 (d, J = 14.53 Hz, 1H) 2.00-2.05 (m, 1H) 2.10 (s, 3H) 2.27 (s, 6H) 2.37 (d, J = 15.29 Hz, 1H) 2.42-2.49 (m, 1H) 2.52-2.60 (m, 1H) 2.65-2.74 (m, 2H) 2.99 (d, J = 9.17 Hz, 1H) 3.20 (s, 3H) 3.26-3.34 (m, 1H) 3.32 (s, 3H) 3.40-3.47 (m, 1H) 3.47-3.60 (m, 2H) 3.66 (d, J = 6.88 Hz, 1H) 3.88 (d, J = 3.06 Hz, 1H) 3.96-4.05 (m, 1H) 4.46 (d, J = 6.88 Hz, 1H) 4.49 (d, J = 4.59 Hz, 2H) 4.74-4.86 (m, 1H) 4.88 (d, J = 4.59 Hz, 1H) 5.12 (d, J = 9.94 Hz, 1H) 5.25 (d, J = 16.05 Hz, 1H) 5.87-6.02 (m, 1H) |
| 224 | Et | H₂N-CH₂CH₂-C(Me)(H)- | | (600 MHz): 0.87 (t, J = 7.57 Hz, 3H) 1.06 (d, J = 6.88 Hz, 3H) 1.08 (d, J = 7.34 Hz, 3H) 1.11 (d, J = 7.34 Hz, 3H) 1.12 (m, 1H) 1.16 (d, J = 6.88 Hz, 3H) 1.22 (d, J = 5.96 Hz, 3H) 1.23 (d, J = 6.42 Hz, 3H) 1.23 (s, 3H) 1.27 (s, 3H) 1.54-1.67 (m, 5H) 1.90 (d, J = 14.67 Hz, 1H) 1.99-2.04 (m, 1H) 2.10 (s, 3H) 2.29 (s, 6H) 2.38 (d, J = 15.13 Hz, 1H) 2.45-2.51 (m, 1H) 2.55-2.61 (m, 1H) 2.72 (s, 2H) 2.95-3.02 (m, 3H) 3.23 (s, 3H) 3.30-3.31 (m, 1H) 3.32 (s, 3H) 3.41-3.45 (m, 1H) 3.47-3.57 (m, 2H) 3.67-3.68 (m, 1H) 3.86-3.90 (m, 1H) 3.98-4.02 (m, 1H) 4.03-4.10 (m, 2H) 4.47 (d, J = 7.34 Hz, 1H) 4.81-4.84 (m, 1H) 4.89 (d, J = 4.59 Hz, 1H) |
| 225 | Et | PhCH₂O-CH₂CH₂-C(Me)(H)- | 866.8 | (500 MHz): 0.87 (t, J = 7.54 Hz, 3H) 1.04 (d, J = 6.58 Hz, 3H) 1.08 (d, J = 7.40 Hz, 3H) 1.11 (d, J = 6.86 Hz, 3H) 1.16 (d, J = 7.13 Hz, 3H) 1.20 (d, J = 6.03 Hz, 3H) 1.21-1.31 (m, 1H) 1.21-1.24 (m, 3H) 1.23 (s, 3H) 1.28 (s, 3H) 1.52-1.66 (m, 5H) 1.92 (d, J = 14.54 Hz, 1H) 2.01-2.07 (m, 1H) 2.11 (s, 3H) 2.13-2.22 (m, 1H) 2.27 (s, 6H) 2.38 (d, J = 15.08 Hz, 1H) 2.42-2.51 (m, 1H) 2.52-2.61 (m, 1H) 2.65-2.75 (m, 2H) 2.95-3.03 (m, 1H) 3.20 (s, 3H) 3.25-3.36 (m, 1H) 3.32 (s, 3H) 3.38-3.47 (m, 1H) 3.47-3.58 (m, 2H) 3.62-3.75 (m, 3H) 3.89 (d, J = 5.48 Hz, 1H) 3.96-4.05 (m, 1H) 4.12-4.22 (m, 2H) 4.46 (d, J = 7.13 Hz, 1H) 4.50-4.58 (m, 2H) 4.78-4.86 (m, 1H) 4.89 (d, J = 4.66 Hz, 1H) 7.21-7.35 (m, 5H) |

TABLE 6-continued formula (M)

| Example | R$^{1M}$ | R$^{3M}$ | ESI MS (M + H) | $^1$H-NMR, CDCl$_3$, δ (ppm) |
|---|---|---|---|---|
| 226 | Et | HO–C(Me)(–)–CH$_2$– (3-hydroxy-3-methylpropyl group) | 776.8 | (500 MHz): 0.88 (t, J = 7.54 Hz, 3H) 1.05 (d, J = 6.86 Hz, 3H) 1.07 (d, J = 7.40 Hz, 3H) 1.12 (d, J = 6.86 Hz, 3H) 1.16 (d, J = 7.13 Hz, 3H) 1.18-1.36 (m, 13H) 1.46-1.74 (m, 5H) 1.80-1.87 (m, 1H) 1.96-2.03 (m, 1H) 2.08 (s, 3H) 2.14 (d, J = 10.97 Hz, 1H) 2.31 (s, 6H) 2.37 (d, J = 15.36 Hz, 1H) 2.42-2.56 (m, 1H) 2.58-2.65 (m, 1H) 2.65-2.74 (m, 2H) 3.01 (t, J = 9.19 Hz, 1H) 3.26 (s, 3H) 3.28-3.34 (m, 1H) 3.32 (s, 3H) 3.42-3.59 (m, 3H) 3.62-3.66 (m, 1H) 3.73-3.85 (m, 2H) 3.87-3.92 (m, 1H) 3.95-4.03 (m, 1H) 4.13 (t, J = 4.25 Hz, 2H) 4.47 (d, J = 7.40 Hz, 1H) 4.79-4.86 (m, 1H) 4.88 (d, J = 4.39 Hz, 1H) |
| 227 | Et | Me$_2$N–CH$_2$–C(Me)(–)– (dimethylaminomethyl branched) | 803.8 | (500 MHz): 0.87 (t, J = 7.54 Hz, 3H) 1.05 (d, J = 6.86 Hz, 3H) 1.06-1.10 (m, 6H) 1.15 (d, J = 7.13 Hz, 3H) 1.18-1.30 (m, 13H) 1.51-1.81 (m, 5H) 1.84-1.95 (m, 1H) 1.97-2.08 (m, 1H) 2.11 (s, 3H) 2.15 (d, J = 9.87 Hz, 1H) 2.23-2.34 (m, 12H) 2.38 (d, J = 15.63 Hz, 1H) 2.42-2.51 (m, 1H) 2.52-2.76 (m, 5H) 3.00 (t, J = 10.56 Hz, 1H) 3.20 (s, 3H) 3.27-3.35 (m, 1H) 3.33 (s, 3H) 3.40-3.47 (m, 1H) 3.47-3.57 (m, 2H) 3.67 (d, J = 6.86 Hz, 1H) 3.88 (d, J = 6.58 Hz, 1H) 3.94-4.05 (m, 1H) 4.07-4.19 (m, 2H) 4.47 (d, J = 7.13 Hz, 1H) 4.77-4.86 (m, 1H) 4.89 (d, J = 4.66 Hz, 1H) |
| 228 | Et | PhCH$_2$–O–C(O)–CH$_2$–C(Me)(–)– (benzyloxycarbonyl-substituted) | 880.8 | (500 MHz): 0.87 (t, J = 7.54 Hz, 3H) 1.01 (d, J = 6.86 Hz, 3H) 1.08 (d, J = 7.40 Hz, 3H) 1.11 (d, J = 7.13 Hz, 3H) 1.16 (d, J = 7.13 Hz, 3H) 1.21 (d, J = 6.31 Hz, 3H) 1.20-1.30 (m, 1H) 1.23 (s, 3H) 1.25 (d, J = 6.31 Hz, 3H) 1.28 (s, 3H) 1.49-1.72 (m, 5H) 1.93-2.08 (m, 2H) 2.10 (s, 3H) 2.16 (d, J = 10.42 Hz, 1H) 2.30 (br. s., 6H) 2.37 (d, J = 14.81 Hz, 1H) 2.43-2.59 (m, 2H) 2.64-2.75 (m, 2H) 3.00 (t, J = 9.87 Hz, 1H) 3.21 (s, 3H) 3.27-3.35 (m, 1H) 3.32 (s, 3H) 3.37-3.45 (m, 1H) 3.46-3.57 (m, 2H) 3.66 (d, J = 6.86 Hz, 1H) 3.89 (d, J = 5.48 Hz, 1H) 3.96-4.05 (m, 1H) 4.46 (d, J = 7.13 Hz, 1H) 4.59 (d, J = 3.29 Hz, 2H) 4.76-4.86 (m, 1H) 4.89 (d, J = 4.39 Hz, 1H) 5.12-5.21 (m, 2H) 7.27-7.37 (m, 5H) |
| 229 | Et | H$_2$N–(CH$_2$)$_3$– (3-aminopropyl) | 789.8 | (500 MHz): 0.88 (t, J = 7.26 Hz, 3H) 1.04-1.10 (m, 6H) 1.11 (d, J = 6.88 Hz, 3H) 1.16 (d, J = 6.88 Hz, 3H) 1.19-1.38 (m, 13H) 1.51-1.61 (m, 3H) 1.61-1.72 (m, 2H) 1.74-1.82 (m, 2H) 1.86-1.93 (m, 1H) 2.01-2.07 (m, 1H) 2.14 (s, 3H) 2.29 (s, 6H) 2.38 (d, J = 15.29 Hz, 1H) 2.44-2.52 (m, 1H) 2.53-2.60 (m, 1H) 2.66-2.75 (m, 2H) 2.77-2.84 (m, 2H) 3.00 (d, J = 9.17 Hz, 1H) 3.22 (s, 3H) 3.26-3.34 (m, 1H) 3.33 (s, 3H) 3.35-3.40 (m, 1H) 3.40-3.47 (m, 1H) 3.47-3.57 (m, 1H) 3.67 (d, J = 6.88 Hz, 1H) 3.89 (d, J = 6.12 Hz, 1H) 3.97-4.04 (m, 1H) 4.04-4.11 (m, 2H) 4.45 (d, J = 6.88 Hz, 1H) 4.77-4.86 (m, 1H) 4.90 (d, J = 4.59 Hz, 1H) |

TABLE 6-continued formula (M)

| Example | $R^{1M}$ | $R^{3M}$ | ESI MS (M + H) | $^1$H-NMR, CDCl$_3$, δ (ppm) |
|---|---|---|---|---|
| 230 | Et | HO-C(=O)-CH$_2$-C(CH$_3$)$_2$- | 790.7 | (600 MHz): 0.86 (t, J = 7.57 Hz, 3H) 1.05 (d, J = 7.34 Hz, 3H) 1.07 (d, J = 6.42 Hz, 3H) 1.13 (d, J = 6.88 Hz, 3H) 1.15 (d, J = 6.88 Hz, 3H) 1.19-1.36 (m, 13H) 1.48-1.59 (m, 3H) 1.72-1.87 (m, 2H) 1.89-1.97 (m, 1H) 1.99-2.06 (m, 1H) 2.16 (s, 6H) 2.35 (d, J = 15.13 Hz, 1H) 2.49-2.59 (m, 1H) 2.54 (s, 3H) 2.67-2.77 (m, 2H) 2.83-2.92 (m, 1H) 2.99 (d, J = 9.17 Hz, 1H) 3.25 (s, 3H) 3.26-3.43 (m, 3H) 3.30 (s, 3H) 3.49-3.58 (m, 1H) 3.61-3.64 (m, 1H) 3.86 (d, J = 6.88 Hz, 1H) 3.93-4.02 (m, 1H) 4.40-4.52 (m, 3H) 4.80-4.86 (m, 1H) 4.87 (d, J = 4.59 Hz, 1H) |
| 231 | Et | quinolin-4-yl-(CH$_2$)$_3$-NH-C(=O)-CH$_2$-C(CH$_3$)$_2$- | 958.6 | (500 MHz): 0.84 (t, J = 7.54 Hz, 3H) 1.04 (d, J = 6.86 Hz, 3H) 1.09 (d, J = 7.40 Hz, 3H) 1.11 (d, J = 7.13 Hz, 3H) 1.16 (d, J = 7.13 Hz, 3H) 1.19 (d, J = 6.03 Hz, 3H) 1.21-1.30 (m, 7H) 1.31 (s, 3H) 1.45-1.71 (m, 5H) 1.94-2.20 (m, 8H) 2.20-2.34 (m, 7H) 2.37 (d, J = 20.02 Hz, 1H) 2.41-2.51 (m, 1H) 2.72-2.77 (m, 2H) 2.98-3.03 (m, 1H) 3.09-3.13 (m, 2H) 3.16-3.27 (m, 1H) 3.21 (s, 3H) 3.32 (s, 3H) 3.34-3.60 (m, 5H) 3.68 (d, J = 7.13 Hz, 1H) 3.83 (d, J = 5.76 Hz, 1H) 3.96-4.04 (m, 1H) 4.45 (d, J = 7.13 Hz, 1H) 4.51 (d, J = 2.47 Hz, 2H) 4.66-4.77 (m, 1H) 4.90 (d, J = 4.66 Hz, 1H) 6.52-6.60 (m, 1H) 7.27 (d, J = 4.66 Hz, 1H) 7.51-7.58 (m, 1H) 7.69 (t, J = 7.68 Hz, 1H) 8.02 (d, J = 9.87 Hz, 1H) 8.09 (d, J = 9.05 Hz, 1H) 8.80 (d, J = 4.39 Hz, 1H) |
| 232 | Et | phthalimido-(CH$_2$)$_2$-NH-(CH$_2$)$_2$-C(CH$_3$)$_2$- | 948.9 | (500 MHz): 0.88 (t, J = 7.65 Hz, 3H) 1.04 (d, J = 6.88 Hz, 3H) 1.06-1.10 (m, 6H) 1.16 (d, J = 6.88 Hz, 3H) 1.20-1.31 (m, 13H) 1.49-1.72 (m, 5H) 1.86-1.95 (m, 1H) 1.99-2.07 (m, 1H) 2.10 (s, 3H) 2.15 (d, J = 10.70 Hz, 1H) 2.29 (br. s., 6H) 2.38 (d, J = 15.29 Hz, 1H) 2.41-2.52 (m, 1H) 2.53-2.61 (m, 1H) 2.66-2.75 (m, 2H) 2.88-2.96 (m, 4H) 3.00 (t, J = 9.94 Hz, 1H) 3.20 (s, 3H) 3.28-3.36 (m, 1H) 3.33 (s, 3H) 3.38-3.44 (m, 1H) 3.44-3.58 (m, 2H) 3.66 (d, J = 6.88 Hz, 1H) 3.79 (t, J = 6.50 Hz, 2H) 3.89 (d, J = 3.82 Hz, 1H) 3.97-4.04 (m, 1H) 4.04-4.12 (m, 2H) 4.46 (d, J = 7.65 Hz, 1H) 4.75-4.86 (m, 1H) 4.89 (d, J = 4.59 Hz, 1H) 7.69 (dd, J = 5.35, 3.06 Hz, 2H) 7.83 (dd, J = 5.35, 3.06 Hz, 2H) |
| 233 | Et | bis[2-(phthalimido)ethyl]amino-(CH$_2$)$_2$-C(CH$_3$)$_2$- | 1122.0 | (600 MHz): 0.84 (t, J = 7.57 Hz, 3H) 1.13 (m, 22H) 1.13 (d, J = 6.88 Hz, 3H) 1.46-1.61 (m, 5H) 1.75-2.38 (m, 13H) 2.39-2.62 (m, 2H) 2.62-2.71 (m, 2H) 2.79-2.94 (m, 6H) 2.98 (t, J = 9.40 Hz, 1H) 3.15 (s, 3H) 3.23-3.56 (m, 4H) 3.29 (s, 3H) 3.61-3.63 (m, 1H) 3.69 (t, J = 6.88 Hz, 4H) 3.81-3.87 (m, 1H) 3.91-4.03 (m, 3H) 4.40-4.48 (m, 1H) 4.73-4.82 (m, 1H) 4.86 (d, J = 4.58 Hz, 1H) 7.59-7.66 (m, 4H) 7.66-7.72 (m, 4H) |

TABLE 6-continued formula (M)

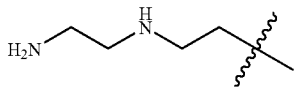

| Example | $R^{1M}$ | $R^{3M}$ | ESI MS (M + H) | $^1$H-NMR, CDCl$_3$, δ (ppm) |
|---|---|---|---|---|
| 234 | Et | 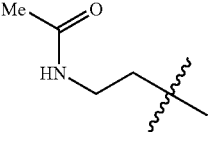 | 818.8 | (500 MHz): 0.88 (t, J = 7.45 Hz, 3H) 1.03-1.10 (m, 6H) 1.11 (d, J = 6.88 Hz, 3H) 1.17 (d, J = 7.26 Hz, 3H) 1.20-1.33 (m, 7H) 1.22 (d, J = 6.12 Hz, 3H) 1.29 (s, 3H) 1.50-1.60 (m, 3H) 1.61-1.69 (m, 2H) 1.73-2.08 (m, 2H) 2.13 (s, 3H) 2.30 (s, 6H) 2.38 (d, J = 14.91 Hz, 1H) 2.44-2.51 (m, 1H) 2.52-2.60 (m, 1H) 2.67-2.79 (m, 4H) 2.79-2.85 (m, 2H) 2.85-2.97 (m, 2H) 3.00 (d, J = 9.17 Hz, 1H) 3.24 (s, 3H) 3.26-3.34 (m, 1H) 3.33 (s, 3H) 3.35-3.60 (m, 3H) 3.67 (d, J = 6.88 Hz, 1H). 3.89 (d, J = 5.73 Hz, 1H) 3.97-4.05 (m, 1H) 4.11-4.17 (m, 2H) 4.45 (d, J = 7.26 Hz, 1H) 4.77-4.87 (m, 1H) 4.90 (d, J = 4.59 Hz, 1H) |
| 235 | Et | 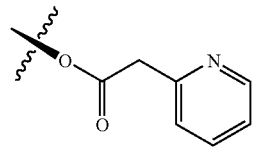 | 817.9 | (500 MHz): 0.88 (t, J = 7.26 Hz, 3H) 1.04-1.10 (m, 6H) 1.11 (d, J = 6.88 Hz, 3H) 1.16 (d, J = 6.88 Hz, 3H) 1.19-1.38 (m, 13H) 1.51-1.61 (m, 3H) 1.61-1.72 (m, 2H) 1.74-1.82 (m, 2H) 1.86-1.93 (m, 1H) 2.01-2.07 (m, 1H) 2.14 (s, 3H) 2.29 (s, 6H) 2.38 (d, J = 15.29 Hz, 1H) 2.44-2.52 (m, 1H) 2.53-2.60 (m, 1H) 2.66-2.75 (m, 2H) 2.77-2.84 (m, 2H) 3.00 (d, J = 9.17 Hz, 1H) 3.22 (s, 3H) 3.26-3.34 (m, 1H) 3.33 (s, 3H) 3.35-3.40 (m, 1H) 3.40-3.47 (m, 1H) 3.47-3.57 (m, 1H) 3.67 (d, J = 6.88 Hz, 1H) 3.89 (d, J = 6.12 Hz, 1H) 3.97-4.04 (m, 1H) 4.04-4.11 (m, 2H) 4.45 (d, J = 6.88 Hz, 1H) 4.77-4.86 (m, 1H) 4.90 (d, J = 4.59 Hz, 1H) |

$R^{2M}$ in the compounds represented by the formula (M) is cladinosyl group except for the compound of Example 218. $R^{2M}$ in the compound of Example 218 is a group represented by the formula:

Example 214

The compound obtained in Example 176 (285 mg) was dissolved in methanol (10 ml), the solution was added with imidazole (163 mg) and hydroxylamine hydrochloride (138 mg), and the mixture was stirred for 4 hours under reflux by heating. The reaction mixture was concentrated under reduced pressure, and the resulting residue was added with ethyl acetate and saturated aqueous ammonium chloride, the layers were separated, and the organic layer was washed with saturated aqueous ammonium chloride, then dried over anhydrous magnesium sulfate and filtered. The filtrate was concentrated under reduced pressure, and the resulting residue was purified by silica gel column chromatography (chloroform:methanol:28% aqueous ammonia=20:1:0.1 to 10:1:0.1) to obtain the compound shown in Table 6 (160 mg).

Example 215

By using the compound obtained in Example 177 (25 mg) as a starting material, the compound shown in Table 6 (5.0 mg) was obtained in the same manner as that of Example 214.

Example 216

By using the compound obtained in Example 180 (50 mg) as a starting material, the compound shown in Table 6 (35.6 mg) was obtained in the same manner as that of Example 214.

Example 217

(1) By using the compound obtained in Example 1 (1.58 g) and the compound obtained in Reference Example 15 (1.36 g) as starting materials, a biaryl compound (0.81 g) was obtained in the same manners as those of Example 7, (1), (2), (3) and Example 23, (2).
(2) By using the compound obtained in (1) mentioned above (0.8 g) as a starting material, the compound shown in Table 6 (154 mg) was obtained in the same manners as those of Example 126, (1), Example 176 and Example 214.

Example 218

The compound obtained in Example 176, (4) (100 mg) was dissolved in 1 N hydrochloric acid (2 ml) and ethanol (1 ml), and the solution was stirred at 50° C. for 5 hours. The reaction mixture was neutralized with 1 N aqueous sodium hydroxide, and then extracted with chloroform. The organic layer was dried over anhydrous magnesium sulfate and filtered, the filtrate was concentrated under reduced pressure, and the resulting residue was purified by column chromatography (chloroform:methanol:28% aqueous ammonia=20:1:0.1). By using the resulting compound (50 mg) as a starting material, the compound shown in Table 6 (12.4 mg) was obtained in the same manners as those of Example 112, (2) and Example 214.

Example 219

(1) By using the compound obtained in Example 70, (1) (606 mg) as a starting material, a 4"-hydroxy compound (401 mg) was obtained in the same manner as that of Example 126, (1).
(2) The compound obtained in (1) mentioned above (394 mg) was dissolved in chloroform (5 ml), the solution was added pyridine (5 ml), 4-dimethylaminopyridine (93.2 mg) and acetic anhydride (108 μl) under ice cooling, and the mixture was stirred at room temperature for 18 hours. The reaction mixture was concentrated under reduced pressure, and the resulting residue was purified by silica gel column chromatography (hexane:acetone=8:1). The purified compound (372 mg) was dissolved in pyridine (7 ml) again, the solution was added with 4-dimethylaminopyridine (93.2 mg) and acetic anhydride (0.32 ml) under ice cooling, and the mixture was stirred at room temperature for 18 hours. The reaction mixture was concentrated under reduced pressure, and the resulting residue was purified by silica gel column chromatography (hexane:acetone=8:1) to obtain a 4"-O-acetyl compound (336 mg).
(3) By using the compound obtained in (2) mentioned above (323 mg) as a starting material, a 9-oxime compound was obtained in the same manners as those of Example 7, (4), Example 176, (3), (4), Example 125, (3) and Example 214.
(4) The compound obtained in (3) mentioned above (22.0 mg) was dissolved in methanol (1.5 ml) and tetrahydrofuran (0.5 ml), the solution was added with sodium methoxide (6.92 mg) under ice cooling, and the mixture was stirred at 50° C. for 6 hours. The reaction mixture was concentrated under reduced pressure, and the resulting residue was added with saturated aqueous ammonium chloride and ethyl acetate, the layers were separated, and the organic layer was dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) to obtain the compound shown in Table 6 (14.0 mg).

Example 220

By using the compound obtained in Example 17, (2) (70 mg) as a starting material, the compound shown in Table 6 (0.84 mg) was obtained in the same manner as that of Example 219 (Example 126, (1), Example 219, (2), Example 7, (4), Example 176, (3), (4), Example 125, (3), Example 214 and Example 219, (4)).

Example 221

(1) By using the compound obtained in Example 1 (3.0 g) and 2-[3-(benzyloxy)propyl]oxirane (3.48 g) obtained by the method described in the literature (European Journal of Organic Chemistry, 2000, p. 1219) as starting materials, a cyclized compound (401 mg) was obtained in the same manners as those of Example 7, (1), (2) and (3).
(2) By using the compound obtained in (1) mentioned above (114 mg) as a starting material, the compound shown in Table 6 (14.6 mg) was obtained in the same manner as that of Example 219 (Example 126, (1), Example 219, (2), Example 7, (4), Example 176, (3), (4), Example 125, (3), Example 214 and Example 219, (4)).

Example 222

The compound obtained in Example 221 (14.6 mg) as a starting material, the compound shown in Table 6 (3.7 mg) was obtained in the same manner as that of Example 73.

Example 223

(1) By using the compound obtained in Example 176, (4) (381 mg) as a starting material, a 9-oxime compound (299 mg) was obtained in the same manner as that of Example 214.
(2) The compound obtained in (1) mentioned above (217 mg) was dissolved in tetrahydrofuran (5 ml), the solution was added with allyl bromide (33 μl) and potassium hydroxide (70.1 mg), and the mixture was stirred at room temperature for 18 hours. The mixture was further added with allyl bromide (7 μl) and potassium hydroxide (14.1 mg), and the mixture was stirred at room temperature for 18 hours. The mixture was further added with allyl bromide (7 μl) and potassium hydroxide (14.1 mg), and the mixture was stirred at room temperature for 18 hours. The reaction mixture was concentrated under reduced pressure, and the resulting residue was purified by silica gel column chromatography (hexane:acetone=8:1) to obtain the compound shown in Table 6 (80 mg).

Example 224

The compound obtained in Example 214 (48.4 mg) was dissolved in tetrahydrofuran (3 ml), the solution was added with 2-bromoethylamine hydrobromide (40.6 mg), potassium hydroxide (37.1 mg) and 18-crown-6-ether (175 mg), and the mixture was stirred at room temperature for 1 hour. The reaction mixture was added with saturated brine and chloroform, the layers were separated, and the organic layer was dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) and silica gel column chromatography (chloroform:methanol:28% aqueous ammonia=9:1:0 to 10:1:0.1) to obtain the compound shown in Table 6 (34.1 mg).

Example 225

By using the compound obtained in Example 214 (50.8 mg) and benzyl 2-bromoethyl ether (44.8 mg) as starting materials, the compound shown in Table 6 (22.7 mg) was obtained in the same manner as that of Example 224.

Example 226

By using the compound obtained in Example 225 (5.6 mg) as a starting material, the compound shown in Table 6 (4.7 mg) was obtained in the same manner as that of Example 43.

Example 227

By using the compound obtained in Example 224 (8.4 mg) as a starting material, the compound shown in Table 6 (5.9 mg) was obtained in the same manner as that of Example 7, (2).

Example 228

By using the compound obtained in Example 214 (78.7 mg) and benzyl bromoacetate (74.0 mg) as starting materials, the compound shown in Table 6 (5.8 mg) was obtained in the same manner as that of Example 224.

Example 229

By using the compound obtained in Example 214 (18.6 mg) and 3-bromopropylamine hydrobromide (16.7 mg) as starting materials, the compound shown in Table 6 (10.2 mg) was obtained in the same manner as that of Example 224.

Example 230

By using the compound obtained in Example 214 (78.7 mg) and benzyl bromoacetate (74.0 mg) as starting materials, the compound shown in Table 6 (25.4 mg) was obtained in the same manner as that of Example 224.

Example 231

The compound obtained in Example 230 (12.1 mg) was dissolved in chloroform, the solution was added with 1-ethyl-3-(3-dimethylaminopropyl)carbodiimide hydrochloride (14.7 mg) and 4-(3-aminopropyl)-quinoline (14.3 mg) obtained by the method described in the patent document (Japanese Patent Unexamined Publication No. 2005-200318) under ice cooling, and the mixture was stirred at room temperature for 4 hours. The reaction mixture was added with chloroform and saturated brine, the layers were separated, and the organic layer was dried over anhydrous magnesium sulfate and filtered. The filtrate was concentrated under reduced pressure, and the resulting residue was purified by silica gel column chromatography (chloroform:methanol:28% aqueous ammonia=10:1:0 to 10:1:0.1) and preparative thin layer chromatography (chloroform:methanol:28% aqueous ammonia=10:1:0.1) to obtain the compound shown in Table 6 (1.7 mg).

Example 232

By using the compound obtained in Example 224 (16.8 mg) and phthalimide acetaldehyde (4.5 mg) as starting materials, the compound shown in Table 6 (12.0 mg) was obtained in the same manner as that of Example 7, (2).

Example 233

By using the compound obtained in Example 224 (16.8 mg) and phthalimide acetaldehyde (4.5 mg) as starting materials, the compound shown in Table 6 (1.7 mg) was obtained in the same manner as that of Example 7, (2).

Example 234

The compound obtained in Example 232 (12.0 mg) was dissolved in ethanol (1 ml), the solution was added with hydrazine monohydrate (0.64 mg) under ice cooling, and the mixture was stirred at room temperature for 18 hours. The reaction mixture was concentrated under reduced pressure, and the resulting residue was purified by preparative thin layer chromatography (chloroform:methanol:28% aqueous ammonia=10:1:0.1) to obtain the compound shown in Table 6 (5.4 mg).

Example 235

(1) By using the compound obtained in Example 224 (8.4 mg) as a starting material, a diacetyl compound (7.7 mg) was obtained in the same manner as that of Example 176, (3).

(2) The compound obtained in (1) mentioned above (6.9 mg) was dissolved in methanol (1 ml), and the solution was stirred at room temperature for 24 hours. The reaction mixture was concentrated under reduced pressure, and the resulting residue was purified by preparative thin layer chromatography (chloroform:methanol:28% aqueous ammonia=10:1:0.1) to obtain the compound shown in Table 6 (3.2 mg).

Syntheses of Examples 236 to 239

Preparation methods of compounds represented by the formula (N) having R defined in Table 7 are shown below.

TABLE 7 formula (N)

| Example | R | ESI MS (M + H) | $^1$H-NMR, CDCl$_3$, δ (ppm) |
|---|---|---|---|
| 236 | benzyl carbamate-ethyl | 882.8 | (500 MHz): 0.85 (t, J = 7.26 Hz, 3H) 0.88-1.31 (m, 25H) 1.45-1.65 (m, 5H) 1.87-1.97 (m, 1H) 1.97-2.15 (m, 1H) 2.08 (s, 3H) 2.20-2.45 (m, 2H) 2.24 (s, 6H) 2.46-2.63 (m, 3H) 2.68-2.79 (m, 1H) 2.89-2.96 (m, 1H) 2.97-3.05 (m, 1H) 3.32 (s, 11H) 3.91-4.04 (m, 1H) 4.09-4.20 (m, 2H) 4.49 (d, J = 6.88 Hz, 1H) 4.72-4.85 (m, 2H) 5.02 (d, J = 13.00 Hz, 1H) 5.16 (d, J = 13.00 Hz, 1H) 6.76 (br. s., 1H) 7.20-7.44 (m, 5H) |
| 237 | benzyloxy-ethyl | 839.7 | (600 MHz): 0.86 (t, J = 7.34 Hz, 3H) 0.97-1.29 (m, 25H) 1.47-1.69 (m, 5H) 1.87-1.99 (m, 1H) 2.07-2.20 (m, 1H) 2.12 (s, 3H) 2.22-2.62 (m, 6H) 2.29 (s, 6H) 2.71-2.82 (m, 1H) 2.94-3.05 (m, 2H) 3.26-3.68 (m, 6H) 3.33 (s, 3H) 3.94-4.18 (m, 3H) 4.48-4.58 (m, 3H) 4.75-4.87 (m, 2H) 7.21-7.36 (m, 5H) |
| 238 | H$_2$N-ethyl | 748.7 | (600 MHz): 0.80-1.34 (m, 28H) 1.50-1.70 (m, 5H) 1.84-2.21 (m, 2H) 2.16 (s, 3H) 2.24-2.64 (m, 7H) 2.29 (s, 6H) 2.72-3.08 (m, 4H) 3.18-3.60 (m, 4H) 3.34 (s, 3H) 3.78-4.16 (m, 4H) 4.50-4.59 (m, 1H) 4.74-4.86 (m, 2H) |
| 239 | HO-ethyl | 749.7 | (600 MHz): 0.86 (t, J = 7.57 Hz, 3H) 0.94-1.36 (m, 25H) 1.47-1.67 (m, 5H) 1.87-1.96 (m, 1H) 2.04-2.17 (m, 1H) 2.09 (s, 3H) 2.23-2.41 (m, 8H) 2.47-2.63 (m, 3H) 2.69-2.78 (m, 1H) 2.91-2.97 (m, 1H) 3.00-3.07 (m, 1H) 3.24-3.39 (m, 1H) 3.34 (s, 3H) 3.43-3.67 (m, 5H) 3.79-3.86 (m, 1H) 3.95-4.04 (m, 1H) 4.10-4.41 (m, 3H) 4.56 (d, J = 6.88 Hz, 1H) 4.74-4.85 (m, 2H) |

Example 236

By using the compound obtained in Example 4 (225 mg) as a starting material, the compound shown in Table 7 (16 mg) was obtained in the same manner as that of Example 7.

Example 237

By using the compound obtained in Example 5 (180 mg) as a starting material, the compound shown in Table 7 (16 mg) was obtained in the same manner as that of Example 7.

Example 238

The compound obtained in Example 236 (24 mg) was dissolved in methanol (0.3 ml), the solution was added with 5% palladium-carbon (4 mg), and the mixture was stirred at room temperature under a hydrogen atmosphere of 1 atm. The reaction mixture was filtered through Celite, then the filtrate was concentrated under reduced pressure, and the resulting residue was purified by silica gel column chromatography (NH-form, acetone:hexane:triethylamine=10:40:0.2) to obtain the compound shown in Table 7 (8.7 mg).

Example 239

The compound obtained in Example 237 (11 mg) was dissolved in methanol (0.1 ml), the solution was added with 20% palladium hydroxide-carbon (2 mg), and the mixture was stirred at room temperature for 6 hours under a hydrogen atmosphere of 1 atm. The reaction mixture was filtered through Celite, and then the filtrate was concentrated under reduced pressure. The resulting residue was dissolved in methanol (0.1 ml), the solution was added with 20% palladium hydroxide-carbon (2 mg), and the mixture was stirred at room temperature for 17 hours under a hydrogen atmosphere of 1 atm. The reaction mixture was filtered through Celite, and then the filtrate was concentrated under reduced pressure. The resulting residue was dissolved in methanol (0.1 ml), the solution was added with 20% palladium hydroxide-carbon (2 mg), and the mixture was stirred at room temperature for 6 hours under a hydrogen atmosphere of 1 atm. The reaction mixture was filtered through Celite, and then the filtrate was concentrated under reduced pressure. The resulting residue was purified by preparative thin layer chromatography (chloroform:methanol:28% aqueous ammonia=10:1:0.1) to obtain the compound shown in Table 7 (1.7 mg).

Syntheses of Examples 240 to 243

Preparation methods of compounds represented by the formula (O) having $R^{10}$, and $R^{20}$ defined in Table 8 are shown below.

TABLE 8 formula (O)

| Example | $R^{1O}$ | $R^{2O}$ | ESI MS (M + H) | $^1$H-NMR, CDCl$_3$, δ (ppm) |
|---|---|---|---|---|
| 240 | H |  | 675.3 | (500 MHz): 0.93 (d, J = 6.88 Hz, 3H) 1.01 (d, J = 6.88 Hz, 3H) 1.07 (d, J = 7.65 Hz, 3H) 1.11 (d, J = 7.65 Hz, 3H) 1.21 (d, J = 6.12 Hz, 3H) 1.21-1.31 (m, 1H) 1.23 (s, 3H) 1.27 (d, J = 6.12 Hz, 3H) 1.30 (s, 3H) 1.53 (dd, J = 15.29, 4.59 Hz, 1H) 1.61-1.73 (m, 2H) 1.80 (t, J = 12.61 Hz, 1H) 1.98-2.08 (m, 1H) 2.10-2.16 (m, 2H) 2.30 (s, 6H) 2.34-2.40 (m, 1H) 2.37 (s, 3H) 2.42-2.53 (m, 1H) 2.60 (q, J = 6.88 Hz, 1H) 2.67-2.76 (m, 1H) 2.77-2.86 (m, 1H) 2.99 (t, J = 9.94 Hz, 1H) 3.06-3.15 (m, 1H) 3.19-3.26 (m, 1H) 3.34 (s, 3H) 3.44-3.52 (m, 1H) 3.63 (d, J = 8.41 Hz, 1H) 3.76 (t, J = 11.09 Hz, 1H) 3.96-4.04 (m, 1H) 4.05-4.08 (m, 1H) 4.41 (d, J = 6.88 Hz, 1H) 4.47 (d, J = 11.47 Hz, 1H) 4.72 (d, J = 4.59 Hz, 1H) |
| 241 | H |  | 690.3 | (300 MHz): 0.98-1.12 (m, 9H) 1.20 (d, J = 7.15 Hz, 3H) 1.21-1.32 (m, 1H) 1.22-1.25 (m, 3H) 1.23 (s, 3H) 1.30 (d, J = 6.22 Hz, 3H) 1.37 (s, 3H) 1.48-2.06 (m, 5H) 2.26 (s, 3H) 2.30 (s, 6H) 2.31-2.53 (m, 2H) 2.64-2.83 (m, 2H) 2.84-2.95 (m, 1H) 2.96-3.06 (m, 1H) 3.27 (dd, J = 10.26, 7.31 Hz, 1H) 3.31 (s, 3H) 3.42-3.58 (m, 3H) 3.74-3.89 (m, 1H) 3.95-4.13 (m, 2H) 4.27-4.39 (m, 2H) 4.43 (d, J = 7.31 Hz, 1H) 4.77 (d, J = 4.51 Hz, 1H) |
| 242 | Et |  | 718.6 | (500 MHz): 0.88 (t, J = 7.55 Hz, 3H) 0.99-1.37 (m, 25H) 1.48-1.68 (m, 5H) 1.90-1.96 (m, 1H) 2.08-2.37 (m, 3H) 2.18 (s, 3H) 2.28 (s, 6H) 2.40-2.49 (m, 1H) 2.53-2.77 (m, 3H) 2.95-3.03 (m, 1H) 3.21-3.69 (m, 5H) 3.30 (s, 3H) 3.73-3.84 (m, 1H) 3.94-4.03 (m, 1H) 4.05-4.13 (m, 1H) 4.42 (d, J = 7.20 Hz, 1H) 4.76-4.81 (m, 1H) 5.00-5.08 (m, 1H) 5.15 (br. s., 1H) |
| 243 | Et |  | 761.6 | (600 MHz): 0.88 (t, J = 7.57 Hz, 3H) 0.91-1.40 (m, 25H) 1.47-1.58 (m, 3H) 1.60-1.68 (m, 1H) 1.89-1.98 (m, 2H) 2.08-2.37 (m, 3H) 2.21 (s, 3H) 2.28 (s, 6H) 2.41-2.48 (m, 1H) 2.52-2.58 (m, 1H) 2.66-2.82 (m, 4H) 2.85-3.03 (m, 3H) 3.20-3.52 (m, 4H) 3.30 (s, 3H) 3.63 (s, 1H) 3.77-3.86 (m, 1H) 3.95-4.11 (m, 3H) 4.42 (d, J = 7.34 Hz, 1H) 4.76-4.82 (m, 1H) 5.01-5.10 (m, 1H) |

Example 240

(1) The compound obtained in Example 2 (30 g) was dissolved in toluene (700 ml), the solution was added with triethylamine (51 ml) and 2-bromoethyl alcohol (22 ml), and the mixture was stirred at 80° C. for 4 hours. The reaction mixture was concentrated under reduced pressure, and the resulting residue was purified by silica gel column chromatography (chloroform:methanol:28% aqueous ammonia=9:1:0.1) to obtain a 10a-N-(2-hydroxyethyl) compound (19.4 g).
(2) By using the compound obtained in (1) mentioned above (19.4 g) as a starting material, a cyclized compound (3.0 g) was obtained in the same manners as those of Example 7, (2) and (3).
(3) By using the compound obtained in (2) mentioned above (0.67 g) as a starting material, a 4"-hydroxy compound (0.52 g) was obtained in the same manner as that of Example 126, (1).
(4) The compound obtained in (3) mentioned above (0.5 g) was dissolved in tetrahydrofuran (5 ml), the solution was added with potassium carbonate (0.3 g) and N,N'-carbonyldiimidazole (0.27 g), the mixture was stirred at room temperature for 80 minutes, and then further added with potassium carbonate (0.3 g) and N,N'-carbonyldiimidazole (0.27 g), and the mixture was stirred at room temperature for 30 minutes. The reaction mixture was filtered, then the filtrate was concentrated under reduced pressure, and the resulting residue was diluted with ethyl acetate, and washed successively with saturated aqueous ammonium chloride and saturated brine. Then, the organic layer was dried over anhydrous magnesium sulfate and filtered. The filtrate was concentrated under reduced pressure, and the resulting residue was dissolved in tetrahydrofuran (5 ml). The solution was added with a solution of sodium hydride (29 mg) and benzyl alcohol (0.11 ml) in tetrahydrofuran (5 ml), and the mixture was stirred at room temperature for 30 minutes. The reaction mixture was added with saturated aqueous ammonium chloride, and the mixture was extracted with ethyl acetate. The organic layer was washed with saturated brine, then dried over anhydrous magnesium sulfate and filtered. The filtrate was concentrated under reduced pressure, and the resulting residue was purified by silica gel column chromatography (hexane:acetone:triethylamine=30:10:0.2) to obtain a 4"-O-benzyloxycarbonyl compound (0.35 g).
(5) By using the compound obtained in (4) mentioned above (0.35 g) as a starting material, a 2'-acetyl compound (105 mg) was obtained in the same manners as those of Example 7, (4) and Example 176, (3).
(6) By using the compound obtained in (5) mentioned above (50 mg) as a starting material, the compound shown in Table 8 (17 mg) was obtained in the same manners as those of Example 176, (4) and (5).

Example 241

The compound obtained in Example 240 (23 mg) was dissolved in methanol (1 ml), the solution was added with 50% aqueous hydroxyamine (30 μl) and acetic acid (15 μl), and the mixture was stirred at 50° C. for 40 hours. The reaction mixture was added with ethyl acetate and 0.5 N aqueous sodium hydroxide, the layers were separated, and the organic layer was washed with saturated brine, then dried over anhydrous magnesium sulfate and filtered. The filtrate was concentrated under reduced pressure, and the resulting residue was purified by silica gel column chromatography (chloroform:methanol:28% aqueous ammonia=9:1:0.1) to obtain the compound shown in Table 8 (6.5 mg).

Example 242

(1) By using the compound obtained in Example 206, (3) (100 mg) as a starting material, a 9-oxime compound (56 mg) was obtained in the same manner as that of Example 214.
(2) By using the compound obtained in (1) mentioned above (20 mg) as a starting material, the compound shown in Table 8 (7 mg) was obtained in the same manner as that of Example 7, (4).

Example 243

(1) By using the compound obtained in Example 242, (1) (29 mg) as a starting material, an aminoethyl compound (14 mg) was obtained in the same manner as that of Example 224.
(2) By using the compound obtained in (1) mentioned above (14 mg) as a starting material, the compound shown in Table 8 (8 mg) was obtained in the same manner as that of Example 7, (4).

Syntheses of Examples 244 to 247

Preparation methods of compounds represented by the formula (P) having R defined in Table 9 are shown below.

TABLE 9 formula (P)

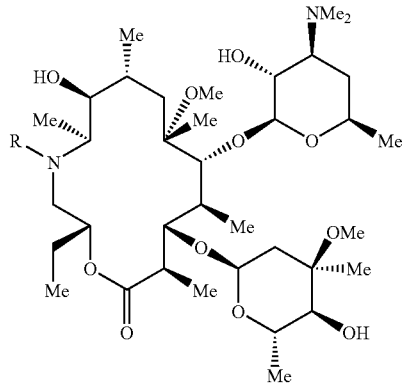

| Example | R | ESI MS (M + H) | $^1$H-NMR, CDCl$_3$, δ (ppm) |
|---|---|---|---|
| 244 | H | 705.4 | |
| 245 | Et | 733.4 | (600 MHz): 0.76-0.83 (m, 6H) 0.90 (t, J = 7.34 Hz, 3H) 0.97 (t, J = 7.79 Hz, 2H) 0.99-1.36 (m, 4H) 1.09 (d, J = 7.34 Hz, 3H) 1.16 (d, J = 7.79 Hz, 3H) 1.22 (d, J = 7.79 Hz, 3H) 1.22 (s, 3H) |

TABLE 9-continued formula (P)

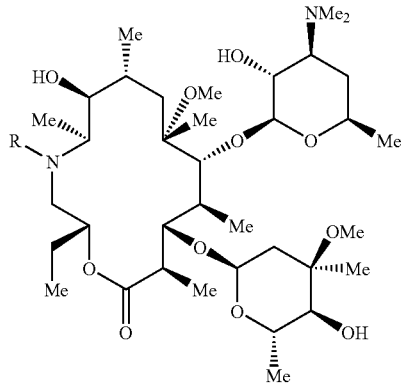

| Example | R | ESI MS (M + H) | ¹H-NMR, CDCl₃, δ (ppm) |
|---|---|---|---|
| | | | 1.29 (d, J = 5.96 Hz, 3H) 1.32 (s, 3H) 1.53 (dd, J = 15.36, 4.81 Hz, 2H) 1.69-1.77 (m, 1H) 1.77-1.87 (m, 1H) 2.21-2.40 (m, 12H) 2.46-2.58 (m, 1H) 2.59-2.70 (m, 1H) 2.77-2.86 (m, 1H) 2.91 (d, J = 14.67 Hz, 1H) 3.00 (t, J = 9.86 Hz, 1H) 3.14-3.25 (m, 1H) 3.15-3.25 (m, 3H) 3.32 (s, 3H) 3.38-3.50 (m, 2H) 3.70 (d, J = 8.25 Hz, 1H) 4.02-4.09 (m, 1H) 4.15-4.22 (m, 1H) 4.37 (d, J = 7.34 Hz, 1H) 4.50-4.62 (m, 1H) 4.95 (d, J = 4.13 Hz, 1H) |
| 246 | allyl/methyl group | 745.4 | (600 MHz): 0.66 (t, J = 8.02 Hz, 3H) 0.75-0.82 (m, 6H) 0.89-0.96 (m, 5H) 1.09 (d, J = 7.34 Hz, 3H) 1.14-1.17 (m, 3H) 1.17-1.24 (m, 5H) 1.28 (d, J = 6.42 Hz, 3H) 1.32 (s, 3H) 1.53 (dd, J = 14.90, 4.81 Hz, 1H) 1.60-1.87 (m, 2H) 2.19-2.40 (m, 10H) 2.45-2.66 (m, 2H) 2.78-2.85 (m, 1H) 2.93 (d, J = 15.13 Hz, 1H) 3.00 (t, J = 9.17 Hz, 1H) 3.21 (s, 3H) 3.13-3.26 (m, 1H) 3.32 (s, 3H) 3.29-3.33 (m, 2H) 3.40-3.51 (m, 2H) 3.70 (d, J = 8.25 Hz, 1H) 4.01-4.08 (m, 1H) 4.15-4.21 (m, 1H) 4.37 (d, J = 7.34 Hz, 1H) 4.55-4.66 (m, 1H) 4.95 (d, J = 5.04 Hz, 1H) 5.10 (m, 2H) 5.78-5.88 (m, 1H) |
| 247 | benzyl group | 795.4 | (600 MHz): 0.53-0.69 (m, 3H) 0.78-0.83 (m, 3H) 0.84-0.90 (m, 3H) 0.91-0.99 (m, 2H) 1.09 (d, J = 7.34 Hz, 3H) 1.18 (d, J = 7.34 Hz, 3H) 1.19-1.25 (m, 8H) 1.29 (d, J = 5.96 Hz, 3H) 1.31 (s, 3H) 1.53 (dd, J = 15.36, 4.81 Hz, 1H) 1.64 (d, J = 11.46 Hz, 1H) 1.75-1.92 (m, 1H) 2.16-2.32 (m, 9H) 2.36 (d, J = 15.13 Hz, 1H) 2.42-2.51 (m, 2H) 2.81-2.88 (m, 1H) 2.98-3.04 (m, 2H) 3.16-3.21 (m, 1H) 3.22 (s, 3H) 3.32 (s, 3H) 3.41-3.49 (m, 1H) 3.51-3.59 (m, 1H) 3.65 (d, J = 13.76 Hz, 1H) 3.70 (d, J = 7.79 Hz, 1H) 3.76 (d, J = 14.21 Hz, 1H) 4.01-4.09 (m, 1H) 4.17-4.22 (m, 1H) 4.36 (d, J = 7.34 Hz, 1H) 4.61-4.70 (m, 1H) 4.97 (d, J = 4.58 Hz, 1H) 7.22 (t, J = 7.34 Hz, 1H) 7.30 (t, J = 7.57 Hz, 2H) 7.35 (d, 2H) |

Example 244

(1) The compound obtained in Example 1 (1.0 g) was dissolved in chloroform (5 ml), the solution was added with benzaldehyde (107 mg) and sodium triacetoxyborohydride (322 mg), and the mixture was stirred at room temperature for 18 hours. The reaction mixture was added with saturated aqueous sodium hydrogencarbonate, the layers were separated, and the organic layer was dried over anhydrous magnesium sulfate and filtered. The filtrate was concentrated under reduced pressure, and the resulting residue was purified by silica gel column chromatography (chloroform:methanol:28% aqueous ammonia=30:1:0.1) to obtain a 10a-N-benzyl compound (717 mg).

(2) By using the compound obtained in (1) mentioned above (710 mg) as a starting material, a cyclized compound (35 mg) was obtained in the same manners as those of Example 7, (1) and (3).

(3) By using the compound obtained in (2) mentioned above (30 mg) as a starting material, the compound shown in Table 9 (1.7 mg) was obtained in the same manners as those of Example 7, (4) and Example 73.

Example 245

(1) By using the compound obtained in Example 1 (5.03 g) and (S)-1,2-epoxybutane as starting materials, an adduct compound (2.39 g) was obtained in the same manner as that of Example 7, (1).

(2) The compound obtained in (1) mentioned above (2.39 g) and triphenylphosphine (2.36 g) were dissolved in tetrahydrofuran (36 ml), the solution was added with a 40% solution of diisopropyl azodicarboxylate in toluene (4.7 ml), and the mixture was stirred at room temperature for 5 hours. The reaction mixture was concentrated under reduced pressure, and the resulting residue was added with distilled water and chloroform. The layers were separated, and the organic layer was dried over anhydrous magnesium sulfate and filtered. The filtrate was concentrated under reduced pressure, and the resulting residue was purified by silica gel column chromatography (hexane:acetone:triethylamine=90:5:0.1 to 45:5:0.1) to obtain a cyclized compound (0.63 g).
(3) By using the compound obtained in (2) mentioned above (50 mg) and acetaldehyde as starting materials, an ethyl compound (24 mg) was obtained in the same manner as that of Example 7, (2).
(4) By using the compound obtained in (3) mentioned above (24 mg) as a starting material, the compound shown in Table 9 (10 mg) was obtained in the same manner as that of Example 7, (4).

Example 246

(1) The compound obtained in Example 245, (2) (70 mg) was dissolved in dimethylformamide (1 ml), the solution was added with allyl bromide (116 mg) and potassium carbonate (186 mg), and the mixture was stirred at room temperature for 21 hours. The reaction mixture was added with distilled water and chloroform, the layers were separated, and the organic layer was dried over anhydrous magnesium sulfate and filtered. The filtrate was concentrated under reduced pressure, and the resulting residue was purified by silica gel column chromatography (chloroform:methanol: 28% aqueous ammonia=50:1:0.1) to obtain an allyl compound (21 mg).
(2) By using the compound obtained in (1) mentioned above (21 mg) as a starting material, the compound shown in Table 9 (5 mg) was obtained in the same manner as that of Example 7, (4).

Example 247

By using the compound obtained in Example 245, (2) (48 mg) and benzyl bromide as starting materials, the compound shown in Table 9 (5 mg) was obtained in the same manners as those of Example 246, (1) and Example 7, (4).

Example 248

Synthesis of the Compound Represented by the Formula (Q)

[Formula 26]

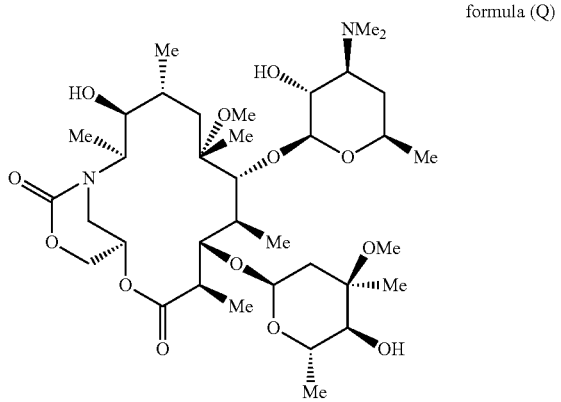

formula (Q)

(1) By using the compound obtained in Example 1 (4.5 g) and benzyl(S)-(+)-glycidyl ether (3.0 g) as starting materials, an adduct compound (2.74 g) was obtained in the same manner as that of Example 7, (1).

(2) The compound obtained in (1) mentioned above (2.0 g) was dissolved in tetrahydrofuran (300 ml), the solution was added with a 2.2 M solution of diethyl azodicarboxylate in toluene (1.57 ml) and triphenylphosphine (0.91 g), and the mixture was stirred at room temperature for 6 hours. The reaction mixture was concentrated under reduced pressure, and the resulting residue was purified by silica gel column chromatography (hexane:acetone:triethylamine=30:10: 0.2) to obtain a cyclized compound (0.3 g).
(3) The compound obtained in (2) mentioned above (0.14 g) was dissolved in tetrahydrofuran (10 ml), the solution was added with 20% palladium hydroxide-carbon (0.5 g), and the mixture was stirred at room temperature for 8 hours under a hydrogen atmosphere of 1 atm. The reaction mixture was filtered, and then the filtrate was concentrated under reduced pressure. The resulting residue (65 mg) was dissolved in chloroform (3 ml) and pyridine (0.05 ml), the solution was added dropwise with a solution of triphosgene (18 mg) in chloroform (1 ml) by small and small, and then the mixture was stirred at room temperature for 5 hours. The reaction mixture was added with chloroform and saturated aqueous sodium hydrogencarbonate, the layers were separated, and the organic layer was washed with saturated brine, then dried over anhydrous magnesium sulfate and filtered. The filtrate was concentrated under reduced pressure, and the resulting residue was purified by silica gel column chromatography (hexane:acetone:triethylamine=30:10:0.2) to obtain a carbamate compound (18 mg).
(4) By using the compound obtained in (3) mentioned above (18 mg) as a starting material, the title compound (11.6 mg) was obtained in the same manner as that of Example 7, (4).
MS (ESI) m/z=733.3 [M+H]$^+$
$^1$H-NMR (300 MHz, CDCl$_3$) δ (ppm):1.06 (d, J=7.34 Hz, 3H), 1.12 (d, J=7.34 Hz, 3H), 1.13-1.32 (m, 2H), 1.19 (d, J=6.88 Hz, 3H), 1.22 (d, J=5.96 Hz, 3H), 1.24-1.25 (m, 6H), 1.36 (d, J=6.42 Hz, 3H), 1.44 (d, J=6.88 Hz, 3H), 1.58 (dd, J=15.36, 4.81 Hz, 1H), 1.60-1.65 (m, 1H), 1.88-2.05 (m, 2H), 2.07-2.13 (m, 1H), 2.28 (s, 1H), 2.28 (s, 6H), 2.36 (d, J=15.13 Hz, 1H), 2.43-2.52 (m, 1H), 2.68-2.77 (m, 1H), 3.09 (t, J=9.17 Hz, 1H), 3.20-3.27 (m, 1H), 3.32-3.40 (m, 2H), 3.34 (s, 3H), 3.36 (s, 3H), 3.41-3.48 (m, 1H), 3.50-3.59 (m, 1H), 3.72 (d, J=3.67 Hz, 1H), 3.74 (d, J=5.50 Hz, 1H), 3.98-4.05 (m, 1H), 4.13-4.20 (m, 1H), 4.23 (d, J=11.92 Hz, 1H), 4.40-4.49 (m, 1H), 4.51-4.59 (m, 2H), 4.97-5.04 (m, 1H)

Example 249

Synthesis of the Compound Represented by the Formula (R)

[Formula 27]

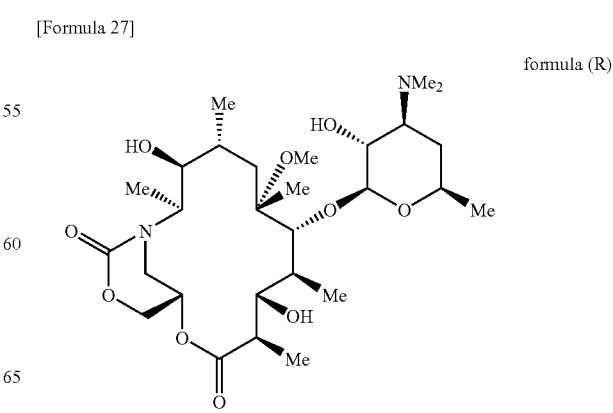

formula (R)

(1) By using the compound obtained in Example 1 (3.0 g) and (R)-1,2-epoxypropane benzyl ether (2.0 g) as starting materials, an adduct compound (1.13 g) was obtained in the same manner as that of Example 7, (1).
(2) The compound obtained in (1) mentioned above (0.6 g) was dissolved in tetrahydrofuran (90 ml), the solution was added with a 1.9 M solution of diisopropyl azodicarboxylate in toluene (0.55 ml) and triphenylphosphine (0.27 g), and the mixture was stirred at room temperature for 6 hours. The reaction mixture was concentrated under reduced pressure, and the resulting residue was purified by silica gel column chromatography (hexane:acetone:triethylamine=30:10:0.2) to obtain a cyclized compound (0.42 g).
(3) By using the compound obtained in (2) mentioned above (59 mg) as a starting material, the title compound (5.7 mg) was obtained in the same manners as those of Example 248, (3) and Example 7, (4).

MS (ESI) m/z=575.2 [M+H]$^+$
$^1$H-NMR (300 MHz, CDCl$_3$) δ (ppm): 1.10 (d, J=6.88 Hz, 3H), 1.15-1.19 (m, 3H), 1.21-1.30 (m, 13H), 1.32 (s, 3H), 1.40 (dd, J=15.36, 6.19 Hz, 1H), 1.61-1.67 (m, 1H), 1.72-1.80 (m, 1H), 1.84-1.92 (m, 1H), 2.00-2.07 (m, 1H), 2.24 (s, 6H), 2.44-2.50 (m, 1H), 2.70-2.77 (m, 1H), 3.15 (s, 3H), 3.23 (dd, J=10.32, 7.57 Hz, 1H), 3.26-3.29 (m, 1H), 3.48-3.54 (m, 1H), 3.57-3.64 (m, 1H), 3.82-3.85 (m, 1H), 3.89-4.02 (m, 1H), 4.03-4.14 (m, 1H), 4.18-4.23 (m, 1H), 4.28-4.34 (m, 1H), 4.47 (d, J=7.34 Hz, 1H), 4.63-4.70 (m, 1H), 5.00-5.04 (m, 1H)

Syntheses of Examples 250 to 258

Preparation methods of compounds represented by the formula (S) having $R^{1S}$, $R^{2S}$ and $R^{3S}$ defined in Table 10 are shown below.

TABLE 10 formula (S)

| Example | X | $R^{1S}$ | $R^{2S}$ | $R^{3S}$ | ESI MS (M + H) | $^1$H-NMR, CDCl$_3$, δ (ppm) |
|---|---|---|---|---|---|---|
| 250 | (HO, Me, Me-N structure) | cladinosyl | H | H | 743.7 | (300 MHz): 0.83-0.93 (m, 9H) 1.04-1.32 (m, 2H) 1.13 (d, J = 7.31 Hz, 3H) 1.17 (d, J = 7.31 Hz, 3H) 1.23 (d, J = 6.22 Hz, 3H) 1.23 (s, 3H) 1.29 (d, J = 6.22 Hz, 3H) 1.38 (s, 3H) 1.49-1.79 (m, 4H) 1.91-2.53 (m, 9H) 2.29 (s, 6H) 2.36 (s, 3H) 2.70-3.08 (m, 3H) 3.17-3.27 (m, 1H) 3.34 (s, 3H) 3.44-3.59 (m, 2H) 3.66 (d, J = 8.24 Hz, 1H) 3.99-4.10 (m, 1H) 4.14-4.24 (m, 2H) 4.30-4.33 (m, 1H) 4.41 (d, J = 7.31 Hz, 1H) 4.64-4.74 (m, 1H) 4.96 (d, J = 4.97 Hz, 1H) |
| 251 | (HO, Me, Me-N structure) | cladinosyl | H | (1,5-naphthyridinyl) | 871.7 | (300 MHz): 0.83 (t, J = 7.38 Hz, 3H) 0.88 (d, J = 7.31 Hz, 3H) 0.91 (d, J = 6.84 Hz, 3H) 1.10-1.37 (m, 2H) 1.16 (d, J = 7.31 Hz, 3H) 1.19 (d, J = 7.46 Hz, 3H) 1.25 (s, 3H) 1.27 (d, J = 6.22 Hz, 3H) 1.34 (d, J = 6.37 Hz, 3H) 1.44-2.10 (m, 5H) 1.47 (s, 3H) 2.23-2.55 (m, 7H) 2.30 (s, 6H) 2.31 (s, 3H) 2.74-2.96 (m, 2H) 3.05 (t, J = 9.25 Hz, 1H) 3.20-3.28 (m, 1H) 3.35 (s, 3H) 3.46-3.60 (m, 2H) 3.75 (d, J = 8.08 Hz, 1H) 4.03-4.15 (m, 1H) 4.30 (d, J = 2.64 Hz, 1H) 4.41-4.71 (m, 4H) 5.07 (d, J = 4.35 Hz, 1H) 7.63 (dd, J = 8.55, 4.20 Hz, 1H) 8.36-8.41 (m, 1H) 8.45-8.48 (m, 1H) 8.98-9.01 (m, 2H) |

TABLE 10-continued formula (S)

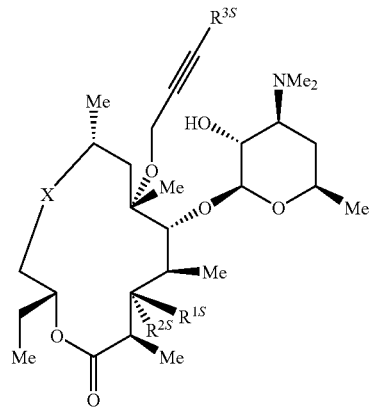

| Example | X | $R^{1S}$ | $R^{2S}$ | $R^{3S}$ | ESI MS (M + H) | $^1$H-NMR, CDCl$_3$, δ (ppm) |
|---|---|---|---|---|---|---|
| 252 | HO, Me,,, Me-N | cladinosyl | H | isoxazole-pyridazine | 888.7 | (300 MHz): 0.84-0.94 (m, 9H) 1.09-1.35 (m, 8H) 1.15 (d, J = 7.31 Hz, 3H) 1.19 (d, J = 7.46 Hz, 3H) 1.32 (d, J = 6.22 Hz, 3H) 1.44 (s, 3H) 1.49-1.88 (m, 4H) 1.95-2.54 (m, 8H) 2.29 (s, 6H) 2.34 (s, 3H) 2.73-2.98 (m, 2H) 3.04 (t, J = 9.17 Hz, 1H) 3.23 (dd, J = 10.65, 7.38 Hz, 1H) 3.34 (s, 3H) 3.45-3.56 (m, 2H) 3.70 (d, J = 8.39 Hz, 1H) 4.01-4.11 (m, 1H) 4.21-4.24 (m, 1H) 4.43 (d, J = 7.15 Hz, 1H) 4.46-4.74 (m, 3H) 5.00 (d, J = 3.89 Hz, 1H) 7.30 (s, 1H) 7.61 (dd, J = 8.55, 4.97 Hz, 1H) 8.26 (dd, J = 8.55, 1.71 Hz, 1H) 9.25 (dd, J = 4.97, 1.71 Hz, 1H) |
| 253 | O=, Me,,, N (oxazolidinone) | cladinosyl | H | H | 755.6 | (300 MHz): 0.93 (t, J = 7.54 Hz, 3H) 1.09 (d, J = 7.46 Hz, 3H) 1.07-1.33 (m, 14H) 1.13 (d, J = 6.53 Hz, 3H) 1.19 (d, J = 7.15 Hz, 3H) 1.30 (d, J = 6.22 Hz, 3H) 1.45-1.83 (m, 6H) 2.07-2.51 (m, 5H) 2.28 (s, 6H) 2.67-2.79 (m, 1H) 2.98-3.10 (m, 2H) 3.17 (dd, J = 10.26, 7.31 Hz, 1H) 3.31 (s, 3H) 3.45 (dd, 1H) 3.58 (dd, J = 10.57, 3.11 Hz, 1H) 3.64 (d, J = 7.62 Hz, 1H) 3.74-3.80 (m, 1H) 3.81-3.90 (m, 1H) 3.93-4.05 (m, 2H) 4.21 (ddd, J = 21.18, 16.44, 2.49 Hz, 2H) 4.37 (d, J = 7.30 Hz, 1H) 4.85-4.98 (m, 2H) |
| 254 | O=, Me,,, N (oxazolidinone) | cladinosyl | H | naphthyridine | 883.7 | (300 MHz): 0.91 (t, J = 7.62 Hz, 3H) 1.09-1.32 (m, 11H) 1.13 (d, J = 7.62 Hz, 3H) 1.17 (d, J = 6.53 Hz, 3H) 1.21 (d, J = 7.15 Hz, 3H) 1.24 (s, 3H) 1.30 (d, J = 6.53 Hz, 3H) 1.51-1.88 (m, 7H) 2.20-2.48 (m, 3H) 2.28 (s, 6H) 2.72-2.81 (m, 1H) 2.98-3.11 (m, 2H) 3.19 (dd, J = 10.26, 7.31 Hz, 1H) 3.32 (s, 3H) 3.41-3.56 (m, 1H) 3.60-3.90 (m, 4H) 3.97-4.05 (m, 2H) 4.40 (d, J = 7.15 Hz, 1H) 4.46-4.61 (m, 2H) 4.91 (d, J = 4.20 Hz, 1H) 4.94-5.03 (m, 1H) 7.61 (dd, J = 8.55, 4.20 Hz, 1H) 8.35-8.40 (m, 1H) 8.45-8.47 (m, 1H) 8.97-9.01 (m, 2H) |
| 255 | O=, Me,,, N (oxazolidinone) | cladinosyl | H | isoxazole-pyridazine | 900.7 | (300 MHz): 0.93 (t, J = 7.54 Hz, 3H) 1.12 (d, J = 7.46 Hz, 3H) 1.10-1.34 (m, 14H) 1.15 (d, J = 6.37 Hz, 3H) 1.21 (d, J = 7.15 Hz, 3H) 1.31 (d, J = 6.22 Hz, 3H) 1.54-1.85 (m, 6H) 2.19-2.30 (m, 3H) 2.32 (s, 6H) 2.43-2.55 (m, 1H) 2.70-2.80 (m, 1H) 2.98-3.25 (m, 3H) 3.32 (s, 3H) 3.45-3.56 (m, 1H) 3.62 (dd, J = 10.10, 2.80 Hz, 1H) 3.71 (d, J = 7.31 Hz, 1H) 3.74-3.83 (m, 2H) 3.96 (d, J = 8.55 Hz, 1H) 3.96-4.06 (m, 2H) 4.41 (d, J = 7.15 Hz, 1H) 4.47-4.61 (m, 2H) 4.90 (d, J = 4.35 Hz, 1H) 4.93-5.05 (m, 1H) 7.31 (s, 1H) 7.61 (dd, J = 8.55, 4.97 Hz, 1H) 8.25 (dd, J = 8.55, 1.71 Hz, 1H) 9.24 (dd, J = 4.97, 1.71 Hz, 1H) |

TABLE 10-continued formula (S)

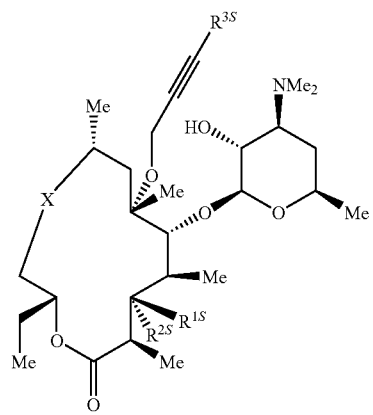

| Example | X | R$^{1S}$ | R$^{2S}$ | R$^{3S}$ | ESI MS (M + H) | $^1$H-NMR, CDCl$_3$, δ (ppm) |
|---|---|---|---|---|---|---|
| 256 | ![] | ![] | ![] | ![] | 740.4 | (300 MHz): 0.95 (t, J = 7.46 Hz, 3H) 1.12-1.77 (m, 12H) 1.19 (d, J = 6.53 Hz, 3H) 1.26 (d, J = 6.06 Hz, 3H) 1.41 (d, J = 6.84 Hz, 3H) 1.59 (s, 3H) 2.08-2.19 (m, 1H) 2.28 (s, 6H) 2.41-2.53 (m, 1H) 2.86-2.99 (m, 1H) 3.10 (dd, J = 15.08, 10.41 Hz, 1H) 3.20 (dd, J = 10.26, 7.31 Hz, 1H) 3.46-3.75 (m, 4H) 3.82 (d, J = 13.37 Hz, 1H) 3.96-4.16 (m, 2H) 4.13 (d, J = 11.04 Hz, 1H) 4.22 (d, J = 9.48 Hz, 1H) 4.33 (d, J = 7.31 Hz, 1H) 4.81-4.93 (m, 1H) 7.30 (s, 1H) 7.60 (dd, J = 8.63, 5.05 Hz, 1H) 8.25 (dd, J = 8.55, 1.71 Hz, 1H) 9.24 (dd, J = 5.13, 1.71 Hz, 1H) |
| 257 | ![] | cladinosyl | H | ![] | 901.5 | (300 MHz): 0.89 (t, J = 7.46 Hz, 3H) 1.05 (d, J = 6.68 Hz, 3H) 1.12 (d, J = 7.62 Hz, 3H) 1.17 (d, J = 7.15 Hz, 3H) 1.20 (d, J = 6.84 Hz, 3H) 1.29 (s, 7H) 1.30 (d, J = 6.06 Hz, 3H) 1.40 (s, 3H) 1.53-1.70 (m, 4H) 1.80-1.85 (m, 2H) 1.94-1.99 (m, 1H) 2.01 (s, 3H) 2.13 (d, J = 10.41 Hz, 1H) 2.30 (s, 6H) 2.37-2.43 (m, 1H) 2.43-2.55 (m, 1H) 2.61-2.72 (m, 3H) 3.03 (t, J = 10.10 Hz, 1H) 3.35 (s, 3H) 3.39 (dd, J = 10.49, 7.07 Hz, 1H) 3.53-3.63 (m, 2H) 3.68 (d, J = 6.06 Hz, 1H) 3.76-3.84 (m, 1H) 3.91-3.94 (m, 1H) 3.96-4.06 (m, 1H) 4.55 (d, J = 7.15 Hz, 1H) 4.61 (d, J = 14.30 Hz, 1H) 4.78 (d, J = 14.45 Hz, 1H) 4.85 (d, J = 4.04 Hz, 1H) 4.85-4.95 (m, 1H) 7.25 (s, 1H) 7.60 (dd, J = 8.55, 4.97 Hz, 1H) 8.25 (dd, J = 8.55, 1.71 Hz, 1H) 9.24 (dd, J = 5.05, 1.79 Hz, 1H) |
| 258 | ![] | ![] | ![] | ![] | 728.4 | (300 MHz): 0.85 (d, J = 6.53 Hz, 3H) 0.86 (d, J = 7.15 Hz, 3H) 0.92 (t, J = 7.38 Hz, 3H) 1.16-1.98 (m, 6H) 1.26 (d, J = 6.06 Hz, 3H) 1.34 (d, J = 6.84 Hz, 3H) 1.43 (d, J = 7.31 Hz, 3H) 1.51 (s, 3H) 2.08 (dd, J = 15.93, 1.32 Hz, 1H) 2.23-2.57 (m, 3H) 2.29 (s, 6H) 2.42 (s, 3H) 3.00 (dd, J = 15.47, 2.56 Hz, 1H) 3.21 (dd, J = 10.34, 7.23 Hz, 1H) 3.33-3.57 (m, 3H) 3.67 (s, 1H) 3.89 (d, J = 9.17 Hz, 1H) 3.94-4.07 (m, 2H) 4.13-4.24 (m, 1H) 4.41 (d, J = 7.31 Hz, 1H) 4.64-4.72 (m, 1H) 7.22 (s, 1H) 7.61 (dd, J = 8.55, 4.97 Hz, 1H) 8.25 (dd, J = 8.55, 1.71 Hz, 1H) 9.25 (dd, J = 5.05, 1.79 Hz, 1H) |

Example 250

(1) By using the compound obtained in Example 6 (650 mg) as a starting material, a cyclized compound (312 mg) was obtained in the same manners as those of Example 7, (1), (2) and (3).
(2) By using the compound obtained in (1) mentioned above (300 mg) as a starting material, the compound shown in Table 10 (166 mg) was obtained in the same manner as that of Example 7, (4).

Example 251

The compound obtained in Example 250 (50 mg) was dissolved in acetonitrile (1.5 ml), the solution was added with 3-bromo-1,5-naphthyridine (21.1 mg) obtained by the method described in the literature (Journal of Organic Chemistry, 1968, vol. 33, p. 1384), tetrakistriphenylphosphine palladium (3.9 mg) and triethylamine (0.3 ml), and the mixture was stirred at 80° C. for 4 hours. The reaction mixture was concentrated under reduced pressure, and the resulting residue was purified by silica gel column chromatography (hexane:acetone:triethylamine=10:10:0.2) to obtain the compound shown in Table 10 (26.8 mg).

Example 252

By using the compound obtained in Example 250 (6.0 mg) and 5-iodo-3-(pyridazin-3-yl)isoxazole (3.3 mg) obtained by the method described in the patent document (WO05/087787) as starting materials, the compound shown in Table 10 (4.24 mg) was obtained in the same manner as that of Example 251.

Example 253

By using the compound obtained in Example 250 (92 mg) as a starting material, the compound shown in Table 10 (48.3 mg) was obtained in the same manners as those of Example 176, (3), Example 207, (1) and Example 125, (3).

Example 254

By using the compound obtained in Example 253 (22 mg) as a starting material, the compound shown in Table 10 (10.1 mg) was obtained in the same manner as that of Example 251.

Example 255

By using the compound obtained in Example 253 (22 mg) as a starting material, the compound shown in Table 10 (21.4 mg) was obtained in the same manner as that of Example 252.

Example 256

(1) By using the compound obtained in Example 255 (15 mg) as a starting material, a 3-hydroxy compound (11.2 mg) was obtained in the same manners as those of Example 125, (2) and Example 176, (3).
(2) By using the compound obtained in (1) mentioned above (11.2 mg) as a starting material, the compound shown in Table 10 (6.71 mg) was obtained in the same manners as those of Example 176, (4) and Example 125, (3).

Example 257

(1) By using the compound obtained in Example 250, (1) (1.0 g) as a starting material, a 9-hydroxy compound (592 mg) was obtained in the same manners as those of Example 126, (1), Example 219, (2) and Example 7, (4).
(2) By using the compound obtained in (1) mentioned above (590 mg) as a starting material, a ketone compound (594 mg) was obtained in the same manners as those of Example 176, (3) and (4).
(3) By using the compound obtained in (2) mentioned above (280 mg) as a starting material, a deacetylated compound (229.5 mg) was obtained in the same manner as that of Example 125, (3).
(4) By using the compound obtained in (3) mentioned above (150 mg) as a starting material, a coupling compound (188 mg) was obtained in the same manner as that of Example 252.
(5) By using the compound obtained in (4) mentioned above (180 mg) as a starting material, an oxime compound (81 mg) was obtained in the same manner as that of Example 214.
(6) By using the compound obtained in (5) mentioned above (49.7 mg) as a starting material, the compound shown in Table 10 (40.0 mg) was obtained in the same manner as that of Example 219, (4).

Example 258

(1) By using the compound obtained in Example 250, (1) (1.0 g) as a starting material, a 3-hydroxy compound (135 mg) was obtained in the same manners as those of Example 125, (2) and Example 112, (1).
(2) By using the compound obtained in (1) mentioned above (135 mg) as a starting material, a 3-ketone compound (72.3 mg) was obtained in the same manners as those of Example 176, (4) and Example 114, (4).
(3) By using the compound obtained in (2) mentioned above (71 mg) as a starting material, a coupling compound (70.6 mg) was obtained in the same manner as that of Example 252.
(4) By using the compound obtained in (3) mentioned above (70.6 mg) as a starting material, the compound shown in Table 10 (38.4 mg) was obtained in the same manner as that of Example 125, (2).

Example 259

Synthesis of the Compound Represented by the Formula (T)

[Formula 28]

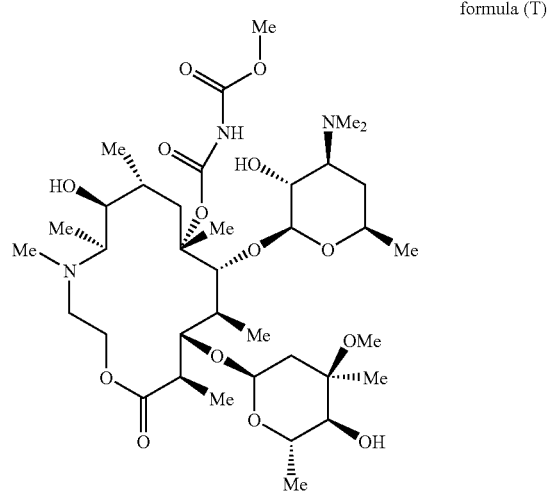

formula (T)

(1) The compound obtained in Example 240, (2) (0.2 g) was dissolved in chloroform (3 ml), the solution was added with trichloroacetyl isocyanate (26 μl) under ice cooling, and the mixture was stirred at room temperature for 3 hours. The reaction mixture was added with methanol (40 μl) and potassium carbonate (40 mg), and the mixture was stirred at room temperature for 2.5 days. The reaction mixture was added with chloroform and saturated aqueous sodium hydrogencarbonate, and the layers were separated. The organic layer was washed with saturated brine, then dried over anhydrous magnesium sulfate and filtered. The filtrate was concentrated under reduced pressure, and the resulting residue was purified by silica gel column chromatography (hexane:acetone:triethylamine=50:10:0.2) to obtain a 6-O-carbamate compound (0.16 g).

(2) By using the compound obtained in (1) mentioned above (80 mg) as a starting material, the title compound (4.7 mg) was obtained in the same manner as that of Example 7, (4).
MS (ESI) m/z=778.5 [M+H]$^+$
$^1$H-NMR (300 MHz, CDCl$_3$) δ (ppm): 0.85 (d, J=6.22 Hz, 3H), 0.90 (d, J=6.68 Hz, 3H), 1.13 (d, J=7.15 Hz, 3H), 1.15-1.32 (m, 14H), 1.27 (d, J=6.37 Hz, 3H), 1.44-1.80 (m, 3H), 2.10-2.61 (m, 6H), 2.29 (s, 6H), 2.32 (s, 3H), 2.76-2.96 (m, 2H), 2.98-3.07 (m, 1H), 3.20-3.33 (m, 2H), 3.33 (s, 3H), 3.42-3.55 (m, 1H), 3.76 (s, 3H), 3.80-4.09 (m, 3H), 4.24-4.49 (m, 3H), 4.73-4.81 (m, 1H)

Example 260

Synthesis of the Compound Represented by the Formula (U)

[Formula 29]

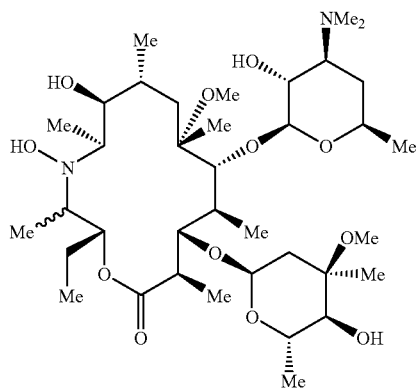

formula (U)

(1) By using the compound obtained in Example 245, (2) (119 mg) as a starting material, a deprotected compound (70 mg) was obtained in the same manner as that of Example 7, (4).

(2) The compound obtained in (1) mentioned above (30 mg) was dissolved in dichloromethane (860 μl), the solution was added with m-chloroperbenzoic acid (30 mg) on an ice bath, and the mixture was stirred at the same temperature for 1 hour. The reaction mixture was added with distilled water and chloroform, the layers were separated, and the organic layer was washed successively with saturated aqueous sodium hydrogencarbonate and saturated brine, then dried over anhydrous magnesium sulfate and filtered. The filtrate was concentrated under reduced pressure, and the resulting residue was purified by silica gel column chromatography (chloroform:methanol:28% aqueous ammonia=10:1:0.1). The resulting compound (27 mg) was dissolved in tetrahydrofuran (4 ml), the solution was added with triphenylphosphine (45 mg), and the mixture was stirred at 70° C. for 60 hours. The reaction mixture was concentrated under reduced pressure, and the resulting residue was purified by silica gel column chromatography (chloroform:methanol:28% aqueous ammonia=10:1:0.1) to obtain a nitrone compound (24 mg).

(3) The compound obtained in (2) mentioned above (8 mg) was dissolved in diethyl ether-dichloromethane-tetrahydrofuran (1:1:1, 3 ml), the solution was added with a 0.84 M solution of methylmagnesium iodide in ether (660 μl) on an ice bath, and the mixture was stirred at room temperature for 2 hours. The reaction mixture was added with saturated aqueous ammonium chloride and chloroform, the layers were separated, and the organic layer was dried over anhydrous magnesium sulfate and filtered. The filtrate was concentrated under reduced pressure, and the resulting residue was purified by silica gel column chromatography (chloroform:methanol:28% aqueous ammonia=10:1:0.1) to obtain the title compound (5 mg).
MS (ESI) m/z=735.5 [M+H]$^+$
$^1$H-NMR (300 MHz, CDCl$_3$) δ (ppm): 0.87 (t, J=7.57 Hz, 3H), 0.97 (d, J=6.88 Hz, 3H), 1.09-1.13 (m, 6H), 1.18 (d, J=6.88 Hz, 3H), 1.19-1.29 (m, 11H), 1.30 (d, J=5.96 Hz, 3H), 1.34 (s, 3H), 1.44-1.77 (m, 4H), 1.98-2.05 (m, 1H), 2.06-2.13 (m, 1H), 2.14-2.22 (m, 2H), 2.28 (s, 6H), 2.36 (d, J=15.13 Hz, 1H), 2.42-2.52 (m, 1H), 2.73-2.81 (m, 1H), 2.92-3.08 (m, 3H), 3.16-3.25 (m, 2H), 3.30 (s, 3H), 3.30 (s, 3H), 3.42-3.54 (m, 1H), 3.73 (d, J=8.71 Hz, 1H), 3.97-4.08 (m, 2H), 4.38 (d, J=7.34 Hz, 1H), 4.86 (d, J=4.58 Hz, 1H), 4.96 (td, J=7.91, 3.44 Hz, 1H), 5.83 (br.s., 1H)

Example 261

Synthesis of the Compound Represented by the Formula (V)

[Formula 30]

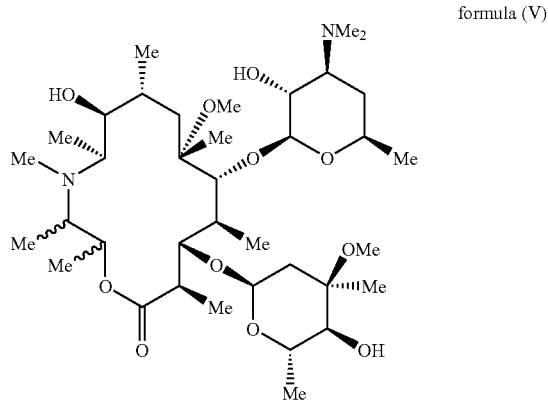

formula (V)

By using the compound obtained in Example 1 (700 mg) and cis-2,3-epoxybutane (254 mg) as starting materials, the title compound (4.0 mg) was obtained in the same manner as that of Example 7.
MS (ESI) m/z=719.2 [M+H]$^+$ Syntheses of Examples 262 to 551

Preparation methods of compounds represented by the formula (W) having $R^{1W}$ and $R^{2W}$ defined in Table 11 are shown below.

TABLE 11 formula (W)

| Example | $R^{1W}$ | $R^{2W}$ | ESI MS (M + H) | $^1$H-NMR, CDCl$_3$, δ (ppm) |
|---|---|---|---|---|
| 262 | H₂N— | —H | 718 | (300 MHz): 0.81-0.84 (m, 6H) 0.89 (t, J = 7.2 Hz, 3H) 1.10 (d, J = 7.2 Hz, 3H) 1.15-1.23 (m, 10H) 1.27-1.32 (m, 6H) 1.48-1.85 (m, 6H) 2.15-2.54 (m, 16H) 2.76-2.91 (m, 2H) 3.18-3.24 (m, 4H) 3.29 (s, 3H) 3.41-3.54 (m, 2H) 3.72 (d, J = 7.8 Hz, 1H) 4.04 (dq, J = 9.6 Hz, J = 6.3 Hz, 1H) 4.14 (d, J = 4.5 Hz, 1H) 4.42 (d, J = 7.2 Hz, 1H) 4.65 (m, 1H) 4.95 (d, J = 4.8 Hz, 1H) |
| 263 | HO— | —H | 719 | (300 MHz): 0.81-0.92 (m, 9H) 1.11 (d, J = 7.2 Hz, 3H) 1.16-1.25 (m, 13H) 1.32 (s, 3H) 1.42-1.85 (m, 7H) 2.07 (d, J = 15.3 Hz, 1H) 2.15-2.55 (m, 14H) 2.77-2.91 (m, 2H) 3.04 (brs, 1H) 3.17-3.24 (m, 4H) 3.32 (s, 3H) 3.40-3.49 (m, 2H) 3.67 (d, J = 7.5 Hz, 1H) 4.18 (d, J = 3.9 Hz, 1H) 4.43 (d, J = 7.2 Hz, 1H) 4.58-4.64 (m, 2H) 4.99 (d, J = 4.8 Hz, 1H) |
| 264 | carbamate linker with ethyl-N(Et)-CH(Me)-(3-methoxyphenyl) | —H | 967.6 | (600 MHz): 0.82 (d, J = 6.42 Hz, 6H) 0.89 (t, J = 7.34 Hz, 3H) 1.00 (t, J = 7.11 Hz, 3H) 1.07-1.26 (m, 2H) 1.10-1.20 (m, 15H) 1.31 (s, 3H) 1.32 (d, J = 6.88 Hz, 3H) 1.50-1.65 (m, 3H) 1.69-1.79 (m, 1H) 1.80-1.88 (m, 1H) 2.11-2.21 (m, 1H) 2.23-2.51 (m, 6H) 2.28 (s, 6H) 2.36 (s, 3H) 2.54-2.64 (m, 3H) 2.77-2.84 (m, 1H) 2.85-2.93 (m, 1H) 3.16-3.22 (m, 3H) 3.23 (s, 3H) 3.34 (s, 3H) 3.35-3.45 (m, 1H) 3.54-3.64 (m, 1H) 3.71 (d, J = 7.79 Hz, 1H) 3.79 (s, 3H) 3.81-3.85 (m, 1H) 4.18-4.25 (m, 1H) 4.35-4.42 (m, 1H) 4.43-4.48 (m, 1H) 4.53 (d, J = 10.09 Hz, 1H) 4.64 (s, 1H) 4.97 (d, J = 3.21 Hz, 1H) 5.19 (s, 1H) 6.76 (d, J = 10.09 Hz, 1H) 6.84 (s, 1H) 6.88 (d, J = 7.34 Hz, 1H) 7.21 (t, J = 7.79 Hz, 1H) |
| 265 | carbamate linker with ethyl-N(Et)-CH(Me)-(4-methoxyphenyl) | —H | 967.6 | (600 MHz): 0.82 (d, J = 6.88 Hz, 6H) 0.89 (t, J = 7.34 Hz, 3H) 0.99 (t, J = 6.88 Hz, 3H) 1.07-1.23 (m, 2H) 1.12 (s, 3H) 1.12-1.18 (m, 9H) 1.19 (d, J = 6.42 Hz, 3H) 1.28-1.32 (m, 6H) 1.50-1.66 (m, 3H) 1.69-1.79 (m, 1H) 1.80-1.88 (m, 1H) 2.11-2.21 (m, 1H) 2.22-2.46 (m, 6H) 2.28 (s, 6H) 2.36 (s, 3H) 2.51-2.61 (m, 3H) 2.78-2.84 (m, 1H) 2.85-2.91 (m, 1H) 3.15-3.22 (m, 3H) 3.23 (s, 3H) 3.35 (s, 3H) 3.35-3.45 (m, 1H) 3.56-3.65 (m, 1H) 3.71 (d, J = 7.79 Hz, 1H) 3.78 (s, 3H) 3.80-3.87 (m, 1H) 4.21 (s, 1H) 4.36-4.42 (m, 1H) 4.46 (d, J = 7.79 Hz, 1H) 4.53 (d, J = 9.63 Hz, 1H) 4.60-4.69 (m, 1H) 4.97 (d, J = 4.58 Hz, 1H) 5.17-5.23 (m, 1H) 6.83 (d, J = 8.71 Hz, 2H) 7.19 (d, J = 8.25 Hz, 2H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 266 | [carbamate-CH₂CH₂-N(Et)-CH(Me)-(4-F-C₆H₄)] | H | 955.6 | (600 MHz): 0.82 (d, J = 6.88 Hz, 6H) 0.89 (t, J = 7.34 Hz, 3H) 1.00 (t, J = 7.11 Hz, 3H) 1.07-1.25 (m, 2H) 1.10 (s, 3H) 1.11-1.14 (m, 3H) 1.14-1.20 (m, 9H) 1.27-1.35 (m, 6H) 1.51-1.65 (m, 3H) 1.69-1.79 (m, 1H) 1.81-1.88 (m, 1H) 2.10-2.21 (m, 1H) 2.23-2.33 (m, 2H) 2.28 (s, 6H) 2.36 (s, 3H) 2.38-2.47 (m, 4H) 2.49-2.62 (m, 3H) 2.78-2.84 (m, 1H) 2.85-2.92 (m, 1H) 3.15-3.26 (m, 3H) 3.23 (s, 3H) 3.35 (s, 3H) 3.36-3.45 (m, 1H) 3.56-3.65 (m, 1H) 3.72 (d, J = 7.79 Hz, 1H) 3.83-3.89 (m, 1H) 4.22 (s, 1H) 4.35-4.43 (m, 1H) 4.44-4.49 (m, 1H) 4.52 (d, J = 9.63 Hz, 1H) 4.63 (s, 1H) 4.97 (d, J = 4.13 Hz, 1H) 5.15 (s, 1H) 6.98 (t, J = 8.71 Hz, 2H) 7.23-7.29 (m, 2H) |
| 267 | [carbamate-CH₂CH₂-N(Et)-CH(Me)-(4-Cl-C₆H₄)] | H | 971.6 | (600 MHz): 0.82 (d, J = 6.88 Hz, 6H) 0.89 (t, J = 7.34 Hz, 3H) 1.00 (t, J = 7.11 Hz, 3H) 1.07-1.25 (m, 2H) 1.10-1.14 (m, 3H) 1.11 (s, 3H) 1.14-1.20 (m, 9H) 1.28-1.33 (m, 6H) 1.50-1.66 (m, 3H) 1.69-1.80 (m, 1H) 1.80-1.89 (m, 1H) 2.10-2.21 (m, 1H) 2.22-2.34 (m, 2H) 2.28 (s, 6H) 2.36 (s, 3H) 2.37-2.48 (m, 4H) 2.50-2.62 (m, 3H) 2.77-2.85 (m, 1H) 2.85-2.93 (m, 1H) 3.15-3.26 (m, 3H) 3.23 (s, 3H) 3.33-3.45 (m, 1H) 3.36 (s, 3H) 3.55-3.65 (m, 1H) 3.72 (d, J = 7.79 Hz, 1H) 3.82-3.89 (m, 1H) 4.18-4.26 (m, 1H) 4.35-4.43 (m, 1H) 4.44-4.49 (m, 1H) 4.53 (d, J = 9.63 Hz, 1H) 4.63 (s, 1H) 4.97 (d, J = 4.58 Hz, 1H) 5.15 (s, 1H) 7.21-7.29 (m, 4H) |
| 268 | [carbamate-CH₂CH₂-N(Et)-CH(Me)-(4-Me-C₆H₄)] | H | 951.6 | (600 MHz): 0.82 (d, J = 5.96 Hz, 6H) 0.89 (t, J = 7.34 Hz, 3H) 0.96-1.03 (m, 3H) 1.07-1.25 (m, 17H) 1.28-1.34 (m, 6H) 1.48-1.66 (m, 3H) 1.69-1.79 (m, 1H) 1.80-1.89 (m, 1H) 2.12-2.20 (m, 1H) 2.22-2.30 (m, 2H) 2.27 (s, 6H) 2.31 (s, 3H) 2.33-2.48 (m, 4H) 2.36 (s, 3H) 2.52-2.63 (m, 3H) 2.78-2.85 (m, 1H) 2.85-2.94 (m, 1H) 3.15-3.23 (m, 3H) 3.23 (s, 3H) 3.35 (s, 3H) 3.36-3.44 (m, 1H) 3.56-3.66 (m, 1H) 3.72 (d, J = 8.25 Hz, 1H) 3.80-3.89 (m, 1H) 4.16-4.25 (m, 1H) 4.35-4.43 (m, 1H) 4.45-4.49 (m, 1H) 4.53 (d, J = 10.09 Hz, 1H) 4.60-4.69 (m, 1H) 4.93-5.00 (m, 1H) 5.22 (s, 1H) 7.10 (d, J = 7.79 Hz, 2H) 7.17 (d, J = 8.25 Hz, 2H) |
| 269 | [carbamate-CH₂CH₂-N(Et)-CH(Me)-(2-F-C₆H₄)] | H | 955.6 | (600 MHz): 0.82 (d, J = 6.42 Hz, 6H) 0.89 (t, J = 8.02 Hz, 3H) 1.00 (t, J = 6.88 Hz, 3H) 1.07-1.27 (m, 2H) 1.10 (s, 3H) 1.12 (d, J = 6.88 Hz, 3H) 1.14-1.18 (m, 6H) 1.19 (d, J = 5.96 Hz, 3H) 1.31 (s, 3H) 1.33 (d, J = 6.88 Hz, 3H) 1.49-1.68 (m, 3H) 1.74 (s, 1H) 1.85 (s, 1H) 2.10-2.20 (m, 1H) 2.21-2.50 (m, 6H) 2.27 (s, 6H) 2.36 (s, 3H) 2.53-2.65 (m, 3H) 2.77-2.84 (m, 1H) 2.89 (d, J = 16.05 Hz, 1H) 3.15-3.28 (m, 3H) 3.23 (s, 3H) 3.34 (s, 3H) 3.36-3.45 (m, 1H) 3.58-3.67 (m, 1H) 3.71 (d, J = 8.25 Hz, 1H) 4.17 (s, 1H) 4.26-4.33 (m, 1H) 4.34-4.42 (m, 1H) 4.49 (d, J = 6.42 Hz, 1H) 4.48-4.56 (m, 1H) 4.64 (s, 1H) 4.96 (d, J = 4.59 Hz, 1H) 5.25-5.33 (m, 1H) 6.98-7.03 (m, 1H) 7.08 (t, J = 7.11 Hz, 1H) 7.17-7.24 (m, 1H) 7.30 (t, J = 7.11 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 270 | [benzyloxy-phenyl-CH(Me)-N(Et)-CH$_2$CH$_2$-NH-C(=O)-O-] | H | 1043.6 | mixture of diastereomers (600 MHz): 0.78 (d, J = 6.42 Hz, 6H) 0.86 (t, J = 7.34 Hz, 3H) 0.90-1.00 (m, 3H) 1.04-1.22 (m, 2H) 1.07-1.17 (m, 15H) 1.24-1.31 (m, 6H) 1.46-1.63 (m, 3H) 1.71 (s, 1H) 1.81 (s, 1H) 2.07-2.17 (m, 1H) 2.18-2.47 (m, 6H) 2.23 (s, 6H) 2.32 (s, 3H) 2.48-2.61 (m, 3H) 2.74-2.81 (m, 1H) 2.85 (d, J = 14.21 Hz, 1H) 3.11-3.23 (m, 3H) 3.20 (s, 3H) 3.31 (s, 3H) 3.33-3.43 (m, 1H) 3.52-3.62 (m, 1H) 3.68 (d, J = 7.79 Hz, 1H) 3.72-3.84 (m, 1H) 4.14-4.22 (m, 1H) 4.32-4.40 (m, 1H) 4.43 (d, J = 5.96 Hz, 1H) 4.47-4.54 (m, 1H) 4.60 (s, 1H) 4.91-4.96 (m, 1H) 5.00 (s, 2H) 5.15-5.25 (m, 1H) 6.87 (d, J = 8.71 Hz, 2H) 7.17 (d, J = 7.79 Hz, 2H) 7.26-7.31 (m, 1H) 7.32-7.37 (m, 2H) 7.37-7.41 (m, 2H) |
| 271 | [3-F-phenyl-CH(Me)-N(Et)-CH$_2$CH$_2$-NH-C(=O)-O-] | H | 955.6 | mixture of diastereomers (600 MHz): 0.81 (d, J = 6.42 Hz, 6H) 0.89 (t, J = 7.79 Hz, 3H) 1.00 (t, J = 7.11 Hz, 3H) 1.07-1.27 (m, 17H) 1.28-1.33 (m, 6H) 1.48-1.67 (m, 3H) 1.69-1.89 (m, 2H) 2.11-2.20 (m, 1H) 2.22-2.63 (m, 9H) 2.28 (s, 6H) 2.36 (s, 3H) 2.77-2.85 (m, 1H) 2.88 (d, J = 15.13 Hz, 1H) 3.16-3.46 (m, 4H) 3.23 (s, 3H) 3.34 (s, 3H) 3.55-3.63 (m, 1H) 3.71 (d, J = 7.79 Hz, 1H) 3.78-3.88 (m, 1H) 4.18-4.25 (m, 1H) 4.34-4.43 (m, 1H) 4.43-4.48 (m, 1H) 4.58 Hz, 1H) 4.63 (s, 1H) 4.97 (d, J = 3.21 Hz, 1H) 5.14-5.21 (m, 1H) 6.90 (t, J = 8.25 Hz, 1H) 7.01 (d, J = 10.09 Hz, 1H) 7.06 (d, J = 7.79 Hz, 1H) 7.22-7.28 (m, 1H), and (600 MHz): 0.81 (d, J = 6.42 Hz, 6H) 0.89 (t, J = 7.79 Hz, 3H) 0.97 (t, J = 7.11 Hz, 3H) 1.07-1.27 (m, 17H) 1.28-1.33 (m, 6H) 1.48-1.67 (m, 3H) 1.69-1.89 (m, 2H) 2.11-2.20 (m, 1H) 2.22-2.63 (m, 9H) 2.28 (s, 6H) 2.36 (s, 3H) 2.77-2.85 (m, 1H) 2.88 (d, J = 15.13 Hz, 1H) 3.16-3.46 (m, 4H) 3.23 (s, 3H) 3.34 (s, 3H) 3.55-3.63 (m, 1H) 3.71 (d, J = 7.79 Hz, 1H) 3.78-3.88 (m, 1H) 4.18-4.25 (m, 1H) 4.34-4.43 (m, 1H) 4.43-4.48 (m, 1H) 4.54 (d, J = 4.13 Hz, 1H) 4.63 (s, 1H) 4.97 (d, J = 3.21 Hz, 1H) 5.14-5.21 (m, 1H) 6.90 (t, J = 8.25 Hz, 1H) 7.01 (d, J = 10.09 Hz, 1H) 7.06 (d, J = 7.79 Hz, 1H) 7.22-7.28 (m, 1H) |
| 272 | [3-Cl-phenyl-CH(Me)-N(Et)-CH$_2$CH$_2$-NH-C(=O)-O-] | H | 971.6 | mixture of diastereomers (600 MHz): 0.81 (d, J = 6.42 Hz, 6H) 0.87-0.93 (m, 3H) 0.94-1.03 (m, 3H) 1.07-1.25 (m, 2H) 1.11-1.21 (m, 15H) 1.30 (s, 3H) 1.32 (d, J = 6.88 Hz, 3H) 1.48-1.65 (m, 3H) 1.75 (s, 1H) 1.84 (s, 1H) 2.10-2.21 (m, 1H) 2.21-2.53 (m, 6H) 2.28 (s, 6H) 2.36 (s, 3H) 2.53-2.64 (m, 3H) 2.77-2.84 (m, 1H) 2.84-2.96 (m, 1H) 3.16-3.26 (m, 3H) 3.22 (s, 3H) 3.33 (s, 3H) 3.35-3.46 (m, 1H) 3.55-3.66 (m, 1H) 3.69-3.74 (m, 1H) 3.76-3.88 (m, 1H) 4.18-4.26 (m, 1H) 4.34-4.42 (m, 1H) 4.43-4.51 (m, 1H) 4.52-4.56 (m, 1H) 4.63 (s, 1H) 4.93-5.00 (m, 1H) 5.12-5.23 (m, 1H) 7.15-7.31 (m, 4H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 273 | (4-ethoxyphenyl)(Me)CH-N(Et)-CH$_2$CH$_2$-NH-C(O)-O- | H | 981.6 | mixture of diastereomers (600 MHz): 0.81 (d, J = 6.88 Hz, 6H) 0.89 (t, J = 7.79 Hz, 3H) 0.93-1.04 (m, 3H) 1.06-1.27 (m, 2H) 1.10-1.21 (m, 15H) 1.27-1.33 (m, 6H) 1.39 (t, J = 7.34 Hz, 3H) 1.49-1.67 (m, 3H) 1.75 (s, 1H) 1.84 (s, 1H) 2.16 (s, 1H) 2.21-2.33 (m, 2H) 2.28 (s, 6H) 2.33-2.49 (m, 4H) 2.35 (s, 3H) 2.50-2.64 (m, 3H) 2.77-2.84 (m, 1H) 2.84-2.92 (m, 1H) 3.14-3.22 (m, 3H) 3.23 (s, 3H) 3.34 (s, 3H) 3.36-3.45 (m, 1H) 3.56-3.66 (m, 1H) 3.69-3.74 (m, 1H) 3.74-3.87 (m, 1H) 3.97-4.02 (m, 2H) 4.18-4.24 (m, 1H) 4.35-4.43 (m, 1H) 4.47 (d, J = 6.88 Hz, 1H) 4.51-4.55 (m, 1H) 4.64 (s, 1H) 4.95-4.99 (m, 1H) 5.18-5.28 (m, 1H) 6.81 (d, J = 8.25 Hz, 2H) 7.18 (d, J = 8.25 Hz, 2H), and (600 MHz): 0.81 (d, J = 6.88 Hz, 6H) 0.89 (t, J = 7.79 Hz, 3H) 0.93-1.04 (m, 3H) 1.06-1.27 (m, 2H) 1.10-1.21 (m, 15H) 1.27-1.33 (m, 6H) 1.39 (t, J = 7.34 Hz, 3H) 1.49-1.67 (m, 3H) 1.75 (s, 1H) 1.84 (s, 1H) 2.16 (s, 1H) 2.21-2.33 (m, 2H) 2.28 (s, 6H) 2.33-2.49 (m, 4H) 2.35 (s, 3H) 2.50-2.64 (m, 3H) 2.77-2.84 (m, 1H) 2.84-2.92 (m, 1H) 3.14-3.22 (m, 3H) 3.23 (s, 3H) 3.35 (s, 3H) 3.36-3.45 (m, 1H) 3.56-3.66 (m, 1H) 3.69-3.74 (m, 1H) 3.74-3.87 (m, 1H) 3.97-4.02 (m, 2H) 4.18-4.24 (m, 1H) 4.35-4.43 (m, 1H) 4.47 (d, J = 6.88 Hz, 1H) 4.51-4.55 (m, 1H) 4.64 (s, 1H) 4.95-4.99 (m, 1H) 5.18-5.28 (m, 1H) 6.81 (d, J = 8.25 Hz, 2H) 7.18 (d, J = 8.25 Hz, 2H) |
| 274 | -O-C(O)-NH-CH$_2$CH$_2$-NH-CH(Me)-(1-methylpyrrol-3-yl) | H | 912.5 | mixture of diastereomers (600 MHz): 0.78-0.84 (m, 6H) 0.89 (t, J = 7.34 Hz, 3H) 1.08-1.24 (m, 17H) 1.29-1.34 (m, 6H) 1.49-1.87 (m, 5H) 2.10-2.45 (m, 5H) 2.28 (s, 6H) 2.35 (s, 3H) 2.54-2.60 (m, 1H) 2.63-2.74 (m, 2H) 2.77-2.83 (m, 1H) 2.86-2.91 (m, 1H) 3.17-3.44 (m, 10H) 3.55-3.62 (m, 4H) 3.65-3.72 (m, 2H) 4.16-4.22 (m, 1H) 4.34-4.40 (m, 1H) 4.42-4.46 (m, 1H) 4.51-4.55 (m, 1H) 4.60-4.67 (m, 1H) 4.97 (d, J = 4.58 Hz, 1H) 5.28-5.33 (m, 1H) 6.01 (br. s., 1H) 6.46 (br. s., 1H) 6.51 (br. s., 1H) |

TABLE 11-continued formula (W)

[Structure of formula (W): macrolide scaffold with substituents R^(1W) and R^(2W)]

| Example | R^(1W) | R^(2W) | ESI MS (M + H) | $^1$H-NMR, CDCl$_3$, δ (ppm) |
|---|---|---|---|---|
| 275 | 2-methylphenyl-CH(Me)-N(Et)-CH$_2$CH$_2$-NH-C(O)-O-⁂ | H | 951.6 | mixture of diastereomers (600 MHz): 0.81 (d, J = 5.96 Hz, 6H) 0.86-0.93 (m, 3H) 0.93-1.03 (m, 3H) 1.04-1.25 (m, 2H) 1.09-1.20 (m, 15H) 1.28 (d, J = 6.42 Hz, 3H) 1.30 (s, 3H) 1.49-1.64 (m, 3H) 1.74 (s, 1H) 1.85 (s, 1H) 2.10-2.21 (m, 1H) 2.23-2.46 (m, 4H) 2.28 (s, 6H) 2.35 (s, 3H) 2.36 (s, 3H) 2.47-2.54 (m, 1H) 2.54-2.69 (m, 4H) 2.77-2.84 (m, 1H) 2.85-2.94 (m, 1H) 3.05-3.16 (m, 2H) 3.17-3.22 (m, 1H) 3.22 (s, 3H) 3.34 (s, 3H) 3.36-3.44 (m, 1H) 3.55-3.66 (m, 1H) 3.69-3.74 (m, 1H) 3.97-4.03 (m, 1H) 4.16-4.25 (m, 1H) 4.33-4.41 (m, 1H) 4.42-4.54 (m, 2H) 4.64 (s, 1H) 4.92-4.99 (m, 1H) 5.02-5.11 (m, 1H) 7.07-7.19 (m, 3H) 7.30-7.39 (m, 1H), and (600 MHz): 0.81 (d, J = 5.96 Hz, 6H) 0.86-0.93 (m, 3H) 0.93-1.03 (m, 3H) 1.04-1.25 (m, 2H) 1.09-1.20 (m, 15H) 1.28 (d, J = 6.42 Hz, 3H) 1.30 (s, 3H) 1.49-1.64 (m, 3H) 1.74 (s, 1H) 1.85 (s, 1H) 2.10-2.21 (m, 1H) 2.23-2.46 (m, 4H) 2.28 (s, 6H) 2.36 (s, 3H) 2.37 (s, 3H) 2.47-2.54 (m, 1H) 2.54-2.69 (m, 4H) 2.77-2.84 (m, 1H) 2.85-2.94 (m, 1H) 3.05-3.16 (m, 2H) 3.17-3.22 (m, 1H) 3.22 (s, 3H) 3.34 (s, 3H) 3.36-3.44 (m, 1H) 3.55-3.66 (m, 1H) 3.69-3.74 (m, 1H) 4.02-4.09 (m, 1H) 4.16-4.25 (m, 1H) 4.33-4.41 (m, 1H) 4.42-4.54 (m, 2H) 4.64 (s, 1H) 4.92-4.99 (m, 1H) 5.00-5.06 (m, 1H) 7.07-7.19 (m, 3H) 7.30-7.39 (m, 1H) |
| 276 | 3-methylphenyl-CH(Me)-N(Et)-CH$_2$CH$_2$-NH-C(O)-O-⁂ | H | 951.6 | mixture of diastereomers (600 MHz): 0.77 (d, J = 6.42 Hz, 6H) 0.84 (t, J = 7.57 Hz, 3H) 0.89-0.99 (m, 3H) 1.01-1.22 (m, 2H) 1.05-1.16 (m, 15H) 1.26 (s, 3H) 1.27 (d, J = 3.67 Hz, 3H) 1.45-1.61 (m, 3H) 1.70 (s, 1H) 1.79 (s, 1H) 2.05-2.17 (m, 1H) 2.16-2.47 (m, 6H) 2.23 (s, 6H) 2.29 (s, 3H) 2.31 (s, 3H) 2.48-2.62 (m, 3H) 2.72-2.79 (m, 1H) 2.84 (d, J = 14.67 Hz, 1H) 3.10-3.20 (m, 3H) 3.18 (s, 3H) 3.29 (s, 3H) 3.31-3.41 (m, 1H) 3.50-3.61 (m, 1H) 3.64-3.69 (m, 1H) 3.69-3.82 (m, 1H) 4.13-4.20 (m, 1H) 4.30-4.38 (m, 1H) 4.38-4.45 (m, 1H) 4.45-4.51 (m, 1H) 4.59 (s, 1H) 4.92 (d, J = 4.58 Hz, 1H) 5.11-5.24 (m, 1H) 6.98 (d, J = 7.34 Hz, 1H) 7.01-7.07 (m, 2H) 7.13 (t, J = 7.57 Hz, 1H) |
| 277 | 4-ethylphenyl-CH(Me)-N(Et)-CH$_2$CH$_2$-NH-C(O)-O-⁂ | H | 965.6 | mixture of diastereomers (600 MHz): 0.82 (d, J = 6.42 Hz, 6H) 0.89 (t, J = 7.57 Hz, 3H) 0.94-1.04 (m, 3H) 1.06-1.28 (m, 2H) 1.11-1.24 (m, 18H) 1.31 (s, 3H) 1.31-1.35 (m, 3H) 1.49-1.66 (m, 3H) 1.75 (s, 1H) 1.85 (s, 1H) 2.11-2.20 (m, 1H) 2.22-2.34 (m, 2H) 2.28 (s, 6H) 2.36 (s, 3H) 2.38-2.50 (m, 4H) 2.53-2.63 (m, 3H) 2.62 (q, J = 7.34 Hz, 2H) 2.77-2.85 (m, 1H) 2.85-2.93 (m, 1H) 3.16-3.23 (m, 3H) 3.23 (s, 3H) 3.35 (s, 3H) 3.36-3.44 (m, 1H) 3.56-3.66 (m, 1H) 3.72 (d, J = 8.25 Hz, 1H) 3.76-3.90 (m, 1H) 4.17-4.24 (m, 1H) 4.35-4.43 (m, 1H) 4.44-4.50 (m, 1H) 4.53 (d, J = 10.09 Hz, 1H) 4.64 (s, 1H) 4.94-5.00 (m, 1H) 5.25 (s, 1H) 7.12 (d, J = 7.79 Hz, 2H) 7.19 (d, J = 7.79 Hz, 2H) |

TABLE 11-continued formula (W)

| Example | R[1W] | R[2W] | ESI MS (M + H) | $^1$H-NMR, CDCl$_3$, δ (ppm) |
|---|---|---|---|---|
| 278 | Me$_2$N-phenyl-CH(Me)-N(Et)-CH$_2$CH$_2$-NH-C(O)-O- | H | | mixture of diastereomers (600 MHz): 0.82 (d, J = 6.42 Hz, 6H) 0.89 (t, J = 7.34 Hz, 3H) 0.94-1.06 (m, 3H) 1.06-1.26 (m, 2H) 1.10-1.22 (m, 15H) 1.30 (s, 3H) 1.31-1.37 (m, 3H) 1.49-1.66 (m, 3H) 1.70-1.80 (m, 1H) 1.80-1.88 (m, 1H) 2.12-2.22 (m, 1H) 2.22-2.34 (m, 2H) 2.28 (s, 6H) 2.35-2.54 (m, 4H) 2.36 (s, 3H) 2.53-2.69 (m, 3H) 2.77-2.85 (m, 1H) 2.85-2.92 (m, 1H) 2.93 (s, 6H) 3.15-3.22 (m, 3H) 3.23 (s, 3H) 3.34 (s, 3H) 3.35-3.44 (m, 1H) 3.56-3.66 (m, 1H) 3.69-3.73 (m, 1H) 3.73-3.84 (m, 1H) 4.17-4.26 (m, 1H) 4.35-4.42 (m, 1H) 4.43-4.49 (m, 1H) 4.53 (d, J = 9.63 Hz, 1H) 4.59-4.69 (m, 1H) 4.97 (d, J = 4.13 Hz, 1H) 5.20-5.29 (m, 1H) 6.57-6.70 (m, 3H) 7.16 (t, J = 7.79 Hz, 1H) |
| 279 | O$_2$N-phenyl-CH(Me)-N(Et)-CH$_2$CH$_2$-NH-C(O)-O- | H | 982.6 | mixture of diastereomers (600 MHz): 0.81 (d, J = 6.42 Hz, 6H) 0.87-0.92 (m, 3H) 0.96-1.04 (m, 3H) 1.06-1.26 (m, 2H) 1.10-1.20 (m, 15H) 1.30 (s, 3H) 1.38 (d, J = 6.42 Hz, 3H) 1.49-1.65 (m, 3H) 1.71-1.80 (m, 1H) 1.79-1.88 (m, 1H) 2.10-2.19 (m, 1H) 2.21-2.67 (m, 9H) 2.28 (s, 6H) 2.36 (s, 3H) 2.77-2.84 (m, 1H) 2.84-2.94 (m, 1H) 3.19-3.40 (m, 4H) 3.22 (s, 3H) 3.33 (s, 3H) 3.55-3.61 (m, 1H) 3.69-3.73 (m, 1H) 3.91-4.01 (m, 1H) 4.18-4.25 (m, 1H) 4.34-4.41 (m, 1H) 4.41-4.49 (m, 1H) 4.51-4.56 (m, 1H) 4.62 (s, 1H) 4.94-4.98 (m, 1H) 5.08-5.16 (m, 1H) 7.47 (t, J = 8.02 Hz, 1H) 7.68 (d, J = 7.79 Hz, 1H) 8.09 (d, J = 8.71 Hz, 1H) 8.17 (s, 1H) |
| 280 | Me-NH-CH$_2$CH$_2$-NH-C(O)-O- | H | 833.5 | (600 MHz): 0.81 (d, J = 6.88 Hz, 6H) 0.89 (t, J = 7.34 Hz, 3H) 1.08 (t, J = 7.11 Hz, 3H) 1.11 (d, J = 7.34 Hz, 3H) 1.13-1.15 (m, 1H) 1.15-1.18 (m, 9H) 1.19 (d, J = 5.96 Hz, 3H) 1.23 (d, J = 11.92 Hz, 1H) 1.30 (s, 3H) 1.50-1.58 (m, 1H) 1.60 (dd, J = 15.13, 5.04 Hz, 1H) 1.65 (d, J = 13.30 Hz, 1H) 1.74 (s, 1H) 1.84 (s, 1H) 2.11-2.21 (m, 1H) 2.22-2.29 (m, 1H) 2.30 (s, 6H) 2.30-2.34 (m, 1H) 2.36 (s, 3H) 2.36-2.47 (m, 1H) 2.40 (d, J = 15.13 Hz, 1H) 2.55-2.67 (m, 3H) 2.70-2.78 (m, 2H) 2.78-2.84 (m, 1H) 2.89 (d, J = 13.30 Hz, 1H) 3.18-3.22 (m, 1H) 3.23 (s, 3H) 3.26-3.31 (m, 2H) 3.33 (s, 3H) 3.40 (s, 1H) 3.55-3.62 (m, 1H) 3.70 (d, J = 7.79 Hz, 1H) 4.20 (s, 1H) 4.33-4.41 (m, 1H) 4.44 (d, J = 6.88 Hz, 1H) 4.53 (d, J = 9.63 Hz, 1H) 4.64 (s, 1H) 4.97 (d, J = 4.59 Hz, 1H) 5.28-5.36 (m, 1H) |
| 281 | -O-C(O)-NH-CH$_2$CH$_2$-N(Et)-CH(Me)-(2-CF$_3$-phenyl) | H | 1005.6 | (600 MHz): 0.81 (d, J = 6.88 Hz, 6H) 0.89 (t, J = 7.34 Hz, 3H) 0.94 (t, J = 7.11 Hz, 3H) 1.06-1.26 (m, 17H) 1.29 (d, J = 6.42 Hz, 3H) 1.31 (s, 3H) 1.50-1.65 (m, 3H) 1.71-1.79 (m, 1H) 1.80-1.88 (m, 1H) 2.10-2.19 (m, 1H) 2.21-2.45 (m, 4H) 2.29 (s, 6H) 2.36 (s, 3H) 2.46-2.75 (m, 5H) 2.77-2.85 (m, 1H) 2.85-2.93 (m, 1H) 3.15-3.26 (m, 3H) 3.22 (s, 3H) 3.34 (s, 3H) 3.35-3.40 (m, 1H) 3.52-3.62 (m, 1H) 3.71 (d, J = 8.25 Hz, 1H) 4.07-4.15 (m, 1H) 4.21-4.29 (m, 1H) 4.35-4.47 (m, 2H) 4.54 (d, J = 9.63 Hz, 1H) 4.63 (s, 1H) 4.93-5.00 (m, 1H) 5.02-5.10 (m, 1H) 7.30 (t, J = 7.57 Hz, 1H) 7.48 (t, J = 7.79 Hz, 1H) 7.58 (d, J = 7.34 Hz, 1H) 7.77 (d, J = 7.79 Hz, 1H) |

TABLE 11-continued formula (W)

| Example | $R^{1W}$ | $R^{2W}$ | ESI MS (M + H) | $^1$H-NMR, CDCl$_3$, δ (ppm) |
|---|---|---|---|---|
| 282 | (carbamate-O-CH2CH2-N(Et)(CH(Me)-3-CF3-C6H4)) | H | 1005.6 | (600 MHz): 0.79 (d, J = 6.88 Hz, 6H) 0.87 (t, J = 7.34 Hz, 3H) 0.97 (t, J = 7.11 Hz, 3H) 1.04-1.23 (m, 17H) 1.28 (s, 3H) 1.33 (d, J = 6.88 Hz, 3H) 1.47-1.64 (m, 3H) 1.68-1.77 (m, 1H) 1.78-1.86 (m, 1H) 2.08-2.17 (m, 1H) 2.20-2.50 (m, 6H) 2.25 (s, 6H) 2.34 (s, 3H) 2.50-2.61 (m, 3H) 2.75-2.82 (m, 1H) 2.82-2.91 (m, 1H) 3.13-3.24 (m, 3H) 3.20 (s, 3H) 3.31 (s, 3H) 3.33-3.38 (m, 1H) 3.50-3.59 (m, 1H) 3.69 (d, J = 8.71 Hz, 1H) 3.85-3.92 (m, 1H) 4.15-4.26 (m, 1H) 4.33-4.45 (m, 2H) 4.52 (d, J = 10.09 Hz, 1H) 4.55-4.66 (m, 1H) 4.92-4.97 (m, 1H) 5.08-5.15 (m, 1H) 7.36-7.42 (m, 1H) 7.44-7.54 (m, 3H) |
| 283 | (carbamate-O-CH2CH2-N(Et)(CH(Me)-4-CF3-C6H4)) | H | 1005.6 | (600 MHz): 0.81 (d, J = 6.42 Hz, 6H) 0.89 (t, J = 7.34 Hz, 3H) 1.00 (t, J = 7.11 Hz, 3H) 1.07-1.27 (m, 17H) 1.30 (s, 3H) 1.34 (d, J = 6.42 Hz, 3H) 1.50-1.64 (m, 3H) 1.70-1.79 (m, 1H) 1.80-1.89 (m, 1H) 2.11-2.19 (m, 1H) 2.21-2.50 (m, 6H) 2.27 (s, 6H) 2.36 (s, 3H) 2.52-2.63 (m, 3H) 2.77-2.84 (m, 1H) 2.85-2.93 (m, 1H) 3.16-3.30 (m, 3H) 3.22 (s, 3H) 3.34 (s, 3H) 3.36-3.46 (m, 1H) 3.54-3.63 (m, 1H) 3.71 (d, J = 8.25 Hz, 1H) 3.88-3.94 (m, 1H) 4.23 (s, 1H) 4.35-4.43 (m, 1H) 4.42-4.48 (m, 1H) 4.54 (d, J = 9.63 Hz, 1H) 4.63 (s, 1H) 4.97 (d, J = 3.67 Hz, 1H) 5.12-5.20 (m, 1H) 7.43 (d, J = 7.79 Hz, 2H) 7.55 (d, J = 8.25 Hz, 2H) |
| 284 | (carbamate-O-CH2CH2-N(Et)(CH(Me)-4-Br-C6H4)) | H | 1015.5 | (600 MHz): 0.82 (d, J = 6.42 Hz, 6H) 0.89 (t, J = 7.34 Hz, 3H) 1.00 (t, J = 7.11 Hz, 3H) 1.07-1.27 (m, 17H) 1.27-1.33 (m, 6H) 1.48-1.67 (m, 3H) 1.69-1.80 (m, 1H) 1.80-1.88 (m, 1H) 2.11-2.20 (m, 1H) 2.22-2.49 (m, 6H) 2.28 (s, 6H) 2.36 (s, 3H) 2.49-2.62 (m, 3H) 2.78-2.84 (m, 1H) 2.85-2.93 (m, 1H) 3.16-3.27 (m, 3H) 3.23 (s, 3H) 3.36 (s, 3H) 3.38-3.47 (m, 1H) 3.55-3.64 (m, 1H) 3.71 (d, J = 7.79 Hz, 1H) 3.80-3.87 (m, 1H) 4.22 (s, 1H) 4.35-4.42 (m, 1H) 4.43-4.50 (m, 1H) 4.53 (d, J = 10.09 Hz, 1H) 4.63 (s, 1H) 4.93-5.00 (m, 1H) 5.13-5.20 (m, 1H) 7.18 (d, J = 8.25 Hz, 2H) 7.41 (d, J = 8.25 Hz, 2H) |
| 285 | (3-NH2-C6H4-CH(Me)-N(Et)-CH2CH2-NH-C(O)-O-carbamate) | H | 952.6 | mixture of diastereomers (600 MHz): 0.81 (d, J = 5.96 Hz, 6H) 0.90 (t, J = 7.34 Hz, 3H) 0.95-1.05 (m, 3H) 1.06-1.26 (m, 17H) 1.27-1.30 (m, 3H) 1.31 (s, 3H) 1.49-1.68 (m, 3H) 1.72-1.79 (m, 1H) 1.80-1.87 (m, 1H) 2.12-2.18 (m, 1H) 2.18-2.69 (m, 9H) 2.26 (s, 6H) 2.36 (s, 3H) 2.75-2.85 (m, 1H) 2.86-2.94 (m, 1H) 3.08-3.46 (m, 4H) 3.22 (s, 3H) 3.33 (s, 3H) 3.53-3.65 (m, 1H) 3.66-3.80 (m, 2H) 4.15-4.28 (m, 1H) 4.35-4.43 (m, 1H) 4.42-4.51 (m, 1H) 4.54 (d, J = 9.63 Hz, 1H) 4.57-4.69 (m, 1H) 4.92-5.00 (m, 1H) 5.05-5.20 (m, 1H) 6.51-6.56 (m, 1H) 6.60-6.67 (m, 1H) 6.68-6.75 (m, 1H) 7.06 (t, J = 7.57 Hz, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 286 | (carbamate linker-NH-CH₂CH₂-N(Et)-CH(Me)-(1-methylpyrrol-3-yl)) | H | 940.6 | mixture of diastereomers (600 MHz): 0.78-0.84 (m, 6H) 0.89 (t, J = 7.34 Hz, 3H) 0.96-1.04 (m, 3H) 1.08-1.33 (m, 23H) 1.49-1.78 (m, 4H) 1.81-1.88 (m, 1H) 2.11-2.64 (m, 10H) 2.28 (s, 6H) 2.35 (s, 3H) 2.77-2.84 (m, 1H) 2.88 (d, J = 15.13 Hz, 1H) 3.15-3.45 (m, 4H) 3.23 (s, 3H) 3.34 (s, 3H) 3.57-3.65 (m, 4H) 3.71 (d, J = 8.25 Hz, 1H) 3.81-3.89 (m, 1H) 4.17-4.23 (m, 1H) 4.36-4.42 (m, 1H) 4.44-4.49 (m, 1H) 4.54 (d, J = 9.63 Hz, 1H) 4.60-4.67 (m, 1H) 4.97 (d, J = 5.04 Hz, 1H) 5.36 (br. s., 1H) 5.99 (d, J = 7.79 Hz, 1H) 6.42 (br. s., 1H) 6.50 (br. s., 1H), and (600 MHz): 0.78-0.84 (m, 6H) 0.89 (t, J = 7.34 Hz, 3H) 0.96-1.04 (m, 3H) 1.08-1.33 (m, 23H) 1.49-1.78 (m, 4H) 1.81-1.88 (m, 1H) 2.11-2.64 (m, 10H) 2.27 (s, 6H) 2.35 (s, 3H) 2.77-2.84 (m, 1H) 2.88 (d, J = 15.13 Hz, 1H) 3.15-3.45 (m, 4H) 3.23 (s, 3H) 3.33 (s, 3H) 3.57-3.65 (m, 4H) 3.71 (d, J = 8.25 Hz, 1H) 3.81-3.89 (m, 1H) 4.17-4.23 (m, 1H) 4.36-4.42 (m, 1H) 4.44-4.49 (m, 1H) 4.54 (d, J = 9.63 Hz, 1H) 4.60-4.67 (m, 1H) 4.97 (d, J = 5.04 Hz, 1H) 5.36 (br. s., 1H) 5.99 (d, J = 7.79 Hz, 1H) 6.42 (br. s., 1H) 6.50 (br. s., 1H) |
| 287 | (carbamate linker-NH-CH₂CH₂-N(Et)-CH(Me)-Ph) | H | 937.6 | (600 MHz): 0.79-0.83 (m, 6H) 0.88 (t, J = 7.34 Hz, 3H) 1.00 (t, J = 7.11 Hz, 3H) 1.07-1.17 (m, 13H) 1.18 (d, J = 5.96 Hz, 3H) 1.20-1.26 (m, 1H) 1.30 (s, 3H) 1.32 (d, J = 6.88 Hz, 3H) 1.49-1.56 (m, 1H) 1.59 (dd, J = 15.13, 5.04 Hz, 1H) 1.62-1.88 (m, 3H) 2.11-2.19 (m, 1H) 2.22-2.27 (m, 2H) 2.29 (s, 6H) 2.35 (s, 3H) 2.39 (d, J = 15.59 Hz, 1H) 2.41-2.47 (m, 3H) 2.52-2.65 (m, 3H) 2.77-2.84 (m, 1H) 2.85-2.91 (m, 1H) 3.16-3.22 (m, 3H) 3.22 (s, 3H) 3.34 (s, 3H) 3.37-3.42 (m, 1H) 3.57-3.64 (m, 1H) 3.71 (d, J = 7.79 Hz, 1H) 3.87 (q, J = 6.88 Hz, 1H) 4.17-4.24 (m, 1H) 4.34-4.42 (m, 1H) 4.46 (d, J = 7.34 Hz, 1H) 4.52 (d, J = 9.63 Hz, 1H) 4.60-4.66 (m, 1H) 4.96 (d, J = 5.04 Hz, 1H) 5.18-5.24 (m, 1H) 7.18-7.23 (m, 1H) 7.27-7.30 (m, 4H) |
| 288 | (carbamate linker-NH-CH₂CH₂-N(Et)-CH(Me)-(naphth-1-yl)) | H | 987.7 | (600 MHz): 0.79-0.83 (m, 6H) 0.89 (t, J = 7.34 Hz, 3H) 1.00 (t, J = 7.11 Hz, 3H) 1.06 (s, 3H) 1.08-1.18 (m, 13H) 1.18-1.25 (m, 1H) 1.29 (s, 3H) 1.45 (d, J = 6.42 Hz, 3H) 1.49-1.62 (m, 3H) 1.69-1.88 (m, 2H) 2.11-2.19 (m, 1H) 2.20-2.32 (m, 2H) 2.28 (s, 6H) 2.35 (s, 3H) 2.38-2.48 (m, 2H) 2.50-2.62 (m, 2H) 2.64-2.73 (m, 3H) 2.78-2.83 (m, 1H) 2.88 (d, J = 15.13 Hz, 1H) 3.00-3.12 (m, 1H) 3.17-3.22 (m, 1H) 3.21 (s, 3H) 3.32 (s, 3H) 3.35-3.41 (m, 1H) 3.48-3.55 (m, 1H) 3.70 (d, J = 8.25 Hz, 1H) 4.16-4.26 (m, 1H) 4.32-4.39 (m, 1H) 4.42 (d, J = 6.88 Hz, 1H) 4.48 (d, J = 10.09 Hz, 1H) 4.59-4.67 (m, 2H) 4.95 (d, J = 4.58 Hz, 1H) 4.98-5.04 (m, 1H) 7.38-7.43 (m, 2H) 7.43-7.47 (m, 1H) 7.48-7.54 (m, 2H) 7.73 (d, J = 8.25 Hz, 1H) 7.83 (d, J = 8.25 Hz, 1H) 8.34 (d, J = 8.71 Hz, 1H) |

TABLE 11-continued formula (W)

[Structure of formula (W): macrolide with NMe2, HO, OMe, Me substituents; R^1W and R^2W groups on the sugar moiety]

| Example | R^1W | R^2W | ESI MS (M + H) | $^1$H-NMR, CDCl$_3$, δ (ppm) |
|---|---|---|---|---|
| 289 | [carbamate linker -O-C(O)-NH-CH$_2$CH$_2$-N(Et)-CH(Me)-(2-naphthyl)] | H | 987.7 | (600 MHz): 0.79-0.84 (m, 6H) 0.89 (t, J = 7.34 Hz, 3H) 1.02 (t, J = 7.11 Hz, 3H) 1.06 (s, 3H) 1.13 (d, J = 7.34 Hz, 8H) 1.13 (d, J = 7.34 Hz, 3H) 1.19-1.27 (m, 1H) 1.30 (s, 3H) 1.42 (d, J = 6.42 Hz, 3H) 1.49-1.64 (m, 2H) 1.58 (dd, J = 15.13, 5.04 Hz, 1H) 1.68-1.79 (m, 1H) 1.80-1.88 (m, 1H) 2.12-2.20 (m, 1H) 2.22-2.25 (m, 1H) 2.26 (s, 6H) 2.28-2.32 (m, 1H) 2.35 (s, 3H) 2.39 (d, J = 15.13 Hz, 1H) 2.46-2.55 (m, 3H) 2.56-2.67 (m, 3H) 2.78-2.83 (m, 1H) 2.88 (d, J = 14.21 Hz, 1H) 3.17-3.23 (m, 3H) 3.23 (s, 3H) 3.36 (s, 3H) 3.37-3.42 (m, 1H) 3.57-3.64 (m, 1H) 3.71 (d, J = 7.79 Hz, 1H) 4.03 (q, J = 6.42 Hz, 1H) 4.17-4.24 (m, 1H) 4.35-4.43 (m, 1H) 4.47 (d, J = 6.88 Hz, 1H) 4.51 (d, J = 10.09 Hz, 1H) 4.60-4.67 (m, 1H) 4.96 (d, J = 5.04 Hz, 1H) 5.19-5.23 (m, 1H) 7.40-7.51 (m, 3H) 7.67 (s, 1H) 7.74-7.83 (m, 3H) |
| 290 | [carbamate linker -O-C(O)-NH-CH$_2$CH$_2$-NH-CH(Me)-(N-methylpyrrol-2-yl)] | H | 912.7 | mixture of diastereomers (600 MHz): 0.81 (d, J = 6.42 Hz, 6H) 0.89 (t, J = 7.34 Hz, 3H) 1.07-1.25 (m, 17H) 1.30 (s, 3H) 1.36-1.39 (m, 3H) 1.50-1.87 (m, 5H) 2.12-2.46 (m, 5H) 2.29 (s, 6H) 2.36 (s, 3H) 2.53-2.61 (m, 1H) 2.66-2.73 (m, 2H) 2.78-2.84 (m, 1H) 2.86-2.92 (m, 1H) 3.17-3.44 (m, 4H) 3.23 (s, 3H) 3.33 (s, 3H) 3.53-3.59 (m, 1H) 3.61 (s, 3H) 3.70 (d, J = 8.25 Hz, 1H) 3.82-3.87 (m, 1H) 4.19-4.24 (m, 1H) 4.35-4.40 (m, 1H) 4.41-4.45 (m, 1H) 4.52-4.55 (m, 1H) 4.61-4.67 (m, 1H) 4.97 (d, J = 5.04 Hz, 1H) 5.17-5.20 (m, 1H) 5.96-5.98 (m, 1H) 6.03-6.04 (m, 1H) 6.51-6.53 (m, 1H) |
| 291 | [carbamate linker -O-C(O)-NH-CH$_2$CH$_2$-NH-CH(Me)-(4-methylsulfonylphenyl)] | H | 987.7 | mixture of diastereomers (600 MHz): 0.81 (d, J = 6.42 Hz, 6H) 0.89 (t, J = 7.34 Hz, 3H) 1.07-1.27 (m, 17H) 1.30 (s, 3H) 1.32 (d, J = 6.42 Hz, 3H) 1.50-1.87 (m, 5H) 2.11-2.46 (m, 5H) 2.29 (s, 6H) 2.36 (s, 3H) 2.50-2.66 (m, 3H) 2.78-2.84 (m, 1H) 2.85-2.91 (m, 1H) 3.04 (s, 3H) 3.17-3.44 (m, 4H) 3.23 (s, 3H) 3.34 (s, 3H) 3.53-3.60 (m, 1H) 3.70 (d, J = 8.25 Hz, 1H) 3.82-3.88 (m, 1H) 4.20-4.26 (m, 1H) 4.35-4.45 (m, 2H) 4.52-4.56 (m, 1H) 4.60-4.66 (m, 1H) 4.95-4.99 (m, 1H) 5.15-5.20 (m, 1H) 7.47-7.51 (m, 2H) 7.85-7.89 (m, 2H), and (600 MHz): 0.81 (d, J = 6.42 Hz, 6H) 0.89 (t, J = 7.34 Hz, 3H) 1.07-1.27 (m, 17H) 1.30 (s, 3H) 1.32 (d, J = 6.42 Hz, 3H) 1.50-1.87 (m, 5H) 2.11-2.46 (m, 5H) 2.29 (s, 6H) 2.36 (s, 3H) 2.50-2.66 (m, 3H) 2.78-2.84 (m, 1H) 2.85-2.91 (m, 1H) 3.04 (s, 3H) 3.17-3.44 (m, 4H) 3.22 (s, 3H) 3.34 (s, 3H) 3.53-3.60 (m, 1H) 3.70 (d, J = 8.25 Hz, 1H) 3.82-3.88 (m, 1H) 4.20-4.26 (m, 1H) 4.35-4.45 (m, 2H) 4.52-4.56 (m, 1H) 4.60-4.66 (m, 1H) 4.95-4.99 (m, 1H) 5.15-5.20 (m, 1H) 7.47-7.51 (m, 2H) 7.85-7.89 (m, 2H) |

TABLE 11-continued formula (W)

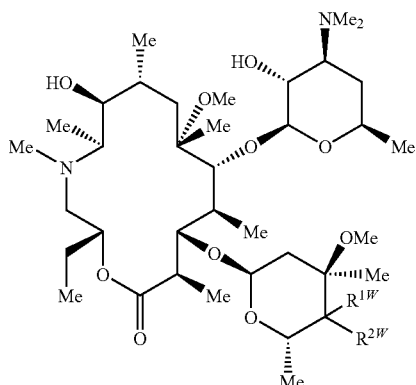

| Example | $R^{1W}$ | $R^{2W}$ | ESI MS (M + H) | $^1$H-NMR, CDCl$_3$, δ (ppm) |
|---|---|---|---|---|
| 292 | (carbamate-NH-CH$_2$CH$_2$-NH-CH(Me)-[1-ethyl-pyrazol-5-yl]) | H | 927.7 | mixture of diastereomers (600 MHz): 0.81 (d, J = 6.88 Hz, 6H) 0.89 (t, J = 7.34 Hz, 3H) 1.07-1.25 (m, 17H) 1.30 (s, 3H) 1.37 (d, J = 6.42 Hz, 3H) 1.42 (t, J = 7.34 Hz, 3H) 1.49-1.87 (m, 5H) 2.11-2.45 (m, 5H) 2.29 (s, 6H) 2.36 (s, 3H) 2.53-2.60 (m, 1H) 2.63-2.70 (m, 2H) 2.78-2.84 (m, 1H) 2.86-2.91 (m, 1H) 3.16-3.45 (m, 10H) 3.52-3.59 (m, 1H) 3.70 (d, J = 8.25 Hz, 1H) 3.90-3.95 (m, 1H) 4.16 (q, J = 7.18 Hz, 2H) 4.20-4.25 (m, 1H) 4.34-4.45 (m, 2H) 4.52-4.55 (m, 1H) 4.61-4.66 (m, 1H) 4.97 (d, J = 4.58 Hz, 1H) 5.15-5.18 (m, 1H) 6.07-6.08 (m, 1H) 7.40-7.42 (m, 1H), and (600 MHz): 0.81 (d, J = 6.88 Hz, 6H) 0.89 (t, J = 7.34 Hz, 3H) 1.07-1.25 (m, 17H) 1.30 (s, 3H) 1.38 (d, J = 6.88 Hz, 3H) 1.42 (t, J = 7.11 Hz, 3H) 1.49-1.87 (m, 5H) 2.11-2.45 (m, 5H) 2.29 (s, 6H) 2.36 (s, 3H) 2.53-2.60 (m, 1H) 2.63-2.70 (m, 2H) 2.78-2.84 (m, 1H) 2.86-2.91 (m, 1H) 3.16-3.45 (m, 10H) 3.52-3.59 (m, 1H) 3.70 (d, J = 8.25 Hz, 1H) 3.90-3.95 (m, 1H) 4.16 (q, J = 7.18 Hz, 2H) 4.20-4.25 (m, 1H) 4.34-4.45 (m, 2H) 4.52-4.55 (m, 1H) 4.61-4.66 (m, 1H) 4.97 (d, J = 4.58 Hz, 1H) 5.15-5.18 (m, 1H) 6.07-6.08 (m, 1H) 7.40-7.42 (m, 1H) |
| 293 | (carbamate-NH-CH$_2$CH$_2$-N(Et)-CH(Me)-[1-methyl-pyrrol-2-yl]) | H | 940.7 | mixture of diastereomers (600 MHz): 0.81 (d, J = 6.88 Hz, 6H) 0.89 (t, J = 7.34 Hz, 3H) 1.03 (t, J = 7.11 Hz, 3H) 1.06-1.23 (m, 17H) 1.26 (d, J = 6.42 Hz, 3H) 1.30 (s, 3H) 1.50-1.87 (m, 5H) 2.10-2.63 (m, 10H) 2.29 (s, 6H) 2.36 (s, 3H) 2.78-3.11 (m, 4H) 3.18-3.23 (m, 1H) 3.22 (s, 3H) 3.33 (s, 3H) 3.36-3.46 (m, 1H) 3.51-3.57 (m, 1H) 3.66 (s, 3H) 3.70 (d, J = 7.79 Hz, 1H) 3.96-4.04 (m, 1H) 4.18-4.24 (m, 1H) 4.33-4.39 (m, 1H) 4.41-4.45 (m, 1H) 4.47-4.51 (m, 1H) 4.60-4.71 (m, 2H) 4.94-4.98 (m, 1H) 5.98-6.02 (m, 2H) 6.52-6.56 (m, 1H), and (600 MHz): 0.81 (d, J = 6.88 Hz, 6H) 0.89 (t, J = 7.34 Hz, 3H) 0.99 (t, J = 7.11 Hz, 3H) 1.06-1.24 (m, 17H) 1.26 (d, J = 6.42 Hz, 3H) 1.30 (s, 3H) 1.49-1.88 (m, 5H) 2.10-2.64 (m, 10H) 2.29 (s, 6H) 2.36 (s, 3H) 2.77-3.11 (m, 4H) 3.17-3.21 (m, 1H) 3.22 (s, 3H) 3.32 (s, 3H) 3.36-3.46 (m, 1H) 3.51-3.58 (m, 1H) 3.65 (s, 3H) 3.70 (d, J = 7.79 Hz, 1H) 3.96-4.04 (m, 1H) 4.17-4.25 (m, 1H) 4.32-4.39 (m, 1H) 4.41-4.45 (m, 1H) 4.47-4.51 (m, 1H) 4.60-4.66 (m, 1H) 4.85-4.89 (m, 1H) 4.94-4.97 (m, 1H) 5.99-6.02 (m, 2H) 6.52-6.56 (m, 1H) |

TABLE 11-continued formula (W)

[Structure of formula (W): a macrolide (azithromycin-like) core bearing substituents R$^{1W}$ and R$^{2W}$ on the sugar moiety]

| Example | R$^{1W}$ | R$^{2W}$ | ESI MS (M + H) | $^1$H-NMR, CDCl$_3$, δ (ppm) |
|---|---|---|---|---|
| 294 | [Structure: thiophene-2-sulfonamide (N-Me) with CH(Me)-NH-CH$_2$CH$_2$-NH-C(=O)-O- linker] | —H | 1008.6 | mixture of diastereomers (600 MHz): 0.81 (d, J = 6.42 Hz, 6H) 0.89 (t, J = 7.34 Hz, 3H) 1.07-1.25 (m, 17H) 1.30 (s, 3H) 1.37-1.41 (m, 3H) 1.48-1.86 (m, 5H) 2.10-2.47 (m, 5H) 2.31 (s, 6H) 2.36 (s, 3H) 2.55-2.73 (m, 3H) 2.70 (s, 3H) 2.78-2.83 (m, 1H) 2.86-2.92 (m, 1H) 3.13-3.31 (m, 3H) 3.22 (s, 3H) 3.33 (s, 3H) 3.36-3.45 (m, 1H) 3.52-3.61 (m, 1H) 3.69 (d, J = 7.79 Hz, 1H) 4.17-4.24 (m, 1H) 4.34-4.53 (m, 4H) 4.60-4.65 (m, 1H) 4.95-4.98 (m, 1H) 5.23-5.29 (m, 1H) 7.12-7.15 (m, 1H) 7.44-7.46 (m, 1H), and (600 MHz): 0.81 (d, J = 6.42 Hz, 6H) 0.89 (t, J = 7.34 Hz, 3H) 1.07-1.25 (m, 17H) 1.30 (s, 3H) 1.37-1.41 (m, 3H) 1.48-1.86 (m, 5H) 2.10-2.47 (m, 5H) 2.31 (s, 6H) 2.36 (s, 3H) 2.55-2.73 (m, 3H) 2.70 (s, 3H) 2.78-2.83 (m, 1H) 2.86-2.92 (m, 1H) 3.13-3.31 (m, 3H) 3.22 (s, 3H) 3.32 (s, 3H) 3.36-3.45 (m, 1H) 3.52-3.61 (m, 1H) 3.69 (d, J = 7.79 Hz, 1H) 4.17-4.24 (m, 1H) 4.34-4.53 (m, 4H) 4.60-4.65 (m, 1H) 4.95-4.98 (m, 1H) 5.23-5.29 (m, 1H) 7.12-7.15 (m, 1H) 7.44-7.46 (m, 1H) |
| 295 | [Structure: -O-C(=O)-NH-CH$_2$CH$_2$-N(Et)-CH(Me)-(4-methylsulfonylphenyl)] | —H | 1015.7 | mixture of diastereomers (600 MHz): 0.81 (d, J = 6.42 Hz, 6H) 0.89 (t, J = 7.34 Hz, 3H) 0.95-1.01 (m, 3H) 1.06-1.26 (m, 17H) 1.30 (s, 3H) 1.35 (d, J = 6.88 Hz, 3H) 1.49-1.87 (m, 5H) 2.10-2.64 (m, 10H) 2.28 (s, 6H) 2.36 (s, 3H) 2.78-2.83 (m, 1H) 2.88 (d, J = 15.59 Hz, 1H) 3.04 (s, 3H) 3.17-3.26 (m, 3H) 3.23 (s, 3H) 3.35 (s, 3H) 3.41-3.46 (m, 1H) 3.54-3.60 (m, 1H) 3.71 (d, J = 8.25 Hz, 1H) 3.88-3.95 (m, 1H) 4.22-4.27 (m, 1H) 4.36-4.46 (m, 2H) 4.54 (d, J = 9.63 Hz, 1H) 4.60-4.66 (m, 1H) 4.97 (d, J = 4.13 Hz, 1H) 5.12-5.15 (m, 1H) 7.52 (d, J = 8.71 Hz, 2H) 7.86 (d, J = 8.25 Hz, 2H) |
| 296 | [Structure: -O-C(=O)-NH-CH$_2$CH$_2$-N(Et)-CH(Me)-(1-ethyl-pyrazol-5-yl)] | —H | 955.8 | mixture of diastereomers (600 MHz): 0.80 (d, J = 6.42 Hz, 6H) 0.88 (t, J = 7.34 Hz, 3H) 1.03 (t, J = 7.11 Hz, 3H) 1.05-1.25 (m, 17H) 1.27-1.32 (m, 6H) 1.40-1.45 (m, 3H) 1.49-1.86 (m, 5H) 2.10-2.59 (m, 10H) 2.28 (s, 6H) 2.35 (s, 3H) 2.76-3.21 (m, 5H) 3.21 (s, 3H) 3.32 (s, 3H) 3.35-3.44 (m, 1H) 3.49-3.58 (m, 1H) 3.69 (d, J = 7.34 Hz, 1H) 4.00-4.06 (m, 1H) 4.13-4.45 (m, 5H) 4.49-4.53 (m, 1H) 4.59-4.66 (m, 1H) 4.88-4.92 (m, 1H) 4.96 (d, J = 5.04 Hz, 1H) 6.09 (s, 1H) 7.39 (s, 1H), and (600 MHz): 0.80 (d, J = 6.42 Hz, 6H) 0.88 (t, J = 7.34 Hz, 3H) 0.99 (t, J = 7.11 Hz, 3H) 1.15 (d, 17H) 1.27-1.32 (m, 6H) 1.40-1.45 (m, 3H) 1.49-1.86 (m, 5H) 2.10-2.59 (m, 10H) 2.28 (s, 6H) 2.35 (s, 3H) 2.76-3.21 (m, 5H) 3.22 (s, 3H) 3.31 (s, 3H) 3.35-3.44 (m, 1H) 3.49-3.58 (m, 1H) 3.69 (d, J = 7.34 Hz, 1H) 4.00-4.06 (m, 1H) 4.13-4.45 (m, 5H) 4.49-4.53 (m, 1H) 4.59-4.66 (m, 1H) 4.84-4.88 (m, 1H) 4.96 (d, J = 5.04 Hz, 1H) 6.09 (s, 1H) 7.39 (s, 1H) |

TABLE 11-continued formula (W)

| Example | $R^{1W}$ | $R^{2W}$ | ESI MS (M + H) | $^1$H-NMR, CDCl$_3$, δ (ppm) |
|---|---|---|---|---|
| 297 | (structure: carbamate-NH-CH$_2$CH$_2$-NH-CH(Me)-1-methyl-pyrazol-5-yl) | H | 913.7 | mixture of diastereomers (600 MHz): 0.81 (d, J = 6.88 Hz, 6H) 0.89 (t, J = 7.34 Hz, 3H) 1.08-1.27 (m, 17H) 1.30 (s, 3H) 1.37 (d, J = 6.42 Hz, 3H) 1.47-1.87 (m, 5H) 2.10-2.46 (m, 5H) 2.29 (s, 6H) 2.36 (s, 3H) 2.52-2.70 (m, 3H) 2.78-2.84 (m, 1H) 2.86-2.92 (m, 1H) 3.17-3.46 (m, 3H) 3.22 (s, 4H) 3.33 (s, 3H) 3.53-3.60 (m, 1H) 3.70 (d, J = 7.79 Hz, 1H) 3.86 (s, 3H) 3.90-3.96 (m, 1H) 4.19-4.26 (m, 1H) 4.35-4.46 (m, 2H) 4.51-4.56 (m, 1H) 4.60-4.67 (m, 1H) 4.97 (d, J = 5.04 Hz, 1H) 5.15-5.19 (m, 1H) 6.08-6.10 (m, 1H) 7.36-7.38 (m, 1H), and (600 MHz): 0.81 (d, J = 6.88 Hz, 6H) 0.89 (t, J = 7.34 Hz, 3H) 1.08-1.27 (m, 17H) 1.30 (s, 3H) 1.37 (d, J = 6.42 Hz, 3H) 1.47-1.87 (m, 5H) 2.10-2.46 (m, 5H) 2.29 (s, 6H) 2.36 (s, 3H) 2.52-2.70 (m, 3H) 2.78-2.84 (m, 1H) 2.86-2.92 (m, 1H) 3.17-3.46 (m, 3H) 3.22 (s, 4H) 3.33 (s, 3H) 3.53-3.60 (m, 1H) 3.70 (d, J = 7.79 Hz, 1H) 3.86 (s, 3H) 3.90-3.96 (m, 1H) 4.19-4.26 (m, 1H) 4.35-4.46 (m, 2H) 4.51-4.56 (m, 1H) 4.60-4.67 (m, 1H) 4.97 (d, J = 5.04 Hz, 1H) 5.15-5.19 (m, 1H) 6.08-6.10 (m, 1H) 7.36-7.38 (m, 1H) |
| 298 | (structure: carbamate-NH-CH$_2$CH$_2$-NH-CH(Me)-1,3-dimethyl-pyrazol-5-yl) | H | 927.7 | mixture of diastereomers (600 MHz): 0.76 (d, J = 6.42 Hz, 6H) 0.84 (t, J = 7.34 Hz, 3H) 1.01-1.20 (m, 17H) 1.25 (s, 3H) 1.29 (d, J = 6.42 Hz, 3H) 1.44-1.81 (m, 5H) 2.03-2.41 (m, 5H) 2.15 (s, 3H) 2.24 (s, 6H) 2.31 (s, 3H) 2.48-2.55 (m, 1H) 2.59-2.63 (m, 2H) 2.73-2.78 (m, 1H) 2.80-2.86 (m, 1H) 3.12-3.39 (m, 4H) 3.17 (s, 3H) 3.28 (s, 3H) 3.47-3.54 (m, 1H) 3.65 (d, J = 8.25 Hz, 1H) 3.72 (s, 3H) 3.78-3.84 (m, 1H) 4.14-4.20 (m, 1H) 4.29-4.41 (m, 2H) 4.47-4.50 (m, 1H) 4.55-4.62 (m, 1H) 4.92 (d, J = 4.58 Hz, 1H) 5.09-5.14 (m, 1H) 5.81 (s, 1H), and (600 MHz): 0.76 (d, J = 6.42 Hz, 6H) 0.84 (t, J = 7.34 Hz, 3H) 1.01-1.20 (m, 17H) 1.25 (s, 3H) 1.29 (d, J = 6.42 Hz, 3H) 1.44-1.81 (m, 5H) 2.03-2.41 (m, 5H) 2.15 (s, 3H) 2.24 (s, 6H) 2.31 (s, 3H) 2.48-2.55 (m, 1H) 2.59-2.63 (m, 2H) 2.73-2.78 (m, 1H) 2.80-2.86 (m, 1H) 3.12-3.39 (m, 4H) 3.17 (s, 3H) 3.28 (s, 3H) 3.47-3.54 (m, 1H) 3.65 (d, J = 8.25 Hz, 1H) 3.72 (s, 3H) 3.78-3.84 (m, 1H) 4.14-4.20 (m, 1H) 4.29-4.41 (m, 2H) 4.47-4.50 (m, 1H) 4.55-4.62 (m, 1H) 4.92 (d, J = 4.58 Hz, 1H) 5.09-5.14 (m, 1H) 5.81 (s, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 299 | | | 1024.8 | mixture of diastereomers (600 MHz): 0.81 (d, J = 6.88 Hz, 6H) 0.89 (t, J = 7.34 Hz, 3H) 1.02-1.07 (m, 6H) 1.07-1.25 (m, 17H) 1.28-1.33 (m, 6H) 1.49-1.88 (m, 5H) 2.09-2.61 (m, 12H) 2.26-2.31 (m, 6H) 2.36 (s, 3H) 2.78-2.83 (m, 1H) 2.88 (d, J = 13.76 Hz, 1H) 3.12-3.44 (m, 4H) 3.23 (s, 3H) 3.34 (s, 3H) 3.53-3.62 (m, 3H) 3.66-3.72 (m, 2H) 3.79 (s, 3H) 4.17-4.24 (m, 1H) 4.35-4.41 (m, 1H) 4.42-4.46 (m, 1H) 4.51-4.55 (m, 1H) 4.61-4.67 (m, 1H) 4.97 (d, J = 5.04 Hz, 1H) 5.25-5.33 (m, 1H) 6.79 (d, J = 8.25 Hz, 1H) 7.09 (d, J = 6.42 Hz, 1H) 7.28 (s, 1H), and (600 MHz): 0.81 (d, J = 6.88 Hz, 6H) 0.89 (t, J = 7.34 Hz, 3H) 1.02-1.07 (m, 6H) 1.07-1.25 (m, 17H) 1.28-1.33 (m, 6H) 1.49-1.88 (m, 5H) 2.09-2.61 (m, 12H) 2.26-2.31 (m, 6H) 2.36 (s, 3H) 2.78-2.83 (m, 1H) 2.88 (d, J = 13.76 Hz, 1H) 3.12-3.44 (m, 4H) 3.23 (s, 3H) 3.33 (s, 3H) 3.53-3.62 (m, 3H) 3.66-3.72 (m, 2H) 3.79 (s, 3H) 4.17-4.24 (m, 1H) 4.35-4.41 (m, 1H) 4.42-4.46 (m, 1H) 4.51-4.55 (m, 1H) 4.61-4.67 (m, 1H) 4.97 (d, J = 5.04 Hz, 1H) 5.25-5.33 (m, 1H) 6.79 (d, J = 8.25 Hz, 1H) 7.09 (d, J = 6.42 Hz, 1H) 7.28 (s, 1H) |
| 300 | | H | | mixture of diastereomers (600 MHz): 0.81 (d, J = 6.88 Hz, 6H) 0.89 (t, J = 7.34 Hz, 3H) 1.07-1.25 (m, 17H) 1.28-1.33 (m, 6H) 1.48-1.87 (m, 9H) 2.11-2.61 (m, 12H) 2.28 (s, 6H) 2.36 (s, 3H) 2.78-2.83 (m, 1H) 2.86-2.92 (m, 1H) 3.13-3.45 (m, 4H) 3.23 (s, 3H) 3.33 (s, 3H) 3.54-3.73 (m, 5H) 3.80 (s, 3H) 4.18-4.24 (m, 1H) 4.35-4.40 (m, 1H) 4.41-4.46 (m, 1H) 4.50-4.56 (m, 1H) 4.60-4.68 (m, 1H) 4.97 (d, J = 4.58 Hz, 1H) 5.25-5.32 (m, 1H) 6.80 (d, J = 8.25 Hz, 1H) 7.11 (d, J = 9.63 Hz, 1H) 7.22 (s, 1H), and (600 MHz): 0.81 (d, J = 6.88 Hz, 6H) 0.89 (t, J = 7.34 Hz, 3H) 1.07-1.25 (m, 17H) 1.28-1.33 (m, 6H) 1.48-1.87 (m, 9H) 2.11-2.61 (m, 12H) 2.28 (s, 6H) 2.36 (s, 3H) 2.78-2.83 (m, 1H) 2.86-2.92 (m, 1H) 3.13-3.45 (m, 4H) 3.23 (s, 3H) 3.34 (s, 3H) 3.54-3.73 (m, 5H) 3.80 (s, 3H) 4.18-4.24 (m, 1H) 4.35-4.40 (m, 1H) 4.41-4.46 (m, 1H) 4.50-4.56 (m, 1H) 4.60-4.68 (m, 1H) 4.97 (d, J = 4.58 Hz, 1H) 5.25-5.32 (m, 1H) 6.80 (d, J = 8.25 Hz, 1H) 7.11 (d, J = 9.63 Hz, 1H) 7.22 (s, 1H) |
| 301 | | H | 1036.7 | mixture of diastereomers (600 MHz): 0.78-0.86 (m, 6H) 0.86-0.95 (m, 6H) 1.07-1.25 (m, 17H) 1.28-1.31 (m, 3H) 1.33-1.37 (m, 3H) 1.49-1.89 (m, 5H) 2.12-2.59 (m, 18H) 2.61 (s, 3H) 2.74-2.91 (m, 3H) 3.17-3.46 (m, 4H) 3.22 (s, 3H) 3.31 (s, 3H) 3.54-3.73 (m, 2H) 4.10-4.21 (m, 1H) 4.37-4.55 (m, 3H) 4.61-4.78 (m, 2H) 4.95-4.98 (m, 1H) 5.39-5.44 (m, 1H) 7.14-7.18 (m, 1H) 7.44-7.47 (m, 1H), and (600 MHz): 0.78-0.86 (m, 6H) 0.86-0.95 (m, 6H) 1.07-1.25 (m, 17H) 1.28-1.31 (m, 3H) 1.33-1.37 (m, 3H) 1.49-1.89 (m, 5H) 2.12-2.59 (m, 18H) 2.60 (s, 3H) 2.74-2.91 (m, 3H) 3.17-3.46 (m, 4H) 3.24 (s, 3H) 3.32 (s, 3H) 3.54-3.73 (m, 2H) 4.10-4.21 (m, 1H) 4.37-4.55 (m, 3H) 4.61-4.78 (m, 2H) 4.95-4.98 (m, 1H) 5.73-5.80 (m, 1H) 7.14-7.18 (m, 1H) 7.44-7.47 (m, 1H) |

TABLE 11-continued formula (W)

| Example | $R^{1W}$ | $R^{2W}$ | ESI MS (M + H) | $^1$H-NMR, CDCl$_3$, δ (ppm) |
|---|---|---|---|---|
| 302 | (carbamate-NH-CH$_2$CH$_2$-N(Et)-CH(Me)-(1-methylpyrazol-5-yl)) | H | 941.8 | mixture of diastereomers (600 MHz): 0.76 (d, J = 6.88 Hz, 6H) 0.84 (t, J = 7.34 Hz, 3H) 0.98 (t, J = 7.34 Hz, 3H) 1.01-1.21 (m, 17H) 1.23-1.27 (m, 6H) 1.44-1.81 (m, 5H) 2.05-2.56 (m, 10H) 2.24 (s, 6H) 2.30 (s, 3H) 2.71-2.79 (m, 1H) 2.79-2.86 (m, 1H) 2.88-3.16 (m, 3H) 3.16 (s, 3H) 3.27 (d, J = 7.34 Hz, 3H) 3.31-3.39 (m, 1H) 3.46-3.52 (m, 1H) 3.64 (d, J = 9.63 Hz, 1H) 3.84 (s, 3H) 3.95-4.02 (m, 1H) 4.13-4.19 (m, 1H) 4.28-4.34 (m, 1H) 4.35-4.40 (m, 1H) 4.43-4.50 (m, 1H) 4.53-4.60 (m, 1H) 4.80-4.88 (m, 1H) 4.91 (d, J = 5.04 Hz, 1H) 6.05 (s, 1H) 7.30 (s, 1H), and (600 MHz): 0.76 (d, J = 6.88 Hz, 6H) 0.84 (t, J = 7.34 Hz, 3H) 0.94 (t, J = 7.11 Hz, 3H) 1.01-1.21 (m, 17H) 1.23-1.27 (m, 6H) 1.44-1.81 (m, 5H) 2.05-2.56 (m, 10H) 2.24 (s, 6H) 2.30 (s, 3H) 2.71-2.79 (m, 1H) 2.79-2.86 (m, 1H) 2.88-3.16 (m, 3H) 3.16 (s, 3H) 3.26 (s, 3H) 3.31-3.39 (m, 1H) 3.46-3.52 (m, 1H) 3.64 (d, J = 9.63 Hz, 1H) 3.84 (s, 3H) 3.95-4.02 (m, 1H) 4.13-4.19 (m, 1H) 4.28-4.34 (m, 1H) 4.35-4.40 (m, 1H) 4.43-4.50 (m, 1H) 4.53-4.60 (m, 1H) 4.80-4.88 (m, 1H) 4.91 (d, J = 5.04 Hz, 1H) 6.05 (s, 1H) 7.30 (s, 1H) |
| 303 | (carbamate-NH-CH$_2$CH$_2$-N(Et)-CH(Me)-(1,3-dimethylpyrazol-5-yl)) | H | 955.8 | mixture of diastereomers (600 MHz): 0.81 (d, J = 6.88 Hz, 6H) 0.88 (t, J = 7.34 Hz, 3H) 1.02 (t, J = 7.11 Hz, 3H) 1.06-1.23 (m, 17H) 1.25-1.28 (m, 3H) 1.30 (s, 3H) 1.49-1.86 (m, 5H) 2.10-2.59 (m, 10H) 2.20 (s, 3H) 2.28 (s, 6H) 2.35 (s, 3H) 2.77-2.83 (m, 1H) 2.85-2.91 (m, 1H) 2.96-3.21 (m, 3H) 3.21 (s, 3H) 3.33 (s, 3H) 3.35-3.44 (m, 1H) 3.51-3.57 (m, 1H) 3.69 (d, J = 7.79 Hz, 1H) 3.81 \ (s, 3H) 3.93-3.99 (m, 1H) 4.19-4.25 (m, 1H) 4.33-4.39 (m, 1H) 4.40-4.45 (m, 1H) 4.49-4.53 (m, 1H) 4.59-4.66 (m, 1H) 4.88-4.94 (m, 1H) 4.96 (d, J = 4.58 Hz, 1H) 5.87 (s, 1H), and (600 MHz): 0.81 (d, J = 6.88 Hz, 6H) 0.88 (t, J = 7.34 Hz, 3H) 0.99 (t, J = 7.11 Hz, 3H) 1.06-1.23 (m, 17H) 1.25-1.28 (m, 3H) 1.30 (s, 3H) 1.49-1.86 (m, 5H) 2.10-2.59 (m, 10H) 2.20 (s, 3H) 2.28 (s, 6H) 2.35 (s, 3H) 2.77-2.83 (m, 1H) 2.85-2.91 (m, 1H) 2.96-3.21 (m, 3H) 3.21 (s, 3H) 3.31 (s, 3H) 3.35-3.44 (m, 1H) 3.51-3.57 (m, 1H) 3.69 (d, J = 7.79 Hz, 1H) 3.80 (s, 3H) 3.93-3.99 (m, 1H) 4.19-4.25 (m, 1H) 4.33-4.39 (m, 1H) 4.40-4.45 (m, 1H) 4.19-4.53 (m, 1H) 4.59-4.66 (m, 1H) 4.88-4.94 (m, 1H) 4.96 (d, J = 4.58 Hz, 1H) 5.87 (s, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 304 | | H | 1052.8 | mixture of diastereomers (600 MHz): 0.81 (d, J = 6.42 Hz, 6H) 0.89 (t, J = 7.34 Hz, 3H) 0.96-1.00 (m, 3H) 1.04 (t, J = 7.11 Hz, 6H) 1.07-1.25 (m, 17H) 1.30 (s, 3H) 1.31-1.34 (m, 3H) 1.49-1.86 (m, 5H) 2.11-2.66 (m, 14H) 2.27 (s, 6H) 2.36 (s, 3H) 2.78-2.91 (m, 2H) 3.16-3.21 (m, 3H) 3.23 (s, 3H) 3.33 (s, 3H) 3.35-3.44 (m, 1H) 3.54-3.58 (m, 3H) 3.71 (d, J = 8.25 Hz, 1H) 3.79 (s, 3H) 3.80-3.84 (m, 1H) 4.19-4.25 (m, 1H) 4.36-4.47 (m, 2H) 4.53-4.56 (m, 1H) 4.61-4.66 (m, 1H) 4.97 (d, J = 4.58 Hz, 1H) 5.27-5.30 (m, 1H) 6.77 (d, J = 7.34 Hz, 1H) 7.10 (d, J = 8.25 Hz, 1H) 7.29 (s, 1H), and (600 MHz): 0.81 (d, J = 6.42 Hz, 6H) 0.89 (t, J = 7.34 Hz, 3H) 0.94-0.99 (m, 3H) 1.04 (t, J = 7.11 Hz, 6H) 1.07-1.25 (m, 17H) 1.30 (s, 3H) 1.31-1.34 (m, 3H) 1.49-1.86 (m, 5H) 2.11-2.66 (m, 14H) 2.78-2.91 (m, 2H) 3.16-3.21 (m, 3H) 3.23 (s, 3H) 3.33 (s, 3H) 3.35-3.44 (m, 1H) 3.54-3.58 (m, 3H) 3.71 (d, J = 8.25 Hz, 1H) 3.79 (s, 3H) 3.80-3.84 (m, 1H) 4.19-4.25 (m, 1H) 4.36-4.47 (m, 2H) 4.53-4.56 (m, 1H) 4.61-4.66 (m, 1H) 4.97 (d, J = 4.58 Hz, 1H) 5.27-5.30 (m, 1H) 6.77 (d, J = 7.34 Hz, 1H) 7.10 (d, J = 8.25 Hz, 1H) 7.29 (s, 1H) |
| 305 | | H | 1050.8 | mixture of diastereomers (600 MHz): 0.81 (d, J = 6.42 Hz, 6H) 0.89 (t, J = 7.34 Hz, 3H) 0.95-1.02 (m, 3H) 1.04-1.35 (m, 23H) 1.49-1.91 (m, 9H) 2.11-2.73 (m, 14H) 2.28 (s, 6H) 2.36 (s, 3H) 2.78-2.92 (m, 2H) 3.16-3.42 (m, 6H) 3.23 (s, 3H) 3.33 (s, 3H) 3.55-3.63 (m, 1H) 3.69-3.73 (m, 1H) 3.79-3.83 (m, 4H) 4.20-4.26 (m, 1H) 4.36-4.49 (m, 2H) 4.52-4.56 (m, 1H) 4.60-4.68 (m, 1H) 4.97 (d, J = 4.58 Hz, 1H) 5.33-5.41 (m, 1H) 6.78-6.84 (m, 1H) 7.14-7.22 (m, 1H) 7.30-7.36 (m, 1H) |
| 306 | | H | 925.7 | mixture of diastereomers (600 MHz): 0.81 (d, J = 6.88 Hz, 6H) 0.89 (t, J = 7.34 Hz, 3H) 1.07-1.27 (m, 17H) 1.31 (s, 3H) 1.39-1.44 (m, 3H) 1.49-1.88 (m, 5H) 2.11-2.18 (m, 1H) 2.22-2.46 (m, 4H) 2.31 (s, 6H) 2.36 (s, 3H) 2.54-2.64 (m, 1H) 2.65-2.74 (m, 1H) 2.75-2.85 (m, 2H) 2.86-2.93 (m, 1H) 3.15-3.48 (m, 4H) 3.22 (s, 3H) 3.33 (s, 3H) 3.50-3.61 (m, 1H) 3.67-3.72 (m, 1H) 3.90-3.97 (m, 1H) 4.18-4.27 (m, 1H) 4.34-4.46 (m, 2H) 4.54 (d, J = 10.09 Hz, 1H) 4.59-4.67 (m, 1H) 4.98 (d, J = 4.59 Hz, 1H) 5.01-5.07 (m, 1H) 6.72-6.79 (m, 2H) 6.90-6.96 (m, 1H) 7.09-7.15 (m, 1H) |
| 307 | | H | 954.6 | mixture of diastereomers (600 MHz): 0.81 (d, J = 6.88 Hz, 6H) 0.89 (t, J = 7.34 Hz, 3H) 1.06-1.26 (m, 2H) 1.10-1.20 (m, 15H) 1.31 (s, 3H) 1.40 (d, J = 6.42 Hz, 3H) 1.47-1.67 (m, 3H) 1.75 (s, 1H) 1.84 (s, 1H) 2.10-2.20 (m, 1H) 2.22-2.45 (m, 4H) 2.29 (s, 6H) 2.36 (s, 3H) 2.47-2.54 (m, 1H) 2.55-2.65 (m, 2H) 2.77-2.84 (m, 1H) 2.88 (d, J = 14.67 Hz, 1H) 3.15-3.31 (m, 3H) 3.22 (s, 3H) 3.34 (s, 3H) 3.35-3.46 (m, 1H) 3.57 (s, 1H) 3.70 (d, J = 8.25 Hz, 1H) 4.21-4.23 (m, 1H) 4.23-4.29 (m, 1H) 4.34-4.41 (m, 1H) 4.42-4.47 (m, 1H) 4.50-4.56 (m, 1H) 4.63 (s, 1H) 4.97 (d, J = 4.58 Hz, 1H) 5.12-5.21 (m, 1H) 7.34-7.39 (m, 1H) 7.53-7.60 (m, 1H) 7.68 (d, J = 8.71 Hz, 1H) 7.74 (d, J = 7.79 Hz, 1H) |

TABLE 11-continued formula (W)

| Example | R^{1W} | R^{2W} | ESI MS (M + H) | $^1$H-NMR, CDCl$_3$, δ (ppm) |
|---|---|---|---|---|
| 308 | 2-chlorophenyl-CH(Me)-NH-CH$_2$CH$_2$-NH-C(O)-O- | H | 943.6 | mixture of diastereomers (600 MHz): 0.81 (d, J = 6.88 Hz, 6H) 0.89 (t, J = 7.34 Hz, 3H) 1.06-1.26 (m, 2H) 1.10-1.20 (m, 15H) 1.29-1.34 (m, 6H) 1.48-1.66 (m, 3H) 1.75 (s, 1H) 1.84 (s, 1H) 2.10-2.20 (m, 1H) 2.20-2.47 (m, 4H) 2.29 (s, 6H) 2.36 (s, 3H) 2.54-2.65 (m, 3H) 2.77-2.84 (m, 1H) 2.89 (d, J = 14.67 Hz, 1H) 3.16-3.33 (m, 3H) 3.23 (s, 3H) 3.34 (s, 3H) 3.36-3.46 (m, 1H) 3.58 (s, 1H) 3.70 (d, J = 8.25 Hz, 1H) 4.21 (s, 1H) 4.22-4.27 (m, 1H) 4.35-4.41 (m, 1H) 4.42-4.47 (m, 1H) 4.51-4.56 (m, 1H) 4.63 (s, 1H) 4.97 (d, J = 4.58 Hz, 1H) 5.21-5.30 (m, 1H) 7.13-7.18 (m, 1H) 7.21-7.25 (m, 1H) 7.29-7.34 (m, 1H) 7.38-7.42 (m, 1H) |
| 309 | 3-hydroxyphenyl-CH(Me)-NH-CH$_2$CH$_2$-NH-C(O)-O- | H | 925.6 | mixture of diastereomers (600 MHz): 0.77-0.85 (m, 6H) 0.90 (t, J = 7.34 Hz, 3H) 1.03-1.37 (m, 23H) 1.49-1.90 (m, 5H) 2.09-2.53 (m, 5H) 2.36 (s, 3H) 2.38-2.45 (m, 6H) 2.55-2.62 (m, 1H) 2.70-2.96 (m, 3H) 3.00-3.10 (m, 1H) 3.21 (s, 3H) 3.29-3.48 (m, 4H) 3.36 (s, 3H) 3.58-3.74 (m, 3H) 4.08-4.17 (m, 1H) 4.29-4.38 (m, 1H) 4.46-4.55 (m, 2H) 4.57-4.66 (m, 1H) 4.93-4.98 (m, 1H) 5.28-5.35 (m, 1H) 6.67-6.76 (m, 2H) 6.86-6.93 (m, 1H) 7.09-7.17 (m, 1H), and (600 MHz): 0.77-0.85 (m, 6H) 0.90 (t, J = 7.34 Hz, 3H) 1.03-1.37 (m, 23H) 1.49-1.90 (m, 5H) 2.09-2.53 (m, 5H) 2.36 (s, 3H) 2.38-2.45 (m, 6H) 2.55-2.62 (m, 1H) 2.70-2.96 (m, 3H) 3.00-3.10 (m, 1H) 3.22 (s, 3H) 3.29-3.48 (m, 4H) 3.34 (s, 3H) 3.58-3.74 (m, 3H) 4.08-4.17 (m, 1H) 4.29-4.38 (m, 1H) 4.46-4.55 (m, 2H) 4.57-4.66 (m, 1H) 4.93-4.98 (m, 1H) 5.01-5.07 (m, 1H) 6.67-6.76 (m, 2H) 6.86-6.93 (m, 1H) 7.09-7.17 (m, 1H) |
| 310 | 2-(CH$_3$CH$_2$O)phenyl-CH(Me)-NH-CH$_2$CH$_2$-NH-C(O)-O- | H | 953.7 | mixture of diastereomers (600 MHz): 0.82 (d, J = 6.42 Hz, 6H) 0.89 (t, J = 7.34 Hz, 3H) 1.05-1.27 (m, 17H) 1.31 (s, 3H) 1.34 (d, J = 5.50 Hz, 3H) 1.41 (t, J = 7.11 Hz, 3H) 1.47-1.71 (m, 3H) 1.71-1.88 (m, 2H) 2.09-2.47 (m, 5H) 2.30 (s, 6H) 2.36 (s, 3H) 2.51-2.64 (m, 3H) 2.77-2.85 (m, 1H) 2.86-2.92 (m, 1H) 3.14-3.36 (m, 3H) 3.23 (s, 3H) 3.33 (s, 3H) 3.37-3.44 (m, 1H) 3.53-3.64 (m, 1H) 3.70 (d, J = 7.79 Hz, 1H) 3.99-4.08 (m, 3H) 4.14-4.22 (m, 1H) 4.32-4.41 (m, 1H) 4.42-4.48 (m, 1H) 4.51-4.55 (m, 1H) 4.60-4.68 (m, 1H) 4.97 (d, J = 4.13 Hz, 1H) 5.33-5.41 (m, 1H) 6.83 (d, J = 7.79 Hz, 1H) 6.87-6.92 (m, 1H) 7.14-7.22 (m, 2H) |

TABLE 11-continued formula (W)

| Example | R$^{1W}$ | R$^{2W}$ | ESI MS (M + H) | $^1$H-NMR, CDCl$_3$, δ (ppm) |
|---------|----------|----------|----------------|------------------------------|
| 311 | (2-nitrophenyl)-CH(Me)-N(Et)-CH$_2$CH$_2$-NH-C(O)-O- | H | 982.7 | mixture of diastereomers (600 MHz): 0.77-0.85 (m, 6H) 0.86-0.92 (m, 6H) 1.05-1.24 (m, 17H) 1.30 (s, 3H) 1.34 (d, J = 6.42 Hz, 3H) 1.48-1.89 (m, 5H) 2.08-2.66 (m, 10H) 2.28 (s, 6H) 2.35 (s, 3H) 2.77-2.84 (m, 1H) 2.84-2.92 (m, 1H) 2.97-3.48 (m, 4H) 3.22 (s, 3H) 3.35 (s, 3H) 3.59-3.75 (m, 2H) 4.08-4.13 (m, 1H) 4.32-4.57 (m, 4H) 4.58-4.69 (m, 1H) 4.92-4.99 (m, 1H) 5.22-5.27 (m, 1H) 7.32-7.38 (m, 1H) 7.45-7.60 (m, 3H), and (600 MHz): 0.77-0.85 (m, 6H) 0.86-0.92 (m, 6H) 1.05-1.24 (m, 17H) 1.31 (s, 3H) 1.36 (d, J = 6.88 Hz, 3H) 1.48-1.89 (m, 5H) 2.08-2.66 (m, 10H) 2.28 (s, 6H) 2.35 (s, 3H) 2.77-2.84 (m, 1H) 2.84-2.92 (m, 1H) 2.97-3.48 (m, 4H) 3.23 (s, 3H) 3.33 (s, 3H) 3.59-3.75 (m, 2H) 4.13-4.19 (m, 1H) 4.32-4.57 (m, 4H) 4.58-4.69 (m, 1H) 4.92-4.99 (m, 1H) 5.14-5.20 (m, 1H) 7.32-7.38 (m, 1H) 7.45-7.60 (m, 3H) |
| 312 | -O-C(O)-NH-CH$_2$CH$_2$-NH-CH(Me)-(4-nitrophenyl) | H | 954.7 | mixture of diastereomers (600 MHz): 0.79 (d, J = 6.88 Hz, 6H) 0.87 (t, J = 7.34 Hz, 3H) 1.04-1.23 (m, 17H) 1.28 (s, 3H) 1.29-1.32 (m, 3H) 1.44-1.67 (m, 3H) 1.67-1.85 (m, 2H) 2.06-2.45 (m, 6H) 2.26 (s, 6H) 2.33 (s, 3H) 2.46-2.54 (m, 1H) 2.57-2.66 (m, 1H) 2.74-2.91 (m, 2H) 3.13-3.42 (m, 4H) 3.20 (s, 3H) 3.31 (s, 3H) 3.49-3.58 (m, 1H) 3.67 (d, J = 7.79 Hz, 1H) 3.82-3.88 (m, 1H) 4.15-4.25 (m, 1H) 4.30-4.45 (m, 2H) 4.48-4.53 (m, 1H) 4.56-4.64 (m, 1H) 4.95 (d, J = 4.58 Hz, 1H) 5.12-5.19 (m, 1H) 7.44 (d, J = 8.71 Hz, 2H) 8.14 (d, J = 8.25 Hz, 2H), and (600 MHz): 0.79 (d, J = 6.88 Hz, 6H) 0.87 (t, J = 7.34 Hz, 3H) 1.04-1.23 (m, 17H) 1.28 (s, 3H) 1.29-1.32 (m, 3H) 1.44-1.67 (m, 3H) 1.67-1.85 (m, 2H) 2.06-2.45 (m, 6H) 2.26 (s, 6H) 2.33 (s, 3H) 2.46-2.54 (m, 1H) 2.57-2.66 (m, 1H) 2.74-2.91 (m, 2H) 3.13-3.42 (m, 4H) 3.20 (s, 3H) 3.32 (s, 3H) 3.49-3.58 (m, 1H) 3.67 (d, J = 7.79 Hz, 1H) 3.82-3.88 (m, 1H) 4.15-4.25 (m, 1H) 4.30-4.45 (m, 2H) 4.48-4.53 (m, 1H) 4.56-4.64 (m, 1H) 4.95 (d, J = 4.58 Hz, 1H) 5.12-5.19 (m, 1H) 7.44 (d, J = 8.71 Hz, 2H) 8.14 (d, J = 8.25 Hz, 2H) |
| 313 | (3-methoxyphenyl)-CH(Me)-NH-CH$_2$CH$_2$-NH-C(O)-O- | H | 939.7 | mixture of diastereomers (600 MHz): 0.81 (d, J = 6.88 Hz, 6H) 0.89 (t, J = 7.34 Hz, 3H) 1.06-1.25 (m, 17H) 1.27-1.34 (m, 6H) 1.47-1.69 (m, 3H) 1.70-1.89 (m, 2H) 2.11-2.46 (m, 5H) 2.30 (s, 6H) 2.36 (s, 3H) 2.53-2.66 (m, 3H) 2.76-2.85 (m, 1H) 2.85-2.94 (m, 1H) 3.14-3.48 (m, 4H) 3.23 (s, 3H) 3.33 (s, 3H) 3.53-3.63 (m, 1H) 3.66-3.74 (m, 2H) 3.80 (s, 3H) 4.21 (s, 1H) 4.33-4.41 (m, 1H) 4.41-4.48 (m, 1H) 4.50-4.56 (m, 1H) 4.63 (s, 1H) 4.97 (d, J = 4.58 Hz, 1H) 5.19-5.30 (m, 1H) 6.74-6.79 (m, 1H) 6.81 (s, 1H) 6.85 (d, J = 7.34 Hz, 1H) 7.19-7.24 (m, 1H) |

TABLE 11-continued formula (W)

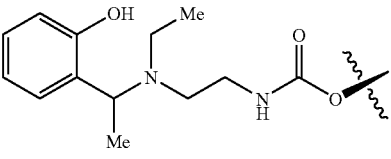

| Example | $R^{1W}$ | $R^{2W}$ | ESI MS (M + H) | $^1$H-NMR, CDCl$_3$, δ (ppm) |
|---|---|---|---|---|
| 314 |  | 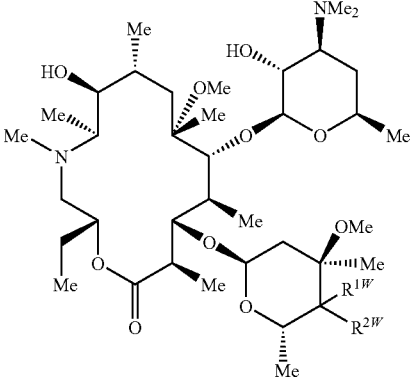 | 953.7 | mixture of diastereomers (600 MHz): 0.81 (d, J = 6.42 Hz, 6H) 0.89 (t, J = 7.11 Hz, 3H) 1.04-1.27 (m, 2H) 1.05-1.20 (m, 18H) 1.30 (s, 3H) 1.37-1.41 (m, 3H) 1.49-1.64 (m, 3H) 1.74 (s, 1H) 1.84 (s, 1H) 2.10-2.21 (m, 1H) 2.20-2.46 (m, 4H) 2.30 (s, 7H) 2.36 (s, 3H) 2.53-2.95 (m, 6H) 3.14-3.48 (m, 4H) 3.22 (s, 3H) 3.32 (s, 3H) 3.55-3.66 (m, 1H) 3.70 (d, J = 7.79 Hz, 1H) 4.10-4.22 (m, 2H) 4.37 (s, 1H) 4.42-4.55 (m, 2H) 7.02 (t, J = 6.19 Hz, 1H) 7.15 (t, J = 7.79 Hz, 1H), and (600 MHz): 0.81 (d, J = 6.42 Hz, 6H) 0.89 (t, J = 7.11 Hz, 3H) 1.04-1.27 (m, 2H) 1.05-1.20 (m, 18H) 1.30 (s, 3H) 1.37-1.41 (m, 3H) 1.49-1.64 (m, 3H) 1.74 (s, 1H) 1.84 (s, 1H) 2.10-2.21 (m, 1H) 2.20-2.46 (m, 4H) 2.30 (s, 7H) 2.36 (s, 3H) 2.53-2.95 (m, 6H) 3.14-3.48 (m, 4H) 3.22 (s, 3H) 3.33 (s, 3H) 3.55-3.66 (m, 1H) 3.70 (d, J = 7.79 Hz, 1H) 4.04-4.09 (m, 1H) 4.14-4.21 (m, 1H) 4.37 (s, 1H) 4.42-4.55 (m, 2H) 4.64 (s, 1H) 4.96 (s, 1H) 5.07-5.17 (m, 1H) 6.72-6.82 (m, 2H) 7.02 (t, J = 6.19 Hz, 1H) 7.15 (t, J = 7.79 Hz, 1H) |
| 315 | 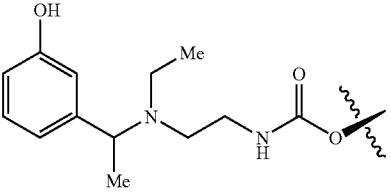 |  | 953.7 | mixture of diastereomers (600 MHz): 0.81 (d, J = 6.88 Hz, 6H) 0.90 (t, J = 7.34 Hz, 3H) 1.04 (t, J = 7.34 Hz, 3H) 1.06-1.31 (m, 2H) 1.08-1.31 (m, 18H) 1.31-1.34 (m, 3H) 1.48-1.88 (m, 5H) 2.08-2.18 (m, 1H) 2.21-2.51 (m, 7H) 2.31-2.39 (m, 9H) 2.55-2.76 (m, 2H) 2.77-2.99 (m, 2H) 3.19-3.24 (m, 3H) 3.23-3.54 (m, 4H) 3.39-3.42 (m, 3H) 3.59-3.75 (m, 2H) 3.92 (q, J = 6.42 Hz, 1H) 4.20 (s, 1H) 4.32-4.42 (m, 1H) 4.45-4.52 (m, 1H) 4.58 (d, J = 9.63 Hz, 1H) 4.66 (s, 1H) 4.96-5.02 (m, 1H) 6.68-6.79 (m, 2H) 6.98 (s, 1H) 7.12 (t, J = 7.79 Hz, 1H), and (600 MHz): 0.81 (d, J = 6.88 Hz, 6H) 0.90 (t, J = 7.34 Hz, 3H) 1.01 (t, J = 7.11 Hz, 3H) 1.06-1.31 (m, 2H) 1.08-1.31 (m, 18H) 1.31-1.34 (m, 3H) 1.48-1.88 (m, 5H) 2.08-2.18 (m, 1H) 2.21-2.51 (m, 7H) 2.31-2.39 (m, 9H) 2.55-2.76 (m, 2H) 2.77-2.99 (m, 2H) 3.19-3.24 (m, 3H) 3.23-3.54 (m, 4H) 3.39-3.42 (m, 3H) 3.59-3.75 (m, 2H) 3.92 (q, J = 6.42 Hz, 1H) 4.17 (s, 1H) 4.32-4.42 (m, 1H) 4.45-4.52 (m, 1H) 4.54 (d, J = 9.63 Hz, 1H) 4.59-4.64 (m, 1H) 4.96-5.02 (m, 1H) 6.68-6.79 (m, 2H) 7.07 (s, 1H) 7.15 (t, J = 7.79 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 316 | HO-C$_6$H$_4$-CH(Me)-NH-CH$_2$CH$_2$-NH-C(O)-O- | —H | 925.6 | mixture of diastereomers (600 MHz): 0.75-0.82 (m, 6H) 0.86 (t, J = 7.34 Hz, 3H) 1.00-1.17 (m, 14H) 1.18-1.30 (m, 9H) 1.43-1.66 (m, 3H) 1.67-1.76 (m, 1H) 1.77-1.86 (m, 1H) 2.10-2.65 (m, 11H) 2.30 (s, 6H) 2.72-2.90 (m, 2H) 3.12-3.46 (m, 4H) 3.20 (s, 3H) 3.31 (s, 3H) 3.50-3.69 (m, 3H) 4.08-4.14 (m, 1H) 4.23-4.31 (m, 1H) 4.41-4.64 (m, 3H) 4.91 (d, J = 4.59 Hz, 1H) 6.63-6.71 (m, 1H) 6.71-6.79 (m, 1H) 7.09 (d, J = 8.71 Hz, 1H) 7.13 (d, J = 8.25 Hz, 1H), and (600 MHz): 0.75-0.82 (m, 6H) 0.86 (t, J = 7.34 Hz, 3H) 1.00-1.17 (m, 14H) 1.18-1.30 (m, 9H) 1.43-1.66 (m, 3H) 1.67-1.76 (m, 1H) 1.77-1.86 (m, 1H) 2.10-2.65 (m, 11H) 2.31 (s, 6H) 2.72-2.90 (m, 2H) 3.12-3.46 (m, 4H) 3.19 (s, 3H) 3.37 (s, 3H) 3.50-3.69 (m, 3H) 4.02-4.08 (m, 1H) 4.23-4.31 (m, 1H) 4.41-4.64 (m, 3H) 4.91 (d, J = 4.59 Hz, 1H) 6.63-6.71 (m, 1H) 6.71-6.79 (m, 1H) 7.09 (d, J = 8.71 Hz, 1H) 7.13 (d, J = 8.25 Hz, 1H) |
| 317 | 2-NH$_2$-C$_6$H$_4$-CH(Me)-N(Et)-CH$_2$CH$_2$-NH-C(O)-O- | —H | 952.7 | mixture of diastereomers (600 MHz): 0.81 (d, J = 6.88 Hz, 6H) 0.89 (t, J = 7.34 Hz, 3H) 1.05 (t, J = 7.34 Hz, 3H) 1.07-1.27 (m, 17H) 1.30 (s, 3H) 1.35 (d, J = 6.88 Hz, 3H) 1.48-1.90 (m, 5H) 2.10-2.20 (m, 1H) 2.21-2.53 (m, 5H) 2.30 (s, 6H) 2.36 (s, 3H) 2.54-2.70 (m, 4H) 2.77-2.84 (m, 1H) 2.89 (d, J = 13.76 Hz, 1H) 3.02-3.30 (m, 3H) 3.22 (s, 3H) 3.34 (s, 3H) 3.37-3.49 (m, 1H) 3.49-3.59 (m, 1H) 3.67-3.72 (m, 1H) 3.93-4.02 (m, 1H) 4.17-4.28 (m, 1H) 4.32-4.39 (m, 1H) 4.40-4.46 (m, 1H) 4.49 (d, J = 9.63 Hz, 1H) 4.58-4.68 (m, 1H) 4.74-4.83 (m, 1H) 4.94-4.98 (m, 1H) 6.60 (d, J = 7.79 Hz, 1H) 6.65-6.71 (m, 1H) 7.02-7.08 (m, 2H), and (600 MHz): 0.81 (d, J = 6.88 Hz, 6H) 0.89 (t, J = 7.34 Hz, 3H) 1.05 (t, J = 7.34 Hz, 3H) 1.07-1.27 (m, 17H) 1.30 (s, 3H) 1.35 (d, J = 6.88 Hz, 3H) 1.48-1.90 (m, 5H) 2.10-2.20 (m, 1H) 2.21-2.53 (m, 5H) 2.30 (s, 6H) 2.36 (s, 3H) 2.54-2.70 (m, 4H) 2.77-2.84 (m, 1H) 2.89 (d, J = 13.76 Hz, 1H) 3.02-3.30 (m, 3H) 3.22 (s, 3H) 3.34 (s, 3H) 3.37-3.49 (m, 1H) 3.49-3.59 (m, 1H) 3.67-3.72 (m, 1H) 3.93-4.02 (m, 1H) 4.17-4.28 (m, 1H) 4.32-4.39 (m, 1H) 4.40-4.46 (m, 1H) 4.49 (d, J = 9.63 Hz, 1H) 4.58-4.68 (m, 1H) 4.93-5.02 (m, 2H) 6.60 (d, J = 7.79 Hz, 1H) 6.65-6.71 (m, 1H) 7.02-7.08 (m, 2H) |
| 318 | -O-C(O)-NH-CH$_2$CH$_2$-N(Et)-CH(Me)-C$_6$H$_4$-4-NO$_2$ | —H | 982.7 | mixture of diastereomers (600 MHz): 0.81 (d, J = 7.34 Hz, 6H) 0.90 (t, J = 7.34 Hz, 3H) 0.96-1.03 (m, 3H) 1.06-1.26 (m, 17H) 1.30 (s, 3H) 1.36 (d, J = 6.88 Hz, 3H) 1.49-1.66 (m, 3H) 1.70-1.90 (m, 2H) 2.10-2.64 (m, 10H) 2.28 (s, 6H) 2.36 (s, 3H) 2.76-2.94 (m, 2H) 3.16-3.48 (m, 4H) 3.22 (s, 3H) 3.35 (s, 3H) 3.52-3.62 (m, 1H) 3.71 (d, J = 8.25 Hz, 1H) 3.88-4.00 (m, 1H) 4.19-4.29 (m, 1H) 4.34-4.49 (m, 2H) 4.51-4.57 (m, 1H) 4.59-4.67 (m, 1H) 4.94-5.00 (m, 1H) 5.07-5.15 (m, 1H) 7.50 (d, J = 8.71 Hz, 2H) 8.16 (d, J = 7.34 Hz, 2H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 319 | (carbamate-CH₂CH₂-NH-CH(Me)-C₆H₄-NMe₂) | H | 952.7 | mixture of diastereomers (600 MHz): 0.81 (d, J = 6.88 Hz, 6H) 0.89 (t, J = 7.34 Hz, 3H) 1.06-1.25 (m, 17H) 1.28-1.33 (m, 6H) 1.49-1.68 (m, 3H) 1.70-1.79 (m, 1H) 1.80-1.87 (m, 1H) 2.11-2.19 (m, 1H) 2.21-2.46 (m, 4H) 2.29 (s, 6H) 2.36 (s, 3H) 2.54-2.64 (m, 3H) 2.77-2.84 (m, 1H) 2.85-2.93 (m, 1H) 2.92 (s, 6H) 3.13-3.31 (m, 3H) 3.23 (s, 3H) 3.34 (s, 3H) 3.36-3.44 (m, 3H) 3.55-3.62 (m, 1H) 3.62-3.68 (m, 1H) 3.70 (d, J = 7.79 Hz, 1H) 4.20 (s, 1H) 4.34-4.41 (m, 1H) 4.42-4.47 (m, 1H) 4.51-4.55 (m, 1H) 4.59-4.68 (m, 1H) 4.97 (d, J = 4.59 Hz, 1H) 5.23-5.31 (m, 1H) 6.68 (d, J = 8.71 Hz, 2H) 7.12 (d, J = 8.71 Hz, 2H) |
| 320 | (2-Cl-C₆H₄-CH(Me)-N(Et)-CH₂CH₂-NH-C(O)O-) | H | 971.7 | mixture of diastereomers (600 MHz): 0.82 (d, J = 6.42 Hz, 6H) 0.89 (t, J = 7.11 Hz, 3H) 0.94 (t, J = 6.88 Hz, 3H) 1.05-1.26 (m, 2H) 1.09-1.20 (m, 15H) 1.27-1.34 (m, 6H) 1.48-1.68 (m, 3H) 1.74 (s, 1H) 1.84 (s, 1H) 2.12-2.49 (m,,5H) 2.27 (s, 6H) 2.36 (s, 3H) 2.49-2.69 (m, 5H) 2.77-2.84 (m, 1H) 2.88 (s, 1H) 3.13-3.45 (m, 4H) 3.23 (s, 3H) 3.34 (s, 3H) 3.61 (s, 1H) 3.71 (d, J = 8.25 Hz, 1H) 4.20 (s, 1H) 4.28-4.36 (m, 1H) 4.38 (s, 1H) 4.47 (s, 1H) 4.49-4.55 (m, 1H) 4.64 (s, 1H) 4.96 (s, 1H) 5.19-5.30 (m, 1H) 7.12-7.18 (m, 1H) 7.19-7.24 (m, 1H) 7.32 (d, J = 7.79 Hz, 1H) 7.39-7.45 (m, 1H), and (600 MHz): 0.82 (d, J = 6.42 Hz, 6H) 0.89 (t, J = 7.11 Hz, 3H) 0.98 (t, J = 7.11 Hz, 3H) 1.05-1.26 (m, 2H) 1.09-1.20 (m, 15H) 1.27-1.34 (m, 6H) 1.48-1.68 (m, 3H) 1.74 (s, 1H) 1.84 (s, 1H) 2.12-2.49 (m,, 5H) 2.27 (s, 6H) 2.36 (s, 3H) 2.49-2.69 (m, 5H) 2.77-2.84 (m, 1H) 2.88 (s, 1H) 3.13-3.45 (m, 4H) 3.23 (s, 3H) 3.34 (s, 3H) 3.61 (s, 1H) 3.71 (d, J = 8.25 Hz, 1H) 4.20 (s, 1H) 4.28-4.36 (m, 1H) 4.38 (s, 1H) 4.47 (s, 1H) 4.49-4.55 (m, 1H) 4.64 (s, 1H) 4.96 (s, 1H) 5.19-5.30 (m, 1H) 7.12-7.18 (m, 1H) 7.19-7.24 (m, 1H) 7.32 (d, J = 7.79 Hz, 1H) 7.39-7.45 (m, 1H) |
| 321 | (3-MeO-C₆H₄-CH(Me)-N(Et)-CH₂CH₂-NH-C(O)O-) | H | 967.8 | mixture of diastereomers (600 MHz): 0.82 (d, J = 6.88 Hz, 6H) 0.89 (t, J = 7.34 Hz, 3H) 0.95-1.04 (m, 3H) 1.07-1.27 (m, 2H) 1.10-1.21 (m, 15H) 1.31 (s, 3H) 1.32 (d, J = 5.96 Hz, 3H) 1.49-1.65 (m, 3H) 1.70-1.79 (m, 1H) 1.80-1.88 (m, 1H) 2.11-2.21 (m, 1H) 2.21-2.53 (m, 6H) 2.28 (s, 6H) 2.36 (s, 3H) 2.53-2.65 (m, 3H) 2.81 (dd, J = 7.34, 5.50 Hz, 1H) 2.85-2.93 (m, 1H) 3.16-3.23 (m, 3H) 3.23 (s, 3H) 3.34 (s, 3H) 3.36-3.45 (m, 1H) 3.55-3.63 (m, 1H) 3.71 (d, J = 7.79 Hz, 1H) 3.80 (s, 3H) 3.80-3.86 (m, 1H) 4.21 (s, 1H) 4.35-4.42 (m, 1H) 4.46 (s, 1H) 4.51-4.56 (m, 1H) 4.64 (s, 1H) 4.94-4.99 (m, 1H) 5.20 (s, 1H) 6.76 (d, J = 7.79 Hz, 1H) 6.83 (s, 1H) 6.88 (d, J = 7.79 Hz, 1H) 7.21 (t, J = 7.57 Hz, 1H) |

TABLE 11-continued formula (W)

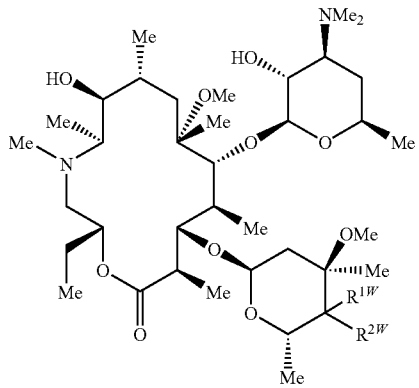

| Example | R$^{1W}$ | R$^{2W}$ | ESI MS (M + H) | $^1$H-NMR, CDCl$_3$, δ (ppm) |
|---|---|---|---|---|
| 322 | [carbamate-NH-CH$_2$CH$_2$-N(Et)-CH(Me)-3,5-bis(trifluoromethyl)phenyl] | H | 1073.7 | (600 MHz): 0.79-0.84 (m, 6H) 0.89 (t, J = 7.34 Hz, 3H) 1.00 (t, J = 7.11 Hz, 3H) 1.07-1.18 (m, 16H) 1.19-1.27 (m, 1H) 1.30 (s, 3H) 1.38 (d, J = 6.88 Hz, 3H) 1.49-1.63 (m, J = 15.13, 5.04 Hz, 2H) 1.60 (dd, J = 15.13, 5.04 Hz, 1H) 1.70-1.88 (m, 2H) 2.11-2.19 (m, 1H) 2.29 (s, 6H) 2.30-2.33 (m, 1H) 2.36 (s, 3H) 2.38-2.46 (m, 3H) 2.49-2.64 (m, 6H) 2.77-2.84 (m, 1H) 2.88 (d, J = 11.92 Hz, 1H) 3.16-3.30 (m, 2H) 3.22 (s, 3H) 3.33 (s, 3H) 3.35-3.39 (m, 1H) 3.52-3.57 (m, 1H) 3.71 (d, J = 8.71 Hz, 1H) 3.96 (q, J = 6.72 Hz, 1H) 4.21-4.30 (m, 1H) 4.36-4.44 (m, 2H) 4.55 (d, J = 9.63 Hz, 1H) 4.59-4.67 (m, 1H) 4.97 (d, J = 4.59 Hz, 1H) 5.06-5.11 (m, 1H) 7.75 (s, 1H) 7.78 (s, 2H) |
| 323 | [2-ethoxyphenyl-CH(Me)-N(Et)-CH$_2$CH$_2$-NH-carbamate] | H | 981.8 | mixture of diastereomers (600 MHz): 0.82 (d, J = 6.42 Hz, 6H) 0.89 (t, J = 7.34 Hz, 3H) 0.92-1.00 (m, 3H) 1.05-1.24 (m, 2H) 1.10-1.19 (m, 15H) 1.25-1.33 (m, 6H) 1.38-1.43 (m, 3H) 1.49-1.65 (m, 3H) 1.74 (s, 1H) 1.84 (s, 1H) 2.12-2.20 (m, 1H) 2.21-2.32 (m, 2H) 2.26 (s, 6H) 2.33-2.65 (m, 7H) 2.36 (s, 3H) 2.78-2.84 (m, 1H) 2.88 (d, J = 16.05 Hz, 1H) 3.15-3.27 (m, 3H) 3.23 (s, 3H) 3.32 (s, 3H) 3.35-3.46 (m, 1H) 3.53-3.63 (m, 1H) 3.69-3.74 (m, 1H) 3.96-4.05 (m, 2H) 4.22 (s, 1H) 4.33-4.49 (m, 3H) 4.50-4.56 (m, 1H) 4.64 (s, 1H) 4.97 (d, J = 4.58 Hz, 1H) 5.39-5.50 (m, 1H) 6.84 (d, J = 8.25 Hz, 1H) 6.86-6.93 (m, 1H) 7.17 (t, J = 7.11 Hz, 1H) 7.27 (s, 1H), and (600 MHz): 0.82 (d, J = 6.42 Hz, 6H) 0.89 (t, J = 7.34 Hz, 3H) 0.92-1.00 (m, 3H) 1.05-1.24 (m, 2H) 1.10-1.19 (m, 15H) 1.25-1.33 (m, 6H) 1.38-1.43 (m, 3H) 1.49-1.65 (m, 3H) 1.74 (s, 1H) 1.84 (s, 1H) 2.12-2.20 (m, 1H) 2.21-2.32 (m, 2H) 2.27 (s, 6H) 2.33-2.65 (m, 7H) 2.36 (s, 3H) 2.78-2.84 (m, 1H) 2.88 (d, J = 16.05 Hz, 1H) 3.15-3.27 (m, 3H) 3.23 (s, 3H) 3.33 (s, 3H) 3.35-3.46 (m, 1H) 3.53-3.63 (m, 1H) 3.69-3.74 (m, 1H) 4.04-4.13 (m, 2H) 4.22 (s, 1H) 4.33-4.49 (m, 3H) 4.50-4.56 (m, 1H) 4.64 (s, 1H) 4.97 (d, J = 4.58 Hz, 1H) 5.39-5.50 (m, 1H) 6.84 (d, J = 8.25 Hz, 1H) 6.86-6.93 (m, 1H) 7.17 (t, J = 7.11 Hz, 1H) 7.27 (s, 1H) |
| 324 | [carbamate-NH-CH$_2$CH$_2$-N(Et)-CH(Me)-3-methoxyphenyl] | H | 967.8 | (600 MHz): 0.82 (d, J = 6.88 Hz, 6H) 0.89 (t, J = 7.34 Hz, 3H) 0.98 (t, J = 6.88 Hz, 3H) 1.06-1.25 (m, 2H) 1.13 (d, J = 7.34 Hz, 3H) 1.14 (s, 3H) 1.15-1.18 (m, 6H) 1.19 (d, J = 5.96 Hz, 3H) 1.31 (s, 3H) 1.33 (d, J = 6.88 Hz, 3H) 1.50-1.68 (m, 3H) 1.70-1.79 (m, 1H) 1.80-1.88 (m, 1H) 2.10-2.20 (m, 1H) 2.22-2.34 (m, 2H) 2.29 (s, 6H) 2.36 (s, 3H) 2.38-2.52 (m, 4H) 2.55-2.65 (m, 3H) 2.78-2.84 (m, 1H) 2.85-2.92 (m, 1H) 3.16-3.25 (m, 3H) 3.23 (s, 3H) 3.34 (s, 3H) 3.35-3.42 (m, 1H) 3.56-3.65 (m, 1H) 3.71 (d, J = 8.25 Hz, 1H) 3.76-3.84 (m, 1H) 3.79 (s, 3H) 4.21 (s, 1H) 4.35-4.42 (m, 1H) 4.47 (d, J = 6.88 Hz, 1H) 4.53 (d, J = 10.09 Hz, 1H) 4.64 (s, 1H) 4.97 (d, J = 4.58 Hz, 1H) 5.22 (s, 1H) 6.76 (dd, J = 7.79, 2.29 Hz, 1H) 6.84 (s, 1H) 6.88 (d, J = 7.34 Hz, 1H) 7.21 (t, J = 8.02 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 325 | | | 1010.8 | mixture of diastereomers (600 MHz): 0.81 (d, J = 6.88 Hz, 6H) 0.89 (t, J = 7.34 Hz, 3H) 1.04-1.24 (m, 23H) 1.28 (d, J = 6.42 Hz, 3H) 1.31 (s, 3H) 1.49-1.86 (m, 5H) 2.10-2.45 (m, 5H) 2.29 (s, 6H) 2.36 (s, 3H) 2.54-2.62 (m, 7H) 2.78-2.91 (m, 2H) 3.15-3.46 (m, 4H) 3.23 (s, 3H) 3.33 (s, 3H) 3.54-3.65 (m, 2H) 3.70 (d, J = 7.79 Hz, 1H) 3.73 (s, 2H) 4.18-4.23 (m, 1H) 4.34-4.40 (m, 1H) 4.42-4.46 (m, 1H) 4.52-4.55 (m, 1H) 4.62-4.66 (m, 1H) 4.97 (d, J = 5.04 Hz, 1H) 5.23-5.28 (m, 1H) 6.71-6.73 (m, 1H) 6.82-6.84 (m, 1H) 7.01-7.03 (m, 1H), and (600 MHz): 0.81 (d, J = 6.88 Hz, 6H) 0.89 (t, J = 7.34 Hz, 3H) 1.04-1.24 (m, 23H) 1.28 (d, J = 6.88 Hz, 3H) 1.31 (s, 3H) 1.49-1.86 (m, 5H) 2.10-2.45 (m, 5H) 2.29 (s, 6H) 2.36 (s, 3H) 2.54-2.62 (m, 7H) 2.78-2.91 (m, 2H) 3.15-3.46 (m, 4H) 3.23 (s, 3H) 3.33 (s, 3H) 3.54-3.65 (m, 2H) 3.70 (d, J = 7.79 Hz, 1H) 3.73 (s, 2H) 4.18-4.23 (m, 1H) 4.34-4.40 (m, 1H) 4.42-4.46 (m, 1H) 4.52-4.55 (m, 1H) 4.62-4.66 (m, 1H) 4.97 (d, J = 5.04 Hz, 1H) 5.23-5.28 (m, 1H) 6.71-6.73 (m, 1H) 6.82-6.84 (m, 1H) 7.01-7.03 (m, 1H) |
| 326 | | | 1022.8 | mixture of diastereomers (600 MHz): 0.81 (d, J = 6.42 Hz, 6H) 0.89 (t, J = 7.34 Hz, 3H) 1.08-1.25 (m, 17H) 1.28 (d, J = 6.42 Hz, 3H) 1.31 (s, 3H) 1.49-1.88 (m, 11H) 2.11-2.63 (m, 12H) 2.30 (s, 6H) 2.36 (s, 3H) 2.78-2.84 (m, 1H) 2.86-2.91 (m, 1H) 3.14-3.45 (m, 4H) 3.23 (s, 3H) 3.34 (s, 3H) 3.55-3.62 (m, 2H) 3.63 (s, 2H) 3.70 (d, J = 7.79 Hz, 1H) 4.19-4.23 (m, 1H) 4.35-4.40 (m, 1H) 4.42-4.46 (m, 1H) 4.52-4.55 (m, 1H) 4.61-4.66 (m, 1H) 4.96-4.99 (m, 1H) 5.23-5.26 (m, 1H) 6.72-6.74 (m, 1H) 6.82-6.83 (m, 1H) 7.01-7.04 (m, 1H), and (600 MHz): 0.81 (d, J = 6.42 Hz, 6H) 0.89 (t, J = 7.34 Hz, 3H) 1.08-1.25 (m, 17H) 1.28 (d, J = 6.42 Hz, 3H) 1.31 (s, 3H) 1.49-1.88 (m, 11H) 2.11-2.63 (m, 12H) 2.30 (s, 6H) 2.36 (s, 3H) 2.78-2.84 (m, 1H) 2.86-2.91 (m, 1H) 3.14-3.45 (m, 4H) 3.23 (s, 3H) 3.34 (s, 3H) 3.55-3.62 (m, 2H) 3.63 (s, 2H) 3.70 (d, J = 7.79 Hz, 1H) 4.19-4.23 (m, 1H) 4.35-4.40 (m, 1H) 4.42-4.46 (m, 1H) 4.52-4.55 (m, 1H) 4.61-4.66 (m, 1H) 4.96-4.99 (m, 1H) 5.23-5.26 (m, 1H) 6.72-6.74 (m, 1H) 6.82-6.83 (m, 1H) 7.01-7.04 (m, 1H) |
| 327 | | | 1036.8 | mixture of diastereomers (600 MHz): 0.81 (d, J = 6.88 Hz, 6H) 0.89 (t, J = 7.34 Hz, 3H) 1.06-1.26 (m, 17H) 1.28-1.32 (m, 6H) 1.37-1.86 (m, 11H) 2.10-2.46 (m, 9H) 2.28 (s, 6H) 2.35 (s, 3H) 2.53-2.61 (m, 3H) 2.77-2.92 (m, 2H) 3.12-3.61 (m, 7H) 3.22 (s, 3H) 3.33 (s, 3H) 3.65-3.72 (m, 2H) 3.78 (s, 3H) 4.19-4.23 (m, 1H) 4.35-4.41 (m, 1H) 4.41-4.45 (m, 1H) 4.51-4.55 (m, 1H) 4.60-4.67 (m, 1H) 4.96 (d, J = 4.59 Hz, 1H) 5.25-5.32 (m, 1H) 6.77-6.81 (m, 1H) 7.07-7.13 (m, 1H) 7.21-7.24 (m, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 328 | | H | 1038.8 | mixture of diastereomers (600 MHz): 0.81 (d, J = 6.88 Hz, 6H) 0.89 (t, J = 7.34 Hz, 3H) 1.07-1.25 (m, 17H) 1.28-1.32 (m, 6H) 1.50-1.86 (m, 5H) 2.10-2.62 (m, 12H) 2.29 (s, 6H) 2.36 (s, 3H) 2.79-2.84 (m, 1H) 2.86-2.92 (m, 1H) 3.13-3.45 (m, 4H) 3.23 (s, 3H) 3.33 (s, 3H) 3.53 (s, 3H) 3.54-3.60 (m, 1H) 3.66-3.73 (m, 6H) 3.80 (s, 2H) 4.20-4.24 (m, 1H) 4.35-4.40 (m, 1H) 4.42-4.46 (m, 1H) 4.54 (d, J = 10.09 Hz, 1H) 4.60-4.67 (m, 1H) 4.97 (d, J = 5.04 Hz, 1H) 5.23-5.29 (m, 1H) 6.79-6.83 (m, 1H) 7.11-7.14 (m, 1H) 7.20-7.22 (m, 1H), and (600 MHz): 0.81 (d, J = 6.88 Hz, 6H) 0.89 (t, J = 7.34 Hz, 3H) 1.07-1.25 (m, 17H) 1.28-1.32 (m, 6H) 1.50-1.86 (m, 5H) 2.10-2.62 (m, 12H) 2.29 (s, 6H) 2.36 (s, 3H) 2.79-2.84 (m, 1H) 2.86-2.92 (m, 1H) 3.13-3.45 (m, 4H) 3.23 (s, 3H) 3.35 (s, 3H) 3.53 (s, 3H) 3.54-3.60 (m, 1H) 3.66-3.73 (m, 6H) 3.80 (s, 2H) 4.20-4.24 (m, 1H) 4.35-4.40 (m, 1H) 4.42-4.46 (m, 1H) 4.54 (d, J = 10.09 Hz, 1H) 4.60-4.67 (m, 1H) 4.97 (d, J = 5.04 Hz, 1H) 5.23-5.29 (m, 1H) 6.79-6.83 (m, 1H) 7.11-7.14 (m, 1H) 7.20-7.22 (m, 1H) |
| 329 | | H | 1010.8 | mixture of diastereomers (600 MHz): 0.84 (d, J = 6.88 Hz, 6H) 0.92 (t, J = 7.34 Hz, 3H) 1.10-1.27 (m, 17H) 1.31 (d, J = 6.42 Hz, 3H) 1.33 (s, 3H) 1.53-1.90 (m, 5H) 2.13-2.48 (m, 5H) 2.32 (s, 6H) 2.38 (s, 3H) 2.55-2.66 (m, 3H) 2.80-2.86 (m, 1H) 2.88-2.93 (m, 1H) 3.00 (s, 3H) 3.10 (s, 3H) 3.17-3.49 (m, 4H) 3.26 (s, 3H) 3.36 (s, 3H) 3.57-3.64 (m, 1H) 3.68-3.74 (m, 2H) 4.22-4.25 (m, 1H) 4.37-4.42 (m, 1H) 4.45-4.49 (m, 1H) 4.54-4.58 (m, 1H) 4.64-4.69 (m, 3H) 4.99 (d, J = 4.58 Hz, 1H) 5.23-5.28 (m, 1H) 6.88-6.92 (m, 2H) 7.17-7.22 (m, 2H), and (600 MHz): 0.84 (d, J = 6.88 Hz, 6H) 0.92 (t, J= 7.34 Hz, 3H) 1.10-1.27 (m, 17H) 1.31 (d, J = 6.88 Hz, 3H) 1.33 (s, 3H) 1.53-1.90 (m, 5H) 2.13-2.48 (m, 5H) 2.32 (s, 6H) 2.38 (s, 3H) 2.55-2.66 (m, 3H) 2.80-2.86 (m, 1H) 2.88-2.93 (m, 1H) 3.00 (s, 3H) 3.10 (s, 3H) 3.17-3.49 (m, 4H) 3.26 (s, 3H) 3.36 (s, 3H) 3.57-3.64 (m, 1H) 3.68-3.74 (m, 2H) 4.22-4.25 (m, 1H) 4.37-4.42 (m, 1H) 4.45-4.49 (m, 1H) 4.54-4.58 (m, 1H) 4.64-4.69 (m, 3H) 4.99 (d, J = 4.58 Hz, 1H) 5.23-5.28 (m, 1H) 6.88-6.92 (m, 2H) 7.17-7.22 (m, 2H) |
| 330 | | H | 1052.7 | mixture of diastereomers (600 MHz): 0.82 (d, J = 6.88 Hz, 6H) 0.89 (t, J = 7.34 Hz, 3H) 1.07-1.25 (m, 17H) 1.30 (s, 6H) 1.49-1.88 (m, 5H) 2.10-2.46 (m, 5H) 2.30 (s, 6H) 2.36 (s, 3H) 2.51-2.62 (m, 3H) 2.78-2.83 (m, 1H) 2.86-2.91 (m, 1H) 3.15-3.46 (m, 4H) 3.23 (s, 3H) 3.34 (s, 3H) 3.55-3.72 (m, 11H) 4.18-4.23 (m, 1H) 4.34-4.41 (m, 1H) 4.42-4.47 (m, 1H) 4.51-4.55 (m, 1H) 4.61-4.67 (m, 3H) 4.97 (d, J = 4.13 Hz, 1H) 5.20-5.25 (m, 1H) 6.85-6.90 (m, 2H) 7.17-7.20 (m, 2H) |

TABLE 11-continued formula (W)

| Example | R[1W] | R[2W] | ESI MS (M + H) | $^1$H-NMR, CDCl$_3$, δ (ppm) |
|---|---|---|---|---|
| 331 | | H | 1007.8 | mixture of diastereomers (600 MHz): 0.82 (d, J = 5.96 Hz, 6H) 0.89 (t, J = 7.34 Hz, 3H) 1.07-1.25 (m, 17H) 1.28-1.31 (m, 6H) 1.50-1.88 (m, 5H) 2.12-2.47 (m, 5H) 2.30 (s, 6H) 2.34 (s, 3H) 2.35 (s, 3H) 2.53-2.63 (m, 7H) 2.78-2.84 (m, 1H) 2.86-2.91 (m, 1H) 3.14-3.52 (m, 14H) 3.56-3.62 (m, 1H) 3.63-3.69 (m, 1H) 3.71 (d, J = 8.25 Hz, 1H) 4.18-4.22 (m, 1H) 4.34-4.40 (m, 1H) 4.43-4.48 (m, 1H) 4.53 (d, J = 10.55 Hz, 1H) 4.62-4.67 (m, 1H) 4.95-4.98 (m, 1H) 5.21-5.26 (m, 1H) 6.87 (d, J = 8.71 Hz, 2H) 7.14 (d, J = 8.25 Hz, 2H) |
| 332 | | H | 1038.8 | mixture of diastereomers (600 MHz): 0.81 (d, J = 6.88 Hz, 6H) 0.89 (t, J = 7.34 Hz, 3H) 0.93-1.01 (m, 3H) 1.05-1.25 (m, 23H) 1.27-1.33 (m, 6H) 1.50-1.88 (m, 5H) 2.11-2.66 (m, 14H) 2.28 (s, 6H) 2.36 (s, 3H) 2.79-2.83 (m, 1H) 2.85-2.92 (m, 1H) 3.15-3.79 (m, 9H) 3.23 (s, 3H) 3.35 (s, 3H) 4.20-4.25 (m, 1H) 4.36-4.42 (m, 1H) 4.44-4.48 (m, 1H) 4.52-4.56 (m, 1H) 4.61-4.66 (m, 1H) 4.97 (d, J = 5.04 Hz, 1H) 5.22-5.25 (m, 1H) 6.72 (d, J = 8.25 Hz, 1H) 6.84 (br. s., 1H) 7.05 (d, J = 8.25 Hz, 1H) |
| 333 | | H | 1050.9 | mixture of diastereomers (600 MHz): 0.84 (d, J = 6.88 Hz, 6H) 0.92 (t, J = 7.34 Hz, 3H) 0.95-1.05 (m, 3H) 1.10-1.28 (m, 17H) 1.29-1.35 (m, 6H) 1.49-1.91 (m, 11H) 2.14-2.65 (m, 14H) 2.31 (s, 6H) 2.38 (s, 3H) 2.81-2.87 (m, 1H) 2.88-2.95 (m, 1H) 3.17-3.50 (m, 4H) 3.25 (s, 3H) 3.37 (s, 3H) 3.59-3.82 (m, 5H) 4.23-4.27 (m, 1H) 4.40-4.45 (m, 1H) 4.47-4.51 (m, 1H) 4.54-4.60 (m, 1H) 4.64-4.69 (m, 1H) 5.00 (d, J = 4.59 Hz, 1H) 5.24-5.27 (m, 1H) 6.74-6.76 (m, 1H) 6.84-6.87 (m, 1H) 7.06-7.10 (m, 1H) |
| 334 | | H | 1064.9 | mixture of diastereomers (600 MHz): 0.81 (d, J = 6.88 Hz, 6H) 0.89 (t, J = 7.34 Hz, 3H) 0.95-1.01 (m, 3H) 1.07-1.25 (m, 17H) 1.28-1.34 (m, 6H) 1.37-1.87 (m, 11H) 2.10-2.64 (m, 14H) 2.27 (s, 6H) 2.36 (s, 3H) 2.78-2.83 (m, 1H) 2.86-2.92 (m, 1H) 3.15-3.24 (m, 3H) 3.23 (s, 3H) 3.33 (s, 3H) 3.36-3.61 (m, 4H) 3.71 (d, J = 8.25 Hz, 1H) 3.77-3.86 (m, 4H) 4.21-4.26 (m, 1H) 4.37-4.47 (m, 2H) 4.53-4.57 (m, 1H) 4.61-4.67 (m, 1H) 4.97 (d, J = 5.04 Hz, 1H) 5.31-5.38 (m, 1H) 6.78 (d, J = 8.25 Hz, 1H) 7.08-7.13 (m, 1H) 7.26-7.29 (m, 1H) |
| 335 | | H | 1066.9 | mixture of diastereomers (600 MHz): 0.81 (d, J = 6.88 Hz, 6H) 0.89 (t, J = 7.34 Hz, 3H) 0.95-1.01 (m, 3H) 1.07-1.25 (m, 17H) 1.28-1.35 (m, 6H) 1.50-1.87 (m, 5H) 2.10-2.51 (m, 11H) 2.28 (s, 6H) 2.36 (s, 3H) 2.53-2.64 (m, 3H) 2.78-2.84 (m, 1H) 2.86-2.91 (m, 1H) 3.16-3.24 (m, 3H) 3.23 (s, 3H) 3.33 (s, 3H) 3.35-3.45 (m, 1H) 3.52-3.60 (m, 1H) 3.54 (s, 2H) 3.67-3.73 (m, 5H) 3.77-3.85 (m, 4H) 4.21-4.27 (m, 1H) 4.36-4.47 (m, 2H) 4.53-4.56 (m, 1H) 4.61-4.66 (m, 1H) 4.97 (d, J = 4.59 Hz, 1H) 5.27-5.33 (m, 1H) 6.80 (d, J = 8.25 Hz, 1H) 7.11-7.16 (m, 1H) 7.23-7.26 (m, 1H) |

TABLE 11-continued formula (W)

| Example | $R^{1W}$ | $R^{2W}$ | ESI MS (M + H) | $^1$H-NMR, CDCl$_3$, δ (ppm) |
|---|---|---|---|---|
| 336 | | -H | 1038.8 | mixture of diastereomers (600 MHz): 0.82 (d, J = 6.42 Hz, 6H) 0.89 (t, J = 7.34 Hz, 3H) 0.94-1.01 (m, 3H) 1.07-1.26 (m, 17H) 1.28-1.33 (m, 6H) 1.50-1.88 (m, 5H) 2.12-2.47 (m, 7H) 2.28 (s, 6H) 2.36 (s, 3H) 2.51-2.62 (m, 3H) 2.77-2.92 (m, 2H) 2.98 (s, 3H) 3.08 (s, 3H) 3.16-3.23 (m, 3H) 3.23 (s, 3H) 3.34 (s, 3H) 3.37-3.45 (m, 1H) 3.56-3.64 (m, 1H) 3.71 (d, J = 8.25 Hz, 1H) 3.76-3.84 (m, 1H) 4.19-4.24 (m, 1H) 4.36-4.42 (m, 1H) 4.44-4.48 (m, 1H) 4.52-4.55 (m, 1H) 4.62-4.65 (m, 1H) 4.65 (s, 2H) 4.95-4.99 (m, 1H) 5.19-5.24 (m, 1H) 6.87 (d, J = 8.25 Hz, 2H) 7.19 (d, J = 8.25 Hz, 2H) |
| 337 | | -H | 1080.9 | mixture of diastereomers (600 MHz): 0.77 (d, J = 6.88 Hz, 6H) 0.85 (t, J = 7.34 Hz, 3H) 0.89-0.96 (m, 3H) 1.03-1.21 (m, 17H) 1.24-1.28 (m, 6H) 1.45-1.83 (m, 5H) 2.09-2.43 (m, 7H) 2.24 (s, 6H) 2.31 (s, 3H) 2.47-2.57 (m, 3H) 2.74-2.79 (m, 1H) 2.82-2.86 (m, 1H) 3.13-3.18 (m, 3H) 3.19 (s, 3H) 3.30 (s, 3H) 3.33-3.40 (m, 1H) 3.53-3.63 (m, 9H) 3.67 (d, J = 7.79 Hz, 1H) 3.72-3.80 (m, 1H) 4.16-4.20 (m, 1H) 4.32-4.37 (m, 1H) 4.40-4.43 (m, 1H) 4.48-4.51 (m, 1H) 4.57-4.63 (m, 3H) 4.92-4.94 (m, 1H) 5.15-5.19 (m, 1H) 6.82 (d, J = 8.25 Hz, 2H) 7.16 (d, J= 8.25 Hz, 2H) |
| 338 | | -H | 1035.9 | mixture of diastereomers (600 MHz): 0.77 (d, J = 6.88 Hz, 6H) 0.85 (t, J = 7.34 Hz, 3H) 0.89-0.96 (m, 3H) 1.03-1.21 (m, 17H) 1.24-1.28 (m, 6H) 1.45-1.83 (m, 5H) 2.09-2.43 (m, 7H) 2.24 (s, 6H) 2.31 (s, 3H) 2.47-2.57 (m, 3H) 2.74-2.79 (m, 1H) 2.82-2.86 (m, 1H) 3.13-3.18 (m, 3H) 3.19 (s, 3H) 3.30 (s, 3H) 3.33-3.40 (m, 1H) 3.53-3.63 (m, 9H) 3.67 (d, J = 7.79 Hz, 1H) 3.72-3.80 (m, 1H) 4.16-4.20 (m, 1H) 4.32-4.37 (m, 1H) 4.40-4.43 (m, 1H) 4.48-4.51 (m, 1H) 4.57-4.63 (m, 3H) 4.92-4.94 (m, 1H) 5.15-5.19 (m, 1H) 6.82 (d, J = 8.25 Hz, 2H) 7.16 (d, J = 8.25 Hz, 2H) |

TABLE 11-continued formula (W)

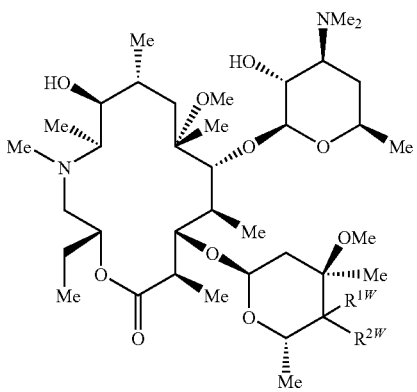

| Example | $R^{1W}$ | $R^{2W}$ | ESI MS (M + H) | $^1$H-NMR, CDCl$_3$, δ (ppm) |
|---|---|---|---|---|
| 339 | 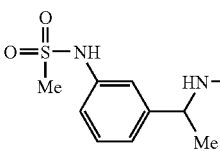 |  | 1002.7 | mixture of diastereomers (600 MHz): 0.81 (d, J = 6.88 Hz, 6H) 0.89 (t, J = 7.34 Hz, 3H) 1.06-1.26 (m, 2H) 1.09-1.19 (m, 15H) 1.28-1.35 (m, 6H) 1.50-1.58 (m, 1H) 1.57-1.63 (m, 1H) 1.68-1.80 (m, 2H) 1.83 (s, 1H) 2.09-2.19 (m, 1H) 2.21-2.45 (m, 4H) 2.32 (s, 6H) 2.36 (s, 3H) 2.49-2.59 (m, 1H) 2.59-2.72 (m, 2H) 2.76-2.84 (m, 1H) 2.89 (d, J = 14.21 Hz, 1H) 3.00 (s, 3H) 3.15-3.28 (m, 3H) 3.22 (s, 3H) 3.33 (s, 3H) 3.35-3.47 (m, 3H) 3.57 (s, 1H) 3.70 (d, J = 7.79 Hz, 1H) 3.74 (q, J = 6.72 Hz, 1H) 4.17-4.26 (m, 1H) 4.34-4.41 (m, 1H) 4.42-4.47 (m, 1H) 4.50-4.55 (m, 1H) 4.63 (s, 1H) 4.94-4.99 (m, 1H) 5.19-5.26 (m, 1H) 7.06-7.14 (m, 2H) 7.18 (s, 1H) 7.26-7.31 (m, 1H), and (600 MHz): 0.81 (d, J = 6.88 Hz, 6H) 0.89 (t, J = 7.34 Hz, 3H) 1.06-1.26 (m, 2H) 1.09-1.19 (m, 15H) 1.28-1.35 (m, 6H) 1.50-1.58 (m, 1H) 1.57-1.63 (m, 1H) 1.68-1.80 (m, 2H) 1.83 (s, 1H) 2.09-2.19 (m, 1H) 2.21-2.45 (m, 4H) 2.32 (s, 6H) 2.36 (s, 3H) 2.49-2.59 (m, 1H) 2.59-2.72 (m, 2H) 2.76-2.84 (m, 1H) 2.89 (d, J = 14.21 Hz, 1H) 3.01 (s, 3H) 3.15-3.28 (m, 3H) 3.22 (s, 3H) 3.33 (s, 3H) 3.35-3.47 (m, 1H) 3.57 (s, 1H) 3.70 (d, J = 7.79 Hz, 1H) 3.74 (q, J = 6.72 Hz, 1H) 4.17-4.26 (m, 1H) 4.34-4.41 (m, 1H) 4.42-4.47 (m, 1H) 4.50-4.55 (m, 1H) 4.63 (s, 1H) 4.94-4.99 (m, 1H) 5.25-5.31 (m, 1H) 7.06-7.14 (m, 2H) 7.18 (s, 1H) 7.26-7.31 (m, 1H) |
| 340 | 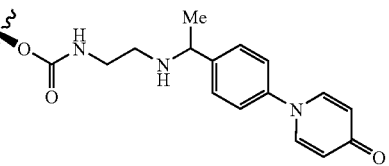 |  | 1002.7 | mixture of diastereomers (600 MHz): 0.79 (d, J = 6.88 Hz, 6H) 0.87 (t, J = 7.34 Hz, 3H) 1.04-1.24 (m, 2H) 1.07-1.19 (m, 15H) 1.28 (s, 3H) 1.29-1.34 (m, 3H) 1.48-1.56 (m, 1H) 1.56-1.61 (m, 1H) 1.60-1.87 (m, 3H) 2.07-2.18 (m, 1H) 2.19-2.45 (m, 4H) 2.30 (s, 6H) 2.34 (s, 3H) 2.49-2.67 (m, 3H) 2.75-2.82 (m, 1H) 2.83-2.90 (m, 1H) 3.13-3.45 (m, 4H) 3.20 (s, 3H) 3.31 (s, 3H) 3.50-3.59 (m, 1H) 3.68 (d, J = 8.25 Hz, 1H) 3.77-3.85 (m, 1H) 4.20 (s, 1H) 4.32-4.39 (m, 1H) 4.39-4.44 (m, 1H) 4.50-4.54 (m, 1H) 4.60 (s, 1H) 4.95 (d, J = 5.04 Hz, 1H) 5.16-5.23 (m, 1H) 6.47 (d, J = 7.79 Hz, 2H) 7.24-7.28 (m, 2H) 7.39-7.45 (m, 2H) 7.54 (d, J = 7.79 Hz, 2H), and (600 MHz): 0.79 (d, J = 6.88 Hz, 6H) 0.87 (t, J = 7.34 Hz, 3H) 1.04-1.24 (m, 2H) 1.07-1.19 (m, 15H) 1.28 (s, 3H) 1.29-1.34 (m, 3H) 1.48-1.56 (m, 1H) 1.56-1.61 (m, 1H) 1.60-1.87 (m, 3H) 2.07-2.18 (m, 1H) 2.19-2.45 (m, 4H) 2.30 (s, 6H) 2.34 (s, 3H) 2.49-2.67 (m, 3H) 2.75-2.82 (m, 1H) 2.83-2.90 (m, 1H) 3.13-3.45 (m, 4H) 3.20 (s, 3H) 3.32 (s, 3H) 3.50-3.59 (m, 1H) 3.68 (d, J = 8.25 Hz, 1H) 3.77-3.85 (m, 1H) 4.20 (s, 1H) 4.32-4.39 (m, 1H) 4.39-4.44 (m, 1H) 4.50-4.54 (m, 1H) 4.60 (s, 1H) 4.95 (d, J = 5.04 Hz, 1H) 5.16-5.23 (m, 1H) 6.47 (d, J = 7.79 Hz, 2H) 7.24-7.28 (m, 2H) 7.39-7.45 (m, 2H) 7.54 (d, J = 7.79 Hz, 2H) |

TABLE 11-continued formula (W)

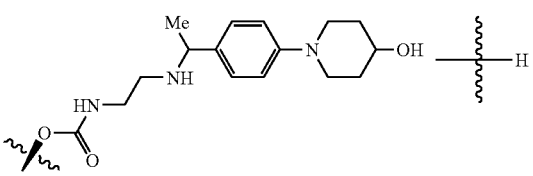

| Example | $R^{1W}$ | $R^{2W}$ | ESI MS (M + H) | $^1$H-NMR, CDCl$_3$, δ (ppm) |
|---|---|---|---|---|
| 341 | 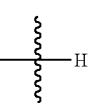 | H | 1008.8 | mixture of diastereomers (500 MHz): 0.81 (d, J = 6.88 Hz, 6H) 0.88 (t, J = 7.45 Hz, 3H) 1.04-1.26 (m, 2H) 1.07-1.21 (m, 15H) 1.27-1.34 (m, 6H) 1.47-1.79 (m, 6H) 1.79-1.89 (m, 1H) 1.92-2.03 (m, 2H) 2.08-2.47 (m, 5H) 2.31 (s, 6H) 2.35 (s, 3H) 2.52-2.68 (m, 3H) 2.75-2.83 (m, 1H) 2.83-2.92 (m, 3H) 3.12-3.45 (m, 4H) 3.22 (s, 3H) 3.32 (s, 3H) 3.47-3.55 (m, 2H) 3.54-3.62 (m, 1H) 3.63-3.72 (m, 2H) 3.76-3.85 (m, 1H) 4.17 (s, 1H) 4.31-4.40 (m, 1H) 4.41-4.47 (m, 1H) 4.48-4.53 (m, 1H) 4.63 (s, 1H) 4.95 (d, J = 4.59 Hz, 1H) 5.36-5.45 (m, 1H) 6.86 (d, J = 8.79 Hz, 2H) 7.13 (d, J = 8.79 Hz, 2H) |
| 342 | 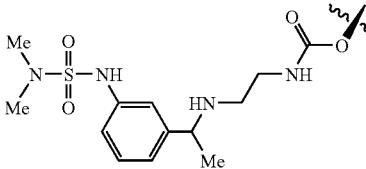 | H | 1031.7 | mixture of diastereomers (500 MHz): 0.82 (d, J = 7.20 Hz, 6H) 0.90 (t, J = 7.20 Hz, 3H) 1.06-1.23 (m, 17H) 1.28-1.33 (m, 6H) 1.48-1.66 (m, 3H) 1.69-1.79 (m, 1H) 1.80-1.89 (m, 1H) 2.10-2.20 (m, 1H) 2.22-2.46 (m, 4H) 2.31 (s, 6H) 2.36 (s, 3H) 2.48-2.70 (m, 3H) 2.77-2.94 (m, 2H) 2.83 (s, 6H) 3.12-3.48 (m, 4H) 3.22 (s, 3H) 3.32 (s, 3H) 3.52-3.63 (m, 1H) 3.67-3.76 (m, 2H) 4.13-4.28 (m, 1H) 4.33-4.49 (m, 2H) 4.50-4.56 (m, 1H) 4.59-4.68 (m, 1H) 4.94-4.99 (m, 1H) 5.22-5.31 (m, 1H) 6.98-7.27 (m, 4H), and (500 MHz): 0.82 (d, J = 7.20 Hz, 6H) 0.90 (t, J = 7.20 Hz, 3H) 1.06-1.23 (m, 17H) 1.28-1.33 (m, 6H) 1.48-1.66 (m, 3H) 1.69-1.79 (m, 1H) 1.80-1.89 (m, 1H) 2.10-2.20 (m, 1H) 2.22-2.46 (m, 4H) 2.31 (s, 6H) 2.36 (s, 3H) 2.48-2.70 (m, 3H) 2.77-2.94 (m, 2H) 2.84 (s, 6H) 3.12-3.48 (m, 4H) 3.22 (s, 3H) 3.34 (s, 3H) 3.52-3.63 (m, 1H) 3.67-3.76 (m, 2H) 4.13-4.28 (m, 1H) 4.33-4.49 (m, 2H) 4.50-4.56 (m, 1H) 4.59-4.68 (m, 1H) 4.94-4.99 (m, 1H) 5.22-5.31 (m, 1H) 6.98-7.27 (m, 4H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 343 | [structure: MeSO₂NH-phenyl-CH(Me)-N(Et)-CH₂CH₂-NH-C(=O)-O-] | H | 1030.7 | mixture of diastereomers (500 MHz): 0.81 (d, J = 6.88 Hz, 6H) 0.90 (t, J = 7.26 Hz, 3H) 0.95-1.03 (m, 3H) 1.05-1.27 (m, 2H) 1.10-1.19 (m, 15H) 1.29-1.34 (m, 6H) 1.50-1.58 (m, 1H) 1.57-1.64 (m, 1H) 1.64-1.90 (m, 3H) 2.10-2.20 (m, 1H) 2.21-2.45 (m, 4H) 2.33 (s, 6H) 2.36 (s, 3H) 2.44-2.65 (m, 4H) 2.66-2.76 (m, 1H) 2.76-2.85 (m, 1H) 2.90 (d, J = 14.91 Hz, 1H) 3.00 (s, 3H) 3.05-3.44 (m, 4H) 3.22 (s, 3H) 3.34 (s, 3H) 3.53-3.62 (m, 1H) 3.70 (d, J = 8.03 Hz, 1H) 3.84 (q, J = 6.75 Hz, 1H) 4.24 (s, 1H) 4.36-4.45 (m, 1H) 4.47 (d, J = 7.26 Hz, 1H) 4.50-4.56 (m, 1H) 4.62 (s, 1H) 4.96 (d, J = 4.59 Hz, 1H) 5.20-5.26 (m, 1H) 7.09 (d, J = 7.26 Hz, 1H) 7.15 (t, J = 7.26 Hz, 1H) 7.26 (t, J = 7.45 Hz, 1H) 7.32 (d, J = 13.00 Hz, 1H), and (500 MHz): 0.81 (d, J = 6.88 Hz, 6H) 0.90 (t, J = 7.26 Hz, 3H) 0.95-1.03 (m, 3H) 1.05-1.27 (m, 2H) 1.10-1.19 (m, 15H) 1.29-1.34 (m, 6H) 1.50-1.58 (m, 1H) 1.57-1.64 (m, 1H) 1.64-1.90 (m, 3H) 2.10-2.20 (m, 1H) 2.21-2.45 (m, 4H) 2.33 (s, 6H) 2.36 (s, 3H) 2.44-2.65 (m, 4H) 2.66-2.76 (m, 1H) 2.76-2.85 (m, 1H) 2.90 (d, J = 14.91 Hz, 1H) 3.00 (s, 3H) 3.13-3.42 (m, 4H) 3.22 (s, 3H) 3.34 (s, 3H) 3.53-3.62 (m, 1H) 3.70 (d, J = 8.03 Hz, 1H) 3.84 (q, J = 6.75 Hz, 1H) 4.24 (s, 1H) 4.36-4.45 (m, 1H) 4.47 (d, J = 7.26 Hz, 1H) 4.50-4.56 (m, 1H) 4.62 (s, 1H) 4.96 (d, J = 4.59 Hz, 1H) 5.25-5.31 (m, 1H) 7.09 (d, J = 7.26 Hz, 1H) 7.15 (t, J = 7.26 Hz, 1H) 7.26 (t, J = 7.45 Hz, 1H) 7.32 (d, J = 13.00 Hz, 1H) |
| 344 | [structure: -O-C(=O)-NH-CH₂CH₂-N(Et)-CH(Me)-phenyl-N(pyridinone)] | H | 1030.8 | mixture of diastereomers (500 MHz): 0.81 (d, J = 6.88 Hz, 6H) 0.89 (t, J = 7.45 Hz, 3H) 0.95-1.05 (m, 3H) 1.06-1.27 (m, 2H) 1.10 (s, 3H) 1.12 (d, J = 6.50 Hz, 3H) 1.14-1.21 (m, 9H) 1.29 (s, 3H) 1.36 (d, J = 4.97 Hz, 3H) 1.49-1.63 (m, 2H) 1.63-1.70 (m, 1H) 1.70-1.79 (m, 1H) 1.79-1.89 (m, 1H) 2.11-2.20 (m, 1H) 2.20-2.68 (m, 9H) 2.31 (s, 6H) 2.35 (s, 3H) 2.76-2.84 (m, 1H) 2.88 (d, (m, 9H) 2.31 (s, 6H) 2.35 (s, 3H) 2.76-2.84 (m, 1H) 2.88 (d, J = 15.29 Hz, 1H) 3.19-3.27 (m, 3H) 3.21 (s, 3H) 3.31 (s, 3H) 3.33-3.40 (m, 1H) 3.53-3.61 (m, 1H) 3.69 (d, J = 8.03 Hz, 1H) 3.90-3.96 (m, 1H) 4.21 (s, 1H) 4.33-4.42 (m, 1H) 4.44 (d, J = 6.50 Hz, 1H) 4.52 (d, J = 9.94 Hz, 1H) 4.62 (s, 1H) 4.96 (d, J = 4.20 Hz, 1H) 5.17-5.28 (m, 1H) 6.49 (d, J = 7.64 Hz, 2H) 7.23-7.30 (m, 2H) 7.47 (d, J = 8.79 Hz, 2H) 7.58 (d, J = 7.65 Hz, 2H), and (500 MHz): 0.81 (d, J = 6.88 Hz, 6H) 0.89 (t, J = 7.45 Hz, 3H) 0.95-1.05 (m, 3H) 1.06-1.27 (m, 2H) 1.10 (s, 3H) 1.12 (d, J = 6.50 Hz, 3H) 1.14-1.21 (m, 9H) 1.29 (s, 3H) 1.36 (d, J = 4.97 Hz, 3H) 1.49-1.63 (m, 2H) 1.63-1.70 (m, 1H) 1.70-1.79 (m, 1H) 1.79-1.89 (m, 1H) 2.11-2.20 (m, 1H) 2.20-2.68 (m, 9H) 2.31 (s, 6H) 2.35 (s, 3H) 2.76-2.84 (m, 1H) 2.88 (d, J = 15.29 Hz, 1H) 3.19-3.27 (m, 3H) 3.21 (s, 3H) 3.32 (s, 3H) 3.33-3.40 (m, 1H) 3.53-3.61 (m, 1H) 3.69 (d, J = 8.03 Hz, 1H) 3.86-3.91 (m, 1H) 4.21 (s, 1H) 4.33-4.42 (m, 1H) 4.44 (d, J = 6.50 Hz, 1H) 4.53 (d, J = 9.56 Hz, 1H) 4.62 (s, 1H) 4.96 (d, J = 4.20 Hz, 1H) 5.17-5.28 (m, 1H) 6.49 (d, J = 7.64 Hz, 2H) 7.23-7.30 (m, 2H) 7.46 (d, J = 8.41 Hz, 2H) 7.58 (d, J = 7.65 Hz, 2H) |

TABLE 11-continued formula (W)

| Example | R[1W] | R[2W] | ESI MS (M + H) | $^1$H-NMR, CDCl$_3$, δ (ppm) |
|---|---|---|---|---|
| 345 | (structure with carbamate-NH-CH$_2$CH$_2$-N(Et)-CH(Me)-phenyl-N-piperidinyl-OH) | H | 1036.8 | mixture of diastereomers (500 MHz): 0.81 (d, J = 6.50 Hz, 6H) 0.89 (t, J = 7.26 Hz, 3H) 0.94-1.02 (m, 3H) 1.07-1.26 (m, 2H) 1.10-1.21 (m, 15H) 1.26-1.35 (m, 6H) 1.46-1.79 (m, 6H) 1.79-1.90 (m, 1H) 1.93-2.02 (m, 2H) 2.11-2.20 (m, 1H) 2.21-2.49 (m, 6H) 2.28-2.31 (m, 6H) 2.35 (s, 3H) 2.51-2.66 (m, 3H) 2.76-2.84 (m, 1H) 2.84-2.92 (m, 3H) 3.14-3.26 (m, 3H) 3.22 (s, 3H) 3.33 (s, 3H) 3.34-3.42 (m, 1H) 3.48-3.56 (m, 2H) 3.55-3.64 (m, 1H) 3.70 (d, J = 7.64 Hz, 1H) 3.74-3.86 (m, 2H) 4.19 (s, 1H) 4.33-4.41 (m, 1H) 4.43-4.49 (m, 1H) 4.52 (d, J = 9.56 Hz, 1H) 4.64 (s, 1H) 4.96 (d, J = 4.59 Hz, 1H) 5.33 (s, 1H) 6.86 (d, J = 8.41 Hz, 2H) 7.14 (d, J = 8.41 Hz, 2H) |
| 346 | (structure with pyridyl-aziridinyl-phenyl-CH(Me)-NH-CH$_2$CH$_2$-NH-carbamate) | H | 1027.8 | mixture of diastereomers (500 MHz): 0.82 (d, J = 6.88 Hz, 6H) 0.90 (t, J = 7.45 Hz, 3H) 1.06-1.26 (m, 17H) 1.27-1.32 (m, 6H) 1.48-1.90 (m, 5H) 2.11-2.20 (m, 1H) 2.22-2.47 (m, 5H) 2.29 (s, 6H) 2.36 (s, 3H) 2.49-2.65 (m, 4H) 2.77-2.85 (m, 1H) 2.89 (d, J = 14.91 Hz, 1H) 3.02-3.06 (m, 1H) 3.14-3.45 (m, 4H) 3.23 (s, 3H) 3.34 (s, 3H) 3.53-3.63 (m, 1H) 3.66-3.73 (m, 2H) 4.21 (s, 1H) 4.34-4.41 (m, 1H) 4.42-4.47 (m, 1H) 4.50-4.57 (m, 1H) 4.64 (s, 1H) 4.97 (d, J = 4.59 Hz, 1H) 5.21-5.28 (m, 1H) 6.95 (d, J = 8.41 Hz, 2H) 7.16 (d, J = 8.41 Hz, 2H) 7.29 (d, J = 6.12 Hz, 2H) 8.56 (d, J = 5.73 Hz, 2H) |
| 347 | (structure with Me$_2$N-SO$_2$-NH-phenyl-CH(Me)-N(Et)-CH$_2$CH$_2$-NH-carbamate) | H | 1059.8 | mixture of diastereomers (500 MHz): 0.81 (d, J = 6.88 Hz, 6H) 0.89 (t, J = 7.45 Hz, 3H) 0.94-1.03 (m, 3H) 1.04-1.26 (m, 2H) 1.11-1.19 (m, 15H) 1.26-1.34 (m, 6H) 1.48-1.69 (m, 3H) 1.69-1.79 (m, 1H) 1.78-1.87 (m, 1H) 2.09-2.19 (m, 1H) 2.21-2.71 (m, 9H) 2.30 (s, 6H) 2.36 (s, 3H) 2.77-2.85 (m, 1H) 2.82 (s, 6H) 2.88 (d, J = 15.29 Hz, 1H) 3.04-3.40 (m, 4H) 3.21 (s, 3H) 3.32 (s, 3H) 3.54-3.61 (m, 1H) 3.71 (d, J = 8.41 Hz, 1H) 3.77-3.87 (m, 1H) 4.26 (s, 1H) 4.38-4.50 (m, 2H) 4.50-4.56 (m, 1H) 4.62 (s, 1H) 4.96 (d, J = 4.20 Hz, 1H) 5.28-5.35 (m, 1H) 6.98-7.11 (m, 2H) 7.18-7.25 (m, 1H) 7.29 (d, J = 14.14 Hz, 1H), and (500 MHz): 0.81 (d, J = 6.88 Hz, 6H) 0.89 (t, J = 7.45 Hz, 3H) 0.94-1.03 (m, 3H) 1.04-1.26 (m, 2H) 1.11-1.19 (m, 15H) 1.26-1.34 (m, 6H) 1.48-1.69 (m, 3H) 1.69-1.79 (m, 1H) 1.78-1.87 (m, 1H) 2.09-2.19 (m, 1H) 2.21-2.71 (m, 9H) 2.30 (s, 6H) 2.36 (s, 3H) 2.77-2.85 (m, 1H) 2.82 (s, 6H) 2.88 (d, J = 15.29 Hz, 1H) 3.10-3.42 (m, 4H) 3.21 (s, 3H) 3.33 (s, 3H) 3.54-3.61 (m, 1H) 3.71 (d, J = 8.41 Hz, 1H) 3.77-3.87 (m, 1H) 4.26 (s, 1H) 4.38-4.50 (m, 2H) 4.50-4.56 (m, 1H) 4.62 (s, 1H) 4.96 (d, J = 4.20 Hz, 1H) 5.22-5.28 (m, 1H) 6.98-7.11 (m, 2H) 7.18-7.25 (m, 1H) 7.29 (d, J = 14.14 Hz, 1H) |

TABLE 11-continued formula (W)

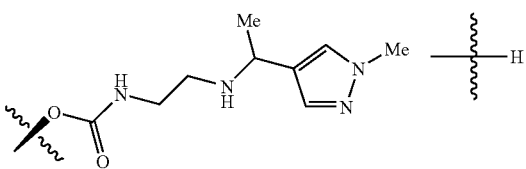

| Example | R$^{1W}$ | R$^{2W}$ | ESI MS (M + H) | $^1$H-NMR, CDCl$_3$, δ (ppm) |
|---|---|---|---|---|
| 348 | 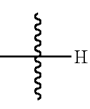 | 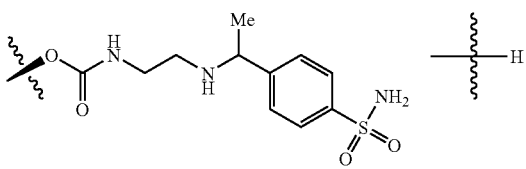 | 913.7 | mixture of diastereomers (600 MHz): 0.82 (d, J = 6.88 Hz, 6H) 0.90 (t, J = 7.34 Hz, 3H) 1.09-1.26 (m, 17H) 1.31 (s, 3H) 1.34 (d, J = 6.88 Hz, 3H) 1.51-1.88 (m, 5H) 2.13-2.46 (m, 5H) 2.30 (s, 6H) 2.37 (s, 3H) 2.55-2.61 (m, 1H) 2.66-2.70 (m, 2H) 2.79-2.84 (m, 1H) 2.87-2.92 (m, 1H) 3.18-3.36 (m, 6H) 3.23 (s, 3H) 3.37-3.42 (m, 1H) 3.54-3.62 (m, 1H) 3.71 (d, J = 8.25 Hz, 1H) 3.74-3.79 (m, 1H) 3.86 (s, 3H) 4.19-4.24 (m, 1H) 4.35-4.41 (m, 1H) 4.42-4.46 (m, 1H) 4.54 (d, J = 9.63 Hz, 1H) 4.62-4.67 (m, 1H) 4.98 (d, J = 4.58 Hz, 1H) 5.26-5.30 (m, 1H) 7.24 (s, 1H) 7.37 (s, 1H), and (600 MHz): 0.82 (d, J = 6.88 Hz, 6H) 0.90 (t, J = 7.34 Hz, 3H) 1.09-1.26 (m, 17H) 1.31 (s, 3H) 1.33 (d, J = 6.88 Hz, 3H) 1.51-1.88 (m, 5H) 2.13-2.46 (m, 5H) 2.30 (s, 6H) 2.37 (s, 3H) 2.55-2.61 (m, 1H) 2.66-2.70 (m, 2H) 2.79-2.84 (m, 1H) 2.87-2.92 (m, 1H) 3.18-3.36 (m, 6H) 3.23 (s, 3H) 3.37-3.42 (m, 1H) 3.54-3.62 (m, 1H) 3.71 (d, J = 8.25 Hz, 1H) 3.74-3.79 (m, 1H) 3.86 (s, 3H) 4.19-4.24 (m, 1H) 4.35-4.41 (m, 1H) 4.42-4.46 (m, 1H) 4.54 (d, J = 9.63 Hz, 1H) 4.62-4.67 (m, 1H) 4.98 (d, J = 4.58 Hz, 1H) 5.26-5.30 (m, 1H) 7.24 (s, 1H) 7.37 (s, 1H) |
| 349 | 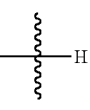 | 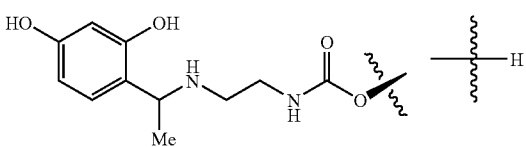 | 988.7 | mixture of diastereomers (600 MHz): 0.82 (d, J = 6.88 Hz, 6H) 0.90 (t, J = 7.34 Hz, 3H) 1.04 (d, J = 5.96 Hz, 3H) 1.07-1.26 (m, 14H) 1.30-1.34 (m, 6H) 1.51-1.88 (m, 5H) 2.10-2.84 (m, 18H) 2.87-2.93 (m, 1H) 3.18-3.34 (m, 9H) 3.37-3.44 (m, 1H) 3.53-3.61 (m, 1H) 3.68-3.72 (m, 1H) 3.81-3.86 (m, 1H) 4.19-4.22 (m, 1H) 4.34-4.46 (m, 2H) 4.52-4.56 (m, 1H) 4.61-4.67 (m, 1H) 4.94-4.99 (m, 1H) 5.32-5.41 (m, 1H) 7.44 (d, J = 8.25 Hz, 2H) 7.83-7.87 (m, 2H), and (600 MHz): 0.82 (d, J = 6.88 Hz, 6H) 0.90 (t, J = 7.34 Hz, 3H) 1.03 (d, J = 5.96 Hz, 3H) 1.07-1.26 (m, 14H) 1.30-1.34 (m, 6H) 1.51-1.88 (m, 5H) 2.10-2.84 (m, 18H) 2.87-2.93 (m, 1H) 3.18-3.34 (m, 9H) 3.37-3.44 (m, 1H) 3.53-3.61 (m, 1H) 3.68-3.72 (m, 1H) 3.81-3.86 (m, 1H) 4.19-4.22 (m, 1H) 4.34-4.46 (m, 2H) 4.52-4.56 (m, 1H) 4.61-4.67 (m, 1H) 4.94-4.99 (m, 1H) 5.32-5.41 (m, 1H) 7.44 (d, J = 8.25 Hz, 2H) 7.83-7.87 (m, 2H) |
| 350 | 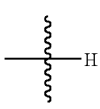 | H | 941.7 | mixture of diastereomers (600 MHz): 0.83 (d, J = 6.88 Hz, 6H) 0.91 (t, J = 7.11 Hz, 3H) 1.04-1.37 (m, 20H) 1.44 (d, J = 6.42 Hz, 3H) 1.52-1.90 (m, 5H) 2.13-2.45 (m, 5H) 2.43 (s, 6H) 2.53 (s, 3H) 2.55-2.98 (m, 5H) 3.08-3.51 (m, 10H) 3.60-3.72 (m, 2H) 3.78-3.99 (m, 1H) 4.04-4.18 (m, 1H) 4.30-4.39 (m, 1H) 4.46-4.55 (m, 2H) 4.60-4.67 (m, 1H) 4.88-4.92 (m, 1H) 4.97-5.00 (m, 1H) 6.11-6.32 (m, 2H) 6.79 (d, J = 8.25 Hz, 1H), and (600 MHz): 0.83 (d, J = 6.88 Hz, 6H) 0.91 (t, J = 6.88 Hz, 6H) 0.91 (t, J = 7.11 Hz, 3H) 1.04-1.37 (m, 20H) 1.42 (d, J = 6.42 Hz, 3H) 1.52-1.90 (m, 5H) 2.13-2.45 (m, 5H) 2.43 (s, 6H) 2.53 (s, 3H) 2.55-2.98 (m, 5H) 3.08-3.51 (m, 10H) 3.60-3.72 (m, 2H) 3.78-3.99 (m, 1H) 4.04-4.18 (m, 1H) 4.30-4.39 (m, 1H) 4.46-4.55 (m, 2H) 4.60-4.67 (m, 1H) 4.88-4.92 (m, 1H) 4.97-5.00 (m, 1H) 6.11-6.32 (m, 2H) 6.79 (d, J = 8.25 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 351 | (3,5-dihydroxyphenyl)-CH(Me)-NH-CH$_2$CH$_2$-NH-C(=O)-O- | -H | 941.8 | mixture of diastereomers (600 MHz): 0.82 (d, J = 5.96 Hz, 6H) 0.89-0.93 (m, 3H) 1.05-1.22 (m, 16H) 1.23-1.34 (m, 7H) 1.50-1.89 (m, 5H) 2.11-3.03 (m, 10H) 2.38 (s, 6H) 2.45 (s, 3H) 3.15-3.55 (m, 4H) 3.22 (s, 3H) 3.38 (s, 3H) 3.57-3.66 (m, 2H) 3.69 (d, J = 7.79 Hz, 1H) 4.11-4.18 (m, 1H) 4.32-4.39 (m, 1H) 4.47-4.56 (m, 2H) 4.59-4.66 (m, 1H) 4.95-4.99 (m, 1H) 5.04-5.08 (m, 1H) 6.24-6.28 (m, 1H) 6.33-6.37 (m, 2H), and (600 MHz): 0.82 (d, J = 5.96 Hz, 6H) 0.89-0.93 (m, 3H) 1.05-1.22 (m, 16H) 1.23-1.34 (m, 7H) 1.50-1.89 (m, 5H) 2.11-3.03 (m, 10H) 2.38 (s, 6H) 2.45 (s, 3H) 3.15-3.55 (m, 4H) 3.22 (s, 3H) 3.36 (s, 3H) 3.57-3.66 (m, 2H) 3.69 (d, J = 7.79 Hz, 1H) 4.11-4.18 (m, 1H) 4.32-4.39 (m, 1H) 4.47-4.56 (m, 2H) 4.59-4.66 (m, 1H) 4.95-4.99 (m, 1H) 5.44-5.49 (m, 1H) 6.24-6.28 (m, 1H) 6.33-6.37 (m, 2H) |
| 352 | -O-C(=O)-NH-CH$_2$CH$_2$-NH-CH(Me)-(2-methoxyphenyl) | -H | 939.7 | (600 MHz): 0.91 (d, J = 6.88 Hz, 6H) 0.99 (t, J = 7.34 Hz, 3H) 1.16-1.32 (m, 2H) 1.22 (d, J = 6.88 Hz, 3H) 1.24-1.29 (m, 12H) 1.40 (s, 3H) 1.42 (d, J = 6.88 Hz, 3H) 1.58-1.74 (m, 3H) 1.79-1.88 (m, 1H) 1.90-1.97 (m, 1H) 2.21-2.30 (m, 1H) 2.30-2.56 (m, 4H) 2.38 (s, 6H) 2.45 (s, 3H) 2.61-2.71 (m, 3H) 2.87-2.94 (m, 1H) 2.98 (d, J = 14.67 Hz, 1H) 3.25-3.40 (m, 3H) 3.33 (s, 3H) 3.43 (s, 3H) 3.50 (s, 1H) 3.63-3.71 (m, 1H) 3.80 (d, J = 8.25 Hz, 1H) 3.91 (s, 3H) 4.15 (q, J = 6.72 Hz, 1H) 4.30 (s, 1H) 4.43-4.51 (m, 1H) 4.54 (d, J = 6.88 Hz, 1H) 4.63 (d, J = 9.63 Hz, 1H) 4.74 (s, 1H) 5.07 (d, J = 4.59 Hz, 1H) 5.41-5.47 (m, 1H) 6.95 (d, J = 8.25 Hz, 1H) 7.01 (t, J = 7.57 Hz, 1H) 7.27-7.34 (m, 2H) |
| 353 | (3-ethylphenyl)-CH(Me)-NH-CH$_2$CH$_2$-NH-C(=O)-O- | -H | 937.8 | mixture of diastereomers (600 MHz): 0.82 (d, J = 6.88 Hz, 6H) 0.89 (t, J = 7.34 Hz, 3H) 1.08-1.26 (m, 2H) 1.12 (d, J = 7.34 Hz, 3H) 1.13-1.21 (m, 12H) 1.21-1.24 (m, 3H) 1.31 (s, 3H) 1.31-1.34 (m, 3H) 1.50-1.68 (m, 3H) 1.70-1.80 (m, 1H) 1.80-1.89 (m, 1H) 2.12-2.20 (m, 1H) 2.22-2.47 (m, 4H) 2.29 (s, 6H) 2.36 (s, 3H) 2.53-2.64 (m, 3H) 2.63 (q, J = 7.79 Hz, 2H) 2.77-2.84 (m, 1H) 2.88 (d, J = 17.42 Hz, 1H) 3.15-3.45 (m, 4H) 3.22-3.24 (m, 3H) 3.33 (s, 3H) 3.53-3.63 (m, 1H) 3.66-3.74 (m, 2H) 4.17-4.26 (m, 1H) 4.34-4.41 (m, 1H) 4.42-4.47 (m, 1H) 4.54 (d, J = 9.63 Hz, 1H) 4.60-4.69 (m, 1H) 4.97 (d, J = 4.58 Hz, 1H) 5.23-5.30 (m, 1H) 7.05-7.10 (m, 3H) 7.19-7.24 (m, 1H), and (600 MHz): 0.82 (d, J = 6.88 Hz, 6H) 0.89 (t, J = 7.34 Hz, 3H) 1.08-1.26 (m,, 2H) 1.12 (d, J = 7.34 Hz, 3H) 1.13-1.21 (m, 12H) 1.21-1.24 (m, 3H) 1.31 (s, 3H) 1.31-1.34 (m, 3H) 1.50-1.68 (m, 3H) 1.70-1.80 (m, 1H) 1.80-1.89 (m, 1H) 2.12-2.20 (m, 1H) 2.22-2.47 (m, 4H) 2.29 (s, 6H) 2.36 (s, 3H) 2.53-2.64 (m, 3H) 2.63 (q, J = 7.79 Hz, 2H) 2.77-2.84 (m, 1H) 2.88 (d, J = 17.42 Hz, 1H) 3.15-3.45 (m, 4H) 3.22-3.24 (m, 3H) 3.34 (s, 3H) 3.53-3.63 (m, 1H) 3.66-3.74 (m, 2H) 4.17-4.26 (m, 1H) 4.34-4.41 (m, 1H) 4.42-4.47 (m, 1H) 4.53 (d, J = 9.63 Hz, 1H) 4.60-4.69 (m, 1H) 4.97 (d, J = 4.58 Hz, 1H) 5.23-5.30 (m, 1H) 7.05-7.10 (m, 3H) 7.19-7.24 (m, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 354 | [structure: carbamate-NH-CH₂CH₂-NH-CH(Me)-phenyl-triazole with two CH₂OH] | H | 1036.8 | mixture of diastereomers (600 MHz): 0.78-0.86 (m, 6H) 0.90 (t, J = 7.57 Hz, 3H) 1.06-1.26 (m,, 2H) 1.09 (d, J = 7.34 Hz, 3H) 1.13-1.20 (m, 12H) 1.28 (s, 3H) 1.36 (d, J = 6.42 Hz, 3H) 1.50-1.68 (m, 3H) 1.69-1.79 (m, 1H) 1.80-1.90 (m, 1H) 2.12-2.47 (m, 5H) 2.27 (s, 6H) 2.35 (s, 3H) 2.48-2.66 (m, 2H) 2.69-2.93 (m, 3H) 3.20-3.36 (m,, 3H) 3.22 (s, 3H) 3.32 (s, 3H) 3.37-3.43 (m, 1H) 3.56 (s, 1H) 3.70 (d, J = 9.17 Hz, 1H) 3.81-3.88 (m, 1H) 4.19 (s, 1H) 4.33-4.40 (m, 1H) 4.43 (d, J = 6.42 Hz, 1H) 4.54 (d, J = 10.09 Hz, 1H) 4.63 (s, 1H) 4.72 (s, 2H) 4.93-4.98 (m, 1H) 4.94 (s, 2H) 5.24-5.27 (m, 1H) 7.44-7.51 (m, 2H) 7.54-7.60 (m, 2H), and (600 MHz): 0.78-0.86 (m, 6H) 0.90 (t, J = 7.57 Hz, 3H) 1.06-1.26 (m,, 2H) 1.09 (d, J = 7.34 Hz, 3H) 1.13-1.20 (m, 12H) 1.29 (s, 3H) 1.36 (d, J = 6.42 Hz, 3H) 1.50-1.68 (m, 3H) 1.69-1.79 (m, 1H) 1.80-1.90 (m, 1H) 2.12-2.47 (m, 5H) 2.30 (s, 6H) 2.34 (s, 3H) 2.48-2.66 (m, 2H) 2.69-2.93 (m, 3H) 3.20-3.36 (m, 3H) 3.23 (s, 3H) 3.34 (s, 3H) 3.37-3.43 (m, 1H) 3.56 (s, 1H) 3.70 (d, J = 9.17 Hz, 1H) 3.81-3.88 (m, 1H) 4.19 (s, 1H) 4.33-4.40 (m, 1H) 4.43 (d, J = 6.42 Hz, 1H) 4.53 (d, J = 9.63 Hz, 1H) 4.63 (s, 1H) 4.72 (s, 2H) 4.92 (s, 2H) 4.93-4.98 (m, 1H) 5.27-5.31 (m, 1H) 7.44-7.51 (m, 2H) 7.57 (m, 2H) |
| 355 | [structure: carbamate-NH-CH₂CH₂-NH-CH(Me)-phenyl-OH] | H | 925.8 | (600 MHz): 0.81 (d, J = 6.88 Hz, 6H) 0.90 (t, J = 7.34 Hz, 3H) 1.04-1.23 (m, 2H) 1.10 (d, J = 7.34 Hz, 3H) 1.13 (d, J = 5.96 Hz, 3H) 1.15-1.19 (m, 9H) 1.29 (d, J = 6.42 Hz, 3H) 1.31 (s, 3H) 1.50-1.58 (m, 1H) 1.63 (dd, J = 15.36, 4.81 Hz, 1H) 1.68 (d, J = 12.38 Hz, 1H) 1.72-1.79 (m, 1H) 1.80-1.87 (m, 1H) 2.11-2.19 (m, 1H) 2.19-2.26 (m, 1H) 2.29-2.52 (m, 4H) 2.37 (s, 3H) 2.40 (s, 6H) 2.74-2.85 (m, 2H) 2.85-3.00 (m, 2H) 3.00-3.08 (m, 1H) 3.22 (s, 3H) 3.30-3.35 (m, 1H) 3.35-3.47 (m, 2H) 3.36 (s, 3H) 3.58-3.65 (m, 1H) 3.66-3.73 (m, 2H) 4.14 (s, 1H) 4.32-4.39 (m, 1H) 4.49 (d, J = 7.34 Hz, 1H) 4.53 (d, J = 10.09 Hz, 1H) 4.62 (s, 1H) 4.97 (d, J = 4.58 Hz, 1H) 5.07 (s, 1H) 6.67-6.74 (m, 2H) 6.90 (s, 1H) 7.13 (t, J = 7.79 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 356 | | | 965.9 | mixture of diastereomers (600 MHz): 0.82 (d, J = 6.88 Hz, 6H) 0.89 (t, J = 7.34 Hz, 3H) 1.00 (t, J = 7.11 Hz, 3H) 1.06-1.27 (m, 2H) 1.11-1.15 (m, 6H) 1.15-1.21 (m, 9H) 1.21-1.24 (m, 3H) 1.31 (s, 3H) 1.33 (d, J = 6.88 Hz, 3H) 1.50-1.67 (m, 3H) 1.69-1.79 (m, 1H) 1.81-1.89 (m, 1H) 2.11-2.21 (m, 1H) 2.23-2.51 (m, 6H) 2.28 (s, 6H) 2.36 (s, 3H) 2.55-2.65 (m, 3H) 2.63 (q, J = 7.79 Hz, 2H) 2.78-2.84 (m, 1H) 2.85-2.93 (m, 1H) 3.17-3.25 (m, 3H) 3.23 (s, 3H) 3.34 (s, 3H) 3.36-3.46 (m, 1H) 3.59 (s, 1H) 3.72 (d, J = 8.25 Hz, 1H) 3.82-3.87 (m, 1H) 4.22 (s, 1H) 4.36-4.43 (m, 1H) 4.43-4.49 (m, 1H) 4.53 (d, J = 9.63 Hz, 1H) 4.64 (s, 1H) 4.97 (d, J = 4.59 Hz, 1H) 5.19-5.28 (m, 1H) 7.04-7.12 (m, 3H) 7.21 (t, J = 7.57 Hz, 1H), and (600 MHz): 0.82 (d, J = 6.88 Hz, 6H) 0.89 (t, J = 7.34 Hz, 3H) 0.97 (t, J = 7.57 Hz, 3H) 1.06-1.27 (m, 2H) 1.11-1.15 (m, 6H) 1.15-1.21 (m, 9H) 1.21-1.24 (m, 3H) 1.31 (s, 3H) 1.34 (d, J = 6.88 Hz, 3H) 1.50-1.67 (m, 3H) 1.69-1.79 (m, 1H) 1.81-1.89 (m, 1H) 2.11-2.21 (m, 1H) 2.23-2.51 (m, 6H) 2.28 (s, 6H) 2.36 (s, 3H) 2.55-2.65 (m, 3H) 2.63 (q, J = 7.79 Hz, 2H) 2.78-2.84 (m, 1H) 2.85-2.93 (m, 1H) 3.17-3.25 (m, 3H) 3.23 (s, 3H) 3.34 (s, 3H) 3.36-3.46 (m, 1H) 3.59 (s, 1H) 3.72 (d, J = 8.25 Hz, 1H) 3.76-3.82 (m, 1H) 4.22 (s, 1H) 4.36-4.43 (m, 1H) 4.43-4.49 (m, 1H) 4.54 (d, J = 9.63 Hz, 1H) 4.64 (s, 1H) 4.97 (d, J = 4.59 Hz, 1H) 5.19-5.28 (m, 1H) 7.04-7.12 (m, 3H) 7.21 (t, J = 7.57 Hz, 1H) |
| 357 | | H | 985.9 | mixture of diastereomers (500 MHz): 0.81 (d, J = 6.58 Hz, 6H) 0.89 (t, J = 7.40 Hz, 3H) 1.05-1.34 (m, 23H) 1.50-1.89 (m, 4H) 2.11-2.45 (m, 15H) 2.48-2.73 (m, 3H) 2.76-2.93 (m, 2H) 3.13-3.43 (m, 10H) 3.50-3.61 (m, 1H) 3.62-3.72 (m, 2H) 3.88 (s, 6H) 4.16-4.24 (m, 1H) 4.30-4.69 (m, 4H) 4.94-4.99 (m, 1H) 5.10-5.32 (m, 1H) 6.50-6.54 (m, 2H) |
| 358 | | H | 833.9 | (500 MHz): 0.78-0.86 (m, 6H) 0.86-0.93 (m, 3H) 1.04-1.28 (m, 17H) 1.31 (s, 3H) 1.47-1.90 (m, 6H) 2.05-2.12 (m, 1H) 2.13-2.58 (m, 8H) 2.21 (s, 6H) 2.30 (s, 7H) 2.77-2.96 (m, 2H) 3.16-3.34 (m, 3H) 3.23 (s, 3H) 3.32 (s, 3H) 3.35-3.52 (m, 2H) 3.64-3.68 (m, 1H) 4.09-4.16 (m, 1H) 4.40-4.47 (m, 1H) 4.51 (s, 1H) 4.53-4.69 (m, 2H) 5.03-5.07 (m, 1H) 5.37-5.43 (m, 1H) |
| 359 | | H | 806.8 | (500 MHz): 0.79-0.86 (m, 6H) 0.89 (t, J = 7.26 Hz, 3H) 1.05-1.27 (m, 17H) 1.31 (s, 3H) 1.47-1.89 (m, 5H) 2.08-2.13 (m, 1H) 2.20-2.34 (m, 8H) 2.36 (s, 3H) 2.40-2.56 (m, 2H) 2.78-2.94 (m, 2H) 3.22-3.25 (m, 4H) 3.32 (s, 3H) 3.34-3.51 (m, 5H) 3.65 (d, J = 7.26 Hz, 1H) 3.73 (t, J = 5.16 Hz, 2H) 4.10-4.16 (m, 1H) 4.41-4.47 (m, 1H) 4.52 (s, 1H) 4.54-4.68 (m, 2H) 5.05 (d, J = 4.97 Hz, 1H) 5.24-5.32 (m, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 360 | carbamate-NH-(CH₂)₃-N(Et)-CH(Me)-(2-methoxyphenyl) | —H | 982.0 | (500 MHz): 0.77-0.86 (m, 6H) 0.89 (t, J = 7.40 Hz, 3H) 1.06 (s, 3H) 1.07-1.12 (m, 1H) 1.07-1.11 (m, 3H) 1.13 (d, J = 6.58 Hz, 3H) 1.15-1.19 (m, 1H) 1.18 (d, J = 6.03 Hz, 3H) 1.19 (s, 3H) 1.22-1.28 (m, 6H) 1.31 (s, 3H) 1.45-1.69 (m, 5H) 1.70-1.79 (m, 1H) 1.81-1.90 (m, 1H) 2.08 (d, J = 15.36 Hz, 1H) 2.14-2.30 (m, 3H) 2.27 (s, 6H) 2.35 (s, 3H) 2.39-2.55 (m, 5H) 2.57-2.64 (m, 1H) 2.71-2.78 (m, 1H) 2.79-2.84 (m, 1H) 2.89 (d, J = 15.36 Hz, 1H) 3.19 (dd, J = 10.28, 7.27 Hz, 1H) 3.22-3.28 (m, 1H) 3.24 (s, 3H) 3.31 (s, 3H) 3.36-3.43 (m, 1H) 3.44-3.51 (m, 1H) 3.67 (d, J = 7.68 Hz, 1H) 3.81 (s, 3H) 4.09-4.17 (m, 1H) 4.37-4.43 (m, 1H) 4.45 (d, J = 6.86 Hz, 1H) 4.48 (s, 1H) 4.50-4.56 (m, 1H) 4.61-4.70 (m, 1H) 5.02 (d, J = 4.39 Hz, 1H) 6.11-6.18 (m, 1H) 6.85 (d, J = 8.25 Hz, 1H) 6.93 (t, J = 7.27 Hz, 1H) 7.18-7.23 (m, 1H) 7.30 (d, J = 7.68 Hz, 1H) |
| 361 | carbamate-NH-(CH₂)₂-N(Et)-CH(Me)-(2-methoxyphenyl) | —H | 968.0 | (500 MHz): 0.77-0.86 (m, 6H) 0.89 (t, J = 7.27 Hz, 3H) 0.94 (t, J = 7.13 Hz, 3H) 1.08 (s, 3H) 1.08-1.18 (m, 2H) 1.10 (d, J = 7.40 Hz, 3H) 1.12 (d, J = 6.58 Hz, 3H) 1.18 (d, J = 6.31 Hz, 6H) 1.28 (d, J = 6.86 Hz, 3H) 1.31 (s, 3H) 1.52-1.68 (m, 3H) 1.69-1.78 (m, 1H) 1.80-1.90 (m, 1H) 2.09 (d, J = 14.81 Hz, 1H) 2.14-2.21 (m, 1H) 2.22-2.32 (m, 2H) 2.27 (s, 6H) 2.36 (s, 3H) 2.40-2.61 (m, 6H) 2.78-2.86 (m, 1H) 2.90 (d, J = 12.34 Hz, 1H) 3.16-3.25 (m, 3H) 3.25 (s, 3H) 3.31 (s, 3H) 3.36-3.50 (m, 2H) 3.66 (d, J = 7.68 Hz, 1H) 3.84 (s, 3H) 4.09-4.15 (m, 1H) 4.35 (q, J = 6.86 Hz, 1H) 4.44 (d, J = 7.40 Hz, 1H) 4.50 (s, 1H) 4.51-4.57 (m, 1H) 4.60-4.70 (m, 1H) 5.04 (d, J = 4.94 Hz, 1H) 5.65-5.69 (m, 1H) 6.87 (d, J = 7.95 Hz, 1H) 6.91 (t, J = 7.54 Hz, 1H) 7.17-7.22 (m, 1H) 7.26-7.30 (m, 1H) |
| 362 | MeO-CH(Me)- | HO (α) | 748.4 | (600 MHz): 0.78-0.83 (m, 6H) 0.89 (t, J = 7.34 Hz, 3H) 1.08 (d, J = 7.34 Hz, 3H) 1.10-1.14 (m, 1H) 1.13-1.18 (m, 6H) 1.18 (s, 3H) 1.23 (d, J = 5.96 Hz, 3H) 1.24-1.29 (m, 2H) 1.31 (s, 3H) 1.47-1.58 (m, 3H) 1.68-1.82 (m, 2H) 1.85 (dd, J = 15.13, 5.04 Hz, 1H) 2.05 (d, J = 15.13 Hz, 1H) 2.10-2.19 (m, 1H) 2.20-2.47 (m, 13H) 2.53-2.63 (m, 1H) 2.75-2.81 (m, 1H) 2.87-2.96 (m, 2H) 3.19 (d, J = 10.09 Hz, 1H) 3.22 (s, 3H) 3.23-3.26 (m, 1H) 3.27 (s, 3H) 3.36 (s, 3H) 3.37-3.41 (m, 1H) 3.42-3.48 (m, 1H) 3.59 (d, J = 10.09 Hz, 1H) 3.70 (d, J = 7.79 Hz, 1H) 4.15-4.21 (m, 1H) 4.35-4.40 (m, 2H) 4.56-4.65 (m, 1H) 4.97 (d, J = 4.58 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 363 | H$_2$N-CH(Me)- | HO (down) | 748.4 | (600 MHz): 0.73-0.79 (m, 6H) 0.84 (t, J = 7.34 Hz, 3H) 1.05 (d, J = 7.34 Hz, 3H) 1.06-1.08 (m, 1H) 1.09 (s, 3H) 1.09-1.12 (m, 6H) 1.16 (d, J = 6.42 Hz, 3H) 1.17-1.23 (m, 1H) 1.27 (s, 3H) 1.44-1.53 (m, 1H) 1.58-1.78 (m, 3H) 1.81 (dd, J = 15.13, 5.04 Hz, 1H) 2.00 (d, J = 15.13 Hz, 1H) 2.07-2.15 (m, 1H) 2.18-2.26 (m, 2H) 2.27 (s, 6H) 2.31 (s, 3H) 2.34-2.42 (m, 1H) 2.45-2.54 (m, 1H) 2.58 (d, J = 13.76 Hz, 1H) 2.71-2.77 (m, 1H) 2.81-2.87 (m, 1H) 2.89 (d, J = 13.76 Hz, 1H) 3.12-3.19 (m, 1H) 3.18 (s, 3H) 3.23 (s, 3H) 3.30-3.38 (m, 1H) 3.41-3.49 (m, 1H) 3.65 (d, J = 8.25 Hz, 1H) 4.11-4.19 (m, 1H) 4.33 (d, J = 7.34 Hz, 1H) 4.35-4.42 (m, 1H) 4.52-4.62 (m, 1H) 4.93 (d, J = 5.04 Hz, 1H) |
| 364 | MeNH-CH(Me)- | HO (down) | 762.5 | (600 MHz): 0.79-0.83 (m, 6H) 0.89 (t, J = 7.34 Hz, 3H) 1.08 (d, J = 6.88 Hz, 3H) 1.10-1.12 (m, 1H) 1.14 (d, J = 7.34 Hz, 3H) 1.18 (s, 3H) 1.21 (d, J = 6.42 Hz, 3H) 1.24 (s, 3H) 1.26-1.30 (m, 1H) 1.33 (s, 3H) 1.49-1.58 (m, 1H) 1.66-1.81 (m, 2H) 1.83 (dd, J = 14.90, 4.81 Hz, 1H) 2.03 (d, J = 15.13 Hz, 1H) 2.11-2.31 (m, 3H) 2.33-2.56 (m, 16H) 2.63-2.83 (m, 3H) 2.91 (d, J = 15.13 Hz, 1H) 3.21 (s, 3H) 3.23-3.28 (m, 1H) 3.30 (s, 3H) 3.36-3.42 (m, 1H) 3.62-3.70 (m, 2H) 4.14-4.22 (m, 1H) 4.36 (d, J = 7.34 Hz, 1H) 4.48-4.65 (m, 2H) 4.93 (d, J = 4.59 Hz, 1H) |
| 365 | Me$_2$N-CH(Me)- | HO (down) | 776.1 | (600 MHz): 0.77-0.83 (m, 6H) 0.88 (t, J = 7.34 Hz, 3H) 1.07 (d, J = 7.79 Hz, 3H) 1.09 (s, 3H) 1.09-1.11 (m, 1H) 1.11-1.17 (m, 6H) 1.21 (d, J = 5.96 Hz, 3H) 1.23-1.27 (m, 1H) 1.30 (s, 3H) 1.48-1.56 (m, 1H) 1.61-1.84 (m, 3H) 1.88 (dd, J = 14.67, 5.04 Hz, 1H) 1.97 (d, J = 14.67 Hz, 1H) 2.05 (d, J = 15.13 Hz, 1H) 2.10-2.20 (m, 1H) 2.20-2.29 (m, 2H) 2.31 (s, 6H) 2.34 (s, 9H) 2.38-2.56 (m, 2H) 2.73 (d, J = 14.67 Hz, 1H) 2.75-2.79 (m, 1H) 2.89 (d, J = 15.59 Hz, 1H) 3.19-3.24 (m, 1H) 3.22 (s, 3H) 3.27 (s, 3H) 3.34-3.46 (m, 2H) 3.69 (d, J = 8.25 Hz, 1H) 4.12-4.20 (m, 2H) 4.36 (d, J = 6.88 Hz, 1H) 4.61 (br. s., 1H) 4.97 (d, J = 5.04 Hz, 1H) |
| 366 | oxazolidine-2-thione | | 790.4 | (600 MHz): 0.78-0.83 (m, 6H) 0.90 (t, J = 7.57 Hz, 3H) 1.07 (d, J = 7.34 Hz, 3H) 1.12-1.17 (m, 7H) 1.18-1.25 (m, 7H) 1.30 (s, 3H) 1.50-1.59 (m, 1H) 1.63-1.84 (m, 3H) 1.88 (dd, J = 15.13, 5.04 Hz, 1H) 2.09-2.16 (m, 1H) 2.20 (d, J = 15.13 Hz, 1H) 2.22-2.27 (m, 1H) 2.27-2.33 (m, 7H) 2.36 (s, 3H) 2.38-2.53 (m, 2H) 2.76-2.83 (m, 1H) 2.85-2.92 (m, 1H) 3.17-3.23 (m, 2H) 3.20 (s, 3H) 3.30 (s, 3H) 3.31-3.37 (m, 2H) 3.63 (d, J = 4.13 Hz, 1H) 3.88 (d, J = 10.55 Hz, 1H) 4.25-4.29 (m, 1H) 4.30 (d, J = 7.34 Hz, 1H) 4.38 (q, J = 6.72 Hz, 1H) 4.56-4.66 (m, 1H) 5.00 (d, J = 4.59 Hz, 1H) |

TABLE 11-continued formula (W)

| Example | R^1W | R^2W | ESI MS (M + H) | ^1H-NMR, CDCl_3, δ (ppm) |
|---|---|---|---|---|
| 367 | Me-S-CH(Me)- | HO- | 779.5 | (600 MHz): 0.77-0.83 (m, 6H) 0.89 (t, J = 7.34 Hz, 3H) 1.04-1.09 (m, 1H) 1.09 (d, J = 7.34 Hz, 3H) 1.11-1.17 (m, 10H) 1.21 (d, J = 5.96 Hz, 3H) 1.22-1.26 (m, 1H) 1.31 (s, 3H) 1.49-1.57 (m, 1H) 1.59-1.83 (m, 3H) 1.84 (dd, J = 15.13, 5.50 Hz, 1H) 2.04-2.08 (m, 1H) 2.09 (s, 3H) 2.11-2.19 (m, 1H) 2.23-2.32 (m, 8H) 2.36 (s, 3H) 2.38-2.46 (m, 1H) 2.47-2.55 (m, 1H) 2.62 (d, J = 14.21 Hz, 1H) 2.75-2.81 (m, 1H) 2.83 (d, J = 14.67 Hz, 1H) 2.90 (d, J = 15.13 Hz, 1H) 3.09 (s, 1H) 3.17-3.21 (m, 1H) 3.21 (s, 3H) 3.28 (s, 3H) 3.36-3.44 (m, 1H) 3.46-3.55 (m, 1H) 3.66 (d, J = 8.25 Hz, 1H) 4.13-4.24 (m, 1H) 4.37 (d, J = 7.34 Hz, 1H) 4.44 (q, J = 6.42 Hz, 1H) 4.54-4.66 (m, 1H) 4.97 (d, J = 5.04 Hz, 1H) |
| 368 | morpholine-CH_2CH_2CH_2-NH-CH(Me)- | HO- | | (600 MHz): 0.79 (d, J = 6.42 Hz, 6H) 0.87 (t, J = 7.34 Hz, 3H) 1.03-1.26 (m, 2H) 1.07 (d, J = 7.34 Hz, 3H) 1.10 (s, 3H) 1.11 (d, J = 6.42 Hz, 3H) 1.13 (d, J = 7.34 Hz, 3H) 1.18 (d, J = 5.96 Hz, 3H) 1.29 (s, 3H) 1.46-1.56 (m, 1H) 1.56-1.88 (m, 6H) 2.02 (d, J = 14.67 Hz, 1H) 2.07-2.18 (m, 1H) 2.20-2.50 (m, 11H) 2.26 (s, 6H) 2.33 (s, 3H) 2.59-2.67 (m, 2H) 2.71-2.80 (m, 2H) 2.83-2.91 (m, 1H) 3.14-3.22 (m, 1H) 3.20 (s, 3H) 3.25 (s, 3H) 3.33-3.43 (m, 1H) 3.46-3.54 (m, 1H) 3.62-3.71 (m, 5H) 4.17 (s, 1H) 4.30-4.38 (m, 2H) 4.59 (s, 1H) 4.94 (d, J = 4.59 Hz, 1H) |
| 369 | 3-HO-C_6H_4-CH(Me)-NH-CH_2CH_2-NH-CH(Me)- | HO- | 911.9 | mixture of diastereomers (600 MHz): 0.82 (d, J = 6.88 Hz, 6H) 0.91 (t, J = 7.34 Hz, 3H) 1.07 (d, J = 7.34 Hz, 3H) 1.08-1.40 (m, 17H) 1.12 (d, J = 5.96 Hz, 3H) 1.52-1.58 (m, 1H) 1.59-1.67 (m, 1H) 1.72-1.88 (m, 3H) 2.01-2.08 (m, 1H) 2.10-2.33 (m, 3H) 2.34-2.70 (m, 16H) 2.72-2.83 (m, 2H) 2.90-2.96 (m, 1H) 3.18-3.32 (m, 6H) 3.32-3.39 (m, 1H) 3.39-3.60 (m, 2H) 3.62-3.77 (m, 3H) 4.12-4.20 (m, 1H) 4.36 (d, J = 6.88 Hz, 1H) 4.40-4.48 (m, 1H) 4.57-4.65 (m, 1H) 4.95 (d, J = 5.04 Hz, 1H) 6.64-6.82 (m, 3H) 7.13-7.21 (m, 1H) |
| 370 | Me_2N-CH_2CH_2-NH-CH(Me)- | HO- | 819.8 | (500 MHz): 0.81 (d, J = 7.13 Hz, 6H) 0.89 (t, J = 7.27 Hz, 3H) 1.09 (d, J = 7.13 Hz, 3H) 1.11-1.17 (m, 1H) 1.12 (s, 3H) 1.13-1.17 (m, 6H) 1.20 (d, J = 6.31 Hz, 3H) 1.21-1.26 (m, 1H) 1.31 (s, 3H) 1.48-1.57 (m, 1H) 1.60-1.66 (m, 1H) 1.68-1.79 (m, 1H) 1.79-1.90 (m, 2H) 2.01-2.06 (m, 1H) 2.11-2.18 (m, 1H) 2.18-2.53 (m, 7H) 2.21 (s, 6H) 2.28 (s, 6H) 2.35 (s, 3H) 2.64-2.94 (m, 5H) 3.16-3.25 (m, 1H) 3.22 (s, 3H) 3.27 (s, 3H) 3.35-3.56 (m, 2H) 3.70 (d, J = 8.23 Hz, 1H) 4.14-4.23 (m, 1H) 4.29-4.41 (m, 2H) 4.53-4.67 (m, 1H) 4.96 (d, J = 4.39 Hz, 1H) |
| 371 | HO-CH_2CH_2-NH-CH(Me)- | HO- | 792.8 | (500 MHz): 0.81 (d, J = 6.86 Hz, 6H) 0.86-0.92 (m, 3H) 1.04-1.36 (m, 20H) 1.38-1.47 (m, 2H) 1.48-1.89 (m, 5H) 2.04 (d, J = 14.81 Hz, 1H) 2.10-2.53 (m, 6H) 2.28 (s, 6H) 2.35 (s, 3H) 2.54-2.60 (m, 2H) 2.73-2.94 (m, 3H) 3.17-3.24 (m, 1H) 3.22 (s, 3H) 3.27 (s, 3H) 3.35-3.45 (m, 1H) 3.51-3.60 (m, 1H) 3.70 (d, J = 7.95 Hz, 1H) 4.14-4.22 (m, 1H) 4.34-4.42 (m, 2H) 4.56-4.67 (m, 1H) 4.96 (d, J = 4.66 Hz, 1H) |

TABLE 11-continued formula (W)

| Example | R<sup>1W</sup> | R<sup>2W</sup> | ESI MS (M + H) | <sup>1</sup>H-NMR, CDCl<sub>3</sub>, δ (ppm) |
|---|---|---|---|---|
| 372 | Me-butyl-NH- | HO (α) | 804.8 | (500 MHz): 0.76-0.84 (m, 6H) 0.89 (t, J = 7.27 Hz, 3H) 1.05-1.30 (m, 20H) 1.34 (s, 3H) 1.48-1.87 (m, 5H) 2.03-2.18 (m, 2H) 2.20-2.45 (m, 4H) 2.28 (s, 6H) 2.36 (s, 3H) 2.51-2.59 (m, 1H) 2.62-2.69 (m, 2H) 2.75-2.82 (m, 3H) 2.87-2.94 (m, 1H) 3.19-3.30 (m, 1H) 3.21 (s, 3H) 3.28 (s, 3H) 3.35-3.41 (m, 1H) 3.51-3.71 (m, 5H) 4.18-4.25 (m, 1H) 4.38 (d, J = 6.58 Hz, 1H) 4.51-4.65 (m, 2H) 4.96 (d, J = 4.66 Hz, 1H) |
| 373 | (ethyl-NH-CH<sub>2</sub>CH<sub>2</sub>-NH-CH(Me)-3-hydroxyphenyl) | OH | 911.9 | (600 MHz): 0.86 (d, J = 6.88 Hz, 6H) 0.95 (t, J = 7.34 Hz, 3H) 1.06-1.33 (m, 17H) 1.35 (s, 3H) 1.36 (d, J = 6.88 Hz, 3H) 1.55-1.63 (m, 1H) 1.65-1.70 (m, 1H) 1.75-1.93 (m, 3H) 2.09 (d, J = 14.67 Hz, 1H) 2.15-2.38 (m, 3H) 2.39-2.75 (m, 8H) 2.41 (s, 3H) 2.45 (s, 6H) 2.79-2.87 (m, 1H) 2.93-3.03 (m, 1H) 3.26 (s, 3H) 3.35 (s, 3H) 3.37-3.52 (m, 2H) 3.59-3.66 (m, 1H) 3.72 (d, J = 7.79 Hz, 1H) 3.77 (q, J = 6.57 Hz, 1H) 4.15-4.21 (m, 1H) 4.40 (d, J = 6.88 Hz, 1H) 4.46-4.53 (m, 1H) 4.62-4.69 (m, 1H) 4.99 (d, J = 5.04 Hz, 1H) 6.72-6.77 (m, 1H) 6.80-6.87 (m, 2H) 7.20 (t, J = 7.79 Hz, 1H) |
| 374 | (4-NO<sub>2</sub>-phenyl-CH(OH)-CH(NH-)-CH<sub>2</sub>OH) | OH | 943.9 | (600 MHz): 0.79-0.83 (m, 6H) 0.90 (t, J = 7.34 Hz, 3H) 1.09 (s, 3H) 1.10 (d, J = 7.34 Hz, 3H) 1.10-1.31 (m, 2H) 1.15 (d, J = 7.79 Hz, 3H) 1.19 (d, J = 6.42 Hz, 3H) 1.23 (d, J = 6.42 Hz, 3H) 1.36 (s, 3H) 1.50-1.85 (m, 5H) 2.05 (d, J = 15.13 Hz, 1H) 2.10-2.17 (m, 1H) 2.23-2.44 (m, 2H) 2.27 (s, 6H) 2.37 (s, 3H) 2.57-2.63 (m, 3H) 2.75-2.93 (m, 4H) 3.20 (s, 3H) 3.21 (s, 3H) 3.30 (dd, J = 9.86, 6.65 Hz, 1H) 3.35-3.39 (m, 1H) 3.45 (dd, J = 11.23, 2.98 Hz, 1H) 3.47-3.51 (m, 1H) 3.52-3.58 (m, 1H) 3.66 (d, J = 8.25 Hz, 1H) 3.69 (dd, J = 11.46, 4.13 Hz, 1H) 4.23-4.26 (m, 1H) 4.37 (d, J = 6.42 Hz, 1H) 4.57-4.62 (m, 1H) 4.64-4.69 (m, 1H) 4.86 (d, J = 5.96 Hz, 1H) 4.95 (d, J = 5.04 Hz, 1H) 7.57 (d, J = 8.25 Hz, 2H) 8.20 (d, J = 8.71 Hz, 2H) |
| 375 | (HOCH<sub>2</sub>)<sub>2</sub>CH-NH- | HO (α) | | (600 MHz): 0.78-0.83 (m, 6H) 0.90 (t, J = 7.34 Hz, 3H) 1.09 (d, J = 7.34 Hz, 3H) 1.16 (d, J = 7.34 Hz, 3H) 1.17-1.27 (m, 2H) 1.20 (s, 3H) 1.21-1.23 (m, 6H) 1.35 (s, 3H) 1.49-1.58 (m, 1H) 1.63-1.69 (m, 1H) 1.71-1.88 (m, 3H) 2.08 (d, J = 15.13 Hz, 1H) 2.09-2.17 (m, 1H) 2.22-2.45 (m, 3H) 2.28 (s, 6H) 2.37 (s, 3H) 2.49-2.55 (m, 1H) 2.59-2.64 (m, 1H) 2.72-2.84 (m, 3H) 2.91 (d, J = 15.59 Hz, 1H) 3.22 (s, 3H) 3.27 (dd, J = 9.86, 6.65 Hz, 1H) 3.29 (s, 3H) 3.36-3.42 (m, 1H) 3.52-3.77 (m, 6H) 4.22 (s, 1H) 4.38 (d, J = 6.42 Hz, 1H) 4.56-4.66 (m, 2H) 4.97 (d, J = 4.58 Hz, 1H) |

TABLE 11-continued formula (W)

| Example | R[1W] | R[2W] | ESI MS (M + H) | $^1$H-NMR, CDCl₃, δ (ppm) |
|---|---|---|---|---|
| 376 | (4-nitrophenethyl)amino-ethyl group | HO·· | 897.9 | (600 MHz): 0.83 (d, J = 6.88 Hz, 6H) 0.91 (t, J = 7.34 Hz, 3H) 1.08-1.29 (m, 2H) 1.11 (d, J = 7.34 Hz, 3H) 1.12 (s, 3H) 1.15 (d, J = 6.42 Hz, 3H) 1.17 (d, J = 7.34 Hz, 3H) 1.21 (d, J = 6.42 Hz, 3H) 1.33 (s, 3H) 1.51-1.59 (m, 1H) 1.62-1.68 (m, 1H) 1.71-1.88 (m, 3H) 2.04 (d, J = 14.67 Hz, 1H) 2.10-2.21 (m, 1H) 2.23-2.47 (m, 3H) 2.29 (s, 6H) 2.38 (s, 3H) 2.47-2.54 (m, 1H) 2.61 (d, J = 13.30 Hz, 1H) 2.77-2.84 (m, 2H) 2.84-2.96 (m, 5H) 3.20-3.26 (m, 7H) 3.35-3.43 (m, 1H) 3.52-3.60 (m, 1H) 3.71 (d, J = 8.25 Hz, 1H) 4.23 (s, 1H) 4.38 (d, J = 6.88 Hz, 1H) 4.47 (q, J = 6.42 Hz, 1H) 4.62 (s, 1H) 4.96 (d, J = 4.59 Hz, 1H) 7.36 (d, J = 8.71 Hz, 2H) 8.17 (d, J = 8.71 Hz, 2H) |
| 377 | isopentylamino group | HO·· | 817.6 | (500 MHz): 0.81 (d, J = 7.13 Hz, 6H) 0.85-0.91 (m, 9H) 1.05-1.36 (m, 22H) 1.48-1.88 (m, 5H) 2.00-2.07 (m, 1H) 2.09-2.19 (m, 1H) 2.20-2.31 (m, 8H) 2.35 (s, 3H) 2.37-2.62 (m, 5H) 2.73-2.81 (m, 2H) 2.86-2.94 (m, 1H) 3.18-3.24 (m, 4H) 3.27 (s, 3H) 3.34-3.45 (m, 2H) 3.51-3.60 (m, 1H) 3.70 (d, J = 8.23 Hz, 1H) 4.15-4.21 (m, 1H) 4.33-4.43 (m, 2H) 4.57-4.66 (m, 1H) 4.96 (d, J = 4.39 Hz, 1H) |
| 378 | 2-piperidinoethylamino group | HO·· | 859.8 | (500 MHz): 0.81 (d, J = 7.13 Hz, 6H) 0.89 (t, J = 7.27 Hz, 3H) 1.06-1.26 (m, 17H) 1.31 (s, 3H) 1.37-1.45 (m, 2H) 1.49-1.58 (m, 4H) 1.60-1.91 (m, 4H) 2.04 (d, J = 14.81 Hz, 1H) 2.09-2.20 (m, 1H) 2.21-2.52 (m, 21H) 2.65-2.82 (m, 4H) 2.85-2.93 (m, 1H) 3.17-3.25 (m, 4H) 3.27 9s, 3H) 3.34-3.56 (m, 2H) 3.70 (d, J = 8.23 Hz, 1H) 4.13-4.22 (m, 1H) 4.33-4.39 (m, 2H) 4.58-4.66 (m, 1H) 4.96 (d, J = 4.66 Hz, 1H) |
| 379 | 2-morpholinoethylamino group | HO·· | 861.8 | (500 MHz): 0.81 (d, J = 6.88 Hz, 6H) 0.89 (t, J = 7.45 Hz, 3H) 1.06-1.33 (m, 20H) 1.48-1.89 (m, 5H) 2.04 (d, J = 14.53 Hz, 1H) 2.09-2.52 (m, 20H) 2.64-2.93 (m, 5H) 3.18-3.24 (m, 4H) 3.28 (s, 3H) 3.35-3.45 (m, 2H) 3.48-3.56 (m, 1H) 3.65-3.72 (m, 5H) 4.16-4.23 (m, 1H) 4.34-4.41 (m, 2H) 4.58-4.66 (m, 1H) 4.97 (d, J = 4.59 Hz, 1H) |
| 380 | 4-(2-aminoethyl)piperazinyl group | HO·· | 860.8 | (500 MHz): 0.81 (d, J = 6.86 Hz, 6H) 0.85-0.92 (m, 3H) 1.05-1.33 (m, 20H) 1.47-1.91 (m, 5H) 1.98-2.20 (m, 3H) 2.20-2.53 (m, 17H) 2.58-2.73 (m, 2H) 2.73-2.92 (m, 7H) 3.18-3.24 (m, 4H) 3.28 (s, 3H) 3.33-3.46 (m, 2H) 3.47-3.56 (m, 1H) 3.66-3.72 (m, 1H) 4.13-4.22 (m, 2H) 4.33-4.39 (m, 2H) 4.57-4.67 (m, 1H) 4.94-4.98 (m, 1H) |
| 381 | 2-(diethylamino)ethylamino group | HO·· | 847.9 | (600 MHz): 0.81 (d, J = 6.88 Hz, 6H) 0.89 (t, J = 7.34 Hz, 3H) 0.99 (t, J = 7.11 Hz, 6H) 1.06-1.28 (m, 2H) 1.09 (d, J = 7.34 Hz, 3H) 1.13 (s, 3H) 1.14 (d, J = 6.42 Hz, 3H) 1.16 (d, J = 7.34 Hz, 3H) 1.20 (d, J = 5.96 Hz, 3H) 1.31 (s, 3H) 1.49-1.57 (m, 1H) 1.57-1.91 (m, 4H) 2.04 (d, J = 14.67 Hz, 1H) 2.11-2.19 (m, 1H) 2.22-2.32 (m, 2H) 2.28 (s, 6H) 2.36 (s, 3H) 2.39-2.68 (m, 11H) 2.74-2.84 (m, 2H) 2.86-2.93 (m, 1H) 3.19-3.22 (m, 1H) 3.22-3.23 (m, 3H) 3.28 (s, 3H) 3.35-3.44 (m, 1H) 3.46-3.55 (m, 1H) 3.71 (d, J = 7.79 Hz, 1H) 4.18 (s, 1H) 4.30-4.42 (m, 2H) 4.62 (s, 1H) 4.97 (d, J = 4.59 Hz, 1H) |

TABLE 11-continued formula (W)

| Example | R<sup>1W</sup> | R<sup>2W</sup> | ESI MS (M + H) | ¹H-NMR, CDCl₃, δ (ppm) |
|---|---|---|---|---|
| 382 | (ethyl-NH-CH₂CH₂-pyrrolidine) | HO⁻ | 845.8 | (600 MHz): 0.81 (d, J = 6.88 Hz, 6H) 0.88 (t, J = 7.34 Hz, 3H) 1.09 (d, J = 7.34 Hz, 3H) 1.10-1.26 (m, 2H) 1.12 (s, 3H) 1.14 (d, J = 6.42 Hz, 3H) 1.15 (d, J = 7.79 Hz, 3H) 1.20 (d, J = 6.42 Hz, 3H) 1.31 (s, 3H) 1.49-1.66 (m, 2H) 1.71-1.90 (m, 7H) 2.04 (d, J = 15.13 Hz, 1H) 2.09-2.32 (m, 3H) 2.28 (s, 3H) 2.35 (s, 3H) 2.37-2.45 (m, 1H) 2.45-2.59 (m, 9H) 2.71 (t, J = 6.42 Hz, 1H) 2.74-2.94 (m, 3H) 3.17-3.22 (m, 1H) 3.22 (s, 3H) 3.27 (s, 3H) 3.36-3.44 (m, 1H) 3.48-3.57 (m, 1H) 3.70 (d, J = 8.25 Hz, 1H) 4.17 (s, 1H) 4.33-4.39 (m, 2H) 4.61 (s, 1H) 4.96 (d, J = 4.59 Hz, 1H) |
| 383 | (CH₂-piperidine) | HO⁻ | 816.8 | (600 MHz): 0.82 (d, J = 6.88 Hz, 6H) 0.89 (t, J = 7.34 Hz, 3H) 1.03-1.28 (m, 4H) 1.07-1.11 (m, 6H) 1.13 (d, J = 6.42 Hz, 3H) 1.16 (d, J = 7.34 Hz, 3H) 1.22 (d, J = 6.42 Hz, 3H) 1.31 (s, 3H) 1.70 (d, 9H) 1.97 (d, J = 14.67 Hz, 1H) 2.06 (d, J = 15.13 Hz, 1H) 2.11-2.21 (m, 1H) 2.22-2.33 (m, 4H) 2.30 (s, 6H) 2.36 (s, 3H) 2.39-2.46 (m, 1H) 2.46-2.53 (m, 1H) 2.53-2.63 (m, 2H) 2.72 (d, J = 15.13 Hz, 1H) 2.75-2.82 (m, 1H) 2.86-2.93 (m, 1H) 3.22 (dd, J = 10.32, 7.11 Hz 1H) 3.24 (s, 3H) 3.29 (s, 3H) 3.37-3.47 (m, 2H) 3.71 (d, J = 7.79 Hz, 1H) 4.13-4.22 (m, 2H) 4.38 (d, J = 7.34 Hz, 1H) 4.59-4.68 (m, 1H) 4.98 (d, J = 5.04 Hz, 1H) |
| 384 | (morpholine-CH₂) | HO⁻ | 818.8 | (600 MHz): 0.83 (d, J = 6.88 Hz, 6H) 0.90 (t, J = 7.34 Hz, 3H) 1.04-1.29 (m, 2H) 1.08-1.12 (m, 6H) 1.15 (d, J = 6.42 Hz, 3H) 1.17 (d, J = 7.79 Hz, 3H) 1.23 (d, J = 5.96 Hz, 3H) 1.32 (s, 3H) 1.51-1.59 (m, 1H) 1.62-1.93 (m, 4H) 2.05 (d, J = 14.67 Hz, 1H) 2.08 (d, J = 15.13 Hz, 1H) 2.12-2.22 (m, 1H) 2.23-2.34 (m, 2H) 2.31 (s, 6H) 2.37 (s, 3H) 2.40-2.46 (m, 1H) 2.46-2.53 (m, 1H) 2.55-2.71 (m, 4H) 2.76-2.84 (m, 2H) 2.86-2.95 (m, 1H) 3.23 (dd, J = 10.55, 7.34 Hz, 1H) 3.25 (s, 3H) 3.30 (s, 3H) 3.37-3.47 (m, 2H) 3.66-3.77 (m, 5H) 4.16-4.26 (m, 2H) 4.38 (d, J = 7.34 Hz, 1H) 4.64 (s, 1H) 4.99 (d, J = 4.58 Hz, 1H) |
| 385 | (NH-CH(CH₂OH)-CH(OH)-Ph) | ⁻OH | 898.9 | (500 MHz): 0.78-0.83 (m, 6H) 0.89 (t, J = 7.26 Hz, 3H) 1.06-1.36 (m, 20H) 1.48-1.86 (m, 4H) 2.01-2.44 (m, J = 15.29 Hz, 14H) 2.55-2.94 (m, 6H) 3.17-3.28 (m, 7H) 3.33-3.69 (m, 6H) 4.19-4.25 (m, 1H) 4.36 (d, J = 6.88 Hz, 1H) 4.56-4.65 (m, 2H) 4.72 (d, J = 6.12 Hz, 1H) 4.95 (d, J = 4.59 Hz, 1H) 7.24-7.37 (m, 5H) |
| 386 | (Me-NH-CH₂CH₂-NH-) | HO⁻ | 805.8 | (500 MHz): 0.81 (d, J = 6.86 Hz, 6H) 0.89 (t, J = 7.40 Hz, 3H) 1.06-1.34 (m, 20H) 1.48-1.89 (m, 5H) 2.04 (d, J = 13.99 Hz, 1H) 2.11-2.53 (m, 18H) 2.62-2.93 (m, 6H) 3.17-3.25 (m, 4H) 3.27 (s, 3H) 3.33-3.55 (m, 3H) 3.70 (d, J = 7.95 Hz, 1H) 4.16-4.23 (m, 1H) 4.33-4.40 (m, 2H) 4.57-4.68 (m, 1H) 4.94-4.98 (m, 1H) |

TABLE 11-continued formula (W)

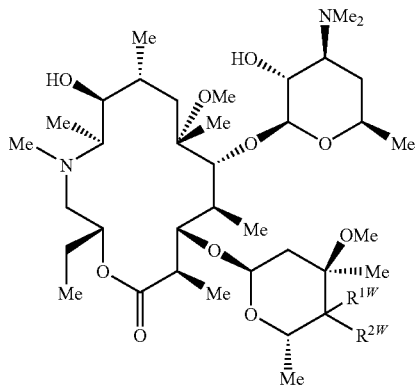

| Example | R$^{1W}$ | R$^{2W}$ | ESI MS (M + H) | $^1$H-NMR, CDCl$_3$, δ (ppm) |
|---|---|---|---|---|
| 387 | H$_2$N-CH$_2$CH$_2$-N(Me)- | HO''''- | 805.8 | (500 MHz): 0.81 (d, J = 6.86 Hz, 6H) 0.88 (t, J = 7.40 Hz, 3H) 1.05-1.28 (m, 17H) 1.31 (s, 3H) 1.48-1.92 (m, 5H) 2.01-2.19 (m, 3H) 2.22-2.38 (m, 15H) 2.38-2.54 (m, 3H) 2.59-2.67 (m, 1H) 2.74-2.92 (m, 4H) 3.18-3.30 (m, 7H) 3.36-3.47 (m, 2H) 3.70 (d, J = 8.23 Hz, 1H) 4.14-4.25 (m, 2H) 4.37 (d, J = 7.13 Hz, 1H) 4.58-4.66 (m, 1H) 4.97 (d, J = 4.66 Hz, 1H) |
| 388 | N-methylpiperazinyl | HO''''- | 831.8 | (500 MHz): 0.81 (d, J = 6.88 Hz, 6H) 0.89 (t, J = 7.45 Hz, 3H) 1.03-1.34 (m, 20H) 1.48-1.92 (m, 6H) 1.99-2.19 (m, 4H) 2.19-2.32 (m, 4H) 2.27 (s, 3H) 2.29 (s, 6H) 2.35 (s, 3H) 2.38-2.53 (m, 2H) 2.56-2.71 (m, 1H) 2.74-2.83 (m, 2H) 2.84-2.94 (m, 1H) 3.15-3.25 (m, 4H) 3.28 (s, 3H) 3.34-3.46 (m, 4H) 3.70 (d, J = 8.03 Hz, 1H) 4.18 (d, 2H) 4.36 (d, J = 7.26 Hz, 1H) 4.43-4.57 (m, 1H) 4.58-4.68 (m, 1H) 4.97 (d, J = 4.59 Hz, 1H) |
| 389 | piperazinyl | HO''''- | 817.8 | (500 MHz): 0.81 (d, J = 6.88 Hz, 6H) 0.89 (t, J = 7.26 Hz, 3H) 1.05-1.33 (m, 20H) 1.48-1.92 (m, 6H) 1.98-2.20 (m, 3H) 2.21-2.33 (m, 9H) 2.35 (s, 3H) 2.38-2.67 (m, 3H) 2.73-2.92 (m, 7H) 3.18-3.26 (m, 4H) 3.28 (s, 3H) 3.35-3.47 (m, 3H) 3.70 (d, J = 8.03 Hz, 1H) 4.14-4.23 (m, 2H) 4.37 (d, J = 7.26 Hz, 1H) 4.58-4.67 (m, 1H) 4.97 (d, J = 4.97 Hz, 1H) |
| 390 | 3-aminopyrrolidinyl | HO''''- | 817.7 | mixture of diastereomers (500 MHz): 0.80 (d, J = 6.88 Hz, 6H) 0.88 (t, J = 7.26 Hz, 3H) 1.03-1.26 (m, 17H) 1.30 (s, 3H) 1.46-1.91 (m, 7H) 2.06 (d, J = 14.91 Hz, 1H) 2.10-2.31 (m, 11H) 2.34 (s, 3H) 2.37-2.53 (m, 3H) 2.61-2.81 (m, 2H) 2.82-3.00 (m, 3H) 3.16-3.25 (m, 4H) 3.27 (s, 3H) 3.34-3.56 (m, 3H) 3.69 (d, J = 8.03 Hz, 1H) 4.11-4.22 (m, 2H) 4.36 (d, J = 7.26 Hz, 1H) 4.57-4.67 (m, 1H) 4.97 (d, J = 4.97 Hz, 1H) |
| 391 | Me$_2$N-CH$_2$CH$_2$CH$_2$-NH- | HO''''- | 833.8 | (500 MHz): 0.81 (d, J = 6.86 Hz, 6H) 0.88 (t, J = 7.40 Hz, 3H) 1.06-1.32 (m, 20H) 1.47-1.90 (m, 7H) 2.03 (d, J = 15.08 Hz, 1H) 2.10-2.53 (m, 22H) 2.60-2.66 (m, 2H) 2.74-2.93 (m, 3H) 3.17-3.24 (m, 4H) 3.27 (s, 3H) 3.33-3.56 (m, 3H) 3.70 (d, J = 7.95 Hz, 1H) 4.14-4.21 (m, 1H) 4.32-4.39 (m, 2H) 4.57-4.67 (m, 1H) 4.96 (d, J = 4.66 Hz, 1H) |
| 392 | HOCH$_2$-CH(NH-)-CH$_2$-NMe$_2$ | HO''''- | 849.9 | (500 MHz): 0.81 (d, J = 6.88 Hz, 6H) 0.90 (t, J = 7.26 Hz, 3H) 1.06-1.30 (m, 17H) 1.32 (s, 3H) 1.47-1.86 (m, 5H) 2.05 (d, J = 15.29 Hz, 1H) 2.10-2.56 (m, 23H) 3.16-3.57 (m, 15H) 3.69 (d, J = 8.41 Hz, 1H) 4.20-4.26 (m, 1H) 4.35 (d, J = 7.26 Hz, 1H) 4.48-4.65 (m, 2H) 4.97 (d, J = 4.97 Hz, 1H) |
| 393 | HOCH$_2$-CH(NH-)-CH$_2$-NMe$_2$ | HO''''- | 849.8 | (500 MHz): 0.81 (d, J = 6.86 Hz, 6H) 0.89 (t, J = 7.40 Hz, 3H) 1.06-1.28 (m, 17H) 1.31 (s, 3H) 1.49-1.89 (m, 5H) 2.00-2.55 (m, 19H) 2.57-2.94 (m, 5H) 3.17-3.29 (m, 7H) 3.35-3.72 (m, 9H) 4.17-4.24 (m, 1H) 4.32-4.43 (m, 2H) 4.58-4.66 (m, 1H) 4.95 (d, J = 5.49 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 394 | (1-methylpyrrolidin-3-yl)(ethyl)amino- | HO•••••• | 831.8 | mixture of diastereomers (500 MHz): 0.81 (d, J = 6.58 Hz, 6H) 0.88 (t, J = 7.27 Hz, 3H) 1.04-1.33 (m, 20H) 1.47-1.92 (m, 7H) 2.00-3.00 (m, 25H) 3.17-3.30 (m, 7H) 3.35-3.46 (m, 2H) 3.65-3.72 (m, 3H) 4.11-4.23 (m, 2H) 4.33-4.42 (m, 1H) 4.57-4.67 (m, 1H) 4.93-4.99 (m, 1H) |
| 395 | (1-hydroxy-2-propyl)amino-ethyl- (HOCH$_2$CH(Me)NH–CH(Et)–) | HO•••••• | 806.7 | mixture of diastereomers (600 MHz): 0.76-0.83 (m, 6H) 0.86-0.92 (m, 3H) 0.97 (d, J = 6.42 Hz, 3H) 1.05-1.28 (m, 14H) 1.07 (d, J = 7.34 Hz, 3H) 1.36 (s, 3H) 1.49-1.58 (m, 1H) 1.61-1.69 (m, 1H) 1.70-1.85 (m, 3H) 2.03-2.09 (m, 1H) 2.09-2.17 (m, 1H) 2.24-2.44 (m 3H) 2.28 (s, 6H) 2.35-2.37 (m, 3H) 2.48-2.57 (m, 1H) 2.67-2.95 (m, 5H) 3.21 (s, 3H) 3.23-3.27 (m, 1H) 3.29 (s, 3H) 3.34-3.43 (m, 2H) 3.49-3.58 (m, 2H) 3.64 (d, J = 7.79 Hz, 1H) 4.16 (s, 1H) 4.34 (d, J = 7.34 Hz, 1H) 4.50-4.55 (m, 1H) 4.56-4.65 (m, 1H) 4.94 (d, J = 4.58 Hz, 1H), and (600 MHz): 0.76-0.83 (m, 6H) 0.86-0.92 (m, 3H) 1.05 (d, J = 6.42 Hz, 3H) 1.05-1.28 (m 14H) 1.10 (d, J = 7.34 Hz, 3H) 1.32 (s, 3H) 1.49-1.58 (m, 1H) 1.61-1.69 (m, 1H) 1.70-1.85 (m, 3H) 2.03-2.09 (m, 1H) 2.09-2.17 (m, 1H) 2.24-2.44 (m 3H) 2.27 (s, 6H) 2.35-2.37 (m, 3H) 2.48-2.57 (m, 2H) 2.61-2.66 (m, 1H) 2.67-2.95 (m, 3H) 3.21 (s, 3H) 3.27-3.42 (m, 3H) 3.29 (s, 3H) 3.49-3.58 (m, 1H) 3.60-3.65 (m, 1H) 3.68 (d, J = 8.71 Hz, 1H) 4.24 (s, 1H) 4.43 (d, J = 5.50 Hz, 1H) 4.56-4.65 (m, 2H) 4.97 (d, J = 5.04 Hz, 1H) |
| 396 | (isobutyl)amino-ethyl- (Me$_2$CHCH$_2$NH–CH(Et)–) | HO•••••• | 818.8 | (600 MHz): 0.81 (d, J = 6.42 Hz, 6H) 0.84-0.91 (m, 9H) 1.06-1.28 (m, 2H) 1.09 (d, J = 7.34 Hz, 3H) 1.13 (s, 3H) 1.14 (d, J = 4.13 Hz, 3H) 1.15 (d, J = 5.04 Hz, 3H) 1.19 (d, J = 5.96 Hz, 3H) 1.29-1.48 (m, 4H) 1.31 (s, 3H) 1.48-1.57 (m, 1H) 1.59-1.65 (m, 1H) 1.68-1.79 (m, 1H) 1.79-1.89 (m, 2H) 2.04 (d, J = 14.67 Hz, 1H) 2.10-2.19 (m, 1H) 2.21-2.31 (m, 3H) 2.28 (s, 6H) 2.35 (s, 3H) 2.37-2.54 (m, 3H) 2.74-2.81 (m, 2H) 2.90 (d, J = 14.67 Hz, 1H) 3.18-3.22 (m, 1H) 3.22 (s, 3H) 3.28 (s, 3H) 3.36-3.43 (m, 1H) 3.53-3.59 (m, 1H) 3.70 (d, J = 8.25 Hz, 1H) 4.17 (s, 1H) 4.35-4.42 (m, 2H) 4.61 (s, 1H) 4.96 (d, J = 4.58 Hz, 1H) |
| 397 | (isopropylaminoethyl)amino-ethyl- (Me$_2$CHNHCH$_2$CH$_2$NH–CH(Et)–) | HO•••••• | 833.8 | (600 MHz): 0.77-0.83 (m, 6H) 0.88 (t, J = 7.34 Hz, 3H) 1.02-1.06 (m, 6H) 1.06-1.27 (m, 2H) 1.09 (d, J = 7.34 Hz, 3H) 1.13 (s, 3H) 1.13-1.16 (m, 6H) 1.20 (d, J = 6.42 Hz, 3H) 1.30 (s, 3H) 1.49-1.57 (m, 1H) 1.59-1.66 (m, 1H) 1.68-1.89 (m, 3H) 2.04 (d, J = 16.05 Hz, 1H) 2.09-2.19 (m, 1H) 2.21-2.32 (m, 2H) 2.28 (s, 6H) 2.35 (s, 3H) 2.37-2.52 (m, 3H) 2.64-2.80 (m, 6H) 2.82 (d, J = 13.30 Hz, 1H) 2.85-2.93 (m, 1H) 3.17-3.24 (m, 1H) 3.22 (s, 3H) 3.27 (s, 3H) 3.33-3.54 (m, 2H) 3.70 (d, J = 8.25 Hz, 1H) 4.20 (s, 1H) 4.33-4.40 (m, 2H) 4.61 (s, 1H) 4.96 (d, J = 4.59 Hz, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 398 | tetrahydropyran-4-yl-NH-CH(Me)- | HO⋯ | 832.8 | mixture of diastereomers (600 MHz): 0.80 (d, J = 6.88 Hz, 6H) 0.89 (t, J = 7.34 Hz, 3H) 1.09 (d, J = 7.34 Hz, 3H) 1.10-1.42 (m, 4H) 1.13-1.17 (m, 9H) 1.20 (d, J = 5.96 Hz, 3H) 1.31 (s, 3H) 1.49-1.57 (m, 1H) 1.59-1.87 (m, 6H) 2.05 (d, J = 14.67 Hz, 1H) 2.09-2.19 (m, 1H) 2.20-2.32 (m, 2H) 2.28 (s, 6H) 2.36 (s, 3H) 2.37-2.60 (m, 4H) 2.73-2.84 (m, 2H) 2.86-2.93 (m, 1H) 3.18-3.22 (m, 1H) 3.22 (s, 3H) 3.27 (s, 3H) 3.31-3.43 (m, 3H) 3.55-3.62 (m, 1H) 3.69 (d, J = 8.25 Hz, 1H) 3.90-3.98 (m, 2H) 4.19 (s, 1H) 4.35 (d, J = 7.34 Hz, 1H) 4.45 (q, J = 6.27 Hz, 1H) 4.61 (s, 1H) 4.96 (d, J = 4.58 Hz, 1H) |
| 399 | (3-aminopyrrolidin-1-yl)-CH(Me)- | OH | | (600 MHz): 0.89 (d, J = 6.42 Hz, 6H) 0.97 (t, J = 7.34 Hz, 3H) 1.12-1.35 (m, 2H) 1.16 (d, J = 7.34 Hz, 3H) 1.17 (s, 3H) 1.20-1.25 (m, 6H) 1.30 (d, J = 5.96 Hz, 3H) 1.39 (s, 3H) 1.55-1.87 (m, 5H) 1.91 (s, 1H) 1.96 (dd, J = 15.13, 5.04 Hz, 1H) 2.15 (d, J = 14.67 Hz, 1H) 2.20-2.60 (m, 9H) 2.37 (s, 6H) 2.43 (s, 3H) 2.71-3.10 (m, 6H) 3.29 (dd, J = 10.55, 7.34 Hz, 1H) 3.32 (s, 3H) 3.36 (s, 3H) 3.44-3.53 (m, 2H) 3.57-3.63 (m, 1H) 3.78 (d, J = 8.25 Hz, 1H) 4.23 (s, 1H) 4.28 (q, J = 6.42 Hz, 1H) 4.45 (d, J = 7.34 Hz, 1H) 4.70 (s, 1H) 5.06 (d, J = 5.04 Hz, 1H) |
| 400 | (1-benzylpyrrolidin-3-yl)-NH-CH(Me)- | HO⋯ | 907.7 | mixture of diastereomers (600 MHz): 0.80 (d, J = 6.88 Hz, 6H) 0.88 (t, J = 7.34 Hz, 3H) 1.04-1.32 (m, 22H) 1.46-1.87 (m, 5H) 1.98-2.93 (m, 23H) 3.15-3.29 (m, 7H) 3.32-3.60 (m, 4H) 3.65-3.74 (m, 2H) 4.14-4.21 (m, 1H) 4.31-4.40 (m, 2H) 4.55-4.66 (m, 1H) 4.95 (d, J = 5.04 Hz, 1H) 7.20-7.32 (m, 5H) |
| 401 | -CH(Me)-NH-CH₂CH₂-(4-methylpiperazin-1-yl) | HO⋯ | 874.7 | (600 MHz): 0.77-0.91 (m, 9H) 1.06-1.34 (m, 20H) 1.48-1.90 (m, 5H) 2.00-2.59 (m, 28H) 2.66-2.93 (m, 5H) 3.16-3.26 (m, 5H) 3.28 (s, 3H) 3.34-3.56 (m, 2H) 3.70 (d, J = 8.25 Hz, 1H) 4.15-4.23 (m, 1H) 4.34-4.39 (m, 2H) 4.58-4.66 (m, 1H) 4.96 (d, J = 4.59 Hz, 1H) |
| 402 | -CH(Me)-NH-(pyrrolidin-3-yl) | HO⋯ | 817.6 | mixture of diastereomers (600 MHz); 0.76-0.84 (m, 6H) 0.89 (t, J = 7.34 Hz, 3H) 1.05-1.27 (m, 17H) 1.31 (s, 3H) 1.40-2.07 (m, 7H) 2.09-2.58 (m, 14H) 2.62-3.04 (m, 8H) 3.14-3.24 (m, 5H) 3.27 (s, 3H) 3.34-3.58 (m, 3H) 3.67-3.72 (m, 1H) 4.16-4.24 (m, 1H) 4.33-4.47 (m, 2H) 4.56-4.65 (m, 1H) 4.94-4.98 (m, 1H) |
| 403 | -CH(Me)-NH-CH₂CH₂-(4-benzyloxycarbonylpiperazin-1-yl) | HO⋯ | 994.7 | (600 MHz): 0.77-0.84 (m, 6H) 0.88 (t, J = 7.34 Hz, 3H) 1.06-1.26 (m, 17H) 1.30 (s, 3H) 1.47-1.89 (m, 5H) 2.03 (d, J = 14.67 Hz, 1H) 2.10-2.51 (m, 20H) 2.63-2.93 (m, 5H) 3.17-3.29 (m, 8H) 3.35-3.55 (m, 6H) 3.69 (d, J = 8.25 Hz, 1H) 4.14-4.23 (m, 1H) 4.33-4.40 (m, 2H) 4.56-4.65 (m, 1H) 4.96 (d, J = 5.04 Hz, 1H) 5.11 (s, 2H) 7.27-7.37 (m, 5H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 404 | –CH(CH₃)–NH–CH₂CH₂–piperazinyl(NH) | HO⟋ (axial) | 860.6 | (600 MHz): 0.76-0.84 (m, 6H) 0.89 (t, J = 7.34 Hz, 3H) 1.06-1.33 (m, 20H) 1.48-1.90 (m, 5H) 2.04 (d, J = 15.13 Hz, 1H) 2.11-2.53 (m, 22H) 2.66-2.93 (m, 8H) 3.18-3.25 (m, 4H) 3.28 (s, 3H) 3.35-3.56 (m, 2H) 3.70 (d, J = 7.79 Hz, 1H) 4.15-4.22 (m, 1H) 4.34-4.40 (m, 2H) 4.58-4.66 (m, 1H) 4.96 (d, J = 4.59 Hz, 1H) |
| 405 | H₂N–CH(CH₃)– | HO– | 748.4 | (600 MHz): 0.78-0.82 (m, 6H) 0.88 (t, J = 7.34 Hz, 3H) 1.09 (d, J = 7.34 Hz, 3H) 1.14 (d, J = 7.34 Hz, 3H) 1.16 (s, 3H) 1.16-1.17 (m, 1H) 1.17-1.19 (m, 1H) 1.20 (d, J = 5.96 Hz, 3H) 1.24 (d, J = 6.88 Hz, 3H) 1.31 (s, 3H) 1.49-1.57 (m, 1H) 1.62-1.85 (m, 3H) 1.88 (dd, J = 15.36, 5.27 Hz, 1H) 2.10-2.27 (m, 2H) 2.24 (d, J = 15.13 Hz, 1H) 2.29 (s, 6H) 2.30-2.32 (m, 1H) 2.36 (s, 3H) 2.38-2.44 (m, 1H) 2.49-2.55 (m, 1H) 2.77-2.99 (m, 4H) 3.17-3.20 (m, 1H) 3.21 (s, 3H) 3.34 (s, 3H) 3.37-3.44 (m, 1H) 3.48-3.57 (m, 1H) 3.67 (d, J = 7.79 Hz, 1H) 4.06-4.14 (m, 1H) 4.40 (d, J = 6.88 Hz, 1H) 4.48 (q, J = 6.88 Hz, 1H) 4.58-4.68 (m, 1H) 4.88 (d, J = 4.59 Hz, 1H) |
| 406 | 3-aminopyrrolidin-1-yl-CH(CH₃)– | –OH | | (600 MHz): 0.79 (d, J = 6.42 Hz, 6H) 0.87 (t, J = 7.34 Hz, 3H) 1.04-1.25 (m, 2H) 1.07 (d, J = 7.34 Hz, 3H) 1.08 (s, 3H) 1.12 (d, J = 6.42 Hz, 3H) 1.14 (d, J = 7.79 Hz, 3H) 1.20 (d, J = 5.96 Hz, 3H) 1.29 (s, 3H) 1.44-1.91 (m, 7H) 2.05 (d, J = 15.13 Hz, 1H) 2.10-2.53 (m, 9H) 2.27 (s, 6H) 2.33 (s, 3H) 2.63-2.98 (m, 6H) 3.16-3.21 (m, 1H) 3.22 (s, 3H) 3.27 (s, 3H) 3.35-3.43 (m, 2H) 3.47-3.53 (m, 1H) 3.68 (d, J = 8.25 Hz, 1H) 4.14 (s, 1H) 4.18 (q, J = 6.11 Hz, 1H) 4.35 (d, J = 7.34 Hz, 1H) 4.61 (s, 1H) 4.96 (d, J = 5.04 Hz, 1H) |
| 407 | Me–O–CH(CH₃)– | 763.2 | 763.2 | (600 MHz): 0.77-0.83 (m, 6H) 0.88 (t, J = 7.34 Hz, 3H) 1.08 (d, J = 7.34 Hz, 3H) 1.14 (d, J = 7.34 Hz, 3H) 1.15-1.17 (m, 1H) 1.17 (s, 3H) 1.20 (d, J = 5.96 Hz, 3H) 1.21-1.25 (m, 1H) 1.26 (d, J = 6.42 Hz, 3H) 1.31 (s, 3H) 1.48-1.57 (m, 1H) 1.62-1.83 (m, 3H) 1.83 (dd, J = 15.13, 5.04 Hz, 1H) 2.05-2.24 (m, 2H) 2.22 (d, J = 15.13 Hz, 1H) 2.27-2.30 (m, 1H) 2.32 (s, 6H) 2.36 (s, 3H) 2.39-2.46 (m, 1H) 2.50-2.58 (m, 1H) 2.77-2.85 (m, 1H) 2.89-2.96 (m, 1H) 3.07 (s, 1H) 3.20 (s, 3H) 3.20-3.24 (m, 1H) 3.34 (s, 3H) 3.34 (s, 3H) 3.37-3.43 (m, 1H) 3.46-3.55 (m, 2H) 3.52 (d, J = 4.58 Hz, 1H) 3.66 (d, J = 7.79 Hz, 1H) 4.05-4.11 (m, 1H) 4.37-4.46 (m, 2H) 4.56-4.66 (m, 1H) 4.90 (d, J = 5.04 Hz, 1H) |
| 408 | Me–S–CH(CH₃)– | HO– | 779.4 | (600 MHz): 0.72-0.78 (m, 6H) 0.84 (t, J = 7.34 Hz, 3H) 1.02 (d, J = 7.34 Hz, 3H) 1.04-1.08 (m, 1H) 1.10 (d, J = 7.34 Hz, 3H) 1.14-1.18 (m, 6H) 1.17-1.20 (m, 1H) 1.22 (d, J = 6.42 Hz, 3H) 1.26 (s, 3H) 1.45-1.54 (m, 1H) 1.56-1.77 (m, 3H) 1.80 (dd, J = 15.13, 5.04 Hz, 1H) 2.06-2.10 (m, 6H) 2.13-2.43 (m, 7H) 2.67 (d, J = 13.76 Hz, 1H) 2.71-2.81 (m, 2H) 2.83-2.90 (m, 1H) 3.13-3.16 (m, 9H) 3.17-3.23 (m, 1H) 3.29 (s, 3H) 3.30-3.35 (m, 1H) 3.44-3.52 (m, 1H) 3.62-3.67 (m, 1H) 4.01-4.09 (m, 1H) 4.36 (d, J = 7.34 Hz, 1H) 4.39 (q, J = 6.57 Hz, 1H) 4.53-4.61 (m, 1H) 4.83 (d, J = 4.13 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 409 | Me-NH-CH(Me)- | HO- | 762.5 | (600 MHz): 0.78-0.82 (m, 6H) 0.89 (t, J = 7.34 Hz, 3H) 1.09 (d, J = 7.34 Hz, 3H) 1.10-1.11 (m, 1H) 1.14 (d, J = 7.34 Hz, 3H) 1.17 (s, 3H) 1.17-1.19 (m, 1H) 1.20 (d, J = 5.96 Hz, 3H) 1.23 (d, J = 6.88 Hz, 3H) 1.32 (s, 3H) 1.50-1.57 (m, 1H) 1.61-1.87 (m, 3H) 2.13 (m, 1H) 2.20 (d, J = 15.13 Hz, 1H) 2.23-2.26 (m, 2H) 2.26-2.22 (m, 7H) 2.36 (s, 3H) 2.38 (s, 3H) 2.39-2.45 (m, 1H) 2.45-2.54 (m, 1H) 2.69-2.73 (m, 2H) 2.77-2.83 (m, 1H) 2.87-2.94 (m, 1H) 3.17-3.20 (m, 1H) 3.20 (s, 3H) 3.34 (s, 3H) 3.38-3.45 (m, 1H) 3.46-3.53 (m, 1H) 3.66 (d, J = 7.34 Hz, 1H) 4.05-4.12 (m, 1H) 4.39 (d, J = 7.34 Hz, 1H) 4.43 (q, J = 6.42 Hz, 1H) 4.58-4.66 (m, 1H) 4.87 (d, J = 4.58 Hz, 1H) |
| 410 | Me$_2$N-CH(Me)- | HO- | 776.5 | (600 MHz): 0.77-0.83 (m, 6H) 0.88 (t, J = 7.34 Hz, 3H) 1.09 (d, J = 7.34 Hz, 3H) 1.12-1.17 (m, 8H) 1.16 (s, 3H) 1.19 (d, J = 6.42 Hz, 3H) 1.32 (s, 3H) 1.46 (dd, J = 15.36, 5.27 Hz, 1H) 1.49-1.57 (m, 1H) 1.63-1.87 (m, 3H) 2.15-2.24 (m, 4H) 2.25-2.33 (m, 7H) 2.34-2.37 (m, 9H) 2.39-2.45 (m, 1H) 2.55-2.64 (m, 1H) 2.74 (d, J = 14.67 Hz, 1H) 2.77-2.83 (m, 1H) 2.87-2.92 (m, 1H) 3.16-3.21 (m, 1H) 3.21 (s, 3H) 3.35 (s, 3H) 3.37-3.43 (m, 1H) 3.59-3.66 (m, 1H) 3.68 (d, J = 7.79 Hz, 1H) 4.04-4.09 (m, 1H) 4.45 (d, J = 7.34 Hz, 1H) 4.59 (q, J = 6.72 Hz, 1H) 4.61-4.66 (m, 1H) 4.82 (d, J = 5.04 Hz, 1H) |
| 411 | oxazolidine-2-thione | | 790.4 | (600 MHz): 0.77-0.93 (m, 9H) 1.08-1.16 (m, 6H) 1.15-1.18 (m, 1H) 1.19 (d, J = 6.42 Hz, 3H) 1.21-1.25 (m, 7H) 1.31 (s, 3H) 1.33-1.43 (m, 1H) 1.51-1.58 (m, 1H) 1.69-1.88 (m, 3H) 2.13-2.49 (m, 14H) 2.54-2.63 (m, 1H) 2.80-2.92 (m, 2H) 3.15-3.21 (m, 1H) 3.21 (s, 3H) 3.37 (s, 3H) 3.39-3.48 (m, 2H) 3.60-3.66 (m, 2H) 3.83 (d, J = 10.55 Hz, 1H) 4.13-4.19 (m, 1H) 4.45 (d, J = 6.88 Hz, 1H) 4.63-4.71 (m, 1H) 4.90 (d, J = 5.04 Hz, 1H) 4.91-4.95 (m, 1H) |
| 412 | H$_2$N-CH$_2$CH$_2$-NH-CH(Me)- | HO- | 791.7 | (500 MHz): 0.80 (d, J = 6.86 Hz, 6H) 0.88 (t, J = 7.40 Hz, 3H) 1.06-1.26 (m, 17H) 1.31 (s, 3H) 1.47-1.88 (m, 4H) 2.26 (s, 6H) 2.26 (s, 6H) 2.36 (s, 3H) 2.37-2.57 (m, 3H) 2.65-2.84 (m, 5H) 2.86-2.93 (m, 1H) 3.14-3.23 (m, 1H) 3.20 (s, 3H) 3.34 (s, 3H) 3.37-3.54 (m, 2H) 3.66 (d, J = 7.95 Hz, 1H) 4.05-4.14 (m, 1H) 4.33-4.48 (m, 2H) 4.58-4.67 (m, 1H) 4.85 (m, 2H) 4.58-4.67 (m, 1H) 4.85-4.89 (m, 1H) |
| 413 | H$_2$N-(CH$_2$)$_3$-NH-CH(Me)- | HO- | 805.7 | (500 MHz): 0.80 (d, J = 6.86 Hz, 6H) 0.88 (t, J = 7.40 Hz, 3H) 1.05-1.24 (m, 17H) 1.31 (s, 3H) 1.47-1.88 (m, 6H) 2.08-2.33 (m, 5H) 2.28 (s, 6H) 2.35 (s, 3H) 2.37-2.59 (m, 3H) 2.63-2.84 (m, 6H) 2.85-2.94 (m, 1H) 3.09-3.24 (m, 1H) 3.20 (s, 3H) 3.34 (s, 3H) 3.36-3.55 (m, 2H) 3.66 (d, J = 7.95 Hz, 1H) 4.04-4.13 (m, 1H) 4.34-4.47 (m, 2H) 4.54-4.68 (m, 1H) 4.86 (d, J = 4.66 Hz, 1H) |
| 414 | H$_2$N-(CH$_2$)$_4$-NH-CH(Me)- | HO- | 819.7 | (500 MHz): 0.80 (d, J = 6.58 Hz, 6H) 0.88 (t, J = 7.27 Hz, 3H) 1.04-1.25 (m, 17H) 1.31 (s, 3H) 1.39-1.88 (m, 8H) 2.08-2.33 (m, 6H) 2.26 (s, 6H) 2.35 (s, 3H) 2.37-2.64 (m, 4H) 2.65-2.94 (m, 5H) 3.15-3.23 (m, 1H) 3.20 (s, 3H) 3.34 (s, 3H) 3.37-3.68 (m, 3H) 3.99-4.14 (m, 1H) 4.33-4.50 (m, 2H) 4.58-4.68 (m, 1H) 4.83-4.89 (m, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 415 | HO-CH₂CH₂-NH- (attached) | HO- | 792.7 | (500 MHz): 0.80 (d, J = 6.86 Hz, 9H) 0.89 (t, J = 7.40 Hz, 3H) 1.05-1.12 (m, 4H) 1.12-1.22 (m, 10H) 1.23-1.28 (m, 3H) 1.31 (s, 3H) 1.48-1.66 (m, 2H) 1.68-1.88 (m, 2H) 2.26 (s, 5H) 2.26 (s, 6H) 2.36 (s, 3H) 2.38-2.50 (m, 2H) 2.59-2.67 (m, 1H) 2.74-2.93 (m, 5H) 3.14-3.26 (m, 2H) 3.34 (s, 3H) 3.36-3.68 (m, 4H) 4.06-4.16 (m, 1H) 4.37 (d, J = 7.13 Hz, 1H) 4.44 (d, 1H) 4.58-4.67 (m, 1H) 4.89 (d, J = 4.66 Hz, 1H) |
| 416 | piperidin-1-yl | HO- | 816.7 | (500 MHz): 0.81 (d, J = 7.13 Hz, 6H) 0.88 (t, J = 7.27 Hz, 3H) 1.07-1.16 (m, 13H) 1.16-1.22 (m, 4H) 1.32 (s, 3H) 1.36-1.89 (m, 12H) 2.10-2.33 (m, 6H) 2.26 (s, 6H) 2.35 (s, 3H) 2.39-2.48 (m, 1H) 2.50-2.66 (m, 2H) 2.70 (d, J = 14.54 Hz, 1H) 2.85 (d, 2H) 3.14-3.30 (m, 2H) 3.22 (s, 3H) 3.36 (s, 3H) 3.38-3.47 (m, 1H) 3.60-3.72 (m, 2H) 4.02-4.10 (m, 1H) 4.47 (d, J = 7.13 Hz, 1H) 4.59-4.67 (m, 2H) 4.82 (d, J = 5.21 Hz, 1H) |
| 417 | HO-(CH₂)₃-NH- | HO- | 806.7 | (500 MHz): 0.80 (d, J = 6.87 Hz, 6H) 0.89 (t, J = 7.44 Hz, 3H) 1.04-1.26 (m, 17H) 1.31 (s, 3H) 1.48-1.85 (m, 6H) 1.90-1.97 (m, 1H) 2.18-2.34 (m, 4H) 2.26 (s, 6H) 2.36 (s, 3H) 2.37-2.49 (m, 2H) 2.64-2.96 (m, 6H) 3.12-3.26 (m, 2H) 3.19 (s, 2H) 3.33 (s, 3H) 3.35-3.51 (m, 2H) 3.65 (d, J = 8.01 Hz, 1H) 3.75-3.79 (m, 2H) 4.07-4.16 (m, 1H) 4.33-4.47 (m, 2H) 4.57-4.66 (m, 1H) 4.88 (d, J = 4.58 Hz, 1H) |
| 418 | piperazin-1-yl | HO- | 817.8 | (500 MHz): 0.80 (d, J = 6.88 Hz, 6H) 0.88 (t, J = 7.26 Hz, 3H) 1.03-1.22 (m, 17H) 1.31 (s, 3H) 1.46-1.88 (m, 6H) 2.25 (s, 4H) 2.25 (s, 6H) 2.35 (s, 3H) 2.37-2.46 (m, 1H) 2.48-2.74 (m, 5H) 2.76-2.93 (m, 6H) 3.12-3.24 (m, 1H) 3.21 (s, 3H) 3.35 (s, 3H) 3.37-3.45 (m, 1H) 3.56-3.65 (m, 1H) 3.68 (d, J = 7.65 Hz, 1H) 4.01-4.11 (m, 1H) 4.28-4.37 (m, 1H) 4.45 (d, J = 7.65 Hz, 1H) 4.54-4.68 (m, 2H) 4.83 (d, J = 5.35 Hz, 1H) |
| 419 | Me₂N-CH₂CH₂-NH- | HO- | 819.7 | (500 MHz): 0.80 (d, J = 6.86 Hz, 6H) 0.88 (t, J = 7.27 Hz, 3H) 1.03-1.27 (m, 17H) 1.31 (s, 3H) 1.47-1.94 (m, 5H) 1.97-2.07 (m, 1H) 2.09-2.45 (m, 6H) 2.20 (s, 6H) 2.26 (s, 7H) 2.35 (s, 3H) 2.45-2.53 (m, 1H) 2.58-2.74 (m, 3H) 2.75-2.84 (m, 2H) 2.85-2.94 (m, 1H) 3.13-3.29 (m, 1H) 3.21 (s, 3H) 3.34 (s, 3H) 3.37-3.56 (m, 2H) 3.67 (d, J = 7.95 Hz, 1H) 4.04-4.14 (m, 1H) 4.36-4.51 (m, 2H) 4.57-4.69 (m, 1H) 4.86 (d, J = 4.94 Hz, 1H) |
| 420 | HO-(CH₂)₄-NH- | HO- | 820.7 | (500 MHz): 0.80 (d, J = 6.88 Hz, 6H) 0.89 (t, J = 7.26 Hz, 3H) 1.04-1.28 (m, 17H) 1.32 (s, 3H) 1.47-1.88 (m, 8H) 1.98-2.19 (m, 2H) 2.17-2.55 (m, 6H) 2.27 (s, 6H) 2.36 (s, 3H) 2.67-2.96 (m, 5H) 3.14-3.26 (m, 1H) 3.20 (s, 3H) 3.34 (s, 3H) 3.32-3.53 (m, 2H) 3.53-3.69 (m, 3H) 4.04-4.16 (m, 1H) 4.32-4.48 (m, 2H) 4.56-4.68 (m, 1H) 4.89 (d, J = 5.35 Hz, 1H) |

TABLE 11-continued formula (W)

| Example | R^1W | R^2W | ESI MS (M + H) | ^1H-NMR, CDCl_3, δ (ppm) |
|---|---|---|---|---|
| 421 | morpholine-N-CH_2- | HO- | 818.7 | (500 MHz): 0.80 (d, J = 7.13 Hz, 6H) 0.88 (t, J = 7.40 Hz, 3H) 1.06-1.22 (m, 17H) 1.31 (s, 3H) 1.47-1.90 (m, 5H) 2.10-2.37 (m, 5H) 2.26 (s, 6H) 2.35 (s, 3H) 2.37-2.46 (m, 1H) 2.47-2.61 (m, 3H) 2.62-2.93 (m, 5H) 3.15-3.25 (m, 1H) 3.21 (s, 3H) 3.35 (s, 3H) 3.37-3.44 (m, 1H) 3.54-3.63 (m, 1H) 3.64-3.70 (m, 5H) 4.02-4.13 (m, 1H) 4.43 (d, J = 7.13 Hz, 1H) 4.53-4.67 (m, 2H) 4.84 (d, J = 4.94 Hz, 1H) |
| 422 | MeO-CH_2CH_2-NH- | HO- | 806.7 | (500 MHz): 0.80 (d, J = 7.13 Hz, 6H) 0.88 (t, J = 7.40 Hz, 3H) 1.05-1.24 (m, 17H) 1.31 (s, 3H) 1.47-1.87 (m, 4H) 1.99-2.54 (m, 7H) 2.25 (s, 6H) 2.35 (s, 3H) 2.67-2.94 (m, 5H) 3.13-3.24 (m, 1H) 3.20 (s, 3H) 3.33 (s, 3H) 3.34 (s, 3H) 3.37-3.55 (m, 5H) 3.67 (d, J = 7.68 Hz, 1H) 4.05-4.13 (m, 1H) 4.39 (d, J = 7.13 Hz, 1H) 4.46 (q, J = 6.58 Hz, 1H) 4.56-4.69 (m, 1H) 4.85 (d, J = 4.66 Hz, 1H) |
| 423 | HO-CH_2CH_2-N(Me)- | HO- | 806.7 | (500 MHz): 0.80 (d, J = 6.88 Hz, 6H) 0.88 (t, J = 7.26 Hz, 3H) 1.06-1.28 (m, 17H) 1.32 (s, 3H) 1.49-1.87 (m, 5H) 2.10-2.52 (m, 7H) 2.26 (s, 6H) 2.34-2.36 (m, 3H) 2.36 (s, 3H) 2.58-2.66 (m, 1H) 2.69-2.93 (m, 4H) 3.15-3.29 (m, 1H) 3.21 (s, 3H) 3.34 (s, 3H) 3.37-3.70 (m, 5H) 4.06-4.11 (m, 1H) 4.40 (d, J = 7.65 Hz, 1H) 4.50 (q, J = 6.88 Hz, 1H) 4.59-4.67 (m, 1H) 4.86 (d, J = 4.59 Hz, 1H) |
| 424 | Me-CH_2CH_2CH_2-NH- | HO- | 804.7 | (500 MHz): 0.80 (d, J = 6.88 Hz, 6H) 0.85-0.92 (m, 6H) 1.05-1.25 (m, 17H) 1.27-1.36 (m, 5H) 1.38-1.47 (m, 2H) 1.48-1.88 (m, 4H) 2.06-2.61 (m, 9H) 2.26 (s, 6H) 2.35 (s, 3H) 2.66-2.84 (m, 3H) 2.86-2.94 (m, 1H) 3.15-3.25 (m, 1H) 3.21 (s, 3H) 3.32-3.55 (m, 2H) 3.34 (s, 3H) 3.66 (d, J = 8.41 Hz, 1H) 4.04-4.14 (m, 1H) 4.37-4.49 (m, 2H) 4.58-4.69 (m, 1H) 4.86 (d, J = 4.59 Hz, 1H) |
| 425 | N≡C-CH_2CH_2-NH- | HO- | 801.6 | (500 MHz): 0.81 (d, J = 6.88 Hz, 6H) 0.90 (t, J = 7.26 Hz, 3H) 1.07-1.29 (m, 17H) 1.32 (s, 3H) 1.49-1.88 (m, 5H) 2.10-2.55 (m, 8H) 2.31 (s, 6H) 2.37 (s, 3H) 2.66-3.02 (m, 6H) 3.15-3.51 (m, 3H) 3.21 (s, 3H) 3.35 (s, 3H) 3.66 (d, J = 7.65 Hz, 1H) 4.08-4.16 (m, 1H) 4.36-4.45 (m, 2H) 4.58-4.68 (m, 1H) 4.89 (d, J = 4.59 Hz, 1H) |
| 426 | Ph-CH_2-NH- | HO- | 838.6 | (500 MHz): 0.80 (d, J = 6.86 Hz, 6H) 0.89 (t, J = 7.40 Hz, 3H) 1.06-1.23 (m, 17H) 1.32 (s, 3H) 1.49-1.86 (m, 4H) 2.26 (s, 5H) 2.26 (s, 6H) 2.36 (s, 3H) 2.38-2.51 (m, 2H) 2.67-2.84 (m, 3H) 2.86-2.94 (m, 1H) 3.15-3.22 (m, 1H) 3.20 (s, 3H) 3.33 (s, 3H) 3.38-3.52 (m, 2H) 3.63-3.80 (m, 3H) 4.06-4.13 (m, 1H) 4.34-4.45 (m, 2H) 4.58-4.68 (m, 1H) 4.88 (d, J = 4.66 Hz, 1H) 7.20-7.35 (m, 5H) |
| 427 | (pyridin-3-yl)-CH_2-NH- | HO- | 839.6 | (500 MHz): 0.80 (d, J = 7.13 Hz, 6H) 0.89 (t, J = 7.40 Hz, 3H) 1.04-1.35 (m, 20H) 1.46-1.95 (m, 4H) 2.07-2.48 (m, 7H) 2.26 (s, 6H) 2.36 (s, 3H) 2.66 (d, J = 12.07 Hz, 1H) 2.76-2.84 (m, 2H) 2.85-2.93 (m, 1H) 3.14-3.49 (m, 4H) 3.19 (s, 3H) 3.33 (s, 3H) 3.61-3.69 (m, 2H) 3.80 (d, J = 13.44 Hz, 1H) 4.06-4.15 (m, 1H) 4.33-4.44 (m, 2H) 4.58-4.67 (m, 1H) 4.88 (d, J = 4.94 Hz, 1H) 7.21-7.25 (m, 1H) 7.59-7.64 (m, 1H) 8.45-8.58 (m, 2H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 428 | (imidazol-1-ylmethyl) | HO— (with Me) | 799.6 | (500 MHz): 0.76-0.84 (m, 6H) 0.86-0.92 (m, 6H) 1.04-1.27 (m, 14H) 1.30 (s, 3H) 1.50-1.87 (m, 5H) 2.09-2.56 (m, 6H) 2.32 (s, 6H) 2.37 (s, 3H) 2.79-2.95 (m, 2H) 3.16-3.25 (m, 1H) 3.19 (s, 3H) 3.32 (s, 3H) 3.34-3.46 (m, 2H) 3.63 (d, J = 7.64 Hz, 1H) 4.11-4.29 (m, 3H) 4.35 (d, J = 6.88 Hz, 1H) 4.48-4.68 (m, 2H) 4.98 (d, J = 4.59 Hz, 1H) 7.00 (s, 1H) 7.07-7.10 (m, 1H) 7.60 (s, 1H) |
| 429 | (phenylamino-methyl) | HO— (with Me) | 824.7 | (500 MHz): 0.81 (d, J = 6.88 Hz, 6H) 0.91 (t, J = 7.26 Hz, 3H) 1.06-1.36 (m, 20H) 1.51-1.89 (m, 4H) 2.01-2.55 (m, 7H) 2.31 (s, 6H) 2.38 (s, 3H) 2.79-2.88 (m, 1H) 2.89-2.97 (m, 1H) 3.14-3.52 (m, 5H) 3.23 (s, 3H) 3.37 (s, 3H) 3.68 (d, J = 8.03 Hz, 1H) 4.17-4.25 (m, 1H) 4.39 (d, J = 7.26 Hz, 1H) 4.50 (q, J = 6.75 Hz, 1H) 4.60-4.69 (m, 1H) 5.01 (d, J = 4.97 Hz, 1H) 6.62 (d, J = 8.03 Hz, 2H) 6.69 (t, J = 7.26 Hz, 1H) 7.18 (t, J = 7.84 Hz, 2H) |
| 430 | (oxazolidin-2-one-yl) |  | 774.6 | (500 MHz): 0.77-0.93 (m, 9H) 1.07-1.28 (m, 17H) 1.32 (s, 3H) 1.40-1.89 (m, 4H) 2.10-2.61 (m, 7H) 2.29 (s, 6H) 2.35 (s, 3H) 2.75-2.92 (m, 2H) 3.14-3.45 (m, 3H) 3.22 (s, 3H) 3.38 (s, 3H) 3.57-3.71 (m, 3H) 4.10-4.19 (m, 1H) 4.43-4.49 (m, 1H) 4.57-4.69 (m, 1H) 4.86-4.93 (m, 2H) 5.00-5.04 (m, 1H) |
| 431 | [complex: –CH(Me)–NH–CH₂CH₂–N(Et)–CH(Me)–(2-methoxyphenyl)] | —OH | 954.0 | (600 MHz): 0.82 (m, 6H) 0.89 (t, J = 7.34 Hz, 3H) 0.94 (t, J = 7.11 Hz, 3H) 1.11-1.29 (m, 17H) 1.27 (d, J = 6.88 Hz, 3H) 1.31 (s, 3H) 1.48-1.75 (m, 3H) 1.80-1.85 (m, 1H) 1.88 (dd, J = 15.13, 5.04 Hz, 1H) 2.04 (d, J = 14.67 Hz, 1H) 2.11-2.19 (m, 1H) 2.25-2.30 (m, 2H) 2.27 (s, 6H) 2.36 (s, 3H) 2.36-2.66 (m, 9H) 2.74-2.81 (m, 2H) 2.86-2.94 (m, 1H) 3.18-3.22 (m, 1H) 3.23 (s, 3H) 3.27 (s, 3H) 3.35-3.42 (m, 1H) 3.43-3.48 (m, 1H) 3.71 (d, J = 8.25 Hz, 1H) 3.80 (s, 3H) 4.15-4.22 (m, 1H) 4.26-4.32 (m, 1H) 4.33-4.39 (m, 2H) 4.59-4.66 (m, 1H) 4.97 (d, J = 5.04 Hz, 1H) 6.84 (d, J = 8.25 Hz, 1H) 6.89-6.94 (m, 1H) 7.17-7.22 (m, 1H) 7.29-7.33 (m, 1H) |
| 432 | [3-hydroxyphenyl-CH(Me)-NH-CH₂CH₂-NH-] | HO— (with Me) | 911.9 | mixture of diastereomers (600 MHz): 0.80-0.88 (m, 6H) 0.89-0.95 (m, 3H) 1.08-1.39 (m, 23H) 1.49-1.91 (m, 4H) 2.09-2.73 (m, 12H) 2.29 (s, 6H) 2.38 (s, 3H) 2.75-2.96 (m, 3H) 3.15-3.56 (m, 9H) 3.63-3.77 (m, 2H) 4.13-4.21 (m, 1H) 4.36-4.48 (m, 2H) 4.66-4.75 (m, 1H) 4.89-4.95 (m, 1H) 6.70-6.90 (m, 3H) 7.15 (t, J = 7.79 Hz, 1H) |
| 433 | [–CH(Me)–NH–CH₂CH₂–NH–CH(Me)–(3-hydroxyphenyl)] | —OH | 911.9 | (600 MHz): 0.82 (d, J = 6.42 Hz, 6H) 0.90 (t, J = 7.34 Hz, 3H) 1.03-1.28 (m, 2H) 1.10 (d, J = 7.34 Hz, 3H) 1.13 (s, 3H) 1.17 (d, J = 7.79 Hz, 3H) 1.20 (d, J = 5.96 Hz, 3H) 1.26 (d, J = 6.42 Hz, 3H) 1.29-1.34 (m, 6H) 1.50-1.60 (m, 1H) 1.60-1.68 (m, 1H) 1.70-1.90 (m, 2H) 2.07-2.46 (m, 6H) 2.27 (s, 6H) 2.36 (s, 3H) 2.46-2.73 (m, 7H) 2.79-2.83 (m, 1H) 2.86-2.93 (m, 1H) 3.19-3.23 (m, 1H) 3.23 (s, 3H) 3.33 (s, 3H) 3.37-3.44 (m, 1H) 3.46-3.55 (m, 1H) 3.65-3.77 (m, 2H) 4.16 (s, 1H) 4.40 (d, J = 7.34 Hz, 1H) 4.44 (q, J = 6.88 Hz, 1H) 4.67 (s, 1H) 4.89 (d, J = 5.04 Hz, 1H) 6.71 (dd, J = 8.02, 2.52 Hz, 1H) 6.75 (d, J = 7.79 Hz, 1H) 6.84-6.88 (m, 1H) 7.13 (t, J = 7.79 Hz, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 434 | (4-nitrophenyl-CH(OH)-CH(NH-CH₂-)-CH₂OH) | -OH | 944.0 | (500 MHz): 0.77-0.85 (m, 6H) 0.90 (t, J = 7.40 Hz, 3H) 1.04-1.26 (m, 17H) 1.30 (s, 3H) 1.50-1.87 (m, 4H) 1.97-2.03 (m, 1H) 2.10-2.52 (m, 6H) 2.25 (s, 6H) 2.37 (s, 3H) 2.61-2.69 (m, 2H) 2.77-2.96 (m, 3H) 3.14-3.23 (m, 1H) 3.15 (s, 3H) 3.29-3.46 (m, 3H) 3.33 (s, 3H) 3.60-3.67 (m, 2H) 4.09-4.17 (m, 1H) 4.33 (d, J = 7.13 Hz, 1H) 4.41 (q, J = 6.40 Hz, 1H) 4.59-4.68 (m, 1H) 4.81 (d, J = 6.31 Hz, 1H) 4.89 (d, J = 4.94 Hz, 1H) 7.57 (d, J = 8.78 Hz, 2H) 8.19 (d, J = 8.78 Hz, 2H) |
| 435 | (4-nitrophenyl-CH(OH)-CH(NH-(CH₂)₄-NH-CH₂-)-CH₂OH) | -OH | | (500 MHz): 0.80 (d, J = 6.86 Hz, 6H) 0.88 (t, J = 7.40 Hz, 3H) 1.05-1.37 (m, 22H) 1.39-1.88 (m, 8H) 2.07-2.32 (m, 11H) 2.32-2.92 (m, 13H) 3.15-3.23 (m, 4H) 3.31-3.43 (m, 5H) 3.46-3.74 (m, 4H) 4.05-4.13 (m, 1H) 4.37-4.48 (m, 2H) 4.58-4.71 (m, 2H) 4.86 (d, J = 4.66 Hz, 1H) 7.58 (d, J = 8.50 Hz, 2H) 8.17-8.21 (m, 2H) |
| 436 | (4-nitrophenyl-CH(OH)-CH(NH-(CH₂)₆-NH-CH₂-)-CH₂OH) | -OH | 1042.8 | (500 MHz): 0.73-0.83 (m, 6H) 0.84-0.90 (m, 3H) 1.03-1.87 (m, 32H) 1.91-1.96 (m, 4H) 2.04-2.91 (m, 20H) 3.11-3.30 (m, 4H) 3.30-3.42 (m, 5H) 3.45-3.55 (m, 1H) 3.63-3.72 (m, 2H) 4.04-4.10 (m, 1H) 4.35-4.47 (m, 2H) 4.55-4.71 (m, 2H) 4.83-4.86 (m, 1H) 5.68-5.76 (m, 1H) 7.56-7.60 (m, 2H) 8.17 (d, J = 8.78 Hz, 2H) |
| 437 | (4-nitrophenyl-CH(OH)-CH(NH-(CH₂)₂-NH-CH₂-)-CH₂OH) | -OH | 987.0 | (600 MHz): 0.82 (d, J = 6.42 Hz, 6H) 0.89 (t, J = 7.34 Hz, 3H) 1.10 (d, J = 7.34 Hz, 3H) 1.10-1.22 (m, 2H) 1.17 (d, J = 7.79 Hz, 3H) 1.18 (s, 3H) 1.22 (d, J = 5.96 Hz, 3H) 1.28 (d, J = 6.88 Hz, 3H) 1.34 (s, 3H) 1.51-1.87 (m, 5H) 2.11-2.26 (m, 3H) 2.28 (s, 6H) 2.30-2.35 (m, 1H) 2.37 (s, 3H) 2.41-2.46 (m, 1H) 2.46-2.51 (m, 1H) 2.56-2.91 (m, 10H) 3.20-3.24 (m, 4H) 3.36 (s, 3H) 3.38-3.43 (m, 2H) 3.45-3.50 (m, 1H) 3.64-3.68 (m, 2H) 4.11-4.17 (m, 1H) 4.38 (d, J = 6.88 Hz, 1H) 4.43-4.48 (m, 1H) 4.59-4.64 (m, 1H) 4.69 (d, J = 6.42 Hz, 1H) 4.94 (d, J = 4.58 Hz, 1H) 7.60 (d, J = 8.71 Hz, 2H) 8.20 (d, J = 8.71 Hz, 2H) |
| 438 | (4-nitrophenyl-CH(OH)-CH(NH-(CH₂)₃-NH-CH₂-)-CH₂OH) | -OH | 1001.1 | (600 MHz): 0.82 (d, J = 6.42 Hz, 6H) 0.89 (t, J = 7.34 Hz, 3H) 1.10 (d, J = 7.34 Hz, 3H) 1.10-1.25 (m, 2H) 1.17 (d, J = 7.79 Hz, 3H) 1.18 (s, 3H) 1.22 (d, J = 5.96 Hz, 3H) 1.27 (d, J = 6.42 Hz, 3H) 1.33 (s, 3H) 1.51-1.87 (m, 7H) 2.10-2.34 (m, 4H) 2.28 (s, 6H) 2.38 (s, 3H) 2.40-2.92 (m, 11H) 3.20 (s, 3H) 3.20-3.24 (m, 1H) 3.36 (s, 3H) 3.36-3.40 (m, 2H) 3.46-3.52 (m, 1H) 3.66 (d, J = 7.79 Hz, 1H) 3.69 (dd, J = 11.00, 3.67 Hz, 1H) 4.11-4.14 (m, 1H) 4.39 (d, J = 7.34 Hz, 1H) 4.42-4.47 (m, 1H) 4.58-4.65 (m, 1H) 4.71 (d, J = 6.88 Hz, 1H) 4.91 (d, J = 4.58 Hz, 1H) 7.61 (d, J = 8.71 Hz, 2H) 8.20 (d, J = 8.71 Hz, 2H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 439 | [4-NO2-phenyl-CH(OH)-CH(CH2OH)-NH-(CH2)4-NH-] | –OH | 1015.1 | (600 MHz): 0.81 (d, J = 6.88 Hz, 6H) 0.89 (t, J = 7.34 Hz, 3H) 1.08-1.24 (m, 8H) 1.10 (d, J = 7.34 Hz, 3H) 1.21 (d, J = 6.42 Hz, 3H) 1.24 (d, J = 6.88 Hz, 3H) 1.33 (s, 3H) 1.44-1.87 (m, 9H) 2.10-2.34 (m, 4H) 2.27 (s, 6H) 2.37 (s, 3H) 2.40-2.51 (m, 4H) 2.58-2.67 (m, 3H) 2.71-2.78 (m, 2H) 2.79-2.92 (m, 3H) 3.19-3.21 (m, 1H) 3.21 (s, 3H) 3.35 (s, 3H) 3.36-3.44 (m, 2H) 3.47-3.53 (m, 1H) 3.67 (d, J = 7.34 Hz, 1H) 3.71 (dd, J = 11.00, 3.67 Hz, 1H) 4.08-4.13 (m, 1H) 4.39 (d, J = 7.34 Hz, 1H) 4.42-4.48 (m, 1H) 4.58-4.64 (m, 1H) 4.70 (d, J = 6.88 Hz, 1H) 4.87-4.90 (m, 1H) 7.60 (d, J = 8.25 Hz, 2H) 8.20 (d, J = 8.71 Hz, 2H) |
| 440 | HO-CH2CH2-N(Et)-CH2CH2-NH– | HO / | 863.9 | (600 MHz): 0.82 (d, J = 6.88 Hz, 6H) 0.90 (t, J = 7.34 Hz, 3H) 1.02 (t, J = 7.11 Hz, 3H) 1.10 (d, J = 7.79 Hz, 3H) 1.11-1.26 (m, 2H) 1.16 (d, J = 7.34 Hz, 3H) 1.19 (s, 3H) 1.21 (d, J = 5.96 Hz, 3H) 1.25 (d, J = 6.88 Hz, 3H) 1.33 (s, 3H) 1.50-1.87 (m, 4H) 2.11-2.34 (m, 5H) 2.28 (s, 6H) 2.37 (s, 3H) 2.40-2.70 (m, 10H) 2.73-2.85 (m, 3H) 2.89-2.95 (m, 1H) 3.17-3.22 (m, 1H) 3.22 (s, 3H) 3.36 (s, 3H) 3.39-3.57 (m, 4H) 3.63-3.69 (m, 2H) 4.08-4.13 (m, 1H) 4.40 (d, J = 7.34 Hz, 1H) 4.43-4.47 (m, 1H) 4.60-4.68 (m, 1H) 4.89 (d, J = 4.59 Hz, 1H) |
| 441 | HO-(CH2)3-N(Et)-CH2CH2-NH– | HO / | 878.0 | (600 MHz): 0.82 (d, J = 6.42 Hz, 6H) 0.90 (t, J = 7.34 Hz, 3H) 1.04 (t, J = 7.11 Hz, 3H) 1.02-1.24 (m, 2H) 1.10 (d, J = 7.34 Hz, 3H) 1.16 (d, J = 7.34 Hz, 3H) 1.18 (s, 3H) 1.21 (d, J = 5.96 Hz, 3H) 1.25 (d, J = 6.88 Hz, 3H) 1.34 (s, 3H) 1.50-1.87 (m, 6H) 2.11-2.33 (m, 5H) 2.28 (s, 6H) 2.37 (s, 3H) 2.39-2.85 (m, 13H) 2.89-2.94 (m, 1H) 3.18-3.22 (m, 1H) 3.22 (s, 3H) 3.36 (s, 3H) 3.41-3.45 (m, 1H) 3.49-3.55 (m, 1H) 3.61-3.69 (m, 2H) 3.75-3.78 (m, 2H) 3.80-3.83 (m, 1H) 4.08-4.12 (m, 1H) 4.41 (d, J = 7.34 Hz, 1H) 4.43-4.48 (m, 1H) 4.61-4.67 (m, 1H) 4.89 (d, J = 4.13 Hz, 1H) |
| 442 | MeC(O)-NH-CH2CH2-NH– | HO / | 833.9 | (500 MHz): 0.80 (d, J = 7.13 Hz, 6H) 0.89 (t, J = 7.27 Hz, 3H) 1.05-1.27 (m, 17H) 1.32 (s, 3H) 1.48-1.87 (m, 4H) 1.96 (s, 3H) 2.06-2.34 (m, 10H) 2.36 (s, 3H) 2.38-2.50 (m, 2H) 2.57-2.65 (m, 1H) 2.72-2.93 (m, 6H) 3.16-3.50 (m, 11H) 3.62-3.67 (m, 1H) 4.07-4.15 (m, 1H) 4.34-4.47 (m, 2H) 4.58-4.69 (m, 1H) 4.89 (d, J = 4.66 Hz, 1H) 5.88-5.94 (m, 1H) |
| 443 | MeSO2-NH-CH2CH2-NH– | HO / | 869.9 | (500 MHz): 0.80 (d, J = 7.13 Hz, 6H) 0.89 (t, J = 7.27 Hz, 3H) 1.04-1.35 (m, 20H) 1.47-1.87 (m, 4H) 2.03-2.17 (m, 2H) 2.20-2.38 (m, 13H) 2.38-2.50 (m, 2H) 2.61-2.93 (m, 6H) 2.95 (s, 3H) 3.11-3.28 (m, 5H) 3.34 (s, 3H) 3.37-3.52 (m, 2H) 3.64 (d, J = 7.95 Hz, 1H) 4.09-4.16 (m, 1H) 4.34-4.46 (m, 2H) 4.58-4.67 (m, 1H) 4.76-4.92 (m, 2H) |
| 444 | Me2N-(CH2)3-NH– | HO / | 833.9 | (500 MHz): 0.80 (d, J = 7.13 Hz, 6H) 0.89 (t, J = 7.40 Hz, 3H) 1.06-1.25 (m, 17H) 1.32 (s, 3H) 1.48-1.88 (m, 6H) 2.06-2.33 (m, 18H) 2.36 (s, 3H) 2.38-2.94 (m, 8H) 3.14-3.26 (m, 5H) 3.34 (s, 3H) 3.38-3.56 (m, 2H) 3.67 (d, J = 7.68 Hz, 1H) 4.06-4.13 (m, 1H) 4.36-4.49 (m, 2H) 4.58-4.69 (m, 1H) 4.86 (d, J = 4.94 Hz, 1H) |

TABLE 11-continued formula (W)

| Example | R¹ᵂ | R²ᵂ | ESI MS (M + H) | ¹H-NMR, CDCl₃, δ (ppm) |
|---------|-----|-----|----------------|------------------------|
| 445 | Me₂N-(CH₂)₄-NH- | HO- (wedge) | 847.9 | (500 MHz): 0.80 (d, J = 7.13 Hz, 6H) 0.89 (t, J = 7.40 Hz, 3H) 1.05-1.25 (m, 17H) 1.32 (s, 3H) 1.42-1.87 (m, 8H) 2.08-2.33 (m, 18H) 2.36 (s, 3H) 2.37-2.65 (m, 4H) 2.68-2.94 (m, 4H) 3.15-3.27 (m, 5H) 3.34 (s, 3H) 3.36-3.55 (m, 2H) 3.66 (d, J = 7.68 Hz, 1H) 4.05-4.12 (m, 1H) 4.36-4.48 (m, 2H) 4.58-4.69 (m, 1H) 4.86 (d, J = 4.66 Hz, 1H) |
| 446 | (2-MeO-C₆H₄)-NH-CH₂-CH(OH)-CH₂-NH- | HO- (wedge) | 928.0 | mixture of diastereomers (600 MHz): 0.81 (d, J = 6.42 Hz, 6H) 0.90 (t, J = 7.34 Hz, 3H) 1.10 (d, J = 7.34 Hz, 3H) 1.14-1.26 (m, 2H) 1.16 (d, J = 7.34 Hz, 3H) 1.19 (d, J = 4.13 Hz, 3H) 1.21 (d, J = 6.42 Hz, 3H) 1.26-1.29 (m, 3H) 1.32 (s, 3H) 1.46-1.88 (m, 4H) 2.03-2.1 (m, 2H) 2.21-2.51 (m, 5H) 2.28 (s, 6H) 2.37 (s, 3H) 2.54 (dd, J = 11.92, 8.71 Hz, 1H) 2.74-2.94 (m, 5H) 3.07-3.29 (m, 3H) 3.20 (s, 3H) 3.35 (s, 3H) 3. 37-3.51 (m, 2H) 3.67 (d, J = 7.79 Hz, 1H) 3.84 (s, 3H) 3.87-3.96 (m, 1H) 4.08-4.17 (m, 1H) 4.38 (d, J = 6.88 Hz, 1H) 4.41-4.47 (m, 1H) 4.59-4.67 (m, 1H) 4.86-4.92 (m, 1H) 6.59-6.64 (m, 1H) 6.65-6.70 (m, 1H) 6.74-6.79 (m, 1H) 6.82-6.88 (m, 1H), and (600 MHz): 0.81 (d, J = 6.42 Hz, 6H) 0.90 (t, J = 7.34 Hz, 3H) 1.10 (d, J = 7.34 Hz, 3H) 1.14-1.26 (m, 2H) 1.16 (d, J = 7.34 Hz, 3H) 1.19 (d, J = 4.13 Hz, 3H) 1.21 (d, J = 6.42 Hz, 3H) 1.26-1.29 (m, 3H) 1.32 (s, 3H) 1.46-1.88 (m, 4H) 2.03-2.18 (m, 2H) 2.21-2.51 (m, 5H) 2.28 (s, 6H) 2.37 (s, 3H) 2.63 (dd, J = 12.38, 3.67 Hz, 1H) 2.74-2.94 (m, 5H) 3.07-3.29 (m, 3H) 3.20 (s, 3H) 3.35 (s, 3H) 3.37-3.51 (m, 2H) 3.67 (d, J = 7.79 Hz, 1H) 3.84 (s, 3H) 3.87-3.96 (m, 1H) 4.08-4.17 (m, 1H) 4.38 (d, J = 6.88 Hz, 1H) 4.41-4.47 (m, 1H) 4.59-4.67 (m, 1H) 4.86-4.92 (m, 1H) 6.59-6.64 (m, 1H) 6.65-6.70 (m, 1H) 6.74-6.79 (m, 1H) 6.82-6.88 (m, 1H) |
| 447 | -NH-CH₂-CH(OH)-CH₂-N(Et)-CH(Me)-(2-MeO-C₆H₄) | -OH (wedge) | 984.0 | mixture of diastereomers (600 MHz): 0.81 (d, J = 6.88 Hz, 6H) 0.86-0.91 (m, 3H) 0.91-0.99 (m, 3H) 1.05-1.36 (m, 23H) 1.47-1.88 (m, 4H) 1.95-2.03 (m, 1H) 2.10-2.33 (m, 4H) 2.27 (s, 6H) 2.36 (s, 3H) 2.38-2.85 (m, 11H) 2.88-2.95 (m, 1H) 3.16-3.21 (m, 1H) 3.21 (s, 3H) 3.35 (s, 3H) 3.37-3.46 (m, 1H) 3.49-3.58 (m, 1H) 3.64-3.78 (m, 2H) 3.82 (s, 3H) 4.05-4.15 (m, 1H) 4.36-4.45 (m, 2H) 4.45-4.52 (m, 1H) 4.57-4.67 (m, 1H) 4.82-4.89 (m, 1H) 6.83-6.96 (m, 2H) 7.18-7.29 (m, 2H), and (600 MHz): 0.81 (d, J = 6.88 Hz, 6H) 0.86-0.91 (m, 3H) 0.91-0.99 (m, 3H) 1.05-1.36 (m, 23H) 1.47-1.88 (m, 4H) 1.95-2.03 (m, 1H) 2.10-2.33 (m, 4H) 2.27 (s, 6H) 2.36 (s, 3H) 2.38-2.85 (m, 11H) 2.88-2.95 (m, 1H) 3.16-3.21 (m, 1H) 3.21 (s, 3H) 3.35 (s, 3H) 3.37-3.46 (m, 1H) 3.49-3.58 (m, 1H) 3.64-3.78 (m, 2H) 3.83 (s, 3H) 4.05-4.15 (m, 1H) 4.36-4.45 (m, 2H) 4.45-4.52 (m, 1H) 4.57-4.67 (m, 1H) 4.82-4.89 (m, 1H) 6.83-6.96 (m, 2H) 7.18-7.29 (m, 2H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 448 | (structure: -NH-CH₂-CH₂-N(CH₂CH₂OH)-CH(Me)-(2-methoxyphenyl)) | OH | 970.0 | (600 MHz): 0.78-0.84 (m, 6H) 0.89 (t, J = 7.34 Hz, 3H) 1.05-1.22 (m, 2H) 1.07 (s, 3H) 1.09 (d, J = 7.34 Hz, 3H) 1.13 (d, J = 6.42 Hz, 3H) 1.15 (d, J = 7.34 Hz, 3H) 1.20 (d, J = 5.96 Hz, 3H) 1.29-1.34 (m, 6H) 1.50-1.58 (m, 1H) 1.60-1.66 (m, 1H) 1.70-1.88 (m, 3H) 2.12-2.20 (m, 1H) 2.21-2.39 (m, 4H) 2.26 (s, 6H) 2.36 (s, 3H) 2.42 (d, J = 12.84 Hz, 1H) 2.46-2.64 (m, 6H) 2.67 (d, J = 12.84 Hz, 1H) 2.70-2.76 (m, 1H) 2.77-2.84 (m, 1H) 2.91 (d, J = 14.21 Hz, 1H) 3.18 (dd, J = 10.09, 7.34 Hz, 1H) 3.21 (s, 3H) 3.32 (s, 3H) 3.37-3.57 (m, 3H) 3.60-3.68 (m, 2H) 3.83 (s, 3H) 4.07 (s, 1H) 4.36-4.48 (m, 3H) 4.63 (s, 1H) 4.83 (d, J = 5.04 Hz, 1H) 6.87 (d, J = 7.34 Hz, 1H) 6.94 (t, J = 7.11 Hz, 1H) 7.20-7.29 (m, 2H) |
| 449 | (structure: HOCH₂-CH(CH₂OH)-NH-) | OH | 822.7 | (600 MHz): 0.81 (d, J = 6.88 Hz, 6H) 0.90 (t, J = 7.11 Hz, 3H) 1.09 (d, J = 7.34 Hz, 3H) 1.10-1.26 (m, 2H) 1.16 (d, J = 7.34 Hz, 3H) 1.19 (s, 3H) 1.21 (d, J = 5.96 Hz, 3H) 1.29 (d, J = 6.88 Hz, 3H) 1.32 (s, 3H) 1.48-1.87 (m, 4H) 2.05 (dd, J = 15.13, 5.04 Hz, 1H) 2.08-2.19 (m, 1H) 2.19-2.52 (m, 5H) 2.28 (s, 6H) 2.37 (s, 3H) 2.64-2.70 (m, 1H) 2.78-2.94 (m, 4H) 3.17-3.23 (m, 1H) 3.20 (s, 3H) 3.29-3.41 (m, 1H) 3.35 (s, 3H) 3.43-3.51 (m, 1H) 3.53 (dd, J = 11.00, 5.04 Hz, 1H) 3.61 (dd, J = 11.00, 5.50 Hz, 1H) 3.65-3.69 (m, 2H) 3.72 (dd, J = 11.00, 4.59 Hz, 1H) 4.14 (s, 1H) 4.38 (d, J = 6.88 Hz, 1H) 4.42-4.48 (m, 1H) 4.62 (s, 1H) 4.90 (d, J = 4.59 Hz, 1H) |
| 450 | (structure: -NH-CH₂-CH(OH)-(4-nitrophenyl)) | OH | 913.8 | mixture of diastereomers (600 MHz): 0.81 (d, J = 6.42 Hz, 6H) 0.87-0.93 (m, 3H) 1.07-1.36 (m, 17H) 1.10 (d, J = 7.34 Hz, 3H) 1.48-1.88 (m, 4H) 2.00-2.19 (m, 2H) 2.20-2.48 (m, 5H) 2.28 (s, 6H) 2.35-2.38 (m, 3H) 2.48-3.02 (m 6H) 3.18-3.24 (m, 1H) 3.21 (s, 3H) 3.34-3.48 (m, 2H) 3.36 (s, 3H) 3.61-3.68 (m, 2H) 4.15 (s, 1H) 4.34-4.39 (m, 1H) 4.41-4.47 (m, 1H) 4.60-4.69 (m, 1H) 4.75-4.82 (m, 1H) 4.93 (d, J = 5.04 Hz, 1H) 7.50-7.57 (m, 2H) 8.18-8.23 (m, 2H) |
| 451 | (structure: -NH-CH(CH₂F)-CH(OH)-(4-methylsulfonylphenyl)) | OH | 978.8 | (600 MHz): 0.76-0.83 (m, 6H) 0.89 (t, J = 7.34 Hz, 3H) 1.05-1.34 (m, 20H) 1.42-1.86 (m, 4H) 1.88-2.54 (m, 15H) 2.60-3.00 (m, 4H) 3.01-3.07 (m, 4H) 3.13-3.68 (m, 13H) 4.10-4.28 (m, 1H) 4.32-4.47 (m, 2H) 4.57 (d, J = 7.79 Hz, 2H) 4.87-4.92 (m, 1H) 7.59 (d, J = 8.25 Hz, 2H) 7.92 (d, J = 8.25 Hz, 2H) |
| 452 | (structure: -NH-CH(CH₂OH)-CH(OH)-phenyl) | OH | 898.9 | (500 MHz): 0.76-0.85 (M, 6H) 0.90 (t, J = 7.40 Hz, 3H) 1.05-1.26 (m, 17H) 1.31 (s, 3H) 1.48-1.66 (m, 2H) 1.69-1.87 (m, 2H) 2.04 (dd, J = 15.08, 5.21 Hz, 1H) 2.10-2.33 (m, 5H) 2.25 (s, 6H) 2.34-2.50 (m, 2H) 2.36 (s, 3H) 2.63-2.74 (m, 2H) 2.77-2.95 (m, 3H) 3.16-3.22 (m, 1H) 3.19 (s, 3H) 3.30-3.39 (m, 1H) 3.33 (s, 3H) 3.40-3.49 (m, 1H) 3.53-3.67 (m, 2H) 4.09-4.16 (m, 1H) 4.32-4.44 (m, 2H) 4.58-4.70 (m, 2H) 4.88 (d, J = 4.94 Hz, 1H) 7.22-7.38 (m, 5H) |

TABLE 11-continued formula (W)

| Example | R[1W] | R[2W] | ESI MS (M + H) | $^1$H-NMR, CDCl$_3$, δ (ppm) |
|---|---|---|---|---|
| 453 | (structure: Me$_2$N-CH$_2$-CH(CH$_2$OH)-NH-) | HO— | 849.8 | (500 MHz): 0.81 (d, J = 7.13 Hz, 6H) 0.89 (t, J = 7.27 Hz, 3H) 1.06-1.35 (m, 20H) 1.49-1.93 (m, 5H) 2.09-2.53 (m, 24H) 2.63-2.71 (m, 1H) 2.74-2.94 (m, 3H) 3.16-3.24 (m, 4H) 3.30-3.70 (m, 8H) 4.08-4.17 (m, 1H) 4.35-4.45 (m, 2H) 4.59-4.68 (m, 1H) 4.86 (d, J = 4.11 Hz, 1H) |
| 454 | (structure: Me$_2$N-CH$_2$-CH(CH$_2$OH)-NH-) | HO— | 849.8 | (500 MHz): 0.80 (d, J = 6.86 Hz, 6H) 0.89 (t, J = 7.40 Hz, 3H) 1.06-1.27 (m, 17H) 1.32 (s, 3H) 1.48-1.87 (m, 5H) 1.99-2.07 (m, 1H) 2.10-2.53 (m, 23H) 2.69-2.94 (m, 4H) 3.16-3.24 (m, 4H) 3.31-3.70 (m, 8H) 4.07-4.15 (m, 1H) 4.36-4.48 (m, 2H) 4.58-4.69 (m, 1H) 4.86 (d, J = 4.94 Hz, 1H) |
| 455 | (structure: -NH-CH(CH$_2$OH)-CH$_2$-C$_6$H$_4$-NO$_2$) | —OH | 927.9 | (500 MHz): 0.78-0.85 (m, 6H) 0.91 (t, J = 7.26 Hz, 3H) 1.06-1.27 (m, 17H) 1.32 (s, 3H) 1.50-1.87 (m, 4H) 1.98-2.05 (m, 1H) 2.10-2.53 (m, 14H) 2.60-2.66 (m, 1H) 2.70-2.75 (m, 1H) 2.79-2.96 (m, 3H) 3.02-3.06 (m, 3H) 3.16-3.24 (m, 4H) 3.31-3.38 (m, 4H) 3.41-3.67 (m, 3H) 4.13-4.19 (m, 1H) 4.36 (d, J = 7.65 Hz, 1H) 4.45 (q, 1H) 4.58-4.67 (m, 1H) 4.74 (d, J = 7.26 Hz, 1H) 4.91 (d, J = 4.97 Hz, 1H) 7.61 (d, J = 8.41 Hz, 2H) 7.92 (d, J = 8.41 Hz, 2H) |
| 456 | (structure: -NH-CH(CH$_2$OH)-CH(OH)-C$_6$H$_4$-SO$_2$Me) | —OH | 976.8 | (500 MHz): 0.78-0.85 (m, 6H) 0.91 (t, J = 7.27 Hz, 3H) 1.06-1.27 (m, 17H) 1.31 (s, 3H) 1.50-1.88 (m, 4H) 1.96-2.04 (m, 1H) 2.10-2.53 (m, 16H) 2.60-2.95 (m, 5H) 3.04 (s, 3H) 3.16-3.24 (m, 4H) 3.32-3.38 (m, 5H) 3.41-3.50 (m, 1H) 3.58-3.67 (m, 2H) 4.12-4.19 (m, 1H) 4.36 (d, J = 7.40 Hz, 1H) 4.44 (q, J = 6.76 Hz, 1H) 4.59-4.67 (m, 1H) 4.74 (d, J = 7.13 Hz, 1H) 4.91 (d, J = 4.94 Hz, 1H) 7.59-7.63 (m, 1H) 7.91 (d, J = 8.50 Hz, 2H) |
| 457 | (structure: -HN-CH$_2$-CH$_2$-C$_6$H$_4$-NO$_2$) | HO— | 897.9 | (600 MHz): 0.77-0.84 (m, 6H) 0.90 (t, J = 7.34 Hz, 3H) 1.05-1.22 (m, 2H) 1.08 (d, J = 7.34 Hz, 3H) 1.10 (s, 3H) 1.13-1.17 (m, 6H) 1.18 (d, J = 6.42 Hz, 3H) 1.31 (s, 3H) 1.49-1.65 (m, 2H) 1.71-1.87 (m, 2H) 2.11-2.20 (m, 3H) 2.21-2.49 (m, 4H) 2.26 (s, 6H) 2.36 (s, 3H) 2.70-2.74 (m, 1H) 2.76-2.94 (m, 7H) 3.17 (s, 3H) 3.17-3.20 (m, 1H) 3.33 (s, 3H) 3.40-3.48 (m, 2H) 3.62 (d, J = 8.25 Hz, 1H) 4.06-4.12 (m, 1H) 4.33-4.41 (m, 2H) 4.62-4.71 (m, 1H) 4.84-4.88 (m, 1H) 7.34 (d, J = 8.71 Hz, 2H) 8.15 (d, J = 8.71 Hz, 2H) |
| 458 | (structure: -NH-CH(CH$_2$OH)-CH$_2$-C$_6$H$_4$-NO$_2$) | —OH | 927.6 | (600 MHz): 0.77-0.84 (m, 6H) 0.91 (t, J = 7.57 Hz, 3H) 1.04-1.35 (m, 20H) 1.49-1.94 (m, 5H) 2.10-2.52 (m, 14H) 2.67-2.94 (m, 6H) 3.16-3.25 (m, 5H) 3.29-3.47 (m, 5H) 3.59-3.66 (m, 3H) 3.76-3.78 (m, 1H) 4.08-4.15 (m, 1H) 4.33-4.43 (m, 2H) 4.58-4.68 (m, 1H) 4.84 (d, J = 5.04 Hz, 1H) 7.36 (d, J = 8.71 Hz, 2H) 8.14-8.16 (m, 2H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 459 | ~NH-C(O)-NH-CH$_2$CH$_2$-N(CH$_2$CH$_2$OH)-CH(Me)-(2-MeO-C$_6$H$_4$) | H | | (600 MHz): 0.81 (d, J = 7.34 Hz, 6H) 0.90 (t, J = 7.34 Hz, 3H) 1.05 (s, 3H) 1.06-1.26 (m, 2H) 1.10 (d, J = 7.34 Hz, 3H) 1.15-1.20 (m, 9H) 1.30-1.35 (m, 6H) 1.50-1.70 (m, 3H) 1.71-1.79 (m, 1H) 1.79-1.86 (m, 1H) 2.09-2.18 (m, 1H) 2.21-2.45 (m, 4H) 2.27 (s, 6H) 2.37 (s, 3H) 2.46-2.61 (m, 3H) 2.63-2.76 (m, 2H) 2.76-2.84 (m, 1H) 2.88-2.93 (m, 1H) 2.99-3.08 (m, 1H) 3.17-3.32 (m, 2H) 3.22 (s, 3H) 3.30 (s, 3H) 3.33-3.50 (m, 3H) 3.60-3.67 (m, 1H) 3.69 (d, J = 8.71 Hz, 1H) 3.90 (s, 3H) 4.03-4.09 (m, 1H) 4.21-4.27 (m, 1H) 4.33 (d, J = 7.34 Hz, 1H) 4.39-4.45 (m, 1H) 4.58-4.67 (m, 2H) 4.81 (s, 1H) 4.95 (d, J = 4.59 Hz, 1H) 6.93 (d, J = 8.25 Hz, 1H) 6.94-6.98 (m, 1H) 7.22-7.30 (m, 2H) |
| 460 | HO-CH$_2$CH$_2$-N(Et)-(CH$_2$)$_4$-NH~ | H | | (600 MHz): 0.83 (d, J = 6.42 Hz, 6H) 0.90 (t, J = 7.34 Hz, 3H) 1.02 (t, J = 7.11 Hz, 3H) 1.07-1.24 (m, 8H) 1.09 (d, J = 7.34 Hz, 3H) 1.16 (d, J = 7.34 Hz, 3H) 1.26 (d, J = 6.42 Hz, 3H) 1.31 (s, 3H) 1.44-1.78 (m, 6H) 1.83-1.90 (m, 1H) 1.93 (d, J = 10.09 Hz, 1H) 2.15-2.35 (m, 4H) 2.29 (s, 6H) 2.36 (s, 3H) 2.41-2.63 (m, 7H) 2.78-2.91 (m, 3H) 3.21 (dd, J = 10.09, 7.34 Hz, 1H) 3.25 (s, 3H) 3.28 (s, 3H) 3.37-3.45 (m, 5H) 3.53 (t, J = 5.50 Hz, 2H) 3.66-3.70 (m, 1H) 3.72 (d, J = 7.79 Hz, 1H) 3.98-4.04 (m, 1H) 4.08-4.11 (m, 1H) 4.45 (d, J = 6.88 Hz, 1H) 4.63-4.70 (m, 1H) 4.93 (d, J = 5.04 Hz, 1H) |
| 461 | HO-CH$_2$CH$_2$-N(Et)-(CH$_2$)$_3$-C(O)-NH~ | H | 876.9 | (500 MHz): 0.81 (d, J = 7.13 Hz, 6H) 0.89 (t, J = 7.27 Hz, 3H) 1.01 (t, J = 7.13 Hz, 3H) 1.08 (d, J = 7.40 Hz, 3H) 1.07-1.12 (m, 1H) 1.12 (s, 3H) 1.15 (d, J = 7.40 Hz, 3H) 1.20 (d, J = 6.03 Hz, 3H) 1.22 (d, J = 6.31 Hz, 3H) 1.21-1.28 (m, 1H) 1.34 (s, 3H) 1.49-1.58 (m, 2H) 1.63-1.70 (m, 1H) 1.71-1.79 (m, 1H) 1.78-1.86 (m, 1H) 2.10-2.18 (m, 1H) 2.18-2.25 (m, 1H) 2.26-2.33 (m, 2H) 2.29 (s, 6H) 2.36 (s, 3H) 2.38-2.44 (m, 1H) 2.52-2.65 (m, 7H) 2.74-2.82 (m, 1H) 2.92 (d, J = 13.99 Hz, 1H) 3.21 (s, 3H) 3.21-3.33 (m, 3H) 3.26 (s, 3H) 3.36-3.42 (m, 1H) 3.42-3.49 (m, 2H) 3.54-3.58 (m, 2H) 3.66 (d, J = 7.95 Hz, 1H) 4.07-4.13 (m, 1H) 4.13-4.19 (m, 1H) 4.31 (d, J = 7.13 Hz, 1H) 4.56-4.64 (m, 1H) 4.94 (d, J = 4.39 Hz, 1H) 5.08-5.12 (m, 1H) 5.12-5.17 (m, 1H) |
| 462 | (2-MeO-C$_6$H$_4$)-NH-CH$_2$-CH(OH)-CH$_2$-NH-C(O)-NH~ | H | 940.9 | mixture of diastereomers (500 MHz): 0.77-0.85 (m, 6H) 0.89 (t, J = 7.40 Hz, 3H) 1.07 (d, J = 7.40 Hz, 3H) 1.12 (d, J = 2.19 Hz, 3H) 1.12-1.16 (m, 1H) 1.15 (d, J = 7.40 Hz, 3H) 1.18-1.23 (m, 6H) 1.20-1.27 (m, 1H) 1.35 (s, 3H) 1.49-1.58 (m, 2H) 1.59-1.68 (m, 1H) 1.70-1.79 (m, 1H) 1.79-1.85 (m, 1H) 2.16-2.30 (m, 3H) 2.26 (s, 6H) 2.33 (d, J = 15.08 Hz, 1H) 2.36 (s, 3H) 2.38-2.45 (m, 1H) 2.48-2.57 (m, 1H) 2.76-2.80 (m, 1H) 2.92 (d, J = 14.26 Hz, 1H) 3.10-3.16 (m, 1H) 3.21 (s, 3H) 3.24 (d, J = 2.47 Hz, 3H) 3.24-3.36 (m, 3H) 3.37-3.52 (m, 4H) 3.66 (d, J = 7.40 Hz, 1H) 3.82 (s, 3H) 3.91-3.98 (m, 1H) 4.07-4.19 (m, 2H) 4.28 (d, J = 7.13 Hz, 1H) 4.48-4.56 (m, 1H) 4.56-4.64 (m, 1H) 4.93 (d, J = 4.11 Hz, 1H) 5.24-5.31 (m, 1H) 5.31-5.38 (m, 1H) 6.59-6.63 (m, 1H) 6.64-6.69 (m, 1H) 6.73-6.77 (m, 1H) 6.80-6.86 (m, 1H) |

TABLE 11-continued formula (W)

| Example | R^1W | R^2W | ESI MS (M + H) | 1H-NMR, CDCl3, δ (ppm) |
|---|---|---|---|---|
| 463 | (urea-CH2-CH(OH)-CH2-N(Et)-CH(Me)-(2-methoxyphenyl)) | H | 997.0 | mixture of diastereomers (500 MHz): 0.74-0.85 (m, 6H) 0.86-0.91 (m, 3H) 0.90-1.01 (m, 3H) 1.06-1.12 (m, 6H) 1.14-1.23 (m, 9H) 1.15-1.19 (m, 1H) 1.21-1.26 (m, 1H) 1.26-1.35 (m, 6H) 1.51-1.59 (m, 2H) 1.61-1.70 (m, 1H) 1.71-1.79 (m, 1H) 1.80-1.86 (m, 1H) 2.10-2.17 (m, 1H) 2.26-2.35 (m, 2H) 2.28-2.31 (m, 6H) 2.35-2.37 (m, 3H) 2.38-2.59 (m, 5H) 2.76-2.83 (m, 1H) 2.89 (d, J = 15.08 Hz, 1H) 2.93-3.06 (m, 1H) 3.19-3.23 (m, 1H) 3.21 (s, 3H) 3.27-3.28 (m, 3H) 3.33-3.50 (m, 6H) 3.58-3.70 (m, 1H) 3.69 (d, J = 8.23 Hz, 1H) 3.83 (s, 3H) 4.03-4.12 (m, 1H) 4.17-4.24 (m, 1H) 4.32-4.41 (m, 2H) 4.60-4.65 (m, 1H) 4.96 (d, J = 4.66 Hz, 1H) 6.86-6.89 (m, 1H) 6.94 (t, J = 7.40 Hz, 1H) 7.20-7.26 (m, 2H) |
| 464 | (urea-(CH2)4-NH-CH(CH2OH)-CH(OH)-(4-nitrophenyl)) | H | 1042.0 | (500 MHz): 0.81 (d, J = 6.88 Hz, 6H) 0.89 (t, J = 7.45 Hz, 3H) 1.03-1.59 (m, 26H) 1.63-1.87 (m, 3H) 2.10-2.47 (m, 8H) 2.28 (s, 6H) 2.36 (s, 3H) 2.51-2.69 (m, 3H) 2.74-2.81 (m, 1H) 2.89-2.97 (m, 1H) 3.07-3.54 (m, 7H) 3.20 (s, 3H) 3.24 (s, 3H) 3.61-3.72 (m, 2H) 4.05-4.14 (m, 2H) 4.28 (d, J = 7.26 Hz, 1H) 4.56-4.69 (m, 2H) 4.93 (d, J = 4.20 Hz, 1H) 4.98-5.13 (m, 2H) 7.60 (d, J = 8.79 Hz, 2H) 8.18 (d, J = 8.79 Hz, 2H) |
| 465 | (urea-(CH2)5-NH-CH(CH2OH)-CH(OH)-(4-nitrophenyl)) | H | 1054.7 | (500 MHz): 0.55-0.64 (m, 1H) 0.76-1.00 (m, 11H) 0.99-1.89 (m, 30H) 1.98-2.48 (m, 6H) 2.30 (s, 6H) 2.37 (s, 3H) 2.50-2.68 (m, 3H) 2.74-2.84 (m, 1H) 2.87-2.97 (m, 1H) 3.06-3.54 (m, 6H) 3.21 (s, 3H) 3.25 (s, 3H) 3.61-3.75 (m, 2H) 4.06-4.19 (m, 2H) 4.30 (d, J = 6.88 Hz, 1H) 4.57-4.73 (m, 2H) 4.83-5.10 (m, 3H) 7.08 (s, 1H) 7.60 (d, J = 8.41 Hz, 2H) 8.19 (d, J = 8.79 Hz, 2H) |
| 466 | (Cl2CH-C(O)-NH-(CH2)5-NH-urea) | H | 956.9 | (500 MHz): 0.80 (d, J = 6.88 Hz, 6H) 0.88 (t, J = 7.26 Hz, 3H) 1.04-1.41 (m, 22H) 1.47-1.87 (m, 8H) 2.09-2.45 (m, 7H) 2.28 (s, 6H) 2.36 (s, 3H) 2.46-2.56 (m, 1H) 2.73-2.94 (m, 2H) 3.08-3.50 (m, 7H) 3.20 (s, 3H) 3.25 (s, 3H) 3.65-3.69 (m, 1H) 4.05-4.14 (m, 1H) 4.15-4.21 (m, 1H) 4.30 (d, J = 7.26 Hz, 1H) 4.57-4.65 (m, 1H) 4.75-4.83 (m, 1H) 4.92-5.02 (m, 2H) 6.00 (s, 1H) 6.99-7.06 (m, 1H) |
| 467 | (HO-(CH2)3-N(Et)-(CH2)2-NH-urea) | H | 890.8 | (600 MHz): 0.77-0.83 (m, 6H) 0.89 (t, J = 7.34 Hz, 3H) 1.03 (t, J = 7.11 Hz, 3H) 1.08 (d, J = 7.34 Hz, 3H) 1.10-1.21 (m, 2H) 1.11 (s, 3H) 1.15 (d, J = 7.79 Hz, 3H) 1.19 (d, J = 6.42 Hz, 3H) 1.21 (d, J = 6.42 Hz, 3H) 1.31 (s, 3H) 1.49-1.58 (m, 2H) 1.61-1.71 (m, 3H) 1.71-1.78 (m, 1H) 1.79-1.87 (m, 1H) 2.11-2.18 (m, 1H) 2.20-2.28 (m, 2H) 2.29 (s, 6H) 2.32-2.35 (m, 1H) 2.35 (s, 3H) 2.37-2.45 (m, 1H) 2.48-2.59 (m, 5H) 2.61-2.70 (m, 2H) 2.76-2.82 (m, 1H) 2.90 (d, J = 14.67 Hz, 1H) 3.21 (s, 3H) 3.21-3.25 (m, 2H) 3.26 (s, 3H) 3.32-3.48 (m, 4H) 3.67 (d, J = 7.79 Hz, 1H) 3.79 (t, J = 5.27 Hz, 2H) 4.05-4.12 (m, 1H) 4.13-4.18 (m, 1H) 4.34 (d, J = 7.34 Hz, 1H) 4.58-4.65 (m, 1H) 4.95 (d, J = 4.59 Hz, 1H) 4.96-4.99 (m, 1H) 5.10-5.20 (m, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 468 | Me-NH-C(O)-NH- (butyl urea) | H | 817.9 | (600 MHz): 0.81 (d, J = 6.88 Hz, 6H) 0.87-0.93 (m, 6H) 1.06-1.29 (m, 2H) 1.09 (d, J = 7.34 Hz, 3H) 1.12 (s, 3H) 1.16 (d, J = 7.79 Hz, 3H) 1.20 (d, J = 6.42 Hz, 3H) 1.22 (d, J = 5.96 Hz, 3H) 1.30-1.39 (m, 2H) 1.32 (s, 3H) 1.44-1.50 (m, 2H) 1.50-1.59 (m, 2H) 1.60-1.69 (m, 1H) 1.71-1.79 (m, 1H) 1.79-1.86 (m, 1H) 2.08-2.18 (m, 1H) 2.20-2.44 (m, 4H) 2.29 (s, 6H) 2.37 (s, 3H) 2.45-2.53 (m, 1H) 2.76-2.83 (m, 1H) 2.90 (d, J = 14.67 Hz, 1H) 3.13-3.19 (m, 2H) 3.20-3.25 (m, 1H) 3.21 (s, 3H) 3.27 (s, 3H) 3.37-3.53 (m, 3H) 3.69 (d, J = 7.79 Hz, 1H) 4.05-4.13 (m, 1H) 4.16-4.24 (m, 1H) 4.25-4.31 (m, 1H) 4.34 (d, J = 6.88 Hz, 1H) 4.56-4.66 (m, 1H) 4.79 (d, J = 9.63 Hz, 1H) 4.96 (d, J = 4.59 Hz, 1H) |
| 469 | Me$_2$N-(CH$_2$)$_6$-NH- | H | 845.9 | (600 MHz): 0.78-0.85 (m, 6H) 0.88 (t, J = 7.34 Hz, 3H) 1.08 (d, J = 7.34 Hz, 3H) 1.09-1.23 (m, 4H) 1.15 (d, J = 7.79 Hz, 3H) 1.18 (s, 3H) 1.19 (d, J = 6.42 Hz, 3H) 1.25 (d, J = 5.96 Hz, 3H) 1.26-1.35 (m, 7H) 1.36-1.66 (m, 7H) 1.68-1.80 (m, 1H) 1.80-1.90 (m, 1H) 1.92 (d, J = 9.63 Hz, 1H) 2.19-2.26 (m, 3H) 2.20 (s, 6H) 2.28 (s, 6H) 2.32 (d, J = 15.13 Hz, 1H) 2.35 (s, 3H) 2.40-2.46 (m, 1H) 2.47-2.52 (m, 1H) 2.54-2.60 (m, 1H) 2.76-2.83 (m, 2H) 2.84-2.92 (m, 1H) 3.17-3.22 (m, 1H) 3.24 (s, 3H) 3.28 (s, 3H) 3.36-3.46 (m, 1H) 3.64-3.70 (m, 1H) 3.71 (d, J = 7.34 Hz, 1H) 3.96-4.03 (m, 1H) 4.08 (s, 1H) 4.44 (d, J = 7.34 Hz, 1H) 4.65 (s, 1H) 4.92 (d, J = 5.04 Hz, 1H) |
| 470 | sulfonamide-propyl-N(Et)-CH(Me)-(2-methoxyphenyl) | H | 1002.1 | (600 MHz): 0.81 (d, J = 6.42 Hz, 6H) 0.89 (t, J = 7.34 Hz, 3H) 0.96 (t, J = 6.88 Hz, 3H) 1.06-1.28 (m, 2H) 1.09 (d, J = 7.34 Hz, 3H) 1.16 (d, J = 7.34 Hz, 3H) 1.21 (d, J = 6.42 Hz, 3H) 1.23 (s, 3H) 1.25 (d, J = 6.42 Hz, 3H) 1.27 (d, J = 6.42 Hz, 3H) 1.31 (s, 3H) 1.49-2.02 (m, 7H) 2.06-2.70 (m, 10H) 2.29 (s, 6H) 2.36 (s, 3H) 2.73-3.34 (m, 6H) 3.23 (s, 3H) 3.28 (s, 3H) 3.37-3.46 (m, 2H) 3.62-3.68 (m, 1H) 3.80 (s, 3H) 4.09-4.23 (m, 2H) 4.29-4.36 (m, 2H) 4.58-4.70 (m, 2H) 4.96 (d, J = 4.59 Hz, 1H) 6.83-6.98 (m, 2H) 7.17-7.34 (m, 2H) |
| 471 | H$_2$N- | H | 718.5 | (300 MHz): 0.81-0.84 (m, 6H) 0.90 (t, J = 7.2 Hz, 3H) 1.10 (d, J = 7.2 Hz, 3H) 1.16-1.26 (m, 13H) 1.32 (s, 3H) 1.51-1.85 (m, 6H) 2.03 (d, J = 15.6 Hz, 1H) 2.14-2.57 (m, 15H) 2.77-2.93 (m, 2H) 3.18-3.25 (m, 4H) 3.33 (s, 3H) 3.41-3.50 (m, 2H) 3.70 (d, J = 7.8 Hz, 1H) 4.14 (d, J = 5.1 Hz, 1H) 4.46 (d, J = 7.2 Hz, 1H) 4.62-4.68 (m, 2H) 4.96 (d, J = 4.8 Hz, 1H) |
| 472 | benzyloxy-methoxy-phenyl-CH(Me)-N(Et)-(CH$_2$)$_2$-NH-C(O)-O- | H | 1073.3 | mixture of diastereomers (300 MHz): 0.82 (d, J = 6.87 Hz, 6H) 0.90 (t, J = 7.14 Hz, 3H) 0.94-1.04 (m, 3H) 1.07-1.35 (m, 23H) 1.49-1.90 (m, 5H) 2.12-2.66 (m, 8H) 2.28 (s, 6H) 2.37 (s, 3H) 2.76-2.95 (m, 2H) 3.16-3.50 (m, 9H) 3.24 (s, 3H) 3.51-3.64 (m, 1H) 3.71 (d, J = 8.24 Hz, 1H) 3.74-3.83 (m, 1H) 3.89 (s, 3H) 4.19-4.27 (m, 1H) 4.34-4.49 (m, 2H) 4.55 (d, J = 9.61 Hz, 1H) 4.59-4.70 (m, 1H) 4.98 (d, J = 4.60 Hz, 1H) 5.13 (s, 2H) 5.18-5.29 (m, 1H) 6.74 (d, J = 8.24 Hz, 1H) 6.82 (d, J = 8.51 Hz, 1H) 6.86 (s, 1H) 7.27-7.46 (m, 5H) |

TABLE 11-continued formula (W)

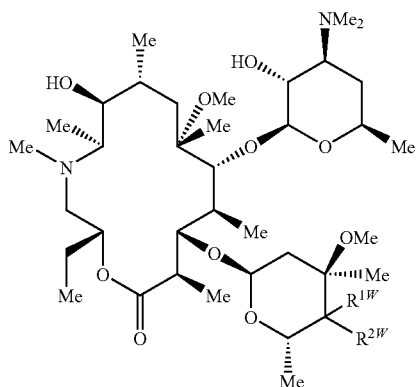

| Example | $R^{1W}$ | $R^{2W}$ | ESI MS (M + H) | $^1$H-NMR, CDCl$_3$, δ (ppm) |
|---|---|---|---|---|
| 473 | (2,6-bis(benzyloxy)phenyl)-CH(Me)-N(Et)-CH$_2$CH$_2$-NH-C(=O)-O- | H | 1149.4 | mixture of diastereomers (300 MHz): 0.82 (d, J = 6.86 Hz, 6H) 0.84-0.94 (m, 3H) 1.05-1.32 (m, 23H) 1.41-1.91 (m, 8H) 2.11-2.76 (m, 8H) 2.21 (s, 3H) 2.23 (s, 3H) 2.37 (s, 3H) 2.76-2.86 (m, 1H) 2.89 (d, J = 15.38 Hz, 1H) 2.99-3.58 (m, 10H) 3.23 (s, 3H) 3.67-3.77 (m, 1H) 4.21-4.54 (m, 4H) 4.58-4.73 (m, 2H) 4.93-4.99 (m, 1H) 5.05-5.13 (m, 4H) 5.43-5.69 (m, 1H) 6.59 (d, J = 8.24 Hz, 2H) 7.05-7.13 (m, 1H) 7.27-7.44 (m, 10H) |
| 474 | -O-C(=O)-NH-CH$_2$CH$_2$-N(Et)-CH(Me)-(3-(piperidinylmethyl)-4-ethoxyphenyl) | H | 1078.4 | mixture of diastereomers (300 MHz): 0.83 (d, J = 6.87 Hz, 6H) 0.91 (t, J = 7.41 Hz, 3H) 0.94-1.04 (m, 3H) 1.08-1.47 (m, 26H) 1.56-1.91 (m, 11H) 2.12-2.68 (m, 12H) 2.28 (s, 6H) 2.37 (s, 3H) 2.77-2.95 (m, 2H) 3.15-3.65 (m, 7H) 3.24 (s, 3H) 3.34 (s, 3H) 3.53 (s, 2H) 3.72 (d, J = 8.24 Hz, 1H) 3.76-3.88 (m, 1H) 4.00 (q, J = 6.87 Hz, 2H) 4.19-4.28 (m, 1H) 4.34-4.49 (m, 2H) 4.56 (d, J = 9.62 Hz, 1H) 4.60-4.69 (m, 1H) 4.98 (d, J = 4.67 Hz, 1H) 5.37-5.45 (m, 1H) 6.77 (d, J = 8.24 Hz, 1H) 7.09 (d, J = 7.97 Hz, 1H) 7.27-7.29 (m, 1H) |
| 475 | -O-C(=O)-NH-CH$_2$CH$_2$-N(Et)-CH(Me)-(3-cyanomethyl-4-methoxyphenyl) | H | 1006.3 | mixture of diastereomers (300 MHz): 0.82 (d, J = 6.87 Hz, 6H) 0.91 (t, J = 7.42 Hz, 3H) 0.95-1.35 (m, 26H) 1.47-1.93 (m, 5H) 2.11-2.64 (m, 8H) 2.29 (s, 6H) 2.37 (s, 3H) 2.76-2.95 (m, 2H) 3.17-3.64 (m, 7H) 3.24 (s, 3H) 3.35 (s, 3H) 3.69 (s, 2H) 3.72 (d, J = 8.51 Hz, 1H) 3.76-3.85 (m, 1H) 3.86 (s, 3H) 4.21-4.29 (m, 1H) 4.34-4.49 (m, 2H) 4.55 (d, J = 9.89 Hz, 1H) 4.60-4.69 (m, 1H) 4.98 (d, J = 4.39 Hz, 1H) 5.17-5.25 (m, 1H) 6.83 (d, J = 8.52 Hz, 1H) 7.21-7.28 (m, 2H) |
| 476 | -O-C(=O)-NH-CH$_2$CH$_2$-N(Et)-CH(Me)-(3,5-dimethylisoxazol-4-yl) | H | 842.3 | mixture of diastereomers (300 MHz): 0.83 (d, J = 6.87 Hz, 6H) 0.91 (t, J = 7.14 Hz, 3H) 0.98-1.35 (m, 26H) 1.47-1.94 (m, 5H) 2.12-2.48 (m, 8H) 2.30 (s, 6H) 2.37 (s, 3H) 2.51-2.67 (m, 3H) 2.76-2.95 (m, 2H) 3.14-3.48 (m, 15H) 3.24 (s, 3H) 3.51-3.63 (m, 1H) 3.72 (d, J = 8.24 Hz, 1H) 3.71-3.89 (m, 1H) 4.20-4.28 (m, 1H) 4.34-4.48 (m, 2H) 4.55 (d, J = 9.89 Hz, 1H) 4.60-4.69 (m, 1H) 4.98 (d, J = 4.67 Hz, 1H) 5.13-5.27 (m, 1H) 8.10 (s, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 477 | (carbamate-NH-CH$_2$CH$_2$-N(Et)-CH(Me)-aryl with morpholinomethyl and OEt) | H | 1080.4 | mixture of diastereomers (300 MHz): 0.82 (d, J = 6.87 Hz, 6H) 0.90 (t, J = 7.41 Hz, 3H) 0.94-1.03 (m, 3H) 1.07-1.36 (m, 23H) 1.40 (t, J = 6.87 Hz, 3H) 1.47-1.90 (m, 5H) 2.12-2.67 (m, 12H) 2.29 (s, 6H) 2.37 (s, 3H) 2.76-2.87 (m, 1H) 2.89 (d, J = 15.66 Hz, 1H) 3.14-3.43 (m, 6H) 3.23 (s, 3H) 3.34 (s, 3H) 3.53-3.64 (m, 1H) 3.56 (s, 2H) 3.67-3.88 (m, 5H) 4.01 (q, J = 6.86 Hz, 2H) 4.20-4.29 (m, 1H) 4.34-4.49 (m, 2H) 4.56 (d, J = 9.89 Hz, 1H) 4.60-4.69 (m, 1H) 4.98 (d, J = 4.39 Hz, 1H) 5.31-5.43 (m, 1H) 6.78 (d, J = 8.51 Hz, 1H) 7.11 (d, J = 8.24 Hz, 1H) 7.23-7.27 (m, 1H) |
| 478 | (carbamate-NH-CH$_2$CH$_2$-N(Et)-CH(Me)-thienyl-CH$_2$CN) | H | 982 | mixture of diastereomers (300 MHz): 0.83 (d, J = 6.87 Hz, 6H) 0.90 (t, J = 7.41 Hz, 3H) 0.99-1.39 (m, 26H) 1.54-1.89 (m, 5H) 2.11-2.69 (m, 8H) 2.30 (s, 6H) 2.37 (s, 3H) 2.76-2.95 (m, 2H) 3.17-3.43 (m, 9H) 3.24 (s, 3H) 3.54-3.67 (m, 1H) 3.72 (d, J = 7.97 Hz, 1H) 3.85 (s, 2H) 4.04-4.12 (m, 1H) 4.19-4.27 (m, 1H) 4.35-4.48 (m, 2H) 4.56 (d, J = 9.88 Hz, 1H) 4.60-4.69 (m, 1H) 4.98 (d, J = 4.67 Hz, 1H) 5.18-5.28 (m, 1H) 6.71 (d, J = 3.30 Hz, 1H) 6.87-6.90 (m, 1H) |
| 479 | (carbamate-NH-CH$_2$CH$_2$-N(Et)-CH(Me)-(3-methylpyrazinyl)) | H | 953 | mixture of diastereomers (300 MHz): 0.83 (d, J = 6.60 Hz, 6H) 0.90 (t, J = 7.15 Hz, 3H) 0.97-1.05 (m, 3H) 1.07-1.29 (m, 17H) 1.31 (s, 3H) 1.37 (d, J = 6.59 Hz, 3H) 1.55-1.93 (m, 5H) 2.10-2.75 (m, 14H) 2.21 (s, 3H) 2.29 (s, 3H) 2.36 (s, 3H) 2.77-2.95 (m, 2H) 2.98-3.75 (m, 15H) 4.14-4.54 (m, 4H) 4.59-4.70 (m, 1H) 4.95-5.00 (m, 1H) 5.08-5.68 (m, 1H) 8.30-8.48 (m, 2H) |
| 480 | (4-pyridyl-CH(Me)-N(Et)-CH$_2$CH$_2$-NH-carbamate) | H | 938 | mixture of diastereomers (300 MHz): 0.83 (d, J = 7.15 Hz, 6H) 0.91 (t, J = 6.59 Hz, 3H) 0.96-1.05 (m, 3H) 1.07-1.37 (m, 24H) 1.49-1.91 (m, 5H) 2.08-2.66 (m, 8H) 2.29 (s, 6H) 2.37 (s, 3H) 2.76-2.95 (m, 2H) 3.18-3.43 (m, 9H) 3.24 (s, 3H) 3.53-3.65 (m, 1H) 3.72 (d, J = 7.97 Hz, 1H) 3.79-3.91 (m, 1H) 4.19-4.27 (m, 1H) 4.36-4.48 (m, 2H) 4.52-4.59 (m, 1H) 4.59-4.69 (m, 1H) 4.98 (d, J = 4.67 Hz, 1H) 5.14-5.23 (m, 1H) 7.25-7.27 (m, 2H) 8.53 (d, J = 6.04 Hz, 2H) |
| 481 | (1-ethyl-3-methylpyrazol-4-yl-CH(Me)-N(Et)-CH$_2$CH$_2$-NH-carbamate) | H | 969.4 | mixture of diastereomers (300 MHz): 0.83 (d, J = 6.87 Hz, 6H) 0.90 (t, J = 7.42 Hz, 3H) 0.96-1.07 (m, 3H) 1.08-1.35 (m, 20H) 1.31 (s, 3H) 1.41-1.48 (m, 3H) 1.50-1.95 (m, 5H) 2.11-2.64 (m, 11H) 2.29 (s, 6H) 2.36 (s, 3H) 2.75-2.88 (m, 1H) 2.89 (d, J = 14.56 Hz, 1H) 3.14-3.48 (m, 9H) 3.24 (s, 3H) 3.52-3.67 (m, 1H) 3.71 (d, J = 7.97 Hz, 1H) 3.81-3.93 (m, 1H) 4.01-4.10 (m, 2H) 4.17-4.25 (m, 1H) 4.34-4.45 (m, 1H) 4.46 (d, J = 7.42 Hz, 1H) 4.51-4.58 (m, 1H) 4.59-4.71 (m, 1H) 4.98 (d, J = 4.40 Hz, 1H) 5.18-5.28 (m, 1H) 7.15-7.18 (m, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 482 | H₂N-(CH₂)₃-NH-C(O)-O-⌇ | -H | 833 | (400 MHz): 0.81-0.89 (m, 6H) 0.91 (t, J = 7.3 Hz, 3H) 1.11-1.28 (m, 18H) 1.32 (s, 3H) 1.49-1.67 (m, 8H) 2.17-2.43 (m, 15H) 2.64-2.66 (m, 1H) 2.73 (t, J = 6.7 Hz, 1H) 2.80-2.83 (m, 1H) 2.90 (d, J = 15.1 Hz, 1H) 3.20-3.23 (m, 6H) 3.34 (s, 3H) 3.39 (m, 1H) 3.56 (m, 1H) 3.70-3.75 (m, 3H) 4.22 (m, 1H) 4.35-4.45 (m, 2H) 4.54 (d, J = 10.0 Hz, 1H) 4.64 (m, 1H) 4.98 (d, J = 4.6 Hz, 1H) 5.07 (m, 1H) |
| 483 | HO-CH₂CH₂-NH-C(O)-O-⌇ | -H | 806 FAB MASS | (400 MHz): 0.82-0.89 (m, 6H) 0.91 (t, J = 7.3 Hz, 3H) 1.01-1.24 (m, 16H) 1.32 (s, 3H) 1.53-2.09 (m, 6H) 2.18-2.45 (m, 14H) 2.58-2.62 (m, 1H) 2.78-2.92 (m, 2H) 3.20-3.23 (m, 4H) 3.34 (s, 3H) 3.36-3.39 (m, 3H) 3.56-3.59 (m, 1H) 3.65-3.75 (m, 3H) 4.21 (m, 1H) 4.36-4.45 (m, 2H) 4.54 (d, J = 9.8 Hz, 1H) 4.64 (m, 1H) 4.98 (d, J = 4.6 Hz, 1H) 5.39 (m, 1H) |
| 484 | MeO-CH₂CH₂-NH-C(O)-O-⌇ | -H | 820.3 | (400 MHz): 0.82-0.83 (m, 6H) 0.91 (t, J = 7.3 Hz, 3H) 1.12-1.27 (m, 16H) 1.32 (s, 3H) 1.52-1.76 (m, 6H) 2.19-2.44 (m, 14H) 2.60 (m, 1H) 2.80-2.92 (m, 2H) 3.17-3.24 (m, 4H) 3.34-3.35 (m, 7H) 3.37-3.47 (m, 4H) 3.56-3.59 (m, 1H) 3.70 (d, J = 8.1 Hz, 1H) 4.21 (m, 1H) 4.34-4.46 (m, 2H) 4.54 (d, J = 9.8 Hz, 1H) 4.65 (m, 1H) 4.98 (d, J = 4.6 Hz, 1H) 5.23 (m, 1H) |
| 485 | HO-CH₂CH₂-N(Me)-C(O)-O-⌇ | -H | 820.3 | (400 MHz): 0.82-0.83 (m, 6H) 0.90 (t, J = 7.3 Hz, 3H) 1.09-1.26 (m, 16H) 1.33 (s, 3H) 1.52-1.85 (m, 6H) 2.15-2.67 (m, 15H) 2.82-2.99 (m, 5H) 3.10 (d, J = 7.6 Hz, 1H) 3.23 (s, 3H) 3.42-3.78 (m, 7H) 4.10 (m, 1H) 4.41-4.47 (m, 2H) 4.58-4.64 (m, 2H) 4.97 (d, J = 4.6 Hz, 1H) |
| 486 | piperidine-N-C(O)-O-⌇ | -H | 830.3 | (400 MHz): 0.82-0.84 (m, 6H) 0.90 (t, J = 7.3 Hz, 3H) 1.10-1.28 (m, 16H) 1.31 (s, 3H) 1.50-1.64 (m, 10H) 1.74 (m, 1H) 1.88 (m, 1H) 2.14-2.47 (m, 14H) 2.56 (m, 1H) 2.80-2.93 (m, 2H) 3.22-3.27 (m, 4H) 3.33 (s, 3H) 3.44 (m, 5H) 3.63 (m, 1H) 3.70 (d, J = 6.8 Hz, 1H) 4.07 (d, J = 4.6 Hz, 1H) 4.39 (m, 1H) 4.55-4.59 (m, 2H) 4.67 (m, 1H) 4.98 (d, J = 4.6 Hz, 1H) |
| 487 | morpholine-N-C(O)-O-⌇ | -H | 832.3 | (400 MHz): 0.82-0.84 (m, 6H) 0.90 (t, J = 7.3 Hz, 3H) 1.10-1.31 (m, 19H) 1.50-1.64 (m, 4H) 1.75 (m, 1H) 1.87 (m, 1H) 2.23-2.37 (m, 4H) 2.42 (s, 3H) 3.41-3.71 (m, 8H) 4.10 (d, J = 4.4 Hz, 1H) 4.40 (m, 1H) 4.53-4.59 (m, 2H) 4.64 (m, 1H) 4.98 (d, J = 4.9 Hz, 1H) |
| 488 | Me-(CH₂)₃-NH-C(O)-O-⌇ | -H | 818.3 | (400 MHz): 0.82-0.83 (m, 6H) 0.86-0.92 (m, 6H) 1.09-1.37 (m, 23H) 1.45-1.93 (m, 6H) 2.14-2.44 (m, 14H) 2.60 (m, 1H) 2.80 (m, 1H) 2.90 (d, J = 15.4 Hz, 1H) 3.19-3.24 (m, 6H) 3.34 (s, 3H) 3.40 (d, J = 8.3 Hz, 1H) 3.55 (m, 1H) 3.71 (d, J = 8.3 Hz, 1H) 4.22 (m, 1H) 4.34-4.44 (m, 2H) 4.55 (d, J = 9.8 Hz, 1H) 4.64 (m, 1H) 4.86 (t, J = 5.5 Hz, 1H) 4.98 (d, J = 4.6 Hz, 1H) |

TABLE 11-continued formula (W)

| Example | R^1W | R^2W | ESI MS (M + H) | $^1$H-NMR, CDCl$_3$, δ (ppm) |
|---|---|---|---|---|
| 489 | Me-NH-C(O)-O- (methylcarbamate linked via tertiary carbon with Me) | H | 776 | (400 MHz): 0.82-0.83 (m, 6H) 0.91 (t, J = 7.3 Hz, 3H) 1.12-1.27 (m, 16H) 1.32 (s, 3H) 1.50-1.88 (m, 6H) 2.14-2.43 (m, 14H) 2.59 (m, 1H) 2.80-2.84 (m, 4H) 2.90 (d, J = 14.2 Hz, 1H) 3.19-3.23 (m, 4H) 3.34 (s, 3H) 3.39 (d, J = 8.6 Hz, 1H) 3.55 (m, 1H) 3.70 (d, J = 8.3 Hz, 1H), 4.22 (m, 1H), 4.34-4.44 (m, 2H) 4.56 (d, J = 9.8 Hz, 1H) 4.64 (m, 1H) 4.80 (m, 1H) 4.98 (d, J = 4.6 Hz, 1H) |
| 490 | H$_2$N-CH$_2$CH$_2$-NH-C(O)-O- | H | 805 | (400 MHz): 0.83 (d, J = 6.82 Hz, 6H) 0.91 (t, J = 7.31 Hz, 3H) 1.08-1.28 (m, 2H) 1.13 (d, J = 7.31 Hz, 3H) 1.17 (s, 3H) 1.18 (d, J = 8.04 Hz, 6H) 1.20 (d, J = 6.09 Hz, 3H) 1.32 (s, 3H) 1.50-1.90 (m, 8H) 2.10-2.46 (m, 6H) 2.32 (s, 6H) 2.37 (s, 3H) 2.58-2.67 (m, 1H) 2.75-2.95 (m, 4H) 3.15-3.31 (m, 3H) 3.24 (s, 3H) 3.34 (s, 3H) 3.40 (d, J = 6.33 Hz, 1H) 3.54-3.63 (m, 1H) 3.71 (d, J = 8.04 Hz, 1H) 4.16-4.25 (m, 1H) 4.34-4.44 (m, 1H) 4.45 (d, J = 7.06 Hz, 1H) 4.54 (d, J = 9.74 Hz, 1H) 4.60-4.70 (m, 1H) 4.98 (d, J = 4.78 Hz, 1H) 5.31 (t, J = 5.60 Hz, 1H) |
| 491 | H$_2$N-(CH$_2$)$_3$-NH-C(O)-O- | H | 819 | (400 MHz): 0.82 (d, J = 6.82 Hz, 6H) 0.95 (t, J = 7.31 Hz, 3H) 1.08-1.26 (m, 2H) 1.12 (d, J = 7.31 Hz, 3H) 1.16 (s, 3H) 1.17 (d, J = 9.01 Hz, 6H) 1.21 (d, J = 6.33 Hz, 3H) 1.32 (s, 3H) 1.49-1.92 (m, 10H) 2.10-2.48 (m, 6H) 2.31 (s, 6H) 2.37 (s, 3H) 2.55-2.64 (m, 1H) 2.78 (t, J = 6.58 Hz, 2H) 2.82 (dd, J = 5.36, 7.31 Hz, 1H) 2.90 (d, J = 15.10 Hz, 1H) 3.18-3.26 (m, 1H) 3.24 (s, 3H) 3.28-3.36 (m, 2H) 3.34 (s, 3H) 3.40 (d, J = 6.57 Hz, 1H) 3.52-3.62 (m, 1H) 3.71 (d, J = 8.29 Hz, 1H) 4.16-4.27 (m, 1H) 4.32-4.43 (m, 1H) 4.44 (d, J = 7.06 Hz, 1H) 4.55 (d, J = 9.74 Hz, 1H) 4.59-4.69 (m, 1H) 4.98 (d, J = 4.63 Hz, 1H) 5.28 (t, J = 5.60 Hz, 1H) |
| 492 | Me$_2$N-CH$_2$CH$_2$-NH-C(O)-O- | H | 833 | (400 MHz): 0.82 (d, J = 6.82 Hz, 6H) 0.90 (t, J = 7.31 Hz, 3H) 1.08-1.24 (m, 2H) 1.12 (d, J = 7.31 Hz, 3H) 1.17 (s, 3H) 1.18 (d, J = 6.09 Hz, 6H) 1.19 (d, J = 7.31 Hz, 3H) 1.32 (s, 3H) 1.45-1.95 (m, 6H) 2.12-2.35 (m, 4H) 2.21 (s, 6H) 2.31 (s, 6H) 2.37 (s, 3H) 2.37-2.48 (m, 4H) 2.55-2.65 (m, 1H) 2.76-2.86 (m, 1H) 2.90 (d, J = 14.8 Hz, 1H) 3.17-3.22 (m, 3H) 3.24 (s, 3H) 3.34 (s, 3H) 3.36-3.50 (m, 1H) 3.55-3.65 (m, 1H) 3.71 (d, J = 8.04 Hz, 1H) 4.14-4.23 (m, 1H) 4.33-4.43 (m, 1H) 4.46 (d, J = 7.06 Hz, 1H) 4.54 (d, J = 9.75 Hz, 1H) 4.60-4.70 (m, 1H) 4.98 (d, J = 4.63 Hz, 1H) 5.39 (t, J = 4.87 Hz, 1H) |
| 493 | N≡C-CH$_2$CH$_2$-NH-C(O)-O- | H | 815 | (400 MHz): 0.82 (d, J = 6.82 Hz, 6H) 0.91 (t, J = 7.31 Hz, 3H) 1.08-1.24 (m, 2H) 1.13 (d, J = 7.31 Hz, 3H) 1.16 (s, 3H) 1.18 (d, J = 5.11 Hz, 6H) 1.21 (d, J = 6.09 Hz, 3H) 1.32 (s, 3H) 1.49-1.95 (m, 6H) 2.11-2.48 (m, 5H) 2.31 (s, 6H) 2.37 (s, 3H) 2.54-2.62 (m, 1H) 2.64 (t, J = 6.33 Hz, 2H) 2.78-2.86 (m, 1H) 2.90 (d, J = 14.61 Hz, 1H) 3.16-3.24 (m, 2H) 3.23 (s, 3H) 3.34 (s, 3H) 3.36-3.61 (m, 4H) 3.70 (d, J = 8.04 Hz, 1H) 4.18-4.27 (m, 1H) 4.35-4.45 (m, 2H) 4.55 (d, J = 9.74 Hz, 1H) 4.58-4.70 (m, 1H) 4.99 (d, J = 4.63 Hz, 1H) 5.38 (t, J = 6.33 Hz, 1H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 494 | HO-propyl-NH-C(O)-O- | H | 820 | (400 MHz): 0.82 (d, J = 6.82 Hz, 6H) 0.91 (t, J = 7.31 Hz, 3H) 1.07-1.29 (m, 2H) 1.12 (d, J = 7.06 Hz, 3H) 1.17 (s, 3H) 1.18 (d, J = 7.80 Hz, 6H) 1.20 (d, J = 6.82 Hz, 3H) 1.32 (s, 3H) 1.48-1.91 (m, 8H) 2.10-2.48 (m, 4H) 2.31 (s, 6H) 2.37 (s, 3H) 2.54-2.67 (m, 1H) 2.75-2.87 (m, 1H) 2.90 (d, J = 14.61 Hz, 1H) 3.12-3.27 (m, 2H) 3.23 (s, 3H) 3.31-3.48 (m, 3H) 3.34 (s, 3H) 3.52-3.75 (m, 4H) 4.16-4.26 (m, 1H) 4.33-4.42 (m, 1H) 4.44 (d, J = 7.07 Hz, 1H) 4.55 (d, J = 9.74 Hz, 1H) 4.58-4.69 (m, 1H) 4.98 (d, J = 4.63 Hz, 1H) 5.19 (t, J = 4.87 Hz, 1H) |
| 495 | HO-butyl-NH-C(O)-O- | H | 834 | (400 MHz): 0.82 (d, J = 6.81 Hz, 6H) 0.91 (t, J = 7.31 Hz, 3H) 1.08-1.28 (m, 2H) 1.12 (d, J = 7.31 Hz, 3H) 1.16 (s, 3H) 1.17 (d, J = 6.33 Hz, 6H) 1.19 (d, J = 7.06 Hz, 3H) 1.39 (s, 3H) 1.50-1.72 (m, 10H) 2.10-2.21 (m, 1H) 2.22-2.47 (m, 3H) 2.32 (s, 6H) 2.37 (s, 3H) 2.54-2.66 (m, 1H) 2.77-2.87 (m, 1H) 2.91 (d, J = 14.61 Hz, 1H) 3.18-3.29 (m, 4H) 3.23 (s, 3H) 3.34 (s, 3H) 3.36-3.50 (m, 2H) 3.51-3.61 (m, 1H) 3.65-3.73 (m, 3H) 4.18-4.26 (m, 1H) 4.33-4.43 (m, 3H) 4.43 (d, J = 7.31 Hz, 1H) 4.55 (d, J = 9.74 Hz, 1H) 4.59-4.61 (m, 1H) 4.98 (d, J = 4.63 Hz, 1H) 5.04 (t, J = 4.87 Hz, 1H) |
| 496 | H$_2$N-C(O)-O- | H | 762 | (400 MHz): 0.82 (d, J = 7.06 Hz, 6H) 0.91 (t, J = 7.31 Hz, 3H) 1.06-1.25 (m, 2H) 1.13 (d, J = 7.30 Hz, 3H) 1.18 (s, 3H) 1.18 (d, J = 8.28 Hz, 3H) 1.21 (d, J = 6.09 Hz, 6H) 1.32 (s, 3H) 1.49-1.93 (m, 7H) 2.16 (d, J = 14.37 Hz, 1H) 2.21-2.49 (m, 3H) 2.31 (s, 6H) 2.37 (s, 3H) 2.56-2.64 (m, 1H) 2.76-2.87 (m, 1H) 2.90 (d, J = 15.10 Hz, 1H) 3.15-3.26 (m, 2H) 3.24 (s, 3H) 3.35 (s, 3H) 3.36-3.44 (m, 1H) 3.50-3.61 (m, 1H) 3.71 (d, J = 8.04 Hz, 1H) 4.19-4.28 (m, 1H) 4.36-4.44 (m, 1H) 4.43 (d, J = 7.07 Hz, 1H) 4.54 (d, J = 9.75 Hz, 1H) 4.59-4.93 (m, 3H) 4.98 (d, J = 4.63 Hz, 1H) |
| 497 | Me$_2$N-C(O)-O- | H | 790 | (300 MHz): 0.78-0.88 (m, 6H) 0.90 (t, J = 7.42 Hz, 3H) 1.09-1.27 (m, 11H) 1.11 (d, J = 5.76 Hz, 3H) 1.12 (s, 3H) 1.31 (s, 3H) 1.44-1.95 (m, 7H) 2.12-2.48 (m, 4H) 2.29 (s, 6H) 2.36 (s, 3H) 2.77-2.95 (m, 2H) 2.92 (s, 3H) 2.94 (s, 3H) 3.15-3.27 (m, 2H) 3.24 (s, 3H) 3.33 (s, 3H) 3.36-3.54 (m, 1H) 3.58-3.69 (m, 1H) 3.71 (d, J = 7.41 Hz, 1H) 4.08 (d, J = 5.50 Hz, 1H) 4.35-4.48 (m, 1H) 4.54 (d, J = 9.62 Hz, 1H) 4.56 (d, J = 7.14 Hz, 1H) 4.61-4.71 (m, 1H) 4.97 (d, J = 4.67 Hz, 1H) |
| 498 | piperazine-1-carbonyloxy | H | 831.4 | (400 MHz): 0.83 (d, J = 6.33 Hz, 6H) 0.90 (t, J = 7.31 Hz, 3H) 1.07-1.28 (m, 11H) 1.11 (d, J = 8.28 Hz, 3H) 1.12 (s, 3H) 1.31 (s, 3H) 1.49-1.94 (m, 8H) 2.13-2.48 (m, 5H) 2.29 (s, 6H) 2.36 (s, 3H) 2.48-2.58 (m, 1H) 2.73-2.95 (m, 6H) 3.16-3.27 (m, 2H) 3.24 (s, 3H) 3.33 (s, 3H) 3.34-3.65 (m, 2H) 3.70 (d, J = 7.06 Hz, 1H) 4.03-4.13 (m, 1H) 4.35-4.45 (m, 1H) 4.52-4.60 (m, 2H) 4.60-4.70 (m, 1H) 4.98 (d, J = 4.38 Hz, 1H) |

TABLE 11-continued formula (W)

| Example | R[1W] | R[2W] | ESI MS (M + H) | $^1$H-NMR, CDCl₃, δ (ppm) |
|---|---|---|---|---|
| 499 | (Me-oxazole-Me-Me carbamate with N-ethyl-ethylenediamine linker) | H | 956.6 | mixture of diastereomers, (400 MHz): 0.82-0.84 (m, 6H) 0.91 (t, J = 7.3 Hz, 3H) 1.01-1.03 (m, 3H) 1.05-1.37 (m, 22H) 1.52-1.85 (m, 6H) 2.06-2.44 (m, 22H) 2.57-2.92 (m, 5H) 3.15-3.41 (m, 9H) 3.59 (m, 1H) 3.72 (d, J = 8.1 Hz, 1H) 3.93 (q, J = 7.1 Hz, 1H) 4.23 (m, 1H) 4.38-4.48 (m, 2H) 4.55-4.59 (m, 1H) 4.65 (m, 1H) 4.99 (d, J = 4.9 Hz, 1H) 5.30-4.35 (m, 1H) |
| 500 | (tetrazole-phenyl with Me-N-ethyl-ethylenediamine carbamate) | H | 1005.5 | mixture of diastereomers, (400 MHz): 0.82-0.83 (m, 6H) 0.92 (t, J = 7.3 Hz, 3H) 0.99-1.32 (m, 22H) 1.40 (d, J = 6.8 Hz) 1.52-1.85 (m, 6H) 2.14-2.67 (m, 19H) 2.80-2.92 (m, 2H) 3.19-3.39 (m, 9H) 3.56 (m, 1H) 3.71 (d, J = 8.3 Hz, 1H) 3.97 (q, J = 7.3 Hz, 1H) 4.25 (m, 1H) 4.36-4.45 (m, 2H) 4.54 (d, J = 9.8 Hz, 1H) 4.64 (m, 1H) 4.98 (d, J = 4.4 Hz, 1H) 5.18-5.20 (m, 1H) 7.52-7.59 (m, 3H) 7.73 (m, 1H) 9.13 (m, 1H) |
| 501 | (1,3,5-trimethylpyrazole with N-ethyl-ethylenediamine carbamate) | H | 969.6 | mixture of diastereomers, (400 MHz): 0.82-0.83 (m, 6H) 0.89-0.97 (m, 6H) 1.12-1.33 (m, 22H) 1.52-1.64 (m, 6H) 2.19-2.71 (m, 25H) 2.80-2.91 (m, 2H) 3.19-3.24 (m, 6H) 3.34-3.40 (m, 4H) 3.51-3.72 (m, 6H) 4.22 (m, 1H) 4.39-4.55 (m, 2H) 4.65 (m, 1H) 4.98 (d, J = 4.6 Hz, 1H) 5.11-5.13 (m, 1H) |
| 502 | (4-morpholinophenyl-Me with N-ethyl-ethylenediamine carbamate) | H | 1022.7 | mixture of diastereomers, (400 MHz): 0.82-0.84 (m, 6H) 0.91 (t, J = 7.3 Hz, 3H) 0.95-1.01 (m, 3H) 1.11-1.33 (m, 22H) 1.47-1.64 (m, 6H) 2.25-2.62 (m, 19H) 2.79-2.91 (m, 2H) 3.13-3.16 (m, 4H) 3.20-3.24 (m, 6H) 3.31-3.39 (m, 4H) 3.61 (m, 1H) 3.72 (d, J = 8.1 Hz, 1H) 3.76-3.87 (m, 5H) 4.22 (m, 1H) 4.37-4.48 (m, 2H) 4.55 (d, J = 9.8 Hz, 1H) 4.65 (m, 1H) 4.98 (d, J = 4.6 Hz, 1H) 5.27-5.30 (m, 1H) 6.85 (d, J = 8.6 Hz, 2H) 7.19 (d, J = 8.6 Hz, 2H) |
| 503 | (4-(morpholinosulfonyl)phenyl-Me with N-ethyl-ethylenediamine carbamate) | H | 1086.7 | mixture of diastereomers, (400 MHz): 0.82-0.84 (m, 6H) 0.91 (t, J = 7.3 Hz, 3H) 0.98-1.02 (m, 3H) 1.10-1.32 (m, 19H) 1.37 (d, J = 6.8 Hz, 3H) 1.50-1.65 (m, 6H) 2.25-2.66 (m, 19H) 2.81-2.91 (m, 2H) 3.01 (m, 4H) 3.20-3.40 (m, 10H) 3.58 (m, 1H) 3.71-3.77 (m, 5H) 3.93 (d, J = 6.8 Hz, 1H) 4.25 (m, 1H) 4.37-4.45 (m, 2H) 4.56 (d, J = 9.8 Hz, 1H) 4.65 (m, 1H) 4.99 (d, J = 4.4 Hz, 1H) 5.19 (m, 1H) 7.51 (d, J = 8.3 Hz, 2H) 7.69 (d, J = 8.3 Hz, 2H) |
| 504 | (1-ethyl-5-methylpyrazole with N-ethyl-ethylenediamine carbamate) | H | 969.6 | mixture of diastereomers, (400 MHz): 0.82-0.84 (m, 6H) 0.91 (t, J = 7.3 Hz, 3H) 0.99-1.42 (m, 22H) 1.52-1.64 (m, 6H) 2.09-2.60 (m, 22H) 2.81-2.92 (m, 2H) 3.19-3.24 (m, 6H) 3.34-3.39 (m, 4H) 3.58 (m, 1H) 3.71 (d, J = 7.8 Hz, 1H) 3.82 (q, J = 7.1 Hz, 1H) 4.05-4.11 (m, 2H) 4.22 (m, 1H) 4.36-4.46 (m, 2H) 4.54 (dd, J = 9.8 Hz, J = 2.0 Hz, 1H) 4.65 (m, 1H) 4.98 (d, J = 4.4 Hz, 1H) 5.16-5.25 (m, 1H) |

TABLE 11-continued formula (W)

| Example | R$^{1W}$ | R$^{2W}$ | ESI MS (M + H) | $^1$H-NMR, CDCl$_3$, δ (ppm) |
|---------|----------|----------|----------------|------------------------------|
| 505 | | H | 1095.6 | mixture of diastereomers, (400 MHz): 0.82-0.84 (m, 6H) 0.91 (t, J = 7.3 Hz, 3H) 0.95-0.99 (m, 3H) 1.10-1.32 (m, 22H) 1.52-1.64 (m, 6H) 2.15-2.62 (m, 19H) 2.81-2.92 (m, 2H) 3.19-3.24 (m, 6H) 3.31-3.39 (m, 4H) 3.60 (m, 1H) 3.71-3.78 (m, 5H) 3.85 (s, 3H) 4.23 (m, 1H) 4.37-4.57 (m, 5H) 4.65 (m, 1H) 4.98 (d, J = 4.4 Hz, 1H) 5.30-5.35 (m, 1H) 6.62 (d, J = 8.5 Hz, 1H) 7.20 (d, J = 8.5 Hz, 1H), 7.27 (brs, 1H) |
| 506 | | H | 1038.6 | mixture of diastereomers, (400 MHz): 0.82-0.84 (m, 6H) 0.91 (t, J = 7.3 Hz, 3H) 1.12-1.32 (m, 28H) 1.52-1.67 (m, 6H) 2.15-2.43 (m, 14H) 2.56-2.62 (m, 3H) 2.80-2.91 (m, 2H) 3.16-3.27 (m, 6H) 3.30-3.44 (m, 8H) 3.59 (m, 1H) 3.69-3.73 (m, 2H) 4.22 (m, 1H) 4.35-4.47 (m, 2H) 4.53-4.56 (dd, J = 9.8 Hz, J = 1.7 Hz, 1H) 4.65 (m, 3H) 4.98 (d, J = 4.6 Hz, 1H) 5.27-5.31 (m, 1H) 6.89 (dd, J = 8.6 Hz, J = 2.0 Hz, 2H) 7.18 (d, J = 8.6 Hz, 1H) |
| 507 | | H | 1036.6 | mixture of diastereomers, (400 MHz): 0.82-0.84 (m, 6H) 0.91 (t, J = 7.3 Hz, 3H) 1.12-1.32 (m, 25H) 1.52-2.01 (m, 10H) 2.25-2.44 (m, 16H) 2.59 (m, 3H) 2.81-2.91 (m, 2H) 3.20-3.73 (m, 17H) 4.22 (m, 1H) 4.37-4.46 (m, 2H) 4.53-4.64 (m, 4H) 4.98 (d, J = 4.6 Hz, 1H) 5.29-5.31 (m, 1H) 6.89 (dd, J = 8.6 Hz, J = 1.9 Hz, 2H) 7.18 (d, J = 8.6 Hz, 1H) |
| 508 | | H | 977.5 | mixture of diastereomers, (400 MHz): 0.82-0.84 (m, 6H) 0.91 (t, J = 7.3 Hz, 3H) 1.12-1.32 (m, 19H) 1.37 (d, J = 6.6 Hz, 3H) 1.52-1.73 (m, 6H) 2.28-2.44 (m, 14H) 2.55-2.69 (m, 3H) 2.81-2.92 (m, 2H) 3.22-3.39 (m, 10H) 3.58 (m, 1H) 3.71 (d, J = 8.1 Hz, 1H) 3.87 (q, J = 6.4 Hz, 1H) 4.23 (m, 1H) 4.37-4.45 (m, 2H) 4.55 (dd, J = 9.8 Hz, J = 2.7 Hz, 1H) 4.64 (m, 1H) 4.98 (d, J = 4.4 Hz, 1H) 5.27-5.28 (m, 1H) 7.53 (d, J = 8.3 Hz, 2H) 7.65 (d, J = 8.3 Hz, 2H) 8.99 (d, J = 2.9 Hz, 1H) |
| 509 | | H | 746 FAB MASS | (300 MHz): 0.80-0.83 (m, 6H) 0.90 (t, J = 7.5 Hz, 3H) 1.07-1.30 (m, 16H) 1.34 (s, 3H) 1.41-1.82 (m, 6H) 2.02-2.54 (m, 22H) 2.74-2.81 (m, 1H) 2.93 (d, J = 14.7 Hz, 1H) 3.15-3.25 (m, 7H) 3.37 (d, J = 8.4 Hz, 1H) 3.46-3.53 (m, 1H) 3.73 (d, J = 8.4 Hz, 1H) 4.20 (d, J = 4.8 Hz, 1H) 4.36 (d, J = 7.2 Hz, 1H) 4.46 (dq, J = 9.9 Hz, J = 6.0 Hz, 1H) 4.62 (m, 1H) 4.90 (d, J = 4.2 Hz, 1H) |
| 510 | | H | 955 | mixture of diastereomers (400 MHz): 0.83 (d, J = 6.84 Hz, 6H) 0.91 (t, J = 7.32 Hz, 3H) 1.08-1.34 (m, 22H) 1.49-1.91 (m, 5H) 2.13-2.76 (m, 6H) 2.30 (s, 3H) 2.37 (s, 6H) 2.77-2.87 (m, 1H) 2.90 (d, J = 14.65 Hz, 1H) 3.11-3.49 (m, 12H) 3.52-3.74 (m, 3H) 3.84-3.91 (m, 3H) 4.15-4.25 (m, 1H) 4.32-4.49 (m, 2H) 4.54 (d, J = 9.76 Hz, 1H) 4.59-4.69 (m, 1H) 4.98 (d, J = 4.64 Hz, 1H) 5.02-5.29 (m, 1H) 6.73-6.85 (m, 3H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 511 | (2-hydroxy-3-methylphenyl-CH(Me)-NH-CH₂CH₂-NH-C(O)-O-) | H | 955 | mixture of diastereomers (400 MHz): 0.83 (d, J = 6.84 Hz, 6H) 0.91 (t, J = 7.33 Hz, 3H) 1.09-1.41 (m, 17H) 1.12 (d, J = 7.73 Hz, 3H) 1.32 (s, 3H) 1.48-1.91 (m, 5H) 2.08-2.48 (m, 6H) 2.30 (s, 3H) 2.33 (s, 3H) 2.37 (s, 3H) 2.57-2.93 (m, 5H) 3.20-3.49 (m, 6H) 3.23 (s, 3H) 3.37 (s, 3H) 3.50-3.64 (m, 1H) 3.71 (d, J = 8.06 Hz, 1H) 3.79-3.88 (m, 1H) 4.15-4.27 (m, 1H) 4.33-4.48 (m, 2H) 4.51-4.57 (m, 1H) 4.59-4.70 (m, 1H) 4.98 (d, J = 4.64 Hz, 1H) 5.08-5.25 (m, 1H) 6.22-6.29 (m, 1H) 6.56-6.64 (m, 1H) |
| 512 | (3,4-dimethoxy-2-hydroxyphenyl-CH(Me)-NH-CH₂CH₂-NH-C(O)-O-) | H | 985 | mixture of diastereomers (400 MHz): 0.82 (d, J = 6.84 Hz, 6H) 0.90 (t, J = 7.33 Hz, 3H) 1.08-1.32 (m, 17H) 1.32 (s, 3H) 1.42 (d, J = 6.83 Hz, 3H) 1.50-1.89 (m, 5H) 2.13-2.45 (m, 3H) 2.30 (s, 6H) 2.37 (s, 3H) 2.54-2.64 (m, 1H) 2.65-2.87 (m, 3H) 2.90 (d, J = 14.9 Hz, 1H) 3.17-3.59 (m, 10H) 3.23 (s, 3H) 3.70 (d, J = 6.83 Hz, 1H) 3.83 (s, 3H) 3.89-3.95 (m, 4H) 4.18-4.27 (m, 1H) 4.35-4.46 (m, 2H) 4.52-4.57 (m, 1H) 4.60-4.68 (m, 1H) 4.98 (d, J = 4.64 Hz, 1H) 5.09-5.17 (m, 1H) 6.36 (d, J = 8.30 Hz, 1H) 6.65 (d, J = 8.55 Hz, 1H) |
| 513 | (4-hydroxy-3-(methoxymethyl)phenyl-CH(Me)-NH-CH₂CH₂-NH-C(O)-O-) | H | 969 | mixture of diastereomers (400 MHz): 0.83 (d, J = 6.83 Hz, 6H) 0.91 (t, J = 7.56 Hz, 3H) 1.08-1.34 (m, 23H) 1.49-1.92 (m, 5H) 2.12-2.69 (m, 6H) 2.30 (s, 3H) 2.34 (s, 3H) 2.37 (s, 3H) 2.77-2.87 (m, 1H) 2.90 (d, J = 14.9 Hz, 1H) 3.12-3.52 (m, 9H) 3.24 (s, 3H) 3.46 (s, 3H) 3.54-3.62 (m, 1H) 3.66 (q, J = 6.59 Hz, 1H) 3.71 (d, J = 8.06 Hz, 1H) 4.15-4.25 (m, 1H) 4.33-4.49 (m, 2H) 4.54 (d, J = 9.76 Hz, 1H) 4.61-4.67 (m, 3H) 4.98 (d, J = 4.64 Hz, 1H) 5.12-5.31 (m, 1H) 6.77-6.84 (m, 1H) 6.93-6.97 (m, 1H) 7.08-7.16 (m, 1H) |
| 514 | (2-hydroxy-5-methoxyphenyl-CH(Me)-NH-CH₂CH₂-NH-C(O)-O-) | H | 955 | mixture of diastereomers (400 MHz): 0.82 (d, J = 7.08 Hz, 6H) 0.91 (t, J = 7.32 Hz, 3H) 1.08-1.34 (m, 17H) 1.32 (s, 3H) 1.40-1.45 (m, 3H) 1.49-1.91 (m, 5H) 2.12-2.46 (m, 3H) 2.30 (s, 6H) 2.37 (s, 3H) 2.53-2.74 (m, 2H) 2.75-2.87 (m, 2H) 2.90 (d, J = 14.64 Hz, 1H) 3.18-3.64 (m, 10H) 3.23 (s, 3H) 3.69-3.73 (m, 1H) 3.74 (s, 3H) 3.85-3.92 (m, 1H) 4.16-4.27 (m, 1H) 4.35-4.47 (m, 2H) 4.54 (d, J = 9.77 Hz, 1H) 4.60-4.70 (m, 1H) 4.99 (d, J = 4.64 Hz, 1H) 5.17 (t, J = 5.86 Hz, 1H) 6.51-6.54 (m, 1H) 6.68-6.71 (m, 2H) |
| 515 | (2,6-dihydroxyphenyl-CH(Me)-NH-CH₂CH₂-NH-C(O)-O-) | H | 941.5 | mixture of diastereomers (400 MHz): 0.83 (d, J = 7.08 Hz, 6H) 0.91 (t, J = 7.32 Hz, 3H) 1.08-1.30 (m, 17H) 1.32 (s, 3H) 1.39 (d, J = 6.59 Hz, 3H) 1.50-1.91 (m, 5H) 2.12-2.49 (m, 4H) 2.31 (s, 3H) 2.32 (s, 3H) 2.38 (s, 3H) 2.58-2.67 (m, 1H) 2.69-2.87 (m, 3H) 2.91 (d, J = 15.14 Hz, 1H) 3.19-3.61 (m, 8H) 3.23 (s, 3H) 3.35 (s, 3H) 3.67-3.74 (m, 1H) 4.16-4.29 (m, 1H) 4.32-4.51 (m, 1H) 4.54 (d, J = 9.77 Hz, 1H) 4.59-4.69 (m, 1H) 4.95-5.20 (m, 1H) 6.26-6.32 (m, 2H) 6.90-6.96 (m, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 516 | naphthyl-NH-CH₂CH₂-NH-C(=O)-O-C(CH₃)₂- | H | 931.6 | (400 MHz): 0.81 (d, J = 7.08 Hz, 6H) 0.90 (d, J = 7.32 Hz, 3H) 1.05-1.33 (m, 14H) 1.13 (s, 3H) 1.29 (s, 3H) 1.48-1.89 (m, 5H) 2.08-2.55 (m, 6H) 2.24 (s, 6H) 2.36 (s, 3H) 2.76-2.94 (m, 2H) 2.14-3.51 (m, 6H) 3.22 (s, 3H) 3.30 (s, 3H) 3.60-3.71 (m, 3H) 4.14-4.25 (m, 1H) 4.34-4.42 (m, 2H) 4.61-4.70 (m, 1H) 4.62 (d, J = 9.76 Hz, 1H) 4.91-4.97 (m, 1H) 4.98 (d, J = 4.64 Hz, 1H) 5.36 (t, J = 6.35 Hz, 1H) 6.55 (d, J = 7.32 Hz, 1H) 7.23 (d, J = 8.30 Hz, 1H) 7.33 (t, J = 7.81 Hz, 1H) 7.39-7.47 (m, 2H) 7.75-7.82 (m, 2H) |
| 517 | tetrahydroisoquinolin-2-yl-CH₂CH₂-NH-C(=O)-O-C(CH₃)₂- | H | 921.5 | (400 MHz): 0.79-0.86 (m, 6H) 0.90 (t, J = 7.30 Hz, 3H) 0.96-1.38 (m, 8H) 1.05 (d, J = 6.08 Hz, 3H) 1.09 (d, J = 7.31 Hz, 3H) 1.16 (s, 3H) 1.29 (s, 3H) 1.48-1.89 (m, 5H) 2.12-2.51 (m, 4H) 2.20 (s, 6H) 2.36 (s, 3H) 2.60-2.95 (m, 8H) 3.13 (dd, J = 2.68, 9.89 Hz, 1H) 3.22 (s, 3H) 3.31 (s, 3H) 3.35-3.53 (m, 4H) 3.61 (s, 2H) 3.67 (d, J = 8.04 Hz, 1H) 4.13-4.20 (m, 1H) 4.28-4.37 (m, 1H) 4.39 (d, J = 7.07 Hz, 1H) 4.52 (d, J = 9.74 Hz, 1H) 4.59-4.71 (m, 1H) 4.96 (d, J = 4.63 Hz, 1H) 5.47 (t, J = 4.88 Hz, 1H) 6.98-7.02 (m, 1H) 7.07-7.16 (m, 3H) |
| 518 | Me-C(=O)-NH-C(CH₃)₂- | H | 760 FAB MASS | (400 MHz): 0.82-0.83 (m, 6H) 0.91 (t, J = 7.3 Hz, 3H) 1.10-1.12 (m, 6H) 1.17-1.32 (m, 13H) 1.48-1.97 (m, 6H) 2.03 (s, 3H) 2.14-2.54 (m, 15H) 2.81 (dq, J = 7.3 Hz, J = 5.1 Hz, 1H) 2.90 (d, J = 14.7 Hz, 1H) 3.23-3.30 (m, 7H) 3.40-3.49 (m, 2H) 3.64-3.74 (m, 2H) 4.12 (dq, J = 10.0 Hz, J = 6.3 Hz, 1H) 4.24 (m, 1H) 4.98 (d, J = 4.4 Hz, 1H) 5.90 (d, J = 9.5 Hz, 1H) |
| 519 | HO-CH₂CH₂-NH-C(CH₃)₂- | H | 762.4 | (400 MHz): 0.82-0.84 (m, 6H) 0.90 (t, J = 7.3 Hz, 3H) 1.09 (d, J = 7.3 Hz, 3H) 1.16-1.32 (m, 16H) 1.51-1.86 (m, 6H) 2.01 (d, J = 9.8 Hz, 1H) 2.20-2.55 (m, 15H) 2.75-2.84 (m, 2H) 2.89 (d, J = 14.4 Hz, 1H) 3.04-3.13 (m, 1H) 3.20-3.25 (m, 4H) 3.30 (s, 3H) 3.42 (m, 1H) 3.52-3.59 (m, 2H) 3.73 (d, J = 5.1 Hz, 1H) 4.06 (dq, J = 9.6 Hz, J = 6.2 Hz, 1H) 4.14 (d, J = 3.9 Hz, 1H) 4.42 (d, J = 7.1 Hz, 1H) 4.66 (m, 1H) 4.95 (d, J = 4.6 Hz, 1H) |
| 520 | Me-S(=O)₂-NH-C(CH₃)₂- | H | 796.3 | (400 MHz): 0.82-0.84 (m, 6H) 0.90 (t, J = 7.3 Hz, 3H) 1.10 (d, J = 7.3 Hz, 3H) 1.14-1.33 (m, 16H) 1.52-1.80 (m, 6H) 2.19-2.53 (m, 15H) 2.81 (dq, J = 7.3 Hz, J = 5.1 Hz, 1H) 2.89 (d, J = 14.4 Hz, 1H) 3.02 (s, 3H) 3.14 (dd, J = 9.5 Hz, J = 9.3 Hz, 1H) 3.20-3.24 (m, 4H) 3.30 (s, 3H) 3.41-3.49 (m, 2H) 3.66 (d, J = 8.1 Hz, 1H) 4.14-4.20 (m, 2H) 4.35 (d, J = 7.3 Hz, 1H) 4.65 (m, 1H) 4.90 (d, J = 9.0 Hz, 1H) 4.98 (d, J = 4.6 Hz, 1H) |
| 521 | -NH-C(=O)-NH-CH₂CH₂-N(Et)-CH(Me)-(2-MeO-C₆H₄) | H | 966.5 | (400 MHz): 0.81-0.83 (m, 6H) 0.91 (t, J = 7.3 Hz, 3H) 0.97 (m, 3H) 0.99-1.27 (m, 19H) 1.33 (s, 3H) 1.52-1.92 (m, 6H) 2.13-2.58 (m, 19H) 2.81 (dq, J = 7.2 Hz, J = 5.2 Hz, 1H) 2.89 (d, J = 15.4 Hz, 1H) 3.20-3.24 (m, 7H) 3.30 (s, 3H) 3.41-3.49 (m, 2H) 3.71 (d, J = 8.3 Hz, 1H) 3.85 (s, 3H) 4.03-4.13 (m, 1H) 4.23 (m, 1H) 4.35-4.40 (m, 2H) 4.63 (m, 1H) 4.71 (m, 1H) 4.98 (d, J = 4.4 Hz, 1H) 6.88-7.00 (m, 2H) 7.21-7.33 (m, 2H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 522 | (structure with amide, butyl chain, N-ethyl, α-methylbenzyl with 2-methoxy) | H | 965.6 | (300 MHz): 0.82 (d, J = 6.87 Hz, 6H) 0.91 (t, J = 7.14 Hz, 3H) 1.13 (t, J = 7.14 Hz, 3H) 1.06-1.35 (m, 17H) 1.09 (s, 3H) 1.32 (s, 3H) 1.48-1.94 (m, 4H) 1.56 (dd, J = 4.94, 15.11 Hz, 1H) 2.10-2.74 (m, 12H) 2.29 (s, 6H) 2.37 (s, 3H) 2.76-2.94 (m, 2H) 3.16-3.26 (m, 1H) 3.22 (s, 3H) 3.29 (s, 3H) 3.34-3.47 (m, 2H) 3.64-3.76 (m, 2H) 3.81 (s, 3H) 4.02-4.17 (m, 1H) 4.20-4.28 (m, 1H) 4.33-4.39 (m, 2H) 4.56-4.70 (m, 1H) 4.98 (d, J = 4.40 Hz, 1H) 5.85 (d, J = 9.61 Hz, 1H) 6.86 (d, J = 8.24 Hz, 1H) 6.94 (t, J = 7.15 Hz, 1H) 7.20 (t, J = 7.42 Hz, 1H) 7.36-7.52 (m, 1H) |
| 523 | Me₂N-propyl-urea | H | 846.5 | (400 MHz): 0.82 (d, J = 6.82 Hz, 6H) 0.84-0.94 (m, 6H) 1.08-1.35 (m, 5H) 1.10 (d, J = 7.07 Hz, 3H) 1.13 (s, 3H) 1.17 (d, J = 7.31 Hz, 3H) 1.33 (s, 3H) 1.52-1.90 (m, 7H) 1.91-2.50 (m, 6H) 2.26 (s, 6H) 2.33 (s, 6H) 2.38 (s, 3H) 2.53-2.63 (m, 1H) 2.75-2.86 (m, 1H) 2.92 (d, J = 15.35 Hz, 1H) 3.21-3.33 (m, 4H) 3.22 (s, 3H) 3.28 (s, 3H) 3.36-3.53 (m, 3H) 3.69 (d, J = 8.08 Hz, 1H) 4.08-4.24 (m, 2H) 4.36 (d, J = 7.31 Hz, 1H) 4.57-4.70 (m, 1H) 4.92-5.02 (m, 1H) 4.97 (d, J = 4.38 Hz, 1H) |
| 524 | (N-ethyl, butyl chain, α-methyl-2-methoxybenzyl amine) | H | 951.5 | (300 MHz): 0.81-0.92 (m, 9H) 0.99-1.37 (m, 25H) 1.46-2.01 (m, 11H) 2.20-2.57 (m, 19H) 2.77-2.91 (m, 4H) 3.16-3.32 (m, 7H) 3.40 (m, 1H) 3.65-3.75 (m, 2H) 3.81 (s, 3H) 3.97-4.11 (m, 2H) 4.33-4.38 (m, 1H) 4.43 (d, J = 7.2 Hz, 1H) 4.66 (m, 1H) 4.92 (d, J = 4.5 Hz, 1H) 6.85 (d, J = 8.1 Hz, 1H) 6.94 (m, 1H) 7.21 (m, 1H) 7.46 (m, 1H) |
| 525 | Me₂N-ethyl-urea | H | 832.4 | (300 MHz): 0.77-0.87 (m, 6H) 0.91 (t, J = 7.14 Hz, 3H) 1.10 (d, J = 7.14 Hz, 3H) 1.13 (s, 3H) 1.17 (d, J = 7.42 Hz, 3H) 1.20-1.32 (m, 8H) 1.33 (s, 3H) 1.49-1.63 (m, 2H) 1.63-1.89 (m, 3H) 1.92-2.11 (m, 2H) 2.11-2.47 (m, 21H) 2.48-2.59 (m, 1H) 2.75-2.86 (m, 1H) 2.87-2.96 (m, 1H) 3.18-3.34 (m, 8H) 3.37-3.56 (m, 3H) 3.70 (d, J = 7.97 Hz, 1H) 4.04-4.24 (m, 2H) 4.35 (d, J = 7.14 Hz, 1H) 4.58-4.68 (m, 1H) 4.97 (d, J = 4.40 Hz, 1H) 4.99-5.08 (m, 2H) |
| 526 | Me₂N-butyl-urea | H | 860.3 | (300 MHz): 0.78-0.87 (m, 6H) 0.91 (t, J = 7.14 Hz, 3H) 1.10 (d, J = 7.14 Hz, 3H) 1.13 (s, 3H) 1.17 (d, J = 7.42 Hz, 3H) 1.19-1.30 (m, 8H) 1.35 (s, 3H) 1.46-1.90 (m, 8H) 2.02-2.46 (m, 21H) 2.47-2.58 (m, 1H) 2.71-2.86 (m, 1H) 2.88-2.98 (m, 2H) 3.12-3.31 (m, 8H) 3.36-3.58 (m, 3H) 3.69 (d, J = 7.97 Hz, 1H) 4.04-4.24 (m, 2H) 4.33 (d, J = 7.42 Hz, 1H) 4.56-4.68 (m, 1H) 4.88 (d, J = 9.62 Hz, 1H) 4.96 (d, J = 4.12 Hz, 1H) 5.00-5.11 (m, 1H) |
| 527 | MeSO₂NH-ethyl-urea | H | 882.2 | (300 MHz): 0.77-0.87 (m, 6H) 0.91 (t, J = 7.42 Hz, 3H) 1.08 (d, J = 7.14 Hz, 3H) 1.13 (s, 3H) 1.17 (d, J = 7.42 Hz, 3H) 1.19-1.30 (m, 8H) 1.37 (s, 3H) 1.49-1.63 (m, 2H) 1.68-1.90 (m, 3H) 2.10-2.50 (m, 14H) 2.54-2.66 (m, 1H) 2.73-2.85 (m, 1H) 2.89-3.00 (m, 4H) 3.18-3.59 (m, 13H) 3.66 (d, J = 7.42 Hz, 1H) 4.07-4.20 (m, 2H) 4.29 (d, J = 7.14 Hz, 1H) 4.57-4.68 (m, 1H) 4.95 (d, J = 4.12 Hz, 1H) 5.27-5.40 (m, 1H) 5.51-5.62 (m, 1H) |

TABLE 11-continued formula (W)

[Structure of macrolide compound with R^1W and R^2W substituents]

| Example | R^1W | R^2W | ESI MS (M + H) | ^1H-NMR, CDCl_3, δ (ppm) |
|---------|------|------|----------------|---------------------------|
| 528 | [Me-C(O)-NH-CH_2-CH_2-NH-C(O)-NH-C(Me)-] | H | 846.3 | (300 MHz): 0.77-0.87 (m, 6H) 0.91 (t, J = 7.42 Hz, 3H) 1.09 (d, J = 7.14 Hz, 3H) 1.12 (s, 3H) 1.14-1.30 (m, 11H) 1.36 (s, 3H) 1.48-1.63 (m, 2H) 1.67-1.89 (m, 3H) 1.95 (s, 3H) 2.02-2.49 (m, 14H) 2.49-2.62 (m, 1H) 2.74-2.85 (m, 1H) 2.88-2.99 (m, 1H) 3.16-3.57 (m, 13H) 3.66 (d, J = 7.42 Hz, 1H) 4.07-4.21 (m, 2H) 4.29 (d, J = 7.14 Hz, 1H) 4.57-4.68 (m, 1H) 4.95 (d, J = 4.12 Hz, 1H) 5.19-5.32 (m, 1H) 5.49-5.59 (m, 1H) 6.85 (br s, 1H) |
| 529 | [2-methoxyphenyl-CH(Me)-N-(pyrrolidin-3-yl)-NH-C(O)-NH-C(Me)-] | H | 964 FAB MASS | mixture of diastereomers (300 MHz): 0.77-0.87 (m, 6H) 0.91 (t, J = 7.14 Hz, 3H) 1.04-1.40 (m, 20H) 1.47-2.05 (m, 6H) 2.10-2.64 (m, 17H) 2.66-3.08 (m, 4H) 3.12-3.32 (m, 8H) 3.36-3.54 (m, 4H) 3.64-3.75 (m, 1H) 3.77-3.89 (m, 4H) 4.02-4.31 (m, 3H) 4.31-4.38 (m, 1H) 4.57-4.69 (m, 1H) 4.78-5.04 (m, 3H) 6.82-6.92 (m, 2H) 7.15-7.24 (m, 1H) 7.39-7.49 (m, 1H) |
| 530 | [2-methoxyphenyl-CH(Me)-piperazinyl-C(O)-NH-C(Me)-] | H | 964.4 | mixture of diastereomers (400 MHz): 0.78-0.88 (m, 6H) 0.91 (t, J = 7.31 Hz, 3H) 1.09 (d, J = 7.14 Hz, 3H) 1.05-1.14 (m, 6H) 1.14-1.29 (m, 11H) 1.29-1.40 (m, 6H) 1.50-1.65 (m, 2H) 1.70-1.93 (m, 3H) 2.11-2.30 (m, 1H) 2.20-2.56 (m, 18H) 2.77-2.87 (m, 1H) 2.90-2.98 (m, 1H) 3.10-3.38 (m, 14H) 3.48-3.55 (m, 1H) 3.68-3.73 (m, 1H) 3.83 (s, 3H) 3.92-4.01 (m, 1H) 4.04-4.13 (m, 1H) 4.17-4.26 (m, 1H) 4.36-4.43 (m, 1H) 4.58-4.68 (m, 1H) 4.98 (d, J = 4.62 Hz, 1H) 5.00-5.07 (m, 1H) 6.88 (d, J = 8.04 Hz, 1H) 6.92-6.98 (m, 1H) 7.19-7.26 (m, 1H) 7.38-7.44 (m, 1H) |
| 531 | [Me_2N-C(O)-CH(Me)-N(Et)-(CH_2)_4-NH-C(Me)-] | H | 916.4 | mixture of diastereomers (300 MHz): 0.79-0.86 (m, 6H) 0.90 (t, J = 7.42 Hz, 3H) 1.12 (t, J = 7.14 Hz, 3H) 1.06-1.96 (m, 26H) 1.20 (s, 3H) 1.31 (s, 3H) 1.93 (d, J = 9.61 Hz, 1H) 2.13-2.67 (m, 12H) 2.30 (s, 6H) 2.36 (s, 3H) 2.70-2.88 (m, 3H) 2.93 (s, 3H) 3.15 (s, 3H) 3.17-3.25 (m, 1H) 3.25 (s, 3H) 3.28 (s, 3H) 3.36-3.47 (m, 1H) 3.60-3.78 (m, 3H) 3.94-4.15 (m, 2H) 4.44 (d, J = 7.42 Hz, 1H) 4.60-4.72 (m, 1H) 4.93 (d, J = 4.67 Hz, 1H) |
| 532 | [2-methoxyphenyl-CH(Me)-piperazinyl-CH_2-] | HO— | 951.5 | (300 MHz): 0.76-0.86 (m, 6H) 0.90 (t, J = 7.14 Hz, 3H) 1.04-1.24 (m, 17H) 1.24-1.38 (m, 6H) 1.46-1.90 (m, 5H) 2.10-2.50 (m, 21H) 2.50-2.83 (m, 5H) 2.85-2.96 (m, 1H) 3.14-3.26 (m, 4H) 3.32-3.48 (m, 4H) 3.56-3.72 (m, 2H) 3.81 (s, 3H) 3.86-3.95 (m, 1H) 4.02-4.10 (m, 1H) 4.46 (d, J = 7.14 Hz, 1H) 4.55-4.70 (m, 2H) 4.83 (d, J = 5.22 Hz, 1H) 6.86 (d, J = 8.24 Hz, 1H) 6.91-7.00 (m, 1H) 7.20 (t, J = 7.69 Hz, 1H) 7.41 (m, J = 6.59 Hz, 1H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 533 | (2-methoxybenzyl-methyl-pyrrolidinyl-amino group) | HO— | 951 FAB MASS | mixture of diastereomers (300 MHz): 0.77-0.87 (m, 6H) 1.46-1.92 (m, 5H) 2.00-2.56 (m, 9H) 2.28 (s, 6H) 2.38 (s, 3H) 2.62-2.87 (m, 6H) 2.87-2.97 (m, 1H) 3.10-3.28 (m, 4H) 2.35 (s, 3H) 3.39-3.60 (m, 2H) 3.62-3.71 (m, 1H) 3.76-3.88 (m, 1H) 3.82 (s, 3H) 4.06-4.14 (m, 1H) 4.37-4.51 (m, 2H) 4.59-4.70 (m, 1H) 4.83-4.91 (m, 1H) 6.86 (d, J = 8.52 Hz, 1H) 6.92-7.00 (m, 1H) 7.14-7.23 (m, 1H) 7.44-7.52 (m, 1H) |
| 534 | (carbamate-ethyl-N-ethyl-methoxyphenyl group) | —H | 967.6 | (400 MHz): 0.81-0.83 (m, 6H) 0.90 (t, J = 7.3 Hz, 3H) 0.94-1.03 (m, 3H) 1.08-1.31 (m, 22H) 1.43-1.84 (m, 6H) 2.13-2.91 (m, 21H) 3.18-3.40 (m, 10H) 3.68 (d, J = 8.1 Hz, 1H) 3.80 (s, 3H) 4.02-4.18 (m, 4H) 4.33-4.40 (m, 2H) 4.63 (m, 1H) 4.98 (d, J = 4.5 Hz, 1H) 5.10 (d, J = 9.9 Hz, 1H) 6.84-6.94 (m, 2H) 7.19 (ddd, J = 8.4 Hz, J = 6.9 Hz, J = 1.5 Hz, 1H) 7.37 (dd, J = 7.8 Hz, J = 1.5 Hz, 1H) |
| 535 | (NH-methyl-methoxyphenyl group) | OH | 882.4 | (400 MHz): 0.82 (d, J = 7.1 Hz, 3H) 0.82 (d, J = 7.1 Hz, 3H) 0.90 (t, J = 7.4 Hz, 3H) 1.07-1.26 (m, 21H) 1.31-1.35 (m, 7H) 1.70-1.90 (m, 4H) 2.04-2.55 (m, 19H) 2.82 (t, J = 6.8 Hz, 1H) 2.92 (d, J = 15.3 Hz, 1H) 3.19 (dd, J = 10.2, 7.4 Hz, 1H) 3.23 (s, 3H) 3.34 (s, 3H) 3.41 (m, 1H) 3.55 (m, 1H) 3.67 (d, J = 7.8 Hz, 1H) 4.04 (q, J = 6.7 Hz, 1H), 4.09 (m, 1H) 4.42 (d, J = 7.3 Hz, 1H) 4.46 (q, J = 6.8 Hz, 1H) 4.65 (m, 1H) 4.86 (d, J = 4.9 Hz, 1H) 6.86 (m, 1H) 6.94 (m, 1H) 7.21 (m, 1H) 7.31 (m, 1H) |
| 536 | (methoxybenzyl-NH group) | HO— | 868.3 | (400 MHz): 0.82 (d, J = 7.0 Hz, 3H) 0.90 (t, J = 7.3 Hz, 3H) 1.08-1.38 (m, 28H) 1.85-2.00 (m, 2H) 2.09-2.55 (m, 18H) 2.63-2.89 (m, 4H) 3.19 (dd, J = 10.2, 8.2 Hz, 1H) 3.21 (s, 3H) 3.35 (s, 3H) 3.41 (m, 1H) 3.51 (m, 1H) 3.67 (d, J = 8.0 Hz, 1H) 3.69 (d, J = 14.4 Hz, 1H) 3.79 (d, J = 14.4 Hz, 1H) 3.81 (s, 3H) 4.09 (m, 1H) 4.40 (d, J = 7.1 Hz, 1H) 4.45 (q, J = 6.6 Hz, 1H) 4.63 (m, 1H) 4.87 (m, 1H) 6.86 (m, 1H) 6.91 (m, 1H) 7.20-7.25 (m, 2H) |
| 537 | (benzyl-NH group) | HO— | 838.3 | (400 MHz): 0.81 (d, J = 7.0 Hz, 3H) 0.81 (d, J = 7.0 Hz, 3H) 0.90 (t, J = 7.3 Hz, 3H) 1.08-1.34 (m, 24H) 1.60-1.80 (m, 3H) 2.14-2.54 (m, 17H) 2.69-2.85 (m, 3H) 2.91 (m, 1H) 3.20 (m, 1H) 3.22 (s, 3H) 3.35 (s, 3H) 3.36-3.52 (m, 3H) 3.66 (d, J = 7.8 Hz, 1H) 3.70 (d, J = 13.3 Hz, 1H) 3.79 (d, J = 13.2 Hz, 1H) 4.10 (m, 1H) 4.39 (d, J = 7.3 Hz, 1H) 4.43 (q, J = 6.6 Hz, 1H) 4.64 (m, 1H) 4.89 (m, 1H) 7.24-7.32 (m, 4H) |
| 538 | (hydroxymethyl-NH-methylthiophenyl-OH group) | OH | 944.3 | (300 MHz): 0.77-0.87 (m, 6H) 0.91 (t, J = 7.14 Hz, 3H) 1.10 (d, J = 7.42 Hz, 3H) 1.13 (s, 3H) 1.13-1.27 (m, 14H) 1.29 (d, J = 6.59 Hz, 3H) 1.33 (s, 3H) 1.47-1.69 (m, 2H) 1.71-1.91 (m, 2H) 1.98 (dd, J = 5.23 Hz, J = 15.4 Hz, 1H) 2.10-2.35 (m, 10H) 2.38 (s, 3H) 2.41-2.54 (m, 5H) 2.56-2.64 (m, 1H) 2.69 (d, J = 12.4 Hz, 3H) 2.77-2.98 (m, 3H) 3.16-3.25 (m, 3H) 3.21 (s, 3H) 3.31-3.54 (m, 3H) 3.35 (s, 3H) 3.64-3.73 (m, 2H) 4.10-4.19 (m, 1H) 4.34-4.49 (m, 2H) 4.56 (d, J = 6.87 Hz, 1H) 4.59-4.69 (m, 1H) 4.91 (d, J = 4.34 Hz, 1H) 7.20-7.34 (m, 5H) |

TABLE 11-continued formula (W)

[Structure of macrolide compound with R$^{1W}$ and R$^{2W}$ substituents]

| Example | R$^{1W}$ | R$^{2W}$ | ESI MS (M + H) | $^1$H-NMR, CDCl$_3$, δ (ppm) |
|---|---|---|---|---|
| 539 | [structure: -NH-CH(CH(OH)-4-NO$_2$-C$_6$H$_4$)-CH$_2$OH] | -OH | 943.5 | (300 MHz): 0.78-0.88 (m, 6H) 0.92 (t, J = 7.14 Hz, 3H) 1.04-1.14 (m, 7H) 1.13 (s, 3H) 1.14-1.24 (m, 7H) 1.27 (d, J = 6.87 Hz, 3H) 1.32 (s, 3H) 1.48-1.69 (m, 2H) 1.71-1.89 (m, 2H) 1.95 (dd, J = 4.67 Hz, J = 15.1 Hz, 1H) 2.11-2.35 (m, 10H) 2.38 (s, 3H) 2.42-2.64 (m, 4H) 2.77-2.98 (m, 3H) 3.16-3.26 (m, 1H) 3.21 (s, 3H) 3.28-3.38 (m, 1H) 3.33 (s, 3H) 3.39-3.56 (m, 2H) 3.67 (d, J = 7.14 Hz, 1H) 3.80 (dd, J = 3.85 Hz, J = 11.0 Hz, 1H) 4.11-4.19 (m, 1H) 4.34-4.48 (m, 2H) 4.60-4.70 (m, 1H) 4.76 (d, J = 5.77 Hz, 1H) 4.90 (d, J = 4.67 Hz, 1H) 7.59 (d, J = 8.79 Hz, 2H) 8.21 (d, J = 8.79 Hz, 2H) |
| 540 | [structure: -NH-CH(CH(OH)-C$_6$H$_5$)-CH$_2$OH] | -OH | 898.7 | (300 MHz): 0.76-0.88 (m, 6H) 0.91 (t, J = 7.14 Hz, 3H) 1.05-1.26 (m, 14H) 1.28 (d, J = 6.87 Hz, 3H) 1.33 (s, 3H) 1.47-1.69 (m, 2H) 1.69-1.91 (m, 2H) 1.96 (dd, J = 5.22 Hz, J = 15.4 Hz, 1H) 2.10-2.36 (m, 10H) 2.36-2.55 (m, 5H) 2.61-2.72 (m, 2H) 2.77-2.98 (m, 3H) 3.16-3.26 (m, 1H) 3.21 (s, 3H) 3.30-3.42 (m, 1H) 3.34 (s, 3H) 3.42-3.54 (m, 2H) 3.64-3.74 (m, 2H) 4.10-4.18 (m, 1H) 4.34-4.48 (m, 2H) 4.58-4.70 (m, 2H) 4.90 (d, J = 4.40 Hz, 1H) 7.23-7.42 (m, 5H) |
| 541 | [structure: -NH-CH$_2$-CH(OH)-C$_6$H$_5$] | -OH | 968.5 | (300 MHz): 0.76-0.87 (m, 6H) 0.92 (t, J = 7.42 Hz, 3H) 1.05-1.15 (m, 1H) 1.11 (d, J = 7.42 Hz, 3H) 1.15-1.30 (m, 13H) 1.33 (s, 3H) 1.48-1.69 (m, 2H) 1.71-1.90 (m, 2H) 2.10-2.34 (m, 11H) 2.34-2.54 (m, 5H) 2.70-2.87 (m, 4H) 2.87-2.98 (m, 2H) 3.16-3.25 (m, 1H) 3.20 (s, 3H) 3.33-3.55 (m, 2H) 3.37 (s, 3H) 3.67 (d, J = 7.97 Hz, 3H) 4.09-4.18 (m, 1H) 4.35-4.49 (m, 2H) 4.59-4.70 (m, 1H) 4.72 (dd, J = 3.85 Hz, J = 8.24 Hz, 1H) 4.91 (d, J = 4.12 Hz, 1H) 7.23-7.40 (m, 5H) |
| 542 | [structure: -NH-CH(CH$_2$-C$_6$H$_5$)-CH$_2$OH] | -OH | 882.5 | (300 MHz): 0.75-0.87 (m, 6H) 0.92 (t, J = 7.42 Hz, 3H) 0.99 (d, J = 6.59 Hz, 3H) 1.04-1.29 (m, 14H) 1.32 (s, 3H) 1.48-1.67 (m, 2H) 1.70-1.90 (m, 2H) 2.11-2.36 (m, 11H) 2.36-2.51 (m, 5H) 2.66-2.89 (m, 4H) 2.90-3.00 (m, 1H) 3.14-3.24 (m, 2H) 3.20 (s, 3H) 3.29-3.48 (m, 3H) 3.34 (s, 3H) 3.56-3.69 (m, 2H) 4.04-4.13 (m, 1H) 4.26-4.38 (m, 2H) 4.60-4.72 (m, 1H) 4.86 (d, J = 3.85 Hz, 1H) 7.12-7.21 (m, 2H) 7.22-7.36 (m, 3H) |
| 543 | [structure: -NH-C(=O)-NH-CH(Me)-(2-OMe-C$_6$H$_4$)] | -OH | 925.3 | (300 MHz): 0.75-0.86 (m, 6H) 0.91 (t, J = 7.42 Hz, 3H) 1.00-1.29 (m, 17H) 1.33 (s, 3H) 1.42 (d, J = 6.59 Hz, 3H) 1.47-1.69 (m, 2H) 1.69-2.00 (m, 3H) 2.08-2.52 (m, 15H) 2.76-2.99 (m, 2H) 3.04-3.26 (m, 2H) 3.21 (s, 3H) 3.31 (s, 3H) 3.35-3.51 (m, 2H) 3.58-3.63 (m, 1H) 3.87 (s, 3H) 4.05-4.18 (m, 1H) 4.30-4.47 (m, 2H) 4.55-4.60 (m, 1H) 4.84-5.01 (m, 3H) 5.01-5.10 (m, 1H) 6.83-6.96 (m, 2H) 7.16-7.31 (m, 3H) |

TABLE 11-continued formula (W)

| Example | R¹ᵂ | R²ᵂ | ESI MS (M + H) | ¹H-NMR, CDCl₃, δ (ppm) |
|---|---|---|---|---|
| 544 | [structure: -NH-C(=O)-CH₂-N(Et)-CH(Me)-(2-methoxyphenyl)] | [structure: -OH] | 967.4 | (300 MHz): 0.81-0.83 (m, 6H) 0.90 (t, J = 7.1 Hz, 3H) 1.02-1.34 (m, 25H) 1.50-1.76 (m, 9H) 2.12-2.63 (m, 17H) 2.80-2.94 (m, 2H) 2.99-3.51 (m, 12H) 3.65-3.73 (m, 3H) 3.82 (s, 3H) 4.18 (m, 1H) 4.37-4.50 (m, 3H) 4.62 (m, 1H) 4.92 (d, J = 4.8 Hz, 1H) 6.84-6.94 (m, 2H) 7.21 (ddd, J = 7.8 Hz, J = 7.8 Hz, J = 1.5 Hz, 1H) 7.31 (dd, J = 7.2 Hz, J = 1.5 Hz, 1H) 7.98 (m, 1H) |
| 545 | [structure: -NH-(CH₂)₃-N(Et)-CH(Me)-(2-methoxyphenyl)] | -H | 937.4 | (300 MHz): 0.81-0.92 (m, 9H) 0.98 (t, J = 6.9 Hz, 3H) 1.07-1.31 (m, 22H) 1.46-1.92 (m, 9H) 2.16-2.68 (m, 21H) 2.75-2.91 (m, 2H) 3.14-3.32 (m, 7H) 3.41 (m, 1H) 3.65-3.73 (m, 2H) 3.80 (s, 3H) 3.95-4.10 (m, 2H) 4.31 (q, J = 6.9 Hz, 1H) 4.43 (q, J = 7.2 Hz, 1H) 4.65 (m, 1H) 4.92 (d, J = 4.8 Hz, 1H) 6.84 (d, J = 8.0 Hz, 1H) 6.93 (dd, J = 7.8 Hz, J = 7.5 Hz, 1H) 7.19 (ddd, J = 8.0 Hz, J = 7.5 Hz, J = 1.5 Hz, 1H) 7.39 (m, 1H) |
| 546 | [structure: -N(Et)-CH(Me)-(2-methoxyphenyl)] | [structure: -OH] | 910.4 | (400 MHz): 0.80-0.85 (m, 6H) 0.91 (m, 3H) 1.02-1.42 (m, 40H) 1.70-1.90 (m, 4H) 1.95-2.65 (m, 18H) 2.76-2.98 (m, 4H) 3.20 (dd, J = 10.2, 7.8 Hz, 1H) 3.24 (s, 3H) 3.32 (s, 3H) 3.42 (m, 1H) 3.64 (m, 1H) 3.70 (d, J = 7.8 Hz, 1H) 3.81 (s, 3H) 4.04 (m, 1H) 4.42-4.49 (m, 1H) 4.61-4.76 (m, 2H) 6.84 (m, 1H) 6.94 (m, 1H) 7.24 (m, 1H) 7.32 (m, 1H) |
| 547 | [structure: -NH-CH₂-CH₂-(4-methoxyphenyl)] | [structure: HO-] | 882.3 | (400 MHz): 0.82 (d, J = 6.9 Hz, 3H) 0.82 (d, J = 6.9 Hz, 3H) 0.89 (t, J = 7.3 Hz, 3H) 1.07-1.39 (m, 26H) 1.69-1.89 (m, 3H) 2.06-2.60 (m, 15H) 2.65-2.87 (m, 8H) 3.17-3.20 (m, 1H) 3.21 (s, 3H) 3.34 (s, 3H) 3.38-3.56 (m, 2H) 3.66 (d, J = 7.8 Hz, 1H) 3.78 (s, 3H) 4.09 (m, 1H) 4.40 (d, J = 7.1 Hz, 1H) 4.43 (q, J = 6.5 Hz, 1H) 4.86 (m, 1H) 6.82-6.90 (m, 2H) 7.11-7.20 (m, 2H) |
| 548 | [structure: (2-methoxyphenyl)-CH₂-CH₂-NH-] | [structure: HO-] | 882.3 | (400 MHz): 0.82 (d, J = 6.9 Hz, 3H) 0.82 (d, J = 6.9 Hz, 3H) 0.91 (t, J = 7.3 Hz, 3H) 1.08-1.38 (m, 32H) 1.70-1.90 (m, 3H) 2.05 (dd, J = 15.1, 6.1 Hz, 1H) 2.12-2.95 (m, 16H) 3.16-3.25 (m, 4H) 3.34 (s, 3H) 3.36-3.56 (m, 2H) 3.82 (s, 3H) 3.66 (d, J = 7.8 Hz, 1H) 4.08 (m, 1H) 4.41 (d, J = 7.1 Hz, 1H) 4.45 (q, J = 6.9 Hz, 1H) 4.64 (m, 1H) 4.86 (m, 1H) 6.83 (m, 2H) 7.11 (m, 2H) |
| 549 | [structure: phenyl-CH₂-CH₂-NH-] | [structure: HO-] | 852.3 | (400 MHz): 0.79-0.85 (m, 6H) 0.91 (t, J = 8.3 Hz, 3H) 1.07-1.36 (m, 26H) 1.70-1.88 (m, 2H) 2.06-2.54 (m, 17H) 2.85-2.95 (m, 7H) 3.16-3.26 (m, 4H) 3.34 (s, 3H) 3.36-3.58 (m, 2H) 3.66 (d, J = 7.5 Hz, 1H) 4.08 (m, 1H) 4.39 (d, J = 7.1 Hz, 1H) 4.43 (q, J = 6.6 Hz, 1H) 4.85 (m, 1H) 7.17-7.31 (m, 5H) |

TABLE 11-continued formula (W)

| Example | R$^{1W}$ | R$^{2W}$ | ESI MS (M + H) | $^1$H-NMR, CDCl$_3$, δ (ppm) |
|---|---|---|---|---|
| 550 | (structure with N-H, phenyl-OMe, CH$_2$OH) | (structure with OH) | 912 | (400 MHz): 0.79-0.84 (m, 6H) 0.92 (t, J = 7.4 Hz, 3H) 1.02-1.25 (m, 17H) 1.32 (s, 3H) 1.72-1.88 (m, 4H) 2.10-2.50 (m, 16H) 2.62-2.77 (m, 5H) 2.83 (m, 1H) 2.94 (m, 1H) 3.16-3.47 (m, 13H) 3.60-3.65 (m, 2H) 3.78 (s, 3H) 4.11 (m, 1H) 4.31-4.37 (m, 2H) 4.66 (m, 1H) 4.89 (m, 1H) 6.83 (m, 2H) 7.09 (m, 2H) |
| 551 | (structure with MeO-phenyl-CH(OH)-CH$_2$-NH) | (structure with HO) | 898 | mixture of diastereomers (400 MHz): 0.82 (m, 3H) 0.82 (m, 3H) 0.91 (t, J = 7.3 Hz, 3H) 1.08-1.35 (m, 20H) 1.60-1.90 (m, 8H) 2.00-2.95 (m, 20H) 3.18-3.60 (m, 12H) 3.67 (m, 1H) 3.81 (s, 3H) 4.14 (m, 1H) 4.32-4.48 (m, 2H) 4.61-4.69 (m, 2H) 4.87-4.97 (m, 1H) 6.89 (m, 2H) 7.28 (m, 2H) |

Example 262

(1) By using the compound obtained in Example 126, (1) (1.00 g) as a starting material, a 4"-ketone compound (0.99 g) was obtained in the same manner as that of Example 113, (2).

(2) The compound obtained in (1) mentioned above (305 mg) was dissolved in methanol (9 ml), the solution was added with ammonium acetate (249 mg) and sodium cyanoborohydride (30.4 mg), and the mixture was stirred overnight at room temperature. The reaction mixture was added with saturated aqueous sodium hydrogencarbonate and chloroform, the layers were separated, and then the organic layer was washed with saturated brine. The organic layer was dried over sodium sulfate and filtered, then the filtrate was concentrated under reduced pressure, and the resulting residue was purified by silica gel column chromatography (chloroform:methanol=30:1) and silica gel column chromatography (NH-form, toluene:ethyl acetate=50:1) to obtain an amine compound (43.3 mg) of which steric configuration of the 4"-position was S and a mixture of epimers (35.3 mg).

(3) By using the amine compound (25.1 mg) obtained in (2) mentioned above of which steric configuration of the 4"-position was S as a starting material, the compound shown in Table 11 (16.1 mg) was obtained in the same manner as that of Example 7, (4).

Example 263

(1) The compound obtained in Example 262, (1) (109 mg) was dissolved in ethanol (7.3 ml), the solution was added with Raney nickel slurry (2 ml), and the mixture was stirred at room temperature for 7 hours under a hydrogen atmosphere of 3.5 kgt/cm$^2$. The reaction mixture was filtered through Celite, and then the filtrate was added with distilled water and ethyl acetate. The layers were separated, and the organic layer was dried over sodium sulfate and filtered. The filtrate was concentrated under reduced pressure, and the resulting residue was purified by silica gel column chromatography (hexane:acetone:triethylamine=60:10:0.2) to obtain a hydroxyl compound (40.1 mg) of which steric configuration of the 4"-position was R.

(2) By using the compound obtained in (1) mentioned above (20.3 mg) as a starting material, the compound shown in Table 11 (14.2 mg) was obtained in the same manner as that of Example 7, (4).

Example 264

By using the compound obtained in Example 126, (2) (100 mg) and the compound obtained in Reference Example 72 (54.7 mg) as starting materials, the compound shown in Table 11 (72 mg) was obtained in the same manners as those of Example 126, (3) and Example 7, (4).

Example 265

By using the compound obtained in Example 126, (2) (100 mg) and the compound obtained in Reference Example 73 (54.7 mg) as starting materials, the compound shown in Table 11 (64 mg) was obtained in the same manners as those of Example 126, (3) and Example 7, (4).

Example 266

By using the compound obtained in Example 126, (2) (100 mg) and the compound obtained in Reference Example 74 (51.7 mg) as starting materials, the compound shown in Table 11 (50 mg) was obtained in the same manners as those of Example 126, (3) and Example 7, (4).

Example 267

By using the compound obtained in Example 126, (2) (100 mg) and the compound obtained in Reference Example 75 (55.8 mg) as starting materials, the compound shown in Table 11 (43 mg) was obtained in the same manners as those of Example 126, (3) and Example 7, (4).

Example 268

By using the compound obtained in Example 126, (2) (100 mg) and the compound obtained in Reference Example 76 (50.8 mg) as starting materials, the compound shown in Table 11 (43 mg) was obtained in the same manners as those of Example 126, (3) and Example 7, (4).

Example 269

By using the compound obtained in Example 126, (2) (150 mg) and the compound obtained in Reference Example 77 (60.6 mg) as starting materials, the compound shown in Table 11 (82 mg) was obtained in the same manners as those of Example 126, (3) and Example 7, (4).

Example 270

By using the compound obtained in Example 126, (2) (250 mg) and the compound obtained in Reference Example 78 (143.3 mg) as starting materials, the compound shown in Table 11 (235 mg) was obtained in the same manners as those of Example 126, (3) and Example 7, (4).

Example 271

By using the compound obtained in Example 126, (2) (150 mg) and the compound obtained in Reference Example 79 (60.6 mg) as starting materials, the compound shown in Table 11 (97 mg) was obtained in the same manners as those of Example 126, (3) and Example 7, (4).

Example 272

By using the compound obtained in Example 126, (2) (150 mg) and the compound obtained in Reference Example 80 (65.3 mg) as starting materials, the compound shown in Table 11 (99 mg) was obtained in the same manners as those of Example 126, (3) and Example 7, (4).

Example 273

By using the compound obtained in Example 126, (2) (150 mg) and the compound obtained in Reference Example 81 (68.1 mg) as starting materials, the compound shown in Table 11 (126 mg) was obtained in the same manners as those of Example 126, (3) and Example 7, (4).

Example 274

By using the compound obtained in Example 126, (2) (150 mg) and the compound obtained in Reference Example 82 (48 mg) as starting materials, the compound shown in Table 11 (95 mg) was obtained in the same manners as those of Example 126, (3) and Example 7, (4).

Example 275

By using the compound obtained in Example 126, (2) (150 mg) and the compound obtained in Reference Example 83 (59.4 mg) as starting materials, the compound shown in Table 11 (113 mg) was obtained in the same manners as those of Example 126, (3) and Example 7, (4).

Example 276

By using the compound obtained in Example 126, (2) (150 mg) and the compound obtained in Reference Example 84 (59.4 mg) as starting materials, the compound shown in Table 11 (119 mg) was obtained in the same manners as those of Example 126, (3) and Example 7, (4).

Example 277

By using the compound obtained in Example 126, (2) (150 mg) and the compound obtained in Reference Example 85 (63.5 mg) as starting materials, the compound shown in Table 11 (125 mg) was obtained in the same manners as those of Example 126, (3) and Example 7, (4).

Example 278

By using the compound obtained in Example 126, (2) (150 mg) and the compound obtained in Reference Example 86 (67.8 mg) as starting materials, the compound shown in Table 11 (130 mg) was obtained in the same manners as those of Example 126, (3) and Example 7, (4).

Example 279

By using the compound obtained in Example 126, (2) (150 mg) and the compound obtained in Reference Example 87 (68.4 mg) as starting materials, the compound shown in Table 11 (83 mg) was obtained in the same manners as those of Example 126, (3) and Example 7, (4).

Example 280

The compound obtained in Example 270 (100 mg) was dissolved in methanol (5 ml), the solution was added with 5% palladium-carbon (20 mg), and the mixture was stirred at room temperature for 3 hours under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=10:1:0.1 to 5:1:0.1) to obtain the compound shown in Table 11 (54 mg).

Example 281

By using the compound obtained in Example 126, (2) (150 mg) and the compound obtained in Reference Example 88 (75.0 mg) as starting materials, the compound shown in Table

Example 282

By using the compound obtained in Example 126, (2) (150 mg) and the compound obtained in Reference Example 89 (75.0 mg) as starting materials, the compound shown in Table 11 (102 mg) was obtained in the same manners as those of Example 126, (3) and Example 7, (4).

Example 283

By using the compound obtained in Example 126, (2) (150 mg) and the compound obtained in Reference Example 90 (75.0 mg) as starting materials, the compound shown in Table 11 (104 mg) was obtained in the same manners as those of Example 126, (3) and Example 7, (4).

Example 284

By using the compound obtained in Example 126, (2) (110 mg) and the compound obtained in Reference Example 91 (57.3 mg) as starting materials, the compound shown in Table 11 (77 mg) was obtained in the same manners as those of Example 126, (3) and Example 7, (4).

Example 285

The compound obtained in Example 279 (50 mg) was dissolved in a mixed solvent of isopropanol (4 ml) and distilled water (2 ml), the solution was added with iron (5.4 mg), and the mixture was stirred at 90° C. for 1 hour. The reaction mixture was concentrated under reduced pressure, and then the resulting residue was purified by silica gel column chromatography (chloroform:methanol:28% aqueous ammonia=10:1:0.1) to obtain the compound shown in Table 11 (32 mg).

Example 286

The compound obtained in Example 274 (53 mg) was dissolved in chloroform (1 ml), the solution was added with acetaldehyde (13 mg) and sodium triacetoxyborohydride (18 mg), and the mixture was stirred at room temperature for 1 hour. The reaction mixture was added with saturated aqueous sodium hydrogencarbonate and chloroform, the layers were separated, and then the organic layer was dried over anhydrous magnesium sulfate and filtered. The filtrate was concentrated under reduced pressure, and the resulting residue was purified by silica gel column chromatography (chloroform:methanol:28% aqueous ammonia=20:1:0.1) to obtain the compound shown in Table 11 (44.8 mg).

Example 287

(1) The compound obtained in Example 126, (2) (150 mg) was dissolved in tetrahydrofuran (0.2 ml), the solution was added with the compound obtained in Reference Example 92 (55 mg), and the mixture was stirred at room temperature for 3 days. The reaction mixture was added with chloroform and distilled water, the layers were separated, and the organic layer was dried over anhydrous magnesium sulfate and filtered. The filtrate was concentrated under reduced pressure, and the resulting residue was purified by silica gel column chromatography (hexane:acetone:triethylamine=15:10:0.2) to obtain a carbamate compound (169 mg).

(2) By using the compound obtained in (1) mentioned above (169 mg) as a starting material, the compound shown in Table 11 (100 mg) was obtained in the same manner as that of Example 7, (4).

Example 288

By using the compound obtained in Example 126, (2) (150 mg) and the compound obtained in Reference Example 93 (70 mg) as starting materials, the compound shown in Table 11 (111 mg) was obtained in the same manners as those of Example 287, (1) and Example 7, (4).

Example 289

By using the compound obtained in Example 126, (2) (150 mg) and the compound obtained in Reference Example 94 (70 mg) as starting materials, the compound shown in Table 11 (110 mg) was obtained in the same manners as those of Example 287, (1) and Example 7, (4).

Example 290

By using the compound obtained in Example 126, (2) (150 mg) and the compound obtained in Reference Example 95 (48 mg) as starting materials, the compound shown in Table 11 (106 mg) was obtained in the same manners as those of Example 126, (3) and Example 7, (4).

Example 291

By using the compound obtained in Example 126, (2) (150 mg) and the compound obtained in Reference Example 96 (70 mg) as starting materials, the compound shown in Table 11 (103 mg) was obtained in the same manners as those of Example 126, (3) and Example 7, (4).

Example 292

By using the compound obtained in Example 126, (2) (150 mg) and the compound obtained in Reference Example 97 (52 mg) as starting materials, the compound shown in Table 11 (107 mg) was obtained in the same manners as those of Example 126, (3) and Example 7, (4).

Example 293

By using the compound obtained in Example 290 (80 mg) as a starting material, the compound shown in Table 11 (65 mg) was obtained in the same manner as that of Example 286.

Example 294

By using the compound obtained in Example 126, (2) (150 mg) and the compound obtained in Reference Example 98 (76 mg) as starting materials, the compound shown in Table 11 (50 mg) was obtained in the same manners as those of Example 126, (3) and Example 7, (4).

Example 295

By using the compound obtained in Example 291 (70 mg) as a starting material, the compound shown in Table 11 (70 mg) was obtained in the same manner as that of Example 286.

Example 296

By using the compound obtained in Example 292 (70 mg) as a starting material, the compound shown in Table 11 (61 mg) was obtained in the same manner as that of Example 286.

Example 297

By using the compound obtained in Example 126, (2) (150 mg) and the compound obtained in Reference Example 99 (48 mg) as starting materials, the compound shown in Table 11 (26 mg) was obtained in the same manners as those of Example 126, (3) and Example 7, (4).

Example 298

By using the compound obtained in Example 126, (2) (150 mg) and the compound obtained in Reference Example 100 (52 mg) as starting materials, the compound shown in Table 11 (117 mg) was obtained in the same manners as those of Example 126, (3) and Example 7, (4).

Example 299

By using the compound obtained in Example 126, (2) (150 mg) and the compound obtained in Reference Example 101 (80 mg) as starting materials, the compound shown in Table 11 (64 mg) was obtained in the same manners as those of Example 126, (3) and Example 7, (4).

Example 300

By using the compound obtained in Example 126, (2) (150 mg) and the compound obtained in Reference Example 102 (80 mg) as starting materials, the compound shown in Table 11 (65 mg) was obtained in the same manners as those of Example 126, (3) and Example 7, (4).

Example 301

By using the compound obtained in Example 294 (35 mg) as a starting material, the compound shown in Table 11 (26 mg) was obtained in the same manner as that of Example 286.

Example 302

By using the compound obtained in Example 297 (17 mg) as a starting material, the compound shown in Table 11 (14 mg) was obtained in the same manner as that of Example 286.

Example 303

By using the compound obtained in Example 298 (70 mg) as a starting material, the compound shown in Table 11 (67 mg) was obtained in the same manner as that of Example 286.

Example 304

By using the compound obtained in Example 299 (43 mg) as a starting material, the compound shown in Table 11 (40 mg) was obtained in the same manner as that of Example 286.

Example 305

By using the compound obtained in Example 300 (65 mg) as a starting material, the compound shown in Table 11 (24 mg) was obtained in the same manner as that of Example 286.

Example 306

By using the compound obtained in Example 126, (2) (150 mg) and the compound obtained in Reference Example 103 (51.9 mg) as starting materials, the compound shown in Table 11 (127 mg) was obtained in the same manners as those of Example 126, (3) and Example 7, (4).

Example 307

By using the compound obtained in Example 126, (2) (150 mg) and the compound obtained in Reference Example 104 (60.3 mg) as starting materials, the compound shown in Table 11 (118 mg) was obtained in the same manners as those of Example 126, (3) and Example 7, (4).

Example 308

By using the compound obtained in Example 126, (2) (150 mg) and the compound obtained in Reference Example 105 (57.2 mg) as starting materials, the compound shown in Table 11 (120 mg) was obtained in the same manners as those of Example 126, (3) and Example 7, (4).

Example 309

By using the compound obtained in Example 126, (2) (150 mg) and the compound obtained in Reference Example 106 (51.9 mg) as starting materials, the compound shown in Table 11 (105 mg) was obtained in the same manners as those of Example 126, (3) and Example 7, (4).

Example 310

By using the compound obtained in Example 126, (2) (150 mg) and the compound obtained in Reference Example 107 (60.0 mg) as starting materials, the compound shown in Table 11 (128 mg) was obtained in the same manners as those of Example 126, (3) and Example 7, (4).

Example 311

By using the compound obtained in Example 307 (65 mg) as a starting material, the compound shown in Table 11 (53 mg) was obtained in the same manner as that of Example 286.

Example 312

By using the compound obtained in Example 126, (2) (150 mg) and the compound obtained in Reference Example 108 (60.3 mg) as starting materials, the compound shown in Table 11 (120 mg) was obtained in the same manners as those of Example 126, (3) and Example 7, (4).

Example 313

By using the compound obtained in Example 126, (2) (150 mg) and the compound obtained in Reference Example 109 (56.0 mg) as starting materials, the compound shown in Table 11 (123 mg) was obtained in the same manners as those of Example 126, (3) and Example 7, (4).

Example 314

By using the compound obtained in Example 306 (65 mg) as a starting material, the compound shown in Table 11 (46 mg) was obtained in the same manner as that of Example 286.

Example 315

By using the compound obtained in Example 309 (60 mg) as a starting material, the compound shown in Table 11 (63 mg) was obtained in the same manner as that of Example 286.

Example 316

By using the compound obtained in Example 126, (2) (150 mg) and the compound obtained in Reference Example 110 (51.9 mg) as starting materials, the compound shown in Table 11 (86 mg) was obtained in the same manners as those of Example 126, (3) and Example 7, (4).

Example 317

By using the compound obtained in Example 311 (35 mg) as a starting material, the compound shown in Table 11 (20 mg) was obtained in the same manner as that of Example 285.

Example 318

By using the compound obtained in Example 312 (65 mg) as a starting material, the compound shown in Table 11 (73 mg) was obtained in the same manner as that of Example 286.

Example 319

By using the compound obtained in Example 126, (2) (150 mg) and the compound obtained in Reference Example 111 (59.7 mg) as starting materials, the compound shown in Table 11 (125 mg) was obtained in the same manners as those of Example 126, (3) and Example 7, (4).

Example 320

By using the compound obtained in Example 308 (60 mg) as a starting material, the compound shown in Table 11 (67 mg) was obtained in the same manner as that of Example 286.

Example 321

By using the compound obtained in Example 313 (70 mg) as a starting material, the compound shown in Table 11 (72 mg) was obtained in the same manner as that of Example 286.

Example 322

By using the compound obtained in Example 126, (2) (164 mg) and the compound obtained in Reference Example 112 (103 mg) as starting materials, the compound shown in Table 11 (110 mg) was obtained in the same manners as those of Example 287, (1) and Example 7, (4).

Example 323

By using the compound obtained in Example 310 (70 mg) as a starting material, the compound shown in Table 11 (66 mg) was obtained in the same manner as that of Example 286.

Example 324

By using the compound obtained in Example 126, (2) (150 mg) and the compound obtained in Reference Example 113 (64.0 mg) as starting materials, the compound shown in Table 11 (130 mg) was obtained in the same manners as those of Example 126, (3) and Example 7, (4).

Example 325

By using the compound obtained in Example 126, (2) (150 mg) and the compound obtained in Reference Example 114 (76 mg) as starting materials, the compound shown in Table 11 (100 mg) was obtained in the same manners as those of Example 126, (3) and Example 7, (4).

Example 326

By using the compound obtained in Example 126, (2) (150 mg) and the compound obtained in Reference Example 115 (80 mg) as starting materials, the compound shown in Table 11 (106 mg) was obtained in the same manners as those of Example 126, (3) and Example 7, (4).

Example 327

By using the compound obtained in Example 126, (2) (150 mg) and the compound obtained in Reference Example 116 (69 mg) as starting materials, the compound shown in Table 11 (96 mg) was obtained in the same manners as those of Example 126, (3) and Example 7, (4).

Example 328

By using the compound obtained in Example 126, (2) (160 mg) and the compound obtained in Reference Example 117 (85 mg) as starting materials, the compound shown in Table 11 (80 mg) was obtained in the same manners as those of Example 126, (3) and Example 7, (4).

Example 329

By using the compound obtained in Example 126, (2) (150 mg) and the compound obtained in Reference Example 118 (76 mg) as starting materials, the compound shown in Table 11 (101 mg) was obtained in the same manners as those of Example 126, (3) and Example 7, (4).

Example 330

By using the compound obtained in Example 126, (2) (150 mg) and the compound obtained in Reference Example 119 (89 mg) as starting materials, the compound shown in Table 11 (123 mg) was obtained in the same manners as those of Example 126, (3) and Example 7, (4).

Example 331

By using the compound obtained in Example 126, (2) (150 mg) and the compound obtained in Reference Example 120 (62 mg) as starting materials, the compound shown in Table 11 (125 mg) was obtained in the same manners as those of Example 126, (3) and Example 7, (4).

Example 332

By using the compound obtained in Example 325 (58 mg) as a starting material, the compound shown in Table 11 (34 mg) was obtained in the same manner as that of Example 286.

Example 333

By using the compound obtained in Example 326 (73 mg) as a starting material, the compound shown in Table 11 (48 mg) was obtained in the same manner as that of Example 286.

Example 334

By using the compound obtained in Example 327 (68 mg) as a starting material, the compound shown in Table 11 (62 mg) was obtained in the same manner as that of Example 286.

Example 335

By using the compound obtained in Example 328 (48 mg) as a starting material, the compound shown in Table 11 (47 mg) was obtained in the same manner as that of Example 286.

Example 336

By using the compound obtained in Example 329 (60 mg) as a starting material, the compound shown in Table 11 (58 mg) was obtained in the same manner as that of Example 286.

Example 337

By using the compound obtained in Example 330 (74 mg) as a starting material, the compound shown in Table 11 (67 mg) was obtained in the same manner as that of Example 286.

Example 338

By using the compound obtained in Example 331 (81 mg) as a starting material, the compound shown in Table 11 (53 mg) was obtained in the same manner as that of Example 286.

Example 339

By using the compound obtained in Example 126, (2) (150 mg) and the compound obtained in Reference Example 121 (74.1 mg) as starting materials, the compound shown in Table 11 (75 mg) was obtained in the same manners as those of Example 126, (3) and Example 7, (4).

Example 340

By using the compound obtained in Example 126, (2) (150 mg) and the compound obtained in Reference Example 122 (74.1 mg) as starting materials, the compound shown in Table 11 (108 mg) was obtained in the same manners as those of Example 126, (3) and Example 7, (4).

Example 341

By using the compound obtained in Example 126, (2) (150 mg) and the compound obtained in Reference Example 123 (75.9 mg) as starting materials, the compound shown in Table 11 (132 mg) was obtained in the same manners as those of Example 126, (3) and Example 7, (4).

Example 342

By using the compound obtained in Example 126, (2) (150 mg) and the compound obtained in Reference Example 124 (82.5 mg) as starting materials, the compound shown in Table 11 (125 mg) was obtained in the same manners as those of Example 126, (3) and Example 7, (4).

Example 343

By using the compound obtained in Example 339 (40 mg) as a starting material, the compound shown in Table 11 (41 mg) was obtained in the same manner as that of Example 286.

Example 344

By using the compound obtained in Example 340 (50 mg) as a starting material, the compound shown in Table 11 (51 mg) was obtained in the same manner as that of Example 286.

Example 345

By using the compound obtained in Example 341 (75 mg) as a starting material, the compound shown in Table 11 (57 mg) was obtained in the same manner as that of Example 286.

Example 346

By using the compound obtained in Example 126, (2) (150 mg) and the compound obtained in Reference Example 125 (81.3 mg) as starting materials, the compound shown in Table 11 (10 mg) was obtained in the same manners as those of Example 126, (3) and Example 7, (4).

Example 347

By using the compound obtained in Example 342 (75 mg) as a starting material, the compound shown in Table 11 (58 mg) was obtained in the same manner as that of Example 286.

Example 348

By using the compound obtained in Example 126, (2) (150 mg) and the compound obtained in Reference Example 126 (40 mg) as starting materials, the compound shown in Table 11 (17 mg) was obtained in the same manners as those of Example 126, (3) and Example 7, (4).

Example 349

By using the compound obtained in Example 126, (2) (150 mg) and the compound obtained in Reference Example 127 (64 mg) as starting materials, the compound shown in Table 11 (15 mg) was obtained in the same manners as those of Example 126, (3) and Example 7, (4).

Example 350

2',4'-Dihydroxyacetophenone (500 mg) was dissolved in dimethylformamide (10 ml), and the solution was added with imidazole (1.34 g) and t-butyldimethylchlorosilane (1.09 g), and the mixture was stirred at room temperature for 48 hours. The reaction mixture was added with ethyl acetate and saturated aqueous ammonium chloride, the layers were separated, and then the organic layer was washed 3 times with distilled water, dried over anhydrous magnesium sulfate and filtered. The filtrate was concentrated under reduced pressure to obtain a crude product (1.34 g). This crude product was dissolved in methanol (10 ml), the solution was added with ethylenediamine (634 mg), and the mixture was stirred at room temperature for 16 hours. The reaction mixture was added to a suspension of sodium borohydride (200 mg) in tetrahydrofuran (50 ml), then the mixture was added with methanol (6 ml), and the mixture was stirred at room temperature for 1 hour. The reaction mixture was concentrated under reduced pressure, and then added with chloroform and saturated aqueous ammonium chloride, the layers were separated, and then the organic layer was dried over anhydrous magnesium sulfate and filtered. The filtrate was concentrated under reduced pressure, and the resulting residue was purified by silica gel column chromatography (chloroform:methanol:

28% aqueous ammonia=10:1:0.1). By using the resulting amine compound (62 mg) and the compound obtained in Example 126, (2) (100 mg) as starting materials, the compound shown in Table 11 (5 mg) was obtained in the same manners as those of Example 126, (3) and Example 7, (4).

Example 351

3',5'-Dihydroxyacetophenone (500 mg) was dissolved in dimethylformamide (10 ml), and the solution was added with imidazole (1.34 g) and t-butyldimethylchlorosilane (1.09 g), and the mixture was stirred at room temperature for 48 hours. The reaction mixture was added with ethyl acetate and saturated aqueous ammonium chloride, the layers were separated, and then the organic layer was washed 3 times with distilled water, dried over anhydrous magnesium sulfate and filtered. The filtrate was concentrated under reduced pressure to obtain a crude product (1.49 g). A portion of the crude product (250 mg) was dissolved in methanol (2 ml), the solution was added with ethylenediamine (118 mg), and the mixture was stirred at room temperature for 16 hours. This mixture was added to a suspension of sodium borohydride (37 mg) in tetrahydrofuran (10 ml), then the mixture was added with methanol (2 ml), and the mixture was stirred at room temperature for 1 hour. The reaction mixture was concentrated under reduced pressure, and then added with chloroform and saturated aqueous ammonium chloride, the layers were separated, and then the organic layer was dried over anhydrous magnesium sulfate and filtered. The filtrate was concentrated under reduced pressure, and the resulting residue was purified by silica gel column chromatography (chloroform:methanol: 28% aqueous ammonia=10:1:0.1). By using the resulting amine compound (58 mg) and the compound obtained in Example 126, (2) (100 mg) as starting materials, the compound shown in Table 11 (5 mg) was obtained in the same manners as those of Example 126, (3) and Example 7, (4).

Example 352

By using the compound obtained in Example 126, (2) (70 mg) and the compound obtained in Reference Example 128 (15.7 mg) as starting materials, the compound shown in Table 11 (54 mg) was obtained in the same manners as those of Example 126, (3) and Example 7, (4).

Example 353

By using the compound obtained in Example 126, (2) (150 mg) and the compound obtained in Reference Example 129 (41.5 mg) as starting materials, the compound shown in Table 11 (142 mg) was obtained in the same manners as those of Example 126, (3) and Example 7, (4).

Example 354

By using the compound obtained in Example 126, (2) (150 mg) and the compound obtained in Reference Example 130 (112.3 mg) as starting materials, the compound shown in Table 11 (131 mg) was obtained in the same manners as those of Example 126, (3) and Example 7, (4).

Example 355

By using the compound obtained in Example 126, (2) (150 mg) and the compound obtained in Reference Example 131 (38.9 mg) as starting materials, the compound shown in Table 11 (113 mg) was obtained in the same manners as those of Example 126, (3) and Example 7, (4).

Example 356

By using the compound obtained in Example 353 (35 mg) as a starting material, the compound shown in Table 11 (32 mg) was obtained in the same manner as that of Example 286.

Example 357

By using the compound obtained in Example 126, (2) (100 mg) and the compound obtained in Reference Example 132 (68 mg) as starting materials, the compound shown in Table 11 (87 mg) was obtained in the same manners as those of Example 126, (3) and Example 7, (4).

Example 358

(1) By using the compound obtained in Example 263, (1) (100 mg) as a starting material, a 4"-O-imidazolylcarbonyl compound (110 mg) was obtained in the same manner as that of Example 126, (2).
(2) By using the compound obtained in (1) mentioned above (20 mg) and N,N-dimethylethylenediamine (16.9 mg) as starting materials, the compound shown in Table 11 (5 mg) was obtained in the same manners as those of Example 126, (3) and Example 7, (4).

Example 359

By using the compound obtained in Example 358, (1) (20 mg) and aminoethanol (11.5 mg) as starting materials, the compound shown in Table 11 (6 mg) was obtained in the same manners as those of Example 126, (3) and Example 7, (4).

Example 360

By using the compound obtained in Example 358, (1) (23 mg) and the compound obtained in Reference Example 57 (10.4 mg) as starting materials, the compound shown in Table 11 (7.4 mg) was obtained in the same manners as those of Example 126, (3) and Example 7, (4).

Example 361

By using the compound obtained in Example 358, (1) (27.2 mg) and the compound obtained in Reference Example 54 (9.8 mg) as starting materials, the compound shown in Table 11 (5.7 mg) was obtained in the same manners as those of Example 126, (3) and Example 7, (4).

Example 362

(1) The compound obtained in Example 168, (1) (80 mg) was dissolved in methanol (8 ml), the solution was added with sodium methoxide (0.16 g), and the mixture was stirred for 3 days under reflux by heating. The mixture was further added with sodium methoxide (0.16 g), and the mixture was stirred for 7 days under reflux by heating. The mixture was further added with sodium methoxide (0.16 g), and the mixture was stirred for 2 days under reflux by heating. The reaction mixture was added with chloroform and saturated aqueous ammonium chloride, the layers were separated, and the organic layer was dried over anhydrous magnesium sulfate and filtered. The filtrate was concentrated under reduced pressure, and the resulting residue was purified by silica gel column chromatography (hexane:acetone:triethylamine=30:10:0.2) to obtain a hydroxy compound (14 mg).
(2) By using the compound obtained in (1) mentioned above (14 mg) as a starting material, the compound shown in Table 11 (8 mg) was obtained in the same manner as that of Example 7, (4).

Example 363

(1) The compound obtained in Example 168, (1) (60 mg) was dissolved in ethanol (3 ml), the solution was added with 24% aqueous ammonia (3 ml) and pyridine hydrochloride (6 mg), and the mixture was stirred at 70° C. for 15 hours in a sealed tube. The reaction mixture was added with chloroform and brine, the layers were separated, and the organic layer was dried over anhydrous magnesium sulfate and filtered. The filtrate was concentrated under reduced pressure, and the resulting residue was purified by silica gel column chromatography (chloroform:methanol:28% aqueous ammonia=30:1:0.1 to 10:1:0.1) to obtain an amine compound (38 mg).
(2) By using the compound obtained in (1) mentioned above (38 mg) as a starting material, the compound shown in Table 11 (4 mg) was obtained in the same manner as that of Example 7, (4).

Example 364

By using the compound obtained in Example 168, (1) (60 mg) and 40% aqueous methylamine (3 ml) as starting materials, the compound shown in Table 11 (15 mg) was obtained in the same manners as those of Example 363, (1) and Example 7, (4).

Example 365

By using the compound obtained in Example 168, (1) (60 mg) and 50% aqueous dimethylamine (3 ml) as starting materials, the compound shown in Table 11 (34 mg) was obtained in the same manners as those of Example 363, (1) and Example 7, (4).

Example 366

(1) The compound obtained in Example 363, (1) (64 mg) was dissolved in dichloromethane (6.6 ml), the solution was added with 1,1'-thiocarbonyldiimidazole (14 mg), and the mixture was stirred at room temperature for 13 hours. The mixture was further added with 1,1'-thiocarbonyldiimidazole (7 mg), and the mixture was stirred at room temperature for 4 hours. The mixture was further added with 1,1'-thiocarbonyldiimidazole (7 mg), and the mixture was stirred at room temperature for 4 hours. The reaction mixture was added with chloroform and saturated aqueous sodium hydrogencarbonate, the layers were separated, and the organic layer was dried over anhydrous magnesium sulfate and filtered. The filtrate was concentrated under reduced pressure, and the resulting residue was purified by preparative thin layer chromatography (chloroform:methanol:28% aqueous ammonia=22:1:0.1) to obtain a cyclized compound (47 mg).
(2) By using the compound obtained in (1) mentioned above (47 mg) as a starting material, the compound shown in Table 11 (34 mg) was obtained in the same manner as that of Example 7, (4).

Example 367

(1) The compound obtained in Example 168, (1) (350 mg) was dissolved in dimethyl sulfoxide (54 ml), the solution was added with sodium methanethiolate (250 mg), and the mixture was stirred at 70° C. for 4 hours. The reaction mixture was added with chloroform and saturated aqueous ammonium chloride, the layers were separated, and the organic layer was dried over anhydrous magnesium sulfate and filtered. The filtrate was concentrated under reduced pressure, and the resulting residue was purified by preparative thin layer chromatography (hexane:acetone:triethylamine=30:10:0.2) to obtain a hydroxy compound (31 mg).
(2) By using the compound obtained in (1) mentioned above (31 mg) as a starting material, the compound shown in Table 11 (17 mg) was obtained in the same manner as that of Example 7, (4).

Example 368

(1) By using the compound obtained in Example 168, (1) (275 mg) as a starting material, a deprotected compound (210 mg) was obtained in the same manner as that of Example 7, (4).
(2) The compound obtained in (1) mentioned above (30 mg) was dissolved in ethanol (0.5 ml), the solution was added with N-(3-aminopropyl)morpholine (29.6 mg) and pyridine hydrochloride (0.95 mg), and the mixture was stirred at 90° C. for 36 hours. The reaction mixture was concentrated under reduced pressure, and the resulting residue was purified by column chromatography (chloroform:methanol:28% aqueous ammonia=30:1:0.1) to obtain the compound shown in Table 11 (24 mg).

Example 369

By using the compound obtained in Example 368, (1) (50 mg) and the compound obtained in Reference Example 106 (62 mg) as starting materials, the compound shown in Table 11 (13 mg) was obtained in the same manner as that of Example 168, (2).

Example 370

By using the compound obtained in Example 368, (1) (30 mg) and N,N-dimethylethylenediamine (45 µl) as starting materials, the compound shown in Table 11 (23 mg) was obtained in the same manner as that of Example 368, (2).

Example 371

By using the compound obtained in Example 368, (1) (30 mg) and aminoethanol (24.8 µl) as starting materials, the compound shown in Table 11 (28 mg) was obtained in the same manner as that of Example 368, (2).

Example 372

By using the compound obtained in Example 368, (1) (30 mg) and n-butylamine (40.6 µl) as starting materials, the compound shown in Table 11 (22 mg) was obtained in the same manner as that of Example 368, (2).

Example 373

By using the compound obtained in Example 368, (1) (30 mg) and the compound obtained in Reference Example 131

(37.0 mg) as starting materials, the compound shown in Table 11 (38 mg) was obtained in the same manner as that of Example 168, (2).

Example 374

The compound obtained in Example 368, (1) (50 mg) was dissolved in ethanol, the solution was added with (1S,2S)-(+)-2-amino-1-(4-nitrophenyl)-1,3-propanediol (73 mg) and pyridine hydrochloride (1.6 mg), and the mixture was heated at 90° C. for 48 hours in a sealed tube. The reaction mixture was concentrated under reduced pressure, and the resulting residue was purified by silica gel column chromatography (chloroform:methanol:28% aqueous ammonia=20:1:0.1) to obtain the compound shown in Table 11 (23 mg).

Example 375

By using the compound obtained in Example 368, (1) (30 mg) and 2-amino-1,3-propanediol (18.7 mg) as starting materials, the compound shown in Table 11 (24 mg) was obtained in the same manner as that of Example 368, (2).

Example 376

By using the compound obtained in Example 368, (1) (30 mg) and 4-nitrophenethylamine (34.1 mg) as starting materials, the compound shown in Table 11 (9 mg) was obtained in the same manner as that of Example 368, (2).

Example 377

By using the compound obtained in Example 368, (1) (30 mg) and isoamylamine (24 µl) as starting materials, the compound shown in Table 11 (29 mg) was obtained in the same manner as that of Example 368, (2).

Example 378

By using the compound obtained in Example 368, (1) (30 mg) and 1-(2-aminoethyl)piperidine (29.2 µl) as starting materials, the compound shown in Table 11 (24 mg) was obtained in the same manner as that of Example 368, (2).

Example 379

By using the compound obtained in Example 368, (1) (30 mg) and 4-(2-aminoethyl)morpholine (26.9 µl) as starting materials, the compound shown in Table 11 (24 mg) was obtained in the same manner as that of Example 368, (2).

Example 380

By using the compound obtained in Example 368, (1) (30 mg) and 1-(2-aminoethyl)piperazine (26.9 µl) as starting materials, the compound shown in Table 11 (15 mg) was obtained in the same manner as that of Example 368, (2).

Example 381

By using the compound obtained in Example 368, (1) (30 mg) and N,N-diethylethylenediamine (23.8 mg) as starting materials, the compound shown in Table 11 (28 mg) was obtained in the same manner as that of Example 368, (2).

Example 382

By using the compound obtained in Example 368, (1) (30 mg) and N-(2-aminoethyl)pyrrolidine (23.4 mg) as starting materials, the compound shown in Table 11 (21 mg) was obtained in the same manner as that of Example 368, (2).

Example 383

By using the compound obtained in Example 368, (1) (30 mg) and piperidine (17.5 mg) as starting materials, the compound shown in Table 11 (36 mg) was obtained in the same manner as that of Example 368, (2).

Example 384

By using the compound obtained in Example 368, (1) (30 mg) and morpholine (17.9 mg) as starting materials, the compound shown in Table 11 (28 mg) was obtained in the same manner as that of Example 368, (2).

Example 385

By using the compound obtained in Example 368, (1) (30 mg) and (1R,2R)-(−)-2-amino-1-phenyl-1,3-propanediol (34.2 mg) as starting materials, the compound shown in Table 11 (36 mg) was obtained in the same manner as that of Example 368, (2).

Example 386

By using the compound obtained in Example 368, (1) (30 mg) and N-methylethylenediamine (18 µl) as starting materials, the compound shown in Table 11 (9 mg) was obtained in the same manner as that of Example 368, (2).

Example 387

By using the compound obtained in Example 368, (1) (30 mg) and N-methylethylenediamine (18 µl) as starting materials, the compound shown in Table 11 (9 mg) was obtained in the same manner as that of Example 368, (2).

Example 388

By using the compound obtained in Example 368, (1) (30 mg) and 1-methylpiperazine (23 µl) as starting materials, the compound shown in Table 11 (18 mg) was obtained in the same manner as that of Example 368, (2).

Example 389

By using the compound obtained in Example 368, (1) (30 mg) and piperazine (17.7 mg) as starting materials, the compound shown in Table 11 (22 mg) was obtained in the same manner as that of Example 368, (2).

Example 390

By using the compound obtained in Example 368, (1) (60 mg) and 3-aminopyrrolidine (36.4 µl) as starting materials, the compound shown in Table 11 (39 mg) was obtained in the same manner as that of Example 368, (2).

Example 391

By using the compound obtained in Example 368, (1) (30 mg) and N,N-dimethyl-1,3-propanediamine (25.8 µl) as starting materials, the compound shown in Table 11 (23 mg) was obtained in the same manner as that of Example 368, (2).

Example 392

By using the compound obtained in Example 368, (1) (30 mg) and the compound obtained in Reference Example 133

(24.2 mg) as starting materials, the compound shown in Table 11 (11 mg) was obtained in the same manner as that of Example 368, (2).

Example 393

By using the compound obtained in Example 368, (1) (30 mg) and the compound obtained in Reference Example 133 (24.2 mg) as starting materials, a diastereomer of the compound of Example 392 shown in Table 11 (5 mg) was obtained in the same manner as that of Example 368, (2).

Example 394

By using the compound obtained in Example 368, (1) (30 mg) and the compound obtained in Reference Example 134 (20.5 mg) as starting materials, the compound shown in Table 11 (16 mg) was obtained in the same manner as that of Example 368, (2).

Example 395

By using the compound obtained in Example 368, (1) (10 mg) and 2-amino-1-propanol (5.1 mg) as starting materials, the compound shown in Table 11 (10.7 mg) was obtained in the same manner as that of Example 368, (2).

Example 396

By using the compound obtained in Example 368, (1) (10 mg) and 3-aminopentane (6.0 mg) as starting materials, the compound shown in Table 11 (10.7 mg) was obtained in the same manner as that of Example 368, (2).

Example 397

By using the compound obtained in Example 368, (1) (10 mg) and N-isopropylethylenediamine (7.0 mg) as starting materials, the compound shown in Table 11 (9.4 mg) was obtained in the same manner as that of Example 368, (2).

Example 398

By using the compound obtained in Example 368, (1) (10 mg) and 4-aminotetrahydropyrane (6.9 mg) as starting materials, the compound shown in Table 11 (10.5 mg) was obtained in the same manner as that of Example 368, (2).

Example 399

By using the compound obtained in Example 368, (1) (30 mg) and (3R)-(+)-3-aminopyrrolidine (17.7 mg) as starting materials, the compound shown in Table 11 (26.1 mg) was obtained in the same manner as that of Example 368, (2).

Example 400

By using the compound obtained in Example 368, (1) (50 mg) and 1-benzyl-3-aminopyrrolidine (60.3 mg) as starting materials, the compound shown in Table 11 (30.7 mg) was obtained in the same manner as that of Example 368, (2).

Example 401

By using the compound obtained in Example 368, (1) (30 mg) and the compound obtained in Reference Example 135 (11 mg) as starting materials, the compound shown in Table 11 (3.2 mg) was obtained in the same manner as that of Example 368, (2).

Example 402

The compound obtained in Example 400 (15 mg) was dissolved in methanol (300 μl), the solution was added with 20% palladium hydroxide-carbon (7.5 mg), and the mixture was stirred at room temperature for 3 hours under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=10:1:0.1) to obtain the compound shown in Table 11 (8.4 mg).

Example 403

By using the compound obtained in Example 368, (1) (50 mg) and the compound obtained in Reference Example 136 (90.1 mg) as starting materials, the compound shown in Table 11 (33.4 mg) was obtained in the same manner as that of Example 368, (2).

Example 404

By using the compound obtained in Example 403 (15 mg) as a starting material, the compound shown in Table 11 (3.0 mg) was obtained in the same manner as that of Example 402.

Example 405

(1) By using the compound obtained in Example 172, (1) (60 mg) and 24% aqueous ammonia (3 ml) as starting materials, an amine compound (52 mg) was obtained in the same manner as that of Example 363, (1).
(2) By using the compound obtained in (1) mentioned above (52 mg) as a starting material, the compound shown in Table 11 (25 mg) was obtained in the same manner as that of Example 7, (4).

Example 406

By using the compound obtained in Example 368, (1) (30 mg) and (3S)-(−)-3-aminopyrrolidine (17.7 mg) as starting materials, the compound shown in Table 11 (30.7 mg) was obtained in the same manner as that of Example 368, (2).

Example 407

(1) By using the compound obtained in Example 172, (1) (80 mg) as a starting material, a hydroxy compound (27 mg) was obtained in the same manner as that of Example 362, (1).
(2) By using the compound obtained in (1) mentioned above (32 mg) as a starting material, the compound shown in Table 11 (22 mg) was obtained in the same manner as that of Example 7, (4).

Example 408

By using the compound obtained in Example 172, (1) (70 mg) as a starting material, the compound shown in Table 11 (8 mg) was obtained in the same manners as those of Example 367, (1) and Example 7, (4).

Example 409

By using the compound obtained in Example 172, (1) (60 mg) and 40% aqueous methylamine (3 ml) as starting materials, the compound shown in Table 11 (20 mg) was obtained in the same manners as those of Example 363, (1) and Example 7, (4).

Example 410

By using the compound obtained in Example 172, (1) (60 mg) and 50% aqueous dimethylamine (3 ml) as starting materials, the compound shown in Table 11 (29 mg) was obtained in the same manners as those of Example 363, (1) and Example 7, (4).

Example 411

By using the compound obtained in Example 405, (1) (43 mg) as a starting material, a cyclized compound (26 mg) was obtained in the same manner as that of Example 366, (1).
(2) By using the compound obtained in (1) mentioned above (32 mg) as a starting material, the compound shown in Table 11 (30 mg) was obtained in the same manner as that of Example 7, (4).

Example 412

(1) By using the compound obtained in Example 172, (1) (2.0 g) as a starting material, a deprotected compound (1.4 g) was obtained in the same manner as that of Example 7, (4).
(2) By using the compound obtained in (1) mentioned above (115 mg) and ethylenediamine (52.6 µl) as starting materials, the compound shown in Table 11 (124 mg) was obtained in the same manner as that of Example 368, (2).

Example 413

By using the compound obtained in Example 412, (1) (100 mg) and 1,3-diaminopropane (57.1 µl) as starting materials, the compound shown in Table 11 (51 mg) was obtained in the same manner as that of Example 368, (2).

Example 414

By using the compound obtained in Example 412, (1) (100 mg) and 1,4-diaminobutane (27.5 µl) as starting materials, the compound shown in Table 11 (51 mg) was obtained in the same manner as that of Example 368, (2).

Example 415

By using the compound obtained in Example 412, (1) (100 mg) and aminoethanol (16.5 µl) as starting materials, the compound shown in Table 11 (82 mg) was obtained in the same manner as that of Example 368, (2).

Example 416

By using the compound obtained in Example 412, (1) (100 mg) and piperidine (27.1 µl) as starting materials, the compound shown in Table 11 (43 mg) was obtained in the same manner as that of Example 368, (2).

Example 417

By using the compound obtained in Example 412, (1) (100 mg) and 3-amino-1-propanol (52.3 µl) as starting materials, the compound shown in Table 11 (41 mg) was obtained in the same manner as that of Example 368, (2).

Example 418

By using the compound obtained in Example 412, (1) (100 mg) and piperazine (58.9 mg) as starting materials, the compound shown in Table 11 (96 mg) was obtained in the same manner as that of Example 368, (2).

Example 419

By using the compound obtained in Example 412, (1) (100 mg) and N,N-dimethylethylenediamine (75 µl) as starting materials, the compound shown in Table 11 (100 mg) was obtained in the same manner as that of Example 368, (2).

Example 420

By using the compound obtained in Example 412, (1) (100 mg) and 4-amino-1-butanol (63 µl) as starting materials, the compound shown in Table 11 (86 mg) was obtained in the same manner as that of Example 368, (2).

Example 421

By using the compound obtained in Example 412, (1) (100 mg) and morpholine (60 µl) as starting materials, the compound shown in Table 11 (47 mg) was obtained in the same manner as that of Example 368, (2).

Example 422

By using the compound obtained in Example 412, (1) (100 mg) and 2-methoxyethylamine (60 µl) as starting materials, the compound shown in Table 11 (71 mg) was obtained in the same manner as that of Example 368, (2).

Example 423

By using the compound obtained in Example 412, (1) (100 mg) and 2-(methylamino)ethanol (55 µl) as starting materials, the compound shown in Table 11 (64 mg) was obtained in the same manner as that of Example 368, (2).

Example 424

By using the compound obtained in Example 412, (1) (100 mg) and n-butylamine (68 µl) as starting materials, the compound shown in Table 11 (66 mg) was obtained in the same manner as that of Example 368, (2).

Example 425

By using the compound obtained in Example 412, (1) (100 mg) and 3-aminopropionitrile (102 µl) as starting materials, the compound shown in Table 11 (14 mg) was obtained in the same manner as that of Example 368, (2).

Example 426

By using the compound obtained in Example 412, (1) (60 mg) and benzylamine (45 µl) as starting materials, the compound shown in Table 11 (61 mg) was obtained in the same manner as that of Example 368, (2).

Example 427

By using the compound obtained in Example 412, (1) (60 mg) and 3-(aminomethyl)pyridine (42 µl) as starting materials, the compound shown in Table 11 (52 mg) was obtained in the same manner as that of Example 368, (2).

Example 428

By using the compound obtained in Example 412, (1) (60 mg) and imidazole (28.2 mg) as starting materials, the compound shown in Table 11 (57 mg) was obtained in the same manner as that of Example 368, (2).

Example 429

By using the compound obtained in Example 412, (1) (60 mg) and aniline (37 μl) as starting materials, the compound shown in Table 11 (58 mg) was obtained in the same manner as that of Example 368, (2).

Example 430

(1) By using the compound obtained in Example 172, (1) (100 mg) and benzylamine (75 μl) as starting materials, an amine compound (84 mg) was obtained in the same manner as that of Example 368, (2).
(2) The compound obtained in (1) mentioned above (84 mg) was dissolved in methanol (200 μl), the solution was added with 20% palladium hydroxide-carbon (42 mg), and the mixture was stirred at room temperature for 14 hours under a hydrogen atmosphere of 1 atm. The reaction mixture was filtered, and then the filtrate was concentrated under reduced pressure. The resulting residue (72 mg) was dissolved in chloroform (200 μl), the solution was added with pyridine (162 μl) and triphosgene (59.4 mg), and the mixture was stirred for 1 hour under ice cooling. The reaction mixture was added with saturated aqueous sodium hydrogencarbonate and chloroform, the layers were separated, and the organic layer was dried over anhydrous magnesium sulfate and filtered. The filtrate was concentrated under reduced pressure to obtain a cyclized compound (12 mg).
(3) By using the compound obtained in (2) mentioned above (12 mg) as a starting material, the compound shown in Table 11 (10 mg) was obtained in the same manner as that of Example 7, (4).

Example 431

By using the compound obtained in Example 172, (1) (40 mg) and the compound obtained in Reference Example 54 (15.3 mg) as starting materials, the compound shown in Table 11 (2.4 mg) was obtained in the same manners as those of Example 168, (2) and Example 7, (4).

Example 432

By using the compound obtained in Example 412, (1) (50 mg) and the compound obtained in Reference Example 106 (62 mg) as starting materials, the compound shown in Table 11 (18 mg) was obtained in the same manner as that of Example 168, (2).

Example 433

By using the compound obtained in Example 412, (1) (30 mg) and the compound obtained in Reference Example 131 (37.0 mg) as starting materials, the compound shown in Table 11 (17 mg) was obtained in the same manner as that of Example 168, (2).

Example 434

By using the compound obtained in Example 412, (1) (50 mg) and D-(−)-threo-2-amino-1-(4-nitrophenyl)-1,3-propanediol (72.6 mg) as starting materials, the compound shown in Table 11 (37 mg) was obtained in the same manner as that of Example 368, (2).

Example 435

By using the compound obtained in Example 412, (1) (50 mg) and the compound obtained in Reference Example 137 (102 mg) as starting materials, the compound shown in Table 11 (23 mg) was obtained in the same manner as that of Example 368, (2).

Example 436

By using the compound obtained in Example 412, (1) (50 mg) and the compound obtained in Reference Example 138 (107 mg) as starting materials, the compound shown in Table 11 (39 mg) was obtained in the same manner as that of Example 368, (2).

Example 437

By using the compound obtained in Example 412, (1) (50 mg) and the compound obtained in Reference Example 139 (87 mg) as starting materials, the compound shown in Table 11 (36 mg) was obtained in the same manner as that of Example 368, (2).

Example 438

By using the compound obtained in Example 412, (1) (50 mg) and the compound obtained in Reference Example 140 (92 mg) as starting materials, the compound shown in Table 11 (52 mg) was obtained in the same manner as that of Example 368, (2).

Example 439

By using the compound obtained in Example 412, (1) (50 mg) and the compound obtained in Reference Example 141 (97 mg) as starting materials, the compound shown in Table 11 (51 mg) was obtained in the same manner as that of Example 368, (2).

Example 440

By using the compound obtained in Example 412, (1) (50 mg) and the compound obtained in Reference Example 142 (84 mg) as starting materials, the compound shown in Table 11 (15 mg) was obtained in the same manner as that of Example 368, (2).

Example 441

By using the compound obtained in Example 412, (1) (50 mg) and the compound obtained in Reference Example 150 (89 mg) as starting materials, the compound shown in Table 11 (21 mg) was obtained in the same manner as that of Example 368, (2).

Example 442

By using the compound obtained in Example 412, (1) (50 mg) and the compound obtained in Reference Example 69 (36.0 mg) as starting materials, the compound shown in Table 11 (37 mg) was obtained in the same manner as that of Example 368, (2).

Example 443

By using the compound obtained in Example 412, (1) (50 mg) and the compound obtained in Reference Example 68 (47.3 mg) as starting materials, the compound shown in Table 11 (37 mg) was obtained in the same manner as that of Example 368, (2).

Example 444

By using the compound obtained in Example 412, (1) (50 mg) and N,N-dimethylpropane-1,4-diamine (34.9 mg) as starting materials, the compound shown in Table 11 (37 mg) was obtained in the same manner as that of Example 368, (2).

Example 445

By using the compound obtained in Example 412, (1) (50 mg) and the compound obtained in Reference Example 67 (39.7 mg) as starting materials, the compound shown in Table 11 (12.5 mg) was obtained in the same manner as that of Example 368, (2).

Example 446

By using the compound obtained in Example 412, (1) (50 mg) and the compound obtained in Reference Example 147 (67.1 mg) as starting materials, the compound shown in Table 11 (31 mg) was obtained in the same manner as that of Example 168, (2).

Example 447

By using the compound obtained in Example 412, (1) (50 mg) and the compound obtained in Reference Example 148 (76.7 mg) as starting materials, the compound shown in Table 11 (32 mg) was obtained in the same manner as that of Example 168, (2).

Example 448

By using the compound obtained in Example 412, (1) (50 mg) and the compound obtained in Reference Example 145 (121 mg) as starting materials, the compound shown in Table 11 (32 mg) was obtained in the same manner as that of Example 168, (2).

Example 449

By using the compound obtained in Example 412, (1) (30 mg) and 2-amino-1,3-propanediol (18.7 mg) as starting materials, the compound shown in Table 11 (36 mg) was obtained in the same manner as that of Example 368, (2).

Example 450

By using the compound obtained in Example 412, (1) (30 mg) and the compound obtained in Reference Example 143 (37.4 mg) as starting materials, the compound shown in Table 11 (34 mg) was obtained in the same manner as that of Example 368, (2).

Example 451

(1) Florfenicolamine hydrochloride (20 mg) was added with 1 N aqueous sodium hydroxide and chloroform, the layers were separated, the aqueous layer was added with potassium carbonate, and the mixture was extracted with chloroform. The organic layer was concentrated under reduced pressure to obtain an amine compound (17 mg).

(2) By using the compound obtained in Example 412, (1) (12.6 mg) and the compound obtained in (1) mentioned above (17 mg) as starting materials, the compound shown in Table 11 (1.0 mg) was obtained in the same manner as that of Example 368, (2).

Example 452

By using the compound obtained in Example 412, (1) (30 mg) and (1R,2R)-(−)-2-amino-1-phenyl-1,3-propanediol (34.3 mg) as starting materials, the compound shown in Table 11 (30 mg) was obtained in the same manner as that of Example 368, (2).

Example 453

By using the compound obtained in Example 412, (1) (30 mg) and the compound obtained in Reference Example 133 (24.2 mg) as starting materials, the compound shown in Table 11 (8 mg) was obtained in the same manner as that of Example 368, (2).

Example 454

By using the compound obtained in Example 412, (1) (30 mg) and the compound obtained in Reference Example 133 (24.2 mg) as starting materials, a diastereomer of the compound of Example 453 shown in Table 11 (10 mg) was obtained in the same manner as that of Example 368, (2).

Example 455

By using the compound obtained in Example 412, (1) (50 mg) and the compound obtained in Reference Example 144 (39.7 mg) as starting materials, the compound shown in Table 11 (12.5 mg) was obtained in the same manner as that of Example 368, (2).

Example 456

By using the compound obtained in Example 412, (1) (30 mg) and D-(+)-threo-[1-(p-methanesulfonyl)phenyl]-2-amino-1,3-propanediol (13 mg) as starting materials, the compound shown in Table 11 (12.5 mg) was obtained in the same manner as that of Example 368, (2).

Example 457

By using the compound obtained in Example 412, (1) (30 mg) and 4-nitrophenethylamine hydrochloride (41.6 mg) as starting materials, the compound shown in Table 11 (13 mg) was obtained in the same manner as that of Example 368, (2).

Example 458

By using the compound obtained in Example 412, (1) (30 mg) and the compound obtained in Reference Example 144 (40.2 mg) as starting materials, the compound shown in Table 11 (4.0 mg) was obtained in the same manner as that of Example 368, (2).

Example 459

(1) The amine compound (50 mg) obtained in Example 262, (2) of which steric configuration of the 4″-position was S was dissolved in dimethylformamide (2 ml), the solution was added with N,N'-carbonyldiimidazole (25.7 mg), and the mixture was stirred at room temperature for 18 hours. The reaction mixture was added with ethyl acetate and saturated aqueous sodium hydrogencarbonate, the layers were separated, and the organic layer was dried over anhydrous magnesium sulfate and filtered. The filtrate was concentrated under reduced pressure, and the resulting residue was dissolved in tetrahydrofuran (2 ml). The solution was added with the compound obtained in Reference Example 145 (55.9 mg), and the mixture was stirred for 1 hour under reflux by heating. The reaction mixture was added with saturated aqueous sodium hydrogencarbonate and ethyl acetate, the layers were separated, and the organic layer was dried over anhydrous magnesium sulfate and filtered. The filtrate was concentrated under reduced pressure, and the resulting residue was purified by silica gel column chromatography (hexane:acetone:triethylamine=30:10:0.2) to obtain a urea compound (71 mg).

(2) By using the compound obtained in (1) mentioned above (65 mg) as a starting material, the compound shown in Table 11 (48 mg) was obtained in the same manner as that of Example 7, (4).

Example 460

(1) The compound obtained in Reference Example 146 (20 mg) was dissolved in chloroform, the solution was added with the Dess-Martin reagent (40 mg), and the mixture was stirred at room temperature for 20 minutes. The reaction mixture was added with saturated aqueous sodium hydrogencarbonate and diethyl ether, the layers were separated, and the organic layer was dried over anhydrous magnesium sulfate and filtered. The filtrate was concentrated under reduced pressure, the resulting aldehyde and the amine compound (50 mg) obtained in Example 262, (2) of which steric configuration of the 4"-position was S were dissolved in chloroform, the solution was added with sodium triacetoxyborohydride (1.38 g), and the mixture was stirred at room temperature for 18 hours. The reaction mixture was added with saturated aqueous sodium hydrogencarbonate, the layers were separated, and the organic layer was dried over anhydrous magnesium sulfate and filtered. The filtrate was concentrated under reduced pressure, and the resulting residue was purified by silica gel column chromatography (hexane:acetone:triethylamine=50:10:0.2) to obtain an adduct compound (30 mg).

(2) By using the compound obtained in (1) mentioned above (30 mg) as a starting material, the compound shown in Table 11 (9.5 mg) was obtained in the same manner as that of Example 7, (4).

Example 461

(1) The amine compound (420 mg) obtained in Example 262, (2) of which steric configuration of the 4"-position was S was dissolved in dimethylformamide (8 ml), the solution was added with N,N'-carbonyldiimidazole (180 mg), and the mixture was stirred at room temperature for 18 hours. The reaction mixture was added with ethyl acetate and saturated aqueous sodium hydrogencarbonate, the layers were separated, and the organic layer was dried over anhydrous magnesium sulfate and filtered. The filtrate was concentrated under reduced pressure to obtain a 4"-N-imidazolylcarbonyl compound (462 mg).

(2) The compound obtained in (1) mentioned above (66 mg) was dissolved in tetrahydrofuran (2 ml), the solution was added with the compound obtained in Reference Example 142 (47 mg), and the mixture was stirred for 1 hour under reflux by heating. The reaction mixture was concentrated under reduced pressure, and the resulting residue was purified by silica gel column chromatography (hexane:acetone:triethylamine=50:10:0.2) to obtain a urea compound (72.2 mg).

(3) By using the compound obtained in (2) mentioned above (71.2 mg) as a starting material, the compound shown in Table 11 (16.6 mg) was obtained in the same manner as that of Example 7, (4).

Example 462

By using the compound obtained in Example 461, (1) (66 mg) and the compound obtained in Reference Example 147 (38 mg) as starting materials, the compound shown in Table 11 (30.4 mg) was obtained in the same manners as those of Example 461, (2) and Example 7, (4).

Example 463

By using the compound obtained in Example 461, (1) (66 mg) and the compound obtained in Reference Example 148 (48 mg) as starting materials, the compound shown in Table 11 (41.3 mg) was obtained in the same manners as those of Example 461, (2) and Example 7, (4).

Example 464

(1) By using the compound obtained in Example 461, (1) (130 mg) and the compound obtained in Reference Example 137 (44.6 mg) as starting materials, a urea compound (111 mg) was obtained in the same manner as that of Example 126, (3).

(2) By using the compound obtained in (1) mentioned above (50 mg) as a starting material, the compound shown in Table 11 (42 mg) was obtained in the same manner as that of Example 7, (4).

Example 465

(1) By using the compound obtained in Example 461, (1) (60 mg) and the compound obtained in Reference Example 138 (15 mg) as starting materials, a urea compound (23 mg) was obtained in the same manner as that of Example 126, (3).

(2) By using the compound obtained in (1) mentioned above (20 mg) as a starting material, the compound shown in Table 11 (14 mg) was obtained in the same manner as that of Example 7, (4).

Example 466

(1) By using the compound obtained in Example 461, (1) (70 mg) and the compound obtained in Reference Example 149 (17.2 mg) as starting materials, a urea compound (54 mg) was obtained in the same manner as that of Example 126, (3).

(2) By using the compound obtained in (1) mentioned above (50 mg) as a starting material, the compound shown in Table 11 (33 mg) was obtained in the same manner as that of Example 7, (4).

Example 467

(1) The amine compound obtained in Example 262, (2) (70 mg) of which steric configuration of the 4"-position was S was dissolved in dimethylformamide (1.5 ml), the solution was added with N,N'-carbonyldiimidazole (30.0 mg), and the mixture was stirred at room temperature for 18 hours. The reaction mixture was added with ethyl acetate and saturated aqueous sodium hydrogencarbonate, the layers were separated, and the organic layer was dried over anhydrous magnesium sulfate and filtered. The filtrate was concentrated under reduced pressure, and the resulting residue was dissolved in tetrahydrofuran (2 ml). The solution was added with the compound obtained in Reference Example 150 (38.5 mg), and the mixture was stirred for 1 hour under reflux by heating. The reaction mixture was concentrated under reduced pressure, and the resulting residue was purified by silica gel column chromatography (hexane:acetone:triethylamine=50:10:0.2) to obtain a urea compound (66.9 mg).

(2) By using the compound obtained in (1) mentioned above (64.3 mg) as a starting material, the compound shown in Table 11 (32.7 mg) was obtained in the same manner as that of Example 7, (4).

Example 468

By using the amine compound obtained in Example 262, (2) (50 mg) of which steric configuration of the 4"-position was S and n-butylamine (11.6 mg) as starting materials, the compound shown in Table 11 (40 mg) was obtained in the same manners as those of Example 459, (1) and Example 7, (4).

Example 469

(1) The amine compound obtained in Example 262, (2) (50 mg) of which steric configuration of the 4"-position was S was dissolved in chloroform (2 ml), the solution was added with the compound obtained in Reference Example 151 (37.8 mg) and sodium triacetoxyborohydride (16.8 mg), and the mixture was stirred at room temperature for 2 hours. The reaction mixture was added with saturated aqueous sodium hydrogencarbonate and chloroform, the layers were separated, and then the organic layer was dried over anhydrous magnesium sulfate and filtered. The filtrate was concentrated under reduced pressure, and the resulting residue was purified by silica gel column chromatography (hexane:acetone:triethylamine=50:10:0.2) to obtain an amine compound (37 mg).

(2) By using the compound obtained in (1) mentioned above (35 mg) as a starting material, the compound shown in Table 11 (23 mg) was obtained in the same manner as that of Example 7, (4).

Example 470

(1) The amine compound obtained in Example 262, (2) (60 mg) of which steric configuration of the 4"-position was S was dissolved in chloroform, the solution was added with triethylamine (64 mg) and 3-chloropropanesulfonyl chloride (32 mg), and the mixture was stirred at room temperature for 1 hour. The reaction mixture was concentrated under reduced pressure, and the resulting residue was purified by silica gel column chromatography (hexane:acetone:triethylamine=10:10:0.2) to obtain a chloro compound (60 mg).

(2) The compound obtained in (1) mentioned above (46 mg) and (1S)-1-(2-methoxyphenyl)ethanamine (19 mg) obtained by the method described in the patent document (Japanese Patent Unexamined Publication No. 54-154724) were dissolved in dimethylformamide (0.5 ml), and the solution was heated at 110° C. for 5 hours. The reaction mixture was added with ethyl acetate and saturated aqueous sodium hydrogencarbonate, the layers were separated, and the organic layer was dried over anhydrous magnesium sulfate and filtered. The filtrate was concentrated under reduced pressure, and the resulting residue was purified by silica gel column chromatography (hexane:acetone:triethylamine=30:10:0.2) to obtain an adduct compound (26 mg).

(3) By using the compound obtained in (2) mentioned above (26 mg) as a starting material, the compound shown in Table 11 (9 mg) was obtained in the same manner as that of Example 7, (4).

Example 471

(1) The epimer mixture (48 mg) obtained in Example 262, (2) was dissolved in dichloromethane (0.5 ml), the solution was added with 9-fluorenylmethylsuccinimidyl carbonate (25 mg) and triethylamine (33 µl), and the mixture was stirred at room temperature for 2 days. The reaction mixture was concentrated under reduced pressure, and the resulting residue was purified by preparative thin layer chromatography (hexane:ethyl acetate:methanol:28% aqueous ammonia=50:10:1:1) to obtain a protected amine compound (8.0 mg) of which steric configuration of the 4"-position was R.

(2) The compound obtained in (1) mentioned above (12.2 mg) was dissolved in piperidine (0.3 ml), and the solution was stirred at room temperature for 20 minutes. The reaction mixture was concentrated under reduced pressure, and the resulting residue was purified by preparative thin layer chromatography (chloroform:methanol=10:1) to obtain an amine compound (9.2 mg) of which steric configuration of the 4"-position was R.

(3) By using the compound obtained in (2) mentioned above (9.2 mg) as a starting material, the compound shown in Table 11 (4.9 mg) was obtained in the same manner as that of Example 7, (4).

Example 472

By using the compound obtained in Example 126, (2) (79 mg) and the compound obtained in Reference Example 163 (47.2 mg) as starting materials, the compound shown in Table 11 (25.5 mg) was obtained in the same manners as those of Example 126, (3) and Example 7, (4).

Example 473

By using the compound obtained in Example 126, (2) (80.5 mg) and the compound obtained in Reference Example 164 (53.2 mg) as starting materials, the compound shown in Table 11 (23.1 mg) was obtained in the same manners as those of Example 126, (3) and Example 7, (4).

Example 474

By using the compound obtained in Example 126, (2) (79.3 mg) and the compound obtained in Reference Example 165 (41.2 mg) as starting materials, the compound shown in Table 11 (21.3 mg) was obtained in the same manners as those of Example 126, (3) and Example 7, (4).

Example 475

By using the compound obtained in Example 126, (2) (80.5 mg) and the compound obtained in Reference Example 166 (37.2 mg) as starting materials, the compound shown in Table 11 (22.3 mg) was obtained in the same manners as those of Example 126, (3) and Example 7, (4).

Example 476

By using the compound obtained in Example 126, (2) (78.3 mg) and the compound obtained in Reference Example 167 (28.7 mg) as starting materials, the compound shown in Table 11 (24.3 mg) was obtained in the same manners as those of Example 126, (3) and Example 7, (4).

Example 477

By using the compound obtained in Example 126, (2) (81.1 mg) and the compound obtained in Reference Example 168 (42.3 mg) as starting materials, the compound shown in Table 11 (15.3 mg) was obtained in the same manners as those of Example 126, (3) and Example 7, (4).

Example 478

By using the compound obtained in Example 126, (2) (81.3 mg) and the compound obtained in Reference Example 169 (33.5 mg) as starting materials, the compound shown in Table 11 (16.3 mg) was obtained in the same manners as those of Example 126, (3) and Example 7, (4).

Example 479

By using the compound obtained in Example 126, (2) (86.7 mg) and the compound obtained in Reference Example 170 (28.4 mg) as starting materials, the compound shown in Table 11 (12.4 mg) was obtained in the same manners as those of Example 126, (3) and Example 7, (4).

Example 480

By using the compound obtained in Example 126, (2) (79.6 mg) and the compound obtained in Reference Example 171 (30.3 mg) as starting materials, the compound shown in Table 11 (17.0 mg) was obtained in the same manners as those of Example 126, (3) and Example 7, (4).

Example 481

By using the compound obtained in Example 126, (2) (79.9 mg) and the compound obtained in Reference Example 172 (27.5 mg) as starting materials, the compound shown in Table 11 (20.0 mg) was obtained in the same manners as those of Example 126, (3) and Example 7, (4).

Example 482

(1) The compound obtained in Example 126, (2) (80 mg) was dissolved in tetrahydrofuran (0.2 ml), the solution was added with 1,4-butanediamine (77 µl), and the mixture was stirred overnight at room temperature. The reaction mixture was added with saturated aqueous ammonium chloride and ethyl acetate, the layers were separated, and then the organic layer was filtered by using a phase separator. The filtrate was concentrated under reduced pressure, and the resulting residue was purified by preparative thin layer chromatography (chloroform:methanol:28% aqueous ammonia=5:1:0.1) to obtain a carbamate compound (52.1 mg).

(2) By using the compound obtained in (1) mentioned above (52.1 mg) as a starting material, the compound shown in Table 11 (2.6 mg) was obtained in the same manner as that of Example 7, (4).

Example 483

By using the compound obtained in Example 126, (2) (80 mg) and 2-aminoethanol (9 µl) as starting materials, the compound shown in Table 11 (10.9 mg) was obtained in the same manners as those of Example 482, (1) and Example 7, (4).

Example 484

By using the compound obtained in Example 126, (2) (80 mg) and 2-methoxyethylamine (13 µl) as starting materials, the compound shown in Table 11 (20.0 mg) was obtained in the same manners as those of Example 482, (1) and Example 7, (4).

Example 485

By using the compound obtained in Example 126, (2) (80 mg) and 2-(N-methylamino)ethanol (12 µl) as starting materials, the compound shown in Table 11 (21.9 mg) was obtained in the same manners as those of Example 482, (1) and Example 7, (4).

Example 486

By using the compound obtained in Example 126, (2) (80 mg) and piperidine (15 µl) as starting materials, the compound shown in Table 11 (36.2 mg) was obtained in the same manners as those of Example 482, (1) and Example 7, (4).

Example 487

By using the compound obtained in Example 126, (2) (80 mg) and morpholine (13 µl) as starting materials, the compound shown in Table 11 (13.3 mg) was obtained in the same manners as those of Example 482, (1) and Example 7, (4).

Example 488

By using the compound obtained in Example 126, (2) (80 mg) and n-butylamine (15 µl) as starting materials, the compound shown in Table 11 (33.5 mg) was obtained in the same manners as those of Example 482, (1) and Example 7, (4).

Example 489

By using the compound obtained in Example 126, (2) (80 mg), methylamine hydrochloride (52 mg) and triethylamine (107 µl) as starting materials, the compound shown in Table 11 (17.0 mg) was obtained in the same manners as those of Example 482, (1) and Example 7, (4).

Example 490

By using the compound obtained in Example 126, (2) (80 mg) and ethylenediamine (51.3 µl) as starting materials, the compound shown in Table 11 (22.5 mg) was obtained in the same manners as those of Example 126, (3) and Example 7, (4).

Example 491

By using the compound obtained in Example 126, (2) (80 mg) and 1,3-propanediamine (64 µl) as starting materials, the compound shown in Table 11 (26.6 mg) was obtained in the same manners as those of Example 126, (3) and Example 7, (4).

Example 492

By using the compound obtained in Example 126, (2) (80 mg) and N,N-dimethylethylenediamine (15.4 μl) as starting materials, the compound shown in Table 11 (28.9 mg) was obtained in the same manners as those of Example 126, (3) and Example 7, (4).

Example 493

By using the compound obtained in Example 126, (2) (80 mg) and 3-aminopropanenitrile (11.3 μl) as starting materials, the compound shown in Table 11 (33.5 mg) was obtained in the same manners as those of Example 126, (3) and Example 7, (4).

Example 494

By using the compound obtained in Example 126, (2) (80 mg) and 3-amino-1-propanol (11.7 μl) as starting materials, the compound shown in Table 11 (26.7 mg) was obtained in the same manners as those of Example 126, (3) and Example 7, (4).

Example 495

By using the compound obtained in Example 126, (2) (80 mg) and 4-amino-1-butanol (14.3 μl) as starting materials, the compound shown in Table 11 (21.7 mg) was obtained in the same manners as those of Example 126, (3) and Example 7, (4).

Example 496

By using the compound obtained in Example 126, (2) (80 mg) and 28% aqueous ammonia (46.7 μl) as starting materials, the compound shown in Table 11 (22.3 mg) was obtained in the same manners as those of Example 126, (3) and Example 7, (4).

Example 497

By using the compound obtained in Example 126, (2) (80 mg) and 50% aqueous dimethylamine (69 μl) as starting materials, the compound shown in Table 11 (31.0 mg) was obtained in the same manners as those of Example 126, (3) and Example 7, (4).

Example 498

By using the compound obtained in Example 126, (2) (80 mg) and piperazine (132 mg) as starting materials, the compound shown in Table 11 (35.1 mg) was obtained in the same manners as those of Example 126, (3) and Example 7, (4).

Example 499

(1) The compound obtained in Example 126, (2) (80 mg) was dissolved in tetrahydrofuran (0.2 ml), the solution was added with the compound obtained in Reference Example 173 (48 mg), and the mixture was stirred at room temperature for 2 days. The reaction mixture was concentrated under reduced pressure, and the resulting residue was purified by preparative thin layer chromatography (chloroform:methanol:28% aqueous ammonia=15:1:0.1) to obtain a carbamate compound (58.2 mg).

(2) By using the compound obtained in (1) mentioned above (58.2 mg) as a starting material, the compound shown in Table 11 (39.0 mg) was obtained in the same manner as that of Example 7, (4).

Example 500

By using the compound obtained in Example 126, (2) (80 mg) and the compound obtained in Reference Example 174 (40 mg) as starting materials, the compound shown in Table 11 (44.0 mg) was obtained in the same manners as those of Example 499, (1) and Example 7, (4).

Example 501

By using the compound obtained in Example 126, (2) (80 mg) and the compound obtained in Reference Example 175 (51 mg) as starting materials, the compound shown in Table 11 (39.0 mg) was obtained in the same manners as those of Example 499, (1) and Example 7, (4).

Example 502

By using the compound obtained in Example 126, (2) (80 mg) and the compound obtained in Reference Example 176 (42 mg) as starting materials, the compound shown in Table 11 (43.5 mg) was obtained in the same manners as those of Example 499, (1) and Example 7, (4).

Example 503

By using the compound obtained in Example 126, (2) (80 mg) and the compound obtained in Reference Example 177 (52 mg) as starting materials, the compound shown in Table 11 (50.8 mg) was obtained in the same manners as those of Example 499, (1) and Example 7, (4).

Example 504

By using the compound obtained in Example 126, (2) (80 mg) and the compound obtained in Reference Example 178 (51 mg) as starting materials, the compound shown in Table 11 (42.2 mg) was obtained in the same manners as those of Example 499, (1) and Example 7, (4).

Example 505

By using the compound obtained in Example 126, (2) (80 mg) and the compound obtained in Reference Example 179 (54 mg) as starting materials, the compound shown in Table 11 (50.8 mg) was obtained in the same manners as those of Example 499, (1) and Example 7, (4).

Example 506

By using the compound obtained in Example 126, (2) (80 mg) and the compound obtained in Reference Example 180 (45 mg) as starting materials, the compound shown in Table 11 (38.8 mg) was obtained in the same manners as those of Example 499, (1) and Example 7, (4).

Example 507

By using the compound obtained in Example 126, (2) (80 mg) and the compound obtained in Reference Example 181

Example 508

By using the compound obtained in Example 126, (2) (80 mg) and the compound obtained in Reference Example 182 (36 mg) as starting materials, the compound shown in Table 11 (10.0 mg) was obtained in the same manners as those of Example 499, (1) and Example 7, (4) except that dimethylformamide was used instead of tetrahydrofuran.

Example 509

The compound obtained in Example 262 (11.0 mg) was dissolved in chloroform, the solution was added with 36% aqueous formaldehyde (12.7 µl) and sodium triacetoxyborohydride (4.9 mg), and the mixture was stirred at room temperature for 4 hours. The reaction mixture was added with saturated aqueous sodium hydrogencarbonate, potassium carbonate and dichloromethane, the layers were separated, and then the organic layer was dried over sodium sulfate and filtered. The filtrate was concentrated under reduced pressure, and the resulting residue was purified by preparative thin layer chromatography (chloroform:methanol:28% aqueous ammonia=5:1:0.1) to obtain the compound shown in Table 11 (6.2 mg).

Example 510

By using the compound obtained in Example 126, (2) (80.0 mg) and the compound obtained in Reference Example 183 (77.0 mg) as starting materials, the compound shown in Table 11 (44.6 mg) was obtained in the same manners as those of Example 126, (3) and Example 7, (4).

Example 511

By using the compound obtained in Example 126, (2) (80.0 mg) and the compound obtained in Reference Example 184 (100 mg) as starting materials, the compound shown in Table 11 (44.3 mg) was obtained in the same manners as those of Example 126, (3) and Example 7, (4).

Example 512

By using the compound obtained in Example 126, (2) (80.0 mg) and the compound obtained in Reference Example 185 (23.5 mg) as starting materials, the compound shown in Table 11 (19.0 mg) was obtained in the same manners as those of Example 126, (3) and Example 7, (4).

Example 513

By using the compound obtained in Example 126, (2) (80.0 mg) and the compound obtained in Reference Example 186 (60.0 mg) as starting materials, the compound shown in Table 11 (47.2 mg) was obtained in the same manners as those of Example 126, (3) and Example 7, (4).

Example 514

By using the compound obtained in Example 126, (2) (80.0 mg) and the compound obtained in Reference Example 187 (35.0 mg) as starting materials, the compound shown in Table 11 (55.9 mg) was obtained in the same manners as those of Example 126, (3) and Example 7, (4).

Example 515

By using the compound obtained in Example 126, (2) (80.0 mg) and the compound obtained in Reference Example 188 (87.7 mg) as starting materials, the compound shown in Table 11 (14.8 mg) was obtained in the same manners as those of Example 126, (3) and Example 7, (4).

Example 516

(1) N-(Naphthalen-1-yl)ethane-1,2-diamine hydrochloride (100 mg) was dissolved in distilled water (5 ml), the solution was added with potassium carbonate and thereby made basic, and then the mixture was extracted with chloroform. The organic layer was dried over anhydrous magnesium sulfate and filtered, and then the filtrate was concentrated under reduced pressure to obtain a desalted compound (40 mg).
(2) By using the compound obtained in Example 126, (2) (80.0 mg) and the desalted compound (40 mg) obtained in (1) mentioned above as starting materials, the compound shown in Table 11 (47.8 mg) was obtained in the same manners as those of Example 126, (3) and Example 7, (4).

Example 517

By using the compound obtained in Example 126, (2) (80.0 mg) and the compound obtained in Reference Example 189 (50.0 mg) as starting materials, the compound shown in Table 11 (41.2 mg) was obtained in the same manners as those of Example 126, (3) and Example 7, (4).

Example 518

(1) The amine compound (50 mg) obtained in Example 262, (2) of which steric configuration of the 4"-position was S was dissolved in dichloromethane (1 ml), the solution was added with acetic anhydride (6.0 µl) and pyridine (6.4 µl) under ice cooling, and the mixture was stirred for 1.5 hours under ice cooling. The reaction mixture was added with saturated brine and ethyl acetate, the layers were separated, and then the organic layer was dried over anhydrous sodium sulfate and filtered. The filtrate was concentrated under reduced pressure, and the resulting residue was purified by preparative thin layer chromatography (hexane:acetone:triethylamine=30:10:0.2) to obtain an acetyl compound (40.6 mg).
(2) By using the compound obtained in (1) mentioned above (40.6 mg) as a starting material, the compound shown in Table 11 (27.3 mg) was obtained in the same manner as that of Example 7, (4).

Example 519

(1) The amine compound (30 mg) obtained in Example 262, (2) of which steric configuration of the 4"-position was S was dissolved in chloroform (0.6 ml), the solution was added with 2-(t-butyldimethylsilyloxy)acetaldehyde (7.4 µml), sodium triacetoxyborohydride (10.1 mg) and acetic acid (1.8 µl), and the mixture was stirred at room temperature for 3 hours. The reaction mixture was added with saturated aqueous sodium hydrogencarbonate and ethyl acetate, the layers were separated, and then the organic layer was washed with saturated brine. The organic layer was dried over anhydrous sodium sulfate and filtered, then the filtrate was concentrated under reduced pressure, and the resulting residue was purified by preparative thin layer chromatography (hexane:acetone:triethylamine=40:10:0.2) to obtain an alkylamine compound (23.1 mg).

(2) By using the compound obtained in (1) mentioned above (23.1 mg) as a starting material, the compound shown in Table 11 (11.9 mg) was obtained in the same manner as that of Example 7, (4).

Example 520

(1) The amine compound obtained in Example 262, (2) (50 mg) of which steric configuration of the 4"-position was S was dissolved in dichloromethane (1 ml), the solution was added with methanesulfonyl chloride (6.1 μl) and triethylamine (14.7 μl) under ice cooling, and the mixture was stirred for 3 hours under ice cooling, and further stirred at room temperature for 4 hours. The reaction mixture was added with saturated brine and ethyl acetate, the layers were separated, and then the organic layer was dried over anhydrous sodium sulfate and filtered. The filtrate was concentrated under reduced pressure, and the resulting residue was purified by preparative thin layer chromatography (hexane:acetone:triethylamine=30:10:0.2) to obtain a sulfonamide compound (31.5 mg).

(2) By using the compound obtained in (1) mentioned above (31.5 mg) as a starting material, the compound shown in Table 11 (17.0 mg) was obtained in the same manner as that of Example 7, (4).

Example 521

(1) The amine compound obtained in Example 262, (2) (40 mg) of which steric configuration of the 4"-position was S was dissolved in tetrahydrofuran (0.4 ml), the solution was added with N,N'-carbonyldiimidazole (41.2 mg), and the mixture was stirred overnight at room temperature, and then further stirred at 40° C. for 3 hours. The reaction mixture was added with distilled water and ethyl acetate, the layers were separated, and then the organic layer was dried over anhydrous sodium sulfate and filtered. The filtrate was concentrated under reduced pressure, and the resulting residue was purified by preparative thin layer chromatography (hexane:acetone:triethylamine=30:10:0.2) to obtain an imidazolamide compound (17.3 mg).

(2) The compound obtained in (1) mentioned above (17.3 mg) was dissolved in tetrahydrofuran (0.1 ml), the solution was added with (1S)-1-(2-methoxyphenyl)ethanamine (7.4 mg) obtained by the method described in the patent document (Japanese Patent Unexamined Publication No. 54-154724), and the mixture was stirred overnight at room temperature. The reaction mixture was concentrated under reduced pressure, and the resulting residue was purified by preparative thin layer chromatography (hexane:acetone:triethylamine=30:10:0.2) to obtain a urea compound (8.7 mg).

(3) By using the compound obtained in (2) mentioned above (11.0 mg) as a starting material, the compound shown in Table 11 (7.5 mg) was obtained in the same manner as that of Example 7, (4).

Example 522

(1) The amine compound obtained in Example 262, (2) (38 mg) of which steric configuration of the 4"-position was S and the compound obtained in Reference Example 191 (33.9 mg) were dissolved in dichloromethane (760 μl), the solution was successively added with 4-dimethylaminopyridine (16.6 mg) and dicyclohexylcarbodiimide (16.6 mg), and the mixture was stirred at room temperature for 12 hours. The reaction mixture was added with saturated aqueous sodium hydrogencarbonate and ethyl acetate, the layers were separated, and the organic layer was dried over anhydrous magnesium sulfate and filtered. The filtrate was concentrated under reduced pressure, and the resulting residue was purified by silica gel column chromatography (NH-form, chloroform) to obtain an amide compound (44.7 mg).

(2) The compound obtained in (1) mentioned above (44.7 mg) was dissolved in dimethylformamide (894 μl), the solution was successively added with benzenethiol (16.9 μl) and potassium carbonate (22.9 mg), and the mixture was stirred at 60° C. for 30 minutes. The reaction mixture was added with saturated aqueous ammonium chloride and ethyl acetate, the layers were separated, the organic layer was concentrated under reduced pressure, and the resulting residue was purified by preparative thin layer chromatography (chloroform:methanol=10:1) to obtain a denitrobenzenesulfonylated compound (20.1 mg).

(3) By using the compound obtained in (2) mentioned above (20.1 mg) and acetaldehyde (4.87 μl) as starting materials, the compound shown in Table 11 (9.8 mg) was obtained in the same manners as those of Example 7, (2) and Example 7, (4).

Example 523

The amine compound obtained in Example 262, (2) (15.5 mg) of which steric configuration of the 4"-position was S was dissolved in dimethylformamide (100 μl), the solution was added with carbonyldiimidazole (3.02 mg), the mixture was stirred at room temperature for 1 hour, and then added with N,N-dimethylpropane-1,3-diamine (6 μl), and the mixture was stirred at room temperature for 1 hour. The reaction mixture was added with ethyl acetate and distilled water, the layers were separated, and the organic layer was dried over anhydrous magnesium sulfate and filtered. Then, the filtrate was concentrated under reduced pressure, and the resulting residue was purified by preparative thin layer chromatography (chloroform:methanol:28% aqueous ammonia=10:1:0.1) to obtain the compound shown in Table 11 (13.2 mg).

Example 524

(1) The amine compound obtained in Example 262, (2) (60 mg) of which steric configuration of the 4"-position was S was dissolved in chloroform (1.2 ml), the solution was added with the compound obtained in Reference Example 190 (30.9 mg), sodium triacetoxyborohydride (20.2 mg) and acetic acid (3.6 μl), and the mixture was stirred at room temperature for 2 hours. The reaction mixture was added with saturated aqueous sodium hydrogencarbonate and chloroform, the layers were separated, and then the organic layer was washed with saturated brine. The organic layer was dried over anhydrous sodium sulfate and filtered, then the filtrate was concentrated under reduced pressure, and the resulting residue was purified by silica gel column chromatography (chloroform:methanol:28% aqueous ammonia=50:1:0.1) to obtain an alkylamine compound (68.4 mg).

(2) By using the compound obtained in (1) mentioned above (40 mg) as a starting material, a denitrobenzenesulfonylated compound (20.0 mg) was obtained in the same manner as that of Example 522, (2).

(3) The compound obtained in (2) mentioned above (20.0 mg) was dissolved in chloroform (0.6 ml), the solution was added with acetaldehyde (1.18 µl) and sodium triacetoxyborohydride (5.5 mg) under ice cooling, and the mixture was stirred for 2 hours under ice cooling, and then at room temperature for 1.5 hours. The reaction mixture was added with saturated aqueous sodium hydrogencarbonate and chloroform, the layers were separated, and then the organic layer was washed with saturated brine. The organic layer was dried over anhydrous sodium sulfate and filtered, then the filtrate was concentrated under reduced pressure, and the resulting residue was purified by silica gel column chromatography (hexane:acetone:triethylamine=60:10:0.2) to obtain a mono-N-ethyl compound (14.0 mg).

(4) By using the compound obtained in (3) mentioned above (14.0 mg) as a starting material, the compound shown in Table 11 (7.0 mg) was obtained in the same manner as that of Example 7, (4).

Example 525

By using the compound obtained in Example 461, (1) (20 mg) and N,N-dimethylethylenediamine (7.7 µl) as starting materials, the compound shown in Table 11 (10 mg) was obtained in the same manners as those of Example 126, (3) and Example 7, (4).

Example 526

By using the compound obtained in Example 461, (1) (20 mg) and the compound obtained in Reference Example 67 (12 mg) as starting materials, the compound shown in Table 11 (11 mg) was obtained in the same manners as those of Example 126, (3) and Example 7, (4).

Example 527

By using the compound obtained in Example 461, (1) (20 mg) and the compound obtained in Reference Example 68 (20 mg) as starting materials, the compound shown in Table 11 (15 mg) was obtained in the same manners as those of Example 126, (3) and Example 7, (4).

Example 528

By using the compound obtained in Example 461, (1) (20 mg) and the compound obtained in Reference Example 69 (15 mg) as starting materials, the compound shown in Table 11 (13 mg) was obtained in the same manners as those of Example 126, (3) and Example 7, (4).

Example 529

By using the compound obtained in Example 461, (1) (17 mg) and the compound obtained in Reference Example 70 (17 mg) as starting materials, the compound shown in Table 11 (13.5 mg) was obtained in the same manners as those of Example 126, (3) and Example 7, (4).

Example 530

By using the compound obtained in Example 461, (1) (20 mg) and the compound obtained in Reference Example 71 (11 mg) as starting materials, the compound shown in Table 11 (14 mg) was obtained in the same manners as those of Example 126, (3) and Example 7, (4).

Example 531

The compound obtained in Reference Example 192 (31.1 mg) was dissolved in dichloromethane (622 µl), the solution was added with the Dess-Martin reagent (79.2 mg), and the mixture was stirred at room temperature for 1.5 hours. The reaction mixture was added with saturated aqueous sodium hydrogencarbonate and saturated aqueous sodium thiosulfate (1:1), the layers were separated, and the organic layer was concentrated under reduced pressure to obtain an aldehyde compound. By using the resulting aldehyde compound and the amine compound obtained in Example 262, (2) (30 mg) of which steric configuration of the 4"-position was S as starting materials, the compound shown in Table 11 (2.3 mg) was obtained in the same manners as those of Example 7, (2) and Example 7, (4).

Example 532

By using the compound obtained in Example 368, (1) (30 mg) and the compound obtained in Reference Example 71 (45 mg) as starting materials, the compound shown in Table 11 (33 mg) was obtained in the same manner as that of Example 168, (2).

Example 533

By using the compound obtained in Example 368, (1) (20 mg) and the compound obtained in Reference Example 70 (30 mg) as starting materials, the compound shown in Table 11 (20 mg) was obtained in the same manner as that of Example 168, (2).

Example 534

(1) The compound obtained in Example 461, (1) (60 mg) was dissolved in dimethylformamide (1.5 ml), the solution was added with the compound obtained in Reference Example 193 (20.1 mg) and sodium t-butoxide (1.7 mg), and the mixture was stirred at room temperature for 30 minutes. The reaction mixture was added with saturated aqueous ammonium chloride and ethyl acetate, the layers were separated, and then the organic layer was washed with distilled water. The organic layer was dried over anhydrous sodium sulfate and filtered, then the filtrate was concentrated under reduced pressure, and the resulting residue was purified by preparative thin layer chromatography (hexane:acetone:triethylamine=30:10:0.2) to obtain a carbamate compound (51.1 mg).

(2) By using the compound obtained in (1) mentioned above (51.1 mg) as a starting material, the compound shown in Table 11 (17.1 mg) was obtained in the same manner as that of Example 7, (4).

Example 535

The compound obtained in Example 412, (1) (23 mg) and (1S)-(2-methoxyphenyl)ethanamine (24 mg) obtained by the method described in the patent document (Japanese Patent Unexamined Publication No. 54-154724) were dissolved in ethanol (0.3 ml), the solution was added with potassium iodide (26 mg), and the mixture was stirred at 120° C. for 30 minutes under microwave irradiation. The reaction mixture was added with ethyl acetate, and the mixture was filtered.

Then, the filtrate was concentrated under reduced pressure, and the resulting residue was purified by preparative thin layer chromatography (hexane:acetone:28% aqueous ammonia=5:5:0.1) to obtain the compound shown in Table 11 (19 mg).

Example 536

By using the compound obtained in Example 412, (1) (23 mg) and 2-methoxybenzylamine (18 μl) as starting materials, the compound shown in Table 11 (10 mg) was obtained in the same manner as that of Example 535.

Example 537

By using the compound obtained in Example 412, (1) (21 mg) and benzylamine (16 μl) as starting materials, the compound shown in Table 11 (17 mg) was obtained in the same manner as that of Example 535.

Example 538

By using the compound obtained in Example 412, (1) (25 mg) and (1S,2S)-thiomicamine (36 mg) as starting materials, the compound shown in Table 11 (25 mg) was obtained in the same manner as that of Example 535.

Example 539

By using the compound obtained in Example 412, (1) (25 mg) and (1S,2S)-2-amino-1-(4-nitrophenyl)propane-1,3-diol (36 mg) as starting materials, the compound shown in Table 11 (23 mg) was obtained in the same manner as that of Example 535.

Example 540

By using the compound obtained in Example 412, (1) (25 mg) and (1S,2S)-2-amino-1-phenyl-1,3-propanediol (29 mg) as starting materials, the compound shown in Table 11 (26 mg) was obtained in the same manner as that of Example 535.

Example 541

By using the compound obtained in Example 412, (1) (25 mg) and (R)-2-amino-1-phenylethanol (23 mg) as starting materials, the compound shown in Table 11 (25 mg) was obtained in the same manner as that of Example 535.

Example 542

By using the compound obtained in Example 412, (1) (25 mg) and L-phenylalaninol (26 mg) as starting materials, the compound shown in Table 11 (23 mg) was obtained in the same manner as that of Example 535.

Example 543

(1) The compound obtained in Example 405, (1) (20 mg) and the compound obtained in Reference Example 194 (15 mg) were dissolved in dimethylformamide (0.1 ml), and the solution was stirred at 90° C. for 4 hours. The reaction mixture was added with distilled water and ethyl acetate, the layers were separated, and the organic layer was washed successively with distilled water and saturated brine, then dried over anhydrous sodium sulfate and filtered. The filtrate was concentrated under reduced pressure, and the resulting residue was purified by preparative thin layer chromatography (chloroform:methanol=15:1) to obtain a urea compound (22 mg).

(2) By using the compound obtained in (1) mentioned above (22 mg) as a starting material, the compound shown in Table 11 (15 mg) was obtained in the same manner as that of Example 7, (4).

Example 544

(1) By using the compound obtained in Example 405, (1) (28.2 mg) and the compound obtained in Reference Example 195 (12.7 mg) as starting materials, the compound shown in Table 11 (3.6 mg) was obtained in the same manners as those of Example 112, (2) and Example 7, (4).

Example 545

By using the amine compound obtained in Example 262, (2) (60 mg) of which steric configuration of the 4"-position was S and the compound obtained in Reference Example 196 (29.9 mg) as starting materials, the compound shown in Table 11 (7.5 mg) was obtained in the same manners as those of Example 524, (1), Example 522, (2), Example 524 (3) and Example 7, (4).

Example 546

By using the compound obtained in Example 412, (1) (20 mg) and the compound obtained in Reference Example 54, (2) (20 mg) as starting materials, the compound shown in Table 11 (8 mg) was obtained in the same manner as that of Example 535.

Example 547

By using the compound obtained in Example 412, (1) (23 mg) and 4-methoxyphenetylamine (21 μl) as starting materials, the compound shown in Table 11 (20 mg) was obtained in the same manner as that of Example 535.

Example 548

By using the compound obtained in Example 412, (1) (22 mg) and 2-methoxyphenetylamine (21 μl) as starting materials, the compound shown in Table 11 (17 mg) was obtained in the same manner as that of Example 535.

Example 549

By using the compound obtained in Example 412, (1) (23 mg) and phenetylamine (20 μl) as starting materials, the compound shown in Table 11 (19 mg) was obtained in the same manner as that of Example 535.

Example 550

By using the compound obtained in Example 412, (1) (29 mg) and the compound obtained in Reference Example 197 (36 mg) as starting materials, the compound shown in Table 11 (30 mg) was obtained in the same manner as that of Example 535.

Example 551

By using the compound obtained in Example 412, (1) (28 mg) and the compound obtained in Reference Example 198 (24 mg) as starting materials, the compound shown in Table 11 (31 mg) was obtained in the same manner as that of Example 535.

Syntheses of Examples 552 to 558

Preparation methods of compounds represented by the formula (X) having R defined in Table 12 are shown below.

TABLE 12 formula (X)

| Example | R | ESI MS (M + H) | $^1$H—NMR, CDCl$_3$, δ (ppm) |
|---|---|---|---|
| 552 | (2,3,4-trimethoxyphenyl)acetate | 769 | (300 MHz): 0.84-0.91 (m, 9H) 1.00 (d, J = 6.9 Hz, 3H) 1.09-1.15 (m, 4H) 1.19 (d, J = 6.0 Hz, 1H) 1.26 (s, 3H) 1.51-1.60 (m, 4H) 1.92 (m, 1H) 2.22-2.30 (m, 8H) 2.38 (s, 3H) 2.47-2.52 (m, 3H) 2.83 (m, 1H) 3.02 (d, J = 14.1 Hz, 1H) 3.18-3.23 (m, 5H) 3.35 (m, 1H) 3.61 (d, J = 16.4 Hz, 1H) 3.71 (d, J = 16.4 Hz, 1H) 3.82-3.93 (m, 10H) 4.09 (m, 1H) 4.72 (m, 1H) 5.26 (m, 1H) 6.62 (d, J = 8.7 Hz, 1H), 6.92 (d, J = 8.7 Hz, 1H) |
| 553 | (4-cyanophenyl)acetate | 704 | (300 MHz): 0.83-0.94 (m, 12H) 1.08 (d, J = 7.2 Hz, 3H) 1.18 (d, J = 6.0 Hz, 3H) 1.22-1.30 (m, 4H) 1.50-1.60 (m, 4H) 1.91 (m, 1H) 2.17-2.28 (m, 8H) 2.38 (s, 3H) 2.44-2.52 (m, 3H) 2.83 (q, J = 7.2 Hz, 1H) 3.02 (d, J = 14.4 Hz, 1H) 3.15-3.27 (m, 6H) 3.70-3.76 (m, 3H) 3.81 (d, J = 3.9 Hz, 1H) 4.02 (m, 1H) 4.69 (m, 1H) 7.46 (d, J = 8.1 Hz, 2H), 7.62 (d, J = 8.1 Hz, 2H) |
| 554 | (3-cyanophenyl)acetate | 704 FAB MASS | (400 MHz): 0.84-0.91 (m, 9H) 0.96 (d, J = 6.8 Hz, 3H) 1.09 (d, J = 7.3 Hz, 3H) 1.19 (d, J = 6.1 Hz, 3H) 1.23-1.27 (m, 4H) 1.53-1.67 (m, 4H) 1.91 (m, 1H) 2.15-2.25 (m, 2H) 2.32 (s, 6H) 2.39 (s, 3H) 2.42-2.50 (m, 3H) 2.85 (t, J = 7.8 Hz, 1H) 3.04 (d, J = 14.6 Hz, 1H) 3.17-3.28 (m, 6H) 3.70-3.78 (m, 3H) 3.83 (d, J = 4.1 Hz, 1H) 4.07 (m, 1H) 4.69 (m, 1H) 5.36 (m, 1H) 7.45 (dd, J = 7.8 Hz, J = 7.8 Hz, 1H) 7.57-7.60 (m, 2H) 7.64 (s, 1H) |
| 555 | (3-methylsulfonylphenyl)acetate | 757 FAB MASS | (400 MHz): 0.84-0.90 (m, 9H) 0.96 (d, J = 6.8 Hz, 3H) 1.06 (d, J = 6.8 Hz, 3H) 1.19 (d, J = 6.1 Hz, 3H) 1.23-1.27 (m, 4H) 1.51-1.68 (m, 4H) 1.89-1.92 (m, 1H) 2.19-2.25 (m, 2H) 2.30 (s, 6H) 2.38-2.51 (m, 6H) 2.81-2.87 (m, 1H) 3.03-3.07 (m, 4H) 3.17-3.23 (m, 5H) 3.28-3.29 (m, 1H) 3.81-3.84 (m, 4H) 4.05-4.07 (m, 1H) 4.70 (m, 1H) 5.35 (m, 1H) 7.55 (dd, J = 7.7 Hz, J = 7.7 Hz, 1H) 7.62 (d, J = 7.7 Hz, 1H), 7.87 (d, J = 7.7 Hz, 1H) 7.93 (s, 1H) |
| 556 | (2-aminophenyl)acetate | 694 | (300 MHz): 0.82-0.95 (m, 12H) 1.07-1.27 (m, 2H) 1.11 (d, J = 7.15 Hz, 3H) 1.14 (d, J = 5.76 Hz, 3H) 1.25 (s, 3H) 1.45-1.95 (m, 4H) 2.10-2.39 (m, 3H) 2.27 (s, 6H) 2.38 (s, 3H) 2.43-2.59 (m, 2H) 2.76-2.89 (m, 1H) 2.93-3.08 (m, 2H) 3.14 (dd, J = 2.75, 9.89 Hz, 2H) 3.20 (s, 3H) 3.60 (d, J = 14.01 Hz, 1H) 3.68 (d, J = 14.01 Hz, 1H) 4.64-4.79 (m, 1H) 5.15-5.33 (m, 1H) 6.69-6.75 (m, 2H) 7.04-7.13 (m, 2H) |
| 557 | (3-aminophenyl)acetate | 694 | (300 MHz): 0.82-1.02 (m, 12H) 1.05-1.27 (m, 2H) 1.09 (d, J = 7.14 Hz, 3H) 1.16 (d, J = 6.32 Hz, 3H) 1.25 (s, 3H) 1.40-2.58 (m, 9H) 2.33 (s, 6H) 2.39 (s, 3H) 2.72-2.86 (m, 1H) 2.96-3.23 (m, 4H) 3.20 (s, 3H) 3.59 (s, 2H) 3.87 (d, J = 4.12 Hz, 1H) 3.94-4.06 (m, 1H) 4.63-4.78 (m, 1H) 5.23-5.31 (m, 1H) 6.55-6.61 (m, 1H) 6.69 (d, J = 7.42 Hz, 1H) 6.71 (s, 1H) 7.09 (t, J = 7.69 Hz, 1H) |
| 558 | (4-aminophenyl)acetate | 694 | (300 MHz): 0.82-0.97 (m, 12H) 1.16-1.27 (m, 2H) 1.09 (d, J = 7.42 Hz, 3H) 1.16 (d, J = 6.32 Hz, 3H) 1.25 (s, 3H) 1.45-1.98 (m, 4H) 2.11-2.58 (m, 5H) 2.30 (s, 6H) 2.38 (s, 3H) 2.75-2.87 (m, 1H) 2.96-3.22 (m, 4H) 3.21 (s, 3H) 3.54 (d, J = 15.39 Hz, 1H) 3.59 (d, J = 15.11 Hz, 1H) 3.85 (d, J = 4.12 Hz, 1H) 3.96 (d, J = 6.60 Hz, 1H) 4.66-4.79 (m, 1H) 5.12-5.31 (m, 1H) 6.62-6.66 (m, 2H) 7.12 (d, J = 8.52 Hz, 2H) |

Example 552

By using the compound obtained in Example 112, (1) (50 mg) and 2,3,4-trimethoxyphenylacetic acid (47 mg) as starting materials, the compound shown in Table 12 (2.5 mg) was obtained in the same manners as those of Example 112, (2) and Example 7, (4).

Example 553

By using the compound obtained in Example 112, (1) (50 mg) and 4-cyanophenylacetic acid (34 mg) as starting materials, the compound shown in Table 12 (2.6 mg) was obtained in the same manners as those of Example 112, (2) and Example 7, (4).

Example 554

(1) The compound obtained in Example 112, (1) (50 mg) was dissolved in dichloromethane (0.5 ml), the solution was added with 3-cyanophenylacetic acid (68 mg), dicyclohexylcarbodiimide (86 mg) and 4-dimethylaminopyridine (17.0 mg), and the mixture was stirred at room temperature for 3 days. The reaction mixture was added with saturated aqueous ammonium chloride and chloroform, the layers were separated, and then the organic layer was filtered by using a phase separator. The filtrate was washed with saturated aqueous sodium hydrogencarbonate, and filtered by using a phase separator, and then the filtrate was concentrated under reduced pressure, the residue was added with methanol, and the mixture was stirred at room temperature for 1 day. The reaction mixture was concentrated under reduced pressure, and the resulting residue was purified by preparative thin layer chromatography (chloroform:methanol:28% aqueous ammonia=15:1:0.1) to obtain an acyl compound (18.5 mg).

(2) By using the compound obtained in (1) mentioned above (18.5 mg) as a starting material, the compound shown in Table 12 (8.0 mg) was obtained in the same manner as that of Example 7, (4).

Example 555

By using the compound obtained in Example 112, (1) (50 mg) and 3-methanesulfonylphenylacetic acid (90 mg) as starting materials, the compound shown in Table 12 (15.4 mg) was obtained in the same manners as those of Example 554, (1) and Example 7, (4).

Example 556

(1) The compound obtained in Example 112, (1) (50 mg) was dissolved in dimethylformamide (1.0 ml), the solution was added with dicyclohexylcarbodiimide (120 mg), 4-dimethylaminopyridine (26.1 mg) and 2-(2-nitrophenyl)acetic acid (114 mg), and the mixture was stirred at room temperature for 3 days. The reaction mixture was added with saturated aqueous ammonium chloride and ethyl acetate, the layers were separated, and the organic layer was dried over anhydrous magnesium sulfate, and then filtered. The filtrate was concentrated under reduced pressure, and the resulting residue was added with methanol (5 ml). The mixture was stirred at room temperature for 24 hours, and then concentrated under reduced pressure, and the resulting residue was purified by preparative thin layer chromatography (chloroform:methanol:28% aqueous ammonia=10:1:0.1) to obtain a condensed compound (41 mg).

(2) By using the compound obtained in (1) mentioned above (41 mg) as a starting material, a detriethylsilylated compound (15.4 mg) was obtained in the same manner as that of Example 7, (4).

(3) The compound obtained in (2) mentioned above (15.4 mg) was dissolved in methanol-ethyl acetate (1:1, 2.0 ml), the solution was added with 10% palladium-carbon (3 mg), and the mixture was stirred at room temperature for 4 hours under a hydrogen atmosphere of 1 atm. The reaction mixture was filtered through Celite, then the filtrate was concentrated under reduced pressure, and the resulting residue was purified by preparative thin layer chromatography (chloroform:methanol:28% aqueous ammonia=10:1:0.1) to obtain the compound shown in Table 12 (7.3 mg).

Example 557

By using the compound obtained in Example 112, (1) (50 mg) and 2-(3-nitrophenyl)acetic acid (114 mg) as starting materials, the compound shown in Table 12 (1.5 mg) was obtained in the same manners as those of Example 556, (1), Example 7, (4) and Example 556 (3).

Example 558

By using the compound obtained in Example 112, (1) (50 mg) and 2-(4-nitrophenyl)acetic acid (114 mg) as starting materials, the compound shown in Table 12 (4.8 mg) was obtained in the same manners as those of Example 556, (1) Example 7, (4) and Example 556, (3).

Example 559

Synthesis of the Compound Represented by the Formula (Y)

[Formula 31]

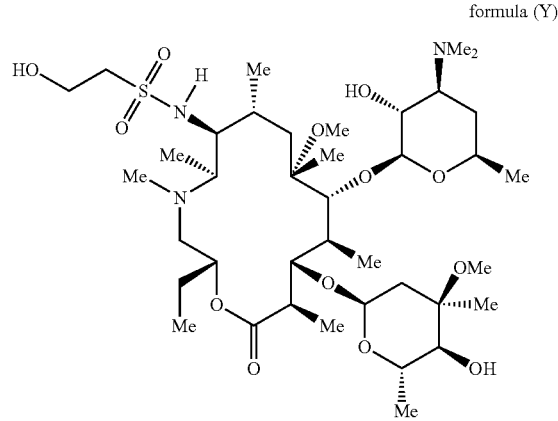

formula (Y)

By using the compound obtained in Example 195 (8 mg) and 2-chloroethanesulfonyl chloride (2 μl) as starting materials, the title compound (8 mg) was obtained in the same manner as that of Example 196.

Syntheses of Examples 560 to 562

Preparation methods of compounds represented by the formula (Z) having R defined in Table 13 are shown below.

TABLE 13 formula (Z)

[Structure of formula (Z) shown]

| Example | R | ESI MS (M + H) | $^1$H—NMR, CDCl$_3$, δ (ppm) |
|---|---|---|---|
| 560 | Me-CH$_2$-C(=CH$_2$)- (3-methyl-2-butenyl type) | 786.5 | (500 MHz): 0.87 (t, J = 7.54 Hz, 3H) 1.06 (d, J = 6.86 Hz, 3H) 1.08 (d, J = 7.68 Hz, 3H) 1.11 (d, J = 6.86 Hz, 3H) 1.16 (d, J = 7.13 Hz, 3H) 1.21 (d, J = 6.31 Hz, 3H) 1.23 (s, 3H) 1.23-1.25 (m, 4H) 1.28 (s, 3H) 1.50-1.67 (m, 5H) 1.73 (s, 3H) 1.92-2.00 (m, 1H) 2.01-2.08 (m, 1H) 2.13 (s, 3H) 2.15 (d, J = 10.42 Hz, 1H) 2.28 (s, 6H) 2.38 (d, J = 15.08 Hz, 1H) 2.42-2.50 (m, 1H) 2.51-2.59 (m, 1H) 2.68-2.75 (m, 2H) 3.00 (t, J = 9.87 Hz, 1H) 3.20 (s, 3H) 3.25-3.32 (m, 1H) 3.32 (s, 3H) 3.38-3.45 (m, 1H) 3.47-3.57 (m, 2H) 3.67 (d, J = 6.86 Hz, 1H) 3.88 (d, J = 4.11 Hz, 1H) 3.97-4.04 (m, 1H) 4.41 (s, 2H) 4.47 (d, J = 7.40 Hz, 1H) 4.80 (br. s., 1H) 4.84 (s, 1H) 4.89 (d, J = 4.66 Hz, 1H) 4.94 (s, 1H) |
| 561 | Me- (methyl) | 746.4 | (500 MHz): 0.88 (t, J = 7.40 Hz, 3H) 1.06 (d, J = 6.86 Hz, 3H) 1.07-1.09 (m, 3) 1.08-1.11 (m, 3H) 1.16 (d, J = 7.13 Hz, 3H) 1.19-1.30 (m, 10H) 1.27 (s, 3H) 1.48-1.68 (m, 5H) 1.89 (d, J = 14.81 Hz, 1H) 1.99-2.06 (m, 1H) 2.11 (s, 3H) 2.14 (d, J = 10.42 Hz, 1H) 2.28 (s, 6H) 2.38 (d, J = 15.36 Hz, 1H) 2.43-2.51 (m, 1H) 2.54-2.61 (m, 1H) 2.67-2.75 (m, 2H) 2.97-3.03 (m, 1H) 3.21 (s, 3H) 3.28-3.32 (m, 1H) 3.33 (s, 3H) 3.38-3.45 (m, 1H) 3.47-3.56 (m, 2H) 3.67 (d, J = 6.86 Hz, 1H) 3.78 (s, 3H) 3.86-3.91 (m, 1H) 4.01 (d, 1H) 4.47 (d, J = 7.40 Hz, 1H) 4.79-4.86 (m, 1H) 4.89 (d, J = 4.66 Hz, 1H) |
| 562 | Me-O-CH$_2$- (methoxymethyl) | 776.4 | (500 MHz): 0.87 (t, J = 7.54 Hz, 3H) 1.08 (dd, J = 6.99, 3.70 Hz, 6H) 1.12 (d, J = 6.86 Hz, 3H) 1.16 (d, J = 7.13 Hz, 3H) 1.18-1.27 (m, 1H) 1.21 (d, J = 6.03 Hz, 3H) 1.23 (s, 3H) 1.24 (d, J = 6.31 Hz, 3H) 1.30 (s, 3H) 1.47-1.67 (m, 5H) 1.99-2.06 (m, 1H) 2.06-2.12 (m, 1H) 2.14-2.17 (m, 1H) 2.17 (s, 3H) 2.28 (s, 6H) 2.35-2.40 (m, 1H) 2.41-2.49 (m, 1H) 2.49-2.56 (m, 1H) 2.65-2.80 (m, 2H) 3.00 (t, J = 9.87 Hz, 1H) 3.22 (s, 3H) 3.25-3.31 (m, 1H) 3.32 (s, 3H) 3.41 (s, 3H) 3.41-3.46 (m, 1H) 3.47-3.56 (m, 2H) 3.67 (d, J = 7.13 Hz, 1H) 3.85-3.90 (m, 1H) 3.97-4.05 (m, 1H) 4.46 (d, J = 7.13 Hz, 1H) 4.78 (br. s., 1H) 4.89 (d, J = 4.39 Hz, 1H) 5.03-5.10 (m, 2H) |

Example 560

The compound obtained in Example 214 (101 mg) was dissolved in tetrahydrofuran (6 ml), the solution was added with 3-chloro-2-methyl-1-propene (41 μl), potassium hydroxide (77.4 mg) and 18-crown-6-ether (365 mg), and the mixture was stirred at room temperature 15 minutes. The reaction mixture was added with saturated brine and chloroform, the layers were separated, and the organic layer was dried over anhydrous magnesium sulfate and filtered. The filtrate was concentrated under reduced pressure, and the resulting residue was purified by silica gel column chromatography (chloroform:methanol=9:1 to chloroform:methanol:28% aqueous ammonia=10:1:0.1) and preparative thin layer chromatography (chloroform:methanol:28% aqueous ammonia=10:1:0.1) to obtain the compound shown in Table 13 (33.8 mg).

Example 561

The compound obtained in Example 214 (104 mg) was dissolved in tetrahydrofuran (6 ml), the solution was added with methyl iodide (9 μl) and potassium hydroxide (23.9 mg), and the mixture was stirred at room temperature for 40 minutes. The reaction mixture was added with saturated brine and chloroform, the layers were separated, and the organic layer was dried over anhydrous magnesium sulfate and filtered. The filtrate was concentrated under reduced pressure, and the resulting residue was purified by preparative thin layer chromatography (chloroform:methanol:28% aqueous ammonia=10:1:0.1) to obtain the compound shown in Table 13 (62.8 mg).

Example 562

By using the compound obtained in Example 214 (104 mg) and chloromethyl methyl ether (32.4 μl) as starting materials, the compound shown in Table 13 (44.0 mg) was obtained in the same manner as that of Example 560.

Syntheses of Examples 563 to 566

Preparation methods of compounds represented by the formula (AA) having R defined in Table 14 are shown below.

TABLE 14 formula (AA)

[Structure of formula (AA) shown]

| Example | R | ESI MS (M + H) | $^1$H—NMR, CDCl$_3$, δ (ppm) |
|---|---|---|---|
| 563 | [Me-O-C(=O)-CH=CH-CH$_2$-CH(wavy)- structure] | 803.5 | (600 MHz): 0.73-0.84 (m, 6H) 0.88 (t, J = 7.34 Hz, 3H) 1.08 (d, J = 7.34 Hz, 3H) 1.10-1.14 (m, 1H) 1.16 (d, J = 7.79 Hz, 3H) 1.19-1.23 (m, 6H) 1.23-1.26 (m, 1H) 1.28 (d, J = 5.96 Hz, 3H) 1.32 (s, 3H) 1.44-1.50 (m, 1H) 1.53 (dd, J = 15.13, 5.04 Hz, 1H) 1.63-1.86 (m, 3H) 2.20-2.33 (m, 9H) 2.35 (d, J = 15.13 Hz, 1H) 2.46-2.56 (m, 2H) 2.76-2.85 (m, 1H) 2.94-3.02 (m, 2H) 3.17-3.25 (m, 2H) 3.21 (s, 3H) 3.31 (s, 3H) 3.37-3.58 (m, 3H) 3.69 (d, J = 7.79 Hz, 1H) 3.72 (s, 3H) 4.01-4.08 (m, 1H) 4.09-4.20 (m, 1H) 4.36 (d, J = 6.88 Hz, 1H) 4.56-4.68 (m, 1H) 4.93 (d, J = 4.58 Hz, 1H) 5.98 (d, J = 16.05 Hz, 1H) 6.87-6.95 (m, 1H) |
| 564 | [N≡C-C$_6$H$_4$-CH$_2$- (4-cyanobenzyl wavy) structure] | 820.5 | (600 MHz): 0.51-0.65 (m, 3H) 0.74-0.84 (m, 6H) 0.99-1.03 (m, 1H) 1.04 (d, J = 7.34 Hz, 3H) 1.12 (d, J = 7.34 Hz, 3H) 1.15 (d, J = 5.96 Hz, 3H) 1.17 (s, 3H) 1.17-1.19 (m, 1H) 1.23 (d, J = 5.96 Hz, 3H) 1.26 (s, 3H) 1.34-1.44 (m, 2H) 1.48 (dd, J = 15.36, 4.81 Hz, 1H) 1.56-1.66 (m, 2H) 1.68-1.81 (m, 1H) 2.07-2.18 (m, 1H) 2.23 (s, 6H) 2.25-2.27 (m, 1H) 2.30 (d, J = 15.13 Hz, 1H) 2.33-2.46 (m, 3H) 2.73-2.80 (m, 1H) 2.91-2.99 (m, 2H) 3.09-3.15 (m, 1H) 3.17 (s, 3H) 3.26 (s, 3H) 3.36-3.43 (m, 1H) 3.49-3.55 (m, 1H) 3.65 (d, J = 7.79 Hz, 1H) 3.70 (s, 2H) 3.96-4.02 (m, 1H) 4.08-4.13 (m, 1H) 4.30 (d, J = 7.34 Hz, 1H) 4.58-4.67 (m, 1H) 4.89 (d, J = 4.59 Hz, 1H) 7.44 (d, J = 8.25 Hz, 2H) 7.53 (d, J = 8.25 Hz, 2H) |
| 565 | [wavy-CH$_2$-C$_6$H$_4$-CH$_2$-C(=O)-O-Me structure] | 867.5 | (600 MHz): 0.50-0.59 (m, 3H) 0.71-0.77 (m, 3H) 0.78-0.85 (m, 3H) 0.94-1.00 (m, 1H) 1.03 (d, J = 7.34 Hz, 3H) 1.12 (d, J = 7.79 Hz, 3H) 1.13-1.19 (m, 9H) 1.20-1.31 (m, 2H) 1.23 Cd, J = 6.42 Hz, 3H) 1.25 (s, 2H) 1.41-1.82 (m, 3H) 1.99-2.59 (m, 7H) 2.23 (s, 6H) 2.30 (d, J = 15.13 Hz, 1H) 2.74-2.83 (m, 1H) 2.93-2.98 (m, 2H) 3.09-3.15 (m, 1H) 3.16 (s, 3H) 3.26 (s, 3H) 3.36-3.44 (m, 1H) 3.45-3.52 (m, 1H) 3.53 (s, 2H) 3.61 (s, 3H) 3.62-3.71 (m, 3H) 3.95-4.03 (m, 1H) 4.11-4.16 (m, 1H) 4.30 (d, J = 6.88 Hz, 1H) 4.56-4.62 (m, 1H) 4.90 (d, J = 4.59 Hz, 1H) 7.15 (d, J = 7.79 Hz, 1H) 7.25 (d, J = 7.79 Hz, 2H) |
| 566 | [HO-C(=O)-CH=CH-CH$_2$-CH(wavy)- structure] | 789.5 | (600 MHz): 0.75-0.83 (m, 6H) 0.84-0.91 (m, 3H) 1.03-1.13 (m, 6H) 1.16 (d, J = 7.34 Hz, 3H) 1.20-1.36 (m, 9H) 1.45-2.17 (m, 5H) 1.53 (dd, J = 14.90, 4.81 Hz, 1H) 2.23-2.43 (m, 4H) 2.45-2.72 (m, 8H) 2.77-2.91 (m, 2H) 2.95-2.99 (m, 1H) 3.00 (d, J = 9.63 Hz, 1H) 3.16-3.19 (m, 1H) 3.22 (s, 3H) 3.31 (s, 3H) 3.34-3.48 (m, 3H) 3.45-3.55 (m, 1H) 3.69 (d, J = 8.25 Hz, 1H) 3.99-4.07 (m, 1H) 4.08-4.17 (m, 1H) 4.41 (d, J = 6.88 Hz, 1H) 4.56-4.69 (m, 1H) 4.92 (d, J = 4.58 Hz, 1H) 5.93-6.04 (m, 1H) 6.79-6.91 (m, 1H) |

Example 563

(1) The compound obtained in Example 245, (2) (200 mg) was dissolved in dimethylformamide (3.8 ml), the solution was added with methyl 4-bromocrotonate (265 µl) and potassium carbonate (260 mg), and the mixture was stirred at room temperature for 16 hours. The reaction mixture was added with distilled water and diethyl ether, and the layers were separated. The organic layer was washed with saturated brine, then dried over anhydrous magnesium sulfate and filtered. The filtrate was concentrated under reduced pressure, and the resulting residue was purified by silica gel column chromatography (chloroform to hexane: acetone:triethylamine=10:10:0.2) to obtain an N-alkyl compound (70 mg).

(2) By using the compound obtained in (1) mentioned above (70 mg) as a starting material, the compound shown in Table 14 (49 mg) was obtained in the same manner as that of Example 7, (4).

Example 564

By using the compound obtained in Example 245, (2) (200 mg) and 4-cyanobenzyl bromide (370 mg) as starting materials, the compound shown in Table 14 (53 mg) was obtained in the same manners as those of Example 563, (1) and Example 7, (4).

Example 565

By using the compound obtained in Example 245, (2) (200 mg) and 4-(bromomethyl)phenylacetic acid methyl ester (460 mg) as starting materials, the compound shown in Table 14 (14 mg) was obtained in the same manners as those of Example 563, (1) and Example 7, (4).

Example 566

The compound obtained in Example 563, (2) (27 mg) was dissolved in a mixed solvent of tetrahydrofuran-methanol-distilled water (3:1:1, 1 ml), the solution was added with lithium hydroxide monohydrate (7 mg), and the mixture was stirred at room temperature for 4 hours. The mixture was further added with lithium hydroxide monohydrate (7 mg), and the mixture was stirred at room temperature for 14 hours. The reaction mixture was added with chloroform and saturated aqueous ammonium chloride, the layers were separated, and the organic layer was dried over anhydrous magnesium sulfate and filtered. The filtrate was concentrated under reduced pressure, and the resulting residue was purified by preparative thin layer chromatography (chloroform:methanol:28% aqueous ammonia=3:1:0.1) to obtain the compound shown in Table 14 (3 mg).

Syntheses of Examples 567 to 663

Preparation methods of compounds represented by the formula (AB) having R defined in Table 15 are shown below.

TABLE 15 formula (AB)

| Example | R | ESI MS (M + H) | $^1$H—NMR, CDCl$_3$, δ (ppm) |
|---|---|---|---|
| 567 | (benzamide-propyl) | 852.6 | (500 MHz): 0.78-0.86 (m, 6H) 1.08 (d, J = 7.40 Hz, 3H) 1.11-1.25 (m, 2H) 1.15 (d, J = 7.40 Hz, 3H) 1.21 (d, J = 6.03 Hz, 3H) 1.22 (s, 3H) 1.27 (d, J = 6.31 Hz, 3H) 1.31 (s, 3H) 1.53 (dd, J = 15.22, 4.80 Hz, 1H) 1.55-1.68 (m, 4H) 1.79-1.89 (m, 2H) 2.22-2.31 (m, 4H) 2.27 (s, 6H) 2.32-2.37 (m, 1H) 2.35 (s, 3H) 2.41-2.50 (m, 2H) 2.74-2.83 (m, 1H) 2.88-2.94 (m, 1H) 3.00 (t, J = 9.32 Hz, 1H) 3.16-3.22 (m, 1H) 3.23 (s, 3H) 3.31 (s, 3H) 3.36-3.56 (m, 4H) 3.69 (d, J = 7.95 Hz, 1H) 3.98-4.08 (m, 1H) 4.07-4.16 (m, 1H) 4.39 (d, J = 7.13 Hz, 1H) 4.69-4.82 (m, 1H) 4.91 (d, J = 4.39 Hz, 1H) 6.36 (br. s., 1H) 7.39-7.44 (m, 2H) 7.45-7.50 (m, 1H) 7.71-7.78 (m, 2H) |
| 568 | (nicotinamide-propyl) | 853.6 | (500 MHz): 0.79-0.87 (m, 6H) 1.08 (d, J = 7.40 Hz, 3H) 1.11-1.26 (m, 2H) 1.15 (d, J = 7.40 Hz, 3H) 1.21 (d, J = 6.03 Hz, 3H) 1.22 (s, 3H) 1.27 (d, J = 6.31 Hz, 3H) 1.31 (s, 3H) 1.50-1.57 (m, 1H) 1.56-1.71 (m, 4H) 1.76-1.93 (m, 2H) 2.15-2.29 (m, 4H) 2.27 (s, 6H) 2.32-2.38 (m, 1H) 2.35 (s, 3H) 2.41-2.52 (m, 2H) 2.76-2.83 (m, 1H) 2.88-2.95 (m, 1H) 3.00 (t, J = 9.74 Hz, 1H) 3.20 (dd, J = 10.28, 7.27 Hz, 1H) 3.23 (s, 3H) 3.26-3.29 (m, 1H) 3.31 (s, 3H) 3.34-3.51 (m, 2H) 3.51-3.60 (m, 1H) 3.69 (d, J = 7.95 Hz, 1H) 4.00-4.07 (m, 1H) 4.07-4.14 (m, 1H) 4.39 (d, J = 7.40 Hz, 1H) 4.75-4.85 (m, 1H) 4.90 (d, J = 4.66 Hz, 1H) 6.58 (br. s., 1H) 7.34-7.40 (m, 1H) 8.07-8.15 (m, 1H) 8.70 (dd, J = 4.94, 1.65 Hz, 1H) 8.97 (d, J = 1.65 Hz, 1H) |

TABLE 15-continued formula (AB)

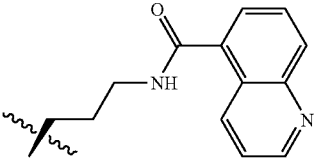

| Example | R | ESI MS (M + H) | $^1$H—NMR, CDCl$_3$, δ (ppm) |
|---|---|---|---|
| 569 | 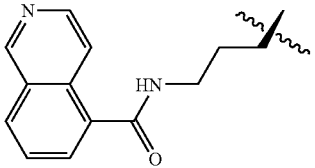 | 903.7 | (500 MHz): 0.75-0.90 (m, 6H) 1.08 (d, J = 7.65 Hz, 3H) 1.14 (d, J = 7.65 Hz, 3H) 1.16-1.28 (m, 2H) 1.20-1.23 (m, 3H) 1.22 (s, 3H) 1.28 (d, J = 6.12 Hz, 3H) 1.31 (s, 3H) 1.52 (dd, J = 15.29, 4.59 Hz, 1H) 1.58-1.91 (m, 6H) 2.13-2.30 (m, 4H) 2.28 (s, 6H) 2.33 (d, J = 15.29 Hz, 1H) 2.38 (s, 3H) 2.41-2.51 (m, 2H) 2.73-2.85 (m, 1H) 2.91-2.97 (m, 1H) 3.00 (t, J = 9.56 Hz, 1H) 3.16-3.21 (m, 1H) 3.22 (s, 3H) 3.30 (s, 3H) 3.34-3.43 (m, 1H) 3.43-3.49 (m, 1H) 3.49-3.64 (m, 2H) 3.69 (d, J = 8.41 Hz, 1H) 4.01-4.08 (m, 1H) 4.08-4.15 (m, 1H) 4.39 (d, J = 6.88 Hz, 1H) 4.74-4.85 (m, 1H) 4.90 (d, J = 4.59 Hz, 1H) 6.28 (br. s., 1H) 7.46 (dd, J = 8.79, 4.20 Hz, 1H) 7.62-7.71 (m, 2H) 8.13-8.19 (m, 1H) 8.74 (d, J = 8.41 Hz, 1H) 8.92-8.96 (m, 1H) |
| 570 | 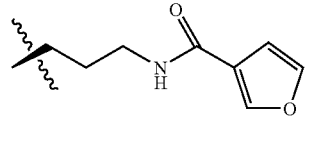 | 903.7 | (500 MHz): 0.75-0.86 (m, 6H) 1.07 (d, J = 6.88 Hz, 3H) 1.10-1.26 (m, 2H) 1.14 (d, J = 7.65 Hz, 3H) 1.17-1.24 (m, 6H) 1.28 (d, J = 6.12 Hz, 3H) 1.31 (s, 3H) 1.52 (dd, J = 15.29, 4.59 Hz, 1H) 1.60-1.74 (m, 4H) 1.78-1.90 (m, 2H) 2.16-2.30 (m, 4H) 2.28 (s, 6H) 2.33 (d, J = 14.53 Hz, 1H) 2.38 (s, 3H) 2.42-2.52 (m, 2H) 2.75-2.84 (m, 1H) 2.91-3.03 (m, 2H) 3.14-3.21 (m, 1H) 3.22 (s, 3H) 3.30 (s, 3H) 3.33-3.41 (m, 1H) 3.43-3.49 (m, 1H) 3.49-3.64 (m, 2H) 3.69 (d, J = 8.41 Hz, 1H) 3.98-4.08 (m, 1H) 4.08-4.16 (m, 1H) 4.38 (d, J = 7.65 Hz, 1H) 4.76-4.85 (m, 1H) 4.89 (d, J = 4.59 Hz, 1H) 6.22-6.37 (m, 1H) 7.56-7.62 (m, 1H) 7.83 (d, J = 6.88 Hz, 1H) 8.04 (d, J = 8.41 Hz, 1H) 8.15 (d, J = 6.12 Hz, 1H) 8.57 (d, J = 6.12 Hz, 1H) 9.26 (s, 1H) |
| 571 | 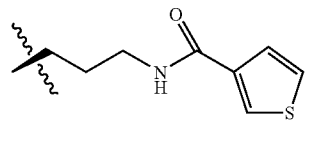 | 842.6 | (500 MHz): 0.78-0.88 (m, 6H) 1.09 (d, J = 6.88 Hz, 3H) 1.16 (d, J = 7.65 Hz, 3H) 1.15-1.26 (m, 2H) 1.21 (d, J = 6.12 Hz, 3H) 1.23 (s, 3H) 1.28 (d, J = 6.12 Hz, 3H) 1.31 (s, 3H) 1.47-1.67 (m, 5H) 1.72-1.83 (m, 1H) 1.83-1.90 (m, 1H) 2.13-2.31 (m, 4H) 2.28 (s, 6H) 2.35 (s, 3H) 2.35-2.39 (m, 1H) 2.41-2.51 (m, 2H) 2.75-2.83 (m, 1H) 2.88-2.95 (m, 1H) 2.97-3.03 (m, 1H) 3.16-3.23 (m, 1H) 3.24 (s, 3H) 3.32 (s, 3H) 3.33-3.40 (m, 2H) 3.43-3.52 (m, 2H) 3.70 (d, J = 7.65 Hz, 1H) 4.00-4.08 (m, 1H) 4.08-4.17 (m, 1H) 4.40 (d, J = 7.65 Hz, 1H) 4.73-4.84 (m, 1H) 4.91 (d, J = 4.59 Hz, 1H) 6.12 (br. s., 1H) 6.64 (s, 1H) 7.39-7.44 (m, 1H) 7.94 (s, 1H) |
| 572 | 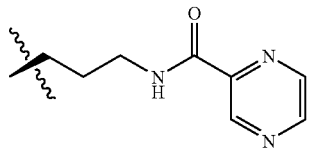 | 858.6 | (500 MHz): 0.73-0.84 (m, 6H) 1.11 (d, J = 7.26 Hz, 3H) 1.19-1.31 (m, 2H) 1.19-1.22 (m, 3H) 1.22 (s, 3H) 1.24 (s, 3H) 1.29 (d, J = 6.12 Hz, 3H) 1.33 (s, 3H) 1.53-1.57 (m, 1H) 1.63-1.71 (m, 1H) 1.79-1.87 (m, 1H) 1.87-1.96 (m, 1H) 2.04-2.12 (m, 1H) 2.22-2.38 (m, 5H) 2.30 (s, 6H) 2.35 (s, 3H) 2.38-2.45 (m, 1H) 2.46-2.54 (m, 1H) 2.82-2.89 (m, 1H) 2.94-3.05 (m, 2H) 3.17-3.24 (m, 1H) 3.22 (s, 3H) 3.33 (s, 3H) 3.38-3.44 (m, 1H) 3.44-3.51 (m, 1H) 3.70 (d, J = 8.03 Hz, 1H) 3.78-3.87 (m, 1H) 3.93-4.01 (m, 1H) 4.02-4.10 (m, 1H) 4.14-4.21 (m, 1H) 4.39 (d, J = 6.88 Hz, 1H) 4.67-4.75 (m, 1H) 4.94 (d, J = 4.20 Hz, 1H) 6.10-6.16 (m, 2H) 6.58-6.63 (m, 2H) |
| 573 | | 854.7 | (500 MHz): 0.77-0.85 (m, 6H) 1.08 (d, J = 7.65 Hz, 3H) 1.10-1.24 (m, 2H) 1.15 (d, J = 7.65 Hz, 3H) 1.19-1.24 (m, 3H) 1.22 (s, 3H) 1.28 (d, J = 6.12 Hz, 3H) 1.31 (s, 3H) 1.53 (dd, J = 15.29, 4.59 Hz, 1H) 1.56-1.74 (m, 4H) 1.79-1.89 (m, 2H) 2.11-2.20 (m, 1H) 2.22-2.37 (m, 4H) 2.28 (s, 6H) 2.35 (s, 3H) 2.39-2.51 (m, 2H) 2.75-2.83 (m, 1H) 2.90-2.96 (m, 1H) 2.97-3.03 (m, 1H) 3.17-3.21 (m, 1H) 3.22 (s, 3H) 3.31 (s, 3H) 3.35-3.54 (m, 4H) 3.69 (d, J = 7.65 Hz, 1H) 3.96-4.09 (m, 1H) 4.11-4.17 (m, 1H) 4.38 (d, J = 6.88 Hz, 1H) 4.68-4.82 (m, 1H) 4.92 (d, J = 4.59 Hz, 1H) 7.81-7.89 (m, 1H) 8.51-8.55 (m, 1H) 8.74 (d, J = 3.06 Hz, 1H) 9.37-9.41 (m, 1H) |

TABLE 15-continued formula (AB)

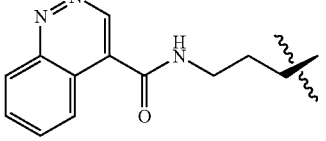

| Example | R | ESI MS (M + H) | $^1$H—NMR, CDCl$_3$, δ (ppm) |
|---|---|---|---|
| 574 | 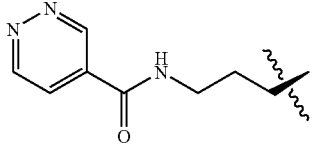 | 904.7 | (500 MHz): 0.74-0.90 (m, 6H) 1.07 (d, J = 7.65 Hz, 3H) 1.09-1.26 (m, 2H) 1.13 (d, J = 7.65 Hz, 3H) 1.19-1.23 (m, 3H) 1.22 (s, 3H) 1.27 (d, J = 6.12 Hz, 3H) 1.30 (s, 3H) 1.52 (dd, J = 14.91, 4.97 Hz, 1H) 1.64 (d, J = 13.00 Hz, 1H) 1.66-1.95 (m, 5H) 2.17-2.36 (m, 5H) 2.28 (s, 6H) 2.37 (s, 3H) 2.41-2.51 (m, 2H) 2.74-2.84 (m, 1H) 2.91-3.04 (m, 2H) 3.16-3.20 (m, 1H) 3.21 (s, 3H) 3.30 (s, 3H) 3.31-3.40 (m, 1H) 3.40-3.51 (m, 1H) 3.54-3.66 (m, 2H) 3.68 (d, J = 7.65 Hz, 1H) 3.94-4.13 (m, 2H) 4.38 (d, J = 6.88 Hz, 1H) 4.76-4.85 (m, 1H) 4.87 (d, J = 4.59 Hz, 1H) 6.76-7.03 (m, 1H) 7.82 (t, J = 8.41 Hz, 1H) 7.85-7.89 (m, 1H) 8.32 (d, J = 7.65 Hz, 1H) 8.52 (d, J = 9.17 Hz, 1H) 9.27 (s, 1H) |
| 575 | 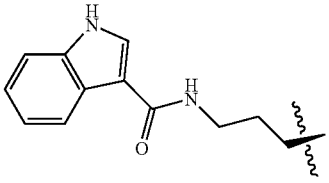 | 854.7 | (500 MHz): 0.76-0.91 (m, 6H) 1.08 (d, J = 7.40 Hz, 3H) 1.11-1.24 (m, 2H) 1.15 (d, J = 7.13 Hz, 3H) 1.21 (s, 3H) 1.23 (s, 3H) 1.27 (d, J = 6.03 Hz, 3H) 1.31 (s, 3H) 1.51-1.71 (m, 5H) 1.74-1.83 (m, 1H) 1.84-1.92 (m, 1H) 2.17-2.29 (m, 4H) 2.26 (s, 6H) 2.34 (s, 3H) 2.34-2.38 (m, 1H) 2.39-2.47 (m, 1H) 2.48-2.56 (m, 1H) 2.75-2.82 (m, 1H) 2.87-2.94 (m, 1H) 3.00 (t, J = 7.82 Hz, 1H) 3.19 (dd, J = 10.15, 7.40 Hz, 1H) 3.23 (s, 3H) 3.26-3.38 (m, 1H) 3.31 (s, 3H) 3.40-3.52 (m, 2H) 3.58-3.67 (m, 1H) 3.69 (d, J = 7.68 Hz, 1H) 3.97-4.11 (m, 2H) 4.40 (d, J = 7.40 Hz, 1H) 4.78-4.86 (m, 1H) 4.89 (d, J = 4.39 Hz, 1H) 7.41 (br. s., 1H) 7.88 (dd, J = 5.21, 2.19 Hz, 1H) 9.29-9.35 (m, 1H) 9.55 (s, 1H) |
| 576 | 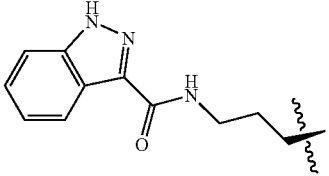 | 891.7 | (500 MHz): 0.72-0.85 (m, 6H) 1.09 (d, J = 7.40 Hz, 3H) 1.11-1.26 (m, 2H) 1.14 (d, J = 7.40 Hz, 3H) 1.20-1.24 (m, 6H) 1.29-1.34 (m, 6H) 1.52 (dd, J = 15.22, 4.80 Hz, 1H) 1.58-1.72 (m, 4H) 1.78-1.93 (m, 2H) 2.15-2.20 (m, 1H) 2.22-2.35 (m, 4H) 2.29 (s, 6H) 2.35 (s, 3H) 2.40-2.51 (m, 2H) 2.79-2.85 (m, 1H) 2.95 (d, J = 14.81 Hz, 1H) 2.98-3.04 (m, 1H) 3.20 (s, 3H) 3.21-3.26 (m, 1H) 3.30 (s, 3H) 3.41-3.54 (m, 4H) 3.69 (d, J = 7.68 Hz, 1H) 4.01-4.10 (m, 1H) 4.11-4.21 (m, 1 H) 4.40 (d, J = 7.40 Hz, 1H) 4.67-4.81 (m, 1H) 4.91 (d, J = 4.39 Hz, 1H) 6.46-6.57 (m, 1H) 7.16-7.23 (m, 2H) 7.36-7.41 (m, 1H) 7.81-7.87 (m, 1H) 8.00-8.11 (m, 1H) 9.72 (br. s.,1H) |
| 577 | 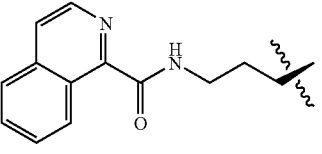 | 892.7 | (500 MHz): 0.75-0.85 (m, 6H) 1.06 (d, J = 7.40 Hz, 3H) 1.08-1.14 (m, 1H) 1.13 (d, J = 7.40 Hz, 3H) 1.15-1.26 (m, 1H) 1.19-1.24 (m, 6H) 1.29 (d, J = 6.31 Hz, 3H) 1.31 (s, 3H) 1.51 (dd, J = 15.08, 4.66 Hz, 1H) 1.57-1.71 (m, 4H) 1.78-1.94 (m, 2H) 2.07-2.18 (m, 1H) 2.23-2.37 (m, 4H) 2.29 (s, 6H) 2.32 (s, 3H) 2.38-2.44 (m, 1H) 2.44-2.53 (m, 1H) 2.77-2.85 (m, 1H) 2.87-2.95 (m, 1H) 3.00 (t, J = 9.19 Hz, 1H) 3.16-3.26 (m, 1H) 3.22 (s, 3H) 3.29 (s, 3H) 3.39-3.57 (m, 4H) 3.71 (d, J = 7.95 Hz, 1H) 3.98-4.10 (m, 1H) 4.12-4.21 (m, 1H) 4.40 (d, J = 6.86 Hz, 1H) 4.72-4.82 (m, 1H) 4.92 (d, J = 4.66 Hz, 1H) 7.20-7.28 (m, 1H) 7.32-7.40 (m, 2H) 7.46 (d, J = 8.23 Hz, 1H) 8.37 (d, J = 8.23 Hz, 1H) 11.30 (br. s., 1H) |
| 578 |  | 903.7 | (500 MHz): 0.77-0.84 (m, 6H) 1.08 (d, J = 7.40 Hz, 3H) 1.09-1.14 (m, 1H) 1.16 (d, J = 7.68 Hz, 3H) 1.19-1.25 (m, 1H) 1.19-1.23 (m, 3H) 1.22 (s, 3H) 1.28 (d, J = 6.31 Hz, 3H) 1.31 (s, 3H) 1.53 (dd, J = 15.22, 4.80 Hz, 1H) 1.60-1.77 (m, 4H) 1.80-1.95 (m, 2H) 2.13-2.21 (m, 1H) 2.22-2.31 (m, 3H) 2.28 (s, 6H) 2.32-2.36 (m, 1H) 2.36 (s, 3H) 2.39-2.51 (m, 2H) 2.74-2.84 (m, 1H) 2.94 (d, J = 14.54 Hz, 1H) 3.00 (t, J = 9.46 Hz, 1H) 3.16-3.22 (m, 1H) 3.23 (s, 3H) 3.31 (s, 3H) 3.35-3.43 (m, 1H) 3.43-3.59 (m, 3H) 3.69 (d, J = 8.23 Hz, 1H) 3.99-4.09 (m, 1H) 4.11-4.19 (m, 1H) 4.38 (d, J = 7.40 Hz, 1H) 4.72-4.83 (m, 1H) 4.92 (d, J = 4.39 Hz, 1H) 7.62-7.74 (m, 2H) 7.79 (d, J = 5.49 Hz, 1H) 7.84 (d, J = 7.68 Hz, 1H) 8.22-8.29 (m, 1H) 8.46 (d, J = 5.48 Hz, 1H) 9.58 (d, J = 8.78 Hz, 1H) |

TABLE 15-continued formula (AB)

| Example | R | ESI MS (M + H) | $^1$H—NMR, CDCl$_3$, δ (ppm) |
|---|---|---|---|
| 579 | quinoline-8-carboxamide-N-propyl | 903.7 | (500 MHz): 0.78-0.86 (m, 6H) 1.08 (d, J = 7.40 Hz, 3H) 1.10-1.24 (m, 2H) 1.16 (d, J = 7.40 Hz, 3H) 1.20-1.22 (m, 3H) 1.22 (s, 3H) 1.28 (d, J = 6.03 Hz, 3H) 1.31 (s, 3H) 1.52 (dd, J = 15.36, 4.94 Hz, 1H) 1.60-1.66 (m, 1H) 1.67-1.87 (m, 4H) 1.90-1.98 (m, 1H) 2.13-2.20 (m, 1H) 2.20-2.38 (m, 4H) 2.28 (s, 6H) 2.36 (s, 3H) 2.39-2.52 (m, 2H) 2.77-2.85 (m, 1H) 2.90-2.97 (m, 1H) 2.97-3.03 (m, 1H) 3.20 (dd, J = 10.15, 7.40 Hz, 1H) 3.22 (s, 3H) 3.31 (s, 3H) 3.36-3.43 (m, 1H) 3.43-3.51 (m, 1H) 3.56-3.65 (m, 2H) 3.69 (d, J = 8.23 Hz, 1H) 3.96-4.09 (m, 1H) 4.11-4.19 (m, 1H) 4.38 (d, J = 7.40 Hz, 1H) 4.71-4.84 (m, 1H) 4.93 (d, J = 4.39 Hz, 1H) 7.49 (dd, J = 8.23, 4.39 Hz, 1H) 7.63-7.70 (m, 1H) 7.95 (dd, J = 8.09, 1.51 Hz, 1H) 8.27 (dd, J = 8.36, 1.78 Hz, 1H) 8.85 (dd, J = 7.27, 1.51 Hz, 1H) 8.92 (dd, J = 4.11, 1.92 Hz, 1H) 11.26-11.34 (m, 1H) |
| 580 | 1,5-naphthyridine-4-carboxamide-N-propyl | 904.7 | (500 MHz): 0.77-0.87 (m, 6H) 1.07 (d, J = 7.40 Hz, 3H) 1.11 (d, J = 7.40 Hz, 3H) 1.12-1.16 (m, 1H) 1.18-1.24 (m, 1H) 1.19-1.22 (m, 3H) 1.22 (s, 3H) 1.27 (d, J = 6.31 Hz, 3H) 1.31 (s, 3H) 1.52 (dd, J = 15.22, 4.80 Hz, 1H) 1.60-1.77 (m, 4H) 1.80-1.95 (m, 2H) 2.15-2.29 (m, 4H) 2.27 (s, 6H) 2.30-2.35 (m, 1H) 2.36 (s, 3H) 2.39-2.52 (m, 2H) 2.71-2.80 (m, 1H) 2.90-2.97 (m, 1H) 2.97-3.03 (m, 1H) 3.15-3.20 (m, 1H) 3.21 (s, 3H) 3.30 (s, 3H) 3.32-3.40 (m, 1H) 3.41-3.50 (m, 1H) 3.53-3.65 (m, 2H) 3.68 (d, J = 7.95 Hz, 1H) 3.98-4.07 (m, 1H) 4.06-4.13 (m, 1H) 4.38 (d, J = 7.13 Hz, 1H) 4.75-4.85 (m, 1H) 4.88 (d, J = 4.66 Hz, 1H) 6.85-7.03 (m, 1H) 7.49 (d, J = 4.39 Hz, 1H) 7.52 (dd, J = 8.50, 4.11 Hz, 1H) 8.68 (dd, J = 8.50, 1.92 Hz, 1H) 9.01 (d, J = 4.39 Hz, 1H) 9.09 (dd, J = 4.11, 1.92 Hz, 1H) |
| 581 | 1,5-naphthyridine-8-carboxamide-N-propyl | 904.6 | (500 MHz): 0.78-0.86 (m, 6H) 1.09 (d, J = 7.40 Hz, 3H) 1.12-1.23 (m, 2H) 1.16 (d, J = 7.40 Hz, 3H) 1.20-1.23 (m, 3H) 1.22 (s, 3H) 1.28 (d, J = 6.31 Hz, 3H) 1.31 (s, 3H) 1.53 (dd, J = 15.22, 5.07 Hz, 1H) 1.59-1.77 (m, 4H) 1.80-1.93 (m, 2H) 2.16-2.21 (m, 1H) 2.21-2.31 (m, 3H) 2.28 (s, 6H) 2.32-2.37 (m, 1H) 2.36 (s, 3H) 2.39-2.50 (m, 2H) 2.76-2.84 (m, 1H) 2.91-2.96 (m, 1H) 3.00 (t, J = 9.32 Hz, 1H) 3.20 (dd, J = 10.42, 7.40 Hz, 1H) 3.23 (s, 3H) 3.31 (s, 3H) 3.35-3.42 (m, 1H) 3.42-3.59 (m, 3H) 3.69 (d, J = 7.95 Hz, 1H) 3.99-4.09 (m, 1H) 4.10-4.20 (m, 1H) 4.38 (d, J = 7.13 Hz, 1H) 4.74-4.84 (m, 1H) 4.92 (d, J = 4.66 Hz, 1H) 7.58 (dd, J = 8.78, 4.11 Hz, 1H) 8.06 (dd, J = 5.62, 0.69 Hz, 1H) 8.29-8.36 (m, 1H) 8.68 (d, J = 5.76 Hz, 1H) 9.09 (dd, J = 4.11, 1.65 Hz, 1H) 9.94-10.03 (m, 1H) |
| 582 | pyridine-2-carboxamide-N-propyl | 853.6 | (500 MHz): 0.79-0.86 (m, 6H) 1.09 (d, J = 7.65 Hz, 3H) 1.11-1.26 (m, 2H) 1.16 (d, J = 7.65 Hz, 3H) 1.20-1.23 (m, 3H) 1.23 (s, 3H) 1.28 (d, J = 6.88 Hz, 3H) 1.32 (s, 3H) 1.53 (dd, J = 15.29, 4.59 Hz, 1H) 1.57-1.73 (m, 4H) 1.78-1.92 (m, 2H) 2.13-2.19 (m, 1H) 2.22-2.32 (m, 3H) 2.28 (s, 6H) 2.33-2.38 (m, 1H) 2.36 (s, 3H) 2.40-2.51 (m, 2H) 2.77-2.84 (m, 1H) 2.90-2.96 (m, 1H) 3.00 (t, J = 9.56 Hz, 1H) 3.16-3.22 (m, 1H) 3.23 (s, 3H) 3.32 (s, 3H) 3.35-3.42 (m, 1H) 3.42-3.52 (m, 3H) 3.70 (d, J = 7.65 Hz, 1H) 4.00-4.09 (m, 1H) 4.12-4.19 (m, 1H) 4.38 (d, J = 7.65 Hz, 1H) 4.70-4.82 (m, 1H) 4.93 (d, J = 4.59 Hz, 1H) 7.39-7.44 (m, 1H) 7.81-7.86 (m, 1H) 8.03-8.10 (m, 1H) 8.18 (d, J = 7.65 Hz, 1H) 8.55 (d, J = 4.59 Hz, 1H) |

TABLE 15-continued formula (AB)

| Example | R | ESI MS (M + H) | ¹H—NMR, CDCl₃, δ (ppm) |
|---|---|---|---|
| 583 | pyridin-4-yl-C(O)NH-CH₂CH₂CH(Me)- | 853.7 | (500 MHz): 0.79-0.88 (m, 6H) 1.09 (d, J = 7.40 Hz, 3H) 1.11-1.26 (m, 2H) 1.15 (d, J = 7.13 Hz, 3H) 1.21 (d, J = 6.03 Hz, 3H) 1.23 (s, 3H) 1.28 (d, J = 6.31 Hz, 3H) 1.31 (s, 3H) 1.54 (dd, J = 15.22, 4.80 Hz, 1H) 1.57-1.91 (m, 6H) 2.16-2.31 (m, 4H) 2.27 (s, 6H) 2.33-2.40 (m, 1H) 2.36 (s, 3H) 2.40-2.54 (m, 2H) 2.75-2.83 (m, 1H) 2.88-2.95 (m, 1H) 3.01 (t, J = 9.60 Hz, 1H) 3.20 (dd, J = 10.15, 7.13 Hz, 1H) 3.23 (s, 3H) 3.32 (s, 3H) 3.33-3.40 (m, 1H) 3.40-3.52 (m, 2H) 3.53-3.63 (m, 1H) 3.70 (d, J = 7.95 Hz, 1H) 3.99-4.07 (m, 1H) 4.07-4.14 (m, 1H) 4.40 (d, J = 7.13 Hz, 1H) 4.75-4.87 (m, 1H) 4.91 (d, J =]4.66 Hz, 1H) 6.66 (br. s., 1H) 7.63 (d, J = 5.76 Hz, 2H) 8.69-8.75 (m, 2H) |
| 584 | pyrimidin-5-yl-C(O)NH-CH₂CH₂CH(Me)- | 854.6 | (500 MHz): 0.79-0.90 (m, 6H) 1.09 (d, J = 7.26 Hz, 3H) 1.12-1.26 (m, 2H) 1.16 (d, J = 7.26 Hz, 3H) 1.21 (d, J = 6.12 Hz, 3H) 1.23 (s, 3H) 1.27 (d, J = 6.12 Hz, 3H) 1.31 (s, 3H) 1.55 (dd, J = 15.29, 4.97 Hz, 2H) 1.59-1.72 (m, 4H) 1.73-1.83 (m, 1H) 1.84-1.96 (m, 1H) 2.18-2.31 (m, 4H) 2.27 (s, 6H) 2.33-2.38 (m, 1H) 2.35 (s, 3H) 2.41-2.53 (m, 2H) 2.76-2.83 (m, 1H) 2.88-2.95 (m, 1H) 3.00 (t, J = 9.37 Hz, 1H) 3.20 (dd, J = 10.32, 7.26 Hz, 1H) 3.23 (s, 3H) 3.28-3.39 (m, 1H) 3.31 (s, 3H) 3.41-3.51 (m, 2H) 3.54-3.64 (m, 1H) 3.70 (d, J = 7.64 Hz, 1H) 3.98-4.09 (m, 2H) 4.40 (d, J = 7.26 Hz, 1H) 4.79-4.87 (m, 1H) 4.89 (d, J = 4.59 Hz, 1H) 9.13 (s, 2H) 9.29 (s, 1H) |
| 585 | 1H-inden-3-yl-C(O)NH-CH₂CH₂CH(Me)- | 890.6 | (500 MHz): 0.77-0.88 (m, 6H) 1.09 (d, J = 7.64 Hz, 3H) 1.11-1.18 (m, 1H) 1.16 (d, J = 7.26 Hz, 3H) 1.19-1.26 (m, 1H) 1.20-1.23 (m, 3H) 1.23 (s, 3H) 1.28 (d, J = 6.50 Hz, 3H) 1.32 (s, 3H) 1.53 (dd, J = 15.29, 4.59 Hz, 1H) 1.56-1.69 (m, 4H) 1.72-1.90 (m, 2H) 2.13-2.22 (m, 1H) 2.22-2.32 (m, 3H) 2.28 (s, 6H) 2.32-2.38 (m, 1H) 2.36 (s, 3H) 2.41-2.52 (m, 2H) 2.75-2.83 (m, 1H) 2.89-2.96 (m, 1H) 3.00 (t, J = 8.60 Hz, 1H) 3.20 (dd, J = 10.32, 7.26 Hz, 1H) 3.23 (s, 3H) 3.31 (s, 3H) 3.35-3.54 (m, 6H) 3.70 (d, J = 8.03 Hz, 1H) 4.00-4.08 (m, 1H) 4.10-4.17 (m, 1H) 4.39 (d, J = 7.26 Hz, 1H) 4.72-4.83 (m, 1H) 4.92 (d, J = 4.20 Hz, 1H) 6.16 (br. s., 1H) 6.91-6.96 (m, 1H) 7.22-7.27 (m, 1H) 7.33 (t, J = 7.64 Hz, 1H) 7.47 (d, J = 7.26 Hz, 1H) 7.88 (d, J = 7.65 Hz, 1H) |
| 586 | benzofuran-3-yl-C(O)NH-CH₂CH₂CH(Me)- | 892.7 | (500 MHz): 0.76-0.87 (m, 6H) 1.09 (d, J = 7.26 Hz, 3H) 1.10-1.26 (m, 2H) 1.17 (d, J = 7.26 Hz, 3H) 1.20-1.23 (m, 3H) 1.22 (s, 3H) 1.28 (d, J = 6.50 Hz, 3H) 1.31 (s, 3H) 1.52 (dd, J = 15.29, 4.97 Hz, 1H) 1.56-1.75 (m, 4H) 1.78-1.90 (m, 2H) 2.13-2.21 (m, 1H) 2.21-2.31 (m, 3H) 2.27 (s, 6H) 2.31-2.38 (m, 1H) 2.36 (s, 3H) 2.40-2.51 (m, 2H) 2.75-2.84 (m, 1H) 2.89-2.95 (m, 1H) 3.00 (t, J = 9.37 Hz, 1H) 3.20 (dd, J = 10.32, 7.26 Hz, 1H) 3.23 (s, 3H) 3.31 (s, 3H) 3.34-3.42 (m, 1H) 3.42-3.57 (m, 3H) 3.70 (d, J = 8.03 Hz, 1H) 4.01-4.09 (m, 1H) 4.09-4.19 (m, 1H) 4.39 (d, J = 7.26 Hz, 1H) 4.73-4.83 (m, 1H) 4.92 (d, J = 4.59 Hz, 1H) 6.65-6.78 (m, 1H) 7.28 (t, J = 7.45 Hz, 1H) 7.37-7.42 (m, 1H) 7.45 (s, 1H) 7.50 (d, J = 8.41 Hz, 1H) 7.66 (d, J = 7.64 Hz, 1H) |
| 587 | benzothiophen-3-yl-C(O)NH-CH₂CH₂CH(Me)- | 908.6 | (500 MHz): 0.79-0.91 (m, 6H) 1.09 (d, J = 7.65 Hz, 3H) 1.13-1.19 (m, 1H) 1.15 (d, J = 7.65 Hz, 3H) 1.19-1.27 (m, 1H) 1.21-1.23 (m, 3H) 1.23 (s, 3H) 1.28 (d, J = 6.12 Hz, 3H) 1.32 (s, 3H) 1.54 (dd, J = 15.29, 5.35 Hz, 1H) 1.59-1.76 (m, 4H) 1.80-1.94 (m, 2H) 2.16-2.32 (m, 4H) 2.28 (s, 6H) 2.32-2.39 (m, 1H) 2.37 (s, 3H) 2.41-2.55 (m, 2H) 2.70-2.84 (m, 1H) 2.90-2.97 (m, 1H) 3.01 (t, J = 9.56 Hz, 1H) 3.20 (dd, J = 9.94, 7.65 Hz, 1H) 3.24 (s, 3H) 3.31 (s, 3H) 3.35-3.41 (m, 1H) 3.43-3.51 (m, 2H) 3.51-3.61 (m, 1H) 3.70 (d, J = 7.65 Hz, 1H) 3.99-4.09 (m, 1H) 4.09-4.18 (m, 1H) 4.40 (d, J = 6.88 Hz, 1H) 4.72-4.86 (m, 1H) 4.91 (d, J = 4.59 Hz, 1H) 6.30 (br. s., 1H) 7.34-7.42 (m, 1H) 7.41-7.47 (m, 1H) 7.85 (d, J = 8.41 Hz, 1H) 7.87 (s, 1H) 8.38 (d, J = 7.65 Hz, 1H) |

TABLE 15-continued formula (AB)

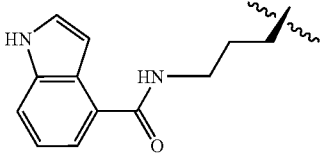

| Example | R | ESI MS (M + H) | $^1$H—NMR, CDCl$_3$, δ (ppm) |
|---|---|---|---|
| 588 | 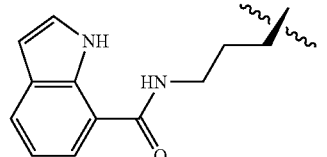 | 891.7 | (500 MHz): 0.76-0.88 (m, 6H) 1.08 (d, J = 7.26 Hz, 3H) 1.10-1.18 (m, 1H) 1.15 (d, J = 7.26 Hz, 3H) 1.19-1.26 (m, 1H) 1.20-1.23 (m, 3H) 1.22 (s, 3H) 1.28 (d, J = 6.50 Hz, 3H) 1.32 (s, 3H) 1.53 (dd, J = 15.29, 4.97 Hz, 1H) 1.60-1.78 (m, 4H) 1.80-1.97 (m, 2H) 2.12-2.21 (m, 1H) 2.21-2.32 (m, 3H) 2.28 (s, 6H) 2.31-2.38 (m, 1 H) 2.36 (s, 3H) 2.40-2.54 (m, 2H) 2.77-2.83 (m, 1H) 2.90-2.97 (m, 1H) 3.00 (t, J = 9.75 Hz, 1H) 3.16-3.22 (m, 1H) 3.23 (s, 3H) 3.31 (s, 3H) 3.36-3.42 (m, 1H) 3.43-3.49 (m, 1H) 3.50-3.60 (m, 2H) 3.70 (d, J = 8.03 Hz, 1H) 4.00-4.11 (m, 1H) 4.11-4.20 (m, 1H) 4.39 (d, J = 7.26 Hz, 1H) 4.72-4.83 (m, 1H) 4.92 (d, J = 4.20 Hz, 1H) 6.25-6.37 (m, 1H) 6.89-6.93 (m, 1H) 7.21 (t, J = 7.84 Hz, 1H) 7.28-7.35 (m, 1H) 7.49 (dd, J = 11.85, 7.64 Hz, 2H) 8.63-8.74 (m, 1H) |
| 589 | 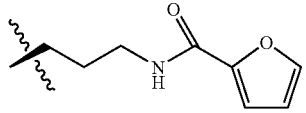 | 891.7 | (500 MHz): 0.79-0.88 (m, 6H) 1.10 (d, J = 6.88 Hz, 3H) 1.13-1.19 (m, 1H) 1.16 (d, J = 7.65 Hz, 3H) 1.20-1.27 (m, 1H) 1.21-1.23 (m, 3H) 1.23 (s, 3H) 1.29 (d, J = 6.12 Hz, 3H) 1.32 (s, 3H) 1.54 (dd, J = 15.29, 4.59 Hz, 1H) 1.58-1.74 (m, 4H) 1.78-1.91 (m, 2H) 2.14-2.22 (m, 1H) 2.22-2.32 (m, 3H) 2.28 (s, 6H) 2.32-2.39 (m, 1H) 2.36 (s, 3H) 2.42-2.53 (m, 2H) 2.74-2.85 (m, 1H) 2.87-2.96 (m, 1H) 3.01 (t, J = 9.94 Hz, 1H)3.21 (dd, J = 10.32, 7.26 Hz, 1H) 3.24 (s, 3H) 3.32 (s, 3H) 3.35-3.42 (m, 1H) 3.43-3.52 (m, 2H) 3.54-3.63 (m, 1H) 3.71 (d, J = 7.65 Hz, 1H) 3.98-4.08 (m, 1H) 4.09-4.18 (m, 1H) 4.40 (d, J = 7.65 Hz, 1H) 4.74-4.87 (m, 1H) 4.93 (d, J = 4.59 Hz, 1H) 6.48-6.65 (m, 2H) 7.10 (t, J = 7.65 Hz, 1H) 7.29-7.34 (m, 1H) 7.38 (d, J = 6.88 Hz, 1H) 7.79 (d, J = 7.65 Hz, 1H) 10.28-10.38 (m, 1H) |
| 590 | 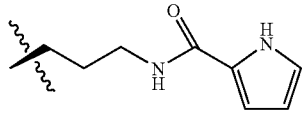 | 842.6 | (500 MHz): 0.75-0.85 (m, 6H) 1.09 (d, J = 7.26 Hz, 3H) 1.11-1.18 (m, 1H) 1.16 (d, J = 7.26 Hz, 3H) 1.19-1.25 (m, 1H) 1.21 (d, J = 6.12 Hz, 3H) 1.22 (s, 3H) 1.28 (d, J = 6.12 Hz, 3H) 1.31 (s, 3H) 1.50-1.67 (m, 5H) 1.71-1.78 m, 1H) 1.79-1.89 (m, 1H) 2.11-2.21 (m, 1H) 2.22-2.32 (m, 3H) 2.28 (s, 6H) 2.32-2.37 (m, 1H) 2.35 (s, 3H) 2.40-2.50 (m, 2H) 2.76-2.83 (m, 1H) 2.89-2.95 (m, 1H) 3.00 (t, J = 9.75 Hz, 1H) 3.20 (dd, J = 10.32, 7.26 Hz, 1H) 3.23 (s, 3H) 3.32 (s, 3H) 3.36-3.50 (m, 4H) 3.69 (d, J = 8.03 Hz, 1H) 4.00-4.09 (m, 1H) 4.10-4.17 (m, 1H) 4.38 (d, J = 7.26 Hz, 1H) 4.64-4.81 (m, 1H) 4.92 (d, J = 4.59 Hz, 1H) 6.38-6.45 (m, 1H) 6.48 (dd, J = 3.44, 1.53 Hz, 1H) 7.07-7.11 (m, 1H) 7.39-7.44 (m, 1H) |
| 591 | 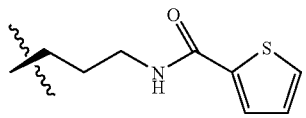 | 841.6 | (500 MHz): 0.80-0.87 (m, 6H) 1.10 (d, J = 7.26 Hz, 3H) 1.13-1.18 (m, 1H) 1.16 (d, J = 7.64 Hz, 3H) 1.20-1.26 (m, 1H) 1.22 (d, J = 6.12 Hz, 3H) 1.23 (s, 3H) 1.28 (d, J = 6.12 Hz, 3H) 1.32 (s, 3H) 1.51-1.73 (m, 5H) 1.75-1.83 (m, 1H) 1.83-1.91 (m, 1H) 2.13-2.21 (m, 1H) 2.23-2.31 (m, 3H) 2.28 (s, 6H) 2.35 (s, 3H) 2.35-2.40 (m, 1H) 2.41-2.52 (m, 2H) 2.76-2.84 (m, 1H) 2.88-2.95 (m, 1H) 3.01 (t, J = 9.75 Hz, 1H) 3.17-3.22 (m, 1H) 3.24 (s, 3H) 3.32 (s, 3H) 3.34-3.43 (m, 2H) 3.43-3.52 (m, 2H) 3.70 (d, J = 8.03 Hz, 1H) 4.00-4.09 (m, 1H) 4.10-4.17 (m, 1H) 4.40 (d, J = 6.88 Hz, 1H) 4.72-4.85 (m, 1H) 4.92 (d, J = 4.59 Hz, 1H) 6.01-6.16 (m, 1H) 6.19-6.24 (m, 1H) 6.54-6.60 (m, 1H) 6.87-6.94 (m, 1H) 9.38 (br. s., 1H) |
| 592 | | 858.6 | (500 MHz): 0.79-0.88 (m, 6H) 1.09 (d, J = 7.40 Hz, 3H) 1.09-1.18 (m, 1H) 1.16 (d, J = 7.40 Hz, 3H) 1.18-1.25 (m, 1H) 1.21 (d, J = 6.03 Hz, 3H) 1.22 (s, 3H) 1.28 (d, J = 6.03 Hz, 3H) 1.31 (s, 3H) 1.53 (dd, J = 15.22, 4.80 Hz, 1H) 1.57-1.66 (m, 4H) 1.73-1.81 (m, 1H) 1.82-1.92 (m, 1H) 2.12-2.22 (m, 1H) 2.22-2.31 (m, 3H) 2.27 (s, 6H) 2.35 (s, 3H) 2.35-2.39 (m, 1H) 2.40-2.50 (m, 2H) 2.73-2.83 (m, 1H) 2.91 (d, J = 14.26 Hz, 1H) 3.00 (t, J = 9.46 Hz, 1H) 3.20 (dd, J = 10.28, 7.27 Hz, 1H) 3.23 (s, 3H) 3.31 (s, 3H) 3.34-3.43 (m, 2H) 3.43-3.54 (m, 2H) 3.70 (d, J = 7.95 Hz, 1H) 3.98-4.08 (m, 1H) 4.09-4.17 (m, 1H) 4.39 (d, J = 7.40 Hz, 1H) 4.72-4.85 (m, 1H) 4.91 (d, J = 4.39 Hz, 1H) 6.24 (br. s., 1H) 7.05 (dd, J = 4.94, 3.84 Hz, 1H) 7.44 (dd, J = 4.94, 1.10 Hz, 1H) 7.50 (dd, J = 3.70, 0.96 Hz, 1H) |

TABLE 15-continued formula (AB)

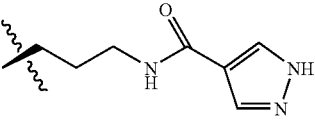

| Example | R | ESI MS (M + H) | $^1$H—NMR, CDCl$_3$, δ (ppm) |
|---|---|---|---|
| 593 | 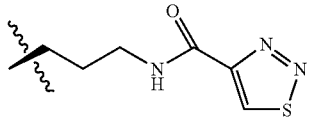 | 842.6 | (500 MHz): 0.75-0.86 (m, 6H) 1.08 (d, J = 7.13 Hz, 3H) 1.12-1.17 (m, 1H) 1.14 (d, J = 7.40 Hz, 3H) 1.20-1.23 (m, 3H) 1.20-1.26 (m, 1H) 1.22 (s, 3H) 1.29 (d, J = 6.31 Hz, 3H) 1.31 (s, 3H) 1.54 (dd, J = 15.22, 5.07 Hz, 1H) 1.57-1.69 (m, 4H) 1.73-1.90 (m, 2H) 2.13-2.28 (m, 3H) 2.29 (s, 6H) 2.31-2.35 (m, 1H) 2.36 (s, 3H) 2.41-2.46 (m, 1H) 2.47-2.53 (m, 1H) 2.79-2.84 (m, 1H) 2.95 (d, J = 13.71 Hz, 1H) 3.01 (d, J = 9.05 Hz, 1H) 3.20 (s, 3H) 3.24 (dd, J = 10.15, 7.40 Hz, 1H) 3.30 (s, 3H) 3.35-3.51 (m, 4H) 3.68 (d, J = 7.40 Hz, 1H) 4.01-4.09 (m, 1H) 4.11-4.19 (m, 1H) 4.38 (d, J = 7.13 Hz, 1H) 4.67-4.83 (m, 1H) 4.90 (d, J = 4.66 Hz, 1H) 6.71-6.77 (m, 1H) 8.02 (s, 2H) |
| 594 | 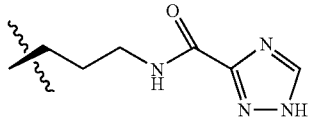 | 860.6 | (500 MHz): 0.78-0.84 (m, 6H) 1.09 (d, J = 7.40 Hz, 3H) 1.10-1.14 (m, 1H) 1.16 (d, J = 7.40 Hz, 3H) 1.19-1.22 (m, 1H) 1.21 (d, J = 6.03 Hz, 3H) 1.22 (s, 3H) 1.27 (d, J = 6.31 Hz, 3H) 1.31 (s, 3H) 1.53 (dd, J = 15.22, 4.80 Hz, 1H) 1.56-1.66 (m, 3H) 1.67-1.80 (m, 2H) 1.81-1.93 (m, 1H) 2.11-2.20 (m, 1H) 2.22-2.34 (m, 2H) 2.27 (s, 6H) 2.34-2.38 (m, 1H) 2.35 (s, 3H) 2.40-2.49 (m, 2H) 2.75-2.83 (m, 1H) 2.93 (d, J = 15.63 Hz, 1H) 3.00 (t, J = 9.46 Hz, 1H) 3.13-3.20 (m, 1H) 3.22 (s, 3H) 3.31 (s, 3H) 3.35-3.41 (m, 1H) 3.42-3.49 (m, 1H) 3.50-3.59 (m, 2H) 3.69 (d, J = 7.95 Hz, 1H) 4.00-4.08 (m, 1H) 4.10-4.17 (m, 1H) 4.38 (d, J = 7.13 Hz, 1H) 4.70-4.84 (m, 1H) 4.92 (d, J = 4.39 Hz, 1H) 7.58-7.64 (m, 1H) 9.21 (s, 1H) |
| 595 | 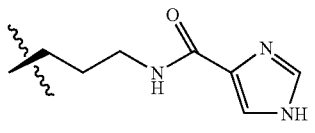 | 843.7 | (500 MHz): 0.77-0.85 (m, 6H) 1.07-1.10 (m, 3H) 1.10-1.17 (m, 1H) 1.13-1.17 (m, 3H) 1.18-1.25 (m, 1H) 1.19-1.23 (m, 3H) 1.22 (s, 3H) 1.28 (d, J = 6.31 Hz, 3H) 1.31 (s, 3H) 1.47-1.71 (m, 5H) 1.73-1.89 (m, 2H) 2.09-2.20 (m, 1H) 2.20-2.32 (m, 2H) 2.28 (s, 6H) 2.31-2.40 (m, 4H) 2.41-2.52 (m, 2H) 2.63-2.84 (m, 3H) 2.87-2.95 (m, 1H) 3.00 (d, J = 9.32 Hz, 1H) 3.17-3.22 (m, 1H) 3.22 (s, 3H) 3.31 (s, 3H) 3.35-3.50 (m, 2H) 3.69 (d, J = 8.23 Hz, 1H) 4.01-4.09 (m, 1H) 4.10-4.18 (m, 1H) 4.38 (d, J = 7.13 Hz, 1H) 4.66-4.79 (m, 1H) 4.89-4.95 (m, 1H) |
| 596 | 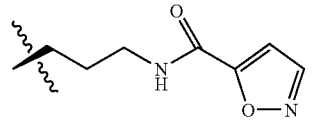 | 842.6 | (500 MHz): 0.73-0.89 (m, 6H) 1.07 (d, J = 7.40 Hz, 3H) 1.10-1.18 (m, 1H) 1.15 (d, J = 7.40 Hz, 3H) 1.18-1.25 (m, 1H) 1.20-1.23 (m, 3H) 1.22 (s, 3H) 1.28 (d, J = 6.31 Hz, 3H) 1.31 (s, 3H) 1.53 (dd, J = 15.22, 4.80 Hz, 1H) 1.56-1.68 (m, 4H) 1.74-1.90 (m, 2H) 2.10-2.18 (m, 1H) 2.19-2.29 (m, 3H) 2.28 (s, 6H) 2.34 (s, 3H) 2.34-2.37 (m, 1H) 2.38-2.44 (m, 1H) 2.44-2.52 (m, 1H) 2.74-2.84 (m, 1H) 2.91 (d, J = 13.44 Hz, 1H) 3.00 (t, J = 9.19 Hz, 1H) 3.14-3.24 (m, 1H) 3.22 (s, 3H) 3.31 (s, 3H) 3.35-3.52 (m, 4H) 3.69 (d, J = 7.95 Hz, 1H) 4.00-4.08 (m, 1H) 4.10-4.18 (m, 1H) 4.38 (d, J = 7.40 Hz, 1H) 4.70-4.79 (m, 1H) 4.91 (d, J = 4.66 Hz, 1H) 7.19 (br. s., 1H) 7.57 (s, 1H) 7.60 (s, 1H) 10.92 (br. s., 1H) |
| 597 |  | 843.6 | (500 MHz): 0.77-0.86 (m, 6H) 1.09 (d, J = 7.26 Hz, 3H) 1.12-1.17 (m, 1H) 1.17 (d, J = 7.26 Hz, 3H) 1.19-1.26 (m, 1H) 1.22 (d, J = 6.12 Hz, 3H) 1.23 (s, 3H) 1.28 (d, J = 6.50 Hz, 3H) 1.32 (s, 3H) 1.50-1.75 (m, 5H) 1.77-1.91 (m, 2H) 2.14-2.23 (m, 1H) 2.22-2.33 (m, 3H) 2.29 (s, 6H) 2.33-2.39 (m, 1H) 2.36 (s, 3H) 2.41-2.55 (m, 2H) 2.77-2.85 (m, 1H) 2.94 (d, J = 15.67 Hz, 1H) 3.01 (t, J = 8.98 Hz, 1H) 3.16-3.22 (m, 1H) 3.23 (s, 3H) 3.32 (s, 3H) 3.36-3.42 (m, 1H) 3.42-3.54 (m, 3H) 3.70 (d, J = 8.03 Hz, 1H) 4.00-4.09 (m, 1H) 4.10-4.18 (m, 1H) 4.39 (d, J = 7.26 Hz, 1H) 4.73-4.83 (m, 1H) 4.92 (d, J = 4.59 Hz, 1H) 6.63-6.77 (m, 1H) 6.90 (d, J = 1.15 Hz, 1H) 8.27-8.37 (m, 1H) |

TABLE 15-continued formula (AB)

| Example | R | ESI MS (M + H) | $^1$H—NMR, CDCl$_3$, δ (ppm) |
|---|---|---|---|
| 598 | *N-linked propyl-NH-C(O)-furazan (1,2,5-oxadiazole)* | 844.5 | (500 MHz): 0.80-0.92 (m, 6H) 1.11 (d, J = 6.88 Hz, 3H) 1.18 (d, J = 6.88 Hz, 3H) 1.17-1.29 (m, 2H) 1.21-1.24 (m, 3H) 1.25 (s, 3H) 1.29 (d, J = 6.50 Hz, 3H) 1.34 (s, 3H) 1.51-1.81 (m, 6H) 1.93-2.16 (m, 2H) 2.30-2.42 (m, 12H) 2.51-2.61 (m, 2H) 2.79-2.88 (m, 2H) 3.01 (d, J = 9.56 Hz, 1H) 3.21-3.27 (m, 1H) 3.27-3.33 (m, 6H) 3.33-3.43 (m, 2H) 3.44-3.55 (m, 2H) 3.72-3.75 (m, 1H) 3.98-4.11 (m, 2H) 4.36-4.41 (m, 1H) 4.80-5.00 (m, 2H) |
| 599 | *N-linked propyl-NH-C(O)-thiazol-4-yl* | 859.6 | (500 MHz): 0.81 (d, J = 6.88 Hz, 6H) 1.09 (d, J = 7.26 Hz, 3H) 1.11-1.16 (m, 1H) 1.16 (d, J = 7.64 Hz, 3H) 1.19-1.26 (m, 1H) 1.20-1.24 (m, 3H) 1.23 (s, 3H) 1.28 (d, J = 6.12 Hz, 3H) 1.32 (s, 3H) 1.53 (dd, J = 15.10, 4.78 Hz, 1H) 1.56-1.75 (m, 4H) 1.77-1.88 (m, 2H) 2.10-2.20 (m, 1H) 2.21-2.32 (m, 3H) 2.28 (s, 6H) 2.34-2.37 (m, 1H) 2.35 (s, 3H) 2.40-2.51 (m, 2H) 2.75-2.85 (m, 1H) 2.93 (d, J = 13.38 Hz, 1H) 3.00 (t, J = 9.75 Hz, 1H) 3.17-3.23 (m, 1H) 3.22-3.23 (m, 3H) 3.32 (s, 3H) 3.34-3.52 (m, 4H) 3.70 (d, J = 8.03 Hz, 1H) 4.01-4.09 (m, 1H) 4.10-4.18 (m, 1H) 4.38 (d, J = 7.26 Hz, 1H) 4.67-4.80 (m, 1H) 4.93 (d, J = 4.59 Hz, 1H) 7.38-7.46 (m, 1H) 8.15 (d, J = 1.91 Hz, 1H) 8.74 (d, J = 2.29 Hz, 1H) |
| 600 | *N-linked propyl-NH-C(O)-pyrrol-3-yl* | 841.6 | (500 MHz): 0.73-0.91 (m, 6H) 1.08 (d, J = 7.26 Hz, 3H) 1.12-1.19 (m, 1H) 1.15 (d, J = 7.26 Hz, 3H) 1.17-1.26 (m, 1H) 1.19-1.25 (m, 3H) 1.23 (s, 3H) 1.28 (d, J = 6.50 Hz, 3H) 1.31 (s, 3H) 1.53 (dd, J = 15.29, 4.59 Hz, 1H) 1.56-1.68 (m, 4H) 1.76-1.89 (m, 2H) 2.11-2.21 (m, 1H) 2.22-2.30 (m, 3H) 2.28 (s, 6H) 2.35 (s, 3H) 2.33-2.38 (m, 1H) 2.39-2.51 (m, 2H) 2.76-2.83 (m, 1H) 2.91 (d, J = 13.76 Hz, 1H) 3.00 (t, J = 9.36 Hz, 1H) 3.18-3.22 (m, 1H) 3.22 (s, 3H) 3.31 (s, 3H) 3.34-3.52 (m, 4H) 3.70 (d, J = 8.03 Hz, 1H) 4.00-4.09 (m, 1H) 4.11-4.19 (m, 1H) 4.39 (d, J = 7.26 Hz, 1H) 4.70-4.81 (m, 1H) 4.92 (d, J = 4.59 Hz, 1H) 6.09 (br. s., 1H) 6.41-6.46 (m, 1H) 6.70-6.76 (m, 1H) 7.33-7.39 (m, 1H) 9.12 (br. s., 1H) |
| 601 | *N-linked propyl-NH-C(O)-thiazol-2-yl* | 859.6 | (500 MHz): 0.81 (d, J = 6.88 Hz, 6H) 1.09 (d, J = 7.26 Hz, 3H) 1.10-1.17 (m, 1H) 1.16 (d, J = 7.64 Hz, 3H) 1.18-1.26 (m, 1H) 1.21 (d, J = 6.12 Hz, 3H) 1.23 (s, 3H) 1.28 (d, J = 6.12 Hz, 3H) 1.31 (s, 3H) 1.53 (dd, J = 15.10, 4.78 Hz, 1H) 1.56-1.78 (m, 4H) 1.79-1.89 (m, 2H) 2.12-2.20 (m, 1H) 2.22-2.32 (m, 3H) 2.28 (s, 6H) 2.33-2.38 (m, 1H) 2.35 (s, 3H) 2.40-2.50 (m, 2H) 2.75-2.84 (m, 1H) 2.93 (d, J = 14.53 Hz, 1H) 3.00 (t, J = 9.56 Hz, 1H) 3.16-3.22 (m, 1H) 3.22 (s, 3H) 3.32 (s, 3H) 3.35-3.42 (m, 1H) 3.42-3.50 (m, 3H) 3.69 (d, J = 8.03 Hz, 1H) 3.99-4.09 (m, 1H) 4.10-4.17 (m, 1H) 4.38 (d, J = 7.26 Hz, 1H) 4.70-4.79 (m, 1H) 4.92 (d, J = 4.59 Hz, 1H) 7.29-7.36 (m, 1H) 7.55 (d, J = 3.06 Hz, 1H) 7.84 (d, J = 3.06 Hz, 1H) |
| 602 | *N-linked ethyl-pyridin-2(1H)-one* | 812.4 | (600 MHz): 0.75-0.84 (m, 6H) 1.06-1.26 (m, 11H) 1.10 (d, J = 7.34 Hz, 3H) 1.28 (d, J = 6.42 Hz, 3H) 1.31 (s, 3H) 1.54 (dd, J = 15.36, 4.81 Hz, 1H) 1.61-1.67 (m, 1H) 1.77-1.86 (m, 1H) 2.02-2.49 (m, 9H) 2.27 (s, 6H) 2.34 (s, 3H) 2.81-2.89 (m, 1H) 2.94-3.03 (m, 2H) 3.19 (dd, J = 10.09, 7.34 Hz, 1H) 3.21 (s, 3H) 3.32 (s, 3H) 3.34-3.41 (m, 1H) 3.42-3.48 (m, 1H) 3.69 (d, J = 7.79 Hz, 1H) 3.86-3.96 (m, 2H) 4.02-4.08 (m, 1H) 4.14-4.20 (m, 1H) 4.38 (d, J = 7.34 Hz, 1H) 4.75-4.78 (m, 1H) 4.93 (d, J = 4.59 Hz, 1H) 6.14 (dd, J = 13.30, 1.38 Hz, 1H) 6.54 (d, J = 9.17 Hz, 1H) 7.20 (d, J = 6.42 Hz, 1H) 7.29-7.32 (m, 1H) |

TABLE 15-continued formula (AB)

| Example | R | ESI MS (M + H) | $^1$H—NMR, CDCl$_3$, δ (ppm) |
|---|---|---|---|
| 603 | [1-(2-oxopyridin-1-yl)propyl, attached via CH with methyl] | 826.4 | (600 MHz): 0.77-0.85 (m, 6H) 1.08 (d, J = 7.34 Hz, 3H) 1.07-1.25 (m, 8H) 1.14 (d, J = 7.34 Hz, 3H) 1.27 (d, J = 5.96 Hz, 3H) 1.31 (s, 3H) 1.50-1.86 (m, 7H) 2.08-2.49 (m, 7H) 2.28 (s, 6H) 2.33 (s, 3H) 2.75-2.81 (m, 1H) 2.87-2.94 (m, 1H) 3.00 (t, J = 9.86 Hz, 1H) 3.16-3.49 (m, 3H) 3.22 (s, 3H) 3.31 (s, 3H) 3.69 (d, J = 7.79 Hz, 1H) 3.86-3.97 (m, 2H) 4.01-4.07 (m, 1H) 4.09-4.15 (m, 1H) 4.38 (d, J = 7.34 Hz, 1H) 4.71-4.78 (m, 1H) 4.91 (d, J = 4.59 Hz, 1H) 6.10-6.16 (m, 1H) 6.54 (d, J = 9.17 Hz, 1H) 7.21-7.23 (m, 1H) 7.27-7.31 (m, 1H) |
| 604 | [oxazolidine-2,4-dione-N-yl methyl] | 804.5 | (500 MHz): 0.87 (d, J = 7.26 Hz, 3H) 0.93 (d, J = 6.50 Hz, 3H) 1.08 (d, J = 7.64 Hz, 3H) 1.11 (d, J = 7.26 Hz, 3H) 1.16-1.29 (m, 2H) 1.21 (d, J = 6.12 Hz, 3H) 1.23 (s, 3H) 1.26 (d, J = 6.12 Hz, 3H) 1.29 (s, 3H) 1.48-1.56 (m, 1H) 1.57-1.64 (m, 1H) 1.87-1.96 (m, 1H) 2.18-2.22 (m, 1H) 2.21-2.41 (m, 13H) 2.42-2.52 (m, 1H) 2.54-2.62 (m, 1H) 2.72-2.80 (m, 1H) 2.91-3.03 (m, 2H) 3.18-3.29 (m, 2H) 3.24 (s, 3H) 3.32 (s, 3H) 3.43-3.52 (m, 1H) 3.59-3.66 (m, 1H) 3.70 (d, J = 7.64 Hz, 1H) 3.80-3.92 (m, 1H) 3.95-4.07 (m, 2H) 4.42 (d, J = 6.88 Hz, 1H) 4.63 (q, J = 15.80 Hz, 2H) 4.79-4.86 (m, 1H) 5.12-5.21 (m, 1H) |
| 605 | [(2-oxopyrimidin-1-yl)methyl] | 799.5 | (500 MHz): 0.79 (d, J = 6.88 Hz, 3H) 0.82 (d, J = 6.50 Hz, 3H) 0.90 (d, J = 6.88 Hz, 3H) 1.07 (d, J = 7.64 Hz, 3H) 1.08-1.30 (m, 8H) 1.26 (d, J = 6.12 Hz, 3H) 1.31 (s, 3H) 1.48 (dd, J = 15.10, 4.78 Hz, 1H) 1.64 (d, J = 12.23 Hz, 1H) 1.75-1.89 (m, 1H) 2.19-2.50 (m, 7H) 2.27 (s, 6H) 2.39 (s, 3H) 2.69 (m, 1H) 2.97 (t, J = 9.56 Hz, 1H) 3.09-3.18 (m, 2H) 3.18 (s, 3H) 3.27 (s, 3H) 3.27-3.34 (m, 1H) 3.37-3.49 (m, 1H) 3.66 (d, J = 8.03 Hz, 1H) 3.70-3.81 (m, 1H) 3.93-4.05 (m, 1H) 4.06-4.14 (m, 1H) 4.34 (d, J = 7.26 Hz, 1H) 4.45-4.71 (m, 1H) 4.81 (d, J = 4.59 Hz, 1H) 4.95-5.16 (m, 1H) 6.22-6.32 (m, 1H) 7.65-7.75 (m, 1H) 8.49-8.66 (m, 1H) |
| 606 | [(pyrimidin-2-yloxy)ethyl] | 799.5 | (500 MHz): 0.79-0.89 (m, 6H) 1.08 (d, J = 7.64 Hz, 3H) 1.10-1.15 (m, 1H) 1.14 (d, J = 7.64 Hz, 3H) 1.19-1.26 (m, 7H) 1.28 (d, J = 6.50 Hz, 3H) 1.32 (s, 3H) 1.49-1.56 (m, 1H) 1.59-1.76 (m, 1H) 1.79-1.90 (m, 1H) 2.17-2.37 (m, 5H) 2.30 (s, 6H) 2.40 (s, 3H) 2.44-2.55 (m, 2H) 2.75-2.83 (m, 1H) 2.95-3.07 (m, 2H) 3.16-3.22 (m, 1H) 3.23 (s, 3H) 3.31 (s, 3H) 3.35-3.52 (m, 2H) 3.70 (d, J = 8.03 Hz, 1H) 3.99-4.08 (m, 1H) 4.10-4.18 (m, 1H) 4.39 (d, J = 7.26 Hz, 1H) 4.44-4.60 (m, 2H) 4.91 (d, J = 4.59 Hz, 1H) 5.07-5.19 (m, 1H) 6.94 (t, J = 4.78 Hz, 1H) 8.50 (d, J = 4.59 Hz, 2H) |
| 607 | [(4-oxoquinazolin-3-yl)methyl] | 849.5 | (500 MHz): 0.78-0.88 (m, 9H) 1.07 (d, J = 7.26 Hz, 3H) 1.10-1.23 (m, 2H) 1.16 (s, 3H) 1.19 (d, J = 6.12 Hz, 3H) 1.24 (d, J = 6.50 Hz, 3H) 1.31 (s, 3H) 1.40 (dd, J = 15.10, 4.78 Hz, 1H) 1.60-1.65 (m, 1H) 1.78-1.87 (m, 1H) 2.15-2.34 (m, 4H) 2.27 (s, 6H) 2.35-2.52 (m, 3H) 2.44 (s, 3H) 2.71-2.79 (m, 1H) 2.94 (t, J = 9.56 Hz, 1H) 3.08-3.17 (m, 2H) 3.18 (s, 3H) 3.24 (s, 3H) 3.30-3.37 (m, 1H) 3.39-3.47 (m, 1H) 3.65 (d, J = 8.03 Hz, 1H) 3.84-3.93 (m, 1H) 3.95-4.02 (m, 1H) 4.03-4.08 (m, 1H) 4.34 (d, J = 7.28 Hz, 1H) 4.50-4.66 (m, 2H) 4.75 (d, J = 4.59 Hz, 1H) 5.05 (br. s., 1H) 7.45-7.52 (m, 1H) 7.65-7.70 (m, 1H) 7.71-7.76 (m, 1H) 8.03 (s, 1H) 8.27 (dd, J = 8.03, 1.53 Hz, 1H) |

TABLE 15-continued formula (AB)

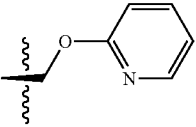

| Example | R | ESI MS (M + H) | ¹H—NMR, CDCl₃, δ (ppm) |
|---|---|---|---|
| 608 | 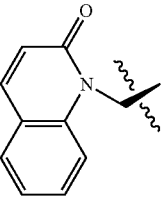 | 798.5 | (500 MHz): 0.79-0.87 (m, 6H) 1.08 (d, J = 7.40 Hz, 3H) 1.13 (d, J = 7.40 Hz, 3H) 1.15-1.25 (m, 2H) 1.20-1.22 (m, 3H) 1.22 (s, 3H) 1.27 (d, J = 6.31 Hz, 3H) 1.32 (s, 3H) 1.52 (dd, J = 15.08, 4.94 Hz, 1H) 1.59-1.68 (m, 1H) 1.81-1.89 (m, 1H) 2.22-2.37 (m, 5H) 2.28 (s, 6H) 2.37 (s, 3H) 2.42-2.51 (m, H) 2.72-2.83 (m, 1H) 2.93-3.04 (m, 2H) 3.14-3.23 (m, 1H) 3.22 (s, 3H) 3.31 (s, 3H) 3.35-3.43 (m, 1H) 3.42-3.52 (m, 1H) 3.69 (d, J = 7.95 Hz, 1H) 3.99-4.08 (m, 1H) 4.11-4.17 (m, 1H) 4.38 (d, J = 7.13 Hz, 1H) 4.39-4.51 (m, 2H) 4.91 (d, J = 4.66 Hz, 1H) 5.11 (br. s., 1H) 6.65-6.71 (m, 1H) 6.82-6.89 (m, 1H) 7.49-7.58 (m, 1H) 8.08-8.15 (m, 1H) |
| 609 | 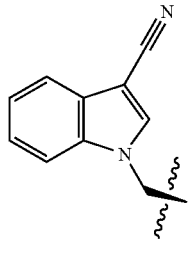 | 848.6 | (500 MHz): 0.22-0.49 (m, 3H) 0.86 (t, J = 6.58 Hz, 6H) 0.99 (d, J = 7.40 Hz, 3H) 1.11-1.25 (m, 2H) 1.16 (s, 3H) 1.19 (d, J = 6.03 Hz, 3H) 1.22 (d, J = 6.31 Hz, 3H) 1.30 (s, 3H) 1.40 (dd, J = 15.22, 3.98 Hz, 1H) 1.60-1.67 (m, 1H) 1.82-1.91 (m, 1H) 2.14-2.30 (m, 4H) 2.27 (s, 6H) 2.33-2.61 (m, 4H) 2.48 (s, 3H) 2.93 (t, J = 9.60 Hz, 1H) 3.01 (d, J = 14.54 Hz, 1H) 3.17 (s, 3H) 3.18-3.25 (m, 2H) 3.22 (s, 3H) 3.40-3.47 (m, 1H) 3.63 (d, J = 7.68 Hz, 1H) 3.91-4.01 (m, 2H) 4.34 (d, J = 6.86 Hz, 1H) 4.45-4.58 (m, 1H) 4.59-4.67 (m, 1H) 4.69-4.73 (m, 1H) 5.17-5.28 (m, 1H) 6.65 (d, J = 9.60 Hz, 1H) 7.20 (t, J = 7.40 Hz, 1H) 7.47-7.52 (m, 1H) 7.54-7.59 (m, 1H) 7.64 (d, J = 9.32 Hz, 2H) |
| 610 | 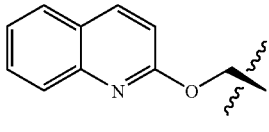 | 845.6 | (500 MHz): 0.49-0.58 (m, 3H) 0.84 (d, J = 7.13 Hz, 3H) 0.87 (d, J = 6.58 Hz, 3H) 1.03 (d, J = 7.40 Hz, 3H) 1.07-1.27 (m, 2H) 1.18 (s, 3H) 1.20 (d, J = 6.31 Hz, 3H) 1.24 (d, J = 6.31 Hz, 3H) 1.31 (s, 3H) 1.43 (dd, J = 15.22, 4.80 Hz, 1H) 1.60-1.67 (m, 1H) 1.81-1.88 (m, 1H) 2.17-2.31 (m, 4H) 2.27 (s, 6H) 2.31-2.39 (m, 1H) 2.39-2.59 (m, 3H) 2.45 (s, 3H) 2.95 (t, J = 9.74 Hz, 1H) 3.09-3.14 (m, 1H) 3.15-3.21 (m, 1H) 3.17 (s, 3H) 3.21-3.32 (m, 1H) 3.25 (s, 3H) 3.37-3.50 (m, 1H) 3.64 (d, J = 7.95 Hz, 1H) 3.89-3.95 (m, 1H) 3.95-4.02 (m, 1H) 4.27 (dd, J = 14.54, 3.02 Hz, 1H) 4.34 (d, J = 7.40 Hz, 1H) 4.43-4.53 (m, 1H) 4.71 (d, J = 4.11 Hz, 1H) 4.97-5.12 (m, 1H) 7.26-7.29 (m, 1H) 7.31-7.36 (m, 1H) 7.43 (d, J = 8.23 Hz, 1H) 7.60 (s, 1H) 7.72 (d, J = 7.68 Hz, 1H) |
| 611 | 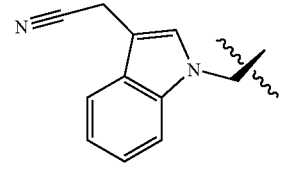 | 848.6 | (500 MHz): 0.84 (d, J = 6.88 Hz, 3H) 0.87 (d, J = 6.88 Hz, 3H) 1.08 (d, J = 6.88 Hz, 3H) 1.10-1.25 (m, 2H) 1.15 (d, J = 6.88 Hz, 3H) 1.21-1.24 (m, 6H) 1.28 (d, J = 6.12 Hz, 3H) 1.33 (s, 3H) 1.53 (dd, J = 14.91, 4.97 Hz, 1H) 1.62-1.69 (m, 1H) 1.82-1.92 (m, 1H) 2.22-2.40 (m, 5H) 2.29 (s, 6H) 2.42 (s, 3H) 2.45-2.52 (m, 2H) 2.76-2.87 (m, 1H) 2.94-3.06 (m, 2H) 3.16-3.24 (m, 1H) 3.24 (s, 3H) 3.32 (s, 3H) 3.37-3.44 (m, 1H) 3.45-3.52 (m, 1H) 3.71 (d, J = 7.65 Hz, 1H) 3.99-4.09 (m, 1H) 4.11-4.17 (m, 1H) 4.39 (d, J = 7.65 Hz, 1H) 4.53-4.62 (m, 1H) 4.70 (dd, J = 11.09, 4.97 Hz, 1H) 4.92 (d, J = 5.35 Hz, 1H) 5.12-5.25 (m, 1H) 6.86 (d, J = 9.17 Hz, 1H) 7.37 (t, J = 7.65 Hz, 1H) 7.57-7.64 (m, 1H) 7.70 (d, J = 7.65 Hz, 1H) 7.82 (d, J = 8.41 Hz, 1H) 7.97 (d, J = 9.17 Hz, 1H) |
| 612 |  | 859.7 | (500 MHz): 0.47-0.61 (m, 3H) 0.84 (d, J = 7.13 Hz, 3H) 0.86 (d, J = 6.86 Hz, 3H) 1.03 (d, J = 7.40 Hz, 3H) 1.12 (d, J = 13.71 Hz, 3H) 1.18 (s, 3H) 1.18-1.23 (m, 1H) 1.20 (d, J = 6.03 Hz, 3H) 1.24 (d, J = 6.31 Hz, 3H) 1.31 (s, 3H) 1.42 (dd, J = 15.08, 4.39 Hz, 1H) 1.56-1.73 (m, 1H) 1.80-1.90 (m, 1H) 2.14-2.39 (m, 6H) 2.31 (s, 6H) 2.45 (s, 3H) 2.47-2.59 (m, 2H) 2.90-2.99 (m, 1H) 3.07 (d, J = 13.71 Hz, 1H) 3.18 (s, 3H) 3.19-3.23 (m, 1H) 3.25 (s, 3H) 3.40-3.48 (m, 2H) 3.64 (d, J = 7.95 Hz, 1H) 3.80 (s, 2H) 3.91-4.01 (m, 2H) 4.16-4.24 (m, 1H) 4.35 (d, J = 7.13 Hz, 1H) 4.39-4.50 (m, 2H) 4.73 (d, J = 4.94 Hz, 1H) 5.01-5.11 (m, 1H) 7.11 (s, 1H) 7.13-7.18 (m, 1H) 7.23-7.29 (m, 1H) 7.37 (d, J = 8.23 Hz, 1H) 7.54 (d, J = 7.95 Hz, 1H) |

TABLE 15-continued formula (AB)

| Example | R | ESI MS (M + H) | $^1$H—NMR, CDCl$_3$, δ (ppm) |
|---|---|---|---|
| 613 | (1-oxo-5-cyano-pyridin-2-yl)ethyl group | 823.7 | (500 MHz): 0.81 (d, J = 7.13 Hz, 3H) 0.83 (d, J = 6.31 Hz, 3H) 0.96 (d, J = 7.40 Hz, 3H) 1.08 (d, J = 7.13 Hz, 3H) 1.10-1.23 (m, 2H) 1.18-1.22 (m, 6H) 1.25 (d, J = 6.31 Hz, 3H) 1.31 (s, 3H) 1.47 (dd, J = 15.08, 4.94 Hz, 1H) 1.58-1.67 (m, 1H) 1.76-1.89 (m, 1H) 2.19-2.32 (m, 4H) 2.26 (s, 6H) 2.31-2.38 (m, 1H) 2.37-2.52 (m, 2H) 2.40 (s, 3H) 2.70-2.80 (m, 1H) 2.91-3.01 (m, 1H) 3.06-3.13 (m, 1H) 3.14-3.19 (m, 1H) 3.18 (s, 3H) 3.29 (s, 3H) 3.29-3.34 (m, 1H) 3.39-3.50 (m, 1H) 3.66 (d, J = 8.23 Hz, 1H) 3.70-3.79 (m, 1H) 3.96-4.04 (m, 1H) 4.05-4.10 (m, 1H) 4.35 (d, J = 7.13 Hz, 1H) 4.51-4.72 (m, 1H) 4.80 (d, J = 4.39 Hz, 1H) 4.94-5.06 (m, 1H) 6.54 (d, J = 9.60 Hz, 1H) 7.36 (dd, J = 9.60, 2.47 Hz, 1H) 7.83-7.90 (m, 1H) |
| 614 | (indol-1-yl)ethyl group | 820.6 | (500 MHz): 0.44-0.56 (m, 3H) 0.84 (d, J = 7.13 Hz, 3H) 0.86 (d, J = 6.86 Hz, 3H) 1.03 (d, J = 7.40 Hz, 3H) 1.08-1.15 (m, 1H) 1.17 (s, 3H) 1.17-1.24 (m, 1H) 1.20 (d, J = 6.03 Hz, 3H) 1.24 (d, J = 6.31 Hz, 3H) 1.31 (s, 3H) 1.41 (dd, J = 15.36, 4.66 Hz, 1H) 1.59-1.72 (m, 1H) 1.79-1.89 (m, 1H) 2.17-2.28 (m, 4H) 2.28 (s, 6H) 2.33-2.39 (m, 1H) 2.39-2.46 (m, 1H) 2.45 (s, 3H) 2.48-2.57 (m, 2H) 2.94 (t, J = 9.60 Hz, 1H) 3.06 (d, J = 14.81 Hz, 1H) 3.18 (s, 3H) 3.18 (s, 1H) 3.25 (s, 3H) 3.38-3.52 (m, 2H) 3.64 (d, J = 7.95 Hz, 1H) 3.92-3.96 (m, 1H) 3.96-4.02 (m, 1H) 4.21 (dd, J = 14.54, 3.29 Hz, 1H) 4.35 (d, J = 7.13 Hz, 1H) 4.42-4.51 (m, 1H) 4.73 (d, J = 4.66 Hz, 1H) 5.06-5.13 (m, 1H) 6.44-6.48 (m, 1H) 7.04-7.10 (m, 2H) 7.16-7.22 (m, 1H) 7.32-7.38 (m, 1H) 7.54-7.61 (m, 1H) |
| 615 | (2-cyano-pyrrol-1-yl)ethyl group | 795.6 | (500 MHz): 0.83 (d, J = 7.26 Hz, 3H) 0.86 (d, J = 6.50 Hz, 3H) 0.89 (d, J = 6.88 Hz, H) 1.08 (d, J = 7.26 Hz, 3H) 1.09-1.14 (m, 1H) 1.19-1.25 (m, 1H) 1.19-1.22 (m, 3H) 1.21 (s, 3H) 1.26 (d, J = 6.12 Hz, 3H) 1.32 (s, 3H) 1.48 (dd, J = 15.29, 4.97 Hz, 1H) 1.61-1.67 (m, 1H) 1.81-1.90 (m, 1H) 2.22-2.35 (m, 5H) 2.28 (s, 6H) 2.41 (s, 3H) 2.42-2.48 (m, 1H) 2.48-2.55 (m, 1H) 2.69-2.77 (m, 1H) 2.98 (t, J = 9.56 Hz, 1H) 3.06 (d, J = 13.76 Hz, 1H) 3.16-3.20 (m, 1H) 3.21 (s, 3H) 3.29 (s, 3H) 3.40-3.50 (m, 2H) 3.67 (d, J = 8.03 Hz, 1H) 3.97-4.05 (m, 2H) 4.17-4.23 (m, 1H) 4.25-4.33 (m, 1H) 4.37 (d, J = 7.26 Hz, 1H) 4.82 (d, J = 4.59 Hz, 1H) 4.97-5.08 (m, 1H) 6.14 (dd, J = 3.82, 2.68 Hz, 1H) 6.76 (dd, J = 3.82, 1.53 Hz, 1H) 6.85 (dd, J = 2.68, 1.53 Hz, 1H) |
| 616 | (2-oxo-1,6-naphthyridin-1-yl)ethyl group | 849.6 | (500 MHz): 0.85 (d, J = 7.13 Hz, 3H) 0.87 (d, J = 6.58 Hz, 3H) 1.00 (d, J = 7.13 Hz, 3H) 1.16 (s, 3H) 1.17-1.20 (m, 1H) 1.19 (d, J = 6.03Hz, 3H) 1.21-1.24 (m, 1H) 1.22 (d, J = 6.31 Hz, 3H) 1.24 (s, 3H) 1.30 (s, 3H) 1.41 (dd, J = 15.50, 4.53 Hz, 1H) 1.58-1.66 (m, 1H) 1.82-1.95 (m, 1H) 2.14-2.25 (m, 4H) 2.26 (s, 6H) 2.36-2.59 (m, 4H) 2.47 (s, 3H) 2.93 (t, J = 8.91 Hz, 1H) 3.04 (d, J = 14.54 Hz, 1H) 3.14-3.20 (m, 1H) 3.17 (s, 3H) 3.22 (s, 3H) 3.36-3.52 (m, 2H) 3.63 (d, J = 7.95 Hz, 1H) 3.87-4.06 (m, 2H) 4.34 (d, J = 7.13Hz, 1H) 4.36-4.46 (m, 1H) 4.51-4.60 (m, 1H) 4.68-4.76 (m, 1H) 5.13-5.24 (m, 1H) 6.71 (d, J = 9.32 Hz, 1H) 7.44-7.50 (m, 1H) 7.71 (d, J = 9.32 Hz, 1H) 8.60 (d, J = 6.31 Hz, 1H) 8.73 (s, 1H) |

TABLE 15-continued formula (AB)

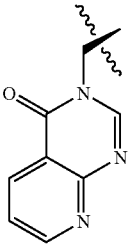

| Example | R | ESI MS (M + H) | ¹H—NMR, CDCl₃, δ (ppm) |
|---|---|---|---|
| 617 | 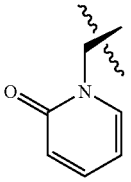 | 850.6 | (500 MHz): 0.81 (d, J = 7.13 Hz, 3H) 0.83-0.89 (m, 3H) 1.06 (d, J = 7.40 Hz, 3H) 1.07-1.13 (m, 1H) 1.16 (s, 3H) 1.17-1.24 (m, 1H) 1.19 (d, J = 6.03Hz, 3H) 1.23 (d, J = 6.31 Hz, 3H) 1.31 (s, 3H) 1.39 (dd, J = 15.08, 4.39 Hz, 1H) 1.59-1.66 (m, 1H) 1.78-1.88 (m, 1H) 2.18-2.30 (m, 4H) 2.26 (s, 6H) 2.34-2.52 (m, 3H) 2.44 (s, 3H) 2.72-2.81 (m, 1H) 2.93 (t, J = 9.46 Hz, 1H) 3.09-3.20 (m, 2H) 3.17 (s, 3H) 3.24 (s, 3H) 3.26-3.38 (m, 1H) 3.39-3.49 (m, 1H) 3.64 (d, J = 8.23 Hz, 1H) 3.88-4.05 (m, 3H) 4.34 (d, J = 7.13 Hz, 1H) 4.49-4.62 (m, 1H) 4.73 (d, J = 4.39 Hz, 1H) 4.96-5.11 (m, 1H) 7.27 (m, 3H) 7.44 (dd, J = 7.95, 4.66 Hz, 1H) 8.26 (s, 1H) 8.60 (dd, J = 7.95, 1.92 Hz, 1H) 8.97 (dd, J = 4.39, 1.92 Hz, 1H) |
| 618 | 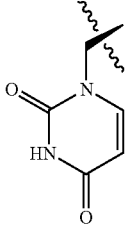 | 798.4 | (600 MHz): 0.78-0.84 (m, 6H) 0.87 (d, J = 6.42 Hz, 3H) 1.07 (d, J = 7.34 Hz, 3H) 1.06-1.11 (m, 1H) 1.16-1.25 (m, 1H) 1.19 (s, 3H) 1.21 (d, J = 5.96 Hz, 3H) 1.26 (d, J = 6.42Hz, 3H) 1.32 (s, 3H) 1.43-1.49 (m, 1H) 1.61-1.67 (m, 1H) 1.77-1.84 (m, 1H) 2.22-2.49 (m, 7H) 2.27 (s, 6H) 2.41 (s, 3H) 2.66-2.72 (m, 1H) 2.97 (t, J = 9.86 Hz, 1H) 3.06-3.11 (m, 1H) 3.14-3.20 (m, 1H) 3.19 (s, 3H) 3.27 (s, 3H) 3.40-3.49 (m, 2H) 3.63-3.72 (m, 2H) 3.97-4.04 (m, 1H) 4.07-4.11 (m, 1H) 4.35 (d, J = 7.34 Hz, 1H) 4.60-4.69 (m, 1H) 4.81 (d, J = 4.58 Hz, 1H) 5.02-5.08 (m, 1H) 6.09-6.14 (m, 1H) 6.51 (d, J = 8.71 Hz, 1H) 7.26-7.31 (m, 2H) |
| 619 | 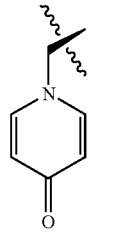 | 815.4 | (600 MHz): 0.78-0.85 (m, 6H) 1.03 (d, J = 7.34 Hz, 3H) 1.06-1.24 (m, 8H) 1.08 (d, J = 7.34 Hz, 3H) 1.27 (d, J = 6.42 Hz, 3H) 1.32 (s, 3H) 1.50 (dd, J = 15.13, 4.59 Hz, 1H) 1.61-1.68 (m, 1H) 1.79-1.87 (m, 1H) 2.20-2.34 (m, 5H) 2.28 (s, 6H) 2.38 (s, 3H) 2.42-2.50 (m, 2H) 2.70-2.76 (m, 1H) 2.99 (t, J = 9.86 Hz, 1H) 3.06 (d, J = 15.59 Hz, 1H) 3.15-3.22 (m, 1H) 3.20 (s, 3H) 3.29 (s, 3H) 3.40-3.48 (m, 2H) 3.62-3.70 (m, 2H) 3.99-4.05 (m, 1H) 4.07-4.13 (m, 1H) 4.23-4.30 (m, 1H) 4.36 (d, J = 7.34 Hz, 1H) 4.84 (d, J = 4.59 Hz, 1H) 4.96-5.04 (m, 1H) 5.66 (d, J = 8.25 Hz, 1H) 7.22 (d, J = 7.79 Hz, 1H) 8.64 (br. s., 1H) |
| 620 | 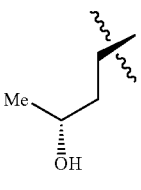 | 798.4 | (600 MHz): 0.79-0.88 (m, 6H) 0.94 (d, J = 6.88 Hz, 3H) 1.08 (d, J = 7.34 Hz, 3H) 1.08 (s, 8H) 1.27 (d, J = 6.42 Hz, 3H) 1.32 (s, 3H) 1.47-1.53 (m 1H) 1.58-1.68 (m, 1H) 1.80-1.87 (m, 1H) 2.17-2.53 (m, 7H) 2.28 (s, 6H) 2.39 (s, 3H) 2.68-2.74 (m, 1H) 2.98 (t, J = 10.09 Hz, 1H) 3.09-3.22 (m, 2H) 3.20 (s, 3H) 3.29 (s, 3H) 3.31-3.48 (m, 2H) 3.67 (d, J = 8.25 Hz, 1H) 3.88-4.06 (m, 4H) 4.36 (d, J = 7.34 Hz, 1H) 4.82 (d, J = 4.59 Hz, 1H) 4.91-5.01 (m, 1H) 6.35 (d, J = 7.79 Hz, 2H) 7.24-7.27 (m, 2H) |
| 621 |  | 763.4 | (500 MHz): 0.79-0.86 (m, 6H) 1.10 (d, J = 7.26 Hz, 3H) 1.16 (d, J = 7.26 Hz, 3H) 1.17-1.24 (m, 2H) 1.19 (d, J = 6.12 Hz, 3H) 1.22 (d, J = 6.12 Hz, 3H) 1.23 (s, 3H) 1.28 (d, J = 6.50 Hz, 3H) 1.32 (s, 3H) 1.35-1.43 (m, 1H) 1.45-1.50 (m, 1H) 1.54 (dd, J = 15.29, 4.97 Hz, 1H) 1.57-1.71 (m, 2H) 1.73-1.81 (m, 1H) 1.82-1.90 (m, 1H) 2.11-2.21 (m, 1H) 2.23-2.39 (m, 4H) 2.29 (s, 6H) 2.38 (s, 3H) 2.43-2.53 (m, 2H) 2.76-2.84 (m, 1H) 2.92 (d, J = 14.91 Hz, 1H) 3.01 (t, J = 9.94 Hz, 1H) 3.16-3.23 (m, 1H) 3.23 (s, 3H) 3.32 (s, 3H) 3.35-3.43 (m, 1H) 3.44-3.51 (m, 1H) 3.70 (d, J = 8.03 Hz, 1H) 3.76-3.84 (m, 1H) 4.01-4.09 (m, 1H) 4.14 (br. s, 1H) 4.39 (d, J = 7.26 Hz, 1H) 4.73 (br. s., 1H) 4.93 (d, J = 4.59 Hz, 1H) |

TABLE 15-continued formula (AB)

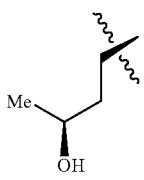

| Example | R | ESI MS (M + H) | $^1$H—NMR, CDCl$_3$, δ (ppm) |
|---|---|---|---|
| 622 | 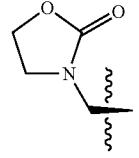 | 763.4 | (500 MHz): 0.79-0.86 (m, 6H) 1.10 (d, J = 7.64 Hz, 3H) 1.16 (d, J = 7.26 Hz, 3H) 1.18 (d, J = 6.12 Hz, 3H) 1.20-1.26 (m, 2H) 1.22 (d, J = 6.12 Hz, 3H) 1.22-1.24 (m, 3H) 1.28 (d, J = 6.12 Hz, 3H) 1.32 (s, 3H) 1.37-1.45 (m, 1H) 1.45-1.73 (m, 4H) 1.78-1.95 (m, 2H) 2.11-2.20 (m, 1H) 2.22-2.36 (m, 4H) 2.29 (s, 6H) 2.38 (s, 3H) 2.41-2.53 (m, 2H) 2.75-2.84 (m, 1H) 2.93 (d, J = 13.76 Hz, 1H) 3.01 (t, J = 9.75 Hz, 1H) 3.16-3.22 (m, 1H) 3.23 (s, 3H) 3.32 (s, 3H) 3.36-3.43 (m, 1H) 3.43-3.51 (m, 1H) 3.70 (d, J = 8.03 Hz, 1H) 3.77-3.85 (m, 1H) 4.00-4.09 (m, 1H) 4.15 (br. s., 1H) 4.39 (d, J = 6.88 Hz, 1H) 4.75 (br. s., 1H) 4.93 (d, J = 4.59 Hz, 1H) |
| 623 | 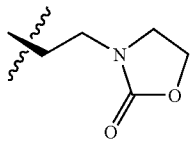 | 790.4 | (500 MHz): 0.84-0.92 (m, 6H) 1.08 (d, J = 7.40 Hz, 3H) 1.15 (d, J = 7.40 Hz, 3H) 1.19-1.29 (m, 2H) 1.21 (d, J = 6.03 Hz, 3H) 1.22-1.25 (m, 3H) 1.28 (d, J = 6.31 Hz, 3H) 1.31 (s, 3H) 1.54 (dd, J = 15.08, 4.94 Hz, 1H) 1.58-1.70 (m, 1H) 1.86-1.97 (m, 1H) 2.20-2.31 (m, 3H) 2.28-2.31 (m, 6H) 2.32-2.38 (m, 2H) 2.34-2.35 (m, 3H) 2.40-2.49 (m, 1H) 2.50-2.58 (m, 1H) 2.76-2.85 (m, 1H) 2.89 (d, J = 14.26 Hz, 1H) 2.97-3.04 (m, 1H) 3.20 (dd, J = 10.15, 7.13 Hz, 1H) 3.25 (s, 3H) 3.26-3.30 (m, 1H) 3.31 (s, 3H) 3.44-3.50 (m, 1H) 3.50-3.60 (m, 3H) 3.68-3.77 (m, 1H) 3.98-4.08 (m, 2H) 4.22-4.29 (m, 2H) 4.41 (d, J = 7.13 Hz, 1H) 4.92 (d, J = 4.39 Hz, 1H) 5.09 (br. s., 1H) |
| 624 | 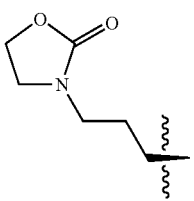 | 804.4 | (600 MHz): 0.77-0.85 (m, 6H) 1.09 (d, J = 7.34 Hz, 3H) 1.17 (d, J = 7.34 Hz, 3H) 1.19-1.26 (m, 2H) 1.21 (d, J = 5.96 Hz, 3H) 1.22 (s, 3H) 1.28 (d, J = 6.42 Hz, 3H) 1.31 (s, 3H) 1.52 (dd, J = 15.36, 4.81 Hz, 1H) 1.61-1.69 (m, 1H) 1.72-1.88 (m, 2H) 1.99-2.10 (m, 1H) 2.10-2.21 (m, 1H) 2.21-2.36 (m, 4H) 2.28 (s, 6H) 2.37 (s, 3H) 2.41-2.50 (m, 2H) 2.75-2.83 (m, 1H) 2.96-3.04 (m, 2H) 3.17-3.22 (m, 1H) 3.21 (s, 3H) 3.23-3.30 (m, 2H) 3.31 (s, 3H) 3.37-3.43 (m, 1H) 3.43-3.49 (m, 1H) 3.55 (t, J = 8.25 Hz, 2H) 3.69 (d, J = 8.25 Hz, 1H) 4.00-4.07 (m, 1H) 4.09-4.18 (m, 1H) 4.28-4.35 (m, 2H) 4.37 (d, J = 7.34 Hz, 1H) 4.72-4.79 (m, 1H) 4.90 (d, J = 4.58 Hz, 1H) |
| 625 | 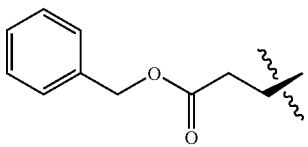 | 818.5 | (500 MHz): 0.77-0.87 (m, 6H) 1.10 (d, J = 7.26 Hz, 3H) 1.16 (d, J = 7.26 Hz, 3H) 1.19-1.28 (m, 8H) 1.28 (d, J = 6.50 Hz, 3H) 1.32 (s, 3H) 1.45-1.70 (m, 5H) 1.72-1.81 (m, 1H) 1.81-1.88 (m, 1H) 2.09-2.19 (m, 1H) 2.21-2.38 (m, 4H) 2.29 (s, 6H) 2.36 (s, 3H) 2.39-2.52 (m, 2H) 2.75-2.83 (m, 1H) 2.88-2.96 (m, 1H) 2.98-3.04 (m, 1H) 3.17-3.22 (m, 1H) 3.23 (s, 3H) 3.24-3.29 (m, 2H) 3.32 (s, 3H) 3.35-3.42 (m, 1H) 3.43-3.49 (m, 1H) 3.51-3.56 (m, 2H) 3.70 (d, J = 8.03 Hz, 1H) 3.99-4.09 (m, 1H) 4.10-4.18 (m, 1H) 4.32 (t, J = 8.03 Hz, 2H) 4.39 (d, J = 7.26 Hz, 1H) 4.74 (br. s., 1H) 4.93 (d, J = 4.59 Hz, 1H) |
| 626 |  | 853.4 | (500 MHz): 0.77-0.84 (m, 6H) 1.08 (d, J = 7.40 Hz, 3H) 1.11 (d, J = 7.68 Hz, 3H) 1.20-1.25 (m, 2H) 1.22 (d, J = 6.31 Hz, 3H) 1.23 (s, 3H) 1.28 (d, J = 6.31 Hz, 3H) 1.32 (s, 3H) 1.53 (dd, J = 15.22, 4.80 Hz, 1H) 1.57-1.65 (m, 1H) 1.77-1.92 (m, 2H) 2.07-2.19 (m, 1H) 2.20-2.53 (m, 18H) 2.74-2.82 (m, 1H) 2.93-3.03 (m, 2H) 3.17-3.25 (m, 1H) 3.22 (s, 3H) 3.31 (s, 3H) 3.35-3.41 (m, 1H) 3.42-3.50 (m, 1H) 3.68 (d, J = 7.95 Hz, 1H) 3.99-4.08 (m, 1H) 4.09-4.17 (m, 1H) 4.38 (d, J = 7.13 Hz, 1H) 4.66-4.76 (m, 1H) 4.91 (d, J = 4.39 Hz, 1H) 5.08-5.13 (m, 2H) 7.28-7.39 (m, 5H) |

TABLE 15-continued formula (AB)

| Example | R | ESI MS (M + H) | ¹H—NMR, CDCl₃, δ (ppm) |
|---|---|---|---|
| 627 | H₂N-C(=O)-CH₂-CH₂-CH(Me)- | 762.5 | (500 MHz): 0.79-0.87 (m, 6H) 1.09 (d, J = 7.40 Hz, 3H) 1.16 (d, J = 7.40 Hz, 3H) 1.20-1.25 (m, 2H) 1.21 (d, J = 6.03 Hz, 3H) 1.23 (s, 3H) 1.28 (d, J = 6.31 Hz, 3H) 1.31 (s, 3H) 1.54 (dd, J = 15.08, 4.94 Hz, 1H) 1.62-1.69 (m, 1H) 1.80-1.96 (m, 2H) 2.00-2.11 (m, 1H) 2.12-2.34 (m, 7H) 2.28 (s, 6H) 2.38 (s, 3H) 2.42-2.51 (m, 2H) 2.74-2.84 (m, 1H) 2.91-2.97 (m, 1H) 3.00 (t, J = 9.87 Hz, 1H) 3.15-3.22 (m, 1H) 3.23 (s, 3H) 3.32 (s, 3H) 3.35-3.41 (m, 1H) 3.42-3.50 (m, 1H) 3.70 (d, J = 8.23 Hz, 1H) 3.99-4.08 (m, 1H) 4.12 (br. s., 1H) 4.39 (d, J = 7.40 Hz, 1H) 4.79 (br. s., 1H) 4.91 (d, J = 4.66 Hz, 1H) 5.35 (br. s., 1H) 5.66 (br. s., 1H) |
| 628 | N≡C-(CH₂)₄-CH(Me)- | 772.5 | (500 MHz): 0.77-0.86 (m, 6H) 1.09 (d, J = 7.64 Hz, 3H) 1.17 (d, J = 7.26 Hz, 3H) 1.20-1.28 (m, 8H) 1.28 (d, J = 6.12 Hz, 3H) 1.32 (s, 3H) 1.38-1.73 (m, 6H) 1.75-1.91 (m, 2H) 2.09-2.20 (m, 1H) 2.22-2.41 (m, 16H) 2.41-2.53 (m, 2H) 2.75-2.85 (m, 1H) 2.89-2.96 (m, 1H) 3.00 (t, J = 9.94 Hz, 1H) 3.15-3.21 (m, 1H) 3.23 (s, 3H) 3.32 (s, 3H) 3.34-3.42 (m, 1H) 3.43-3.50 (m, 1H) 3.70 (d, J = 8.03 Hz, 1H) 3.99-4.09 (m, 1H) 4.11-4.17 (m, 1H) 4.39 (d, J = 7.26 Hz, 1H) 4.74 (br. s., 1H) 4.93 (d, J = 4.59 Hz, 1H) |
| 629 | Me-C(=O)-CH₂-CH₂-CH(Me)- | 761.5 | (500 MHz): 0.77-0.87 (m, 6H) 1.09 (d, J = 7.13 Hz, 3H) 1.12-1.27 (m, 2H) 1.17 (d, J = 7.40 Hz, 3H) 1.20-1.25 (m, 6H) 1.28 (d, J = 6.31 Hz, 3H) 1.31 (s, 3H) 1.46-1.63 (m, 2H) 1.77-1.91 (m, 2H) 1.92-2.05 (m, 1H) 2.13 (s, 3H) 2.14-2.19 (m, 1H) 2.20-2.40 (m, 13H) 2.42-2.55 (m, 4H) 2.76-2.83 (m, 1H) 2.89-2.96 (m, 1H) 3.00 (t, J = 9.87 Hz, 1H) 3.16-3.26 (m, 1H) 3.22 (s, 3H) 3.32 (s, 3H) 3.34-3.42 (m, 1H) 3.43-3.51 (m, 1H) 3.69 (d, J = 7.95 Hz, 1H) 3.99-4.08 (m, 1H) 4.10-4.18 (m, 1H) 4.39 (d, J = 7.13 Hz, 1H) 4.65-4.76 (m, 1H) 4.90-4.95 (m, 1H) |
| 630 | PhCH₂-O-CH(Me)-CH₂-CH(Me)- | 853.6 | (500 MHz): 0.76-0.84 (m, 6H) 1.09 (d, J = 7.40 Hz, 3H) 1.11-1.25 (m, 8H) 1.14 (d, J = 7.40 Hz, 3H) 1.18 (dd, J = 6.17, 3.43 Hz, 3H) 1.28 (d, J = 6.31 Hz, 3H) 1.32 (s, 3H) 1.33-1.45 (m, 1H) 1.45-1.77 (m, 5H) 1.79-1.91 (m, 1H) 2.07-2.19 (m, 1H) 2.20-2.38 (m, 13H) 2.39-2.56 (m, 2H) 2.75-2.83 (m, 1H) 2.86-2.95 (m, 1H) 2.97-3.03 (m, 1H) 3.14-3.25 (m, 1H) 3.22 (s, 3H) 3.32 (s, 3H) 3.36-3.43 (m, 1H) 3.44-3.55 (m, 2H) 3.70 (d, J = 7.95 Hz, 1H) 3.98-4.09 (m, 1H) 4.12-4.19 (m, 1H) 4.38 (d, J = 7.13 Hz, 1H) 4.42 (d, J = 11.79 Hz, 1H) 4.56 (d, J = 11.79 Hz, 1H) 4.63-4.74 (m, 1H) 4.93 (d, J = 4.66 Hz, 1H) 7.26-7.35 (m, 5H) |
| 631 | (pyrrol-1-yl)-CH₂-CH(Me)-CH₂- | 784.6 | (500 MHz): 0.73-0.84 (m, 6H) 1.11 (d, J = 7.26 Hz, 3H) 1.19-1.31 (m, 2H) 1.19-1.22 (m, 3H) 1.22 (d, J = 6.12 Hz, 3H) 1.24 (s, 3H) 1.29 (d, J = 6.12Hz, 3H) 1.33 (s, 3H) 1.53-1.57 (m, 1H) 1.63-1.71 (m, 1H) 1.79-1.87 (m, 1H) 1.87-1.96 (m, 1H) 2.04-2.12 (m, 1H) 2.22-2.38 (m, 5H) 2.30 (s, 6H) 2.35 (s, 3H) 2.38-2.45 (m, 1H) 2.46-2.54 (m, 1H) 2.82-2.89 (m, 1H) 2.94-3.05 (m, 2H) 3.17-3.24 (m, 1H) 3.22 (s, 3H) 3.33 (s, 3H) 3.38-3.44 (m, 1H) 3.44-3.51 (m, 1H) 3.70 (d, J = 8.03 Hz, 1H) 3.78-3.87 (m, 1H) 3.93-4.01 (m, 1H) 4.02-4.10 (m, 1H) 4.14-4.21 (m, 1H) 4.39 (d, J = 6.88 Hz, 1H) 4.67-4.75 (m, 1H) 4.94 (d, J = 4.20 Hz, 1H) 6.10-6.16 (m, 2H) 6.58-6.63 (m, 2H) |
| 632 | -CH(Me)-CH₂-CH₂-CH₂-(pyrrol-1-yl) | 798.6 | (500 MHz): 0.77-0.84 (m, 6H) 1.09 (d, J = 7.26 Hz, 3H) 1.10-1.13 (m, 1H) 1.16 (d, J = 7.26 Hz, 3H) 1.22 (d, J = 6.12 Hz, 3H) 1.23-1.26 (m, 1H) 1.23 (s, 3H) 1.29 (d, J = 6.12 Hz, 3H) 1.32 (s, 3H) 1.39-1.48 (m, 1H) 1.49-1.88 (m, 6H) 2.04-2.15 (m, 1H) 2.19-2.38 (m, 13 H) 2.39-2.44 (m, 1H) 2.45-2.55 (m, 1H) 2.75-2.84 (m, 1H) 2.87-2.95 (m, 1H) 2.97-3.04 (m, 1H) 3.19-3.28 (m, 1H) 3.23 (s, 3H) 3.32 (s, 3H) 3.34-3.42 (m, 1H) 3.43-3.52 (m, 1H) 3.70 (d, J = 8.03 Hz, 1H) 3.81-3.95 (m, 2H) 4.00-4.08 (m, 1H) 4.11-4.17 (m, 1H) 4.39 (d, J = 7.26 Hz, 1H) 4.69-4.78 (m, 1H) 4.93 (d, J = 4.20 Hz, 1H) 6.00-6.21 (m, 2H) 6.55-6.67 (m, 2H) |

TABLE 15-continued formula (AB)

| Example | R | ESI MS (M + H) | ¹H—NMR, CDCl₃, δ (ppm) |
|---|---|---|---|
| 633 | benzyl carbamate-CH(Me)- linker | 882.5 | (500 MHz): 0.81 (d, J = 6.88 Hz, 6H) 1.09 (d, J = 7.65 Hz, 3H) 1.12-1.25 (m, 2H) 1.14 (d, J = 7.65 Hz, 3H) 1.20-1.23 (m, 6H) 1.28 (d, J = 6.12 Hz, 3H) 1.31 (s, 3H) 1.41-1.59 (m, 4H) 1.62-1.69 (m, 1H) 1.71-1.81 (m, 1H) 1.80-1.89 (m, 1H) 2.07-2.18 (m, 1H) 2.21-2.38 (m, 4H) 2.29 (s, 6H) 2.34 (s, 3H) 2.39-2.52 (m, 2H) 2.73-2.82 (m, 1H) 2.86-2.95 (m, 1H) 3.00 (t, J = 9.94 Hz, 1H) 3.13-3.26 (m, 3H) 3.22 (s, 3H) 3.32 (s, 3H) 3.34-3.42 (m, 1H) 3.43-3.50 (m, 1H) 3.69 (d, J = 7.65 Hz, 1H) 3.98-4.09 (m, 1H) 4.09-4.17 (m, 1H) 4.38 (d, J = 7.65 Hz, 1H) 4.71 (br. s., 1H) 4.77-4.84 (m, 1H) 4.92 (d, J = 4.59 Hz, 1H) 5.08 (s, 2H) 7.27-7.39 (m, 5H) |
| 634 | benzyloxy-ethyl carbamate-CH(Me)- linker | 898 FAB MASS | (300 MHz): 0.80-0.92 (m, 6H) 1.10 (d, J = 7.42 Hz, 3H) 1.16 (d, J = 7.42 Hz, 3H) 1.18-1.26 (m, 2H) 1.23 (d, J = 6.32 Hz, 3H) 1.24 (s, 3H) 1.29 (d, J = 6.32 Hz, 3H) 1.33 (s, 3H) 1.54 (dd, J = 5.00 Hz, 15.4 Hz, 1H) 1.53-1.58 (m, 1H) 1.64-1.73 (m, 1H) 1.85-1.94 (m, 1H) 2.17-2.40 (m, 12H) 2.41-2.54 (m, 2H) 2.75-2.87 (m, 1H) 2.91-3.06 (m, 2H) 3.21 (dd, J = 7.42 Hz, 10.2 Hz, 1H) 3.24 (s, 3H) 3.32 (s, 3H) 3.26-3.56 (m, 4H) 3.65 (t, J = 4.40 Hz, 2H) 3.70 (d, J = 7.69 Hz, 1H) 3.99-4.14 (m, 2H) 4.20-4.29 (m, 1H) 4.40 (d, J = 7.14 Hz, 1H) 4.56 (s, 2H) 4.76-4.88 (m, 1H) 4.90 (d, J = 4.40 Hz, 1H) 7.25-7.39 (m, 5H) |
| 635 | propargyl carbamate-CH(Me)- linker | 802.2 | (300 MHz): 0.80-0.92 (m, 6H) 1.10 (d, J = 7.14 Hz, 3H) 1.17 (d, J = 7.42 Hz, 3H) 1.23 (d, J = 6.04 Hz, 3H) 1.24 (s, 3H) 1.29 (d, J = 6.32 Hz, 3H) 1.33 (s, 3H) 1.55 (dd, J = 4.95 Hz, 15.1 Hz, 1H) 1.62-1.72 (m, 1H) 1.81-1.94 (m, 1H) 2.17-2.40 (m, 12H) 2.41-2.54 (m, 3H) 2.75-2.87 (m, 1H) 2.94-3.07 (m, 2H) 3.21 (dd, J = 6.87 Hz, 10.2 Hz, 1H) 3.24 (s, 3H) 3.26-3.58 (m, 7H) 3.71 (d, J = 7.97 Hz, 1H) 3.99-4.14 (m, 2H) 4.41 (d, J = 7.14 Hz, 1H) 4.56 (s, 2H) 4.60-4.74 (m, 2H) 4.77-4.94 (m, 2H) 5.10-5.22 (m, 1H) |
| 636 | hydroxyethyl carbamate-CH(Me)- linker | 808 FAB MASS | (300 MHz): 0.81-0.94 (m, 6H) 1.11 (d, J = 7.14 Hz, 3H) 1.18 (d, J = 7.42 Hz, 3H) 1.23 (d, J = 7.69 Hz, 3H) 1.24 (s, 3H) 1.29 (d, J = 6.32 Hz, 3H) 1.33 (s, 3H) 1.55 (dd, J = 4.67 Hz, 15.1 Hz, 1H) 1.62-1.71 (m, 1H) 1.81-1.94 (m, 1H) 2.17-2.58 (m, 14H) 2.75-2.87 (m, 1H) 2.94-3.07 (m, 2H) 3.21 (dd, J = 6.87 Hz, 10.2 Hz, 1H) 3.24 (s, 3H) 3.30-3.39 (m, 4H) 3.40-3.62 (m, 2H) 3.71 (d, J = 7.69 Hz, 1H) 3.75-3.85 (m, 3H) 3.99-4.19 (m, 2H) 4.21-4.30 (m, 2H) 4.41 (d, J = 7.14 Hz, 1H) 4.56 (s, 2H) 4.80-4.94 (m, 2H) 5.28-5.38 (m, 1H) |
| 637 | NC-CH₂CH₂-CH(Me)- linker | 758 FAB MASS | (300 MHz): 0.90-1.05 (m, 6H) 1.14 (d, J = 7.42 Hz, 3H) 1.18-1.39 (m, 15H) 1.55 (dd, J = 4.67 Hz, 15.1 Hz 1H) 1.60-1.74 (m, 1H) 1.75-1.87 (m, 1H) 2.05-2.42 (m, 12H) 2.45-2.56 (m, 1H) 2.61-2.83 (m, 2H) 2.98-3.08 (m, 1H) 3.24-3.44 (m, 8H) 3.47-3.60 (m, 1H) 3.81 (d, J = 6.87 Hz, 1H) 3.97-4.09 (m, 1H) 4.24-4.34 (m, 1H) 4.53 (d, J = 7.14 Hz, 1H) 4.62 (d, J = 4.40 Hz, 1H) 4.87-5.20 (m, 1H) |
| 638 | HO-(CH₂)₅-CH(Me)- linker | 791.2 | (300 MHz): 0.82 (d, J = 6.86 Hz, 6H) 1.06-1.92 (m, 17H) 1.10 (d, J = 7.41 Hz, 3H) 1.16 (d, J = 7.41 Hz, 3H) 1.23 (d, J = 6.04 Hz, 3H) 1.24 (s, 3H) 1.29 (d, J = 6.32 Hz, 3H) 2.08-2.52 (m, 6H) 2.29 (s, 6H) 2.37 (s, 3H) 2.73-2.87 (m, 1H) 2.91 (d, J = 14.55 Hz, 1H) 3.01 (t, J = 9.89 Hz, 1H) 3.15-3.25 (m, 2H) 3.23 (s, 3H) 3.33 (s, 3H) 3.37-3.54 (m, 2H) 3.64 (t, J = 6.59 Hz, 2H) 3.70 (d, J = 8.25 Hz, 1H) 4.00-4.19 (m, 2H) 4.39 (d, J = 7.14 Hz, 1H) 4.66-4.76 (m, 1H) 4.94 (d, J = 4.40 Hz, 1H) |

TABLE 15-continued formula (AB)

| Example | R | ESI MS (M + H) | $^1$H—NMR, CDCl$_3$, δ (ppm) |
|---|---|---|---|
| 639 | HO—(CH$_2$)$_5$—CH(Me)— | 777.3 | (300 MHz): 0.83 (d, J = 6.86 Hz, 6H) 1.08-1.92 (m, 15H) 1.10 (d, J = 7.41 Hz, 3H) 1.16 (d, J = 7.42 Hz, 3H) 1.23 (d, J = 6.04 Hz, 3H) 1.24 (s, 3H) 1.29 (d, J = 6.59 Hz, 3H) 1.33 (s, 3H) 2.07-2.53 (m, 6H) 2.29 (s, 6H) 2.37 (s, 3H) 2.72-2.86 (m, 1H) 2.91 (d, J = 14.56 Hz, 1H) 2.98 (t, J = 9.88 Hz, 1H) 3.16-3.27 (m, 2H) 3.23 (s, 3H) 3.33 (s, 3H) 3.37-3.53 (m, 2H) 3.63 (t, J = 6.60 Hz, 2H) 3.71 (d, J = 8.24 Hz, 1H) 4.00-4.20 (m, 2H) 4.40 (d, J = 7.42 Hz, 1H) 4.65-4.80 (m, 1H) 4.94 (d, J = 4.40 Hz, 1H) |
| 640 | quinolin-3-yl-CH=CH-CH(Me)- | 858 | (300 MHz): 0.84 (d, J = 6.86 Hz, 6H) 0.87 (d, J = 4.67 Hz, 3H) 1.03-1.36 (m, 2H) 1.03 (d, J = 7.42 Hz, 3H) 1.08 (d, J = 7.14 Hz, 3H) 1.21 (s, 3H) 1.22 (d, J = 6.05 Hz, 3H) 1.28 (d, J = 6.32 Hz, 3H) 1.33 (s, 3H) 1.50 (dd, J = 4.67, 14.84 Hz, 1H) 1.59-1.75 (m, 1H) 1.81-1.94 (m, 1H) 2.22-2.36 (m, 5H) 2.28 (s, 6H) 2.43 (s, 3H) 2.43-2.56 (m, 2H) 2.65-2.86 (m, 2H) 2.93-3.06 (m, 2H) 3.16-3.24 (m, 2H) 3.25 (s, 3H) 3.28 (s, 3H) 3.36-3.54 (m, 2H) 3.70 (d, J = 7.97 Hz, 1H) 3.97-4.16 (m, 2H) 4.38 (d, J = 7.14 Hz, 1H) 4.90 (d, J = 4.67 Hz, 1H) 4.95-5.03 (m, 1H) 6.30-6.43 (m, 1H) 6.59 (d, J = 15.93 Hz, 1H), 7.49-7.56 (m, 1H) 7.63-7.69 (m, 1H) 7.78 (d, J = 8.24 Hz, 1H) 7.98 (d, J = 1.93 Hz, 1H) 8.06 (d, J = 8.52 Hz, 1H) 8.94 (d, J = 2.20 Hz, 1H) |
| 641 | 1-hydroxycyclohexyl-CH(Me)- | 803 | mixture of diastereomers, (300 MHz): 0.85 (d, J = 6.87 Hz, 6H) 1.07-1.79 (m, 9H) 1.09 (d, J = 7.42 Hz, 3H) 1.16 (d, J = 7.42 Hz, 3H) 1.23 (d, J = 6.04 Hz, 3H) 1.24 (s, 3H) 1.29 (d, J = 6.32 Hz, 3H) 1.33 (s, 3H) 1.80-2.57 (m, 6H) 2.33 (s, 6H) 2.42 (s, 3H) 2.71-2.82 (m, 1H) 2.96-3.09 (m, 2H) 3.17-3.39 (m, 2H) 3.25 (s, 3H) 3.32 (s, 3H) 3.42-3.54 (m, 1H) 3.71 (d, J = 7.97 Hz, 1H) 3.98-4.19 (m, 2H) 4.40 (d, J = 7.14 Hz, 1H) 4.92 (d, J = 4.39 Hz, 1H) 5.01-5.11 (m, 1H) |
| 642 | Ph-C(Me)(OH)-CH(Me)- | 825 | (300 MHz): 0.79-2.70 (m, 18H) 0.79 (d, J = 7.15 Hz, 3H) 0.89 (d, J = 6.87 Hz, 3H) 1.04 (d, J = 7.42 Hz, 3H) 1.22 (d, J = 4.40 Hz, 3H) 1.24 (s, 3H) 1.26 (d, J = 6.32 Hz, 3H) 1.30 (s, 3H) 1.49 (s, 3H) 2.35 (s, 9H) 2.91-3.09 (m, 2H) 3.20-3.33 (m, 2H) 3.25 (s, 3H) 3.29 (s, 3H) 3.33-3.54 (m, 2H) 3.70 (d, J = 7.15 Hz, 1H) 3.90-4.07 (m, 2H) 4.40 (d, J = 7.14 Hz, 1H) 4.76 (d, J = 3.85 Hz, 1H) 4.95-5.07 (m, 1H) 7.18-7.34 (m, 3H) 7.46 (d, J = 7.14 Hz, 2H) |
| 643 | Me-CH$_2$-C(Me)(OH)-CH(Me)- | 777 | mixture of diastereomers, (300 MHz): 0.80-0.94 (m, 9H) 1.10-1.74 (m, 9H) 1.10 (d, J = 7.15 Hz, 3H) 1.16 (s, 3H) 1.17 (d, J = 6.04 Hz, 3H) 1.23 (d, J = 5.77 Hz, 3H) 1.24 (s, 3H) 1.30 (d, J = 6.32 Hz, 3H) 1.33 (s, 3H) 1.79-2.55 (m, 6H) 2.31 (s, 6H) 2.43 (s, 3H) 2.71-2.84 (m, 1H) 2.95-3.10 (m, 2H) 3.18-3.42 (m, 2H) 3.25 (s, 3H) 3.32 (s, 3H) 3.42-3.53 (m, 1H) 3.71 (d, J = 7.97 Hz, 1H) 4.00-4.21 (m, 2H) 4.40 (d, J = 7.14 Hz, 1H) 4.93 (d, J = 4.39 Hz, 1H) 4.99-5.08 (m, 1H) |
| 644 | HO-CH(Me)-CH(Me)- | 749 FAB MASS | mixture of diastereomers, (300 MHz): 0.82-0.95 (m, 6H) 1.07-1.49 (m, 22H) 1.49-1.98 (m, 5H) 2.14-2.62 (m, 16H) 2.74-2.87 (m, 1H) 2.87-3.11 (m, 3H) 3.16-3.31 (m, 4H) 3.33 and 3.34 (s, 3H) 3.38-3.55 (m, 2H) 3.59-3.69 and 3.81-3.93 (m, 1H) 3.73 (d, J = 7.69 Hz, 1H) 3.99-4.17 (m, 2H) 4.37-4.46 (m, 1H) |
| 645 | HO-CH$_2$-CH(OH)-CH$_2$-CH(Me)- | 779 | (300 MHz): 0.78-0.92 (m, 6H) 1.10 (d, J = 7.14 Hz, 3H) 1.16 (d, J = 7.42 Hz, 3H) 1.10 (d, J = 7.14 Hz, 3H) 1.19-1.27 (m, 6H) 1.29 (d, J = 6.32 Hz, 3H) 1.33 (s, 3H) 1.37-1.98 (m, 6H) 2.29 (s, 9H) 2.38 (s, 3H) 2.41-2.53 (m, 2H) 2.74-2.86 (m, 1H) 2.89-3.00 (m, 1H) 3.02 (t, J = 10.2 Hz 1H) 3.17-3.30 (m, 5H) 3.33 (s, 3H) 3.36-3.54 (m, 2H) 3.59-3.77 (m, 3H) 4.00-4.18 (m, 2H) 4.39 (d, J = 7.42 Hz, 1H) 4.70-4.83 (m, 1H) 4.93 (d, J = 4.4 Hz, 1H) |

TABLE 15-continued formula (AB)

| Example | R | ESI MS (M + H) | $^1$H—NMR, CDCl$_3$, δ (ppm) |
|---|---|---|---|
| 646 | allyl-O-C(=O)-NH-CH< | 804 | (300 MHz): 0.92 (d, J = 6.32 Hz, 3H) 1.07 (d, J = 7.14 Hz, 3H) 1.17 (d, J = 7.42 Hz, 3H) 1.21-1.29 (m, 7H) 1.32 (d, J = 6.32 Hz, 3H) 1.33 (s, 3H) 1.55 (dd, J = 4.95 Hz, 15.7 Hz 1H) 1.59-1.67 (m, 1H) 1.86-1.99 (m, 1H) 2.11-2.20 (m, 1H) 2.16 (s, 3H) 2.23-2.41 (m, 9H) 2.43-2.60 (m, 3H) 2.91-3.10 (m, 3H) 3.21-3.49 (m, 9H) 3.50-3.66 (m, 2H) 3.81 (d, J = 6.04 Hz, 1H) 4.03-4.15 (m, 1H) 4.49-4.57 (m, 3H) 4.60 (d, J = 7.14 Hz, 1H) 5.15-5.31 (m, 2H) 5.31-5.43 (m, 1H) 5.81-5.96 (m, 1H) 7.00 (br s, 1H) |
| 647 | quinolin-3-yl-CH=CH-CH< | 858.4 | (400 MHz): 0.94-1.04 (m, 6H) 1.05-1.36 (m, 2H) 1.13 (d, J = 9.01 Hz, 3H) 1.15 (s, 3H) 1.19 (d, J = 6.82 Hz, 3H) 1.24 (d, J = 6.09 Hz, 3H) 1.28 (d, J = 6.33 Hz, 3H) 1.31 (s, 3H) 1.61-1.90 (m, 3H) 2.05-3.04 (m, 11H) 2.25 (s, 3H) 2.31 (s, 6H) 3.24-3.43 (m, 3H) 3.30 (s, 3H) 3.38 (s, 3H) 3.47-3.60 (m, 2H) 3.83 (d, J = 6.82 Hz, 1H) 3.97-4.08 (m, 1H) 4.27-4.35 (m, 1H) 4.47-4.57 (m, 1H) 4.60 (d, J = 4.62 Hz, 1H) 5.02-5.29 (m, 1H) 6.33-6.44 (m, 1H) 6.62 (d, J = 16.07 Hz, 1H) 7.53 (t, J = 7.06 Hz, 1H) 7.67 (dd, J = 7.06, 8.52 Hz, 1H) 7.78 (d, J = 8.28 Hz, 1H) 7.99 (s, 1H) 8.06 (d, J = 8.53 Hz, 1H) 8.96 (d, J = 1.46 Hz, 1H) |
| 648 | quinolin-4-yl-CH=CH-CH< | 858.5 | (300 MHz): 0.94-1.06 (m, 6H) 1.08-1.32 (m, 2H) 1.10 (s, 3H) 1.30 (s, 3H) 1.44-1.79 (m, 3H) 2.03-3.04 (m, 11H) 2.27 (s, 3H) 2.33 (s, 6H) 3.15-3.58 (m, 3H) 3.27 (s, 3H) 3.37 (s, 3H) 3.82 (d, J = 6.60 Hz, 1H) 3.91-4.01 (m, 1H) 4.27-4.35 (m, 1H) 4.47-4.55 (m, 2H) 6.37-6.49 (m, 1H) 7.20 (d, J = 15.38 Hz, 1H) 7.42 (d, J = 4.67 Hz, 1H) 7.53-7.60 (m, 1H) 7.68-7.77 (m, 1H) 8.10 (d, J = 9.34 Hz, 2H) 8.84 (d, J = 4.67 Hz, 1H) |
| 649 | 2-hydroxyphenyl-CH< | 797.4 | (300 MHz): 0.96 (d, J = 6.87 Hz, 3H) 1.03 (d, J = 5.76 Hz, 3H) 1.05-1.37 (m, 2H) 1.13 (d, J = 7.42 Hz, 6H) 1.22 (s, 3H) 1.23 (d, J = 4.39 Hz, 3H) 1.26 (d, J = 6.31 Hz, 3H) 1.33 (s, 3H) 1.50 (dd, J = 4.95, 15.11 Hz, 1H) 1.55-1.76 (m, 2H) 1.95-2.06 (m, 1H) 2.16-2.51 (m, 5H) 2.28 (s, 3H) 2.40 (s, 3H) 2.75-2.92 (m, 3H) 2.93-3.05 (m, 2H) 3.17-3.38 (m, 3H) 3.28 (s, 3H) 3.32 (s, 3H) 3.40-3.56 (m, 2H) 3.77 (d, J = 6.59 Hz, 1H) 3.96-4.18 (m, 2H) 4.40 (d, J = 7.42 Hz, 1H) 4.75 (d, J = 4.40 Hz, 1H) 4.84-4.93 (m, 1H) 6.76-6.88 (m, 2H) 7.06-7.16 (m, 2H) |
| 650 | allyl-O-C(=O)-NH-propyl | 818 | (300 MHz): 0.79-0.90 (m, 6H) 1.11 (d, J = 7.14 Hz, 3H) 1.18 (d, J = 7.42 Hz, 3H) 1.21-1.27 (m, 6H) 1.29 (d, J = 6.32 Hz, 3H) 1.33 (s, 3H) 1.55 (dd, J = 4.95 Hz, 15.4 Hz, 1H) 1.60-1.81 (m, 2H) 1.81-1.96 (m, 1H) 2.12-2.33 (m, 8H) 2.33-2.41 (m, 4H) 2.41-2.53 (m, 2H) 2.75-2.87 (m, 1H) 2.88-3.07 (m, 3H) 3.17-3.29 (m, 5H) 3.30-3.54 (m, 5H) 3.71 (d, J = 7.69 Hz, 1H) 4.00-4.18 (m, 2H) 4.40 (d, J = 7.14 Hz, 1H) 4.55 (d, J = 5.77 Hz, 2H) 4.79-4.90 (m, 1H) 4.92 (d, J = 4.40 Hz, 1H) 5.07 (br s, 1H) 5.18-5.35 (m, 2H) 5.84-5.99 (m, 1H) |
| 651 | 3-methoxy-4-acetoxyphenyl-CH(Me)-CH< | 869 FAB MASS | (300 MHz): 0.73-0.89 (m, 9H) 1.06 (d, J = 7.14 Hz, 3H) 1.17-1.25 (m, 6H) 1.27 (d, J = 6.32 Hz, 3H) 1.33 (s, 3H) 1.47 (dd, J = 4.67 Hz, 15.1 Hz, 1H) 1.56-1.71 (m, 2H) 1.77-1.92 (m, 1H) 2.18-2.33 (m, 14H) 2.39-2.54 (m, 4H) 2.57-2.69 (m, 1H) 2.77 (dd, J = 3.57, 13.7 Hz, 1H) 2.94-3.10 (m, 3H) 3.15-3.25 (m, 5H) 3.28 (s, 3H) 3.39-3.53 (m, 2H) 3.67 (d, J = 7.97 Hz, 1H) 3.81 (s, 3H) 3.96-4.09 (m, 2H) 4.36 (d, J = 7.14 Hz, 1H) 4.84 (d, J = 4.40 Hz, 2H) 4.90-5.02 (m, 1H) 6.74-6.83 (m, 2H) 6.92 (d, J = 797 Hz, 1H) |

TABLE 15-continued formula (AB)

| Example | R | ESI MS (M + H) | $^1$H—NMR, CDCl$_3$, δ (ppm) |
|---|---|---|---|
| 652 | propargyl carbamate group (HC≡C-CH$_2$-O-C(O)-NH-) | 802.5 | (300 MHz): 0.92 (d, J = 6.60 Hz, 3H) 1.07 (d, J = 7.42 Hz, 3H) 1.17 (d, J = 7.42 Hz, 3H) 1.21-1.30 (m, 12H) 1.33-1.41 (m, 4H) 1.33 (s, 3H) 1.56-1.75 (m, 2H) 1.86-1.98 (m, 1H) 2.11-2.19 (m, 3H) 2.20-2.39 (m, 10H) 2.42 (t, J = 2.47 Hz, 3H) 2.44-2.58 (m, 3H) 2.94-3.07 (m, 2H) 3.12 (t, J = 9.89 Hz, 1H) 3.24-3.48 (m, 9H) 3.50-3.64 (m, 2H) 3.81 (d, J = 6.32 Hz, 1H) 4.04-4.16 (m, 1H) 4.52 (d, J = 4.95 Hz, 1H) 4.54-4.66 (m, 3H) 5.30-5.42 (m, 1H) |
| 653 | 4-hydroxy-3-methoxybenzyl group | 827 FAB MASS | (300 MHz): 0.76-0.89 (m, 9H) 1.07 (d, J = 7.42 Hz, 3H) 1.17-1.25 (m, 6H) 1.27 (d, J = 6.32 Hz, 3H) 1.32 (s, 3H) 1.48 (dd, J = 4.95 Hz, 15.4 Hz, 1H) 1.60-1.92 (m, 3H) 2.19-2.35 (m, 9H) 2.38-2.54 (m, 5H) 2.60-2.75 (m, 2H) 2.91-3.04 (m, 3H) 3.16-3.25 (m, 5H) 3.29 (s, 3H) 3.39-3.53 (m, 2H) 3.68 (d, J = 7.97 Hz, 1H) 3.87 (s, 3H) 3.97-4.10 (m, 2H) 4.37 (d, J = 7.14 Hz, 1H) 4.85 (d, J = 4.40 Hz, 2H) 4.88-4.98 (m, 1H) 6.65-6.72 (m, 2H) 6.80 (d, J = 7.97 Hz, 1H) |
| 654 | 2-hydroxy-2-phenylethyl group (with methyl branch) | 811.4 | mixture of diastereomers, (400 MHz): 0.82-0.91 (m, 6H) 1.07-1.38 (m, 14H) 1.25 (s, 3H) 1.34 (s, 3H) 1.57 (dd, J = 4.88, 15.35 Hz, 1H) 1.66 (d, J = 12.66 Hz, 1H) 1.73-2.02 (m, 3H) 2.15-2.63 (m, 15H) 2.29 (s, 6H) 2.77-2.93 (m, 1H) 2.94-3.12 (m, 2H) 3.18-3.38 (m, 5H) 3.34 (s, 3H) 3.38-3.61 (m, 2H) 3.73 (d, J = 7.80 Hz, 1H) 4.01-4.22 (m, 2H) 4.37-4.45 (m, 1H) 4.55-4.78 (m, 1H) 4.75-5.22 (m, 1H) 4.88-4.97 (m, 1H) 7.24-7.37 (m, 5H) |
| 655 | 2-hydroxyheptyl group | 791.5 | mixture of diastereomers, (400 MHz): 0.82-0.94 (m, 9H) 1.08-1.98 (m, 27H) 1.24 (s, 3H) 1.55 (dd, J = 4.87, 15.34 Hz, 1H) 2.19-2.56 (m, 9H) 2.29 (s, 6H) 2.75-2.86 (m, 1H) 2.87-3.08 (m, 3H) 3.18-3.28 (m, 2H) 3.26 (s, 3H) 3.32-3.35 (m, 2H) 3.37-3.58 (m, 2H) 3.62-3.73 (m, 1H) 3.73 (d, J = 8.03 Hz, 1H) 4.00-4.17 (m, 2H) 4.34-4.45 (m, 1H) 4.88-5.11 (m, 2H) |
| 656 | 4-methyl-3-hydroxypentyl group | 777.5 | mixture of diastereomers, (400 MHz): 0.79-0.94 (m, 12H) 1.09-1.35 (m, 14H) 1.24 (s, 3H) 1.32 (s, 3H) 1.41-1.49 (m, 1H) 1.55 (dd, J = 4.87, 15.10 Hz, 1H) 1.60-1.96 (m, 4H) 2.19-2.54 (m, 9H) 2.29 (s, 6H) 2.74-2.86 (m, 1H) 2.89-3.07 (m, 2H) 3.14-3.27 (m, 2H) 3.25 (s, 3H) 3.34 (s, 3H) 3.38-3.55 (m, 2H) 3.73 (d, J = 7.80 Hz, 1H) 4.00-4.19 (m, 2H) 4.41 (d, J = 7.06 Hz, 1H) 4.87-5.10 (m, 2H) |
| 657 | 3-hydroxypentyl group (with methyl) | 777.5 | mixture of diastereomers, (400 MHz): 0.81-0.95 (m, 9H) 1.08-1.97 (m, 25H) 1.24 (s, 3H) 1.55 (dd, J = 4.39, 15.11 Hz, 1H) 2.16-2.54 (m, 9H) 2.29 (s, 6H) 2.74-2.87 (m, 1H) 2.89-3.08 (m, 2H) 3.17-3.30 (m, 2H) 3.26 (s, 3H) 3.32-3.35 (m, 3H) 3.38-3.56 (m, 2H) 3.60-3.75 (m, 1H) 3.72 (d, J = 7.80 Hz, 1H) 4.01-4.18 (m, 2H) 4.37-4.46 (m, 1H) 4.88-5.12 (m, 2H) |
| 658 | allyl carbamate group (CH$_2$=CH-CH$_2$-O-C(O)-NH-CH$_2$CH$_2$-) | 832.6 | (300 MHz): 0.78-0.88 (m, 6H) 1.10 (d, J = 7.14 Hz, 3H) 1.16 (d, J = 7.42 Hz, 3H) 1.19-1.27 (m, 6H) 1.29 (d, J = 6.32 Hz, 3H) 1.33 (s, 3H) 1.43-1.91 (m, 4H) 2.09-2.41 (m, 12H) 2.41-2.53 (m, 2H) 2.74-2.85 (m, 1H) 2.87-2.97 (m, 1H) 3.02 (t, J = 9.34 Hz, 1H) 3.13-3.26 (m, 5H) 3.33 (s, 3H) 3.36-3.53 (m, 2H) 3.70 (d, J = 7.97 Hz, 1H) 4.00-4.18 (m, 2H) 4.39 (d, J = 7.14 Hz, 1H) 4.55 (d, J = 5.77 Hz, 2H) 4.68-4.83 (m, 2H) 4.93 (d, J = 4.40 Hz, 1H) 5.17-5.35 (m, 2H) 5.84-6.00 (m, 1H) |

TABLE 15-continued

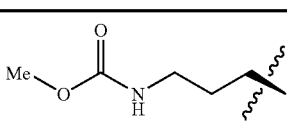

formula (AB)

| Example | R | ESI MS (M + H) | $^1$H—NMR, CDCl$_3$, δ (ppm) |
|---|---|---|---|
| 659 | 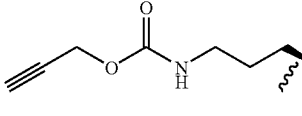 | 806.6 | (300 MHz): 0.78-0.88 (m, 6H) 1.10 (d, J = 7.14 Hz, 3H) 1.16 (d, J = 7.42 Hz, 3H) 1.19-1.27 (m, 6H) 1.29 (d, J = 6.32 Hz, 3H) 1.33 (s, 3H) 1.42-1.91 (m, 4H) 2.09-2.41 (m, 12H) 2.41-2.54 (m, 2H) 2.74-2.85 (m, 1H) 2.87-2.97 (m, 1H) 3.02 (t, J = 9.34 Hz, 1H) 3.13-3.27 (m, 5H) 3.33 (s, 3H) 3.36-3.53 (m, 2H) 3.66 (s, 3H) 3.70 (d, J = 7.97 Hz, 1H) 4.00-4.19 (m, 2H) 4.40 (d, J = 7.14 Hz, 1H) 4.68-4.79 (m, 2H) 4.93 (d, J = 4.40 Hz, 1H) |
| 660 | 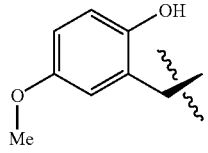 | 830.3 | (300 MHz): 0.77-0.90 (m, 6H) 1.10 (d, J = 7.42 Hz, 3H) 1.16 (d, J = 7.14 Hz, 3H) 1.20-1.27 (m, 6H) 1.29 (d, J = 6.32 Hz, 3H) 1.33 (s, 3H) 1.43-1.94 (m, 4H) 2.10-2.41 (m, 12H) 2.41-2.56 (m, 2H) 2.74-2.85 (m, 1H) 2.89-3.06 (m, 2H) 3.15-3.28 (m, 5H) 3.33 (s, 3H) 3.36-3.54 (m, 2H) 3.70 (d, J = 7.97 Hz, 1H) 4.00-4.18 (m, 2H) 4.40 (d, J = 7.14 Hz, 1H) 4.63-4.78 (m, 3H) 4.88 (br s, 1H) 4.93 (d, J = 4.12 Hz, 1H) |
| 661 | 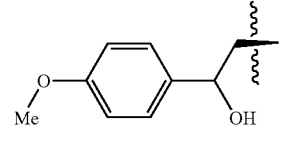 | 827.4 | (300 MHz): 0.91-1.06 (m, 6H) 1.06-1.17 (m, 6H) 1.19-1.31 (m, 9H) 1.34 (s, 3H) 1.51 (dd, J = 4.67 Hz, 15.4 Hz, 1H) 1.64-1.73 (m, 1H) 1.94-2.09 (m, 1H) 2.13-2.35 (m, 9H) 2.35-2.54 (m, 6H) 2.75-2.90 (m, 2H) 2.93-3.04 (m, 2H) 3.18-3.36 (m, 8H) 3.43-3.56 (m, 2H) 3.67-3.81 (m, 4H) 3.96-4.07 (m, 1H) 4.09-4.18 (m, 1H) 4.41 (d, J = 7.14 Hz, 1H) 4.76 (d, J = 4.40 Hz, 2H) 4.87-4.97 (m, 1H) 6.61-6.75 (m, 2H) 6.81 (d, J = 8.52 Hz, 1H) |
| 662 | 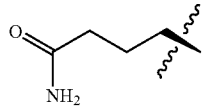 | 841.5 | (300 MHz): 0.79-0.92 (m, 6H) 1.12 (d, J = 7.14 Hz, 3H) 1.15-1.27 (m, 11H) 1.29 (d, J = 6.32 Hz, 3H) 1.33 (s, 3H) 1.56 (dd, J = 4.95 Hz, 15.1 Hz, 1H) 1.62-1.71 (m, 1H) 1.80-1.98 (m, 2H) 2.12-2.38 (m, 9H) 2.38-2.60 (m, 5H) 2.77-2.88 (m, 1H) 2.97-3.09 (m, 2H) 3.17-3.27 (m, 4H) 3.27-3.37 (m, 4H) 3.39-3.54 (m, 2H) 3.72 (d, J = 7.97 Hz, 1H) 3.80 (s, 3H) 4.00-4.18 (m, 2H) 4.40 (d, J = 7.14 Hz, 1H) 4.66-4.82 (m, 2H) 4.91 (d, J = 4.67 Hz, 1H) 6.87 (d, J = 8.79 Hz, 1H) 7.23 (d, J = 8.79 Hz, 1H) |
| 663 |  | 776 FAB MASS | (300 MHz): 0.77-0.88 (m, 6H) 1.10 (d, J = 7.42 Hz, 3H) 1.17 (d, J = 7.42 Hz, 3H) 1.19-1.27 (m, 8H) 1.29 (d, J = 6.32 Hz, 3H) 1.33 (s, 3H) 1.49-1.92 (m, 4H) 2.11-2.33 (m, 10H) 2.33-2.41 (m, 4H) 2.41-2.54 (m, 2H) 2.75-2.86 (m, 1H) 2.87-2.97 (m, 1H) 3.02 (t, J = 9.07 Hz, 1H) 3.17-3.26 (m, 5H) 3.33 (s, 3H) 3.35-3.54 (m, 2H) 3.71 (d, J = 7.97 Hz, 1H) 4.00-4.17 (m, 2H) 4.40 (d, J = 7.14 Hz, 1H) 4.71-4.84 (m, 1H) 4.93 (d, J = 4.40 Hz, 1H) 5.31 (br s, 1H) 5.55 (br s, 1H) |

Example 567

(1) By using the compound obtained in Example 1 (9.0 g) and the compound obtained in Reference Example 160 (8.52 g) as starting materials, a cyclized compound (2.57 g) was obtained in the same manners as those of Example 7, (1), (2) and (3).

(2) The compound obtained in (1) mentioned above (2.25 g) was dissolved in methanol (110 ml), the solution was added with 5% palladium-carbon (51 mg), and the mixture was stirred at room temperature for 18 hours under a hydrogen atmosphere of 1 atm. The reaction mixture was filtered, and then the filtrate was concentrated under reduced pressure. The resulting residue was added with saturated aqueous sodium hydrogencarbonate and ethyl acetate, the layers were separated, and the organic layer was dried over anhydrous magnesium sulfate and filtered. The filtrate was concentrated under reduced pressure to obtain an amine compound (1.92 g).

(3) The compound obtained in (2) mentioned above (100 mg) was dissolved in a mixed solvent of chloroform-methanol (2:1, 3 ml), the solution was added with benzoic acid (34 mg), 1-ethyl-3-(3-dimethylaminopropyl)carbodiimide hydrochloride (53 mg) and 4-dimethylaminopyridine (11.2 mg), and the mixture was stirred at room temperature for 18 hours. The reaction mixture was concentrated under reduced pressure, and the resulting residue was purified by silica gel column chromatography (hexane:acetone:triethylamine=90:10:0.2 to 30:10:0.2) to obtain an amide compound (96.9 mg).

521

(4) By using the compound obtained in (3) mentioned above (93.9 mg) as a starting material, the compound shown in Table 15 (66.4 mg) was obtained in the same manner as that of Example 7, (4).

Example 568

By using the compound obtained in Example 567, (2) (100 mg) and nicotinic acid (34 mg) as starting materials, the compound shown in Table 15 (41.5 mg) was obtained in the same manners as those of Example 567, (3) and Example 7, (4).

Example 569

By using the compound obtained in Example 567, (2) (100 mg) and quinoline-5-carboxylic acid (47.6 mg) as starting materials, the compound shown in Table 15 (25.7 mg) was obtained in the same manners as those of Example 567, (3) and Example 7, (4).

Example 570

By using the compound obtained in Example 567, (2) (100 mg) and isoquinoline-5-carboxylic acid (47.6 mg) as starting materials, the compound shown in Table 15 (31.1 mg) was obtained in the same manners as those of Example 567, (3) and Example 7, (4).

Example 571

(1) The compound obtained in Example 567, (2) (100 mg) was dissolved in chloroform (2 ml), the solution was added with 3-furancarboxylic acid (30.8 mg), 1-ethyl-3-(3-dimethylaminopropyl)carbodiimide hydrochloride (53 mg) and 4-dimethylaminopyridine (11.2 mg), and the mixture was stirred at room temperature for 18 hours. The reaction mixture was concentrated under reduced pressure, and the resulting residue was purified by silica gel column chromatography (hexane:acetone:triethylamine=90:10:0.2 to 30:10:0.2) to obtain an amide compound (91.2 mg).
(2) By using the compound obtained in (1) mentioned above (89.5 mg) as a starting material, the compound shown in Table 15 (38.4 mg) was obtained in the same manner as that of Example 7, (4).

Example 572

By using the compound obtained in Example 567, (2) (100 mg) and 3-thenoic acid (35.2 mg) as starting materials, the compound shown in Table 15 (39.5 mg) was obtained in the same manner as that of Example 571, (1) and Example 7, (4).

Example 573

By using the compound obtained in Example 567, (2) (100 mg) and pyrazinecarboxylic acid (34.1 mg) as starting materials, the compound shown in Table 15 (52.4 mg) was obtained in the same manners as those of Example 571, (1) and Example 7, (4).

Example 574

By using the compound obtained in Example 567, (2) (100 mg) and cinnoline-4-carboxylic acid (47.9 mg) as starting

522 materials, the compound shown in Table 15 (24.9 mg) was obtained in the same manners as those of Example 571, (1) and Example 7, (4).

Example 575

By using the compound obtained in Example 567, (2) (100 mg) and 4-pyridazinecarboxylic acid (34.1 mg) as starting materials, the compound shown in Table 15 (42.9 mg) was obtained in the same manners as those of Example 571, (1) and Example 7, (4).

Example 576

By using the compound obtained in Example 567, (2) (101 mg) and indole-3-carboxylic acid (44.9 mg) as starting materials, the compound shown in Table 15 (33.1 mg) was obtained in the same manners as those of Example 571, (1) and Example 7, (4).

Example 577

By using the compound obtained in Example 567, (2) (100 mg) and indazole-3-carboxylic acid (44.6 mg) as starting materials, the compound shown in Table 15 (39.2 mg) was obtained in the same manners as those of Example 571, (1) and Example 7, (4).

Example 578

(1) The compound obtained in Example 567, (2) (88 mg) was dissolved in chloroform (2 ml), the solution was added with 1-isoquinolinecarboxylic acid (41.9 mg) and 1-ethyl-3-(3-dimethylaminopropyl)carbodiimide hydrochloride (46.2 mg), and the mixture was stirred at room temperature for 18 hours. The reaction mixture was concentrated under reduced pressure, and the resulting residue was purified by silica gel column chromatography (hexane:acetone:triethylamine=100:10:0.2 to 30:10:0.2) to obtain an amide compound (55.9 mg).
(2) By using the compound obtained in (1) mentioned above (53.9 mg) as a starting material, the compound shown in Table 15 (35.5 mg) was obtained in the same manner as that of Example 7, (4).

Example 579

By using the compound obtained in Example 567, (2) (88 mg) and quinoline-8-carboxylic acid (41.9 mg) as starting materials, the compound shown in Table 15 (43.9 mg) was obtained in the same manners as those of Example 578, (1) and Example 7, (4).

Example 580

By using the compound obtained in Example 567, (2) (88 mg) and [1,8]naphthylidine-4-carboxylic acid (42.2 mg) as starting materials, the compound shown in Table 15 (29.0 mg) was obtained in the same manners as those of Example 578, (1) and Example 7, (4).

Example 581

By using the compound obtained in Example 567, (2) (88 mg) and [1,6]naphthylidine-5-carboxylic acid (42.2 mg) as starting materials, the compound shown in Table 15 (27.2 mg) was obtained in the same manners as those of Example 578, (1) and Example 7, (4).

Example 582

By using the compound obtained in Example 567, (2) (88 mg) and picolinic acid (29.8 mg) as starting materials, the compound shown in Table 15 (30.1 mg) was obtained in the same manners as those of Example 578, (1) and Example 7, (4).

starting materials, the compound shown in Table 15 (27.2 mg) was obtained in the same manners as those of Example 578, (1) and Example 7, (4).

Example 583

By using the compound obtained in Example 567, (2) (63 mg) and isonicotinic acid (21.4 mg) as starting materials, the compound shown in Table 15 (19.4 mg) was obtained in the same manners as those of Example 578, (1) and Example 7, (4).

Example 584

By using the compound obtained in Example 567, (2) (100 mg) and 5 pyrimidinecarboxylic acid (34.1 mg) as starting materials, the compound shown in Table 15 (28.2 mg) was obtained in the same manners as those of Example 578, (1) and Example 7, (4).

Example 585

By using the compound obtained in Example 567, (2) (100 mg) and 1H-indene-3-carboxylic acid (44.1 mg) as starting materials, the compound shown in Table 15 (43 mg) was obtained in the same manners as those of Example 578, (1) and Example 7, (4).

Example 586

By using the compound obtained in Example 567, (2) (100 mg) and 1-benzofuran-3-carboxylic acid (44.6 mg) as starting materials, the compound shown in Table 15 (72 mg) was obtained in the same manners as those of Example 578, (1) and Example 7, (4).

Example 587

By using the compound obtained in Example 567, (2) (100 mg) and 1-benzothiophene-3-carboxylic acid (49 mg) as starting materials, the compound shown in Table 15 (38 mg) was obtained in the same manners as those of Example 578, (1) and Example 7, (4).

Example 588

By using the compound obtained in Example 567, (2) (100 mg) and indole-4-carboxylic acid (44.3 mg) as starting materials, the compound shown in Table 15 (57.1 mg) was obtained in the same manners as those of Example 578, (1) and Example 7, (4).

Example 589

By using the compound obtained in Example 567, (2) (100 mg) and indole-7-carboxylic acid (44.3 mg) as starting materials, the compound shown in Table 15 (44.1 mg) was obtained in the same manners as those of Example 578, (1) and Example 7, (4).

Example 590

By using the compound obtained in Example 567, (2) (100 mg) and 2-furancarboxylic acid (30.8 mg) as starting materials, the compound shown in Table 15 (51.1 mg) was obtained in the same manners as those of Example 578, (1) and Example 7, (4).

Example 591

By using the compound obtained in Example 567, (2) (100 mg) and pyrrole-2-carboxylic acid (30.6 mg) as starting materials, the compound shown in Table 15 (52.9 mg) was obtained in the same manners as those of Example 578, (1) and Example 7, (4).

Example 592

By using the compound obtained in Example 567, (2) (100 mg) and 2-thenoic acid (35.2 mg) as starting materials, the compound shown in Table 15 (35.8 mg) was obtained in the same manners as those of Example 578, (1) and Example 7, (4).

Example 593

By using the compound obtained in Example 567, (2) (100 mg) and 4-pyrazolecarboxylic acid (30.8 mg) as starting materials, the compound shown in Table 15 (42.6 mg) was obtained in the same manners as those of Example 578, (1) and Example 7, (4).

Example 594

By using the compound obtained in Example 567, (2) (100 mg) and 1,2,3-thiadiazole-4-carboxylic acid (35.8 mg) as starting materials, the compound shown in Table 15 (68.6 mg) was obtained in the same manners as those of Example 578, (1) and Example 7, (4).

Example 595

By using the compound obtained in Example 567, (2) (100 mg) and 1H-[1,2,4]triazole-3-carboxylic acid (31.1 mg) as starting materials, the compound shown in Table 15 (12.2 mg) was obtained in the same manners as those of Example 578, (1) and Example 7, (4).

Example 596

By using the compound obtained in Example 567, (2) (100 mg) and 4-imidazolecarboxylic acid (30.8 mg) as starting materials, the compound shown in Table 15 (13.6 mg) was obtained in the same manners as those of Example 578, (1) and Example 7, (4).

Example 597

By using the compound obtained in Example 567, (2) (100 mg) and isoxazole-5-carboxylic acid (31.1 mg) as starting materials, the compound shown in Table 15 (17.2 mg) was obtained in the same manners as those of Example 578, (1) and Example 7, (4).

Example 598

By using the compound obtained in Example 567, (2) (100 mg) and 1,2,5-oxadiazole-3-carboxylic acid (31.4 mg) as starting materials, the compound shown in Table 15 (9.3 mg) was obtained in the same manners as those of Example 578, (1) and Example 7, (4).

Example 599

By using the compound obtained in Example 567, (2) (100 mg) and 4-thiazolecarboxylic acid (35.5 mg) as starting materials, the compound shown in Table 15 (14.2 mg) was obtained in the same manners as those of Example 578, (1) and Example 7, (4).

Example 600

By using the compound obtained in Example 567, (2) (100 mg) and pyrrole-3-carboxylic acid monohydrate (30.6 mg) as starting materials, the compound shown in Table 15 (31.1 mg) was obtained in the same manners as those of Example 578, (1) and Example 7, (4).

Example 601

By using the compound obtained in Example 567, (2) (100 mg) and thiazole-2-carboxylic acid (35.5 mg) as starting materials, the compound shown in Table 15 (51.6 mg) was obtained in the same manners as those of Example 578, (1) and Example 7, (4).

Example 602

By using the compound obtained in Example 1 (480 mg) and the compound obtained in Reference Example 161 (470 mg) as starting materials, the compound shown in Table 15 (49 mg) was obtained in the same manner as that of Example 7.

Example 603

By using the compound obtained in Example 1 (1.5 g) and the compound obtained in Reference Example 162 (1.62 g) as starting materials, the compound shown in Table 15 (148 mg) was obtained in the same manner as that of Example 7.

Example 604

(1) The compound obtained in Example 52, (1) (140 mg) was dissolved in dimethylformamide (5 ml), the solution was added with 2,4-oxazolidinedione (65.3 mg) and potassium carbonate (179 mg), and the mixture was stirred at 120° C. for 1.5 hours. The reaction mixture was added with ethyl acetate and distilled water, the layers were separated, and the organic layer was dried over anhydrous magnesium sulfate and filtered. The filtrate was concentrated under reduced pressure, and the resulting residue was purified by silica gel column chromatography (hexane:acetone:triethylamine=60:10:0.2) to obtain an N-alkyl compound (101 mg).

(2) By using the compound obtained in (1) mentioned above (98.0 mg) as a starting material, the compound shown in Table 15 (45.8 mg) was obtained in the same manner as that of Example 7, (4).

Example 605

By using the compound obtained in Example 52, (1) (130 mg) and 2-hydroxypyrimidine (157 mg) as starting materials, the compound shown in Table 15 (42.5 mg) was obtained in the same manners as those of Example 604, (1) and Example 7, (4).

Example 606

By using the compound obtained in Example 52, (1) (130 mg) and 2-hydroxypyrimidine (157 mg) as starting materials, the compound shown in Table 15 (12.3 mg) was obtained in the same manners as those of Example 604, (1) and Example 7, (4).

Example 607

By using the compound obtained in Example 52, (1) (150 mg) and 4-hydroxyquinazoline (101 mg) as starting materials, the compound shown in Table 15 (77.3 mg) was obtained in the same manners as those of Example 604, (1) and Example 7, (4).

Example 608

By using the compound obtained in Example 52, (1) (750 mg) and 2-hydroxypyridine (330 mg) as starting materials, the compound shown in Table 15 (108 mg) was obtained in the same manners as those of Example 604, (1) and Example 7, (4).

Example 609

By using the compound obtained in Example 52, (1) (150 mg) and 2-quinolinol (101 mg) as starting materials, the compound shown in Table 15 (43.2 mg) was obtained in the same manners as those of Example 604, (1) and Example 7, (4).

Example 610

By using the compound obtained in Example 52, (1) (150 mg) and 3-cyanoindole (98.5 mg) as starting materials, the compound shown in Table 15 (71.0 mg) was obtained in the same manners as those of Example 604, (1) and Example 7, (4).

Example 611

By using the compound obtained in Example 52, (1) (150 mg) and 2-quinolinol (101 mg) as starting materials, the compound shown in Table 15 (32.6 mg) was obtained in the same manners as those of Example 604, (1) and Example 7, (4).

Example 612

By using the compound obtained in Example 52, (1) (150 mg) and 3-indoleacetonitrile (108 mg) as starting materials, the compound shown in Table 15 (16.1 mg) was obtained in the same manners as those of Example 604, (1) and Example 7, (4).

Example 613

By using the compound obtained in Example 52, (1) (150 mg) and 6-oxo-1,6-dihydro-3-pyridinecarbonitrile (83.5 mg) as starting materials, the compound shown in Table 15 (74.3 mg) was obtained in the same manners as those of Example 604, (1) and Example 7, (4).

Example 614

By using the compound obtained in Example 52, (1) (300 mg) and indole (162 mg) as starting materials, the compound shown in Table 15 (37.8 mg) was obtained in the same manners as those of Example 604, (1) and Example 7, (4).

Example 615

By using the compound obtained in Example 52, (1) (150 mg) and pyrrole-2-carbonitrile (63.8 mg) as starting materials, the compound shown in Table 15 (55.0 mg) was obtained in the same manners as those of Example 604, (1) and Example 7, (4).

Example 616

By using the compound obtained in Example 52, (1) (150 mg) and 1,6-naphthylidin-2(1H)-one (101 mg) as starting materials, the compound shown in Table 15 (48.6 mg) was obtained in the same manners as those of Example 604, (1) and Example 7, (4).

Example 617

By using the compound obtained in Example 52, (1) (150 mg) and pyrido[2,3-d]pyrimidin-4(3H)-one (102 mg) as starting materials, the compound shown in Table 15 (76.6 mg) was obtained in the same manners as those of Example 604, (1) and Example 7, (4).

Example 618

By using the compound obtained in Example 52, (1) (150 mg) and 2-hydroxypyridine (132 mg) as starting materials, the compound shown in Table 15 (55 mg) was obtained in the same manners as those of Example 604, (1) and Example 7, (4).

Example 619

By using the compound obtained in Example 52, (1) (150 mg) and uracil (156 mg) as starting materials, the compound shown in Table 15 (44 mg) was obtained in the same manners as those of Example 604, (1) and Example 7, (4).

Example 620

By using the compound obtained in Example 52, (1) (150 mg) and 4-hydroxypyridine (132 mg) as starting materials, the compound shown in Table 15 (32 mg) was obtained in the same manners as those of Example 604, (1) and Example 7, (4).

Example 621

(1) By using the compound obtained in Example 1 (1.5 g) and the compound obtained in Reference Example 152 (1.55 g) as starting materials, a cyclized compound (276 mg) was obtained in the same manners as those of Example 7, (1), (2) and (3).
(2) By using the compound obtained in (1) mentioned above (170 mg) as a starting material, the compound shown in Table 15 (85.6 mg) was obtained in the same manner as that of Example 7, (4).

Example 622

(1) By using the compound obtained in Example 1 (1.5 g) and the compound obtained in Reference Example 153 (1.45 g) as starting materials, a cyclized compound (244 mg) was obtained in the same manners as those of Example 7, (1), (2) and (3).
(2) By using the compound obtained in (1) mentioned above (176 mg) as a starting material, the compound shown in Table 15 (77.7 mg) was obtained in the same manner as that of Example 7, (4).

Example 623

By using the compound obtained in Example 1 (1.18 g) and the compound obtained in Reference Example 154 (511 mg) as starting materials, the compound shown in Table 15 (133 mg) was obtained in the same manner as that of Example 7.

Example 624

By using the compound obtained in Example 1 (811 mg) and the compound obtained in Reference Example 155 (385 mg) as starting materials, the compound shown in Table 15 (16.3 mg) was obtained in the same manner as that of Example 7.

Example 625

(1) By using the compound obtained in Example 1 (1.5 g) and the compound obtained in Reference Example 156 (1.22 g) as starting materials, a cyclized compound (314 mg) was obtained in the same manners as those of Example 7, (1), (2) and (3).
(2) By using the compound obtained in (1) mentioned above (250 mg) as a starting material, the compound shown in Table 15 (194 mg) was obtained in the same manner as that of Example 7, (4).

Example 626

(1) By using the compound obtained in Example 1 (3.0 g) and the compound obtained in Reference Example 157 (3.8 g) as starting materials, a cyclized compound (257 mg) was obtained in the same manners as those of Example 7, (1), (2) and (3).
(2) By using the compound obtained in (1) mentioned above (50.1 mg) as a starting material, the compound shown in Table 15 (25.1 mg) was obtained in the same manner as that of Example 7, (4).

Example 627

(1) The compound obtained in Example 626, (1) (102 mg) was dissolved in a mixed solvent of methanol-ethyl acetate (2:1, 3 ml), the solution was added with 5% palladium-carbon (51 mg), and the mixture was stirred at room temperature for 1 hour under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=10:1:0.1) to obtain a debenzylated compound (93.9 mg).
(2) The compound obtained in (1) mentioned above (30.6 mg) was dissolved in chloroform (1 ml), the solution was added with triethylamine (19.2 µl) and isobutyl chloroformate (18 µl) under ice cooling, and the mixture was stirred at the same temperature for 1 hour. The mixture was added with a 0.5 N solution of ammonia in 1,4-dioxane (0.83 ml), and the mixture was stirred at room temperature for 40 minutes. The reaction mixture was neutralized with saturated aqueous ammonium chloride, and then the reaction mixture was added with chloroform and saturated aqueous ammonium chloride. The layers were separated, and the organic layer was washed with saturated brine, then dried over anhydrous magnesium sulfate and filtered. The filtrate was concentrated under reduced pressure, and the resulting residue was purified by silica gel column chromatography (hexane:acetone:triethylamine=60:10:0.2) to obtain an amide compound (40.7 mg).

(3) By using the compound obtained in (2) mentioned above (40.7 mg) as a starting material, the compound shown in Table 15 (10.0 mg) was obtained in the same manner as that of Example 7, (4).

Example 628

By using the compound obtained in Example 1 (1.50 g) and the compound obtained in Reference Example 158 (2.0 g) as starting materials, the compound shown in Table 15 (93 mg) was obtained in the same manner as that of Example 7.

Example 629

(1) By using the compound obtained in Example 1 (3.0 g) and the compound obtained in Reference Example 159 (3.0 g) as starting materials, a cyclized compound (514 mg) was obtained in the same manners as those of Example 7, (1), (2) and (3).
(2) The compound obtained in (1) mentioned above (200 mg) was dissolved in methanol (5 ml), the solution was added with 5% palladium-carbon (100 mg), and the mixture was stirred at room temperature for 2 hours under a hydrogen atmosphere of 1 atm. The reaction mixture was filtered, and then the filtrate was concentrated under reduced pressure. The resulting residue was dissolved in methanol (5 ml), the solution was added with 20% palladium hydroxide-carbon (500 mg), and the mixture was stirred at room temperature for 2 hours under a hydrogen atmosphere of 1 atm. The reaction mixture was filtered, and then the filtrate was concentrated under reduced pressure. The resulting residue was dissolved in tetrahydrofuran (4 ml), the solution was added with 20% palladium hydroxide-carbon (500 mg), and the mixture was stirred at room temperature for 1.5 hours under a hydrogen atmosphere of 1 atm. The reaction mixture was filtered, then the filtrate was concentrated under reduced pressure, and the resulting residue was purified by silica gel column chromatography (hexane:acetone:triethylamine=60:10:0.2) to obtain a debenzylated compound (73.9 mg).
(3) By using the compound obtained in (2) mentioned above (72.2 mg) as a starting material, a ketone compound (73.3 mg) was obtained in the same manner as that of Example 113, (2).
(4) By using the compound obtained in (3) mentioned above (73.3 mg) as a starting material, the compound shown in Table 15 (27.4 mg) was obtained in the same manner as that of Example 7, (4).

Example 630

By using the compound obtained in Example 629, (1) (130 mg) as a starting material, the compound shown in Table 15 (59.4 mg) was obtained in the same manner as that of Example 7, (4).

Example 631

By using the compound obtained in Example 1 (719 mg) and 1-(2-oxiran-2-ylethyl)-1H-pyrrole (497 mg) obtained by the method described in the literature (Journal of Organic Chemistry, 1987, vol. 52, 5, p. 819) as starting materials, the compound shown in Table 15 (64.9 mg) was obtained in the same manner as that of Example 7.

Example 632

By using the compound obtained in Example 1 (604 mg) and 1-(3-oxiran-2-ylpropyl)-1H-pyrrole (460 mg) obtained by the method described in the literature (Journal of Organic Chemistry, 1987, vol. 52, 5, p. 819) as starting materials, the compound shown in Table 15 (29.3 mg) was obtained in the same manner as that of Example 7.

Example 633

By using the compound obtained in Example 567, (1) (100 mg) as a starting material, the compound shown in Table 15 (67.6 mg) was obtained in the same manner as that of Example 7, (4).

Example 634

(1) The compound obtained in Example 1 (800 mg) was dissolved in tetrahydrofuran (5.4 ml), the solution was added with the compound obtained in Reference Example 199 (3.03 g) and ytterbium triflate monohydrate (50 mg), and the mixture was stirred at 90° C. for 10 minutes under microwave irradiation. The reaction mixture was concentrated under reduced pressure, and the resulting residue was purified by silica gel column chromatography (chloroform:methanol=30:1 to chloroform:methanol:28% aqueous ammonia=30:1:0.1) to obtain a 10a-N-(4-((2-(benzyloxy)ethoxy)carbonylamino)-2-hydroxypropyl) compound (290 mg).
(2) By using the compound obtained in (1) mentioned above (289 mg) as a starting material, a 10a-N-methyl compound (288 mg) was obtained in the same manner as that of Example 7, (2).
(3) Dimethylaminopyridine (83 mg) and 2-methyl-6-nitrobenzoic acid anhydride (117 mg) were dissolved in dichloromethane (24 ml), the solution was added dropwise with a solution of the compound obtained in (2) mentioned above (281 mg) in dichloromethane (16 ml) at room temperature over 1 hour and 20 minutes, and then the mixture was further stirred at room temperature for 1 hour. The reaction mixture was added with 20% aqueous ammonium chloride, the layers were separated, and the organic layer was washed with saturated brine, then dried over anhydrous sodium sulfate and filtered. The filtrate was concentrated under reduced pressure, and the resulting residue was purified by silica gel column chromatography (hexane:ethyl acetate=5:1 to 2:1) to obtain a cyclized compound (148 mg).
(4) By using the compound obtained in (3) mentioned above (146 mg) as a starting material, the compound shown in Table 15 (104 mg) was obtained in the same manner as that of Example 7, (4).

Example 635

By using the compound obtained in Example 1 (800 mg) and the compound obtained in Reference Example 200 (1.87 g) as starting materials, the compound shown in Table 15 (76 mg) was obtained in the same manners as those of Example 634, (1), Example 7, (2), Example 634, (3) and Example 7, (4).

Example 636

By using the compound obtained in Example 634 (91 mg) as a starting material, the compound shown in Table 15 (15 mg) was obtained in the same manner as that of Example 81.

Example 637

By using the compound obtained in Example 1 (800 mg) and the compound obtained in Reference Example 42 (1.34 g) as starting materials, the compound shown in Table 15 (12.9 mg) was obtained in the same manners as those of Example 634, (1), Example 7, (2), Example 634, (3) and Example 7, (4).

Example 638

By using the compound obtained in Example 1 (800 mg) and the compound obtained in Reference Example 201 (3.12 g) as starting materials, the compound shown in Table 15 (105 mg) was obtained in the same manners as those of Example 634, (1), Example 7, (2), Example 634, (3) and Example 7, (4).

Example 639

By using the compound obtained in Example 1 (800 mg) and the compound obtained in Reference Example 202 (2.95 g) as starting materials, the compound shown in Table 15 (125 mg) was obtained in the same manners as those of Example 634, (1), Example 7, (2), Example 634, (3) and Example 7, (4).

Example 640

(1) By using the compound obtained in Example 1 (800 mg) and (R)-2-allyloxirane (1.02 g) obtained by the method described in the literature (Journal of American Chemical Society, 2004, vol. 126, p. 2495) as starting materials, a cyclized compound (442 mg) was obtained in the same manners as those of Example 634, (1), Example 7, (2) and Example 634, (3).

(2) The compound obtained in (1) mentioned above (160 mg) was dissolved in a 2% solution of 1-methyl-2-pyrrolidinone in dioxane, the solution was added with trisdibenzylideneacetone dipalladium (13.7 mg), 3-bromoquinoline (40.5 mg), dicyclohexylmethylamine (63.5 μl) and a 0.52 N solution of tri-t-butylphosphine in dioxane (57.5 μl), and the mixture was stirred at 90° C. for 1 hour under microwave irradiation. The reaction mixture was added with saturated aqueous ammonium chloride and ethyl acetate, the layers were separated, and the organic layer was dried over anhydrous magnesium sulfate and filtered. The filtrate was concentrated under reduced pressure, and the resulting residue was purified by silica gel column chromatography (hexane:tetrahydrofuran=20:1) to obtain a coupling compound (95.6 mg).

(3) By using the compound obtained in (2) mentioned above (95.6 mg) as a starting material, the compound shown in Table 15 (61.4 mg) was obtained in the same manner as that of Example 7, (4).

Example 641

By using the compound obtained in Example 1 (800 mg) and the compound obtained in Reference Example 203 (3.26 g) as starting materials, a mixture of deprotected compounds was obtained in the same manners as those of Example 634, (1), Example 7, (2), Example 634, (3) and Example 7, (4). This mixture was dissolved in dimethylformamide (150 μl), the solution was added with 18-crown-6-ether (43.8 mg) and potassium fluoride (9.6 mg), and the mixture was stirred at 60° C. for 26 hours. The reaction mixture was concentrated, and the resulting residue was purified by preparative thin layer chromatography (chloroform:methanol:28% aqueous ammonia=5:1:0.1) to obtain the compound shown in Table 15 (10 mg).

Example 642

By using the compound obtained in Example 1 (800 mg) and the compound obtained in Reference Example 204 (1.63 g) as starting materials, the compound shown in Table 15 (2.1 mg) was obtained in the same manner as that of Example 641.

Example 643

By using the compound obtained in Example 1 (1.5 g) and the compound obtained in Reference Example 205 (1.15 g) as starting materials, the compound shown in Table 15 (27.6 mg) was obtained in the same manners as those of Example 634, (1), Example 7, (2), Example 634, (3) and Example 7, (4).

Example 644

By using the compound obtained in Example 1 (1.5 g) and the compound obtained in Reference Example 206 (3.3 g) as starting materials, the compound shown in Table 15 (105 mg) was obtained in the same manners as those of Example 634, (1), Example 7, (2), Example 634, (3) and Example 7, (4).

Example 645

By using the compound obtained in Example 1 (1.5 g) and the compound obtained in Reference Example 207 (5.4 g) as starting materials, the compound shown in Table 15 (208 mg) was obtained in the same manners as those of Example 634, (1), Example 7, (2), Example 634, (3) and Example 7, (4).

Example 646

(1) By using the compound obtained in Example 1 (800 mg) and the compound obtained in Reference Example 208 (978 mg) as starting materials, a 10a-N-methyl compound (110 mg) was obtained in the same manners as those of Example 634, (1) and Example 7, (2).

(2) 2-Chloro-1-methylpyridinium iodide (37 mg) was dissolved in acetonitrile (23 ml), the solution was added dropwise with a solution of the compound obtained in (1) mentioned above (110 mg) and triethylamine (40 μl) in acetonitrile (10 ml) over 20 minutes under reflux by heating, and then the mixture was further stirred for 0.5 hour under reflux by heating. The reaction mixture was added with 20% aqueous ammonium chloride and ethyl acetate, the layers were separated, and the organic layer was washed with saturated brine, then dried over anhydrous sodium sulfate and filtered. The filtrate was concentrated under reduced pressure, and the resulting residue was purified by silica gel column chromatography (hexane:ethyl acetate=15:1 to 10:1) to obtain a cyclized compound (36 mg).

(3) By using the compound obtained in (2) mentioned above (35 mg) as a starting material, the compound shown in Table 15 (22 mg) was obtained in the same manner as that of Example 7, (4).

Example 647

(1) By using the compound obtained in Example 1 (0.55 g) and the compound obtained in Reference Example 209 (441 mg) as starting materials, a cyclized compound (88.1 mg) was obtained in the same manners as those of Example 634, (1), Example 7, (2) and Example 646, (2).
(2) By using the compound obtained in (1) mentioned above (29.4 mg) and 3-bromoquinoline (7.4 μl) as starting materials, the compound shown in Table 15 (9.0 mg) was obtained in the same manners as those of Example 640, (2) and Example 7, (4).

Example 648

By using the compound obtained in Example 647, (1) (29.4 mg) and 4-bromoquinoline (28.5 mg) as starting materials, the compound shown in Table 15 (2.7 mg) was obtained in the same manners as those of Example 640, (2) and Example 7, (4).

Example 649

By using the compound obtained in Example 1 (1.0 g) and the compound obtained in Reference Example 210 (3.99 g) as starting materials, the compound shown in Table 15 (198.9 mg) was obtained in the same manners as those of Example 634, (1), Example 7, (2), Example 634, (3) and Example 7, (4).

Example 650

By using the compound obtained in Example 1 (1.2 g) and the compound obtained in Reference Example 211 (1.64 g) as starting materials, the compound shown in Table 15 (134 mg) was obtained in the same manners as those of Example 634, (1), Example 7, (2), Example 634, (3) and Example 7, (4).

Example 651

(1) By using the compound obtained in Example 1 (1.2 g) and the compound obtained in Reference Example 212 (1.64 g) as starting materials, a cyclized compound (496 mg) was obtained in the same manners as those of Example 634, (1), Example 7, (2) and Example 634, (3).
(2) By using the compound obtained in (1) mentioned above (250 mg) as a starting material, the compound shown in Table 15 (170 mg) was obtained in the same manner as that of Example 7, (4).

Example 652

By using the compound obtained in Example 1 (2.0 g) and the compound obtained in Reference Example 200 (3.06 g) as starting materials, the compound shown in Table 15 (80 mg) was obtained in the same manners as those of Example 634, (1) Example 7, (2), Example 646, (2) and Example 7, (4).

Example 653

The compound obtained in Example 651 (30 mg) was dissolved in methanol (2 ml), and the solution was stirred for 19 hours under reflux by heating. The reaction mixture was concentrated under reduced pressure, and the resulting residue was purified by preparative thin layer chromatography (chloroform:methanol:28% aqueous ammonia=10:1:0.1) to obtain the compound shown in Table 15 (26 mg).

Example 654

By using the compound obtained in Example 1 (1.0 g) and the compound obtained in Reference Example 213 (4.2 g) as starting materials, the compound shown in Table 15 (71.1 mg) was obtained in the same manners as those of Example 634, (1), Example 7, (2), Example 634, (3) and Example 7, (4).

Example 655

By using the compound obtained in Example 1 (1.0 g) and the compound obtained in Reference Example 214 (3.9 g) as starting materials, the compound shown in Table 15 (76.0 mg) was obtained in the same manners as those of Example 634, (1), Example 7, (2), Example 634, (3) and Example 7, (4).

Example 656

By using the compound obtained in Example 1 (1.0 g) and the compound obtained in Reference Example 215 (3.69 g) as starting materials, the compound shown in Table 15 (51.3 mg) was obtained in the same manners as those of Example 634, (1), Example 7, (2), Example 634, (3) and Example 7, (4).

Example 657

By using the compound obtained in Example 1 (1.0 g) and the compound obtained in Reference Example 216 (3.69 g) as starting materials, the compound shown in Table 15 (63 mg) was obtained in the same manners as those of Example 634, (1), Example 7, (2), Example 634, (3) and Example 7, (4).

Example 658

(1) The compound obtained in Example 54, (1) (50 mg) was dissolved in dichloromethane (1 ml), the solution was added with triethylamine (7.7 μl) and allyl chloroformate (5.4 μl), and the mixture was stirred for 1 hour under ice cooling. The reaction mixture was added with distilled water and chloroform, the layers were separated, and the organic layer was washed with saturated brine, then dried over anhydrous sodium sulfate and filtered. The filtrate was concentrated under reduced pressure, and the resulting residue was purified by silica gel column chromatography (hexane:ethyl acetate=3:1) to obtain a carbamate compound (44 mg).
(2) By using the compound obtained in (1) mentioned above (43 mg) as a starting material, the compound shown in Table 15 (29 mg) was obtained in the same manner as that of Example 7, (4).

Example 659

By using the compound obtained in Example 54, (1) (40 mg) and methyl chloroformate (3.1 μl) as starting materials, the compound shown in Table 15 (24 mg) was obtained in the same manners as those of Example 658, (1) and Example 7, (4).

Example 660

By using the compound obtained in Example 54, (1) (40 mg) and propargyl alcohol (30 μl) as starting materials, the compound shown in Table 15 (5 mg) was obtained in the same manners as those of Example 54, (2) and Example 7, (4).

Example 661

By using the compound obtained in Example 1 (405 mg) and the compound obtained in Reference Example 217 (600 mg) as starting materials, the compound shown in Table 15 (23 mg) was obtained in the same manners as those of Example 634, (1), Example 7, (2), Example 634, (3) and Example 7, (4).

Example 662

(1) By using the compound obtained in Example 1 (1.0 g) and the compound obtained in Reference Example 218 (2.4 g) as starting materials, a cyclized compound (92 mg) was obtained in the same manners as those of Example 634, (1), Example 7, (2) and Example 634, (3).
(2) By using the compound obtained in (1) mentioned above (42 mg) as a starting material, the compound shown in Table 15 (13 mg) was obtained in the same manner as that of Example 7, (4).

Example 663

(1) By using the compound obtained in Example 1 (1.5 g) and the compound obtained in Reference Example 219 (3.3 g) as starting materials, a cyclized compound (349 mg) was obtained in the same manners as those of Example 634, (1), Example 7, (2) and Example 634, (3).
(2) By using the compound obtained in (1) mentioned above (150 mg) as a starting material, a carboxylic acid compound (138 mg) was obtained in the same manner as that of Example 64.
(3) By using the compound obtained in (2) mentioned above (75 mg) as a starting material, the compound shown in Table 15 (20 mg) was obtained in the same manners as those of Example 91, (2) and Example 7, (4).

Syntheses of Examples 664 to 668

Preparation methods of compounds represented by the formula (AC) having $R^{1AC}$ and $R^{2AC}$ defined in Table 16 are shown below.

TABLE 16 formula (AC)

[Structure of formula (AC) shown]

| Example | $R^{1AC}$ | $R^{2AC}$ | ESI MS (M + H) | $^1$H—NMR, CDCl$_3$, δ (ppm) |
|---|---|---|---|---|
| 664 | _tc,6 [3-hydroxyphenyl-CH(Me)-NH-CH$_2$CH$_2$-NH-C(O)-O-] | H | 965.0 | mixture of diastereomers (600 MHz): 0.76-0.88 (m, 6H) 1.02-1.25 (m, 17H) 1.26-1.34 (m, 8H) 1.57-1.97 (m, 7H) 2.10-2.32 (m, 3H) 2.32-2.52 (m, 4H) 2.35 (s, 3H) 2.36-2.38 (m, 6H) 2.53-2.61 (m, 1H) 2.67-2.85 (m, 3H) 2.93-3.01 (m, 1H) 3.22 (s, 3H) 3.29-3.45 (m, 3H) 3.34 (s, 3H) 3.58-3.74 (m, 3H) 4.05-4.17 (m, 1H) 4.31-4.40 (m, 1H) 4.43-4.56 (m, 2H) 4.69-4.79 (m, 1H) 4.91-4.97 (m, 1H) 5.37-5.45 (m, 1H) 6.67-6.75 (m, 2H) 6.88-6.93 (m, 1H) 7.10-7.17 (m, 1H), and (600 MHz): 0.76-0.88 (m, 6H) 1.02-1.25 (m, 17H) 1.26-1.34 (m, 8H) 1.57-1.97 (m, 7H) 2.10-2.32 (m, 3H) 2.32-2.52 (m, 5H) 2.36-2.38 (m, 6H) 2.39 (s, 3H) 2.67-2.85 (m, 3H) 2.93-3.01 (m, 1H) 3.01-3.09 (m, 1H) 3.21 (s, 3H) 3.35 (d, J = 10.09 Hz, 3H) 3.36 (s, 3H) 3.58-3.74 (m, 3H) 4.05-4.17 (m, 1H) 4.31-4.40 (m, 1H) 4.43-4.56 (m, 2H) 4.69-4.79 (m, 1H) 4.91-4.97 (m, 1H) 5.09-5.15 (m, 1H) 6.67-6.75 (m, 2H) 6.88-6.93 (m, 1H) 7.10-7.17 (m, 1H) |
| 665 | [-O-C(O)-NH-CH$_2$CH$_2$-NH-CH(Me)-3-hydroxyphenyl] | H | 964.9 | (600 MHz): 0.76-0.84 (m, 6H) 1.00-1.26 (m, 2H) 1.07 (d, J = 7.34 Hz, 3H) 1.11 (d, J = 6.42 Hz, 3H) 1.13-1.16 (m, 6H) 1.21 (s, 3H) 1.27 (d, J = 6.42 Hz, 3H) 1.29 (s, 3H) 1.53-1.98 (m, 7H) 2.09-2.31 (m, 3H) 2.32-2.51 (m, 5H) 2.35 (s, 3H) 2.37 (s, 6H) 2.71-2.83 (m, 3H) 2.95 (d, J = 14.21 Hz, 1H) 3.00-3.07 (m, 1H) 3.20 (s, 3H) 3.26-3.41 (m, 3H) 3.34 (s, 3H) 3.55-3.62 (m, 1H) 3.63-3.70 (m, 2H) 4.06-4.15 (m, 1H) 4.29-4.39 (m, 1H) 4.45 (d, J = 7.34 Hz, 1H) 4.51 (d, J = 10.09 Hz, 1H) 4.67-4.77 (m, 1H) 4.93 (d, J = 4.59 Hz, 1H) 5.10-5.14 (m, 1H) 6.65-6.71 (m, 2H) 6.88 (s, 1H) 7.10 (t, J = 7.79 Hz, 1H) |

TABLE 16-continued formula (AC)

| Example | R$^{1AC}$ | R$^{2AC}$ | ESI MS (M + H) | $^1$H—NMR, CDCl$_3$, δ (ppm) |
|---|---|---|---|---|
| 666 | [structure: carbamate-NH-CH2CH2-N(Me)-CH(Me)-(2-methoxyphenyl) with N-Et] | H | 1007.0 | (600 MHz): 0.77-0.85 (m, 6H) 0.92 (t, J = 6.88 Hz, 3H) 1.06-1.25 (m, 2H) 1.11 (d, J = 7.34 Hz, 3H) 1.13 (s, 3H) 1.14-1.19 (m, 9H) 1.28 (d, J = 6.88 Hz, 3H) 1.30 (s, 3H) 1.50-1.56 (m, 1H) 1.56-1.97 (m, 6H) 2.10-2.19 (m, 1H) 2.20-2.31 (m, 2H) 2.24 (s, 6H) 2.31-2.65 (m, 9H) 2.36 (s, 3H) 2.76-2.84 (m, 1H) 2.93 (d, J = 15.59 Hz, 1H) 3.12-3.42 (m, 4H) 3.22 (s, 3H) 3.31 (s, 3H) 3.50-3.59 (m, 1H) 3.70 (d, J = 8.25 Hz, 1H) 3.84 (s, 3H) 4.17 (s, 1H) 4.32-4.46 (m, 3H) 4.53 (d, J = 10.09 Hz, 1H) 4.75 (s, 1H) 4.94 (d, J = 4.58 Hz, 1H) 5.54-5.62 (m, 1H) 6.86 (d, J = 7.79 Hz, 1H) 6.90 (t, J = 7.57 Hz, 1H) 7.19 (t, J = 6.88 Hz, 1H) 7.27 (d, J = 7.34 Hz, 1H) |
| 667 | [structure: NH-CH2CH2-N(Et)-CH(Me)-(2-methoxyphenyl)] | OH | 993.0 | (600 MHz): 0.78-0.88 (m, 6H) 0.97-1.02 (m, 3H) 1.09-1.13 (m, 6H) 1.12-1.23 (m, 12H) 1.28 (d, J = 6.88 Hz, 3H) 1.34 (s, 3H) 1.56-1.70 (m, 3H) 1.72-1.90 (m, 2H) 1.91-1.97 (m, 1H) 2.10-2.24 (m, 2H) 2.23-2.31 (m, 2H) 2.27 (s, 6H) 2.35-2.41 (m, 2H) 2.38 (s, 3H) 2.41-2.68 (m, 9H) 2.72-2.77 (m, 1H) 2.79-2.83 (m, 1H) 2.94-3.00 (m, 1H) 3.16-3.20 (m, 1H) 3.22-3.25 (m, 3H) 3.35 (s, 3H) 3.37-3.45 (m, 1H) 3.54-3.60 (m, 1H) 3.68-3.71 (m, 1H) 3.749-3.82 (m, 3H) 4.03-4.13 (m, 1H) 4.32-4.39 (m, 1H) 4.41-4.46 (m, 1H) 4.47-4..53 (m, 1H) 4.70-4.81 (m, 1H) 4.85 (d, J = 5.04 Hz, 1H) 6.83-6.87 (m, 1H) 6.93 (t, J = 6.88 Hz, 1H) 7.16-7.22 (m, 1H) 7.32-7.36 (m, 1H) |
| 668 | [structure: (3-hydroxyphenyl)-CH(Me)-NH-CH2CH2-NH-] | HO- | 951.1 | (600 MHz): 0.76-0.89 (m, 6H) 1.06-1.37 (m, 24H) 1.58-1.95 (m, 5H) 2.05-2.27 (m, 5H) 2.27 (s, 6H) 2.33-2.40 (m, 5H) 2.42-2.77 (m, 8H) 2.78-2.86 (m, 1H) 2.89-2.98 (m, 1H) 3.14-3.25 (m, 4H) 3.31-3.35 (m, 3H) 3.35-3.45 (m, 1H) 3.45-3.55 (m, 1H) 3.61-3.76 (m, 2H) 4.07-4.19 (m, 1H) 4.34-4.47 (m, 2H) 4.73-4.85 (m, 1H) 4.86-4.91 (m, 1H) 6.68-6.77 (m, 2H) 6.83-6.86 (m, 1H) 7.13 (t, J = 7.79 Hz, 1H) |

Example 664

(1) By using the compound obtained in Example 104, (1) (740 mg) as a starting material, a 4"-hydroxy compound (630 mg) was obtained in the same manner as that of Example 126, (1).
(2) By using the compound obtained in (1) mentioned above (100 mg) as a starting material, an imidazolylcarbonyl compound (109 mg) was obtained in the same manner as that of Example 126, (2).
(3) By using the compound obtained in (2) mentioned above (30 mg) and the compound obtained in Reference Example 106 (10.1 mg) as starting materials, the compound shown in Table 16 (21 mg) was obtained in the same manners as those of Example 126, (3) and Example 7, (4).

Example 665

By using the compound obtained in Example 664, (2) (30 mg) and the compound obtained in Reference Example 131 (10.1 mg) as starting materials, the compound shown in Table 16 (17 mg) was obtained in the same manners as those of Example 126, (3) and Example 7, (4).

Example 666

By using the compound obtained in Example 664, (2) (30 mg) and the compound obtained in Reference Example 54 (12.3 mg) as starting materials, the compound shown in Table 16 (21 mg) was obtained in the same manners as those of Example 126, (3) and Example 7, (4).

Example 667

(1) By using the compound obtained in Example 664, (1) (500 mg) as a starting material, a ketone compound (401 mg) was obtained in the same manner as that of Example 113, (2).

(2) By using the compound obtained in (1) mentioned above (200 mg) as a starting material, an epoxy compound (146 mg) was obtained in the same manner as that of Example 172, (1).
(3) By using the compound obtained in (2) mentioned above (142 mg) as a starting material, a deprotected compound (106 mg) was obtained in the same manner as that of Example 7, (4).
(4) By using the compound obtained in (3) mentioned above (30 mg) and the compound obtained in Reference Example 54 (43.4 mg) as starting materials, the compound shown in Table 16 (14.2 mg) was obtained in the same manner as that of Example 168, (2).

Example 668

By using the compound obtained in Example 667, (2) (30 mg) and the compound obtained in Reference Example 106 (35.1 mg) as starting materials, the compound shown in Table 16 (10.3 mg) was obtained in the same manner as that of Example 168, (2).

The "cladinosyl" mentioned in the aforementioned tables means a group represented by the following formula.

[Formula 32]

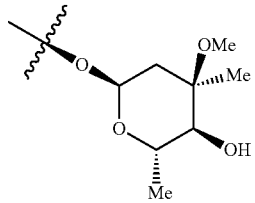

Syntheses of Examples 669 to 675

Preparation methods of compounds represented by the formula (AD) having $R^{1AD}$ and $R^{2AD}$ defined in Table 17 are shown below.

TABLE 17

[Formula 33]

(formula AD)

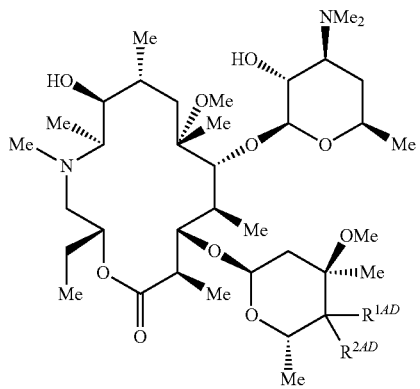

| Example | $R^{1AD}$ | $R^{2AD}$ | MS (M + H) | $^1$H—NMR, CDCl$_3$, δ (ppm) |
|---|---|---|---|---|
| 669 | Me-N(Me)-CH(Me)-NH-* | HO''''''-* | 833.7 | (500 MHz): 0.81 (d, J = 6.86 Hz, 6H) 0.89 (t, J = 7.40 Hz, 3H) 0.95 (d, J = 6.03 Hz, 3H) 1.05-1.28 (m, 11H) 1.10 (d, J = 7.40 Hz, 3H) 1.21 (d, J = 6.03 Hz, 3H) 1.31 (s, 3H) 1.48-1.91 (m, 5H) 1.98-2.10 (m, 2H) 2.11-2.57 (m, 7H) 2.18 (s, 6H) 2.29 (s, 6H) 2.35 (s, 3H) 2.65-2.73 (m, 1H) 2.74-2.83 (m, 2H) 2.85-2.94 (m, 1H) 3.17-3.23 (m, 1H) 3.23 (s, 3H) 3.29 (s, 3H) 3.33-3.45 (m, 1H) 3.47-3.58 (m, 1H) 3.71 (d, J = 8.23 Hz, 1H) 4.13-4.22 (m, 1H) 4.34-4.42 (m, 2H) 4.57-4.66 (m, 1H) 4.97 (d, J = 4.66 Hz, 1H) |
| 670 | Me-N(Me)-CH(Me)-NH-* | HO''''''-* | 833.6 | (500 MHz): 0.81 (d, J = 7.13 Hz, 6H) 0.89 (t, J = 7.40 Hz, 3H) 0.99 (d, J = 5.48 Hz, 3H) 1.05-1.28 (m, 8H) 1.09 (d, J = 7.40 Hz, 3H) 1.12 (s, 3H) 1.21 (d, J = 6.03 Hz, 3H) 1.31 (s, 3H) 1.48-1.94 (m, 5H) 1.97-2.04 (m, 1H) 2.09-2.55 (m, 8H), 2.20 (s, 6H) 2.29 (s, 6H) 2.36 (s, 3H) 2.64-2.74 (m, 1H) 2.74-2.81 (m, 1H) 2.90 (d, J = 14.54 Hz, 1H) 2.95 (d, J = 13.16) Hz, 1H) 3.16-3.23 (m, 1H) 3.23 (s, 3H) 3.28 (s, 3H) 3.34-3.45 (m, 1H) 3.46-3.56 (m, 1H) 3.72 (d, J = 7.68 Hz, 1H) 4.12-4.22 (m, 1H) 4.32 (q, J = 6.40 Hz, 1H) 4.38 (d, J = 7.40 Hz, 1H) 4.57-4.68 (m, 1H) 4.96 (d, J = 4.94 Hz, 1H) |

TABLE 17-continued

[Formula 33]

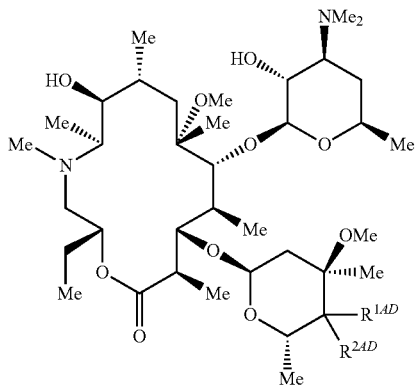

(formula AD)

| Example | R$^{1AD}$ | R$^{2AD}$ | MS (M + H) | $^1$H—NMR, CDCl$_3$, δ (ppm) |
|---|---|---|---|---|
| 671 | [structure: CH$_2$NH-CH$_2$-(N-ethyl pyrrolidinyl)] | [structure: HO] | 859.6 | (500 MHz): 0.81 (d, J = 6.88 Hz, 6H) 0.89 (t, J = 7.45 Hz, 3H) 1.03-1.28 (m, 20 H) 1.31 (s, 3H) 1.46-1.94 (m, 9H) 2.01-2.33 (m, 6H) 2.29 (s, 6H) 2.36 (s, 3H) 2.38-2.69 (m, 5H) 2.73-2.84 (m, 3H) 2.90 (d, J = 15.29 Hz, 1H) 3.09-3.22 (m, 3H) 3.23 (s, 3H) 3.28 (s, 3H) 3.36-3.44 (m, 1H) 3.46-3.55 (m, 1H) 3.71 (d, J = 8.41 Hz, 1H) 4.15-4.23 (m, 1H) 4.32-4.40 (m, 2H) 4.57-4.67 (m, 1H) 4.97 (d, J = 4.97 Hz, 1H) |
| 672 | [structure: 2-methoxyphenyl-CH(Me)-CH$_2$-NH-] | [structure: HO] | 896.4 | mixture of diastereomers (400 MHz): 0.80-0.84 (m, 6H) 0.88-0.93 (m, 3H) 1.03-1.37 (m, 23H) 2.06-2.50 (m, 19H) 2.61-2.96 (m, 6H) 3.16-3.68 (m, 15H) 3.80-3.83 (m, 4H) 4.06 (m, 1H) 4.36-4.42 (m, 2H) 4.65 (m, 1H) 4.79 (d, J = 4.9 Hz, 1H) 6.82-6.94 (m, 2H) 7.18-7.23 (m, 2H) |
| 673 | [structure: 2-methoxybenzyl-NH-] | [structure: HO] | 868.3 | (400 MHz): 0.82 (d, J = 6.9 Hz, 3H) 0.82 (d, J = 6.9 Hz, 3H) 0.90 (t, J = 7.3 Hz, 3H) 1.05 (s, 3H) 1.08 (d, J = 7.3 Hz, 3H) 1.15-1.20 (m, 11H) 1.32 (s, 3H) 1.50-1.89 (m, 10H) 2.00-2.46 (m, 15H) 3.20 (dd, J = 10.3, 7.1 Hz, 1H) 3.23 (s, 3H) 3.26 (s, 3H) 3.50 (m, 1H) 3.62 (d, J = 13.4 Hz, 1H) 3.68 (d, J = 8.1 Hz, 1H) 3.84 (s, 3H) 3.85 (d, J = 13.4 Hz, 1H) 4.14 (m, 1H) 4.37 (d, J = 7.1 Hz, 1H) 4.39 (q, J = 6.4 Hz, 1H) 4.62 (m, 1H) 4.96 (m, 1H) 6.85-6.93 (m, 2H) 7.15-7.26 (m, 2H) |
| 674 | [structure: 2-methoxyphenyl-CH(Me)-NH-CH$_2$-] | [structure: HO] | 882.3 | (400 MHz): 0.81 (d, J = 7.0 Hz, 3H) 0.81 (d, J = 7.0 Hz, 3H) 0.84 (t, J = 7.3 Hz, 3H) 1.08-1.17 (m, 17H) 1.30 (s, 3H) 1.35 (d, J = 6.9 Hz, 3H) 1.43-2.05 (m, 10H) 2.13-2.46 (m, 15H) 2.73-2.94 (m, 3H) 3.18 (dd, J = 10.0, 7.3 Hz, 1H) 3.23 (s, 3H) 3.26 (s, 3H) 3.34-3.45 (m, 2H) 3.67 (d, J = 7.8 Hz, 1H) 3.83 (s, 3H) 4.02 (m, 1H) 4.08-4.14 (m, 1H) 4.30 (q, J = 6.4 Hz, 1H) 4.35 (d, J = 7.4 Hz, 1H) 4.62 (m, 1H) 4.96 (m, 1H) 6.84-6.94 (m, 2H) 7.18-7.24 (m, 2H) |
| 675 | [structure: 2-methoxyphenyl-CH(Me)-N(Et)-CH$_2$-] | [structure: HO] | 910.4 | (400 MHz): 0.82 (d, J = 7.1 Hz, 3H) 0.82 (d, J = 7.1 Hz, 3H) 0.90 (t, J = 7.4 Hz, 3H) 1.08-1.44 (m, 24H) 1.50-1.80 (m, 10H) 1.95-2.60 (m, 18H) 2.72-2.93 (m, 3H) 3.20 (m, 1H) 3.23 (s, 3H) 3.32 (s, 3H) 3.39 (m, 2H) 3.72 (d, J = 8.1 Hz, 1H) 3.85 (s, 3H) 4.15-4.25 (m, 2H) 4.35-4.40 (m, 2H) 4.63 (m, 1H) 4.99 (m, 1H) 6.84-6.95 (m, 2H) 7.24-7.34 (m, 2H) |

Example 669

By using the compound obtained in Example 368, (1) (30 mg) and 1-dimethylamino-2-propylamine (21.0 mg) as starting materials, the compound shown in Table 17 (8.1 mg) was obtained in the same manner as that of Example 368, (2).

Example 670

By using the compound obtained in Example 368, (1) (30 mg) and 1-dimethylamino-2-propylamine (21.0 mg) as starting materials, a diastereomer of the compound of Example 669 shown in Table 17 (11.0 mg) was obtained in the same manner as that of Example 368, (2).

Example 671

By using the compound obtained in Example 368, (1) (30 mg) and (S)-(−)-2-aminomethyl-1-ethylpyrrolidine (26.3 mg) as starting materials, the compound shown in Table 17 (21.7 mg) was obtained in the same manner as that of Example 368, (2).

Example 672

By using the compound obtained in Example 412, (1) (30 mg) and the compound obtained in Reference Example 220 (32 mg) as starting materials, the compound shown in Table 17 (25 mg) was obtained in the same manner as that of Example 535.

Example 673

(1) By using the compound obtained in Example 168, (1) (25 mg) and 2-methoxybenzylamine (23 µl) as starting materials, an amine compound (29 mg) was obtained in the same manner as that of Example 535.
(2) By using the compound obtained in (1) mentioned above (19 mg) as a starting material, the compound shown in Table 17 (13 mg) was obtained in the same manner as that of Example 7, (4).

Example 674

(1) By using the compound obtained in Example 168, (1) (26 mg) and (1S)-(2-methoxyphenyl)ethanamine (26 mg) obtained by the method described in the patent document (Japanese Patent Unexamined Publication No. 54-154724) as starting materials, an amine compound (30 mg) was obtained in the same manner as that of Example 535.
(2) By using the compound obtained in (1) mentioned above (19 mg) as a starting material, the compound shown in Table 17 (13 mg) was obtained in the same manner as that of Example 7, (4).

Example 675

By using the compound obtained in Example 368, (1) (33 mg) and the compound obtained in Reference Example 54, (2) (40 mg) as starting materials, the compound shown in Table 17 (21 mg) was obtained in the same manner as that of Example 535.

Syntheses of Examples 676 to 778

By using the compound obtained in Example 368, (1) and amine reagents as starting materials, compounds represented by the formula (AE) having R defined in Table 18 were obtained in the same manner as that of Example 368, (2).

TABLE 18

[Formula 34]

Formula (AE)

| Example | R | ESI MS (M + H) |
|---|---|---|
| 676 | (cyclopropylmethyl)amino | 788.93 |
| 677 | (cyclobutyl)amino | 802.97 |
| 678 | 3-(2-oxopyrrolidin-1-yl)propylamino | 873.99 |
| 679 | (2S)-1-hydroxy-3-methylbutan-2-ylamino | 849.00 |
| 680 | (tetrahydrofuran-2-ylmethyl)amino | 832.97 |
| 681 | (2-amino-2-methylpropyl)amino | 820.00 |
| 682 | (3-methylbutan-2-yl)amino | 819.00 |
| 683 | (propan-2-yl)amino | 790.97 |

TABLE 18-continued
[Formula 34]
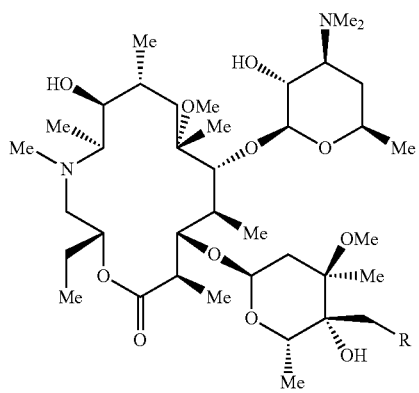
Formula (AE)
| Example | R | ESI MS (M + H) |
|---|---|---|
| 684 | 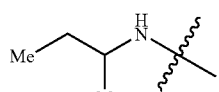 | 804.99 |
| 685 | 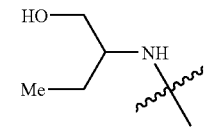 | 820.99 |
| 686 | 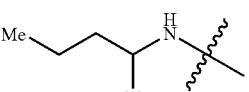 | 819.01 |
| 687 | 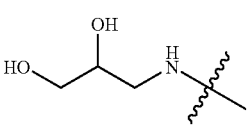 | 822.97 |
| 688 | 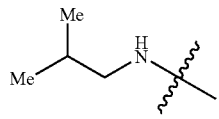 | 805.01 |
| 689 | 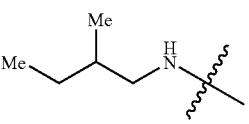 | 819.01 |
| 690 | 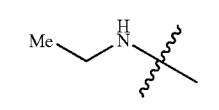 | 776.95 |
| 691 | 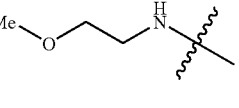 | 806.98 |
| 692 | 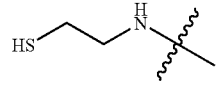 | 808.02 |
TABLE 18-continued
[Formula 34]
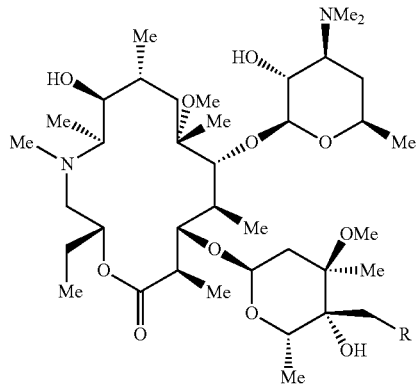
Formula (AE)
| Example | R | ESI MS (M + H) |
|---|---|---|
| 693 | 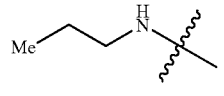 | 790.98 |
| 694 | 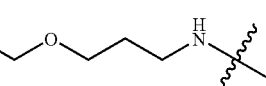 | 835.01 |
| 695 | 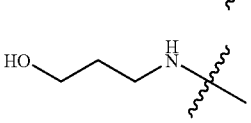 | 806.98 |
| 696 | 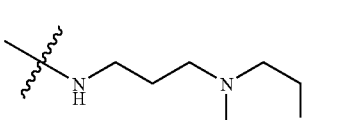 | 889.04 |
| 697 | 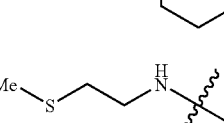 | 822.96 |
| 698 | 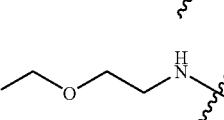 | 820.99 |
| 699 | 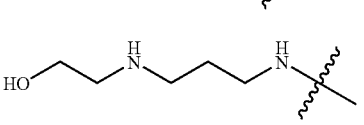 | 850.01 |
| 700 | 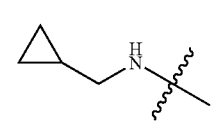 | 802.99 |
| 701 | 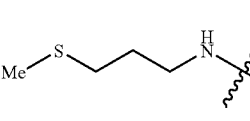 | 836.97 |
| 702 | 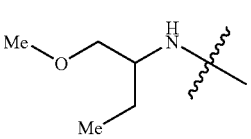 | 835.01 |

TABLE 18-continued

[Formula 34]

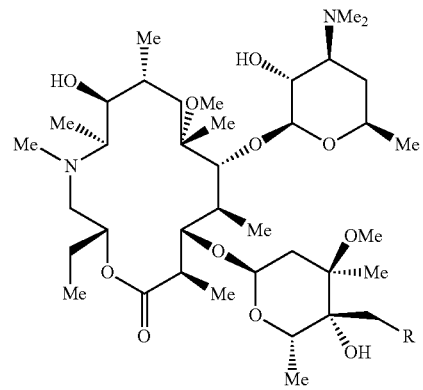

Formula (AE)

| Example | R | ESI MS (M + H) |
|---|---|---|
| 703 | ![structure with =CH2, Me, NH] | 802.98 |
| 704 | Me-CH2-CH(OH)-CH2-NH- | 820.99 |
| 705 | HO-CH2-C(Me)2-CH2-NH- | 835.00 |
| 706 | HO-CH2-CH(NH-)-CH(Me)2 | 835.02 |
| 707 | HO-CH2-CH(Me)-NH- | 806.98 |
| 708 | HO-CH2-CH(CH2Me)-NH- | 820.99 |
| 709 | HO-CH2-CH(CH2Me)-NH- | 821.00 |
| 710 | Me-CH(OH)-CH2-NH- | 806.99 |

TABLE 18-continued

[Formula 34]

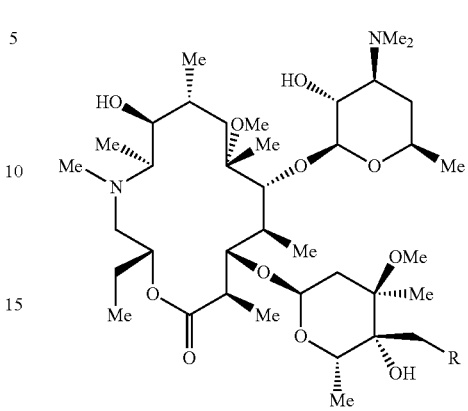

Formula (AE)

| Example | R | ESI MS (M + H) |
|---|---|---|
| 711 | 4-hydroxycyclohexyl-NH- | 847.00 |
| 712 | (tetrahydrofuran-2-yl)methyl-NH- | 832.99 |
| 713 | (piperidin-2-yl)methyl-NH- | 846.02 |
| 714 | HOCH2-CH(NH-)-CH(OH)-Me | 836.98 |
| 715 | (tetrahydrofuran-2-yl)methyl-NH- | 832.99 |
| 716 | H2N-C(O)-CH(NH-)-CH2-CH(Me)2 | 862.01 |
| 717 | HO-CH2-CH(OH)-CH2-NH- | 822.97 |

TABLE 18-continued
[Formula 34]
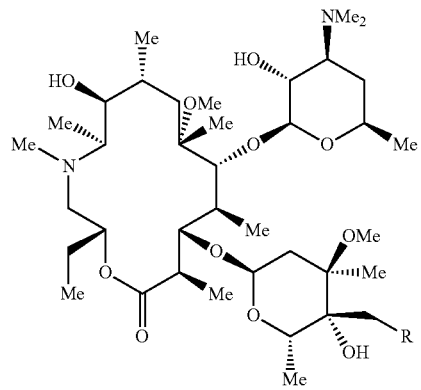
Formula (AE)
| Example | R | ESI MS (M + H) |
|---|---|---|
| 718 | 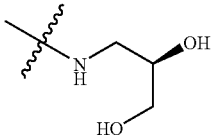 | 822.97 |
| 719 | 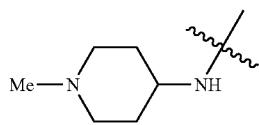 | 846.01 |
| 720 | 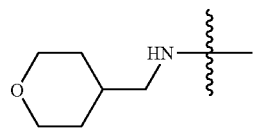 | 846.99 |
| 721 | 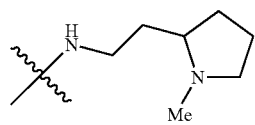 | 860.04 |
| 722 | 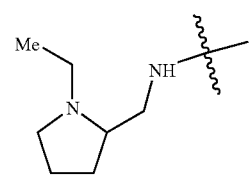 | 860.05 |
| 723 | 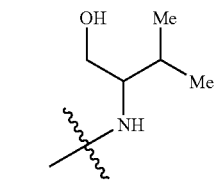 | 835.01 |
| 724 | 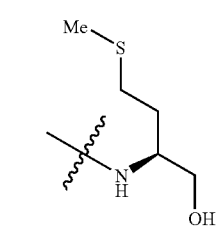 | 866.97 |
TABLE 18-continued
[Formula 34]
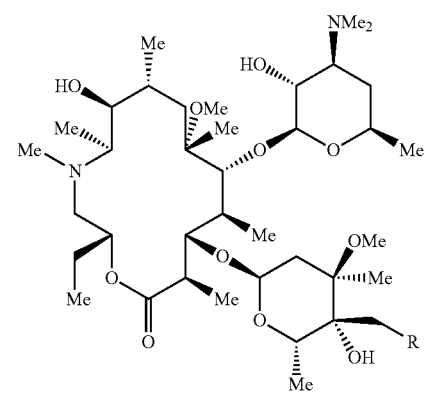
Formula (AE)
| Example | R | ESI MS (M + H) |
|---|---|---|
| 725 | 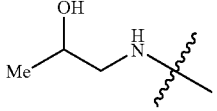 | 806.98 |
| 726 | 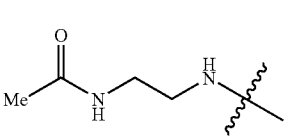 | 833.99 |
| 727 | 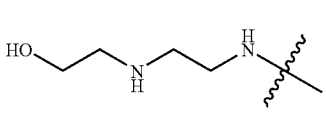 | 836.01 |
| 728 | 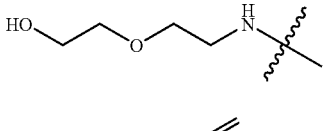 | 836.99 |
| 729 | 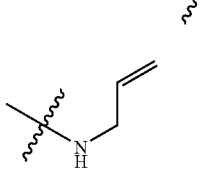 | 788.97 |
| 730 | 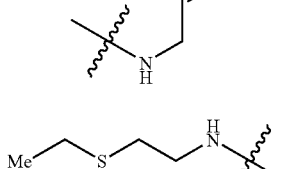 | 836.97 |
| 731 | 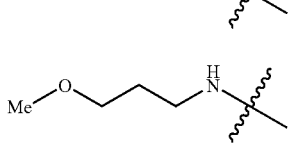 | 821.00 |
| 732 | 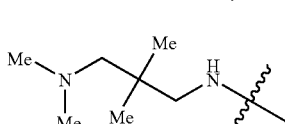 | 862.06 |
| 733 | 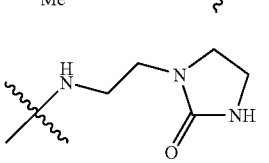 | 860.99 |

TABLE 18-continued
[Formula 34]
Formula (AE)
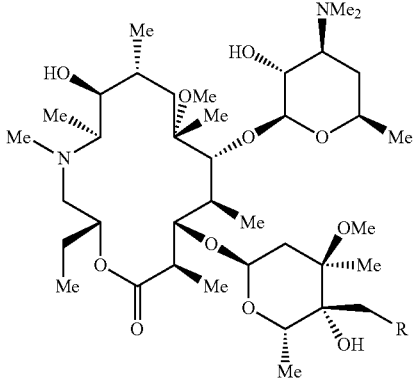
| Example | R | ESI MS (M + H) |
|---|---|---|
| 734 | 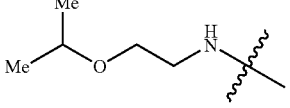 | 835.02 |
| 735 | 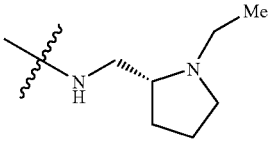 | 860.03 |
| 736 | 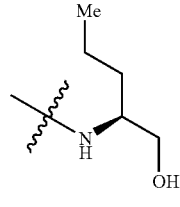 | 835.00 |
| 737 | 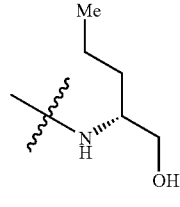 | 835.01 |
| 738 | 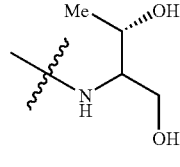 | 836.99 |
| 739 | 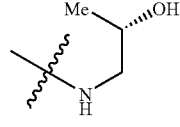 | 806.97 |
TABLE 18-continued
[Formula 34]
Formula (AE)
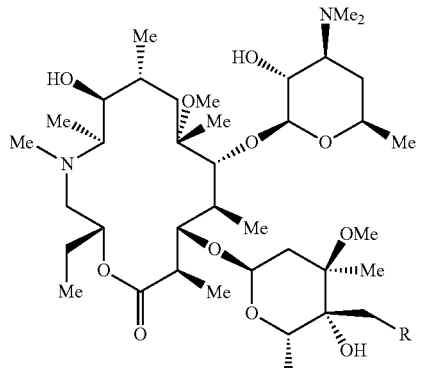
| Example | R | ESI MS (M + H) |
|---|---|---|
| 740 | 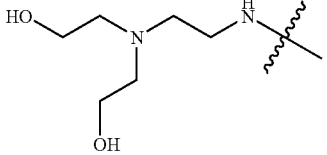 | 880.01 |
| 741 | 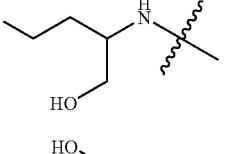 | 835.00 |
| 742 | 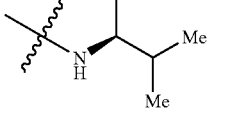 | 835.00 |
| 743 | 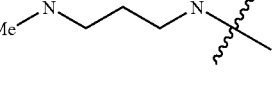 | 820.00 |
| 744 | 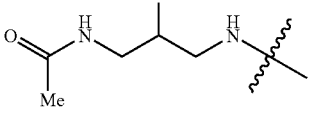 | 862.00 |
| 745 | 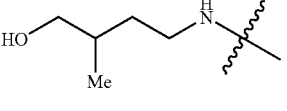 | 835.00 |
| 746 | 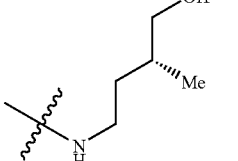 | 834.99 |
| 747 | 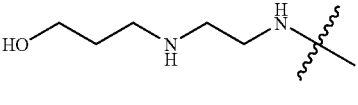 | 850.00 |

TABLE 18-continued
[Formula 34]
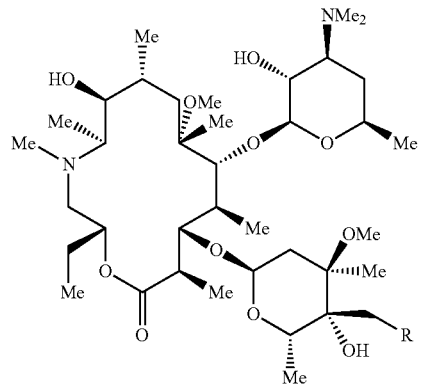
Formula (AE)
| Example | R | ESI MS (M + H) |
|---|---|---|
| 748 | 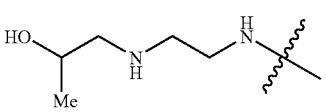 | 850.01 |
| 749 | 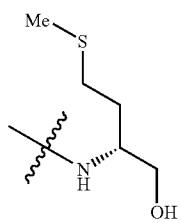 | 866.96 |
| 750 | 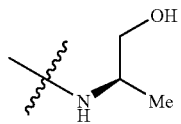 | 806.97 |
| 751 | 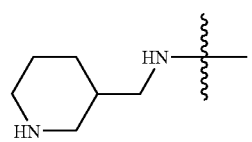 | 846.01 |
| 752 | 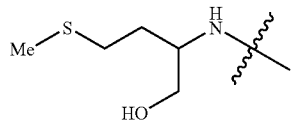 | 867.03 |
| 753 | 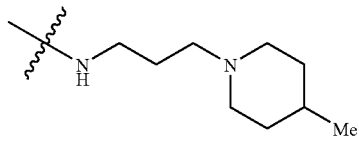 | 888.11 |
TABLE 18-continued
[Formula 34]
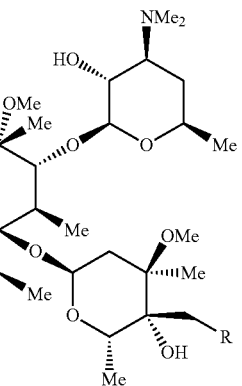
Formula (AE)
| Example | R | ESI MS (M + H) |
|---|---|---|
| 754 | 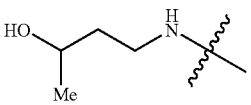 | 821.04 |
| 755 | 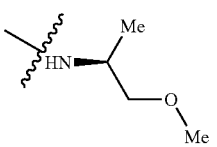 | 821.04 |
| 756 | 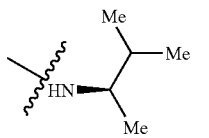 | 819.06 |
| 757 | 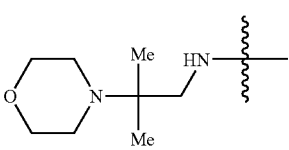 | 890.09 |
| 758 | 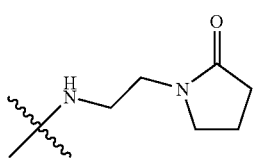 | 860.05 |
| 759 | 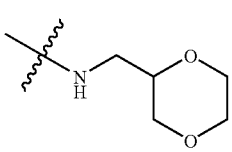 | 849.04 |
| 760 | 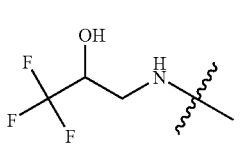 | 861.00 |

TABLE 18-continued

[Formula 34]

Formula (AE)

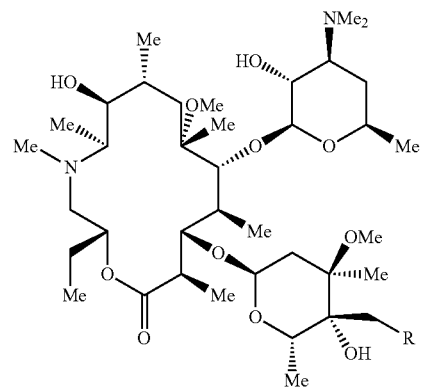

| Example | R | ESI MS (M + H) |
|---|---|---|
| 761 | [structure: NH-CH2CH2-N(piperazine)-Et] | 889.09 |
| 762 | [structure: NH-(1-ethylpiperidin-4-yl)] | 860.08 |
| 763 | [structure: NH-CH2-(1-ethylpiperidin-4-yl)] | 874.09 |
| 764 | [structure: NH-CH2-(1-methylpiperidin-2-yl)] | 860.08 |
| 765 | [structure: NH-CH2-CH(Me)-OEt] | 835.06 |
| 766 | [structure: NH-CH2-CH(OMe)-Et with Me] | 835.05 |
| 767 | [structure: NH-(2,5-dihydrothiophene-1,1-dioxide-3-yl)] | 865.03 (APCI) |

TABLE 18-continued

[Formula 34]

Formula (AE)

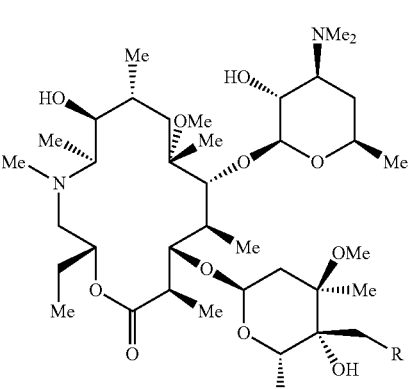

| Example | R | ESI MS (M + H) |
|---|---|---|
| 768 | [structure: NH-CH2-(1-(2-hydroxyethyl)piperidin-4-yl)] | 890.08 |
| 769 | [structure: NH-CH(piperidin-4-yl)-CH2-CH=CH2] | 886.09 |
| 770 | [structure: NH-CH2-C(=O)-NH-Et] | 834.03 |
| 771 | [structure: NH-CH2-C(=O)-NH-cyclopropyl] | 846.03 |
| 772 | [structure: NH-CH2-C(=O)-NH-CH(Me)2] | 848.04 |
| 773 | [structure: NH-CH2-C(=O)-NH-C(Me)3] | 862.06 |

TABLE 18-continued
[Formula 34]
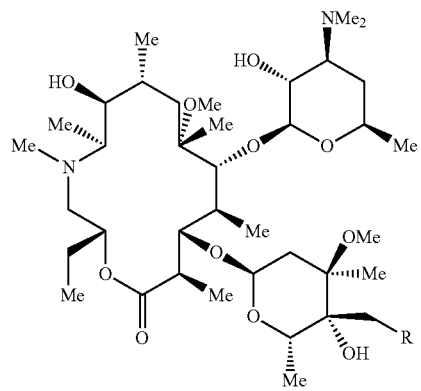
Formula (AE)
| Example | R | ESI MS (M + H) |
|---|---|---|
| 774 | 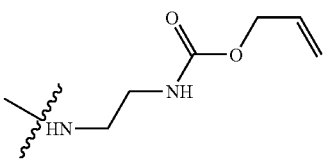 | 890.08 |
| 775 | 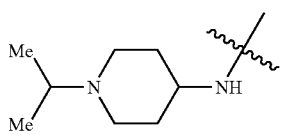 | 876.02 |
| 776 | 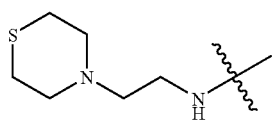 | 874.07 |
| 777 | 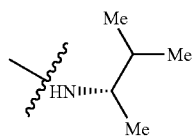 | 878.01 |
| 778 | 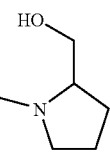 | 819.04 |
Syntheses of Examples 779 to 822
By using the compound obtained in Example 412, (1) and amine reagents as starting materials, compounds represented by the formula (AF) having R defined in Table 19 were obtained in the same manner as that of Example 368, (2).
TABLE 19
[Formula 35]
Formula (AF)
| Example | R | ESI MS (M + H) |
|---|---|---|
| 779 | 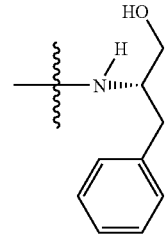 | 882.94 |
| 780 | 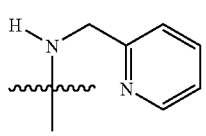 | 839.94 |
| 781 | 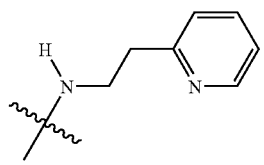 | 853.97 |
| 782 | 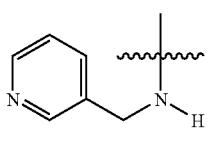 | 839.95 |
| 783 | 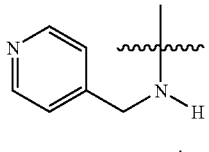 | 839.95 |
| 784 | 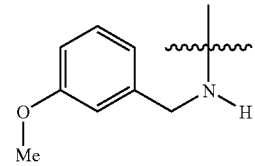 | 868.98 |
| 785 | 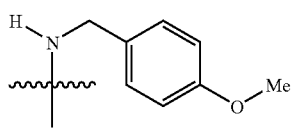 | 868.98 |

TABLE 19-continued
[Formula 35]
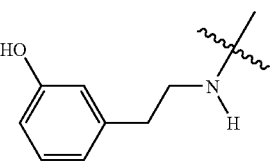
Formula (AF)
| Example | R | ESI MS (M + H) |
|---|---|---|
| 786 | 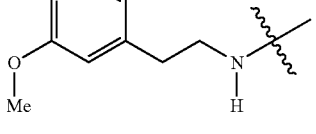 | 868.99 |
| 787 | 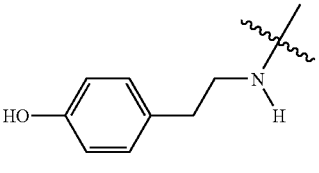 | 883.00 |
| 788 | 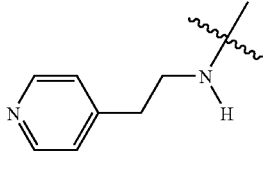 | 868.98 |
| 789 | 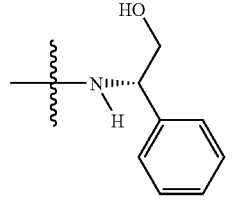 | 853.99 |
| 790 | 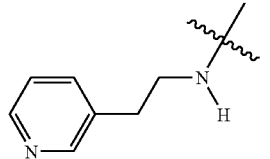 | 868.99 |
| 791 | 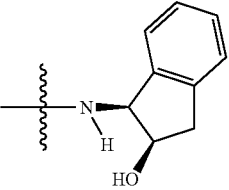 | 853.99 |
| 792 | 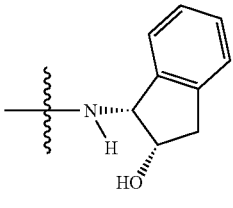 | 881.00 |
| 793 | 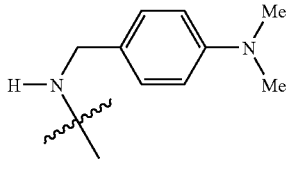 | 880.99 |
| 794 | 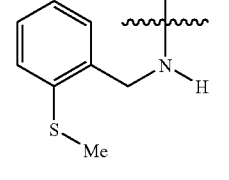 | 882.03 |
| 795 | 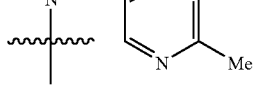 | 884.97 |
| 796 | 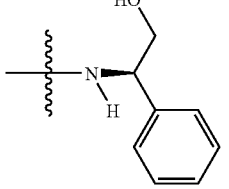 | 855.00 |
| 797 |  | 869.00 |

TABLE 19-continued
[Formula 35]
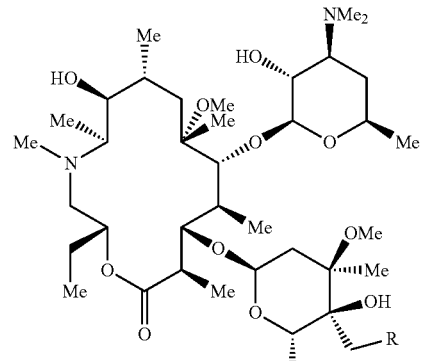
Formula (AF)
| Example | R | ESI MS (M + H) |
|---|---|---|
| 798 | 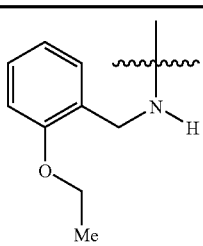 | 883.02 |
| 799 | 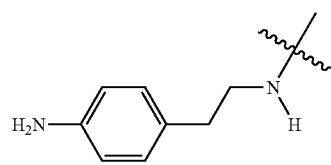 | 868.03 |
| 800 | 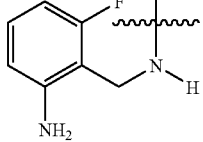 | 872.00 |
| 801 | 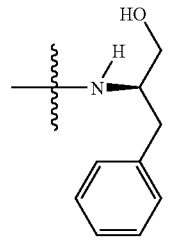 | 883.03 |
| 802 | 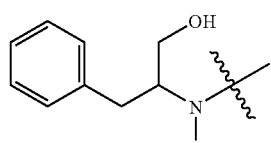 | 883.02 |
| 803 | 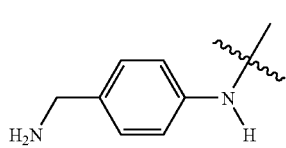 | 854.02 |
TABLE 19-continued
[Formula 35]
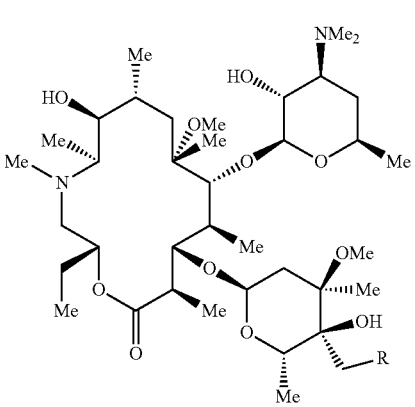
Formula (AF)
| Example | R | ESI MS (M + H) |
|---|---|---|
| 804 | 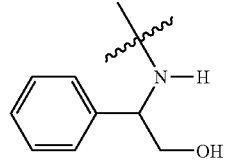 | 869.02 |
| 805 | 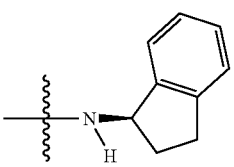 | 865.01 |
| 806 | 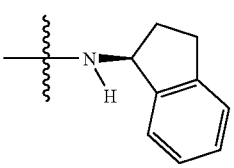 | 865.02 |
| 807 | 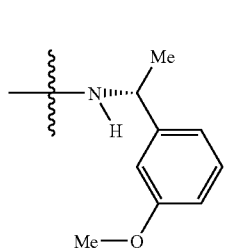 | 883.03 |
| 808 | 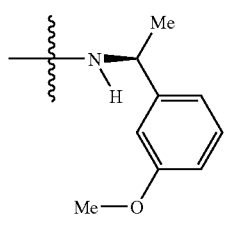 | 883.03 |

TABLE 19-continued
[Formula 35]
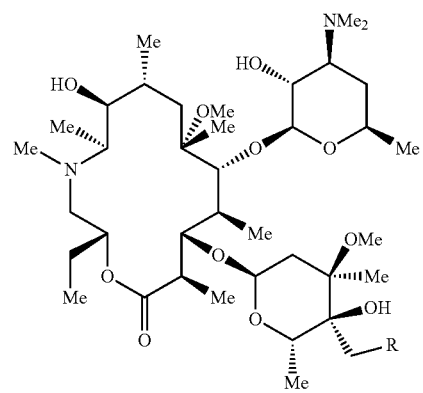
Formula (AF)
| Example | R | ESI MS (M + H) |
|---|---|---|
| 809 | 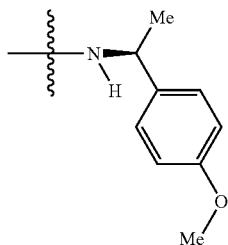 | 883.03 |
| 810 | 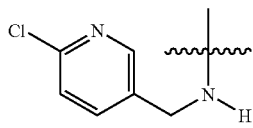 | 873.95 |
| 811 | 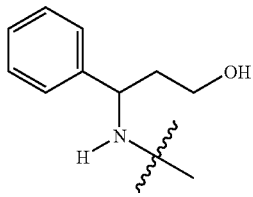 | 883.03 |
| 812 | 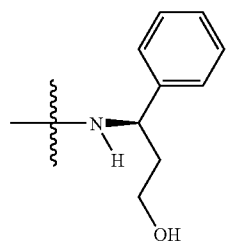 | 883.04 |
| 813 | 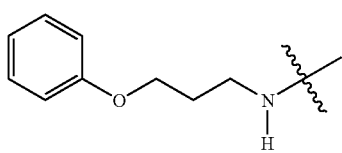 | 883.03 |
TABLE 19-continued
[Formula 35]
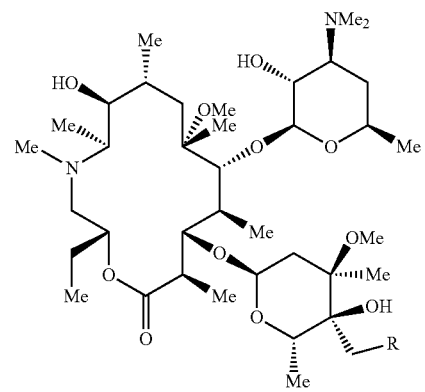
Formula (AF)
| Example | R | ESI MS (M + H) |
|---|---|---|
| 814 | 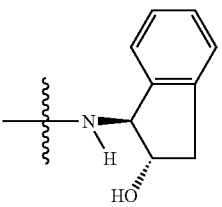 | 881.02 |
| 815 | 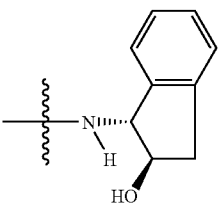 | 881.02 |
| 816 | 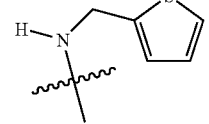 | 844.99 |
| 817 | 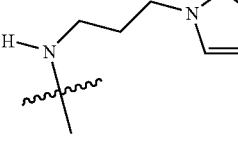 | 857.05 |
| 818 | 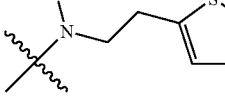 | 858.99 |
| 819 | 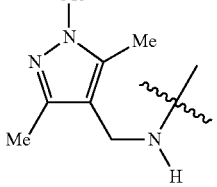 | 871.04 |

565
TABLE 19-continued

[Formula 35]

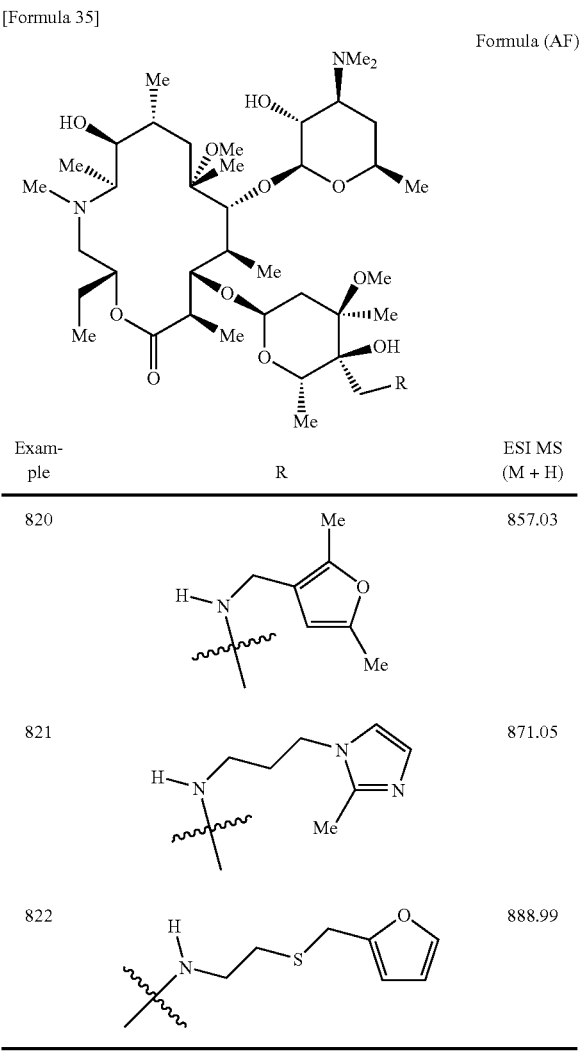

Formula (AF)

| Example | R | ESI MS (M + H) |
|---|---|---|
| 820 | | 857.03 |
| 821 | | 871.05 |
| 822 | | 888.99 |

Test Example 1

In Vitro Antibacterial Activity

In vitro antibacterial activities of the compounds of the present invention against various test bacteria were measured according to the microbroth dilution method (NCCLS method). As test compounds, the compounds of Examples 7, 23, 114, 126, 131, 210, 214, 231, 257, 261, 287, 363, 366, 563 and Comparative agent 1: clarithromycin were used. The test bacteria used are shown in Table 20. The results are shown as MIC values (minimum inhibitory concentration, μg/ml) in Table 21.

TABLE 20

| Test bacteria | Symbols of bacteria |
|---|---|
| H. influenzae ATCC 43095 | A |
| S. pneumoniae ATCC 49619 | B |
| S. pneumoniae 205 | C |

566
TABLE 21

| | Compound | | |
|---|---|---|---|
| | A | B | C |
| Comparative agent 1 | 4 | 0.03 | >128 |
| Example 7 | 1 | 0.03 | >128 |
| Example 23 | 4 | 0.03 | 8 |
| Example 114 | 8 | 0.016 | 0.06 |
| Example 126 | 4 | 0.06 | 0.03 |
| Example 131 | 16 | 0.03 | 0.12 |
| Example 210 | 4 | 0.06 | 32 |
| Example 214 | 1 | 0.03 | >128 |
| Example 231 | 8 | 0.06 | 2 |
| Example 257 | 8 | 0.03 | 4 |
| Example 261 | 4 | 0.12 | 64 |
| Example 287 | 8 | 0.06 | 0.12 |
| Example 363 | 2 | 0.12 | 4 |
| Example 366 | 4 | 0.12 | 2 |
| Example 563 | 16 | 0.25 | 64 |

INDUSTRIAL APPLICABILITY

The compounds of the present invention have superior antibacterial activity against *Hemophilus influenzae*, erythromycin resistant pneumococci and the like, and therefore, they can be used as therapeutic agents of infectious diseases.

What is claimed is:

1. A 10a-azalide compound represented by the formula (I):

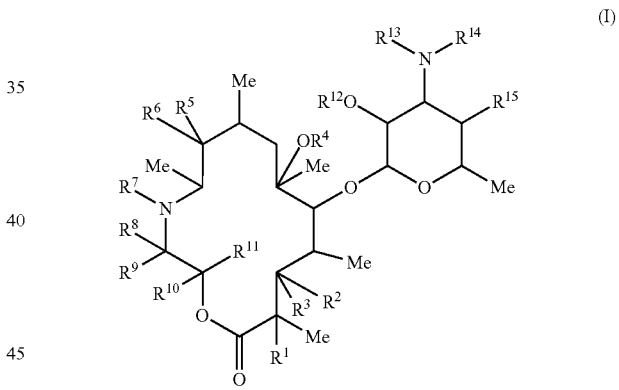

{wherein, in the formula (I), $R^1$ is:
hydrogen atom,
a halogen atom, or
a $C_{1-10}$ alkyl group which may be substituted,
$R^2$ and $R^3$ combine together to represent oxo group, or one of them is hydrogen atom, and the other is:
hydrogen atom,
hydroxyl group,
a protected hydroxyl group,
a group represented by the formula —$X^{031}$—$R^{031}$,
a group represented by the formula —$X^{031}$-$A^{031}$-$X^{032}$—$R^{031}$,
a group represented by the formula —$X^{031}$-$A^{031}$-$X^{032}$-$A^{032}$-$X^{033}$—$R^{031}$,
a group represented by the formula —$X^{031}$-$A^{031}$-$X^{032}$-$A^{032}$-$X^{033}$-$A^{033}$-$X^{034}$—$R^{031}$, or a group represented by the formula 2:

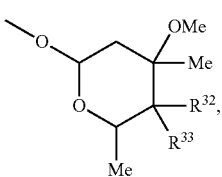

(2)

wherein $X^{031}$ is:
a group represented by the formula —O—,
a group represented by the formula —OCO—,
a group represented by the formula —OCO$_2$—, or
a group represented by the formula —OCON(R$^{20}$)—,
one of $R^{32}$ and $R^{33}$ is hydrogen atom, and the other is:
hydrogen atom,
amino group,
hydroxyl group,
a protected hydroxyl group,
a group represented by the formula —OCON(R$^{24}$)R$^{25}$ (in the formula, $R^{24}$ and $R^{25}$ both represent hydrogen atom, or represent groups which combine to form a cyclic amino group together with the adjacent nitrogen atom),
a group represented by the formula —X$^{331}$—R$^{331}$,
a group represented by the formula —X$^{331}$-A$^{331}$-X$^{332}$—R$^{331}$,
a group represented by the formula —X$^{331}$-A$^{331}$-X$^{332}$-A$^{332}$-X$^{333}$—R$^{331}$, or
a group represented by the formula —X$^{331}$-A$^{331}$-X$^{332}$-A$^{332}$-X$^{333}$-A$^{333}$-X$^{334}$—R$^{331}$,
wherein $X^{331}$ is:
a single bond,
a group represented by the formula —O—,
a group represented by the formula —OCO—,
a group represented by the formula —OCO$_2$—,
a group represented by the formula —OCON(R$^{20}$)—,
a group represented by the formula —N(R$^{20}$)—,
a group represented by the formula —N(R$^{20}$)CO—,
a group represented by the formula —N(R$^{20}$)CO$_2$—,
a group represented by the formula —N(R$^{20}$)CON(R$^{21}$)—, or
a group represented by the formula —N(R$^{20}$)SO$_2$—,
or one of $R^{32}$ and $R^{33}$ is hydroxyl group, and the other is:
a group represented by the formula —CH$_2$NH$_2$,
a group represented by the formula —X$^{335}$—R$^{332}$,
a group represented by the formula —X$^{335}$-A$^{334}$-X$^{336}$—R$^{332}$,
a group represented by the formula —X$^{335}$-A$^{334}$-X$^{336}$-A$^{335}$-X$^{337}$—R$^{332}$, or
a group represented by the formula —X$^{335}$-A$^{334}$-X$^{336}$-A$^{335}$-X$^{337}$-A$^{336}$-X$^{338}$—R$^{332}$,
wherein $X^{335}$ is:
a single bond,
a group represented by the formula —(CH$_2$)$_n$—N(R$^{20}$)—,
a group represented by the formula —(CH$_2$)$_n$—N(R$^{20}$)CO—,
a group represented by the formula —(CH$_2$)$_n$—N(R$^{20}$)CO$_2$—,
a group represented by the formula —(CH$_2$)$_n$—N(R$^{20}$)CON(R$^{21}$)—,
a group represented by the formula —(CH$_2$)$_n$—N(R$^{20}$)O—,
a group represented by the formula —(CH$_2$)$_n$—OCON(R$^{20}$)—,
a group represented by the formula —(CH$_2$)$_n$—ON(R$^{20}$)CO—,
a group represented by the formula —(CH$_2$)$_n$—O—,
a group represented by the formula —(CH$_2$)$_n$—OCO—,
a group represented by the formula —(CH$_2$)$_n$—OCO$_2$—,
a group represented by the formula —(CH$_2$)$_n$—OC(NR$^{20}$)—, or
a group represented by the formula —(CH$_2$)$_n$—S(O)$_p$—,
or $R^{32}$ and $R^{33}$ combine together to represent:
oxo group,
oxime group,
a group represented by the formula =N—X$^{339}$—R$^{333}$,
a group represented by the formula =N—X$^{339}$-A$^{337}$-X$^{340}$—R$^{333}$,
a group represented by the formula =N—X$^{339}$-A$^{337}$-X$^{340}$-A$^{338}$-X$^{341}$—R$^{333}$,
a group represented by the formula =N—X$^{339}$-A$^{337}$-X$^{340}$-A$^{338}$-X$^{341}$-A$^{339}$-X$^{342}$—R$^{333}$, or a group represented by the formula 3:

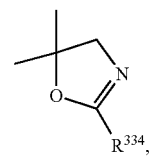

(3)

wherein $X^{339}$ is:
a single bond,
a group represented by the formula —O—,
a group represented by the formula —N(R$^{20}$)—,
a group represented by the formula —N(R$^{20}$)CO—,
a group represented by the formula —N(R$^{20}$)CO$_2$—,
a group represented by the formula —N(R$^{20}$)CON(R$^{21}$)—, or
a group represented by the formula —N(R$^{20}$)SO$_2$—,
and
$R^{334}$ is:
a group represented by the formula —SH,
a group represented by the formula —OH,
a group represented by the formula —X$^{343}$—R$^{335}$,
a group represented by the formula —X$^{343}$-A$^{340}$-X$^{344}$—R$^{335}$,
a group represented by the formula —X$^{343}$-A$^{340}$-X$^{344}$-A$^{341}$-X$^{345}$—R$^{335}$, or
a group represented by the formula —X$^{343}$-A$^{340}$-X$^{344}$-A$^{341}$-X$^{345}$-A$^{342}$-X$^{346}$—R$^{335}$,
wherein $X^{343}$ is:
a single bond,
a group represented by the formula —S—, or
a group represented by the formula —(CH$_2$)$_n$CO—,
$R^4$ is:
hydrogen atom,
a group represented by the formula —CONHCO$_2$Me
a group represented by the formula —X$^{041}$—R$^{041}$,
a group represented by the formula —X$^{041}$-A$^{041}$-X$^{042}$—R$^{041}$,
a group represented by the formula —X$^{041}$-A$^{041}$-X$^{042}$-A$^{042}$-X$^{043}$—R$^{041}$, or
a group represented by the formula —X$^{041}$-A$^{041}$-X$^{042}$-A$^{042}$-X$^{043}$-A$^{043}$-X$^{044}$—R$^{041}$, wherein $X^{041}$ is:
a single bond,
a group represented by the formula —CO—,
a group represented by the formula —CON($R^{20}$)—, or
a group represented by the formula —$CO_2$—,
or $R^4$ may combine with $R^6$ to form cyclic carbonate [—$CO_2$—],
one of $R^5$ and $R^6$ is hydrogen atom, and the other is:
hydrogen atom,
hydroxyl group,
a protected hydroxyl group,
amino group,
a protected amino group,
a halogen atom,
a group represented by the formula —$OCONH_2$,
a group represented by the formula —$X^{061}$—$R^{061}$,
a group represented by the formula —$X^{061}$-$A^{061}$-$X^{062}$—$R^{061}$,
a group represented by the formula —$X^{061}$-$A^{061}$-$X^{062}$-$A^{062}$-$X^{063}$—$R^{061}$, or
a group represented by the formula —$X^{061}$-$A^{061}$-$X^{062}$-$A^{062}$-$X^{063}$-$A^{063}$-$X^{064}$—$R^{061}$,
or may combine with $R^7$ to form cyclic carbamate [—OCO—],
wherein $X^{061}$ is:
a single bond,
a group represented by the formula —O—,
a group represented by the formula —OCO—,
a group represented by the formula —$OCO_2$—,
a group represented by the formula —OCON($R^{20}$)—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—,
a group represented by the formula —N($R^{20}$)$SO_2$—, or
a group represented by the formula —$CH_2$N($R^{20}$)—,
or $R^5$ and $R^6$ combine together to represent
oxo group,
oxime group,
a group represented by the formula =N—$NH_2$,
a protected oxime group,
a group represented by the formula =N—$X^{065}$—$R^{062}$,
a group represented by the formula =N—$X^{065}$-$A^{064}$-$X^{066}$—$R^{062}$,
a group represented by the formula =N—$X^{065}$-$A^{064}$-$X^{066}$-$A^{065}$-$X^{067}$—$R^{062}$, or
a group represented by the formula =N—$X^{065}$-$A^{064}$-$X^{066}$-$A^{065}$-$X^{067}$-$A^{066}$-$X^{068}$—$R^{062}$
wherein $X^{065}$ is:
a single bond,
a group represented by the formula —O—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—, or
a group represented by the formula —N($R^{20}$)$SO_2$—,
$R^7$ is:
hydrogen atom,
hydroxyl group,
a protective group of amino group,
a group represented by the formula —$X^{071}$—$R^{071}$,
a group represented by the formula —$X^{071}$-$A^{071}$-$X^{072}$—$R^{071}$, or
a group represented by the formula —$X^{071}$-$A^{071}$-$X^{072}$-$A^{072}$-$X^{073}$—$R^{071}$, or may combine with $R^{10}$ to form cyclic carbamate [—$CO_2CH_2$—],
wherein $X^{071}$ is:
a single bond,
a group represented by the formula —O—,
a group represented by the formula —CO—,
a group represented by the formula —$CO_2$—, or
a group represented by the formula —$SO_2$—,
$R^8$ and $R^9$, which are the same or different, represent:
hydrogen atom,
a group represented by the formula —$X^{081}$—$R^{081}$,
a group represented by the formula —$X^{081}$-$A^{081}$-$X^{082}$—$R^{081}$, or
a group represented by the formula —$X^{081}$-$A^{081}$-$X^{082}$-$A^{082}$-$X^{083}$—$R^{081}$,
wherein $X^{081}$ is:
a single bond,
a group represented by the formula —CO—,
a group represented by the formula —$CO_2$—, or
a group represented by the formula —CON($R^{20}$)—,
$R^{10}$ and $R^{11}$, which are the same or different, represent
hydrogen atom,
a group represented by the formula —$X^{101}$—$R^{101}$,
a group represented by the formula —$X^{101}$-$A^{101}$-$X^{102}$—$R^{101}$,
a group represented by the formula —$X^{101}$-$A^{101}$-$X^{102}$-$A^{102}$-$X^{103}$—$R^{101}$, or
a group represented by the formula —$X^{101}$-$A^{101}$-$X^{102}$-$A^{102}$-$X^{103}$-$A^{103}$-$X^{104}$—$R^{101}$,
wherein $X^{101}$ is:
a single bond,
a group represented by the formula —CO—,
a group represented by the formula —$CO_2$—, or
a group represented by the formula —CON($R^{20}$)—,
$R^{12}$ is:
hydrogen atom,
a protective group of hydroxyl group,
a group represented by the formula —$X^{121}$—$R^{121}$,
a group represented by the formula —$X^{121}$-$A^{121}$-$X^{122}$—$R^{121}$, or
a group represented by the formula —$X^{121}$-$A^{121}$-$X^{122}$-$A^{122}$-$X^{123}$—$R^{121}$,
wherein $X^{121}$ is:
a single bond,
a group represented by the formula —CO—,
a group represented by the formula —$CO_2$—, or
a group represented by the formula —CON($R^{20}$)—,
$R^{13}$ and $R^{14}$, which are the same or different, represent
hydrogen atom,
a protective group of amino group,
a group represented by the formula —$X^{131}$—$R^{131}$,
a group represented by the formula —$X^{131}$-$A^{131}$-$X^{132}$—$R^{131}$, or
a group represented by the formula —$X^{131}$-$A^{131}$-$X^{132}$-$A^{132}$-$X^{133}$—$R^{131}$,
wherein $X^{131}$ is:
a single bond,
a group represented by the formula —CO—,
a group represented by the formula —$CO_2$—, or
a group represented by the formula —CON($R^{20}$)—,
$R^{15}$ is:
hydrogen atom,
hydroxyl group,
a protected hydroxyl group,
a group represented by the formula —$X^{151}$—$R^{151}$, a group represented by the formula $-X^{151}-A^{151}-X^{152}-R^{151}$, or a group represented by the formula $-X^{151}-A^{151}-X^{152}-A^{152}-X^{153}-R^{151}$, wherein $X^{151}$ is:

a single bond, a group represented by the formula $-OCO-$, a group represented by the formula $-OCO_2-$, or a group represented by the formula $-OCON(R^{20})-$, $X^{032}, X^{033}, X^{034}, X^{332}, X^{333}, X^{334}, X^{336}, X^{337}, X^{338}, X^{340}, X^{341}, X^{342}, X^{344}, X^{345}, X^{346}, X^{042}, X^{043}, X^{044}, X^{062}, X^{063}, X^{064}, X^{066}, X^{067}, X^{068}, X^{072}, X^{073}, X^{082}, X^{083}, X^{102}, X^{103}, X^{104}, X^{122}, X^{123}, X^{132}, X^{133}, X^{152}$ and $X^{153}$ mentioned above, which are the same or different, represent a single bond a group represented by the formula $-O-$, a group represented by the formula $-OCO-$, a group represented by the formula $-OCO_2-$, a group represented by the formula $-OCON(R^{20})-$, a group represented by the formula $-S(O)_p-$, a group represented by the formula $-SO_2N(R^{20})-$, a group represented by the formula $-OCS-$, a group represented by the formula $-CO-$, a group represented by the formula $-CO_2-$, a group represented by the formula $-CON(R^{20})-$, a group represented by the formula $-CH=N-$, a group represented by the formula $-CH=N-O-$, a group represented by the formula $-CH=N(R^{20})-$, a group represented by the formula $-CH=N(R^{20})O-$, a group represented by the formula $-CH=N(R^{20})N(R^{21})-$, a group represented by the formula $-CH=N(OR^{20})-$, a group represented by the formula $-CH=N-N(R^{20})R^{21}-$, a group represented by the formula $-CS-$, a group represented by the formula $-C(S)O-$, a group represented by the formula $-CSN(R^{20})-$, a group represented by the formula $-O-N=CH-$, a group represented by the formula $-N=CH-$, a group represented by the formula $-N(R^{20})-$, a group represented by the formula $-N(R^{20})CO-$, a group represented by the formula $-N(R^{20})CS-$, a group represented by the formula $-N(R^{20})SO_2$, a group represented by the formula $-N(R^{20})CO_2-$, or a group represented by the formula $-N(R^{20})CON(R^{21})-$, $A^{031}, A^{032}, A^{033}, A^{331}, A^{332}, A^{333}, A^{334}, A^{335}, A^{336}, A^{337}, A^{338}, A^{339}, A^{340}, A^{341}, A^{342}, A^{041}, A^{042}, A^{043}, A^{061}, A^{062}, A^{063}, A^{064}, A^{065}, A^{066}, A^{071}, A^{072}, A^{081}, A^{082}, A^{101}, A^{102}, A^{103}, A^{121}, A^{122}, A^{131}, A^{132}, A^{151}$ and $A^{152}$ mentioned above, which are the same or different, represent a divalent $C_{1-10}$ aliphatic hydrocarbon group which may be substituted with hydroxyl group, an arylene group, or a divalent heterocyclic group, $R^{031}, R^{331}, R^{332}, R^{333}, R^{335}, R^{041}, R^{061}, R^{062}, R^{071}, R^{081}, R^{101}, R^{121}, R^{131}$ and $R^{151}$ mentioned above, which are the same or different, represent a $C_{1-10}$ alkyl group which may be substituted, a $C_{2-10}$ alkenyl group which may be substituted, a $C_{2-10}$ alkynyl group which may be substituted, a $C_{3-10}$ cycloalkyl group which may be substituted, a $C_{3-10}$ cycloalkyl group condensed with an aryl group, which may be substituted, an aryl group which may be substituted, or a heterocyclic group which may be substituted, substituents of the groups "which may be substituted" mentioned above each mean arbitrary 1 to 5 substituents selected from the following group of substituents, and the group of substituents consists of:

carboxyl group, a halogen atom, oxo group, hydroxyl group, cyano group, nitro group, oxido group, sulfonic acid group, and thiol group, as well as the following group which may be substituted with groups of the group A:

a $C_{1-10}$ alkyl group, a $C_{2-12}$ alkenyl group, a $C_{2-12}$ alkynyl group, a $C_{3-10}$ cycloalkyl group, a $C_{1-10}$ alkoxy group, a $C_{1-10}$ hydroxyalkoxy group, a $C_{2-12}$ alkenyloxy group, a carboxy($C_{1-6}$ alkyloxy) group, a cyano($C_{1-6}$ alkyloxy) group, a $C_{1-10}$ alkylthio group, a $C_{1-6}$ alkylsulfonyl group, an arylsulfonyl group which may be substituted with a $C_{1-6}$ alkyl group or a halogen atom, a $C_{1-10}$ haloalkylthio group, a $C_{2-10}$ alkenylthio group, a ($C_{1-6}$ alkoxy)($C_{1-6}$ alkyl) group, a ($C_{1-6}$ alkoxy)($C_{1-6}$ alkoxy) group, a $C_{1-10}$ haloalkyl group, a $C_{2-12}$ alkanoyl group, a $C_{2-12}$ alkanoyloxy group, a ($C_{2-12}$ alkanoyloxy)($C_{1-6}$ alkyl) group, a benzoyl group which may be substituted with 1 to 3 of halogen atoms or nitro groups, a $C_{2-6}$ alkanoylamino group, an aminosulfonyl group which may be substituted with 1 or 2 of $C_{1-6}$ alkyl groups, a $C_{1-6}$ alkylsulfonyl group, a $C_{1-6}$ alkylsulfonylamino group, a benzenesulfonylamino group which may be substituted with $C_{1-6}$ alkyl, succinimido group, maleimido group, phthalimido group, a $C_{2-10}$ alkoxycarbonyl group, a $C_{2-10}$ alkoxycarbonylalkoxy group, tri-($C_{1-6}$ alkyl)silyloxy group, a group represented by the formula $-N(R^{22})R^{23}$ (in the formula, $R^{22}$ and $R^{23}$ each represent hydrogen atom, a $C_{1-6}$ alkyl group, a $C_{1-6}$ hydroxyalkyl group, a $C_{3-10}$ alkoxycarbonylalkyl group or a cyano($C_{1-6}$ alkyl) group, or represent groups which combine to form, together with the adjacent nitrogen atom, a cyclic amino group, which may be substituted with "a $C_{1-6}$ alkyl group, a cyano($C_{1-6}$ alkyl) group, a $C_{3-10}$ cycloalkyl group, a $C_{2-6}$ alkanoyl group, benzoyl group, an aryloxy($C_{2-6}$ alkanoyl) group which may be substituted with "a $C_{1-6}$ alkyl group or a $C_{1-6}$ alkoxy group", a ($C_{1-6}$ alkoxy)($C_{1-6}$ alkyl) group, a $C_{2-6}$ alkoxycarbonyl group, oxo group, or hydroxyl group"), a group represented by the formula $-CON(R^{22})R^{23}$ (in the formula, $R^{22}$ and $R^{23}$ have the same meanings as those defined above), a group represented by the formula —OCON($R^{22}$)$R^{23}$ (in the formula, $R^{22}$ and $R^{23}$ have the same meanings as those defined above), a group represented by the formula —$CH_2$N($R^{22}$)$R^{23}$ (in the formula, $R^{22}$ and $R^{23}$ have the same meanings as those defined above), a group represented by the formula —O($CH_2$)$_m$N($R^{22}$)$R^{23}$ (in the formula, $R^{22}$ and $R^{23}$ have the same meanings as those defined above), and "an aryl group, a heterocyclic group, an aryloxy group, an arylthio group, a heterocyclyloxy group or a heterocyclylthio group" which may be substituted with 1 to 5 of groups arbitrarily selected from the group consisting of "a $C_{1-6}$ alkyl group, a $C_{1-6}$ haloalkyl group, a halogen atom, a $C_{1-6}$ alkoxy group, an aminosulfonyl group which may be substituted with 1 or 2 of $C_{1-6}$ alkyl groups, an aminosulfonylamino group which may be substituted with 1 or 2 of $C_{1-6}$ alkyl groups, an amino ($C_{1-6}$ alkyl) group which may be substituted with 1 or 2 of $C_{1-6}$ alkyl groups, a saturated heterocyclic group, a $C_{1-6}$ alkyl group substituted with a saturated heterocyclic group, carboxyl group, a $C_{2-10}$ alkoxycarbonyl group, a $C_{1-6}$ hydroxyalkyl group, cyano group, a cyano ($C_{1-6}$ alkyl) group, an amino group which may be substituted with 1 or 2 of $C_{1-6}$ alkyl groups, hydroxyl group, a $C_{1-10}$ alkylthio group, a $C_{1-6}$ alkylsulfonyl group, a $C_{1-6}$ alkylsulfonylamino group and nitro group", which may be substituted with groups of the group A, wherein group A consists of "an aryl group, a heterocyclic group, a heterocyclylthio group or an aryloxy group" which may be substituted with "a halogen atom, a $C_{1-6}$ alkyl group, a hydroxy($C_{1-6}$ alkyl) group, hydroxyl group or nitro group", cyano group, cyanothio group, carboxyl group, hydroxyl group, a $C_{2-10}$ alkoxycarbonyl group, and a $C_{1-10}$ alkoxy group, $R^{20}$ and $R^{21}$ mentioned above, which are the same or different, represent a group suitably selected from hydrogen atom, and a $C_{1-10}$ alkyl group which may be substituted with the substituents mentioned above, p mentioned above is an integer of 0 to 2, n mentioned above is 1 or 2, and m mentioned above is an integer of 2 to 4}, or a pharmaceutically acceptable salt thereof.

2. The 10a-azalide compound, or pharmaceutically acceptable salt thereof according to claim 1, wherein $R^{13}$ and $R^{14}$ are methyl groups, and $R^{15}$ is hydrogen atom.

3. The 10a-azalide compound, or pharmaceutically acceptable salt thereof according to claim 2, wherein $R^1$, $R^8$, $R^9$ and $R^{12}$ are hydrogen atom, one of $R^2$ and $R^3$ is hydrogen atom, and the other is a group represented by the formula 2

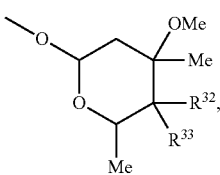

(2)

$R^4$ is hydrogen atom, or a group represented by the formula —$R^{041}$, one of $R^5$ and $R^6$ is hydrogen atom, and the other is hydroxyl group, or $R^5$ and $R^6$ combine together to represent oxo group, oxime group, a protected oxime group, a group represented by the formula =N—$X^{065}$—$R^{062}$, a group represented by the formula =N—$X^{065}$-$A^{064}$-$X^{066}$—$R^{062}$, a group represented by the formula =N—$X^{065}$-$A^{064}$-$X^{066}$-$A^{065}$-$X^{067}$—$R^{062}$, or a group represented by the formula =N—$X^{065}$-$A^{064}$-$X^{066}$-$A^{065}$-$X^{067}$-$A^{066}$-$X^{068}$—$R^{062}$, and $R^7$ is methyl group.

4. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is a group represented by the formula 2:

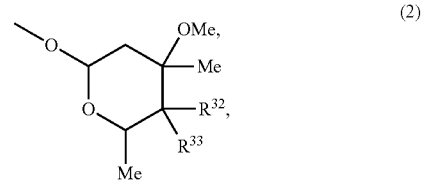

(2)

$R^4$ is hydrogen atom, or a group represented by the formula —$R^{041}$, one of $R^5$ and $R^6$ is hydrogen atom, and the other is hydroxyl group, amino group, a group represented by the formula —$OCONH_2$, a group represented by the formula —$X^{061}$—$R^{061}$, or a group represented by the formula —$X^{061}$-$A^{061}$-$X^{062}$—$R^{061}$, or $R^5$ and $R^6$ combine together to represent oxo group, oxime group, a group represented by the formula =N—$NH_2$, a group represented by the formula =N—O—$R^{062}$, or a group represented by the formula =N—O-$A^{064}$-$X^{066}$—$R^{062}$, $R^7$ is methyl group, one of $R^{10}$ and $R^{11}$ is hydrogen atom, and the other is hydrogen atom, a group represented by the formula —$X^{101}$—$R^{101}$, or a group represented by the formula —$X^{101}$-$A^{101}$-$X^{102}$—$R^{101}$, and $X^{101}$ is a single bond, or a group represented by the formula —$CO_2$—.

5. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is a group represented by the formula 41:

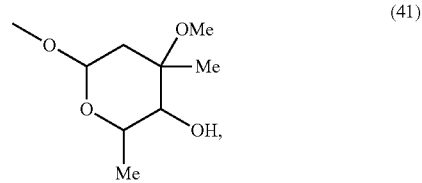

(41)

$R^4$ is hydrogen atom, methyl group, or a group represented by the formula —$CONHCO_2Me$, $R^7$ is methyl group, one of $R^5$ and $R^6$ is hydrogen atom, and the other is hydroxyl group, one of $R^{10}$ and $R^{11}$ is hydrogen atom, and the other is hydrogen atom, a group represented by the formula —$X^{101}$—$R^{101}$, or a group represented by the formula —$X^{101}$-$A^{101}$-$X^{102}$—$R^{101}$, and $X^{101}$ is a single bond, or a group represented by the formula —$CO_2$—.

6. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is hydroxyl group, a group represented by the formula —OCO—$R^{031}$, or a group represented by the formula —OCO-$A^{031}$-$X^{032}$-$A^{032}$-$X^{033}$-$A^{033}$-$X^{034}$—$R^{031}$, or $R^2$ and $R^3$ combine together to represent oxo group, $R^4$ and $R^7$ are methyl groups, one of $R^5$ and $R^6$ is hydrogen atom, and the other is hydroxyl group, one of $R^{10}$ and $R^{11}$ is hydrogen atom, and the other is ethyl group, or a group represented by the formula -$A^{101}$-$X^{102}$—$R^{101}$.

7. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is a group represented by the formula 2:

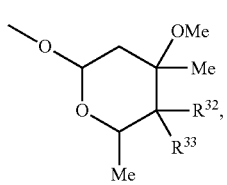

(2)

one of $R^{32}$ and $R^{33}$ is hydrogen atom, and the other is hydroxyl group, amino group, a group represented by the formula —$X^{331}$-$A^{331}$-$X^{332}$—$R^{331}$, or a group represented by the formula —$X^{331}$-$A^{331}$-$X^{332}$-$A^{332}$-$X^{333}$—$R^{331}$, $X^{331}$ is:

a group represented by the formula —OCO—, or a group represented by the formula —OCONH—, or one of $R^{32}$ and $R^{33}$ is hydroxyl group, and the other is methyl group, or a group represented by the formula —$X^{335}$-$A^{334}$-$X^{336}$—$R^{332}$, $X^{335}$ is:

a group represented by the formula —$CH_2$—NH—, or a group represented by the formula —$CH_2$—NHCO—, or $R^{32}$ and $R^{33}$ combine together to represent oxo group, or oxime group, $R^4$ is hydrogen atom, or methyl group, $R^7$ is methyl group, one of $R^5$ and $R^6$ is hydrogen atom, and the other is hydroxyl group, or $R^5$ and $R^6$ combine together to represent oxo group, or oxime group, one of $R^{10}$ and $R^{11}$ is hydrogen atom, and the other is hydrogen atom, methyl group, ethyl group, or cyanopropyl group.

8. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is a group represented by the formula 41:

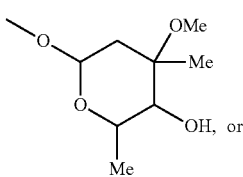

(41)

a group represented by the formula —OCO—$R^{031}$, $R^4$ and $R^7$ are methyl groups, one of $R^5$ and $R^6$ is hydrogen atom, and the other is amino group, a group represented by the formula —OCONH$_2$, a group represented by the formula —$X^{061}$—$R^{061}$, or a group represented by the formula —$X^{061}$-$A^{061}$-$X^{062}$—$R^{061}$, or $R^5$ and $R^6$ combine together to represent oxo group, oxime group, a group represented by the formula =N—NH$_2$, a group represented by the formula =N—O—$R^{062}$, or a group represented by the formula =N—O-$A^{064}$-$X^{066}$—$R^{062}$, one of $R^{10}$ and $R^{11}$ is hydrogen atom, and the other is hydrogen atom, a group represented by the formula —$R^{101}$, or a group represented by the formula -$A^{101}$-$X^{102}$—$R^{101}$.

9. The 10a-azalide compound, or pharmaceutically acceptable salt thereof according to claim 2, wherein $R^1$, $R^8$, $R^9$ and $R^{12}$ are hydrogen atoms, $R^2$ and $R^3$ combine together to represent oxo group, or one of them is hydrogen atom, and the other is a group represented by the formula 41:

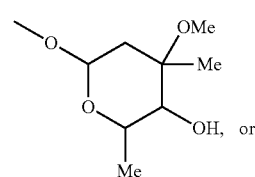

(41)

a group represented by the formula —OCO—$R^{031}$, $R^4$ is methyl group, one of $R^5$ and $R^6$ is hydrogen atom, and the other combines with $R^7$ to form cyclic carbamate [—OCO—], one of $R^{10}$ and $R^{11}$ is hydrogen atom, and the other is ethyl group, or a group represented by the formula -$A^{101}$-$X^{102}$—$R^{101}$.

10. The 10a-azalide compound, or pharmaceutically acceptable salt thereof according to claim 2, wherein $R^1$, $R^8$, $R^9$ and $R^{12}$ are hydrogen atoms, $R^2$ and $R^3$ combine together to represent oxo group, or one of them is hydrogen atom, and the other is a group represented by the formula 41:

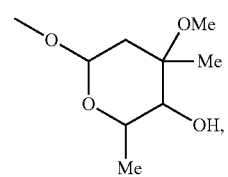

(41)

$R^4$ is:

a group represented by the formula —$R^{041}$, one of $R^5$ and $R^6$ is hydrogen atom, and the other is hydroxyl group, $R^7$ is methyl group, or may combine with one of $R^5$ and $R^6$ to form cyclic carbamate [—OCO—], one of $R^{10}$ and $R^{11}$ is hydrogen atom, and the other is ethyl group.

11. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is a group represented by the formula 2:

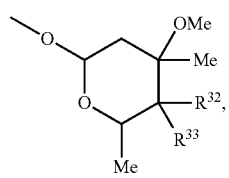

(2)

one of $R^{32}$ and $R^{33}$ is hydrogen atom, and the other is amino group, hydroxyl group, a group represented by the formula —OCON($R^{24}$)$R^{25}$ (in the formula, $R^{24}$ and $R^{25}$ both represent hydrogen atom, or represent groups which combine to form a cyclic amino group together with the adjacent nitrogen atom),
a group represented by the formula —$X^{331}$—$R^{331}$,
a group represented by the formula —$X^{331}$-$A^{331}$-$X^{332}$—$R^{331}$, or
a group represented by the formula —$X^{331}$-$A^{331}$-$X^{332}$-$A^{332}$-$X^{333}$-$A^{333}$-$X^{334}$—$R^{331}$, $R^4$ and $R^7$ are methyl groups, one of $R^5$ and $R^6$ is hydrogen atom, and the other is hydroxyl group, one of $R^{10}$ and $R^{11}$ is hydrogen atom, and the other is ethyl group.

12. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is a group represented by the formula 2:

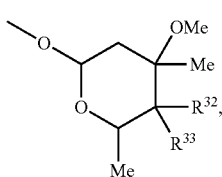

(2)

one of $R^{32}$ and $R^{33}$ is hydroxyl group, and the other is:
a group represented by the formula —$CH_2NH_2$,
a group represented by the formula —$X^{335}$—$R^{332}$,
a group represented by the formula —$X^{335}$-$A^{334}$-$X^{336}$—$R^{332}$, or
a group represented by the formula —$X^{335}$-$A^{334}$-$X^{336}$-$A^{335}$-$X^{337}$—$R^{332}$, $R^4$ and $R^7$ are methyl groups, one of $R^5$ and $R^6$ is hydrogen atom, and the other is hydroxyl group, one of $R^{10}$ and $R^{11}$ is hydrogen atom, and the other is ethyl group.

13. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is a group represented by the formula 2:

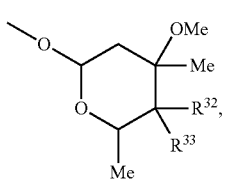

(2)

$R^{32}$ and $R^{33}$ combine together to represent a group represented by the formula 3:

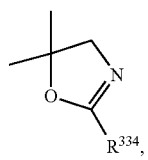

(3)

$R^{334}$ is:
a group represented by the formula —SH, or
a group represented by the formula —OH, $R^4$ and $R^7$ are methyl group, one of $R^5$ and $R^6$ is hydrogen atom, and the other is hydroxyl group, one of $R^{10}$ and $R^{11}$ is hydrogen atom, and the other is ethyl group.

14. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is a group represented by the formula 41:

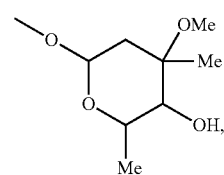

(41)

$R^4$ is methyl group, one of $R^5$ and $R^6$ is hydrogen atom, and the other is hydroxyl group, $R^7$ is:
a group represented by the formula —$R^{071}$, one of $R^{10}$ and $R^{11}$ is hydrogen atom, and the other is ethyl group.

15. The 10a-azalide compound, or pharmaceutically acceptable salt thereof according to claim 2, wherein $R^1$, $R^8$, $R^9$ and $R^{12}$ are hydrogen atoms, one of $R^2$ and $R^3$ is hydrogen atom, and the other is hydroxyl group, or a group represented by the formula 41:

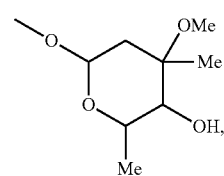

(41)

$R^4$ is methyl group, one of $R^5$ and $R^6$ is hydrogen atom, and the other is hydroxyl group, $R^7$ combines with $R^{10}$ to form cyclic carbamate [—$CO_2CH_2$—], and $R^{11}$ is hydrogen atom.

16. The 10a-azalide compound, or pharmaceutically acceptable salt thereof according to claim 2, wherein $R^1$ and $R^{12}$ are hydrogen atoms, one of $R^2$ and $R^3$ is hydrogen atom, and the other is a group represented by the formula 41:

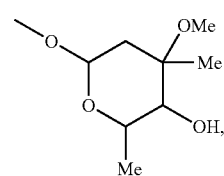

(41)

$R^4$ is methyl group, one of $R^5$ and $R^6$ is hydrogen atom, and the other is hydroxyl group, $R^7$ is methyl group, or hydroxyl group, one of $R^8$ and $R^9$ is hydrogen atom, and the other is methyl group, one of $R^{10}$ and $R^{11}$ is hydrogen atom, and the other is methyl group, or ethyl group.

17. A compound represented by the formula (II):

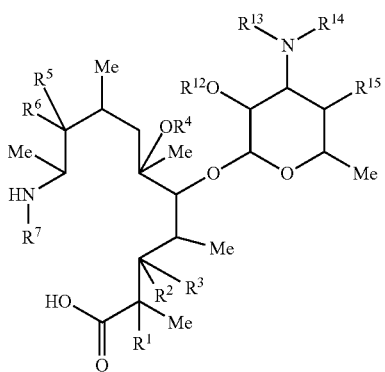

(II)

{wherein, in the formula (II), $R^1$ is:
hydrogen atom,
a halogen atom, or
a $C_{1-10}$ alkyl group which may be substituted,
$R^2$ and $R^3$ combine to represent oxo group or
one of them is hydrogen atom, and the other is:
hydrogen atom,
hydroxyl group,
a protected hydroxyl group,
a group represented by the formula $-X^{031}-R^{031}$,
a group represented by the formula $-X^{031}-A^{031}-X^{032}-R^{031}$,
a group represented by the formula $-X^{031}-A^{031}-X^{032}-A^{032}-X^{033}-R^{031}$,
a group represented by the formula $-X^{031}-A^{031}-X^{032}-A^{032}-X^{033}-A^{033}-X^{034}-R^{031}$, or a
group represented by the formula 2:

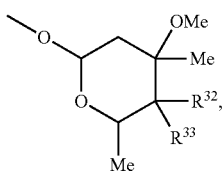

(2)

wherein $X^{031}$ is:
a group represented by the formula $-O-$,
a group represented by the formula $-OCO-$,
a group represented by the formula $-OCO_2-$, or
a group represented by the formula $-OCON(R^{20})-$,
one of $R^{32}$ and $R^{33}$ is hydrogen atom, and the other is:
hydrogen atom,
amino group,
hydroxyl group,
protected hydroxyl group,
a group represented by the formula $-OCON(R^{24})R^{25}$ (in the formula, $R^{24}$ and $R^{25}$ both represent hydrogen atom, or represent groups which combine to form a cyclic amino group together with the adjacent nitrogen atom),
a group represented by the formula $-X^{331}-R^{331}$,
a group represented by the formula $-X^{331}-A^{331}-X^{332}-R^{331}$,
a group represented by the formula $-X^{331}-A^{331}-X^{332}-A^{332}-X^{333}-R^{331}$, or a group represented by the formula $-X^{331}-A^{331}-X^{332}-A^{332}-X^{333}-A^{333}-X^{334}-R^{331}$,
wherein $X^{331}$ is:
a single bond,
a group represented by the formula $-O-$,
a group represented by the formula $-OCO-$,
group represented by the formula $-OCO_2-$,
a group represented by the formula $-OCON(R^{20})-$,
a group represented by the formula $-N(R^{20})-$,
a group represented by the formula $-N(R^{20})CO_2-$,
a group represented by the formula $-N(R^{20})CON(R^{21})-$, or
a group represented by the formula $-N(R^{20})SO_2-$,
or one of $R^{32}$ and $R^{33}$ is hydroxyl group, and the other is:
a group represented by the formula $-CH_2NH_2$,
a group represented by the formula $-X^{335}-R^{332}$,
a group represented by the formula $-X^{335}-A^{334}-X^{336}-R^{332}$,
a group represented by the formula $-X^{335}-A^{334}-X^{336}-A^{335}-X^{337}-R^{332}$, or
a group represented by the formula $-X^{335}-A^{334}-X^{336}-A^{335}-X^{337}-A^{336}-X^{338}-R^{332}$,
wherein $X^{335}$ is:
a single bond,
a group represented by the formula $-(CH_2)_n-N(R^{20})-$,
a group represented by the formula $-(CH_2)_n-N(R^{20})CO-$,
a group represented by the formula $-(CH_2)_n-N(R^{20})CO_2-$,
a group represented by the formula $-(CH_2)_n-N(R^{20})CON(R^{21})-$,
a group represented by the formula $-(CH_2)_n-N(R^{20})O-$,
a group represented by the formula $-(CH_2)_n-OCON(R^{20})-$,
a group represented by the formula $-(CH_2)_n-ON(R^{20})CO-$,
a group represented by the formula $-(CH_2)_n-O-$,
a group represented by the formula $-(CH_2)_n-OCO-$,
a group represented by the formula $-(CH_2)_n-OCO_2-$,
a group represented by the formula $-(CH_2)_n-OC(NR^{20})-$, or
a group represented by the formula $-(CH_2)_n-S(O)_p-$,
or $R^{32}$ and $R^{33}$ combine together to represent:
oxo group,
oxime group,
a group represented by the formula $=N-X^{339}-R^{333}$,
a group represented by the formula $=N-X^{339}-A^{337}-X^{340}-R^{333}$,
a group represented by the formula $=N-X^{339}-A^{337}-X^{340}-A^{338}-X^{341}-R^{333}$,
a group represented by the formula $=N-X^{339}-A^{337}-X^{340}-A^{338}-X^{341}-A^{339}-X^{342}-R^{333}$, or a group represented by the formula 3:

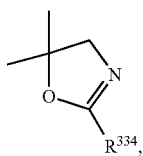
(3)

wherein $X^{339}$ is:
a single bond,
a group represented by the formula —O—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—, or
a group represented by the formula —N($R^{20}$)$SO_2$—, and
$R^{334}$ is:
a group represented by the formula —SH,
a group represented by the formula —OH,
a group represented by the formula —$X^{343}$—$R^{335}$,
a group represented by the formula —$X^{343}$-$A^{340}$-$X^{344}$—$R^{335}$,
a group represented by the formula —$X^{343}$-$A^{340}$-$X^{344}$-$A^{341}$-$X^{345}$—$R^{335}$, or
a group represented by the formula —$X^{343}$-$A^{340}$-$X^{344}$-$A^{341}$-$X^{345}$-$A^{342}$-$X^{346}$—$R^{335}$,
wherein $X^{343}$ is:
a single bond,
a group represented by the formula —S—, or
a group represented by the formula —$(CH_2)_n$CO—,
$R^4$ is:
hydrogen atom,
a group represented by the formula —$CONHCO_2Me$
a group represented by the formula —$X^{041}$—$R^{041}$,
a group represented by the formula —$X^{041}$-$A^{041}$-$X^{042}$—$R^{041}$,
a group represented by the formula —$X^{041}$-$A^{041}$-$X^{042}$-$A^{042}$-$X^{043}$—$R^{041}$, or
a group represented by the formula —$X^{041}$-$A^{041}$$X^{042}$-$A^{042}$-$X^{043}$-$A^{043}$-$X^{044}$—$R^{041}$,
wherein $X^{041}$ is:
a single bond,
a group represented by the formula —CO—,
a group represented by the formula —CON($R^{20}$)—, or
a group represented by the formula —$CO_2$—,
or $R^4$ may combine with $R^6$ to form cyclic carbonate [—$CO_2$—],
one of $R^5$ and $R^6$ is hydrogen atom, and the other is:
hydrogen atom,
hydroxyl group,
a protected hydroxyl group,
amino group,
a protected amino group,
a halogen atom,
a group represented by the formula —$OCONH_2$,
a group represented by the formula —$X^{061}$—$R^{061}$,
a group represented by the formula —$X^{061}$-$A^{061}$-$X^{062}$—$R^{061}$,
a group represented by the formula —$X^{061}$-$A^{061}$-$X^{062}$-$A^{062}$-$X^{063}$—$R^{061}$, or
a group represented by the formula —$X^{061}$-$A^{061}$-$X^{062}$-$A^{062}$-$X^{063}$-$A^{063}$-$X^{064}$—$R^{061}$, wherein $X^{061}$ is:
a single bond,
a group represented by the formula —O—,
a group represented by the formula —OCO—,
a group represented by the formula —$OCO_2$—,
a group represented by the formula —OCON($R^{20}$)—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—,
a group represented by the formula —N($R^{20}$)$SO_2$—, or
a group represented by the formula —$CH_2$N($R^{20}$)—,
or $R^5$ and $R^6$ combine together to represent
oxo group,
oxime group,
a group represented by the formula =N—$NH_2$,
a protected oxime group,
a group represented by the formula =N—$X^{065}$—$R^{062}$,
a group represented by the formula =N—$X^{065}$-$A^{064}$-$X^{066}$—$R^{062}$,
a group represented by the formula =N—$X^{065}$-$A^{064}$-$X^{066}$-$A^{065}$-$X^{067}$—$R^{062}$, or
a group represented by the formula =N—$X^{065}$-$A^{064}$-$X^{066}$-$A^{065}$-$X^{067}$-$A^{066}$-$X^{068}$—$R^{062}$
wherein $X^{065}$ is:
a single bond,
a group represented by the formula —O—,
a group represented by the formula —N($R^{20}$)—,
a group represented by the formula —N($R^{20}$)CO—,
a group represented by the formula —N($R^{20}$)$CO_2$—,
a group represented by the formula —N($R^{20}$)CON($R^{21}$)—, or
a group represented by the formula —N($R^{20}$)$SO_2$—,
$R^7$ is:
hydrogen atom,
hydroxyl group,
a protective group of amino group,
a group represented by the formula —$X^{071}$—$R^{071}$,
a group represented by the formula —$X^{071}$-$A^{071}$-$X^{072}$—$R^{071}$, or
a group represented by the formula —$X^{071}$-$A^{071}$-$X^{072}$-$A^{072}$-$X^{073}$—$R^{071}$, or
may combine with $R^{10}$ to form cyclic carbamate [—$CO_2CH_2$—],
wherein $X^{071}$ is:
a single bond,
a group represented by the formula —O—,
a group represented by the formula —CO—,
a group represented by the formula —$CO_2$—, or
a group represented by the formula —$SO_2$—,
$R^{12}$ is:
hydrogen atom,
a protective group of hydroxyl group,
a group represented by the formula —$X^{121}$—$R^{121}$,
a group represented by the formula —$X^{121}$-$A^{121}$-$X^{122}$—$R^{121}$, or
a group represented by the formula —$X^{121}$-$A^{121}$-$X^{122}$-$A^{122}$-$X^{123}$—$R^{121}$,
wherein $X^{121}$ is:
a single bond,
a group represented by the formula —CO—,
a group represented by the formula —$CO_2$—, or
a group represented by the formula —CON($R^{20}$)—, $R^{13}$ and $R^{14}$, which are the same or different, represent
hydrogen atom,
a protective group of amino group,
a group represented by the formula —$X^{131}$—$R^{131}$,
a group represented by the formula —$X^{131}$-$A^{131}$-$X^{132}$—$R^{131}$, or
a group represented by the formula —$X^{131}$-$A^{131}$-$X^{132}$-$A^{132}$-$X^{133}$—$R^{131}$,
  wherein $X^{131}$ is:
  a single bond,
  a group represented by the formula —CO—,
  a group represented by the formula —$CO_2$—, or
  a group represented by the formula —$CON(R^{20})$—,
$R^{15}$ is:
hydrogen atom,
hydroxyl group,
a protected hydroxyl group,
a group represented by the formula —$X^{151}$—$R^{151}$,
a group represented by the formula —$X^{151}$-$A^{151}$-$X^{152}$—$R^{151}$, or
a group represented by the formula —$X^{151}$-$A^{151}$-$X^{152}$-$A^{152}$-$X^{153}$—$R^{151}$,
  wherein $X^{151}$ is:
  a single bond,
  a group represented by the formula —OCO—,
  a group represented by the formula —$OCO_2$13, or
  a group represented by the formula —$OCON(R^{20})$—,
$X^{032}, X^{033}, X^{034}, X^{332}, X^{333}, X^{334}, X^{336}, X^{337}, X^{338}, X^{340}, X^{341}, X^{342}, X^{344}, X^{345}, X^{346}, X^{042}, X^{043}, X^{044}, X^{062}, X^{063}, X^{064}, X^{066}, X^{067}, X^{068}, X^{072}, X^{073}, X^{122}, X^{123}, X^{132}, X^{133}, X^{152}$ and $X^{153}$ mentioned above, which are the same or different, represent
a single bond
a group represented by the formula —O—,
a group represented by the formula —OCO—,
a group represented by the formula —$OCO_2$—,
a group represented by the formula —$OCON(R^{20})$—,
a group represented by the formula —$S(O)_p$—,
a group represented by the formula —$SO_2N(R^{20})$—,
a group represented by the formula —OCS—,
a group represented by the formula —CO—,
a group represented by the formula —$CO_2$—,
a group represented by the formula —$CON(R^{20})$—,
a group represented by the formula —CH=N—,
a group represented by the formula —CH=N—O—,
a group represented by the formula —CH=$N(R^{20})$—,
a group represented by the formula —CH=$N(R^{20})$O—,
a group represented by the formula —CH=$N(R^{20})N(R^{21})$—,
a group represented by the formula —CH=$N(OR^{20})$—,
a group represented by the formula —CH=N—$N(R^{20})R^{21}$—,
a group represented by the formula —CS—,
a group represented by the formula —C(S)O—,
a group represented by the formula —$CSN(R^{20})$—,
a group represented by the formula —O—N=CH—,
a group represented by the formula —N=CH—,
a group represented by the formula —$N(R^{20})$—,
a group represented by the formula —$N(R^{20})CO$—,
a group represented by the formula —$N(R^{20})CS$—,
a group represented by the formula —$N(R^{20})SO_2$—,
a group represented by the formula —$N(R^{20})CO_2$—, or
a group represented by the formula —$N(R^{20})CON(R^{21})$—,
$A^{031}, A^{032}, A^{033}, A^{331}, A^{332}, A^{333}, A^{334}, A^{335}, A^{336}, A^{337}, A^{338}, A^{339}, A^{340}, A^{341}, A^{342}, A^{041}, A^{042}, A^{043}, A^{061}, A^{062}, A^{063}, A^{064}, A^{065}, A^{066}, A^{071}, A^{072}, A^{121}, A^{122}$,
$A^{131}, A^{132}, A^{151}$ and $A^{152}$ mentioned above, which are the same or different, represent
a divalent $C_{1-10}$ aliphatic hydrocarbon group which may be substituted with hydroxyl group,
an arylene group, or
a divalent heterocyclic group,
$R^{031}, R^{331}, R^{332}, R^{333}, R^{335}, R^{041}, R^{061}, R^{062}, R^{071}, R^{121}, R^{131}$ and $R^{151}$ mentioned above, which are the same or different, represent
a $C_{1-10}$ alkyl group which may be substituted,
a $C_{2-10}$ alkenyl group which may be substituted,
a $C_{2-10}$ alkynyl group which may be substituted,
a $C_{3-10}$ cycloalkyl group which may be substituted,
a $C_{3-10}$ cycloalkyl group condensed with an aryl group, which may be substituted,
an aryl group which may be substituted, or
a heterocyclic group which may be substituted,
substituents of the groups "which may be substituted" mentioned above each mean arbitrary 1 to 5 substituents selected from the following group of substituents, and the group of substituents consists of:
carboxyl group,
a halogen atom,
oxo group,
hydroxyl group,
cyano group,
nitro group,
oxido group,
sulfonic acid group, and
thiol group,
as well as the following group which may be substituted with groups of the group A:
a $C_{1-10}$ alkyl group,
a $C_{2-12}$ alkenyl group,
a $C_{2-12}$ alkynyl group,
a $C_{3-10}$ cycloalkyl group,
a $C_{1-10}$ alkoxy group,
a $C_{1-10}$ hydroxyalkoxy group,
a $C_{2-12}$ alkenyloxy group,
a carboxy($C_{1-6}$ alkyloxy) group,
a cyano($C_{1-6}$ alkyloxy) group,
a $C_{1-10}$ alkylthio group,
a $C_{1-6}$ alkylsulfonyl group,
an arylsulfonyl group which may be substituted with a $C_{1-6}$ alkyl group or a halogen atom,
a $C_{1-10}$ haloalkylthio group,
a $C_{2-10}$ alkenylthio group,
a ($C_{1-6}$ alkoxy)($C_{1-6}$ alkyl) group,
a ($C_{1-6}$ alkoxy)($C_{1-6}$ alkoxy) group,
a $C_{1-10}$ haloalkyl group,
a $C_{2-12}$ alkanoyl group,
a $C_{2-12}$ alkanoyloxy group,
a ($C_{2-12}$ alkanoyloxy)($C_{1-6}$ alkyl) group,
a benzoyl group which may be substituted with 1 to 3 of halogen atoms or nitro groups,
a $C_{2-6}$ alkanoylamino group,
an aminosulfonyl group which may be substituted with 1 or 2 of $C_{1-6}$ alkyl groups,
a $C_{1-6}$ alkylsulfonyl group,
a $C_{1-6}$ alkylsulfonylamino group,
a benzenesulfonylamino group which may be substituted with $C_{1-6}$ alkyl,
succinimido group,
maleimido group,
phthalimido group,
a $C_{2-10}$ alkoxycarbonyl group,
a $C_{2-10}$ alkoxycarbonylalkoxy group,
tri-($C_{1-6}$ alkyl)silyloxy group, a group represented by the formula —N(R$^{22}$)R$^{23}$ (in the formula, R$^{22}$ and R$^{23}$ each represent hydrogen atom, a C$_{1-6}$ alkyl group, a C$_{1-6}$ hydroxyalkyl group, a C$_{3-10}$ alkoxycarbonylalkyl group or a cyano(C$_{1-6}$ alkyl) group, or represent groups which combine to form, together with the adjacent nitrogen atom, a cyclic amino group, which may be substituted with "a C$_{1-6}$ alkyl group, a cyano(C$_{1-6}$ alkyl) group, a C$_{3-10}$ cycloalkyl group, a C$_{2-6}$ alkanoyl group, benzoyl group, an aryloxy(C$_{2-6}$ alkanoyl) group which may be substituted with "a C$_{1-6}$ alkyl group or a C$_{1-6}$ alkoxy group", a (C$_{1-6}$ alkoxy)(C$_{1-6}$ alkyl) group, a C$_{2-6}$ alkoxycarbonyl group, oxo group, or hydroxyl group"), a group represented by the formula —CON(R$^{22}$)R$^{23}$ (in the formula, R$^{22}$ and R$^{23}$ have the same meanings as those defined above), a group represented by the formula —OCON(R$^{22}$)R$^{23}$ (in the formula, R$^{22}$ and R$^{23}$ have the same meanings as those defined above), a group represented by the formula —CH$_2$N(R$^{22}$)R$^{23}$ (in the formula, R$^{22}$ and R$^{23}$ have the same meanings as those defined above), a group represented by the formula —O(CH$_2$)$_m$N(R$^{22}$)R$^{23}$ (in the formula, R$^{22}$ and R$^{23}$ have the same meanings as those defined above), and "an aryl group, a heterocyclic group, an aryloxy group, an arylthio group, a heterocyclyloxy group or a heterocyclylthio group" which may be substituted with 1 to 5 of groups arbitrarily selected from the group consisting of "a C$_{1-6}$ alkyl group, a C$_{1-6}$ haloalkyl group, a halogen atom, a C$_{1-6}$ alkoxy group, an aminosulfonylamino group which may be substituted with 1 or 2 of C$_{1-6}$ alkyl groups, an aminosulfonylamino group which may be substituted with 1 or 2 of C$_{1-6}$ alkyl groups, an amino (C$_{1-6}$ alkyl) group which may be substituted with 1 or 2 of C$_{1-6}$ alkyl groups, a saturated heterocyclic group, a C$_{1-6}$ alkyl group substituted with a saturated heterocyclic group, carboxyl group, a C$_{2-10}$ alkoxycarbonyl group, a C$_{1-6}$ hydroxyalkyl group, cyano group, a cyano (C$_{1-6}$ alkyl) group, an amino group which may be substituted with 1 or 2 of C$_{1-6}$ alkyl groups, hydroxyl group, a C$_{1-10}$ alkylthio group, a C$_{1-6}$ alkylsulfonyl group, a C$_{1-6}$ alkylsulfonylamino group and nitro group", which may be substituted with groups of the group A, wherein group A consists of "an aryl group, a heterocyclic group, a heterocyclylthio group or an aryloxy group" which may be substituted with "a halogen atom, a C$_{1-6}$ alkyl group, a hydroxy(C$_{1-6}$ alkyl) group, hydroxyl group or nitro group", cyano group, cyanothio group, carboxyl group, hydroxyl group, a C$_{2-10}$ alkoxycarbonyl group, and a C$_{1-10}$ alkoxy group, R$^{20}$ and R$^{21}$ mentioned above, which are the same or different, represent a group suitably selected from hydrogen atom, and a C$_{1-10}$ alkyl group which may be substituted with the substituents mentioned above, p mentioned above is an integer of 0 to 2, n mentioned above is 1 or 2, and m mentioned above is an integer of 2 to 4}.

* * * * *